(12) United States Patent
Martini et al.

(10) Patent No.: US 12,377,136 B2
(45) Date of Patent: Aug. 5, 2025

(54) POLYNUCLEOTIDES ENCODING PORPHOBILINOGEN DEAMINASE FOR THE TREATMENT OF ACUTE INTERMITTENT PORPHYRIA

(71) Applicants: ModernaTX, Inc., Cambridge, MA (US); Fundacion Para La Investigacion Medica Aplicada, Pamplona (ES)

(72) Inventors: Paolo Martini, Boston, MA (US); Stephen Hoge, Brookline, MA (US); Kerry Benenato, Sudbury, MA (US); Vladimir Presnyak, Manchester, NH (US); Lei Jiang, Cambridge, MA (US); Iain McFadyen, Arlington, MA (US); Ellalahewage Sathyajith Kumarasinghe, Harvard, MA (US); Antonio Fontanellas Roma, Pamplona (ES); Pedro Berraondo Lopez, Pamplona (ES); Matias Antonio Avila Zaragoza, Pamplona (ES); Lin Tung Guey, Lexington, MA (US); Staci Sabnis, Medford, MA (US)

(73) Assignees: ModernaTX, Inc., Cambridge, MA (US); Fundacion Para La Investigacion Medica Aplicada, Pamplona (ES)

( * ) Notice: Subject to any disclaimer, the term of this patent is extended or adjusted under 35 U.S.C. 154(b) by 352 days.

(21) Appl. No.: 17/813,984

(22) Filed: Jul. 21, 2022

(65) Prior Publication Data
US 2023/0112986 A1    Apr. 13, 2023

Related U.S. Application Data

(63) Continuation of application No. 16/302,339, filed as application No. PCT/US2017/033418 on May 18, 2017, now abandoned.

(30) Foreign Application Priority Data

May 9, 2017 (EP) ................................. 17382259

(51) Int. Cl.
| A61K 38/43 | (2006.01) |
| A61K 38/45 | (2006.01) |
| A61K 48/00 | (2006.01) |
| A61P 7/08 | (2006.01) |
| C12N 9/10 | (2006.01) |
| C12N 15/88 | (2006.01) |

(52) U.S. Cl.
CPC .......... *A61K 38/45* (2013.01); *A61K 48/0033* (2013.01); *A61K 48/005* (2013.01); *A61P 7/08* (2018.01); *C12N 9/1085* (2013.01); *C12N 15/88* (2013.01); *C12Y 205/01061* (2013.01)

(58) Field of Classification Search
None
See application file for complete search history.

(56) References Cited

U.S. PATENT DOCUMENTS

| 9,095,552 | B2 | 8/2015 | Chakraborty et al. |
| 9,107,886 | B2 | 8/2015 | Chakraborty et al. |
| 9,114,113 | B2 | 8/2015 | Chakraborty et al. |
| 9,220,792 | B2 | 12/2015 | Chakraborty et al. |
| 9,233,141 | B2 | 1/2016 | Chakraborty et al. |
| 9,814,760 | B2 | 11/2017 | Bancel et al. |
| 2013/0280305 | A1 | 10/2013 | Kuboyama et al. |
| 2014/0010861 | A1* | 1/2014 | Bancel .................. C07K 16/40 536/23.4 |
| 2014/0148502 | A1 | 5/2014 | Bancel et al. |
| 2014/0155472 | A1 | 6/2014 | Bancel et al. |
| 2014/0155473 | A1 | 6/2014 | Bancel et al. |
| 2014/0155474 | A1 | 6/2014 | Bancel et al. |
| 2014/0155475 | A1 | 6/2014 | Bancel et al. |
| 2014/0193482 | A1 | 7/2014 | Bancel et al. |
| 2014/0200263 | A1 | 7/2014 | Bancel et al. |
| 2014/0275227 | A1* | 9/2014 | Hoge ................. A61K 48/0066 536/23.5 |

(Continued)

FOREIGN PATENT DOCUMENTS

| WO | WO 17/075531 | * 7/1999 |
| WO | WO199937325 | 7/1999 |

(Continued)

OTHER PUBLICATIONS

Sequence alignment, 2024.*

(Continued)

*Primary Examiner* — Ileana Popa

(74) *Attorney, Agent, or Firm* — Fish & Richardson P.C.

(57) ABSTRACT

The invention relates to mRNA therapy for the treatment of Acute Intermittent Porphyria (AIP). mRNAs for use in the invention, when administered in vivo, encode human porphobilinogen deaminase (PBGD), isoforms thereof, functional fragments thereof, and fusion proteins comprising PBGD. mRNAs of the invention are preferably encapsulated in lipid nanoparticles (LNPs) to affect efficient delivery to cells and/or tissues in subjects, when administered thereto. mRNA therapies of the invention increase and/or restore deficient levels of PBGD expression and/or activity in subjects. mRNA therapies of the invention further decrease levels of toxic metabolites associated with deficient PBGD activity in subjects, namely porphobilinogen and aminolevulinate (PBG and ALA).

11 Claims, 51 Drawing Sheets
Specification includes a Sequence Listing.

(56) References Cited

U.S. PATENT DOCUMENTS

| | | | |
|---|---|---|---|
| 2014/0275229 A1 | 9/2014 | Bancel et al. |
| 2018/0311381 A1 | 11/2018 | Bancel et al. |
| 2019/0175517 A1 | 6/2019 | Martini et al. |
| 2019/0298657 A1 | 10/2019 | Martini et al. |
| 2019/0298658 A1 | 10/2019 | Benenato et al. |
| 2019/0300906 A1 | 10/2019 | Martini et al. |
| 2019/0390181 A1 | 12/2019 | Benenato et al. |
| 2020/0078314 A1 | 3/2020 | Martini et al. |
| 2020/0085916 A1 | 3/2020 | Martini |

FOREIGN PATENT DOCUMENTS

| | | |
|---|---|---|
| WO | WO200107065 | 2/2001 |
| WO | WO2010036118 | 4/2010 |
| WO | WO2011068810 | 6/2011 |
| WO | WO2013086373 | 6/2013 |
| WO | WO2013151665 | 10/2013 |
| WO | WO2013151666 | 10/2013 |
| WO | WO2017075531 | 10/2015 |
| WO | WO2015199952 | 12/2015 |
| WO | WO2017049245 | 3/2017 |

OTHER PUBLICATIONS

Badminton et al., "Management of acute cutaneous porphyrias", International Journal of Clinical Practice, May 2002, vol. 56, pp. 272-278.

Elder et al., "The incidence of inherited porphyrias in Europe", Journal of Inherited Metabolic Disease, Nov. 2012, vol. 36, pp. 849-857.

European Communication Pursuant to Article 94(3), in EP Application No. 17727452.9, dated Mar. 10, 2020, 6 pages.

Hrdinka et al., "May 2006 update in porphobilinogen deaminase gene polymorphisms and mutations causing acute intermittent porphyria. Comparison with the situation in Slavic population", Physiological Research, 2006, vol. 55, pp. S119-S136, 18 pages.

JP Office Action in Japanese Appln. No. 2019512957, dated Jun. 3, 2021, 5 pages with English Translation.

Kauffman et al., "Optimization of Lipid Nanoparticle Formulations for mRNA Delivery in Vivo with Fractional Factorial and Definitive Screening Designs", Nano Letters, 2015, 15(11):7300-7306.

Paneda et al., "Safety and liver transduction efficacy of rAAV5-cohPBGD in nonhuman primates: a potential therapy for acute intermittent porphyria", Human Gene Therapy, vol. 24, Dec. 2013, pp. 1007-1017, XP002772550, Mary Ann Liebert, Inc. Publishers ISSN: 1043-0342.

PCT International Search Report and Written Opinion in International Application No. PCT/US2017/033418, dated Aug. 8, 2017, 3 pages.

Seth et al., "Liver Transplantation for Porphyria: Who, When and How?", Liver Transplantation, 2007, vol. 13, pp. 1219-1227.

Song et al. "Structural insight into acute intermittent porphyria." The FASEB Journal 23.2 (2009): 396-404.

Tjensvoll et al., "Haplotype analysis of Norwegian and Swedish patients with acute intermittent porphyria (AIP): Extreme haplotype heterogeneity for mutation R116W", Disease Markers, Dec. 2003, vol. 19, pp. 41-46.

Unzo et al., "Helper-dependent adenoviral liver gene therapy protects against induced attacks and corrects protein folding stress in acute intermittent porphyria mice", Human Molecular Genetics, vol. 22, No. 14, 2013, pp. 2929-2940, XP002772551, Oxford University Press ISSN: 0964-6906.

Wang et al., "Cloning and prokaryotic expression of porphyria-associated porphobilinogen deaminase gene", XP002772549, retrieved from CAS Database Accession No. 163.578058 abstract.

* cited by examiner

FIG. 1A

SEQ ID NO: 1 (PBGD; porphobilinogen deaminase, wt, isoform 1)

MSGNGNAAATAEENSPKMRVIRVGTRKSQLARIQTDSVVATLKASYPGLQFEIIAMSTTGDKILDTALSKIGEKSLFTKELEH
ALEKNEVDLVVHSLKDLPTVLPPGFTIGAICKRENPHDAVVFHPKFVGKTLETLPEKSVVGTSSLRRAAQLQRKFPHLEFRSI
RGNLNTRLRKLDEQEFSAIILATAGLQRMGWHNRVGQILHPEECMYAVGQALGVEVRAKDQDILDLVGVLHDPETLLRCIA
ERAFLRHLEGGCSVPVAVHTAMKDGQLYLTGGVWSLDGSDSIQETMQATIHVPAQHEDGPEDDPQLVGITARNIPRGPQLAAQ
NLGISLANLLLSKGAKNILDVARQLNDAH

See Porphobilinogen deaminase, Uniprot Acc. No. P08397. This is the 'canonical' sequence. All positional information in related variants and isoforms refers to it.

FIG. 1B

| Feature | Position | Length | Description |
|---|---|---|---|
| Initiator methionine | 1 | 1 | Removed |
| Mature Chain | 2-361 | 360 | Porphobilinogen deaminase |

FIG. 1C

Porphobilinogen_deaminase

FIG. 1D

SEQ ID NO: 2

ATGTCTGGTAACGGCAATGCGGCTGCAACGGGCGGAAGAAAACAGCCCAAAGATGAGAGTGATTCGCGTGGGTACCCGCAAGAG
CCAGCTTGCTCGCATACAGACAAGATTCTTGATACTGCACTCTCTAAGATTGGAGAGAAAAGCCTGTTTACCAAGGAGCTTGAACAT
GCCCTGGAGAATCTGAAGTGAAGCGGGAAATGCGGGAAAACCCCGGAAGTTCCCGCATCCAGATCCTGGCATCGATTCGCATGAT
AGCCATCTGCAAGCGGGAGAATCCCCAGCTGCTCATGATGCTGCGAAGAGCAGCGAGAGTTCAGTGCCATCATCCTGGCATCGCTGCA
CGGGAAACCTCAACACCGGCTGGCACAACCGGGTGGGACATCTTGGATCCTGGGGTGGTCGTGCCAGTGCGACGGAAGCGGAAGAGCCGCTGGCCCTTGGGCG
TGGAAGTGCGAGCGGCCAAGGACCAGGACATCCTGGATCTGGTGGGTGTGCTGCACGATCCCGAGACTCTGCTTCGCTGCATCGCT
GAAAGGGCCTTCCTGAGGCATCTGGAAGGAGGCTGCAGTGTGCCAGTAGCACATACAAGACCACCATCCAGGAGGGCAGTTGCGCCCCAGC
CTGACTGGAGGGAGTCCCTGAGGATGATGGCCCAGTTGTAAGGACCCACAGTTGCTAGGCATCCTCGTAACATCCAGCGCCAAAAACATCCTGATGTTGCACGGACCTTAACGATCG
AACTTGGGCATCAGCCTGGCCACTTGCTGAGCAACAGGAAGCAGCCAAAAACATCCTGATGTTGCACGGACCTTAACGATCG
CCAT

FIG. 2A SEQ ID NO: 3 (PBGD; porphobilinogen deaminase, wt, isoform 2)

MRVIRVGTRKSQLARIQTDSVVATLKASYPGLQFEIIAMSTTGDKILDTALSKIGERSLFTKELEHALEKNEVDLVVHSLKDL
PTVLPPGFTIGAICKRENPHDAVVFHPKFVGKTLETLPEKSVVGTSSLRRAAQLQRKFPHLEFRSIRGNLNTRLRKLDEQQEF
SAIILATAGLQRMGWHNRVGQILHPEECMYAVGQGALGVEVRAKDQDILDLVGVLHDPETLLRCIAERAFLRHLEGGCSVPVA
VHTAMKDGQLYLTGGVWSLDGSDSIQETMQATIHVPAQHEDGPEDDPQLVGITARNIPRGPQLAAQNLGISLANLLLSKGAKN
ILDVARQLNDAH

See Porphobilinogen deaminase, Uniprot Acc. No. P08397. Also known as erythrocyte form. The sequence of this isoform differs from the canonical sequence as follows: 1-17: Missing.

FIG. 2B

| Feature | Position | Length | Description |
|---|---|---|---|
| Mature Chain | 1-344 | 344 | Porphobilinogen deaminase |

FIG. 2C Porphobilinogen_deaminase

FIG. 2D SEQ ID NO: 4

ATGAGAGTGATTCGCTGGGTACCCGCAAGAGCCAGTCTTGCTCGCATACAGACGGACAGTGTGGTGGCAACATTGAAAGCCTC
GTACCCTGGCCTGCAGTTTGAAATCATTGCTATGTCCACCACAGGGGACAAGATTCTTGATACTGCACTCTCTAAGATTGGAG
AGAAAAGCCTGTTTACCAAGGAGCTTGAACATGCCCTGGAGAAGAATGAAGTGGACCTTGTTGTTCACTCCTTGAAGGACCTG
CCCACTGTGCTTCCTCCTGGCTTTACCATCGGGCCATCTGCCAAGAGAGAGTCGCCAAGCGCTGAACACCCGGCTTGTGTTCC
ATTTGTTGGAAGACCCTAGAATGTTCGGGAGTATTCCCAGCGCCATGGCCCTTGGGGCGCATCCTGGTGTGGGCCTTGAAGGGG
GAAAGTTCCCGCATCATCCTGGCCAACAGCTGGCCTGCAGCGCCTTCGGGAGAAGTCCTGCAGTTGGGGCAGATCCTGGAGAA
AGTGCCATCATCCTGGCCAACAGCTGGCCTGCAGCGCCTTCGGGAGAAGTGGACGAGCTGCCACCCTGAGCGCCTGGTGTGCT
GCATGTATGCCGAGACAGTCTGCGGCTACGTACCCAGATCGCCAGCAATGGGGCAACTGTCCCTGCCAGTGACCACAGTAGCC
ACGATCCCAGAGACAGTCTGCGGCTACGTACCCAGATCGCCAGCAATGGGGCAACTGTCCCCGTGTGCCCACAGTAGCCACAGA
GTGCATAGCAGCTTGGGCCTTGGGGATGGCCAACTGCTGCTGGAGTTGGTAGGCATCACTGGTTGGTAGGCATCACTACAAGAGAC
CATGCAGGCTACCACATGTCCCCAGCATGGCCCAGCATGAACGCTTGCCAACTTGTTGCTGAGCAAAGGAGCCAAAAAC
ATCCTGGATGTTGCACGGCAGCAGCTTTAACGATGCCCAT

FIG. 3A SEQ ID NO: 5 (PBGD; porphobilinogen deaminase, wt, isoform 3)

MSGNGNAAATAEENSPKMRVIRVGTRKSQLARIQTDSVVATLKASYPGLQFEIIAMSTTGDKILDTALSKIGEKSLFTKELEH
ALEKNEVDLVVHSLKDLPTVLPPGFTIGAICKRENPHDAVVFHPKFVGKTLETLPEKSVVGTSSLRRAAQLQRKFPHLEFRSI
RGNLNTRLRKLDEQQEFSAIILATAGLQRMGWHNRVGQILHPEECMYAVGQEGGCSVPVAVHTAMKDGQLYLTGGVWSLDGSD
SIQETMQATIHVPAQHEDGPEDDPQLVGITARNIPRGPQLAAQNLGISLANLLLSKGAKNILDVARQLNDAH

See Porphobilinogen deaminase, Uniprot Acc. No. P08397. The sequence of this isoform differs from the canonical sequence as follows:
218-257: Missing

FIG. 3B

| Feature | Position | Length | Description |
|---|---|---|---|
| Initiator methionine | 1 | 1 | Removed |
| Mature Chain | 2-321 | 320 | Porphobilinogen deaminase |

FIG. 3C Porphobilinogen_deaminase

FIG. 3D SEQ ID NO: 6

ATGTCTGGTAACGGCAATGCGGCTGCAACGGCGGAAGAAAACAGCCCAAAGATGAGAGTGATTCGCGTGGGTACCCGCAAGAG
CCAGCTTGCTCGCATACAGACAGACGGACAGTGTTGTAGCTACTCTGAAGGCCTCGTAAGATTGGAGAGAAAAGCCTGAAAGCCTGAATCATTGCTA
TGTCCACCACAGGGGACAAGATTCTTGATACTGCTTTGTCTAAGATTGGAGAGAAAAGCCTGTTTACCAAGGAGTTGAACAT
GCCCTGGAGAAGAATGAAGTGGACCTGGTGGTTCACTCCCTGAAGGACCTGCCAACTGTGTTCCCTCCTGGCTTCACCATCGG
AGCCATCTGCAAGCGGGAAAATCCGGGACCAGTGCCCGTCATGATGCTGTGTTTTCACCCAAAAATTGTTGGGAAGACCCTGGAAGACCCTGCCAG
AGAAGAGTGTGGTTGGGAACCTGAACACCCGGCTTCGAAAGCTTGACAGTTCAGTGCCATCATCCCTGGCAACAGCTGGCCTGCA
CGGCGCATGGCCAGTCGACAGCCGTGGCCAGATCCTGCAACCTGAGGAGTTCAGTGCCATCATCCTGGCAACAGCTGGCTGCA
GTGTGCCAGTAGCCGTCATACAGCCAGGCTACATGGAAGATGGGCAACTGTACCTGACTGGAGGAGTCTGGAGCCTGGATGGCTCAGAT
AGCATACAAGAGACAATGCAGGCCACCATCCACGAGGCCCAGTGCCTGCCCAGAACTTGGCCTCCCCCAGAACTTGGCCTGCCCCAGAATACAGCCCTGGGCATCAGCCTGGCCAACTGTTGCTGAGCA
AAGGAGCCAAAAACATCCTGGATGTTGCACGGCAGCTTAACGATGCCCAT

FIG. 4A

SEQ ID NO: 7 (PBGD; porphobilinogen deaminase, wt, isoform 4)

MRVIRVGTRKSQLARIQTDSVVATLKASYPGLQFEIIAMSTTGDKILDTALSKIGEKSLFTKELEHALEKNEVDLVVHSLKDL
PTVLPPGFTIGAICKRENPHDAVVFHPKFVGKTLETLPEKSVVGTSSLRRAAQLQRKFPHLEFRSIRGNLNTRLRKLDEQQEF
SAIILATAGLQRMGWHNRVGQILHPEECMYAVGQEGGCSVPVAVHTAMKDGQLYLTGGVWSLDGSDSIQETMQATIHVPAQHE
DGPEDDPQLVGITARNIPRGPQLAAQNLGISLANLLLSKGAKNILDVARQLNDAH

See Porphobilinogen deaminase, Uniprot Acc. No. P08397. The sequence of this isoform differs from the canonical sequence as follows:
   1-17: Missing.
   218-257: Missing.

FIG. 4B

| Feature | Position | Length | Description |
|---|---|---|---|
| Mature Chain | 1-304 | 304 | Porphobilinogen deaminase |

FIG. 4C

Porphobilinogen_deaminase

FIG. 4D

SEQ ID NO: 8

ATGAGAGTGATTCGCGTGGGTACCCGCAAGAGCCAGCTTGCTCGCATACAGACGGACAGTGTTGTGGCAACATTGAAAGCCTC
GTACCCTGGCCTGCAGTTTGAAATCATTGCTATGTCCACCACAGGGGACAAGATTCTTGATACTGCACTCTCTAAGATTGGAG
AGAAAAGCCTGTTTACCAAGGAGCTTGAACATGCCCTGGAGAAGAATGAAGTGGACCTGGTTGTTCACTCCTTGAAGGACCTG
CCCACTGTGCTTCCTCCGGCTTCACCATCGGAGCCATCTGCAAGAGAGAATCCCCAGCACCCGAGCTTGAAGAGCCAGCTGCCCAAA
ATTTGTTGGGAAGACCCTCAGAAACCTCGGAGAGTTCGGGAGCAGCTATTCGGAGCAAACCTCAACACTCGGCTTCGGAAGCTGGACGAGCAGGAGTTC
AGTGCCATCATCCTGGCAACAGCAGGGCTCCAGAGAATGGGCTGGCACAACCGGGTGGGACAGATCCTGCACCCTGAGGAATG
CATGTATGCTGTGGGACAGGAAGGAGGCTGCTCAGATAGCAGCTCCAGTGTGCCAGTTGCTGTACATGCCACAATGAAGGATGGGCAACTGTACCTGA
CTGGAGGAGTCTGGAGCCTGGATGGATCCGATAGCATCCAGGAGACCATGCAGGCCACCATCCATGTCCCTGCCCAGCACGAG
GATGGCCCTGAGGATGACCCACAGTTGGTAGGCATCACTGCTCGTAACATTCCTCGAGGCCCCCAGTTGGCTGCCCAGAACTT
GGGCATCAGCCTGGCCAACTTGTTGCTGAGCAAAGGAGCCAAAAACATCCTGGATGTTGCACGGCAGCTTAACGATGCCCAT

| Protein | Length | Theoretical Minimum U (%) | Theoretical Minimum U (abs) | | | | | | |
|---|---|---|---|---|---|---|---|---|---|
| PGBD | 361 | 10.99% | 119 | | | | | | |

| Nucleic Acid | Length | U Content(abs) | U Content(%) | U Content v WT(%) | U Content v Theoretical Minimum (%) | UU pairs | UU pairs v WT(%) | UUU | UUUU | UUUUU |
|---|---|---|---|---|---|---|---|---|---|---|
| PBGD WT | 1083 | 215 | 19.85% | 100.00% | 180.67% | 32 | 100.00% | 4 | 0 | 0 |
| PBGD-CO01 | 1083 | 157 | 14.50% | 73.02% | 131.93% | 8 | 25.00% | 3 | 1 | 0 |
| PBGD-CO02 | 1083 | 150 | 13.85% | 69.77% | 126.05% | 9 | 28.13% | 1 | 0 | 0 |
| PBGD-CO03 | 1083 | 154 | 14.22% | 71.63% | 129.41% | 10 | 31.25% | 2 | 0 | 0 |
| PBGD-CO04 | 1083 | 141 | 13.02% | 65.58% | 118.49% | 10 | 31.25% | 1 | 0 | 0 |
| PBGD-CO05 | 1083 | 145 | 13.39% | 67.44% | 121.85% | 11 | 34.38% | 0 | 0 | 0 |
| PBGD-CO06 | 1083 | 149 | 13.76% | 69.30% | 125.21% | 13 | 40.63% | 2 | 0 | 0 |
| PBGD-CO07 | 1083 | 148 | 13.67% | 68.84% | 124.37% | 10 | 31.25% | 1 | 0 | 0 |
| PBGD-CO08 | 1083 | 144 | 13.30% | 66.98% | 121.01% | 10 | 31.25% | 3 | 0 | 0 |
| PBGD-CO09 | 1083 | 152 | 14.04% | 70.70% | 127.73% | 13 | 40.63% | 0 | 0 | 0 |
| PBGD-CO10 | 1083 | 148 | 13.67% | 68.84% | 124.37% | 9 | 28.13% | 4 | 0 | 0 |
| PBGD-CO11 | 1083 | 151 | 13.94% | 70.23% | 126.89% | 11 | 34.38% | 3 | 0 | 0 |
| PBGD-CO12 | 1083 | 153 | 14.13% | 71.16% | 128.57% | 11 | 34.38% | 4 | 0 | 0 |
| PBGD-CO13 | 1083 | 151 | 13.94% | 70.23% | 126.89% | 9 | 28.13% | 3 | 0 | 0 |
| PBGD-CO14 | 1083 | 152 | 14.04% | 70.70% | 127.73% | 11 | 34.38% | 1 | 0 | 0 |
| PBGD-CO15 | 1083 | 151 | 13.94% | 70.23% | 126.89% | 10 | 31.25% | 2 | 0 | 0 |
| PBGD-CO16 | 1083 | 148 | 13.67% | 68.84% | 124.37% | 10 | 31.25% | 2 | 0 | 0 |
| PBGD-CO17 | 1083 | 154 | 14.22% | 71.63% | 129.41% | 16 | 50.00% | 1 | 0 | 0 |
| PBGD-CO18 | 1083 | 149 | 13.76% | 69.30% | 125.21% | 9 | 28.13% | 2 | 0 | 0 |
| PBGD-CO19 | 1083 | 147 | 13.57% | 68.37% | 123.53% | 11 | 34.38% | 1 | 0 | 0 |
| PBGD-CO20 | 1083 | 152 | 14.04% | 70.70% | 127.73% | 8 | 25.00% | 3 | 0 | 0 |
| PBGD-CO21 | 1083 | 152 | 14.04% | 70.70% | 127.73% | 10 | 31.25% | 3 | 0 | 0 |
| PBGD-CO22 | 1083 | 153 | 14.13% | 71.16% | 128.57% | 14 | 43.75% | 1 | 0 | 0 |
| PBGD-CO23 | 1083 | 145 | 13.39% | 67.44% | 121.85% | 9 | 28.13% | 2 | 0 | 0 |
| PBGD-CO24 | 1083 | 148 | 13.67% | 68.84% | 124.37% | 15 | 46.88% | 0 | 0 | 0 |
| PBGD-CO25 | 1083 | 148 | 13.67% | 68.84% | 124.37% | 12 | 37.50% | 2 | 0 | 0 |
| | MAX | 157 | 14.50% | 73.02% | 131.93% | 16 | 50.00% | 4 | 1 | 0 |
| | MIN | 141 | 13.02% | 65.58% | 118.49% | 8 | 25.00% | 0 | 0 | 0 |
| | MEAN | 149.68 | 13.82% | 69.62% | 125.78% | 10.76 | 33.63% | 1.88 | 0.04 | 0 |
| | MEDIAN | 150 | 13.85% | 69.77% | 126.05% | 10 | 31.25% | 2 | 0 | 0 |
| | STD DEV | 3.61 | 0.33% | 1.68% | 3.04% | 2.07 | 6.46% | | | |

FIG. 5

| Protein | Length | Theoretical Maximum G (%) | Theoretical Maximum G (abs) | | |
|---|---|---|---|---|---|
| PGBD | 361 | 43.03% | 466 | | |
| Nucleic Acid | Length | G Content(abs) | G Content(%) | G Content v WT(%) | G Content v Theoretical Maximum (%) |
| PBGD WT | 1083 | 319 | 29.46% | 100.00% | 68.45% |
| PBGD-CO01 | 1083 | 340 | 31.39% | 106.58% | 72.96% |
| PBGD-CO02 | 1083 | 345 | 31.86% | 108.15% | 74.03% |
| PBGD-CO03 | 1083 | 337 | 31.12% | 105.64% | 72.32% |
| PBGD-CO04 | 1083 | 343 | 31.67% | 107.52% | 73.61% |
| PBGD-CO05 | 1083 | 348 | 32.13% | 109.09% | 74.68% |
| PBGD-CO06 | 1083 | 351 | 32.41% | 110.03% | 75.32% |
| PBGD-CO07 | 1083 | 334 | 30.84% | 104.70% | 71.67% |
| PBGD-CO08 | 1083 | 348 | 32.13% | 109.09% | 74.68% |
| PBGD-CO09 | 1083 | 347 | 32.04% | 108.78% | 74.46% |
| PBGD-CO10 | 1083 | 352 | 32.50% | 110.34% | 75.54% |
| PBGD-CO11 | 1083 | 338 | 31.21% | 105.96% | 72.53% |
| PBGD-CO12 | 1083 | 345 | 31.86% | 108.15% | 74.03% |
| PBGD-CO13 | 1083 | 335 | 30.93% | 105.02% | 71.89% |
| PBGD-CO14 | 1083 | 343 | 31.67% | 107.52% | 73.61% |
| PBGD-CO15 | 1083 | 346 | 31.95% | 108.46% | 74.25% |
| PBGD-CO16 | 1083 | 336 | 31.02% | 105.33% | 72.10% |
| PBGD-CO17 | 1083 | 349 | 32.23% | 109.40% | 74.89% |
| PBGD-CO18 | 1083 | 343 | 31.67% | 107.52% | 73.61% |
| PBGD-CO19 | 1083 | 346 | 31.95% | 108.46% | 74.25% |
| PBGD-CO20 | 1083 | 336 | 31.02% | 105.33% | 72.10% |
| PBGD-CO21 | 1083 | 358 | 33.06% | 112.23% | 76.82% |
| PBGD-CO22 | 1083 | 345 | 31.86% | 108.15% | 74.03% |
| PBGD-CO23 | 1083 | 355 | 32.78% | 111.29% | 76.18% |
| PBGD-CO24 | 1083 | 346 | 31.95% | 108.46% | 74.25% |
| PBGD-CO25 | 1083 | 349 | 32.23% | 109.40% | 74.89% |
| | MAX | 358 | 33.06% | 112.23% | 76.82% |
| | MIN | 334 | 30.84% | 104.70% | 71.67% |
| | MEAN | 344.6 | 31.82% | 108.03% | 73.95% |
| | MEDIAN | 345 | 31.86% | 108.15% | 74.03% |
| | STD DEV | 6.26 | 0.58% | 1.96% | 1.34% |

FIG. 6

| Protein | Length | Theoretical Maximum C (%) | Theoretical Maximum C (abs) | | |
|---|---|---|---|---|---|
| PGBD | 361 | 45.71% | 495 | | |
| Nucleic Acid | Length | C Content(abs) | C Content(%) | C Content v WT(%) | C Content v Theoretical Maximum (%) |
| PBGD WT | 1083 | 285 | 26.32% | 100.00% | 57.58% |
| PBGD-CO01 | 1083 | 349 | 32.23% | 122.46% | 70.51% |
| PBGD-CO02 | 1083 | 354 | 32.69% | 124.21% | 71.52% |
| PBGD-CO03 | 1083 | 357 | 32.96% | 125.26% | 72.12% |
| PBGD-CO04 | 1083 | 373 | 34.44% | 130.88% | 75.35% |
| PBGD-CO05 | 1083 | 359 | 33.15% | 125.96% | 72.53% |
| PBGD-CO06 | 1083 | 350 | 32.32% | 122.81% | 70.71% |
| PBGD-CO07 | 1083 | 369 | 34.07% | 129.47% | 74.55% |
| PBGD-CO08 | 1083 | 366 | 33.80% | 128.42% | 73.94% |
| PBGD-CO09 | 1083 | 343 | 31.67% | 120.35% | 69.29% |
| PBGD-CO10 | 1083 | 338 | 31.21% | 118.60% | 68.28% |
| PBGD-CO11 | 1083 | 349 | 32.23% | 122.46% | 70.51% |
| PBGD-CO12 | 1083 | 343 | 31.67% | 120.35% | 69.29% |
| PBGD-CO13 | 1083 | 367 | 33.89% | 128.77% | 74.14% |
| PBGD-CO14 | 1083 | 356 | 32.87% | 124.91% | 71.92% |
| PBGD-CO15 | 1083 | 351 | 32.41% | 123.16% | 70.91% |
| PBGD-CO16 | 1083 | 359 | 33.15% | 125.96% | 72.53% |
| PBGD-CO17 | 1083 | 339 | 31.30% | 118.95% | 68.48% |
| PBGD-CO18 | 1083 | 358 | 33.06% | 125.61% | 72.32% |
| PBGD-CO19 | 1083 | 349 | 32.23% | 122.46% | 70.51% |
| PBGD-CO20 | 1083 | 363 | 33.52% | 127.37% | 73.33% |
| PBGD-CO21 | 1083 | 340 | 31.39% | 119.30% | 68.69% |
| PBGD-CO22 | 1083 | 352 | 32.50% | 123.51% | 71.11% |
| PBGD-CO23 | 1083 | 340 | 31.39% | 119.30% | 68.69% |
| PBGD-CO24 | 1083 | 354 | 32.69% | 124.21% | 71.52% |
| PBGD-CO25 | 1083 | 351 | 32.41% | 123.16% | 70.91% |
| | MAX | 373 | 34.44% | 130.88% | 75.35% |
| | MIN | 338 | 31.21% | 118.60% | 68.28% |
| | MEAN | 353.16 | 32.61% | 123.92% | 71.35% |
| | MEDIAN | 352 | 32.50% | 123.51% | 71.11% |
| | STD DEV | 9.72 | 0.90% | 3.41% | 1.96% |

FIG. 7

| Protein | Length | Theoretical Maximum GC (%) | Theoretical Maximum GC (abs) | |
|---|---|---|---|---|
| PGBD | 361 | 69.34% | 751 | |
| Nucleic Acid | Length | GC Content (abs) | GC Content(%) | GC Content v WT(%) | GC Content v Theoretical Maximum (%) |
| PBGD WT | 1083 | 604 | 55.77% | 100.00% | 80.43% |
| PBGD-CO01 | 1083 | 689 | 63.62% | 114.07% | 91.74% |
| PBGD-CO02 | 1083 | 699 | 64.54% | 115.73% | 93.08% |
| PBGD-CO03 | 1083 | 694 | 64.08% | 114.90% | 92.41% |
| PBGD-CO04 | 1083 | 716 | 66.11% | 118.54% | 95.34% |
| PBGD-CO05 | 1083 | 707 | 65.28% | 117.05% | 94.14% |
| PBGD-CO06 | 1083 | 701 | 64.73% | 116.06% | 93.34% |
| PBGD-CO07 | 1083 | 703 | 64.91% | 116.39% | 93.61% |
| PBGD-CO08 | 1083 | 714 | 65.93% | 118.21% | 95.07% |
| PBGD-CO09 | 1083 | 690 | 63.71% | 114.24% | 91.88% |
| PBGD-CO10 | 1083 | 690 | 63.71% | 114.24% | 91.88% |
| PBGD-CO11 | 1083 | 687 | 63.43% | 113.74% | 91.48% |
| PBGD-CO12 | 1083 | 688 | 63.53% | 113.91% | 91.61% |
| PBGD-CO13 | 1083 | 702 | 64.82% | 116.23% | 93.48% |
| PBGD-CO14 | 1083 | 699 | 64.54% | 115.73% | 93.08% |
| PBGD-CO15 | 1083 | 697 | 64.36% | 115.40% | 92.81% |
| PBGD-CO16 | 1083 | 695 | 64.17% | 115.07% | 92.54% |
| PBGD-CO17 | 1083 | 688 | 63.53% | 113.91% | 91.61% |
| PBGD-CO18 | 1083 | 701 | 64.73% | 116.06% | 93.34% |
| PBGD-CO19 | 1083 | 695 | 64.17% | 115.07% | 92.54% |
| PBGD-CO20 | 1083 | 699 | 64.54% | 115.73% | 93.08% |
| PBGD-CO21 | 1083 | 698 | 64.45% | 115.56% | 92.94% |
| PBGD-CO22 | 1083 | 697 | 64.36% | 115.40% | 92.81% |
| PBGD-CO23 | 1083 | 695 | 64.17% | 115.07% | 92.54% |
| PBGD-CO24 | 1083 | 700 | 64.64% | 115.89% | 93.21% |
| PBGD-CO25 | 1083 | 700 | 64.64% | 115.89% | 93.21% |
| | MAX | 716 | 66.11% | 118.54% | 95.34% |
| | MIN | 687 | 63.43% | 113.74% | 91.48% |
| | MEAN | 697.76 | 64.43% | 115.52% | 92.91% |
| | MEDIAN | 698 | 64.45% | 115.56% | 92.94% |
| | STD DEV | 7.37 | 0.68% | 1.22% | 0.98% |

FIG. 8

| Sequence | SEQ ID NO | GC | GC 1st | GC 2nd | GC 3rd |
|---|---|---|---|---|---|
| PBGD_WT | 2 | 55.77 | 63.16 | 40.72 | 63.43 |
| PBGD-CO01 | 9 | 63.62 | 63.16 | 40.72 | 86.98 |
| PBGD-CO02 | 10 | 64.54 | 64.54 | 40.72 | 88.37 |
| PBGD-CO03 | 11 | 64.08 | 64.27 | 40.72 | 87.26 |
| PBGD-CO04 | 12 | 66.11 | 64.27 | 40.72 | 93.35 |
| PBGD-CO05 | 13 | 65.28 | 64.54 | 40.72 | 90.58 |
| PBGD-CO06 | 14 | 64.73 | 63.16 | 40.72 | 90.30 |
| PBGD-CO07 | 15 | 64.91 | 63.71 | 40.72 | 90.30 |
| PBGD-CO08 | 16 | 65.93 | 65.10 | 40.72 | 91.97 |
| PBGD-CO09 | 17 | 63.71 | 62.60 | 40.72 | 87.81 |
| PBGD-CO10 | 18 | 63.71 | 63.16 | 40.72 | 87.26 |
| PBGD-CO11 | 19 | 63.43 | 62.60 | 40.72 | 86.98 |
| PBGD-CO12 | 20 | 63.53 | 63.16 | 40.72 | 86.70 |
| PBGD-CO13 | 21 | 64.82 | 63.99 | 40.72 | 89.75 |
| PBGD-CO14 | 22 | 64.54 | 64.27 | 40.72 | 88.64 |
| PBGD-CO15 | 23 | 64.36 | 63.99 | 40.72 | 88.37 |
| PBGD-CO16 | 24 | 64.17 | 63.71 | 40.72 | 88.09 |
| PBGD-CO17 | 25 | 63.53 | 63.43 | 40.72 | 86.43 |
| PBGD-CO18 | 26 | 64.73 | 63.99 | 40.72 | 89.47 |
| PBGD-CO19 | 27 | 64.17 | 63.71 | 40.72 | 88.09 |
| PBGD-CO20 | 28 | 64.54 | 64.82 | 40.72 | 88.09 |
| PBGD-CO21 | 29 | 64.45 | 64.27 | 40.72 | 88.37 |
| PBGD-CO22 | 30 | 64.36 | 63.99 | 40.72 | 88.37 |
| PBGD-CO23 | 31 | 64.17 | 62.33 | 40.72 | 89.47 |
| PBGD-CO24 | 32 | 64.64 | 64.54 | 40.72 | 88.64 |
| PBGD-CO25 | 33 | 64.64 | 62.88 | 40.72 | 90.30 |
| | MAX | 66.11 | 65.1 | 40.72 | 93.35 |
| | MIN | 63.43 | 62.33 | 40.72 | 86.43 |
| | MEAN | 64.43 | 63.77 | 40.72 | 88.80 |
| | MEDIAN | 64.45 | 63.99 | 40.72 | 88.37 |
| | STD DEV | 0.68 | 0.74 | 0.00 | 1.67 |

FIG. 9

FIG. 10A SEQ ID NO: 152 (PBGD GoF; porphobilinogen deaminase, I291M/N340S)

MSGNGNAAATAEENSPKMRVIRVGTRKSQLARIQTDSVVATLKASYPGLQFEIIAMSTTGDKILDTALSKIGEKSLFTKEL
EHALEKNEVDLVVHSLKDLPTVLPPGFTIGAICKRENPHDAVVFHPKFVGKTLETLPEKSVVGTSSLRRAAQLQRKFPHLE
FRSIRGNLNTRLRKLDEQQEFSAIILATAGLQRMGWHNRVGQILHPEECMYAVGQGALGVEVRAKDQDILDLVGVLHDPET
LLRCIAERAFLRHLEGGCSVPVAVHTAMKDGQLYITGGVWSLDGSDSMQETMQATIHVPAQHEDGPEDDPQLVGITARNIP
RGPQLAAQNLGISLAS<u>L</u>LLSKGAKNILDVARQLNDAH

See Porphobilinogen deaminase, Uniprot Acc. No. P08397. Underlined amino acids indicate mutations I291M and N340S with respect to the 'canonical' sequence

FIG. 10B

| Feature | Position | Length | Description |
|---|---|---|---|
| Initiator methionine | 1 | 1 | Removed |
| Mature Chain | 2-361 | 360 | Porphobilinogen deaminase |

FIG. 10C

Porphobilinogen_deaminase

FIG. 11

SEQ ID NO: 153

ATGAGCGGGAACGGCAACGCGGGCAGCCACCGCTGAGGAAACTCTCCAAAAATGAGAGTCATTAGGGTGGGCACCAGAAAGAGTCAACT
CGCAAGGATCCAGACCGACTCTGTGGTGGCCACTCTAAAAGCGAGCTACCCCGGAGTTCGAAATCATCGCGATGAGCACCACCG
GCGATAAAATCCTAGATACCGCCTTGAGCAAGATCGGAGAAGAGCCTCTTTACCAAGGAGCTGGACACGCCCTGGAGAAAAACGAG
GTGGATCTGGTGGTCCATAGCCTAAAAGGATCTCCCTACAGTGCTGCCCCCGGGTTTACCATCGGCGCCATTTGTAAGCGGGAGAACCC
GCACGACGCAGTGGTCTTCCACCCCAAGTTTGTGGGCAAGACCCTGCCGGAAAAGTCCGTGGCACCTCCAGCCTGA
GACGAGCCCGCCGCCCCAAGTTTCCCACCACCTGGCAGCGCCATCATCCTGGACTCCTGCCAGGGAAACCTCAGGGGAAACCTCAACACCAGACTGAGAAAGCTGGAC
GAACAGCAGGAGTTCAGCGCCATCTGTGGGCCAGGGCGCATAGCTGAGGTGCATAATCAGGATGGGCTGGCATAATCAGGACATCAGGGGGATCAGGACATCCTGGACCTCGTGGGCGTGC
CGAGGAATGCATGTATGCTGAGGTGCATAGCCAGCTGTGTACTTGACTTGGTGGGCGTCGGCGTCGGCCGCGACAATGCAGGC
TTCACGACCCGGAAACCCTGCTGAAAGGACACGGGCCCAGCACGACGGCCCGACGCCCCCGAGGACGACGCCCAGCTGGTGGGCATTACCGCCAGGAAAATATCCTAGGGAC
CATACAGCCATGAATGAGAAGGACGGCCCTGCCAGCACGACGGCCCGAGGACGACGCCCAGCTGGTGGGCATTACCGCCAGGAAAATATCCTAGGGAC
CACTATCCACGTGCCTGCCCAAAAACTTGGGCATCAGCCTGCTGAGCAAAGGAGCTAAAACATCCTGGATGTGGCCAGGCAG
CCCAGCTGGCTGCCCCAAAAACTTGGGCATCAGCCTGCTGAGCAAAGGAGCTAAAACATCCTGGATGTGGCCAGGCAG
CTGAATGACGCCCAC

FIG. 12A

SEQ ID NO: 154 (ApoA1-PBGD; ApoA1-PBGD fusion, ApoA1 fusion)

MDEPPQSPWDRVKDLATVYVDVLKDSGRDYVSQFEGSALGKQLNLKLLDNWDSVTSTFSKLREQLGPVTQEFWDNLEKETE
GLRQEMSKDLEEVKAKVQPYLDDFQKKWQEEMELYRQKVEPLRAELQEGARQKLHELQEKLSPLGEEMRDRARAHVDALRT
HLAPYSDELRQRLAARLEALKENGGARLAEYHAKATEHLSTLSEKAKPALEDLRQGLLPVLESFKVSFLSALEEYTKKLNT
QSGNGNAAATAEENSPKMRVIRVGTRKSQLARIQTDSVVATLKASYPGLQFEIIAMSTTGDKILDTALSKIGEKSLFTKEL
EHALEKNEVDLVVHSLKDLPTVLPPGFTIGAICKRENPHDAVVFHPKFVGKTLETLPEKSVVGTSSLRRAAQLQRKFPHLE
FRSIRGNLNTRLRKLDEQQEFSAIILATAGLQRMGWHNRVGQILHPEECMYAVGQGALGVEVRAKDQDILDLVGVLHDPET
LLRCIAERAFLRHLEGGCSVPVAVHTAMKDGQLYLTGGVWSLDGSDSMQETMQATIHVPAQHEDGPEDDPQLVGITARNIP
RGPQLAAQNLGISLASLLLSKGAKNILDVARQLNDAH

See Porphobilinogen deaminase, Uniprot Acc. No. P08397 and also Apoliprotein A-I, Uniprot Acc No. P02647. The PBGD sequence includes the I291M and N340S mutations (numbered with respect to the PBGD 'canonical' sequence)

Underlined amino acids indicate the location of PBGD.

FIG. 12B

| Feature | Position | Length | Description |
|---|---|---|---|
| Initiator methionine | 1 | 1 | |
| ApoA1 Fusion component | 2-244 | 243 | Apolipoprotein A1 (mature form without signal peptide and propeptide) |
| PBGD Fusion component | 245-604 | 360 | Porphobilinogen deaminase |

FIG. 12C

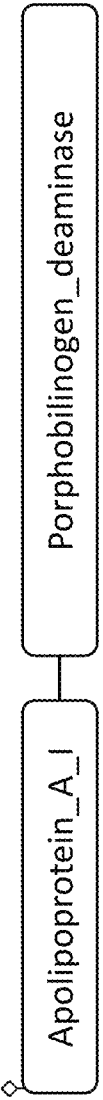

Apolipoprotein_A_I — Porphobilinogen_deaminase

FIG. 12D

SEQ ID NO: 155

ATGGACGAACCACCCCAGTCACCCTGGGATAGAGTCAAAGACCTGGCCACTGTGTACTGTGGACGTGCTGAAAGATAGCGGGCGGGATTAC
GTCTCGCAGTTCGAGGGCTCCGCCTTAGGCAAAGACTGAAACTGCTGGACAATTGGGACTCCGTCACTAGCACATTCTCCAAG
CTGAGAGAGCAGCTGGGACCTGTGACTCAGGAGTTCTGGGACAACCTGGAGAAGGAAACTGAGGGCCTGAGGCAGGAGCTATACCGGCAAAAGGTG
CTGGAGGAGGTTAAGGCAAAGTGCAACCTGACCTCCAAGGAGATGCAAGGAGATGGAGCTGAGCCCCTCGGGCTATACCGGCGAGGAAATGCGT
GAGCCTCTCCGGGCCGAGCTCCAGGAGGGCGCTCGGACAGCCCTGCGCTGGCCCACGTGCCACGTGGACGCCCTGCGCGCCAGACTCGAA
GATAGACACGTGCCAGAGCTCCAGGAGGCGCTGCGCGCCCTGCGCTGGCCCACGTGCCACGTGGACGCCCTGCGCGCCAGACTCGAA
GCTCTGAAGGAGAATGGCGCGCAGGCCTGAGGCGTTACCGTGCTTACCCGTGTTACCGTGAGAGCTTCAAGGTGAGTTTGTCCACTCTGTGCCTTGAGCGCTAAGCCT
GCCCTGGAGGACCTGAGGCGTTACCGTGCTTACCCGTGTTACCGCGAACGGCAGGCCTGTTACCCGCGAACGGCAGGCCTGTTACCCGCGAACGGCAGGCC
CTGAACACCCAGAGCGGGCAACGGCAGGCCTGCAACGGCAGGCCTGCAACGGCAGGCCTGCAACGGCAGGCCTGAACACCCAGAGCGGGCAACGGCAGG
TCCCAGCTTGCACGAATCCAGACGACCGCCGATTCAGTCGTGCGCACGGCAAGCCATCTTACCCCGGACCCTGCGTCAGTTCGAGATTATCGCCATGTCT
ACAACCGGCGACAAGATCCTCGATACCGCCCTGAGCAGTAGACGCACGCCCTCGAGAAA
AACGAGGTGGACCTTGTGCGTGTTCCATCCGAGAAAGTTTCCTCACCTGGAGCACATCCGGGCAACCTGAACATCCGGCGCTGCGGAAGCTG
AATCCCACGATGCCAGGCCCAACTTCAGCGCTATCATTCTAGCAACAGCCGGCCTGCGGGGGATGCAGAGCGCATGAGCAGCAAGGACCAGGTGGGA
CTGAGAAGAGCGGCCAAGAGTTCAGGCTATACCGCCGTTGGCCAAGGCGGCATAGCGCCGGCCTGGCCGAGATCTTGATCTGTCGGGGTG
CCCGAGGAATGCATTGCATGTGAGACCCCATGGAGGTCAGAGAGGTCAGCGCATCTGAGCGGCTTGAGCGGCTTGGACGGCTGGACGGCCGTG
CTGCACGACCCCATGAAGGAACGGCCAGCTCCAGCACGGCCAGCTGTACCTGACCGGAGATGGCCCGAAGATGGCCCCGAAGATGACCCTCAGCTGGTGGGATTACTGCTAGAAACATCCCCGCGGCCCC
CACACAGCCATGAAGGAACGGCCAGCTTCCAGCACGGCCCAAACCTGGGAATCTCTGGCCTCCTCTAAAGGAGCCAAGAATATTCTGGACGTGGCACGGCAGCTC
AACGATGCACAC

Underlined nucleobases indicate the region encoding Porphobilinogen deaminase (PBGD). The non-underlined portion of the sequence encodes Apolipoprotein A1.

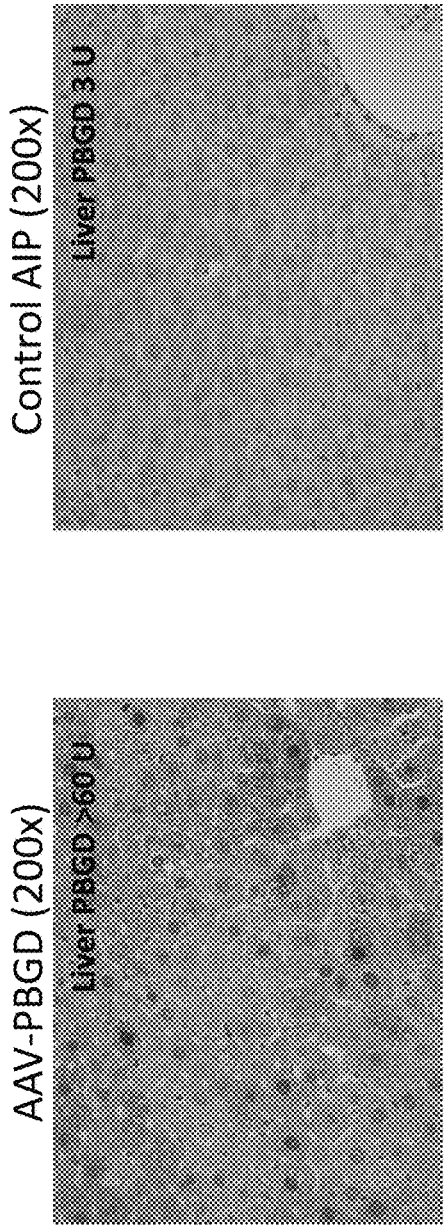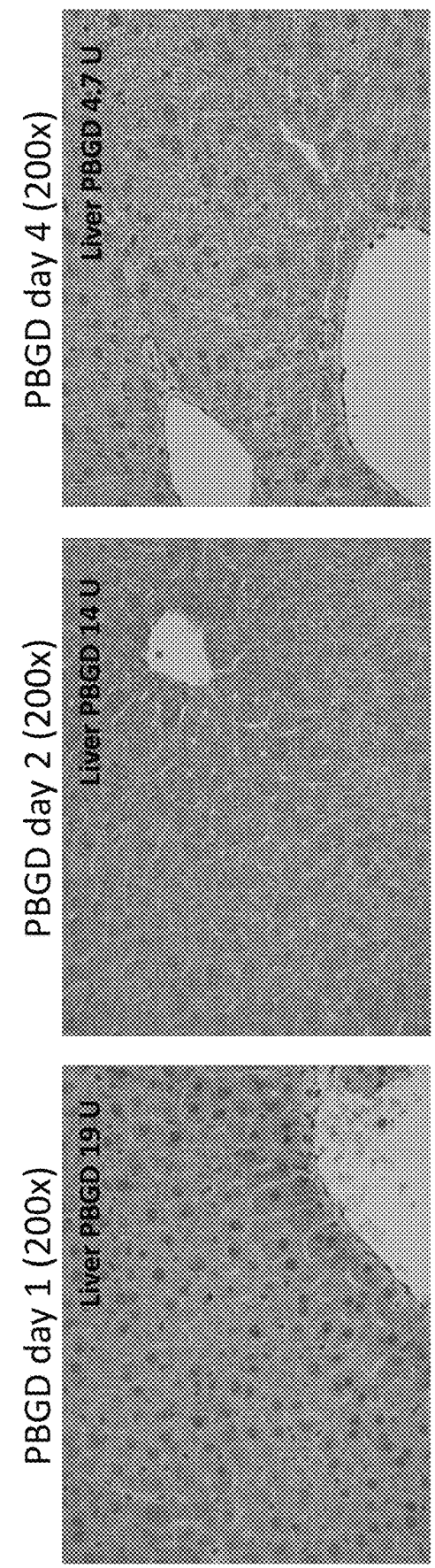

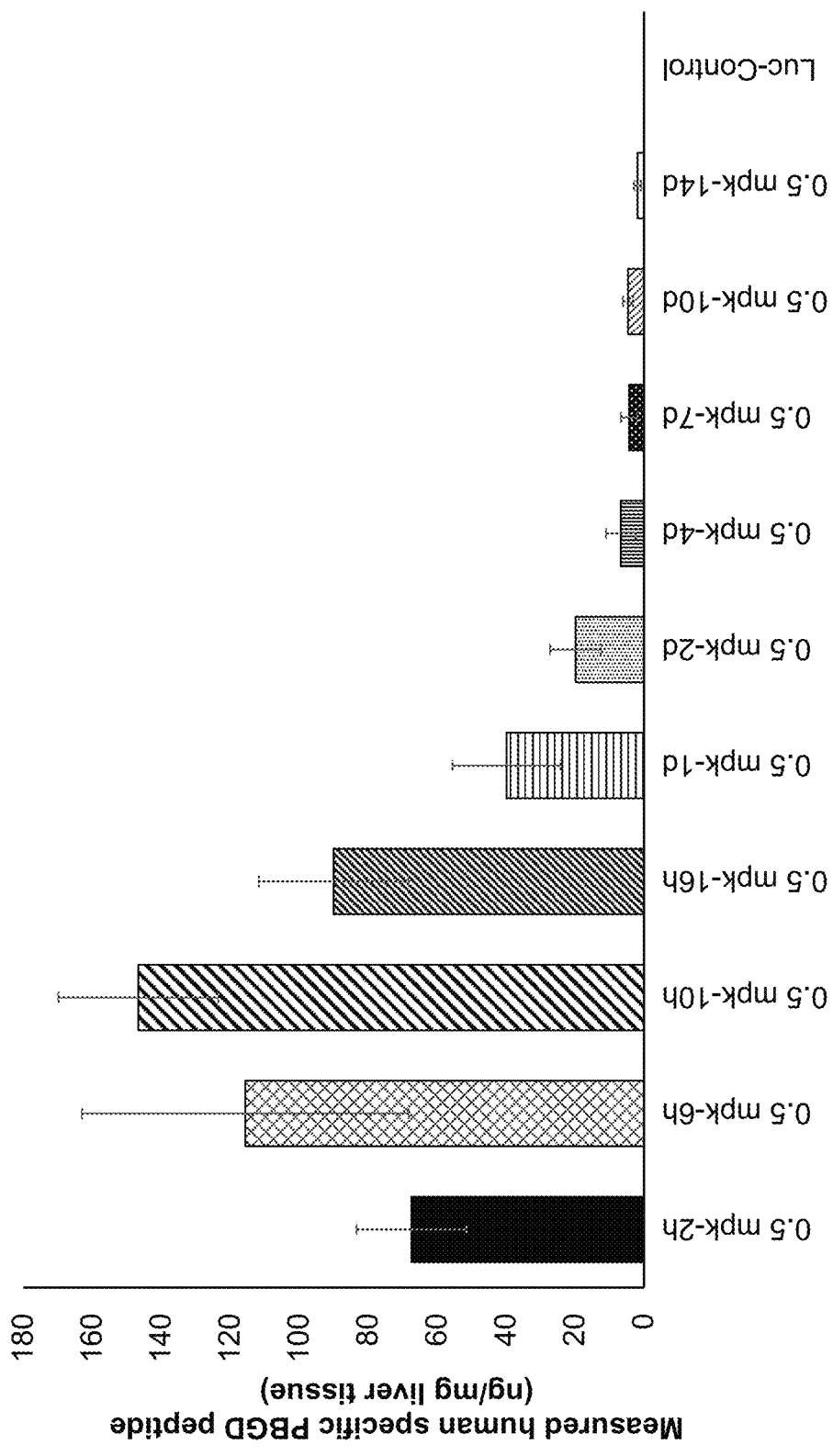

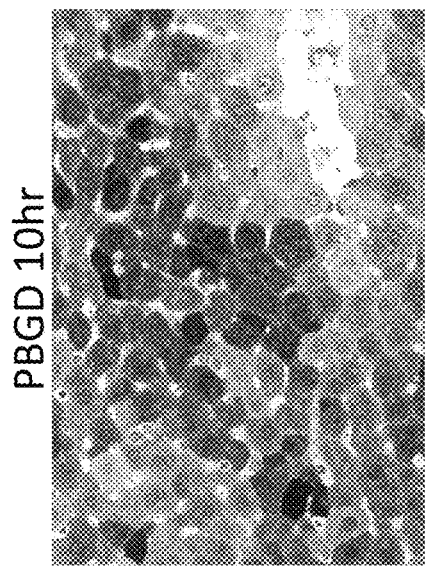
FIG. 38C PBGD 10hr
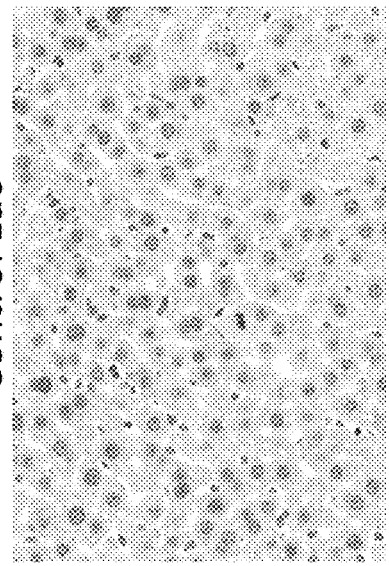
FIG. 38F Control Luc
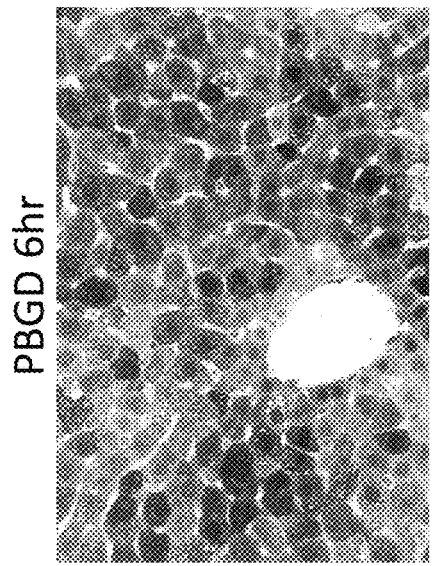
FIG. 38B PBGD 6hr
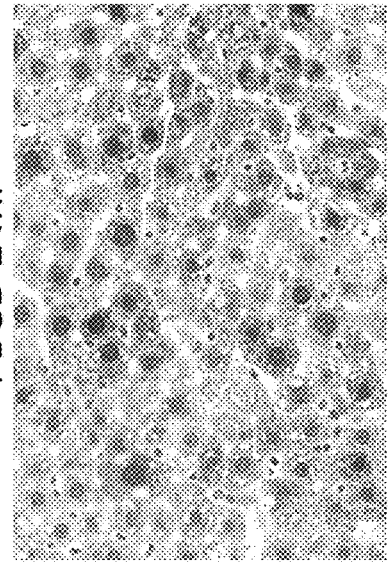
FIG. 38E PBGD 24hr
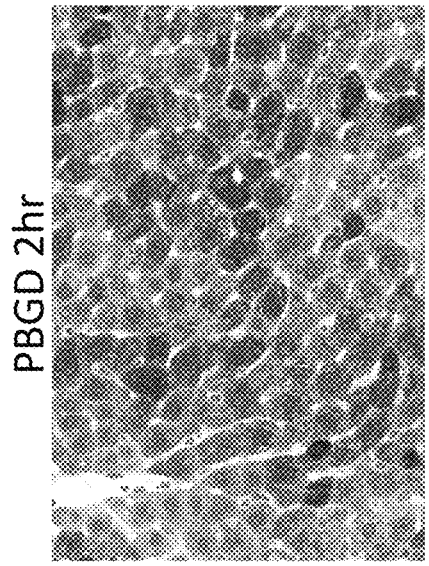
FIG. 38A PBGD 2hr
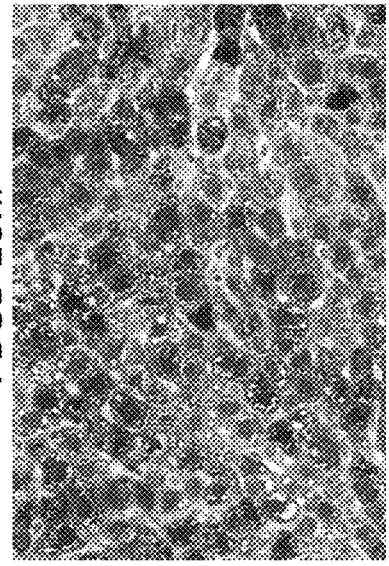
FIG. 38D PBGD 16hr Hepatic PBGD protein level in WT (Sprague Dawley) rats PBS 24hr PBGD / compound 18, 1mpk, 24hr

SEQUENCE LISTING

```
Sequence total quantity: 199
SEQ ID NO: 1            moltype = AA  length = 361
FEATURE                 Location/Qualifiers
REGION                  1..361
                        note = polypeptide sequence of wild type PBGD, isoform 1
source                  1..361
                        mol_type = protein
                        organism = synthetic construct
SEQUENCE: 1
MSGNGNAAAT AEENSPKMRV IRVGTRKSQL ARIQTDSVVA TLKASYPGLQ FEIIAMSTTG    60
DKILDTALSK IGEKSLFTKE LEHALEKNEV DLVVHSLKDL PTVLPPGFTI GAICKRENPH   120
DAVVFHPKFV GKTLETLPEK SVVGTSSLRR AAQLQRKFPH LEFRSIRGNL NTRLRKLDEQ   180
QEFSAIILAT AGLQRMGWHN RVGQILHPEE CMYAVGQGAL GVEVRAKDQD ILDLVGVLHD   240
PETLLRCIAE RAFLRHLEGG CSVPVAVHTA MKDGQLYLTG GVWSLDGSDS IQETMQATIH   300
VPAQHEDGPE DDPQLVGITA RNIPRGPQLA AQNLGISLAN LLLSKGAKNI LDVARQLNDA   360
H                                                                  361

SEQ ID NO: 2            moltype = DNA  length = 1083
FEATURE                 Location/Qualifiers
```

```
misc_feature             1..1083
                         note = nucleotide sequence of wild type PBGD, isoform 1
source                   1..1083
                         mol_type = other DNA
                         organism = synthetic construct
SEQUENCE: 2
atgtctggta acggcaatgc ggctgcaacg gcggaagaaa acagcccaaa gatgagagtg    60
attcgcgtgg gtacccgcaa gagccagctt gctcgcatac agacggacag tgtggtggca   120
acattgaaag cctcgtaccc tggcctgcag tttgaaatca ttgctatgtc caccacaggg   180
gacaagattc ttgatactgc actctctaag attggagaga aagcctgttt taccaaggag   240
cttgaacatg ccctggagaa gaatgaagtg gacctggttg ttcactcctt gaaggacctg   300
cccactgtgc ttcctcctgg cttcaccatc ggagccatct gcaagcggga aaaccctcat   360
gatgctgttg tctttcaccc aaaatttgtt gggaagaccc tagaaccct gccagagaag    420
agtgtggtgg gaaccagctc cctgcgaaga gcagcccagc tgcagagaaa gttcccgcat   480
ctggagttca ggagtattcg ggaaacctca acaccggc ttcggaagct ggacgagcag     540
caggagttca gtgccatcat cctggcaaca gctggcctgc agcgcatggg ctggcacaac   600
cgggtggggc agatcctgca ccctgaggaa tgcatgtatg ctgtgggcca gggggccttg   660
ggcgtggaag tgcgagccaa ggaccaggac atcttggatc tggtgggtgt gctgcacgat   720
cccgagactc tgcttcgctg catcgctgaa agggccttcc tgaggcacct ggaaggaggc   780
tgcagtgtgc cagtagccgt gcatacagct atgaaggatg gcaactgta cctgactgga    840
ggagtctgga cctagacgg ctcagatagc atacaagaga ccatgcaggc taccatccat    900
gtccctgccc agcatgaaga tgggcctgag gatgacccac agttggtagg catcactgct   960
cgtaacattc cacgagggcc ccagttggct gcccagaact tgggcatcag cctggccaac  1020
ttgttgctga gcaaggagc caaaaacatc ctggatgttg cacggcagct taacgatgcc   1080
cat                                                                1083

SEQ ID NO: 3              moltype = AA   length = 344
FEATURE                  Location/Qualifiers
REGION                   1..344
                         note = polypeptide sequence of wild type PBGD, isoform 2
source                   1..344
                         mol_type = protein
                         organism = synthetic construct
SEQUENCE: 3
MRVIRVGTRK SQLARIQTDS VVATLKASYP GLQFEIIAMS TTGDKILDTA LSKIGEKSLF    60
TKELEHALEK NEVDLVVHSL KDLPTVLPPG FTIGAICKRE NPHDAVVFHP KFVGKTLETL   120
PEKSVVGTSS LRRAAQLQRK FPHLEFRSIR GNLNTRLRKL DEQQEFSAII LATAGLQRMG   180
WHNRVGQILH PEECMYAVGQ GALGVEVRAK DQDILDLVGV LHDPETLLRC IAERAFLRHL   240
EGGCSVPVAV HTAMKDGQLY LTGGVWSLDG SDSIQETMQA TIHVPAQHED GPEDDPQLVG   300
ITARNIPRGP QLAAQNLGIS LANLLLSKGA KNILDVARQL NDAH                    344

SEQ ID NO: 4              moltype = DNA   length = 1032
FEATURE                  Location/Qualifiers
misc_feature             1..1032
                         note = nucleotide sequence of wild type PBGD, isoform 2
source                   1..1032
                         mol_type = other DNA
                         organism = synthetic construct
SEQUENCE: 4
atgagagtga ttcgcgtggg tacccgcaag agccagcttg ctcgcataca gacggacagt    60
gtggtggcaa cattgaaagc ctcgtaccct ggcctgcagt ttgaaatcat tgctatgtcc   120
accacagggg acaagattct tgatactgca ctctctaaga ttggagagaa agcctgtttt   180
accaaggagc ttgaacatgc cctggagaag aatgaagtgg acctggttgt tcactccttg   240
aaggacctgc ccactgtgct tcctcctggc ttcaccatcg gagccatctg caagcgggaa   300
aaccctcatg atgctgttgt ctttcaccca aaatttgttg ggaagaccct agaaaccctg   360
ccagagaaga gtgtggtggg aaccagctcc ctgcgaagag cagcccagct gcagagaaag   420
ttcccgcatc tggagttcag gagtattcgg gaaacctca acaccggct cggaagctg      480
gacgagcagc aggagttcag tgccatcatc ctggcaacag ctggcctgca gcgcatgggc   540
tggcacaacc gggtggggca gatcctgcac cctgaggaat gcatgtatgc tgtgggccag   600
ggggccttgg gcgtggaagt gcgagccaag gaccaggaca tcttggatct ggtgggtgtg   660
ctgcacgatc ccgagactct gcttcgctgc atcgctgaaa gggccttcct gaggcacctg   720
gaaggaggct gcagtgtgcc agtagccgtg catacagcta tgaaggatgg caactgtac    780
ctgactggag gagtctggag cctagacggc tcagatagca tacaagagac catgcaggct   840
accatccatg tccctgccca gcatgaagat gggcctgagg atgacccaca gttggtaggc   900
atcactgctc gtaacattcc acgagggccc cagttggctg cccagaactt gggcatcagc   960
ctggccaact tgttgctgag caaggagcc aaaaacatcc tggatgttgc acggcagctt   1020
aacgatgccc at                                                      1032

SEQ ID NO: 5              moltype = AA   length = 321
FEATURE                  Location/Qualifiers
REGION                   1..321
                         note = polypeptide sequence of wild type PBGD, isoform 3
source                   1..321
                         mol_type = protein
                         organism = synthetic construct
SEQUENCE: 5
MSGNGNAAAT AEENSPKMRV IRVGTRKSQL ARIQTDSVVA TLKASYPGLQ FEIIAMSTTG    60
DKILDTALSK IGEKSLFTKE LEHALEKNEV DLVVHSLKDL PTVLPPGFTI GAICKRENPH   120
DAVVFHPKFV GKTLETLPEK SVVGTSSLRR AAQLQRKFPH LEFRSIRGNL NTRLRKLDEQ   180
```

```
QEFSAIILAT AGLQRMGWHN RVGQILHPEE CMYAVGQEGG CSVPVAVHTA MKDGQLYLTG    240
GVWSLDGSDS IQETMQATIH VPAQHEDGPE DDPQLVGITA RNIPRGPQLA AQNLGISLAN    300
LLLSKGAKNI LDVARQLNDA H                                             321

SEQ ID NO: 6              moltype = DNA   length = 963
FEATURE                   Location/Qualifiers
misc_feature              1..963
                          note = nucleotide sequence of wild type PBGD, isoform 3
source                    1..963
                          mol_type = other DNA
                          organism = synthetic construct
SEQUENCE: 6
atgtctggta acggcaatgc ggctgcaacg gcggaagaaa acagcccaaa gatgagagtg     60
attcgcgtgg gtacccgcaa gagccagctt gctcgcatac agacggacag tgtggtggca    120
acattgaaag cctcgtaccc tggcctgcag tttgaaatca ttgctatgtc caccacaggg    180
gacaagattc ttgatactgc actctctaag attggagaga aagcctgttt taccaaggag    240
cttgaacatg ccctggagaa gaatgaagtg gacctggttg ttcactcctt gaaggacctg    300
cccactgtgc ttcctcctgg cttcaccatc ggagccatct gcaagcggga aaaccctcat    360
gatgctgttg tctttcaccc aaaatttgtt gggaagaccc tagaaaccct gccagagaag    420
agtgtggtgg gaaccagctc cctgcgaaga gcagcccagc tgcagagaaa gttcccgcat    480
ctggagttca ggagtattcg ggaaacctca acacccggc ttcggaagct ggacgagcag    540
caggagttca gtgccatcat cctggcaaca gctggcctgc agcgcatggg tggcacaac    600
cggggtgggc agatcctgca ccctgaggaa tgcatgtatg ctgtgggcca ggaaggaggc    660
tgcagtgtgc cagtagccgt gcatacagct atgaaggatg gcaactgta cctgactgga    720
ggagtctgga gcctagacgg ctcagatagc atacaagaga ccatgcaggc taccatccat    780
gtccctgccc agcatgaaga tggccctgag gatgacccac agttggtagg catcactgct    840
cgtaacattc cacgagggcc ccagttggcg cccagaact gggcatcagc cctggccaac    900
ttgttgctga gcaaggagc caaaaacatc ctggatgttg cacggcagct taacgatgcc    960
cat                                                                 963

SEQ ID NO: 7              moltype = AA   length = 304
FEATURE                   Location/Qualifiers
REGION                    1..304
                          note = polypeptide sequence of wild type PBGD, isoform 4
source                    1..304
                          mol_type = protein
                          organism = synthetic construct
SEQUENCE: 7
MRVIRVGTRK SQLARIQTDS VVATLKASYP GLQFEIIAMS TTGDKILDTA LSKIGEKSLF     60
TKELEHALEK NEVDLVVHSL KDLPTVLPPG FTIGAICKRE NPHDAVVFHP KFVGKTLETL    120
PEKSVVGTSS LRRAAQLQRK FPHLEFRSIR GNLNTRLRKL DEQQEFSAII LATAGLQRMG    180
WHNRVGQILH PEECMYAVGQ EGGCSVPVAV HTAMKDGQLY LTGGVWSLDG SDSIQETMQA    240
TIHVPAQHED GPEDDPQLVG ITARNIPRGP QLAAQNLGIS LANLLLSKGA KNILDVARQL    300
NDAH                                                                304

SEQ ID NO: 8              moltype = DNA   length = 912
FEATURE                   Location/Qualifiers
misc_feature              1..912
                          note = nucleotide sequence of wild type PBGD, isoform 4
source                    1..912
                          mol_type = other DNA
                          organism = synthetic construct
SEQUENCE: 8
atgagagtga ttcgcgtggg tacccgcaag agccagcttg ctcgcataca gacggacagt     60
gtggtggcaa cattgaaagc ctcgtaccct ggcctgcagt ttgaaatcat tgctatgtcc    120
accacagggg acaagattct tgatactgca ctctctaaga ttggagagaa aagcctgttt    180
accaaggagc ttgaacatgc cctggagaag aatgaagtgg acctggttgt tcactccttg    240
aaggacctgc ccactgtgct tcctcctggc ttcaccatcg gagccatctg caagcgggaa    300
aaccctcatg atgctgttgt ctttcacccc aaaatttgtt ggaagaccct agaaaccctg    360
ccagagaaga gtgtggtggg aaccagctcc ctgcgaagag cagcccagct gcagagaaag    420
ttcccgcatc tggagttcag gagtattcgg gaaacctcaa cacccggct cggaagctg    480
gacgagcagc aggagttcag tgccatcatc ctggcaacag ctggcctgca gcgcatgggc    540
tggcacaacc gggtggggca gatcctgcac cctgaggaat gcatgtatgc tgtgggccag    600
gaaggaggct gcagtgtgcc agtagccgtg catacagcta tgaaggatgg caactgtac    660
ctgactggag gagtctggag cctagacggc tcagatagca tacaagagac catgcaggct    720
accatccatg tccctgccca gcatgaagat ggccctgagg atgacccaca gttggtaggc    780
atcactgctc gtaacattcc acgagggccc cagttggctg cccagaactt gggcatcagc    840
ctggccaact tgttgctgag caaggagcc aaaaacatcc tggatgttgc acggcagctt    900
aacgatgccc at                                                       912

SEQ ID NO: 9              moltype = RNA   length = 1083
FEATURE                   Location/Qualifiers
misc_feature              1..1083
                          note = PBGD-CO01
source                    1..1083
                          mol_type = other RNA
                          organism = synthetic construct
SEQUENCE: 9
atgagcggga acggcaacgc cgcagccacc gccgaggaga acagccccaa gatgcgggtc     60
```

```
atcagggtgg gcacgcggaa gtcccagttg gcacgcatac agaccgcacg cgtagtggcg   120
accctgaagg cctcctaccc cggcctccag ttcgagatca tcgccatgag caccaccggg   180
gacaagatcc tcgataccgc cctgtccaag atcggcgaga agtccttgtt taccaaggag   240
ctggagcacg ccctggagaa gaatgaggtg gaccttgtgg tgcacagcct caaggacctg   300
cccaccgtgc tgcccccagg gttcaccata ggagccatac gcaagaggga gaacccgcac   360
gacgcagtcg tgttccaccc caagtttgtg gtaagacac tggagaccct gcccgagaag   420
agcgtggtg gtacctccag cctccgccga gcagcccagc tgcagaggaa gttcccgcac   480
ctggaattcc gatccatcag gggcaatctg aacaccagac tgaggaagct ggatgagcag   540
caggaatttt ccgcgataat cctcgcgacc gccgggctgc agaggatggg ctggcataac   600
agggtgggcc aaatcctgca ccccgaggag tgcatgtacg ccgtgggcca gggcgccctc   660
ggcgtggagg tgagggccaa agaccaagac atcctggacc tggtgggggt cctgcacgat   720
ccggagactc tgctgaggtg catcgccgag cgggcgtttc tcaggcacct cgagggcggc   780
tgctccgtgc ccgtggccgt ccataccgcc atgaaggacg ccagctgta cctcaccggc   840
ggcgtgtgga gcctggacgg cagcgactcc atacaggaaa ccatgcaagc gaccatacat   900
gtccccgccc agcacgagga cgggcccgag gatgacccgc agctggtcgg tatcaccgca   960
aggaatatcc ccggggccc acagctggcc gcccagaatc tgggcatctc cctggccaat   1020
ctgctgctgt ccaagggcgc caagaacatc ctcgacgtgg ccaggcaact gaacgacgca   1080
cac                                                                 1083

SEQ ID NO: 10              moltype = RNA    length = 1083
FEATURE                    Location/Qualifiers
misc_feature               1..1083
                           note = PBGD-CO02
source                     1..1083
                           mol_type = other RNA
                           organism = synthetic construct
SEQUENCE: 10
atgagcggca acggtaacgc cgccgccacc gccgaggaga actcgcccaa gatgcgggtc   60
atcagggtgg gaacgaggaa gtcccagctg gccaggatcc agaccgacag cgtggtggcg   120
acgctgaagg ccagctaccc cggcctgcag tttgagtaa tcgccatgtc aaccaccggg   180
gacaagatcc tcgacaccgc gctgagcaag atcggcgaga agtccctgtt caccaaggag   240
ctggagcacg ccttggaaaa gaacgaggtg gatctggtcg tgcacagcct gaaggacctg   300
cccaccgtgc tgcccccgg cttcaccatc ggcgccatct gcaagcggga aaatccccat   360
gacgccgtgg tgttccaccc caagttcgtg gggaagaccc tggagaccct gcccgagaag   420
agcgtggtg gaaccagctc actgcggcgg gccgcccagc tgcaacgtaa gttccccat   480
ctggagttcc gatccatccg aggcaatctg aacaccaggc tgagaaagct ggatgaacaa   540
caggagttca gcgccatcat cctggcaacc gccggtctgc agaggatggg ctggcacaac   600
agggtgggcc aaatcctgca ccccgaggag tgcatgtatg cagtggggca gggcgcgctg   660
ggtgtcgagg tgcgagcgaa ggaccaggac atcctcgacc tggtgggagt gctgcacgac   720
cccgagaccc tgctgcggtg catcgccgag agggccttcc tgcgccacct cgagggcggc   780
tgctcagtgc ccgtggccgt gcataccgcc atgaaggacg ccagctgta cctgaccggc   840
ggtgtgtgga gcctcgacgg cagcgactcc atccaggaaa cgatgcaggc gactatccac   900
gtgcccgcac agcacgagga cgggcccgaa gacgaccccc agctggtcgg gatcaccgcc   960
aggaacatcc ccgagggcc ccagctggcg gcccaaaacc tcggcatatc cctggccaac   1020
ctgctgctgt ccaagggcgc caagaacatc ctggatgtgg cccgccaact gaacgacgcc   1080
cac                                                                 1083

SEQ ID NO: 11              moltype = RNA    length = 1083
FEATURE                    Location/Qualifiers
misc_feature               1..1083
                           note = PBGD-CO03
source                     1..1083
                           mol_type = other RNA
                           organism = synthetic construct
SEQUENCE: 11
atgagcggta acggcaacgc cgccgccaca gccgaagaga actcccccaa gatgagggtg   60
attagggtgg gtacccgaaa gagccagctg gcccggatcc agaccgactc cgtggtggcc   120
accctcaagg caagctaccc cggcctgcag ttcgagatca tcgccatgag caccaccggg   180
gacaaaattc tcgacaccgc cctgagcaag atcggcgaga agtccttgtt caccaaggag   240
ctagagcacg ccctcgaaaa gaacgaggtg gatctggtcg tgcactccct gaaggacctg   300
cccaccgtgc tgcccccgg cttcacgatc ggcgcgatct gcaagaggga gaacccgcat   360
gacgccgtgg tgtttcatcc caaatttgtg ggaaaaaccc tggagactct ccccgagaag   420
agcgtcgtcg ggacctcctc cctgcggcgg gccgcccagc tgcagcgcaa gttcccgcac   480
ctggagttcc gcagcatcag gggaaacctg aacaccagac tgaggaagct gacgagcag   540
caggagttca gcgctatcat cctcgccacc gccggcctcc agcgaatggg ctggcataac   600
cgggtgggcc agatcctgca cccgaagaa tgtatgtacg cggtgggcca gggcgcgctg   660
ggcgtggagg tgagggccaa ggaccaggac atcctggatc tcgtgggcgt gctgcacgac   720
cccgagaccc tgctgagatg catcgccgaa cgggccttcc tgaggcacct ggagggcggc   780
tgctccgtgc cggtggccgt acataccgca atgaaagacg ccagctcta cctgacgggg   840
ggggtgtgga gcctcgacgg ctccgactcc atccaggaga ccatgcaggc gacgatccat   900
gtacccgccc agcacgagga cgggcccgag gatgatcccc aactcgtggg catcaccgcc   960
cgcaacatcc cgaggggccc ccagctggcc gcacagaacc tgggaatatc actgccaac   1020
ctcctgctca gcaggggcgc caagaatatc ctcgacgtgg ccaggcagct gaatgacgcc   1080
cac                                                                 1083

SEQ ID NO: 12              moltype = RNA    length = 1083
FEATURE                    Location/Qualifiers
misc_feature               1..1083
                           note = PBGD-CO04
```

| source | 1..1083 |
| --- | --- |
| | mol_type = other RNA |
| | organism = synthetic construct |

SEQUENCE: 12
```
atgagcggca acggcaacgc cgccgccacc gccgaggaga acagccccaa aatgcgcgtg    60
atcagggtgg gcaccaggaa gagccagctg gcccgcatcc agaccgacag tgtcgtggcc   120
accctcaagg ccagctatcc gggcctgcaa ttcgagatca tcgccatgag caccaccggc   180
gacaagatcc tcgacaccgc cctcagcaag atcggcgaga agtccctgtt caccaaggag   240
ctggagcacg ccctggagaa gaacgaggtg gacctggtgg tgcacagcct caaggacctg   300
cccaccgtgc tgccccccgg cttcaccatc ggcgccatct gcaagcggga gaaccccac    360
gacgccgtgg tgttccatcc caagttcgtg ggcaagaccc tggagaccct gcccgagaag   420
agcgtggtcg gcaccagctc cctcaggaga gccgcccagc tgcagcgaaa gttccccac    480
ctggaattcc gcagcatccg ggggaacctg aacacccgcc tgaggaagct ggacgagcag   540
caagaattca gcgccatcat cctggccacc gcgggcctgc agaggatggg gtggcacaac   600
cgcgtcggcc agatcctgca cccagaggag tgcatgtacg cggtggggca gggggccttg   660
ggggtggaag tgcgcgccaa ggaccaggac atcctggacc tggtcggcgt gctgcatgac   720
cccgagaccc tgctcaggtg catcgccgag agggcctttc tgcgccacct cgaggggggt   780
tgcagcgtgc cggtcgccgt ccatacggcc atgaaggacg gccagctgta cctgaccggc   840
ggcgtgtggt ccctggacgg ctccgacagc atccaggaga ccatgcaggc caccatccac   900
gtgcccgccc aacacgagga cggccccgag gacgacccgc agctcgtcgg catcaccgcc   960
aggaatatac cccgtggccc ccagctggcc gcccagaatc tcggcatcag cctggccaat  1020
ctgctgctga gcaaggggc caagaacatc ctggacgtgg ccaggcagct gaatgatgcc  1080
cac                                                               1083
```

| SEQ ID NO: 13 | moltype = RNA length = 1083 |
| --- | --- |
| FEATURE | Location/Qualifiers |
| misc_feature | 1..1083 |
| | note = PBGD-CO05 |
| source | 1..1083 |
| | mol_type = other RNA |
| | organism = synthetic construct |

SEQUENCE: 13
```
atgagcggca acggaaacgc cgccgcgacg gccgaggaga actcccccaa aatgagggtc    60
atcagggtgg gcacccggaa gagccagctg gcgcggatcc agaccgacag cgtcgtggcc   120
accctcaaag ccagctaccc aggcctgcag ttcgagatca tcgccatgtc gaccaccggc   180
gacaagatcc tggataccgc cctcagcaag atcggcgaga agtccctgtt caccaaggag   240
ctcgagcacg ccctggagaa gaatgaggtg gatctggtgg tgcattccct gaaagacctg   300
ccgaccgtcc tgccccccgg cttcacgatc ggagccatct gcaaacggga gaaccccac    360
gacgcgtgg tgttccaccc gaagttcgtg ggtaagaccc tggaaacact gcccgagaag   420
tccgtggtgg gcaccagcag cctgaggcgg gcgcccaac tgcagaggaa gttccccac    480
ctcgagttca gaagcatccg ggggaacctg aataccggc tgcgcaagct ggacgagcag   540
caggagttca gcgccatcat cctggccacc gctggcctgc agaggatggg atggcacaac   600
cgtgtgggcc agatcctgca cccggaggag tgcatgtacg ccgtggggca ggggcgcctg   660
ggcgtggagg tgcgcgcgaa ggaccaggac atcctggacc ttgtcggcgt gctgcacgat   720
cccgagacgc tgctgaggtg catcgccgag agggccttcc tgaggcacct ggaaggggc    780
tgtagcgtcc ccgtggctgt ccacaccgcc atgaaggacg ccagctgta cctgaccggc   840
ggcgtgtggt ccctggacgg cagcgacagc atccaggaga ccatgcaggc caccatccac   900
gtcccccgccc aacacgaaga cggccccgag gacgaccccc agctggtagg cataactgcc   960
cgcaatatcc caggggcc ccaactggcc gcccagaacc tggcataag cctggcaaac  1020
ctgctgctgt ccaagggcgc caagaacatc ctggacgtcg cccgccagct gaacgacgcc  1080
cac                                                               1083
```

| SEQ ID NO: 14 | moltype = RNA length = 1083 |
| --- | --- |
| FEATURE | Location/Qualifiers |
| misc_feature | 1..1083 |
| | note = PBGD-CO06 |
| source | 1..1083 |
| | mol_type = other RNA |
| | organism = synthetic construct |

SEQUENCE: 14
```
atgagcggca acggcaacgc cgccgccacc gccgaggaga attcccccaa aatgagggtg    60
atccgcgtgg gcacgaggaa gagccagctg gcccggatcc agacggacag cgtggtggcc   120
accctgaagg cctcgtatcc cgggctgcag ttcgagatca tcgccatgag caccaccggc   180
gacaagatcc tcgacaccgc cctgtccaag atcggcgaga aaagcctgtt caccaaggaa   240
ctggagcacg cactgaaaa gaacgaggta gacctcgtgg tgcattccct gaaggacctg   300
cccaccgtgc tgccccagg cttcaccatc ggcgccatct gcaagcgaga gaaccccat    360
gatgccgtgg tgttccaccc gaagtttgtt ggcaagacgc tggagaccct gcccgagaag   420
agcgtagtgg gcaccagctc gctgcggagg gccgcccagc tgcagaggaa gttccccac    480
ctggagttta ggagcattag gggaacctg aacaccagc tcaggaagct ggacgagcag   540
caggagttct ccgctataat cctggccacc gccgggctgc agaggatggg gtggcacaac   600
agggtggggc aaatcctgca ccccgaagag tgcatgtacg ccgtcggcca gggggccctg   660
ggcgttgagg ttcgcgccaa ggatcaggac atcctggacc tggtgggggt gctgcatgac   720
cccgagaccc tgctgaggtg catcgcgaaa gggccttcc tgcgccacct ggagggcggc    780
tgcagcgtgc ccgtcgccgt ccacaccgcg atgaaggacg gccagctgta cctgaccggc   840
ggggtctggt ccctggacgg ctccgacagc atccaggaga cgatgcaggc cacgatccac   900
gtgcccgccc aacacgagga cggtcccgaa gatgatcccc agctggtcgg catcaccgca   960
aggaacatcc caggggccc ccagctggcc gcacagaacc tggcatctc gctgccaac    1020
ctgctgctga gcaaggggc caagaacatc ctcgacgtgg ccaggcagct aaacgacgcc  1080
cac                                                               1083
```

| SEQ ID NO: 15 | moltype = RNA length = 1083 |
| FEATURE | Location/Qualifiers |
| misc_feature | 1..1083 |
| | note = PBGD-C007 |
| source | 1..1083 |
| | mol_type = other RNA |
| | organism = synthetic construct |

SEQUENCE: 15
```
atgtccggca acggcaacgc tgccgccacg gccgaggaga acagcccaa gatgagggtg    60
atccgggtgg gcaccagaaa gtcccagctc gccaggatcc agactgatag cgtggtcgcc   120
accctcaaag ccagctaccc gggcctgcag tttgagatca tcgccatgtc cacaaccggc   180
gacaagatcc tggacacagc gctgtcgaag atcggcgaaa aaagcctctt caccaaggag   240
ctggagcacg ccctggagaa gaatgaggtg gacctggtgg tgcattccct gaaggacctg   300
cccaccgtgc tgcccccgg cttcaccatc ggcgccatct gcaagaggga gaacccacac   360
gacgccgtgg tcttccaccc caagttcgtg gggaaaaccc tcgaaccct ccccgaaaag   420
tccgtggtgg gcacctccag cctgaggcgg cggcccagc tgcagaggaa gttcccacac   480
ctcgagttcc gcagcatccg gggcaatctg aacaccaggc tcaggaagct ggacgagcag   540
caggagttca gcgccatcat cctggccacc gcgggcctcc agaggatggg ctggcacaac   600
agggtggggcc agatcctcca ccccgaggaa tgtatgtacg ccgtgggca aggcgccctg   660
ggcgtggagg tccgggcgaa ggaccaggac atcctgacc tggtcggcgt gctgcacgat   720
cccgagacgc tgtcaggtg catcgccgaa cgcgccttcc tccggcacct cgagggggcg   780
tgcagcgtgc cggtgccgt ccacaccgcc atgaaggacg ccagctgta cctgaccggc   840
ggcgtctgga gcctggacgg ctccgactcc atccaggaga cgatgcaggc caccatccat   900
gtgccagccc agcatgagga cggccggaa gacgaccccc aactggtggg catcaccgcc   960
cggaacatcc caggggccc tcagctcgcc gcacagaatc ttggcatcag cctgccaat  1020
ctcctgctga gcaagggagc caagaacatc ctcgacgtgg ccaggcagct gaacgacgcc  1080
cat                                                                1083
```

| SEQ ID NO: 16 | moltype = RNA length = 1083 |
| FEATURE | Location/Qualifiers |
| misc_feature | 1..1083 |
| | note = PBGD-C008 |
| source | 1..1083 |
| | mol_type = other RNA |
| | organism = synthetic construct |

SEQUENCE: 16
```
atgagcggca acggcaacgc cgccgccacc gccgaggaga atagcccaa gatgcgggtg    60
atccgcgtgg gcacccgcaa gagccagctg gccggatcc agaccgactc cgtcgtgcc   120
accctgaagg ccagctaccc cggactccag ttcgagatca tcgccatgtc gaccacgggc   180
gacaagatcc tcgacaccgc cctcagcaaa atcggagaga agtccctgtt caccaaggag   240
ctcgaacacg ccctggaaaa gaacgaggtg gacctggtgg tgcactccct gaaggacctg   300
cccaccgtgc tccccccgg atttaccatc ggagccatct gcaagcggga gaaccctcac   360
gacgccgtgg tgttccatcc caagttcgtg gggaagacgc tggaaaccct gccggagaag   420
agcgtagtgg gcaccagcag cctgcggagg gccgcccagc tgcagaggaa gttccccac   480
ctggagtttc gtagcatccg cggcaatctg aacacgcggc tgcgcaagct cgacgagcag   540
caggagttct ccgcgatcat actggccacc gccggcctgc agcggatggg gtggcacaac   600
cgggtcggcc agatcctgca ccccgaggag tgcatgtacg ccgtgggcca gggggccttg   660
ggcgtggagg tgagggccaa ggaccaggac atcctggacc tcgtgggcgt cttgcacgac   720
cccgaaaccc tgctgaggtg catcgccgag cgggcctttc tgaggcacct ggaggcggg   780
tgcagcgtgc ccgtggccgt ccacaccgca atgaaggacg ccagctgta cctgaccggc   840
ggggtctgga gcctgacgg cagcgattcg atacaggaga caatgcaagc cacgatccac   900
gtccccgccc agcacgagga cggcccgag gacgaccccc aactggtcgg gatcaccgcc   960
cggaacatcc caggggggcc gcagctggcc gcccagaacc tgggcatctc cctgccaac  1020
ctgctgctga gcaaaggcgc caagaacatt ctggatgtgg cccgcagct gaacgatgcc  1080
cac                                                                1083
```

| SEQ ID NO: 17 | moltype = RNA length = 1083 |
| FEATURE | Location/Qualifiers |
| misc_feature | 1..1083 |
| | note = PBGD-C009 |
| source | 1..1083 |
| | mol_type = other RNA |
| | organism = synthetic construct |

SEQUENCE: 17
```
atgagcggga acggcaacgc cgccgccacc gccgaggaga acagtccgaa gatgagggta    60
atcagggtcg ggacccgtaa gagccagctc gccaggatcc agaccgacag cgtggtggcc   120
accctgaagg ccagctatcc agggctgcag ttcgagatca tcgccatgtc caccaccggg   180
gacaaaatcc tggacaccgc cctgagcaag ataggcgaaa gagcctgtt caccaaggag   240
ctggagcatg ccctggaaaa gaacgaggtg gacctggtcg tgcacagcct gaaggacctg   300
cccaccgtgc tgcccccgg cttcaccatc ggcgcgatct gcaaaggga gaaccccac   360
gacgctgtgg tcttccaccc aaaattcgtg gggaagactc tcgagaccct gccgagaag   420
agcgtggtgg gtacttccag cctgaggagg gccgcccagc tgcaaaggaa gttccccat   480
ctggagttca ggagcatccg gggcaacctg aataccaggc tgcaagct ggatgagcag   540
caggaattca gcgccatcat cctggccacc gccggcctgc agaggatggg ctggcacaac   600
agggtcggcc agatcctgca ccccgaggag tgcatgtatg ccgtgggcca gggtgccctg   660
ggagtggagg tcagggcgaa ggaccaggac atccttgacc ttgtcggcgt gctgcacgac   720
cccgagaccc tgtcaggtg catcgccgag agggccttcc tgaggcatct ggagggggcg   780
tgtagcgtgc ccgtcgcagt gcacaccgcc atgaaggacg ccaactgta cctgaccggc   840
```

```
ggcgtgtgga gcctggacgg ctctgattcg atccaagaga ccatgcaagc cactatacac   900
gtgcccgccc agcacgagga cgggcccgag gatgacccac agctggtcgg aataccgcc    960
cggaacatcc ccagggggacc ccagctggcc gcgcagaatc tgggcatctc actgccaac  1020
ctgctgctct ccaagggggc caagaacatc tggacgtgg ctaggcagct gaacgacgcc  1080
cac                                                                1083
```

| SEQ ID NO: 18 | moltype = RNA  length = 1083 |
|---|---|
| FEATURE | Location/Qualifiers |
| misc_feature | 1..1083 |
| | note = PBGD-CO10 |
| source | 1..1083 |
| | mol_type = other RNA |
| | organism = synthetic construct |

SEQUENCE: 18
```
atgagcggca acggaaacgc cgccgccacc gccgaggaaa actcccccaa aatgcgggtc    60
atcagggtgg gcaccaggaa gtcccagctc gccaggatac aaaccgactc cgtggtagcc   120
accctgaagg ccagctaccc cgggctccag ttcgagatca tcgccatgag cacaaccggt   180
gacaagattc ttgacaccgc cctcagcaag ataggcgaga agagcctgtt caccaaggag   240
ctggaacatg ccctggaaaa gaacgaggtc gacctcgtcg tgcacagcct gaaggacctg   300
cccacggtgc tgccacccgg cttcacgatc ggcgccatct gcaaaagaga gaatcccat   360
gacgcggtgg tgtttcaccc caagtttgtg gggaagaccc tggagaccct gcccgagaag   420
agcgtggtgg ggacgagcag cctgcgcagg gccgcccacc tgcagcggaa gttccccat   480
ctggagttta ggagcatcag gggggaacctg aacacgaggc tgaggaagct ggacgagcag   540
caggaattca gcgccatcat cctggcgacc gccggcctgc agcggatggg ctggcataac   600
cgcgtgggac agatactgca ccccgaggaa tgcatgtacg cggtcggcca aggcgcgctg   660
ggcgtggagg tgagggccaa agatcaggat atcctagacc tcgtgggcgt gcttcacgac   720
cccgagacac tgctgaggtg catcgccgag agggcgtttc tgcggcacct ggagggcggg   780
tgcagcgtgc cggtggccgt gcataccgcc atgaaggacg ccagctgta cctgacgggg   840
ggggtgtgga gcctcgacgg ctcggacagc atccaggaga cgatgcaggc cacgatacac   900
gtgcccgccc agcacgaaga cgggcccgag gatgaccccc agctggtggg gatcacagcc   960
aggaacatcc caggggcccc caactcgcc gcccagaacc tggggattag cctggccaac  1020
ctgctcctct ccaagggcgc caagaacatc tggacgtgg ccaggcagct gaacgatgcc  1080
cat                                                                1083
```

| SEQ ID NO: 19 | moltype = RNA  length = 1083 |
|---|---|
| FEATURE | Location/Qualifiers |
| misc_feature | 1..1083 |
| | note = PBGD-CO11 |
| source | 1..1083 |
| | mol_type = other RNA |
| | organism = synthetic construct |

SEQUENCE: 19
```
atgtccggca acgggaacgc agccgcgacc gccgaggaga actcccccaa gatgcgcgtg    60
attagggtcg ggacgaggaa gagccagctg gccaggatac agaccgattc cgtggtggcc   120
accctcaagg ccagctaccc tgggctgcaa ttcgagatca tagccatgag caccaccggc   180
gataagatac tggacaccgc cctcagcaag atcggtgaga agtcgctgtt taccaaggaa   240
ctggaagcag ccctggagaa gaatgaagtg gatctcgtcg tacacagctt gaaggaacctg   300
cccaccgtgc tgcccccgg attcaccatc ggggccatct gcaagaggga gaaccccac    360
gacgccgtgg tgttccaccc caaattcgtc ggcaagaccc tggaaccct gcccgaaaag    420
agcgtggtgg gcacctccag cctgcgcagg gccgcccagc tgcagaggaa gttccccac    480
ctggagttca ggagcatacg ggggcaacctg aacacccgag tgaggaagct ggacgaacag    540
caagagttca gcgccatcat cctggcaacc gccggcctgc agaggatggg ctggcacaac   600
agggtgggcc agatcctgca ccccgaggag tgtatgtacg ccgtaggcca gggcgccctc   660
ggagtggagg tcagggccaa ggaccaggac atcctcgacc tggtggggtgt gctgcacgac   720
cccgagacac tgctgaggtg catcgccgag agggcctttc tgaggcacct cgaaggcggc   780
tgctccgtgc ccgtggccgt gcacaccgcc atgaaagacg gtcagctgta cttgaccggt   840
ggcgtgtgga gcctcgacgg cagcgacagc atccaggaga caatgcaggc caccatcac   900
gtccccgcac agcacgaaga cgggcctgag gacgaccccc agctggtggg aataccgcc   960
aggaatatcc ccgaggccc ccagctggcg cccagaacc tgggcattc cctggccaac   1020
ctcctgctga gcaaaggtgc caagaatatc ctggacgtgg cccggcagct gaatgacgcc  1080
cac                                                                1083
```

| SEQ ID NO: 20 | moltype = RNA  length = 1083 |
|---|---|
| FEATURE | Location/Qualifiers |
| misc_feature | 1..1083 |
| | note = PBGD-CO12 |
| source | 1..1083 |
| | mol_type = other RNA |
| | organism = synthetic construct |

SEQUENCE: 20
```
atgagcggga acgggaacgc cgccgccacc gccgaggaga attcccccaa gatgagggtg    60
ataagggtag ggaccaggaa gagccagctg gccaggatcc agactgacag cgtggttgcc   120
accctgaagg ccagctaccc cggtctgcag ttcgagatca tcgccatgtc caccaccggt   180
gacaagattc tggacaccgc cctgtccaag atcggagaaa agagcctgtt caccaaggag   240
ctcgaacacg cccttgagaa gaatgaagtg gacctggtgg tgcactccct caaggaccta   300
cccaccgtgc tgccccccgg ctttaccatc ggcgccatct gcaagaggga gaaccccat   360
gacgcggtgg tgtttcaccc caaattcgtc ggaaagaccc tggagacact gcccgagaag   420
tccgtggtgg gcaccagcag cctgaggagg gccgcccagc tgcagaggaa gttccccat   480
ctggagttta ggagcatcag gggcaacctg aacacccggc tgaggaagct ggatgaacag   540
```

```
caggagttca gcgccatcat cctggccacg gcgggcctgc agcggatggg gtggcataac  600
cgggtggggc agatcctgca ccccgaagaa tgcatgtatg cggtagggca aggggccctg  660
ggcgtcgagg tgcgggccaa ggaccaggac atactggacc tggtgggggt gctgcatgat  720
cccgaaaccc tgctccggtg catcgccgag agggccttcc tcaggcacct ggagggcgga  780
tgctcggtgc ccgtcgccgt gcataccgcc atgaaggacg gccagctcta cctcaccggc  840
ggcgtttggt ccctggatgg aagcgacagc attcaggaaa ccatgcaggc caccatccac  900
gtgccagcgc agcacgagga cggccccgag gacgaccccc agctagtggg catcaccgcc  960
aggaacatcc ccggggcccc ccagctggcc gcacagaacc taggcatcag cctggccaac  1020
ctcctgctga gcaagggcgc caagaacatc ctggatgtgg ccaggcagct gaacgacgcc  1080
cac                                                                1083
```

| SEQ ID NO: 21 | moltype = RNA length = 1083 |
|---|---|
| FEATURE | Location/Qualifiers |
| misc_feature | 1..1083 |
| | note = PBGD-CO013 |
| source | 1..1083 |
| | mol_type = other RNA |
| | organism = synthetic construct |

SEQUENCE: 21
```
atgtccggta acggcaacgc ggccgccacc gccgaggaga acagccccaa gatgagggtg  60
atccgcgtgg gcaccaggaa gagccagctg gccaggatcc aaaccgacag cgtggtcgcc  120
acgctgaagg ccagctaccc aggtctgcaa ttcgagatca tcgccatgag caccaccggc  180
gacaaaatcc tggataccgc cctgtccaag atcggcgaga gagcctgtt caccaaggag  240
ctggaacacg ccctggagaa gaacgaggtg gacctggtcg tgcacagcct gaaggacctg  300
cccaccgtcc tgcccccgg gttcaccatc ggcgccattt gcaagcgaga gaacccacac  360
gacgccgtcg tgttccaccc caagttcgtc ggcaagacgc tcgagaccct gcccgagaag  420
agcgtggtcg ggacgagctc cctccggcgc gccgcccagc tccagcgcaa atttccccat  480
ttagagttcc gtagcatccg tgcaacctg aacacgcgtc tgaggaagct ggatgaacaa  540
caggagttca gcgccatcat cctggccacc gccggcctgc agaggatggg ctggcacaac  600
cgtgtgggcc agatccttca tcccgaggag tgcatgtacg ctgtcggcca ggggctctg  660
gggtggaag tcagggccaa ggaccaggac atcctggatc tggtcggcgt gctccacgac  720
cccgagactc tgctgaggtg tatcgcagag agggcgttcc tcaggcacct cgagggcggg  780
tgcagcgtcc ctgtggcggt gcacaccgcc atgaaggacg gcagctgta cctcaccggc  840
ggcgtgtggt cctggatgg cagcgacagc atcaggagga cgatgcaggc caccatccac  900
gtgcccgccc agcacgagga cggccccgag gacgacccc aactggtcgg catcaccgcc  960
cgcaacatcc caggggcc caactggcc gcccagaatc tgggcatctc cctggccaac  1020
ctgctcctga gcaagggtgc caagaacatc ctcgacgtgg ccaggcagct caacgacgcc  1080
cac                                                                1083
```

| SEQ ID NO: 22 | moltype = RNA length = 1083 |
|---|---|
| FEATURE | Location/Qualifiers |
| misc_feature | 1..1083 |
| | note = PBGD-CO014 |
| source | 1..1083 |
| | mol_type = other RNA |
| | organism = synthetic construct |

SEQUENCE: 22
```
atgagcggca acggcaacgc cgcagccacc gccgaggaga actcccccaa gatgagggtg  60
atcagggtgg gcaccaggaa gtcccaactg gcgcggatcc agaccgacag cgtggtggcc  120
accctgaagg cgtcctaccc cggcctccag ttcgagatta cgccatgag caccaccggc  180
gacaagatcc tggataccgc cctgagcaag atcggggaaa aaagcctgtt caccaaggag  240
ctggagcacg ccctggagaa gaacgaggtg gatctcgtgg tacactccct gaaggatttg  300
cccaccgtcc tgcccccgg gttcaccatc ggggccatct gtaaaaggga gaatcccac  360
gacgccgtgg tgttccaccc caagttcgtg ggcaagaccc tggagaccct ccccgagaag  420
agcgtggtcg gaaccagcag cctgcgccgc gccgctcagc tacaacgcaa gttcccccac  480
ctggagttcc ggagcatcag ggggaacctg aacaccgtc tgcggaagct cgacgagcag  540
caggagttca gcgctatcat cctggctacg gccgggctgc agaggatggg atggcacaac  600
agggtcgggc agatcctgca tcccgaggag tgcatgtacg ccgtgggcca aggcgccctc  660
ggagtggaag tcagggccaa agaccaagac atcctggacc tagtcggcgt gctgcatgac  720
cccgagaccc tgctccgctg catcgccgag agggcgttcc tgcgccatct ggagggggc  780
tgcagcgtgc cggtggccgt gcataccaget atgaaagatg ccaactgta cctcaccggc  840
ggcgtctgga gcctggacgg ctcggactcc attcaagaga cgatgcaggc cacgatccac  900
gtgcccgcgc agcacgagga tgggcccgag gacgatcccc agctggtagg catcaccgcc  960
cggaacatcc ccggggcccc gcagctggcc gcccagaacc tggggatctc cctggccaac  1020
ctcctgctgt cgaaggggc caagaacatc ctggatgtcg ccaggcagct gaacgacgcc  1080
cac                                                                1083
```

| SEQ ID NO: 23 | moltype = RNA length = 1083 |
|---|---|
| FEATURE | Location/Qualifiers |
| misc_feature | 1..1083 |
| | note = PBGD-CO015 |
| source | 1..1083 |
| | mol_type = other RNA |
| | organism = synthetic construct |

SEQUENCE: 23
```
atgtccggga acgggaacgc ggccgccacg gcggaggaga actcccccaa aatgagggtg  60
ataagggtgg gcacccggaa aagccagctg gctcgaatcc agaccgacag cgtggtggcc  120
accctgaaag cctcctaccc cggcctccag tttgagatca tcgccatgag caccaccggc  180
gacaagatcc tcgacaccgc cctgagcaag atcggtgaaa agtcgctgtt cacgaaggag  240
```

```
ctggagcacg ccctagagaa gaacgaggtc gacctggtgg tccacagcct gaaggacctg    300
cccaccgtcc tccccccggg atttaccatt ggagccatat gcaaacggga gaaccccat    360
gacgccgtgg tcttccaccc caagttcgtc ggcaagaccc tggagaccct cccggagaag    420
tccgtggtgg ggaccagcag cctgcgcagg ccgcccagc tgcagaggaa attccccat    480
ctggaattca ggtccatcag ggggaacctc aacacccggc tggaaagct cgacgaacaa    540
caggaattca gcgccatcat cctggccacc gcggggctgc agaggatggg gtggcacaac    600
agggtgggac agatcctgca ccccgaggag tgtatgtacg ccgtgggca gggagccctg    660
ggcgtcgagg taagggcgaa ggatcaggac atcctggatc tggtgggggt gctgcacgac    720
cccgagaccc tgctccggtg cattgccgag agggccttcc tgaggcacct ggagggcggc    780
tgtagcgtgc ccgtggccgt gcacacagcg atgaaagacg gccagctgta tctgaccggg    840
ggcgtgtggt ccctcgatgg ctcagactcc atccaggaga cgatgcaggc caccatccat    900
gtgcccgccc agcacgagga cggccccgag gacgaccccc agctcgtggg gatcaccgcc    960
cgtaacatac ccaggggccc ccagctggcc gcccagaatc tggggattag cctcgccaac    1020
ctgctgctga gcaagggcgc caagaacatc ctggacgtgg cccggcagct gaacgacgcc    1080
cat                                                                 1083

SEQ ID NO: 24           moltype = RNA  length = 1083
FEATURE                 Location/Qualifiers
misc_feature            1..1083
                        note = PBGD-CO016
source                  1..1083
                        mol_type = other RNA
                        organism = synthetic construct
SEQUENCE: 24
atgtccggca acgggaacgc cgccgccact gccgaggaga acagccccaa gatgagggtg    60
attagggtgg gcaccgtaa gagccagctc gccaggatcc agaccgacag cgtggtcgcg    120
accctcaagg cctcctaccc cggcctgcag ttcgaaatca tcgccatgag caccacgggg    180
gacaaaatcc tggataccgc cctgagcaag ataggtgaga gagcctgtt caccaaggaa    240
ctggagcacg ccctggaaaa gaacgaagtc gacctcgtgg tgcactccct gaaggacctc    300
cccaccgtgc tgccgcccgg cttcaccatc ggagccatct gcaagaggga gaaccccac    360
gacgccgtgg tatttcaccc caagttcgtc ggcaagaccc tggagaccct gcccgagaag    420
agcgtggtag gcaccagctc cctccgcagg ccgcccaac tccaaggaa gttccccac    480
ctcgagttcc ggagcatcag gggaaatctg aacaccaggc tgaggaagct cgatgagcag    540
caggagttct ccgccatcat cctggccacc gccggactgc aaaggatggg gtggcacaac    600
cgcgttgggc aaatcctgca ccccgaagag tgcatgtacg ccgtggggca gggcgcactc    660
ggggtggagg tgagggccaa ggaccaggac atcctggacc tcgtaggcgt actgcacgac    720
cccgagaccc tgctgcgctg tatcgctgag agggcctttc tgcggcacct ggagggcggc    780
tgcagcgtgc ccgtcgccgt gcacaccgcc atgaaagacg ccagctcta tctgacgggg    840
ggggtggcga gcctggaagg cagcgacagc atccaggaga caatgcaggc caccatccac    900
gtgcccgccc agcacgagga cgggcccgaa gacgaccccc agctcgtggg catcacggcc    960
cgtaacatcc caggggccc gcaactggcc gcgcagaacc tgggcatctc gctggccaat    1020
ctgctgctga gcaagggtgc caagaacatc tggatgttg cccgacagct gaatgacgcc    1080
cac                                                                 1083

SEQ ID NO: 25           moltype = RNA  length = 1083
FEATURE                 Location/Qualifiers
misc_feature            1..1083
                        note = PBGD-CO017
source                  1..1083
                        mol_type = other RNA
                        organism = synthetic construct
SEQUENCE: 25
atgagcggca acggtaacgc cgccgcgacc gcggaggaga actcacccaa gatgcgggtc    60
atcagggtag gcaccaggaa gagccagctg gccaggatac agaccgacag cgtggtggcc    120
acgctgaagg cgtcctatcc gggcctgcaa ttcgaaatta tcgccatgag cacgaccggg    180
gacaagatcc tggacaccgc gctgagcaaa atcggcgaga gagcctcttc caccaaaagg    240
ctggagcatg ccctggagaa gaacgaggtg gacctggtcg tgcattcact gaaggatctc    300
cccaccgtgg tgcccctgg ctttaccatc ggagccatct gcaagcgcga aaaccccac    360
gatgccgtgg tcttccaccc caagttcgta gggaagaccc ttgagcccct gccggagaag    420
tcggtggtcg ggaccagcag cctgcggagg gccgcccagc tccagaggaa gttcccgcac    480
cttgagttca ggagcatccg gggcaatctg aataccaggc tgaggaagct ggacgagcag    540
caagagttca gtgccatcat cctcgccacc gcggcctgc agaggatggg gtggcacaac    600
agggtgggac agatcctgca tcccgaggag tgcatgtacg ccgtgggcca gggcgccctc    660
ggcgtggaag tgcgggccaa ggaccaggac atttctggat tggtgggggt gctgcacgat    720
cccgagaccc tgctgcgatg catcgccgag cgcgccttct taaggcacct cgaggggggt    780
tgcagcgtgc ccgtggcagt gcacaccgcc atgaaggacg gccagctgta cctgaccggg    840
ggcgtgtgga gcctggacgg ctcggacagc atccaggaga caatgcaggc caccatccac    900
gtgccagctc aacatgagga tggccccgag gacgatccgc agctggtggg aatcaccgcc    960
cggaacatcc ctaggggccc ccaactggca gcccaaaacc tggcataag cctggccaac    1020
ctgctgctct ccaagggcgc caagaacatt ctggacgtcg cgaggcagct gaacgacgcc    1080
cac                                                                 1083

SEQ ID NO: 26           moltype = RNA  length = 1083
FEATURE                 Location/Qualifiers
misc_feature            1..1083
                        note = PBGD-CO018
source                  1..1083
                        mol_type = other RNA
                        organism = synthetic construct
```

```
SEQUENCE: 26
atgagcggca acggcaacgc cgccgcgacc gccgaggaga atagcccaa aatgagggtg    60
atccgggtgg gcacccggaa gtcccagctg gcccggatcc agaccgacag cgtggtggcc   120
accctcaagg ccagctaccc cggcctgcaa ttcgaaatca tcgccatgag caccaccggc   180
gacaagatcc tggataccgc cctgagcaag atcggcaggc aaaagcctct cactaaggag   240
ctggagcacg ccctggagaa aaacgaagtg gacctggtgg tccatagcct taaggacctg   300
cccaccgtgc tgcccccgg cttcaccatc ggcgccatct gtaagcgtga gaacccgcac    360
gacgccgtgg tgttccaccc caagtttgtg gggaagaccc tcgagactct ccccgagaaa   420
agcgtggtgg gcactagctc tctgaggagg gcagcccagc tccagaggaa attccccac    480
ctcgagttca ggagcatcag gggcaacctg aacacccggc tgaggaagct ggacgagcag   540
caggagttct ccgcgatcat cctggccacc gcgggactgc agcgaatggg ctggcacaac   600
cgggtgggcc aaatcctgca ccccgaggag tgcatgtacg ccgtgggcca gggggcacta   660
ggggtggagg tgcgggccaa ggatcaggac atcctggacc tggtcgggt gctgcacgac    720
cccgagaccc tgctcagatg catcgccgag cgggcgttcc tccggcattt ggagggtgcc   780
tgtagcgtgc ccgtcgccgt gcacaccgcc atgaaggacg tcagctgta cctcaccggg    840
ggcgtgtggt ccctcgacgg cagcgacagc atccaggaga ccatgcaggc caccatccat   900
gtgcccgccc agcacgagga cggccccgag gacgaccccc agctggtcgg catcaccgcc   960
aggaacatcc cagggggcc tcagctggcc gctcaaaacc taggcatcag cctggccaac  1020
ctcctgctca gcaagggcgc caagaatatc ctggacgtcg ccaggcagct gaacgacgcg  1080
cat                                                               1083

SEQ ID NO: 27        moltype = RNA  length = 1083
FEATURE              Location/Qualifiers
misc_feature         1..1083
                     note = PBGD-CO019
source               1..1083
                     mol_type = other RNA
                     organism = synthetic construct
SEQUENCE: 27
atgagcggca acgggaacgc cgccgccacc gccgaggaga acagccccaa gatgagggtg    60
atccgggtcg gtaccaggaa gagccagctg gcccgaatcc agaccgatag cgtggtggcc   120
acgctgaagg ccagctaccc cggactgcag ttcgagataa tcgcgatgag cacaacgggg   180
gacaagatcc tggacaccgc cctctccaag atcggcgaga aaagcctctt caccaaagag   240
ctggagcacg ccctggagaa gaacgaggta gacctcgtag tccatagcct gaaggacctg   300
cccaccgtgc tgcccccgg attcaccatc ggcgccatct gtaagcgcga gaaccccac    360
gacgccgtgg tcttccaccc caagttcgtc ggaaagacac tggagaccct gcccgaaaag   420
agcgtggtgg gcaccagcag cctgaggagg gccgcccagc tgcagcgcaa gttccccac    480
ctagaattca ggagcatccg gggcaactta aacaccaggc tgaggaagct ggatgagcag   540
caggaattca gcgccatcat cctcgcccacg gccgggctgc agaggatggg ctggcacaac   600
cgggtgggcc agatcctgca tccggaagag tgcatgtacg ccgtgggcca gggagccctg   660
ggcgtggagg tccgggccaa ggatcaagat atcctggatc tggtgggggt gctgcacgac   720
cccgagaccc tgctgcgctg catcgccgag agggcctttc tgcgccatct ggaggggggc   780
tgcagcgtgc ccgtggcggt gcataccgcc atgaaggacg gccagctcta tctgaccggc   840
ggggtctgga gcctcgacgg gagcgacagc atccaggaga ccatgcaggc gaccatccac   900
gtgcccgccc agcacgagga cggccccgaa gatgaccccc agctggtggg gatcaccgcg   960
aggaacatcc caggggccc ccagctagcc gcccagaacc ttggcatctc cctggccaac    1020
ctgctactca gcaagggtgc caagaatatc ctggatgtcg ccaggcagct gaacgacgcc  1080
cat                                                               1083

SEQ ID NO: 28        moltype = RNA  length = 1083
FEATURE              Location/Qualifiers
misc_feature         1..1083
                     note = PBGD-CO020
source               1..1083
                     mol_type = other RNA
                     organism = synthetic construct
SEQUENCE: 28
atgtccggca acggcaacgc cgccgccacc gccgaggaaa atagcccaa gatgcgggtg    60
atccgggtgg gaacacgaaa gtcccagctc gcccggatcc agaccgacag cgtggtggcc   120
accctgaagg ccagctaccc tggcctgcag ttcgagatca tcgccatgag caccaccggc   180
gacaagatcc tggatacggc cctgagcaag atcggggaga atccctctt caccaaggaa    240
ctggagcacg ccctggagaa gaacgaggtg gacctggtgg tccactccct gaaggacctg   300
cccacagtgc tcccacccgg cttcaccatc ggcgccatct gcaaacgcga gaaccccac    360
gacgccgtgg tctttcaccc caagttcgtc ggtaaaggac tggagaccct gcccgaaaag   420
agcgtggtgg gcacctccag cctgaggcgg gccgcccagc tgcagaggaa atttccccac   480
ctggagttcc ggagcatcag gggcaacctc aacaccaggc tgaggaagct ggacgagcag   540
caggaattta gcgcgatcat cctggccacc gccggcctgc agaggatggg gtggcacaac   600
agggtgggac aaatcctgca tccgaggag tgcatgtacg ccgtgggcca aggagctctg    660
ggcgtggaag tgagggccaa ggaccaggac atcctgacc tcgtgggcgt actgcacgac    720
cccgagaccc tgctgcggtg cattgccgag cgggccttcc tcgtcacct cgagggcggc    780
tgttccgtgc ccgtggccgt gcataccgcc atgaaggatg acagctgta tctgacgggc    840
ggcgtgtggt cactggacgg gtcggactcc atccaggaga ccatgcaggc caccatccac   900
gtgcccgccc agcacgagga cggcccagaa gacgaccccc agctcgtcgg gataaccgcc   960
cgcaatatcc ctaggggccc ccagctggcc gcccagaacc tcgggatcag cctggccaac  1020
ctcctgctgt ccaagggcgc caagaacata ctggacgtcg cccggcagct gaacgatgcc  1080
cat                                                               1083

SEQ ID NO: 29        moltype = RNA  length = 1083
FEATURE              Location/Qualifiers
```

| | | |
|---|---|---|
| misc_feature | 1..1083 | |
| | note = PBGD-CO021 | |
| source | 1..1083 | |
| | mol_type = other RNA | |
| | organism = synthetic construct | |

SEQUENCE: 29

```
atgagcggca acgggaacgc cgccgcaacc gccgaggaga actcaccaaa gatgagggtg   60
atccgagtgg gcaccaggaa gtcgcagctg ccaggatcc  agaccgacag cgtggtggcg  120
accctcaagg cctcctaccc cggcctgcag ttcgagataa tcgccatgtc caccaccggc  180
gacaagatcc tggataccgc cctcagcaag atcggcgaaa agagcctgtt caccaaggag  240
ctcgagcacg ctctggagaa gaacgaggtg gacctggtcg tgcactccct gaaagacctg  300
cccaccgtgt gcccccgggg cttcaccata ggggccatct gcaagcggga gaaccccac   360
gacgccgtgg tgttccatcc gaagttcgtg ggcaagaccc tggagaccct gcccgagaag  420
agcgtggtgg gcacgagcag cctaagaagg gccgcacagt tccagaggaa gttccccac   480
ctcgagttcc gcagcatcag aggcaacctg aacaccaggc tgcggaagct cgacgagcag  540
caggagttta cgccatcat  cctcgccacc gccggcctgc agaggatggg atggcataac  600
cgggtggggc agatcctgca cccccgaggag tgtatgtacg ccgtggggca gggggccctg  660
ggcgtggagg tgcgggccaa ggatcaggac atcctcgacc tggtgggcgt gcttcacgat  720
cccgagaccc ttctgcggtg catcgccgag cgggcctttc tgaggcatct ggagggcggg  780
tgtagtgtgc cagtggcagt tcacaccgcc atgaaggacg ccagctgta  cctgaccggt  840
ggggtttgga gcctggacgg gtccgacagc atccaggaga ccatgcaggc cacgatccat  900
gtgccccgctc agcatgagga cggaccagaa gacgacccgc agctggtggg catcacgccc  960
cggaacatac ccaggggggcc ccagctggcg gcccagaacc tgggcatcag cctggccaac 1020
ctgctgctga gcaagggcgc caagaacatc ctggatgtgg cgcggcagct gaatgatgcc 1080
cac                                                               1083
```

| | | |
|---|---|---|
| SEQ ID NO: 30 | moltype = RNA   length = 1083 | |
| FEATURE | Location/Qualifiers | |
| misc_feature | 1..1083 | |
| | note = PBGD-CO022 | |
| source | 1..1083 | |
| | mol_type = other RNA | |
| | organism = synthetic construct | |

SEQUENCE: 30

```
atgtcgggca acggcaacgc ggccgccacc gcggaggaga atagccccaa gatgcgggtg   60
atcagggtgg gcaccaggaa gagccagctg ccaggatcc  agaccgacag tgtggtggcc  120
accctgaagg ccagctaccc agggctgcag ttcgagatca ttgccatgtc taccaccggc  180
gacaagatcc tcgacaccgc cctgagcaaa atcgggggaga gagcctgtt  taccaaagag  240
ctggagcacg ccctggagaa gaatgaggtg gacctggtcg tgcactccct gaaggacctg  300
cccaccgtgc tgccacccgg cttcaccatc ggcgccatct gtaagaggga gaatcccac   360
gacgcagttg tgttccaccc caagttcgtg ggcaagaccc tggagaccct gcccgagaag  420
agcgtggtgg gcacgtcgag cctgcgacgg gccgctcagc tgcagcggaa attcccccac  480
ctcgagttcc ggtctattag gggcaacctc aacacccgcc tcaggaaact ggacgagcag  540
caggagttct cggccatcat cctcgccacc gccggactgc aaaggatggg gtggcacaac  600
cgcgtgggac agatcctgca tcccgaggag tgcatgtacg ccgtgggcca gggcgcgctg  660
ggagtggagg tcagggctaa agaccaggac atactcgacc tcgtgggcgt gctgcacgac  720
cccgagaccg tgctgcggtg catagccgag cgggcctttc ttaggcacct ggagggcggc  780
tgctccgtgc ccgtgccgt  gcacaccgcc atgaaggacg ccaactgta  cctgaccggc  840
ggggtgtggt cctggacgg  ctcagacagc atacaggaga ccatgcaagc gaccatccac  900
gtgccccgcc agcacgagga cggcccccgag gatgaccccc agctggtggg gatcacagcc  960
cgcaacatcc cagggggccc ccagctggcc gcccagaact tgggcattag cctggcaaac 1020
ctcctgctgt ccaagggagc caaaaatatc ctggacgtgg ccaggcagct gaacgacgcc 1080
cat                                                               1083
```

| | | |
|---|---|---|
| SEQ ID NO: 31 | moltype = RNA   length = 1083 | |
| FEATURE | Location/Qualifiers | |
| misc_feature | 1..1083 | |
| | note = PBGD-CO023 | |
| source | 1..1083 | |
| | mol_type = other RNA | |
| | organism = synthetic construct | |

SEQUENCE: 31

```
atgagcggca acggcaacgc cgcggccacc gcggaggaga acagccccaa gatgagggtg   60
atcagggtgg gcaccaggaa gtcccaactg gctaggatcc agaccgacag cgtggtggcc  120
accctgaaag catcctaccc cggcctccag ttcgagataa tcgccatgag caccacaggc  180
gacaagatcc tggacaccgc cctgagcaag atcggcgaga gtcgctgtt  taccaaggag  240
ctggagcacg cgctggagaa aaacgaggtg gacctggtcg tgcacagcct gaaggatctg  300
cccacagtgc tccccccagg cttcaccatc ggagccatct gcaagaggga gaatcccac   360
gacgcggtgg tgtttcatcc caagttcgtg gggaagaccc tggagaccct gcccgagaag  420
agcgtggtgg gaccagcag  cctgaggcgg gccgcccagc tgcagaggaa attcccccat  480
ctggagttca aagcatcag  gggcaacctg aacaccaggc tgaggaagct cgacgagcag  540
caggaattca cgccatcat  cctcgccacg gccgggctgc agaggatggg ctggcataac  600
agggtggggc agatcctcca cccccgaagag tgcatgtacg ccgtgggcca gggcgccctc  660
ggcgtggagg taggggccaa ggaccaggac atcctgatga ctggtgggcgt cctgcatgac  720
cccgagaccc tgctgcggtg catcgccgag cgggccttcc tcaggcacct ggagggcggc  780
tgcagcgtgc ccgtggccgt acacaccgcc atgaaagatg ccagctgta  cctgaccggc  840
ggcgtgtgga gcctggacgg gtccgacagc atccaggaga ccatgcaggc caccatccat  900
gtgccccgcc agcacgagga cggcccagag gacgatcccc agcttgtggg aatcaccgcc  960
aggaacatcc ctaggggccc cacagctggcc gccaaaaatc tcgggataag cctggctaac 1020
```

```
ctgctgctga gcaagggcgc gaagaacatc ctggacgtgg cgcgacagct gaacgacgcc    1080
cat                                                                  1083

SEQ ID NO: 32           moltype = RNA   length = 1083
FEATURE                 Location/Qualifiers
misc_feature            1..1083
                        note = PBGD-CO024
source                  1..1083
                        mol_type = other RNA
                        organism = synthetic construct
SEQUENCE: 32
atgagcggca acggcaacgc ggcggccacg gccgaggaga acagccccaa aatgagggtt    60
atcagggtgg gcacccgcaa gtcacagctg gccaggatcc agacagattc cgtggtggcc    120
accttgaagg cctcctaccc cggcctgcag ttcgaaatca tagccatgtc aacgaccggc    180
gacaagatcc tcgacaccgc cctgagcaag atcggggaga agtcactgtt cacaaaggaa    240
ctggaacacg cccttgagaa gaacgaggtt gacctggtgg tccactccct gaaggactgg    300
ccaaccgtgc tgccgccggg cttcaccatc ggggccatct gcaagcggga gaaccccac    360
gacgccgtcg tgttccaccc gaaattcgtg gggaaaaccc tcgagaccct gcccgagaag    420
agcgtggtgg gcacgtccag cctgcggagg gccgcccagc tgcagcggaa gttccccac    480
ctggagttca ggtccatccg ggggaacctg aatacgaggc tgaggaagct ggacgaacag    540
caggagttca gcgccatcat cctggcgacc gccggcctgc agcggatggg ctggcacaat    600
cgggtgggcc agatcctgca cccggaggag tgcatgtacg ccgtggggca ggcgccctc    660
ggcgtcgagg tgcgggccaa ggaccaggat atcctggacc tggtaggagt cctgcacgat    720
cccgaaaccc tgctccggtg tatagccgag cgtgccttcc tgaggcatct ggaaggcgga    780
tgctccgtcc ccgtggccgt gcacaccgca atgaaagacg ccagctgta cctgaccggc    840
ggcgtctgga gcctggacgg ctcagacagc atccaagaga ccatgcaggc caccatccac    900
gtccctgccc agcacgagga cggccccgaa gacgacccgc agctggtggg catcacagcc    960
aggaacatcc ccgggggccc gcagctggcc gcccagaatc tgggaattag cctgccaac    1020
ctcctgctga gcaagggagc caagaacatc ctggacgtgg cccggcagct gaacgacgcc    1080
cac                                                                  1083

SEQ ID NO: 33           moltype = RNA   length = 1083
FEATURE                 Location/Qualifiers
misc_feature            1..1083
                        note = PBGD-CO025
source                  1..1083
                        mol_type = other RNA
                        organism = synthetic construct
SEQUENCE: 33
atgagcggca acggcaacgc ggccgccacc gccgaagaga acagccccaa gatgagggtg    60
atcagggtgg gcacgaggaa gagccagctg gccaggatcc agaccgacag cgtggtggcg    120
accctgaagg cctcttaccc tggcctgcag tttgagatca tcgccatgag caccaccggg    180
gataagatcc tcgacaccgc cctgtccaag attggagaaa aatcgctgtt caccaaggaa    240
ctggagcacg cccttgagaa gaacgaggta gacctggtgg tgcatagcct caaggatctg    300
ccaaccgtgc tgccccccgg gtttaccatc ggcgccatat gcaagaggga gaaccccac    360
gacgcggtgg tgttccaccc caagttcgtg ggcaaaaccc tcgagacgct gcccgagaag    420
agcgtcgttg gcacctccag cctgaggcgg gccgcccagc tgcaggagga gttccccac    480
ctcgagttca aagcatcag gggcaacctg aacaccaggc tgaggaagct ggacgagcag    540
caggagttca gcgccatcat cctggccacc gccggcctgc agaggatggg atggcacaat    600
agggtgggcc agatcctgca ccccgaggag tgcatgtacg ccgtcggaca gggcgcgctg    660
ggcgtggagg tcagggcgaa ggaccaggac atcctggacc tggtcggggt cctgcacgac    720
ccggagaccc tgctgaggtg catcgccgag cgggccttcc tccggcacct ggagggcggt    780
tgcagcgtgc cagtggccgt gcacaccgcc atgaaggatg gcagctgta tctgaccggc    840
ggagtgtgga gcctcgacgg tagcgactcc atccaggaaa ccatgcaggc cactatccac    900
gtgcccgccc agcacgagga tggccccgag gacgatcccc agctggtcgg gattacggcc    960
cggaacatcc caggggcccc gcagctcgcc gcacagaacc tcggcatctc cctggccaac    1020
ctgctgctct ccaagggcgc caagaacatc ctcgacgtgg cccggcaact gaacgacgcc    1080
cac                                                                  1083

SEQ ID NO: 34           moltype = RNA   length = 87
FEATURE                 Location/Qualifiers
misc_feature            1..87
                        note = miR-142
source                  1..87
                        mol_type = other RNA
                        organism = synthetic construct
SEQUENCE: 34
gacagtgcag tcacccataa agtagaaagc actactaaca gcactggagg gtgtagtgtt    60
tcctacttta tggatgagtg tactgtg                                        87

SEQ ID NO: 35           moltype = RNA   length = 23
FEATURE                 Location/Qualifiers
misc_feature            1..23
                        note = miR 142-3p sequence
source                  1..23
                        mol_type = other RNA
                        organism = synthetic construct
SEQUENCE: 35
tgtagtgttt cctactttat gga                                            23
```

```
SEQ ID NO: 36            moltype = RNA  length = 23
FEATURE                  Location/Qualifiers
misc_feature             1..23
                         note = miR 142-3p binding site
source                   1..23
                         mol_type = other RNA
                         organism = synthetic construct
SEQUENCE: 36
tccataaagt aggaaacact aca                                             23

SEQ ID NO: 37            moltype = RNA  length = 21
FEATURE                  Location/Qualifiers
misc_feature             1..21
                         note = miR 142-5p sequence
source                   1..21
                         mol_type = other RNA
                         organism = synthetic construct
SEQUENCE: 37
cataaagtag aaagcactac t                                               21

SEQ ID NO: 38            moltype = RNA  length = 21
FEATURE                  Location/Qualifiers
misc_feature             1..21
                         note = miR-142-5p binding site
source                   1..21
                         mol_type = other RNA
                         organism = synthetic construct
SEQUENCE: 38
agtagtgctt tctactttat g                                               21

SEQ ID NO: 39            moltype = RNA  length = 47
FEATURE                  Location/Qualifiers
misc_feature             1..47
                         note = 5'UTR-001 (Upstream UTR)
source                   1..47
                         mol_type = other RNA
                         organism = synthetic construct
SEQUENCE: 39
gggaataaag agagaaaaga agagtaagaa gaaatataag agccacc                   47

SEQ ID NO: 40            moltype = RNA  length = 47
FEATURE                  Location/Qualifiers
misc_feature             1..47
                         note = 5'UTR-002 (Upstream UTR)
source                   1..47
                         mol_type = other RNA
                         organism = synthetic construct
SEQUENCE: 40
gggagatcag agagaaaaga agagtaagaa gaaatataag agccacc                   47

SEQ ID NO: 41            moltype = RNA  length = 145
FEATURE                  Location/Qualifiers
misc_feature             1..145
                         note = 5'UTR-003 (Upstream UTR)
source                   1..145
                         mol_type = other RNA
                         organism = synthetic construct
SEQUENCE: 41
ggaataaaag tctcaacaca acatatacaa aacaaacgaa tctcaagcaa tcaagcattc      60
tacttctatt gcagcaattt aaatcatttc ttttaaagca aaagcaattt tctgaaaatt    120
ttcaccattt acgaacgata gcaac                                          145

SEQ ID NO: 42            moltype = RNA  length = 42
FEATURE                  Location/Qualifiers
misc_feature             1..42
                         note = 5'UTR-004 (Upstream UTR)
source                   1..42
                         mol_type = other RNA
                         organism = synthetic construct
SEQUENCE: 42
gggagacaag cttggcattc cggtactgtt ggtaaagcca cc                        42

SEQ ID NO: 43            moltype = RNA  length = 47
FEATURE                  Location/Qualifiers
misc_feature             1..47
                         note = 5'UTR-005 (Upstream UTR)
source                   1..47
                         mol_type = other RNA
```

```
                                organism = synthetic construct
SEQUENCE: 43
gggagatcag agagaaaaga agagtaagaa gaaatataag agccacc            47

SEQ ID NO: 44           moltype = RNA   length = 145
FEATURE                 Location/Qualifiers
misc_feature            1..145
                        note = 5'UTR-006 (Upstream UTR)
source                  1..145
                        mol_type = other RNA
                        organism = synthetic construct
SEQUENCE: 44
ggaataaaag tctcaacaca acatatacaa aacaaacgaa tctcaagcaa tcaagcattc   60
tacttctatt gcagcaattt aaatcatttc ttttaaagca aaagcaattt tctgaaaatt  120
ttcaccattt acgaacgata gcaac                                       145

SEQ ID NO: 45           moltype = RNA   length = 42
FEATURE                 Location/Qualifiers
misc_feature            1..42
                        note = 5'UTR-007 (Upstream UTR)
source                  1..42
                        mol_type = other RNA
                        organism = synthetic construct
SEQUENCE: 45
gggagacaag cttggcattc cggtactgtt ggtaaagcca cc                  42

SEQ ID NO: 46           moltype = RNA   length = 47
FEATURE                 Location/Qualifiers
misc_feature            1..47
                        note = 5'UTR-008 (Upstream UTR)
source                  1..47
                        mol_type = other RNA
                        organism = synthetic construct
SEQUENCE: 46
gggaattaac agagaaaaga agagtaagaa gaaatataag agccacc            47

SEQ ID NO: 47           moltype = RNA   length = 47
FEATURE                 Location/Qualifiers
misc_feature            1..47
                        note = 5'UTR-009 (Upstream UTR)
source                  1..47
                        mol_type = other RNA
                        organism = synthetic construct
SEQUENCE: 47
gggaaattag acagaaaaga agagtaagaa gaaatataag agccacc            47

SEQ ID NO: 48           moltype = RNA   length = 47
FEATURE                 Location/Qualifiers
misc_feature            1..47
                        note = 5'UTR-010 (Upstream UTR)
source                  1..47
                        mol_type = other RNA
                        organism = synthetic construct
SEQUENCE: 48
gggaaataag agagtaaaga acagtaagaa gaaatataag agccacc            47

SEQ ID NO: 49           moltype = RNA   length = 47
FEATURE                 Location/Qualifiers
misc_feature            1..47
                        note = 5'UTR-011 (Upstream UTR)
source                  1..47
                        mol_type = other RNA
                        organism = synthetic construct
SEQUENCE: 49
gggaaaaaag agagaaaaga agactaagaa gaaatataag agccacc            47

SEQ ID NO: 50           moltype = RNA   length = 47
FEATURE                 Location/Qualifiers
misc_feature            1..47
                        note = 5'UTR-012 (Upstream UTR)
source                  1..47
                        mol_type = other RNA
                        organism = synthetic construct
SEQUENCE: 50
gggaaataag agagaaaaga agagtaagaa gatatataag agccacc            47

SEQ ID NO: 51           moltype = RNA   length = 47
FEATURE                 Location/Qualifiers
misc_feature            1..47
```

```
                          note = 5'UTR-013 (Upstream UTR)
source                    1..47
                          mol_type = other RNA
                          organism = synthetic construct
SEQUENCE: 51
gggaaataag agacaaaaca agagtaagaa gaaatataag agccacc            47

SEQ ID NO: 52             moltype = RNA   length = 47
FEATURE                   Location/Qualifiers
misc_feature              1..47
                          note = 5'UTR-014 (Upstream UTR)
source                    1..47
                          mol_type = other RNA
                          organism = synthetic construct
SEQUENCE: 52
gggaaattag agagtaaaga acagtaagta gaattaaaag agccacc            47

SEQ ID NO: 53             moltype = RNA   length = 47
FEATURE                   Location/Qualifiers
misc_feature              1..47
                          note = 5'UTR-015 (Upstream UTR)
source                    1..47
                          mol_type = other RNA
                          organism = synthetic construct
SEQUENCE: 53
gggaaataag agagaataga agagtaagaa gaaatataag agccacc            47

SEQ ID NO: 54             moltype = RNA   length = 47
FEATURE                   Location/Qualifiers
misc_feature              1..47
                          note = 5'UTR-016 (Upstream UTR)
source                    1..47
                          mol_type = other RNA
                          organism = synthetic construct
SEQUENCE: 54
gggaaataag agagaaaaga agagtaagaa gaaaattaag agccacc            47

SEQ ID NO: 55             moltype = RNA   length = 47
FEATURE                   Location/Qualifiers
misc_feature              1..47
                          note = 5'UTR-017 (Upstream UTR)
source                    1..47
                          mol_type = other RNA
                          organism = synthetic construct
SEQUENCE: 55
gggaaataag agagaaaaga agagtaagaa gaaatttaag agccacc            47

SEQ ID NO: 56             moltype = RNA   length = 92
FEATURE                   Location/Qualifiers
misc_feature              1..92
                          note = 5'UTR-018 (Upstream UTR)
source                    1..92
                          mol_type = other RNA
                          organism = synthetic construct
SEQUENCE: 56
tcaagctttt ggaccctcgt acagaagcta atacgactca ctatagggaa ataagagaga   60
aaagaagagt aagaagaaat ataagagcca cc                                92

SEQ ID NO: 57             moltype = RNA   length = 142
FEATURE                   Location/Qualifiers
misc_feature              1..142
                          note = 142-3p 3'UTR (UTR including miR142-3p binding site)
source                    1..142
                          mol_type = other RNA
                          organism = synthetic construct
SEQUENCE: 57
tgataatagt ccataaagta ggaaacacta cagctggagc ctcggtggcc atgcttcttg   60
cccttgggc ctcccccag cccctcctcc ccttcctgca cccgtacccc cgtggtcttt    120
gaataaagtc tgagtgggcg gc                                           142

SEQ ID NO: 58             moltype = RNA   length = 142
FEATURE                   Location/Qualifiers
misc_feature              1..142
                          note = 142-3p 3'UTR (UTR including miR142-3p binding site)
source                    1..142
                          mol_type = other RNA
                          organism = synthetic construct
SEQUENCE: 58
tgataatagg ctggagcctc ggtggctcca taaagtagga aacactacac atgcttcttg   60
```

```
cccttgggc tcccccccag ccctcctcc ccttcctgca cccgtacccc cgtggtcttt    120
gaataaagtc tgagtgggcg gc                                            142
```

| SEQ ID NO: 59 | moltype = RNA length = 142 |
|---|---|
| FEATURE | Location/Qualifiers |
| misc_feature | 1..142 |
| | note = 142-3p 3'UTR (UTR including miR142-3p binding site) |
| source | 1..142 |
| | mol_type = other RNA |
| | organism = synthetic construct |

SEQUENCE: 59
```
tgataatagg ctggagcctc ggtggccatg cttcttgccc cttccataaa gtaggaaaca    60
ctacatgggc tcccccag cccctcctcc ccttcctgca cccgtacccc cgtggtcttt    120
gaataaagtc tgagtgggcg gc                                            142
```

| SEQ ID NO: 60 | moltype = RNA length = 142 |
|---|---|
| FEATURE | Location/Qualifiers |
| misc_feature | 1..142 |
| | note = 142-3p 3'UTR (UTR including miR142-3p binding site) |
| source | 1..142 |
| | mol_type = other RNA |
| | organism = synthetic construct |

SEQUENCE: 60
```
tgataatagg ctggagcctc ggtggccatg cttcttgccc cttgggcctc ccccagtcc     60
ataaagtagg aaacactaca ccctcctcc ccttcctgca cccgtacccc cgtggtcttt    120
gaataaagtc tgagtgggcg gc                                            142
```

| SEQ ID NO: 61 | moltype = RNA length = 142 |
|---|---|
| FEATURE | Location/Qualifiers |
| misc_feature | 1..142 |
| | note = 142-3p 3'UTR (UTR including miR142-3p binding site) |
| source | 1..142 |
| | mol_type = other RNA |
| | organism = synthetic construct |

SEQUENCE: 61
```
tgataatagg ctggagcctc ggtggccatg cttcttgccc cttgggcctc ccccagccc     60
ctcctcccct tctccataaa gtaggaaaca ctacactgca cccgtacccc cgtggtcttt    120
gaataaagtc tgagtgggcg gc                                            142
```

| SEQ ID NO: 62 | moltype = RNA length = 142 |
|---|---|
| FEATURE | Location/Qualifiers |
| misc_feature | 1..142 |
| | note = 142-3p 3'UTR (UTR including miR142-3p binding site) |
| source | 1..142 |
| | mol_type = other RNA |
| | organism = synthetic construct |

SEQUENCE: 62
```
tgataatagg ctggagcctc ggtggccatg cttcttgccc cttgggcctc ccccagccc     60
ctcctcccct tctgcaccc gtaccccctc cataaagtag gaaacactac agtggtcttt    120
gaataaagtc tgagtgggcg gc                                            142
```

| SEQ ID NO: 63 | moltype = RNA length = 142 |
|---|---|
| FEATURE | Location/Qualifiers |
| misc_feature | 1..142 |
| | note = 142-3p 3'UTR (UTR including miR142-3p binding site) |
| source | 1..142 |
| | mol_type = other RNA |
| | organism = synthetic construct |

SEQUENCE: 63
```
tgataatagg ctggagcctc ggtggccatg cttcttgccc cttgggcctc ccccagccc     60
ctcctcccct tctgcaccc gtaccccgt ggtctttgaa taaagttcca taaagtagga    120
aacactacac tgagtgggcg gc                                            142
```

| SEQ ID NO: 64 | moltype = RNA length = 371 |
|---|---|
| FEATURE | Location/Qualifiers |
| misc_feature | 1..371 |
| | note = 3'UTR-001 (Creatine Kinase UTR) |
| source | 1..371 |
| | mol_type = other RNA |
| | organism = synthetic construct |

SEQUENCE: 64
```
gcgcctgccc acctgccacc gactgctgga acccagccag tgggagggcc tggcccacca    60
gagtcctgct ccctcactcc tcgccccgcc cctgtcccca gagtcccacc tggggggctct   120
ctccaccctt ctcagagttc cagtttcaac cagagttcca accaatgggc tccatcctct   180
ggattctggc caatgaaata tctccctggc agggtcctct tcttttccca gagctccacc   240
ccaaccagga gctctagtta atggagagct cccagcacac tcggagcttg tgcttttgtct   300
ccacgcaaag cgataaataa aagcattggt ggcctttggt ctttgaataa agcctgagta    360
ggaagtctag a                                                        371
```

| SEQ ID NO: 65 | moltype = RNA length = 568 |
|---|---|
| FEATURE | Location/Qualifiers |
| misc_feature | 1..568 |
| | note = 3'UTR-002 (Myoglobin UTR) |
| source | 1..568 |
| | mol_type = other RNA |
| | organism = synthetic construct |

SEQUENCE: 65

```
gcccctgccg ctcccacccc cacccatctg ggccccgggt tcaagagaga gcggggtctg    60
atctcgtgta gccatataga gtttgcttct gagtgtctgc tttgtttagt agaggtgggc   120
aggaggagct gaggggctgg ggctggggtg ttgaagttgg ctttgcatgc ccagcgatgc   180
gcctccctgt gggatgtcat caccctggga accgggagtg gcccttggct cactgtgttc   240
tgcatggttt ggatctgaat taattgtcct ttcttctaaa tcccaaccga acttcttcca   300
acctccaaac tggctgtaac cccaaatcca agccattaac tacacctgac agtagcaatt   360
gtctgattaa tcactggccc cttgaagaca gcagaatgtc cctttgcaat gaggaggaga   420
tctgggctgg gcgggccagc tggggaagca tttgactatc tggaacttgt gtgtgcctcc   480
tcaggtatgg cagtgactca cctggtttta ataaaacaac ctgcaacatc tcatggtctt   540
tgaataaagc ctgagtagga agtctaga                                       568
```

| SEQ ID NO: 66 | moltype = RNA length = 289 |
|---|---|
| FEATURE | Location/Qualifiers |
| misc_feature | 1..289 |
| | note = 3'UTR-003 (alpha-actin UTR) |
| source | 1..289 |
| | mol_type = other RNA |
| | organism = synthetic construct |

SEQUENCE: 66

```
acacactcca cctccagcac gcgacttctc aggacgacga atcttctcaa tggggggcg    60
gctgagctcc agccaccccg cagtcacttt ctttgtaaca acttccgttg ctgccatcgt   120
aaactgacac agtgtttata acgtgtacat acattaactt attacctcat tttgttattt   180
ttcgaaacaa agccctgtgg aagaaaatgg aaaacttgaa gaagcattaa agtcattctg   240
ttaagctgcg taaatggtct ttgaataaag cctgagtagg aagtctaga                289
```

| SEQ ID NO: 67 | moltype = RNA length = 379 |
|---|---|
| FEATURE | Location/Qualifiers |
| misc_feature | 1..379 |
| | note = 3'UTR-004 (Albumin UTR) |
| source | 1..379 |
| | mol_type = other RNA |
| | organism = synthetic construct |

SEQUENCE: 67

```
catcacattt aaaagcatct cagcctacca tgagaataag agaaagaaaa tgaagatcaa    60
aagcttattc atctgttttt cttttcgtt ggtgtaaagc caacaccctg tctaaaaaac    120
ataaatttct ttaatcattt tgcctctttt ctctgtgctt caattaataa aaaatgaaa    180
gaatctaata gagtggtaca gcactgttat ttttcaaaga tgtgttgcta tcctgaaaat   240
tctgtaggtt ctgtggaagt tccagtgttc tctcttattc cacttcggta gaggatttct   300
agtttcttgt gggctaatta aataaatcat taatactctt ctaatggtct tgaataaag   360
cctgagtagg aagtctaga                                                 379
```

| SEQ ID NO: 68 | moltype = RNA length = 118 |
|---|---|
| FEATURE | Location/Qualifiers |
| misc_feature | 1..118 |
| | note = 3'UTR-005 (alpha-globin UTR) |
| source | 1..118 |
| | mol_type = other RNA |
| | organism = synthetic construct |

SEQUENCE: 68

```
gctgccttct gcggggcttg ccttctggcc atgcccttct tctctccctt gcacctgtac    60
ctcttggtct tgaataaag cctgagtagg aaggcggccg ctcgagcatg catctaga      118
```

| SEQ ID NO: 69 | moltype = RNA length = 908 |
|---|---|
| FEATURE | Location/Qualifiers |
| misc_feature | 1..908 |
| | note = 3'UTR-006 (G-CSF UTR) |
| source | 1..908 |
| | mol_type = other RNA |
| | organism = synthetic construct |

SEQUENCE: 69

```
gccaagccct ccccatccca tgtatttatc tctatttaat atttatgtct atttaagcct    60
catatttaaa gacagggaag agcagaacgg agccccaggc ctctgtgtcc ttccctgcat   120
ttctgagttt cattctcctg cctgtagcag tgagaaaaag ctcctgtcct cccatcccct   180
ggactgggag gtagataggt aaataccaag tatttattac tatgactgct ccccagccct   240
ggctctgcaa tgggcactgg gatgagccgc tgtgagcccc tggtcctgag ggtccccacc   300
tgggacccct gagagtca ggtctcccac gtgggagaca agaaatccct gtttaatatt   360
taaacagcag tgttcccat ctgggtcctt gcacccctca ctctggcctc agccgactgc   420
acagcggccc ctgcatcccc ttggctgtga ggccccggga caagcagagg tggcagagc   480
tgggaggcat ggccctgggg tcccacgaat tgctgggga atctcgtttt tcttcttaag   540
acttttggga catggtttga ctcccgaaca tcaccgacgc gtcctcctgt tttctgggtg   600
gcctcggac acctgccctg ccccacgag ggtcaggact gtgactcttt ttagggccag   660
```

```
gcaggtgcct ggacatttgc cttgctggac ggggactggg gatgtgggag ggagcagaca   720
ggaggaatca tgtcaggcct gtgtgtgaaa ggaagctcca ctgtcaccct ccacctcttc   780
accccccact caccagtgtc ccctccactg tcacattgta actgaacttc aggataaataa  840
agtgtttgcc tccatggtct ttgaataaag cctgagtagg aaggcggccg ctcgagcatg   900
catctaga                                                            908
```

| | |
|---|---|
| SEQ ID NO: 70 | moltype = RNA length = 835 |
| FEATURE | Location/Qualifiers |
| misc_feature | 1..835 |
| | note = 3'UTR-007 (Col1a2; collagen, type I, alpha 2 UTR) |
| source | 1..835 |
| | mol_type = other RNA |
| | organism = synthetic construct |

```
SEQUENCE: 70
actcaatcta aattaaaaaa gaaagaaatt tgaaaaaact ttctctttgc catttcttct    60
tcttcttttt taactgaaag ctgaatcctt ccatttcttc tgcacatcta cttgcttaaa  120
ttgtgggcaa aagagaaaaa gaaggattga tcagagcatt gtgcaataca gtttcattaa  180
ctccttcccc cgctcccca aaaatttgaa ttttttttc aacactctta cacctgttat   240
ggaaaatgtc aacctttgta agaaaaccaa aataaaaatt gaaaaataaa aaccataaac  300
atttgcacca cttgtggctt ttgaatatct tccacagagg gaagtttaaa acccaaactt  360
ccaaggtttt aaactacctc aaaacacttt cccatgagtg tgatccacat tgttaggtgc  420
tgacctagac agagatgaac tgaggtcctt gttttgtttt gttcataata caaaggtgct  480
aattaatagt atttcagata cttgaagaat gttgatggtg ctagaagaat ttgagaagaa  540
atactcctgt attgagttgt atcgtgtggt gtatttttta aaaaatttga tttagcattc  600
atattttcca tctattccc aattaaaagt atgcagatta tttgcccaaa tcttcttcag   660
attcagcatt tgttctttgc cagtctcatt ttcatctttt tccatggttc cacagaagct  720
ttgtttcttg ggcaagcaga aaaattaaat tgtacctatt ttgtatatgt gagatgttta  780
aataaattgt gaaaaaaatg aaataaagca tgtttggttt tccaaaagaa catat        835
```

| | |
|---|---|
| SEQ ID NO: 71 | moltype = RNA length = 297 |
| FEATURE | Location/Qualifiers |
| misc_feature | 1..297 |
| | note = 3'UTR-008 (Col6a2; collagen, type VI, alpha 2 UTR) |
| source | 1..297 |
| | mol_type = other RNA |
| | organism = synthetic construct |

```
SEQUENCE: 71
cgccgccgcc cgggcccgc agtcgagggt cgtgagccca ccccgtccat ggtgctaagc    60
gggcccgggt cccacacggc cagcaccgct gctcactcgg acgacgccct gggcctgcac  120
ctctccagct cctcccacgg ggtccccgta gccccggccc ccgcccagcc ccaggtctcc  180
ccaggccctc cgcaggctgc ccggcctccc tccccctgca gccatcccaa ggctcctgac  240
ctacctggcc cctgagctct ggagcaagcc ctgacccaat aaaggctttg aacccat      297
```

| | |
|---|---|
| SEQ ID NO: 72 | moltype = RNA length = 602 |
| FEATURE | Location/Qualifiers |
| misc_feature | 1..602 |
| | note = 3'UTR-009 (RPN1; ribophorin I UTR) |
| source | 1..602 |
| | mol_type = other RNA |
| | organism = synthetic construct |

```
SEQUENCE: 72
ggggctagag ccctctccgc acagcgtgga gacggggcaa ggaggggggt tattaggatt    60
ggtggttttg ttttgctttg tttaaagccg tgggaaaatg gcacaacttt acctctgtgg  120
gagatgcaac actgagagcc aaggggtggg agttgggata attttttatat aaaagaagtt  180
tttccacttt gaattgctaa aagtggcatt tttcctatgc cagtcactc ctctcatttc   240
taaaataggg acgtggccag gcacggtggc tcatgcctgt aatcccagca ctttgggagg  300
ccgaggcagg cggctcacga ggtcaggaga tcgagactat cctggctaac acggtaaaac  360
cctgtctcta ctaaaagtac aaaaaattag ctgggcgtgg tggtgggcac ctgtagtccc  420
agctactcgg gaggctgagg caggagaaag gcatgaatcc aagaggcaga gcttgcagtg  480
agctgagatc acgccattgc actccagcct gggcaacagt gttaagactc tgtctcaaat  540
ataaataaat aaataaataa ataaataaat aaataaaaat aaagcgagat gttgcccta   600
aa                                                                 602
```

| | |
|---|---|
| SEQ ID NO: 73 | moltype = RNA length = 785 |
| FEATURE | Location/Qualifiers |
| misc_feature | 1..785 |
| | note = 3'UTR-010 (LRP1; low density lipoprotein receptor-related protein1 UTR) |
| source | 1..785 |
| | mol_type = other RNA |
| | organism = synthetic construct |

```
SEQUENCE: 73
ggccctgccc cgtcggactg ccccagaaa gcctcctgcc cctgccagt gaagtccttc     60
agtgagcccc tccccagcca gcccttccct ggccccgccg gatgtataaa tgtaaaaatg  120
aaggaattac atttttatatg tgagcgagca agccggcaag cgagcacagt attatttctc  180
catcccctcc ctgcctgctc cttgcacccc ccatgctgcc ttcagggaga caggcaggga  240
gggcttgggg ctgcacctcc taccctccca ccagaacgca cccactggg agagctggtg   300
gtgcagcctt cccctcctg tataagacac tttgccaagg ctccccctc tcgcccatc     360
cctgcttgcc cgctcccaca gcttcctgag ggctaattcc gggaagggag agttctttgc  420
```

```
tgcccctgtc tggaagacgt ggctctgggt gaggtaggcg ggaaaggatg gagtgtttta    480
gttcttgggg gaggccaccc caaacccag  ccccaactcc aggggcacct atgagatggc    540
catgctcaac cccctccca  gacaggccct cctgtctcc  agggccccca ccgaggttcc    600
cagggctgga gacttcctct ggtaaacatt cctccagcct cccctcccct ggggacgcca    660
aggaggtggg ccacacccag gaagggaaag cgggcagccc cgttttgggg acgtgaacgt    720
tttaataatt tttgctgaat tccttttacaa ctaaataaca cagatattgt tataaataaa    780
attgt                                                                 785

SEQ ID NO: 74           moltype = RNA   length = 3001
FEATURE                 Location/Qualifiers
misc_feature            1..3001
                        note = 3'UTR-011 (Nnt1; cardiotrophin-like cytokine factor
                        1 UTR)
source                  1..3001
                        mol_type = other RNA
                        organism = synthetic construct
SEQUENCE: 74
atattaagga tcaagctgtt agctaataat gccacctctg cagttttggg aacaggcaaa     60
taaagtatca gtatacatgg tgatgtacat ctgtagcaaa gctcttggag aaaatgaaga    120
ctgaagaaag caaagcaaaa actgtataga gagattttc  aaaagcagta atccctcaat    180
tttaaaaaag gattgaaaat tctaaatgtc tttctgtgca tattttttgt gttaggaatc    240
aaaagtattt tataaaagga gaagaacag  cctcatttta gatgtagtcc tgttggattt    300
tttatgcctc ctcagtaacc agaaatgttt taaaaaacta agtgtttagg atttcaagac    360
aacattatac atggctctga aatatctgac acaatgtaaa cattgcaggc acctgcattt    420
tatgtttttt ttttcaacaa atgtgactaa tttgaaactt ttatgaactt ctgagctgtc    480
cccttgcaat tcaaccgcag tttgaattaa tcatatcaaa tcagttttaa ttttttaaat    540
tgtacttcag agtctatatt tcaagggcac atttttctcac tactatttta atacattaaa    600
ggactaaata atctttcaga gatgctgaa  acaaatcatt tgctttatat gtttcattag    660
aataccaatg aaacatacaa cttgaaaatt agtaatagta ttttgaaga  tcccatttct    720
aattggagat ctctttaatt tcgatcaact tataatgtgt agtactatat taagtgcact    780
tgagtggaat tcaacatttg actaataaaa tgagttcatc atgttggcaa gtgatgtggc    840
aattatctct ggtgacaaaa gagtaaaatc aaatatttct gcctgttaca aatatcaagg    900
aagacctgct actatgaaat agatgacatt aatctgtctt cactgtttat aatacggatg    960
gatttttttt caaatcagtg tgtgttttga ggtcttatgt aattgatgac atttgagaga   1020
aatggtggct ttttttagct acctctttgt tcatttagc  accagtaaag atcatgtctt   1080
tttatagaag tgtagatttt ctttgtgact ttgctatcgt gcctaaagct ctaaatatag   1140
gtgaatgtgt gatgaatact cagatttattt gtctctctat ataattagtt tggtactaag   1200
tttctcaaaa aattattaac acatgaaaga caatctctaa accagaaaaa gaagtagtac   1260
aaatttgtt  actgtaatgc tcgcgtttag tgagtttaaa acacacagta tcttttggtt   1320
ttataatcag tttctatttt gctgtgcctg agattaagac ctgtgtatgt gtgtgtgtgt   1380
gtgtgtgcgt ttgtgtgtta aagcagaaaa gactttttta aaagtttaa gtgataaatg   1440
caatttgtta attgatctta gatcactagt aaactcaggg ctgaattata ccatgtatat   1500
tctattagaa gaaagtaaac accatcttta ttcctgccct ttttcttctc tcaaagtagt   1560
tgtagttata tctagaaaga agcaattttg attcttaaa  aaggtagttc ctgcactcag   1620
tttaaactaa aaataatcat acttggattt tattttatttt tgtcatagta aaaattttaa   1680
tttatatata tttttattta gtattatctt attctttgct atttgccaat cctttgtcat   1740
caattgtgtt aaatgaattg aaaattcatg ccctgttcat tttattttac tttattggtt   1800
aggatattta aaggatttt  gtatatataa tttcttaaat taatattcca aaaggttagt   1860
ggacttagat tataaattat ggcaaaaatc taaaaacaac aaaaatgatt tttatacatt   1920
ctatttcatt attcctctt  ttccaataag tcatacaatt ggtagatatg acttatttta   1980
ttttttgtatt ttcactata tctttatgat atttaagtat aaataattaa aaaaatttat   2040
tgtaccttat agtctgtcac caaaaaaaaa aaattatctg taggtagtga aatgctaatg   2100
ttgatttgtc tttaagggct tgttaactat cctttatttt ctcatttgtc ttaaattagg   2160
agtttgtgtt taaattactc atctaagcaa aaaatgtata taaatcccat tactgggtat   2220
atacccaaag gattataaat catgctgcta taaagacaca tgcacacgta tgtttattgc   2280
agcactattc acaatagcaa agacttgaa  ccaaccaaa  tgtccatcaa tgatagactt   2340
gattaagaaa atgtgcacat ataccatg   gaatactatg cagccataaa aaaggatgag   2400
ttcatgtcct ttgtagggac atggataaag ctggaaacca tcattctgag caaactattg   2460
caaggacaga aaaccaaaca ctgcatgttc tcactcagtg gtgggaattg aacaatgaga   2520
acacttggac acaaggtggg gaacaccaca caccagggcc tgtcatgggg tgggggagt    2580
ggggagggat agcattagga gatataccta atgtaaatga tgagtaatg  ggtgcagcac   2640
accaacatgg cacatgtata catatgtagc aaacctgcac gttgtgcaca tgtaccctag   2700
aacttaaagt ataattaaaa aaaaaaagaa aacagaagct atttataag  aagttatttg   2760
ctgaaataaa tgtgatcttt cccattaaaa aaataaaga atttgggt   aaaaaaacac   2820
aatatattgt attcttgaaa aattctaaga gagtggatgt gaagtgttct caccacaaaa   2880
gtgataacta attgaggtaa tgcacatatt aattagaaag attttgtcat tccacaatgt   2940
atatatactt aaaaatatgt tatacacaat aaatacatac attaaaaaat aagtaaatgt   3000
a                                                                  3001

SEQ ID NO: 75           moltype = RNA   length = 1037
FEATURE                 Location/Qualifiers
misc_feature            1..1037
                        note = 3'UTR-012 (Col6a1; collagen, type VI, alpha 1 UTR)
source                  1..1037
                        mol_type = other RNA
                        organism = synthetic construct
SEQUENCE: 75
cccaccctga acgccggcac caaaccctgt cctcccaccc ctcccactc  atcactaaac     60
agagtaaaat gtgatgcgaa ttttcccgac caacctgatt cgctagattt tttttaagga    120
```

```
aaagcttgga aagccaggac acaacgctgc tgcctgcttt gtgcagggtc ctccggggct    180
cagccctgag ttggcatcac ctgcgcaggg ccctctgggg ctcagccctg agctagtgtc    240
acctgcacag ggccctctga ggctcagccc tgagctggcg tcacctgtgc agggccctct    300
ggggctcagc cctgagctgg cctcacctgg gttccccacc ccgggctctc ctgccctgcc    360
ctcctgcccg ccctccctcc tgcctgcgca gctccttccc taggcacctc tgtgctgcat    420
cccaccagcc tgagcaagac gccctctcgg ggcctgtgcc gcactagcct ccctctcctc    480
tgtccccata gctggttttt cccaccaatc ctcacctaac agttacttta caattaaact    540
caaagcaagc tcttctcctc agcttggggc agccattggc ctctgtctcg ttttgggaaa    600
ccaaggtcag gaggccgttg cagacataaa tctcggcgac tcggccccgt ctcctgaggg    660
tcctgctggt gaccggcctg gaccttggcc ctacagccct ggaggccgct gctgaccagc    720
actgaccccg acctcagaga gtactcgcag gggcgctggc tgcactcaag acctctcgaga   780
ttaacggtgc taacccgtc tgctcctccc tcccgcagag actggggcct ggactggaca     840
tgagagcccc ttggtgccac agagggctgt gtcttactag aaacaacgca aacctctcct    900
tcctcagaat agtgatgtgt tcgacgtttt atcaaaggcc cccttctat gttcatgtta     960
gttttgctcc ttctgtgttt ttttctgaac catatccatg ttgctgactt ttccaaataa    1020
aggttttcac tcctctc                                                   1037

SEQ ID NO: 76            moltype = RNA  length = 577
FEATURE                  Location/Qualifiers
misc_feature             1..577
                         note = 3'UTR-013 (Calr; calreticulin UTR)
source                   1..577
                         mol_type = other RNA
                         organism = synthetic construct
SEQUENCE: 76
agaggcctgc ctccagggct ggactgaggc ctgagcgctc ctgccgcaga gctggccgcg    60
ccaaataatg tctctgtgag actcgagaac tttcatttt ttccaggctg gttcggattt     120
ggggtggatt ttggttttgt tccctcctc cactctcccc cacccctcc ccgcccttt       180
ttttttttt ttttaaactg gtattttatc tttgattctc cttcagccct caccctggt     240
tctcatcttt cttgatcaac atcttttctt gcctctgtcc ccttctctca tctcttagct    300
ccctccaac ctgggggca gtggtgtgga aagcacag gcctgagatt tcatctgctc        360
tccttcctgg agcccagagg agggcagcag aaggggtgg tgtctccaac cccccagcac    420
tgaggaagaa cggggctctt ctcatttcac ccctccctt ctccctgcc cccaggactg     480
ggccacttct gggtgggca gtgggtccca gattggctca cactgagaat gtaagaacta    540
caaacaaat ttctattaaa ttaaattttg tgtctcc                             577

SEQ ID NO: 77            moltype = RNA  length = 2212
FEATURE                  Location/Qualifiers
misc_feature             1..2212
                         note = 3'UTR-014 (Col1a1; collagen, type I, alpha 1 UTR)
source                   1..2212
                         mol_type = other RNA
                         organism = synthetic construct
SEQUENCE: 77
ctccctccat cccaacctgg ctccctccca cccaaccaac tttccccca acccggaaac      60
agacaagcaa cccaaactga acccctcaa aagccaaaaa atgggagaca atttcacatg      120
gactttggaa aatatttttt tcctttgcat tcatctctca aacttagttt ttatctttga    180
ccaaccgaac atgaccaaaa accaaaagtg cattcaacct taccaaaaaa aaaaaaaaa     240
aaagaataaa taaataactt tttaaaaaag gaagcttggt ccacttgctt gaagacccat    300
gcgggggtaa gtcccttct gcccgttggg cttatgaaac cccaatgctg ccctttctgc     360
tccttctcc acacccccct tggggcctcc cctccactcc ttcccaaatc tgtctcccca    420
gaagacacag gaaacaatgt attgtctgcc cagcaatcaa aggcaatgct caaacaccca    480
agtggcccc ccctcagcc cgctcctgcc cgcccagcac cccaggcc tgggggacct        540
ggggttctca gactgccaaa gaagccttgc catctggcgc tcccatggct cttgcaacat    600
ctcccttcg ttttgaggg ggtcatgccg gggagccac cagcccctca ctgggttcgg       660
aggagagtca ggaagggcca cgacaaagca gaaacatcgg atttgggaa cgcgtgtcaa    720
tcccttgtgc cgcagggctg ggcgggagag actgttctgt tccttgtgta actgtgttgc    780
tgaaagacta cctcgttctt gtcttgatgt gtcaccgggg caactgcctg ggggcgggga    840
tggggggcagg gtggaagcgg ctcccccattt tataccaaag gtgctacatc tatgtgatgg    900
gtgggtggg gagggaatca ctggtgctat agaaattgag atgccccccc aggccagcaa    960
atgttccttt ttgttcaaag tctattttta ttccttgata ttttttcttt tttttttttt  1020
tttttgtgga tggggacttg tgaattttc taaaggtgct atttaacatg ggaggagagc    1080
gtgtgcggct ccagcccagc ccgctgctca ctttccaccc tctctccacc tgcctctggc    1140
ttctcaggcc tctgctctcc gacctctctc tctgaaacc ctcctccaca gctgcagccca   1200
atcctcccgg ctccctccta gtctgtcctg cgtcctctgt cccgggtttt cagagacaac    1260
ttcccaaagc acaaagcagt ttttcccct aggggtggga ggaagcaaaa gactctgtac    1320
ctattttgta tgtgtataat aatttgagat gttttttaatt attttgattg ctggaataaa   1380
gcatgtggaa atgacccaaa cataatccgc agtggcctcc taatttcctt ctttggagtt    1440
ggggggaggg tagacatggg gaagggggctt tggggtgatg ggcttgctcc ccattcctgc    1500
cctttccctc cccactattc tcttctagat ccctccataa ccccactccc ctttctctca    1560
cccttcttat accgcaaacc tttctacttc ctctttcatt ttctattctt gcaatttcct    1620
tgcacctttt ccaaatcctc ttctccctg caataccata caggcaatcc acgtgcacaa    1680
cacacacaca cactcttcac atctgggtt gtccaaacct catacccact ccccttcaag    1740
cccatccact ctccaccccc tggatgccct gcacttgggt gcggtgggat gctcatggat    1800
actgggaggg tgaggggagt ggaaccccgtg aggaggacct ggggccctct ccttgaactg    1860
acatgaaggg tcatctggcc tctgctccct tctcacccac gctgacctcc tgccgaagga    1920
gcaacgcaac aggagagggg tctgctgagc ctggcgaggg tctggagggg accaggagga    1980
aggcgtgctc cctgctcgct gtcctggccc tgggggagtg agggagacag acacctggga    2040
gagctgtggg gaaggcactc gcaccgtgct cttgggaagg aaggagacct ggccctgctc    2100
```

```
accacggact gggtgcctcg acctcctgaa tccccagaac acaaccccc tgggctgggg    2160
tggtctgggg aaccatcgtg cccccgcctc ccgcctactc cttttaagc tt            2212
```

| | | |
|---|---|---|
| SEQ ID NO: 78 | moltype = RNA   length = 729 | |
| FEATURE | Location/Qualifiers | |
| misc_feature | 1..729 | |
| | note = 3'UTR-015 (Plod1; procollagen-lysine,<br>2-oxoglutarate5-dioxygenase 1 UTR) | |
| source | 1..729 | |
| | mol_type = other RNA | |
| | organism = synthetic construct | |

```
SEQUENCE: 78
ttggccaggc ctgaccctct tggacctttc ttctttgccg acaaccactg cccagcagcc    60
tctgggacct cggggtccca gggaacccag tccagcctcc tggctgttga cttcccattg   120
ctcttggagc caccaatcaa agagattcaa agagattcct gcaggccaga ggcggaacac   180
acctttatgg ctggggctct ccgtggtgtt ctggacccag cccctggaga caccattcac   240
ttttactgct ttgtagtgac tcgtgctctc caacctgtct tcctgaaaaa ccaaggcccc   300
cttccccac ctcttccatg ggggtgagact tgagcagaac aggggcttcc ccaagttgcc   360
cagaaagact gtctgggtga aagccatgg ccagagcttc tcccaggcac aggtgttgca   420
ccagggactt ctgcttcaag ttttgggta aagacacctg gatcagactc caagggctgc   480
cctgagtctg ggacttctgc ctccatggct ggtcatgaga gcaaaccgta gtcccctgga   540
gacagcgact ccagagaacc tcttgggaga cagaagagtg atctgtgcag actcgatct    600
tctacttgcc tgtggggagg ggagtgacag gtccacacac cacactgggt cacccctgtcc   660
tggatgcctc tgaagagagg gacagaccgt cagaaactgg agagtttcta ttaaaggtca   720
tttaaaacca                                                          729
```

| | | |
|---|---|---|
| SEQ ID NO: 79 | moltype = RNA   length = 847 | |
| FEATURE | Location/Qualifiers | |
| misc_feature | 1..847 | |
| | note = 3'UTR-016 (Nucb1; nucleobindin 1 UTR) | |
| source | 1..847 | |
| | mol_type = other RNA | |
| | organism = synthetic construct | |

```
SEQUENCE: 79
tcctccggga ccccagccct caggattcct gatgctccaa ggcgactgat gggcgctgga    60
tgaagtggca cagtcagctt ccctgggggc tggtgtcatg ttgggctcct ggggcggggg   120
cacggcctgg catttcacgc attgctgcca cccaggtcc acctgtctcc actttcacag    180
cctccaagtc tgtggctctt cccttctgtc ctccgagggg cttgccttct ctcgtgtcca   240
gtgaggtgct cagtgatcgg cttaacttag agaagcccgc ccctccccct tctccgtcgg   300
tcccaagagg gtctgctctg agcctgcgtt cctaggtggc tcggcctcag ctgcctgggt   360
tgtgccgcc ctagcatcct gtatgcccac agctactgga atcccgctg ctgctccggg    420
ccaagcttcc ggttgattaa tgagggcatg gggtggtccc tcaagacctt ccctacctt    480
ttgtgaacc agtgatgcct caaagacagt gtcccctcca cagctgggtg ccaggggcag    540
gggatcctca gtatagccgg tgaaccctga taccaggagc ctgggcctcc ctgaacccct   600
ggcttccagc catctcatcg ccagcctcct cctggacctc ttggccccca gcccttccc    660
cacacagccc cagaagggtc ccagagctga ccccactcca ggacctaggc ccagccctc    720
agcctcatct ggagccctg aagaccagtc ccacccacct ttctggcctc atctgacact    780
gctccgcatc ctgctgtgtg tcctgttcca tgttccggtt ccatccaaat acactttctg   840
gaacaaa                                                             847
```

| | | |
|---|---|---|
| SEQ ID NO: 80 | moltype = RNA   length = 110 | |
| FEATURE | Location/Qualifiers | |
| misc_feature | 1..110 | |
| | note = 3'UTR-017 (alpha-globin) | |
| source | 1..110 | |
| | mol_type = other RNA | |
| | organism = synthetic construct | |

```
SEQUENCE: 80
gctggagcct cggtggccat gcttcttgcc ccttgggcct ccccccagcc cctcctcccc    60
ttcctgcacc cgtaccccg tggtctttga ataaagtctg agtgggcggc                110
```

| | | |
|---|---|---|
| SEQ ID NO: 81 | moltype = RNA   length = 119 | |
| FEATURE | Location/Qualifiers | |
| misc_feature | 1..119 | |
| | note = 3'UTR-018 | |
| source | 1..119 | |
| | mol_type = other RNA | |
| | organism = synthetic construct | |

```
SEQUENCE: 81
tgataatagg ctggagcctc ggtggccatg cttcttgccc cttgggcctc ccccagccc    60
ctcctccccct tcctgcaccc gtaccccgt ggtctttgaa taaagtctga gtgggcggc   119
```

| | | |
|---|---|---|
| SEQ ID NO: 82 | moltype = DNA   length = 18 | |
| FEATURE | Location/Qualifiers | |
| misc_feature | 1..18 | |
| | note = Syn5 promoter | |
| source | 1..18 | |
| | mol_type = other DNA | |
| | organism = synthetic construct | |

```
SEQUENCE: 82
attgggcacc cgtaaggg                                                   18

SEQ ID NO: 83         moltype = DNA  length = 92
FEATURE               Location/Qualifiers
misc_feature          1..92
                      note = 5'UTR of mRNA encoding human PBGD
source                1..92
                      mol_type = other DNA
                      organism = synthetic construct
SEQUENCE: 83
tcaagctttt ggaccctcgt acagaagcta atacgactca ctatagggaa ataagagaga     60
aaagaagagt aagaagaaat ataagagcca cc                                   92

SEQ ID NO: 84         moltype = DNA  length = 119
FEATURE               Location/Qualifiers
misc_feature          1..119
                      note = 3'UTR of mRNA encoding human PBGD
source                1..119
                      mol_type = other DNA
                      organism = synthetic construct
SEQUENCE: 84
tgataatagg ctggagcctc ggtggccatg cttcttgccc cttgggcctc cccccagccc     60
ctcctcccct tcctgcaccc gtaccccgt ggtctttgaa taaagtctga gtgggcggc     119

SEQ ID NO: 85         moltype = AA   length = 19
FEATURE               Location/Qualifiers
REGION                1..19
                      note = human specific peptide
source                1..19
                      mol_type = protein
                      organism = synthetic construct
SEQUENCE: 85
ASYPGLQFEI IAMSTTGDK                                                  19

SEQ ID NO: 86         moltype = RNA  length = 1650
FEATURE               Location/Qualifiers
misc_feature          1..1650
                      note = PBGD-CO27
source                1..1650
                      mol_type = other RNA
                      organism = synthetic construct
SEQUENCE: 86
atggaagatg cgaagaacat caagaaggga cctgccccgt tttacccttt ggaggacggt     60
acagcaggag aacagctcca caaggcgatg aaacgctacg ccctggtccc cggaacgatt    120
gcgtttaccg atgcacatat tgaggtagac atcatacg cagaatactt cgaaatgtcg    180
gtgaggctgg cggaagcgat gaagagatat ggtcttaaca ctaatcaccg catcgtggtg    240
tgttcggaga actcattgca gtttttcatg ccggtccttg gagcactttt catcgggtc    300
gcagtcgcgc cagcgaacga catctacaat gagcgggaac tcttgaatag catgggaatc    360
tcccagccga cggtcgtgtt tgtctccaaa aaggggctgc agaaaatcct caacgtgcag    420
aagaagctcc ccattattca aaagatcatc attatggata gcaagacaga ttaccaaggg    480
ttccagtcga tgtataccct tgtgacatcg catttgccgc cagggtttaa cgagtatgac    540
ttcgtccccg agtcatttga cagagataaa accatcgcgc tgattatgaa ttcctcgggt    600
agcaccggtt tgccaagggg ggtggcgttg ccccaccgca ctgcttgtgt gcggttctcg    660
cacgctaggg atcctatctt tggtaatcag atcattcccg acacagcaat cctgtccgtg    720
gtaccttttc atcacggttt tggcatgttc acgactctcg gctatttgat ttgcggtttc    780
agggtcgtac ttatgtatcg gttcgaggaa gaactgtttt tgagatcctt gcaagattac    840
aagatccagt cggccctcct tgtgccaacg cttttctcat tctttgcgaa atcgacactt    900
attgataagt atgaccttc caatctgcat gagattgcct caggggggag gccgcttagc    960
aaggaagtcg gggaggcagt ggccaagcgc ttccacttc ccggaattcg gcagggatac   1020
gggctcacgg agacaacatc cgcgatcctt atcacgcccg agggtgacga taagcccgga   1080
gccgtcggaa aagtggtccc cttctttgaa gccaaggtcg tagacctcga cacgggaaaa   1140
accctcggag tgaaccagag gggcgagctc tgcgtgagag ggccgatgat catgtcaggt   1200
tacgtgaata accctgaagc gacgaatgcg ctgatccgca agggggtg gttgcattcg   1260
ggagacattg cctattggga tgaggatgag cacttcttta tcgtagatcg acttaagagc   1320
ttgatcaaat acaaaggcta tcaggtagcc cctgccgagc tcgagtcaat cctgctccag   1380
cacccccaaca ttttcgacgc cggagtggcc gggttgcccg atgacgacgc gggtgagctg   1440
ccagcggccg tggtagtcct cgaacatggg aaaacaatga ccgaaaagga gatcgtggac   1500
tacgtagcat cacaagtgac gactgcgaag aaactgaggg gaggggtagt ctttgtggac   1560
gaggtcccga aaggcttgac tgggaagctt gacgctcgca aaatccggga aatcctgatt   1620
aaggcaaaga aaggcgggaa aatcgctgtc                                   1650

SEQ ID NO: 87         moltype = RNA  length = 1083
FEATURE               Location/Qualifiers
misc_feature          1..1083
                      note = PBGD-CO26
source                1..1083
                      mol_type = other RNA
                      organism = synthetic construct
```

```
SEQUENCE: 87
atgtctggta acggcaatgc ggctgcaacg gcggaagaaa acagcccaaa gatgagagtg    60
attcgcgtgg gtacccgcaa gagccagctt gctcgcatac agacggacag tgtggtggca   120
acattgaaag cctcgtaccc tggcctgcag tttgaaatca ttgctatgtc caccacaggg   180
gacaagattc ttgatactgc actctctaag atggagagaa aaagcctgtt taccaaggag   240
cttgaacatg ccctggagaa gaatgaagtg gacctggttg ttcactcctt gaaggacctg   300
cccactgtgc ttcctcctgg cttcaccatc ggagccatct gcaagcggga aaaccctcat   360
gatgctgttg tctttcaccc aaaatttgtt gggaagaccc tagaaccct gccagagaag   420
agtgtggtgg gaaccagctc cctgcgaaga gcagcccagc tgcagagaaa gttcccgcat   480
ctggagttca ggagtattcg gggaaacctc aacacccggc ttcggaagct ggacgagcag   540
caggagttca gtgccatcat cctggcaaca gctggcctgc agcgcatggg ctggcacaac   600
cgggtggggc agatcctgca ccctgaggaa tgcatgtatg ctgtgggcca gggggccttg   660
ggcgtggaag tgcgagccaa ggaccaggac atcttggatc tggtgggtgt gctgcacgat   720
cccgagactc tgcttcgctg catcgctgaa agggccttcc tgaggcaccc tgaaggaggc   780
tgcagtgtgc cagtagccgt gcatacagct atgaaggatg gcaactgta cctgactgga   840
ggagtctgga gcctagacgg ctcagatagc atacaagaga ccatgcaggc taccatccat   900
gtccctgccc agcatgaaga tggccctgag gatgacccac agttggtagg catcactgct   960
cgtaacattc cacgagggcc ccagttggct gcccagaact gggcatcag cctgccaac   1020
ttgttgctga gcaaaggagc caaaaacatc ctggatgttg cacggcagct taacgatgcc  1080
cat                                                                1083

SEQ ID NO: 88           moltype = RNA   length = 1083
FEATURE                 Location/Qualifiers
misc_feature            1..1083
                        note = PBGD-CO28
source                  1..1083
                        mol_type = other RNA
                        organism = synthetic construct
SEQUENCE: 88
atgagtggca acggaaacgc cgccgctaca gcagaggaga actccccgaa gatgcgcgtg    60
attagggtag gcaccagaaa gtctcagctg gccagaatcc aaaccgatag cgttgtggcc   120
acattgaagg ctagctatcc cggcctgcag ttcgagatca tcgccatgag caccaccggc   180
gacaagatac tcgacaccgc tctgagtaaa atcggcgaga gagcctgtt taccaaggag   240
ctggagcacg ccctggaaaa gaacgaagtg gacctggtgg tgcatagtct gaaagacctt   300
cccaccgtcc ttccaccagg cttcactatc ggcgccatct gcaagaggga gaatcctcac   360
gatgccgtcg tgtttcatcc caagttcgtg ggcaagacct tagaaccct gccagagaaa   420
agcgtcgttg gaacctcctc cctgcgacgg gccgcccagc tgcagagaaa gttccccac   480
ttggaattca gatccatcag agggaatctg aatactcgcc tgagaaagct ggacgagcag   540
caggagttta gcgctattcat cctggccacg gctggtttgc agagaatggg ctggcacaac   600
cgggtgggac agatcctgca ccccgaggag tgcatgtatg cagtaggcca gggggccctg   660
ggggtggagg tcagagccaa agatcaggac atcctggacc tggtcggcgt gctgcacgat   720
cccgaaaacac tgctgcggtg tatcgccgag agggcttcc tccggcactt agagggcggc   780
tgctccgtcc ccgtggccgt tcacactgcc atgaaagacg gcagctgta cctgacgggc   840
ggcgtgtggt ccctgacggg ctcagactcc attcaggaga ccatgcaagc taccatccac   900
gtccctgccc aacacgaaga tggccccgag gacgaccccc agctggtggg catcaccgcc   960
aggaatatcc aagaggccc ccagttggcc gcccagaacc tgggcatcag tctggccaac  1020
ctgctgctga gtaagggcgc caaaaacatc ctggacgtgg ctcggcagct gaatgacgcc  1080
cac                                                                1083

SEQ ID NO: 89           moltype = RNA   length = 1083
FEATURE                 Location/Qualifiers
misc_feature            1..1083
                        note = PBGD-CO30
source                  1..1083
                        mol_type = other RNA
                        organism = synthetic construct
SEQUENCE: 89
atgagcggca acggcaacgc cgcagccacc gccgaggaaa acagcccaa gatgcgggtg    60
atcagagtgg gcaccggaa gagccagctg gcccggatcc agaccgacag cgtggtggcc   120
accctgaagg cctcctaccc cggcctgcag ttcgagatca ttgccatgag caccaccggc   180
gacaagatcc tggacaccgc cctgagcaag atcggcgaga gagcctgtt cacaaaagag   240
ctggaacacg ccctggaaaa gaacgaggtg gacctggtgg tgcacagcct gaaggacctg   300
cccaccgtgc tgccctgg cttcaccatc ggcgccatct gcaagagaga gaaccccac   360
gacgccgtgg tgttccaccc taagttcgtg ggcaagacc tggaaacct gccagagaag   420
tccgtggtgg gcaccagcag cctgcggaga gccgcccagc tgcagcggaa gttccccac   480
ctggaatttc ggagcatccg gggcaacctg aacacccggc tgcggaagct ggacgagcag   540
caggaatttt ccgctatcat cctggccaca gccggactgc agcggatggg ctggcacaac   600
agagtgggcc agatcctgca ccccgaggaa tgcatgtacg ccgtgggcca gggagccctg   660
ggcgtggaag tgcgggccaa ggaccaggac atcctgatc tggtgggcgt gctgcatgac   720
cccgagacac tgctgcggtg tatcgccgag cgggccttcc tgcggcacct ggaaggcggc   780
tgcagcgtgc ccgtggccgt gcacaccgcc atgaaggacg acagctgta cctgacaggc   840
ggcgtgtgga gcctggacgg cagcgacagc atccaggaga ccatgcaggc caccatccac   900
gtgcccgccc agcacgagga cggccccgag gacgaccctc agctggtcgg catcaccgcc   960
cggaacatcc cacggggccc ccagttggcc gcccagaacc tgggcatcag cctgccaac  1020
ctgctgctgt ccaagggcgc caagaacatc ctggacgtgg cccggcagct gaacgacgcc  1080
cac                                                                1083

SEQ ID NO: 90           moltype = RNA   length = 1083
FEATURE                 Location/Qualifiers
```

```
misc_feature           1..1083
                       note = PBGD-CO31
source                 1..1083
                       mol_type = other RNA
                       organism = synthetic construct
SEQUENCE: 90
atgagcggca acggcaacgc cgccgctacc gccgaagaga acagcccaaa gatgcgcgtg    60
atcagggtcg gcacgcgcaa gtcccagctc gcccggatcc aaaccgatag cgtggtggcc   120
acgctcaagg cgagctatcc gggcttacag ttcgagatca tcgccatgag caccaccggc   180
gataagatac tggacaccgc cctgtccaag atcggcgaaa agagcctgtt caccaaggaa   240
ctggagcacg cgctggagaa gaacgaggtg gacctggtgg tgcacagcct gaaggacctg   300
ccgaccgtgt gccgccgggg attcaccatc ggcgccatct gcaagaggga gaatccgcac   360
gatgccgtgg tgttccaccc aaagttcgtg ggcaagacct tggaaaccct gccagagaag   420
tctgtggtcg gcacctccag cctgcggcga gccgcccagc tgcagcgaaa gttcccgcaa   480
ctggagttca ggtccatccg cggaaatctg aacaccagge tgcgcaagct cgacgagcag   540
caggagttct ccgccatcat cctgccaccg cagcctcc aaagaatggg ctggcataac    600
cgagtcggcc agatcctcca cccggaggag tgcatgtacg cagtgggcca aggcgccctg   660
ggcgtcgagg tgcgtgccaa ggaccaggac atcctggacc tggtgggcgt gctccacgat   720
ccagagacac tgctgagatg catcgcggag cgcgccttcc tgcgccatct ggagggaggc   780
tgctccgtcc cggtggccgt acataccgcc atgaaggacg tcagctgta cctcaccggc    840
ggcgtatggt ccctcgacgg tagcgacagc atacaggaga cgatgcaggc caccatccac   900
gtgccggcgc agcacgagga tggaccagag gacgacccgc agctggtggg tatcaccgcc   960
aggaatatcc cgcggggacc tcagctggcc gcccagaacc tgggcatctc cctcgccaac  1020
ctcctgctga gcaagggcgc caagaacatc ctggacgtgg ccaggcagct caacgatgcc  1080
cat                                                                1083

SEQ ID NO: 91           moltype = RNA   length = 1083
FEATURE                 Location/Qualifiers
misc_feature           1..1083
                       note = PBGD-CO32
source                 1..1083
                       mol_type = other RNA
                       organism = synthetic construct
SEQUENCE: 91
atgagcggca acggcaacgc cgccgccacc gccgaggaaa acagcccgaa gatgcgggtg    60
atcagggtgg gcaccaggaa gtcccagctc gcccggatcc agaccgacag cgtggtcgcc   120
accttgaagg cctcctaccc gggcctccag ttcgagatca tcgccatgtc cacaaccggc   180
gacaagatcc tggataccgc cctcagcaag atcggcgaga gtccctgtt caccaaggag    240
ctggagcacg ccctggagaa gaatgaggtg gacctggtgg tgcacagcct gaaggacctg   300
cctaccgtgc tgccaccagg cttcacaatc ggcgccatct gcaagagaga gaacccgcac   360
gacgccgtgg tgttccatcc gaagttcgtg ggcaagaccc tggaaccct gccggagaag    420
tccgtagtgg gaacctcaag cctgaggcgc gccgcccagc tccagaggaa gttccctcac   480
ctggaattcc ggtccatcag gggcaacctg aacacgacc tgaggaagct cgacgagcag    540
caggagttct ccgccatcat cctggccaca gccggccttc agcgcatggg ctggcacaac   600
agggtggggcc agatcctgca cccggaagaa tgcatgtacg ccgtgggcca aggcgccctc   660
ggcgtggaag tgcgtgccaa ggaccaggac atcctggacc tggtgggcgt gctgcacgac   720
cctgagacgc tgctcaggtg catcgccgaa cgcgcgttc tgcgccatct ggagggaggc    780
tgcagcgtcc cggtgccgt ccacaccgcc atgaaggacg ccagctcta cctgactggc     840
ggcgtgtgga gcctggacgg cagcgacagc attcaggaaa ccatgcaggc caccatccac   900
gtgcctgccg agcacgagga cggcccggag gacgaccctc aactggtggg cattactgcg   960
cgaaacatcc cgcgcggacc tcagctggcc gcccagaacc tgggcatcag cctggccaac  1020
ctgctcctgt ccaagggcgc caagaacatc ctcgacgtgg ccaggcagct gaacgacgcg  1080
cac                                                                1083

SEQ ID NO: 92           moltype = RNA   length = 1083
FEATURE                 Location/Qualifiers
misc_feature           1..1083
                       note = PBGD-CO33
source                 1..1083
                       mol_type = other RNA
                       organism = synthetic construct
SEQUENCE: 92
atgagcggca acggaaacgc cgccgcgacc gcggaggaga actcgcctaa gatgagagtg    60
ataagggtag gcacccggaa gtctcaactc gccaggatcc agaccgacag cgtggtgacc   120
accctcaagg ccagctatcc aggactccag ttcgaaatca tcgccatgtc caccacaggc   180
gataagatcc tggacaccgc cctgtccaag atcggcgaga gtccctcttc caccaaggaa   240
ctggagcacg ccctggagaa gaacgaggtc gatctggtcg tgcacagcct gaaggatctg   300
cctaccgtgc tccgccgggg cttcaccatc ggcgccatct gcaagaggga gaatcctcac   360
gacgccgtgg tgttccaccc gaagttcgtg ggcaagaccc tggagacact gccagaaaag   420
tcggtggtgg gcaccagcag cctgcggcgg gcggcccagc tgcagcggaa gttcccacac   480
ctggagttca ggtccatccg tgcaatctg aacaccggc tgcgtaagct ggacgagcag     540
caggaattca gcgcgatcat cctggcaacc gccggtctgc aaaggatggg ctggcacaac   600
agggtggggcc agatcctgca ccctgaggag tgcatgtacg ccgtgggcca gggagccctg   660
ggcgtggaag tgcgggccaa ggaccaggac atcctggacc tggtgggtgt gctccacgat   720
cctgaaaccc tgctgcggtg catcgccgaa agggccttcc tgaggcacct cgagggcggc   780
tgcagcgtgc cggtcgccgt gcacaccgcc atgaaggacg ccagctgta cctgaccgga    840
ggagtgtgga gcctggacgg ctccgactcc atccaggaga ctatgcaggc caccattcat   900
gtgccggccc agcatgagga cggtccggag gacgatccac agctggtcgg catcaccgcg   960
cggaacatcc caagagggccc gcaactggcc gctcagaacc tgggcatatc cctggccaac  1020
```

```
ctgctcctga gcaagggcgc caagaacatc ctggacgtgg ccaggcagct gaatgacgcc  1080
cac                                                                1083
```

SEQ ID NO: 93          moltype = RNA   length = 1083
FEATURE                Location/Qualifiers
misc_feature           1..1083
                       note = PBGD-CO34
source                 1..1083
                       mol_type = other RNA
                       organism = synthetic construct
SEQUENCE: 93
```
atgtccggca acggcaacgc cgccgctacc gccgaggaga actcccctaa gatgcgggtc   60
atcagggtgg gcacccgaaa gtcccaactt gcccggatcc agaccgactc cgtcgtggcc  120
accctcaagg ctagctatcc aggcctccag ttcgaaatca tcgccatgag caccaccggc  180
gacaagattc tggacaccgc cctgtccaag atcggcgaga gagtctgtt  cacgaaggag   240
ctcgagcacg ccctggaaaa gaacgaggtg gacctggtgg tgcattccct gaaggacctg  300
ccaaccgtgt gccgccggg  cttcactata ggagccatct gcaagcggga gaacccgcac   360
gacgcggtgg tgttccatcc gaagttcgtg ggcaagactc tggaaaccct gccggagaag  420
tccgtggtgg gaactagctc cctgcggcgg gccgcccagc tgcagaggaa gttcccgcac  480
ctggagttca ggagcatacg cggcaacctg aacacccgcc tgcgtaagct cgacgagcag  540
caggaattca gtgccatcat cctggccacg gcgggcctgc agcggatggg ctggcacaac  600
agggtgggcc agatcctcca cccggaggaa tgtatgtacg ccgtgggcca gggcgcactg  660
ggcgtggagg tccgcgccaa ggaccaagac atcctggacc tggtcggcgt gctgcacgac  720
cctgaaaccc tgctgaggtg cattgccgag agagccttcc tgaggcatct ggagggcggc  780
tgcagcgtgc ctgtggccgt gcacacagcc atgaaggacg tcagctgta  cctgaccggc   840
ggcgtgtgga gcctggacgg cagcgactcc atccaggaga caatgcaggc caccatccac  900
gtcccggccc aacacgagga cggacctgag gacgatcctc agctggtggg catcaccgcc  960
aggaacatcc tcggggccc  gcagctggcc gcccagaacc tggcatctc  cctgccaac   1020
ctgctgctgt ccaagggcgc caagaacatc ctcgacgtgg ccagacagct gaacgacgcc  1080
cac                                                                1083
```

SEQ ID NO: 94          moltype = RNA   length = 1083
FEATURE                Location/Qualifiers
misc_feature           1..1083
                       note = PBGD-CO35
source                 1..1083
                       mol_type = other RNA
                       organism = synthetic construct
SEQUENCE: 94
```
atgagcggca acggcaacgc cgccgccacc gccgaggaga acagcccgaa gatgagggtg   60
ataagggtgg gcacacggaa gtcccagctc gcccgcatcc aaaccgactc cgtggtggcc  120
accctcaagg ccagctaccc gggcctccaa ttcgagatca tcgccatgag caccaccggc  180
gacaagatcc tggacaccgc cctgtctaag ataggcgaga agagtctgt  caccaaggag   240
ctggagcatg ccctggagaa gaacgaggtg gacctggtgg tccacagtct caaggacctg  300
ccaaccgtgc tgccgccagg cttcaccatc ggcgccatct gcaagcgtga aacccgcac   360
gatgctgtgt tgttccaccc taagttcgtg ggaaagaccc tggagacgct gccggaaaag  420
agcgtggtcg gcacctccag cctgcggagg gccgcccaac tccagaggaa gttcccgcac  480
ctggagttca ggagcatccg cggcaacctg aacaccaggc tgcgaaagct ggacgagcag  540
caggaattct cggccatcat cctcgccacc gccggcttgc aaagaatggg ctggcataat  600
cgcgtgggcc agatcctgca ccctgaggag tgcatgtacg ccgtgggcca gggtgctctg  660
ggagtggagg tgcggccaa  ggaccaggat atcctgatcc tggtcggcgt gcttcatgac   720
ccggagacgc tcctgaggtg catcgccgag cgggccttcc tgagacacct ggagggcggc  780
tgctccgtgc cagtggccgt gcacaccgcc atgaaggacg acagctgta  cctgaccggc   840
ggcgtgtgga gcctggacgg aagcgacagc atccaagaaa ccatgcaggc gaccattcac  900
gtccctgccc agcacgagga tggaccagag gacgacccgc agctggtggg catcaccgcc  960
cgcaacatcc ctagaggccc acagctggcc gcccagaatc tgggcatcag cctggccaac 1020
ctgctgctgt ctaagggagc caagaacatc ctggacgtgg ccaggcagct gaacgacgcc 1080
cat                                                                1083
```

SEQ ID NO: 95          moltype = RNA   length = 1083
FEATURE                Location/Qualifiers
misc_feature           1..1083
                       note = PBGD-CO36
source                 1..1083
                       mol_type = other RNA
                       organism = synthetic construct
SEQUENCE: 95
```
atgtccggca acggcaacgc cgcagccacc gccgaggaga attccccgaa gatgcgggtg   60
atccgggtgg gcaccagaaa gagccagctc gcccgcatcc aaaccgactc cgtggtggcc  120
accctcaagg cctcctaccc aggcttgcag ttcgaaatca tcgccatgag caccaccggc  180
gacaagatcc tggacaccgc cctgagcaag attggcgaga gtccctgtt  caccaaggag   240
ctggagcatg ctctggagaa gaacgaggtg gacctcgtgg tgcactccct gaaggacctg  300
ccgactgtgc tgccgcctgg cttcacgatc ggcgccatat gcaagcggga aaaccacac   360
gacgcggtgg tcttccaccc aaagttcgtg ggcaagactc tggaaaccct gccggaaaag  420
agcgtggtcg gcacaagctc cctgaggaga gccgcccaac tgcaaaggaa gttccctcac  480
ctcgagttca ggtccatccg gggcaacctg aacaccaggc tgagaaagct cgacgaacag  540
caggagttca gcgccatcat cctggccacg gccggcctgc agaggatggg atggcataac  600
agggtgggcc agatcctgca cccggaggag tgcatgtacg ccgtgggcca gggagccctc  660
ggcgtggagg tcagggccaa ggatcaggat atcctggacc tggtgggcgt gctgcacgat  720
```

```
cctgagacgc tgctgaggtg catcgccgag cgggccttcc tgcggcacct agagggcgga   780
tgcagcgtgc cggtcgcggt ccacaccgcg atgaaggacg ccagctgta cctgaccggc    840
ggcgtgtggt ccctgacgg cagcgattca atccaggaga cgatgcaggc caccatccac    900
gtgccagccc agcacgagga tggcccggag gacgacccgc agctggtggg cattacagcc   960
aggaacatcc ctcggggccc gcagctggcc gcccagaatc tgggcatcag cctggcgaac  1020
ctgctgctca gcaagggagc gaagaacatc ctggacgtgg cccgccagct gaacgatgcc  1080
cac                                                                1083

SEQ ID NO: 96              moltype = RNA   length = 1083
FEATURE                    Location/Qualifiers
misc_feature               1..1083
                           note = PBGD-CO37
source                     1..1083
                           mol_type = other RNA
                           organism = synthetic construct
SEQUENCE: 96
atgagcggca acggcaacgc cgccgccacc gccgaggaga acagcccaaa gatgcgggtg    60
atcagggtgg gcacccgcaa gagccaactc gccagaatcc agaccgacag cgtggtggcc   120
accttgaagg ccagctaccc gggcctccaa ttcgagatca tcgctatgtc caccaccggc   180
gacaagatcc tggacaccgc gctgtccaag atcggcgaaa agagcctgtt caccaaggaa   240
ctggagcacg ccctcgagaa gaacgaggtg gacctggtgg tgcactccct gaaggacctg   300
ccgaccgtcc tgccgccggg cttcaccatc ggcgccatct gcaagcggga aaacccgcac   360
gacgctgtgg tgttccaccc aaagttcgtg ggcaagaccc tggaaaccct gccagaaaag   420
agcgtggtgg gcaccagcag cctcaggaga gccgcccagc tgcagaggaa gttcccgcac   480
ctggagttca ggagcatcag gggcaacctg aacaccaggc tgcgtaagct ggacgagcag   540
caggagttct ccgccatcat cctcgcccaca gccggcctcc agaggatggg ttggcacaac   600
agggtgggcc agatcctgca cccggaagag tgcatgtacg cagtgggcca gggcgccctt   660
ggcgtggaag tgcgagccaa ggatcaggat atcctggacc tggtgggcgt gctgcacgac   720
ccggaaactc tgctgcggtg catcgccgaa agggccttcc tgcgccacct cgaaggcggc   780
tgtagcgtgc cggtggccgt gcacaccgcc atgaaggacg gccagctgta cctgaccggc   840
ggcgtgtgga gcctcgacgg cagcgacagc atccaggaga caatgcaggc caccatccac   900
gtgccggccc agcatgagga tggcccggag gacgaccctc agctggtggg catcaccgcc   960
cgcaacatcc caagaggacc gcaactggcc gcccagaacc tgggcatctc cctggccaac  1020
ctgctcctga gcaagggcgc gaagaacatc ctcgacgtcg cacggcagct gaacgacgcc  1080
cac                                                                1083

SEQ ID NO: 97              moltype = RNA   length = 1083
FEATURE                    Location/Qualifiers
misc_feature               1..1083
                           note = PBGD-CO38
source                     1..1083
                           mol_type = other RNA
                           organism = synthetic construct
SEQUENCE: 97
atgagcggca acggcaacgc cgccgcgacg gccgaggaaa atagcccgaa gatgcgggtg    60
atcagggtgg gcaccaggaa gtcccagctc gccaggatcc agaccgacag cgtggtggcc   120
accctcaagg cctcctaccc gggcctccaa ttcgagatca tcgccatgtc caccaccggc   180
gacaagatcc tcgacaccgc cctgagcaag atcggcgaaa agtcgctgtt caccaaggag   240
ctggagcacg ccctcgagaa gaacgaggtg gacctggtag tgcactccct aaaggacctg   300
ccgaccgtcc tgccgccggg cttcacgatc ggcgccatct gcaagcgcga gaacccgcat   360
gatgccgtcg ttttccaccc taagttcgtg ggcaagaccc tggagacgct gccggagaag   420
tcggtggtgg gaaccagcag cctgaggagg gccgcacaac tgcagaggaa gttcccgcat   480
ctggagttcc gcagcattcg aggcaacctg aacacgcgcc tgagaaagct cgatgaacag   540
caggagttca cgccatcat tctggccact gccggactgc agcggatggg ctggcacaac   600
agagtggcc agatcctgca tccggaagag tgtatgtacg ccgtgggcca gggtgccctg   660
ggcgtggagg tgcgggccaa ggaccaggat atactggatc tggtcggcgt gctccacgac   720
ccagaaacac tcctgaggtg catcgctgag agagccttcc tccggcacct cgagggcggc   780
tgttccgtgc cggtggccgt ccataccgcc atgaaggacg tcagctgta cctgaccgga   840
ggcgtttggt ccctggacgg cagcgacagc atccaggaaa ccatgcaggc caccatccac   900
gtgccggcgc agcacgagga cggcccggaa gacgacccgc agctggtcgg catcacggcc   960
agaaacatcc cgcggggccc gcagctggcc gcccagaacc tggaatctc cctggccaac  1020
ctgctgctga gcaagggcgc gaagaacatc ctggacgtgg ccggcagct gaacgatgcc  1080
cac                                                                1083

SEQ ID NO: 98              moltype = RNA   length = 1083
FEATURE                    Location/Qualifiers
misc_feature               1..1083
                           note = PBGD-CO39
source                     1..1083
                           mol_type = other RNA
                           organism = synthetic construct
SEQUENCE: 98
atgagcggta acggcaacgc cgccgccacc gccgaggaga actcccgaa gatgcgcgtg     60
attcgggtcg gcacaagaaa gtctcaactc gcccgaatcc aaacggacag cgtggtgcc   120
accctcaagg cgagctaccc gggcctccaa ttcgaaatca tcgccatgag caccaccggc   180
gacaagatcc tggacaccgc cctgtcgaag attggcgaaa agtccctgtt caccaaggag   240
ctggagcacg ccctggagaa gaacgaagtg gacctggtcg tgcacagcct gaaggacctg   300
ccgaccgttc tgccgccggg cttcaccatc ggagccatct gcaagcggga gatccgcac    360
gacgccgtgg tcttccaccc aaagttcgtg ggaaagaccc tcgagacact gccggagaag   420
```

```
tccgtggtgg gaacctcctc cctgcgagg gccgcccaac tgcagcggaa gttcccacac    480
ctggaattcc ggtccatcag aggcaacctc aacaccaggc tgaggaagct cgatgagcag    540
caggagttca gcgccatcat cctgccaca gccggactgc agcgcatggg ctggcataac    600
agagtgggcc agatcctcca cccggaggag tgcatgtacg ccgtgggaca aggcgcgctg    660
ggcgtggaag ttcggccaa ggaccaggat atcctgacc tggtgggcgt gctccacgac    720
ccagagacgc tgctgcggtg catcgccgag cgcgccttcc tgcggcacct cgagggcgga    780
tgcagcgtgc cggtcgctgt gcacacagcc atgaaggacg ccagctgta cctgaccggc    840
ggcgtgtgga gtctggacgg cagcgactcc atccaggaga ctatgcaagc caccatccat    900
gtgccggccc aacatgagga cggcccggag gacgaccgc aactggtggg catcaccgcc    960
cggaacatcc cgagggggccc gcagctggcc gcccagaacc tggcattag cctggccaac   1020
ctgctcctga gcaagggcgc taagaacatc ctggacgtcg ccagacagct gaacgacgcc   1080
cac                                                                 1083

SEQ ID NO: 99           moltype = RNA  length = 1083
FEATURE                 Location/Qualifiers
misc_feature            1..1083
                        note = PBGD-CO40A
source                  1..1083
                        mol_type = other RNA
                        organism = synthetic construct
SEQUENCE: 99
atgagcggca acggcaacgc cgccgccacc gccgaggaga acagcccaa gatgcgggtg     60
atccgggtgg gcaccgtaa gagccagctg gcccggatcc agaccgacag cgtggtggcc    120
accctgaagg ccagctaccc cggcctgcag ttcgagatca tcgccatgag caccaccggc    180
gacaagatcc tggacaccgc cctgagcaag atcggcgaga agtccctgtt caccaaggag    240
ctggagcacg ccctggagaa gaacgaggtg gacctggtgg tgcacagcct gaaggacctg    300
cccaccgtgc tgcctccagg cttcaccatc ggcgccatct gcaagcggga gaaccccac    360
gacgccgtgg tgttccaccc caagttcgtg ggcaagaccc tggaaaccct gcctgagaag    420
tccgtcgtag gaaccagcag cctgcggcgg ccgcccagc tgcagcggaa gttccccac    480
ctggagttcc ggagcatccg gggcaacctg aacaccggc tggaagct ggacgagcag    540
caggagttca gcgccatcat cctggctacc gccggtctgc aacgaatggg ctggcacaat    600
agggtgggcc agatcctgca cccggaggag tgcatgtacg cggtgggaca gggcgccctg    660
ggcgtggagg tgcgggccaa ggaccaggac atccttgatc tggtgggcgt gctgcacgac    720
cccgagacgc tgctgcggtg catcgccgag cggggccttcc tgcggcattt ggagggcgga    780
tgcagcgtgc ccgtggccgt gcacaccgcc atgaaggacg ccagctgta cctgaccggc    840
ggcgtgtgga gcctggacgg cagcgacagc atccaggaaa ccatgcaggc caccatccac    900
gtgcctgctc agcacgaaga cggcccgag gacgaccccc agctggtagg catcaccgcc    960
cggaacatcc ccggggggccc tcagctcgcc gcacagaacc ttggaatcag cctggccaac   1020
ctgctgttgt caaagggcgc caagaatatc ctcgacgtgg cccggcagct gaacgacgcc   1080
cac                                                                 1083

SEQ ID NO: 100          moltype = RNA  length = 1083
FEATURE                 Location/Qualifiers
misc_feature            1..1083
                        note = PBGD-CO41A
source                  1..1083
                        mol_type = other RNA
                        organism = synthetic construct
SEQUENCE: 100
atgagcggca acggcaacgc cgccgccacc gccgaggaga acagcccaa gatgcgggtg     60
atccgggtgg gcaccagaaa gagccagctg gcccggatcc agaccgacag cgtggtggcc    120
accctgaagg ccagctaccc cggcctgcag ttcgagatca tcgccatgag caccaccggc    180
gacaagatcc tggacaccgc cctgagcaag atcggcgaga agagtctgtt caccaaggag    240
ctggagcacg ccctggagaa gaacgaggtg gacctggtgg tgcacagcct gaaggacctg    300
cccaccgtgc tgccgcctgg cttcaccatc ggcgccatct gcaagcggga gaaccccac    360
gacgccgtgg tgttcaccc caagttcgtg ggcaagactc tggaaaccct gcctgagaag    420
tccgtggtcg gaacaagcag cctgcggcgg ccgcccagc tgcagcggaa gttccccac    480
ctggagttcc ggagcatccg gggcaacctg aacaccggc tgcggaagct ggacgagcag    540
caggagttca gcgccatcat cctggccaca gccggcctc agaggatggg ctggcacaat    600
cgggtaggcc agatcctgca cccggaggag tgcatgtacg cggtaggtca gggcgccctg    660
ggcgtggagg tgcgggccaa ggaccaggac atccttagatc tggttggcgt gctgcacgac    720
cccgaaacac tgctgcggtg catcgccgag cggggccttcc tgcggcacct cgagggcgga    780
tgcagtgtgc ccgtggccgt gcacaccgcc atgaaggacg ccagctgta cctgaccggc    840
ggcgtgtgga gcctggacgg cagcgacagc atccaggaca caatgcaggc caccatccac    900
gtgccagctc agcacgaaga cggaccagag gacgaccccc agttagtggg aatcaccgcc    960
cggaacatcc ccggggggccc tcagctcgcg gcccagaacc tggcatcag cctggccaac   1020
ctgctgctgt ctaagggcgc caagaacatc ctagacgtgg cccggcagct gaacgacgcc   1080
cac                                                                 1083

SEQ ID NO: 101          moltype = RNA  length = 1083
FEATURE                 Location/Qualifiers
misc_feature            1..1083
                        note = PBGD-CO42A
source                  1..1083
                        mol_type = other RNA
                        organism = synthetic construct
SEQUENCE: 101
atgagcggca acggcaacgc cgccgccacc gccgaggaga acagcccaa gatgcgggtg     60
atccgggtgg gcaccaggaa gtcacagctg gcccggatcc agaccgacag cgtggtggcc    120
```

```
accctgaagg ccagctaccc cggcctgcag ttcgagatca tcgccatgag caccaccggc    180
gacaagatcc tggacaccgc cctgagcaag atcggcgaga agtccctgtt caccaaggag    240
ctggagcacg ccctggagaa gaacgaggtg gacctggtgg tgcacagcct gaaggacctg    300
cccaccgtgc tgccgccagg cttcaccatc ggcgccatct gcaagcggga gaaccccac     360
gacgccgtgc tgttccaccc caagttcgtg ggcaagaccc ttgaaaccct gccagagaag    420
tctgtggtcg gcaccagcag cctgcggcgg ccgcccagc tgcagcggaa gttccccac      480
ctggagttcc ggagcatccg gggcaacctg aacaccggc tgcggaagct ggacgagcag     540
caggagttca cgccatcat cctggccacc gctggcctac agcggatggg ctggcacaat    600
agagttggtc agatcctgca ccccgaggag tgcatgtacg ccgtcggcca gggcgccctg    660
ggcgtgagg tgcgggccaa ggaccaggac atactagacc tcgtgggcgt gctgcacgac     720
cccgaaacct tgctgcggtg catcgccgag cgggccttcc tgcggcacct ggaaggcggt    780
tgcagcgtgc ccgtggccgt gcacaccgcc atgaaggacg ccagctgta cctgaccggc      840
ggcgtgtgga gcctggacgg cagcgacagc atccaggaga caatgcaggc caccatccac    900
gtgccggccc aacacgagga cggacctgag gacgaccccc agcttgtggg aatcaccgcc    960
cggaacatcc cccggggccc tcaactggca gcccagaact taggcataag cctggccaac   1020
ctgctgctgt ccaagggcgc caagaacatc ctcgatgtgg cccggcagct gaacgacgcc   1080
cac                                                                 1083

SEQ ID NO: 102           moltype = RNA   length = 1083
FEATURE                  Location/Qualifiers
misc_feature             1..1083
                         note = PBGD-C043A
source                   1..1083
                         mol_type = other RNA
                         organism = synthetic construct
SEQUENCE: 102
atgagcggca acggcaacgc cgccgccacc gccgaggaga acagcccaa gatgcgggtg       60
atccgggtgg gcacccgcaa gagtcagctg gcccggatcc agaccgacag cgtggtggcc    120
accctgaagg ccagctaccc cggcctgcag ttcgagatca tcgccatgag caccaccggc    180
gacaagatcc tggacaccgc cctgagcaag atcggcgaga agtctctgtt caccaaggag    240
ctggagcacg ccctggagaa gaacgaggtg gacctggtgg tgcacagcct gaaggacctg    300
cccaccgtgc tgccacctgg cttcaccatc ggcgccatct gcaagcggga gaaccccac     360
gacgccgtgc tgttccaccc caagttcgtg ggcaagacac tggaaaccct gccggagaag    420
tccgtggtag gcaccagcag cctgcggcgg ccgcccagc tgcagcggaa gttcccccac     480
ctggagttcc ggagcatccg gggcaacctg aacaccggc tgcggaagct ggacgagcag     540
caggagttca cgccatcat cctggccaca gccggcttac agcgtatggg ctggcacaac     600
agggtgggac agatcctgca ccccgaggag tgcatgtacg ctgtgggcca gggcgccctg    660
ggcgtggagg tgcgggccaa ggaccaggac atcttagatc tcgtcggcgt gctgcacgac    720
cccgaaacct tgctgcggtg catcgccgag cgggccttcc tgcggcatct tgagggcgga    780
tgctccgtgc ccgtggccgt gcacaccgcc atgaaggacg ccagctgta cctgaccggc      840
ggcgtgtgga gcctggacgg cagcgacagc atccaggaga ctatgcaggc caccatccac    900
gtgccagccc agcacgaaga cggcccgag gacgaccccc agctggtggg aatcaccgcc     960
cggaacatcc cccggggccc tcaactggca gcacagaacc taggcatcag cctggccaac   1020
ctgctgctca gcaagggcgc caagaatatc ttggacgtgg cccggcagct gaacgacgcc   1080
cac                                                                 1083

SEQ ID NO: 103           moltype = RNA   length = 1083
FEATURE                  Location/Qualifiers
misc_feature             1..1083
                         note = PBGD-C044A
source                   1..1083
                         mol_type = other RNA
                         organism = synthetic construct
SEQUENCE: 103
atgagcggca acggcaacgc cgccgccacc gccgaggaga acagcccaa gatgcgggtg       60
atccgggtgg gcaccagaaa gagccagctg gcccggatcc agaccgacag cgtggtggcc    120
accctgaagg ccagctaccc cggcctgcag ttcgagatca tcgccatgag caccaccggc    180
gacaagatcc tggacaccgc cctgagcaag atcggcgaga agtctctgtt caccaaggag    240
ctggagcacg ccctggagaa gaacgaggtg gacctggtgg tgcacagcct gaaggacctg    300
cccaccgtgc tgcctcctgg cttcaccatc ggcgccatct gcaagcggga gaaccccac     360
gacgccgtgc tgttccaccc caagttcgtg ggcaagaccc ttgagactct gccagagaag    420
tctgtagtgg gaaccagcag cctgcggcgg ccgcccagc tgcagcggaa gttcccccac     480
ctggagttcc ggagcatccg gggcaacctg aacaccggc tgcggaagct ggacgagcag     540
caggagttca cgccatcat cctggccacg gccggattac agagaatggg ctggcacaac     600
cgagtgggac agatcctgca ccccgaggag tgcatgtatg ccgttggcca aggcgccctg    660
ggcgtggagg tgcgggccaa ggaccaggac atcctcgatc tcgtgggcgt gctgcacgac    720
cccgagactt tgctgcggtg catcgccgag cgggccttcc tgcggcacct agaggcggc      780
tgctcggtgc ccgtggccgt gcacaccgcc atgaaggacg ccagctgta cctgaccggc      840
ggcgtgtgga gcctggacgg cagcgacagc atccaggaga caatgcaggc caccatccac    900
gtgccagccc agcacgagga tggcctgaa gacgaccccc agctggtggg catcaccgcc     960
cggaacatcc cccggggccc acaattggcc gctcagaact taggcattag cctggccaac   1020
ctgctgctgt ctaagggcgc caagaacata ctggacgtgg cccggcagct gaacgacgcc   1080
cac                                                                 1083

SEQ ID NO: 104           moltype = RNA   length = 1083
FEATURE                  Location/Qualifiers
misc_feature             1..1083
                         note = PBGD-C045A
source                   1..1083
```

```
                    mol_type = other RNA
                    organism = synthetic construct
SEQUENCE: 104
atgagcggca acggcaacgc cgccgccacc gccgaggaga acagccccaa gatgcgggtg      60
atccgggtgg gcacccggaa gagccagctg gcccggatcc agaccgacag cgtggtggcc    120
accctgaagg ccagctaccc cggcctgcag ttcgagatca tcgccatgag caccaccggc    180
gacaagatcc tggacaccgc cctgagcaag atcggcgaga gagcctgtt caccaaggag     240
ctggagcacg ccctggagaa gaacgaggtg gacctggtgg tgcacagcct gaaggacctg    300
cccaccgtgc tgccccccgg cttcaccatc ggcgccatct gcaagcggga aaccccgac    360
gacgccgtgg tgttccaccc caagttcgtg ggcaagaccc tggagaccct gcccgagaag   420
agcgtggtgg gcaccagcag cctgcggcgg gccgcccagc tgcagcggaa gttccccac    480
ctggagttcc ggagcatccg gggcaacctg aacacccggc tgcggaagct ggacgagcag    540
caggagttca gcgccatcat cctggccacc gccggcctgc agcggatggg ctggcacaac    600
cgggtgggcc agatcctgca ccccgaggag tgcatgtacg ccgtgggcca gggcgccctg    660
ggcgtggagg tgcgggccaa ggaccaggac atcctggacc tggtgggcgt gctgcacgac    720
cccgagaccc tgctgcggtg catcgccgag cgggccttcc tgcggcacct ggagggcggc    780
tgcagcgtgc ccgtggccgt gcacaccgcc atgaaggacg ccagctgta cctgaccggc     840
ggcgtgtgga gcctggacgg cagcgacagc atccaggaga ccatgcaggc caccatccac   900
gtgcccgccc agcacgagga cggccccgag gacgacccc agctggtggg catcaccgcc     960
cggaacatcc ccgggggccc ccagctggcc gcccagaacc tgggcatcag cctgccaac   1020
ctgctgctga gcaagggcgc caagaacatc ctggacgtgg cccggcagct gaacgacgcc   1080
cac                                                                  1083

SEQ ID NO: 105          moltype = RNA   length = 1083
FEATURE                 Location/Qualifiers
misc_feature            1..1083
                        note = PBGD-C046A
source                  1..1083
                        mol_type = other RNA
                        organism = synthetic construct
SEQUENCE: 105
atgagcggca acggcaacgc cgccgccacc gccgaggaga acagccccaa gatgcgggtg      60
atccgggtgg gcacccggaa gagccagctg gcgaggatcc agacgacag cgtggtggcg    120
acgctgaagg cgagctaccc ggggctgcag ttcgagatca tcgcgatga cacgacgggg    180
gacaagatcc tggacaccgc gctgagcaag atcggcgaga gagcctgtt cacgaaggac    240
ctggagcacg cgctggagaa gaacgaggtg gacctggtgg tgcacagcct gaaggacctg    300
ccgacggtgt tgccgccggg gttcacgatc ggggcgatct gcaagaggga gaacccgcac    360
gacgcggtgg tgttccaccc gaagttcgtg gggaagacgc tggagacgct gccggagaag   420
agcgtggtgg ggacgagcag cctgaggagg gcggcgcagc tgcagaggaa gttcccgcac    480
ctggagttca ggagcatcag ggggaacctg aacacgaggc tgaggaagct ggacgagcag    540
caggagttca gcgcgatcat cctggacggcg cgggggctgc agaggatggg gtggacaac    600
agggtggggc agatcctgca ccccggaggag tgcatgtacg cggtggggca ggggcgctg   660
gggggtggagg tgagggcgaa ggaccaggac atcctggacc tggtgggggt gctgcacgac    720
ccggagacgc tgctgaggtg catcgccgag agggcgttcc tgaggcacct ggaggggggc    780
tgcagcgtgc cggtggcgat gcacacgcg atgaaggacg gcagctgta cctgacgggg    840
ggggtgtgga gcctggacgg gagcgacagc atccaggaga cgatgcaggc gacgatccac   900
gtgccgcgc agcacgagga cggccggag gacgacccg agctggtgg gatcacggcg       960
aggaacatcc cgaggggccc gcagctggcc gcgcagaacc tggggatcag cctggcgaac    1020
ctgctgctga gcaagggggc gaagaacatc ctggacgtgg cgaggcagct gaacgacgcg   1080
cac                                                                  1083

SEQ ID NO: 106          moltype = RNA   length = 1083
FEATURE                 Location/Qualifiers
misc_feature            1..1083
                        note = PBGD-C047A
source                  1..1083
                        mol_type = other RNA
                        organism = synthetic construct
SEQUENCE: 106
atgagcggca acggcaacgc cgccgccacc gccgaggaga acagccccaa gatgcgggtg      60
atccgggtgg gcacccggaa gagccagctg gcccgcatcc agaccgactc cgtcgtcgcc    120
accctcaagg cctcctaccc cggcctccag ttcgagatca tcgccatgtc caccaccggc    180
gacaagatcc tcgacaccgc cctctccaag atcggcgaga gtccctctt caccaaggag     240
ctcgagcacg ccctcgagaa gaacgaggtc gacctcgtgg tccactccct caaggacctc    300
cccaccgtcc tcccccccgg cttcaccatc ggcgccatct gcaagcgcga acccccac     360
gacgccgtcg tcttccaccc caagttcgtc ggcaagaccc tcgagaccct ccccgagaag   420
tccgtcgtcg gcacctcctc cctccgccgc cgcgcccagc tccagcgcaa gttccccac    480
ctcgagttcc gctccatccg cggcaacctc aacacccgcc tgcggaagct cgacgagcag    540
caggagttct ccgccatcat cctcgccacc gccggcctgc agcgcatggg ctggcacaac    600
cgcgtcggcc agatcctcca ccccgaggag tgcatgtacg ccgtcggcca gggcgccctc    660
ggcgtcgagg tccgcgccaa ggaccaggac atcctcgacc tcgtcggcgt cctccacgac    720
cccgagaccc tcctccgctg catcgccgag cgcgccttcc tccgccacct cgagggcggc    780
tgctccgtcc ccgtcgccgt ccacaccgcc atgaaggacg ccagctcta cctcaccggc     840
ggcgtctggt ccctcgacgg ctccgactcc atccaggaga ccatgcaggc caccatccac   900
gtcccgccc agcacgagga cggccccgag gacgacccc agctcgtcgg catcaccgcc     960
cgcaacatcc ccggggccc ccagctcgcc gcccagaacc tcggcatctc cctcgccaac   1020
ctcctcctct ccaagggcgc caagaacatc ctcgacgtcg ccggccagct caacgacgcc   1080
cac                                                                  1083
```

```
SEQ ID NO: 107          moltype = RNA   length = 1083
FEATURE                 Location/Qualifiers
misc_feature            1..1083
                        note = PBGD-CO40B
source                  1..1083
                        mol_type = other RNA
                        organism = synthetic construct
SEQUENCE: 107
atgagcggca acggcaacgc cgccgccacc gccgaggaga acagcccaa gatgcgggtg    60
atccgggtgg gcaccgtaa gagccagctg gcccggatcc agaccgacag cgtggtggcc   120
accctgaagg ccagctaccc cggcctgcag ttcgagatca tcgccatgag caccaccggc   180
gacaagatcc tggacaccgc cctgagcaag atcggcgaga agtccctgtt caccaaggag   240
ctggagcacg ccctggagaa gaacgaggtg gacctggtgt gcacagcct gaaggacctg   300
cccaccgtgc tgcctccagg cttcaccatc ggcgccatct gcaagcggga gaaccctgcc   360
gacgccgtgg tgttccaccc caagttcgtg ggcaagaccc tggaaaccct gcctgagaag   420
tccgtcgtag gaaccagcag cctgcggcgg ccgcccagc tgcagcggaa gttcccacac    480
ctggagttcg gagcatccg gggcaacctg aacacccggc tgcggaagct ggacgagcag   540
caggagttca gcgccatcat cctggctacc gccggtctgc aacgaatggg ctggcacaat   600
agggtgggcc agatcctgca ccccgaggag tgcatgtacg cggtgggaca gggcgccctg   660
ggcgtggagg tgcgggccaa ggaccaggac atccttgatc tggtgggcgt gctgcacgac   720
cccgagacg tgctgcggtg catcgccgag cgggccttcc tgcggcattt ggagggcgga    780
tgcagcgtgc ccgtggccgt gcacaccgcc atgaaggacg gccagctgta cctgaccggc   840
ggcgtgtgga gcctggacgg cagcgacagc atccaggaaa ccatgcaggc caccatccac   900
gtgcctgctc agcacgaaga cggcccagag gacgaccctc agctggtagg catcaccgcc   960
cggaacatcc tcggggccc tcagctcgcc gcacagaacc ttggaatcag cctggccaac  1020
ctgctgtgt caaagggcgc caagaatatc ctcgacgtgg cccggcagct gaacgacgcc  1080
cac                                                               1083

SEQ ID NO: 108          moltype = RNA   length = 1083
FEATURE                 Location/Qualifiers
misc_feature            1..1083
                        note = PBGD-CO41B
source                  1..1083
                        mol_type = other RNA
                        organism = synthetic construct
SEQUENCE: 108
atgagcggca acggcaacgc cgccgccacc gccgaggaga acagcccaa gatgcgggtg    60
atccgggtgg gcaccagaaa gagccagctg gcccggatcc agaccgacag cgtggtggcc   120
accctgaagg ccagctaccc cggcctgcag ttcgagatca tcgccatgag caccaccggc   180
gacaagatcc tggacaccgc cctgagcaag atcggcgaga agtctctgtt caccaaggag   240
ctggagcacg ccctggagaa gaacgaggtg gacctggtgg tgcacagcct gaaggacctg   300
cccaccgtgc tgccgcctgg cttcaccatc ggcgccatct gcaagcggga gaacccgcac   360
gacgccgtgg tgttccaccc caagttcgtg ggcaagactc tggaaaccct gcctgagaag   420
tccgtggtcg gaacaagcag cctgcggcgg ccgcccagc tgcagcggaa gttcccacac    480
ctggagttcc ggagcatccg gggcaacctg aacacccggc tgcggaagct ggacgagcag   540
caggagttca gcgccatcat cctggccaca gccggcttc agaggatggg ctggcacaat    600
cgggtgggcc agatcctgca ccccgaggag tgcatgtacg cggtaggtca gggcgccctg   660
ggcgtggagg tgcgggccaa ggaccaggac atcttagatc tggttggcgt gctgcacgac   720
cccgaaacac tgctgcggtg catcgccgag cgggccttcc tgcggcacct cgagggcggg   780
tgcagtgtgc ccgtggccgt gcacaccgcc atgaaggacg ccagctgta cctgaccggc    840
ggcgtgtgga gcctggacgg cagcgacagc atccaggaga caatgcaggc caccatccac   900
gtgccagctc agcacgaaga cggaccagag gacgacccac agttagtggg aatcaccgcc   960
cggaacatcc gcggggccc tcagctcgcg gcccagaacc tgggcatcag cctggccaac  1020
ctgctgctgt ctaagggcgc caagaacatc ctagacgtgg cccggcagct gaacgacgcc  1080
cac                                                               1083

SEQ ID NO: 109          moltype = RNA   length = 1083
FEATURE                 Location/Qualifiers
misc_feature            1..1083
                        note = PBGD-CO42B
source                  1..1083
                        mol_type = other RNA
                        organism = synthetic construct
SEQUENCE: 109
atgagcggca acggcaacgc cgccgccacc gccgaggaga acagcccaa gatgcgggtg    60
atccgggtgg gcaccaggaa gtcacagctg gcccggatcc agaccgacag cgtggtggcc   120
accctgaagg ccagctaccc cggcctgcag ttcgagatca tcgccatgag caccaccggc   180
gacaagatcc tggacaccgc cctgagcaag atcggcgaga agtccctgtt caccaaggag   240
ctggagcacg ccctggagaa gaacgaggtg gacctggtgt gcacagcct gaaggacctg   300
cccaccgtgc tgccgccagg cttcaccatc ggcgccatct gcaagcggga gaacccgcac   360
gacgccgtgg tgttccaccc caagttcgtg ggcaagaccc ttgaaaccct gcagagaag    420
tctgtggtcg gcaccagcag cctgcggcgg ccgcccagc tgcagcggaa gttcccgcac    480
ctggagttcc ggagcatccg gggcaacctg aacacccggc tgcggaagct ggacgagcag   540
caggagttca gcgccatcat cctggccacc gctggcctac agcggatggg ctggcacaat   600
agagttggtc agatcctgca ccccgaggag tgcatgtacg ccgtcggcca gggcgccctg   660
ggcgtggagg tgcgggccaa ggaccaggac atactagacc tcgtgggcgt gctgcacgac   720
cccgaaacct tgctgcggtg catcgccgag cgggccttcc tgcggcacct ggaaggcggt   780
tgcagcgtgc ccgtggccgt gcacaccgcc atgaaggacg ccagctgta cctgaccggc    840
ggcgtgtgga gcctggacgg cagcgacagc atccaggaga caatgcaggc caccatccac   900
```

```
gtgccggccc aacacgagga cggacctgag gacgacccac agcttgtggg aatcaccgcc    960
cggaacatcc cacggggccc tcaactggca gcccagaact taggcataag cctggccaac   1020
ctgctgctgt ccaagggcgc caagaacatc ctcgatgtgg cccggcagct gaacgacgcc   1080
cac                                                                 1083

SEQ ID NO: 110         moltype = RNA  length = 1083
FEATURE                Location/Qualifiers
misc_feature           1..1083
                       note = PBGD-C043B
source                 1..1083
                       mol_type = other RNA
                       organism = synthetic construct
SEQUENCE: 110
atgagcggca acggcaacgc cgccgccacc gccgaggaga acagcccaa gatgcgggtg      60
atccgggtgg gcacccgcaa gagtcagctg gcccggatcc agaccgacag cgtggtggcc   120
accctgaagg ccagctaccc cggcctgcag ttcgagatca tcgccatgag caccaccggc   180
gacaagatcc tggacaccgc cctgagcaag atcggcgaga gagtctctgtt caccaaggag   240
ctggagcacg ccctggagaa gaacgaggtg gacctggtg tgcacagcct gaaggacctg   300
cccaccgtgc tgccacctgg cttcaccatc ggcgccatct gcaagcggga gaacccacac   360
gacgccgtgg tgttccaccc caagttcgtg ggcaagacac tggaaaccct gccggagaag   420
tccgtggtag gcaccagcag cctgcggcgg ccgcccagc tgcagcggaa gttcccgcac   480
ctggagttcc ggagcatccg gggcaacctg aacacccggc tgcggaagct ggacgagcag   540
caggagttca gcgccatcat cctggcaaca gccggcttac agcgtatggg ctggcacaac   600
agggtgggac agatcctgca ccccgaggag tgcatgtacg ctgtgggcca gggcgccctg   660
ggcgtggagg tgcgggccaa ggaccaggac atcttagatc tcgtcggcgt gctgcacgac   720
cccgaaacct tgctgcggtg catcgccgag cgggccttcc tgcggcatct tgagggcgga   780
tgctccgtgc ccgtgccgt gcacaccgcc atgaaggacg ccagctgta cctgaccggc   840
ggcgtgtgga gcctggacgg cagcgacagc atccaggaga ctatgcaggc caccatccac   900
gtgccagccc agcacgaaga cggcccgagg gacgacccac agctggtggg aatcaccgcc   960
cggaacatcc cgcggggccc tcaactggca gcacagaacc taggcatcag cctggccaac  1020
ctgctgctca gcaagggcgc caagaatatc ttggacgtgg cccggcagct gaacgacgcc  1080
cac                                                                 1083

SEQ ID NO: 111         moltype = RNA  length = 1083
FEATURE                Location/Qualifiers
misc_feature           1..1083
                       note = PBGD-C044B
source                 1..1083
                       mol_type = other RNA
                       organism = synthetic construct
SEQUENCE: 111
atgagcggca acggcaacgc cgccgccacc gccgaggaga acagcccaa gatgcgggtg      60
atccgggtgg gcaccagaaa gagccagctg gcccggatcc agaccgacag cgtggtggcc   120
accctgaagg ccagctaccc cggcctgcag ttcgagatca tcgccatgag caccaccggc   180
gacaagatcc tggacaccgc cctgagcaag atcggcgaga gtctctgtt caccaaggag   240
ctggagcacg ccctggagaa gaacgaggtg gacctggtg tgcacagcct gaaggacctg   300
cccaccgtgc tgcctcctgg cttcaccatc ggcgccatct gcaagcggga gaacccacac   360
gacgccgtgg tgttccaccc caagttcgtg ggcaagaccc ttgagactct gccagagaag   420
tctgtagtgg gaaccagcag cctgcggcgg ccgcccagc tgcagcggaa gttccctcac   480
ctggagttcc ggagcatccg gggcaacctg aacacccggc tgcggaagct ggacgagcag   540
caggagttca gcgccatcat cctggccacg gccggattac agagaatggg ctggcacaac   600
cgagtgggac agatcctgca ccccgaggag tgcatgtatg ccgttggcca aggcgccctg   660
ggcgtggagg tgcgggccaa ggaccaggac atcctcgatc tcgtgggcgt gctgcacgac   720
cccgagactt tgctgcggtg catcgccgag cgggccttcc tgcggcacct agagggcggc   780
tgctcggtgc ccgtggccgt gcacaccgcc atgaaggacg ccagctgta cctgaccggc   840
ggcgtgtgga gcctggacgg cagcgacagc atccaggaga caatgcaggc caccatccac   900
gtgccagccc agcacgagga tggccctgaa gacgacccac agctggtggg catcaccgcc   960
cggaacatcc cgcggggccc acaattggcc gctcagaact taggcattag cctggccaac  1020
ctgctgctgt ctaagggcgc caagaacata ctggacgtgg cccggcagct gaacgacgcc  1080
cac                                                                 1083

SEQ ID NO: 112         moltype = RNA  length = 1083
FEATURE                Location/Qualifiers
misc_feature           1..1083
                       note = PBGD-C045B
source                 1..1083
                       mol_type = other RNA
                       organism = synthetic construct
SEQUENCE: 112
atgagcggca acggcaacgc cgccgccacc gccgaggaga acagcccaa gatgcgggtg      60
atccgggtgg gcacccggaa gagccagctg gcccggatcc agaccgacag cgtggtggcc   120
accctgaagg ccagctaccc cggcctgcag ttcgagatca tcgccatgag caccaccggc   180
gacaagatcc tggacaccgc cctgagcaag atcggcgaga gagcctctgtt caccaaggag   240
ctggagcacg ccctggagaa gaacgaggtg gacctggtg tgcacagcct gaaggacctg   300
cccaccgtgc tgccgccggg cttcaccatc ggcgccatct gcaagcggga gaacccgcac   360
gacgccgtgg tgttccaccc caagttcgtg ggcaagaccc tggagaccct gccgagaag    420
agcgtggtgg gcaccagcag cctgcggcgg ccgcccagc tgcagcggaa gttccctcac   480
ctggagttcc ggagcatccg gggcaacctg aacacccggc tgcggaagct ggacgagcag   540
caggagttca gcgccatcat cctggccacc gccggcctgc agcggatggg ctggcacaac   600
```

```
cgggtgggcc agatcctgca ccccgaggag tgcatgtacg ccgtgggcca gggcgccctg   660
ggcgtggagg tgcgggccaa ggaccaggac atcctggacc tggtgggcgt gctgcacgac   720
cccgagaccc tgctgcggtg catcgccgag cgggccttcc tgcggcacct ggagggcggc   780
tgcagcgtgc ccgtggccgt gcacaccgcc atgaaggacg ccagctgta cctgaccggc   840
ggcgtgtgga gcctggacgg cagcgacagc atccaggaga ccatgcaggc caccatccac   900
gtgcccgccc agcacgagga cggccccgag gacgaccctc agctggtggg catcaccgcc   960
cggaacatcc cacggggccc tcagctggcc gcccagaacc tgggcatcag cctggccaac  1020
ctgctgctga gcaagggcgc caagaacatc ctggacgtgg cccggcagct gaacgacgcc  1080
cac                                                                1083

SEQ ID NO: 113         moltype = RNA   length = 1083
FEATURE                Location/Qualifiers
misc_feature           1..1083
                       note = PBGD-C046B
source                 1..1083
                       mol_type = other RNA
                       organism = synthetic construct
SEQUENCE: 113
atgagcggca acggcaacgc cgccgccacc gccgaggaga acagcccaa gatgcgggtg    60
atccgggtgg gcacccggaa gagccagctg gcgaggatcc agacggacag cgtggtggcg   120
acgctgaagg cgagctaccc ggggctgcag ttcgagatca tcgcgatgag cacgacgggc   180
gacaagatcc tggacacggc gctcaagaag atcgggaga gcctgtt cacgaaggag       240
ctggagcacg cgctggagaa gaacgaggtg gacctggtgg tgcacagcct gaaggacctg   300
ccgacggtgc tgccgccggg gttcacgatc ggggcgatct gcaagaggga gaacccgcac   360
gacgcggtgg tgttccaccc gaagttcgtg gggaagacgc tggagacgct gccggagaag   420
agcgtggtgg ggacgagcag cctgaggagg cgggccagc tgcagaggaa gttcccgcag    480
ctggagttca ggagcatcag gggtaacctg aacacgagc tgaggaagct ggacgagcag    540
caggagttca cgcgcgatcat cctggcgacg cggggctgc agaggatggg gtggcacaac   600
agggtggggc agatcctgca cccggaggag tgcatgtacg cggtggggca gggcgcgctg   660
ggcgtggagg tgagggcgaa ggaccaggac atcctggacc tggtgggcgt gctgcacgac   720
ccggagacgc tgctgaggtg catcgcggag agggcgttcc tgaggcacct ggagggcggg   780
tgcagcgtgc cggtggcggt gcacacggcg atgaaggacg gcagctgta cctgacggga   840
ggggtgtgga gcctggacgg gagcgacagc atccaggaga cgatgcaggc gacgatccac   900
gtgccggcgc agcacgagga cgggccggag gacgaccgc agctggtggg gatcacggcg   960
aggaacatcc cgaggggtcc gcagctggcg gcgcagaacc tggggatcag cctggcgaac  1020
ctgctgctga gcaagggagc gaagaacatc ctggacgtgg cgaggcagct gaacgacgcg  1080
cac                                                                1083

SEQ ID NO: 114         moltype = RNA   length = 1083
FEATURE                Location/Qualifiers
misc_feature           1..1083
                       note = PBGD-C047B
source                 1..1083
                       mol_type = other RNA
                       organism = synthetic construct
SEQUENCE: 114
atgagcggca acggcaacgc cgccgccacc gccgaggaga acagcccaa gatgcgggtg    60
atccgggtgg gcacccggaa gagccagctg gcccgcatcc agaccgactc cgtcgtcgcc   120
accctcaagg cctcctaccc cggcctccag ttcgagatca tcgccatgtc caccaccggc   180
gacaagatcc tcgacaccgc cctctccaag atcggcgaga agtccctctt caccaaggag   240
ctcgagcacg ccctcgagaa gaacgaggtc gacctggtcg tccactccct caaggacctg   300
cccaccgtcc tcccacccgg cttcaccatc ggcgccatct gcaagcgcga gaaccctcac   360
gacgccgtcg tcttccaccc caagttcgtc ggcaagaccc tcgagaccct ccccgagaag   420
tccgtcgtcg gcacctcctc cctccgccgc cgcgccagc tccagcgcaa gttcccacac   480
ctcgagttcc gctccatccg cggcaacctc aacacccgc tccgcaagct cgacgagcag   540
caggagttct ccgccatcat cctcgccacc cgcggcctcc agcgcatggg ctggcacaac   600
cgcgtcggcc agatcctcca cccggaggag tgcatgtacg ccgtcggcca gggcgccctc   660
ggcgtcgagg tccgcgccaa ggaccaggac atcctcgacc tcgtcggcgt cctccacgac   720
cccgagaccc tcctccgctg catcgccgag cgcgccttcc tccgccacct cgagggcggc   780
tgctccgtcc ccgtcgccgt ccacaccgcc atgaaggacg ccagctcta cctcaccggc   840
ggcgtctggt ccctcgacgg ctccgactcc atccaggaga ccatgcaggc caccatccac   900
gtccccgccc agcacgagga cggccccgag gacgaccctc agctcgtcgg catcaccgcc   960
cgcaacatcc cgcgcggccc tcagctcgcc gcccagaacc tcggcatctc cctcgccaac  1020
ctcctcctct ccaagggcgc caagaacatc ctcgacgtcg cccgccagct caacgacgcc  1080
cac                                                                1083

SEQ ID NO: 115         moltype = RNA   length = 1083
FEATURE                Location/Qualifiers
misc_feature           1..1083
                       note = CONSTRUCT #29
source                 1..1083
                       mol_type = other RNA
                       organism = synthetic construct
SEQUENCE: 115
atgtccggaa acggaaacgc cgccgctacc gccgaggaaa atagcccgaa gatgagagtg    60
atccgggtgg gtaccaggaa gtcccagctc gccaggatcc aaacggactc ggtggtggcc   120
accctcaagg ctagctaccc gggcctgcaa ttcgagatca ttgctatgtc caccaccggc   180
gacaagatcc tggatacggc cctgtccaag atcggcaaaa gagctctt caccaaggag      240
ctggaacacg cgctcgagaa gaacgaggtg gacctggtcg tccacagcct caaggacctg   300
```

```
cctacggtgc tgccgccggg attcaccatc ggcgccatct gtaagcggga gaatccgcac   360
gacgccgtgg tgttccaccc taagttcgtg ggcaagaccc tcgagacact gccgaaaaag   420
tccgtcgtgg gcacctcctc cctgagaagg gccgctcagc tccagagaaa gttcccgcac   480
ctggaattca ggagcatccg gggcaacctg aatacccggc ttcgcaagct ggacgagcag   540
caggagttca gcgccatcat cctggccacc gccggcctgc agcggatggg ctggcacaac   600
cgggtgggcc agatcctgca cccggaggag tgcatgtatg ccgtgggtca gggagccctg   660
ggcgtggagg tccgggccaa ggaccaggac atcctggacc tcgtgggcgt gctccacgac   720
cctgaaaccc tcctgaggtg catcgccgag agggccttcc tccggcacct ggagggcggc   780
tgttccgtcc ctgtggccgt gcataccgcc gtgaaggacg gacagctgta cctgaccggc   840
ggcgtgtggt ccctggacgg ctccgacagc atccaggaaa ccatgcaggc cactatccac   900
gtgccggccc agcacgaaga cggcccagag gatgacccgc aactggtcgg cattaccgcc   960
aggaacatac caaggggccc gcagctggcc gcccagaacc tgggcatctc cctggccaac  1020
ctgctgctgt ccaagggagc caagaacatt ctggacgtgg ccaggcagct caatgatgcc  1080
cac                                                                1083

SEQ ID NO: 116          moltype = RNA   length = 1083
FEATURE                 Location/Qualifiers
misc_feature            1..1083
                        note = CONSTRUCT #30
source                  1..1083
                        mol_type = other RNA
                        organism = synthetic construct
SEQUENCE: 116
atgagcggca acggcaacgc cgccgccacc gcagaggaga atagcccgaa gatgagggtg    60
atccgagtgg gcaccaggaa gtcccagctt gcgcgaattc agaccgacag cgtggtggcc   120
accctcaagg cctcctaccc gggactccag ttcgagatca ttcccatgag caccacggga   180
gacaagatcc tggacaccgc cctgtccaag atcggcgaaa agagcctctt caccaaggag   240
ctggagcacg ccctggagaa gaacgaggtc gatctggtgg tgcacagcct gaaggacctg   300
ccgaccgtct tgccgccggg attcaccatc ggtgccatct gtaagcggga gaacccgcac   360
gacgccgtgg tgttccaccc gaagttcgtc ggcaagaccc tggaaaccct gccggagaag   420
tccgtggtgg gcaccagcag cctgaggcgg gccgcccagc tgcagcggaa gttcccgcac   480
ctggaattca ggagcatccg gggcaacctg aacacccggc tgcggaagct ggacgagcag   540
caggagttca gcgccatcat cctggccacc gcaggcctcc agcgcatggg atggcacaac   600
agggtaggcc aaatcctgca cccggaggag tgtatgtacg ccgtgggcca gggagccctg   660
ggcgtggagg tgagagccaa ggaccaggac atcctagacc tggtcggcgt gctgcacgac   720
ccggagcacac tgctgagatg catcgcggag agagccttcc tgcgacacct ggagggcggc   780
tgctccgtgc cggtggccgt gcacaccgcc atgaaggacg ccagctgta tctgaccggc   840
ggcgtgtgga cctggacgg cagcgactcc atccaagaaa ccatgcaggc taccatccac   900
gtgccggccc agcacgagga tggaccagag gacgatcctc aactggtggg catcactgcc   960
aggaacatcc aagaggccc gcagctggcc gcccagaacc tgggcatcag cctggccaac  1020
ctgctgctgt ccaagggcgc caagaacatt ctcgatgtgg ccaggcagct gaacgatgcc  1080
cac                                                                1083

SEQ ID NO: 117          moltype = RNA   length = 1083
FEATURE                 Location/Qualifiers
misc_feature            1..1083
                        note = CONSTRUCT #31
source                  1..1083
                        mol_type = other RNA
                        organism = synthetic construct
SEQUENCE: 117
atgtcgggaa acggcaacgc cgccgccacg gccgaggaga acagcccgaa gatgagagtg    60
attagggtgg gcacccggaa gtcccaactc gcgcggatcc agaccgactc cgtggtggcc   120
accctcaagg ccagctaccc gggcctccag ttcgagatta tcgccatgtc caccacaggc   180
gacaagatcc tcgacaccgc actctcgaag atcggcgaga gtccctgtt caccaaggaa   240
ctggagcacg ccctggagaa gaacgaggtg gacctggtgg tgcactccct gaaggacctg   300
ccgaccgtgc tcccaccagg cttcaccatc ggcgcaatct gtaagcgcga gaatccgcac   360
gacgccgtgg tgttccaccc aaagttcgtg ggcaagaccc tcgaaccct ccggaaaaag   420
agcgtggtgg gtaccagctc cctgcggaga gctgcccagc tgcagagaaa gttcccgcat   480
ctggaattca ggagcatcag gggaaatctg aataccagc tgcgcaagct ggacgagcag   540
caggagttca gcgccatcat cctggccacc gccggcctgc agcggatggg ctggcacaac   600
agggtgggcc agatactgca tccggaggag tgtatgtacg ccgtgggcca gggcgccctc   660
ggcgtggagg tgagagccaa ggaccaagac atcctggacc tagtgggcgt gctgcatgac   720
cctgaaaccc tgctcaggtg catcgccgag agggccttcc tgcggcaccct ggagggcggc   780
tgcagcgtgc cggtggccgt ccacaccgcc atgaaggacg ccagctgta cctgaccggc   840
ggcgtctgga cctggacgg atccgacagc atccaggaaa ccatgcaggc caccatccac   900
gtgccggccc agcacgagga cggccctgag gacgaccctc agctggtggg catcaccgct   960
aggaacatcc aagggggccc gcagctggcc gcccagaacc tcggcatcag cctggccaac  1020
ctgctgctgt ccaagggcgc caagaatatc ctggacgtgg ccaggcagct gaacgacgcc  1080
cac                                                                1083

SEQ ID NO: 118          moltype = RNA   length = 1294
FEATURE                 Location/Qualifiers
misc_feature            1..1294
                        note = CONSTRUCT #1
source                  1..1294
                        mol_type = other RNA
                        organism = synthetic construct
SEQUENCE: 118
```

```
gggaaataag agagaaaaga agagtaagaa gaaatataag agccaccatg agcggcaacg   60
gcaacgccgc agccaccgcc gaggaaaaca gccccaagat gcgggtgatc agagtgggca  120
cccggaagag ccagctggcc cggatccaga ccgacagcgt ggtggccacc ctgaaggcct  180
cctacccgcg cctgcagttc gagatcattg ccatgagcac caccggcgac aagatcctgg  240
acaccgccct gagcaagatc ggcgagaaga gcctgttcac aaaaagagctg gaacacgccc  300
tggaaaagaa cgaggtggac ctggtggtgc acagcctgaa ggacctgccc accgtgctgc  360
cccctggctt caccatcggc gccatctgca agagagagaa ccccacgac gccgtggtgt  420
tccaccctaa gttcgtgggc aagacactgg aaaccctgcc cgagaagtcc gtggtgggca  480
ccagcagcct gcggagagcc gcccagctgc agcggaagtt cccccacctg gaattccgga  540
gcatccgggg caacctgaac acccggctgc ggaagctgga cgagcagcag gaattttccg  600
ctatcatcct ggccacagcc ggactgcagc ggatgggctg gcacaacaga gtgggccaga  660
tcctgcaccc cgaggaatgc atgtacgccg tgggccaggg agccctgggc gtggaagtgc  720
gggccaagga ccaggacatc ctggatctgg tgggcgtgct gcatgacccc gagacactgc  780
tgcggtgtat cgccgagcgg gccttcctgc ggcacctgga aggcggctgc agcgtgccgc  840
tggccgtgca caccgccatg aaggacggac agctgtacct gacaggcggc gtgtggagcc  900
tggacggcag cgacagcatc caggagacca tgcaggccac catccacgtg cccgcccagc  960
acgaggacgg ccccgaggac gaccctcagc tggtcggcat caccgcccgg aacatccca  1020
gaggccccca gctggccgcc cagaacctgg gcatcagcct ggccaacctg ctgctgtcca 1080
agggcgccaa gaacatcctg gacgtggccc ggcagctgga cgacgccac tgataatagt 1140
ccataaagta ggaaacacta cagctggagc ctcggtggcc atgcttcttg ccccttgggc 1200
ctccccccag cccctcctcc ccttcctgca cccgtacccc ccgcattatt actcacggta 1260
cgagtggtct ttgaataaag tctgagtggg cggc                             1294

SEQ ID NO: 119         moltype = RNA  length = 1294
FEATURE                Location/Qualifiers
misc_feature           1..1294
                       note = CONSTRUCT #2
source                 1..1294
                       mol_type = other RNA
                       organism = synthetic construct
SEQUENCE: 119
gggaaataag agagaaaaga agagtaagaa gaaatataag agccaccatg agcggcaacg   60
gcaacgccgc cgctaccgcc gaagagaaca gcccaaagat gcgcgtgatc agggtcggca  120
cgcgcaagtc ccagctcgcc cggatccaaa ccgatagcgt ggtggccacc ctcaaggcga  180
gctatccggg cttacagttc gagatcatcg ccatgagcac caccggcgat aagatactgg  240
acaccgccct gtccaagatc ggcgaaaaga gcctgttcac caaggaactg gagcacgcgc  300
tggagaagaa cgaggtggac ctggtggtgc acagcctgaa ggacctgccg accgtgctgc  360
cgccgggatt caccatcggc gccatctgca agaggggagaa tccgcacgat gccgtggtgt  420
tccacccaaa gttcgtgggc aagaccttgg aaaccctgcc cgagaagtct gtggtcggca  480
cctccagcct gcggcgagcc gcccagctgc agcgaaagtt cccgcacctg gagttcaggt  540
ccatccgcgg aaatctgaac accaggctgc gcaagctcga cgagcagcag gagttctccg  600
ccatcatcct ggccaccgca ggcctccaaa gaatgggctg gcataaccga gtcggccaga  660
tcctccaccc ggaggagtgc atgtacgcag tgggccaagg cgccctgggc gtcgaggtgc  720
gtgccaagga ccaggacatc ctggacctgg tgggcgtgct ccacgatcca gagacactgc  780
tgagatgcat cgccggagcg gccttcctgc gccatctgga gggaggctgc tccgtcccgg  840
tggccgtaca taccgccatg aaggacggtc agctgtacct caccggcggc gtatggtccc  900
tcgacggtag cgacagcata caggacgca tgcaggccac catccacgtg ccggcgcagc  960
acgaggatgg accagaggac gacccgcagc tggtgggtat caccgccagg aatatcccgc 1020
ggggacctca gctggccgcc cagaacctgg gcatctccct cgccaacctc ctgctgagca 1080
agggcgccaa gaacatcctg gacgtggcca ggcagctcaa cgatgcccat tgataatagt 1140
ccataaagta ggaaacacta cagctggagc ctcggtggcc atgcttcttg ccccttgggc 1200
ctcccccag cccctcctcc ccttcctgca cccgtacccc ccgcattatt actcacggta 1260
cgagtggtct ttgaataaag tctgagtggg cggc                             1294

SEQ ID NO: 120         moltype = RNA  length = 1294
FEATURE                Location/Qualifiers
misc_feature           1..1294
                       note = CONSTRUCT #3
source                 1..1294
                       mol_type = other RNA
                       organism = synthetic construct
SEQUENCE: 120
gggaaataag agagaaaaga agagtaagaa gaaatataag agccaccatg agcggcaacg   60
gcaacgccgc cgccaccgcc gaggaaaaca gcccgaagat gcgggtgatc agggtgggca  120
ccaggaagtc ccagctcgcc cggatccaga ccgacagcgt ggtcgccacc ttgaaggcct  180
cctaccgggc cctccagttc gagatcatcg ccatgtccac aaccggcgac aagatcctgg  240
ataccgccct cagcaagatc ggcgagaagt ccctgttcac caaggagctg gagcacgccc  300
tggagaagaa tgaggtggac ctggtggtgc acagcctgaa ggacctgcct accgtgctgc  360
caccaggctt cacaatcggc gccatctgca agagagagaa ccgcacgacg ccgtggtgt   420
tccatccgaa gttcgtgggc aagaccctgg aaaccctgcc ggagaagtcc gtagtggaa   480
cctcaagcct gaggcgcgcc gcccagctcc agaggaagtt ccctcacctg gaattccggt  540
ccatcagggg caacctgaac acgcgcctgc ggaagctcga cgagcagcag gagttctccg  600
ccatcatcct ggccacagcc ggccttcagc gcatgggctg gcacaacagg gtgggccaga  660
tcctgcaccc ggaagaatgc atgtacgccg tgggccaggg agccctgggc gtggaagtgc  720
gtgccaagga ccaggacatc ctggacctgg tgggcgtgct gcacgaccct gagacgctgc  780
tcaggtgcat cgccgaacgc gcgttcctgc ggcacctgga gggaggctgc agcgtcccgg  840
tggccgtcca caccgccatg aaggacgcc agctctacct gactggcggc gtgtggagcc  900
tggacggcag cgacagcatt caggaaacca tgcaggccac catccacgtg cctgcccagc  960
acgaggacgg ccccggagac gaccctcaac tggtgggcat tactgcgcga acatcccgc  1020
```

```
gcggacctca gctggccgcc cagaacctgg gcatcagcct ggccaacctg ctcctgtcca   1080
agggcgccaa gaacatcctc gacgtggcca ggcagctgaa cgacgcgcac tgataatagt   1140
ccataaagta ggaaacacta cagctggagc tcggtggcc atgcttcttg ccccttgggc    1200
ctcccccag ccctcctcc ccttcctgca cccgtacccc ccgcattatt actcacggta     1260
cgagtggtct ttgaataaag tctgagtggg cggc                                1294

SEQ ID NO: 121          moltype = RNA   length = 1294
FEATURE                 Location/Qualifiers
misc_feature            1..1294
                        note = CONSTRUCT #4
source                  1..1294
                        mol_type = other RNA
                        organism = synthetic construct
SEQUENCE: 121
gggaaataag agagaaaaga agagtaagaa gaaatataag agccaccatg agcggcaacg   60
gaaacgccgc cgcgaccgcg gaggagaact cgcctaagat gagagtgata agggtaggca   120
cccggaagtc tcaactcgcc aggatccaga ccgacagcgt ggtggccacc ctcaaggcca   180
gctatccagg actccagttc gaaatcatcg ccatgtccac cacaggcgat aagatcctgg   240
acaccgccct gtccaagatc ggcgagaagt ccctcttcac caaggaactg gagcacgccc   300
tggagaagaa cgaggtcgat ctggtcgtgc acagccgaa ggatctgcct accgtgctcc    360
cgccgggctt caccatcggc gccatctgca gagggagaa tcctcacgac gccgtggtgt    420
tccacccgaa gttcgtgggc aagacccga agacactgac agaaaagtcg gtggtgggca    480
ccagcagcct gcggcgggcg gcccagctgc agcggaagtt cccacacctg gagttcaggt    540
ccatccgtgg caatctgaac acccggctgc gtaagctgga cgagcagcag gaattcagcg   600
cgatcatcct ggcaaccgcc ggtctgcaaa ggatgggctg gcacaacagg gtgggccaga   660
tcctgcaccc tgaggagtgc atgtacgccg tgggccaagg agccgtggaa gtgc           720
gggccaagga ccaggacatc ctggacctcg tgggtgtgct ccacgaccct gaaacctgc     780
tgcggtgcat cgccgaaagg gccttcctga ggcacctcga gggcggctgc agcgtgccgg   840
tcgccgtgca caccgccatg aaggacggcc agctgtacct gaccggagga gtgtggagcc   900
tggacggctc cgactccatc caggagacta tgcaggccac cattcatgtg ccggcccagc   960
atgaggacgg tccggaggac gatccacagc tggtcggcat caccgcgcgg aacatcccaa   1020
gaggcccgca actggccgct cagaacctgg gcatatcccc ggccaacctg ctcctgagca   1080
agggcgccaa gaacatcctg gacgtggcca ggcagctgaa tgacgcccac tgataatagt   1140
ccataaagta ggaaacacta cagctggagc tcggtggcc atgcttcttg ccccttgggc    1200
ctcccccag ccctcctcc ccttcctgca cccgtacccc ccgcattatt actcacggta     1260
cgagtggtct ttgaataaag tctgagtggg cggc                                1294

SEQ ID NO: 122          moltype = RNA   length = 1294
FEATURE                 Location/Qualifiers
misc_feature            1..1294
                        note = CONSTRUCT #5
source                  1..1294
                        mol_type = other RNA
                        organism = synthetic construct
SEQUENCE: 122
gggaaataag agagaaaaga agagtaagaa gaaatataag agccaccatg tccggcaacg   60
gcaacgccgc cgctaccgcc gaggagaact ccccctaagat gcggtcatc agggtgggca   120
cccgaaagtc ccaacttgcc cggatccaga ccgactccgt cgtggccacc ctcaaggcta   180
gctatccagg cctccagttc gaaatcatcg ccatgagcac caccggcgac aagattctgg   240
acaccgccct gtccaagatc ggcgagaaga gtctgttcac gaaggagctc gagcacgccc   300
tggaaaagaa cgaggtggac ctggtggtgc atccctgca ggacctgcca accgtgctcc    360
cgccgggctt cactataggn gccatctgca agcgggagaa cccgcacgac gcggtggtgt    420
tccatccgaa gttcgtgggc aagactctgg aaacccgcc ggagaagtcc gtggtgggaa    480
ctagctccct gcggcgggcc gcccagctgc agaggaagtt cccgcacctg gagttcagga   540
gcatacgcgg caacctgaac acccgcctgc gtaagctgcg cgagcagcag gaattcagtg   600
ccatcatcct ggccacgcg ggcctgcagc ggatgggctg gcacaacagg gtgggccaga    660
tcctccaccc ggaggaatgt atgtacgccg tgggccaggg cgcactgggc gtggaggtcc   720
gcgccaagga ccaagacatc ctggacctgg tcggcgtgct gcacgaccct gaaaccctgc   780
tgaggtgcat tgccgagaga gccttcctga ggcatctgga gggcggctgc agcgtgcctg   840
tggccgtgca cacagccatg aaggacggtc agctgtacct gaccggccgg gtgtggagcc   900
tggacgcag cgactccatc caggagacaa tgcaggccac catccacgtc ccggcccaac    960
acgaggacgg acctgaggac gatcctcagc tggtgggcat caccgccagg aacatccctc   1020
ggggcccgca gctggccgcc cagaacctgg gcatctccc cgccaacctg ctgctgtcca    1080
agggcgccaa gaacatcctc gacgtggcca gacagcccac tgataatagt                 1140
ccataaagta ggaaacacta cagctggagc tcggtggcc atgcttcttg ccccttgggc    1200
ctcccccag ccctcctcc ccttcctgca cccgtacccc ccgcattatt actcacggta     1260
cgagtggtct ttgaataaag tctgagtggg cggc                                1294

SEQ ID NO: 123          moltype = RNA   length = 1294
FEATURE                 Location/Qualifiers
misc_feature            1..1294
                        note = CONSTRUCT #6
source                  1..1294
                        mol_type = other RNA
                        organism = synthetic construct
SEQUENCE: 123
gggaaataag agagaaaaga agagtaagaa gaaatataag agccaccatg agcggcaacg   60
gcaacgccgc cgcaccgcc gaggagaaca gcccgaagat gagggtgata agggtgggca    120
cacggaagtc ccagctcgcc cgcatccaaa ccgactccgt ggtggccacc ctcaaggcca   180
```

```
gctacccggg cctccaattc gagatcatcg ccatgagcac caccggcgac aagatcctgg    240
acaccgccct gtctaagata ggcgaaaaga gcctgttcac caaggagctg gagcatgccc    300
tggagaagaa cgaggtggac ctggtggtcc acagtctcaa ggacctgcca accgtgctgc    360
cgccaggctt caccatcggc gccatctgca agcgtgagaa cccgcacgat gctgtggtgt    420
tccaccctaa gttcgtggga aagacccctg gacgctggtg ggaaaagagc gtggtcggca    480
cctccagcct gcggagggcc gcccaactcc agaggaagtt cccgcacctg gagttcagga    540
gcatccgcgg caacctgaac accaggctgc gaaagctgga cgagcagcag gaattctcgg    600
ccatcatcct cgccaccgcc ggcttgcaaa gaatgggctg gcataatcgc gtgggccaga    660
tcctgcaccc tgaggagtgc atgtacgccg tgggccaggg tgctctggga gtggaggtgc    720
gggccaagga ccaggatatc ctggacctgg tcggcgtgct tcatgacccg gagacgctcc    780
tgaggtgcat cgccgagcgg gccttcctga cacctgga ggggcggctg tccgtgccag    840
tggccgtgca caccgccatg aaggacggac agctgtacct gaccggcggc gtgtggagcc    900
tggacggaag cgacagcatc caagaaacca tgcaggcgac cattcacgtc cctgcccagc    960
acgaggatgg accagaggac gacccgcagc tggtgggcat caccgcccgc aacatcccta   1020
gaggcccaca gctggccgcc cagaatctgg gcatcagcct ggccaacctg ctgctgtcta   1080
agggagccaa gaacatcctg gacgtggcca ggcagctgaa cgacgcccat tgataatagt   1140
ccataaagta ggaaacacta cagctggagc ctcggtggcc atgcttcttg ccccttgggc   1200
ctccccccag cccctcctcc ccttcctgca cccgtacccc ccgcattatt actcacggta   1260
cgagtggtct ttgaataaag tctgagtggg cggc                                1294

SEQ ID NO: 124           moltype = RNA   length = 1294
FEATURE                  Location/Qualifiers
misc_feature             1..1294
                         note = CONSTRUCT #7
source                   1..1294
                         mol_type = other RNA
                         organism = synthetic construct
SEQUENCE: 124
gggaaataag agagaaaaga agagtaagaa gaaatataag agccaccatg tccggcaacg     60
gcaacgccgc agccaccgcc gaggagaatt ccccgaagat gcgggtgatc cgggtgggca    120
ccagaaagag ccagctcgcc cgcatccaaa ccgactccgt ggtggccacc ctcaaggcct    180
cctacccagg cttgcagttc gaaatcatcg ccatgagcac caccggcgac aagatcctgg    240
acaccgccct gagcaagatt ggcgagaagt ccctgttcac caaggagctg gagcatgctc    300
tggagaagaa cgaggtggac ctcgtggtgc actcccgaa ggacctgccg actgtgctgc    360
cgcctggctt cacgatcggc gccatatgca agcgggaaaa cccacacgac gccgtggtct    420
tccacccaaa gttcgtgggc aagaccctgg aaacccgtgcc ggaaaagagc gtggtcggca    480
caagctccct gaggagagcc gcccaactgc aaaggaagtt ccctcacctc gagttcaggt    540
ccatccgggg caacctgaac accaggctga gaaagctcga cgaacagcag gagttcagcg    600
ccatcatcct ggccacggcc ggcctgcaga ggatgggatg gcataacagg gtgggccaga    660
tcctgcaccc ggaggagtgc atgtacgccg tgggccaggg agccctcggc gtggaggtca    720
gggccaagga tcaggatatc ctggacctgg tgggcgtgct gcacgatcct gagacgctgc    780
tgaggtgcat cgccgagcgg gccttcctgc ggcacctaga ggggcggatgc agcgtgccgg    840
tcgcggtcca caccgcgatg aaggacggcc agctgtacct gaccggccgg gtgtggctcca    900
tggacggcag cgattcaatc caggagacga tgcaggccac catccacgtg ccagcccagc    960
acgaggatgg cccggaggac gacccgcagc tggtgggcat tacagccagg aacatccctc   1020
ggggcccgca gctggccgcc cagaatctgg gcatcagcct ggcgaacctg ctgctcagca   1080
agggagcgaa gaacatcctg gacgtggccc gccagctgaa cgatgcccac tgataatagt   1140
ccataaagta ggaaacacta cagctggagc ctcggtggcc atgcttcttg ccccttgggc   1200
ctccccccag cccctcctcc ccttcctgca cccgtacccc ccgcattatt actcacggta   1260
cgagtggtct ttgaataaag tctgagtggg cggc                                1294

SEQ ID NO: 125           moltype = RNA   length = 1294
FEATURE                  Location/Qualifiers
misc_feature             1..1294
                         note = CONSTRUCT #8
source                   1..1294
                         mol_type = other RNA
                         organism = synthetic construct
SEQUENCE: 125
gggaaataag agagaaaaga agagtaagaa gaaatataag agccaccatg agcggcaacg     60
gcaacgccgc cgccaccgcc gaggagaaca gcccaaagat gcgggtgatc agggtgggca    120
cccgcaagag ccaactcgcc agaatccaga ccgacagcgt ggtggccacc ttgaaggcca    180
gctacccggg cctccagttc gagatcatcg ctatgtccac caccggcgac aagatcctgg    240
acaccgccgct gtccaagatc ggcgaaaaga gcctgttcac caaggaactg gagcatgctc    300
tcgagaagaa cgaggtggac ctggtggtgc actcccctgaa ggacctgccg acggtcctgc    360
cgccgggctt caccatcggc gccatctgca gcgggaaaa cccgcacgac gctgtggtgt    420
tccacccaaa gttcgtgggc aagaccctgg aaaccctgcc agaaaagagc gtggtgggca    480
ccagcagcct caggagagcc gcccagctgc agaggaagtt cccgcacctg gagttcagga    540
gcatcagggg caacctgaac accaggctgc gtaagctgga cgagcagcag gagttctccg    600
ccatcatcct cgccacagcc ggcctccaga ggatgggttg gcacaacagg gtgggccaga    660
tcctgcaccc ggaagagtgc atgtacgcag tgggccaggg cgcccttggc gtggaagtgc    720
gagccaagga tcaggatatc ctggacctgg tgggcgtgct gcacgacccg gaaactctgc    780
tgcggtgcat cgccgaaagg gccttcctgc gccacctcga aggcggctgt agcgtgccgg    840
tggccgtgca caccgccatg aaggacggcc agctgtacct gaccggccgg gtgtggagcc    900
tcgacgcag cgacagcatc caggagacaa tgcaggccac catccacgtg ccggcccagc    960
atgaggatgg cccggaggac gaccctcagc tggtgggcat caccgcccgc aacatccaa   1020
gaggaccgca actggccgcc cagaacctgg gcatctccct ggccaacctg ctcctgagca   1080
agggcgcgaa gaacatcctc gacgtcgcac ggcagctgaa cgacgcccac tgataatagt   1140
ccataaagta ggaaacacta cagctggagc ctcggtggcc atgcttcttg ccccttgggc   1200
```

```
ctcccccag ccctcctcc ccttcctgca cccgtacccc ccgcattatt actcacggta    1260
cgagtggtct ttgaataaag tctgagtggg cggc                              1294

SEQ ID NO: 126          moltype = RNA   length = 1294
FEATURE                 Location/Qualifiers
misc_feature            1..1294
                        note = CONSTRUCT #9
source                  1..1294
                        mol_type = other RNA
                        organism = synthetic construct
SEQUENCE: 126
gggaaataag agagaaaaga agagtaagaa gaaatataag agccaccatg agcggcaacg    60
gcaacgccgc cgcgacggcc gaggaaaata gcccgaagat gcgggtgatc agggtgggca   120
ccaggaagtc ccagctcgcc aggatccaga ccgacagcgt ggtggccacc ctcaaggcct   180
cctaccgggg cctccaattc gagatcatcg ccatgtccac caccggcgac aagatcctcc   240
acaccgccct gagcaagatc ggcgaaaagt cgctgttcac caaggagctg gagcacgccc   300
tcgagaagaa cgaggtggac ctggtagtgc actccctaaa ggacctgccg accgtgctgc   360
cgccggggctt cacgatcggc gccatctgca agcgcgagaa cccgcatgat gccgtcgttt   420
tccaccctaa gttcgtgggc aagacccctg gagacgctgcc ggagaagtcg gtggtgggaa   480
ccagcagcct gaggagggcc gcacaactgc agaggaagtt cccgcatctg gagttccgca   540
gcattcgagg caacctgaac acgcgcctga gaaagctcga tgaacagcag gagttcagcg   600
ccatcattct ggccactgcc ggactgcagc ggatggccac gcacaacaga gtgggccaga   660
tcctgcatcc ggaagagtgt atgtacgccg tgggccaggg tgcccgggc gtggaggtgc   720
gggccaagga ccaggatata ctggatctgg tcggcgtgct ccacgaccca gaaacactcc   780
tgaggtgcat cgctgagaga gccttcctcc ggcacctcga gggcggctgt tccgtgccgg   840
tggccgtcca taccgccatg aaggacggtc agctgtaccc gaccggaggc gtttggtccc   900
tggacggcag cgacagcatc caggaaacca tgcaggccac catccacgtg ccggcgcagc   960
acgaggacgg cccggaagac gacccgcagc tggtcggcat cacggccaga aacatcccgc   1020
gggcccgca gctggcggcc cagaacctgg gaatctccct ggccaacctg ctgctgagca    1080
agggcgcgaa gaacatcctg gacgtggcca ggcagctgga cgatgcccac tgataatagt    1140
ccataaagta ggaaacacta cagctggagc ctcggtggcc atgcttcttg ccccttgggc    1200
ctcccccag ccctcctcc ccttcctgca cccgtacccc ccgcattatt actcacggta    1260
cgagtggtct ttgaataaag tctgagtggg cggc                              1294

SEQ ID NO: 127          moltype = RNA   length = 1294
FEATURE                 Location/Qualifiers
misc_feature            1..1294
                        note = CONSTRUCT #10
source                  1..1294
                        mol_type = other RNA
                        organism = synthetic construct
SEQUENCE: 127
gggaaataag agagaaaaga agagtaagaa gaaatataag agccaccatg agcggtaacg    60
gcaacgccgc cgccaccgcc gaggagaact ccccgaagat gcgcgtgatt cgggtcggca   120
caagaaagtc tcaactcgcc cgaatccaaa cggacagcgt ggtggccacc ctcaaggcga   180
gctacccggg cctccagttc gaaatcatcg ccatgagcac caccggcgac aagatcctgg   240
acaccgccct gtcgaagatt ggcgaaaagt ccctgttcac caaggagctg gagcacgccc   300
tggagaagaa cgaagtcgac ctggtcgtgc acagccctgaa ggacctgccg accgttctgc   360
cgccgggctt caccatcgga gccatctgca gcgggagaa tccgcacgac gccgtggtct   420
tccacccaaa gttcgtggga agacccctcg agacactgcc ggagaagtcc gtggtgggaa   480
cctcctccct gcggagggcc gcccaactgc agcggaagtt cccacacctg gaattccgca   540
ccatcagagg caacctcaac accaggctga ggaagctcga tgagcagcag gagttcagcg   600
ccatcatcct ggccacagcc ggactgcagc gcatgggctg gcataacaga gtgggccaga   660
tcctccaccc ggaggagtgc atgtacgccg tgggacaagg cgcgctgggc gtggaagttc   720
gggccaagga ccaggatatc ctggacctgg tgggcgtgct ccacgaccca gagacgctgg   780
tgcggtgcat cgccgagcgc gccttcctgc ggcacctcga gggcggctgc agcgtgccgg   840
tcgctgtgca cacagccatg aaggacggcc agctgtacct gaccggcggc gtgtggagtc   900
tggacggcag cgactccatc caggagacta tgcaagccac catccatgtg ccggcccaac   960
atgaggacgg cccggaggac gacccgcaac tggtgggcat caccgcccgg aacatcccga   1020
gggcccgca gctggcgcc cagaacctgg gcattagccc ggccaacctg ctcctgagca    1080
agggcgctaa gaacatcctg gacgtcgcca gacagctgaa cgacgcccac tgataatagt    1140
ccataaagta ggaaacacta cagctggagc ctcggtggcc atgcttcttg ccccttgggc    1200
ctcccccag ccctcctcc ccttcctgca cccgtacccc ccgcattatt actcacggta    1260
cgagtggtct ttgaataaag tctgagtggg cggc                              1294

SEQ ID NO: 128          moltype = RNA   length = 1294
FEATURE                 Location/Qualifiers
misc_feature            1..1294
                        note = CONSTRUCT #11
source                  1..1294
                        mol_type = other RNA
                        organism = synthetic construct
SEQUENCE: 128
gggaaataag agagaaaaga agagtaagaa gaaatataag agccaccatg agcggcaacg    60
gcaacgccgc cgccaccgcc gaggagaaca gccccaagat gcgggtgatc cgggtgggca   120
cccgtaagag ccagctggcc cggatccaga ccgacagcgt ggtggccacc ctgaaggcca   180
gctacccccgg cctgcagttc gagatcatcg ccatgagcac caccggcgac aagatcctgg   240
acaccgccct gagcaagatc ggcgagaagt ccctgttcac caaggagctg gagcacgccc   300
tggagaagaa cgaggtggac ctggtggtgc acagcctgaa ggacctgccc accgtgctgc   360
```

```
ctccaggctt caccatcggc gccatctgca agcgggagaa ccccacgac gccgtggtgt  420
tccaccccaa gttcgtgggc aagaccctgg aaaccctgcc tgagaagtcc gtcgtaggaa  480
ccagcagcct gcggcgggcc gcccagctgc agcggaagtt cccccacctg gagttccgga  540
gcatccgggg caacctgaac acccggctgc ggaagctgga cgagcagcag gagttcagcg  600
ccatcatcct ggctaccgcc ggtctgcaac gaatgcgctg gcaaaatagg gtgggccaga  660
tcctgcaccc cgaggagtgc atgtacgcgg tgggacaggg cgccctgggc gtggaggtgc  720
gggccaagga ccaggacatc cttgatctgg tgggcgtgct gcacgacccc gagacgctgc  780
tgcggtgcat cgccgagcgg gccttcctgc ggcatttgga gggcggatgc agcgtgcccg  840
tggccgtgca caccgccatg aaggacggcc agctgtacct gaccggcgcg gtgtggaggg  900
tggacggcag cgacagcatc caggaaacca tgcaggccac catccacgtg cctgctcagc  960
acgaagacgg cccagaggac gacccccagc tggtaggcat caccgcccgg aacatccccc 1020
ggggccctca gctcgccgca cagaaccttg gaatcagcct ggccaacctg ctgttgtcaa 1080
agggcgccaa gaatatcctc gacgtggccc ggcagctgaa cgacgcccac tgataatagt 1140
ccataaagta ggaaacacta cagctggagc ctcggtggcc atgcttcttg ccccttgggc 1200
ctccccccag cccctcctcc ccttcctgca cccgtacccc ccgcattatt actcacggta 1260
cgagtggtct ttgaataaag tctgagtggg cggc                             1294
```

SEQ ID NO: 129       moltype = RNA   length = 1294
FEATURE              Location/Qualifiers
misc_feature         1..1294
                     note = CONSTRUCT #12
source               1..1294
                     mol_type = other RNA
                     organism = synthetic construct
SEQUENCE: 129

```
gggaaataag agagaaaaga agagtaagaa gaaatataag agccaccatg agcggcaacg   60
gcaacgccgc cgccaccgcc gaggagaaca gccccaagat gcgggtgatc cgggtgggca  120
ccagaaagag ccagctggcc cggatccaga ccgacagcgt ggtggccacc ctgaaggcca  180
gctaccccgg cctgcagttc gagatcatcg ccatgagcac caccggcgac aagatcctgg  240
acaccgccct gagcaagatc ggcgagaaga gtctgttcac caaggagctg gagcacgccc  300
tggagaagaa cgaggtggac ctggtggtgc acagcctgaa ggacctgccc accgtgctgc  360
cgcctggctt caccatcggc gccatctgca agcgggagaa ccccacgac gccgtggtgt   420
tccaccccaa gttcgtgggc aagactctgg aaaccctgcc tgagaagtcc gtggtcgaa   480
caagcagcct gcggcgggcc gcccagctgc agcggaagtt cccccacctg gagttccgga  540
gcatccgggg caacctgaac acccggctgc ggaagctgga cgagcagcag gagttcagcg  600
ccatcatcct ggccacagcc ggccttcaga ggatgggctg gcacaatcgg gtaggccaga  660
tcctgcaccc cgaggagtgc atgtacgcgg taggtcaggg cgccctgggc gtggaggtgc  720
gggccaagga ccaggacatc ttagatctgg ttggcgtgct gcacgacccc gaaacactgc  780
tgcggtgcat cgccgagcgg gccttcctgc ggcacctcga gggcggctgc agtgtgcccg  840
tggccgtgca caccgccatg aaggacggcc agctgtacct gaccggcggc gtgtggagcc  900
tggacggcag cgacagcatc caggagacaa tgcaggccac catccacgtg ccagctcagc  960
acgaagacgg accagaggac gacccccagt tagtgggaat caccgcccgg aacatccccc 1020
ggggccctca gctcgcgccc cagaacctgg gcatcagcct ggccaacctg ctgctgtcta 1080
agggcgccaa gaacatccta gacgtggccc ggcagctgaa cgacgcccac tgataatagt 1140
ccataaagta ggaaacacta cagctggagc ctcggtggcc atgcttcttg ccccttgggc 1200
ctccccccag cccctcctcc ccttcctgca cccgtacccc ccgcattatt actcacggta 1260
cgagtggtct ttgaataaag tctgagtggg cggc                             1294
```

SEQ ID NO: 130       moltype = RNA   length = 1294
FEATURE              Location/Qualifiers
misc_feature         1..1294
                     note = CONSTRUCT #13
source               1..1294
                     mol_type = other RNA
                     organism = synthetic construct
SEQUENCE: 130

```
gggaaataag agagaaaaga agagtaagaa gaaatataag agccaccatg agcggcaacg   60
gcaacgccgc cgccaccgcc gaggagaaca gccccaagat gcgggtgatc cgggtgggca  120
ccaggaagtc acagctggcc cggatccaga ccgacagcgt ggtggccacc ctgaaggcca  180
gctaccccgg cctgcagttc gagatcatcg ccatgagcac caccggcgac aagatcctgg  240
acaccgccct gagcaagatc ggcgagaagt ccctgttcac caaggagctg gagcacgccc  300
tggagaagaa cgaggtggac ctggtggtgc acagcctgaa ggacctgccc accgtgctgc  360
cgccaggctt caccatcggc gccatctgca agcgggagaa ccccacgac gccgtggtgt   420
tccaccccaa gttcgtgggc aagacccttg aaaccctgcc agaaagtct gtggtcgaa    480
ccagcagcct gcggcgggcc gcccagctgc agcggaagtt cccccacctg gagttccgga  540
gcatccgggg caacctgaac acccggctgc ggaagctgga cgagcagcag gagttcagcg  600
ccatcatcct ggccaccgct ggcctacagc ggatgggctg gcacaataga gttggtcaga  660
tcctgcaccc cgaggagtgc atgtacgccg tcggccaggg cgccctgggc gtggaggtgc  720
gggccaagga ccaggacata ctagacctcg tgggcgtgct gcacgacccc gaaacccttg  780
tgcggtgcat cgccgagcgg gccttcctgc ggcacctgga aggcggttgc agcgtgcccg  840
tggccgtgca caccgccatg aaggacggcc agctgtacct gaccggcggc gtgtggagcc  900
tggacggcag cgacagcatc caggagacaa tgcaggccac catccacgtg ccggcccaac  960
acgaggacgg acctgaggac gacccccagc tgtgggaat caccgcccgg aacatccccc  1020
ggggccctca actcgccagc cagaacttag gcataagcct ggcagctgaa cgacgcccac 1080
agggcgccaa gaacatcctc gatgtggccc ggcagctgaa cgacgcccac tgataatagt 1140
ccataaagta ggaaacacta cagctggagc ctcggtggcc atgcttcttg ccccttgggc 1200
ctccccccag cccctcctcc ccttcctgca cccgtacccc ccgcattatt actcacggta 1260
cgagtggtct ttgaataaag tctgagtggg cggc                             1294
```

```
SEQ ID NO: 131          moltype = RNA   length = 1294
FEATURE                 Location/Qualifiers
misc_feature            1..1294
                        note = CONSTRUCT #14
source                  1..1294
                        mol_type = other RNA
                        organism = synthetic construct
SEQUENCE: 131
gggaaataag agagaaaaga agagtaagaa gaaatataag agccaccatg agcggcaacg    60
gcaacgccgc cgccaccgcc gaggagaaca gccccaagat gcgggtgatc cgggtgggca   120
cccgcaagag tcagctggcc cggatccaga ccgacagcgt ggtggccacc ctgaaggcca   180
gctaccccgg cctgcagttc gagatcatcg ccatgagcac caccggcgac aagatcctgg   240
acaccgccct gagcaagatc ggcgagaaga gtctgttcac caaggagctg gagcacgccc   300
tggagaagaa cgaggtggac ctggtggtgc acagcctgga ggacctgccc accgtgctgc   360
cacctggctt caccatcggc gccatctgca gcgggagaa ccccacgac gccgtggtgt   420
tccaccccaa gttcgtgggc aagacactgg aaaccctgcc ggagaagtcc gtggtaggca   480
ccagcagcct gcggcgggcc gcccagctgc agcggaagtt cccccacctg gagttccgga   540
gcatccgggg caacctgaac acccggctgc ggaagctgga cgagcagcag gagttcagcg   600
ccatcatcct ggcaacagcc ggcttacagc gtatgggctg gcacaacagg gtgggacaga   660
tcctgcaccc cgaggagtgc atgtacgctg tgggccaggg cgccctgggc gtggaggtgc   720
gggccaagga ccaggacatc ttagatctcg tcggcgtgct gcacgacccc gaaaccttgc   780
tgcggtgcat cgccgagcgg gccttcctgc ggcatcttga gggcggatgc tccgtgccgc   840
tggccgtgca caccgccatg aaggacggcc agctgtacct gaccggcggc gtgtggagcc   900
tggacggcag cgacagcatc caggagacta tgcaggccac catccacgtg ccagcccagc   960
acgaagacgg cccagaggac gacccccagc tggtgggaat caccgccggg aacatccccc  1020
ggggcccctca actggccgca cagaacctag gcatcagcct ggccaactcg ctgctcagca  1080
agggcgccaa gaatatcttg gacgtggccc ggcagctgaa cgacgcccac tgataatagt  1140
ccataaagta ggaaacacta cagctggagc ctcggtggcc atgcttcttg ccccttgggc  1200
ctccccccag cccctcctcc ccttcctgca cccgtaccc ccgcattatt actcacggta   1260
cgagtggtct tgaataaag tctgagtggg cggc                             1294

SEQ ID NO: 132          moltype = RNA   length = 1294
FEATURE                 Location/Qualifiers
misc_feature            1..1294
                        note = CONSTRUCT #15
source                  1..1294
                        mol_type = other RNA
                        organism = synthetic construct
SEQUENCE: 132
gggaaataag agagaaaaga agagtaagaa gaaatataag agccaccatg agtggcaacg    60
gaaacgccgc cgctacagca gaggagaact ccccgaagat gcgcgtgatt agggtaggca   120
ccagaaagtc tcagctggcc agaatccaaa ccgatagcgt tgtggccaca ttgaaggcta   180
gctatcccgg cctgcagttc gagatcatcg ccatgagcac caccggcgac aagatactcg   240
acaccgctct gagtaaaatc ggcgagaaga gcctgtttac caaggagctg gagcacgccc   300
tggaaaagaa cgaagtggac ctggtggtgc atagtctgaa agaccttccc accgtccttc   360
caccaggctt cactatcggc gccatctgca gagggagaa tcctcacgat gccgtcgtgt   420
ttcatcccaa gttcgtgggc aagacccttag aaaccctgcc agagaaaagc gtcgttggga   480
cctcctccct gcgacgggcc gcccagctgc agagaaagtt ccccccacttg gaattcagat   540
ccatcagagg gaatctgaat actgcctga gaaagctgga cgagcagcag gagttttagcg   600
ctatcatcct ggccacggct ggtttgcaga gaatgggctg gcacaaccgg gtgggacaga   660
tcctgcaccc cgaggagtgc atgtatgcag taggccaggg gcctgggc gtggaggtca   720
gagccaaaga tcaggacatc ctggacctgg tcggcgtgct gcacgatccc gaaactgcc   780
tgcggtgtat cgccgagagg gctttcctcc ggcacttaga gggcggctgc tccgtccccg   840
tggccgttca cactgccatg aaagacgggc agctgtacct gacgggcggc gtggtgtccc   900
tggccggctc agactccatt caggagacca tgcaagctac catccacgtc cctgcccaac   960
acgaagatgg ccccgaggac gacccccagc tggtgggcat caccgccagg aatatcccaa  1020
gaggccccca gttggccgcc cagaacctgg gcatcagtct ggccaacctg ctgctagta   1080
agggcgccaa aaacatcctg gacgtggctc ggcagctgaa tgacgcccac tgataatagt  1140
ccataaagta ggaaacacta cagctggagc ctcggtggcc atgcttcttg ccccttgggc  1200
ctccccccag cccctcctcc ccttcctgca cccgtaccc ccgcattatt actcacggta   1260
cgagtggtct tgaataaag tctgagtggg cggc                             1294

SEQ ID NO: 133          moltype = RNA   length = 1294
FEATURE                 Location/Qualifiers
misc_feature            1..1294
                        note = CONSTRUCT #16
source                  1..1294
                        mol_type = other RNA
                        organism = synthetic construct
SEQUENCE: 133
gggaaataag agagaaaaga agagtaagaa gaaatataag agccaccatg agcggcaacg    60
gcaacgccgc cgccaccgcc gaggagaaca gccccaagat gcgggtgatc cgggtgggca   120
cccggaagag ccagctggcc cggatccaga ccgacagcgt ggtggccacc ctgaaggcca   180
gctaccccgg cctgcagttc gagatcatcg ccatgagcac caccggcgac aagatcctgg   240
acaccgccct gagcaagatc ggcgagaaga gcctgttcac caaggagctg gagcacgccc   300
tggagaagaa cgaggtggac ctggtggtgc acagcctgaa ggacctgccc accgtgctgc   360
cccccggctt caccatcggc gccatctgca gcgggagaa ccccacgac gccgtggtgt   420
tccaccccaa gttcgtgggc aagacctgg agaccctgcc cgaagagc gtggtgggca   480
ccagcagcct gcggcgggcc gcccagctgc agcggaagtt cccccacctg gagttccgga   540
```

-continued

```
gcatccgggg caacctgaac acccggctgc ggaagctgga cgagcagcag gagttcagcg  600
ccatcatcct ggccaccgcc ggcctgcagc ggatgggctg gcacaaccgg gtgggcaga   660
tcctgcaccc cgaggagtgc atgtacgccg tgggccaggg cgcccggggc gtggaggtgc   720
gggccaagga ccaggacatc ctggacctgg tgggcgtgct gcacgacccc gagaccctgc   780
tgcggtgcat cgccgagcgg gccttcctgc ggcacctggc ggcggctgc agcgtgcccg   840
tggccgtgca caccgccatg aaggacggcc agctgtacct gaccggcggc gtgtggagcc   900
tggacggcag cgacagcatc caggagacca tgcaggccac catccacgtg cccgcccagc   960
acgaggacgg ccccgaggac gaccccagc tggtgggcat caccgccggg aacatccccc  1020
ggggccccca gctggccgcc cagaacctgg gcatcagcct ggccaacctg ctgctgagca  1080
agggcgccaa gaacatcctg gacgtggccc ggcagctgaa cgacgcccac tgataatagt  1140
ccataaagta ggaaacacta cagctggagc ctcggtggcc atgcttcttg ccccttgggc  1200
ctcccccag ccctcctcc ccttcctgca cccgtacccc ccgcattatt actcacggta  1260
cgagtggtct ttgaataaag tctgagtggg cggc                              1294

SEQ ID NO: 134         moltype = RNA   length = 1294
FEATURE                Location/Qualifiers
misc_feature           1..1294
                       note = CONSTRUCT #16
source                 1..1294
                       mol_type = other RNA
                       organism = synthetic construct
SEQUENCE: 134
gggaaataag agagaaaaga agagtaagaa gaaatataag agccaccatg agcggcaacg   60
gcaacgccgc cgccaccgcc gaggagaaca gccccaagat gcgggtgatc cgggtgggca  120
cccgggaagag ccagctggcg aggatccaga cggacagcgt ggtggcgacg ctgaaggcga  180
gctacccggg gctgcagttc gagatcatcg cgatgagcac ggcggggac aagatcctgg   240
acacggcgct gagcaagatc ggggagaaga gcctgttcac gaaggagctg gagcacgcgc  300
tggagaagaa cgaggtggac ctggtggtgc acagcctgaa ggacctgccg acggtgctgc  360
cgccggggtt cacgatcggg gcgatctgca agagggagaa cccgcacgac gcggtggtgt  420
tccacccgaa gttcgtgggg aagacgctgg agacgctgcc ggagaagagc gtggtgggga  480
cgagcagcct gaggagggcg gcgcagctgc agaggaagtt cccgcacctg gagttcagga  540
gcatcagggg gaacctgaac acgaggctga ggaagctgga cgagcagcag gagttcagcg  600
cgatcatcct ggcgacggcg gggctgcaga ggatgggggtg gcacaacagg gtggggcaga  660
tcctgcaccc ggaggagtgc atgtacgcgg tgggcaggg ggcgctgggg gtggaggtga   720
gggcgaagga ccaggacatc ctggacctgg tggggtgct gcacgacccg gagacgctgc   780
tgaggtgcat cgcggagagg gcgttcctga ggcacctgga gggggggtgc agcgtgccgg  840
tggcggtgca caccggcatg aaggacggcc agctgtacct gacgggggggg gtgtggagcc  900
tggacggag cgacagcatc caggagacga tgcaggcgac gatccacgtg ccggcgcagc  960
acgaggacgg gccggaggac gacccgcagc tggtgggat caccggcagg aacatcccga  1020
gggggccgca gctggcggcg cagaacctgg ggatcagcct ggcgaacctg ctgctgagca  1080
aggggcgaa gaacatcctg gacgtggcga ggcagctgaa cgacgcgcac tgataatagt   1140
ccataaagta ggaaacacta cagctggagc ctcggtggcc atgcttcttg ccccttgggc  1200
ctcccccag ccctcctcc ccttcctgca cccgtacccc ccgcattatt actcacggta  1260
cgagtggtct ttgaataaag tctgagtggg cggc                              1294

SEQ ID NO: 135         moltype = RNA   length = 1294
FEATURE                Location/Qualifiers
misc_feature           1..1294
                       note = CONSTRUCT #17
source                 1..1294
                       mol_type = other RNA
                       organism = synthetic construct
SEQUENCE: 135
gggaaataag agagaaaaga agagtaagaa gaaatataag agccaccatg agcggcaacg   60
gcaacgccgc cgccaccgcc gaggagaaca gccccaagat gcgggtgatc cgggtgggca  120
cccggaagag ccagctggcc cgcatccaga ccgactccgt cgtcgccacc ctcaaggcct  180
cctaccccgg cctccagttc gagatcatcg ccatgtccac caccggcgac aagatcctcg  240
acaccgccct ctccaagatc ggcgagaagt ccctcttcac caaggagctc gagcacgccc  300
tcgagaagaa cgaggtcgac ctcgtcgtcc actccctcaa ggacctcccc accgtcctcc  360
cccccggctt caccatcggc gccatctgca agcgcgagaa ccccacgac gccgtcgtct  420
tccacccca gttcgtcggc aagaccctcg agaccctccc cgagaagtcc gtcgtcggca  480
cctcctccct ccgccgcgcc gcccagctcc agcgcaagtt cccccacctc gagttccgct  540
ccatccgcgg caacctcaac acccgcctcc gcaagctcga cgagcagcag gagttctccg  600
ccatcatcct cgccaccgcc ggcctccagc gcatgggctg gcacaaccgg gtcggccaga  660
tcctccaccc cgaggagtgc atgtacgccg tcgccaggg cgcccgcggc gtcgaggtcc  720
gcgccaagga ccaggacatc ctcgacctcg tcggcgtcct ccacgacccc gagaccctcc  780
tccgctgcat cgccgagcgc gccttcctcc gccacctcga gggcggctgc tccgtccccg  840
tcgccgtcca caccgccatg aaggacggcc agctctacct caccggcggc gtctggtccc  900
tcgacggctc cgactccatc caggagacca tgcaggccac catccacgtg ccccgcccagc  960
acgaggacgg ccccgaggac gaccccagc tcgtcggcat caccgccgc aacatccccc  1020
gcggccccca gctcgccgcc cagaacctcg gcatctccct cgccaacctc ctcctctca  1080
agggcgccaa gaacatcctc gacgtcgccc gccagctcaa cgacgcccac tgataatagt  1140
ccataaagta ggaaacacta cagctggagc ctcggtggcc atgcttcttg ccccttgggc  1200
ctcccccag ccctcctcc ccttcctgca cccgtacccc ccgcattatt actcacggta  1260
cgagtggtct ttgaataaag tctgagtggg cggc                              1294

SEQ ID NO: 136         moltype = RNA   length = 1294
FEATURE                Location/Qualifiers
misc_feature           1..1294
```

|  | note = CONSTRUCT #18 |  |
|---|---|---|
| source | 1..1294 |  |
|  | mol_type = other RNA |  |
|  | organism = synthetic construct |  |

SEQUENCE: 136

```
gggaaataag agagaaaaga agagtaagaa gaaatataag agccaccatg agcggcaacg    60
gcaacgccgc cgccaccgcc gaggagaaca gccccaagat gcgggtgatc cgggtgggca   120
cccgtaagag ccagctggcc cggatccaga ccgacagcgt ggtggccacc ctgaaggcca   180
gctaccccgg cctgcagttc gagatcatcg ccatgagcac caccggcgac aagatcctgg   240
acaccgccct gagcaagatc ggcgagaagt ccctgttcac caaggagctg gagcacgccc   300
tggagaagaa cgaggtggac ctggtggtgc acagcctgaa ggacctgccc accgtgctgc   360
ctccaggctt caccatcggc gccatctgca agcgggagaa ccctcacgac gccgtggtgt   420
tccaccccaa gttcgtgggc aagaccctgg aaaccctgcc tgagaagtcc gtcgtaggaa   480
ccagcagcct gcggcgggcc gcccagctgc agcggaagtt cccacacctg gagttccagc   540
gcatccgggg caacctgaac acccggctgc ggaagctgga cgagcagcag gagttcagcg   600
ccatcatcct ggctaccgcc ggtctgcaac gaatgggctg gcacaatagg gtgggccaga   660
tcctgcaccc cgaggagtgc atgtacgcgg tgggacaggg cgccctgggc gtggaggtgc   720
gggccaagga ccaggacatc cttgatctgg tgggcgtgct gcacgacccc gagacgctgc   780
tgcggtgcat cgccgagcgg gccttcctgc ggcatttgga gggcggatgc agcgtgcccg   840
tggccgtgca caccgccatg aaggacggcc agctgtacct gaccggcggc gtgtggagcc   900
tggacggcag cgacagcatc caggaaacca tgcaggccac catccacgtg cctgctcagc   960
acgaagacgg cccagaggac gaccctcagc tggtaggcat caccgcccgg aacatccctc  1020
ggggccctca gctcgccgca cagaaccttg aatcagcct ggccaacctg ctgttgtcaa   1080
agggcgccaa gaatatcctc gacgtggccc ggcagctgaa cgacgcccac tgataatagt   1140
ccataaagta ggaaacacta cagctggagc ctcggtggcc atgcttcttg ccccttgggc   1200
ctccccccag cccctcctcc ccttcctgca cccgtacccc ccgcattatt actcacggta   1260
cgagtggtct ttgaataaag tctgagtggg cggc                               1294
```

| SEQ ID NO: 137 | moltype = RNA length = 1294 |
|---|---|
| FEATURE | Location/Qualifiers |
| misc_feature | 1..1294 |
|  | note = CONSTRUCT #19 |
| source | 1..1294 |
|  | mol_type = other RNA |
|  | organism = synthetic construct |

SEQUENCE: 137

```
gggaaataag agagaaaaga agagtaagaa gaaatataag agccaccatg agcggcaacg    60
gcaacgccgc cgccaccgcc gaggagaaca gccccaagat gcgggtgatc cgggtgggca   120
ccagaaagag ccagctggcc cggatccaga ccgacagcgt ggtggccacc ctgaaggcca   180
gctaccccgg cctgcagttc gagatcatcg ccatgagcac caccggcgac aagatcctgg   240
acaccgccct gagcaagatc ggcgagaaga gtctgttcac caaggagctg gagcacgccc   300
tggagaagaa cgaggtggac ctggtggtgc acagcctgaa ggacctgccc accgtgctgc   360
cgcctggctt caccatcggc gccatctgca gcgggagaa cccgcacgac gccgtggtgt   420
tccaccccaa gttcgtgggc aagactctgg aaaccctgcc tgagaagtcc gtggtcggaa   480
caagcagcct gcggcgggcc gcccagctgc agcggaagtt cccacacctg gagttccgga   540
gcatccgggg caacctgaac acccggctgc ggaagctgga cgagcagcag gagttcagcg   600
ccatcatcct ggccacagcc ggccttcaga ggatgggctg gcacaatcgg gtaggccaga   660
tcctgcaccc cgaggagtgc atgtacgcgg taggtcaggg cgccctgggc gtggaggtgc   720
gggccaagga ccaggacatc ttagatctgg ttggcgtgct gcacgacccc gaaacactgc   780
tgcggtgcat cgccgagcgg gccttcctgc ggcacctcga gggcggctgc agtgtgcccg   840
tggccgtgca caccgccatg aaggacggcc agctgtacct gaccggcggc gtgtggagcc   900
tggacggcag cgacagcatc caggagacaa tgcaggccac catccacgtg ccagctcagc   960
acgaagacgg accagaggac gacccacagt tagtgggaat caccgcccgg aacatcccgc  1020
ggggccctca gctcgcggcc cagaacctgg gcatcagcct ggccaacctg ctgctgtcta  1080
agggcgccaa gaacatccta gacgtggccc ggcagctgaa cgacgcccac tgataatagt  1140
ccataaagta ggaaacacta cagctggagc ctcggtggcc atgcttcttg ccccttgggc  1200
ctccccccag cccctcctcc ccttcctgca cccgtacccc ccgcattatt actcacggta  1260
cgagtggtct ttgaataaag tctgagtggg cggc                               1294
```

| SEQ ID NO: 138 | moltype = RNA length = 1294 |
|---|---|
| FEATURE | Location/Qualifiers |
| misc_feature | 1..1294 |
|  | note = CONSTRUCT #20 |
| source | 1..1294 |
|  | mol_type = other RNA |
|  | organism = synthetic construct |

SEQUENCE: 138

```
gggaaataag agagaaaaga agagtaagaa gaaatataag agccaccatg agcggcaacg    60
gcaacgccgc cgccaccgcc gaggagaaca gccccaagat gcgggtgatc cgggtgggca   120
ccaggaagtc acagctggcc cggatccaga ccgacagcgt ggtggccacc ctgaaggcca   180
gctaccccgg cctgcagttc gagatcatcg ccatgagcac caccggcgac aagatcctgg   240
acaccgccct gagcaagatc ggcgagaagt ccctgttcac caaggagctg gagcacgccc   300
tggagaagaa cgaggtggac ctggtggtgc acagcctgaa ggacctgccc accgtgctgc   360
cgccaggctt caccatcggc gccatctgca gcgggagaa cccgcacgac gccgtggtgt   420
tccaccccaa gttcgtgggc aagacccttg aaaccctgcc agagaagtct gtggtcggaa   480
ccagcagcct gcggcgggcc gcccagctgc agcggaagtt cccgcacctg gagttccgga   540
gcatccgggg caacctgaac acccggctgc ggaagctgga cgagcagcag gagttcagcg   600
ccatcatcct ggcaccgct ggcctacagc ggatgggctg gcacaataga gttggtcaga   660
tcctgcaccc cgaggagtgc atgtacgcgg tcggccaggg cgccctgggc gtggaggtgc   720
```

```
gggccaagga ccaggacata ctagacctcg tgggcgtgct gcacgacccc gaaaccttgc    780
tgcggtgcat cgccgagcgg gccttcctgc ggcacctgga aggcggttgc agcgtgcccg    840
tggccgtgca caccgccatg aaggacggcc agctgtacct gaccggcggc gtgtggagcc    900
tggacggcag cgacagcatc caggagacaa tgcaggccac catccacgtg ccggcccaac    960
acgaggacgg acctgaggac gacccacagc ttgtggggaat caccgcccgg aacatcccac   1020
ggggccctca actggcagcc cagaacttag gcataagcct ggccaacctg ctgctgtcca   1080
agggcgccaa gaacatcctc gatgtggccc ggcagctgaa cgacgcccac tgataatagt   1140
ccataaagta ggaaacacta cagctggagc ctcggtggcc atgcttcttg ccccttgggc   1200
ctcccccccag cccctcctcc ccttcctgca cccgtacccc ccgcattatt actcacggta   1260
cgagtggtct ttgaataaag tctgagtggg cggc                                1294

SEQ ID NO: 139          moltype = RNA   length = 1294
FEATURE                 Location/Qualifiers
misc_feature            1..1294
                        note = CONSTRUCT #21
source                  1..1294
                        mol_type = other RNA
                        organism = synthetic construct
SEQUENCE: 139
gggaaataag agagaaaaga agagtaagaa gaaatataag agccaccatg agcggcaacg    60
gcaacgccgc cgccaccgcc gaggagaaca gccccaagat gcgggtgatc cgggtgggca   120
cccgcaagag tcagctggcc cggatccaga ccgacagcgt ggtggccacc ctgaaggcca   180
gctaccccgg cctgcagttc gagatcatcg ccatgagcac caccggcgac aagatcctga   240
acaccgccct gagcaagatc ggcgagaaga gtctgttcac caaggagctg gagcacgccc   300
tggagaagaa cgaggtggac ctggtggtgc acagcctgaa ggacctgccc accgtgctgc   360
cacctggctt caccatcggc gccatctgca agcgggagaa cccacacgac gccgtggtgt   420
tccaccccaa gttcgtgggc aagacactgg aaacccgtgcc ggagaagtcc gtggtaggca   480
ccagcagcct gcggcgggcc gcccagctgc agcggaagtt cccgcacctg gagttccgga   540
gcatccgggg caacctgaac acccggctgc ggaagctgga cgagcagcag gagttcagcg   600
ccatcatcct ggcaacagcc ggcttacagc gtatgggctg gcacaacagg gtgggacaga   660
tcctgcaccc cgaggagtgc atgtacgctg tgggccaggg cgccctgggc gtggaggtgc   720
gggccaagga ccaggacatc ttagatctcg tcggcgtgct gcacgacccc gaaaccttgc    780
tgcggtgcat cgccgagcgg gccttcctgc ggcatcttga gggcggatgc tccgtgcccg    840
tggccgtgca caccgccatg aaggacggcc agctgtacct gaccggcgcg gtgtggagcc    900
tggacggcag cgacagcatc caggagacta tgcaggccac catccacgtg ccagcccaac    960
acgaagacgg cccagaggac gacccacagc tggtgggaat caccgcccgg aacatcccgc   1020
ggggccctca actggccgca cagaacctag gcatagcct ggccaacctg ctgctcagca   1080
agggcgccaa gaatatcttg gacgtggccc ggcagctgaa cgacgcccac tgataatagt   1140
ccataaagta ggaaacacta cagctggagc ctcggtggcc atgcttcttg ccccttgggc   1200
ctcccccccag cccctcctcc ccttcctgca cccgtacccc ccgcattatt actcacggta   1260
cgagtggtct ttgaataaag tctgagtggg cggc                                1294

SEQ ID NO: 140          moltype = RNA   length = 1294
FEATURE                 Location/Qualifiers
misc_feature            1..1294
                        note = CONSTRUCT #22
source                  1..1294
                        mol_type = other RNA
                        organism = synthetic construct
SEQUENCE: 140
gggaaataag agagaaaaga agagtaagaa gaaatataag agccaccatg agcggcaacg    60
gcaacgccgc cgccaccgcc gaggagaaca gccccaagat gcgggtgatc cgggtgggca   120
ccagaaaagag ccagctggcc cggatccaga ccgacagcgt ggtggccacc ctgaaggcca   180
gctaccccgg cctgcagttc gagatcatcg ccatgagcac caccggcgac aagatcctgg   240
acaccgccct gagcaagatc ggcgagaagt ctctgttcac caaggagctg gagcacgccc   300
tggagaagaa cgaggtggac ctggtggtgc acagcctgaa ggacctgccc accgtgctgc   360
ctcctggctt caccatcggc gccatctgca agcgggagaa cccacacgac gccgtggtgt   420
tccaccccaa gttcgtgggc aagacccttg agactctgcc agagaagtct gtagtgggaa   480
ccagcagcct gcggcgggcc gcccagctgc agcggaagtt ccctcacctg gagttccgga   540
gcatccgggg caacctgaac acccggctgc ggaagctgga cgagcagcag gagttcagcg   600
ccatcatcct ggccacggcc ggattacaga gaatgggctg gcacaaccga gtgggacaga   660
tcctgcaccc cgaggagtgc atgtatgccg ttggccaagg cgccctgggc gtggaggtgc   720
gggccaagga ccaggacatc ctcgatctcg tgggcgtgct gcacgacccc gagactttgc    780
tgcggtgcat cgccgagcgg gccttcctgc ggcacctgga gggcgctgc tcggtgcccg    840
tggccgtgca caccgccatg aaggacggcc agctgtacct gaccggcggc gtgtggagcc    900
tggacggcag cgacagcatc caggagacaa tgcaggccac catccacgtg ccagcccagc    960
acgaggatgg ccctgaagac gacccacagc tggtgggcat caccgcccgg aacatcccgc   1020
ggggccccaca attggccgct cagaacttag gcattagcct ggccaacctg ctgctgtcta   1080
agggcgccaa gaacatactg gacgtggccc ggcagctgaa cgacgcccac tgataatagt   1140
ccataaagta ggaaacacta cagctggagc ctcggtggcc atgcttcttg ccccttgggc   1200
ctcccccccag cccctcctcc ccttcctgca cccgtacccc ccgcattatt actcacggta   1260
cgagtggtct ttgaataaag tctgagtggg cggc                                1294

SEQ ID NO: 141          moltype = RNA   length = 1294
FEATURE                 Location/Qualifiers
misc_feature            1..1294
                        note = CONSTRUCT #24
source                  1..1294
                        mol_type = other RNA
```

```
                        organism = synthetic construct
SEQUENCE: 141
gggaaataag agagaaaaga agagtaagaa gaaatataag agccaccatg agcggcaacg    60
gcaacgccgc cgccaccgcc gaggagaaca gccccaagat gcgggtgatc cgggtgggca   120
cccggaagag ccagctggcc cggatccaga ccgacagcgg ggtggccacc ctgaaggcca   180
gctaccccgg cctgcagttc gagatcatcg ccatgagcac caccggcgac aagatcctga   240
acaccgccct gagcaagatc ggcgagaaga gcctgttcac caaggagctg gagcacgccc   300
tggagaagaa cgaggtggac ctggtggtgc acagcctgaa ggacctgccc accgtgctgc   360
cgcccggctt caccatcggc gccatctgca gcgggagaa cccgcacgac gccgtggtgt   420
tccaccccaa gttcgtgggc aagaccctgg agacccgcc cgagaagagc gtggtgggca   480
ccagcagcct gcggcgggcc gcccagctgc agcggaagtt ccctcacctg gagttccgga   540
gcatccgggg caacctgaac acccggctgc ggaagctgga cgagcagcag gagttcagcg   600
ccatcatcct ggccaccgcc ggcctgcagc ggatgggctg gcacaaccgg gtgggccaga   660
tcctgcaccc cgaggagtgc atgtacgccg tgggccaggg cgccctgggc gtggaggtgc   720
gggccaagga ccaggacatc ctggacctgg tgggcgtgct gcacgacccc gagacctgc   780
tgcggtgcat cgccgagcgg gccttcctgc ggcacctgga gggcggctgc agcgtgcccg   840
tggccgtgca caccgccatg aaggacggcc agctgtacct gaccggcggc gtgtggagcc   900
tggacgggcag cgacagcatc caggagacca tgcaggccac catccacgtg cccgcccagc   960
acgaggacgg ccccgaggac gaccctcagc tggtgggcat caccgcccgg aacatcccac  1020
ggggccctca gctggccgcc cagaacctgg gcatcagcct ggccaacctg ctgctgagca  1080
agggcgccaa gaacatcctg gacgtggccc ggcagctgaa cgacgccac tgataatagt  1140
ccataaagta ggaaacacta cagctggagc ctcggtggcc atgcttcttg ccccttgggc  1200
ctccccccag cccctcctcc ccttcctgca cccgtacccc ccgcattatt actcacgta  1260
cgagtggtct ttgaataaag tctgagtggg cggc                             1294

SEQ ID NO: 142         moltype = RNA  length = 1294
FEATURE                Location/Qualifiers
misc_feature           1..1294
                        note = CONSTRUCT #23
source                 1..1294
                        mol_type = other RNA
                        organism = synthetic construct
SEQUENCE: 142
gggaaataag agagaaaaga agagtaagaa gaaatataag agccaccatg agcggcaacg    60
gcaacgccgc cgccaccgcc gaggagaaca gccccaagat gcgggtgatc cgggtgggca   120
cccggaagag ccagctggcg aggatccaga cggacagcgt ggtggcgacg ctgaaggcga   180
gctaccgggg gctgcagttc gagatcatcg cgatgagcac gacgggcgac aagatcctgg   240
acacggcgct gagcaagatc ggggagaaga gcctgttcac gaaggagctg gagcacgcgc   300
tggagaagaa cgaggtggac ctggtggtgc acagcctgaa ggacctgccc acggtgctgc   360
cgccggggtt cacgatcggg gcgatctgca gagggagaa cccgcacgac gcggtggtgt   420
tccaccccgaa gttcgtgggg aagacgctgg agacgctgcc ggagaagagc gtggtgggga   480
cgagcagcct gaggagggcg gcgcagctgc agaggaagtt cccgcacctg gagttcagga   540
gcatcagggg taacctgaac acgaggctga ggaagctgga cgagcagcag gagttcagcg   600
cgatcatcct ggcgacgccg ggctgcaga ggatgggctg gcacaacagg gtggggcaga   660
tcctgcaccc ggaggagtgc atgtacgccg tgggccaggg cgccctgggc gtggaggtga   720
gggcgaagga ccaggacatc ctggacctgg tgggcgtgct gcacgaccccg agacgctgc   780
tgaggtgcat cgccgagagg gcgttcctga ggcacctggag ggcggggtgc agcgtgccga   840
tggcggtgca caccgccatg aaggacgggc agctgtacct gacgggaggg gtgtggagcc   900
tggacggggag cgacagcatc caggagacga tgcaggcgac gatccacgtg ccggcgcagc   960
acgaggacgg gccggaggac gacccgcagc tggtgggat cacggcgagg aacatcccga  1020
ggggtccgca gctggcgggcg cagaacctgg gcatcagcct ggcgaacctg ctgctgagca  1080
agggagcgaa gaacatcctg gacgtggcga ggcagctgaa cgacgcgcac tgataatagt  1140
ccataaagta ggaaacacta cagctggagc ctcggtggcc atgcttcttg ccccttgggc  1200
ctccccccag cccctcctcc ccttcctgca cccgtacccc ccgcattatt actcacgta  1260
cgagtggtct ttgaataaag tctgagtggg cggc                             1294

SEQ ID NO: 143         moltype = RNA  length = 1294
FEATURE                Location/Qualifiers
misc_feature           1..1294
                        note = CONSTRUCT #24
source                 1..1294
                        mol_type = other RNA
                        organism = synthetic construct
SEQUENCE: 143
gggaaataag agagaaaaga agagtaagaa gaaatataag agccaccatg agcggcaacg    60
gcaacgccgc cgccaccgcc gaggagaaca gccccaagat gcgggtgatc cgggtgggca   120
cccggaagag ccagctggcc cgcatccaga ccgactccgt cgtcgccacc ctcaaggcct   180
cctaccccgg cctccagttc gagatcatcg ccatgtccac caccggcgac aagatcctcg   240
acaccgccct ctccaagatc ggcgagaagt ccctcttcac caaggagctc gagcacgccc   300
tcgagaagaa cgaggtcgac ctcgtcgtcc actcccccaa ggacctcccc accgtcctcc   360
cacccggctt caccatcggc gccatctgca gcgcgagaa ccctcacgac gccgtcgtct   420
tccaccccaa gttcgtcggc aagaccctcg agaccctccc cgagagtcc gtcgtcggca   480
cctcctcct ccgccgcgcc gcccagctcc agcgcaagtt cccacacctc gagttccgct   540
ccatccgcgg caacctcaac acccgcctgc ggaagctgga cgagcagcag gagttctcgc   600
ccatcatcct cgccaccgcc ggcctccagc gcatgggctg gcacaaccgc gtcggccaga   660
tcctccaccc cgaggagtgc atgtacgccg tcgccaggg cgccctcggc gtcgaggtcc   720
gcgccaagga ccaggacatc ctcgacctcg tcggcgtcct ccacgacccc gagaccctgc   780
tccgctgcat cgccgagcgc gccttcctcc gccacctcga gggcggctgc tccgtcccg   840
tcgccgtcca caccgccatg aaggacggcc agctctacct caccggcggc gtctggtccc   900
```

```
tcgacggctc cgactccatc caggagacca tgcaggccac catccacgtc ccgcccagc    960
acgaggacgg ccccgaggac gaccctcagc tcgtcggcat caccgcccgc aacatcccgc  1020
gcggccctca gctcgccgcc cagaacctcg gcatctccct cgccaacctc ctcctctcca  1080
agggcgccaa gaacatcctc gacgtcgccc gccagctcaa cgacgcccac tgataatagt  1140
ccataaagta ggaaacacta cagctggagc ctcggtggcc atgcttcttg ccccttgggc  1200
ctccccccag cccctcctcc ccttcctgca cccgtacccc ccgcattatt actcacggta  1260
cgagtggtct tgaataaagc tctgagtggg cggc                              1294

SEQ ID NO: 144          moltype = RNA   length = 1294
FEATURE                 Location/Qualifiers
misc_feature            1..1294
                        note = CONSTRUCT #27
source                  1..1294
                        mol_type = other RNA
                        organism = synthetic construct
SEQUENCE: 144
gggaaataag agagaaaaga agagtaagaa gaaatataag agccaccatg agcggcaacg    60
gcaacgccgc cgccaccgcc gaggagaaca gccccaagat gcgggtgatc cgggtgggca   120
cccggaagag ccagctggcc cggatccaga ccgacagcgt ggtggccacc ctgaaggcca   180
gctaccccgg cctgcagttc gagatcatcg ccatgagcac caccggcgac aagatcctgg   240
acaccgccct gagcaagatc ggcgagaaga gcctgttcac caaggagctg gagcacgccc   300
tggagaagaa cgaggtggac ctggtggtgc acagcctgaa ggacctgccc accgtgctgc   360
cgccggctt caccatcggc gccatctgca gcggggagaa cccgcacgac gccgtggtgt   420
tccaccccaa gttcgtgggc aagaccctgg agaccctgcc cgagaagagc gtggtgggca   480
ccagcagcct gcggcgggcc gcccagctgc agcggaagtt ccctcacctg gagttccgga   540
gcatccgggg caacctgaac acccggctgc ggaagctgga cgagcagcag gagttcagcg   600
ccatcatcct ggccaccgcc ggcctgcagc ggatgggctg gcacaaccgg gtgggccaga   660
tcctgcaccc cgaggagtgc atgtacgccg tgggccaggg cgccctgggc gtggaggtgc   720
gggccaagga ccaggacatc ctggacctgg tgggcgtgct gcacgacccc gagaccctgc   780
tgcggtgcat cgccgagcgg gccttcctgc ggcacctgga gggcggctgc agcgtgcccg   840
tggccgtgca caccgccatg aaggacggcc agctgtacct gaccggcggc gtgtggagcc   900
tggacggcag cgacagcatc caggagacca tgcaggccac catccacgtg cccgcccagc   960
acgaggacgg ccccgaggac gaccctcagc tggtgggcat caccgccgg aacatcccac  1020
ggggccctca gctggccgcc cagaacctgg gcatcagcct ggccaacctg ctgctgagca  1080
agggcgccaa gaacatcctg gacgtggccc ggcagctgaa cgacgcccac tgataatagt  1140
ccataaagta ggaaacacta cagctggagc ctcggtggcc tagcttcttg ccccttgggc  1200
ctccccccag cccctcctcc ccttcctgca cccgtacccc ccgcattatt actcacggta  1260
cgagtggtct tgaataaagc tctgagtggg cggc                              1294

SEQ ID NO: 145          moltype = RNA   length = 1272
FEATURE                 Location/Qualifiers
misc_feature            1..1272
                        note = CONSTRUCT #28
source                  1..1272
                        mol_type = other RNA
                        organism = synthetic construct
SEQUENCE: 145
gggaaataag agagaaaaga agagtaagaa gaaatataag agccaccatg agcggcaacg    60
gcaacgccgc cgccaccgcc gaggagaaca gccccaagat gcgggtgatc cgggtgggca   120
cccggaagag ccagctggcc cggatccaga ccgacagcgt ggtggccacc ctgaaggcca   180
gctaccccgg cctgcagttc gagatcatcg ccatgagcac caccggcgac aagatcctgg   240
acaccgccct gagcaagatc ggcgagaaga gcctgttcac caaggagctg gagcacgccc   300
tggagaagaa cgaggtggac ctggtggtgc acagcctgaa ggacctgccc accgtgctgc   360
cgccggctt caccatcggc gccatctgca gcggggagaa cccgcacgac gccgtggtgt   420
tccaccccaa gttcgtgggc aagaccctgg agaccctgcc cgagaagagc gtggtgggca   480
ccagcagcct gcggcgggcc gcccagctgc agcggaagtt ccctcacctg gagttccgga   540
gcatccgggg caacctgaac acccggctgc ggaagctgga cgagcagcag gagttcagcg   600
ccatcatcct ggccaccgcc ggcctgcagc ggatgggctg gcacaaccgg gtgggccaga   660
tcctgcaccc cgaggagtgc atgtacgccg tgggccaggg cgccctgggc gtggaggtgc   720
gggccaagga ccaggacatc ctggacctgg tgggcgtgct gcacgacccc gagaccctgc   780
tgcggtgcat cgccgagcgg gccttcctgc ggcacctgga gggcggctgc agcgtgcccg   840
tggccgtgca caccgccatg aaggacggcc agctgtacct gaccggcggc gtgtggagcc   900
tggacggcag cgacagcatc caggagacca tgcaggccac catccacgtg cccgcccagc   960
acgaggacgg ccccgaggac gaccctcagc tggtgggccc cccgccccgg aacatccac  1020
ggggccctca gctggccgcc cagaacctgg gcatcagcct ggccaacctg ctgctgagca  1080
agggcgccaa gaacatcctg gacgtggccc ggcagctgaa cgacgcccac tgataatagg  1140
ctggagcctc ggtggcctag cttcttgccc cttgggcctc ccccagccc ctcctcccct  1200
tcctgcaccc gtaccccctc cataaagtag gaaacactac agtggtcttt gaataaagtc  1260
tgagtgggcg gc                                                     1272

SEQ ID NO: 146          moltype = RNA   length = 1294
FEATURE                 Location/Qualifiers
misc_feature            1..1294
                        note = CONSTRUCT #25
source                  1..1294
                        mol_type = other RNA
                        organism = synthetic construct
SEQUENCE: 146
gggaaataag agagaaaaga agagtaagaa gaaatataag agccaccatg tccggaaacg    60
```

```
gaaacgccgc cgctaccgcc gaggaaaata gcccgaagat gagagtgatc cgggtgggta   120
ccaggaagtc ccagctcgcc aggatccaaa cggactcggt ggtggccacc ctcaaggcta   180
gctaccgggg cctgcaattc gagatcattg ctatgtccac caccggcgac aagatcctgg   240
atacggccct gtccaagatc ggcgaaaaga gcctcttcac caaggagctg aacacgcgc    300
tcgagaagaa cgaggtggac ctggtcgtcc acagcctcaa ggacctgcct acggtgctgc   360
cgccgggatt caccatcggc gccatctgta agcgggagaa tccgcacgac gccgtggtgt   420
tccaccctaa gttcgtgggc aagaccctcg agacactgcc ggaaaagtcc gtcgtgggca   480
cctcctccct gagaagggcc gctcagctcc agagaaagtt cccgcacctg gaattcagga   540
gcatccgggg caacctgaat acccggcttc gcaagctgga cgagcagcag gagttcagcg   600
ccatcatcct ggccaccgcc ggcctgcagc ggatgggctg gcacaacgg gtgggccaga    660
tcctgcaccc ggaggagtgc atgtatgccg tgggtcaggg agccctgggc gtggaggtcc   720
gggcaaagga ccaggacatc ctggaccctcg tgggcgtgct ccacgaccct gaaaccctcc   780
tgaggtgcat cgccgagagg gccttcctcc ggcacctgga gggcggctgt tccgtccctg   840
tggccgtgca taccgccatg aaggacggac agctgtacct gaccggccgg gtgtggtccc   900
tggacggctc cgacagcatc caggaaacca tgcaggccac tatccacgtg ccggcccagc   960
acgaagacgg cccagaggat gacccgcaac tggtcggcat taccgccagg aacataccaa  1020
ggggcccgca gctggccgcc cagaacctgg gcatctccct ggccaacctg ctgctgtcca  1080
agggagccaa gaacattctg gacgtgggcc aggcagctcaa tgatgcccac tgataatagt  1140
ccataaagta ggaaacacta cagctggagc ctcggtggcc atgcttcttg ccccttgggc  1200
ctcccccag cccctcctcc ccttcctgca cccgtacccc ccgcattatt actcacggta    1260
cgagtggtct ttgaataaag tctgagtggg cggc                               1294

SEQ ID NO: 147          moltype = RNA  length = 1294
FEATURE                 Location/Qualifiers
misc_feature            1..1294
                        note = CONSTRUCT #26
source                  1..1294
                        mol_type = other RNA
                        organism = synthetic construct
SEQUENCE: 147
gggaaataag agagaaaaga agagtaagaa gaaatataag agccaccatg agcggcaacg    60
gcaacgccgc cgccaccgca gaggagaata gcccgaagat gagggtgatc cgagtgggca   120
ccaggaagtc ccagcttgcg cgaattcaga ccgacagcgt ggtggccacc ctcaaggcct   180
cctaccgggg actccagttc gagatcatcg ccatgagcac gacgggagac aagatcctgg   240
acaccgccct gtccaagatc ggcgaaaaga gcctcttcac caaggagctg gagcacgccc   300
tggagaagaa cgaggtcgat ctggtggtgc acagcctgaa ggacctgccg accgtcctgc   360
cgccgggatt caccatcggt gccatctgta agcgggagaa cccgcacgac gccgtggtgt   420
tccacccgaa gttcgtcggc aagaccctgg aaaccctgcc ggagaagtcc gtggtgggca   480
ccagcagcct gaggcgggcc gccagctgc agcggaagtt cccgcacctg gaattcagga   540
gcatccgggg caacctgaac acccggctgc ggaagctgga cgagcagcag gagttcagcg   600
ccatcatcct ggccaccgca ggcctccagc gcatgggatg gcacaacagg gtaggccaaa   660
tcctgcaccc ggaggagtgt atgtacgccg tgggccaggg agccctgggc gtggaggtga   720
gagccaagga ccaggacatc ctagacctgg tcggcgtgct gcatgaccct gagacactgc   780
tgagatgcat cgcggagaga gccttcctgc gacacctgga gggcggctgc tccgtgccgt   840
tggccgtgca caccgccatg aaggacggcc agctgtatct gaccggccgg gtgtggagcc   900
tggacggcag cgactccatc caagaaacca tgcaggctac catccacgtg ccggcccagc   960
acgaggatgg accagaggac gatcctcaac tggtgggcat cactgccagg aacatcccaa  1020
gaggcccgca gctggccgcc cagaacctgg gcatcagcct ggccaacctg ctgctgtcca  1080
agggcgccaa gaacattctc gatgtggcca ggcagctgaa cgatgcccac tgataatagt  1140
ccataaagta ggaaacacta cagctggagc ctcggtggcc atgcttcttg ccccttgggc  1200
ctcccccag cccctcctcc ccttcctgca cccgtacccc ccgcattatt actcacggta    1260
cgagtggtct ttgaataaag tctgagtggg cggc                               1294

SEQ ID NO: 148          moltype = RNA  length = 1294
FEATURE                 Location/Qualifiers
misc_feature            1..1294
                        note = CONSTRUCT #27
source                  1..1294
                        mol_type = other RNA
                        organism = synthetic construct
SEQUENCE: 148
gggaaataag agagaaaaga agagtaagaa gaaatataag agccaccatg tcggaaaacg    60
gcaacgccgc cgccacggcc gaggagaaca gcccgaagat gagagtgatt agggtgggca   120
cccggaagtc ccaactcgcg cggatccaga ccgactcggt ggtggccacc ctcaaggcca   180
gctaccgggg cctccagttc gagattatcg ccatgtccac cacaggcgac aagatcctga   240
acaccgcact ctcgaagatc ggcgagaagt ccctgttcac caaggaactg gagcacgccc   300
tggagaagaa cgaggtggac ctggtggtgc actccctgaa ggacctgccg accgtgctcc   360
caccaggctt caccatcggc gcaatctgta gcgcgcgagaa tccgcacgac gccgtggtgt   420
tccacccaaa gttcgtgggc aagaccctcg aaaccctccc ggaaaagagc gtggtgggta   480
ccagctccct gcgagagct gcccagctcc agagaaagtt cccgcatctg gaattcagga   540
gcatcagggg aaatctgaat accagactgc gcaagctgga cgagcagcag gagttcagcg   600
ccatcatcct ggccaccgcc ggcctgcagc ggatgggctg gcacaacagg gtgggccaga   660
tactgcatcc ggaggagtgt atgtacgccg tgggccaggg cgccctcggc gtggaggtga   720
gagccaagga ccaagacatc ctggacctag tgggcgtgct gcatgaccct gaaaccctcc   780
tcaggtgcat cgccgagagg gccttcctgc ggcacctgga gggcggctgc agcgtgccgt   840
tggccgtcca caccgccatg aaggacggcc agctgtacct gaccggcggg gtctggagcc   900
tggacggatc cgacagcatc caggaaacca tgcaggccac catccacgtg ccggcccagc   960
acgaggacgg ccctgaggac gaccctcagc tggtgggcat caccgctagg aacatcccaa  1020
ggggcccgca gctggccgcc cagaacctcg gcatcagcct ggccaacctg ctgctgtcca  1080
```

```
agggcgccaa gaatatcctg gacgtggcca ggcagctgaa cgacgcccac tgataatagt   1140
ccataaagta ggaaacacta cagctggagc ctcggtggcc atgcttcttg ccccttgggc   1200
ctcccccag  ccctcctcc  ccttcctgca cccgtacccc ccgcattatt actcacggta   1260
cgagtggtct tgaataaag  tctgagtggg cggc                               1294
```

```
SEQ ID NO: 149              moltype = RNA    length = 164
FEATURE                     Location/Qualifiers
misc_feature                1..164
                            note = 3'UTR (miR142+miR126 variant 1)
source                      1..164
                            mol_type = other RNA
                            organism = synthetic construct
SEQUENCE: 149
tgataatagt ccataaagta ggaaacacta cagctggagc ctcggtggcc atgcttcttg    60
ccccttgggc ctcccccag  ccctcctcc  ccttcctgca cccgtacccc ccgcattatt   120
actcacggta cgagtggtct tgaataaag  tctgagtggg cggc                    164

SEQ ID NO: 150              moltype = RNA    length = 164
FEATURE                     Location/Qualifiers
misc_feature                1..164
                            note = 3'UTR (miR142+miR126 variant 2)
source                      1..164
                            mol_type = other RNA
                            organism = synthetic construct
SEQUENCE: 150
tgataatagt ccataaagta ggaaacacta cagctggagc ctcggtggcc tagcttcttg    60
ccccttgggc ctcccccag  ccctcctcc  ccttcctgca cccgtacccc ccgcattatt   120
actcacggta cgagtggtct tgaataaag  tctgagtggg cggc                    164

SEQ ID NO: 151              moltype = RNA    length = 142
FEATURE                     Location/Qualifiers
misc_feature                1..142
                            note = 3'UTR (miR142)
source                      1..142
                            mol_type = other RNA
                            organism = synthetic construct
SEQUENCE: 151
tgataatagg ctggagcctc ggtggcctag cttcttgccc cttgggcctc ccccagccc    60
ctcctcccct tcctgcaccc gtaccccctc cataaagtag gaaacactac agtggtcttt   120
gaataaagtc tgagtgggcg gc                                             142

SEQ ID NO: 152              moltype = AA    length = 361
FEATURE                     Location/Qualifiers
REGION                      1..361
                            note = PBGD GoF I291M/N340S
source                      1..361
                            mol_type = protein
                            organism = synthetic construct
SEQUENCE: 152
MSGNGNAAAT AEENSPKMRV IRVGTRKSQL ARIQTDSVVA TLKASYPGLQ FEIIAMSTTG    60
DKILDTALSK IGEKSLFTKE LEHALEKNEV DLVVHSLKDL PTVLPPGFTI GAICKRENPH   120
DAVVFHPKFV GKTLETLPEK SVVGTSSLRR AAQLQRKFPH LEFRSIRGNL NTRLRKLDEQ   180
QEFSAIILAT AGLQRMGWHN RVGQILHPEE CMYAVGQGAL GVEVRAKDQD ILDLVGVLHD   240
PETLLRCIAE RAFLRHLEGG CSVPVAVHTA MKDGQLYLTG GVWSLDGSDS MQETMQATIH   300
VPAQHEDGPE DDPQLVGITA RNIPRGPQLA AQNLGISLAS LLLSKGAKNI LDVARQLNDA   360
H                                                                   361

SEQ ID NO: 153              moltype = DNA    length = 1083
FEATURE                     Location/Qualifiers
misc_feature                1..1083
                            note = I291M / N340S
source                      1..1083
                            mol_type = other DNA
                            organism = synthetic construct
SEQUENCE: 153
atgagcggga acggcaacgc ggcagccacc gctgaggaaa actctccaaa aatgagagtc    60
attgggtgg  gcaccagaaa gagtcaactc gcaaggatcc agaccgactc tgtggtggcc   120
actctaaaag cgagctaccc cggactccag ttcgaaatca tcgccatgag caccaccggc   180
gataaaatcc tagataccgc cttgagcaag atcggcgaga agtccctctt taccaaggag   240
ctggagcacg ccctgagaa  aaacgaggtg atctggtgg  tccatagcct aaaggatctc   300
cctacagtgc tgcccccgg  gtttaccatc ggcgccattt gtaagcggga gaacccgcac   360
gacgcagtgg tcttccaccc caagtttgtg ggcaagacac tggagaccct gccggaaaag   420
tccgtggtgg gcacctccag cctgagacga ccgcccagc  tgcagcgcaa gtttccccac   480
ctggagttta gagcatcag  gggaaacctc aacaccagga agaaagct ggacgaacag   540
caggagttca gcgccatcat cctggcgact gcaggactcc agaggatggg ctggcataat   600
agggtgggac aaattctgca ccccgaggaa tgcatgtatg ctgtggggca gggcgcactc   660
ggggtggagg tgcgggccaa ggatcaggac atcctggacc tcgtgggcgt gcttcacgac   720
ccggaaaccc tgctgaggtg catagcagaa agagcttttcc tgcggcacct ggaggggga   780
tgcagcgtcc ctgtggccgt gcatacagcc atgaaggacg gccagctgta cttgactggt   840
```

```
ggcgtctggt cccttgatgg ctctgacagc atgcaggaaa caatgcaggc cactatccac  900
gtgcctgccc agcacgagga cggccccgag gacgaccctc agctggtggg cattaccgcc  960
agaaatatcc ctaggggacc ccagctggct gcccaaaact tgggcatcag cctggccagc 1020
ctgctgctga gcaaaggagc taaaaacatc ctggatgtgg ccaggcagct gaatgacgcc 1080
cac                                                                1083
```

```
SEQ ID NO: 154          moltype = AA   length = 604
FEATURE                 Location/Qualifiers
REGION                  1..604
                        note = APOA1-PBGD
source                  1..604
                        mol_type = protein
                        organism = synthetic construct
SEQUENCE: 154
MDEPPQSPWD RVKDLATVYV DVLKDSGRDY VSQFEGSALG KQLNLKLLDN WDSVTSTFSK  60
LREQLGPVTQ EFWDNLEKET EGLRQEMSKD LEEVKAKVQP YLDDFQKKWQ EEMELYRQKV 120
EPLRAELQEG ARQKLHELQE KLSPLGEEMR DRARAHVDAL RTHLAPYSDE LRQRLAARLE 180
ALKENGGARL AEYHAKATEH LSTLSEKAKP ALEDLRQGLL PVLESFKVSF LSALEEYTKK 240
LNTQSGNGNA AATAEENSPK MRVIRVGTRK SQLARIQTDS VVATLKASYP GLQFEIIAMS 300
TTGDKILDTA LSKIGEKSLF TKELEHALEK NEVDLVVHSL KDLPTVLPPG FTIGAICKRE 360
NPHDAVVFHP KFVGKTLETL PEKSVVGTSS LRRAAQLQRK FPHLEFRSIR GNLNTRLRKL 420
DEQQEFSAII LATAGLQRMG WHNRVGQILH PEECMYAVGQ GALGVEVRAK DQDILDLVGV 480
LHDPETLLRC IAERAFLRHL EGGCSVPVAV HTAMKDGQLY LTGGVWSLDG SDSMQETMQA 540
TIHVPAQHED GPEDDPQLVG ITARNIPRGP QLAAQNLGIS LASLLLSKGA KNILDVARQL 600
NDAH                                                              604
```

```
SEQ ID NO: 155          moltype = DNA   length = 1812
FEATURE                 Location/Qualifiers
misc_feature            1..1812
                        note = APOA1-PBGD
source                  1..1812
                        mol_type = other DNA
                        organism = synthetic construct
SEQUENCE: 155
atggacgaac cacccagtc accctgggat agagtcaaag acctggccac tgtgtacgtg   60
gacgtgctga agatagcgg gcgggattac gtctcgcagt tcgagggctc cgccttaggc  120
aaacagctga acctcaaact gctggacaat tgggactccg tcactagcac attctccaag  180
ctgagagagc agctgggacc tgtgactcag gagttctggg acaatctgga aggaaaact   240
gagggcctga ggcaggagat gtccaaggat ctggaggagg ttaaggcaaa ggtgcaaccc  300
tacctcgacg acttccagaa aaaatggcaa gaagagatgg agctataccg gcaaaaggtg  360
gagcctctcc gggccgagct ccaggagggc gctcggcaaa agctgcatga gctgcaggag  420
aagctgagcc ccctcggcga ggaaatgcgt gatagagcac gtgccccacgt ggacgccctg  480
cggacacatc tggctcccta cagcgatgag cttaggcaga gactgcgcgc  540
gctctgaagg agaatggcgg cgctcggctg gccgagtatc atgccaaggc caccgagcat  600
ttgtccactc tgagtgagaa ggctaagcct gccctggagg acctgaggca gggcctgtta  660
cccgtgctga gagcttcaa ggtgagcttt ctgagcgcct tggaggagta caccaaaaaa  720
ctgaacaccc agagcggcaa cggaaacgcc gccgctaccg ccgaggagaa cagccctaag  780
atgagggtga tcagggtggg cacccgcaag tcccagcttg cacgaatcca gaccgattca  840
gtcgtggcga ccctgaaggc atcttacccc ggcctgcagt tcgagattat cgccatgtct  900
acaaccggcg acaagatcct cgataccgcc ctgagcaaga tcggcgaaaa gagcctgttc  960
accaaagagc tagagcacgc cctcgagaaa aacgaggtgg accttgtggt gcatagcctc 1020
aaggatcttc ctaccgtgct gccccccggt ttcaccattg gggcaatctg caagagggag 1080
aatccccacg atgccgtggt gttccatccc aaattcgtgg gcaaaacgtt ggagaccctg 1140
cccgagaaaa gtgtggtcgg cactagcagc ctgagaagag cggcccaact tcagagaaag 1200
tttcctcacc tggagttcag gagcatccgg ggcaacctga cacccggcct gcggaagctg 1260
gacgagcagc aagagttcag cgctatcatt ctagcaacag ccggcctgca gcgcatggga 1320
tggcataaca gggtgggaca gattctccaa cccgaggaat gcatgtacgc cgttggccaa 1380
ggcgcgctgg gggtggaggt cagagcaaag gaccaggaca ttcttgatct ggtcggggtg 1440
ctgcacgacc ccgagacact gctgagatgc atagctgagc gggccttcct gcggcatctg 1500
gagggcggct gctcagtccc cgtggccgtg cacacagcca tgaaggacgg ccagctgtac 1560
ctgaccggag gggtgtggag cttggacggc agcgattcaa tgcaggagac aatgcaggca 1620
accatccacg ttccagctca gcacgaggat ggccccgaag atgaccctca gctggtgggg 1680
attactgcta gaaacatccc ccgcggcccc agctggccg cccaaaacct gggaatctct 1740
ctggcctccc tgctcctctc taaggagcc aagaatattc tggacgtggc acggcagctc 1800
aacgatgcac ac                                                    1812
```

```
SEQ ID NO: 156          moltype = RNA   length = 85
FEATURE                 Location/Qualifiers
misc_feature            1..85
                        note = miR-126
source                  1..85
                        mol_type = other RNA
                        organism = synthetic construct
SEQUENCE: 156
cgctggcgac gggacattat tactttggt acgcgctgtg acacttcaaa ctcgtaccgt   60
gagtaataat cgccgtcca cggca                                        85
```

```
SEQ ID NO: 157          moltype = RNA   length = 22
FEATURE                 Location/Qualifiers
```

```
misc_feature           1..22
                       note = miR 126-3p sequence
source                 1..22
                       mol_type = other RNA
                       organism = synthetic construct
SEQUENCE: 157
tcgtaccgtg agtaataatg cg                                                 22

SEQ ID NO: 158         moltype = RNA  length = 22
FEATURE                Location/Qualifiers
misc_feature           1..22
                       note = miR-126-3p binding site
source                 1..22
                       mol_type = other RNA
                       organism = synthetic construct
SEQUENCE: 158
cgcattatta ctcacggtac ga                                                 22

SEQ ID NO: 159         moltype = RNA  length = 21
FEATURE                Location/Qualifiers
misc_feature           1..21
                       note = miR 126-5p sequence
source                 1..21
                       mol_type = other RNA
                       organism = synthetic construct
SEQUENCE: 159
cattattact tttggtacgc g                                                  21

SEQ ID NO: 160         moltype = RNA  length = 21
FEATURE                Location/Qualifiers
misc_feature           1..21
                       note = miR-126-5p binding site
source                 1..21
                       mol_type = other RNA
                       organism = synthetic construct
SEQUENCE: 160
cgcgtaccaa aagtaataat g                                                  21

SEQ ID NO: 161         moltype = RNA  length = 133
FEATURE                Location/Qualifiers
misc_feature           1..133
                       note = 3'UTR with miR 142-3p binding site
source                 1..133
                       mol_type = other RNA
                       organism = synthetic construct
SEQUENCE: 161
gctggagcct cggtggccat gcttcttgcc ccttgggcct cccccagcc cctcctcccc         60
ttcctgcacc cgtacccct ccataaagta ggaaacacta cagtggtctt tgaataaagt        120
ctgagtgggc ggc                                                          133

SEQ ID NO: 162         moltype = RNA  length = 141
FEATURE                Location/Qualifiers
misc_feature           1..141
                       note = 3'UTR with miR 126-3p binding site
source                 1..141
                       mol_type = other RNA
                       organism = synthetic construct
SEQUENCE: 162
tgataatagg ctggagcctc ggtggccatg cttcttgccc cttgggcctc ccccagccc         60
ctcctcccct tcctgcaccc gtaccccccg cattattact cacggtacga gtggtctttg       120
aataaagtct gagtgggcgg c                                                 141

SEQ ID NO: 163         moltype = RNA  length = 119
FEATURE                Location/Qualifiers
misc_feature           1..119
                       note = (3' UTR, no miR binding sites variant 2)
source                 1..119
                       mol_type = other RNA
                       organism = synthetic construct
SEQUENCE: 163
tgataatagg ctggagcctc ggtggcctag cttcttgccc cttgggcctc ccccagccc         60
ctcctcccct tcctgcaccc gtaccccgt ggtctttgaa taaagtctga gtgggcggc        119

SEQ ID NO: 164         moltype = RNA  length = 141
FEATURE                Location/Qualifiers
misc_feature           1..141
                       note = (3' UTR with miR 126-3p binding site variant 3)
source                 1..141
                       mol_type = other RNA
```

```
                        organism = synthetic construct
SEQUENCE: 164
tgataatagg ctggagcctc ggtggcctag cttcttgccc cttgggcctc ccccccagccc    60
ctcctcccct tcctgcaccc gtaccccccg cattattact cacggtacga gtggtctttg    120
aataaagtct gagtgggcgg c                                              141

SEQ ID NO: 165          moltype = RNA   length = 188
FEATURE                 Location/Qualifiers
misc_feature            1..188
                        note = 3' UTR with 3 miR 142-3p binding sites
source                  1..188
                        mol_type = other RNA
                        organism = synthetic construct
SEQUENCE: 165
tgataatagt ccataaagta ggaaacacta cagctggagc ctcggtggcc atgcttcttg     60
cccccttggg c ctccataaag taggaaacac tacatccccc cagcccctcc tcccttcct   120
gcacccgtac ccctccata aagtaggaaa cactacagtg gtctttgaat aaagtctgag    180
tgggcggc                                                             188

SEQ ID NO: 166          moltype = RNA   length = 140
FEATURE                 Location/Qualifiers
misc_feature            1..140
                        note = 3'UTR with miR 142-5p binding site
source                  1..140
                        mol_type = other RNA
                        organism = synthetic construct
SEQUENCE: 166
tgataatagg ctggagcctc ggtggccatg cttcttgccc cttgggcctc ccccccagccc   60
ctcctcccct tcctgcaccc gtaccccag tagtgctttc tactttatgg tggtctttga    120
ataaagtctg agtgggcggc                                                140

SEQ ID NO: 167          moltype = RNA   length = 182
FEATURE                 Location/Qualifiers
misc_feature            1..182
                        note = 3' UTR with 3 miR 142-5p binding sites
source                  1..182
                        mol_type = other RNA
                        organism = synthetic construct
SEQUENCE: 167
tgataataga gtagtgcttt ctactttatg gctggagcct cggtggccat gcttcttgcc    60
ccttgggcca gtagtgcttt ctactttatg tccccccagc ccctcctccc cttcctgcac   120
ccgtaccccc agtagtgctt tctactttat ggtggtcttt gaataaagtc tgagtgggcg   180
gc                                                                   182

SEQ ID NO: 168          moltype = RNA   length = 184
FEATURE                 Location/Qualifiers
misc_feature            1..184
                        note = 3'UTR with 2 miR 142-5p binding sites and 1 miR
                         142-3p bindingsite
source                  1..184
                        mol_type = other RNA
                        organism = synthetic construct
SEQUENCE: 168
tgataataga gtagtgcttt ctactttatg gctggagcct cggtggccat gcttcttgcc    60
ccttgggcct ccataaagta ggaaacacta catccccccca gccctcctc cccttcctgc    120
acccgtaccc ccagtagtgc tttctacttt atggtggtct tgaataaag tctgagtggg    180
cggc                                                                 184

SEQ ID NO: 169          moltype = RNA   length = 142
FEATURE                 Location/Qualifiers
misc_feature            1..142
                        note = 3'UTR with miR 155-5p binding site
source                  1..142
                        mol_type = other RNA
                        organism = synthetic construct
SEQUENCE: 169
tgataatagg ctggagcctc ggtggccatg cttcttgccc cttgggcctc ccccccagccc   60
ctcctcccct tcctgcaccc gtaccccac ccctatcaca attagcatta agtggtcttt    120
gaataaagtc tgagtgggcg gc                                             142

SEQ ID NO: 170          moltype = RNA   length = 188
FEATURE                 Location/Qualifiers
misc_feature            1..188
                        note = 3' UTR with 3 miR 155-5p binding sites
source                  1..188
                        mol_type = other RNA
                        organism = synthetic construct
SEQUENCE: 170
tgataataga cccctatcac aattagcatt aagctggagc ctcggtggcc atgcttcttg    60
```

```
cccttgggc caccccctatc acaattagca ttaatccccc cagcccctcc tcccttcct    120
gcacccgtac ccccacccct atcacaatta gcattaagtg gtctttgaat aaagtctgag    180
tgggcggc                                                              188

SEQ ID NO: 171         moltype = RNA   length = 188
FEATURE                Location/Qualifiers
misc_feature           1..188
                       note = 3'UTR with 2 miR 155-5p binding sites and 1 miR
                        142-3p bindingsite
source                 1..188
                       mol_type = other RNA
                       organism = synthetic construct
SEQUENCE: 171
tgataataga cccctatcac aattagcatt aagctggagc ctcggtggcc atgcttcttg    60
cccttgggc ctccataaag taggaaacac tacatccccc cagcccctcc tcccttcct    120
gcacccgtac ccccacccct atcacaatta gcattaagtg gtctttgaat aaagtctgag    180
tgggcggc                                                              188

SEQ ID NO: 172         moltype = RNA   length = 142
FEATURE                Location/Qualifiers
misc_feature           1..142
                       note = 3'UTR with miR 142-3p binding site, P3 insertion
source                 1..142
                       mol_type = other RNA
                       organism = synthetic construct
SEQUENCE: 172
tgataatagg ctggagcctc ggtggccatg cttcttgccc cttgggcctc cataaagtag    60
gaaacactac atccccccag ccctcctcc ccttcctgca cccgtacccc cgtggtcttt    120
gaataaagtc tgagtgggcg gc                                              142

SEQ ID NO: 173         moltype = RNA   length = 22
FEATURE                Location/Qualifiers
misc_feature           1..22
                       note = miR 146-3p sequence
source                 1..22
                       mol_type = other RNA
                       organism = synthetic construct
SEQUENCE: 173
cctctgaaat tcagttcttc ag                                              22

SEQ ID NO: 174         moltype = RNA   length = 22
FEATURE                Location/Qualifiers
misc_feature           1..22
                       note = miR 146-5p sequence
source                 1..22
                       mol_type = other RNA
                       organism = synthetic construct
SEQUENCE: 174
tgagaactga attccatggg tt                                              22

SEQ ID NO: 175         moltype = RNA   length = 22
FEATURE                Location/Qualifiers
misc_feature           1..22
                       note = miR 155-3p sequence
source                 1..22
                       mol_type = other RNA
                       organism = synthetic construct
SEQUENCE: 175
ctcctacata ttagcattaa ca                                              22

SEQ ID NO: 176         moltype = RNA   length = 23
FEATURE                Location/Qualifiers
misc_feature           1..23
                       note = 3' UTR
source                 1..23
                       mol_type = other RNA
                       organism = synthetic construct
SEQUENCE: 176
ttaatgctaa tcgtgatagg ggt                                             23

SEQ ID NO: 177         moltype = RNA   length = 22
FEATURE                Location/Qualifiers
misc_feature           1..22
                       note = miR 16-3p sequence
source                 1..22
                       mol_type = other RNA
                       organism = synthetic construct
SEQUENCE: 177
ccagtattaa ctgtgctgct ga                                              22
```

```
SEQ ID NO: 178          moltype = RNA   length = 22
FEATURE                 Location/Qualifiers
misc_feature            1..22
                        note = miR 16-5p sequence
source                  1..22
                        mol_type = other RNA
                        organism = synthetic construct
SEQUENCE: 178
tagcagcacg taaatattgg cg                                                  22

SEQ ID NO: 179          moltype = RNA   length = 21
FEATURE                 Location/Qualifiers
misc_feature            1..21
                        note = miR 21-3p sequence
source                  1..21
                        mol_type = other RNA
                        organism = synthetic construct
SEQUENCE: 179
caacaccagt cgatgggctg t                                                   21

SEQ ID NO: 180          moltype = RNA   length = 22
FEATURE                 Location/Qualifiers
misc_feature            1..22
                        note = miR 21-5p sequence
source                  1..22
                        mol_type = other RNA
                        organism = synthetic construct
SEQUENCE: 180
tagcttatca gactgatgtt ga                                                  22

SEQ ID NO: 181          moltype = RNA   length = 22
FEATURE                 Location/Qualifiers
misc_feature            1..22
                        note = miR 223-3p sequence
source                  1..22
                        mol_type = other RNA
                        organism = synthetic construct
SEQUENCE: 181
tgtcagtttg tcaaataccc ca                                                  22

SEQ ID NO: 182          moltype = RNA   length = 22
FEATURE                 Location/Qualifiers
misc_feature            1..22
                        note = miR 223-5p sequence
source                  1..22
                        mol_type = other RNA
                        organism = synthetic construct
SEQUENCE: 182
cgtgtatttg acaagctgag tt                                                  22

SEQ ID NO: 183          moltype = RNA   length = 22
FEATURE                 Location/Qualifiers
misc_feature            1..22
                        note = miR 24-3p sequence
source                  1..22
                        mol_type = other RNA
                        organism = synthetic construct
SEQUENCE: 183
tggctcagtt cagcaggaac ag                                                  22

SEQ ID NO: 184          moltype = RNA   length = 22
FEATURE                 Location/Qualifiers
misc_feature            1..22
                        note = miR 24-5p sequence
source                  1..22
                        mol_type = other RNA
                        organism = synthetic construct
SEQUENCE: 184
tgcctactga gctgatatca gt                                                  22

SEQ ID NO: 185          moltype = RNA   length = 21
FEATURE                 Location/Qualifiers
misc_feature            1..21
                        note = miR 27-3p sequence
source                  1..21
                        mol_type = other RNA
                        organism = synthetic construct
SEQUENCE: 185
```

```
ttcacagtgg ctaagttccg c                                              21

SEQ ID NO: 186          moltype = RNA   length = 22
FEATURE                 Location/Qualifiers
misc_feature            1..22
                        note = miR 27-5p sequence
source                  1..22
                        mol_type = other RNA
                        organism = synthetic construct
SEQUENCE: 186
agggcttagc tgcttgtgag ca                                             22

SEQ ID NO: 187          moltype = RNA   length = 23
FEATURE                 Location/Qualifiers
misc_feature            1..23
                        note = miR 155-5p sequence
source                  1..23
                        mol_type = other RNA
                        organism = synthetic construct
SEQUENCE: 187
ttaatgctaa ttgtgatagg ggt                                            23

SEQ ID NO: 188          moltype = RNA   length = 23
FEATURE                 Location/Qualifiers
misc_feature            1..23
                        note = miR 155-5p binding site
source                  1..23
                        mol_type = other RNA
                        organism = synthetic construct
SEQUENCE: 188
acccctatca caattagcat taa                                            23

SEQ ID NO: 189          moltype = RNA   length = 70
FEATURE                 Location/Qualifiers
misc_feature            1..70
                        note = 5' UTR with miR142-3p binding site at position p1
source                  1..70
                        mol_type = other RNA
                        organism = synthetic construct
SEQUENCE: 189
gggaaataag agtccataaa gtaggaaaca ctacaagaaa agaagagtaa gaagaaatat     60
aagagccacc                                                           70

SEQ ID NO: 190          moltype = RNA   length = 70
FEATURE                 Location/Qualifiers
misc_feature            1..70
                        note = 5' UTR with miR142-3p binding site at position p2
source                  1..70
                        mol_type = other RNA
                        organism = synthetic construct
SEQUENCE: 190
gggaaataag agagaaaaga agagtaatcc ataaagtagg aaacactaca gaagaaatat     60
aagagccacc                                                           70

SEQ ID NO: 191          moltype = RNA   length = 70
FEATURE                 Location/Qualifiers
misc_feature            1..70
                        note = 5' UTR with miR142-3p binding site at position p3
source                  1..70
                        mol_type = other RNA
                        organism = synthetic construct
SEQUENCE: 191
gggaaataag agagaaaaga agagtaagaa gaaatataat ccataaagta ggaaacacta     60
cagagccacc                                                           70

SEQ ID NO: 192          moltype = RNA   length = 188
FEATURE                 Location/Qualifiers
misc_feature            1..188
                        note = (3' UTR with 3 miR 142-3p binding sites variant 2)
source                  1..188
                        mol_type = other RNA
                        organism = synthetic construct
SEQUENCE: 192
tgataatagt ccataaagta ggaaacacta cagctggagc ctcggtggcc tagcttcttg     60
cccttgggc ctccataaag taggaaacac tacatccccc cagcccctcc tccccttcct    120
gcacccgtac cccctccata agtaggaaa cactacagtg gtctttgaat aaagtctgag    180
tgggcggc                                                            188

SEQ ID NO: 193          moltype = RNA   length = 142
```

```
FEATURE                  Location/Qualifiers
misc_feature             1..142
                         note = (3'UTR with miR 142-3p binding site, P1 insertion
                          variant 2)
source                   1..142
                         mol_type = other RNA
                         organism = synthetic construct
SEQUENCE: 193
tgataatagt ccataaagta ggaaacacta cagctggagc ctcggtggcc tagcttcttg    60
ccccttgggc ctcccccag ccctcctcc ccttcctgca cccgtacccc cgtggtcttt    120
gaataaagtc tgagtgggcg gc                                            142

SEQ ID NO: 194           moltype = RNA  length = 142
FEATURE                  Location/Qualifiers
misc_feature             1..142
                         note = (3'UTR with miR 142-3p binding site, P2 insertion
                          variant 2)
source                   1..142
                         mol_type = other RNA
                         organism = synthetic construct
SEQUENCE: 194
tgataatagg ctggagcctc ggtggctcca taaagtagga aacactacac tagcttcttg    60
ccccttgggc ctcccccag ccctcctcc ccttcctgca cccgtacccc cgtggtcttt    120
gaataaagtc tgagtgggcg gc                                            142

SEQ ID NO: 195           moltype = RNA  length = 181
FEATURE                  Location/Qualifiers
misc_feature             1..181
                         note = (3'UTR with 3 miR 142-5p binding sites)
source                   1..181
                         mol_type = other RNA
                         organism = synthetic construct
SEQUENCE: 195
tgataataga gtagtgcttt ctactttatg gctggagcct cggtggccat gcttcttgcc    60
ccttgggcca gtagtgcttt ctactttatg tccccccagc ccctctcccc ttcctgcacc    120
cgtaccccca gtagtgcttt ctactttatg gtggtctttg aataaagtct gagtgggcgg    180
c                                                                    181

SEQ ID NO: 196           moltype = RNA  length = 142
FEATURE                  Location/Qualifiers
misc_feature             1..142
                         note = (3'UTR with miR 142-3p binding site, P3 insertion
                          variant 2)
source                   1..142
                         mol_type = other RNA
                         organism = synthetic construct
SEQUENCE: 196
tgataatagg ctggagcctc ggtggcctag cttcttgccc cttgggcctc cataaagtag    60
gaaacactac atccccccag ccctcctcc ccttcctgca cccgtacccc cgtggtcttt    120
gaataaagtc tgagtgggcg gc                                            142

SEQ ID NO: 197           moltype = RNA  length = 142
FEATURE                  Location/Qualifiers
misc_feature             1..142
                         note = (3'UTR with miR 155-5p binding site variant 2)
source                   1..142
                         mol_type = other RNA
                         organism = synthetic construct
SEQUENCE: 197
tgataatagg ctggagcctc ggtggcctag cttcttgccc cttgggcctc ccccagccc    60
ctcctcccct tcctgcaccc gtaccccac ccctatcaca attagcatta agtggtcttt    120
gaataaagtc tgagtgggcg gc                                            142

SEQ ID NO: 198           moltype = RNA  length = 188
FEATURE                  Location/Qualifiers
misc_feature             1..188
                         note = (3' UTR with 3 miR 155-5p binding sites variant 2)
source                   1..188
                         mol_type = other RNA
                         organism = synthetic construct
SEQUENCE: 198
tgataataga cccctatcac aattagcatt aagctggagc ctcggtggcc tagcttcttg    60
ccccttgggc cacccctatc acaattagca ttaatccccc cagcccctcc tcccttcct    120
gcacccgtac ccccacccct atcacaatta gcattaagtg tctttgaat aaagtctgag    180
tgggcggc                                                             188

SEQ ID NO: 199           moltype = RNA  length = 188
FEATURE                  Location/Qualifiers
misc_feature             1..188
```

```
                    note = (3'UTR with 2 miR 155-5p binding sites and 1 miR
                    142-3p bindingsite variant 2)
source              1..188
                    mol_type = other RNA
                    organism = synthetic construct
SEQUENCE: 199
tgataataga cccctatcac aattagcatt aagctggagc ctcggtggcc tagcttcttg  60
ccccttgggc ctccataaag taggaaacac tacatccccc cagcccctcc tccccttcct  120
gcaccegtac ccccacccct atcacaatta gcattaagtg gtctttgaat aaagtctgag  180
tgggcggc                                                            188
```

POLYNUCLEOTIDES ENCODING PORPHOBILINOGEN DEAMINASE FOR THE TREATMENT OF ACUTE INTERMITTENT PORPHYRIA

CROSS-REFERENCE TO RELATED APPLICATIONS

This application is a continuation of U.S. application Ser. No. 16/302,339, filed on Nov. 16, 2018, which is the National Stage of International Application No. PCT/US2017/033418, filed on May 18, 2017, which claims the priority benefit of U.S. Provisional Application No. 62/338,161, filed May 18, 2016 and EP Application No. EP17382259.4, filed May 9, 2017, each of which is hereby incorporated by reference herein in its entirety.

REFERENCE TO A SEQUENCE LISTING SUBMITTED ELECTRONICALLY VIA EFS-WEB

This application contains a Sequence Listing that has been submitted electronically as an XML file named 45817-0011002_SL_ST26.xml. The XML file, created on Jul. 20, 2022, is 382,804 bytes in size. The material in the XML file is hereby incorporated by reference in its entirety.

BACKGROUND

Acute intermittent porphyria (AIP) is an autosomal dominant metabolic disorder associated with impaired production of heme, the oxygen-binding prosthetic group of hemoglobin. The causative gene for AIP is porphobilinogen deaminase (PBGD) (NM_000190; NP_000181; also referred to as hydroxymethylbilane synthase (HMBS or HM-synthase) and uroporphyrinogen I synthase). Song G et al., *FASEB J.* 23: 396-404 (2009). PBGD (E.C. 2.5.1.61) is one of the eight enzymes involved in the porphyrin-heme biosynthetic pathway. PBGD's biological function is to catalyze the head to tail condensation of four porphobilinogen molecules into the linear hydroxymethylbilane. There are two primary isoforms of PBGD: the 44-kDa housekeeping enzyme (isoform 1), which is expressed in all tissues, and the 42-kDa erythrocyte-specific enzyme (isoform 2). The ubiquitous PBGD isoform 1 is 361 amino acid residues, while the erythrocyte-specific variant (PBGD isoform 2) is 344 amino acids. Id.

Mutations within the PBGD gene can result in the complete or partial loss of PBGD function, resulting in impaired heme production and the abnormal accumulation of aminolevulinic acid (ALA) and porphobilinogen (PBG) in cytoplasm of cells, plasma and urine. Id.

While signs and symptoms can be variable, patients suffering from AIP often exhibit neurological (e.g., agitation, delirium, seizures, loss of motor function, respiratory paralysis) and gastrointestinal (e.g., extreme abdominal pain, vomiting, painful urination) issues. These signs and symptoms can be triggered by various factors (e.g., drugs, hormones, and alcohol) and usually occur as episodes or attacks that develop over course of several hours or few days. Hrdinka M et al., *Physiol Res.* 2: S119-36 (2006). In between these episodes or attacks, AIP patients can otherwise appear healthy. However, if left untreated, AIP can potentially cause life-threatening complications, including death. AIP has an estimate prevalence of about 5.9 per million people worldwide (Elder G et al., *J. Inherit. Metab. Dis.* 36:849-57 (2012)). While AIP patients from all ethnic groups have been reported, the disorder is much more prevalent in both the Dutch and Swedish populations (1 in 10,000 to 8 in 10,000). Tjensvoll K et al., *Dis Markers.* 19: 41-6 (2003-2004).

Historic treatment for AIP was primarily via lifestyle modification (e.g., avoiding alcohol, smoking and known porphyrogenic drugs and diet) and management of individual sign and symptoms. Badminton M N et al., *Int J Clin Pract.* 56: 272-8 (2002). In extreme cases, regular hematin infusions and/or liver transplantation had been recommended. Seth A K et al., *Liver Transpl.* 13: 1219-27 (2007).

Today, the current Standard of Care (SOC) for AIP is Panhematin therapy, also known as "hemin" therapy. The SOC therapy is based on a down-regulation of hepatic heme synthesis using heme administration. Notably however, heme therapy is indicated only if an acute attack of porphyria is proven by a marked increase in urine PBG. Moreover, there remain several unmet medical needs including ineffectiveness in chronic AIP, and short-acting efficacy (lasts only 1-2 days). Moreover, recurrent hyper-activation of the hepatic heme synthesis pathway can be associated with neurological and metabolic manifestations and long-term complications including chronic kidney disease and increased risk of hepatocellular carcinoma in certain AIP patients. Prophylactic heme infusion can be an effective strategy in some of these patients, but it induces tolerance and its frequent application may be associated with thromboembolic disease and hepatic siderosis.

Emerging therapies including enzyme replacement therapy (ERT) or gene therapy (e.g., HMBS-gene transfer), as well as a potential therapy based on ALAS1-gene expression inhibition, are being developed. Zymenex (also known as "Porphozym"), a recombinant human PBGD, failed in Phase 3 clinical trials in 2009. While the therapy had an excellent safety profile, the treatment failed to sufficiently reduce the levels of the surrogate markers of PBGD activity (i.e., PBG and ALA). In the trial, PBG declined, but ALA did not. Moreover, the PBG enzyme wasn't targeted to hepatocytes. In a Phase I open label liver-directed gene therapy clinical trial for acute intermittent porphyria, D'Avola and colleagues reported the results of the first gene therapy trial for AIP and the first-in-human use of AAV5 in which they showed evidence of safety, although there was no clear efficacy signal. It is possible that the biology of the disease and the lack of reliable read-outs might account for the lack of efficacy. To date, orthotopic liver transplantation is the only curative treatment in patients with recurrent acute attacks.

Thus, with the exception of liver transplants, most treatments often fail to completely and reliably treat the disorder. Therefore, there is an ongoing need for improved therapeutics to treat AIP.

BRIEF SUMMARY

The present invention provides mRNA therapeutics for the treatment of acute intermittent porphyria (AIP). The mRNA therapeutics of the invention are particularly well-suited for the treatment of AIP as the technology provides for the intracellular delivery of mRNA encoding PBGD followed by de novo synthesis of functional PBGD protein within target cells. The instant invention features the incorporation of modified nucleotides within therapeutic mRNAs to (1) minimize unwanted immune activation (e.g., the innate immune response associated with the in vivo introduction of foreign nucleic acids) and (2) optimize the translation efficiency of mRNA to protein. Exemplary aspects of the invention feature a combination of nucleotide modifications to reduce the innate immune response and sequence optimization, in particular, within the open reading frame (ORF) of therapeutic mRNAs encoding PBGD to enhance protein expression.

In further embodiments, the mRNA therapeutic technology of the instant invention also features delivery of mRNA encoding PBGD via a lipid nanoparticle (LNP) delivery system. The instant invention features novel ionizable lipid-based LNPs which have improved properties when combined with mRNA encoding PBGD and administered in vivo, for example, cellular uptake, intracellular transport and/or endosomal release or endosomal escape. The LNP formulations of the invention also demonstrate reduced immunogenicity associated with the in vivo administration of LNPs.

In certain aspects, the invention relates to compositions and delivery formulations comprising a polynucleotide, e.g., a ribonucleic acid (RNA), e.g., a messenger RNA (mRNA), encoding porphobilinogen deaminase and methods for treating acute intermittent porphyria (AIP) in a subject in need thereof by administering the same.

The present disclosure provides a pharmaceutical composition comprising a lipid nanoparticle encapsulated mRNA that comprises an open reading frame (ORF) encoding an porphobilinogen deaminase (PBGD) polypeptide, wherein the composition is suitable for administration to a human subject in need of treatment for acute intermittent porphyria (AIP).

The present disclosure further provides a pharmaceutical composition comprising: (a) a mRNA that comprises (i) an open reading frame (ORF) encoding an porphobilinogen deaminase (PBGD) polypeptide, wherein the ORF comprises at least one chemically modified nucleobase, sugar, backbone, or any combination thereof, (ii) an untranslated region (UTR) comprising a microRNA (miRNA) binding site; and (b) a delivery agent, wherein the pharmaceutical composition is suitable for administration to a human subject in need of treatment for acute intermittent porphyria (AIP).

The present disclosure further provides a pharmaceutical composition comprising an mRNA comprising an open reading frame (ORF) encoding a human porphobilinogen deaminase (PBGD) polypeptide, wherein the composition when administered to a subject in need thereof as a single intravenous dose is sufficient to reduce urinary excretion of: (i) aminolevulinate acid (ALA) at least 2-fold, at least 5-fold, at least 10-fold, at least 20-fold or at least 50-fold as compared to a reference ALA excretion level (e.g., during an acute porphyria attack), for at least 24 hours, at least 48 hours, at least 72 hours, at least 96 hours, or at least 120 hours post-administration, (ii) porphobilinogen (PBG) at least 2-fold, at least 5-fold, at least 10-fold, at least 20-fold or at least 50-fold as compared to a reference PBG excretion level (e.g., during an acute porphyria attack), for at least 24 hours, at least 48 hours, at least 72 hours, at least 96 hours, or at least 120 hours post-administration, and/or (iii) porphyrin at least at least 2-fold, at least 5-fold, at least 10-fold, at least 20-fold or at least 50-fold as compared to a reference porphyrin excretion level (e.g., during an acute porphyria attack), for at least 24 hours, at least 48 hours, at least 72 hours, at least 96 hours, or at least 120 hours post-administration.

The present disclosure further provides a pharmaceutical composition comprising an mRNA comprising an open reading frame (ORF) encoding a human porphobilinogen deaminase (PBGD) polypeptide, wherein the composition when administered to a subject in need thereof as a single intravenous dose is sufficient to reduce urinary excretion of: (i) aminolevulinate acid (ALA) by at least 50%, at least 60%, at least 70%, at least 80%, at least 90%, at least 95% or at least 98%, at least 99%, or 100% as compared to the subject's baseline level or a reference ALA excretion level (e.g., in a subject with AIP or during an acute porphyria attack), for at least 24 hours, at least 48 hours, at least 72 hours, at least 96 hours, or at least 120 hours post-administration, (ii) porphobilinogen (PBG) by at least 50%, at least 60%, at least 70%, at least 80%, at least 90%, at least 95% or at least 98%, at least 99%, or 100% as compared to the subject's baseline level or a reference PBG excretion level (e.g., in a subject with AIP or during an acute porphyria attack), for at least 24 hours, at least 48 hours, at least 72 hours, at least 96 hours, or at least 120 hours post-administration, and/or (iii) porphyrin by at least 50%, at least 60%, at least 70%, at least 80%, at least 90%, at least 95% or at least 98%, at least 99%, or 100% as compared to the subject's baseline level or a reference porphyrin excretion level (e.g., in a subject with AIP or during an acute porphyria attack), for at least 24 hours, at least 48 hours, at least 72 hours, at least 96 hours, or at least 120 hours post-administration.

The present disclosure further provides a pharmaceutical composition comprising an mRNA comprising an open reading frame (ORF) encoding a human porphobilinogen deaminase (PBGD) polypeptide, wherein the composition when administered to a subject in need thereof as a single intravenous dose is sufficient to reduce serum levels of: (i) alanine transaminase (ALT) to at least within 10-fold, at least within 5-fold, at least within 2-fold, or at least within 1.5-fold or to within at least 50%, at least 40%, at least 30%, at least 20%, or at least 10% of a reference ALT serum level within at least 24 hours, at least 48 hours, at least 72 hours, at least 96 hours, or at least 120 hours post-administration, (ii) aspartate transaminase (AST) to at least within 10-fold, at least within 5-fold, at least within 2-fold, or at least within 1.5-fold or within at least 50%, at least 40%, at least 30%, at least 20%, or at least 10% of a reference AST serum level, for at least 24 hours, at least 48 hours, at least 72 hours, at least 96 hours, or at least 120 hours post-administration, and/or (iii) bilirubin to at least within 10-fold, at least within 5-fold, at least within 2-fold, or at least within 1.5 fold or within at least 50%, at least 40%, at least 30%, at least 20%, or at least 10% of a reference bilirubin serum level, for at least 24 hours, at least 48 hours, at least 72 hours, at least 96 hours, or at least 120 hours post-administration.

The present disclosure further provides a pharmaceutical composition comprising an mRNA comprising an open reading frame (ORF) encoding a human porphobilinogen deaminase (PBGD) polypeptide, wherein the composition when administered to a subject in need thereof as a single intravenous dose is sufficient to reduce serum levels of: (i) alanine transaminase (ALT) by at least 90%, at least 80%, at least 70%, at least 60%, at least 50%, at least 40%, or at least 30% as compared to the subject's baseline level or a reference ALT serum level (e.g., in a subject with AIP or during an acute porphyria attack), within at least 24 hours, at least 48 hours, at least 72 hours, at least 96 hours, or at least 120 hours post-administration, (ii) aspartate transaminase (AST) by at least 90%, at least 80%, at least 70%, at least 60%, at least 50%, at least 40%, or at least 30% as compared to the subject's baseline level or a reference AST serum level (e.g., in a subject with AIP or during an acute porphyria attack), for at least 24 hours, at least 48 hours, at least 72 hours, at least 96 hours, or at least 120 hours post-administration, and/or (iii) bilirubin by at least 90%, at least 80%, at least 70%, at least 60%, at least 50%, at least 40%, or at least 30% as compared to the subject's baseline level or a reference bilirubin serum level (e.g., in a subject with AIP or during an acute porphyria attack), for at least 24 hours, at least 48 hours, at least 72 hours, at least 96 hours, or at least 120 hours post-administration.

The present disclosure further provides a pharmaceutical composition comprising an mRNA comprising an open reading frame (ORF) encoding a human porphobilinogen deaminase (PBGD) polypeptide, wherein the composition when administered to a subject in need thereof as a single intravenous dose is sufficient to: (i) maintain hepatic PBGD activity levels at or above a reference physiological level or at a supraphysiological level for at least 24 hours, at least 48 hours, at least 72 hours, at least 96 hours, or at least 120 hours post-administration, and/or (ii) maintain hepatic PBGD activity levels at 50% or more of a reference hepatic PBGD activity level for at least 24 hours, at least 48 hours, at least 72 hours, or at least 96 hours post-administration.

In some embodiments, the pharmaceutical compositions disclosed herein further comprise a delivery agent.

The present disclosure provides a polynucleotide comprising an open reading frame (ORF) encoding a porphobilinogen deaminase (PBGD) polypeptide, wherein the uracil or thymine content of the ORF relative to the theoretical minimum uracil or thymine content of a nucleotide sequence encoding the PBGD polypeptide (% $U_{TM}$ or % $T_{TM}$), is between about 100% and about 150%. In some embodiments, the % $U_{TM}$ or % $T_{TM}$ is between about 105% and about 145%, between about 105% and about 140%, between about 110% and about 140%, between about 110% and about 145%, between about 115% and about 135%, between about 105% and about 135%, between about 110% and about 135%, between about 115% and about 145%, or between about 115% and about 140%. In some embodiments, the uracil or thymine content of the ORF relative to the uracil or thymine content of the corresponding wild-type ORF (% $U_{WT}$ or % $T_{WT}$) is less than 100%. In some embodiments, the % $U_{WT}$ or % $T_{WT}$ is less than about 95%, less than about 90%, less than about 85%, less than 80%, less than 79%, less than 78%, less than 77%, less than 76%, less than 75%, less than 74%, or less than 73%. In some embodiments, the % $U_{WT}$ or % $T_{WT}$ is between 65% and 73%. In some embodiments, the uracil or thymine content in the ORF relative to the total nucleotide content in the ORF (% $U_{TL}$ or % $T_{TL}$) is less than about 50%, less than about 40%, less than about 30%, or less than about 19%. In some embodiments, the % $U_{TL}$ or % $T_{TL}$ is less than about 19%. In some embodiments, the % $U_{TL}$ or % $T_{TL}$ is between about 13% and about 15%. In some embodiments, the guanine content of the ORF with respect to the theoretical maximum guanine content of a nucleotide sequence encoding the PBGD polypeptide (% $G_{TMX}$) is at least 69%, at least 70%, at least 75%, at least about 80%, at least about 85%, at least about 90%, at least about 95%, or about 100%. In some embodiments, the % $G_{TMX}$ is between about 70% and about 80%, between about 71% and about 79%, between about 71% and about 78%, or between about 71% and about 77%.

In some embodiments, the cytosine content of the ORF relative to the theoretical maximum cytosine content of a nucleotide sequence encoding the PBGD polypeptide (% $C_{TMX}$) is at least 59%, at least 60%, at least about 65%, at least about 70%, at least about 75%, at least about 80%, at least about 85%, at least about 90%, at least about 95%, or about 100%. In some embodiments, the % $C_{TMX}$ is between about 60% and about 80%, between about 62% and about 80%, between about 63% and about 79%, or between about 68% and about 76%. In some embodiments, the guanine and cytosine content (G/C) of the ORF relative to the theoretical maximum G/C content in a nucleotide sequence encoding the PBGD polypeptide (% $G/G_{TMX}$) is at least about 81%, at least about 85%, at least about 90%, at least about 95%, or about 100%. In some embodiments, the % $G/G_{TMX}$ is between about 80% and about 100%, between about 85% and about 99%, between about 90% and about 97%, or between about 91% and about 96%. In some embodiments, the G/C content in the ORF relative to the G/C content in the corresponding wild-type ORF (% $G/C_{WT}$) is at least 102%, at least 103%, at least 104%, at least 105%, at least 106%, at least 107%, at least 110%, at least 115%, or at least 120%. In some embodiments, the average G/C content in the $3^{rd}$ codon position in the ORF is at least 20%, at least 21%, at least 22%, at least 23%, at least 24%, at least 25%, at least 26%, at least 27%, at least 28%, at least 29%, or at least 30% higher than the average G/C content in the $3^{rd}$ codon position in the corresponding wild-type ORF.

In some embodiments, the ORF has at least 87%, at least 88%, at least 89%, at least 90%, at least 91%, at least 92%, at least 93%, at least 94%, at least 95%, at least 96%, at least 97%, at least 98%, at least 99%, or 100% sequence identity to a sequence selected from the group consisting of SEQ ID NOs: 9 to 33, and 89 to 117. In some embodiments, the ORF has at least 85%, at least 90%, at least 91%, at least 92%, at least 93%, at least 94%, at least 95%, at least 96%, at least 97%, at least 98%, at least 99%, or 100% sequence identity to a nucleic acid sequence selected from the group consisting of SEQ ID NOs: 9 to 33, and 89 to 117. In some embodiments, the ORF has at least 85%, at least 90%, at least 91%, at least 92%, at least 93%, at least 94%, at least 95%, at least 96%, at least 97%, at least 98%, at least 99%, or 100% sequence identity to the nucleic acid sequence of SEQ ID NO: 104, 112, or 114. In some embodiments, the ORF has at least 95%, at least 96%, at least 97%, at least 98%, at least 99%, or 100% sequence identity to the nucleic acid sequence of SEQ ID NO: 104, 112, or 114. In some embodiments, the ORF comprises the nucleic acid sequence of SEQ ID NO: 104, 112, or 114.

In some embodiments, the PBGD polypeptide comprises an amino acid sequence at least about 95%, at least about 96%, at least about 97%, at least about 98%, at least about 99%, or about 100% identical to (i) the polypeptide sequence of wild type PBGD, isoform 1 (SEQ ID NO: 1), (ii) the polypeptide sequence of wild type PBGD, isoform 2 (SEQ ID NO: 3), the polypeptide sequence of wild type PBGD, isoform 3 (SEQ ID NO: 5), or the polypeptide sequence of wild type PBGD, isoform 4 (SEQ ID NO: 7), and wherein the PBGD polypeptide has porphobilinogen deaminase activity. In some embodiments, the PBGD polypeptide is a variant, derivative, or mutant having a porphobilinogen deaminase activity (e.g., the SM gain of function variant, SEQ ID NO: 152). In some embodiments, the gain-of-function mutant PBGD comprises an I291M mutation, an N340S mutation, or a combination thereof. In some embodiments, the gain-of-function mutant PBGD comprises the polypeptide sequence of SEQ ID NO:152. In some embodiments, the PBGD polypeptide is a PBGD fusion protein. In some embodiments, the PBGD fusion protein comprises heterologous protein moiety. In some embodiments, the heterologous protein moiety is an apolipoprotein. In some embodiments, the apolipoprotein is human apolipoprotein A1. In some embodiments, the human apolipoprotein A1 is mature human apolipoprotein A1. In some embodiments, a fusion protein comprising PBGD and mature human apolipoprotein A1 comprises the polypeptide sequence of SEQ ID NO: 154.

In some embodiments, the polynucleotide sequence further comprises a nucleotide sequence encoding a transit peptide.

In some embodiments, the polynucleotide is single stranded. In some embodiments, the polynucleotide is double stranded. In some embodiments, the polynucleotide is DNA. In some embodiments, the polynucleotide is RNA. In some embodiments, the polynucleotide is mRNA. In some embodiments, the polynucleotide comprises at least one chemically modified nucleobase, sugar, backbone, or any combination thereof. In some embodiments, the at least one chemically modified nucleobase is selected from the group consisting of pseudouracil (ψ), N1-methylpseudouracil (m1ψ), 2-thiouracil (s2U), 4'-thiouracil, 5-methylcytosine, 5-methyluracil, and any combination thereof. In some embodiments, the at least one chemically modified nucleobase is selected from the group consisting of pseudouracil (ψ), N1-methylpseudouracil (m1ψ), 1-ethylpseudouracil, 2-thiouracil (s2U), 4'-thiouracil, 5-methylcytosine, 5-methyluracil, 5-methoxyuracil, and any combination thereof. In some embodiments, the at least one chemically modified nucleobase is 5-methoxyuracil. In some embodiments, at least about 25%, at least about 30%, at least about 40%, at least about 50%, at least about 60%, at least about 70%, at least about 80%, at least about 90%, at least about 95%, at least about 99%, or 100% of the uracils are 5-methoxyuracils. In some embodiments, at least about 25%, at least about 30%, at least about 40%, at least about 50%, at least about 60%, at least about 70%, at least about 80%, at least about 90%, at least about 95%, at least about 99%, or 100% of the uracils or thymines are chemically modified. In some embodiments, at least about 25%, at least about 30%, at least about 40%, at least about 50%, at least about 60%, at least about 70%, at least about 80%, at least about 90%, at least about 95%, at least about 99%, or 100% of the guanines are chemically modified. In some embodiments, at least about 25%, at least about 30%, at least about 40%, at least about 50%, at least about 60%, at least about 70%, at least about 80%, at least about 90%, at least about 95%, at least about 99%, or 100% of the cytosines are chemically modified. In some embodiments, at least about 25%, at least about 30%, at least about 40%, at least about 50%, at least about 60%, at least about 70%, at least about 80%, at least about 90%, at least about 95%, at least about 99%, or 100% of the adenines are chemically modified.

In some embodiments, the polynucleotide further comprises a miRNA binding site.

In some embodiments, the polynucleotide comprises at least two different microRNA (miR) binding sites.

In some embodiments, the microRNA is expressed in an immune cell of hematopoietic lineage or a cell that expresses TLR7 and/or TLR8 and secretes pro-inflammatory cytokines and/or chemokines, and wherein the polynucleotide (e.g., mRNA) comprises one or more modified nucleobases.

In some embodiments, the mRNA comprises at least one first microRNA binding site of a microRNA abundant in an immune cell of hematopoietic lineage and at least one second microRNA binding site is of a microRNA abundant in endothelial cells.

In some embodiments, the mRNA comprises multiple copies of a first microRNA binding site and at least one copy of a second microRNA binding site.

In some embodiments, the mRNA comprises first and second microRNA binding sites of the same microRNA.

In some embodiments, the microRNA binding sites are of the 3p and 5p arms of the same microRNA.

In some embodiments, the microRNA binding site comprises one or more nucleotide sequences selected from Table 3 or Table 4.

In some embodiments, the microRNA binding site binds to miR-126, miR-142, miR-144, miR-146, miR-150, miR-155, miR-16, miR-21, miR-223, miR-24, miR-27 or miR-26a, or any combination thereof.

In some embodiments, the microRNA binding site binds to miR126-3p, miR-142-3p, miR-142-5p, or miR-155, or any combination thereof.

In some embodiments, the microRNA binding site is a miR-126 binding site. In some embodiments, at least one microRNA binding site is a miR-142 binding site. In some embodiments, one microRNA binding site is a miR-126 binding site and the second microRNA binding site is for a microRNA selected from the group consisting of miR-142-3p, miR-142-5p, miR-146-3p, miR-146-5p, miR-155, miR-16, miR-21, miR-223, miR-24 and miR-27.

In some embodiments, the mRNA comprises at least one miR-126-3p binding site and at least one miR-142-3p binding site. In some embodiments, the mRNA comprises at least one miR-142-3p binding site and at least one 142-5p binding site.

In some embodiments, the microRNA binding sites are located in the 5' UTR, 3' UTR, or both the 5' UTR and 3' UTR of the mRNA. In some embodiments, the microRNA binding sites are located in the 3' UTR of the mRNA. In some embodiments, the microRNA binding sites are located in the 5' UTR of the mRNA. In some embodiments, the microRNA binding sites are located in both the 5' UTR and 3' UTR of the mRNA. In some embodiments, at least one microRNA binding site is located in the 3' UTR immediately adjacent to the stop codon of the coding region of the mRNA. In some embodiments, at least one microRNA binding site is located in the 3' UTR 70-80 bases downstream of the stop codon of the coding region of the mRNA. In some embodiments, at least one microRNA binding site is located in the 5' UTR immediately preceding the start codon of the coding region of the mRNA. In some embodiments, at least one microRNA binding site is located in the 5' UTR 15-20 nucleotides preceding the start codon of the coding region of the mRNA. In some embodiments, at least one microRNA binding site is located in the 5' UTR 70-80 nucleotides preceding the start codon of the coding region of the mRNA.

In some embodiments, the mRNA comprises multiple copies of the same microRNA binding site positioned immediately adjacent to each other or with a spacer of less than 5, 5-10, 10-15, or 15-20 nucleotides.

In some embodiments, the mRNA comprises multiple copies of the same microRNA binding site located in the 3' UTR, wherein the first microRNA binding site is positioned immediately adjacent to the stop codon and the second and third microRNA binding sites are positioned 30-40 bases downstream of the 3' most residue of the first microRNA binding site.

In some embodiments, the microRNA binding site comprises one or more nucleotide sequences selected from SEQ ID NO:36 and SEQ ID NO:38. In some embodiments, the miRNA binding site binds to miR-142. In some embodiments, the miRNA binding site binds to miR-142-3p or miR-142-5p. In some embodiments, the miR-142 comprises SEQ ID NO: 34.

In some embodiments, the microRNA binding site comprises one or more nucleotide sequences selected from SEQ ID NO:158 and SEQ ID NO:160. In some embodiments, the miRNA binding site binds to miR-126. In some embodiments, the miRNA binding site binds to miR-126-3p or miR-126-5p. In some embodiments, the miR-126 comprises SEQ ID NO: 156.

In some embodiments, the mRNA comprises a 3' UTR comprising a microRNA binding site that binds to miR-142, miR-126, or a combination thereof.

In some embodiments, the polynucleotide, e.g., mRNA, further comprises a 3' UTR. In some embodiments, the 3' UTR comprises a nucleic acid sequence at least about 90%, at least about 95%, at least about 96%, at least about 97%, at least about 98%, at least about 99%, or 100% identical to a 3'UTR sequence selected from the group consisting of SEQ ID NOs: 57 to 81, 84, 149 to 151, 161 to 172, 192 to 199, or any combination thereof. In some embodiments, the miRNA binding site is located within the 3' UTR.

In some embodiments, the 3' UTR comprises a nucleic acid sequence selected from the group consisting of SEQ ID NOs: 57 to 81, 84, 149 to 151, 161 to 172, 192 to 199, and any combination thereof. In some embodiments, the mRNA comprises a 3' UTR comprising a nucleic acid sequence selected from the group consisting of SEQ ID NOs: 149 to 151, or any combination thereof. In some embodiments, the mRNA comprises a 3' UTR comprising a nucleic acid sequence of SEQ ID NO: 150. In some embodiments, the mRNA comprises a 3' UTR comprising a nucleic acid sequence of SEQ ID NO: 151.

In some embodiments, the polynucleotide, e.g., mRNA, further comprises a 5' UTR. In some embodiments, the 5' UTR comprises a nucleic acid sequence at least 90%, at least about 95%, at least about 96%, at least about 97%, at least about 98%, at least about 99%, or about 100% identical to a 5'UTR sequence selected from the group consisting of SEQ ID NO: 39 to 56, 83, 189 to 191, or any combination thereof. In some embodiments, the 5' UTR comprises a sequence selected from the group consisting of SEQ ID NO: 39 to 56, 83, 189 to 191, and any combination thereof. In some embodiments, the mRNA comprises a 5' UTR comprising the nucleic acid sequence of SEQ ID NO: 39.

In some embodiments, the polynucleotide, e.g., mRNA, further comprises a 5' terminal cap. In some embodiments, the 5' terminal cap comprises a Cap0, Cap1, ARCA, inosine, N1-methyl-guanosine, 2'-fluoro-guanosine, 7-deaza-guanosine, 8-oxo-guanosine, 2-amino-guanosine, LNA-guanosine, 2-azidoguanosine, Cap2, Cap4, 5' methylG cap, or an analog thereof. In some embodiments, the 5' terminal cap comprises a Cap1.

In some embodiments, the polynucleotide, e.g., mRNA, further comprises a poly-A region. In some embodiments, the poly-A region is at least about 10, at least about 20, at least about 30, at least about 40, at least about 50, at least about 60, at least about 70, at least about 80, or at least about 90 nucleotides in length. In some embodiments, the poly-A region has about 10 to about 200, about 20 to about 180, about 50 to about 160, about 70 to about 140, about 80 to about 120 nucleotides in length.

In some embodiments, the polynucleotide, e.g., mRNA, encodes a PBGD polypeptide that is fused to one or more heterologous polypeptides. In some embodiments, the one or more heterologous polypeptides increase a pharmacokinetic property of the PBGD polypeptide. In some embodiments, upon administration to a subject, the polynucleotide has (i) a longer plasma half-life; (ii) increased expression of a PBGD polypeptide encoded by the ORF; (iii) a lower frequency of arrested translation resulting in an expression fragment; (iv) greater structural stability; or (v) any combination thereof, relative to a corresponding polynucleotide comprising SEQ ID NO: 2, 4, 6, 8, or 153. In some embodiments, the polynucleotide encodes a PBGD polypeptide that is fused to human apolipoprotein A1 (e.g., SEQ ID NO: 155).

In some embodiments, the polynucleotide, e.g., mRNA, comprises (i) a 5'-terminal cap; (ii) a 5'-UTR; (iii) an ORF encoding a PBGD polypeptide; (iv) a 3'-UTR; and (v) a poly-A region. In some embodiments, the 3'-UTR comprises a miRNA binding site. In some embodiments, the polynucleotide comprises a nucleic acid sequence selected from the group consisting of SEQ ID NO: 118-148, for example, SEQ ID NO: 133, 141, 144, or 145. In some embodiments the polynucleotide further comprises a 5'-terminal cap (e.g., Cap1) and a poly-A-tail region (e.g., about 100 nucleotides in length).

The present disclosure also provides a method of producing a polynucleotide, e.g., mRNA, of the present invention, the method comprising modifying an ORF encoding a PBGD polypeptide by substituting at least one uracil nucleobase with an adenine, guanine, or cytosine nucleobase, or by substituting at least one adenine, guanine, or cytosine nucleobase with a uracil nucleobase, wherein all the substitutions are synonymous substitutions. In some embodiments, the method further comprises replacing at least about 90%, at least about 95%, at least about 99%, or about 100% of uracils with 5-methoxyuracils.

The present disclosure also provides a composition comprising (a) a polynucleotide, e.g., mRNA, of the invention; and (b) a delivery agent. In some embodiments, the delivery agent comprises a lipidoid, a liposome, a lipoplex, a lipid nanoparticle, a polymeric compound, a peptide, a protein, a cell, a nanoparticle mimic, a nanotube, or a conjugate. In some embodiments, the delivery agent comprises a lipid nanoparticle. In some embodiments, the lipid nanoparticle comprises a lipid selected from the group consisting of 3-(didodecylamino)-N1,N1,4-tridodecyl-1-piperazineethanamine (KL10), N1-[2-(didodecylamino)ethyl]-N1,N4,N4-tridodecyl-1,4-piperazinediethanamine (KL22), 14,25-ditridecyl-15,18,21,24-tetraaza-octatriacontane (KL25),
1,2-dilinoleyloxy-N,N-dimethylaminopropane (DLinDMA),
2,2-dilinoleyl-4-dimethylaminomethyl-[1,3]-dioxolane (DLin-K-DMA), heptatriaconta-6,9,28,31-tetraen-19-yl 4-(dimethylamino)butanoate (DLin-MC3-DMA),
2,2-dilinoleyl-4-(2-dimethylaminoethyl)[1,3]-dioxolane (DLin-KC2-DMA),
1,2-dioleyloxy-N,N-dimethylaminopropane (DODMA), (13Z,16SZ)—N,N-dimethyl-3-nonydocosa-13-16-dien-1-amine (L608),
2-({8-[(3β)-cholest-5-en-3-yloxy]octyl}oxy)-N,N-dimethyl-3-[(9Z,12Z)-octadeca-9,12-dien-1-yloxy]propan-1-amine (Octyl-CLinDMA),
(2R)-2-({8-[(3β)-cholest-5-en-3-yloxy]octyl}oxy)-N,N-dimethyl-3-[(9Z,12Z)-octadeca-9,12-dien-1-yloxy]propan-1-amine (Octyl-CLinDMA (2R)),
(2S)-2-({8-[(3β)-cholest-5-en-3-yloxy]octyl}oxy)-N,N-dimethyl-3-[(9Z,12Z)-octadeca-9,
12-dien-1-yloxy]propan-1-amine (Octyl-CLinDMA (2S)), and any combinations thereof.

In some embodiments, the lipid nanoparticle comprises DLin-MC3-DMA.

In some embodiments, the delivery agent comprises a compound having the Formula (I)

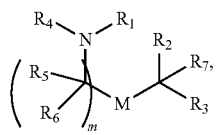

(I)

or a salt or stereoisomer thereof, wherein
$R_1$ is selected from the group consisting of $C_{5-30}$ alkyl, $C_{5-20}$ alkenyl, —R*YR", —YR", and —R"M'R';
$R_2$ and $R_3$ are independently selected from the group consisting of H, $C_{1-14}$ alkyl, $C_{2-14}$ alkenyl, —R*YR", —YR", and —R*OR", or $R_2$ and $R_3$, together with the atom to which they are attached, form a heterocycle or carbocycle;
$R_4$ is selected from the group consisting of a $C_{3-6}$ carbocycle, —$(CH_2)_nQ$, —$(CH_2)_nCHQR$, —CHQR, —$CQ(R)_2$, and unsubstituted $C_{1-6}$ alkyl, where Q is selected from a carbocycle, heterocycle, —OR, —$O(CH_2)_nN(R)_2$, —C(O)OR, —OC(O)R, —$CX_3$, —$CX_2H$, —$CXH_2$, —CN, —$N(R)_2$, —$C(O)N(R)_2$, —N(R)C(O)R, —$N(R)S(O)_2R$, —$N(R)C(O)N(R)_2$, —$N(R)C(S)N(R)_2$, —$N(R)R_8$, —$O(CH_2)_nOR$, —$N(R)C(=NR_9)N(R)_2$, —$N(R)C(=CHR_9)N(R)_2$, —OC(O)N(R)_2$, —N(R)C(O)OR, —N(OR)C(O)R, —$N(OR)S(O)_2R$, —N(OR)C(O)OR, —$N(OR)C(O)N(R)_2$, —$N(OR)C(S)N(R)_2$, —$N(OR)C(=NR_9)N(R)_2$, —$N(OR)C(=CHR_9)N(R)_2$, —$C(=NR_9)N(R)_2$, —$C(=NR_9)R$, —C(O)N(R)OR, and —$C(R)N(R)_2C(O)OR$, and each n is independently selected from 1, 2, 3, 4, and 5;
each $R_5$ is independently selected from the group consisting of $C_{1-3}$ alkyl, $C_{2-3}$ alkenyl, and H;
each $R_6$ is independently selected from the group consisting of $C_{1-3}$ alkyl, $C_{2-3}$ alkenyl, and H;
M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —$S(O)_2$—, —S—S—, an aryl group, and a heteroaryl group;
$R_7$ is selected from the group consisting of $C_{1-3}$ alkyl, $C_{2-3}$ alkenyl, and H;
$R_8$ is selected from the group consisting of $C_{3-6}$ carbocycle and heterocycle;
$R_9$ is selected from the group consisting of H, CN, $NO_2$, $C_{1-6}$ alkyl, —OR, —$S(O)_2R$, —$S(O)_2N(R)_2$, $C_{2-6}$ alkenyl, $C_{3-6}$ carbocycle and heterocycle;
each R is independently selected from the group consisting of $C_{1-3}$ alkyl, $C_{2-3}$ alkenyl, and H;
each R' is independently selected from the group consisting of $C_{1-18}$ alkyl, $C_{2-18}$ alkenyl, —R*YR", —YR", and H;
each R" is independently selected from the group consisting of $C_{3-14}$ alkyl and $C_{3-14}$ alkenyl;
each R* is independently selected from the group consisting of $C_{1-12}$ alkyl and $C_{2-12}$ alkenyl;
each Y is independently a $C_{3-6}$ carbocycle;
each X is independently selected from the group consisting of F, Cl, Br, and I; and
m is selected from 5, 6, 7, 8, 9, 10, 11, 12, and 13; and
provided when $R_4$ is —$(CH_2)_nQ$, —$(CH_2)_nCHQR$, —CHQR, or —$CQ(R)_2$, then (i) Q is not —$N(R)_2$ when n is 1, 2, 3, 4 or 5, or (ii) Q is not 5, 6, or 7-membered heterocycloalkyl when n is 1 or 2.

The present disclosure also provides a composition comprising a nucleotide sequence encoding a PBGD polypeptide and a delivery agent, wherein the delivery agent comprises a compound having the Formula (I)

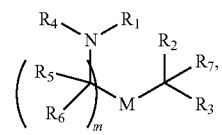

(I)

or a salt or stereoisomer thereof, wherein
$R_1$ is selected from the group consisting of $C_{5-30}$ alkyl, $C_{5-20}$ alkenyl, —R*YR", —YR", and —R"M'R';
$R_2$ and $R_3$ are independently selected from the group consisting of H, $C_{1-14}$ alkyl, $C_{2-14}$ alkenyl, —R*YR", —YR", and —R*OR", or $R_2$ and $R_3$, together with the atom to which they are attached, form a heterocycle or carbocycle;
$R_4$ is selected from the group consisting of a $C_{3-6}$ carbocycle, —$(CH_2)_nQ$, —$(CH_2)_nCHQR$, —CHQR, —$CQ(R)_2$, and unsubstituted $C_{1-6}$ alkyl, where Q is selected from a carbocycle, heterocycle, —OR, —$O(CH_2)_nN(R)_2$, —C(O)OR, —OC(O)R, —$CX_3$, —$CX_2H$, —$CXH_2$, —CN, —$N(R)_2$, —$C(O)N(R)_2$, —N(R)C(O)R, —$N(R)S(O)_2R$, —$N(R)C(O)N(R)_2$, —$N(R)C(S)N(R)_2$, —$N(R)R_8$, —$O(CH_2)_nOR$, —$N(R)C(=NR_9)N(R)_2$, —$N(R)C(=CHR_9)N(R)_2$, —$OC(O)N(R)_2$, —N(R)C(O)OR, —N(OR)C(O)R, —$N(OR)S(O)_2R$, —N(OR)C(O)OR, —$N(OR)C(O)N(R)_2$, —$N(OR)C(S)N(R)_2$, —$N(OR)C(=NR_9)N(R)_2$, —$N(OR)C(=CHR_9)N(R)_2$, —$C(=NR_9)N(R)_2$, —$C(=NR_9)R$, —C(O)N(R)OR, and —$C(R)N(R)_2C(O)OR$, and each n is independently selected from 1, 2, 3, 4, and 5;
each $R_5$ is independently selected from the group consisting of $C_{1-3}$ alkyl, $C_{2-3}$ alkenyl, and H;
each $R_6$ is independently selected from the group consisting of $C_{1-3}$ alkyl, $C_{2-3}$ alkenyl, and H;
M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —$S(O)_2$—, —S—S—, an aryl group, and a heteroaryl group;
$R_7$ is selected from the group consisting of $C_{1-3}$ alkyl, $C_{2-3}$ alkenyl, and H;
$R_8$ is selected from the group consisting of $C_{3-6}$ carbocycle and heterocycle;
$R_9$ is selected from the group consisting of H, CN, $NO_2$, $C_{1-6}$ alkyl, —OR, —$S(O)_2R$, —$S(O)_2N(R)_2$, $C_{2-6}$ alkenyl, $C_{3-6}$ carbocycle and heterocycle;
each R is independently selected from the group consisting of $C_{1-3}$ alkyl, $C_{2-3}$ alkenyl, and H;
each R' is independently selected from the group consisting of $C_{1-18}$ alkyl, $C_{2-18}$ alkenyl, —R*YR", —YR", and H;
each R" is independently selected from the group consisting of $C_{3-14}$ alkyl and $C_{3-14}$ alkenyl;
each R* is independently selected from the group consisting of $C_{1-12}$ alkyl and $C_{2-12}$ alkenyl;
each Y is independently a $C_{3-6}$ carbocycle;
each X is independently selected from the group consisting of F, Cl, Br, and I; and
m is selected from 5, 6, 7, 8, 9, 10, 11, 12, and 13; and
provided when $R_4$ is —$(CH_2)_nQ$, —$(CH_2)_nCHQR$, —CHQR, or —$CQ(R)_2$, then (i) Q is not —$N(R)_2$ when n is 1, 2, 3, 4 or 5, or (ii) Q is not 5, 6, or 7-membered heterocycloalkyl when n is 1 or 2.

In some embodiments, the delivery agent comprises a compound having the Formula (I), or a salt or stereoisomer thereof, wherein $R_1$ is selected from the group consisting of $C_{5-20}$ alkyl, $C_{5-20}$ alkenyl, —R*YR", —YR", and —R"M'R';

$R_2$ and $R_3$ are independently selected from the group consisting of H, $C_{1-14}$ alkyl, $C_{2-14}$ alkenyl, —R*YR", —YR", and —R*OR", or $R_2$ and $R_3$, together with the atom to which they are attached, form a heterocycle or carbocycle;

$R_4$ is selected from the group consisting of a $C_{3-6}$ carbocycle, —$(CH_2)_nQ$, —$(CH_2)_n$CHQR, —CHQR, —CQ$(R)_2$, and unsubstituted $C_{1-6}$ alkyl, where Q is selected from a carbocycle, heterocycle, —OR, —O$(CH_2)_n$N$(R)_2$, —C(O)OR, —OC(O)R, —$CX_3$, —$CX_2$H, —$CXH_2$, —CN, —N$(R)_2$, —C(O)N$(R)_2$, —N(R)C(O)R, —N(R)S$(O)_2$R, —N(R)C(O)N$(R)_2$, —N(R)C(S)N$(R)_2$, and —C(R)N$(R)_2$C(O)OR, and each n is independently selected from 1, 2, 3, 4, and 5;

each $R_5$ is independently selected from the group consisting of $C_{1-3}$ alkyl, $C_{2-3}$ alkenyl, and H;

each $R_6$ is independently selected from the group consisting of $C_{1-3}$ alkyl, $C_{2-3}$ alkenyl, and H;

M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —S(O)$_2$—, an aryl group, and a heteroaryl group;

$R_7$ is selected from the group consisting of $C_{1-3}$ alkyl, $C_{2-3}$ alkenyl, and H;

each R is independently selected from the group consisting of $C_{1-3}$ alkyl, $C_{2-3}$ alkenyl, and H;

each R' is independently selected from the group consisting of $C_{1-18}$ alkyl, $C_{2-18}$ alkenyl, —R*YR", —YR", and H;

each R" is independently selected from the group consisting of $C_{3-14}$ alkyl and $C_{3-14}$ alkenyl;

each R* is independently selected from the group consisting of $C_{1-12}$ alkyl and $C_{2-12}$ alkenyl;

each Y is independently a $C_{3-6}$ carbocycle;

each X is independently selected from the group consisting of F, Cl, Br, and I; and m is selected from 5, 6, 7, 8, 9, 10, 11, 12, and 13; and provided when $R_4$ is —$(CH_2)_nQ$, —$(CH_2)_n$CHQR, —CHQR, or —CQ$(R)_2$, then (i) Q is not —N$(R)_2$ when n is 1, 2, 3, 4 or 5, or (ii) Q is not 5, 6, or 7-membered heterocycloalkyl when n is 1 or 2.

In some embodiments, the compound is of Formula (IA):

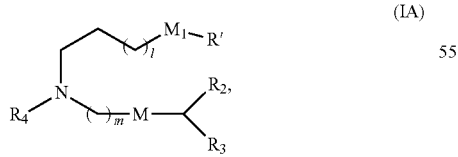

or a salt or stereoisomer thereof, wherein
l is selected from 1, 2, 3, 4, and 5;
m is selected from 5, 6, 7, 8, and 9;
$M_1$ is a bond or M';
$R_4$ is unsubstituted $C_{1-3}$ alkyl, or —$(CH_2)_nQ$, in which n is 1, 2, 3, 4, or 5 and Q is OH, —NHC(S)N$(R)_2$, —NHC(O)N$(R)_2$, —N(R)C(O)R, —N(R)S$(O)_2$R,
—N(R)$R_8$, —NHC(=N$R_9$)N$(R)_2$, —NHC(=CH$R_9$)N$(R)_2$, —OC(O)N$(R)_2$, —N(R)C(O)OR, heteroaryl, or heterocycloalkyl;
M and M' are independently selected from —C(O)O—, —OC(O)—, —C(O)N(R')—, —P(O)(OR')O—, —S—S—, an aryl group, and a heteroaryl group; and
$R_2$ and $R_3$ are independently selected from the group consisting of H, $C_{1-14}$ alkyl, and $C_{2-14}$ alkenyl.

In some embodiments, m is 5, 7, or 9.

In some embodiments, the compound is of Formula (IA), or a salt or stereoisomer thereof, wherein
l is selected from 1, 2, 3, 4, and 5;
m is selected from 5, 6, 7, 8, and 9;
$M_1$ is a bond or M';
$R_4$ is unsubstituted $C_{1-3}$ alkyl, or —$(CH_2)_nQ$, in which n is 1, 2, 3, 4, or 5 and Q is OH, —NHC(S)N$(R)_2$, or —NHC(O)N$(R)_2$;
M and M' are independently selected from —C(O)O—, —OC(O)—, —C(O)N(R')—, —P(O)(OR')O—, an aryl group, and a heteroaryl group; and
$R_2$ and $R_3$ are independently selected from the group consisting of H, $C_{1-14}$ alkyl, and $C_{2-14}$ alkenyl.

In some embodiments, m is 5, 7, or 9.

In some embodiments, the compound is of Formula (II):

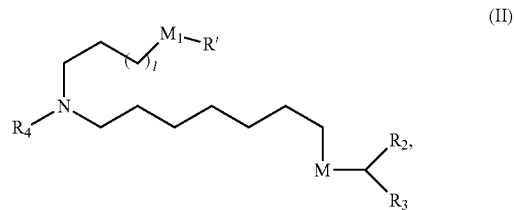

or a salt or stereoisomer thereof, wherein
l is selected from 1, 2, 3, 4, and 5;
$M_1$ is a bond or M';
$R_4$ is unsubstituted $C_{1-3}$ alkyl, or —$(CH_2)_nQ$, in which n is 2, 3, or 4 and Q is OH, —NHC(S)N$(R)_2$, —NHC(O)N$(R)_2$, —N(R)C(O)R, —N(R)S$(O)_2$R, —N(R)$R_8$, —NHC(=N$R_9$)N$(R)_2$, —NHC(=CH$R_9$)N$(R)_2$, —OC(O)N$(R)_2$, —N(R)C(O)OR, heteroaryl, or heterocycloalkyl;
M and M' are independently selected from —C(O)O—, —OC(O)—, —C(O)N(R')—, —P(O)(OR')O—, —S—S—, an aryl group, and a heteroaryl group; and
$R_2$ and $R_3$ are independently selected from the group consisting of H, $C_{1-14}$ alkyl, and $C_{2-14}$ alkenyl.

In some embodiments, the compound is of Formula (II), or a salt or stereoisomer thereof, wherein
l is selected from 1, 2, 3, 4, and 5;
$M_1$ is a bond or M';
$R_4$ is unsubstituted $C_{1-3}$ alkyl, or —$(CH_2)_nQ$, in which n is 2, 3, or 4 and Q is OH, —NHC(S)N$(R)_2$, or —NHC(O)N$(R)_2$;
M and M' are independently selected from —C(O)O—, —OC(O)—, —C(O)N(R')—, —P(O)(OR')O—, an aryl group, and a heteroaryl group; and
$R_2$ and $R_3$ are independently selected from the group consisting of H, $C_{1-14}$ alkyl, and $C_{2-14}$ alkenyl.

In some embodiments, $M_1$ is M'.

In some embodiments, M and M' are independently —C(O)O— or —OC(O)—.

In some embodiments, l is 1, 3, or 5.

In some embodiments, the compound is selected from the group consisting of Compound 1 to Compound 232, salts and stereoisomers thereof, and any combination thereof.

In some embodiments, the compound is selected from the group consisting of Compound 1 to Compound 147, salts and stereoisomers thereof, and any combination thereof.

In some embodiments, the compound is of the Formula (IIa),

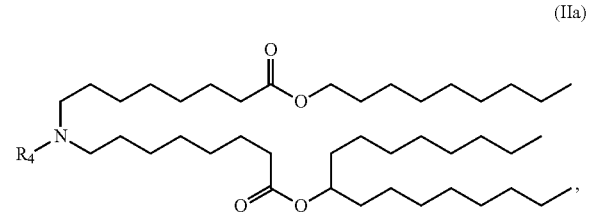

or a salt or stereoisomer thereof.

In some embodiments, the compound is of the Formula (IIb),

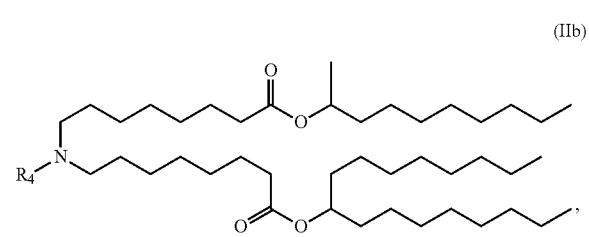

or a salt or stereoisomer thereof.

In some embodiments, the compound is of the Formula (IIc) or (IIe),

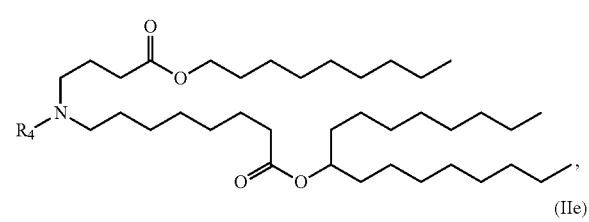

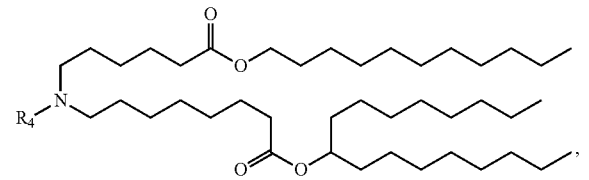

or a salt or stereoisomer thereof.

In some embodiments, $R_4$ is as described herein. In some embodiments, $R_4$ is selected from —$(CH_2)_nQ$ and —$(CH_2)_nCHQR$.

In some embodiments, the compound is of the Formula (IId),

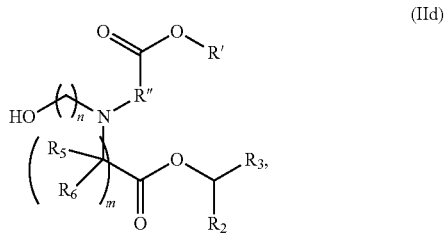

or a salt or stereoisomer thereof,
wherein n is selected from 2, 3, and 4, and m, R', R", and $R_2$ through $R_6$ are as described herein. For example, each of $R_2$ and $R_3$ may be independently selected from the group consisting of $C_{5-14}$ alkyl and $C_{5-14}$ alkenyl.

In some embodiments, the compound is of the Formula (IId), or a salt or stereoisomer thereof,
wherein $R_2$ and $R_3$ are independently selected from the group consisting of $C_{5-14}$ alkyl and $C_{5-14}$ alkenyl, n is selected from 2, 3, and 4, and R', R", $R_5$, $R_6$ and m are as defined herein.

In some embodiments, $R_2$ is $C_8$ alkyl.

In some embodiments, $R_3$ is $C_5$ alkyl, $C_6$ alkyl, $C_7$ alkyl, $C_8$ alkyl, or $C_9$ alkyl.

In some embodiments, m is 5, 7, or 9.

In some embodiments, each $R_5$ is H.

In some embodiments, each $R_6$ is H. In some embodiments, the delivery agent comprises a compound having the Formula (III)

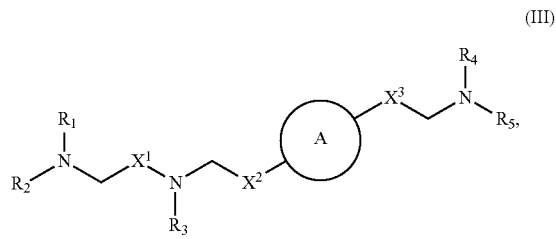

or salts or stereoisomers thereof, wherein
ring A is

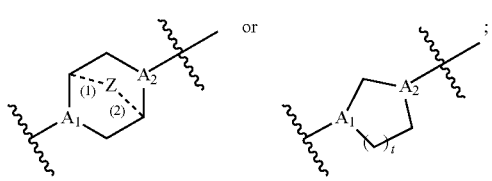

t is 1 or 2;
$A_1$ and $A_2$ are each independently selected from CH or N;
Z is $CH_2$ or absent wherein when Z is $CH_2$, the dashed lines (1) and (2) each represent a single bond; and when Z is absent, the dashed lines (1) and (2) are both absent;
$R_1$, $R_2$, $R_3$, $R_4$, and $R_5$ are independently selected from the group consisting of $C_{5-20}$ alkyl, $C_{5-20}$ alkenyl, —R"MR', —R*YR", —YR", and —R*OR";
each M is independently selected from the group consisting of —C(O)O—, —OC(O)—, —OC(O)O—, —C(O)N(R')—, —N(R')C(O)—, —C(O)—, —C(S)—, —C(S)S—, —SC(S)—, —CH(OH)—, —P(O)(OR') O—, —S(O)$_2$—, an aryl group, and a heteroaryl group;

$X^1$, $X^2$, and $X^3$ are independently selected from the group consisting of a bond, —CH$_2$—, —(CH$_2$)$_2$—, —CHR—, —CHY—, —C(O)—, —C(O)O—, —OC(O)—, —C(O)—CH$_2$—, —CH$_2$—C(O)—, —C(O)O—CH$_2$—, —OC(O)—CH$_2$—, —CH$_2$—C(O)O—, —CH$_2$—OC(O)—, —CH(OH)—, —C(S)—, and —CH(SH)—;

each Y is independently a $C_{3-6}$ carbocycle;

each R* is independently selected from the group consisting of $C_{1-12}$ alkyl and $C_{2-12}$ alkenyl;

each R is independently selected from the group consisting of $C_{1-3}$ alkyl and a $C_{3-6}$ carbocycle;

each R' is independently selected from the group consisting of $C_{1-12}$ alkyl, $C_{2-12}$ alkenyl, and H; and each R" is independently selected from the group consisting of $C_{3-12}$ alkyl and $C_{3-12}$ alkenyl, wherein when ring A is

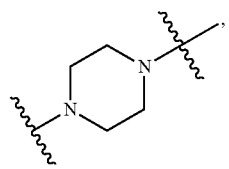 [SMILES: *N1CCN(*)CC1]

then i) at least one of $X^1$, $X^2$, and $X^3$ is not —CH$_2$—; and/or ii) at least one of $R_1$, $R_2$, $R_3$, $R_4$, and $R_5$ is —R"MR'.

In some embodiments, the compound is of any of Formulae (IIIa1)-(IIIa6):

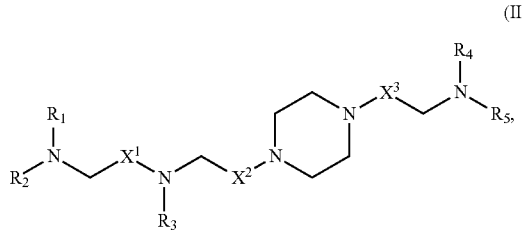
(IIIa1)

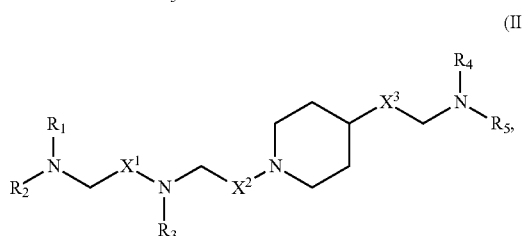
(IIIa2)

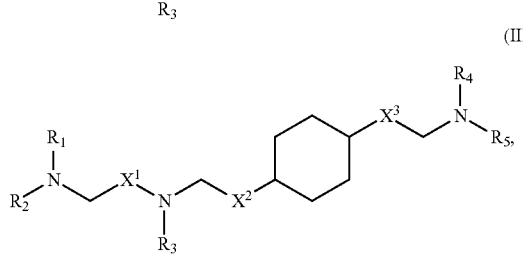
(IIIa3)

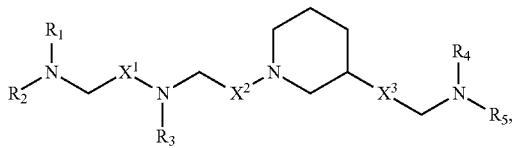
(IIIa4)

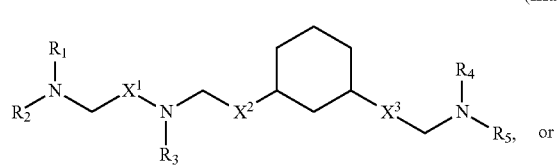
(IIIa5)

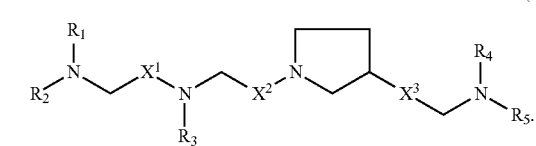
(IIIa6)

The compounds of Formula (III) or any of (IIIa1)-(IIIa6) include one or more of the following features when applicable.

In some embodiments, ring A is

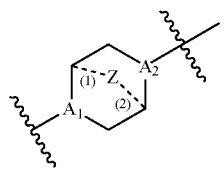

In some embodiments, ring A is

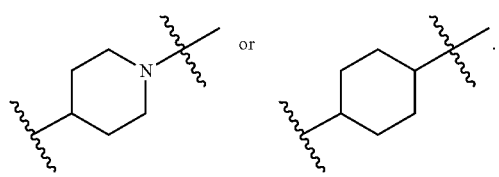 [SMILES: *C1CCN(*)CC1 ; *C1CCC(*)CC1]

In some embodiments, ring A is

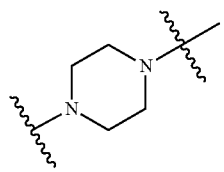

In some embodiments, ring A is

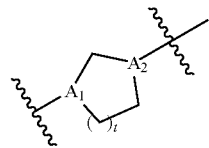

In some embodiments, ring A is

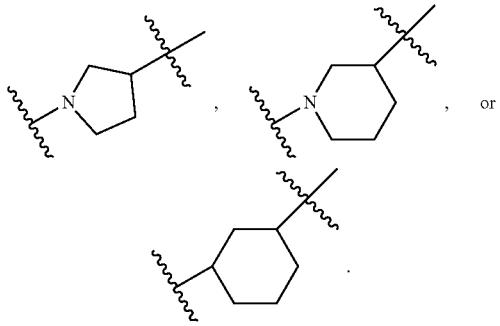

In some embodiments, ring A is

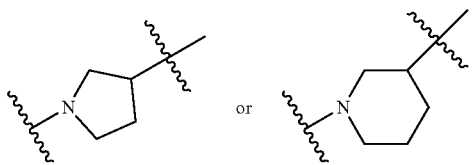 [SMILES: *C1CCN(*)C1 ; *C1CCCN(*)C1]

wherein ring, in which the N atom is connected with $X^2$.

In some embodiments, Z is $CH_2$.

In some embodiments, Z is absent.

In some embodiments, at least one of $A_1$ and $A_2$ is N.

In some embodiments, each of $A_1$ and $A_2$ is N.

In some embodiments, each of $A_1$ and $A_2$ is CH.

In some embodiments, $A_1$ is N and $A_2$ is CH.

In some embodiments, $A_1$ is CH and $A_2$ is N.

In some embodiments, at least one of $X^1$, $X^2$, and $X^3$ is not —$CH_2$—. For example, in certain embodiments, $X^1$ is not —$CH_2$—. In some embodiments, at least one of $X^1$, $X^2$, and $X^3$ is —C(O)—.

In some embodiments, $X^2$ is —C(O)—, —C(O)O—, —OC(O)—, —C(O)—$CH_2$—, —$CH_2$—C(O)—, —C(O)O—$CH_2$—, —OC(O)—$CH_2$—, —$CH_2$—C(O)O—, or —$CH_2$—OC(O)—.

In some embodiments, $X^3$ is —C(O)—, —C(O)O—, —OC(O)—, —C(O)—$CH_2$—, —$CH_2$—C(O)—, —C(O)O—$CH_2$—, —OC(O)—$CH_2$—, —$CH_2$—C(O)O—, or —$CH_2$—OC(O)—. In other embodiments, $X^3$ is —$CH_2$—.

In some embodiments, $X^3$ is a bond or —$(CH_2)_2$—.

In some embodiments, $R_1$ and $R_2$ are the same. In certain embodiments, $R_1$, $R_2$, and $R_3$ are the same. In some embodiments, $R_4$ and $R_5$ are the same. In certain embodiments, $R_1$, $R_2$, $R_3$, $R_4$, and $R_5$ are the same.

In some embodiments, at least one of $R_1$, $R_2$, $R_3$, $R_4$, and $R_5$ is —R"MR'. In some embodiments, at most one of $R_1$, $R_2$, $R_3$, $R_4$, and $R_5$ is —R"MR'. For example, at least one of $R_1$, $R_2$, and $R_3$ may be —R"MR', and/or at least one of $R_4$ and $R_5$ is —R"MR'. In certain embodiments, at least one M is —C(O)O—. In some embodiments, each M is —C(O)O—. In some embodiments, at least one M is —OC(O)—. In some embodiments, each M is —OC(O)—. In some embodiments, at least one M is —OC(O)O—. In some embodiments, each M is —OC(O)O—. In some embodiments, at least one R" is $C_3$ alkyl. In certain embodiments, each R" is $C_3$ alkyl. In some embodiments, at least one R" is $C_5$ alkyl. In certain embodiments, each R" is $C_5$ alkyl. In some embodiments, at least one R" is $C_6$ alkyl. In certain embodiments, each R" is $C_6$ alkyl. In some embodiments, at least one R" is $C_7$ alkyl. In certain embodiments, each R" is $C_7$ alkyl. In some embodiments, at least one R' is $C_5$ alkyl. In certain embodiments, each R' is $C_5$ alkyl. In other embodiments, at least one R' is $C_1$ alkyl. In certain embodiments, each R' is $C_1$ alkyl. In some embodiments, at least one R' is $C_2$ alkyl. In certain embodiments, each R' is $C_2$ alkyl.

In some embodiments, at least one of $R_1$, $R_2$, $R_3$, $R_4$, and $R_5$ is $C_{12}$ alkyl. In certain embodiments, each of $R_1$, $R_2$, $R_3$, $R_4$, and $R_5$ are $C_{12}$ alkyl.

In some embodiments, the delivery agent comprises a compound having the Formula (IV)

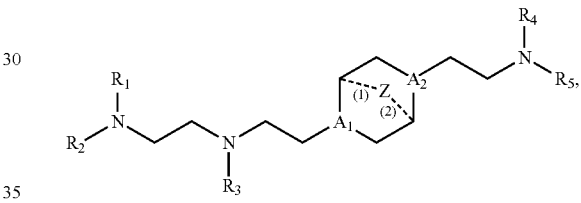

or salts or stereoisomer thereof, wherein
  $A_1$ and $A_2$ are each independently selected from CH or N and at least one of $A_1$ and $A_2$ is N;
  Z is $CH_2$ or absent wherein when Z is $CH_2$, the dashed lines (1) and (2) each represent a single bond; and when Z is absent, the dashed lines (1) and (2) are both absent;
  $R_1$, $R_2$, $R_3$, $R_4$, and $R_5$ are independently selected from the group consisting of $C_{6-20}$ alkyl and $C_{6-20}$ alkenyl;
  wherein when ring A is

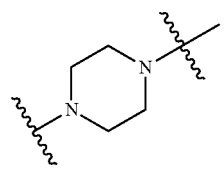

then
  i) $R_1$, $R_2$, $R_3$, $R_4$, and $R_5$ are the same, wherein $R_1$ is not $C_{12}$ alkyl, $C_{18}$ alkyl, or $C_{18}$ alkenyl;
  ii) only one of $R_1$, $R_2$, $R_3$, $R_4$, and $R_5$ is selected from $C_{6-20}$ alkenyl;
  iii) at least one of $R_1$, $R_2$, $R_3$, $R_4$, and $R_5$ have a different number of carbon atoms than at least one other of $R_1$, $R_2$, $R_3$, $R_4$, and $R_5$;
  iv) $R_1$, $R_2$, and $R_3$ are selected from $C_{6-20}$ alkenyl, and $R_4$ and $R_5$ are selected from $C_{6-20}$ alkyl; or
  v) $R_1$, $R_2$, and $R_3$ are selected from $C_{6-20}$ alkyl, and $R_4$ and $R_5$ are selected from $C_{6-20}$ alkenyl.

In some embodiments, the compound is of Formula (IVa):

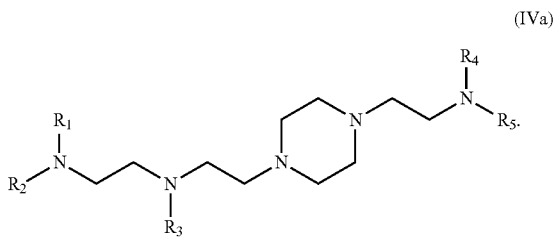

(IVa)

The compounds of Formula (IV) or (IVa) include one or more of the following features when applicable.

In some embodiments, Z is $CH_2$.

In some embodiments, Z is absent.

In some embodiments, at least one of $A_1$ and $A_2$ is N.

In some embodiments, each of $A_1$ and $A_2$ is N.

In some embodiments, each of $A_1$ and $A_2$ is CH.

In some embodiments, $A_1$ is N and $A_2$ is CH.

In some embodiments, $A_1$ is CH and $A_2$ is N.

In some embodiments, $R_1$, $R_2$, $R_3$, $R_4$, and $R_5$ are the same, and are not $C_{12}$ alkyl, $C_{18}$ alkyl, or $C_{18}$ alkenyl. In some embodiments, $R_1$, $R_2$, $R_3$, $R_4$, and $R_5$ are the same and are $C_9$ alkyl or $C_{14}$ alkyl.

In some embodiments, only one of $R_1$, $R_2$, $R_3$, $R_4$, and $R_5$ is selected from $C_{6-20}$ alkenyl. In certain such embodiments, $R_1$, $R_2$, $R_3$, $R_4$, and $R_5$ have the same number of carbon atoms. In some embodiments, $R_4$ is selected from $C_{5-20}$ alkenyl. For example, $R_4$ may be $C_{12}$ alkenyl or $C_{18}$ alkenyl.

In some embodiments, at least one of $R_1$, $R_2$, $R_3$, $R_4$, and $R_5$ have a different number of carbon atoms than at least one other of $R_1$, $R_2$, $R_3$, $R_4$, and $R_5$.

In certain embodiments, $R_1$, $R_2$, and $R_3$ are selected from $C_{6-20}$ alkenyl, and $R_4$ and $R_5$ are selected from $C_{6-20}$ alkyl. In other embodiments, $R_1$, $R_2$, and $R_3$ are selected from $C_{6-20}$ alkyl, and $R_4$ and $R_5$ are selected from $C_{6-20}$ alkenyl. In some embodiments, $R_1$, $R_2$, and $R_3$ have the same number of carbon atoms, and/or $R_4$ and $R_5$ have the same number of carbon atoms. For example, $R_1$, $R_2$, and $R_3$, or $R_4$ and $R_5$, may have 6, 8, 9, 12, 14, or 18 carbon atoms. In some embodiments, $R_1$, $R_2$, and $R_3$, or $R_4$ and $R_5$, are $C_{18}$ alkenyl (e.g., linoleyl). In some embodiments, $R_1$, $R_2$, and $R_3$, or $R_4$ and $R_5$, are alkyl groups including 6, 8, 9, 12, or 14 carbon atoms.

In some embodiments, $R_1$ has a different number of carbon atoms than $R_2$, $R_3$, $R_4$, and $R_5$. In other embodiments, $R_3$ has a different number of carbon atoms than $R_1$, $R_2$, $R_4$, and $R_5$. In further embodiments, $R_4$ has a different number of carbon atoms than $R_1$, $R_3$, and $R_5$.

In other embodiments, the delivery agent comprises a compound having the Formula (V)

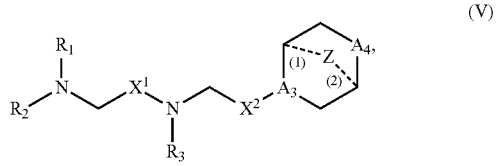

(V)

or salts or stereoisomers thereof, in which $A_3$ is CH or N;

$A_4$ is $CH_2$ or NH; and at least one of $A_3$ and $A_4$ is N or NH;

Z is $CH_2$ or absent wherein when Z is $CH_2$, the dashed lines (1) and (2) each represent a single bond; and when Z is absent, the dashed lines (1) and (2) are both absent;

$R_1$, $R_2$, and $R_3$ are independently selected from the group consisting of $C_{5-20}$ alkyl, $C_{5-20}$ alkenyl, —R"MR', —R*YR", —YR", and —R*OR";

each M is independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —S(O)$_2$—, an aryl group, and a heteroaryl group;

$X^1$ and $X^2$ are independently selected from the group consisting of —$CH_2$—, —$(CH_2)_2$—, —CHR—, —CHY—, —C(O)—, —C(O)O—, —OC(O)—, —C(O)—$CH_2$—, —$CH_2$—C(O)—, —C(O)O—$CH_2$—, —OC(O)—$CH_2$—, —$CH_2$—C(O)O—, —$CH_2$—OC(O)—, —CH(OH)—, —C(S)—, and —CH(SH)—;

each Y is independently a $C_{3-6}$ carbocycle;

each R* is independently selected from the group consisting of $C_{1-12}$ alkyl and $C_{2-12}$ alkenyl;

each R is independently selected from the group consisting of $C_{1-3}$ alkyl and a $C_{3-6}$ carbocycle;

each R' is independently selected from the group consisting of $C_{1-12}$ alkyl, $C_{2-12}$ alkenyl, and H; and each R" is independently selected from the group consisting of $C_{3-12}$ alkyl and $C_{3-12}$ alkenyl.

In some embodiments, the compound is of Formula (Va):

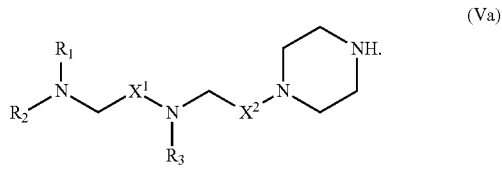

(Va)

The compounds of Formula (V) or (Va) include one or more of the following features when applicable.

In some embodiments, Z is $CH_2$.

In some embodiments, Z is absent.

In some embodiments, at least one of $A_3$ and $A_4$ is N or NH.

In some embodiments, $A_3$ is N and $A_4$ is NH.

In some embodiments, $A_3$ is N and $A_4$ is $CH_2$.

In some embodiments, $A_3$ is CH and $A_4$ is NH.

In some embodiments, at least one of $X^1$ and $X^2$ is not —$CH_2$—. For example, in certain embodiments, $X^1$ is not —$CH_2$—. In some embodiments, at least one of $X^1$ and $X^2$ is —C(O)—.

In some embodiments, $X^2$ is —C(O)—, —C(O)O—, —OC(O)—, —C(O)—$CH_2$—, —$CH_2$—C(O)—, —C(O)O—$CH_2$—, —OC(O)—$CH_2$—, —$CH_2$—C(O)O—, or —$CH_2$—OC(O)—.

In some embodiments, $R_1$, $R_2$, and $R_3$ are independently selected from the group consisting of $C_{5-20}$ alkyl and $C_{5-20}$ alkenyl. In some embodiments, $R_1$, $R_2$, and $R_3$ are the same. In certain embodiments, $R_1$, $R_2$, and $R_3$ are $C_6$, $C_9$, $C_{12}$, or $C_{14}$ alkyl. In other embodiments, $R_1$, $R_2$, and $R_3$ are $C_{18}$ alkenyl. For example, $R_1$, $R_2$, and $R_3$ may be linoleyl.

In other embodiments, the delivery agent comprises a compound having the Formula (VI):

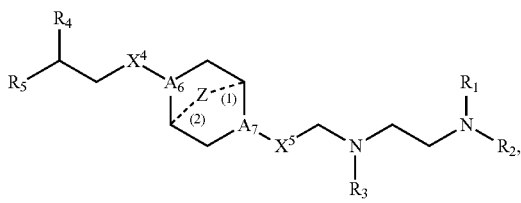

(VI)

or salts or stereoisomers thereof, in which
$A_6$ and $A_7$ are each independently selected from CH or N, wherein at least one of $A_6$ and $A_7$ is N;
Z is $CH_2$ or absent wherein when Z is $CH_2$, the dashed lines (1) and (2) each represent a single bond; and when Z is absent, the dashed lines (1) and (2) are both absent;
$X^4$ and $X^5$ are independently selected from the group consisting of —$CH_2$—, —$(CH_2)_2$—, —CHR—, —CHY—, —C(O)—, —C(O)O—, —OC(O)—, —C(O)—$CH_2$—, —$CH_2$—C(O)—, —C(O)O—$CH_2$—, —OC(O)—$CH_2$—, —$CH_2$—C(O)O—, —$CH_2$—OC(O)—, —CH(OH)—, —C(S)—, and —CH(SH)—;
$R_2$, $R_3$, $R_4$, and $R_5$ each are independently selected from the group consisting of $C_{5-20}$ alkyl, $C_{5-20}$ alkenyl, —R"MR', —R*YR", —YR", and —R*OR";
each M is independently selected from the group consisting of —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —S(O)$_2$—, an aryl group, and a heteroaryl group;
each Y is independently a $C_{3-6}$ carbocycle;
each R* is independently selected from the group consisting of $C_{1-12}$ alkyl and $C_{2-12}$ alkenyl;
each R is independently selected from the group consisting of $C_{1-3}$ alkyl and a $C_{3-6}$ carbocycle;
each R' is independently selected from the group consisting of $C_{1-12}$ alkyl, $C_{2-12}$ alkenyl, and H; and
each R" is independently selected from the group consisting of $C_{3-12}$ alkyl and $C_{3-12}$ alkenyl.

In some embodiments, $R_1$, $R_2$, $R_3$, $R_4$, and $R_5$ each are independently selected from the group consisting of $C_{6-20}$ alkyl and $C_{6-20}$ alkenyl.

In some embodiments, $R_1$ and $R_2$ are the same. In certain embodiments, $R_1$, $R_2$, and $R_3$ are the same. In some embodiments, $R_4$ and $R_5$ are the same. In certain embodiments, $R_1$, $R_2$, $R_3$, $R_4$, and $R_5$ are the same.

In some embodiments, at least one of $R_1$, $R_2$, $R_3$, $R_4$, and $R_5$ is $C_{9-12}$ alkyl. In certain embodiments, each of $R_1$, $R_2$, $R_3$, $R_4$, and $R_5$ independently is $C_9$, $C_{12}$ or $C_{14}$ alkyl. In certain embodiments, each of $R_1$, $R_2$, $R_3$, $R_4$, and $R_5$ is $C_9$ alkyl.

In some embodiments, $A_6$ is N and $A_7$ is N. In some embodiments, $A_6$ is CH and $A_7$ is N.

In some embodiments, $X^4$ is —$CH_2$— and $X^5$ is —C(O)—. In some embodiments, $X^4$ and $X^5$ are —C(O)—.

In some embodiments, when $A_6$ is N and $A_7$ is N, at least one of $X^4$ and $X^5$ is not —$CH_2$—, e.g., at least one of $X^4$ and $X^5$ is —C(O)—. In some embodiments, when $A_6$ is N and $A_7$ is N, at least one of $R_1$, $R_2$, $R_3$, $R_4$, and $R_5$ is —R"MR'.

In some embodiments, at least one of $R_1$, $R_2$, $R_3$, $R_4$, and $R_5$ is not —R"MR'.

In some embodiments, the composition disclosed herein is a nanoparticle composition. In some embodiments, the delivery agent further comprises a phospholipid. In some embodiments, the phospholipid is selected from the group consisting of
1,2-dilinoleoyl-sn-glycero-3-phosphocholine (DLPC),
1,2-dimyristoyl-sn-glycero-phosphocholine (DMPC),
1,2-dioleoyl-sn-glycero-3-phosphocholine (DOPC),
1,2-dipalmitoyl-sn-glycero-3-phosphocholine (DPPC),
1,2-distearoyl-sn-glycero-3-phosphocholine (DSpC),
1,2-diundecanoyl-sn-glycero-phosphocholine (DUPC),
1-palmitoyl-2-oleoyl-sn-glycero-3-phosphocholine (POPC),
1,2-di-O-octadecenyl-sn-glycero-3-phosphocholine (18:0 Diether PC),
1-oleoyl-2-cholesterylhemisuccinoyl-sn-glycero-3-phosphocholine (OChemsPC),
1-hexadecyl-sn-glycero-3-phosphocholine (C16 Lyso PC),
1,2-dilinolenoyl-sn-glycero-3-phosphocholine,
1,2-diarachidonoyl-sn-glycero-3-phosphocholine,
1,2-didocosahexaenoyl-sn-glycero-3-phosphocholine,
1,2-dioleoyl-sn-glycero-3-phosphoethanolamine (DOPE),
1,2-diphytanoyl-sn-glycero-3-phosphoethanolamine (ME 16:0 PE),
1,2-distearoyl-sn-glycero-3-phosphoethanolamine,
1,2-dilinoleoyl-sn-glycero-3-phosphoethanolamine,
1,2-dilinolenoyl-sn-glycero-3-phosphoethanolamine,
1,2-diarachidonoyl-sn-glycero-3-phosphoethanolamine,
1,2-didocosahexaenoyl-sn-glycero-3-phosphoethanolamine,
1,2-dioleoyl-sn-glycero-3-phospho-rac-(1-glycerol) sodium salt (DOPG), sphingomyelin, and any mixtures thereof.

In some embodiments, the delivery agent further comprises a structural lipid. In some embodiments, the structural lipid is selected from the group consisting of cholesterol, fecosterol, sitosterol, ergosterol, campesterol, stigmasterol, brassicasterol, tomatidine, ursolic acid, alpha-tocopherol, and any mixtures thereof.

In some embodiments, the delivery agent further comprises a PEG lipid. In some embodiments, the PEG lipid is selected from the group consisting of a PEG-modified phosphatidylethanolamine, a PEG-modified phosphatidic acid, a PEG-modified ceramide, a PEG-modified dialkylamine, a PEG-modified diacylglycerol, a PEG-modified dialkylglycerol, and any mixtures thereof. In some embodiments, the PEG lipid has the Formula:

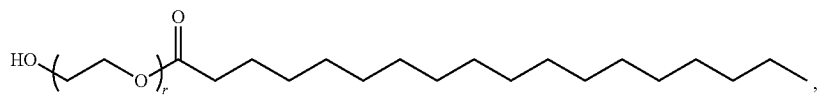

wherein r is an integer between 1 and 100. In some embodiments, the PEG lipid is Compound 428.

In some embodiments, the delivery agent further comprises an ionizable lipid selected from the group consisting of
3-(didodecylamino)-N1,N1,4-tridodecyl-1-piperazineethanamine (KL10),
N1-[2-(didodecylamino)ethyl]-N1,N4,N4-tridodecyl-1,4-piperazinediethanamine (KL22), 14,25-ditridecyl-15,18,21,24-tetraaza-octatriacontane (KL25),
1,2-dilinoleyloxy-N,N-dimethylaminopropane (DLinDMA),
2,2-dilinoleyl-4-dimethylaminomethyl-[1,3]-dioxolane (DLin-K-DMA),
heptatriaconta-6,9,28,31-tetraen-19-yl 4-(dimethylamino)butanoate (DLin-MC3-DMA),
2,2-dilinoleyl-4-(2-dimethylaminoethyl)[1,3]-dioxolane (DLin-KC2-DMA),
1,2-dioleyloxy-N,N-dimethylaminopropane (DODMA),
2-({8-[(3β)-cholest-5-en-3-yloxy]octyl}oxy)-N,N-dimethyl-3-[(9Z,12Z)-octadeca-9,12-di en-1-yloxy]propan-1-amine (Octyl-CLinDMA),
(2R)-2-({8-[(3β)-cholest-5-en-3-yloxy]octyl}oxy)-N,N-dimethyl-3-[(9Z,12Z)-octadeca-9, 12-dien-1-yloxy]propan-1-amine (Octyl-CLinDMA (2R)), and
(2S)-2-({8-[(3β)-cholest-5-en-3-yloxy]octyl}oxy)-N,N-dimethyl-3-[(9Z,12Z)-octadeca-9, 12-dien-1-yloxy]propan-1-amine (Octyl-CLinDMA (2S)).

In some embodiments, the delivery agent further comprises a phospholipid, a structural lipid, a PEG lipid, or any combination thereof. In some embodiments, the delivery agent comprises Compound 18, DSPC, Cholesterol, and Compound 428, e.g., with a mole ratio of about 50:10:38.5:1.5.

In some embodiments, the composition is formulated for in vivo delivery. In some embodiments, the composition is formulated for intramuscular, subcutaneous, or intradermal delivery.

The present disclosure further provides a polynucleotide comprising an mRNA comprising: (i) a 5' UTR, (ii) an open reading frame (ORF) encoding a human porphobilinogen deaminase (PBGD) polypeptide, wherein the ORF comprises a nucleic acid sequence selected from the group consisting of SEQ ID NOs: 9 to 33 and 89 to 117, and (iii) a 3' UTR comprising a microRNA binding site selected from miR-142, miR-126, or a combination thereof, wherein the mRNA comprises at least one chemically modified nucleobase.

The present disclosure further provides a polynucleotide comprising an mRNA comprising: (i) a 5'-terminal cap; (ii) a 5' UTR comprising a sequence selected from the group consisting of SEQ ID NO: 39 to 56, 83, 189 to 191, and any combination thereof, (iii) an open reading frame (ORF) encoding a human porphobilinogen deaminase (PBGD) polypeptide, wherein the ORF comprises a sequence selected from the group consisting of SEQ ID NOs: 9 to 33 and 89 to 117, wherein the mRNA comprises at least one chemically modified nucleobase selected from the group consisting of pseudouracil (ψ), N1-methylpseudouracil (m1ψ), 1-ethylpseudouracil, 2-thiouracil (s2U), 4'-thiouracil, 5-methylcytosine, 5-methyluracil, 5-methoxyuracil, and any combination thereof; and (iv) a 3' UTR comprising a nucleic acid sequence selected from the group consisting of SEQ ID NOs: 57 to 81, 84, 149 to 151, 161 to 172, 192 to 199, and any combination thereof, and (v) a poly-A-region.

In some embodiments, the polynucleotide comprises a nucleic acid sequence selected from the group consisting of SEQ ID NO: 133, 141, 144, and 145.

The present disclosure further provides a pharmaceutical composition comprising the polynucleotide, e.g., an mRNA, and a delivery agent. In some embodiments, the delivery agent is a lipid nanoparticle comprising Compound 18, Compound 236, a salt or a stereoisomer thereof, or any combination thereof. In some embodiments, the polynucleotide comprising a nucleotide sequence encoding a PBGD polypeptide disclosed herein is formulated with a delivery agent comprising, e.g., a compound having the Formula (I), e.g., any of Compounds 1-232, e.g., Compound 18; a compound having the Formula (III), (IV), (V), or (VI), e.g., any of Compounds 233-342, e.g., Compound 236; or a compound having the Formula (VIII), e.g., any of Compounds 419-428, e.g., Compound 428, or any combination thereof. In some embodiments, the delivery agent comprises Compound 18, DSPC, Cholesterol, and Compound 428, e.g., with a mole ratio of about 50:10:38.5:1.5.

In one aspect of the embodiments disclosed herein, the subject is a human subject in need of treatment or prophylaxis for acute intermittent porphyria (AIP) and/or an acute porphyria attack.

In one aspect of the embodiments disclosed herein, upon administration to the subject, the mRNA has: (i) a longer plasma half-life; (ii) increased expression of a PBGD polypeptide encoded by the ORF; (iii) a lower frequency of arrested translation resulting in an expression fragment; (iv) greater structural stability; or (v) any combination thereof, relative to a corresponding mRNA having the nucleic acid sequence of SEQ ID NO: 2, 4, 6, or 8 and/or administered as naked mRNA.

In some embodiments, a pharmaceutical composition or polynucleotide disclosed herein is suitable for administration as a single unit dose or a plurality of single unit doses.

In some embodiments, a pharmaceutical composition or polynucleotide disclosed herein is suitable for reducing the level of one or more biomarkers of AIP in the subject.

In some embodiments, a pharmaceutical composition or polynucleotide disclosed herein is for use in treating, preventing or delaying the onset of AIP signs or symptoms in the subject. In some embodiments, the signs or symptoms include pain, seizures, paralysis, neuropathy, death, or a combination thereof.

The present disclosure also provides a host cell comprising a polynucleotide of the invention. In some embodiments, the host cell is a eukaryotic cell. The present disclosure also provides a vector comprising a polynucleotide of the invention. Also provided is a method of making a polynucleotide of the invention comprising synthesizing the polynucleotide enzymatically or chemically. The present disclosure also provides a polypeptide encoded by a polynucleotide of the invention, a composition comprising a polynucleotide of the invention, a host cell comprising a polynucleotide of the invention, a vector comprising a polynucleotide of the invention, or produced by the method of making disclosed herein.

The present disclosure also provides a method of expressing in vivo an active PBGD polypeptide in a subject in need thereof comprising administering to the subject an effective amount of the polynucleotide of the invention, a composition comprising a polynucleotide of the invention, a host cell comprising a polynucleotide of the invention, a vector comprising a polynucleotide of the invention. Also provided is a method of treating acute intermittent porphyria (AIP) in a subject in need thereof comprising administering to the subject a therapeutically effective amount of the polynucleotide of the invention, a composition comprising a polynucleotide of the invention, a host cell comprising a polynucleotide of the invention, a vector comprising a polynucleotide of the invention, wherein the administration alleviates the signs or symptoms of AIP in the subject.

The present disclosure also provides a method to prevent or delay the onset of AIP signs or symptoms in a subject in need thereof comprising administering to the subject a prophylactically effective amount of the polynucleotide of the invention, a composition comprising a polynucleotide of the invention, a host cell comprising a polynucleotide of the invention, a vector comprising a polynucleotide of the invention before AIP signs or symptoms manifest, wherein the administration prevents or delays the onset of AIP signs or symptoms in the subject. Also provided is a method to ameliorate the signs or symptoms of AIP in a subject in need thereof comprising administering to the subject a therapeutically effective amount of the polynucleotide of the invention, a composition comprising a polynucleotide of the invention, a host cell comprising a polynucleotide of the invention, a vector comprising a polynucleotide of the invention before AIP signs or symptoms manifest, wherein the administration ameliorates AIP signs or symptoms in the subject.

The present disclosure further provides a method of expressing a porphobilinogen deaminase (PBGD) polypeptide in a human subject in need thereof comprising administering to the subject an effective amount of a pharmaceutical composition or a polynucleotide, e.g., an mRNA, described herein, wherein the pharmaceutical composition or polynucleotide is suitable for administrating as a single dose or as a plurality of single unit doses to the subject.

The present disclosure further provides a method of treating, preventing or delaying the onset of acute intermittent porphyria (AIP) signs or symptoms in a human subject in need thereof comprising administering to the subject an effective amount of a pharmaceutical composition or a polynucleotide, e.g., an mRNA, described herein, wherein the administration treats, prevents or delays the onset of one or more of the signs or symptoms of AIP in the subject.

The present disclosure further provides a method for the treatment of acute intermittent porphyria (AIP), comprising administering to a human subject suffering from AIP a single intravenous dose of a pharmaceutical composition or a polynucleotide, e.g., an mRNA, described herein.

The present disclosure further provides a method of reducing an aminolevulinate acid (ALA), a porphobilinogen (PBG) and/or a porphyrin urinary excretion level in a human subject comprising administering to the subject an effective amount of a pharmaceutical composition or a polynucleotide, e.g., an mRNA, described herein, wherein the administration reduces the ALA, PBG and/or porphyrin urinary excretion level in the subject. In some embodiments,
  (i) ALA urinary excretion level is reduced at least 2-fold, at least 5-fold, at least 10-fold, at least 20-fold or at least 50-fold as compared to a reference ALA excretion level during an acute porphyria attack, for at least 24 hours, at least 48 hours, at least 72 hours, at least 96 hours, or at least 120 hours post-administration,
  (ii) PBG urinary excretion level is reduced at least 2-fold, at least 5-fold, at least 10-fold, at least 20-fold or at least 50-fold as compared to a reference PBG excretion level during an acute porphyria attack, for at least 24 hours, at least 48 hours, at least 72 hours, at least 96 hours, or at least 120 hours post-administration, and/or
  (iii) porphyrin urinary excretion level is reduced at least at least 2-fold, at least 5-fold, at least 10-fold, at least 20-fold or at least 50-fold as compared to a reference porphyrin excretion level during an acute porphyria attack, for at least 24 hours, at least 48 hours, at least 72 hours, at least 96 hours, or at least 120 hours post-administration.

The present disclosure further provides a method of reducing an aminolevulinate acid (ALA), a porphobilinogen (PBG) and/or a porphyrin urinary excretion level in a human subject comprising administering to the subject an effective amount of a pharmaceutical composition or a polynucleotide described herein, wherein the administration reduces the ALA, PBG and/or porphyrin urinary excretion level in the subject. In some embodiments,
  (i) ALA urinary excretion level is reduced by at least 50%, at least 60%, at least 70%, at least 80%, at least 90%, at least 95%, at least 98%, at least 99%, or at least 100% as compared to the subject's baseline level or a reference ALA excretion level (e.g., in a subject with AIP or during an acute porphyria attack), for at least 24 hours, at least 48 hours, at least 72 hours, at least 96 hours, or at least 120 hours post-administration,
  (ii) PBG urinary excretion level is reduced by at least 50%, at least 60%, at least 70%, at least 80%, at least 90%, at least 95%, at least 98%, at least 99%, or at least 100% as compared to the subject's baseline level or a reference PBG excretion level (e.g., in a subject with AIP or during an acute porphyria attack), for at least 24 hours, at least 48 hours, at least 72 hours, at least 96 hours, or at least 120 hours post-administration, and/or
  (iii) porphyrin urinary excretion level is reduced by at least 50%, at least 60%, at least 70%, at least 80%, at least 90%, at least 95%, at least 98%, at least 99%, or at least 100% as compared to the subject's baseline level or a reference porphyrin excretion level (e.g., in a subject with AIP or during an acute porphyria attack), for at least 24 hours, at least 48 hours, at least 72 hours, at least 96 hours, or at least 120 hours post-administration.

The present disclosure further provides a method of reducing an alanine transaminase (ALT), a aspartate transaminase (AST) and/or a bilirubin serum level in a human subject comprising administering to the subject an effective amount of a pharmaceutical composition or a polynucleotide, e.g., an mRNA, described herein, wherein the administration reduces the ALT, AST and/or bilirubin serum level in the subject. In some embodiments,
  (i) ALT serum level is reduced to at least within 10-fold, at least within 5-fold, at least within 2-fold, or at least within 1.5-fold as compared to a reference ALT serum level within at least 24 hours, at least 48 hours, at least 72 hours, at least 96 hours, or at least 120 hours post-administration,
  (ii) AST serum level is reduced to at least within 10-fold, at least within 5-fold, at least within 2-fold, or at least within 1.5-fold, as compared to a reference AST serum level, for at least 24 hours, at least 48 hours, at least 72 hours, at least 96 hours, or at least 120 hours post-administration, and/or
  (iii) bilirubin serum level is reduced to at least within 10-fold, at least within 5-fold, at least within 2-fold, or at least within 1.5 fold as compared to a reference bilirubin serum level, for at least 24 hours, at least 48 hours, at least 72 hours, at least 96 hours, or at least 120 hours post-administration.

The present disclosure further provides a method of reducing an alanine transaminase (ALT), a aspartate transaminase (AST) and/or a bilirubin serum level in a human subject comprising administering to the subject an effective amount of a pharmaceutical composition or a polynucleotide described herein, wherein the administration reduces the ALT, AST and/or bilirubin serum level in the subject. In some embodiments,
  (i) ALT serum level is reduced by at least 90%, at least 80%, at least 70%, at least 60% at least 50%, at least 40%, or at least 30% as compared to the subject's baseline level or a reference ALT serum level (e.g., in a subject with AIP or during an acute porphyria attack) within at least 24 hours, at least 48 hours, at least 72 hours, at least 96 hours, or at least 120 hours post-administration, (ii) AST serum level is reduced by at least 90%, at least 80%, at least 70%, at least 60%, at least 50%, at least 40%, or at least 30% as compared to the subject's baseline level or a reference AST serum level (e.g., in a subject with AIP or during an acute porphyria attack), for at least 24 hours, at least 48 hours, at least 72 hours, at least 96 hours, or at least 120 hours post-administration, and/or (iii) bilirubin serum level is reduced by at least 90%, at least 80%, at least 70%, at least 60%, at least 50%, at least 40%, or at least 30% as compared to the subject's baseline level or a reference bilirubin serum level (e.g., in a subject with AIP or during an acute porphyria attack), for at least 24 hours, at least 48 hours, at least 72 hours, at least 96 hours, or at least 120 hours post-administration.

In some embodiments, 12 hours after the pharmaceutical composition or polynucleotide is administered to the subject, the PBGD activity in the subject is increased at least 20%, at least 30%, at least 40%, at least 50%, at least 60%, at least 70%, at least 80%, at least 90%, at least 100%, at least 150%, at least 200%, at least 300%, at least 400%, at least 500%, or at least 600% compared to the subject's baseline PBGD activity.

In some embodiments, the PBGD activity is increased in the liver of the subject.

In some embodiments, the increased PBGD activity persists for greater than 24, 36, 48, 60, 72, or 96 hours.

In some embodiments, the pharmaceutical composition or polynucleotide is administered to the subject during an acute porphyria attack.

In some embodiments, after administration of the pharmaceutical composition or polynucleotide to the subject, e.g., within 24 hours, the level of ALA in the subject is reduced by at least about 20%, at least about 30%, at least about 40%, at least about 50%, at least about 60%, at least about 70%, at least about 80%, at least about 90%, or 100% compared to the subject's baseline ALA.

In some embodiments, the level of ALA is reduced in one or more of the urine, plasma, serum, and/or liver of the subject.

In some embodiments, after administration to the subject the level of ALA in the subject is reduced compared to the baseline level in the subject for at least one day, at least two days, at least three days, at least four days, at least five days, at least one week, at least two weeks, at least three weeks, or at least one month.

In some embodiments, after administration of the pharmaceutical composition or polynucleotide to the subject, e.g., within 24 hours, the level of PBG in the subject is reduced by at least about 20%, at least about 30%, at least about 40%, at least about 50%, at least about 60%, at least about 70%, at least about 80%, at least about 90%, or 100% compared to the subject's baseline ALA.

In some embodiments, the level of PBG is reduced in one or more of the urine, plasma, serum, and/or liver of the subject.

In some embodiments, after administration to the subject the level of PBG in the subject is reduced compared to the baseline level in the subject for at least one day, at least two days, at least three days, at least four days, at least five days, at least one week, at least two weeks, at least three weeks, or at least one month.

In some embodiments, after administration of the pharmaceutical composition or polynucleotide to the subject, e.g., within 24 hours, the level of porphyrin in the subject is reduced by at least about 20%, at least about 30%, at least about 40%, at least about 50%, at least about 60%, at least about 70%, at least about 80%, at least about 90%, or 100% compared to the subject's baseline ALA.

In some embodiments, the level of porphyrin is reduced in one or more of the urine, plasma, serum, and/or liver of the subject.

In some embodiments, after administration to the subject the level of porphyrin in the subject is reduced compared to the baseline level in the subject for at least one day, at least two days, at least three days, at least four days, at least five days, at least one week, at least two weeks, at least three weeks, or at least one month.

In some embodiments, after administration of the pharmaceutical composition or polynucleotide to the subject, e.g., within 24 hours, the level of ALT in the subject is reduced by at least about 20%, at least about 30%, at least about 40%, at least about 50%, at least about 60%, at least about 70%, at least about 80%, at least about 90%, or 100% compared to the subject's baseline ALT.

In some embodiments, the level of ALT is reduced in one or more of the urine, plasma, serum, and/or liver of the subject.

In some embodiments, after administration to the subject the level of ALT in the subject is reduced compared to the baseline level in the subject for at least one day, at least two days, at least three days, at least four days, at least five days, at least one week, at least two weeks, at least three weeks, or at least one month.

In some embodiments, after administration of the pharmaceutical composition or polynucleotide to the subject, e.g., within 24 hours, the level of AST in the subject is reduced by at least about 20%, at least about 30%, at least about 40%, at least about 50%, at least about 60%, at least about 70%, at least about 80%, at least about 90%, or 100% compared to the subject's baseline AST.

In some embodiments, the level of AST is reduced in one or more of the urine, plasma, serum, and/or liver of the subject.

In some embodiments, after administration to the subject the level of AST in the subject is reduced compared to the baseline level in the subject for at least one day, at least two days, at least three days, at least four days, at least five days, at least one week, at least two weeks, at least three weeks, or at least one month.

In some embodiments, after administration of the pharmaceutical composition or polynucleotide to the subject, e.g., within 24 hours, the level of bilirubin in the subject is reduced by at least about 20%, at least about 30%, at least about 40%, at least about 50%, at least about 60%, at least about 70%, at least about 80%, at least about 90%, or 100% compared to the subject's baseline bilirubin.

In some embodiments, the level of bilirubin is reduced in one or more of the urine, plasma, serum, and/or liver of the subject.

In some embodiments, after administration to the subject the level of bilirubin in the subject is reduced compared to the baseline level in the subject for at least one day, at least two days, at least three days, at least four days, at least five days, at least one week, at least two weeks, at least three weeks, or at least one month.

In some embodiments, the AIP is clinically manifest (overt) AIP.

In some embodiments, the AIP is clinically presymptomatic (latent) AIP.

In some embodiments, the level the PBGD polypeptide activity level is sufficient to reduce the risk of or prevent the onset of an acute attack and/or sufficient to treat an acute attack.

In some embodiments, the pharmaceutical composition or polynucleotide is administered as a single dose of less than 1.5 mg/kg, less than 1.25 mg/kg, less than 1 mg/kg, or less than 0.75 mg/kg.

In some embodiments, the administration to the subject is about once a week, about once every two weeks, or about once a month.

In some embodiments, the pharmaceutical composition or polynucleotide is administered intravenously.

BRIEF DESCRIPTION OF THE DRAWINGS/FIGURES

FIG. 1A-D shows the protein sequence (FIG. 1A), table with domain features (FIG. 1B), graphic representation of domain structure (FIG. 1C), and nucleic acid sequence (FIG. 1D) of isoform 1 of PBGD.

FIG. 2A-D shows the protein sequence (FIG. 2A), table with domain features (FIG. 2B), graphic representation of domain structure (FIG. 2C), and nucleic acid sequence (FIG. 2D) of isoform 2 of PBGD.

FIG. 3A-D shows the protein sequence (FIG. 3A), table with domain features (FIG. 3B), graphic representation of domain structure (FIG. 3C), and nucleic acid sequence (FIG. 3D) of isoform 3 of PBGD.

FIG. 4A-D shows the protein sequence (FIG. 4A), table with domain features (FIG. 4B), graphic representation of domain structure (FIG. 4C), and nucleic acid sequence (FIG. 4D) of isoform 4 of PBGD.

FIG. 5 shows uracil (U) metrics corresponding to wild type isoform 1 of PBGD and 25 sequence optimized PBGD polynucleotides. The column labeled "U content (%)" corresponds to the % $U_{TL}$ parameter. The column labeled "U Content v. WT (%)" corresponds to % $U_{WT}$. The column labeled "U Content v. Theoretical Minimum (%)" corresponds to % $U_{TM}$. The column labeled "UU pairs v. WT (%)" corresponds to % $UU_{WT}$.

FIG. 6 shows guanine (G) metrics corresponding to wild type isoform 1 of PBGD and 25 sequence optimized PBGD polynucleotides. The column labeled "G Content (%)" corresponds to % $G_{TL}$. The column labeled "G Content v. WT (%)" corresponds to % $G_{WT}$. The column labeled "G Content v. Theoretical Maximum (%)" corresponds to % $G_{TMX}$.

FIG. 7 shows cytosine (C) metrics corresponding to wild type isoform 1 of PBGD and 25 sequence optimized PBGD polynucleotides. The column labeled "C Content (%)" corresponds to % Cm. The column labeled "C Content v. WT (%)" corresponds to % $C_{WT}$. The column labeled "C Content v. Theoretical Maximum (%)" corresponds to % $C_{TMX}$.

FIG. 8 shows guanine plus cytosine (G/C) metrics corresponding to wild type isoform 1 of PBGD and 25 sequence optimized PBGD polynucleotides. The column labeled "G/C Content (%)" corresponds to % G/Cm. The column labeled "G/C Content v. WT (%)" corresponds to % G/$C_{WT}$. The column labeled "G/C Content v. Theoretical Maximum (%)" corresponds to % G/$C_{MTX}$.

FIG. 9 shows a comparison between the G/C compositional bias for codon positions 1, 2, 3 corresponding to the wild type isoform 1 of PBGD and 25 sequence optimized PBGD polynucleotides.

FIG. 10A-C shows the protein sequence (FIG. 10A), table with domain features (FIG. 10B), graphic representation of domain structure (FIG. 10C) of the I291M/N340S gain of function mutant of isoform 1 of PBGD.

FIG. 11 shows the nucleic acid sequence of the I291M/N340S gain of function mutant of isoform 1 of PBGD.

FIG. 12A-D shows the protein sequence (FIG. 12A), table with domain features (FIG. 12B), graphic representation of domain structure (FIG. 12C), and nucleic acid sequence (FIG. 12D) of a fusion construct comprising the mature form of apolipoprotein A1 (sequence without signal peptide and propeptide) and isoform 1 of PBGD.

FIG. 13 shows the levels of hepatic PBGD activity after IV administration of chemically modified mRNAs encoding wild type PBGD (COV1 and COV2), PBGD-SM protein variant, and ApoAI-PBGD-SM conjugate to AIP mice. A single IV dose of mRNA construct at 1 nmol/kg was administered. PBGD activity in liver was quantitated as pmol of uroporphyrin produced per mg of protein per hour. Levels of hepatic PBGD activity observed in wild type mice and AIP mice are also shown for comparison. Data are expressed as mean±SD.

FIG. 14 shows the design of a pharmacodynamics study to evaluate the effects of the administration of a single IV dose of modified mRNA encoding wild type or SM variant of PBGD to AIP mice subjected to three acute porphyria attacks triggered by phenobarbital challenges. Intraperitoneal injections of phenobarbital and intravenous administration of PBGD mRNA are indicated by arrows above the time line of the study.

FIG. 15 shows urinary ALA excretion levels (micrograms of ALA per mg of creatinine) in AIP mice subjected to porphyria attacks caused by intraperitoneal phenobarbital challenges. In accordance with the study design shown in FIG. 14, AIP mice were administered a single intravenous injection of a chemically modified mRNA encoding PBGD, SM variant of PBGD, or luciferase, all formulated in MC3 and at 0.5 mg/kg. Data are expressed as mean±SD.

FIG. 16 shows urinary PBG excretion levels (micrograms of PBG per mg of creatinine) in AIP mice subjected to porphyria attacks caused by intraperitoneal phenobarbital challenges. In accordance with the study design shown in FIG. 14, AIP mice were administered a single intravenous injection of a chemically modified mRNA encoding PBGD, SM variant of PBGD, or luciferase, all formulated in MC3 and at 0.5 mg/kg. Data are expressed as mean±SD.

FIG. 17 shows pain measurements in AIP mice subjected to porphyria attacks caused by intraperitoneal phenobarbital challenges. In accordance with the study design shown in FIG. 14, AIP mice were administered a single intravenous injection of a chemically modified mRNA encoding PBGD, SM variant of PBGD, or luciferase, all formulated in MC3 and at 0.5 mg/kg. Pain levels were measured after the first, second, and third phenobarbital challenge (pain scale was measured using the method reported in Langford et al., Nat. Methods. 7(6): 447-9 (2010); Matsumiya et al., J. Am. Assoc. Lab. Anim. Sci. 51(1): 42-9 (2012)). Data are expressed as mean±SD.

FIGS. 18A and 18B present assessments of peripheral neuropathy as determined by rotarod (FIG. 18A) and footprint measurements (gait patterns) (FIG. 18B) following a single IV administration of PBGD, SM variant of PBGD, or luciferase mRNA (0.5 mg/kg) according to the study design shown in FIG. 14. Baseline measurements and measurements after each phenobarbital challenge are shown. Data are expressed as mean±SD.

FIGS. 19A, 19B, 19C, 19D and 19E show correction of sciatic nerve dysfunction following a single IV administration of PBGD or SM variant of PBGD mRNA (0.5 mg/kg) compared to luciferase mRNA (0.5 mg/kg) in AIP mice induced by three consecutive phenobarbital challenges according to the study design shown in FIG. 14. FIG. 19A shows sciatic nerve conduction data corresponding to AIP mice administered mRNA encoding luciferase. FIG. 19B and FIG. 19C shows sciatic nerve conduction data corresponding to AIP mice administered modified mRNA encoding wild type PBGD (FIG. 19B) and modified mRNA encoding PBGD-SM protein variant (FIG. 19C). FIG. 19D and FIG. 19E, respectively, show latency and amplitude values from sciatic nerve conduction data corresponding to AIP mice administered mRNA encoding luciferase or modified mRNA encoding wild type PBGD or modified mRNA encoding PBGD-SM variant.

FIGS. 20A, 20B, 20C, 20D, and 20E show hepatic expression of PBGD protein observed after IV administration of modified mRNA encoding wild type PBGD, or an AAV-PBGD vector. FIG. 20A shows hepatic PBGD protein expression after administration of AAV-PBGD. FIG. 20B shows basal PBGD protein expression levels.

FIG. 20C, FIG. 20D and FIG. 20E shows hepatic PBGD protein levels on day 1, day 2 and day 4, respectively, after administration of modified mRNA encoding wild type PBGD.

FIG. 21A and FIG. 21B show urinary ALA excretion levels (micrograms of ALA per mg of creatinine) (FIG. 21A) and urinary PBG excretion levels (micrograms of PBG per mg of creatinine) (FIG. 21B) in AIP mice subjected to porphyria attacks caused by intraperitoneal phenobarbital challenges. AIP mice were administered a single intravenous injection of a chemically modified mRNA encoding PBGD or mRNA encoding luciferase. mRNAs were formulated in MC3 or Compound 18 lipid nanoparticles. The mRNA encoding luciferase was administered at 0.5 mg/kg. The mRNA encoding PBGD was administered at 0.5 mg/kg and 0.1 mg/kg. Data are expressed as mean±SD.

FIG. 22A shows pain measurements in AIP mice subjected to porphyria attacks caused by intraperitoneal phenobarbital challenges. Pain levels were measured using a method reported in Langford et al., Nature Methods. 7(6): 447-9 (2010) after the first, second and third phenobarbital challenges. AIP mice were administered a single intravenous injection of a chemically modified mRNA encoding PBGD or mRNA encoding luciferase. mRNAs were formulated in MC3 or Compound 18 lipid nanoparticles. The mRNA encoding luciferase was administered at 0.5 mg/kg. The mRNA encoding PBGD was administered at 0.5 mg/kg and 0.1 mg/kg. Data are expressed as mean±SD.

FIG. 22B shows rotarod measurements in AIP mice subjected to porphyria attacks caused by intraperitoneal phenobarbital challenges. Time spent on rotarod was measured before the phenobarbital challenge as baseline, and after the first, second and third phenobarbital challenges. AIP mice were administered a single intravenous injection of a chemically modified mRNA encoding PBGD or an mRNA encoding luciferase at the beginning of the study (day 1). mRNAs were formulated in MC3 or Compound 18 lipid nanoparticles. The mRNA encoding luciferase was administered at 0.5 mg/kg. The mRNA encoding PBGD was administered at 0.5 mg/kg and 0.1 mg/kg. Data are expressed as mean±SD.

FIGS. 23A-B shows in vivo hepatic PBGD activity (expressed as nM uroporphyrin 1 concentration) (FIG. 23A) and in vivo hepatic PBGD protein expression (FIG. 23B) in wild type CD-1 mice administered modified mRNA constructs encoding wild type PBGD or luciferase as a control.

FIG. 24 shows the design of a multi-dose pharmacodynamics/dose-response study to evaluate the effects of the administration of a multiple doses of modified mRNA encoding human wild type PBGD to AIP mice subjected to three acute porphyria attacks triggered by phenobarbital challenges. Intraperitoneal injections of phenobarbital and intravenous administration of PBGD mRNA are indicated by arrows above the time line of the study. During each induced porphyria attack, the AIP mice were administered intravenous injections of a chemically modified mRNA encoding PBGD (Construct #14) formulated in Compound 18 lipid nanoparticles, which was administered at a dose of 0.5 mg/kg, 0.2 mg/kg, or 0.05 mg/kg every other week during each attack. PBS and an mRNA encoding luciferase were used as controls.

Figure 24:
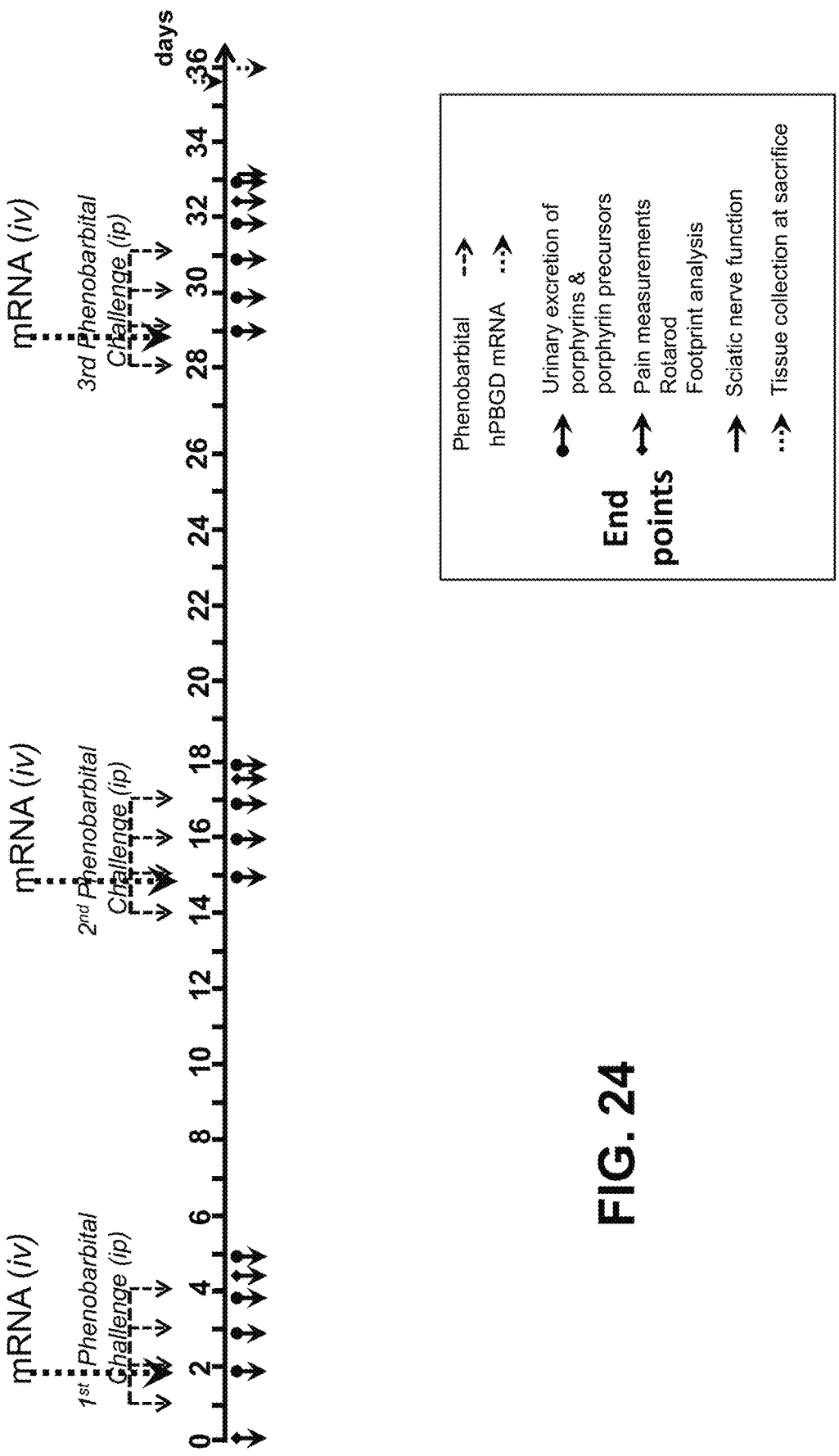
Figure 28:
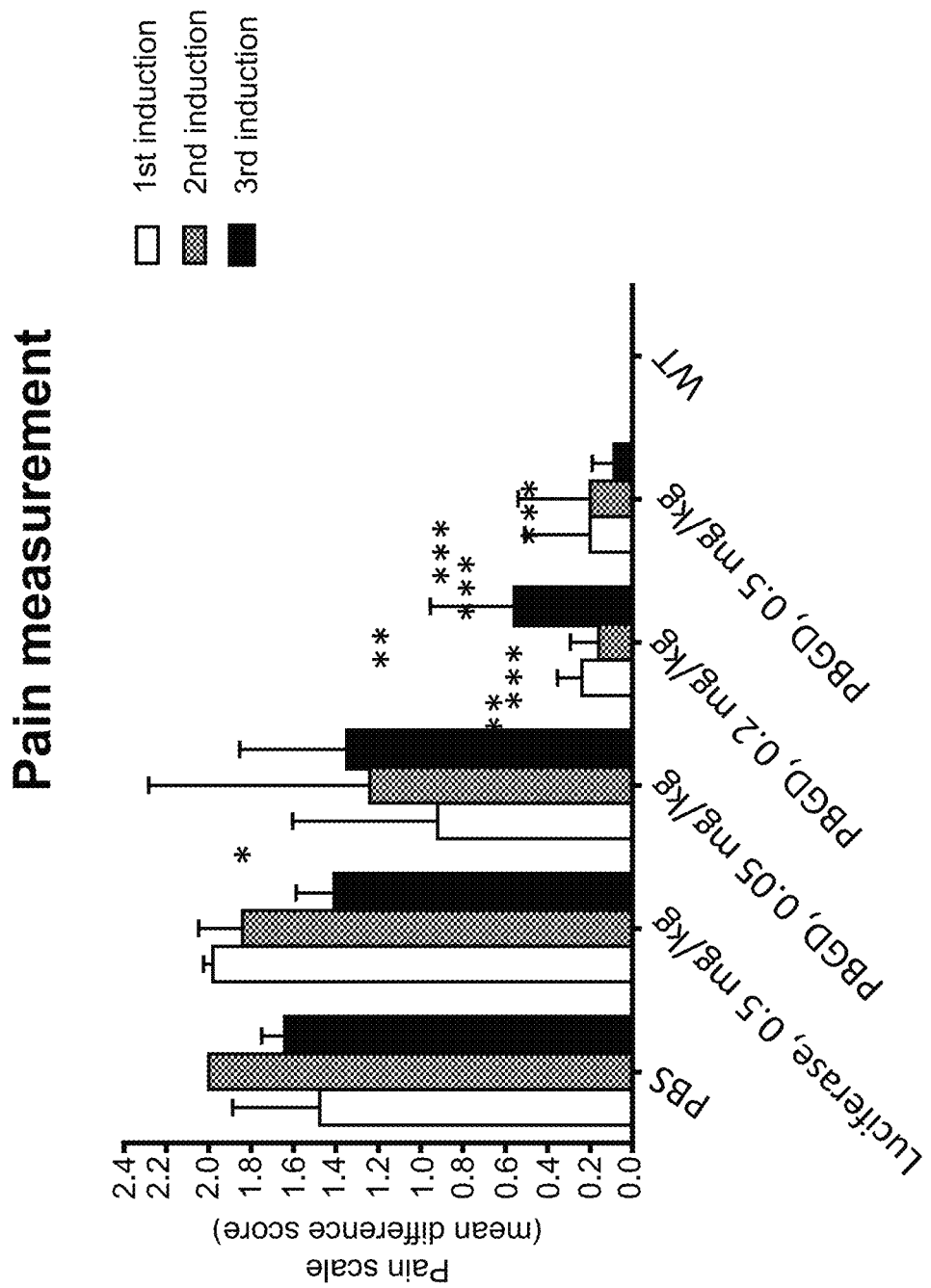
Figure 29:
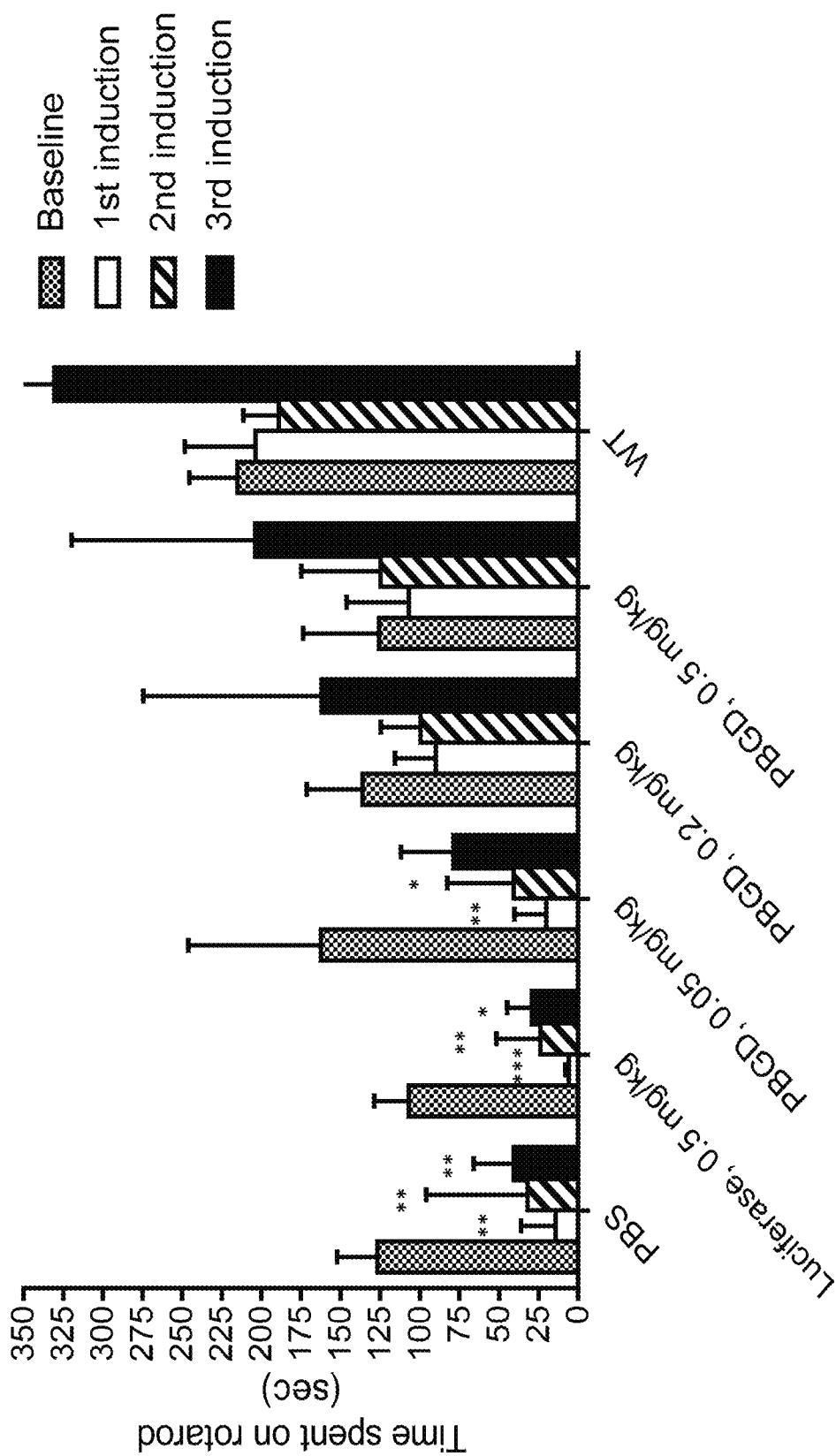
Figure 30:
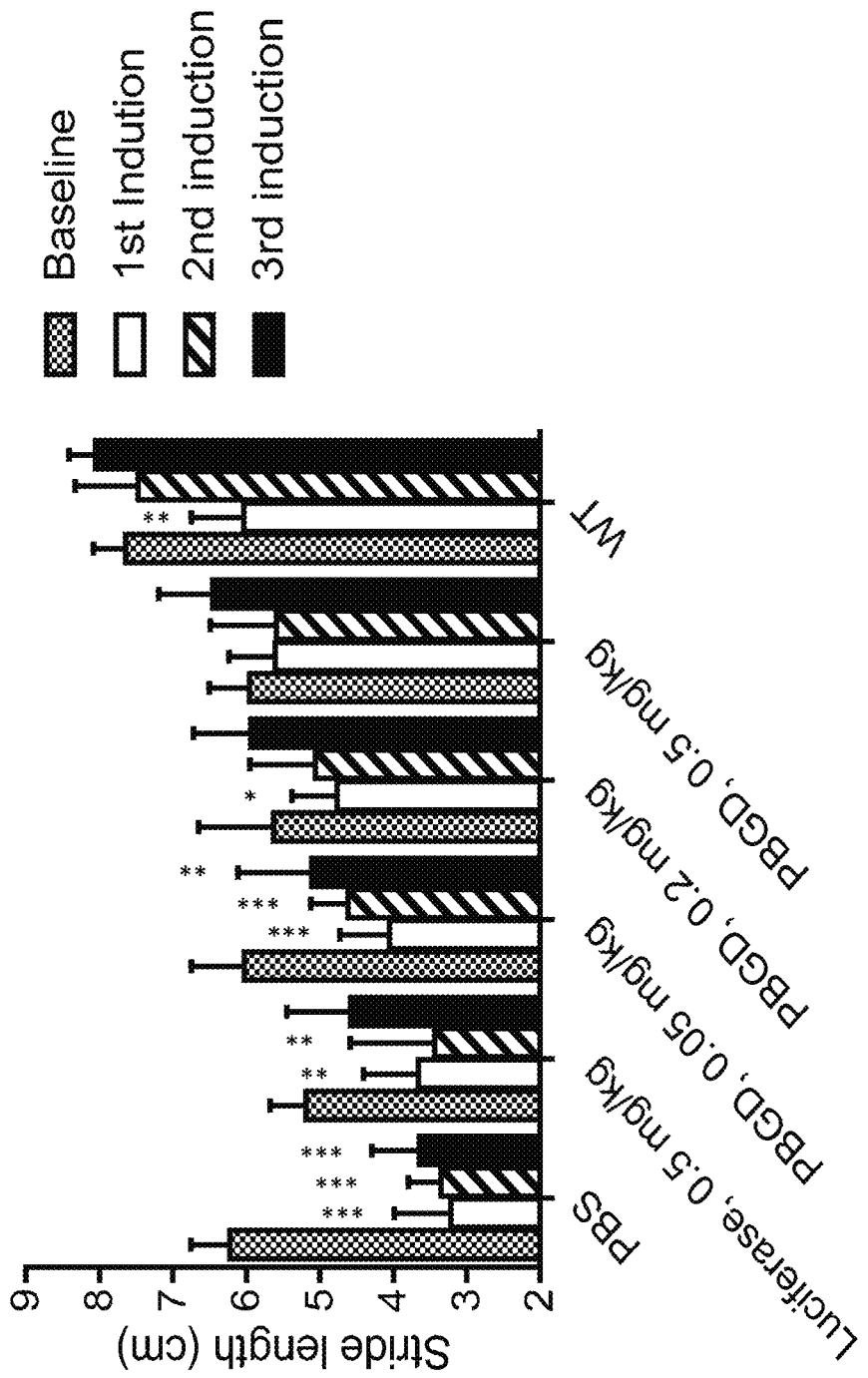
Figure 31:
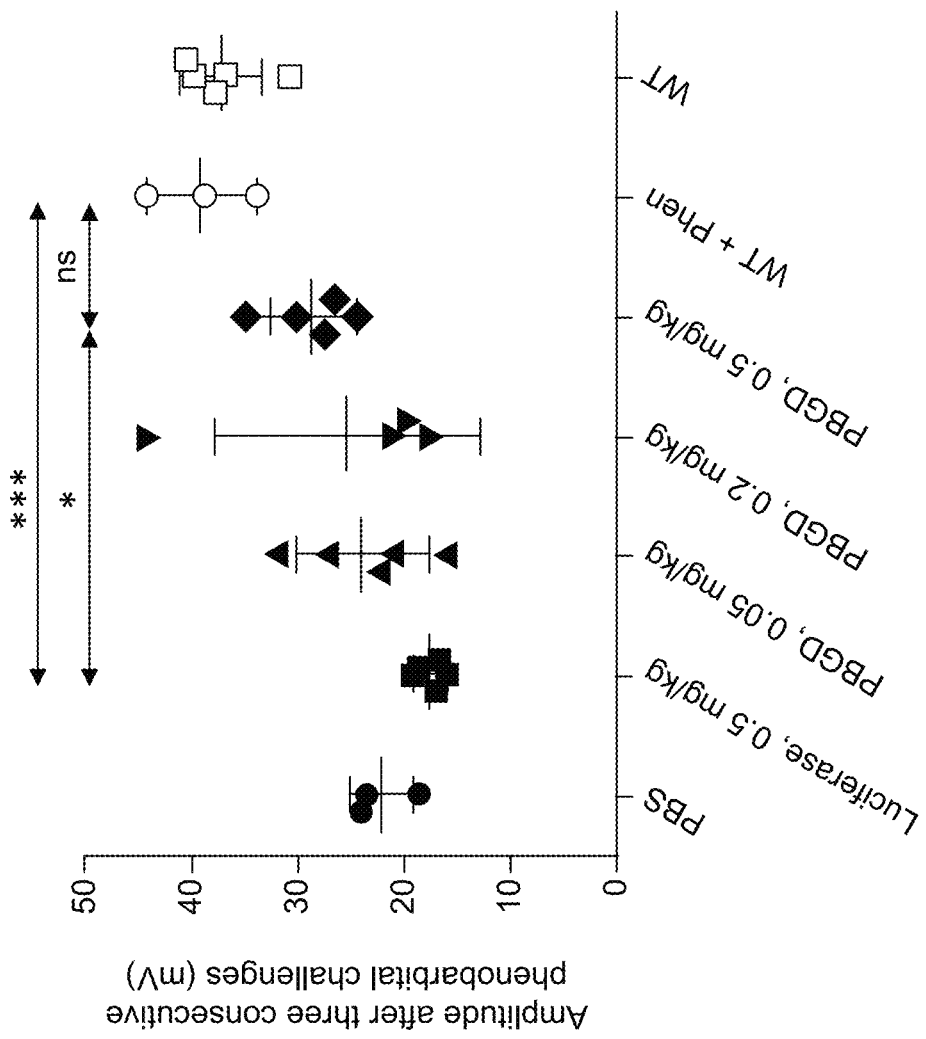

FIG. 28 shows pain measurements in AIP mice subjected to multiple porphyria attacks induced by intraperitoneal phenobarbital challenges according to the study design shown in FIG. 24. Pain levels were measured using a method reported in Langford et al., Nature Methods, 7(6): 447-9 (2010) after the first, second and third phenobarbital challenges. Data are expressed as mean±SD. P-values obtained from repeated measures ANOVA. $p<0.01$, *$p<0.001$ FIG. 29 present assessments of peripheral neuropathy as determined by rotarod. Measurement at baseline and measurements after each phenobarbital challenge are shown. AIP mice were subjected to three porphyria attacks induced by intraperitoneal phenobarbital challenges according to the study design shown in FIG. 24. The figure also shows data corresponding to untreated wild type animals (WT). Data are expressed as mean with SD. In case of the statistical analysis (see asterisks), data were log transformed prior to repeated measures ANOVA analysis to equalize variances and comparisons between baseline and marks obtained after each induction were made using Bonferroni+s multiple comparisons. *$p<0.05$, $p<0.01$, *$p<0.001$ FIG. 30 present assessments of peripheral neuropathy as determined by gait pattern analysis. Measurements at baseline and measurements after each phenobarbital challenge are shown. AIP mice were subjected to three porphyria attacks induced by intraperitoneal phenobarbital challenges according to the study design shown in FIG. 24. The figure also shows data corresponding to untreated wild type animals (WT). The stride length was measured in the two hind legs of each of the animals. The bars represent mean with S.D. Data were log transformed prior to repeated measures ANOVA analysis to equalize variances and comparisons between baseline and footprint marks obtained after each induction were made using Bonferroni's multiple comparisons. *$p<0.05$, $p<0.01$, *$p<0.001$ FIG. 31 present assessments of sciatic nerve dysfunction due to recurrent acute porphyria attacks in AIP mice induced by phenobarbital challenge according to the study design shown in FIG. 24. Amplitude values from sciatic nerve conduction data correspond to mice under control conditions or after administration of a modified mRNA encoding wild type human PBGD (at doses, e.g., 0.05 mg/kg, 0.2 mg/kg, and 0.5 mg/kg). Control measurements correspond to: AIP mice treated with buffer, AIP mice administered mRNA encoding luciferase, untreated wild type mice, and wild type mice treated with phenobarbital. The bars represent mean with S.D. P-values were obtained from a one-way ANOVA. *p<0.05, ***p<0.001

Figure 32B:
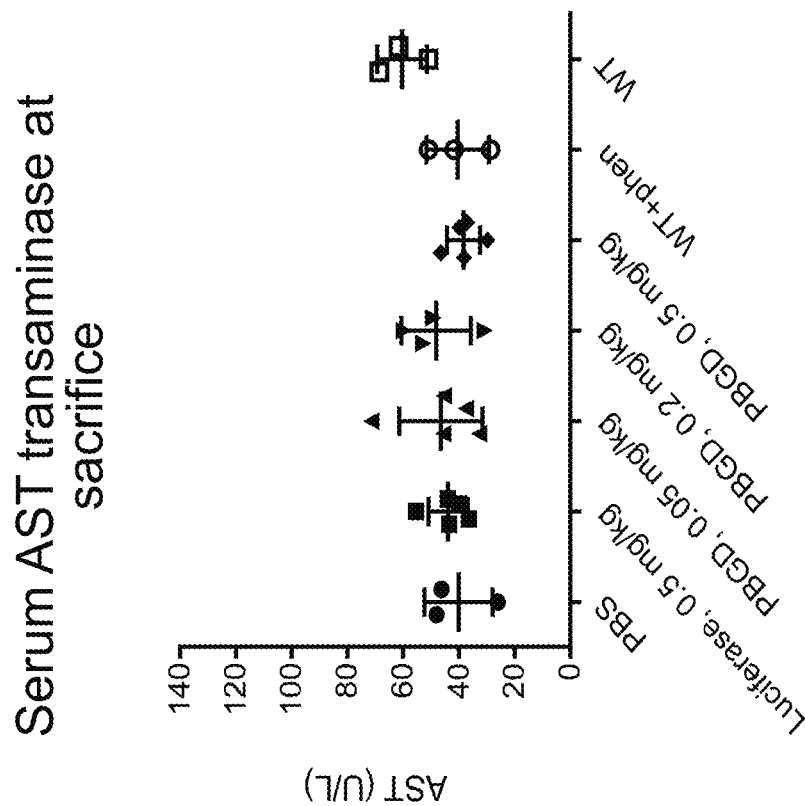
Figure 32A:
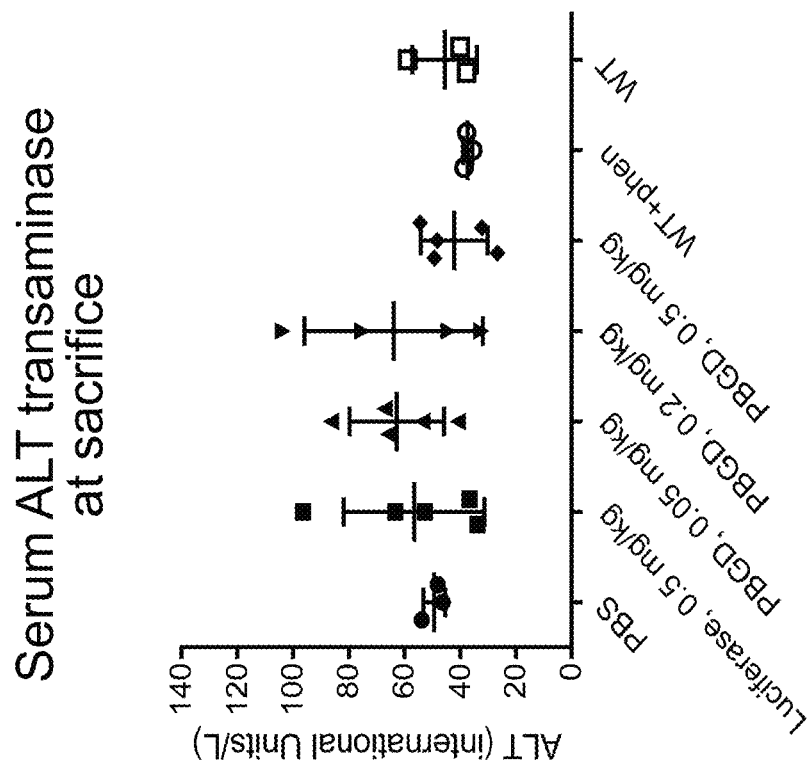
Figure 32C:
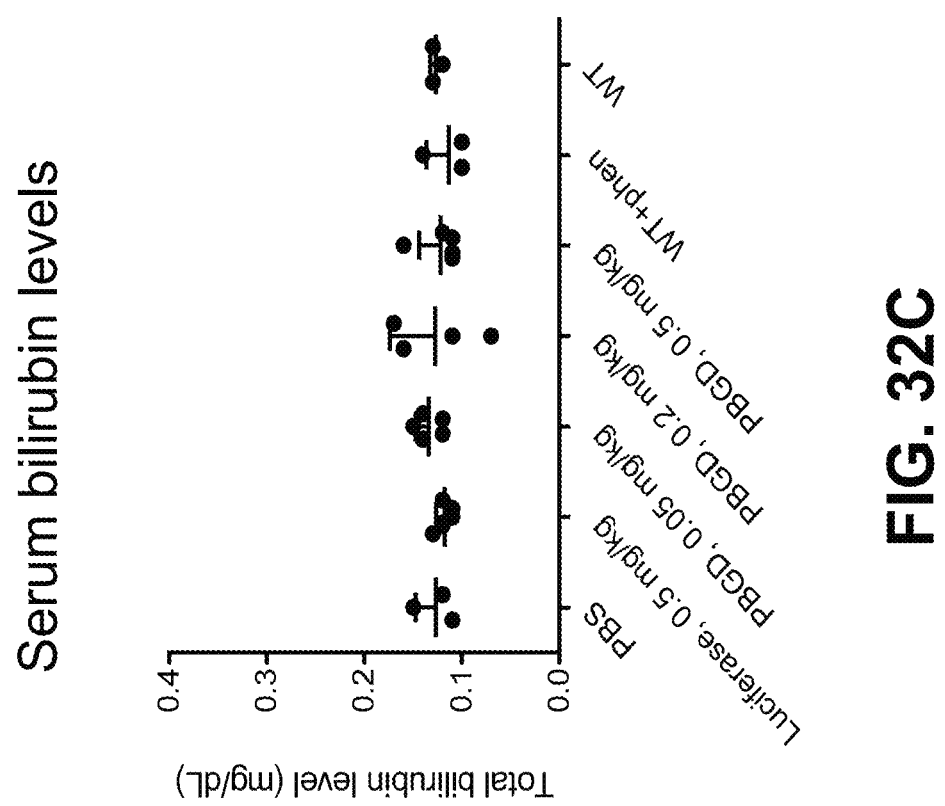

FIGS. 32A, 32B, and 32C present assessments of serum transaminases and bilirubin levels in AIP mice according to the study design shown in FIG. 24. Each drawing presents measurements from mice under control conditions or after 3 IV administrations of modified mRNA encoding human wild type PBGD (at doses of 0.05 mg/kg, 0.2 mg/kg, and 0.5 mg/kg). Control measurements correspond to: AIP mice treated with buffer, AIP mice treated with mRNA encoding luciferase, untreated wild type mice, and wild type mice treated with phenobarbital. The bars represent mean with S.D. FIG. 32A shows levels of serum ALT transaminase (I.U./L) at sacrifice. FIG. 32B shows levels of serum AST transaminase (I.U./L) at sacrifice. FIG. 32C shows serum bilirubin levels (mg/dL).

Figures 33A, 33B, 33C:
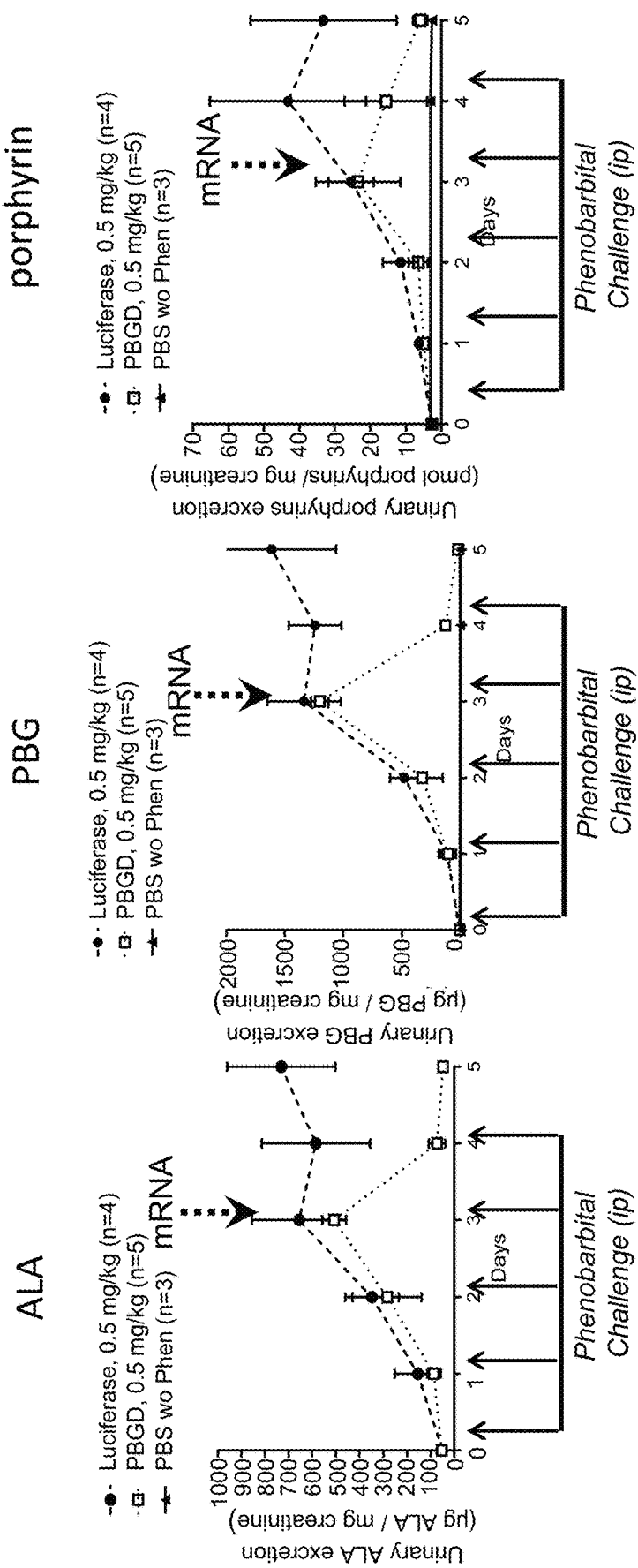

FIGS. 33A, 33B, and 33C show the effect of the administration of a modified mRNA encoding wild type PBGD on AIP urine biomarker levels (ALA, PBG, and porphyrin, respectively) during a porphyria attack triggered by phenobarbital challenges. Each drawing shows results corresponding to AIP mice treated with PBS without phenobarbital, mice treated with mRNA encoding luciferase, and a modified mRNA encoding wild type human PBGD. FIG. 33A shows the effect on urine ALA levels, FIG. 33B shows the effect on urine PBG levels, and FIG. 33C shows the effect on urine porphyrin levels.

Figure 34:
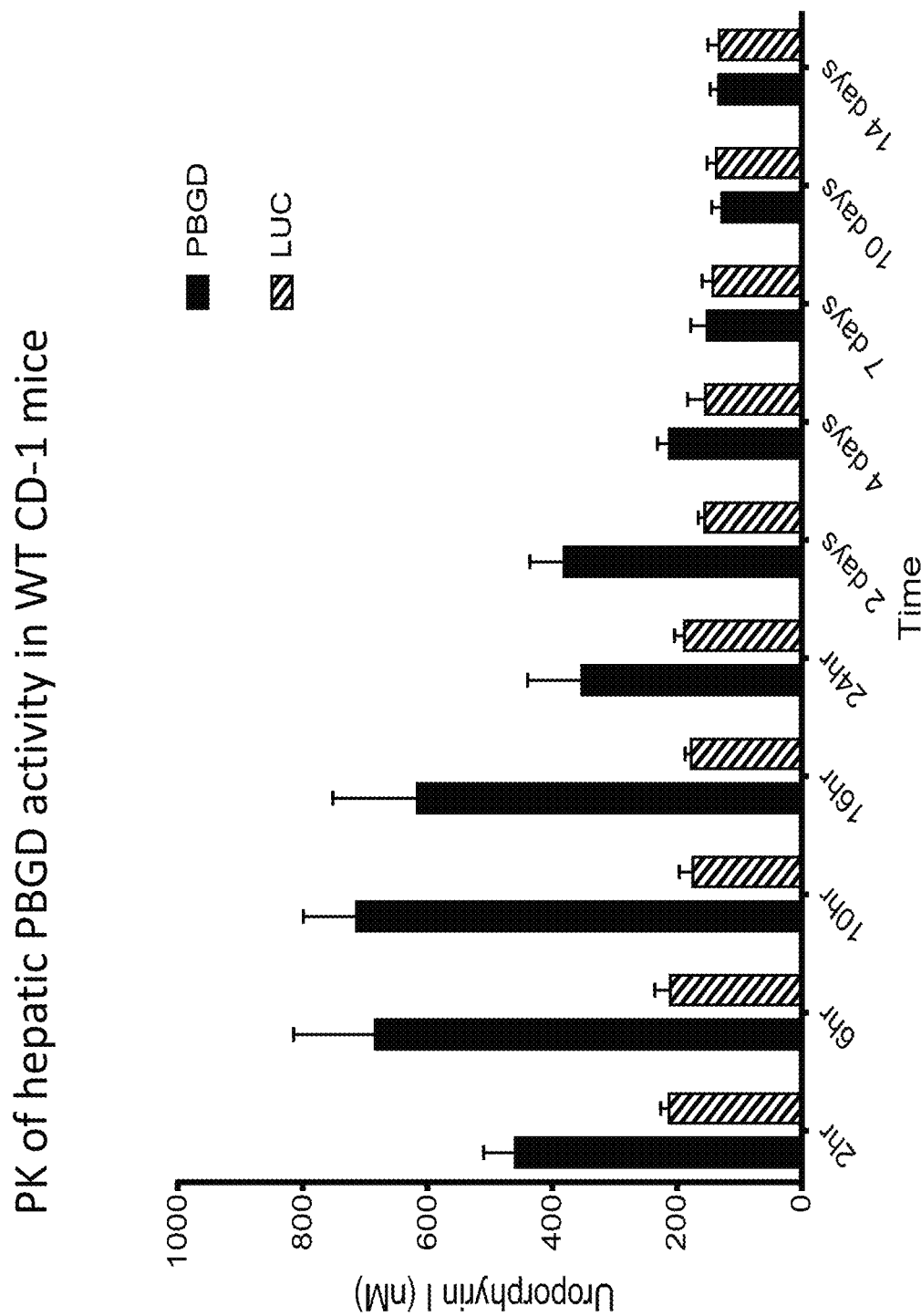

FIG. 34 shows the pharmacokinetic profile of hepatic PBGD activity in WT CD-1 mice after IV administration of either a control mRNA encoding luciferase, or a modified mRNA encoding human wild type PBGD (0.5 mg/kg). The error bars represent S.D. Hepatic PBGD activity was quantitated based on uroporphyrin levels (nM). Splenic PBGD activity did not differ between mice administered luciferase (vehicle control) mRNA and hPBGD mRNA (data not shown).

Figure 35A:
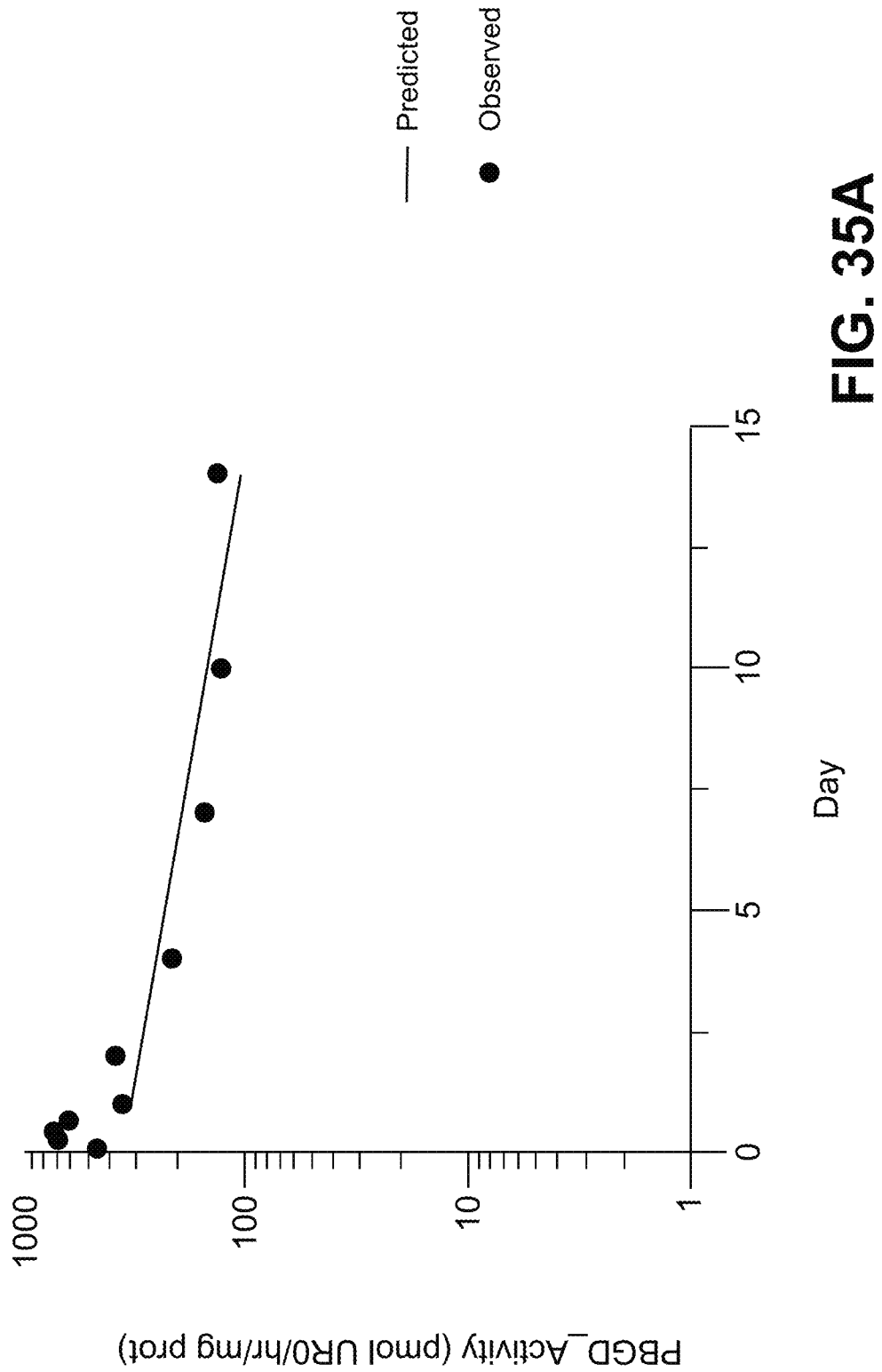
Figure 35B:
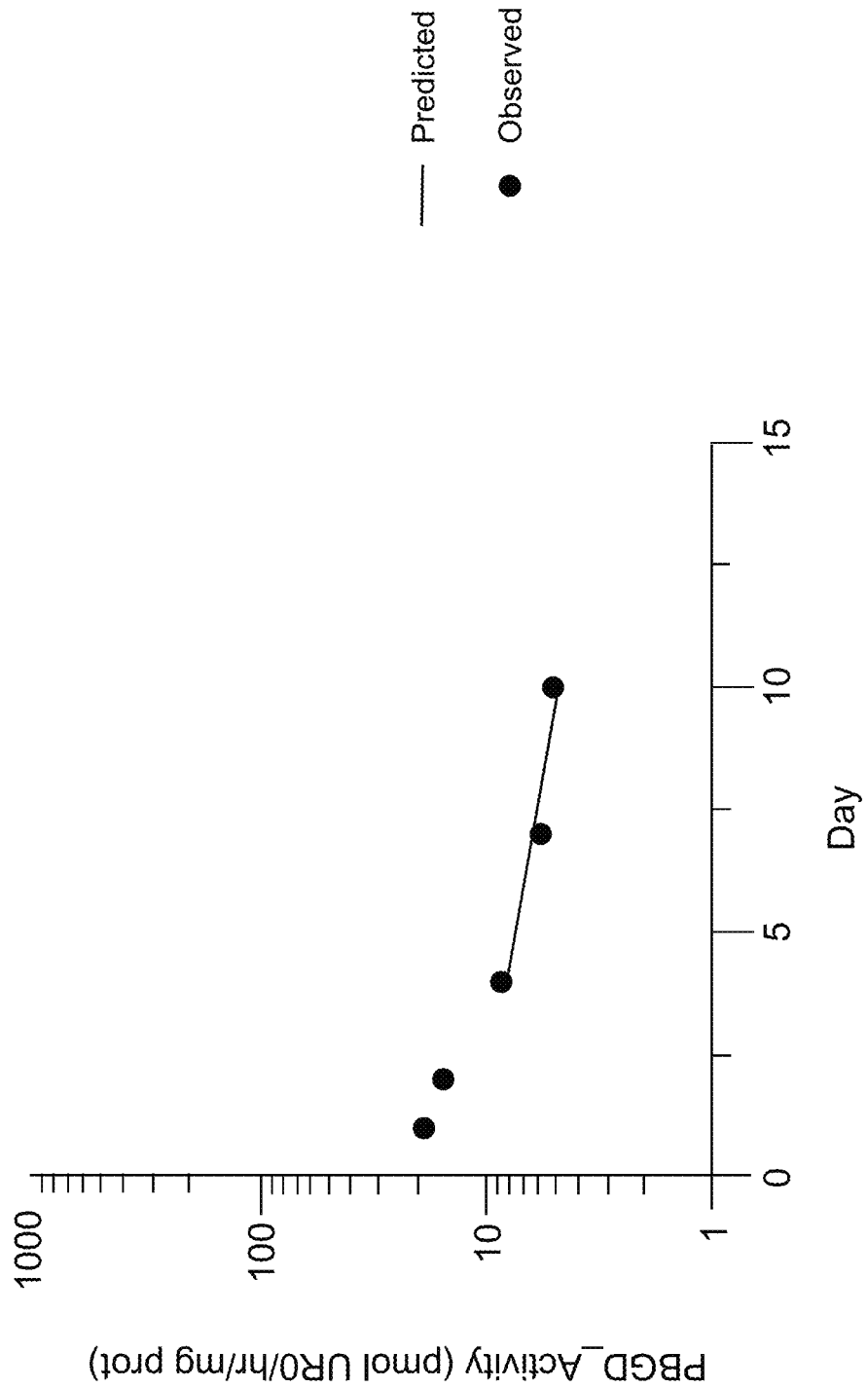

FIG. 35A shows the decay in hepatic PBGD activity in WT CD-1 mice after IV administration of a modified mRNA encoding human wild type PBGD (0.5 mg/kg). FIG. 35B shows the decay in hepatic PBGD activity in AIP mice after IV administration of a modified mRNA encoding human wild type PBGD. In both cases, the terminal $t_{1/2}$ of the PBGD activity, determined by noncompartmental analysis, was 8 days.

FIG. 36 shows the pharmacokinetic of hepatic human PBGD protein concentration in WT CD-1 mice after IV administration of either a control mRNA encoding luciferase, or a modified mRNA encoding human wild type PBGD (0.5 mg/kg). The error bars represent S.D. Human PBGD protein levels in liver were quantified by LC-MS/MS using a human specific peptide (ASYPGLQFEIIAMSTTGDK; SEQ ID NO: 85).

Figure 37:
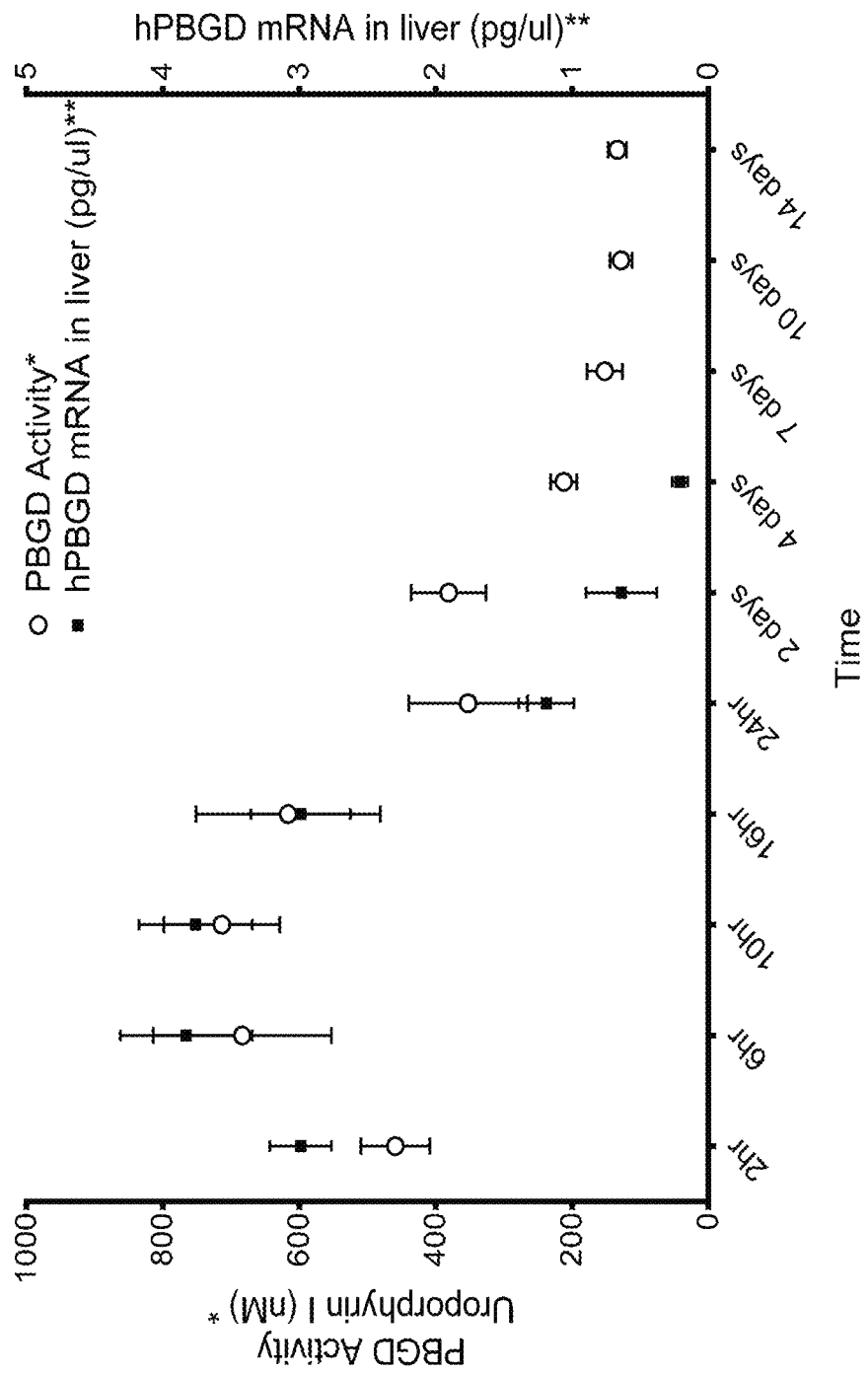

FIG. 37 shows hepatic PBGD activity (measured as uroporphyrin production, nM; left axis) and hPBGD mRNA levels in liver (pg/uL; right axis) in WT CD1 mice administered a single IV bolus of human PBGD mRNA (0.5 mg/kg).

FIGS. 38A, 38B, 38C, 38D, 38E, and 38F show hepatic expression of PBGD protein observed in WT CD1 mice after IV administration of modified mRNA encoding human wild type PBGD (0.5 mg/kg). FIGS. 38A, 38B, 38C, 38D, and 38E show hepatic PBGD protein levels at 2 hours, 6 hours, 10 hours, 16 hours, and 24 hours, respectively, after administration of modified mRNA encoding human wild type PBGD. FIG. 38F shows basal PBGD protein expression levels detected by Novus anti-PBGD antibody which doesn't cross-react with endogenous mouse PBGD protein.

Figure 39:
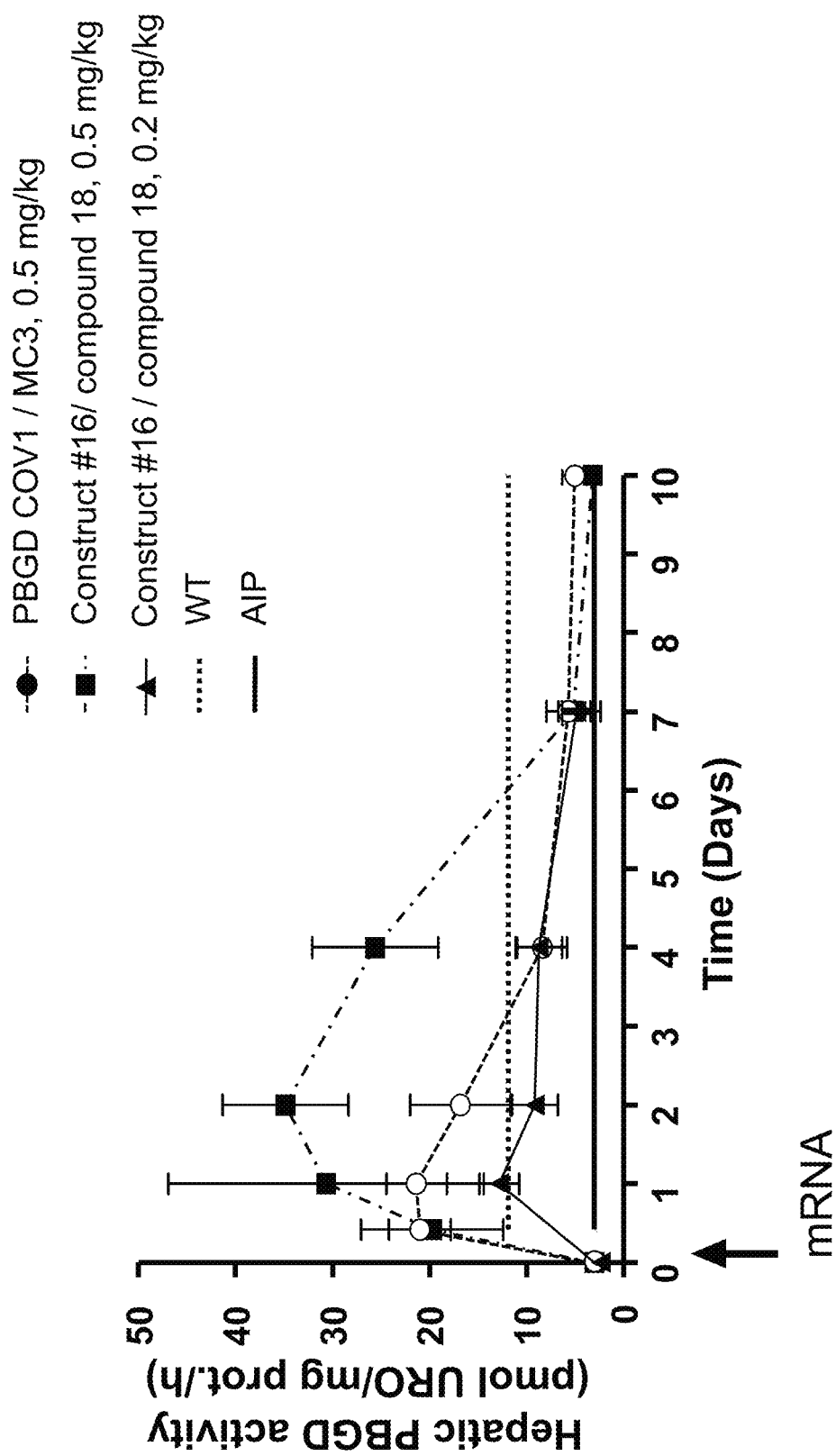

FIG. 39 shows hepatic PBGD activity levels after a single IV administration of 5-methoxyuracil comprising chemically modified mRNAs encoding wild type PBGD to AIP mice. A single IV dose of mRNA construct at 0.2 mg/kg or 0.5 mg/kg was administered. Levels of hepatic PBGD activity observed in wild type mice and AIP mice are also shown for comparison. Data are expressed as mean±SD.

Figure 40A:
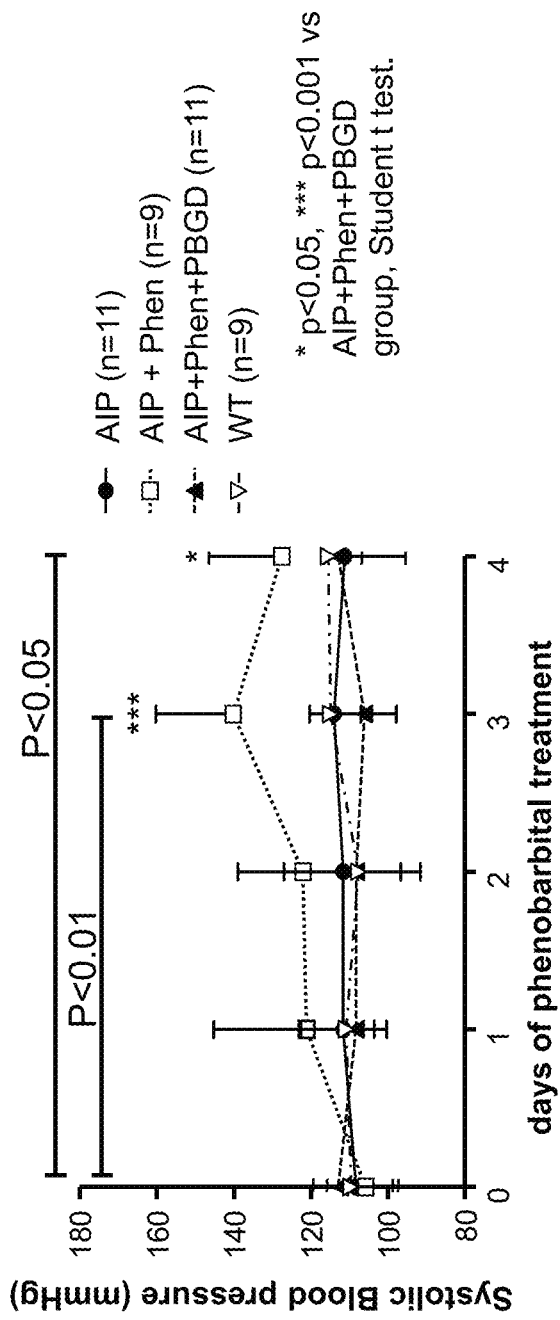
Figure 40B:
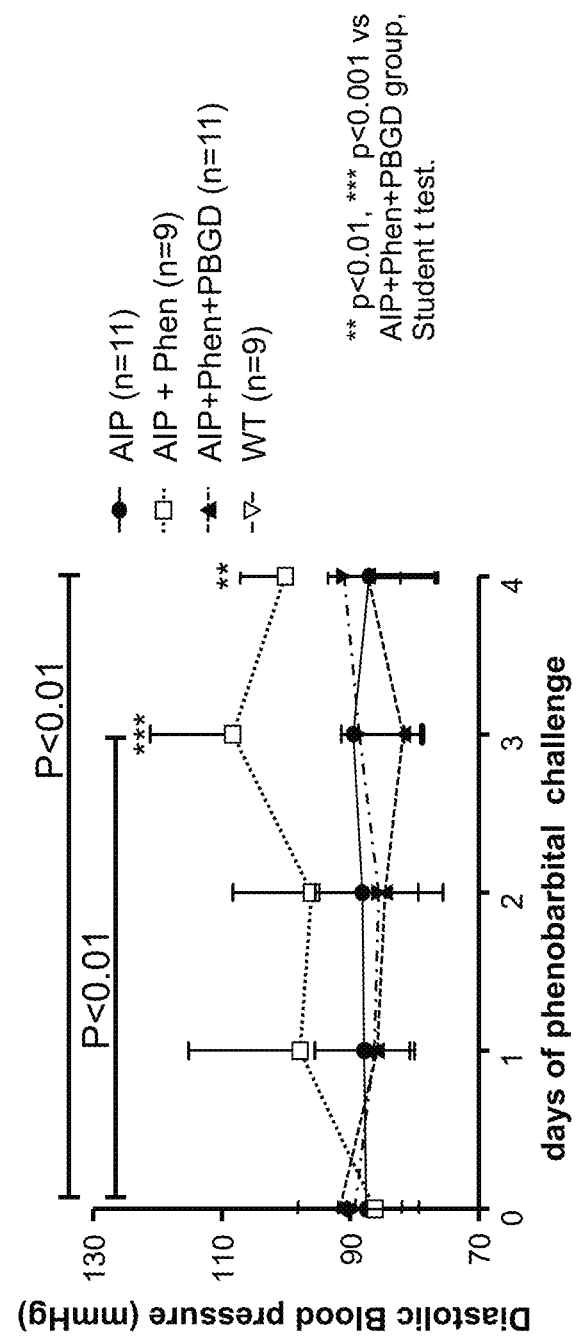

FIGS. 40A and 40B shows a decrease in systolic (FIG. 40A) and diastolic (FIG. 40B) blood pressure in AIP mice administered a single IV injection of human PBGD mRNA (0.5 mg/kg). A porphyric attack was induced in AIP mice by daily intraperitoneal phenobarbital injections. Blood pressure in WT and AIP mice that were not administered phenobarbital are shown as control groups.

Figure 41:
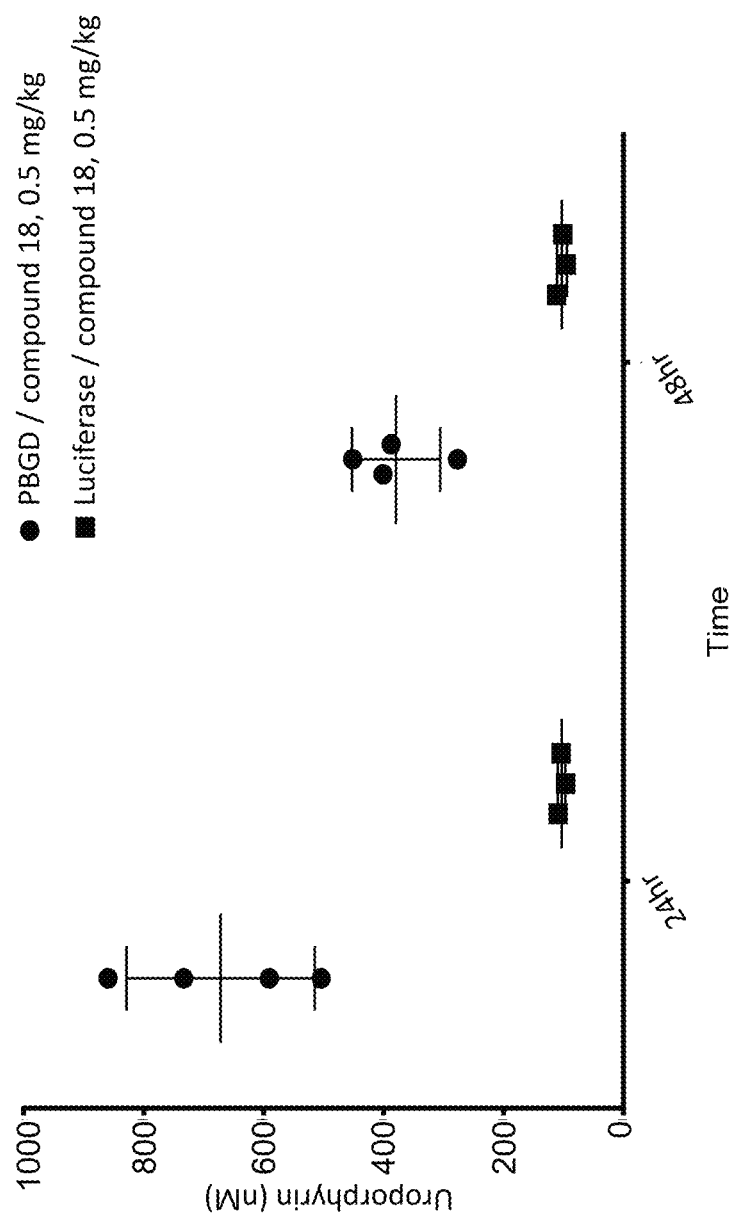

FIG. 41 shows the hepatic PBGD activity 1 and 2 days after a single IV administration of human PBGD mRNA or luciferase vehicle control mRNA (0.5 mg/kg) to Sprague Dawley rats. Data are presented as mean±SD. In contrast, PBGD activity levels in spleen did not differ between treatment arms 1-2 days post-injection in these rats.

Figure 42B:
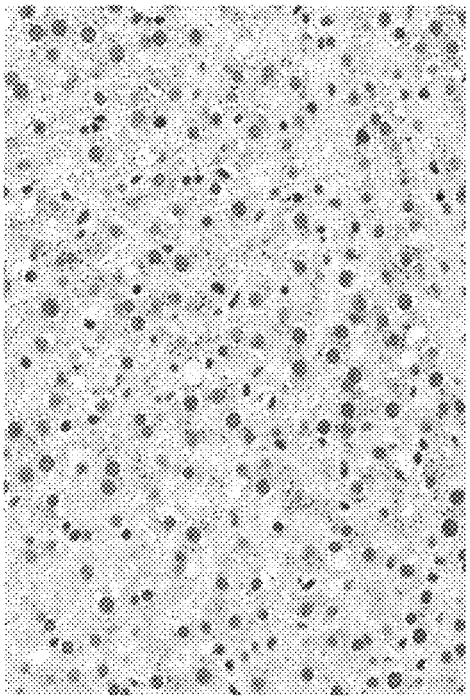
Figure 42A:
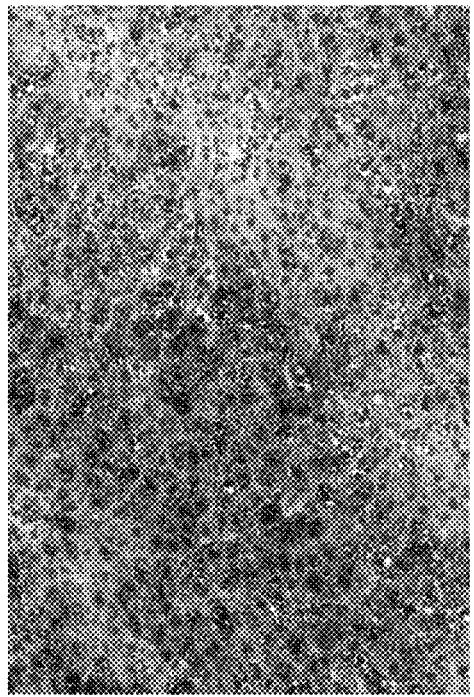

FIG. 42A shows hepatic expression of PBGD protein observed in Sprague Dawley rats at 24 hours after IV administration of modified mRNA encoding human wild type PBGD (1 mg/kg). FIG. 42B shows basal PBGD protein expression levels detected by Novus anti-PBGD antibody which doesn't cross-react with endogenous rat PBGD protein significantly.

Figure 43B:
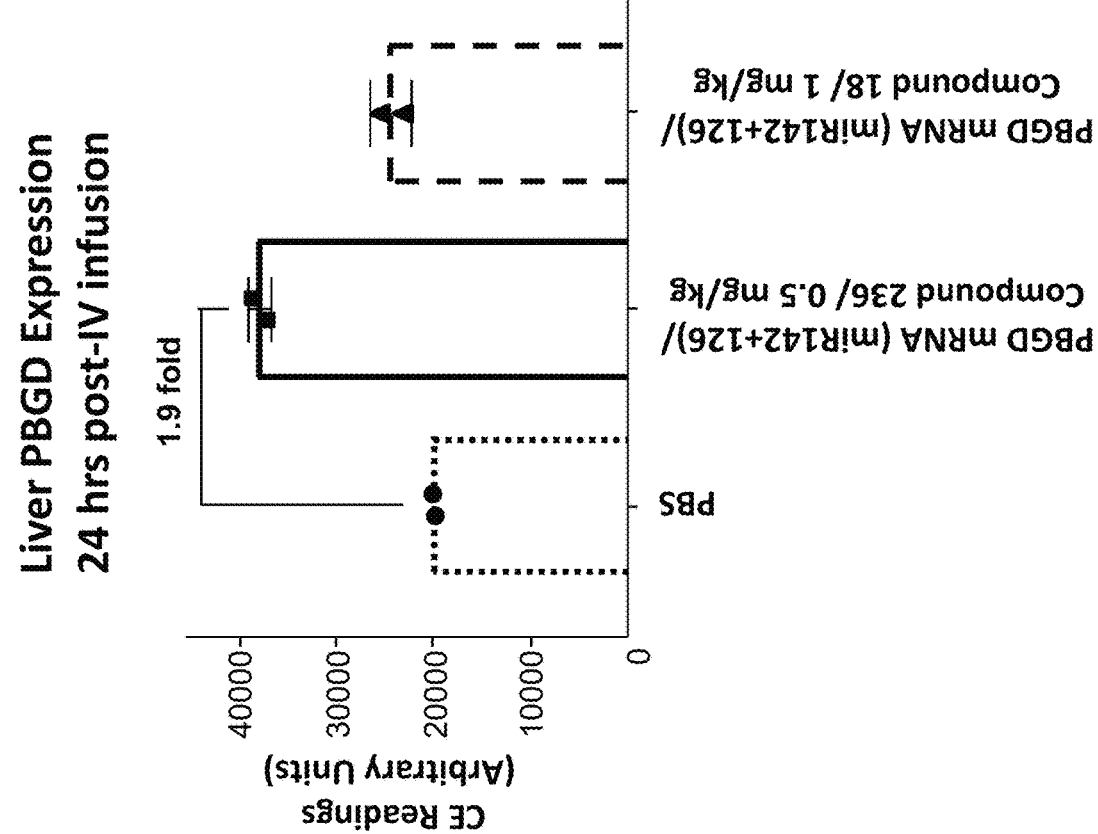
Figure 43A:
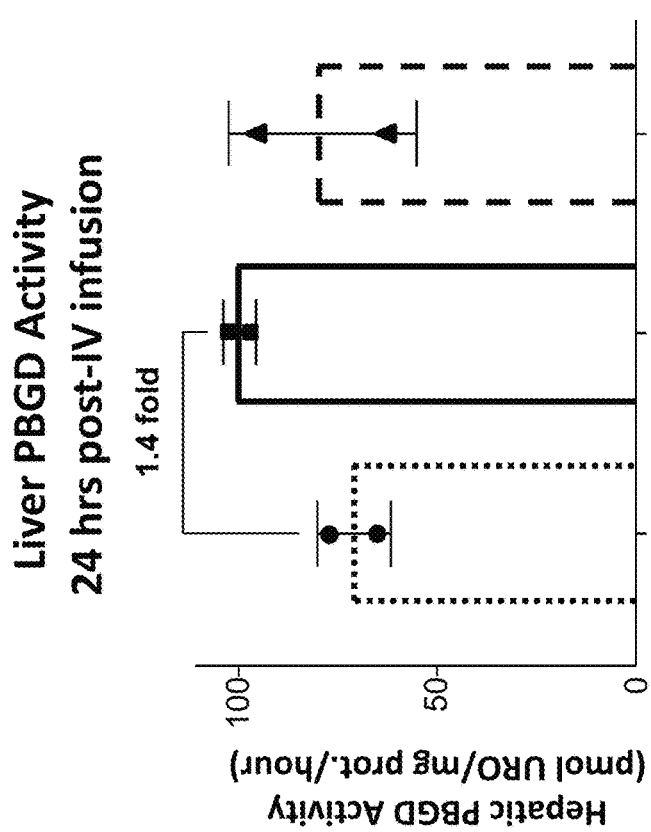

FIGS. 43A-B shows in vivo hepatic PBGD activity (expressed as expressed as pmol uroporphyrinogen/mg protein/hour) (FIG. 43A) and in vivo hepatic PBGD protein expression (FIG. 43B) in Cynomolgus macaque liver following administration of modified mRNA constructs encoding wild type PBGD.

DETAILED DESCRIPTION

The present invention provides mRNA therapeutics for the treatment of acute intermittent porphyria (AIP). Acute intermittent porphyria (AIP) is a genetic metabolic disorder affecting the production of heme, the oxygen-binding prosthetic group of hemoglobin. AIP is caused by mutations in the HMBS gene, which codes for the enzyme porphobilinogen deaminase (PBGD). Without porphobilinogen deaminase (PBGD), a necessary cytoplasmic enzyme, heme synthesis cannot finish, and the metabolite porphobilinogen accumulates in the cytoplasm. mRNA therapeutics are particularly well-suited for the treatment of AIP as the technology provides for the intracellular delivery of mRNA encoding PBGD followed by de novo synthesis of functional PBGD protein within target cells. After delivery of mRNA to the target cells, the desired PBGD protein is expressed by the cells' own translational machinery, and hence, fully functional PBGD protein replaces the defective or missing protein.

One challenge associated with delivering nucleic acid-based therapeutics (e.g., mRNA therapeutics) in vivo stems from the innate immune response which can occur when the body's immune system encounters foreign nucleic acids. Foreign mRNAs can activate the immune system via recognition through toll-like receptors (TLRs), in particular TLR7/8, which is activated by single-stranded RNA (ssRNA). In nonimmune cells, the recognition of foreign mRNA can occur through the retinoic acid-inducible gene I (RIG-I). Immune recognition of foreign mRNAs can result in unwanted cytokine effects including interleukin-1β (IL-1β) production, tumor necrosis factor-α (TNF-α) distribution and a strong type I interferon (type I IFN) response. The instant invention features the incorporation of different modified nucleotides within therapeutic mRNAs to minimize the immune activation and optimize the translation efficiency of mRNA to protein. Particular aspects of the invention feature a combination of nucleotide modification to reduce the innate immune response and sequence optimization, in particular, within the open reading frame (ORF) of therapeutic mRNAs encoding PBGD to enhance protein expression.

Certain embodiments of the mRNA therapeutic technology of the instant invention also feature delivery of mRNA encoding PBGD via a lipid nanoparticle (LNP) delivery system. Lipid nanoparticles (LNPs) are an ideal platform for the safe and effective delivery of mRNAs to target cells. LNPs have the unique ability to deliver nucleic acids by a mechanism involving cellular uptake, intracellular transport and endosomal release or endosomal escape. The instant invention features novel ionizable lipid-based LNPs combined with mRNA encoding PBGD which have improved properties when administered in vivo. Without being bound in theory, it is believed that the novel ionizable lipid-based LNP formulations of the invention have improved properties, for example, cellular uptake, intracellular transport and/or endosomal release or endosomal escape. LNPs administered by systemic route (e.g., intravenous (IV) administration), for example, in a first administration, can accelerate the clearance of subsequently injected LNPs, for example, in further administrations. This phenomenon is known as accelerated blood clearance (ABC) and is a key challenge, in particular, when replacing deficient enzymes (e.g., PBGD) in a therapeutic context. This is because repeat administration of mRNA therapeutics is in most instances essential to maintain necessary levels of enzyme in target tissues in subjects (e.g., subjects suffering from AIP.) Repeat dosing challenges can be addressed on multiple levels. mRNA engineering and/or efficient delivery by LNPs can result in increased levels and or enhanced duration of protein (e.g., PBGD) being expressed following a first dose of administration, which in turn, can lengthen the time between first dose and subsequent dosing. It is known that the ABC phenomenon is, at least in part, transient in nature, with the immune responses underlying ABC resolving after sufficient time following systemic administration. As such, increasing the duration of protein expression and/or activity following systemic delivery of an mRNA therapeutic of the invention in one aspect, combats the ABC phenomenon. Moreover, LNPs can be engineered to avoid immune sensing and/or recognition and can thus further avoid ABC upon subsequent or repeat dosing. Exemplary aspect of the invention feature novel LNPs which have been engineered to have reduced ABC.

1. PORPHOBILINOGEN DEAMINASE (PBGD)

Porphobilinogen deaminase (PBGD; EC 4.3.1.8) is the third enzyme of the biosynthetic pathway leading to the production of heme. It catalyzes the synthesis of hydroxymethylbilane by stepwise condensation of 4 porphobilinogen units. Hydroxymethylbilane is then converted to uroporphyrinogen III by uroporphyrinogen III synthetase. The structure of 40-42 kDa porphobilinogen deaminase, which is highly conserved amongst organisms, consists of three domains. Domains 1 and 2 are structurally very similar: each consisting of five beta-sheets and three alpha helices in humans. Domain 3 is positioned between the other two and has a flattened beta-sheet geometry. A dipyrrole, a cofactor of this enzyme consisting of two condensed porphobilinogen molecules, is covalently attached to domain 3 and extends into the active site, the cleft between domains 1 and 2. Several positively charged arginine residues, positioned to face the active site from domains 1 and 2, have been shown to stabilize the carboxylate functionalities on the incoming porphobilinogen as well as the growing pyrrole chain. These structural features presumably favor the formation of the final hydroxymethylbilane product. Porphobilinogen deaminase usually exists in dimer units in the cytoplasm of the cell.

The most well-known health issue involving porphobilinogen deaminase is acute intermittent porphyria (AIP), an autosomal dominant genetic disorder where insufficient hydroxymethylbilane is produced, leading to a build-up of porphobilinogen in the cytoplasm as well as elevation in ALA and PBG levels in plasma and urine. This is caused by a gene mutation that, in 90% of cases, causes decreased amounts of enzyme. However, mutations where less-active enzymes and/or different isoforms have been described. See Grandchamp et al. (1989) Nucleic Acids Res. 17:6637-49; and Astrin et al. (1994) Hum. Mut. 4:243-52.

The coding sequence (CDS) for wild type PBGD canonical mRNA sequence, corresponding to isoform 1, is described at the NCBI Reference Sequence database (RefSeq) under accession number NM_000109.3 ("*Homo sapiens* hydroxymethylbilane synthase (HBMS), transcript variant 1, mRNA"). The wild type PBGD canonical protein sequence, corresponding to isoform 1, is described at the RefSeq database under accession number NP_000181.2 ("Porphobilinogen deaminase isoform 1 [*Homo sapiens*]"). The PBGD isoform 1 protein is 361 amino acids long. It is noted that the specific nucleic acid sequences encoding the reference protein sequence in the Ref Seq sequences are the coding sequence (CDS) as indicated in the respective RefSeq database entry.

Isoforms 2, 3, and 4 are produced by alternative splicing.

The RefSeq protein and mRNA sequences for isoform 2 of PBGD are NP_001019553.1 and NM_001024382.1, respectively. The RefSeq protein and mRNA sequences for isoform 3 of PBGD are NP_001245137.1 and NM_001258208.1, respectively. The RefSeq protein and mRNA sequences for isoform 4 of PBGD are NP_001245138.1 and NM_001258209.1, respectively. Isoforms 2, 3, and 4 PBGD are encoded by the CDS disclosed in each one of the above mentioned mRNA RefSeq entries.

The isoform 2 polynucleotide contains an alternate, in-frame exon in the 5' coding region and uses a downstream start codon, compared to variant 1. It encodes a PBGD isoform 2 polypeptide, which has a shorter N-terminus compared to isoform 1. The PBGD isoform 2 protein is 344 amino acids long and lacks the amino acids corresponding to positions 1-17 in isoform 1.

The isoform 3 polynucleotide lacks an alternate in-frame exon compared to variant 1. The resulting PBGD isoform 3 polypeptide has the same N- and C-termini but is shorter compared to isoform 1. The PBGD isoform 3 protein is 321 amino acids long and lacks the amino acids corresponding to positions 218-257 in isoform 1.

The isoform 4 polynucleotide uses an alternate splice junction at the 3' end of the first exon and lacks an alternate in-frame exon compared to variant 1. The resulting PBGD isoform 4 polypeptide is shorter at the N-terminus and lacks an alternate internal segment compared to isoform 1. The PBGD isoform 4 protein is 304 amino acids long and lacks the amino acids corresponding to positions 1-17 and positions 218-257 in isoform 1.

In certain aspects, the invention provides a polynucleotide (e.g., a ribonucleic acid (RNA), e.g., a messenger RNA (mRNA)) comprising a nucleotide sequence (e.g., an open reading frame (ORF)) encoding a PBGD polypeptide. In some embodiments, the PBGD polypeptide of the invention is a wild type PBGD isoform 1, 2, 3, or 4 protein. In some embodiments, the PBGD polypeptide of the invention is a variant, a peptide or a polypeptide containing a substitution, and insertion and/or an addition, a deletion and/or a covalent modification with respect to a wild-type PBGD isoform 1, 2, 3, or 4 sequence. In some embodiments, sequence tags or amino acids, can be added to the sequences encoded by the polynucleotides of the invention (e.g., at the N-terminal or C-terminal ends), e.g., for localization. In some embodiments, amino acid residues located at the carboxy, amino terminal, or internal regions of a polypeptide of the invention can optionally be deleted providing for fragments.

In some embodiments, the polynucleotide (e.g., a RNA, e.g., an mRNA) comprising a nucleotide sequence (e.g., an ORF) of the invention encodes a substitutional variant of a PBGD isoform 1, 2, 3, or 4 sequence, which can comprise one, two, three or more than three substitutions. In some embodiments, the substitutional variant can comprise one or more conservative amino acids substitutions. In other embodiments, the variant is an insertional variant. In other embodiments, the variant is a deletional variant.

As recognized by those skilled in the art, PBGD isoform 1, 2, 3, or 4 protein fragments, functional protein domains, variants, and homologous proteins (orthologs) are also considered to be within the scope of the PBGD polypeptides of the invention. Nonlimiting examples of polypeptides encoded by the polynucleotides of the invention are shown in FIGS. 1 to 4. For example, FIG. 1 shows the amino acid sequence of human PBGD wild type isoform 1.

Certain compositions and methods presented in this disclosure refer to the protein or polynucleotide sequences of PBGD isoform 1. A person skilled in the art will understand that such disclosures are equally applicable to any other isoforms of PBGD known in the art.

2. POLYNUCLEOTIDES AND OPEN READING FRAMES (ORFS)

The instant invention features mRNAs for use in treating (i.e., prophylactically and/or therapeutically treating) AIP. The mRNAs featured for use in the invention are administered to subjects and encode human porphobilinogen deaminase (PBGD) proteins(s) in vivo. Accordingly, the invention relates to polynucleotides, e.g., mRNA, comprising an open reading frame of linked nucleosides encoding human porphobilinogen deaminase (PBGD), isoforms thereof, functional fragments thereof, and fusion proteins comprising PBGD. In some embodiments, the open reading frame is sequence-optimized. In particular embodiments, the invention provides sequence-optimized polynucleotides comprising nucleotides encoding the polypeptide sequence of isoforms 1, 2, 3 or 4 of human PBGD, or sequence having high sequence identity with those sequence optimized polynucleotides.

In certain aspects, the invention provides polynucleotides (e.g., a RNA, e.g., an mRNA) that comprise a nucleotide sequence (e.g., an ORF) encoding one or more PBGD polypeptides. In some embodiments, the encoded PBGD polypeptide of the invention can be selected from:
(i) a full length PBGD polypeptide (e.g., having the same or essentially the same length as wild-type PBGD isoform 1, 2, 3 or 4);
(ii) a functional fragment of any of the PBGD isoforms described herein (e.g., a truncated (e.g., deletion of carboxy, amino terminal, or internal regions) sequence shorter than one of wild-type isoforms 1, 2, 3 or 4; but still retaining PBGD enzymatic activity);
(iii) a variant thereof, e.g., full length or truncated isoform 1, 2, 3, or 4 protein in which one or more amino acids have been replaced, e.g., variants that retain all or most of the PBGD activity of the polypeptide with respect to a reference isoform (such as, e.g., T59I, D178N, or any other natural or artificial variants known in the art, or a variant comprising the I291M and N340S mutations); or
(iv) a fusion protein comprising (i) a full length PBGD isoform 1, 2, 3, or 4 protein, a functional fragment or a variant thereof, and (ii) at least one heterologous protein (e.g., Apolipoprotein A1).

In certain embodiments, the encoded PBGD polypeptide is a mammalian PBGD polypeptide, such as a human PBGD polypeptide, a functional fragment or a variant thereof.

In some embodiments, the polynucleotide (e.g., a RNA, e.g., an mRNA) of the invention increases PBGD protein expression levels and/or detectable PBGD enzymatic activity levels in cells when introduced in those cells, e.g., by at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100%, compared to PBGD protein expression levels and/or detectable PBGD enzymatic activity levels in the cells prior to the administration of the polynucleotide of the invention. PBGD protein expression levels and/or PBGD enzymatic activity can be measured according to methods know in the art. In some embodiments, the polynucleotide is introduced to the cells in vitro. In some embodiments, the polynucleotide is introduced to the cells in vivo.

In some embodiments, the polynucleotides (e.g., a RNA, e.g., an mRNA) of the invention comprise a nucleotide sequence (e.g., an ORF) that encodes a wild-type human PBGD, e.g., wild-type isoform 1 of human PBGD (SEQ ID NO: 1, see FIG. 1), wild-type isoform 2 of human PBGD (SEQ ID NO: 3, see FIG. 2), wild-type isoform 3 of human PBGD (SEQ ID NO: 5, see FIG. 3), or wild-type isoform 4 of human PBGD (SEQ ID NO: 7, see FIG. 4).

In some embodiments, the polynucleotide (e.g., a RNA, e.g., an mRNA) of the invention comprises a sequence optimized nucleic acid sequence, wherein the open reading frame (ORF) of the sequence optimized nucleic acid sequence is derived from a wild-type PBGD sequence (e.g., wild-type isoforms 1, 2, 3 or 4). For example, for polynucleotides of invention comprising a sequence optimized ORF encoding PBGD isoform 2, the corresponding wild type sequence is the native PBGD isoform 2. Similarly, for a sequence optimized mRNA encoding a functional fragment of isoform 1, the corresponding wild type sequence is the corresponding fragment from PBGD isoform 1.

In some embodiments, the polynucleotides (e.g., a RNA, e.g., an mRNA) of the invention comprise a nucleotide sequence encoding PBGD isoform 1 having the full length sequence of human PBGD isoform 1 (i.e., including the initiator methionine). In mature human PBGD isoform 1, the initiator methionine can be removed to yield a "mature PBGD" comprising amino acid residues of 2-361 of the translated product. The teachings of the present disclosure directed to the full sequence of human PBGD (amino acids 1-361) are also applicable to the mature form of human PBGD lacking the initiator methionine (amino acids 2-361). Thus, in some embodiments, the polynucleotides (e.g., a RNA, e.g., an mRNA) of the invention comprise a nucleotide sequence encoding PBGD isoform 1 having the mature sequence of human PBGD isoform 1 (i.e., lacking the initiator methionine). In some embodiments, the polynucleotide (e.g., a RNA, e.g., an mRNA) of the invention comprising a nucleotide sequence encoding PBGD isoform 1 having the full length or mature sequence of human PBGD isoform 1 is sequence optimized.

In some embodiments, the polynucleotides (e.g., a RNA, e.g., an mRNA) of the invention comprise a nucleotide sequence (e.g., an ORF) encoding a mutant PBGD polypeptide, e.g., a double mutant I291M/N340S PBGD. The protein (SEQ ID NO: 152) and polynucleotide (SEQ ID NO: 153) of double mutant I291M/N340S human PBGD isoform 1 ("SM PBGD") are shown in FIG. 10A and FIG. 11. In some embodiments, the polynucleotides of the invention comprise an ORF encoding a PBGD polypeptide that comprises at least one point mutation in the PBGD sequence and retains PBGD enzymatic activity. In some embodiments, the mutant PBGD polypeptide has a PBGD activity which is at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100% of the PBGD activity of the corresponding wild-type PBGD (i.e., the same PBGD isoform but without the mutation(s)). In some embodiments, the polynucleotide (e.g., a RNA, e.g., an mRNA) of the invention comprising an ORF encoding a mutant PBGD polypeptide is sequence optimized.

In some embodiments, the polynucleotide (e.g., a RNA, e.g., an mRNA) of the invention comprises a nucleotide sequence (e.g., an ORF) that encodes a PBGD polypeptide with mutations that do not alter PBGD enzymatic activity. Such mutant PBGD polypeptides can be referred to as function-neutral. In some embodiments, the polynucleotide comprises an ORF that encodes a mutant PBGD polypeptide comprising one or more function-neutral point mutations.

In some embodiments, the mutant PBGD polypeptide has higher PBGD enzymatic activity than the corresponding wild-type PBGD. In some embodiments, the mutant PBGD polypeptide has a PBGD activity that is at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100% higher than the activity of the corresponding wild-type PBGD (i.e., the same PBGD isoform but without the mutation(s)).

In some embodiments, the polynucleotides (e.g., a RNA, e.g., an mRNA) of the invention comprise a nucleotide sequence (e.g., an ORF) encoding a functional PBGD fragment, e.g., where one or more fragments correspond to a polypeptide subsequence of a wild type PBGD polypeptide and retain PBGD enzymatic activity. In some embodiments, the PBGD fragment has a PBGD activity which is at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100% of the PBGD activity of the corresponding full length PBGD. In some embodiments, the polynucleotide (e.g., a RNA, e.g., an mRNA) of the invention comprising an ORF encoding a functional PBGD fragment is sequence optimized.

In some embodiments, the polynucleotide (e.g., a RNA, e.g., an mRNA) of the invention comprises a nucleotide sequence (e.g., an ORF) encoding a PBGD fragment that has higher PBGD enzymatic activity than the corresponding full length PBGD. Thus, in some embodiments the PBGD fragment has a PBGD activity which is at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100% higher than the PBGD activity of the corresponding full length PBGD.

In some embodiments, the polynucleotide (e.g., a RNA, e.g., an mRNA) of the invention comprises a nucleotide sequence (e.g., an ORF) encoding a PBGD fragment that is at least 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24% or 25% shorter than wild-type isoform 1, 2, 3, or 4 of PBGD.

In some embodiments, the polynucleotide (e.g., a RNA, e.g., an mRNA) of the invention comprises a nucleotide sequence (e.g., an ORF) encoding a PBGD polypeptide (e.g., the wild-type sequence, functional fragment, or variant thereof), wherein the nucleotide sequence is at least 70%, at least 75%, at least 80%, at least 85%, at least 90%, at least 95%, at least 96%, at least 97%, at least 98%, at least 99%, or 100% identical to the sequence of SEQ ID NO:2, 4, 6 or 8 (see, e.g., panel D in FIGS. 1, 2, 3 and 4, respectively).

In some embodiments, the polynucleotide (e.g., a RNA, e.g., an mRNA) of the invention comprises a nucleotide sequence (e.g., an ORF) encoding a PBGD polypeptide (e.g., the wild-type sequence, functional fragment, or variant thereof), wherein the nucleotide sequence has at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to a sequence selected from the group consisting of SEQ ID NOs: 9 to 33, and 89 to 117. See TABLE 2.

In some embodiments, the polynucleotide (e.g., a RNA, e.g., an mRNA) of the invention comprises a nucleotide sequence (e.g., an ORF) encoding a PBGD polypeptide (e.g., the wild-type sequence, functional fragment, or variant thereof), wherein the nucleotide sequence has 70% to 100%, 75% to 100%, 80% to 100%, 85% to 100%, 70% to 95%, 80% to 95%, 70% to 85%, 75% to 90%, 80% to 95%, 70% to 75%, 75% to 80%, 80% to 85%, 85% to 90%, 90% to 95%, or 95% to 100%, sequence identity to a sequence selected from the group consisting of SEQ ID NOs: 9 to 33, and 89 to 117. See TABLE 2.

In some embodiments, the polynucleotide (e.g., a RNA, e.g., an mRNA) of the invention comprises an ORF encoding a PBGD polypeptide (e.g., the wild-type sequence, functional fragment, or variant thereof), wherein the polynucleotide comprises a nucleic acid sequence having 70% to 100%, 75% to 100%, 80% to 100%, 85% to 100%, 70% to 95%, 80% to 95%, 70% to 85%, 75% to 90%, 80% to 95%, 70% to 75%, 75% to 80%, 80% to 85%, 85% to 90%, 90% to 95%, or 95% to 100%, sequence identity to a sequence selected from the group consisting of SEQ ID NOs: 118-148. See TABLE 5.

In some embodiments, the polynucleotide (e.g., a RNA, e.g., an mRNA) of the invention comprises a nucleotide sequence (e.g., an ORF) encoding a PBGD polypeptide (e.g., the wild-type sequence, functional fragment, or variant thereof), wherein the nucleotide sequence is at least 75%, at least 76%, at least 77%, at least 78%, at least 79%, least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to the sequence of SEQ ID NO:2, 4, 6 or 8 (see, e.g., panel D FIGS. 1, 2, 3 and 4, respectively).

In some embodiments, the polynucleotide (e.g., a RNA, e.g., an mRNA) of the invention comprises a nucleotide sequence (e.g., an ORF) encoding a PBGD polypeptide (e.g., the wild-type sequence, functional fragment, or variant thereof), wherein the nucleotide sequence is between 70% and 90% identical; between 75% and 85% identical; between 76% and 84% identical; between 77% and 83% identical, between 77% and 82% identical, or between 78% and 81% identical to the sequence of SEQ ID NO:2, 4, 6 or 8 (see, e.g., panel D in FIGS. 1, 2, 3, and 4, respectively).

In some embodiments, the polynucleotide (e.g., a RNA, e.g., an mRNA) of the invention comprises from about 900 to about 100,000 nucleotides (e.g., from 900 to 1,000, from 900 to 1,100, from 900 to 1,200, from 900 to 1,300, from 900 to 1,400, from 900 to 1,500, from 1,000 to 1,100, from 1,000 to 1,100, from 1,000 to 1,200, from 1,000 to 1,300, from 1,000 to 1,400, from 1,000 to 1,500, from 1,083 to 1,200, from 1,083 to 1,400, from 1,083 to 1,600, from 1,083 to 1,800, from 1,083 to 2,000, from 1,083 to 3,000, from 1,083 to 5,000, from 1,083 to 7,000, from 1,083 to 10,000, from 1,083 to 25,000, from 1,083 to 50,000, from 1,083 to 70,000, or from 1,083 to 100,000).

In some embodiments, the polynucleotide of the invention (e.g., a RNA, e.g., an mRNA) comprises a nucleotide sequence (e.g., an ORF) encoding a PBGD polypeptide (e.g., the wild-type sequence, functional fragment, or variant thereof), wherein the length of the nucleotide sequence (e.g., an ORF) is at least 500 nucleotides in length (e.g., at least or greater than about 500, 600, 700, 80, 900, 1,000, 1,050, 1,083, 1,100, 1,200, 1,300, 1,400, 1,500, 1,600, 1,700, 1,800, 1,900, 2,000, 2,100, 2,200, 2,300, 2,400, 2,500, 2,600, 2,700, 2,800, 2,900, 3,000, 3,100, 3,200, 3,300, 3,400, 3,500, 3,600, 3,700, 3,800, 3,900, 4,000, 4,100, 4,200, 4,300, 4,400, 4,500, 4,600, 4,700, 4,800, 4,900, 5,000, 5,100, 5,200, 5,300, 5,400, 5,500, 5,600, 5,700, 5,800, 5,900, 6,000, 7,000, 8,000, 9,000, 10,000, 20,000, 30,000, 40,000, 50,000, 60,000, 70,000, 80,000, 90,000 or up to and including 100,000 nucleotides).

In some embodiments, the polynucleotide of the invention (e.g., a RNA, e.g., an mRNA) comprises a nucleotide sequence (e.g., an ORF) encoding a PBGD polypeptide (e.g., the wild-type sequence, functional fragment, or variant thereof), and further comprises at least one nucleic acid sequence that is noncoding, e.g., a miRNA binding site. In some embodiments, the polynucleotide (e.g., a RNA, e.g., an mRNA) of the invention further comprises a 5'-UTR (e.g., selected from the sequences of SEQ ID NOs: 39 to 56, 83, 189 to 191) and a 3'UTR (e.g., selected from the sequences of SEQ ID NOs: 57 to 81, 84, 149 to 151, 161 to 172, 192 to 199). In some embodiments, the polynucleotide (e.g., a RNA, e.g., an mRNA) of the invention comprises a sequence selected from the group consisting of SEQ ID NO: 118-148, e.g., SEQ ID NO: 133, 141, 144 or 145. In a further embodiment, the polynucleotide (e.g., a RNA, e.g., an mRNA) comprises a 5' terminal cap (e.g., Cap0, Cap1, ARCA, inosine, N1-methyl-guanosine, 2'-fluoro-guanosine, 7-deaza-guanosine, 8-oxo-guanosine, 2-amino-guanosine, LNA-guanosine, 2-azidoguanosine, Cap2, Cap4, 5' methylG cap, or an analog thereof) and a poly-A-tail region (e.g., about 100 nucleotides in length). In a further embodiment, the polynucleotide (e.g., a RNA, e.g., an mRNA) a comprises a 3' UTR comprising a nucleic acid sequence selected from the group consisting of SEQ ID NOs: 149 to 151, or any combination thereof. In a further embodiment, the polynucleotide (e.g., a RNA, e.g., an mRNA) comprises a 3' UTR comprising a nucleic acid sequence of SEQ ID NO: 150. In a further embodiment, the polynucleotide (e.g., a RNA, e.g., an mRNA) comprises a 3' UTR comprising a nucleic acid sequence of SEQ ID NO: 151.

In some embodiments, the polynucleotide of the invention (e.g., a RNA, e.g., an mRNA) comprising a nucleotide sequence (e.g., an ORF) encoding a PBGD polypeptide is single stranded or double stranded.

In some embodiments, the polynucleotide of the invention comprising a nucleotide sequence (e.g., an ORF) encoding a PBGD polypeptide (e.g., the wild-type sequence, functional fragment, or variant thereof) is DNA or RNA. In some embodiments, the polynucleotide of the invention is RNA. In some embodiments, the polynucleotide of the invention is, or functions as, a messenger RNA (mRNA). In some embodiments, the mRNA comprises a nucleotide sequence (e.g., an ORF) that encodes at least one PBGD polypeptide, and is capable of being translated to produce the encoded PBGD polypeptide in vitro, in vivo, in situ, or ex vivo.

In some embodiments, the polynucleotide of the invention (e.g., a RNA, e.g., an mRNA) comprises a sequence-optimized nucleotide sequence (e.g., an ORF) encoding a PBGD polypeptide (e.g., the wild-type sequence, functional fragment, or variant thereof), wherein the polynucleotide comprises at least one chemically modified nucleobase, e.g., 5-methoxyuracil. In some embodiments, the polynucleotide further comprises a miRNA binding site, e.g., a miRNA binding site that binds to miR-142 and/or a miRNA binding site that binds to miR-126. In some embodiments, the polynucleotide (e.g., a RNA, e.g., an mRNA) disclosed herein is formulated with a delivery agent comprising, e.g., a compound having the Formula (I), e.g., any of Compounds 1-232, e.g., Compound 18; a compound having the Formula (III), (IV), (V), or (VI), e.g., any of Compounds 233-342, e.g., Compound 236; or a compound having the Formula (VIII), e.g., any of Compounds 419-428, e.g., Compound 428, or any combination thereof. In some embodiments, the delivery agent comprises Compound 18, DSPC, Cholesterol, and Compound 428, e.g., with a mole ratio of about 50:10:38.5:1.5.

3. SIGNAL SEQUENCES

The polynucleotides (e.g., a RNA, e.g., an mRNA) of the invention can also comprise nucleotide sequences that encode additional features that facilitate trafficking of the encoded polypeptides to therapeutically relevant sites. One such feature that aids in protein trafficking is the signal sequence, or targeting sequence. The peptides encoded by these signal sequences are known by a variety of names, including targeting peptides, transit peptides, and signal peptides. In some embodiments, the polynucleotide (e.g., a RNA, e.g., an mRNA) comprises a nucleotide sequence (e.g., an ORF) that encodes a signal peptide operably linked to a nucleotide sequence that encodes a PBGD polypeptide described herein.

In some embodiments, the "signal sequence" or "signal peptide" is a polynucleotide or polypeptide, respectively, which is from about 9 to 200 nucleotides (3-70 amino acids) in length that, optionally, is incorporated at the 5' (or N-terminus) of the coding region or the polypeptide, respectively. Addition of these sequences results in trafficking the encoded polypeptide to a desired site, such as the endoplasmic reticulum or the mitochondria through one or more targeting pathways. Some signal peptides are cleaved from the protein, for example by a signal peptidase after the proteins are transported to the desired site.

In some embodiments, the polynucleotide of the invention comprises a nucleotide sequence encoding a PBGD polypeptide, wherein the nucleotide sequence further comprises a 5' nucleic acid sequence encoding a heterologous signal peptide.

4. FUSION PROTEINS

In some embodiments, the polynucleotide of the invention (e.g., a RNA, e.g., an mRNA) can comprise more than one nucleic acid sequence (e.g., an ORF) encoding a polypeptide of interest. In some embodiments, polynucleotides of the invention comprise a single ORF encoding a PBGD polypeptide, a functional fragment, or a variant thereof. However, in some embodiments, the polynucleotide of the invention can comprise more than one ORF, for example, a first ORF encoding a PBGD polypeptide (a first polypeptide of interest), a functional fragment, or a variant thereof, and a second ORF expressing a second polypeptide of interest. In some embodiments, two or more polypeptides of interest can be genetically fused, i.e., two or more polypeptides can be encoded by the same ORF. In some embodiments, the polynucleotide can comprise a nucleic acid sequence encoding a linker (e.g., a G45 peptide linker or another linker known in the art) between two or more polypeptides of interest.

In some embodiments, a polynucleotide of the invention (e.g., a RNA, e.g., an mRNA) can comprise two, three, four, or more ORFs, each expressing a polypeptide of interest.

In some embodiments, the polynucleotide of the invention (e.g., a RNA, e.g., an mRNA) can comprise a first nucleic acid sequence (e.g., a first ORF) encoding a PBGD polypeptide and a second nucleic acid sequence (e.g., a second ORF) encoding a second polypeptide of interest.

In some embodiments, the polynucleotide of the invention (e.g., an mRNA) comprises a nucleic acid encoding a PBGD fusion protein, wherein said fusion protein comprises an apolipoprotein A1 fused to PBGD. In a particular embodiment, the apolipoprotein A1 (ApoA1) fusion component is a mature form of human apolipoprotein A1 without the native signal peptide and propeptide sequence. See FIGS. 12A-D. In a particular embodiment, the ApoA1-PBGD fusion protein comprises, consists, or consists essentially of the sequence of SEQ ID NO: 154 (see FIG. 12A). In a particular embodiment, the polypeptide of the invention is encoded by a nucleic acid sequence encoding an ApoA1-PBGD fusion protein, wherein said nucleic acid comprises, consists, or consists essentially of the sequence of SEQ ID NO: 155 (see FIG. 12D).

In some embodiments, a polynucleotide of the invention can comprise a portion encoding PBGD (e.g., a wild type PBGD or a variant such as the SM gain of function variant), and, in some embodiments, an ApoA1 component. For example, the polynucleotides of the invention (e.g., mRNA) can comprise, for example, polynucleotides encoding (i) human PBGD isoform 1 (human housekeeping PBGD), (ii) human PBGD isoform 2 (human erythroid-specific PBGD), (iii) SM variant (I291M and N340S double mutant) of PBGD1, (iv) SM variant of PBGD2, (v) human apolipoprotein A1 fused to human PBGD1, (vi) human apolipoprotein A1 fused to PBGD2, (vii) human apolipoprotein A1 fused to SM variant of PBGD1, (viii) human apolipoprotein A1 fused to SM variant of PBGD2, or (ix) combinations thereof. In some embodiments, the polynucleotides have been sequence optimized (e.g., see TABLE 2 and the sequences disclosed in International Publication WO2010/036118, which is herein incorporated by reference in its entirety).

5. SEQUENCE OPTIMIZATION OF NUCLEOTIDE SEQUENCE ENCODING A PBGD POLYPEPTIDE

In some embodiments, the polynucleotide (e.g., a RNA, e.g., an mRNA) of the invention is sequence optimized. In some embodiments, the polynucleotide (e.g., a RNA, e.g., an mRNA) of the invention comprises a nucleotide sequence (e.g., an ORF) encoding a PBGD polypeptide, a nucleotide sequence (e.g., an ORF) encoding another polypeptide of interest, a 5'-UTR, a 3'-UTR, a miRNA, a nucleotide sequence encoding a linker, or any combination thereof, that is sequence optimized.

A sequence optimized nucleotide sequence, e.g., a codon optimized mRNA sequence encoding a PBGD polypeptide, is a sequence comprising at least one synonymous nucleobase substitution with respect to a reference sequence (e.g., a wild type nucleotide sequence encoding a PBGD polypeptide).

A sequence optimized nucleotide sequence can be partially or completely different in sequence from the reference sequence. For example, a reference sequence encoding polyserine uniformly encoded by TCT codons can be sequence optimized by having 100% of its nucleobases substituted (for each codon, T in position 1 replaced by A, C in position 2 replaced by G, and T in position 3 replaced by C) to yield a sequence encoding polyserine which would be uniformly encoded by AGC codons. The percentage of sequence identity obtained from a global pairwise alignment between the reference polyserine nucleic acid sequence and the sequence optimized polyserine nucleic acid sequence would be 0%. However, the protein products from both sequences would be 100% identical.

Some sequence optimization (also sometimes referred to codon optimization) methods are known in the art (and discussed in more detail below) and can be useful to achieve one or more desired results. These results can include, e.g., matching codon frequencies in certain tissue targets and/or host organisms to ensure proper folding; biasing G/C content to increase mRNA stability or reduce secondary structures; minimizing tandem repeat codons or base runs that can impair gene construction or expression; customizing transcriptional and translational control regions; inserting or removing protein trafficking sequences; removing/adding post translation modification sites in an encoded protein (e.g., glycosylation sites); adding, removing or shuffling protein domains; inserting or deleting restriction sites; modifying ribosome binding sites and mRNA degradation sites;

adjusting translational rates to allow the various domains of the protein to fold properly; and/or reducing or eliminating problem secondary structures within the polynucleotide. Sequence optimization tools, algorithms and services are known in the art, non-limiting examples include services from GeneArt (Life Technologies), DNA2.0 (Menlo Park CA) and/or proprietary methods.

Codon options for each amino acid are given in TABLE 1.

TABLE 1

Codon Options

| Amino Acid | Single Letter Code | Codon Options |
|---|---|---|
| Isoleucine | I | ATT, ATC, ATA |
| Leucine | L | CTT, CTC, CTA, CTG, TTA, TTG |
| Valine | V | GTT, GTC, GTA, GTG |
| Phenylalanine | F | TTT, TTC |
| Methionine | M | ATG |
| Cysteine | C | TGT, TGC |
| Alanine | A | GCT, GCC, GCA, GCG |
| Glycine | G | GGT, GGC, GGA, GGG |
| Proline | P | CCT, CCC, CCA, CCG |
| Threonine | T | ACT, ACC, ACA, ACG |
| Serine | S | TCT, TCC, TCA, TCG, AGT, AGC |
| Tyrosine | Y | TAT, TAC |
| Tryptophan | W | TGG |
| Glutamine | Q | CAA, CAG |
| Asparagine | N | AAT, AAC |
| Histidine | H | CAT, CAC |
| Glutamic acid | E | GAA, GAG |
| Aspartic acid | D | GAT, GAC |
| Lysine | K | AAA, AAG |
| Arginine | R | CGT, CGC, CGA, CGG, AGA, AGG |
| Selenocysteine | Sec | UGA in mRNA in presence of Selenocysteine insertion element (SECIS) |
| Stop codons | Stop | TAA, TAG, TGA |

In some embodiments, a polynucleotide (e.g., a RNA, e.g., an mRNA) of the invention comprises a sequence-optimized nucleotide sequence (e.g., an ORF) encoding a PBGD polypeptide, a functional fragment, or a variant thereof, wherein the PBGD polypeptide, functional fragment, or a variant thereof encoded by the sequence-optimized nucleotide sequence has improved properties (e.g., compared to a PBGD polypeptide, functional fragment, or a variant thereof encoded by a reference nucleotide sequence that is not sequence optimized), e.g., improved properties related to expression efficacy after administration in vivo. Such properties include, but are not limited to, improving nucleic acid stability (e.g., mRNA stability), increasing translation efficacy in the target tissue, reducing the number of truncated proteins expressed, improving the folding or prevent misfolding of the expressed proteins, reducing toxicity of the expressed products, reducing cell death caused by the expressed products, increasing and/or decreasing protein aggregation.

In some embodiments, the sequence optimized nucleotide sequence is codon optimized for expression in human subjects, having structural and/or chemical features that avoid one or more of the problems in the art, for example, features which are useful for optimizing formulation and delivery of nucleic acid-based therapeutics while retaining structural and functional integrity; overcoming a threshold of expression; improving expression rates; half-life and/or protein concentrations; optimizing protein localization; and avoiding deleterious bio-responses such as the immune response and/or degradation pathways.

In some embodiments, the polynucleotides of the invention comprise a nucleotide sequence (e.g., a nucleotide sequence (e.g., an ORF) encoding a PBGD polypeptide, a nucleotide sequence (e.g., an ORF) encoding another polypeptide of interest, a 5'-UTR, a 3'-UTR, a microRNA binding site, a nucleic acid sequence encoding a linker, or any combination thereof) that is sequence-optimized according to a method comprising:

(i) substituting at least one codon in a reference nucleotide sequence (e.g., an ORF encoding a PBGD polypeptide) with an alternative codon to increase or decrease uridine content to generate a uridine-modified sequence;

(ii) substituting at least one codon in a reference nucleotide sequence (e.g., an ORF encoding a PBGD polypeptide) with an alternative codon having a higher codon frequency in the synonymous codon set;

(iii) substituting at least one codon in a reference nucleotide sequence (e.g., an ORF encoding a PBGD polypeptide) with an alternative codon to increase G/C content; or (iv) a combination thereof.

In some embodiments, the sequence optimized nucleotide sequence (e.g., an ORF encoding a PBGD polypeptide) has at least one improved property with respect to the reference nucleotide sequence.

In some embodiments, the sequence optimization method is multiparametric and comprises one, two, three, four, or more methods disclosed herein and/or other optimization methods known in the art.

Features, which can be considered beneficial in some embodiments of the invention, can be encoded by or within regions of the polynucleotide and such regions can be upstream (5') to, downstream (3') to, or within the region that encodes the PBGD polypeptide. These regions can be incorporated into the polynucleotide before and/or after sequence-optimization of the protein encoding region or open reading frame (ORF). Examples of such features include, but are not limited to, untranslated regions (UTRs), microRNA sequences, Kozak sequences, oligo(dT) sequences, poly-A tail, and detectable tags and can include multiple cloning sites that can have XbaI recognition.

In some embodiments, the polynucleotide of the invention comprises a 5' UTR, a 3' UTR and/or a miRNA binding site. In some embodiments, the polynucleotide comprises two or more 5' UTRs and/or 3' UTRs, which can be the same or different sequences. In some embodiments, the polynucleotide comprises two or more miRNA, which can be the same or different sequences. Any portion of the 5' UTR, 3' UTR, and/or miRNA binding site, including none, can be sequence-optimized and can independently contain one or more different structural or chemical modifications, before and/or after sequence optimization.

In some embodiments, after optimization, the polynucleotide is reconstituted and transformed into a vector such as, but not limited to, plasmids, viruses, cosmids, and artificial chromosomes. For example, the optimized polynucleotide can be reconstituted and transformed into chemically competent E. coli, yeast, neurospora, maize, drosophila, etc. where high copy plasmid-like or chromosome structures occur by methods described herein.

6. SEQUENCE-OPTIMIZED NUCLEOTIDE SEQUENCES ENCODING PBGD POLYPEPTIDES

In some embodiments, the polynucleotide of the invention comprises a sequence optimized nucleotide sequence encoding a PBGD polypeptide disclosed herein. In some embodiments, the polynucleotide of the invention comprises an open reading frame (ORF) encoding a PBGD polypeptide, wherein the ORF has been sequence optimized.

Exemplary sequence optimized nucleotide sequences encoding human PBGD isoform 1 are set forth as SEQ ID Nos: 9-33 (PBGD-CO01, PBGD-CO02, PBGD-CO03, PBGD-CO04, PBGD-COOS, PBGD-CO06, PBGD-CO07, PBGD-CO08, PBGD-CO09, PBGD-CO10, PBGD-CO11, PBGD-CO12, PBGD-CO13, PBGD-CO14, PBGD-CO15, PBGD-CO16, PBGD-CO17, PBGD-CO18, PBGD-CO19, PBGD-CO20, PBGD-CO21, PBGD-CO22, PBGD-CO23, PBGD-CO24, and PBGD-CO25, respectively. Further exemplary sequence optimized nucleotide sequences encoding human PBGD isoform 1 are shown in TABLE 2. In some embodiments, the sequence optimized PBGD sequences set forth as SEQ ID Nos: 9-33 or shown in TABLE 2, fragments, and variants thereof are used to practice the methods disclosed herein. In some embodiments, the sequence optimized PBGD sequences set forth as SEQ ID Nos: 9-33 or shown in TABLE 2, fragments and variants thereof are combined with or alternatives to the wild-type sequences disclosed in FIGS. 1-4

Exemplary sequence optimized nucleotide sequences encoding human PBGD isoform 1 are set forth as SEQ ID Nos: 89 to 117 (PBGD-CO30, PBGD-CO31, PBGD-CO32, PBGD-CO33, PBGD-CO34, PBGD-CO35, PBGD-CO36, PBGD-CO37, PBGD-CO38, PBGD-CO39, PBGD-CO40A, PBGD-CO41A, PBGD-CO42A, PBGD-CO43A, PBGD-CO44A, PBGD-CO45A, PBGD-CO46A, PBGD-CO47A, PBGD-CO40B, PBGD-CO41B, PBGD-CO42B, PBGD-CO43B, PBGD-CO44B, PBGD-CO45B, PBGD-CO46B, PBGD-CO47B, PBGD-CO48, PBGD-CO49, PBGD-CO50, respectively). Further exemplary sequence optimized nucleotide sequences encoding human PBGD isoform 1 are shown in TABLE 2. In some embodiments, the sequence optimized PBGD sequences set forth as SEQ ID Nos: 89 to 117, or shown in TABLE 2, fragments, and variants thereof are used to practice the methods disclosed herein. In some embodiments, the sequence optimized PBGD sequences set forth as SEQ ID Nos: 89 to 117, or shown in TABLE 2, fragments and variants thereof are combined with or alternatives to the wild-type sequences disclosed in FIGS. 1-4.

In some embodiments, a polynucleotide of the present disclosure, for example a polynucleotide comprising an mRNA nucleotide sequence encoding a PBGD polypeptide, comprises from 5' to 3' end:
(i) a 5' cap provided herein, for example, CAP1;
(ii) a 5' UTR, such as the sequences provided herein, for example, SEQ ID NO: 39;
(iii) an open reading frame encoding a PBGD polypeptide, e.g., a sequence optimized nucleic acid sequence encoding PBGD set forth as SEQ ID Nos: 9 to 33 and 89 to 117, or shown in TABLE 2;
(iv) at least one stop codon;
(v) a 3' UTR, such as the sequences provided herein, for example, SEQ ID NOs 149 to 151; and
(vi) a poly-A tail provided above.

TABLE 2

Sequence optimized sequences for human PBGD, isoform 1

| SEQ ID NO | Name | Sequence |
|---|---|---|
| 9 | PBGD-CO01 | See Sequence Listing |
| 10 | PBGD-CO02 | See Sequence Listing |
| 11 | PBGD-CO03 | See Sequence Listing |
| 12 | PBGD-CO04 | See Sequence Listing |
| 13 | PBGD-CO05 | See Sequence Listing |
| 14 | PBGD-CO06 | See Sequence Listing |
| 15 | PBGD-CO07 | See Sequence Listing |
| 16 | PBGD-CO08 | See Sequence Listing |
| 17 | PBGD-CO09 | See Sequence Listing |
| 18 | PBGD-CO10 | See Sequence Listing |
| 19 | PBGD-CO11 | See Sequence Listing |
| 20 | PBGD-CO12 | See Sequence Listing |
| 21 | PBGD-CO13 | See Sequence Listing |
| 22 | PBGD-CO14 | See Sequence Listing |
| 23 | PBGD-CO15 | See Sequence Listing |
| 24 | PBGD-CO16 | See Sequence Listing |
| 25 | PBGD-CO17 | See Sequence Listing |
| 26 | PBGD-CO18 | See Sequence Listing |
| 27 | PBGD-CO19 | See Sequence Listing |

TABLE 2-continued

Sequence optimized sequences for human PBGD, isoform 1

| SEQ ID NO | Name | Sequence |
|---|---|---|
| 28 | PBGD-CO20 | See Sequence Listing |
| 29 | PBGD-CO21 | See Sequence Listing |
| 30 | PBGD-CO22 | See Sequence Listing |
| 31 | PBGD-CO23 | See Sequence Listing |
| 32 | PBGD-CO24 | See Sequence Listing |
| 33 | PBGD-CO25 | See Sequence Listing |
| 89 | PBGD-CO30 | AUGAGCGGCAACGGCAACGCCGCAGCCACCGCCGAGGAAAACAGCCCCAAGAUGCGGGUGAUCAGAGUGG<br>GCACCCGGAAGAGCCAGCUGGCCCGGAUCCAGACCGACAGCGUGGUGGCCACCCUGAAGGCCUCCUACCC<br>CGGCCUGCAGUUCGAGAUCAUUGCCAUGAGCACCACCGGCGACAAGAUCCUGGACACCGCCCUGAGCAAG<br>AUCGGCGAGAAGAGCCUGUUCACAAAAGAGCUGGAACACGCCCUGGAAAAGAACGAGGUGGACCUGGUGG<br>UGCACAGCCUGAAGGACCUGCCCACCGUGCUGCCCCUGGCUUCACCAUCGGCGCCAUCUGCAAGAGAGA<br>GAACCCCCACGACGCCGUGGUGUUCCACCCUAAGUUCGUGGGCAAGACACUGGAAACCCUGCCCGAGAAG<br>UCCGUGGUGGGCACCAGCAGCCUGCGGAGAGCCGCCCAGCUGCAGCGGAAGUUCCCCCACCUGGAAUUUC<br>GGAGCAUCCGGGGCAACCUGAACACCCGGCUGCGGAAGCUGGACGAGCAGCAGGAAUUUCCGCUAUCAU<br>CCUGGCCACAGCCGGACUGCAGCGGAUGGGCUGGCACAACAGAGUGGGCCAGAUCCUGCACCCCGAGGAA<br>UGCAUGUACGCCGUGGGGCCAGGGAGCCCUGGGCGUGGAAGUGCGGGCCAAGGACCAGGACAUCCUGGAUC<br>UGGUGGGCGUGCUGCAUGACCCCGAGACACUGCUGCGGUGUAUCGCCGAGCGGGCCUUCCUGCGGCACCU<br>GGAAGGCGGCUGCAGCGUGCCCGUGGCCGUCACACCGCCAUGAAGGACGGACAGCUGUACCUGACAGGC<br>GGCGUGUGGAGCCUGGACGGCAGCGACAGCAUCCAGGAGACCAUGCAGGCCACCAUCCACGUGCCCGCCC<br>AGCACGAGGACGGCCCCGAGGACGACCUCAGCUGGUCGGCAUCACCGCCCGGAACAUCCCCAGAGGCCC<br>CCAGCUGGCCGCCCAGAACCUGGGCAUCAGCCUGGCCAACCUGCUGCUGUCCAAGGGCGCCAAGAACAUC<br>CUGGACGUGGCCCGGCAGCUGAACGACGCCCAC |
| 90 | PBGD-CO31 | AUGAGCGGCAACGGCAACGCCGCCGCUACCGCCGAAGAGAACAGCCCAAAGAUGCGCGUGAUCAGGGUCG<br>GCACGCGCAAGUCCCAGCUCGCCCGGAUCCAAACCGAUAGCGUGGUGGCCACGCUCAAGGCGAGCUAUCC<br>GGGCUUACAGUUCGAGAUCAUCGCCAUGAGCACCACCGGCGAUAAGAUACUGGACACCGCCCUGUCCAAG<br>AUCGGCGAAAAGAGCCUGUUCACCAAGGAACUGGAGCACGCGCUGGAGAAGAACGAGGUGGACCUGGUGG<br>UGCACAGCCUGAAGGACCUGCCGACCGUGCUGCCGCCGGGAUUCACCAUCGGCGCCAUCUGCAAGAGGGA<br>GAAUCCGCACGAUGCCGUGGUGUUCCACCCAAAGUUCGUGGGCAAGACCUUGGAAACCCUGCCAGAGAAG<br>UCUGUGGUCGGCACCUCCAGCCUGCGGCGAGCCGCCCAGCUGCAGCGAAAGUUCCCGCACCUGGAGUUCA<br>GGUCCAUCCGCGGAAAUCUGAACACCAGGCUGCGCAAGCUCGACGAGCAGCAGGAGUUCUCCGCCAUCAU<br>CCUGGCCACCGCAGGCCUCCAAAGAAUGGGCUGGCAUAACCGAGUCGCCAGAUCCUCCACCCGGAGGAG<br>UGCAUGUACGCCGUGGGGCCAAGGCGCCCUGGGCGUCGAGGUGCGUGCCAAGGACCAGGACAUCCUGGAC<br>UGGUGGGCGUGCUCCACGAUCCAGAGACACUGCUGAGAUGCAUCGCGGAGCGCGCCUUCCUGCGCCAUCU<br>GGAGGGAGGCUGCUCCGUCCCGGUGGCCGUACAUACCGCCAUGAAGGACGGUCAGCUGUACCUCACCGGC<br>GGCGUAUGGUCCCUCGACGGUAGCGACAGCAUACAGGAGACGAUGCAGGCCACCAUCCACGUGCCGGCGC<br>AGCACGAGGAUGACCAGAGGACGACCCGCAGCUGGUGGGUAUCACCGCCAGGAAUAUCCCGCGGGGACC<br>UCAGCUGGCCGCCCAGAACCUGGGCAUCUCCCUCGCCAACCUCCUGCUGAGCAAGGGCGCCAAGAACAUC<br>CUGGACGUGGCCCAGGCAGCUCAACGAUGCCCAU |
| 91 | PBGD-CO32 | AUGAGCGGCAACGGCAACGCCGCCGCCACCGCCGAGGAAAACAGCCCCAAGAUGCGGGUGAUCAGGGUGG<br>GCACCAGGAAGUCCCAGCUCGCCCGGAUCCAGACCGACAGCGUGGUCGCCACCUUGAAGGCCUCCUACCC<br>GGGCCUCCAGUUCGAGAUCAUCGCCAUGUCCACAACCGGCGACAAGAUCCUGGAUACCGCCCUCAGCAAG<br>AUCGGCGAGAAGUCCCUGUUCACCAAGGAGCUGGAGCACGCCCUGGAGAAGAAUGAGGUGGACCUGGUGG<br>UGCACAGCCUGAAGGACCUGCCUACCGUGCUGCCACCAGGCUUCACAAUCGGCGCCAUCUGCAAGAGAGA<br>GAACCCGCACGACGCCGUGGUGUUCCAUCCGAAGUUCGUGGGCAAGACCCUGGAAACCCUGCCGGAGAAG<br>UCCGUAGUGGGAACCUCAAGCCUGAGGCGCGCCGCCCAGCUCCAGAGGAAGUUCCCUCACCUGGAAUUCC<br>GGUCCAUCAGGGGCAACCUGAACACGCGCCUGCGGAAGCUCGACGAGCAGCAGGAGUUCUCCGCCAUCAU<br>CCUGGCCACAGCCGGCCUUCAGCGCAUGGGCUGGCACAACAGGGUGGGCCAGAUCCUGCACCCGGAAGAA<br>UGCAUGUACGCCGUGGGCCAAGGCGCCCUCGCGUGGAAGUGCGGGCCAAGGACCAGGACAUCCUGGACC<br>UGGUGGGCGUGCUGCACGACCCUGAGACGCUGCUCAGGUGCAUCGCCGAACGCGCGUUCCUGCGGCACCU<br>GGAGGGAGGCUGCAGCGUCCCGGUGGCCGUCCACACCGCCAUGAAGGACGGCCAGCUCUACCUGACUGGC<br>GGCGUGUGGAGCCUGGACGGCAGCGACAGCAUUCAGGAAACCAUGCAGGCCACCAUCCACGUGCCUGCCC<br>AGCACGAGGACGGCCCGGAGGACGACCCUCAACUGGUGGGCAUUACUGCGAAACAUCCCGCGCGGACCC<br>UCAGCUGGCCGCCCAGAACCUGGGCAUCAGCCUGGCCAACCUGCUGCUGUCCAAGGGCGCCAAGAACAUC<br>CUCGACGUGGCCAGGCAGCUGAACGACGCGCAC |
| 92 | PBGD-CO33 | AUGAGCGGCAACGGAAACGCCGCCGCGACCGCGGAGGAGAACUCGCCUAAGAUGAGAGUGAUAAGGGUAG<br>GCACCCGGAAGUCUCAACUCGCCAGGAUCCAGACCGACAGCGUGGUGGCCACCCUCAAGGCCAGCUAUCC<br>AGGACUCCAGUUCGAAAUCAUCGCCAUGUCCACCACAGGCGAUAAGAUCCUGGACACCGCCCUGUCCAAG<br>AUCGGCGAGAAGUCCCUCUUCACCAAGGAACUGGAGCACGCCCUGGAGAAGAACGAGGUCGAUCUGGUCG<br>UGCACAGCCUGAAGGAUCUGCCUACCGUGCUCCCCGGCUUCACCAUCGGCGCCAUCUGCAAGAGGGA<br>GAAUCCUCACGACGCCGUGGUGUUCCACCCGAAGUUCGUGGGCAAGACCCUGGAGACUGCCAGAAAAG<br>UCGUGGUGGGCACCAGCAGCCUGCGGCGGGCCGCCCAGCUGCAGCGGAAGUUCCCACACCUGGAGUUCA<br>GGUCCAUCCGUGGCAAUCUGAACACCCGGCUGCGUAAGCUGGACGAGCAGCAGGAAUUCAGCGCGAUCAU<br>CCUGGCAACCGCCGGUCUGCAAAGGAUGGGCUGGCACAACAGGGUGGGCCAGAUCCUGCACCCUGAGGAG<br>UGCAUGUACGCCGUGGGCCAGGGAGCCCUGGGCGUGGAAGUGCGGGCCAAGGACCAGGACAUCCUGGACC |

TABLE 2-continued

Sequence optimized sequences for human PBGD, isoform 1

| SEQ ID NO | Name | Sequence |
|---|---|---|
| | | UGGUGGGUGUGCUCCACGACCCUGAAACCCUGCUGCGGUGCAUCGCCGAAAGGGCCUUCCUGAGGCACCU CGAGGGCGGCUGCAGCGUGCCGGUCGCCGUGCACACCGCCAUGAAGGACGGCCAGCUGUACCUGACCGGA GGAGUGUGGAGCCUGGACGGCUCCGACUCCAUCCAGGAGACUAUGCAGGCCACCAUUCAUGUGCCGGCCC AGCAUGAGGACGUCCGGAGGACGAUCCACAGCUGGUCGGCAUCACCGCGCGGAACAUCCAAGAGGCCC GCAACUGGCCGCUCAGAACCUGGGCAUAUCCCUGGCCAACCUGCUCCUGAGCAAGGGCGCCAAGAACAUC CUGGACGUGGCCAGGCAGCUGAAUGACGCCCAC |
| 93 | PBGD-CO34 | AUGUCCGGCAACGGCAACGCCGCCGCUACCGCCGAGGAGAACUCCCCUAAGAUGCGGGUCAUCAGGGUGG GCACCCGAAAGUCCCAACUUGCCGGAUCCAGACCGACUCCGUCGUGGCCACCCUCAAGGCUAGCUAUCC AGGCCUCCAGUUCGAAAUCAUCGCCAUGAGCACCACCGGCGACAAGAUUCUGGACACCGCCCUGUCCAAG AUCCGCGAGAAGAGUCUGUUCACCAAGGAGCUCGAGCACGCCCUGGAAAAGAACGAGGUGGACCUGGUGG UGCAUUCCCUGAAGGACCUGCCAACCGUGCUGCCGCCGGGCUUCACUAUAGGAGCCAUCUGCAAGCGGGA GAACCCGCACGACGCGGUGGUGUUCCAUCCGAAGUUCGUGGGCAAGACUCUGGAAACCCUGCCGGAGAAG UCCGUGGUGGGAACUAGCUCCCUGCGGCGGGCCGCCCAGCUGCAGAGGAAGUUCCCGCACCUGGAGUUCA GGAGCAUACGCGGCAACCUGAACACCCGCUGCGUAAGCGCGACGAGCAGCAGGAAUUCAGUGCCAUCAU CCUGGCCACGGCGGGCCUGCAGCGGAUGGGCUGGCACAACAGGGUGGGCCAGAUCCUCCACCCGGAGGAA UGUAUGUACGCCGUGGGCCAGGGCGCACUGGGCGUGGAGGUCCGCGCCAAGGACCAAGACAUCCUGGACC UGGUCGGCGUGCUGCACGACCCUGAAACCCUGCUGAGGUGCAUUGCCGAGAGAGCCUUCCUGAGGCAUCU GGAGGGCGGCUGCAGCGUGCCUGUGGCCGUGCACACAGCCAUGAAGGACACCGGUCAGCUGUACCUGACC GGCGUGUGGAGCCUGGACGCAGCGACUCCAUCCAGGAGACAAUGCAGGCCACCAUCCACGUCCCGGCCC AACACGAGGACGACCUGAGGACGAUCCUCAGCUGGUGGGCAUCACCGCCAGGAACAUCCUCGGGGCCC GCAGCUGGCCGCCCAGAACCUGGGCAUCUCCCUCGCCAACCUGCUGCUGUCCAAGGGCGCCAAGAACAUC CUCGACGUGGCCAGACAGCUGAACGACGCCCAC |
| 94 | PBGD-CO35 | AUGAGCGGCAACGGCAACGCCGCCGCCACCGCCGAGGAGAACAGCCCGAAGAUGAGGGUGAUAAGGGUGG GCACACGGAAGUCCCAGCUCGCCCGCAUCCAAACCGACUCCGUGGUGGCCACCCUCAAGGCCAGCUACCC GGGCCUCCAAUUCGAGAUCAUCGCCAUGAGCACCACCGGCGACAAGAUCCUGGACACCGCCCUGUCCUAAG AUAGGCGAAAAGAGCCUGUUCACCAAGGAGCUGGAGCAUGCCCUGGAGAAGAACGAGGUGGACCUGGUGG UCCACAGUCUCAAGGACCUGCCAACCGUGCUGCCGCCAGGCUUCACCAUCGGCGCCAUCUGCAAGCGUGA GAACCCGCACGAUGCUGUGGUGUUCCACCCUAAGUUCGUGGGAAAGACCCUGGAGACGCUGCCGGAAAAG AGCGUGGUCGGCACCUCCAGCCUGCGGAGGGCCGCCCAACUCCAGAGGAAGUUCCCGCACCUGGAGUUCA GGAGCAUCCGCGGCAACCUGAACACCAGGCUGCGAAAGCUGGACGAGCAGCAGGAAUUCGGCCAUCAU CCUCGCCACCGCCGGCUUGCAAAGAAUGGGCUGGCAUAAUCGCGUGGGCCAGAUCCUGCACCCUGAGGAG UGCAUGUACGCCGUGGGCCAGGGUGCUCUGGGAGUGGAGGUGCGGGCAAGGACCAGGAUAUCCUGGACC UGGUCGGCGUGCUUCAUGACCCGGAGACGCUCCUGAGGUGCAUCGCCGAGCGGGCCUUCCUGAGACACCU GGAGGGCGGCUGCUCCGUGCCAGUGGCCGUGCACACCGCAUGAAGGACGGACAGCUGUACCUGACCGGC GGCGUGUGGAGCCUGGACGGAAGCGACAGCAUCCAAGAAACCAUGCAGGCGACCAUUCACGUCCCCUGCCC AGCACGAGGAUGACCAGAGGACGACCCGCAGCUGGUGGGCAUCACCGCCCGAACAUCCUAGAGGCCC ACAGCUGGCCGCCCAGAAUCUGGGCAUCAGCCUGGCCAACCUGCUGCUGUCUAAGGGAGCCAAGAACAUC CUGGACGUGGCCAGGCAGCUGAACGACGCCCAU |
| 95 | PBGD-CO36 | AUGUCCGGCAACGGCAACGCCGCAGCCACCGCCGAGGAGAAUUCCCCGAAGAUGCGGGUGAUCCGGGUGG GCACCAGAAAGAGCCAGCUCGCCCGCAUCCAAACCGACUCCGUGGUGGCCACCCUCAAGGCCUCCUACCC AGGCUUGCAGUUCGAAAUCAUCGCCAUGAGCACCACCGGCGACAAGAUCCUGGACACCGCCCUGAGCAAG AUUGGCGAGAAGUCCCUGUUCACCAAGGAGCUGGAGCAUGCUCUGGAGAAGAACGAGGUGGACCUCGUGG UGCACUCCCUGAAGGACCUGCCGACUGUGCUGCCGCCUGGCUUCACGAUCGGCGCCAUAUGCAAGCGGGA AAACCCACACGACGCCGUGGUCUUCCACCCAAAGUUCGUGGGCAAGACCCUGGAAACCCUGCCGGAAAAG AGCGUGGUCGGCACAAGCUCCCUGAGGAGAGCCGCCCAACUGCAAAGGAAGUUCCCCGCACCUGGAGUUCA GGUCCAUCCGGGGCAACCUGAACACCAGGCUGAGAAAGCUCGACGAACAGCAGGAGUUCAGCGCCAUCAU CCUGGCCACGGCCGGCCUGCAGAGGAUGGGAUGGCAUAACAGGGUGGGCCAGAUCCUGCACCCGGAGGAG UGCAUGUACGCCGUGGGCCAGGGAGCCCUCGGCGUGGAGGUCAGGGCCAAGGAUCAGGAUAUCCUGGACC UGGUGGGCGUGCUGCACGAUCCUGAGACGCUGCUGAGGUGCAUCGCCGAGCGGGCCUUCCUGCGGCACCU AGAGGGCGGAUGCAGCGUGCCGGUCGCGGUCCACACCGCGAUGAAGGACGGCCAGCUGUACCUGACCGGC GGCGUGUGGUCCUGGACGGCAGCGAUUCAAUCCAGGAGACGAUGCAGGCCACCAUCCACGUGCCAGCCC AGCACGAGGAUGCCCGGAGGACGACCCGCAGCUGGUGGGCAUUACAGCCAGGAACAUCCCUCGGGGCCC GCAGCUGGCCGCCCAGAAUCUGGGCAUCAGCCUGGCGAACCUGCUGCUCAGCAAGGGAGCGAAGAACAUC CUGGACGUGGCCCGCCAGCUGAACGAUGCCCAC |
| 96 | PBGD-CO37 | AUGAGCGGCAACGGCAACGCCGCCGCCACCGCCGAGGAGAACAGCCCAAAGAUGCGGGUGAUCAGGGUGG GCACCCGCAAGAGCCAACUGCCAGAAUCCAGACCGACAGCGUGGUGGCCACCUUGAAGGCCAGCUACCC GGGCCUCCAGUUCGAGAUCAUCGCUAUGUCCACCACCGGCGACAAGAUCCUGGACACCGCCGCUGUCCAAG AUCCGGGAAAAGAGCCUGUUCACCAAGGAACUGGAGCACGCCCUCGAGAAGAACGAGGUGGACCUGGUGG UGCACUCCCUGAAGGACCUGCCGACGGUCCUGCCGCCGGGCUUCACCAUCGGCGCCAUCUGCAAGCGGGA AAACCCGCACGACGCUGUGGUGUUCCACCCAAAGUUCGUGGGCAAGACCCUGGAAACCCUGCCAGAAAAG AGCGUGGUGGGCACCAGCAGCCUCAGGAGAGCCGCCCAGCUGCAGAGGAAGUUCCCCGCACCUGGAGUUCA GGAGCAUCAGGGGCAACCUGAACACCAGGCUGCGUAAGCUGGACGAGCAGCAGGAGUUCUCCGCCAUCAU CCUCGCCACAGCCGGCCUCCAGAGGAUGGGUUGGCACAACAGGGUGGGCCAGAUCCUGCACCCGGAAGAG UGCAUGUACGCAGUGGGCCAGGGCGCCCUUGGCGUGGAAGUGCGAGCCAAGGAUCAGGAUAUCCUGGACC UGGUGGGCGUGCUGCACGACCCGGAAACUCUGCUGAGGUGCAUCGCCGAAAGGGCCUUCCUGCGCCACCU CGAAGGCGGCUGUAGCGUGCCGGUGGCCGUGCACACCGCCAUGAAGGACGGCCAGCUGUACCUGACCGGC GGCGUGUGGAGCCUCGACGGCAGCGACAGCAUCCAGGAGCAAUGCAGGCCACCAUCCACGUGCCGGCCC AGCAUGAGGAUGGCCCGGAGGACGACCCUCAGCUGGUGGGCAUCACCGCCCGCAACAUCCCAAGAGGACC GCAACUGGCCGCCCAGAACCUGGGCAUCUCCCUGGCCAACCUGCUCCUGAGCAAGGGCGCGAAGAACAUC CUCGACGUCGCACGGCAGCUGAACGACGCCCAC |

TABLE 2-continued

Sequence optimized sequences for human PBGD, isoform 1

| SEQ ID NO | Name | Sequence |
|---|---|---|
| 97 | PBGD-CO38 | AUGAGCGGCAACGGCAACGCCGCCGCGACGGCCGAGGAAAAUAGCCCGAAGAUGCGGGUGAUCAGGGUGG GCACCAGGAAGUCCCAGCUCGCCAGGAUCCAGACCGACAGCGUGGUGGCCACCCUCAAGGCCUCCUACCC GGGCCUCCAAUUCGAGAUCAUCGCCAUGUCCACCACCGGCGACAAGAUCCUCGACACCGCCCUGAGCAAG AUCGGCGAAAAGUCGCUGUUCACCAAGGAGCUGGAGCACGCCCUCGAGAAGAACGAGGUGGACCUGGUAG UGCACUCCCUAAAGGACCUGCCGACCGUGCUGCCGCCGGGCUUCACGAUCGGCGCCAUCUGCAAGCGCGA GAACCCCGAUGAUGCCGUCGUUUUCCACCCUAAGUUCGUGGGCAAGACCCUGGAGACGCUGCCGGAGAAG UCGGUGGUGGGAACCAGCAGCCUGAGGAGGGCCGCACAACUGCAGAGGAAGUUCCCGCAUCUGGAGUUCC GCAGCAUUCGAGGCAACCUGAACACGCGCCUGAGAAAGCUCGAUGAACAGCAGGAGUUCAGCGCCAUCAU UCUGGCCACUGCCGGACUGCAGCGGAUGGGCUGGCACAACAGAGUGGGCCAGAUCCUGCAUCCGGAAGAG UGUAUGUACGCCGUGGGCCAGGGUGCCCUGGGCGUGGAGGUGCGGCCAAGGACCAGGAUAUACUGGAUC UGGUCGGCGUGCUCCACGACCCAGAAACACUCCUGAGGUGCAUCGCUGAGAGAGCCUUCCUCCGGCACCU CGAGGGCGGCUGUUCCGUGCCGUGGCCGUCCAUACCGCCAUGAAGGACGGUCAGCUGUACCUGACCGGA GGCGUUUGGUCCCUGGACGGCAGCGACAGCAUCCAGGAAACCAUGCAGGCCACCAUCCACGUGCCGGCGC AGCACGAGGACGGCCCGGAAGACGACCCGCAGCUGGUCGGCAUCACGCCCAGAACAUCCCGCGGGGCCC GCAGCUGGCGGCCCAGAACCUGGGAAUCUCCCUGGCCAACCUGCUGUGAGCAAGGGCGCGAAGAACAUC CUGGACGUGGCCAGGCAGCUGAACGAUGCCCAC |
| 98 | PBGD-CO39 | AUGAGCGGUAACGGCAACGCCGCCGCCACCGCCGAGGAGAACUCCCCGAAGAUGCGCGUGAUUCGGGUCG GCACAAGAAAGUCUCAACUCGCCCGAAUCCAAACGGACAGCGUGGUGGCCACCCUCAAGGCGAGCUACCC GGGCCUCCAGUUCGAAAUCAUCGCCAUGAGCACCACCGGCGACAAGAUCCUGGACACCGCCCUGUCGAAG AUUGGCGAAAAGUCCCUGUUCACCAAGGAGCUGGAGCACGCCCUGGAGAAGAACGAAGUCGACCUGGUCG UGCACAGCCUGAAGGACCUGCCGACCGUUCUGCCGCCGGGCUUCACCAUCGGAGCCAUCUGCAAGCGGGA GAAUCCGCACGACGCCGUGGUCUUCCACCCAAAGUUCGUGGGGAAAACCCUCGAGACACUGCCGGAGAAG UCCGUGGUGGGAACCUCCUCCCUGCGGAGGGCCGCCCAACUGCAGCGGAAGUUCCCACACCUGGAAUUCC GGUCCAUCAGAGGCAACCUCAACACCAGGCUGAGGAAGCUCGAUGAGCAGCAGGAGUUCAGCGCCAUCAU CCUGGCCACAGCCGGACUGCAGCGCAUGGGCUGGCAUAACAGAGUGGGCCAGAUCCUCCACCCGGAGGAG UGCAUGUACGCCGUGGGACAAGGCGCGCUGGGCGUGGAAGUUCGGGCAAGGACCAGGAUAUCCUGGACC UGGUGGGCGUGCUCCACGACCCAGAGACGCUGCUGCGUGCAUCGCCGAGCGCGCCUUCCUGCGGCACCU CGAGGGCGGCUGCAGCGUGCCGUCGCUGUGCACACAGCCAUGAAGGACGGCCAGCUGUACCUGACCGGC GGCGUGUGGAGUCUGGACGGCAGCGACUCCAUCCAGGAGACAUGCAAGCCACCAUCCAUGUGCCGGCCC AACAUGAGGACGGCCCGGAGGACGACCCGCAACUGGUGGGCAUCACCGCCCGGAACAUCCCGAGGGGCCC GCAGCUGGCCGCCCAGAACCUGGGCAUUAGCCUGGCCAACCUGCUCCUGAGCAAGGGCGCUAAGAACAUC CUGGACGUCGCCAGACAGCUGAACGACGCCCAC |
| 99 | PBGD-CO40A | AUGAGCGGCAACGGCAACGCCGCCGCCACCGCCGAGGAGAACAGCCCCAAGAUGCGGGUGAUCCGGGUGG GCACCCGUAAGAGCCAGCUGGCCCGGAUCCAGACCGACAGCGUGGUGGCCACCCUGAAGGCCAGCUACCC CGGCCUGCAGUUCGAGAUCAUCGCCAUGAGCACCACCGGCGACAAGAUCCUGGACACCGCCCUGAGCAAG AUCGGCGAGAAGUCCCUGUUCACCAAGGAGCUGGAGCACGCCCUGGAGAAGAACGAGGUGGACCUGGUGG UGCACAGCCUGAAGGACCUGCCCACCGUGCUGCCUCCAGGCUUCACCAUCGGCGCCAUCUGCAAGCGGGA GAACCCCCACGACGCCGUGGUGUUCCACCCCAAGUUCGUGGGCAAGACCCUGGAAACCCUGCCUGAGAAG UCCGUCUAGGAACCAGCAGCCUGCGGCGGGCCGCCCAGCUGCAGCGGAAGUUCCCCCACCUGGAGUUCC GGAGCAUCCGGGGCAACCUGAACACCCGGCUGCGGAAGCUGGACGAGCAGCAGGAGUUCAGCGCCAUCAU CCUGGCCUACCGCCGGUCUGCAACGAAUGGGCUGGCACAAUAGGGUGGCCAGAUCCUGCACCCCGAGGAG UGCAUGUACGCGGUGGGACAGGGCGCCCUGGGCGUGGAGGUGCGGGCCAAGGACCAGGACAUCCUUGAUC UGGUGGGCGUGCUGCACGACCCCGAGACGCUGCUGCGUGCAUCGCCGAGCGGGCCUUCCUGCGGCAUUU GGAGGGCGGAUGCAGCGUGCCCGUGGCCGUGCACACCGCCAUGAAGGACGGCCAGCUGUACCUGACCGGC GGCGUGUGGAGCCUGGACGGCAGCGACAGCAUCCAGGAAACCAUGCAGGCCACCAUCCACGUGCCGCUC AGCACGAAGACGGCCCAGAGGACGACCCCCAGCUGGUAGGCAUCACCGCCCGGAACAUCCCCGGGGCCC UCAGCUCGCCGCACAGAACCUUGGAAUCAGCCUGGCCAACCUGCUGUUGUCAAAGGGCGCCAAGAAUAUC CUCGACGUGGCCCGGCAGCUGAACGACGCCCAC |
| 100 | PBGD-CO41A | AUGAGCGGCAACGGCAACGCCGCCGCCACCGCCGAGGAGAACAGCCCCAAGAUGCGGGUGAUCCGGGUGG GCACCAGAAAGAGCCAGCUGGCCCGGAUCCAGACCGACAGCGUGGUGGCCACCCUGAAGGCCAGCUACCC CGGCCUGCAGUUCGAGAUCAUCGCCAUGAGCACCACCGGCGACAAGAUCCUGGACACCGCCCUGAGCAAG AUCGGCGAGAAGAGUCUGUUCACCAAGGAGCUGGAGCACGCCCUGGAGAAGAACGAGGUGGACCUGGUGG UGCACAGCCUGAAGGACCUGCCCACCGUGCUGCCCUGGCUUCACCAUCGGCGCCAUCUGCAAGCGGGA GAACCCCCACGACGCCGUGGUGUUCCACCCCAAGUUCGUGGGCAAGACUCUGGAAACCCUGCCUGAGAAG UCCGUGGUCGGAACAAGCAGCCUGCGGCGGGCCGCCCAGCUGCAGCGGAAGUUCCCCCACCUGGAGUUCC GGAGCAUCCGGGGCAACCUGAACACCCGGCUGCGGAAGCUGGACGAGCAGCAGGAGUUCAGCGCCAUCAU CCUGGCCACAGCCGGCCUUCAGAGGAUGGCCACAAUCGGUGGCCAGAUCCUGCACCCCGAGGAG UGCAUGUACGCGGUAGGUCAGGGCGCCCUGGGCGUGGAGGUGCGGGCCAAGGACCAGGACAUCUUAGAUC UGGUUGGCGUGCUGCACGACCCCGAAACACUGCUGCGUGCAUCGCCGAGCGGGCCUUCCUGCGGCACCU CGAGGGCGGCUGCAGUGUGCCCGUGGCCGUGCACACCGCCAUGAAGGACGGCCAGCUGUACCUGACCGGC GGCGUGUGGAGCCUGGACGGCAGCGACAGCAUCCAGGAGACAUGCAUCCACCUCCACGUGCCGCUC AGCACGAAGACGGACCAGACGACGACCCCCAGUUAGUGGGAAUCACCGCCCGGAACAUCCCCGGGGCCC UCAGCUCGCGGCCCAGAACCUGGGCAUCAGCCUGGCCAACCUGCUGCUGUCUAAGGGCGCCAAGAACAUC CUAGACGUGGCCCGGCAGCUGAACGACGCCCAC |
| 101 | PBGD-CO42A | AUGAGCGGCAACGGCAACGCCGCCGCCACCGCCGAGGAGAACAGCCCCAAGAUGCGGGUGAUCCGGGUGG GCACCAGGAAGUCACAGCUGGCCCGGAUCCAGACCGACAGCGUGGUGGCCACCCUGAAGGCCAGCUACCC CGGCCUGCAGUUCGAGAUCAUCGCCAUGAGCACCACCGGCGACAAGAUCCUGGACACCGCCCUGAGCAAG AUCGGCGAGAAGUCCCUGUUCACCAAGGAGCUGGAGCACGCCCUGGAGAAGAACGAGGUGGACCUGGUGG UGCACAGCCUGAAGGACCUGCCCACCGUGCUGCCGCCAGGCUUCACCAUCGGCGCCAUCUGCAAGCGGGA |

TABLE 2-continued

Sequence optimized sequences for human PBGD, isoform 1

| SEQ ID NO | Name | Sequence |
|---|---|---|
| | | GAACCCCCACGACGCCGUGGUGUUCCACCCCAAGUUCGUGGGCAAGACCCUUGAAACCCUGCCAGAGAAG<br>UCUGUGGUCGGCACCAGCAGCCUGCGGCGGGCCGCCCAGCUGCAGCGGAAGUUCCCCCACCUGGAGUUCC<br>GGAGCAUCCGGGGCAACCUGAACACCCGGCUGCGGAAGCUGGACGAGCAGCAGGAGUUCAGCGCCAUCAU<br>CCUGGCCACCGCUGGCCUACAGCGGAUGGGCUGGCACAAUAGAGUUGGUCAGAUCCUGCACCCCGAGGAG<br>UGCAUGUACGCCGUCGGCCAGGGCGCCCUGGGCGUGGAGGUGCGGGCAAGGACCAGGACAUACUAGACC<br>UCGUGGGCGUGCUGCACGACCCCGAAACCUUGCUGCCGGUGCAUCGCCGAGCGGGCCUUCCUGCGGCACCU<br>GGAAGGCGGUUGCAGCGUGCCCGUGGCCGUGCACACCGCCAUGAAGGACGGCCAGCUGUACCUGACCGGC<br>GGCGUGUGGAGCCUGGACGGCAGCGACAGCAUCCAGGAGACAAUGCAGGCCACCAUCCACGUGCCGGCCC<br>AACACGAGGACGACCUGAGGACGACCCCCAGCUUUGUGGGAAUCACCGCCCGGAACAUCCCCGGGGCCC<br>UCAACUGGCAGCCCAGAACUUAGGCAUAAGCCUGGCCAACCUGCUGCUGUCCAAGGGCGCCAAGAACAUC<br>CUCGAUGUGGCCCGGCAGCUGAACGACGCCCAC |
| 102 | PBGD-CO43A | AUGAGCGGCAACGGCAACGCCGCCGCCACCGCCGAGGAGAACAGCCCCAAGAUGCGGGUGAUCCGGGUGG<br>GCACCCGCAAGAGUCAGCUGGCCCGGAUCCAGACCGACAGCGUGGUGGCCACCCUGAAGGCCAGCUACCC<br>CGGCCUGCAGUUCGAGAUCAUCGCCAUGAGCACCACCGGCGACAAGAUCCUGGACACCGCCCUGAGCAAG<br>AUCGGCGAGAAGAGUCUGUUCACCAAGGAGCUGGAGCACGCCCUGGAGAAGAACGAGGUGGACCUGGUGG<br>UGCACAGCCUGAAGGACCUGCCCACCGUGCUGCCACCUGGCUUCACCAUCGGCGCCAUCUGCAAGCGGGA<br>GAACCCCCACGACGCCGUGGUGUUCCACCCCAAGUUCGUGGGCAAGACACUGGAAACCCUGCCGGAGAAG<br>UCCGUGGUAGGCACCAGCAGCCUGCGGCGGGCCGCCCAGCUGCAGCGGAAGUUCCCCCACCUGGAGUUCC<br>GGAGCAUCCGGGGCAACCUGAACACCCGGCUGCGGAAGCUGGACGAGCAGCAGGAGUUCAGCGCCAUCAU<br>CCUGGCAACAGCCGGCUUACAGCGUAUGGGCUGGCACAACAGGGUGGACAGAUCCUGCACCCCGAGGAG<br>UGCAUGUACGCUGUGGGCCAGGGCGCCCUGGGCGUGGAGGUGCGGGCAAGGACCAGGACAUCUUAGAUC<br>UCGUCGGCGUGCUGCACGACCCCGAAACCUUGCUGCCGGUGCAUCGCCGAGCGGGCCUUCCUGCGGCAUCU<br>UGAGGGCGGAUGCUCCGUGCCCGUGGCCGUGCACACCGCCAUGAAGGACGGCCAGCUGUACCUGACCGGC<br>GGCGUGUGGAGCCUGGACGGCAGCGACAGCAUCCAGGAGACAUGCAGGCCACCAUCCACGUGCCAGCCC<br>AGCACGAAGACGCCCAGAGGACGACCCCCAGCUGGUGGGAAUCACCGCCCGGAACAUCCCCGGGGCCC<br>UCAACUGGCCGCACAGAACCUAGGCAUCAGCCUGGCCAACCUGCUGCUCAGCAAGGGCGCCAAGAAUAUC<br>UUGGACGUGGCCCGGCAGCUGAACGACGCCCAC |
| 103 | PBGD-CO44A | AUGAGCGGCAACGGCAACGCCGCCGCCACCGCCGAGGAGAACAGCCCCAAGAUGCGGGUGAUCCGGGUGG<br>GCACCAGAAAGAGCCAGCUGGCCCGGAUCCAGACCGACAGCGUGGUGGCCACCCUGAAGGCCAGCUACCC<br>CGGCCUGCAGUUCGAGAUCAUCGCCAUGAGCACCACCGGCGACAAGAUCCUGGACACCGCCCUGAGCAAG<br>AUCGGCGAGAAGUCUCUGUUCACCAAGGAGCUGGAGCACGCCCUGGAGAAGAACGAGGUGGACCUGGUGG<br>UGCACAGCCUGAAGGACCUGCCCACCGUGCUGCCUCCUGGCUUCACCAUCGGCGCCAUCUGCAAGCGGGA<br>GAACCCCCACGACGCCGUGGUGUUCCACCCCAAGUUCGUGGGCAAGACCCUUGAGACUCUGCCAGAGAAG<br>UCUGUAGUGGGAACCAGCAGCCUGCGGCGGGCCGCCCAGCUGCAGCGGAAGUUCCCCCACCUGGAGUUCC<br>GGAGCAUCCGGGGCAACCUGAACACCCGGCUGCGGAAGCUGGACGAGCAGCAGGAGUUCAGCGCCAUCAU<br>CCUGGCCACGGCCGGAUUACAGAGAAUGGGCUGGCACAACCGAGUGGACAGAUCCUGCACCCCGAGGAG<br>UGCAUGUAUGCCGUUGGCCAAGGCGCCCUGGGCGUGGAGGUGCGGGCAAGGACCAGGACAUCCUCGAUC<br>UCGUGGGCGUGCUGCACGACCCCGAGACUUUGCUGCCGGUGCAUCGCCGAGCGGGCCUUCCUGCGGCACCU<br>AGAGGGCGGCUGCUCGGUGCCCGUGGCCGUGCACACCGCCAUGAAGGACGGCCAGCUGUACCUGACCGGC<br>GGCGUGUGGAGCCUGGACGGCAGCGACAGCAUCCAGGAGACAAUGCAGGCCACCAUCCACGUGCCAGCCC<br>AGCACGAGGAUGCCCUGAAGACGACCCCCAGCUGGUGGGCAUCACCGCCCGGAACAUCCCCGGGGCCC<br>ACAAUUGGCCGCUCAGAACUUAGGCAUUAGCCUGGCCAACCUGCUGCUGUCUAAGGGCGCCAAGAACAUA<br>CUGGACGUGGCCCGGCAGCUGAACGACGCCCAC |
| 104 | PBGD-CO45A | AUGAGCGGCAACGGCAACGCCGCCGCCACCGCCGAGGAGAACAGCCCCAAGAUGCGGGUGAUCCGGGUGG<br>GCACCCGGAAGAGCCAGCUGGCCCGGAUCCAGACCGACAGCGUGGUGGCCACCCUGAAGGCCAGCUACCC<br>CGGCCUGCAGUUCGAGAUCAUCGCCAUGAGCACCACCGGCGACAAGAUCCUGGACACCGCCCUGAGCAAG<br>AUCGGCGAGAAGAGCCUGUUCACCAAGGAGCUGGAGCACGCCCUGGAGAAGAACGAGGUGGACCUGGUGG<br>UGCACAGCCUGAAGGACCUGCCCACCGUGCUGCCCCCGGCUUCACCAUCGGCGCCAUCUGCAAGCGGGA<br>GAACCCCCACGACGCCGUGGUGUUCCACCCCAAGUUCGUGGGCAAGACCCUGGAAACCCUGCCGGAGAAG<br>AGCGUGGUGGGCACCAGCAGCCUGCGGCGGGCCGCCCAGCUGCAGCGGAAGUUCCCCCACCUGGAGUUCC<br>GGAGCAUCCGGGGCAACCUGAACACCCGGCUGCGGAAGCUGGACGAGCAGCAGGAGUUCAGCGCCAUCAU<br>CCUGGCCACCGCCGGCCUGCAGCGGAUGGGCUGGCACAACCGGGUGGGCCAGAUCCUGCACCCCGAGGAG<br>UGCAUGUACGCCGUGGGCCAGGGCGCCCUGGGCGUGGAGGUGCGGGCAAGGACCAGGACAUCCUGGACC<br>UGGUGGGCGUGCUGCACGACCCCGAGACCCUGCUGCCGGUGCAUCGCCGAGCGGGCCUUCCUGCGGCACCU<br>GGAGGGCGGCUGCAGCGUGCCCGUGGCCGUGCACACCGCCAUGAAGGACGGCCAGCUGUACCUGACCGGC<br>GGCGUGUGGAGCCUGGACGGCAGCGACAGCAUCCAGGAGACCAUGCAGGCCACCAUCCACGUGCCCGCCC<br>AGCACGAGGACGCCCCGGAGGACGACCCCCAGCUGGUGGGCAUCACCGCCCGGAACAUCCCCGGGGCCC<br>CCAGCUGGCCGCCCAGAACCUGGGCAUCAGCCUGGCCAACCUGCUGCUGAGCAAGGGCGCCAAGAACAUC<br>CUGGACGUGGCCCGGCAGCUGAACGACGCCCAC |
| 105 | PBGD-CO46A | AUGAGCGGCAACGGCAACGCCGCCGCCACCGCCGAGGAGAACAGCCCCAAGAUGCGGGUGAUCCGGGUGG<br>GCACCCGGAAGAGCCAGCUGGCGAGGAUCCAGACCGACAGCGUGGUGGCCACCCUGAAGGCCAGCUACCC<br>GGGGCUGCAGUUCGAGAUCAUCGCGAUGAGCACGACGGGGGACAAGAUCCUGGACACCGCGCUGAGCAAG<br>AUCGGGGAGAAGAGCCUGUUCACGAAGGAGCUGGAGCACGCGCUGGAAGAACGAGGUGGACCUGGUGG<br>UGCACAGCCUGAAGGACCUGCCGACGGUGCUGCCGCCGGGGUUCACGAUCGGGGCGAUCUGCAAGAGGGA<br>GAACCCCCACGACGCGGUGGUGUUCCACCCGAAGUUCGUGGGGCAAGACGCUGGAAACGCUGCCGGAGAA<br>AGCGUGGUGGGACGAGCAGCCUGAGGAGGGCGGCCAGCUGCAGAGGAAGUUCCCGCACCUGGAGUUCA<br>GGAGCAUCAGGGGGAACCUGAACACGAGGCUGAGGAAGCUGGACGAGCAGCAGGAUUCAGCGCGAUCAU<br>CCUGGCGACGGCGGGGCUGCAGAGGAUGGGGUGGCACAACAGGGUGGGGCAGAUCCUGCACCCGGAGGAG<br>UGCAUGUACGCGGUGGGCAGGGGCGCUGGGGGUGGAGGUGAGGGCAAGGACCAGGACAUCCUGGACC<br>UGGUGGGGGUGCUGCACGACCCCGGAGACGCUGCUGAGGUGCAUCGCGGAGAGGGCGUUCCUGAGGCACCU |

TABLE 2-continued

Sequence optimized sequences for human PBGD, isoform 1

| SEQ ID NO | Name | Sequence |
|---|---|---|
|  |  | GGAGGGGGGUGCAGCGUGCCGGUGGCGGUGCACACGGCGAUGAAGGACGGGCAGCUGUACCUGACGGGG<br>GGGGUGUGGAGCCUGGACGGGAGCGACAGCAUCCAGGAGACGGCAGGCGACGAUCCACGUGCCGGCGC<br>AGCACGAGGACGGGCCGGAGGACGACCCGCAGCUGGUGGGGAUCACGGCGAGGAACAUCCCGAGGGGGCC<br>GCAGCUGGCGGCGCAGAACCUGGGGAUCAGCCUGGCGAACCUGCUGAGCAAGGGGGCGAAGAACAUC<br>CUGGACGUGGCGAGGCAGCUGAACGACGCGCAC |
| 106 | PBGD-CO47A | AUGAGCGGCAACGGCAACGCCGCCGCCACCGCCGAGGAGAACAGCCCCAAGAUGCGGGUGAUCCGGGUGG<br>GCACCCGGAAGAGCCAGCUGGCCCGCAUCCAGACCGACUCCGUCGUCGCCACCCUCAAGGCCUCCUACCC<br>CGGCCUCCAGUUCGAGAUCAUCGCCAUGUCCACCACCGGCGACAAGAUCCUCGACACCGCCCUCUCCAAG<br>AUCGGCGAGAAGUCCCUCUUCACCAAGGAGCUCGAGCACGCCCUCGAGAAGAACGAGGUCGACCUCGUCG<br>UCCACUCCCUCAAGGACCUCCCCACCGUCCUCCCCCCCGGCCUAACCAUCGGCGCCAUCUGCAAGCGCGA<br>GAACCCCACGACGCCGUCGUCUUCCACCCCAAGUUCGUCGGCAAGACCCUCGAGACCCUCCCCGAGAAG<br>UCCGUCGUCGGCACCUCCUCCCUCCGCCGCGCCGCCCAGCUCCAGCGCAAGUCCCCCACCUCGAGUUCC<br>GCUCCAUCCGCGGCAACCUCAACACCCGCCUCCGCAAGCUCGACGAGCAGCAGGAGUUCUCCGCCAUCAU<br>CCUCGCCACCGCCGGCCUCCAGCGCAUGGGCUGGCACAACCGCGUCGGCCAGAUCCUGCACCCCGAGGAG<br>UGCAUGUACGCCGUCGGCCAGGGCGCCCUCGGCGUCGAGGUCCGCGCCAAGGACCAGGACAUCCUCGACC<br>UCGUCGGCGUCCUCCACGACCCCGAGACCCUCCUCCGCUGCAUCGCCGAGCGCGCCUUCCUCCGCCACCU<br>CGAGGGCGGCUGCUCCGUCCCCGUCGCCGUCCACACCGCCAUGAAGGACGGCCAGCUCUACCUCACCGGC<br>GGCGUCUGGUCCCUCGACGGCUCCGACUCCAUCCAGGAGACCAUGCAGGCCACCAUCCACGUCCCCGCCC<br>AGCACGAGGACGGCCCCGAGGACGACCCCCAGCUCGUCGGCAUCACCGCCCGAACAUCCCCGCGGCCC<br>CCAGCUCGCCGCCCAGAACCUCGGCAUCUCCCUCGCCAACCUCCUCCUCUCCAAGGGCGCCAAGAACAUC<br>CUCGACGUCGCCCGCCAGCUCAACGACGCCCAC |
| 107 | PBGD-CO40B | AUGAGCGGCAACGGCAACGCCGCCGCCACCGCCGAGGAGAACAGCCCCAAGAUGCGGGUGAUCCGGGUGG<br>GCACCCGUAAGAGCCAGCUGGCCCGGAUCCAGACCGACAGCGUGGUGGCCACCCUGAAGGCCAGCUACCC<br>CGGCCUGCAGUUCGAGAUCAUCGCCAUGAGCACCACCGGCGACAAGAUCCUGGACACCGCCCUGAGCAAG<br>AUCGGCGAGAAGUCCCUGUUCACCAAGGAGCUGGAGCACGCCCUGGAGAAGAACGAGGUGGACCUGGUG<br>UGCACAGCCUGAAGGACCUGCCCACCGUGCUGCCUCCAGGCUUCACCAUCGGCGCCAUCUGCAAGCGGGA<br>GAACCCUCACGACGCCGUGGUGUUCCACCCCAAGUUCGUGGGCAAGACCCUGGAAACCCUGCCUGAGAAG<br>UCCGUCGUAGGAACCAGCAGCCUGCGGCGGGCCGCCCAGCUGCAGCGGAAGUUCCCACACCUGGAGUUCC<br>GGAGCAUCCGGGGCAACCUGAACACCCGGCUGCGGAAGCUGGACGAGCAGCAGGAGUUCAGCGCCAUCAU<br>CCUGGCUACCGCCGGUCUGCAACGAAUGGGCUGGCACAAUAGGGUGGGCCAGAUCCUGCACCCCGAGGAG<br>UGCAUGUACGCGCGUGGGACAGGGCGCCCUGGGCGUGGAGGUGCGGGCCAAGGACCAGGACAUCCUUGAUC<br>UGGUGGGCGUGCUGCACGACCCCGAGACGCUGCUGCGUGCAUCGCCGAGCGGGCCUUCCUGCGGCAUUU<br>GGAGGGCGGAUGCAGCGUGCCCGUGGCCGUGCACACCGCCAUGAAGGACGGCCAGCUGUACCUGACCGGC<br>GGCGUGUGGAGCCUGGACGGCAGCGACAGCAUCCAGGAAACCAUGCAGGCCACCAUCCACGUGCCUGCUC<br>AGCACGAAGACGGCCCAGAGGACGACCCUCAGCUGGUAGGCAUCACCGCCCGAACAUCCCUCGGGGCCC<br>UCAGCUCGCCGCACAGAACCUUGGAAUCAGCCUGGCCAACCUGCUGUUGUCAAGGGCGCCAAGAAUAUC<br>CUCGACGUGGCCCGGCAGCUGAACGACGCCCAC |
| 108 | PBGD-CO41B | AUGAGCGGCAACGGCAACGCCGCCGCCACCGCCGAGGAGAACAGCCCCAAGAUGCGGGUGAUCCGGGUGG<br>GCACCAGAAAGAGCCAGCUGGCCCGGAUCCAGACCGACAGCGUGGUGGCCACCCUGAAGGCCAGCUACCC<br>CGGCCUGCAGUUCGAGAUCAUCGCCAUGAGCACCACCGGCGACAAGAUCCUGGACACCGCCCUGAGCAAG<br>AUCGGCGAGAAGAGUCUGUUCACCAAGGAGCUGGAGCACGCCCUGGAGAAGAACGAGGUGGACCUGGUGG<br>UGCACAGCCUGAAGGACCUGCCCACCGUGCUGCCGCCUGGCUUCACCAUCGGCGCCAUCUGCAAGCGGGA<br>GAACCCGCACGACGCCGUGGUGUUCCACCCCAAGUUCGUGGGCAAGACUCUGGAAACCCUGCCUGAGAAG<br>UCCGUGGUCGGAACAAGCAGCCUGCGGCGGGCCGCCCAGCUGCAGCGGAAGUUCCCACACCUGGAGUUCC<br>GGAGCAUCCGGGGCAACCUGAACACCCGGCUGCGGAAGCUGGACGAGCAGCAGGAGUUCAGCGCCAUCAU<br>CCUGGCCACAGCCGGCCUUCAGAGGAUGGGCUGGCACAAUCGGGUAGGCCAGAUCCUGCACCCCGAGGAG<br>UGCAUGUACGCGGUAGGUCAGGGCGCCCUGGGCGUGGAGGUGCGGGCCAAGGACCAGGACAUCUUAGAUC<br>UGGUUGGCGUGCUGCACGACCCCGAAACACUGCUGCGGUGCAUCGCCGAGCGGGCCUUCCUGCGGCACCU<br>CGAGGGCGGCUGCAGUGUGCCCGUGGCCGUGCACACCGCCAUGAAGGACGGCCAGCUGUACCUGACCGGC<br>GGCGUGUGGAGCCUGGACGGCAGCGACAGCAUCCAGGAGACAAUGCAGGCCACCAUCCACGUGCCAGCUC<br>AGCACGAAGACGGACCAGAGGACGACCCACAGUUAGUGGGAAUCACCGCCCGAACAUCCCGCGGGGCCC<br>UCAGCUCGCGGCCCAGAACCUGGGCAUCAGCCUGGCCAACCUGCUGCUGUCUAAGGGCGCCAAGAACAUC<br>CUAGACGUGGCCCGGCAGCUGAACGACGCCCAC |
| 109 | PBGD-CO42B | AUGAGCGGCAACGGCAACGCCGCCGCCACCGCCGAGGAGAACAGCCCCAAGAUGCGGGUGAUCCGGGUGG<br>GCACCAGGAAGUCACAGCUGGCCCGGAUCCAGACCGACAGCGUGGUGGCCACCCUGAAGGCCAGCUACCC<br>CGGCCUGCAGUUCGAGAUCAUCGCCAUGAGCACCACCGGCGACAAGAUCCUGGACACCGCCCUGAGCAAG<br>AUCGGCGAGAAGUCCCUGUUCACCAAGGAGCUGGAGCACGCCCUGGAGAAGAACGAGGUGGACCUGGUGG<br>UGCACAGCCUGAAGGACCUGCCCACCGUGCUGCCGCCAGGCUUCACCAUCGGCGCCAUCUGCAAGCGGGA<br>GAACCCGCACGACGCCGUGGUGUUCCACCCCAAGUUCGUGGGCAAGACCCUUGAAACCCUGCAGAGAAG<br>UCUGUGGUCGGCACCAGCAGCCUGCGGCGGGCCGCCCAGCUGCAGCGGAAGUUCCCGCACCUGGAGUUCC<br>GGAGCAUCCGGGGCAACCUGAACACCCGCCUGCGGAAGCUGGACGAGCAGCAGGAGUUCAGCGCGCAUCAU<br>CCUGGCCACCGCUGGCCUACAGCGGAUGGGCUGGCACAAUAGAGUUGGUCAGAUCCUGCACCCCGAGGAG<br>UGCAUGUACGCCGUCGGCCAGGGCGCCCUGGGCGUGGAGGUGCGGGCCAAGGACCAGGACAUACUAGACC<br>UCGUGGGCGUGCUGCACGACCCCGAAACCUUGCUGCGGUGCAUCGCCGAGCGGGCCUUCCUGCGGCACCU<br>GGAAGGCGGUUGCAGCGUGCCCGUGGCCGUGCACACCGCCAUGAAGGACGGCCAGCUGUACCUGACCGGC<br>GGCGUGUGGAGCCUGGACGGCAGCGACAGCAUCCAGGAGACAAUGCAGGCCACCAUCCACGUGCCGGCCC<br>AACACGAGGACGGACCUGAGGACGACCCACAGCUUUGGGAAUCACCGCCCGAACAUCCCACGGGGCCC<br>UCAACUGGCAGCCCAGAACUUAGGCAUAAGCCUGGCCAACCUGCUGCUGUCCAAGGGCGCCAAGAACAUC<br>CUCGAUGUGGCCCGGCAGCUGAACGACGCCCAC |

TABLE 2-continued

Sequence optimized sequences for human PBGD, isoform 1

| SEQ ID NO | Name | Sequence |
|---|---|---|
| 110 | PBGD-CO43B | AUGAGCGGCAACGGCAACGCCGCCGCCACCGCCGAGGAGAACAGCCCCAAGAUGCGGGUGAUCCGGGUGG<br>GCACCCGCAAGAGUCAGCUGGCCCGGAUCCAGACCGACAGCAGCGUGGUGGCCACCCUGAAGGCCAGCUACCC<br>CGGCCUGCAGUUCGAGAUCAUCGCCAUGAGCACCACCGGCGACAAGAUCCUGGACACCGCCCUGAGCAAG<br>AUCGGCGAGAAGAGUCUGUUCACCAAGGAGCUGGAGCACGCCCUGGAGAAGAACGAGGUGGACCUGGUGG<br>UGCACAGCCUGAAGGACCUGCCCACCGUGCUGCCACCUGGCUUCACCAUCGGCGCCAUCUGCAAGCGGGA<br>GAACCCACACGACGCCGUGGUGUUCCACCCCAAGUUCGUGGGCAAGACACUGGAAACCCUGCCGGAGAAG<br>UCCGUGGUAGGCACCAGCAGCCUGCGCCGGGCCGCCCAGCUGCAGCGGAAGUUCCCGCACCUGGAGUUCC<br>GGAGCAUCCGGGGCAACCUGAACACCCGGCUGCGGAAGCUGGACGAGCAGCAGGAGUUCAGCGCCAUCAU<br>CCUGGCAACAGCCGGCUUACAGCGUAUGGGCUGGCACAACAGGGUGGGACAGAUCCUGCACCCCGAGGAG<br>UGCAUGUACGCUGUGGGCCAGGGCGCCCUGGGCGUGGAGGUGCGGGCCAAGGACCAGGACAUCUUAGAUC<br>UCGUCGGCUGCUGCACGACCCCGAAACCUUGCUGCUCGCUGAGCGGCCGAGCGGGCCUUCCUGCGGCAUCU<br>UGAGGGCGGAUGCUCCGUGCCCGUGGCCGUGCACACCGCCAUGAAGGACGGCCAGCUGUACCUGACCGGC<br>GGCGUGUGGAGCCUGGACGGCAGCGACAGCAUCCAGGAGACUAUGCAGGCCACCAUCCACGUGCCAGCCC<br>AGCACGAAGACGCCCAGAGGACGACCCACAGCUGGUGGGAAUCACCGCCCGGAACAUCCCGCGGGGCCC<br>UCAACUGGCCGCACAGAACCUAGGCAUCAGCCUGGCCAACCUGCUGCUCAGCAAGGGCGCCAAGAAUAUC<br>UUGGACGUGGCCCGGCAGCUGAACGACGCCCAC |
| 111 | PBGD-CO44B | AUGAGCGGCAACGGCAACGCCGCCGCCACCGCCGAGGAGAACAGCCCCAAGAUGCGGGUGAUCCGGGUGG<br>GCACCAGAAAGAGCCAGCUGGCCCGGAUCCAGACCGACAGCAGCGUGGUGGCCACCCUGAAGGCCAGCUACCC<br>CGGCCUGCAGUUCGAGAUCAUCGCCAUGAGCACCACCGGCGACAAGAUCCUGGACACCGCCCUGAGCAAG<br>AUCGGCGAGAAGUCUCUGUUCACCAAGGAGCUGGAGCACGCCCUGGAGAAGAACGAGGUGGACCUGGUGG<br>UGCACAGCCUGAAGGACCUGCCCACCGUGCUGCCUCCUGGCUUCACCAUCGGCGCCAUCUGCAAGCGGGA<br>GAACCCACACGACGCCGUGGUGUUCCACCCCAAGUUCGUGGGCAAGACCCUUGAGACUCAGAGAAG<br>UCUGUAGUGGGAACCAGCAGCCUGCGGCGGGCCGCCCAGCUGCAGCGGAAGUUCCCUCACCUGGAGUUCC<br>GGAGCAUCCGGGGCAACCUGAACACCCGGCUGCGGAAGCUGGACGAGCAGCAGGAGUUCAGCGCCAUCAU<br>CCUGGCCACGGCCGGAUUACAGAGAAUGGGCUGGCACAACCGAGUGGGACAGAUCCUGCACCCCGAGGAG<br>UGCAUGUAUGCCGUUGGCCAAGGCGCCCUGGGCGUGGAGGUGCGGGCCAAGGACCAGGACAUCUCGAUC<br>UCGUGGGCGUGCUGCACGACCCCGAGACUUUGCUGCGGUGCAUCGCCGAGCGGGCCUUCCUGCGGCACCU<br>AGAGGGCGGCUGCUCGGUGCCCGUGGCCGUGCACACCGCCAUGAAGGACGGCCAGCUGUACCUGACCGGC<br>GGCGUGUGGAGCCUGGACGGCAGCGACAGCAUCCAGGAGACAAUGCAGGCCACCAUCCACGUGCCAGCCC<br>AGCACGAGGAUGCCCUGAAGACGACCCACAGCUGGUGGGCAUCACCGCCCGGAACAUCCCGCGGGGCCC<br>ACAAUUGGCCGCUCAGAACUUAGGCAUUAGCCUGGCCAACCUGCUGCUGUCUAAGGGCGCCAAGAACAUA<br>CUGGACGUGGCCCGGCAGCUGAACGACGCCCAC |
| 112 | PBGD-CO45B | AUGAGCGGCAACGGCAACGCCGCCGCCACCGCCGAGGAGAACAGCCCCAAGAUGCGGGUGAUCCGGGUGG<br>GCACCCGGAAGAGCCAGCUGGCCCGGAUCCAGACCGACAGCAGCGUGGUGGCCACCCUGAAGGCCAGCUACCC<br>CGGCCUGCAGUUCGAGAUCAUCGCCAUGAGCACCACCGGCGACAAGAUCCUGGACACCGCCCUGAGCAAG<br>AUCGGCGAGAAGAGCCUGUUCACCAAGGAGCUGGAGCACGCCCUGGAGAAGAACGAGGUGGACCUGGUGG<br>UGCACAGCCUGAAGGACCUGCCCACCGUGCUGCCCCCGGCUUCACCAUCGGCGCCAUCUGCAAGCGGGA<br>GAACCCACGACGCCGUGGUGUUCCACCCCAAGUUCGUGGGCAAGACCCUGGAGACCCUGCCCGAGAAG<br>AGCGUGGUGGGCACCAGCAGCCUGCGGCGGGCCGCCCAGCUGCAGCGGAAGUUCCCCUCACCUGGAGUUCC<br>GGAGCAUCCGGGGCAACCUGAACACCCGGCUGCGGAAGCUGGACGAGCAGCAGGAGUUCAGCGCCAUCAU<br>CCUGGCCACCGCCGGCCUGCAGCGGAUGGGCUGGCACAACCGGGUGGGCCAGAUCCUGCACCCCGAGGAG<br>UGCAUGUACGCCGUGGGCCAGGGCGCCCUGGGCGUGGAGGUGCGGGCCAAGGACCAGGACAUCCUGGACC<br>UGGUGGGCGUGCUGCACGACCCCGAGACCCUGCUGCGGUGCAUCGCCGAGCGGGCCCUUCCCUGCGGCACCU<br>GGAGGGCGGCUGCAGCGUGCCCGUGGCCGUGCACACCGCCAUGAAGGACGGCCAGCUGUACCUGACCGGC<br>GGCGUGUGGAGCCUGGACGGCAGCGACAGCAUCCAGGAGACCAUGCAGGCCACCAUCCACGUGCCCGCCC<br>AGCACGAGGACGCCCCGAGGACGACCCUCAGCUGGUGGGCAUCACCGCCCGGAACAUCCCACGGGGCCC<br>UCAGCUGGCCGCCCAGAACCUGGGCAUCAGCCUGGCCAACCUGCUGCUGAGCAAGGGCGCCAAGAACAUC<br>CUGGACGUGGCCCGGCAGCUGAACGACGCCCAC |
| 113 | PBGD-CO46B | AUGAGCGGCAACGGCAACGCCGCCGCCACCGCCGAGGAGAACAGCCCCAAGAUGCGGGUGAUCCGGGUGG<br>GCACCCGGAAGAGCCAGCUGGCGAGGAUCCAGACCGGACAGCGUGGUGGCGACGCUGAAGGCGAGCUACCC<br>GGGGCUGCAGUUCGAGAUCAUCGCGAUGAGCACGACGGGCGACAAGAUCCUGGACACGGCGCUGAGCAAG<br>AUCGGGGAGAAGAGCCUGUUCACGAAGGAGCUGGAGCACGCGCUGGAGAAGAACGAGGUGGACCUGGUGG<br>UGCACAGCCUGAAGGACCUGCGACGGUGCUGCCGGGGUUCACGAUCGGGGGCGAUCUGCAAGCGGGA<br>GAACCCGCACGACGCGGUGGUGUUCCACCCCAAGUUCGUGGGGAAGACGCUGGAGAGCGCUGCCGGAGAAG<br>AGCGUGGUGGGGACGAGCAGCCUGAGGAGGGCGGCGCAGCUGCAGAGGAAGUUCCCGCACCUGGAGUUCA<br>GGAGCAUCAGGGGUAACCUGAACACGGAGCUGAGGAAGCUGGACGAGCAGCAGGAGUUCAGCGCGAUCAU<br>CCUGGCGACGGCGGGGCUGCAGAGGAUGGGGUGGCACAACAGGGUGGGGCAGAUCCUGCACCCGGAGGAG<br>UGCAUGUACGCGGUGGGGCAGGGCGCCCUGGGCGUGGAGGUGCGGGCCAAGGACCAGGACAUCCUGGACC<br>UGGUGGGCGUGCUGCACGACCCGGAGACCCUGCUGAGGUGCAUCGCGGAGAGGGCGUUCCUGAGGCACCU<br>GGAGGGCGGGUGCAGCGUGCCGUGGCCGUGCACACGGCGAUGAAGGACGGCAGCUGUACCUGACGGGA<br>GGGGUGUGGAGCCUGGACGGGAGCGACAGCAUCCAGGAGACGAUGCAGGCGACGAUCCACGUGCCGGCGC<br>AGCACGAGGACGGCCGGAGGACGACCCGCAGCUGGUGGGAUACGGCGAGGAACAUCCCGAGGGGUCC<br>GCAGCUGGCGGCGCAGAACCUGGGGAUCAGCCUGGCGAACCUGCUGCUGAGCAAGGGGAGCGAAGAACAUC<br>CUGGACGUGGCGAGGCAGCUGAACGACGCGCAC |
| 114 | PBGD-CO47B | AUGAGCGGCAACGGCAACGCCGCCGCCACCGCCGAGGAGAACAGCCCCAAGAUGCGGGUGAUCCGGGUGG<br>GCACCCGGAAGAGCCAGCUGGCCCGCAUCCAGACCGACUCCGUCGUCGCCACCCUCAAGGCCUCCUACCC<br>CGGCCUCCAGUUCGAGAUCAUCGCCAUGUCCACCACCGGCGACAAGAUCCUCGACACCGCCCUCUCCAAG<br>AUCGGCGAGAAGUCCCUCUUCACCAAGGAGCUCGAGCACGCCCUCGAGAAGAACGAGGUCGACCUCGUCG<br>UCCACUCCCUCAAGGACCUCCCCACCGUCCUCCCACCCGGCUUCACCAUCGGCGCCAUCUGCAAGCGCGA<br>GAACCCUCACGACGCCGUCGUCUUCCACCCCAAGUUCGUCGGCAAGACCCUCGAGACCCUCCCCGAGAAG |

TABLE 2-continued

Sequence optimized sequences for human PBGD, isoform 1

| SEQ ID NO | Name | Sequence |
|---|---|---|
| | | UCCGUCGUCGGCACCUCCUCCCUCCGCCGCGCCGCCCAGCUCCAGCGCAAGUUCCCACACCUCGAGUUCC<br>GCUCCAUCCGCGGCAACCUCAACACCCGCCUCCGCAAGCUCGACGAGCAGCAGGAGUUCUCCGCCAUCAU<br>CCUCGCCACCGCCGGCCUCCAGCGCAUGGGCUGGCACAACCGCGUCGGCCAGAUCCUCCACCCCGAGGAG<br>UGCAUGUACGCCGUCGGCCAGGGCGCCCUCGGCGUCGAGGUCCGCGCCAAGGACCAGGACAUCCUCGACC<br>UCGUCGGCGUCCUCCACGACCCCGAGACCCUCCUCCGCUGCAUCGCCGAGCGCGCCUUCCUCCGCCACCU<br>CGAGGGCGGCUGCUCCGUCCCCGUCGCCGUCCACACCGCCAUGAAGGACGGCCAGCUCUACCUCACCGGC<br>GGCGUCUGGUCCCUCGACGGCUCCGACUCCAUCCAGGAGACCAUGCAGGCCACCAUCCACGUCCCCGCC<br>AGCACGAGGACGGCCCCGAGGACGACCCUCAGCUCGUCGGCAUCACCGCCCGCAACAUCCCGCGCGGCCC<br>UCAGCUCGCCGCCCAGAACCUCGGCAUCUCCCUCGCCAACCUCCUCCUCUCCAAGGGCGCCAAGAACAUC<br>CUCGACGUCGCCCGCCAGCUCAACGACGCCCAC |
| 115 | PBGD-C048 | AUGUCCGGAAACGGAAACGCCGCCGCUACCGCCGAGGAAAAUAGCCCGAAGAUGAGAGUGAUCCGGGUGG<br>GUACCAGGAAGUCCCAGCUCGCCAGGAUCCAAACGGACUCGGUGGUGGCCACCCUCAAGGCUAGCUACCC<br>GGGCCUGCAAUUCGAGAUCAUUGCUAUGUCCACCACCGGCGACAAGAUCCUGGAUACGGCCCUGUCCAAG<br>AUCGGCGAAAAGAGCCUCUUCACCAAGGAGCUGGAACACGCGCUCGAGAAGAACGAGGUGGACCUGGUCG<br>UCCACAGCCUCAAGGACCUGCCUACGGUGCUGCCGCCGGGAUUCACCAUCGGCGCCAUCUGUAAGCGGGA<br>GAAUCCGCACGACGCCGUGGUGUUCCACCCUAAGUUCGUGGGCAAGACCCUCGAGACACUGCCGGAAAAG<br>UCCGUCGUGGGCACCUCCUCCCUGAGAAGGGCCGCUCAGCUCCAGAGAAAGUUCCCGCACCUGGAAUUCA<br>GGAGCAUCCGGGGCAACCUGAAUACCCGGCUUCGCAAGCUGGACGAGCAGCAGGAGUUCAGCGCCAUCAU<br>CCUGGCCACCGCCGGCCUGCAGCGGAUGGGCUGGCACAACCGGGUGGGCCAGAUCCUGCACCCGGAGGAG<br>UGCAUGUAUGCCGUGGGUCAGGGAGCCCUGGGCGUGGAGGUCCGGGCCAAGGACCAGGACAUCCUGGACC<br>UCGUGGGCGUGCUCCACGACCCUGAAACCCUCCUGAGGUGCAUCGCCGAGAGGGCCUUCCUCCGGCACCU<br>GGAGGGCGGCUGUUCCGUCCCUGUGGCCGUGCAUACCGCCAUGAAGGACGGACAGCUGUACCUGACCGGC<br>GGCGUGUGGUCCCUGGACGGCUCCGACAGCAUCCAGGAAACCAUGCAGGCCACUAUCCACGUGCCGGCCC<br>AGCACGAAGACGGCCCAGAGGAUGACCCGCAACUGGUCGGCAUUACCGCCAGGAACAUACCAAGGGGCCC<br>GCAGCUGGCCGCCCAGAACCUGGGCAUCUCCCUGGCCAACCUGCUGCUGUCCAAGGGAGCCAAGAACAUU<br>CUGGACGUGGCCAGGCAGCUCAAUGAUGCCCAC |
| 116 | PBGD-C049 | AUGAGCGGCAACGGCAACGCCGCCGCCACCGCAGAGGAGAAUAGCCCGAAGAUGAGGGUGAUCCGAGUGG<br>GCACCAGGAAGUCCCAGCUUGCGCGAAUUCAGACCGACAGCGUGGUGGCCACCCUCAAGGCCUCCUACCC<br>GGGCACUCCAGUUCGAGAUCAUCGCCAUGAGCACCACGGGAGACAAGAUCCUGGACACCGCCCUGUCCAAG<br>AUCGGCGAAAAGAGCCUCUUCACCAAGGAGCUGGAGCACGCCCUGGAGAAGAACGAGGUCGAUCUGGUGG<br>UGCACAGCCUGAAGGACCUGCCGACCGUCCUGCCGCCGGGAUUCACCAUCGGUGCCAUCUGUAAGCGGGA<br>GAACCCGCACGACGCCGUGGUGUUCCACCCGAAGUUCGUCGGCAAGACCCUGGAAACCCUGCCGGAGAAG<br>UCCGUGGUGGGCACCAGCAGCCUGAGGCGGGCCGCCCAGCUGCAGCGGAAGUUCCCGCACCUGGAAUUCA<br>GGAGCAUCCGGGGCAACCUGAACACCCGCUGCGGAAGCUGGACGAGCAGCAGGAGUUCAGCGCCAUCAU<br>CCUGGCCACCGCAGGCCUCCAGCGCAUGGGAUGGCACAACAGGGUAGGCCAAAUCCUGCACCCGGAGGAG<br>UGUAUGUACGCCGUGGGCCAGGGAGCCCUGGGCGUGGAGGUGAGAGCCAAGGACCAGGACAUCCUAGACC<br>UGGUCGGCGUGCUGCACGACCCGGAGACACUGCUGAGAUGCAUCGCGGAGAGAGCCUUCCUGCGACACCU<br>GGAGGGCGGCUGCUCCGUGCCGGUGGCCGUGCACACCGCCAUGAAGGACGGCCAGCUGUAUCUGACCGGC<br>GGCGUGUGGAGCCUGGACGGCAGCGACUCCAUCCAAGAAACCAUGCAGGCUACCAUCCACGUGCCGGCCC<br>AGCACGAGGAUGACCAGAGGACGAUCCUCAACUGGUGGGCAUCACUGCCAGGAACAUCCAAGAGGCCC<br>GCAGCUGGCCGCCCAGAACCUGGGCAUCAGCCUGGCCAACCUGCUGCUGUCCAAGGGCGCCAAGAACAUU<br>CUCGAUGUGGCCAGGCAGCUGAACGAUGCCCAC |
| 117 | PBGD-C050 | AUGUCGGGAAACGGCAACGCCGCCGCCACGGCCGAGGAGAACAGCCCGAAGAUGAGAGUGAUUAGGGUGG<br>GCACCCGGAAGUCCCAACUCGCGCGGAUCCAGACCGACUCCGUGGUGGCCACCCUCAAGGCCAGCUACCC<br>GGGCUCCCAGUUCGAGAUUAUCGCCAUGUCCACCACAGGCGACAAGAUCCUCGACACCGCACUCUCGAAG<br>AUCGGCGAGAAGUCCCUGUUCACCAAGGAACUGGAGCACGCCCUGGAGAAGAACGAGGUGGACCUGGUGG<br>UGCACUCCCUGAAGGACCUGCCGACCGUGCUCCCACCAGGCUUCACCAUCGGCGCAAUCUGUAAGCGCGA<br>GAAUCCGCACGACGCCGUGGUGUUCCACCCAAAGUUCGUGGGCAAGACCCUCGAAACCCUCCCCGGAAAAG<br>AGCGUGGUGGGUACCAGCUCCCUGCGGAGAGCUGCCCAGCUGCAGAGAAAGUUCCCGCACUGGAAUUCA<br>GGAGCAUCAGGGGAAAUCUGAAUACCAGACUGCGCAAGCUGGACGAGCAGCAGGAGUUCAGCGCCAUCAU<br>CCUGGCCACCGCCGGCCUGCAGCGGAUGGGCUGGCACAACAGGGUGGGCCAGAUACUGCAUCGGAGGAG<br>UGUAUGUACGCCGUGGGCCAGGGCGCCCUCGGCGUGGAGGUGAGAGCCAAGGACCAAGACAUCCUGGACC<br>UAGUGGGCGUGCUGCAUGACCCUGAAACCCUGCUCAGGUGCAUCGCCGAGAGGGCCUUCCUGCGGCACCU<br>GGAGGGCGGCUGCAGCGUGCCGGUGGCCGUCCACACCGCCAUGAAGGACGGCCAGCUGUACCUGACCGGC<br>GGCGUCUGGAGCCUGGACGGAUCCGACAGCAUCCAGGAAACCAUGCAGGCCACCAUCCACGUGCCGGCCC<br>AGCACGAGGACGCCCUGAGGACGACCCUCAGCUGGUGGGCAUCACCGCUAGGAACAUCCAAGGGGCCC<br>GCAGCUGGCCGCCCAGAACCUCGGCAUCAGCCUGGCCAACCUGCUGCUGUCCAAGGGCGCCAAGAAUAUC<br>CUGGACGUGGCCAGGCAGCUGAACGACGCCCAC |

The sequence optimized nucleotide sequences disclosed herein are distinct from the corresponding wild type nucleotide acid sequences and from other known sequence optimized nucleotide sequences, e.g., these sequence optimized nucleic acids have unique compositional characteristics.

In some embodiments, the percentage of uracil or thymine nucleobases in a sequence optimized nucleotide sequence (e.g., encoding a PBGD polypeptide, a functional fragment, or a variant thereof) is modified (e.g., reduced) with respect to the percentage of uracil or thymine nucleobases in the reference wild-type nucleotide sequence. Such a sequence is referred to as a uracil-modified or thymine-modified sequence. The percentage of uracil or thymine content in a nucleotide sequence can be determined by dividing the number of uracils or thymines in a sequence by the total number of nucleotides and multiplying by 100. In some embodiments, the sequence optimized nucleotide sequence has a lower uracil or thymine content than the uracil or thymine content in the reference wild-type sequence. In some embodiments, the uracil or thymine content in a sequence-optimized nucleotide sequence of the invention is greater than the uracil or thymine content in the reference wild-type sequence and still maintain beneficial effects, e.g., increased expression and/or reduced Toll-Like Receptor (TLR) response when compared to the reference wild-type sequence.

The uracil or thymine content of wild-type PBGD isoform 1 is about 20%. In some embodiments, the uracil or thymine content of a uracil- or thymine-modified sequence encoding a PBGD polypeptide is less than 20%. In some embodiments, the uracil or thymine content of a uracil- or thymine-modified sequence encoding a PBGD polypeptide of the invention is less than 19%, less that 18%, less than 17%, less than 16%, less than 15%, less than 14%, less than 13%, less than 12%, less than 11%, or less than 10%. In some embodiments, the uracil or thymine content is not less than 18%, 17%, 16%, 15%, 14%, 13%, 12%, 11%, or 10%. The uracil or thymine content of a sequence disclosed herein, i.e., its total uracil or thymine content is abbreviated herein as % $U_{TL}$ or % $T_{TL}$.

A uracil- or thymine-modified sequence encoding a PBGD polypeptide of the invention can also be described according to its uracil or thymine content relative to the uracil or thymine content in the corresponding wild-type nucleic acid sequence (% $U_{WT}$ or % $T_{WT}$), or according to its uracil or thymine content relative to the theoretical minimum uracil or thymine content of a nucleic acid encoding the wild-type protein sequence (% $U_{TM}$ or (% $T_{TM}$).

The phrases "uracil or thymine content relative to the uracil or thymine content in the wild type nucleic acid sequence," refers to a parameter determined by dividing the number of uracils or thymines in a sequence-optimized nucleic acid by the total number of uracils or thymines in the corresponding wild-type nucleic acid sequence and multiplying by 100. This parameter is abbreviated herein as % $U_{WT}$ or % $T_{WT}$.

In some embodiments, the % $U_{WT}$ or % $T_{WT}$ of a uracil- or thymine-modified sequence encoding a PBGD polypeptide of the invention is above 50%, above 55%, above 60%, above 65%, above 70%, above 75%, above 80%, above 85%, above 90%, or above 95%.

Uracil- or thymine-content relative to the uracil or thymine theoretical minimum, refers to a parameter determined by dividing the number of uracils or thymines in a sequence-optimized nucleotide sequence by the total number of uracils or thymines in a hypothetical nucleotide sequence in which all the codons in the hypothetical sequence are replaced with synonymous codons having the lowest possible uracil or thymine content and multiplying by 100. This parameter is abbreviated herein as % $U_{TM}$ or % $T_{TM}$.

For DNA it is recognized that thymine is present instead of uracil, and one would substitute T where U appears. Thus, all the disclosures related to, e.g., % $U_{TM}$, % $U_{WT}$, or % $U_{TL}$, with respect to RNA are equally applicable to % $T_{TM}$, % $T_{WT}$, or % $T_{TL}$ with respect to DNA.

In some embodiments, the % $U_{TM}$ of a uracil-modified sequence encoding a PBGD polypeptide of the invention is between about 118% and about 132%.

In some embodiments, a uracil-modified sequence encoding a PBGD polypeptide of the invention has a reduced number of consecutive uracils with respect to the corresponding wild-type nucleic acid sequence. For example, two consecutive leucines can be encoded by the sequence CUUUUG, which includes a four uracil cluster. Such a subsequence can be substituted, e.g., with CUGCUC, which removes the uracil cluster.

Phenylalanine can be encoded by UUC or UUU. Thus, even if phenylalanines encoded by UUU are replaced by UUC, the synonymous codon still contains a uracil pair (UU). Accordingly, the number of phenylalanines in a sequence establishes a minimum number of uracil pairs (UU) that cannot be eliminated without altering the number of phenylalanines in the encoded polypeptide. For example, if the polypeptide (e.g., wild type PBGD isoform 1) has, e.g., 7, 8, or 9 phenylalanines, the absolute minimum number of uracil pairs (UU) in that a uracil-modified sequence encoding the polypeptide (e.g., wild type PBGD isoform 1) can contain is 7, 8, or 9, respectively.

Wild type PBGD isoform 1 contains 32 uracil pairs (UU), and four uracil triplets (UUU). In some embodiments, a uracil-modified sequence encoding a PBGD polypeptide of the invention has a reduced number of uracil triplets (UUU) with respect to the wild-type nucleic acid sequence. In some embodiments, a uracil-modified sequence encoding a PBGD polypeptide of the invention contains 4, 3, 2, 1 or no uracil triplets (UUU).

In some embodiments, a uracil-modified sequence encoding a PBGD polypeptide has a reduced number of uracil pairs (UU) with respect to the number of uracil pairs (UU) in the wild-type nucleic acid sequence. In some embodiments, a uracil-modified sequence encoding a PBGD polypeptide of the invention has a number of uracil pairs (UU) corresponding to the minimum possible number of uracil pairs (UU) in the wild-type nucleic acid sequence, e.g., 9 uracil pairs in the case of wild type PBGD isoform 1.

In some embodiments, a uracil-modified sequence encoding a PBGD polypeptide of the invention has at least 1, 2, 3, 4, 5, 6, 7, 8, 9, 10, 11, 12, 13, 14, 15, 16, 17, 18, 19, 20, 21, 22, or 24 uracil pairs (UU) less than the number of uracil pairs (UU) in the wild-type nucleic acid sequence. In some embodiments, a uracil-modified sequence encoding a PBGD polypeptide of the invention has between 8 and 16 uracil pairs (UU).

The phrase "uracil pairs (UU) relative to the uracil pairs (UU) in the wild type nucleic acid sequence," refers to a parameter determined by dividing the number of uracil pairs (UU) in a sequence-optimized nucleotide sequence by the total number of uracil pairs (UU) in the corresponding wild-type nucleotide sequence and multiplying by 100. This parameter is abbreviated herein as % $UU_{wt}$.

In some embodiments, a uracil-modified sequence encoding a PBGD polypeptide of the invention has a % $UU_{wt}$ less than 90%, less than 85%, less than 80%, less than 75%, less than 70%, less than 65%, less than 60%, less than 65%, less than 60%, less than 55%, less than 50%, less than 40%, less than 30%, or less than 20%.

In some embodiments, a uracil-modified sequence encoding a PBGD polypeptide has a % $UU_{wt}$ between 20% and 55%. In a particular embodiment, a uracil-modified sequence encoding a PBGD polypeptide of the invention has a % $UU_{wt}$ between 25% and 55%.

In some embodiments, the polynucleotide of the invention comprises a uracil-modified sequence encoding a PBGD polypeptide disclosed herein. In some embodiments, the uracil-modified sequence encoding a PBGD polypeptide comprises at least one chemically modified nucleobase, e.g., 5-methoxyuracil. In some embodiments, at least 95% of a nucleobase (e.g., uracil) in a uracil-modified sequence encoding a PBGD polypeptide of the invention are modified nucleobases. In some embodiments, at least 95% of uracil in a uracil-modified sequence encoding a PBGD polypeptide is 5-methoxyuracil. In some embodiments, the polynucleotide comprising a uracil-modified sequence further comprises a miRNA binding site, e.g., a miRNA binding site that binds to miR-142 and/or a miRNA binding site that binds to miR-126. In some embodiments, the polynucleotide (e.g., a RNA, e.g., an mRNA) comprising a uracil-modified sequence disclosed herein is formulated with a delivery agent comprising, e.g., a compound having the Formula (I), e.g., any of Compounds 1-232, e.g., Compound 18; a compound having the Formula (III), (IV), (V), or (VI), e.g., any of Compounds 233-342, e.g., Compound 236; or a compound having the Formula (VIII), e.g., any of Compounds 419-428, e.g., Compound 428, or any combination thereof. In some embodiments, the delivery agent comprises Compound 18, DSPC, Cholesterol, and Compound 428, e.g., with a mole ratio of about 50:10:38.5:1.5.

In some embodiments, the "guanine content of the sequence optimized ORF encoding PBGD with respect to the theoretical maximum guanine content of a nucleotide sequence encoding the PBGD polypeptide," abbreviated as % $G_{TMX}$ is at least 69%, at least 70%, at least 75%, at least about 80%, at least about 85%, at least about 90%, at least about 95%, or about 100%. In some embodiments, the % $G_{TMX}$ is between about 70% and about 80%, between about 71% and about 79%, between about 71% and about 78%, or between about 71% and about 77%.

In some embodiments, the "cytosine content of the ORF relative to the theoretical maximum cytosine content of a nucleotide sequence encoding the PBGD polypeptide," abbreviated as % $C_{TMX}$, is at least 59%, at least 60%, at least about 65%, at least about 70%, at least about 75%, at least about 80%, at least about 85%, at least about 90%, at least about 95%, or about 100%. In some embodiments, the % $C_{TMX}$ is between about 60% and about 80%, between about 62% and about 80%, between about 63% and about 79%, or between about 68% and about 76%.

In some embodiments, the "guanine and cytosine content (G/C) of the ORF relative to the theoretical maximum G/C content in a nucleotide sequence encoding the PBGD polypeptide," abbreviated as % $G/C_{TMX}$ is at least about 81%, at least about 85%, at least about 90%, at least about 95%, or about 100%. The % $G/C_{TMX}$ is between about 80% and about 100%, between about 85% and about 99%, between about 90% and about 97%, or between about 91% and about 96%.

In some embodiments, the "G/C content in the ORF relative to the G/C content in the corresponding wild-type ORF," abbreviated as % $G/C_{WT}$ is at least 102%, at least 103%, at least 104%, at least 105%, at least 106%, at least 107%, at least 110%, at least 115%, or at least 120%.

In some embodiments, the average G/C content in the 3rd codon position in the ORF is at least 20%, at least 21%, at least 22%, at least 23%, at least 24%, at least 25%, at least 26%, at least 27%, at least 28%, at least 29%, or at least 30% higher than the average G/C content in the 3rd codon position in the corresponding wild-type ORF.

In some embodiments, the polynucleotide of the invention comprises an open reading frame (ORF) encoding a PBGD polypeptide, wherein the ORF has been sequence optimized, and wherein each of % $U_{TL}$, % $U_{WT}$, % $U_{TM}$, % $G_{TL}$, % $G_{WT}$, % $G_{TMX}$, % $C_{TL}$, % $C_{WT}$, % $C_{TMX}$, % $G/C_{TL}$, % $G/C_{WT}$, or % $G/C_{TMX}$, alone or in a combination thereof is in a range between (i) a maximum corresponding to the parameter's maximum value (MAX) plus about 0.5, 1, 1.5, 2, 2.5, 3, 3.5, 4, 4.5, 5, 5.5, 6, 6.5, 7, 7.5, 8, 8.5, 9, 9.5, or 10 standard deviations (STD DEV), and (ii) a minimum corresponding to the parameter's minimum value (MIN) less 0.5, 1, 1.5, 2, 2.5, 3, 3.5, 4, 4.5, 5, 5.5, 6, 6.5, 7, 7.5, 8, 8.5, 9, 9.5, or 10 standard deviations (STD DEV).

7. METHODS FOR SEQUENCE OPTIMIZATION

In some embodiments, a polynucleotide, e.g., mRNA, of the invention (e.g., a polynucleotide comprising a nucleotide sequence encoding a PBGD polypeptide, e.g., the wild-type sequence, functional fragment, or variant thereof) is sequence optimized. A sequence optimized nucleotide sequence (nucleotide sequence is also referred to as "nucleic acid" herein) comprises at least one codon modification with respect to a reference sequence (e.g., a wild-type sequence encoding a PBGD polypeptide). Thus, in a sequence optimized nucleic acid, at least one codon is different from a corresponding codon in a reference sequence (e.g., a wild-type sequence).

In general, sequence optimized nucleic acids are generated by at least a step comprising substituting codons in a reference sequence with synonymous codons (i.e., codons that encode the same amino acid). Such substitutions can be effected, for example, by applying a codon substitution map (i.e., a table providing the codons that will encode each amino acid in the codon optimized sequence), or by applying a set of rules (e.g., if glycine is next to neutral amino acid, glycine would be encoded by a certain codon, but if it is next to a polar amino acid, it would be encoded by another codon). In addition to codon substitutions (i.e., "codon optimization") the sequence optimization methods disclosed herein comprise additional optimization steps which are not strictly directed to codon optimization such as the removal of deleterious motifs (destabilizing motif substitution). Compositions and formulations comprising these sequence optimized nucleic acids (e.g., a RNA, e.g., an mRNA) can be administered to a subject in need thereof to facilitate in vivo expression of functionally active PBGD.

The recombinant expression of large molecules in cell cultures can be a challenging task with numerous limitations (e.g., poor protein expression levels, stalled translation resulting in truncated expression products, protein misfolding, etc.). These limitations can be reduced or avoided by administering the polynucleotides (e.g., a RNA, e.g., an mRNA), which encode a functionally active PBGD or compositions or formulations comprising the same to a patient suffering from AIP, so the synthesis and delivery of the PBGD polypeptide to treat AIP takes place endogenously.

Changing from an in vitro expression system (e.g., cell culture) to in vivo expression requires the redesign of the nucleic acid sequence encoding the therapeutic agent. Redesigning a naturally occurring gene sequence by choosing different codons without necessarily altering the encoded amino acid sequence can often lead to dramatic increases in protein expression levels (Gustafsson et al., 2004, Trends Biotechnol 22:346-53). Variables such as codon adaptation index (CAI), mRNA secondary structures, cis-regulatory sequences, GC content and many other similar variables have been shown to somewhat correlate with protein expression levels (Villalobos et al., 2006, BMC Bioinformatics 7:285). However, due to the degeneracy of the genetic code, there are numerous different nucleic acid sequences that can all encode the same therapeutic agent. Each amino acid is encoded by up to six synonymous codons; and the choice between these codons influences gene expression. In addition, codon usage (i.e., the frequency with which different organisms use codons for expressing a polypeptide sequence) differs among organisms (for example, recombinant production of human or humanized therapeutic antibodies frequently takes place in hamster cell cultures).

In some embodiments, a reference nucleic acid sequence can be sequence optimized by applying a codon map. The skilled artisan will appreciate that T bases are present in DNA, whereas the T bases would be replaced by U bases in corresponding RNAs. For example, a sequence optimized nucleic acid disclosed herein in DNA form, e.g., a vector or an in-vitro translation (IVT) template, would have its T bases transcribed as U based in its corresponding transcribed mRNA. In this respect, both sequence optimized DNA sequences (comprising T) and their corresponding RNA sequences (comprising U) are considered sequence optimized nucleic acid of the present invention. A skilled artisan would also understand that equivalent codon-maps can be generated by replaced one or more bases with non-natural bases. Thus, e.g., a TTC codon (DNA map) would correspond to a UUC codon (RNA map), which in turn can correspond to a ΨΨC codon (RNA map in which U has been replaced with pseudouridine).

In one embodiment, a reference sequence encoding PBGD can be optimized by replacing all the codons encoding a certain amino acid with only one of the alternative codons provided in a codon map. For example, all the valines in the optimized sequence would be encoded by GTG or GTC or GTT.

Sequence optimized polynucleotides of the invention can be generated using one or more optimization methods, or a combination thereof. Sequence optimization methods which can be used to sequence optimize nucleic acid sequences are described in detail herein. This list of methods is not comprehensive or limiting.

It will be appreciated that the design principles and rules described for each one of the sequence optimization methods discussed below can be combined in many different ways, for example high G/C content sequence optimization for some regions or uridine content sequence optimization for other regions of the reference nucleic acid sequence, as well as targeted nucleotide mutations to minimize secondary structure throughout the sequence or to eliminate deleterious motifs.

The choice of potential combinations of sequence optimization methods can be, for example, dependent on the specific chemistry used to produce a synthetic polynucleotide. Such a choice can also depend on characteristics of the protein encoded by the sequence optimized nucleic acid, e.g., a full sequence, a functional fragment, or a fusion protein comprising PBGD, etc. In some embodiments, such a choice can depend on the specific tissue or cell targeted by the sequence optimized nucleic acid (e.g., a therapeutic synthetic mRNA).

The mechanisms of combining the sequence optimization methods or design rules derived from the application and analysis of the optimization methods can be either simple or complex. For example, the combination can be:
(i) Sequential: Each sequence optimization method or set of design rules applies to a different subsequence of the overall sequence, for example reducing uridine at codon positions 1 to 30 and then selecting high frequency codons for the remainder of the sequence.
(ii) Hierarchical: Several sequence optimization methods or sets of design rules are combined in a hierarchical, deterministic fashion. For example, use the most GC-rich codons, breaking ties (which are common) by choosing the most frequent of those codons.
(iii) Multifactorial/Multiparametric: Machine learning or other modeling techniques are used to design a single sequence that best satisfies multiple overlapping and possibly contradictory requirements. This approach would require the use of a computer applying a number of mathematical techniques, for example, genetic algorithms.

Ultimately, each one of these approaches can result in a specific set of rules which in many cases can be summarized in a single codon table, i.e., a sorted list of codons for each amino acid in the target protein (i.e., PBGD), with a specific rule or set of rules indicating how to select a specific codon for each amino acid position.

a. Uridine Content Optimization

The presence of local high concentrations of uridine in a nucleic acid sequence can have detrimental effects on translation, e.g., slow or prematurely terminated translation, especially when modified uridine analogs are used in the production of synthetic mRNAs. Furthermore, high uridine content can also reduce the in vivo half-life of synthetic mRNAs due to TLR activation.

Accordingly, a nucleic acid sequence can be sequence optimized using a method comprising at least one uridine content optimization step. Such a step comprises, e.g., substituting at least one codon in the reference nucleic acid with an alternative codon to generate a uridine-modified sequence, wherein the uridine-modified sequence has at least one of the following properties:
(i) increase or decrease in global uridine content;
(ii) increase or decrease in local uridine content (i.e., changes in uridine content are limited to specific subsequences);
(iii) changes in uridine distribution without altering the global uridine content;
(iv) changes in uridine clustering (e.g., number of clusters, location of clusters, or distance between clusters); or
(v) combinations thereof.

In some embodiments, the sequence optimization process comprises optimizing the global uridine content, i.e., optimizing the percentage of uridine nucleobases in the sequence optimized nucleic acid with respect to the percentage of uridine nucleobases in the reference nucleic acid sequence. For example, 30% of nucleobases can be uridines in the reference sequence and 10% of nucleobases can be uridines in the sequence optimized nucleic acid.

In other embodiments, the sequence optimization process comprises reducing the local uridine content in specific regions of a reference nucleic acid sequence, i.e., reducing the percentage of uridine nucleobases in a subsequence of the sequence optimized nucleic acid with respect to the percentage of uridine nucleobases in the corresponding subsequence of the reference nucleic acid sequence. For example, the reference nucleic acid sequence can have a 5'-end region (e.g., 30 codons) with a local uridine content of 30%, and the uridine content in that same region could be reduced to 10% in the sequence optimized nucleic acid.

In specific embodiments, codons can be replaced in the reference nucleic acid sequence to reduce or modify, for example, the number, size, location, or distribution of uridine clusters that could have deleterious effects on protein translation. Although as a general rule it is desirable to reduce the uridine content of the reference nucleic acid sequence, in certain embodiments the uridine content, and in particular the local uridine content, of some subsequences of the reference nucleic acid sequence can be increased.

The reduction of uridine content to avoid adverse effects on translation can be done in combination with other optimization methods disclosed here to achieve other design goals. For example, uridine content optimization can be combined with ramp design, since using the rarest codons for most amino acids will, with a few exceptions, reduce the U content.

In some embodiments, the uridine-modified sequence is designed to induce a lower Toll-Like Receptor (TLR) response when compared to the reference nucleic acid sequence. Several TLRs recognize and respond to nucleic acids. Double-stranded (ds)RNA, a frequent viral constituent, has been shown to activate TLR3. See Alexopoulou et al. (2001) Nature, 413:732-738 and Wang et al. (2004) Nat. Med., 10:1366-1373. Single-stranded (ss)RNA activates TLR7. See Diebold et al. (2004) Science 303:1529-1531. RNA oligonucleotides, for example RNA with phosphorothioate internucleotide linkages, are ligands of human TLR8. See Heil et al. (2004) Science 303:1526-1529. DNA containing unmethylated CpG motifs, characteristic of bacterial and viral DNA, activate TLR9. See Hemmi et al. (2000) Nature, 408: 740-745.

As used herein, the term "TLR response" is defined as the recognition of single-stranded RNA by a TLR7 receptor, and in some embodiments encompasses the degradation of the RNA and/or physiological responses caused by the recognition of the single-stranded RNA by the receptor. Methods to determine and quantitate the binding of an RNA to a TLR7 are known in the art. Similarly, methods to determine whether an RNA has triggered a TLR7-mediated physiological response (e.g., cytokine secretion) are well known in the art. In some embodiments, a TLR response can be mediated by TLR3, TLR8, or TLR9 instead of TLR7.

Suppression of TLR7-mediated response can be accomplished via nucleoside modification. RNA undergoes over hundred different nucleoside modifications in nature (see the RNA Modification Database, available at mods.rna.albany.edu). Human rRNA, for example, has ten times more pseudouridine (Ψ) and 25 times more 2'-O-methylated nucleosides than bacterial rRNA. Bacterial mRNA contains no nucleoside modifications, whereas mammalian mRNAs have modified nucleosides such as 5-methylcytidine (m5C), N6-methyladenosine (m6A), inosine and many 2'-O-methylated nucleosides in addition to N7-methylguanosine (m7G).

Uracil and ribose, the two defining features of RNA, are both necessary and sufficient for TLR7 stimulation, and short single-stranded RNA (ssRNA) act as TLR7 agonists in a sequence-independent manner as long as they contain several uridines in close proximity. See Diebold et al. (2006) Eur. J. Immunol. 36:3256-3267, which is herein incorporated by reference in its entirety. Accordingly, one or more of the optimization methods disclosed herein comprises reducing the uridine content (locally and/or globally) and/or reducing or modifying uridine clustering to reduce or to suppress a TLR7-mediated response.

In some embodiments, the TLR response (e.g., a response mediated by TLR7) caused by the uridine-modified sequence is at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or at least about 100% lower than the TLR response caused by the reference nucleic acid sequence.

In some embodiments, the TLR response caused by the reference nucleic acid sequence is at least about 1-fold, at least about 1.1-fold, at least about 1.2-fold, at least about 1.3-fold, at least about 1.4-fold, at least about 1.5-fold, at least about 1.6-fold, at least about 1.7-fold, at least about 1.8-fold, at least about 1.9-fold, at least about 2-fold, at least about 3-fold, at least about 4-fold, at least about 5-fold, at least about 6-fold, at least about 7-fold, at least about 8-fold, at least about 9-fold, or at least about 10-fold higher than the TLR response caused by the uridine-modified sequence.

In some embodiments, the uridine content (average global uridine content) (absolute or relative) of the uridine-modified sequence is higher than the uridine content (absolute or relative) of the reference nucleic acid sequence. Accordingly, in some embodiments, the uridine-modified sequence contains at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or at least about 100% more uridine that the reference nucleic acid sequence.

In other embodiments, the uridine content (average global uridine content) (absolute or relative) of the uridine-modified sequence is lower than the uridine content (absolute or relative) of the reference nucleic acid sequence. Accordingly, in some embodiments, the uridine-modified sequence contains at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or at least about 100% less uridine that the reference nucleic acid sequence.

In some embodiments, the uridine content (average global uridine content) (absolute or relative) of the uridine-modified sequence is less than 50%, 49%, 48%, 47%, 46%, 45%, 44%, 43%, 42%, 41%, 40%, 39%, 38%, 37%, 36%, 35%, 34%, 33%, 32%, 31%, 30%, 29%, 28%, 27%, 26%, 25%, 24%, 23%, 22%, 21%, 20%, 19%, 18%, 17%, 16%, 15%, 14%, 13%, 12%, 11%, 10%, 9%, 8%, 7%, 6%, 5%, 4%, 3%, 2% or 1% of the total nucleobases in the uridine-modified sequence. In some embodiments, the uridine content of the uridine-modified sequence is between about 10% and about 20%. In some particular embodiments, the uridine content of the uridine-modified sequence is between about 12% and about 16%.

In some embodiments, the uridine content of the reference nucleic acid sequence can be measured using a sliding window. In some embodiments, the length of the sliding window is 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 nucleobases. In some embodiments, the sliding window is over 40 nucleobases in length. In some embodiments, the sliding window is 20 nucleobases in length. Based on the uridine content measured with a sliding window, it is possible to generate a histogram representing the uridine content throughout the length of the reference nucleic acid sequence and sequence optimized nucleic acids.

In some embodiments, a reference nucleic acid sequence can be modified to reduce or eliminate peaks in the histogram that are above or below a certain percentage value. In some embodiments, the reference nucleic acid sequence can be modified to eliminate peaks in the sliding-window representation which are above 65%, 60%, 55%, 50%, 45%, 40%, 35%, or 30% uridine. In another embodiment, the reference nucleic acid sequence can be modified so no peaks are over 30% uridine in the sequence optimized nucleic acid, as measured using a 20 nucleobase sliding window. In some embodiments, the reference nucleic acid sequence can be modified so no more or no less than a predetermined number of peaks in the sequence optimized nucleic sequence, as measured using a 20 nucleobase sliding window, are above or below a certain threshold value. For example, in some embodiments, the reference nucleic acid sequence can be modified so no peaks or no more than 1, 2, 3, 4, 5, 6, 7, 8, 9 or 10 peaks in the sequence optimized nucleic acid are above 10%, 15%, 20%, 25% or 30% uridine. In another embodiment, the sequence optimized nucleic acid contains between 0 peaks and 2 peaks with uridine contents 30% of higher.

In some embodiments, a reference nucleic acid sequence can be sequence optimized to reduce the incidence of consecutive uridines. For example, two consecutive leucines could be encoded by the sequence CUUUUG, which would include a four uridine cluster. Such subsequence could be substituted with CUGCUC, which would effectively remove the uridine cluster. Accordingly, a reference nucleic sequence can be sequence optimized by reducing or eliminating uridine pairs (UU), uridine triplets (UUU) or uridine quadruplets (UUUU). Higher order combinations of U are not considered combinations of lower order combinations. Thus, for example, UUUU is strictly considered a quadruplet, not two consecutive U pairs; or UUUUUU is considered a sextuplet, not three consecutive U pairs, or two consecutive U triplets, etc.

In some embodiments, all uridine pairs (UU) and/or uridine triplets (UUU) and/or uridine quadruplets (UUUU) can be removed from the reference nucleic acid sequence. In other embodiments, uridine pairs (UU) and/or uridine triplets (UUU) and/or uridine quadruplets (UUUU) can be reduced below a certain threshold, e.g., no more than 1, 2, 3, 4, 5, 6, 7, 8, 9, 10, 11, 12, 13, 14, 15, 16, 17, 18, 19, or 20 occurrences in the sequence optimized nucleic acid. In a particular embodiment, the sequence optimized nucleic acid contains less than 20, 19, 18, 17, 16, 15, 14, 13, 12, 11, 10, 9, 8, 7, 6, 5, 4, 3, 2, or 1 uridine pairs. In another particular embodiment, the sequence optimized nucleic acid contains no uridine pairs and/or triplets.

Phenylalanine codons, i.e., UUC or UUU, comprise a uridine pair or triplet and therefore sequence optimization to reduce uridine content can at most reduce the phenylalanine U triplet to a phenylalanine U pair. In some embodiments, the occurrence of uridine pairs (UU) and/or uridine triplets (UUU) refers only to non-phenylalanine U pairs or triplets. Accordingly, in some embodiments, non-phenylalanine uridine pairs (UU) and/or uridine triplets (UUU) can be reduced below a certain threshold, e.g., no more than 1, 2, 3, 4, 5, 6, 7, 8, 9, 10, 11, 12, 13, 14, 15, 16, 17, 18, 19, or 20 occurrences in the sequence optimized nucleic acid. In a particular embodiment, the sequence optimized nucleic acid contains less than 20, 19, 18, 17, 16, 15, 14, 13, 12, 11, 10, 9, 8, 7, 6, 5, 4, 3, 2, or 1 non-phenylalanine uridine pairs and/or triplets. In another particular embodiment, the sequence optimized nucleic acid contains no non-phenylalanine uridine pairs and/or triplets.

In some embodiments, the reduction in uridine combinations (e.g., pairs, triplets, quadruplets) in the sequence optimized nucleic acid can be expressed as a percentage reduction with respect to the uridine combinations present in the reference nucleic acid sequence.

In some embodiments, a sequence optimized nucleic acid can contain about 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, or 65% of the total number of uridine pairs present in the reference nucleic acid sequence. In some embodiments, a sequence optimized nucleic acid can contain about 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, or 65% of the total number of uridine triplets present in the reference nucleic acid sequence. In some embodiments, a sequence optimized nucleic acid can contain about 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, or 65% of the total number of uridine quadruplets present in the reference nucleic acid sequence.

In some embodiments, a sequence optimized nucleic acid can contain about 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, or 65% of the total number of non-phenylalanine uridine pairs present in the reference nucleic acid sequence. In some embodiments, a sequence optimized nucleic acid can contain about 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, or 65% of the total number of non-phenylalanine uridine triplets present in the reference nucleic acid sequence.

In some embodiments, the uridine content in the sequence optimized sequence can be expressed with respect to the theoretical minimum uridine content in the sequence. The term "theoretical minimum uridine content" is defined as the uridine content of a nucleic acid sequence as a percentage of the sequence's length after all the codons in the sequence have been replaced with synonymous codon with the lowest uridine content. In some embodiments, the uridine content of the sequence optimized nucleic acid is identical to the theoretical minimum uridine content of the reference sequence (e.g., a wild type sequence). In some aspects, the uridine content of the sequence optimized nucleic acid is about 100%, about 105%, about 110%, about 115%, about 120%, about 125%, about 130%, about 135%, about 140%, about 145%, about 150%, about 155%, about 160%, about 165%, about 170%, about 175%, about 180%, about 185%, about 190%, about 195%, about 200%, about 210%, about 220%, about 230%, about 240% or about 250% of the theoretical minimum uridine content of the reference sequence (e.g., a wild type sequence).

In some embodiments, the uridine content of the sequence optimized nucleic acid is identical to the theoretical minimum uridine content of the reference sequence (e.g., a wild type sequence).

The reference nucleic acid sequence (e.g., a wild type sequence) can comprise uridine clusters which due to their number, size, location, distribution or combinations thereof have negative effects on translation. As used herein, the term "uridine cluster" refers to a subsequence in a reference nucleic acid sequence or sequence optimized nucleic sequence with contains a uridine content (usually described as a percentage) which is above a certain threshold. Thus, in certain embodiments, if a subsequence comprises more than about 10%, 15%, 20%, 25%, 30%, 35%, 40%, 45%, 50%, 55%, 60% or 65% uridine content, such subsequence would be considered a uridine cluster.

The negative effects of uridine clusters can be, for example, eliciting a TLR7 response. Thus, in some implementations of the nucleic acid sequence optimization methods disclosed herein it is desirable to reduce the number of clusters, size of clusters, location of clusters (e.g., close to the 5' and/or 3' end of a nucleic acid sequence), distance between clusters, or distribution of uridine clusters (e.g., a certain pattern of cluster along a nucleic acid sequence, distribution of clusters with respect to secondary structure elements in the expressed product, or distribution of clusters with respect to the secondary structure of an mRNA).

In some embodiments, the reference nucleic acid sequence comprises at least one uridine cluster, wherein said uridine cluster is a subsequence of the reference nucleic acid sequence wherein the percentage of total uridine nucleobases in said subsequence is above a predetermined threshold. In some embodiments, the length of the subsequence is at least about 10, at least about 15, at least about 20, at least about 25, at least about 30, at least about 35, at least about 40, at least about 45, at least about 50, at least about 55, at least about 60, at least about 65, at least about 70, at least about 75, at least about 80, at least about 85, at least about 90, at least about 95, or at least about 100 nucleobases. In some embodiments, the subsequence is longer than 100 nucleobases. In some embodiments, the threshold is 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24% or 25% uridine content. In some embodiments, the threshold is above 25%.

For example, an amino acid sequence comprising A, D, G, S and R could be encoded by the nucleic acid sequence GCU, GAU, GGU, AGU, CGU. Although such sequence does not contain any uridine pairs, triplets, or quadruplets, one third of the nucleobases would be uridines. Such a uridine cluster could be removed by using alternative codons, for example, by using GCC, GAC, GGC, AGC, and CGC, which would contain no uridines.

In other embodiments, the reference nucleic acid sequence comprises at least one uridine cluster, wherein said uridine cluster is a subsequence of the reference nucleic acid sequence wherein the percentage of uridine nucleobases of said subsequence as measured using a sliding window that is above a predetermined threshold. In some embodiments, the length of the sliding window is 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 nucleobases. In some embodiments, the sliding window is over 40 nucleobases in length. In some embodiments, the threshold is 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24% or 25% uridine content. In some embodiments, the threshold is above 25%.

In some embodiments, the reference nucleic acid sequence comprises at least two uridine clusters. In some embodiments, the uridine-modified sequence contains fewer uridine-rich clusters than the reference nucleic acid sequence. In some embodiments, the uridine-modified sequence contains more uridine-rich clusters than the reference nucleic acid sequence. In some embodiments, the uridine-modified sequence contains uridine-rich clusters with are shorter in length than corresponding uridine-rich clusters in the reference nucleic acid sequence. In other embodiments, the uridine-modified sequence contains uridine-rich clusters which are longer in length than the corresponding uridine-rich cluster in the reference nucleic acid sequence.

See, Kariko et al. (2005) *Immunity* 23:165-175; Kormann et al. (2010) *Nature Biotechnology* 29:154-157; or Sahin et al. (2014) *Nature Reviews Drug Discovery | AOP*, published online 19 Sep. 2014m doi:10.1038/nrd4278; all of which are herein incorporated by reference their entireties.

b. Guanine/Cytosine (G/C) Content

A reference nucleic acid sequence can be sequence optimized using methods comprising altering the Guanine/Cytosine (G/C) content (absolute or relative) of the reference nucleic acid sequence. Such optimization can comprise altering (e.g., increasing or decreasing) the global G/C content (absolute or relative) of the reference nucleic acid sequence; introducing local changes in G/C content in the reference nucleic acid sequence (e.g., increase or decrease G/C in selected regions or subsequences in the reference nucleic acid sequence); altering the frequency, size, and distribution of G/C clusters in the reference nucleic acid sequence, or combinations thereof.

In some embodiments, the sequence optimized nucleic acid encoding PBGD comprises an overall increase in G/C content (absolute or relative) relative to the G/C content (absolute or relative) of the reference nucleic acid sequence. In some embodiments, the overall increase in G/C content (absolute or relative) is at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or at least about 100% relative to the G/C content (absolute or relative) of the reference nucleic acid sequence.

In some embodiments, the sequence optimized nucleic acid encoding PBGD comprises an overall decrease in G/C content (absolute or relative) relative to the G/C content of the reference nucleic acid sequence. In some embodiments, the overall decrease in G/C content (absolute or relative) is at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or at least about 100% relative to the G/C content (absolute or relative) of the reference nucleic acid sequence.

In some embodiments, the sequence optimized nucleic acid encoding PBGD comprises a local increase in Guanine/Cytosine (G/C) content (absolute or relative) in a subsequence (i.e., a G/C modified subsequence) relative to the G/C content (absolute or relative) of the corresponding subsequence in the reference nucleic acid sequence. In some embodiments, the local increase in G/C content (absolute or relative) is by at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or at least about 100% relative to the G/C content (absolute or relative) of the corresponding subsequence in the reference nucleic acid sequence.

In some embodiments, the sequence optimized nucleic acid encoding PBGD comprises a local decrease in Guanine/Cytosine (G/C) content (absolute or relative) in a subsequence (i.e., a G/C modified subsequence) relative to the G/C content (absolute or relative) of the corresponding subsequence in the reference nucleic acid sequence. In some embodiments, the local decrease in G/C content (absolute or relative) is by at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or at least about 100% relative to the G/C content (absolute or relative) of the corresponding subsequence in the reference nucleic acid sequence.

In some embodiments, the G/C content (absolute or relative) is increased or decreased in a subsequence which is at least about 5, 10, 15, 20, 25, 30, 35, 40, 45, 50, 55, 60, 65, 70, 75, 80, 85, 90, 95, or 100 nucleobases in length.

In some embodiments, the G/C content (absolute or relative) is increased or decreased in a subsequence which is at least about 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, or 1000 nucleobases in length.

In some embodiments, the G/C content (absolute or relative) is increased or decreased in a subsequence which is at least about 1100, 1200, 1300, 1400, 1500, 1600, 1700, 1800, 1900, 2000, 2100, 2200, 2300, 2400, 2500, 2600, 2700, 2800, 2900, 3000, 3100, 3200, 3300, 3400, 3500, 3600, 3700, 3800, 3900, 4000, 4100, 4200, 4300, 4400, 4500, 4600, 4700, 4800, 4900, 5000, 5100, 5200, 5300, 5400, 5500, 5600, 5700, 5800, 5900, 6000, 6100, 6200, 6300, 6400, 6500, 6600, 6700, 6800, 6900, 7000, 7100, 7200, 7300, 7400, 7500, 7600, 7700, 7800, 7900, 8000, 8100, 8200, 8300, 8400, 8500, 8600, 8700, 8800, 8900, 9000, 9100, 9200, 9300, 9400, 9500, 9600, 9700, 9800, 9900, or 10000 nucleobases in length.

The increases or decreases in G and C content (absolute or relative) described herein can be conducted by replacing synonymous codons with low G/C content with synonymous codons having higher G/C content, or vice versa. For example, L has 6 synonymous codons: two of them have 2 G/C (CUC, CUG), 3 have a single G/C (UUG, CUU, CUA), and one has no G/C (UUA). So if the reference nucleic acid had a CUC codon in a certain position, G/C content at that position could be reduced by replacing CUC with any of the codons having a single G/C or the codon with no G/C.

See, U.S. Publ. Nos. US20140228558, US20050032730 A1; Gustafsson et al. (2012) Protein Expression and Purification 83: 37-46; all of which are incorporated herein by reference in their entireties.

c. Codon Frequency—Codon Usage Bias

Numerous codon optimization methods known in the art are based on the substitution of codons in a reference nucleic acid sequence with codons having higher frequencies. Thus, in some embodiments, a nucleic acid sequence encoding PBGD disclosed herein can be sequence optimized using methods comprising the use of modifications in the frequency of use of one or more codons relative to other synonymous codons in the sequence optimized nucleic acid with respect to the frequency of use in the non-codon optimized sequence.

As used herein, the term "codon frequency" refers to codon usage bias, i.e., the differences in the frequency of occurrence of synonymous codons in coding DNA/RNA. It is generally acknowledged that codon preferences reflect a balance between mutational biases and natural selection for translational optimization. Optimal codons help to achieve faster translation rates and high accuracy. As a result of these factors, translational selection is expected to be stronger in highly expressed genes. In the field of bioinformatics and computational biology, many statistical methods have been proposed and used to analyze codon usage bias. See, e.g., Comeron & Aguade (1998) J. Mol. Evol. 47: 268-74. Methods such as the "frequency of optimal codons" (Fop) (Ikemura (1981) J. Mol. Biol. 151 (3): 389-409), the "Relative Codon Adaptation" (RCA) (Fox & Eril (2010) DNA Res. 17 (3): 185-96) or the "Codon Adaptation Index" (CAI) (Sharp & Li (1987) Nucleic Acids Res. 15 (3): 1281-95) are used to predict gene expression levels, while methods such as the "effective number of codons" (Nc) and Shannon entropy from information theory are used to measure codon usage evenness. Multivariate statistical methods, such as correspondence analysis and principal component analysis, are widely used to analyze variations in codon usage among genes (Suzuki et al. (2008) DNA Res. 15 (6): 357-65; Sandhu et al., In Silico Biol. 2008; 8(2):187-92).

The nucleic acid sequence encoding a PBGD polypeptide disclosed herein (e.g., a wild type nucleic acid sequence, a mutant nucleic acid sequence, a chimeric nucleic acid sequence, etc. which can be, for example, an mRNA), can be codon optimized using methods comprising substituting at least one codon in the reference nucleic acid sequence with an alternative codon having a higher or lower codon frequency in the synonymous codon set; wherein the resulting sequence optimized nucleic acid has at least one optimized property with respect to the reference nucleic acid sequence.

In some embodiments, at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 99%, or 100% of the codons in the reference nucleic acid sequence encoding PBGD are substituted with alternative codons, each alternative codon having a codon frequency higher than the codon frequency of the substituted codon in the synonymous codon set.

In some embodiments, at least one codon in the reference nucleic acid sequence encoding PBGD is substituted with an alternative codon having a codon frequency higher than the codon frequency of the substituted codon in the synonymous codon set, and at least one codon in the reference nucleic acid sequence is substituted with an alternative codon having a codon frequency lower than the codon frequency of the substituted codon in the synonymous codon set.

In some embodiments, at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, or at least about 75% of the codons in the reference nucleic acid sequence encoding PBGD are substituted with alternative codons, each alternative codon having a codon frequency higher than the codon frequency of the substituted codon in the synonymous codon set.

In some embodiments, at least one alternative codon having a higher codon frequency has the highest codon frequency in the synonymous codon set. In other embodiments, all alternative codons having a higher codon frequency have the highest codon frequency in the synonymous codon set.

In some embodiments, at least one alternative codon having a lower codon frequency has the lowest codon frequency in the synonymous codon set. In some embodiments, all alternative codons having a higher codon frequency have the highest codon frequency in the synonymous codon set.

In some specific embodiments, at least one alternative codon has the second highest, the third highest, the fourth highest, the fifth highest or the sixth highest frequency in the synonymous codon set. In some specific embodiments, at least one alternative codon has the second lowest, the third lowest, the fourth lowest, the fifth lowest, or the sixth lowest frequency in the synonymous codon set.

Optimization based on codon frequency can be applied globally, as described above, or locally to the reference nucleic acid sequence encoding a PBGD polypeptide. In some embodiments, when applied locally, regions of the reference nucleic acid sequence can modified based on codon frequency, substituting all or a certain percentage of codons in a certain subsequence with codons that have higher or lower frequencies in their respective synonymous codon sets. Thus, in some embodiments, at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 99%, or 100% of the codons in a subsequence of the reference nucleic acid sequence are substituted with alternative codons, each alternative codon having a codon frequency higher than the codon frequency of the substituted codon in the synonymous codon set.

In some embodiments, at least one codon in a subsequence of the reference nucleic acid sequence encoding a PBGD polypeptide is substituted with an alternative codon having a codon frequency higher than the codon frequency of the substituted codon in the synonymous codon set, and at least one codon in a subsequence of the reference nucleic acid sequence is substituted with an alternative codon having a codon frequency lower than the codon frequency of the substituted codon in the synonymous codon set.

In some embodiments, at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, or at least about 75% of the codons in a subsequence of the reference nucleic acid sequence encoding a PBGD polypeptide are substituted with alternative codons, each alternative codon having a codon frequency higher than the codon frequency of the substituted codon in the synonymous codon set.

In some embodiments, at least one alternative codon substituted in a subsequence of the reference nucleic acid sequence encoding a PBGD polypeptide and having a higher codon frequency has the highest codon frequency in the synonymous codon set. In other embodiments, all alternative codons substituted in a subsequence of the reference nucleic acid sequence and having a lower codon frequency have the lowest codon frequency in the synonymous codon set.

In some embodiments, at least one alternative codon substituted in a subsequence of the reference nucleic acid sequence encoding a PBGD polypeptide and having a lower codon frequency has the lowest codon frequency in the synonymous codon set. In some embodiments, all alternative codons substituted in a subsequence of the reference nucleic acid sequence and having a higher codon frequency have the highest codon frequency in the synonymous codon set.

In specific embodiments, a sequence optimized nucleic acid encoding a PBGD polypeptide can comprise a subsequence having an overall codon frequency higher or lower than the overall codon frequency in the corresponding subsequence of the reference nucleic acid sequence at a specific location, for example, at the 5' end or 3' end of the sequence optimized nucleic acid, or within a predetermined distance from those region (e.g., at least 1, 2, 3, 4, 5, 6, 7, 8, 9, 10, 15, 20, 25, 30, 35, 40, 45, 50, 55, 60, 65, 70, 75, 80, 85, 90, 95 or 100 codons from the 5' end or 3' end of the sequence optimized nucleic acid).

In some embodiments, a sequence optimized nucleic acid encoding a PBGD polypeptide can comprise more than one subsequence having an overall codon frequency higher or lower than the overall codon frequency in the corresponding subsequence of the reference nucleic acid sequence. A skilled artisan would understand that subsequences with overall higher or lower overall codon frequencies can be organized in innumerable patterns, depending on whether the overall codon frequency is higher or lower, the length of the subsequence, the distance between subsequences, the location of the subsequences, etc.

See, U.S. Pat. Nos. 5,082,767, 8,126,653, 7,561,973, 8,401,798; U.S. Publ. No. US 20080046192, US 20080076161; Int'l. Publ. No. WO2000018778; Welch et al. (2009) *PLoS ONE* 4(9): e7002; Gustafsson et al. (2012) *Protein Expression and Purification* 83: 37-46; Chung et al. (2012) *BMC Systems Biology* 6:134; all of which are incorporated herein by reference in their entireties.

d. Destabilizing Motif Substitution

There is a variety of motifs that can affect sequence optimization, which fall into various non-exclusive categories, for example:

(i) Primary sequence based motifs: Motifs defined by a simple arrangement of nucleotides.

(ii) Structural motifs: Motifs encoded by an arrangement of nucleotides that tends to form a certain secondary structure.

(iii) Local motifs: Motifs encoded in one contiguous subsequence.

(iv) Distributed motifs: Motifs encoded in two or more disjoint subsequences.

(v) Advantageous motifs: Motifs which improve nucleotide structure or function.

(vi) Disadvantageous motifs: Motifs with detrimental effects on nucleotide structure or function.

There are many motifs that fit into the category of disadvantageous motifs. Some examples include, for example, restriction enzyme motifs, which tend to be relatively short, exact sequences such as the restriction site motifs for Xba1 (TCTAGA), EcoRI (GAATTC), EcoRII (CCWGG, wherein W means A or T, per the IUPAC ambiguity codes), or HindIII (AAGCTT); enzyme sites, which tend to be longer and based on consensus not exact sequence, such in the T7 RNA polymerase (GnnnnWnCRnCTCnCnnWnD, wherein n means any nucleotide, R means A or G, W means A or T, D means A or G or T but not C); structural motifs, such as GGGG repeats (Kim et al. (1991) *Nature* 351(6324):331-2); or other motifs such as CUG-triplet repeats (Querido et al. (2014) *J. Cell Sci.* 124:1703-1714).

Accordingly, the nucleic acid sequence encoding a PBGD polypeptide disclosed herein can be sequence optimized using methods comprising substituting at least one destabilizing motif in a reference nucleic acid sequence, and removing such disadvantageous motif or replacing it with an advantageous motif.

In some embodiments, the optimization process comprises identifying advantageous and/or disadvantageous motifs in the reference nucleic sequence, wherein such motifs are, e.g., specific subsequences that can cause a loss of stability in the reference nucleic acid sequence prior or during the optimization process. For example, substitution of specific bases during optimization can generate a subsequence (motif) recognized by a restriction enzyme. Accordingly, during the optimization process the appearance of disadvantageous motifs can be monitored by comparing the sequence optimized sequence with a library of motifs known to be disadvantageous. Then, the identification of disadvantageous motifs could be used as a post-hoc filter, i.e., to determine whether a certain modification which potentially could be introduced in the reference nucleic acid sequence should be actually implemented or not.

In some embodiments, the identification of disadvantageous motifs can be used prior to the application of the sequence optimization methods disclosed herein, i.e., the identification of motifs in the reference nucleic acid sequence encoding a PBGD polypeptide and their replacement with alternative nucleic acid sequences can be used as a preprocessing step, for example, before uridine reduction.

In other embodiments, the identification of disadvantageous motifs and their removal is used as an additional sequence optimization technique integrated in a multiparametric nucleic acid optimization method comprising two or more of the sequence optimization methods disclosed herein. When used in this fashion, a disadvantageous motif identified during the optimization process would be removed, for example, by substituting the lowest possible number of nucleobases in order to preserve as closely as possible the original design principle(s) (e.g., low U, high frequency, etc.).

See, e.g., U.S. Publ. Nos. US20140228558, US20050032730, or US20140228558, which are herein incorporated by reference in their entireties.

e. Limited Codon Set Optimization

In some particular embodiments, sequence optimization of a reference nucleic acid sequence encoding a PBGD polypeptide can be conducted using a limited codon set, e.g., a codon set wherein less than the native number of codons is used to encode the 20 natural amino acids, a subset of the 20 natural amino acids, or an expanded set of amino acids including, for example, non-natural amino acids.

The genetic code is highly similar among all organisms and can be expressed in a simple table with 64 entries which would encode the 20 standard amino acids involved in protein translation plus start and stop codons. The genetic code is degenerate, i.e., in general, more than one codon specifies each amino acid. For example, the amino acid leucine is specified by the UUA, UUG, CUU, CUC, CUA, or CUG codons, while the amino acid serine is specified by UCA, UCG, UCC, UCU, AGU, or AGC codons (difference in the first, second, or third position). Native genetic codes comprise 62 codons encoding naturally occurring amino acids. Thus, in some embodiments of the methods disclosed herein optimized codon sets (genetic codes) comprising less than 62 codons to encode 20 amino acids can comprise 61, 60, 59, 58, 57, 56, 55, 54, 53, 52, 51, 50, 49, 48, 47, 46, 45, 44, 43, 42, 41, 40, 39, 38, 37, 36, 35, 34, 33, 32, 31, 30, 30, 29, 28, 27, 26, 25, 24, 23, 22, 21, or 20 codons.

In some embodiments, the limited codon set comprises less than 20 codons. For example, if a protein contains less than 20 types of amino acids, such protein could be encoded by a codon set with less than 20 codons. Accordingly, in some embodiments, an optimized codon set comprises as many codons as different types of amino acids are present in the protein encoded by the reference nucleic acid sequence. In some embodiments, the optimized codon set comprises 19, 18, 17, 16, 15, 14, 13, 12, 11, 10, 9, 8, 7, 6, 5, 4, 3, 2 or even 1 codon.

In some embodiments, at least one amino acid selected from the group consisting of Ala, Arg, Asn, Asp, Cys, Gln, Glu, Gly, His, Ile, Leu, Lys, Phe, Pro, Ser, Thr, Tyr, and Val, i.e., amino acids which are naturally encoded by more than one codon, is encoded with less codons than the naturally occurring number of synonymous codons. For example, in some embodiments, Ala can be encoded in the sequence optimized nucleic acid by 3, 2 or 1 codons; Cys can be encoded in the sequence optimized nucleic acid by 1 codon; Asp can be encoded in the sequence optimized nucleic acid by 1 codon; Glu can be encoded in the sequence optimized nucleic acid by 1 codon; Phe can be encoded in the sequence optimized nucleic acid by 1 codon; Gly can be encoded in the sequence optimized nucleic acid by 3 codons, 2 codons or 1 codon; His can be encoded in the sequence optimized nucleic acid by 1 codon; Ile can be encoded in the sequence optimized nucleic acid by 2 codons or 1 codon; Lys can be encoded in the sequence optimized nucleic acid by 1 codon; Leu can be encoded in the sequence optimized nucleic acid by 5 codons, 4 codons, 3 codons, 2 codons or 1 codon; Asn can be encoded in the sequence optimized nucleic acid by 1 codon; Pro can be encoded in the sequence optimized nucleic acid by 3 codons, 2 codons, or 1 codon; Gln can be encoded in the sequence optimized nucleic acid by 1 codon; Arg can be encoded in the sequence optimized nucleic acid by 5 codons, 4 codons, 3 codons, 2 codons, or 1 codon; Ser can be encoded in the sequence optimized nucleic acid by 5 codons, 4 codons, 3 codons, 2 codons, or 1 codon; Thr can be encoded in the sequence optimized nucleic acid by 3 codons, 2 codons, or 1 codon; Val can be encoded in the sequence optimized nucleic acid by 3 codons, 2 codons, or 1 codon; and, Tyr can be encoded in the sequence optimized nucleic acid by 1 codon.

In some embodiments, at least one amino acid selected from the group consisting of Ala, Arg, Asn, Asp, Cys, Gln, Glu, Gly, His, Ile, Leu, Lys, Phe, Pro, Ser, Thr, Tyr, and Val, i.e., amino acids which are naturally encoded by more than one codon, is encoded by a single codon in the limited codon set.

In some specific embodiments, the sequence optimized nucleic acid is a DNA and the limited codon set consists of 20 codons, wherein each codon encodes one of 20 amino acids. In some embodiments, the sequence optimized nucleic acid is a DNA and the limited codon set comprises at least one codon selected from the group consisting of GCT, GCC, GCA, and GCG; at least a codon selected from the group consisting of CGT, CGC, CGA, CGG, AGA, and AGG; at least a codon selected from AAT or ACC; at least a codon selected from GAT or GAC; at least a codon selected from TGT or TGC; at least a codon selected from CAA or CAG; at least a codon selected from GAA or GAG; at least a codon selected from the group consisting of GGT, GGC, GGA, and GGG; at least a codon selected from CAT or CAC; at least a codon selected from the group consisting of ATT, ATC, and ATA; at least a codon selected from the group consisting of TTA, TTG, CTT, CTC, CTA, and CTG; at least a codon selected from AAA or AAG; an ATG codon; at least a codon selected from TTT or TTC; at least a codon selected from the group consisting of CCT, CCC, CCA, and CCG; at least a codon selected from the group consisting of TCT, TCC, TCA, TCG, AGT, and AGC; at least a codon selected from the group consisting of ACT, ACC, ACA, and ACG; a TGG codon; at least a codon selected from TAT or TAC; and, at least a codon selected from the group consisting of GTT, GTC, GTA, and GTG.

In other embodiments, the sequence optimized nucleic acid is an RNA (e.g., an mRNA) and the limited codon set consists of 20 codons, wherein each codon encodes one of 20 amino acids. In some embodiments, the sequence optimized nucleic acid is an RNA and the limited codon set comprises at least one codon selected from the group consisting of GCU, GCC, GCA, and GCG; at least a codon selected from the group consisting of CGU, CGC, CGA, CGG, AGA, and AGG; at least a codon selected from AAU or ACC; at least a codon selected from GAU or GAC; at least a codon selected from UGU or UGC; at least a codon selected from CAA or CAG; at least a codon selected from GAA or GAG; at least a codon selected from the group consisting of GGU, GGC, GGA, and GGG; at least a codon selected from CAU or CAC; at least a codon selected from the group consisting of AUU, AUC, and AUA; at least a codon selected from the group consisting of UUA, UUG, CUU, CUC, CUA, and CUG; at least a codon selected from AAA or AAG; an AUG codon; at least a codon selected from UUU or UUC; at least a codon selected from the group consisting of CCU, CCC, CCA, and CCG; at least a codon selected from the group consisting of UCU, UCC, UCA, UCG, AGU, and AGC; at least a codon selected from the group consisting of ACU, ACC, ACA, and ACG; a UGG codon; at least a codon selected from UAU or UAC; and, at least a codon selected from the group consisting of GUU, GUC, GUA, and GUG.

In some specific embodiments, the limited codon set has been optimized for in vivo expression of a sequence optimized nucleic acid (e.g., a synthetic mRNA) following administration to a certain tissue or cell.

In some embodiments, the optimized codon set (e.g., a 20 codon set encoding 20 amino acids) complies at least with one of the following properties:
  (i) the optimized codon set has a higher average G/C content than the original or native codon set; or,
  (ii) the optimized codon set has a lower average U content than the original or native codon set; or,
  (iii) the optimized codon set is composed of codons with the highest frequency; or,
  (iv) the optimized codon set is composed of codons with the lowest frequency; or,
  (v) a combination thereof.

In some specific embodiments, at least one codon in the optimized codon set has the second highest, the third highest, the fourth highest, the fifth highest or the sixth highest frequency in the synonymous codon set. In some specific embodiments, at least one codon in the optimized codon has the second lowest, the third lowest, the fourth lowest, the fifth lowest, or the sixth lowest frequency in the synonymous codon set.

As used herein, the term "native codon set" refers to the codon set used natively by the source organism to encode the reference nucleic acid sequence. As used herein, the term "original codon set" refers to the codon set used to encode the reference nucleic acid sequence before the beginning of sequence optimization, or to a codon set used to encode an optimized variant of the reference nucleic acid sequence at the beginning of a new optimization iteration when sequence optimization is applied iteratively or recursively.

In some embodiments, 5%, 10%, 15%, 20%, 25%, 30%, 35%, 40%, 45%, 50%, 55%, 60%, 65%, 70%, 75%, 80%, 85%, 90%, 95% or 100% of codons in the codon set are those with the highest frequency. In other embodiments, 5%, 10%, 15%, 20%, 25%, 30%, 35%, 40%, 45%, 50%, 55%, 60%, 65%, 70%, 75%, 80%, 85%, 90%, 95% or 100% of codons in the codon set are those with the lowest frequency.

In some embodiments, 5%, 10%, 15%, 20%, 25%, 30%, 35%, 40%, 45%, 50%, 55%, 60%, 65%, 70%, 75%, 80%, 85%, 90%, 95% or 100% of codons in the codon set are those with the highest uridine content. In some embodiments, 5%, 10%, 15%, 20%, 25%, 30%, 35%, 40%, 45%, 50%, 55%, 60%, 65%, 70%, 75%, 80%, 85%, 90%, 95% or 100% of codons in the codon set are those with the lowest uridine content.

In some embodiments, the average G/C content (absolute or relative) of the codon set is 5%, 10%, 15%, 20%, 25%, 30%, 35%, 40%, 45%, 50%, 55%, 60%, 65%, 70%, 75%, 80%, 85%, 90%, 95% or 100% higher than the average G/C content (absolute or relative) of the original codon set. In some embodiments, the average G/C content (absolute or relative) of the codon set is 5%, 10%, 15%, 20%, 25%, 30%, 35%, 40%, 45%, 50%, 55%, 60%, 65%, 70%, 75%, 80%, 85%, 90%, 95% or 100% lower than the average G/C content (absolute or relative) of the original codon set.

In some embodiments, the uracil content (absolute or relative) of the codon set is 5%, 10%, 15%, 20%, 25%, 30%, 35%, 40%, 45%, 50%, 55%, 60%, 65%, 70%, 75%, 80%, 85%, 90%, 95% or 100% higher than the average uracil content (absolute or relative) of the original codon set. In some embodiments, the uracil content (absolute or relative) of the codon set is 5%, 10%, 15%, 20%, 25%, 30%, 35%, 40%, 45%, 50%, 55%, 60%, 65%, 70%, 75%, 80%, 85%, 90%, 95% or 100% lower than the average uracil content (absolute or relative) of the original codon set.

See also U.S. Appl. Publ. No. 2011/0082055, and Int'l. Publ. No. WO2000018778, both of which are incorporated herein by reference in their entireties.

8. CHARACTERIZATION OF SEQUENCE OPTIMIZED NUCLEIC ACIDS

In some embodiments of the invention, the polynucleotide (e.g., a RNA, e.g., an mRNA) comprising a sequence optimized nucleic acid disclosed herein encoding a PBGD polypeptide can be tested to determine whether at least one nucleic acid sequence property (e.g., stability when exposed to nucleases) or expression property has been improved with respect to the non-sequence optimized nucleic acid.

As used herein, "expression property" refers to a property of a nucleic acid sequence either in vivo (e.g., translation efficacy of a synthetic mRNA after administration to a subject in need thereof) or in vitro (e.g., translation efficacy of a synthetic mRNA tested in an in vitro model system). Expression properties include but are not limited to the amount of protein produced by an mRNA encoding a PBGD polypeptide after administration, and the amount of soluble or otherwise functional protein produced. In some embodiments, sequence optimized nucleic acids disclosed herein can be evaluated according to the viability of the cells expressing a protein encoded by a sequence optimized nucleic acid sequence (e.g., a RNA, e.g., an mRNA) encoding a PBGD polypeptide disclosed herein.

In a particular embodiment, a plurality of sequence optimized nucleic acids disclosed herein (e.g., a RNA, e.g., an mRNA) containing codon substitutions with respect to the non-optimized reference nucleic acid sequence can be characterized functionally to measure a property of interest, for example an expression property in an in vitro model system, or in vivo in a target tissue or cell.

a. Optimization of Nucleic Acid Sequence Intrinsic Properties

In some embodiments of the invention, the desired property of the polynucleotide is an intrinsic property of the nucleic acid sequence. For example, the nucleotide sequence (e.g., a RNA, e.g., an mRNA) can be sequence optimized for in vivo or in vitro stability. In some embodiments, the nucleotide sequence can be sequence optimized for expression in a particular target tissue or cell. In some embodiments, the nucleic acid sequence is sequence optimized to increase its plasma half-life by preventing its degradation by endo and exonucleases.

In other embodiments, the nucleic acid sequence is sequence optimized to increase its resistance to hydrolysis in solution, for example, to lengthen the time that the sequence optimized nucleic acid or a pharmaceutical composition comprising the sequence optimized nucleic acid can be stored under aqueous conditions with minimal degradation.

In other embodiments, the sequence optimized nucleic acid can be optimized to increase its resistance to hydrolysis in dry storage conditions, for example, to lengthen the time that the sequence optimized nucleic acid can be stored after lyophilization with minimal degradation.

b. Nucleic Acids Sequence Optimized for Protein Expression

In some embodiments of the invention, the desired property of the polynucleotide is the level of expression of a PBGD polypeptide encoded by a sequence optimized sequence disclosed herein. Protein expression levels can be measured using one or more expression systems. In some embodiments, expression can be measured in cell culture systems, e.g., CHO cells or HEK293 cells. In some embodiments, expression can be measured using in vitro expression systems prepared from extracts of living cells, e.g., rabbit reticulocyte lysates, or in vitro expression systems prepared by assembly of purified individual components. In other embodiments, the protein expression is measured in an in vivo system, e.g., mouse, rabbit, monkey, etc.

In some embodiments, protein expression in solution form can be desirable.

Accordingly, in some embodiments, a reference sequence can be sequence optimized to yield a sequence optimized nucleic acid sequence having optimized levels of expressed proteins in soluble form. Levels of protein expression and other properties such as solubility, levels of aggregation, and the presence of truncation products (i.e., fragments due to proteolysis, hydrolysis, or defective translation) can be measured according to methods known in the art, for example, using electrophoresis (e.g., native or SDS-PAGE) or chromatographic methods (e.g., HPLC, size exclusion chromatography, etc.).

c. Optimization of Target Tissue or Target Cell Viability

In some embodiments, the expression of heterologous therapeutic proteins encoded by a nucleic acid sequence can have deleterious effects in the target tissue or cell, reducing protein yield, or reducing the quality of the expressed product (e.g., due to the presence of protein fragments or precipitation of the expressed protein in inclusion bodies), or causing toxicity.

Accordingly, in some embodiments of the invention, the sequence optimization of a nucleic acid sequence disclosed herein, e.g., a nucleic acid sequence encoding a PBGD polypeptide, can be used to increase the viability of target cells expressing the protein encoded by the sequence optimized nucleic acid.

Heterologous protein expression can also be deleterious to cells transfected with a nucleic acid sequence for autologous or heterologous transplantation. Accordingly, in some embodiments of the present disclosure the sequence optimization of a nucleic acid sequence disclosed herein can be used to increase the viability of target cells expressing the protein encoded by the sequence optimized nucleic acid sequence. Changes in cell or tissue viability, toxicity, and other physiological reaction can be measured according to methods known in the art.

d. Reduction of Immune and/or Inflammatory Response

In some cases, the administration of a sequence optimized nucleic acid encoding PBGD polypeptide or a functional fragment thereof can trigger an immune response, which could be caused by (i) the therapeutic agent (e.g., an mRNA encoding a PBGD polypeptide), or (ii) the expression product of such therapeutic agent (e.g., the PBGD polypeptide encoded by the mRNA), or (iv) a combination thereof. Accordingly, in some embodiments of the present disclosure the sequence optimization of nucleic acid sequence (e.g., an mRNA) disclosed herein can be used to decrease an immune or inflammatory response triggered by the administration of a nucleic acid encoding a PBGD polypeptide or by the expression product of PBGD encoded by such nucleic acid.

In some aspects, an inflammatory response can be measured by detecting increased levels of one or more inflammatory cytokines using methods known in the art, e.g., ELISA. The term "inflammatory cytokine" refers to cytokines that are elevated in an inflammatory response. Examples of inflammatory cytokines include interleukin-6 (IL-6), CXCL1 (chemokine (C—X—C motif) ligand 1; also known as GROα, interferon-γ (IFNγ), tumor necrosis factor α (TNFα), interferon γ-induced protein 10 (IP-10), or granulocyte-colony stimulating factor (G-CSF). The term inflammatory cytokines includes also other cytokines associated with inflammatory responses known in the art, e.g., interleukin-1 (IL-1), interleukin-8 (IL-8), interleukin-12 (IL-12), interleukin-13 (Il-13), interferon α (IFN-α), etc.

9. MODIFIED NUCLEOTIDE SEQUENCES ENCODING PBGD POLYPEPTIDES

In some embodiments, the polynucleotide of the invention (e.g., a RNA, e.g., an mRNA) comprises a chemically modified nucleobase, e.g., 5-methoxyuracil. In some embodiments, the mRNA is a uracil-modified sequence comprising an ORF encoding a PBGD polypeptide, wherein the mRNA comprises a chemically modified nucleobase, e.g., 5-methoxyuracil.

In certain aspects of the invention, when the 5-methoxyuracil base is connected to a ribose sugar, as it is in polynucleotides, the resulting modified nucleoside or nucleotide is referred to as 5-methoxyuridine. In some embodiments, uracil in the polynucleotide is at least about 25%, at least about 30%, at least about 40%, at least about 50%, at least about 60%, at least about 70%, at least about 80%, at least about 90%, at least 95%, at least 99%, or about 100% 5-methoxyuracil. In one embodiment, uracil in the polynucleotide is at least 95% 5-methoxyuracil. In another embodiment, uracil in the polynucleotide is 100% 5-methoxyuracil.

In embodiments where uracil in the polynucleotide is at least 95% 5-methoxyuracil, overall uracil content can be adjusted such that the polynucleotide of the invention (e.g., a RNA, e.g., an mRNA) provides suitable protein expression levels while inducing little to no immune response. In some embodiments, the uracil content of the ORF is between about 105% and about 145%, about 105% and about 140%, about 110% and about 140%, about 110% and about 145%, about 115% and about 135%, about 105% and about 135%, about 110% and about 135%, about 115% and about 145%, or about 115% and about 140% of the theoretical minimum uracil content in the corresponding wild-type ORF (% $U_{TM}$). In other embodiments, the uracil content of the ORF is between about 117% and about 134% or between 118% and 132% of the % $U_{TM}$. In some embodiments, the uracil content of the ORF encoding a PBGD polypeptide is about 115%, about 120%, about 125%, about 130%, about 135%, about 140%, about 145%, or about 150% of the % $U_{TM}$. In this context, the term "uracil" can refer to 5-methoxyuracil and/or naturally occurring uracil.

In some embodiments, the uracil content in the ORF of the mRNA encoding a
PBGD polypeptide of the invention is less than about 50%, about 40%, about 30%, or about 20% of the total nucleobase content in the ORF. In some embodiments, the uracil content in the ORF is between about 15% and about 25% of the total nucleobase content in the ORF. In other embodiments, the uracil content in the ORF is between about 20% and about 30% of the total nucleobase content in the ORF. In one embodiment, the uracil content in the ORF of the mRNA encoding a PBGD polypeptide is less than about 20% of the total nucleobase content in the open reading frame. In this context, the term "uracil" can refer to 5-methoxyuracil and/or naturally occurring uracil.

In further embodiments, the ORF of the mRNA encoding a PBGD polypeptide having 5-methoxyuracil and adjusted uracil content has increased Cytosine (C), Guanine (G), or Guanine/Cytosine (G/C) content (absolute or relative). In some embodiments, the overall increase in C, G, or G/C content (absolute or relative) of the ORF is at least about 2%, at least about 3%, at least about 4%, at least about 5%, at least about 6%, at least about 7%, at least about 10%, at least about 15%, at least about 20%, at least about 40%, at least about 50%, at least about 60%, at least about 70%, at least about 80%, at least about 90%, at least about 95%, or at least about 100% relative to the G/C content (absolute or relative) of the wild-type ORF. In some embodiments, the G, the C, or the G/C content in the ORF is less than about 100%, less than about 90%, less than about 85%, or less than about 80% of the theoretical maximum G, C, or G/C content of the corresponding wild type nucleotide sequence encoding the PBGD polypeptide (% $G_{TMX}$; % $C_{MTX}$, or % $G/C_{MTX}$). In other embodiments, the G, the C, or the G/C content in the ORF is between about 70% and about 80%, between about 71% and about 79%, between about 71% and about 78%, or between about 71% and about 77% of the % $G_{TMX}$, % $C_{MTX}$, or % $G/C_{MTX}$. In some embodiments, the increases in G and/or C content (absolute or relative) described herein can be conducted by replacing synonymous codons with low G, C, or G/C content with synonymous codons having higher G, C, or G/C content. In other embodiments, the increase in G and/or C content (absolute or relative) is conducted by replacing a codon ending with U with a synonymous codon ending with G or C.

In further embodiments, the ORF of the mRNA encoding a PBGD polypeptide of the invention comprises 5-methoxyuracil and has an adjusted uracil content containing less uracil pairs (UU) and/or uracil triplets (UUU) and/or uracil quadruplets (UUUU) than the corresponding wild-type nucleotide sequence encoding the PBGD polypeptide. In some embodiments, the ORF of the mRNA encoding a PBGD polypeptide of the invention contains no uracil pairs and/or uracil triplets and/or uracil quadruplets. In some embodiments, uracil pairs and/or uracil triplets and/or uracil quadruplets are reduced below a certain threshold, e.g., no more than 1, 2, 3, 4, 5, 6, 7, 8, 9, 10, 11, 12, 13, 14, 15, 16, 17, 18, 19, or 20 occurrences in the ORF of the mRNA encoding the PBGD polypeptide. In a particular embodiment, the ORF of the mRNA encoding the PBGD polypeptide of the invention contains less than 20, 19, 18, 17, 16, 15, 14, 13, 12, 11, 10, 9, 8, 7, 6, 5, 4, 3, 2, or 1 non-phenylalanine uracil pairs and/or triplets. In another embodiment, the ORF of the mRNA encoding the PBGD polypeptide contains no non-phenylalanine uracil pairs and/or triplets.

In further embodiments, the ORF of the mRNA encoding a PBGD polypeptide of the invention comprises 5-methoxyuracil and has an adjusted uracil content containing less uracil-rich clusters than the corresponding wild-type nucleotide sequence encoding the PBGD polypeptide. In some embodiments, the ORF of the mRNA encoding the PBGD polypeptide of the invention contains uracil-rich clusters that are shorter in length than corresponding uracil-rich clusters in the corresponding wild-type nucleotide sequence encoding the PBGD polypeptide.

In further embodiments, alternative lower frequency codons are employed. At least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 99%, or 100% of the codons in the PBGD polypeptide-encoding ORF of the 5-methoxyuracil-comprising mRNA are substituted with alternative codons, each alternative codon having a codon frequency lower than the codon frequency of the substituted codon in the synonymous codon set. The ORF also has adjusted uracil content, as described above. In some embodiments, at least one codon in the ORF of the mRNA encoding the PBGD polypeptide is substituted with an alternative codon having a codon frequency lower than the codon frequency of the substituted codon in the synonymous codon set.

In some embodiments, the adjusted uracil content, PBGD polypeptide-encoding ORF of the 5-methoxyuracil-comprising mRNA exhibits expression levels of PBGD when administered to a mammalian cell that are higher than expression levels of PBGD from the corresponding wild-type mRNA. In other embodiments, the expression levels of PBGD when administered to a mammalian cell are increased relative to a corresponding mRNA containing at least 95% 5-methoxyuracil and having a uracil content of about 160%, about 170%, about 180%, about 190%, or about 200% of the theoretical minimum. In yet other embodiments, the expression levels of PBGD when administered to a mammalian cell are increased relative to a corresponding mRNA, wherein at least about 50%, at least about 60%, at least about 70%, at least about 80%, at least about 90%, or about 100% of uracils are 1-methylpseudouracil or pseudouracils. In some embodiments, the mammalian cell is a mouse cell, a rat cell, or a rabbit cell. In other embodiments, the mammalian cell is a monkey cell or a human cell. In some embodiments, the human cell is a HeLa cell, a BJ fibroblast cell, or a peripheral blood mononuclear cell (PBMC). In some embodiments, PBGD is expressed when the mRNA is administered to a mammalian cell in vivo. In some embodiments, the mRNA is administered to mice, rabbits, rats, monkeys, or humans. In one embodiment, mice are null mice. In some embodiments, the mRNA is administered to mice in an amount of about 0.01 mg/kg, about 0.05 mg/kg, about 0.1 mg/kg, or about 0.15 mg/kg. In some embodiments, the mRNA is administered intravenously or intramuscularly. In other embodiments, the PBGD polypeptide is expressed when the mRNA is administered to a mammalian cell in vitro. In some embodiments, the expression is increased by at least about 2-fold, at least about 5-fold, at least about 10-fold, at least about 50-fold, at least about 500-fold, at least about 1500-fold, or at least about 3000-fold. In other embodiments, the expression is increased by at least about 10%, about 20%, about 30%, about 40%, about 50%, 60%, about 70%, about 80%, about 90%, or about 100%.

In some embodiments, adjusted uracil content, PBGD polypeptide-encoding ORF of the 5-methoxyuracil-comprising mRNA exhibits increased stability. In some embodiments, the mRNA exhibits increased stability in a cell relative to the stability of a corresponding wild-type mRNA under the same conditions. In some embodiments, the mRNA exhibits increased stability including resistance to nucleases, thermal stability, and/or increased stabilization of secondary structure. In some embodiments, increased stability exhibited by the mRNA is measured by determining the half-life of the mRNA (e.g., in a plasma, serum, cell, or tissue sample) and/or determining the area under the curve (AUC) of the protein expression by the mRNA over time (e.g., in vitro or in vivo). An mRNA is identified as having increased stability if the half-life and/or the AUC is greater than the half-life and/or the AUC of a corresponding wild-type mRNA under the same conditions.

In some embodiments, the mRNA of the present invention induces a detectably lower immune response (e.g., innate or acquired) relative to the immune response induced by a corresponding wild-type mRNA under the same conditions. In other embodiments, the mRNA of the present disclosure induces a detectably lower immune response (e.g., innate or acquired) relative to the immune response induced by an mRNA that encodes for a PBGD polypeptide but does not comprise 5-methoxyuracil under the same conditions, or relative to the immune response induced by an mRNA that encodes for a PBGD polypeptide and that comprises 5-methoxyuracil but that does not have adjusted uracil content under the same conditions. The innate immune response can be manifested by increased expression of pro-inflammatory cytokines, activation of intracellular PRRs (RIG-I, MDA5, etc.), cell death, and/or termination or reduction in protein translation. In some embodiments, a reduction in the innate immune response can be measured by expression or activity level of Type 1 interferons (e.g., IFN-α, IFN-β, IFN-κ, IFN-δ, IFN-ε, IFN-τ, IFN-ω, and IFN-ζ) or the expression of interferon-regulated genes such as the toll-like receptors (e.g., TLR7 and TLR8), and/or by decreased cell death following one or more administrations of the mRNA of the invention into a cell.

In some embodiments, the expression of Type-1 interferons by a mammalian cell in response to the mRNA of the present disclosure is reduced by at least 10%, 20%, 30%, 40%, 50%, 60%, 70%, 80%, 90%, 95%, 99%, 99.9%, or greater than 99.9% relative to a corresponding wild-type mRNA, to an mRNA that encodes a PBGD polypeptide but does not comprise 5-methoxyuracil, or to an mRNA that encodes a PBGD polypeptide and that comprises 5-methoxyuracil but that does not have adjusted uracil content. In some embodiments, the interferon is IFN-β. In some embodiments, cell death frequency caused by administration of mRNA of the present disclosure to a mammalian cell is 10%, 25%, 50%, 75%, 85%, 90%, 95%, or over 95% less than the cell death frequency observed with a corresponding wild-type mRNA, an mRNA that encodes for a PBGD polypeptide but does not comprise 5-methoxyuracil, or an mRNA that encodes for a PBGD polypeptide and that comprises 5-methoxyuracil but that does not have adjusted uracil content. In some embodiments, the mammalian cell is a BJ fibroblast cell. In other embodiments, the mammalian cell is a splenocyte. In some embodiments, the mammalian cell is that of a mouse or a rat. In other embodiments, the mammalian cell is that of a human. In one embodiment, the mRNA of the present disclosure does not substantially induce an innate immune response of a mammalian cell into which the mRNA is introduced.

In some embodiments, the polynucleotide is an mRNA that comprises an ORF that encodes a PBGD polypeptide, wherein uracil in the mRNA is at least about 95% 5-methoxyuracil, wherein the uracil content of the ORF is between about 115% and about 135% of the theoretical minimum uracil content in the corresponding wild-type ORF, and wherein the uracil content in the ORF encoding the PBGD polypeptide is less than about 30% of the total nucleobase content in the ORF. In some embodiments, the ORF that encodes the PBGD polypeptide is further modified to increase G/C content of the ORF (absolute or relative) by at least about 40%, as compared to the corresponding wild-type ORF. In yet other embodiment, the ORF encoding the PBGD polypeptide contains less than 20 non-phenylalanine uracil pairs and/or triplets. In some embodiments, at least one codon in the ORF of the mRNA encoding the PBGD polypeptide is further substituted with an alternative codon having a codon frequency lower than the codon frequency of the substituted codon in the synonymous codon set. In some embodiments, the expression of the PBGD polypeptide encoded by an mRNA comprising an ORF wherein uracil in the mRNA is at least about 95% 5-methoxyuracil, and wherein the uracil content of the ORF is between about 115% and about 135% of the theoretical minimum uracil content in the corresponding wild-type ORF, is increased by at least about 10-fold when compared to expression of the PBGD polypeptide from the corresponding wild-type mRNA. In some embodiments, the mRNA comprises an open ORF wherein uracil in the mRNA is at least about 95% 5-methoxyuracil, and wherein the uracil content of the ORF is between about 115% and about 135% of the theoretical minimum uracil content in the corresponding wild-type ORF, and wherein the mRNA does not substantially induce an innate immune response of a mammalian cell into which the mRNA is introduced.

10. METHODS FOR MODIFYING POLYNUCLEOTIDES

The invention includes modified polynucleotides comprising a polynucleotide described herein (e.g., a polynucleotide, e.g., an mRNA, comprising a nucleotide sequence encoding a PBGD polypeptide). The modified polynucleotides can be chemically modified and/or structurally modified. When the polynucleotides of the present invention are chemically and/or structurally modified the polynucleotides can be referred to as "modified polynucleotides."

The present disclosure provides for modified nucleosides and nucleotides of a polynucleotide (e.g., RNA polynucleotides, such as mRNA polynucleotides) encoding a PBGD polypeptide. A "nucleoside" refers to a compound containing a sugar molecule (e.g., a pentose or ribose) or a derivative thereof in combination with an organic base (e.g., a purine or pyrimidine) or a derivative thereof (also referred to herein as "nucleobase"). A "nucleotide" refers to a nucleoside including a phosphate group. Modified nucleotides can be synthesized by any useful method, such as, for example, chemically, enzymatically, or recombinantly, to include one or more modified or non-natural nucleosides. Polynucleotides can comprise a region or regions of linked nucleosides. Such regions can have variable backbone linkages. The linkages can be standard phosphodiester linkages, in which case the polynucleotides would comprise regions of nucleotides.

The modified polynucleotides disclosed herein can comprise various distinct modifications. In some embodiments, the modified polynucleotides contain one, two, or more (optionally different) nucleoside or nucleotide modifications. In some embodiments, a modified polynucleotide, introduced to a cell can exhibit one or more desirable properties, e.g., improved protein expression, reduced immunogenicity, or reduced degradation in the cell, as compared to an unmodified polynucleotide.

a. Structural Modifications

In some embodiments, a polynucleotide of the present invention (e.g., a polynucleotide comprising a nucleotide sequence encoding a PBGD polypeptide) is structurally modified. As used herein, a "structural" modification is one in which two or more linked nucleosides are inserted, deleted, duplicated, inverted or randomized in a polynucleotide without significant chemical modification to the nucleotides themselves. Because chemical bonds will necessarily be broken and reformed to effect a structural modification, structural modifications are of a chemical nature and hence are chemical modifications. However, structural modifications will result in a different sequence of nucleotides. For example, the polynucleotide "ATCG" can be chemically modified to "AT-5meC-G". The same polynucleotide can be structurally modified from "ATCG" to "ATCCCG". Here, the dinucleotide "CC" has been inserted, resulting in a structural modification to the polynucleotide.

b. Chemical Modifications

In some embodiments, the polynucleotides of the present invention (e.g., a polynucleotide comprising a nucleotide sequence encoding a PBGD polypeptide) are chemically modified. As used herein in reference to a polynucleotide, the terms "chemical modification" or, as appropriate, "chemically modified" refer to modification with respect to adenosine (A), guanosine (G), uridine (U), thymidine (T) or cytidine (C) ribo- or deoxyribonucleosides in one or more of their position, pattern, percent or population, including, but not limited to, its nucleobase, sugar, backbone, or any combination thereof. Generally, herein, these terms are not intended to refer to the ribonucleotide modifications in naturally occurring 5'-terminal mRNA cap moieties.

In some embodiments, the polynucleotides of the invention (e.g., a polynucleotide comprising a nucleotide sequence encoding a PBGD polypeptide) can have a uniform chemical modification of all or any of the same nucleoside type or a population of modifications produced by downward titration of the same starting modification in all or any of the same nucleoside type, or a measured percent of a chemical modification of all any of the same nucleoside type but with random incorporation, such as where all uridines are replaced by a uridine analog, e.g., 5-methoxyuridine. In another embodiment, the polynucleotides can have a uniform chemical modification of two, three, or four of the same nucleoside type throughout the entire polynucleotide (such as all uridines and/or all cytidines, etc. are modified in the same way).

Modified nucleotide base pairing encompasses not only the standard adenine-thymine, adenine-uracil, or guanine-cytosine base pairs, but also base pairs formed between nucleotides and/or modified nucleotides comprising non-standard or modified bases, wherein the arrangement of hydrogen bond donors and hydrogen bond acceptors permits hydrogen bonding between a non-standard base and a standard base or between two complementary non-standard base structures. One example of such non-standard base pairing is the base pairing between the modified nucleobase inosine and adenine, cytosine or uracil. Any combination of base/sugar or linker can be incorporated into polynucleotides of the present disclosure.

The skilled artisan will appreciate that, except where otherwise noted, polynucleotide sequences set forth in the instant application will recite "T"s in a representative DNA sequence but where the sequence represents RNA, the "T"s would be substituted for "U"s.

Modifications of polynucleotides (e.g., RNA polynucleotides, such as mRNA polynucleotides) that are useful in the compositions, methods and synthetic processes of the present disclosure include, but are not limited to the following nucleotides, nucleosides, and nucleobases: 2-methylthio-N6-(cis-hydroxyisopentenyl)adenosine; 2-methylthio-N6-methyladenosine; 2-methylthio-N6-threonyl carbamoyladenosine; N6-glycinylcarbamoyladenosine; N6-isopentenyladenosine; N6-methyladenosine; N6-threonylcarbamoyladenosine; 1,2'-O-dimethyladenosine; 1-methyladenosine; 2'-O-methyladenosine; 2'-O-ribosyladenosine (phosphate); 2-methyladenosine; 2-methylthio-N6 isopentenyladenosine; 2-methylthio-N6-hydroxynorvalyl carbamoyladenosine; 2'-O-methyladenosine; 2'-O-ribosyladenosine (phosphate); Isopentenyladenosine; N6-(cis-hydroxyisopentenyl)adenosine; N6,2'-O-dimethyladenosine; N6,2'-O-dimethyladenosine; N6,N6,2'-O-trimethyladenosine; N6,N6-dimethyladenosine; N6-acetyladenosine; N6-hydroxynorvalylcarbamoyladenosine; N6-methyl-N6-threonylcarbamoyladenosine; 2-methyladenosine; 2-methylthio-N6-isopentenyladenosine; 7-deaza-adenosine; N1-methyl-adenosine; N6, N6 (dimethyl)adenine; N6-cis-hydroxy-isopentenyl-adenosine; α-thio-adenosine; 2 (amino)adenine; 2 (aminopropyl)adenine; 2 (methylthio) N6 (isopentenyl)adenine; 2-(alkyl)adenine; 2-(aminoalkyl)adenine; 2-(aminopropyl)adenine; 2-(halo)adenine; 2-(halo) adenine; 2-(propyl)adenine; 2'-Amino-2'-deoxy-ATP; 2'-Azido-2'-deoxy-ATP; 2'-Deoxy-2'-a-aminoadenosine TP; 2'-Deoxy-2'-a-azidoadenosine TP; 6 (alkyl)adenine; 6 (methyl)adenine; 6-(alkyl)adenine; 6-(methyl)adenine; 7 (deaza)adenine; 8 (alkenyl)adenine; 8 (alkynyl)adenine; 8 (amino)adenine; 8 (thioalkyl)adenine; 8-(alkenyl)adenine; 8-(alkyl)adenine; 8-(alkynyl)adenine; 8-(amino)adenine; 8-(halo)adenine; 8-(hydroxyl)adenine; 8-(thioalkyl)adenine; 8-(thiol)adenine; 8-azido-adenosine; aza adenine; deaza adenine; N6 (methyl)adenine; N6-(isopentyl)adenine; 7-deaza-8-aza-adenosine; 7-methyladenine; 1-Deazaadenosine TP; 2'Fluoro-N6-Bz-deoxyadenosine TP; 2'-OMe-2-Amino-ATP; 2'O-methyl-N6-Bz-deoxyadenosine TP; 2'-a-Ethynyladenosine TP; 2-aminoadenine; 2-Aminoadenosine TP; 2-Amino-ATP; 2'-a-Trifluoromethyladenosine TP; 2-Azidoadenosine TP; 2'-b-Ethynyladenosine TP; 2-Bromoadenosine TP; 2'-b-Trifluoromethyladenosine TP; 2-Chloroadenosine TP; 2'-Deoxy-2', 2'-difluoroadenosine TP; 2'-Deoxy-2'-a-mercaptoadenosine TP; 2'-Deoxy-2'-a-thiomethoxyadenosine TP; 2'-Deoxy-2'-b-aminoadenosine TP; 2'-Deoxy-2'-b-azidoadenosine TP; 2'-Deoxy-2'-b-bromoadenosine TP; 2'-Deoxy-2'-b-chloroadenosine TP; 2'-Deoxy-2'-b-fluoroadenosine TP; 2'-Deoxy-2'-b-iodoadenosine TP; 2'-Deoxy-2'-b-mercaptoadenosine TP; 2'-Deoxy-2'-b-thiomethoxyadenosine TP; 2-Fluoroadenosine TP; 2-Iodoadenosine TP; 2-Mercaptoadenosine TP; 2-methoxy-adenine; 2-methylthio-adenine; 2-Trifluoromethyladenosine TP; 3-Deaza-3-bromoadenosine TP; 3-Deaza-3-chloroadenosine TP; 3-Deaza-3-fluoroadenosine TP; 3-Deaza-3-iodoadenosine TP; 3-Deazaadenosine TP; 4'-Azidoadenosine TP; 4'-Carbocyclic adenosine TP; 4'-Ethynyladenosine TP; 5'-Homo-adenosine TP; 8-Aza-ATP; 8-bromo-adenosine TP; 8-Trifluoromethyladenosine TP; 9-Deazaadenosine TP; 2-aminopurine; 7-deaza-2,6-diaminopurine; 7-deaza-8-aza-2,6-diaminopurine; 7-deaza-8-aza-2-aminopurine; 2,6-diaminopurine; 7-deaza-8-aza-adenine, 7-deaza-2-aminopurine; 2-thiocytidine; 3-methylcytidine; 5-formylcytidine; 5-hydroxymethylcytidine; 5-methylcytidine; N4-acetylcytidine; 2'-O-methylcytidine; 2'-O-methylcytidine; 5,2'-O-dimethylcytidine; 5-formyl-2'-O-methylcytidine; Lysidine; N4,2'-O-dimethylcytidine; N4-acetyl-2'-O-methylcytidine; N4-methylcytidine; N4,N4-Dimethyl-2'-OMe-Cytidine TP; 4-methylcytidine; 5-aza-cytidine; Pseudo-iso-cytidine; pyrrolo-cytidine; α-thio-cytidine; 2-(thio)cytosine; 2'-Amino-2'-deoxy-CTP; 2'-Azido-2'-deoxy-CTP; 2'-Deoxy-2'-aminocytidine TP; 2'-Deoxy-2'-a-azidocytidine TP; 3 (deaza) 5 (aza)cytosine; 3 (methyl)cytosine; 3-(alkyl)cytosine; 3-(deaza) 5 (aza)cytosine; 3-(methyl)cytidine; 4,2'-O-dimethylcytidine; 5 (halo)cytosine; 5 (methyl)cytosine; 5 (propynyl)cytosine; 5 (trifluoromethyl)cytosine; 5-(alkyl)cytosine; 5-(alkynyl)cytosine; 5-(halo)cytosine; 5-(propynyl)cytosine; 5-(trifluoromethyl)cytosine; 5-bromo-cytidine; 5-iodo-cytidine; 5-propynyl cytosine; 6-(azo)cytosine; 6-aza-cytidine; aza cytosine; deaza cytosine; N4 (acetyl) cytosine; 1-methyl-1-deaza-pseudoisocytidine; 1-methyl-pseudoisocytidine; 2-methoxy-5-methyl-cytidine; 2-methoxy-cytidine; 2-thio-5-methyl-cytidine; 4-methoxy-1-methyl-pseudoisocytidine; 4-methoxy-pseudoisocytidine; 4-thio-1-methyl-1-deaza-pseudoisocytidine; 4-thio-1-methyl-pseudoisocytidine; 4-thio-pseudoisocytidine; 5-aza-zebularine; 5-methyl-zebularine; pyrrolo-pseudoisocytidine; Zebularine; (E)-5-(2-Bromo-vinyl)cytidine TP; 2,2'-anhydro-cytidine TP hydrochloride; 2'Fluor-N4-Bz-cytidine TP; 2'Fluoro-N4-Acetyl-cytidine TP; 2'-O-Methyl-N4-Acetyl-cytidine TP; 2'O-methyl-N4-Bz-cytidine TP; 2'-a-Ethynylcytidine TP; 2'-a-Trifluoromethylcytidine TP; 2'-b-Ethynylcytidine TP; 2'-b-Trifluoromethylcytidine TP; 2'-Deoxy-2',2'-difluorocytidine TP; 2'-Deoxy-2'-a-mercaptocytidine TP; 2'-Deoxy-2'-a-thiomethoxycytidine TP; 2'-Deoxy-2'-b-aminocytidine TP; 2'-Deoxy-2'-b-azidocytidine TP; 2'-Deoxy-2'-b-bromocytidine TP; 2'-Deoxy-2'-b-chlorocytidine TP; 2'-Deoxy-2'-b-fluorocytidine TP; 2'-Deoxy-2'-b-iodocytidine TP; 2'-Deoxy-2'-b-mercaptocytidine TP; 2'-Deoxy-2'-b-thiomethoxycytidine TP; 2'-O-Methyl-5-(1-propynyl)cytidine TP; 3'-Ethynylcytidine TP; 4'-Azidocytidine TP; 4'-Carbocyclic cytidine TP; 4'-Ethynylcytidine TP; 5-(1-Propynyl)ara-cytidine TP; 5-(2-Chloro-phenyl)-2-thiocytidine TP; 5-(4-Amino-phenyl)-2-thiocytidine TP; 5-Aminoallyl-CTP; 5-Cyanocytidine TP; 5-Ethynylara-cytidine TP; 5-Ethynylcytidine TP; 5'-Homo-cytidine TP; 5-Methoxycytidine TP; 5-Trifluoromethyl-Cytidine TP; N4-Amino-cytidine TP; N4-Benzoyl-cytidine TP; Pseudoisocytidine; 7-methylguanosine; N2,2'-O-dimethylguanosine; N2-methylguanosine; Wyosine; 1,2'-O-dimethylguanosine; 1-methylguanosine; 2'-O-methylguanosine; 2'-O-ribosylguanosine (phosphate); 2'-O-methylguanosine; 2'-O-ribosylguanosine (phosphate); 7-aminomethyl-7-deazaguanosine; 7-cyano-7-deazaguanosine; Archaeosine; Methylwyosine; N2,7-dimethylguanosine; N2,N2,2'-O-trimethylguanosine; N2,N2,7-trimethylguanosine; N2,N2-dimethylguanosine; N2,7,2'-O-trimethylguanosine; 6-thio-guanosine; 7-deaza-guanosine; 8-oxo-guanosine; N1-methyl-guanosine; α-thio-guanosine; 2 (propyl)guanine; 2-(alkyl)guanine; 2'-Amino-2'-deoxy-GTP; 2'-Azido-2'-deoxy-GTP; 2'-Deoxy-2'-a-aminoguanosine TP; 2'-Deoxy-2'-a-azidoguanosine TP; 6 (methyl)guanine; 6-(alkyl)guanine; 6-(methyl)guanine; 6-methyl-guanosine; 7 (alkyl)guanine; 7 (deaza)guanine; 7 (methyl)guanine; 7-(alkyl)guanine; 7-(deaza)guanine; 7-(methyl)guanine; 8 (alkyl)guanine; 8 (alkynyl)guanine; 8 (halo)guanine; 8 (thioalkyl)guanine; 8-(alkenyl)guanine; 8-(alkyl)guanine; 8-(alkynyl)guanine; 8-(amino)guanine; 8-(halo)guanine; 8-(hydroxyl)guanine; 8-(thioalkyl)guanine; 8-(thiol)guanine; aza guanine; deaza guanine; N (methyl)guanine; N-(methyl)guanine; 1-methyl-6-thio-guanosine; 6-methoxy-guanosine; 6-thio-7-deaza-8-aza-guanosine; 6-thio-7-deaza-guanosine; 6-thio-7-methyl-guanosine; 7-deaza-8-aza-guanosine; 7-methyl-8-oxo-guanosine; N2,N2-dimethyl-6-thio-guanosine; N2-methyl-6-thio-guanosine; 1-Me-GTP; 2'Fluoro-N2-isobutyl-guanosine TP; 2'O-methyl-N2-isobutyl-guanosine TP; 2'-a-Ethynylguanosine TP; 2'-a-Trifluoromethylguanosine TP; 2'-b-Ethynylguanosine TP; 2'-b-Trifluoromethylguanosine TP; 2'-Deoxy-2',2'-difluoroguanosine TP; 2'-Deoxy-2'-a-mercaptoguanosine TP; 2'-Deoxy-2'-a-thiomethoxyguanosine TP; 2'-Deoxy-2'-b-aminoguanosine TP; 2'-Deoxy-2'-b-azidoguanosine TP; 2'-Deoxy-2'-b-bromoguanosine TP; 2'-Deoxy-2'-b-chloroguanosine TP; 2'-Deoxy-2'-b-fluoroguanosine TP; 2'-Deoxy-2'-b-iodoguanosine TP; 2'-Deoxy-2'-b-mercaptoguanosine TP; 2'-Deoxy-2'-b-thiomethoxyguanosine TP; 4'-Azidoguanosine TP; 4'-Carbocyclic guanosine TP; 4'-Ethynylguanosine TP; 5'-Homo-guanosine TP; 8-bromo-guanosine TP; 9-Deazaguanosine TP; N2-isobutyl-guanosine TP; 1-methylinosine; Inosine; 1,2'-O-dimethylinosine; 2'-O-methylinosine; 7-methylinosine; 2'-O-methylinosine; Epoxyqueosine; galactosyl-queuosine; Mannosylqueuosine; Queuosine; allyamino-thymidine; aza thymidine; deaza thymidine; deoxy-thymidine; 2'-O-methyluridine; 2-thiouridine; 3-methyluridine; 5-carboxymethyluridine; 5-hydroxyuridine; 5-methyluridine; 5-taurinomethyl-2-thiouridine; 5-taurinomethyluridine; Dihydrouridine; Pseudouridine; (3-(3-amino-3-carboxypropyl)uridine; 1-methyl-3-(3-amino-5-carboxypropyl)pseudouridine; 1-methylpseudouridine; 1-ethyl-pseudouridine; 2'-O-methyluridine; 2'-O-methylpseudouridine; 2'-O-methyluridine; 2-thio-2'-O-methyluridine; 3-(3-amino-3-carboxypropyl)uridine; 3,2'-O-dimethyluridine; 3-Methyl-pseudo-Uridine TP; 4-thiouridine; 5-(carboxyhydroxymethyl)uridine; 5-(carboxyhydroxymethyl)uridine methyl ester; 5,2'-O-dimethyluridine; 5,6-di-hydro-uridine; 5-aminomethyl-2-thiouridine; 5-carbamoyl-methyl-2'-O-methyluridine; 5-carbamoylmethyluridine; 5-carboxyhydroxymethyluridine; 5-carboxyhydroxymethyluridine methyl ester; 5-carboxymethylaminomethyl-2'-O-methyluridine; 5-carboxymethylaminomethyl-2-thiouridine; 5-carboxymethylaminomethyl-2-thiouridine; 5-carboxymethylaminomethyluridine; 5-carboxymethylaminomethyluridine; 5-Carbamoylmethyluridine TP; 5-methoxycarbonylmethyl-2'-O-methyluridine; 5-methoxycarbonylmethyl-2-thiouridine; 5-methoxycarbonylmethyluridine; 5-methyluridine,), 5-methoxyuridine; 5-methyl-2-thiouridine; 5-methylaminomethyl-2-selenouridine; 5-methylaminomethyl-2-thiouridine; 5-methylaminomethyluridine; 5-Methyldihydrouridine; 5-Oxyacetic acid-Uridine TP; 5-Oxyacetic acid-methyl ester-Uridine TP; N1-methyl-pseudo-uracil; N1-ethyl-pseudo-uracil; uridine 5-oxyacetic acid; uridine 5-oxyacetic acid methyl ester; 3-(3-Amino-3-carboxypropyl)-Uridine TP; 5-(iso-Pentenylaminomethyl)-

2-thiouridine TP; 5-(iso-Pentenylaminomethyl)-2'-O-methyluridine TP; 5-(iso-Pentenylaminomethyl)uridine TP; 5-propynyl uracil; α-thio-uridine; 1 (aminoalkylamino-carbonylethylenyl)-2(thio)-pseudouracil; 1 (aminoalkylaminocarbonylethylenyl)-2,4-(dithio)pseudouracil; 1 (aminoalkylaminocarbonylethylenyl)-4 (thio)pseudouracil; 1 (aminoalkylaminocarbonylethylenyl)-pseudouracil; 1 (aminocarbonylethylenyl)-2(thio)-pseudouracil; 1 (aminocarbonylethylenyl)-2,4-(dithio)pseudouracil; 1 (aminocarbonylethylenyl)-4 (thio)pseudouracil; 1 (aminocarbonylethylenyl)-pseudouracil; 1 substituted 2(thio)-pseudouracil; 1 substituted 2,4-(dithio)pseudouracil; 1 substituted 4 (thio)pseudouracil; 1 substituted pseudouracil; 1-(aminoalkylamino-carbonylethylenyl)-2-(thio)-pseudouracil; 1-Methyl-3-(3-amino-3-carboxypropyl) pseudouridine TP; 1-Methyl-3-(3-amino-3-carboxypropyl) pseudo-UTP; 1-Methyl-pseudo-UTP; 1-Ethyl-pseudo-UTP; 2 (thio)pseudouracil; 2' deoxy uridine; 2' fluorouridine; 2-(thio)uracil; 2,4-(dithio)pseudouracil; 2' methyl, 2'amino, 2'azido, 2'fluro-guanosine; 2'-Amino-2'-deoxy-UTP; 2'-Azido-2'-deoxy-UTP; 2'-Azido-deoxyuridine TP; 2'-O-methylpseudouridine; 2' deoxy uridine; 2' fluorouridine; 2'-Deoxy-2'-a-aminouridine TP; 2'-Deoxy-2'-a-azidouridine TP; 2-methylpseudouridine; 3 (3 amino-3 carboxypropyl) uracil; 4 (thio)pseudouracil; 4-(thio)pseudouracil; 4-(thio) uracil; 4-thiouracil; 5 (1,3-diazole-1-alkyl)uracil; 5 (2-aminopropyl)uracil; 5 (aminoalkyl)uracil; 5 (dimethylaminoalkyl)uracil; 5 (guanidiniumalkyl)uracil; 5 (methoxycarbonylmethyl)-2-(thio)uracil; 5 (methoxycarbonyl-methyl)uracil; 5 (methyl) 2 (thio)uracil; 5 (methyl) 2,4 (dithio)uracil; 5 (methyl) 4 (thio)uracil; 5 (methylaminomethyl)-2 (thio)uracil; 5 (methylaminomethyl)-2,4 (dithio) uracil; 5 (methylaminomethyl)-4 (thio)uracil; 5 (propynyl) uracil; 5 (trifluoromethyl)uracil; 5-(2-aminopropyl)uracil; 5-(alkyl)-2-(thio)pseudouracil; 5-(alkyl)-2,4 (dithio) pseudouracil; 5-(alkyl)-4 (thio)pseudouracil; 5-(alkyl) pseudouracil; 5-(alkyl)uracil; 5-(alkynyl)uracil; 5-(allylamino)uracil; 5-(cyanoalkyl)uracil; 5-(dialkylaminoalkyl) uracil; 5-(dimethylaminoalkyl)uracil; 5-(guanidiniumalkyl) uracil; 5-(halo)uracil; 5-(1,3-diazole-1-alkyl)uracil; 5-(methoxy)uracil; 5-(methoxycarbonylmethyl)-2-(thio) uracil; 5-(methoxycarbonyl-methyl)uracil; 5-(methyl) 2(thio)uracil; 5-(methyl) 2,4 (dithio)uracil; 5-(methyl) 4 (thio)uracil; 5-(methyl)-2-(thio)pseudouracil; 5-(methyl)-2,4 (dithio)pseudouracil; 5-(methyl)-4 (thio)pseudouracil; 5-(methyl)pseudouracil; 5-(methylaminomethyl)-2 (thio)uracil; 5-(methylaminomethyl)-2,4(dithio)uracil; 5-(methylaminomethyl)-4-(thio)uracil; 5-(propynyl)uracil; 5-(trifluoromethyl)uracil; 5-aminoallyl-uridine; 5-bromo-uridine; 5-iodo-uridine; 5-uracil; 6 (azo)uracil; 6-(azo)uracil; 6-aza-uridine; allyamino-uracil; aza uracil; deaza uracil; N3 (methyl)uracil; Pseudo-UTP-1-2-ethanoic acid; Pseudouracil; 4-Thio-pseudo-UTP; 1-carboxymethyl-pseudouridine; 1-methyl-1-deaza-pseudouridine; 1-propynyl-uridine; 1-taurinomethyl-1-methyl-uridine; 1-taurinomethyl-4-thio-uridine; 1-taurinomethyl-pseudouridine; 2-methoxy-4-thio-pseudouridine; 2-thio-1-methyl-1-deaza-pseudouridine; 2-thio-1-methyl-pseudouridine; 2-thio-5-aza-uridine; 2-thio-dihydropseudouridine; 2-thio-dihydrouridine; 2-thio-pseudouridine; 4-methoxy-2-thio-pseudouridine; 4-methoxy-pseudouridine; 4-thio-1-methyl-pseudouridine; 4-thio-pseudouridine; 5-aza-uridine; Dihydropseudouridine; (±)1-(2-Hydroxypropyl)pseudouridine TP; (2R)-1-(2-Hydroxypropyl)pseudouridine TP; (2S)-1-(2-Hydroxypropyl) pseudouridine TP; (E)-5-(2-Bromo-vinyl)ara-uridine TP; (E)-5-(2-Bromo-vinyl)uridine TP; (Z)-5-(2-Bromo-vinyl) ara-uridine TP; (Z)-5-(2-Bromo-vinyl)uridine TP; 1-(2,2,2-Trifluoroethyl)-pseudo-UTP; 1-(2,2,3,3,3-Pentafluoropropyl)pseudouridine TP; 1-(2,2-Diethoxyethyl)pseudouridine TP; 1-(2,4,6-Trimethylbenzyl)pseudouridine TP; 1-(2,4,6-Trimethyl-benzyl)pseudo-UTP; 1-(2,4,6-Trimethyl-phenyl) pseudo-UTP; 1-(2-Amino-2-carboxyethyl)pseudo-UTP; 1-(2-Amino-ethyl)pseudo-UTP; 1-(2-Hydroxyethyl) pseudouridine TP; 1-(2-Methoxyethyl)pseudouridine TP; 1-(3,4-Bis-trifluoromethoxybenzyl)pseudouridine TP; 1-(3, 4-Dimethoxybenzyl)pseudouridine TP; 1-(3-Amino-3-carboxypropyl)pseudo-UTP; 1-(3-Amino-propyl)pseudo-UTP; 1-(3-Cyclopropyl-prop-2-ynyl)pseudouridine TP; 1-(4-Amino-4-carboxybutyl)pseudo-UTP; 1-(4-Amino-benzyl) pseudo-UTP; 1-(4-Amino-butyl)pseudo-UTP; 1-(4-Amino-phenyl)pseudo-UTP; 1-(4-Azidobenzyl)pseudouridine TP; 1-(4-Bromobenzyl)pseudouridine TP; 1-(4-Chlorobenzyl) pseudouridine TP; 1-(4-Fluorobenzyl)pseudouridine TP; 1-(4-Iodobenzyl)pseudouridine TP; 1-(4-Methanesulfonylbenzyl)pseudouridine TP; 1-(4-Methoxybenzyl)pseudouridine TP; 1-(4-Methoxy-benzyl)pseudo-UTP; 1-(4-Methoxyphenyl)pseudo-UTP; 1-(4-Methylbenzyl)pseudouridine TP; 1-(4-Methyl-benzyl)pseudo-UTP; 1-(4-Nitrobenzyl) pseudouridine TP; 1-(4-Nitro-benzyl)pseudo-UTP; 1(4-Nitro-phenyl)pseudo-UTP; 1-(4-Thiomethoxybenzyl) pseudouridine TP; 1-(4-Trifluoromethoxybenzyl) pseudouridine TP; 1-(4-Trifluoromethylbenzyl) pseudouridine TP; 1-(5-Amino-pentyl)pseudo-UTP; 1-(6-Amino-hexyl)pseudo-UTP; 1,6-Dimethyl-pseudo-UTP; 1-[3-(2-{2-[2-(2-Aminoethoxy)-ethoxy]-ethoxy}-ethoxy)-propionyl]pseudouridine TP; 1-{3-[2-(2-Aminoethoxy)-ethoxy]-propionyl} pseudouridine TP; 1-Acetylpseudouridine TP; 1-Alkyl-6-(1-propynyl)-pseudo-UTP; 1-Alkyl-6-(2-propynyl)-pseudo-UTP; 1-Alkyl-6-allyl-pseudo-UTP; 1-Alkyl-6-ethynyl-pseudo-UTP; 1-Alkyl-6-homoallyl-pseudo-UTP; 1-Alkyl-6-vinyl-pseudo-UTP; 1-Allylpseudouridine TP; 1-Aminomethyl-pseudo-UTP; 1-Benzoylpseudouridine TP; 1-Benzyloxymethylpseudouridine TP; 1-Benzyl-pseudo-UTP; 1-Biotinyl-PEG2-pseudouridine TP; 1-Biotinylpseudouridine TP; 1-Butyl-pseudo-UTP; 1-Cyanomethylpseudouridine TP; 1-Cyclobutylmethyl-pseudo-UTP; 1-Cyclobutyl-pseudo-UTP; 1-Cycloheptylmethyl-pseudo-UTP; 1-Cycloheptyl-pseudo-UTP; 1-Cyclohexylmethyl-pseudo-UTP; 1-Cyclohexyl-pseudo-UTP; 1-Cyclooctylmethyl-pseudo-UTP; 1-Cyclooctyl-pseudo-UTP; 1-Cyclopentylmethyl-pseudo-UTP; 1-Cyclopentyl-pseudo-UTP; 1-Cyclopropylmethyl-pseudo-UTP; 1-Cyclopropyl-pseudo-UTP; 1-Ethyl-pseudo-UTP; 1-Hexyl-pseudo-UTP; 1-Homoallylpseudouridine TP; 1-Hydroxymethylpseudouridine TP; 1-iso-propyl-pseudo-UTP; 1-Me-2-thio-pseudo-UTP; 1-Me-4-thio-pseudo-UTP; 1-Me-alpha-thio-pseudo-UTP; 1-Methanesulfonylmethylpseudouridine TP; 1-Methoxymethylpseudouridine TP; 1-Methyl-6-(2,2,2-Trifluoroethyl)pseudo-UTP; 1-Methyl-6-(4-morpholino)-pseudo-UTP; 1-Methyl-6-(4-thiomorpholino)-pseudo-UTP; 1-Methyl-6-(substituted phenyl) pseudo-UTP; 1-Methyl-6-amino-pseudo-UTP; 1-Methyl-6-azido-pseudo-UTP; 1-Methyl-6-bromo-pseudo-UTP; 1-Methyl-6-butyl-pseudo-UTP; 1-Methyl-6-chloro-pseudo-UTP; 1-Methyl-6-cyano-pseudo-UTP; 1-Methyl-6-dimethylamino-pseudo-UTP; 1-Methyl-6-ethoxy-pseudo-UTP; 1-Methyl-6-ethylcarboxylate-pseudo-UTP; 1-Methyl-6-ethyl-pseudo-UTP; 1-Methyl-6-fluoro-pseudo-UTP; 1-Methyl-6-formyl-pseudo-UTP; 1-Methyl-6-hydroxyamino-pseudo-UTP; 1-Methyl-6-hydroxy-pseudo-UTP; 1-Methyl-6-iodo-pseudo-UTP; 1-Methyl-6-iso-propyl-pseudo-UTP; 1-Methyl-6-methoxy-pseudo-UTP; 1-Methyl-6-methylamino-pseudo-UTP; 1-Methyl-6-phenyl-pseudo-UTP; 1-Methyl-6-propyl-pseudo-UTP; 1-Methyl-6- tert-butyl-pseudo-UTP; 1-Methyl-6-trifluoromethoxy-pseudo-UTP; 1-Methyl-6-trifluoromethyl-pseudo-UTP; 1-Morpholinomethylpseudouridine TP; 1-Pentyl-pseudo-UTP; 1-Phenyl-pseudo-UTP; 1-Pivaloylpseudouridine TP; 1-Propargylpseudouridine TP; 1-Propyl-pseudo-UTP; 1-propynyl-pseudouridine; 1-p-tolyl-pseudo-UTP; 1-tert-Butyl-pseudo-UTP; 1-Thiomethoxymethylpseudouridine TP; 1-Thiomorpholinomethylpseudouridine TP; 1-Trifluoroacetylpseudouridine TP; 1-Trifluoromethyl-pseudo-UTP; 1-Vinylpseudouridine TP; 2,2'-anhydro-uridine TP; 2'-bromo-deoxyuridine TP; 2'-F-5-Methyl-2'-deoxy-UTP; 2'-OMe-S-Me-UTP; 2'-OMe-pseudo-UTP; 2'-a-Ethynyluridine TP; 2'-a-Trifluoromethyluridine TP; 2'-b-Ethynyluridine TP; 2'-b-Trifluoromethyluridine TP; 2'-Deoxy-2',2'-difluorouridine TP; 2'-Deoxy-2'-a-mercaptouridine TP; 2'-Deoxy-2'-a-thiomethoxyuridine TP; 2'-Deoxy-2'-b-aminouridine TP; 2'-Deoxy-2'-b-azidouridine TP; 2'-Deoxy-2'-b-bromouridine TP; 2'-Deoxy-2'-b-chlorouridine TP; 2'-Deoxy-2'-b-fluorouridine TP; 2'-Deoxy-2'-b-iodouridine TP; 2'-Deoxy-2'-b-mercaptouridine TP; 2'-Deoxy-2'-b-thiomethoxyuridine TP; 2-methoxy-4-thio-uridine; 2-methoxyuridine; 2'-O-Methyl-5-(1-propynyl)uridine TP; 3-Alkyl-pseudo-UTP; 4'-Azidouridine TP; 4'-Carbocyclic uridine TP; 4'-Ethynyluridine TP; 5-(1-Propynyl)ara-uridine TP; 5-(2-Furanyl)uridine TP; 5-Cyanouridine TP; 5-Dimethylaminouridine TP; 5'-Homo-uridine TP; 5-iodo-2'-fluoro-deoxyuridine TP; 5-Phenylethynyluridine TP; 5-Trideuteromethyl-6-deuterouridine TP; 5-Trifluoromethyl-Uridine TP; 5-Vinylarauridine TP; 6-(2,2,2-Trifluoroethyl)-pseudo-UTP; 6-(4-Morpholino)-pseudo-UTP; 6-(4-Thiomorpholino)-pseudo-UTP; 6-(Substituted-Phenyl)-pseudo-UTP; 6-Amino-pseudo-UTP; 6-Azido-pseudo-UTP; 6-Bromo-pseudo-UTP; 6-Butyl-pseudo-UTP; 6-Chloro-pseudo-UTP; 6-Cyano-pseudo-UTP; 6-Dimethylamino-pseudo-UTP; 6-Ethoxy-pseudo-UTP; 6-Ethylcarboxylate-pseudo-UTP; 6-Ethyl-pseudo-UTP; 6-Fluoro-pseudo-UTP; 6-Formyl-pseudo-UTP; 6-Hydroxyamino-pseudo-UTP; 6-Hydroxy-pseudo-UTP; 6-Iodo-pseudo-UTP; 6-iso-Propyl-pseudo-UTP; 6-Methoxy-pseudo-UTP; 6-Methylamino-pseudo-UTP; 6-Methyl-pseudo-UTP; 6-Phenyl-pseudo-UTP; 6-Phenyl-pseudo-UTP; 6-Propyl-pseudo-UTP; 6-tert-Butyl-pseudo-UTP; 6-Trifluoromethoxy-pseudo-UTP; 6-Trifluoromethyl-pseudo-UTP; Alpha-thio-pseudo-UTP; Pseudouridine 1-(4-methylbenzenesulfonic acid) TP; Pseudouridine 1-(4-methylbenzoic acid) TP; Pseudouridine TP 1-[3-(2-ethoxy)]propionic acid; Pseudouridine TP 1-[3-{2-(2-[2-(2-ethoxy)-ethoxy]-ethoxy)-ethoxy}]propionic acid; Pseudouridine TP 1-[3-{2-(2-[2-{2 (2-ethoxy]-ethoxy}-ethoxy]-ethoxy)-ethoxy}]propionic acid; Pseudouridine TP 1-[3-{2-(2-[2-ethoxy]-ethoxy)-ethoxy}]propionic acid; Pseudouridine TP 1-[3-{2-(2-ethoxy)-ethoxy}]propionic acid; Pseudouridine TP 1-methylphosphonic acid; Pseudouridine TP 1-methylphosphonic acid diethyl ester; Pseudo-UTP-N1-3-propionic acid; Pseudo-UTP-N1-4-butanoic acid; Pseudo-UTP-N1-5-pentanoic acid; Pseudo-UTP-N1-6-hexanoic acid; Pseudo-UTP-N1-7-heptanoic acid; Pseudo-UTP-N1-methyl-p-benzoic acid; Pseudo-UTP-N1-p-benzoic acid; Wybutosine; Hydroxywybutosine; Isowyosine; Peroxywybutosine; undermodified hydroxywybutosine; 4-demethylwyosine; 2,6-(diamino)purine; 1-(aza)-2-(thio)-3-(aza)-phenoxazin-1-yl: 1,3-(diaza)-2-(oxo)-phenthiazin-1-yl; 1,3-(diaza)-2-(oxo)-phenoxazin-1-yl; 1,3,5-(triaza)-2,6-(dioxa)-naphthalene; 2 (amino)purine; 2,4,5-(trimethyl)phenyl; 2' methyl, 2'amino, 2'azido, 2'fluro-cytidine; 2' methyl, 2'amino, 2'azido, 2'fluro-adenine; 2'methyl, 2'amino, 2'azido, 2'fluro-uridine; 2'-amino-2'-deoxyribose; 2-amino-6-Chloro-purine; 2-aza-inosinyl; 2'-azido-2'-deoxyribose; 2'fluoro-2'-deoxyribose; 2'-fluoro-modified bases; 2'-O-methyl-ribose; 2-oxo-7-aminopyridopyrimidin-3-yl; 2-oxo-pyridopyrimidine-3-yl; 2-pyridinone; 3 nitropyrrole; 3-(methyl)-7-(propynyl) isocarbostyrilyl; 3-(methyl)isocarbostyrilyl; 4-(fluoro)-6-(methyl)benzimidazole; 4-(methyl)benzimidazole; 4-(methyl)indolyl; 4,6-(dimethyl)indolyl; 5 nitroindole; 5 substituted pyrimidines; 5-(methyl)isocarbostyrilyl; 5-nitroindole; 6-(aza)pyrimidine; 6-(azo)thymine; 6-(methyl)-7-(aza)indolyl; 6-chloro-purine; 6-phenyl-pyrrolo-pyrimidin-2-on-3-yl; 7-(aminoalkylhydroxy)-1-(aza)-2-(thio)-3-(aza)-phenthiazin-1-yl; 7-(aminoalkylhydroxy)-1-(aza)-2-(thio)-3-(aza)-phenoxazin-1-yl; 7-(aminoalkylhydroxy)-1,3-(diaza)-2-(oxo)-phenoxazin-1-yl; 7-(aminoalkylhydroxy)-1, 34 diaza)-2-(oxo)-phenthiazin-1-yl; 7-(aminoalkylhydroxy)-1,3-(diaza)-2-(oxo)-phenoxazin-1-yl; 7-(aza)indolyl; 7-(guanidiniumalkylhydroxy)-1-(aza)-2-(thio)-3-(aza)-phenoxazin1-yl; 7-(guanidiniumalkylhydroxy)-1-(aza)-2-(thio)-3-(aza)-phenthiazin-1-yl; 7-(guanidiniumalkylhydroxy)-1-(aza)-2-(thio)-3-(aza)-phenoxazin-1-yl; 7-(guanidiniumalkylhydroxy)-1,3-(diaza)-2-(oxo)-phenoxazin-1-yl; 7-(guanidiniumalkyl-hydroxy)-1,3-(diaza)-2-(oxo)-phenthiazin-1-yl; 7-(guanidiniumalkylhydroxy)-1,3-(diaza)-2-(oxo)-phenoxazin-1-yl; 7-(propynyl)isocarbostyrilyl; 7-(propynyl)isocarbostyrilyl, propynyl-7-(aza)indolyl; 7-deaza-inosinyl; 7-substituted 1-(aza)-2-(thio)-3-(aza)-phenoxazin-1-yl; 7-substituted 1,3-(diaza)-2-(oxo)-phenoxazin-1-yl; 9-(methyl)-imidizopyridinyl; Aminoindolyl; Anthracenyl; bis-ortho-(aminoalkylhydroxy)-6-phenyl-pyrrolo-pyrimidin-2-on-3-yl; bis-ortho-substituted-6-phenyl-pyrrolo-pyrimidin-2-on-3-yl; Difluorotolyl; Hypoxanthine; Imidizopyridinyl; Inosinyl; Isocarbostyrilyl; Isoguanisine; N2-substituted purines; N6-methyl-2-amino-purine; N6-substituted purines; N-alkylated derivative; Napthalenyl; Nitrobenzimidazolyl; Nitroimidazolyl; Nitroindazolyl; Nitropyrazolyl; Nubularine; O6-substituted purines; O-alkylated derivative; ortho-(aminoalkylhydroxy)-6-phenyl-pyrrolo-pyrimidin-2-on-3-yl; ortho-substituted-6-phenyl-pyrrolo-pyrimidin-2-on-3-yl; Oxoformycin TP; para-(aminoalkylhydroxy)-6-phenyl-pyrrolo-pyrimidin-2-on-3-yl; para-substituted-6-phenyl-pyrrolo-pyrimidin-2-on-3-yl; Pentacenyl; Phenanthracenyl; Phenyl; propynyl-7-(aza)indolyl; Pyrenyl; pyridopyrimidin-3-yl; pyridopyrimidin-3-yl, 2-oxo-7-amino-pyridopyrimidin-3-yl; pyrrolo-pyrimidin-2-on-3-yl; Pyrrolopyrimidinyl; Pyrrolopyrizinyl; Stilbenzyl; substituted 1,2,4-triazoles; Tetracenyl; Tubercidine; Xanthine; Xanthosine-5'-TP; 2-thio-zebularine; 5-aza-2-thio-zebularine; 7-deaza-2-amino-purine; pyridin-4-one ribonucleoside; 2-Amino-riboside-TP; Formycin A TP; Formycin B TP; Pyrrolosine TP; 2'-OH-ara-adenosine TP; 2'-OH-ara-cytidine TP; 2'-OH-ara-uridine TP; 2'-OH-ara-guanosine TP; 5-(2-carbomethoxyvinyl)uridine TP; and N6-(19-Amino-pentaoxanonadecyl)adenosine TP.

In some embodiments, the polynucleotide (e.g., RNA polynucleotide, such as mRNA polynucleotide) includes a combination of at least two (e.g., 2, 3, 4 or more) of the aforementioned modified nucleobases.

In some embodiments, the mRNA comprises at least one chemically modified nucleoside. In some embodiments, the at least one chemically modified nucleoside is selected from the group consisting of pseudouridine (ψ), 2-thiouridine (s2U), 4'-thiouridine, 5-methylcytosine, 2-thio-1-methyl-1-deaza-pseudouridine, 2-thio-1-methyl-pseudouridine, 2-thio-5-aza-uridine, 2-thio-dihydropseudouridine, 2-thio-dihydrouridine, 2-thio-pseudouridine, 4-methoxy-2-thio-pseudouridine, 4-methoxy-pseudouridine, 4-thio-1-methylpseudouridine, 4-thio-pseudouridine, 5-aza-uridine, dihydropseudouridine, 5-methyluridine, 5-methoxyuridine, 2'-O-methyl uridine, 1-methyl-pseudouridine (m1ψ), 1-ethyl-pseudouridine (e1ψ), 5-methoxy-uridine (mo5U), 5-methyl-cytidine (m5C), α-thio-guanosine, α-thio-adenosine, 5-cyano uridine, 4'-thio uridine 7-deaza-adenine, 1-methyl-adenosine (m1A), 2-methyl-adenine (m2A), N6-methyl-adenosine (m6A), and 2,6-Diaminopurine, (I), 1-methyl-inosine (m1I), wyosine (imG), methylwyosine (mimG), 7-deaza-guanosine, 7-cyano-7-deaza-guanosine (preQ0), 7-aminomethyl-7-deaza-guanosine (preQ1), 7-methyl-guanosine (m7G), 1-methyl-guanosine (m1G), 8-oxo-guanosine, 7-methyl-8-oxo-guanosine, 2,8-dimethyladenosine, 2-geranylthiouridine, 2-lysidine, 2-selenouridine, 3-(3-amino-3-carboxypropyl)-5,6-dihydrouridine, 3-(3-amino-3-carboxypropyl)pseudouridine, 3-methylpseudouridine, 5-(carboxyhydroxymethyl)-2'-O-methyluridine methyl ester, 5-aminomethyl-2-geranylthiouridine, 5-aminomethyl-2-selenouridine, 5-aminomethyluridine, 5-carbamoylhydroxymethyluridine, 5-carbamoylmethyl-2-thiouridine, 5-carboxymethyl-2-thiouridine, 5-carboxymethylaminomethyl-2-geranylthiouridine, 5-carboxymethylaminomethyl-2-selenouridine, 5-cyanomethyluridine, 5-hydroxycytidine, 5-methylaminomethyl-2-geranylthiouridine, 7-aminocarboxypropyl-demethylwyosine, 7-aminocarboxypropylwyosine, 7-aminocarboxypropylwyosine methyl ester, 8-methyladenosine, N4,N4-dimethylcytidine, N6-formyladenosine, N6-hydroxymethyladenosine, agmatidine, cyclic N6-threonylcarbamoyladenosine, glutamylqueuosine, methylated undermodified hydroxywybutosine, N4,N4,2'-O-trimethylcytidine, geranylated 5-methylaminomethyl-2-thiouridine, geranylated 5-carboxymethylaminomethyl-2-thiouridine, Qbase, preQ0base, preQ1base, and two or more combinations thereof. In some embodiments, the at least one chemically modified nucleoside is selected from the group consisting of pseudouridine, 1-methylpseudouridine, 1-ethyl-pseudouridine, 5-methylcytosine, 5-methoxyuridine, and a combination thereof. In some embodiments, the polynucleotide (e.g., RNA polynucleotide, such as mRNA polynucleotide) includes a combination of at least two (e.g., 2, 3, 4 or more) of the aforementioned modified nucleobases.

(i) Base Modifications

In certain embodiments, the chemical modification is at nucleobases in the polynucleotides (e.g., RNA polynucleotide, such as mRNA polynucleotide). In some embodiments, modified nucleobases in the polynucleotide (e.g., RNA polynucleotide, such as mRNA polynucleotide) are selected from the group consisting of 1-methyl-pseudouridine (m1ψ), 1-ethyl-pseudouridine (elm), 5-methoxy-uridine (mo5U), 5-methyl-cytidine (m5C), pseudouridine (ψ), α-thio-guanosine and α-thio-adenosine. In some embodiments, the polynucleotide includes a combination of at least two (e.g., 2, 3, 4 or more) of the aforementioned modified nucleobases.

In some embodiments, the polynucleotide (e.g., RNA polynucleotide, such as mRNA polynucleotide) comprises pseudouridine (ψ) and 5-methyl-cytidine (m5C). In some embodiments, the polynucleotide (e.g., RNA polynucleotide, such as mRNA polynucleotide) comprises 1-methyl-pseudouridine (m1ψ). In some embodiments, the polynucleotide (e.g., RNA polynucleotide, such as mRNA polynucleotide) comprises 1-ethyl-pseudouridine (e1ψ). In some embodiments, the polynucleotide (e.g., RNA polynucleotide, such as mRNA polynucleotide) comprises 1-methyl-pseudouridine (m1ψ) and 5-methyl-cytidine (m5C). In some embodiments, the polynucleotide (e.g., RNA polynucleotide, such as mRNA polynucleotide) comprises 1-ethyl-pseudouridine (e1ψ) and 5-methyl-cytidine (m5C). In some embodiments, the polynucleotide (e.g., RNA polynucleotide, such as mRNA polynucleotide) comprises 2-thiouridine (s2U). In some embodiments, the polynucleotide (e.g., RNA polynucleotide, such as mRNA polynucleotide) comprises 2-thiouridine and 5-methyl-cytidine (m5C). In some embodiments, the polynucleotide (e.g., RNA polynucleotide, such as mRNA polynucleotide) comprises methoxy-uridine (mo5U). In some embodiments, the polynucleotide (e.g., RNA polynucleotide, such as mRNA polynucleotide) comprises 5-methoxy-uridine (mo5U) and 5-methyl-cytidine (m5C). In some embodiments, the polynucleotide (e.g., RNA polynucleotide, such as mRNA polynucleotide) comprises 2'-O-methyl uridine. In some embodiments, the polynucleotide (e.g., RNA polynucleotide, such as mRNA polynucleotide) comprises 2'-O-methyl uridine and 5-methyl-cytidine (m5C). In some embodiments, the polynucleotide (e.g., RNA polynucleotide, such as mRNA polynucleotide) comprises N6-methyl-adenosine (m6A). In some embodiments, the polynucleotide (e.g., RNA polynucleotide, such as mRNA polynucleotide) comprises N6-methyl-adenosine (m6A) and 5-methyl-cytidine (m5C).

In some embodiments, the polynucleotide (e.g., mRNA polynucleotide, such as mRNA polynucleotide) is uniformly modified (e.g., fully modified, modified throughout the entire sequence) for a particular modification. For example, a polynucleotide can be uniformly modified with 5-methyl-cytidine (m5C), meaning that all cytosine residues in the mRNA sequence are replaced with 5-methyl-cytidine (m5C). Similarly, a polynucleotide can be uniformly modified for any type of nucleoside residue present in the sequence by replacement with a modified residue such as any of those set forth above.

In some embodiments, the chemically modified nucleosides in the open reading frame are selected from the group consisting of uridine, adenine, cytosine, guanine, and any combination thereof.

In some embodiments, the modified nucleobase is a modified cytosine. Examples of nucleobases and nucleosides having a modified cytosine include N4-acetyl-cytidine (ac4C), 5-methyl-cytidine (m5C), 5-halo-cytidine (e.g., 5-iodo-cytidine), 5-hydroxymethyl-cytidine (hm5C), 1-methyl-pseudoisocytidine, 2-thio-cytidine (s2C), 2-thio-5-methyl-cytidine.

In some embodiments, a modified nucleobase is a modified uridine. Example nucleobases and nucleosides having a modified uridine include 5-cyano uridine or 4'-thio uridine.

In some embodiments, a modified nucleobase is a modified adenine. Example nucleobases and nucleosides having a modified adenine include 7-deaza-adenine, 1-methyl-adenosine (m1A), 2-methyl-adenine (m2A), N6-methyl-adenine (m6A), and 2,6-Diaminopurine.

In some embodiments, a modified nucleobase is a modified guanine. Example nucleobases and nucleosides having a modified guanine include inosine (I), 1-methyl-inosine (m1I), wyosine (imG), methylwyosine (mimG), 7-deaza-guanosine, 7-cyano-7-deaza-guanosine (preQ0), 7-aminomethyl-7-deaza-guanosine (preQ1), 7-methyl-guanosine (m7G), 1-methyl-guanosine (m1G), 8-oxo-guanosine, 7-methyl-8-oxo-guanosine.

In some embodiments, the nucleobase modified nucleotides in the polynucleotide (e.g., RNA polynucleotide, such as mRNA polynucleotide) are 5-methoxyuridine.

In some embodiments, the polynucleotide (e.g., RNA polynucleotide, such as mRNA polynucleotide) includes a combination of at least two (e.g., 2, 3, 4 or more) of modified nucleobases.

In some embodiments, at least 95% of a type of nucleobases (e.g., uracil) in a polynucleotide of the invention (e.g., an mRNA polynucleotide encoding PBGD) are modified nucleobases. In some embodiments, at least 95% of uracil in a polynucleotide of the present invention (e.g., an mRNA polynucleotide encoding PBGD) is 5-methoxyuracil.

In some embodiments, the polynucleotide (e.g., RNA polynucleotide, such as mRNA polynucleotide) comprises 5-methoxyuridine (5mo5U) and 5-methyl-cytidine (m5C).

In some embodiments, the polynucleotide (e.g., RNA polynucleotide, such as mRNA polynucleotide) is uniformly modified (e.g., fully modified, modified throughout the entire sequence) for a particular modification. For example, a polynucleotide can be uniformly modified with 5-methoxyuridine, meaning that substantially all uridine residues in the mRNA sequence are replaced with 5-methoxyuridine. Similarly, a polynucleotide can be uniformly modified for any type of nucleoside residue present in the sequence by replacement with a modified residue such as any of those set forth above.

In some embodiments, the modified nucleobase is a modified cytosine.

In some embodiments, a modified nucleobase is a modified uracil. Example nucleobases and nucleosides having a modified uracil include 5-methoxyuracil.

In some embodiments, a modified nucleobase is a modified adenine.

In some embodiments, a modified nucleobase is a modified guanine.

In some embodiments, the nucleobases, sugar, backbone, or any combination thereof in the open reading frame encoding a PBGD polypeptide are chemically modified by at least 10%, at least 20%, at least 30%, at least 40%, at least 50%, at least 60%, at least 70%, at least 80%, at least 90%, at least 95%, at least 99%, or 100%.

In some embodiments, the uridine nucleosides in the open reading frame encoding a PBGD polypeptide are chemically modified by at least 10%, at least 20%, at least 30%, at least 40%, at least 50%, at least 60%, at least 70%, at least 80%, at least 90%, at least 95%, at least 99%, or 100%.

In some embodiments, the adenosine nucleosides in the open reading frame encoding a PBGD polypeptide are chemically modified by at least 10%, at least 20%, at least 30%, at least 40%, at least 50%, at least 60%, at least 70%, at least 80%, at least 90%, at least 95%, at least 99%, or 100%.

In some embodiments, the cytidine nucleosides in the open reading frame encoding a PBGD polypeptide are chemically modified by at least at least 10%, at least 20%, at least 30%, at least 40%, at least 50%, at least 60%, at least 70%, at least 80%, at least 90%, at least 95%, at least 99%, or 100%.

In some embodiments, the guanosine nucleosides in the open reading frame encoding a PBGD polypeptide are chemically modified by at least at least 10%, at least 20%, at least 30%, at least 40%, at least 50%, at least 60%, at least 70%, at least 80%, at least 90%, at least 95%, at least 99%, or 100%.

In some embodiments, the polynucleotides can include any useful linker between the nucleosides. Such linkers, including backbone modifications, that are useful in the composition of the present disclosure include, but are not limited to the following: 3'-alkylene phosphonates, 3'-amino phosphoramidate, alkene containing backbones, aminoalkylphosphoramidates, aminoalkylphosphotriesters, boranophosphates, —$CH_2$—O—N($CH_3$)—$CH_2$—, —$CH_2$—N($CH_3$)—N($CH_3$)—$CH_2$—, —$CH_2$—NH—$CH_2$—, chiral phosphonates, chiral phosphorothioates, formacetyl and thioformacetyl backbones, methylene (methylimino), methylene formacetyl and thioformacetyl backbones, methyleneimino and methylenehydrazino backbones, morpholino linkages, —N($CH_3$)—$CH_2$—$CH_2$—, oligonucleosides with heteroatom internucleoside linkage, phosphinates, phosphoramidates, phosphorodithioates, phosphorothioate internucleoside linkages, phosphorothioates, phosphotriesters, PNA, siloxane backbones, sulfamate backbones, sulfide sulfoxide and sulfone backbones, sulfonate and sulfonamide backbones, thionoalkylphosphonates, thionoalkylphosphotriesters, and thionophosphoramidates.

(ii) Sugar Modifications

The modified nucleosides and nucleotides (e.g., building block molecules), which can be incorporated into a polynucleotide (e.g., RNA or mRNA, as described herein), can be modified on the sugar of the ribonucleic acid. For example, the 2' hydroxyl group (OH) can be modified or replaced with a number of different substituents. Exemplary substitutions at the 2'-position include, but are not limited to, H, halo, optionally substituted $C_{1-6}$ alkyl; optionally substituted $C_{1-6}$ alkoxy; optionally substituted $C_{6-10}$ aryloxy; optionally substituted $C_{3-8}$ cycloalkyl; optionally substituted $C_{3-8}$ cycloalkoxy; optionally substituted $C_{6-10}$ aryloxy; optionally substituted $C_{6-10}$ aryl-$C_{1-6}$ alkoxy, optionally substituted $C_{1-12}$ (heterocyclyl)oxy; a sugar (e.g., ribose, pentose, or any described herein); a polyethyleneglycol (PEG), —O($CH_2CH_2O$)$_n$$CH_2CH_2$OR, where R is H or optionally substituted alkyl, and n is an integer from 0 to 20 (e.g., from 0 to 4, from 0 to 8, from 0 to 10, from 0 to 16, from 1 to 4, from 1 to 8, from 1 to 10, from 1 to 16, from 1 to 20, from 2 to 4, from 2 to 8, from 2 to 10, from 2 to 16, from 2 to 20, from 4 to 8, from 4 to 10, from 4 to 16, and from 4 to 20); "locked" nucleic acids (LNA) in which the 2'-hydroxyl is connected by a $C_{1-6}$ alkylene or $C_{1-6}$ heteroalkylene bridge to the 4'-carbon of the same ribose sugar, where exemplary bridges included methylene, propylene, ether, or amino bridges; aminoalkyl, as defined herein; aminoalkoxy, as defined herein; amino as defined herein; and amino acid, as defined herein Generally, RNA includes the sugar group ribose, which is a 5-membered ring having an oxygen. Exemplary, non-limiting modified nucleotides include replacement of the oxygen in ribose (e.g., with S, Se, or alkylene, such as methylene or ethylene); addition of a double bond (e.g., to replace ribose with cyclopentenyl or cyclohexenyl); ring contraction of ribose (e.g., to form a 4-membered ring of cyclobutane or oxetane); ring expansion of ribose (e.g., to form a 6- or 7-membered ring having an additional carbon or heteroatom, such as for anhydrohexitol, altritol, mannitol, cyclohexanyl, cyclohexenyl, and morpholino that also has a phosphoramidate backbone); multicyclic forms (e.g., tricyclo; and "unlocked" forms, such as glycol nucleic acid (GNA) (e.g., R-GNA or S-GNA, where ribose is replaced by glycol units attached to phosphodiester bonds), threose nucleic acid (TNA, where ribose is replace with α-L-threofuranosyl-(3'→2')), and peptide nucleic acid (PNA, where 2-amino-ethyl-glycine linkages replace the ribose and phosphodiester backbone). The sugar group can also contain one or more carbons that possess the opposite stereochemical configuration than that of the corresponding carbon in ribose. Thus, a polynucleotide molecule can include nucleotides containing, e.g., arabinose, as the sugar. Such sugar modifications are taught International Patent Publication Nos. WO2013052523 and WO2014093924, the contents of each of which are incorporated herein by reference in their entireties.

(iii) Combinations of Modifications

The polynucleotides of the invention (e.g., a polynucleotide comprising a nucleotide sequence encoding a PBGD polypeptide or a functional fragment or variant thereof) can include a combination of modifications to the sugar, the nucleobase, and/or the internucleoside linkage. These combinations can include any one or more modifications described herein.

Combinations of modified nucleotides can be used to form the polynucleotides of the invention. Unless otherwise noted, the modified nucleotides can be completely substituted for the natural nucleotides of the polynucleotides of the invention. As a non-limiting example, the natural nucleotide uridine can be substituted with a modified nucleoside described herein. In another non-limiting example, the natural nucleotide uridine can be partially substituted or replaced (e.g., about 0.1%, 1%, 5%, 10%, 15%, 20%, 25%, 30%, 35%, 40%, 45%, 50%, 55%, 60%, 65%, 70%, 75%, 80%, 85%, 90%, 95% or 99.9%) with at least one of the modified nucleoside disclosed herein. Any combination of base/sugar or linker can be incorporated into the polynucleotides of the invention and such modifications are taught in International Patent Publications WO2013052523 and WO2014093924, and U.S. Publ. Nos. US 20130115272 and US20150307542, the contents of each of which are incorporated herein by reference in its entirety.

11. UNTRANSLATED REGIONS (UTRS)

Untranslated regions (UTRs) are nucleic acid sections of a polynucleotide before a start codon (5'UTR) and after a stop codon (3'UTR) that are not translated. In some embodiments, a polynucleotide (e.g., a ribonucleic acid (RNA), e.g., a messenger RNA (mRNA)) of the invention comprising an open reading frame (ORF) encoding a PBGD polypeptide further comprises UTR (e.g., a 5'UTR or functional fragment thereof, a 3'UTR or functional fragment thereof, or a combination thereof).

A UTR can be homologous or heterologous to the coding region in a polynucleotide. In some embodiments, the UTR is homologous to the ORF encoding the PBGD polypeptide. In some embodiments, the UTR is heterologous to the ORF encoding the PBGD polypeptide. In some embodiments, the polynucleotide comprises two or more 5'UTRs or functional fragments thereof, each of which has the same or different nucleotide sequences. In some embodiments, the polynucleotide comprises two or more 3'UTRs or functional fragments thereof, each of which has the same or different nucleotide sequences.

In some embodiments, the 5'UTR or functional fragment thereof, 3' UTR or functional fragment thereof, or any combination thereof is sequence optimized.

In some embodiments, the 5'UTR or functional fragment thereof, 3' UTR or functional fragment thereof, or any combination thereof comprises at least one chemically modified nucleobase, e.g., 1-methylpseudouridine or 5-methoxyuracil.

UTRs can have features that provide a regulatory role, e.g., increased or decreased stability, localization and/or translation efficiency. A polynucleotide comprising a UTR can be administered to a cell, tissue, or organism, and one or more regulatory features can be measured using routine methods. In some embodiments, a functional fragment of a 5'UTR or 3'UTR comprises one or more regulatory features of a full length 5' or 3' UTR, respectively.

Natural 5'UTRs bear features that play roles in translation initiation. They harbor signatures like Kozak sequences that are commonly known to be involved in the process by which the ribosome initiates translation of many genes. Kozak sequences have the consensus CCR(A/G)CCAUGG, where R is a purine (adenine or guanine) three bases upstream of the start codon (AUG), which is followed by another 'G'. 5'UTRs also have been known to form secondary structures that are involved in elongation factor binding.

By engineering the features typically found in abundantly expressed genes of specific target organs, one can enhance the stability and protein production of a polynucleotide. For example, introduction of 5'UTR of liver-expressed mRNA, such as albumin, serum amyloid A, Apolipoprotein A/B/E, transferrin, alpha fetoprotein, erythropoietin, or Factor VIII, can enhance expression of polynucleotides in hepatic cell lines or liver. Likewise, use of 5'UTR from other tissue-specific mRNA to improve expression in that tissue is possible for muscle (e.g., MyoD, Myosin, Myoglobin, Myogenin, Herculin), for endothelial cells (e.g., Tie-1, CD36), for myeloid cells (e.g., C/EBP, AML1, G-CSF, GM-CSF, CD11b, MSR, Fr-1, i-NOS), for leukocytes (e.g., CD45, CD18), for adipose tissue (e.g., CD36, GLUT4, ACRP30, adiponectin) and for lung epithelial cells (e.g., SP-A/B/C/D).

In some embodiments, UTRs are selected from a family of transcripts whose proteins share a common function, structure, feature or property. For example, an encoded polypeptide can belong to a family of proteins (i.e., that share at least one function, structure, feature, localization, origin, or expression pattern), which are expressed in a particular cell, tissue or at some time during development. The UTRs from any of the genes or mRNA can be swapped for any other UTR of the same or different family of proteins to create a new polynucleotide.

In some embodiments, the 5'UTR and the 3'UTR can be heterologous. In some embodiments, the 5'UTR can be derived from a different species than the 3'UTR. In some embodiments, the 3'UTR can be derived from a different species than the 5'UTR.

Co-owned International Patent Application No. PCT/US2014/021522 (Publ. No. WO/2014/164253, incorporated herein by reference in its entirety) provides a listing of exemplary UTRs that can be utilized in the polynucleotide of the present invention as flanking regions to an ORF.

Exemplary UTRs of the application include, but are not limited to, one or more 5'UTR and/or 3'UTR derived from the nucleic acid sequence of: a globin, such as an α- or β-globin (e.g., a *Xenopus*, mouse, rabbit, or human globin); a strong Kozak translational initiation signal; a CYBA (e.g., human cytochrome b-245 α polypeptide); an albumin (e.g., human albumin7); a HSD17B4 (hydroxysteroid (17β) dehydrogenase); a virus (e.g., a tobacco etch virus (TEV), a Venezuelan equine encephalitis virus (VEEV), a Dengue virus, a cytomegalovirus (CMV) (e.g., CMV immediate early 1 (IE1)), a hepatitis virus (e.g., hepatitis B virus), a sindbis virus, or a PAV barley yellow dwarf virus); a heat shock protein (e.g., hsp70); a translation initiation factor (e.g., eIF4G); a glucose transporter (e.g., hGLUT1 (human glucose transporter 1)); an actin (e.g., human α or β actin); a GAPDH; a tubulin; a histone; a citric acid cycle enzyme; a topoisomerase (e.g., a 5'UTR of a TOP gene lacking the 5' TOP motif (the oligopyrimidine tract)); a ribosomal protein Large 32 (L32); a ribosomal protein (e.g., human or mouse ribosomal protein, such as, for example, rps9); an ATP synthase (e.g., ATP5A1 or the β subunit of mitochondrial H+-ATP synthase); a growth hormone e (e.g., bovine (bGH) or human (hGH)); an elongation factor (e.g., elongation factor 1 α1 (EEF1A1)); a manganese superoxide dismutase (MnSOD); a myocyte enhancer factor 2A (MEF2A); a β-F1-ATPase, a creatine kinase, a myoglobin, a granulocyte-colony stimulating factor (G-CSF); a collagen (e.g., collagen type I, alpha 2 (Col1A2), collagen type I, alpha 1 (Col1A1), collagen type VI, alpha 2 (Col6A2), collagen type VI, alpha 1 (Col6A1)); a ribophorin (e.g., ribophorin I (RPNI)); a low density lipoprotein receptor-related protein (e.g., LRP1); a cardiotrophin-like cytokine factor (e.g., Nnt1); calreticulin (Calr); a procollagen-lysine, 2-oxoglutarate 5-dioxygenase 1 (Plod1); and a nucleobindin (e.g., Nucb1).

In some embodiments, the 5'UTR is selected from the group consisting of a β-globin 5'UTR; a 5'UTR containing a strong Kozak translational initiation signal; a cytochrome b-245 α polypeptide (CYBA) 5'UTR; a hydroxysteroid (17-β) dehydrogenase (HSD17B4) 5'UTR; a Tobacco etch virus (TEV) 5'UTR; a Venezuelen equine encephalitis virus (TEEV) 5'UTR; a 5' proximal open reading frame of rubella virus (RV) RNA encoding nonstructural proteins; a Dengue virus (DEN) 5'UTR; a heat shock protein 70 (Hsp70) 5'UTR; a eIF4G 5'UTR; a GLUT1 5'UTR; functional fragments thereof and any combination thereof.

In some embodiments, the 3'UTR is selected from the group consisting of a β-globin 3'UTR; a CYBA 3'UTR; an albumin 3'UTR; a growth hormone (GH) 3'UTR; a VEEV 3'UTR; a hepatitis B virus (HBV) 3'UTR; α-globin 3'UTR; a DEN 3'UTR; a PAV barley yellow dwarf virus (BYDV-PAV) 3'UTR; an elongation factor 1 α1 (EEF1A1) 3'UTR; a manganese superoxide dismutase (MnSOD) 3'UTR; a β subunit of mitochondrial H(+)-ATP synthase (β-mRNA) 3'UTR; a GLUT1 3'UTR; a MEF2A 3'UTR; a β-F1-ATPase 3'UTR; functional fragments thereof and combinations thereof.

Wild-type UTRs derived from any gene or mRNA can be incorporated into the polynucleotides of the invention. In some embodiments, a UTR can be altered relative to a wild type or native UTR to produce a variant UTR, e.g., by changing the orientation or location of the UTR relative to the ORF; or by inclusion of additional nucleotides, deletion of nucleotides, swapping or transposition of nucleotides. In some embodiments, variants of 5' or 3' UTRs can be utilized, for example, mutants of wild type UTRs, or variants wherein one or more nucleotides are added to or removed from a terminus of the UTR.

Additionally, one or more synthetic UTRs can be used in combination with one or more non-synthetic UTRs. See, e.g., Mandal and Rossi, Nat. Protoc. 2013 8(3):568-82, and sequences available at www.addgene.org/Derrick_Rossi/, the contents of each are incorporated herein by reference in their entirety.

UTRs or portions thereof can be placed in the same orientation as in the transcript from which they were selected or can be altered in orientation or location. Hence, a 5' and/or 3' UTR can be inverted, shortened, lengthened, or combined with one or more other 5' UTRs or 3' UTRs.

In some embodiments, the polynucleotide comprises multiple UTRs, e.g., a double, a triple or a quadruple 5'UTR or 3'UTR. For example, a double UTR comprises two copies of the same UTR either in series or substantially in series. For example, a double beta-globin 3'UTR can be used (see US2010/0129877, the contents of which are incorporated herein by reference in its entirety).

In certain embodiments, the polynucleotides of the invention comprise a 5'UTR and/or a 3'UTR selected from any of the UTRs disclosed herein. In some embodiments, the 5'UTR comprises:

```
5'UTR-001 (Upstream UTR)
                                        (SEQ ID NO. 39)
(GGGAAAUAAGAGAGAAAAGAAGAGUAAGAAGAAAUAUAAGAGCCACC);

5'UTR-002 (Upstream UTR)
                                        (SEQ ID NO. 40)
(GGGAGAUCAGAGAGAAAAGAAGAGUAAGAAGAAAUAUAAGAGCCACC);

5'UTR-003 (Upstream UTR)
(See SEQ ID NO. 41);

5'UTR-004 (Upstream UTR)
                                        (SEQ ID NO. 42)
(GGGAGACAAGCUUGGCAUUCCGGUACUGUUGGUAAAGCCACC);

5'UTR-005 (Upstream UTR)
                                        (SEQ ID NO. 43)
(GGGAGAUCAGAGAGAAAAGAAGAGUAAGAAGAAAUAUAAGAGCCACC);

5'UTR-006 (Upstream UTR)
(See SEQ ID NO. 44);

5'UTR-007 (Upstream UTR)
                                        (SEQ ID NO. 45)
(GGGAGACAAGCUUGGCAUUCCGGUACUGUUGGUAAAGCCACC);

5'UTR-008 (Upstream UTR)
                                        (SEQ ID NO. 46)
(GGGAAUUAACAGAGAAAAGAAGAGUAAGAAGAAAUAUAAGAGCCACC);

5'UTR-009 (Upstream UTR)
                                        (SEQ ID NO. 47)
(GGGAAAUUAGACAGAAAAGAAGAGUAAGAAGAAAUAUAAGAGCCACC);

UTR 5'UTR-010, Upstream
                                        (SEQ ID NO. 48)
(GGGAAAUAAGAGAGUAAAGAACAGUAAGAAGAAAUAUAAGAGCCACC);

5'UTR-011 (Upstream UTR)
                                        (SEQ ID NO. 49)
(GGGAAAAAGAGAGAAAAGAAGACUAAGAAGAAAUAUAAGAGCCACC);

5'UTR-012 (Upstream UTR)
                                        (SEQ ID NO. 50)
(GGGAAAUAAGAGAGAAAAGAAGAGUAAGAAGAUAUAUAAGAGCCACC);

5'UTR-013 (Upstream UTR)
                                        (SEQ ID NO. 51)
(GGGAAAUAAGAGACAAAACAAGAGUAAGAAGAAAUAUAAGAGCCACC);

5'UTR-014 (Upstream UTR)
                                        (SEQ ID NO. 52)
(GGGAAAUUAGAGAGUAAAGAACAGUAAGUAGAAUUAAAAGAGCCACC);

5'UTR-15 (Upstream UTR)
                                        (SEQ ID NO. 53)
(GGGAAAUAAGAGAGAAUAGAAGAGUAAGAAGAAAUAUAAGAGCCACC);

5'UTR-016 (Upstream UTR)
                                        (SEQ ID NO. 54)
(GGGAAAUAAGAGAGAAAAGAAGAGUAAGAAGAAAAUUAAGAGCCACC);

5'UTR-017 (Upstream UTR)
                                        (SEQ ID NO. 55)
(GGGAAAUAAGAGAGAAAAGAAGAGUAAGAAGAAAUUUAAGAGCCACC);
or 5'UTR-018 (Upstream UTR)
                                        (SEQ ID NO. 56)
(UCAAGCUUUUGGACCCUCGUACAGAAGCUAAUACGACUCACUAUAGGGA

AAUAAGAGAGAAAAGAAGAGUAAGAAGAAAUAUAAGAGCCACC).
```

In some embodiments, the 3'UTR comprises:

142-3p 3'UTR (UTR including miR142-3p
binding site)
(SEQ ID NO. 57)
(UGAUAAUAGUCCAUAAAGUAGGAAACACUACAGCUGGAGCCUCGGUGGC

CAUGCUUCUUGCCCCUUGGGCCUCCCCCCAGCCCCUCCUCCCCUUCCUGC

ACCCGUACCCCCGUGGUCUUUGAAUAAAGUCUGAGUGGGCGGC);

142-3p 3'UTR (UTR including miR142-3p
binding site)
(SEQ ID NO. 58)
(UGAUAAUAGGCUGGAGCCUCGGUGGCUCCAUAAAGUAGGAAACACUACA

CAUGCUUCUUGCCCCUUGGGCCUCCCCCCAGCCCCUCCUCCCCUUCCUGC

ACCCGUACCCCCGUGGUCUUUGAAUAAAGUCUGAGUGGGCGGC);

142-3p 3'UTR (UTR including miR142-3p
binding site)
(SEQ ID NO. 59)
(UGAUAAUAGGCUGGAGCCUCGGUGGCCAUGCUUCUUGCCCCUUCCAUAA

AGUAGGAAACACUACAUGGGCCUCCCCCCAGCCCCUCCUCCCCUUCCUGC

ACCCGUACCCCCGUGGUCUUUGAAUAAAGUCUGAGUGGGCGGC);

142-3p 3'UTR (UTR including miR142-3p
binding site)
(SEQ ID NO. 60)
(UGAUAAUAGGCUGGAGCCUCGGUGGCCAUGCUUCUUGCCCCUUGGGCCU

CCCCCCAGUCCAUAAAGUAGGAAACACUACACCCCUCCUCCCCUUCCUGC

ACCCGUACCCCCGUGGUCUUUGAAUAAAGUCUGAGUGGGCGGC);

142-3p 3'UTR (UTR including miR142-3p
binding site)
(SEQ ID NO. 61)
(UGAUAAUAGGCUGGAGCCUCGGUGGCCAUGCUUCUUGCCCCUUGGGCCU

CCCCCCAGCCCCUCCUCCCCUUCUCCAUAAAGUAGGAAACACUACACUGC

ACCCGUACCCCCGUGGUCUUUGAAUAAAGUCUGAGUGGGCGGC);

142-3p 3'UTR (UTR including miR142-3p
binding site)
(SEQ ID NO. 62)
(UGAUAAUAGGCUGGAGCCUCGGUGGCCAUGCUUCUUGCCCCUUGGGCCU

CCCCCCAGCCCCUCCUCCCCUUCCUGCACCCGUACCCCCUCCAUAAAGUA

GGAAACACUACAGUGGUCUUUGAAUAAAGUCUGAGUGGGCGGC);

142-3p 3'UTR (UTR including miR142-3p
binding site)
(SEQ ID NO. 63)
(UGAUAAUAGGCUGGAGCCUCGGUGGCCAUGCUUCUUGCCCCUUGGGCCU

CCCCCCAGCCCCUCCUCCCCUUCCUGCACCCGUACCCCCGUGGUCUUUGA

AUAAAGUUCCAUAAAGUAGGAAACACUACACUGAGUGGGCGGC);

3'UTR-001 (Creatine Kinase UTR)
(See SEQ ID NO. 64);

3'UTR-002 (Myoglobin UTR)
(See SEQ ID NO. 65);

3'UTR-003 (α-actin UTR)
(See SEQ ID NO. 66);

3'UTR-004 (Albumin UTR)
(See SEQ ID NO. 67);

3'UTR-005 (α-globin UTR)
(See SEQ ID NO. 68);

3'UTR-006 (G-CSF UTR)
(See SEQ ID NO. 69);

3'UTR-007 (Col1a2; collagen, type I,
alpha 2 UTR)
(See SEQ ID NO. 70);

3'UTR-008 (Col6a2; collagen, type VI,
alpha 2 UTR)
(See SEQ ID NO. 71);

3'UTR-009 (RPN1; ribophorin I UTR)
(See SEQ ID NO. 72);

3'UTR-010 (LRP1; low density lipoprotein
receptor-related protein 1 UTR)
(See SEQ ID NO. 73);

3'UTR-011 (Nnt1; cardiotrophin-like
cytokine factor 1 UTR)
(See SEQ ID NO. 74);

3'UTR-012 (Col6a1; collagen, type VI,
alpha 1 UTR)
(See SEQ ID NO. 75);

3'UTR-013 (Calr; calreticulin UTR)
(See SEQ ID NO. 76);

3'UTR-014 (Col1a1; collagen, type I,
alpha 1 UTR)
(See SEQ ID NO. 77);

3'UTR-015 (Plod1; procollagen-lysine,
2-oxoglutarate 5-dioxygenase 1 UTR)
(See SEQ ID NO. 78);

3'UTR-016 (Nucb1; nucleobindin 1 UTR)
(See SEQ ID NO. 79);

3'UTR-017 (α-globin)
(See SEQ ID NO. 80);

3'UTR-018 (See SEQ ID NO. 81);

3'UTR (miR 142-3p and miR 126-3p
bindinG sites variant 1)
(SEQ ID NO. 149)
UGAUAAUAGUCCAUAAAGUAGGAAACACUACAGCUGGAGCCUCGGUGGCC

AUGCUUCUUGCCCCUUGGGCCUCCCCCCAGCCCCUCCUCCCCUUCCUGCA

CCCGUACCCCCGCAUUAUUACUCACGGUACGAGUGGUCUUUGAAUAAAG

UCUGAGUGGGCGGC;

3'UTR (miR 142-3p and miR 126-3p
binding sites variant 2)
(SEQ ID NO. 150)
UGAUAAUAGUCCAUAAAGUAGGAAACACUACAGCUGGAGCCUCGGUGGCC

UAGCUUCUUGCCCCUUGGGCCUCCCCCCAGCCCCUCCUCCCCUUCCUGCA

CCCGUACCCCCGCAUUAUUACUCACGGUACGAGUGGUCUUUGAAUAAAG

UCUGAGUGGGCGGC;

or

3'UTR (miR 142-3p binding site
variant 3)
(SEQ ID NO. 151)
UGAUAAUAGGCUGGAGCCUCGGUGGCCUAGCUUCUUGCCCCUUGGGCCUC

CCCCCAGCCCCUCCUCCCCUUCCUGCACCCGUACCCCCUCCAUAAAGUAG

GAAACACUACAGUGGUCUUUGAAUAAAGUCUGAGUGGGCGGC.

In certain embodiments, the 5'UTR and/or 3'UTR sequence of the invention comprises a nucleotide sequence at least about 60%, at least about 70%, at least about 80%, at least about 90%, at least about 95%, at least about 96%, at least about 97%, at least about 98%, at least about 99%, or about 100% identical to a sequence selected from the group consisting of 5'UTR sequences comprising any of SEQ ID NOs: 39 to 56, 83, 189 to 191 and/or 3'UTR sequences comprises any of SEQ ID NOs: 57 to 81, 84, 149 to 151, 161 to 172, 192 to 199, and any combination thereof.

The polynucleotides of the invention can comprise combinations of features. For example, the ORF can be flanked by a 5'UTR that comprises a strong Kozak translational initiation signal and/or a 3'UTR comprising an oligo(dT) sequence for templated addition of a poly-A tail. A 5'UTR can comprise a first polynucleotide fragment and a second polynucleotide fragment from the same and/or different UTRs (see, e.g., US2010/0293625, herein incorporated by reference in its entirety).

Other non-UTR sequences can be used as regions or subregions within the polynucleotides of the invention. For example, introns or portions of intron sequences can be incorporated into the polynucleotides of the invention. Incorporation of intronic sequences can increase protein production as well as polynucleotide expression levels. In some embodiments, the polynucleotide of the invention comprises an internal ribosome entry site (IRES) instead of or in addition to a UTR (see, e.g., Yakubov et al., Biochem. Biophys. Res. Commun. 2010 394(1):189-193, the contents of which are incorporated herein by reference in their entirety). In some embodiments, the polynucleotide comprises an IRES instead of a 5'UTR sequence. In some embodiments, the polynucleotide comprises an ORF and a viral capsid sequence. In some embodiments, the polynucleotide comprises a synthetic 5'UTR in combination with a non-synthetic 3'UTR.

In some embodiments, the UTR can also include at least one translation enhancer polynucleotide, translation enhancer element, or translational enhancer elements (collectively, "TEE," which refers to nucleic acid sequences that increase the amount of polypeptide or protein produced from a polynucleotide. As a non-limiting example, the TEE can include those described in US2009/0226470, incorporated herein by reference in its entirety, and others known in the art. As a non-limiting example, the TEE can be located between the transcription promoter and the start codon. In some embodiments, the 5'UTR comprises a TEE.

In one aspect, a TEE is a conserved element in a UTR that can promote translational activity of a nucleic acid such as, but not limited to, cap-dependent or cap-independent translation.

In one non-limiting example, the TEE comprises the TEE sequence in the 5'-leader of the Gtx homeodomain protein. See Chappell et al., PNAS 2004 101:9590-9594, incorporated herein by reference in its entirety.

In some embodiments, the polynucleotide of the invention comprises one or multiple copies of a TEE. The TEE in a translational enhancer polynucleotide can be organized in one or more sequence segments. A sequence segment can harbor one or more of the TEEs provided herein, with each TEE being present in one or more copies. When multiple sequence segments are present in a translational enhancer polynucleotide, they can be homogenous or heterogeneous. Thus, the multiple sequence segments in a translational enhancer polynucleotide can harbor identical or different types of the TEE provided herein, identical or different number of copies of each of the TEE, and/or identical or different organization of the TEE within each sequence segment. In one embodiment, the polynucleotide of the invention comprises a translational enhancer polynucleotide sequence. Non-limiting examples of TEE sequences are described in U.S. Publication 2014/0200261, the contents of which are incorporated herein by reference in their entirety.

12. MICRORNA (miRNA) BINDING SITES

Polynucleotides of the invention can include regulatory elements, for example, microRNA (miRNA) binding sites, transcription factor binding sites, structured mRNA sequences and/or motifs, artificial binding sites engineered to act as pseudo-receptors for endogenous nucleic acid binding molecules, and combinations thereof. In some embodiments, polynucleotides including such regulatory elements are referred to as including "sensor sequences". Non-limiting examples of sensor sequences are described in U.S. Publication 2014/0200261, the contents of which are incorporated herein by reference in their entirety.

In some embodiments, a polynucleotide (e.g., a ribonucleic acid (RNA), e.g., a messenger RNA (mRNA)) of the invention comprises an open reading frame (ORF) encoding a polypeptide of interest and further comprises one or more miRNA binding site(s). Inclusion or incorporation of miRNA binding site(s) provides for regulation of polynucleotides of the invention, and in turn, of the polypeptides encoded therefrom, based on tissue-specific and/or cell-type specific expression of naturally-occurring miRNAs.

The present invention also provides pharmaceutical compositions and formulations that comprise any of the polynucleotides described above. In some embodiments, the composition or formulation further comprises a delivery agent.

In some embodiments, the composition or formulation can contain a polynucleotide comprising a sequence optimized nucleic acid sequence disclosed herein which encodes a polypeptide. In some embodiments, the composition or formulation can contain a polynucleotide (e.g., a RNA, e.g., an mRNA) comprising a polynucleotide (e.g., an ORF) having significant sequence identity to a sequence optimized nucleic acid sequence disclosed herein which encodes a polypeptide. In some embodiments, the polynucleotide further comprises a miRNA binding site, e.g., a miRNA binding site that binds A miRNA, e.g., a natural-occurring miRNA, is a 19-25 nucleotide long noncoding RNA that binds to a polynucleotide and down-regulates gene expression either by reducing stability or by inhibiting translation of the polynucleotide. A miRNA sequence comprises a "seed" region, i.e., a sequence in the region of positions 2-8 of the mature miRNA. A miRNA seed can comprise positions 2-8 or 2-7 of the mature miRNA. In some embodiments, a miRNA seed can comprise 7 nucleotides (e.g., nucleotides 2-8 of the mature miRNA), wherein the seed-complementary site in the corresponding miRNA binding site is flanked by an adenosine (A) opposed to miRNA position 1. In some embodiments, a miRNA seed can comprise 6 nucleotides (e.g., nucleotides 2-7 of the mature miRNA), wherein the seed-complementary site in the corresponding miRNA binding site is flanked by an adenosine (A) opposed to miRNA position 1. See, for example, Grimson A, Farh K K, Johnston W K, Garrett-Engele P, Lim L P, Bartel D P; Mol Cell. 2007 Jul. 6; 27(1):91-105. miRNA profiling of the target cells or tissues can be conducted to determine the presence or absence of miRNA in the cells or tissues. In some embodiments, a polynucleotide (e.g., a ribonucleic acid (RNA), e.g., a messenger RNA (mRNA)) of the invention comprises one or more microRNA binding sites, microRNA target sequences, microRNA complementary sequences, or microRNA seed complementary sequences. Such sequences can correspond to, e.g., have complementarity to, any known microRNA such as those taught in US Publication US2005/0261218 and US Publication US2005/0059005, the contents of each of which are incorporated herein by reference in their entirety.

microRNAs derive enzymatically from regions of RNA transcripts that fold back on themselves to form short hairpin structures often termed a pre-miRNA (precursor-miRNA). A pre-miRNA typically has a two-nucleotide overhang at its 3' end, and has 3' hydroxyl and 5' phosphate groups. This precursor-mRNA is processed in the nucleus and subsequently transported to the cytoplasm where it is further processed by DICER (a RNase III enzyme), to form a mature microRNA of approximately 22 nucleotides. The mature microRNA is then incorporated into a ribonuclear particle to form the RNA-induced silencing complex, RISC, which mediates gene silencing. Art-recognized nomenclature for mature miRNAs typically designates the arm of the pre-miRNA from which the mature miRNA derives; "5p" means the microRNA is from the 5 prime arm of the pre-miRNA hairpin and "3p" means the microRNA is from the 3 prime end of the pre-miRNA hairpin. A miR referred to by number herein can refer to either of the two mature microRNAs originating from opposite arms of the same pre-miRNA (e.g., either the 3p or 5p microRNA). All miRs referred to herein are intended to include both the 3p and 5p arms/sequences, unless particularly specified by the 3p or 5p designation.

As used herein, the term "microRNA (miRNA or miR) binding site" refers to a sequence within a polynucleotide, e.g., within a DNA or within an RNA transcript, including in the 5'UTR and/or 3'UTR, that has sufficient complementarity to all or a region of a miRNA to interact with, associate with or bind to the miRNA. In some embodiments, a polynucleotide of the invention comprising an ORF encoding a polypeptide of interest and further comprises one or more miRNA binding site(s). In exemplary embodiments, a 5'UTR and/or 3'UTR of the polynucleotide (e.g., a ribonucleic acid (RNA), e.g., a messenger RNA (mRNA)) comprises the one or more miRNA binding site(s).

A miRNA binding site having sufficient complementarity to a miRNA refers to a degree of complementarity sufficient to facilitate miRNA-mediated regulation of a polynucleotide, e.g., miRNA-mediated translational repression or degradation of the polynucleotide. In exemplary aspects of the invention, a miRNA binding site having sufficient complementarity to the miRNA refers to a degree of complementarity sufficient to facilitate miRNA-mediated degradation of the polynucleotide, e.g., miRNA-guided RNA-induced silencing complex (RISC)-mediated cleavage of mRNA. The miRNA binding site can have complementarity to, for example, a 19-25 nucleotide long miRNA sequence, to a long 19-23 nucleotide miRNA sequence, or to a long 22 nucleotide miRNA sequence. A miRNA binding site can be complementary to only a portion of a miRNA, e.g., to a portion less than 1, 2, 3, or 4 nucleotides of the full length of a naturally-occurring miRNA sequence, or to a portion less than 1, 2, 3, or 4 nucleotides shorter than a naturally-occurring miRNA sequence. Full or complete complementarity (e.g., full complementarity or complete complementarity over all or a significant portion of the length of a naturally-occurring miRNA) is preferred when the desired regulation is mRNA degradation.

In some embodiments, a miRNA binding site includes a sequence that has complementarity (e.g., partial or complete complementarity) with an miRNA seed sequence. In some embodiments, the miRNA binding site includes a sequence that has complete complementarity with a miRNA seed sequence. In some embodiments, a miRNA binding site includes a sequence that has complementarity (e.g., partial or complete complementarity) with an miRNA sequence. In some embodiments, the miRNA binding site includes a sequence that has complete complementarity with a miRNA sequence. In some embodiments, a miRNA binding site has complete complementarity with a miRNA sequence but for 1, 2, or 3 nucleotide substitutions, terminal additions, and/or truncations.

In some embodiments, the miRNA binding site is the same length as the corresponding miRNA. In other embodiments, the miRNA binding site is one, two, three, four, five, six, seven, eight, nine, ten, eleven or twelve nucleotide(s) shorter than the corresponding miRNA at the 5' terminus, the 3' terminus, or both. In still other embodiments, the microRNA binding site is two nucleotides shorter than the corresponding microRNA at the 5' terminus, the 3' terminus, or both. The miRNA binding sites that are shorter than the corresponding miRNAs are still capable of degrading the mRNA incorporating one or more of the miRNA binding sites or preventing the mRNA from translation.

In some embodiments, the miRNA binding site binds the corresponding mature miRNA that is part of an active RISC containing Dicer. In another embodiment, binding of the miRNA binding site to the corresponding miRNA in RISC degrades the mRNA containing the miRNA binding site or prevents the mRNA from being translated. In some embodiments, the miRNA binding site has sufficient complementarity to miRNA so that a RISC complex comprising the miRNA cleaves the polynucleotide comprising the miRNA binding site. In other embodiments, the miRNA binding site has imperfect complementarity so that a RISC complex comprising the miRNA induces instability in the polynucleotide comprising the miRNA binding site. In another embodiment, the miRNA binding site has imperfect complementarity so that a RISC complex comprising the miRNA represses transcription of the polynucleotide comprising the miRNA binding site.

In some embodiments, the miRNA binding site has one, two, three, four, five, six, seven, eight, nine, ten, eleven or twelve mismatch(es) from the corresponding miRNA.

In some embodiments, the miRNA binding site has at least about ten, at least about eleven, at least about twelve, at least about thirteen, at least about fourteen, at least about fifteen, at least about sixteen, at least about seventeen, at least about eighteen, at least about nineteen, at least about twenty, or at least about twenty-one contiguous nucleotides complementary to at least about ten, at least about eleven, at least about twelve, at least about thirteen, at least about fourteen, at least about fifteen, at least about sixteen, at least about seventeen, at least about eighteen, at least about nineteen, at least about twenty, or at least about twenty-one, respectively, contiguous nucleotides of the corresponding miRNA.

By engineering one or more miRNA binding sites into a polynucleotide of the invention, the polynucleotide can be targeted for degradation or reduced translation, provided the miRNA in question is available. This can reduce off-target effects upon delivery of the polynucleotide. For example, if a polynucleotide of the invention is not intended to be delivered to a tissue or cell but ends up is said tissue or cell, then a miRNA abundant in the tissue or cell can inhibit the expression of the gene of interest if one or multiple binding sites of the miRNA are engineered into the 5'UTR and/or 3'UTR of the polynucleotide. Thus, in some embodiments, incorporation of one or more miRNA binding sites into an mRNA of the disclosure may reduce the hazard of off-target effects upon nucleic acid molecule delivery and/or enable tissue-specific regulation of expression of a polypeptide encoded by the mRNA. In yet other embodiments, incorporation of one or more miRNA binding sites into an mRNA of the disclosure can modulate immune responses upon nucleic acid delivery in vivo. In further embodiments, incorporation of one or more miRNA binding sites into an mRNA of the disclosure can modulate accelerated blood clearance (ABC) of lipid-comprising compounds and compositions described herein.

Conversely, miRNA binding sites can be removed from polynucleotide sequences in which they naturally occur in order to increase protein expression in specific tissues. For example, a binding site for a specific miRNA can be removed from a polynucleotide to improve protein expression in tissues or cells containing the miRNA.

Regulation of expression in multiple tissues can be accomplished through introduction or removal of one or more miRNA binding sites, e.g., one or more distinct miRNA binding sites. The decision whether to remove or insert a miRNA binding site can be made based on miRNA expression patterns and/or their profilings in tissues and/or cells in development and/or disease. Identification of MiRNAs, miRNA binding sites, and their expression patterns and role in biology have been reported (e.g., Bonauer et al., Curr Drug Targets 2010 11:943-949; Anand and Cheresh Curr Opin Hematol 2011 18:171-176; Contreras and Rao Leukemia 2012 26:404-413 (2011 Dec. 20. doi: 10.1038/leu.2011.356); Bartel Cell 2009 136:215-233; Landgraf et al, Cell, 2007 129:1401-1414; Gentner and Naldini, Tissue Antigens. 2012 80:393-403 and all references therein; each of which is incorporated herein by reference in its entirety).

miRNAs and miRNA binding sites can correspond to any known sequence, including non-limiting examples described in U.S. Publication Nos. 2014/0200261, 2005/0261218, and 2005/0059005, each of which are incorporated herein by reference in their entirety.

Examples of tissues where miRNA are known to regulate mRNA, and thereby protein expression, include, but are not limited to, liver (miR-122), muscle (miR-133, miR-206, miR-208), endothelial cells (miR-17-92, miR-126), myeloid cells (miR-142-3p, miR-142-5p, miR-16, miR-21, miR-223, miR-24, miR-27), adipose tissue (let-7, miR-30c), heart (miR-1d, miR-149), kidney (miR-192, miR-194, miR-204), and lung epithelial cells (let-7, miR-133, miR-126).

Specifically, miRNAs are known to be differentially expressed in immune cells (also called hematopoietic cells), such as antigen presenting cells (APCs) (e.g., dendritic cells and macrophages), macrophages, monocytes, B lymphocytes, T lymphocytes, granulocytes, natural killer cells, etc. Immune cell specific miRNAs are involved in immunogenicity, autoimmunity, the immune-response to infection, inflammation, as well as unwanted immune response after gene therapy and tissue/organ transplantation. Immune cells specific miRNAs also regulate many aspects of development, proliferation, differentiation and apoptosis of hematopoietic cells (immune cells). For example, miR-142 and miR-146 are exclusively expressed in immune cells, particularly abundant in myeloid dendritic cells. It has been demonstrated that the immune response to a polynucleotide can be shut-off by adding miR-142 binding sites to the 3'-UTR of the polynucleotide, enabling more stable gene transfer in tissues and cells. miR-142 efficiently degrades exogenous polynucleotides in antigen presenting cells and suppresses cytotoxic elimination of transduced cells (e.g., Annoni A et al., blood, 2009, 114, 5152-5161; Brown B D, et al., Nat med. 2006, 12(5), 585-591; Brown B D, et al., blood, 2007, 110(13): 4144-4152, each of which is incorporated herein by reference in its entirety).

An antigen-mediated immune response can refer to an immune response triggered by foreign antigens, which, when entering an organism, are processed by the antigen presenting cells and displayed on the surface of the antigen presenting cells. T cells can recognize the presented antigen and induce a cytotoxic elimination of cells that express the antigen.

Introducing a miR-142 binding site into the 5'UTR and/or 3'UTR of a polynucleotide of the invention can selectively repress gene expression in antigen presenting cells through miR-142 mediated degradation, limiting antigen presentation in antigen presenting cells (e.g., dendritic cells) and thereby preventing antigen-mediated immune response after the delivery of the polynucleotide. The polynucleotide is then stably expressed in target tissues or cells without triggering cytotoxic elimination.

In one embodiment, binding sites for miRNAs that are known to be expressed in immune cells, in particular, antigen presenting cells, can be engineered into a polynucleotide of the invention to suppress the expression of the polynucleotide in antigen presenting cells through miRNA mediated RNA degradation, subduing the antigen-mediated immune response. Expression of the polynucleotide is maintained in non-immune cells where the immune cell specific miRNAs are not expressed. For example, in some embodiments, to prevent an immunogenic reaction against a liver specific protein, any miR-122 binding site can be removed and a miR-142 (and/or mirR-146) binding site can be engineered into the 5'UTR and/or 3'UTR of a polynucleotide of the invention.

To further drive the selective degradation and suppression in APCs and macrophage, a polynucleotide of the invention can include a further negative regulatory element in the 5'UTR and/or 3'UTR, either alone or in combination with miR-142 and/or miR-146 binding sites. As a non-limiting example, the further negative regulatory element is a Constitutive Decay Element (CDE).

Immune cell specific miRNAs include, but are not limited to, hsa-let-7a-2-3p, hsa-let-7a-3p, hsa-7a-5p, hsa-let-7c, hsa-let-7e-3p, hsa-let-7e-5p, hsa-let-7g-3p, hsa-let-7g-5p, hsa-let-7i-3p, hsa-let-7i-5p, miR-10a-3p, miR-10a-5p, miR-1184, hsa-let-7f-1-3p, hsa-let-7f-2-5p, hsa-let-7f-5p, miR-125b-1-3p, miR-125b-2-3p, miR-125b-5p, miR-1279, miR-130a-3p, miR-130a-5p, miR-132-3p, miR-132-5p, miR-142-3p, miR-142-5p, miR-143-3p, miR-143-5p, miR-146a-3p, miR-146a-5p, miR-146b-3p, miR-146b-5p, miR-147a, miR-147b, miR-148a-5p, miR-148a-3p, miR-150-3p, miR-150-5p, miR-151b, miR-155-3p, miR-155-5p, miR-15a-3p, miR-15a-5p, miR-15b-5p, miR-15b-3p, miR-16-1-3p, miR-16-2-3p, miR-16-5p, miR-17-5p, miR-181a-3p, miR-181a-5p, miR-181a-2-3p, miR-182-3p, miR-182-5p, miR-197-3p, miR-197-5p, miR-21-5p, miR-21-3p, miR-214-3p, miR-214-5p, miR-223-3p, miR-223-5p, miR-221-3p, miR-221-5p, miR-23b-3p, miR-23b-5p, miR-24-1-5p, miR-24-2-5p, miR-24-3p, miR-26a-1-3p, miR-26a-2-3p, miR-26a-5p, miR-26b-3p, miR-26b-5p, miR-27a-3p, miR-27a-5p, miR-27b-3p, miR-27b-5p, miR-28-3p, miR-28-5p, miR-2909, miR-29a-3p, miR-29a-5p, miR-29b-1-5p, miR-29b-2-5p, miR-29c-3p, miR-29c-5p, miR-30e-3p, miR-30e-5p, miR-331-5p, miR-339-3p, miR-339-5p, miR-345-3p, miR-345-5p, miR-346, miR-34a-3p, miR-34a-5p, miR-363-3p, miR-363-5p, miR-372, miR-377-3p, miR-377-5p, miR-493-3p, miR-493-5p, miR-542, miR-548b-5p, miR548c-5p, miR-548i, miR-548j, miR-548n, miR-574-3p, miR-598, miR-718, miR-935, miR-99a-3p, miR-99a-5p, miR-99b-3p, and miR-99b-5p. Furthermore, novel miRNAs can be identified in immune cell through micro-array hybridization and microtome analysis (e.g., Jima D D et al, Blood, 2010, 116:e118-e127; Vaz C et al., BMC Genomics, 2010, 11,288, the content of each of which is incorporated herein by reference in its entirety.)

miRNAs that are known to be expressed in the liver include, but are not limited to, miR-107, miR-122-3p, miR-122-5p, miR-1228-3p, miR-1228-5p, miR-1249, miR-129-5p, miR-1303, miR-151a-3p, miR-151a-5p, miR-152, miR-194-3p, miR-194-5p, miR-199a-3p, miR-199a-5p, miR-199b-3p, miR-199b-5p, miR-296-5p, miR-557, miR-581, miR-939-3p, and miR-939-5p. MiRNA binding sites from any liver specific miRNA can be introduced to or removed from a polynucleotide of the invention to regulate expression of the polynucleotide in the liver. Liver specific miRNA binding sites can be engineered alone or further in combination with immune cell (e.g., APC) miRNA binding sites in a polynucleotide of the invention.

miRNAs that are known to be expressed in the lung include, but are not limited to, let-7a-2-3p, let-7a-3p, let-7a-5p, miR-126-3p, miR-126-5p, miR-127-3p, miR-127-5p, miR-130a-3p, miR-130a-5p, miR-130b-3p, miR-130b-5p, miR-133a, miR-133b, miR-134, miR-18a-3p, miR-18a-5p, miR-18b-3p, miR-18b-5p, miR-24-1-5p, miR-24-2-5p, miR-24-3p, miR-296-3p, miR-296-5p, miR-32-3p, miR-337-3p, miR-337-5p, miR-381-3p, and miR-381-5p. miRNA binding sites from any lung specific miRNA can be introduced to or removed from a polynucleotide of the invention to regulate expression of the polynucleotide in the lung. Lung specific miRNA binding sites can be engineered alone or further in combination with immune cell (e.g., APC) miRNA binding sites in a polynucleotide of the invention.

miRNAs that are known to be expressed in the heart include, but are not limited to, miR-1, miR-133a, miR-133b, miR-149-3p, miR-149-5p, miR-186-3p, miR-186-5p, miR-208a, miR-208b, miR-210, miR-296-3p, miR-320, miR-451a, miR-451b, miR-499a-3p, miR-499a-5p, miR-499b-3p, miR-499b-5p, miR-744-3p, miR-744-5p, miR-92b-3p, and miR-92b-5p. mMiRNA binding sites from any heart specific microRNA can be introduced to or removed from a polynucleotide of the invention to regulate expression of the polynucleotide in the heart. Heart specific miRNA binding sites can be engineered alone or further in combination with immune cell (e.g., APC) miRNA binding sites in a polynucleotide of the invention.

miRNAs that are known to be expressed in the nervous system include, but are not limited to, miR-124-5p, miR-125a-3p, miR-125a-5p, miR-125b-1-3p, miR-125b-2-3p, miR-125b-5p, miR-1271-3p, miR-1271-5p, miR-128, miR-132-5p, miR-135a-3p, miR-135a-5p, miR-135b-3p, miR-135b-5p, miR-137, miR-139-5p, miR-139-3p, miR-149-3p, miR-149-5p, miR-153, miR-181c-3p, miR-181c-5p, miR-183-3p, miR-183-5p, miR-190a, miR-190b, miR-212-3p, miR-212-5p, miR-219-1-3p, miR-219-2-3p, miR-23a-3p, miR-23a-5p, miR-30a-5p, miR-30b-3p, miR-30b-5p, miR-30c-1-3p, miR-30c-2-3p, miR-30c-5p, miR-30d-3p, miR-30d-5p, miR-329, miR-342-3p, miR-3665, miR-3666, miR-380-3p, miR-380-5p, miR-383, miR-410, miR-425-3p, miR-425-5p, miR-454-3p, miR-454-5p, miR-483, miR-510, miR-516a-3p, miR-548b-5p, miR-548c-5p, miR-571, miR-7-1-3p, miR-7-2-3p, miR-7-5p, miR-802, miR-922, miR-9-3p, and miR-9-5p. miRNAs enriched in the nervous system further include those specifically expressed in neurons, including, but not limited to, miR-132-3p, miR-132-3p, miR-148b-3p, miR-148b-5p, miR-151a-3p, miR-151a-5p, miR-212-3p, miR-212-5p, miR-320b, miR-320e, miR-323a-3p, miR-323a-5p, miR-324-5p, miR-325, miR-326, miR-328, miR-922 and those specifically expressed in glial cells, including, but not limited to, miR-1250, miR-219-1-3p, miR-219-2-3p, miR-219-5p, miR-23a-3p, miR-23a-5p, miR-3065-3p, miR-3065-5p, miR-30e-3p, miR-30e-5p, miR-32-5p, miR-338-5p, and miR-657. miRNA binding sites from any CNS specific miRNA can be introduced to or removed from a polynucleotide of the invention to regulate expression of the polynucleotide in the nervous system. Nervous system specific miRNA binding sites can be engineered alone or further in combination with immune cell (e.g., APC) miRNA binding sites in a polynucleotide of the invention.

miRNAs that are known to be expressed in the pancreas include, but are not limited to, miR-105-3p, miR-105-5p, miR-184, miR-195-3p, miR-195-5p, miR-196a-3p, miR-196a-5p, miR-214-3p, miR-214-5p, miR-216a-3p, miR-216a-5p, miR-30a-3p, miR-33a-3p, miR-33a-5p, miR-375, miR-7-1-3p, miR-7-2-3p, miR-493-3p, miR-493-5p, and miR-944. MiRNA binding sites from any pancreas specific miRNA can be introduced to or removed from a polynucleotide of the invention to regulate expression of the polynucleotide in the pancreas. Pancreas specific miRNA binding sites can be engineered alone or further in combination with immune cell (e.g. APC) miRNA binding sites in a polynucleotide of the invention.

miRNAs that are known to be expressed in the kidney include, but are not limited to, miR-122-3p, miR-145-5p, miR-17-5p, miR-192-3p, miR-192-5p, miR-194-3p, miR-194-5p, miR-20a-3p, miR-20a-5p, miR-204-3p, miR-204-5p, miR-210, miR-216a-3p, miR-216a-5p, miR-296-3p, miR-30a-3p, miR-30a-5p, miR-30b-3p, miR-30b-5p, miR-30c-1-3p, miR-30c-2-3p, miR30c-5p, miR-324-3p, miR-335-3p, miR-335-5p, miR-363-3p, miR-363-5p, and miR-562. miRNA binding sites from any kidney specific miRNA can be introduced to or removed from a polynucleotide of the invention to regulate expression of the polynucleotide in the kidney. Kidney specific miRNA binding sites can be engineered alone or further in combination with immune cell (e.g., APC) miRNA binding sites in a polynucleotide of the invention.

miRNAs that are known to be expressed in the muscle include, but are not limited to, let-7g-3p, let-7g-5p, miR-1, miR-1286, miR-133a, miR-133b, miR-140-3p, miR-143-3p, miR-143-5p, miR-145-3p, miR-145-5p, miR-188-3p, miR-188-5p, miR-206, miR-208a, miR-208b, miR-25-3p, and miR-25-5p. MiRNA binding sites from any muscle specific miRNA can be introduced to or removed from a polynucleotide of the invention to regulate expression of the polynucleotide in the muscle. Muscle specific miRNA binding sites can be engineered alone or further in combination with immune cell (e.g., APC) miRNA binding sites in a polynucleotide of the invention.

miRNAs are also differentially expressed in different types of cells, such as, but not limited to, endothelial cells, epithelial cells, and adipocytes.

miRNAs that are known to be expressed in endothelial cells include, but are not limited to, let-7b-3p, let-7b-5p, miR-100-3p, miR-100-5p, miR-101-3p, miR-101-5p, miR-126-3p, miR-126-5p, miR-1236-3p, miR-1236-5p, miR-130a-3p, miR-130a-5p, miR-17-5p, miR-17-3p, miR-18a-3p, miR-18a-5p, miR-19a-3p, miR-19a-5p, miR-19b-1-5p, miR-19b-2-5p, miR-19b-3p, miR-20a-3p, miR-20a-5p, miR-217, miR-210, miR-21-3p, miR-21-5p, miR-221-3p, miR-221-5p, miR-222-3p, miR-222-5p, miR-23a-3p, miR-23a-5p, miR-296-5p, miR-361-3p, miR-361-5p, miR-421, miR-424-3p, miR-424-5p, miR-513a-5p, miR-92a-1-5p, miR-92a-2-5p, miR-92a-3p, miR-92b-3p, and miR-92b-5p. Many novel miRNAs are discovered in endothelial cells from deep-sequencing analysis (e.g., Voellenkle C et al., RNA, 2012, 18, 472-484, herein incorporated by reference in its entirety). miRNA binding sites from any endothelial cell specific miRNA can be introduced to or removed from a polynucleotide of the invention to regulate expression of the polynucleotide in the endothelial cells.

miRNAs that are known to be expressed in epithelial cells include, but are not limited to, let-7b-3p, let-7b-5p, miR-1246, miR-200a-3p, miR-200a-5p, miR-200b-3p, miR-200b-5p, miR-200c-3p, miR-200c-5p, miR-338-3p, miR-429, miR-451a, miR-451b, miR-494, miR-802 and miR-34a, miR-34b-5p, miR-34c-5p, miR-449a, miR-449b-3p, miR-449b-5p specific in respiratory ciliated epithelial cells, let-7 family, miR-133a, miR-133b, miR-126 specific in lung epithelial cells, miR-382-3p, miR-382-5p specific in renal epithelial cells, and miR-762 specific in corneal epithelial cells. miRNA binding sites from any epithelial cell specific miRNA can be introduced to or removed from a polynucleotide of the invention to regulate expression of the polynucleotide in the epithelial cells.

In addition, a large group of miRNAs are enriched in embryonic stem cells, controlling stem cell self-renewal as well as the development and/or differentiation of various cell lineages, such as neural cells, cardiac, hematopoietic cells, skin cells, osteogenic cells and muscle cells (e.g., Kuppusamy K T et al., Curr. Mol Med, 2013, 13(5), 757-764; Vidigal J A and Ventura A, Semin Cancer Biol. 2012, 22(5-6), 428-436; Goff L A et al., PLoS One, 2009, 4:e7192; Morin R D et al., Genome Res, 2008,18, 610-621; Yoo J K et al., Stem Cells Dev. 2012, 21(11), 2049-2057, each of which is herein incorporated by reference in its entirety). MiRNAs abundant in embryonic stem cells include, but are not limited to, let-7a-2-3p, let-a-3p, let-7a-5p, let7d-3p, let-7d-5p, miR-103a-2-3p, miR-103a-5p, miR-106b-3p, miR-106b-5p, miR-1246, miR-1275, miR-138-1-3p, miR-138-2-3p, miR-138-5p, miR-154-3p, miR-154-5p, miR-200c-3p, miR-200c-5p, miR-290, miR-301a-3p, miR-301a-5p, miR-302a-3p, miR-302a-5p, miR-302b-3p, miR-302b-5p, miR-302c-3p, miR-302c-5p, miR-302d-3p, miR-302d-5p, miR-302e, miR-367-3p, miR-367-5p, miR-369-3p, miR-369-5p, miR-370, miR-371, miR-373, miR-380-5p, miR-423-3p, miR-423-5p, miR-486-5p, miR-520c-3p, miR-548e, miR-548f, miR-548g-3p, miR-548g-5p, miR-548i, miR-548k, miR-548l, miR-548m, miR-548n, miR-5480-3p, miR-5480-5p, miR-548p, miR-664a-3p, miR-664a-5p, miR-664b-3p, miR-664b-5p, miR-766-3p, miR-766-5p, miR-885-3p, miR-885-5p, miR-93-3p, miR-93-5p, miR-941, miR-96-3p, miR-96-5p, miR-99b-3p and miR-99b-5p. Many predicted novel miRNAs are discovered by deep sequencing in human embryonic stem cells (e.g., Morin R D et al., Genome Res, 2008,18, 610-621; Goff L A et al., PLoS One, 2009, 4:e7192; Bar M et al., Stem cells, 2008, 26, 2496-2505, the content of each of which is incorporated herein by reference in its entirety).

In one embodiment, the binding sites of embryonic stem cell specific miRNAs can be included in or removed from the 3'UTR of a polynucleotide of the invention to modulate the development and/or differentiation of embryonic stem cells, to inhibit the senescence of stem cells in a degenerative condition (e.g. degenerative diseases), or to stimulate the senescence and apoptosis of stem cells in a disease condition (e.g. cancer stem cells).

In some embodiments, miRNAs are selected based on expression and abundance in immune cells of the hematopoietic lineage, such as B cells, T cells, macrophages, dendritic cells, and cells that are known to express TLR7/TLR8 and/or able to secrete cytokines such as endothelial cells and platelets. In some embodiments, the miRNA set thus includes miRs that may be responsible in part for the immunogenicity of these cells, and such that a corresponding miR-site incorporation in polynucleotides of the present invention (e.g., mRNAs) could lead to destabilization of the mRNA and/or suppression of translation from these mRNAs in the specific cell type. Non-limiting representative examples include miR-142, miR-144, miR-150, miR-155 and miR-223, which are specific for many of the hematopoietic cells; miR-142, miR150, miR-16 and miR-223, which are expressed in B cells; miR-223, miR-451, miR-26a, miR-16, which are expressed in progenitor hematopoietic cells; and miR-126, which is expressed in plasmacytoid dendritic cells, platelets and endothelial cells. For further discussion of tissue expression of miRs see e.g., Teruel-Montoya, R. et al. (2014) *PLoS One* 9:e102259; Landgraf, P. et al. (2007) *Cell* 129:1401-1414; Bissels, U. et al. (2009) *RNA* 15:2375-2384. Any one miR-site incorporation in the 3'UTR and/or 5' UTR may mediate such effects in multiple cell types of interest (e.g., miR-142 is abundant in both B cells and dendritic cells).

In some embodiments, it may be beneficial to target the same cell type with multiple miRs and to incorporate binding sites to each of the 3p and 5p arm if both are abundant (e.g., both miR-142-3p and miR142-5p are abundant in hematopoietic stem cells). Thus, in certain embodiments, polynucleotides of the invention contain two or more (e.g., two, three, four or more) miR bindings sites from: (i) the group consisting of miR-142, miR-144, miR-150, miR-155 and miR-223 (which are expressed in many hematopoietic cells); or (ii) the group consisting of miR-142, miR150, miR-16 and miR-223 (which are expressed in B cells); or the group consisting of miR-223, miR-451, miR-26a, miR-16 (which are expressed in progenitor hematopoietic cells).

In some embodiments, it may also be beneficial to combine various miRs such that multiple cell types of interest are targeted at the same time (e.g., miR-142 and miR-126 to target many cells of the hematopoietic lineage and endothelial cells). Thus, for example, in certain embodiments, polynucleotides of the invention comprise two or more (e.g., two, three, four or more) miRNA bindings sites, wherein: (i) at least one of the miRs targets cells of the hematopoietic lineage (e.g., miR-142, miR-144, miR-150, miR-155 or miR-223) and at least one of the miRs targets plasmacytoid dendritic cells, platelets or endothelial cells (e.g., miR-126); or (ii) at least one of the miRs targets B cells (e.g., miR-142, miR150, miR-16 or miR-223) and at least one of the miRs targets plasmacytoid dendritic cells, platelets or endothelial cells (e.g., miR-126); or (iii) at least one of the miRs targets progenitor hematopoietic cells (e.g., miR-223, miR-451, miR-26a or miR-16) and at least one of the miRs targets plasmacytoid dendritic cells, platelets or endothelial cells (e.g., miR-126); or (iv) at least one of the miRs targets cells of the hematopoietic lineage (e.g., miR-142, miR-144, miR-150, miR-155 or miR-223), at least one of the miRs targets B cells (e.g., miR-142, miR150, miR-16 or miR-223) and at least one of the miRs targets plasmacytoid dendritic cells, platelets or endothelial cells (e.g., miR-126); or any other possible combination of the foregoing four classes of miR binding sites (i.e., those targeting the hematopoietic lineage, those targeting B cells, those targeting progenitor hematopoietic cells and/or those targeting plamacytoid dendritic cells/platelets/endothelial cells).

In one embodiment, to modulate immune responses, polynucleotides of the present invention can comprise one or more miRNA binding sequences that bind to one or more miRs that are expressed in conventional immune cells or any cell that expresses TLR7 and/or TLR8 and secrete pro-inflammatory cytokines and/or chemokines (e.g., in immune cells of peripheral lymphoid organs and/or splenocytes and/or endothelial cells). It has now been discovered that incorporation into an mRNA of one or more miRs that are expressed in conventional immune cells or any cell that expresses TLR7 and/or TLR8 and secrete pro-inflammatory cytokines and/or chemokines (e.g., in immune cells of peripheral lymphoid organs and/or splenocytes and/or endothelial cells) reduces or inhibits immune cell activation (e.g., B cell activation, as measured by frequency of activated B cells) and/or cytokine production (e.g., production of IL-6, IFN-γ and/or TNFα). Furthermore, it has now been discovered that incorporation into an mRNA of one or more miRs that are expressed in conventional immune cells or any cell that expresses TLR7 and/or TLR8 and secrete pro-inflammatory cytokines and/or chemokines (e.g., in immune cells of peripheral lymphoid organs and/or splenocytes and/or endothelial cells) can reduce or inhibit an anti-drug antibody (ADA) response against a protein of interest encoded by the mRNA.

In another embodiment, to modulate accelerated blood clearance of an polynucleotide delivered in a lipid-comprising compound or composition, polynucleotides of the invention can comprise one or more miR binding sequences that bind to one or more miRNAs expressed in conventional immune cells or any cell that expresses TLR7 and/or TLR8 and secrete pro-inflammatory cytokines and/or chemokines (e.g., in immune cells of peripheral lymphoid organs and/or splenocytes and/or endothelial cells). It has now been discovered that incorporation into an mRNA of one or more miR binding sites reduces or inhibits accelerated blood clearance (ABC) of the lipid-comprising compound or composition for use in delivering the mRNA. Furthermore, it has now been discovered that incorporation of one or more miR binding sites into an mRNA reduces serum levels of anti-PEG anti-IgM (e.g, reduces or inhibits the acute production of IgMs that recognize polyethylene glycol (PEG) by B cells) and/or reduces or inhibits proliferation and/or activation of plasmacytoid dendritic cells following administration of a lipid-comprising compound or composition comprising the mRNA.

In some embodiments, miR sequences may correspond to any known microRNA expressed in immune cells, including but not limited to those taught in US Publication US2005/0261218 and US Publication US2005/0059005, the contents of which are incorporated herein by reference in their entirety. Non-limiting examples of miRs expressed in immune cells include those expressed in spleen cells, myeloid cells, dendritic cells, plasmacytoid dendritic cells, B cells, T cells and/or macrophages. For example, miR-142-3p, miR-142-5p, miR-16, miR-21, miR-223, miR-24 and miR-27 are expressed in myeloid cells, miR-155 is expressed in dendritic cells, B cells and T cells, miR-146 is upregulated in macrophages upon TLR stimulation and miR-126 is expressed in plasmacytoid dendritic cells. In certain embodiments, the miR(s) is expressed abundantly or preferentially in immune cells. For example, miR-142 (miR-142-3p and/or miR-142-5p), miR-126 (miR-126-3p and/or miR-126-5p), miR-146 (miR-146-3p and/or miR-146-5p) and miR-155 (miR-155-3p and/or miR155-5p) are expressed abundantly in immune cells. These microRNA sequences are known in the art and, thus, one of ordinary skill in the art can readily design binding sequences or target sequences to which these microRNAs will bind based upon Watson-Crick complementarity.

Accordingly, in various embodiments, polynucleotides of the present invention comprise at least one microRNA binding site for a miR selected from the group consisting of miR-142, miR-146, miR-155, miR-126, miR-16, miR-21, miR-223, miR-24 and miR-27. In another embodiment, the mRNA comprises at least two miR binding sites for microRNAs expressed in immune cells. In various embodiments, the polynucleotide of the invention comprises 1-4, one, two, three or four miR binding sites for microRNAs expressed in immune cells. In another embodiment, the polynucleotide of the invention comprises three miR binding sites. These miR binding sites can be for microRNAs selected from the group consisting of miR-142, miR-146, miR-155, miR-126, miR-16, miR-21, miR-223, miR-24, miR-27, and combinations thereof. In one embodiment, the polynucleotide of the invention comprises two or more (e.g., two, three, four) copies of the same miR binding site expressed in immune cells, e.g., two or more copies of a miR binding site selected from the group of miRs consisting of miR-142, miR-146, miR-155, miR-126, miR-16, miR-21, miR-223, miR-24, miR-27.

In one embodiment, the polynucleotide of the invention comprises three copies of the same miR binding site. In certain embodiments, use of three copies of the same miR binding site can exhibit beneficial properties as compared to use of a single miR binding site. Non-limiting examples of sequences for 3' UTRs containing three miR bindings sites are shown in SEQ ID NO: 165 (three miR-142-3p binding sites), and SEQ ID NO: 167 (three miR-142-5p binding sites).

In another embodiment, the polynucleotide of the invention comprises two or more (e.g., two, three, four) copies of at least two different miR binding sites expressed in immune cells. Non-limiting examples of sequences of 3' UTRs containing two or more different miR binding sites are shown in SEQ ID NO: 164 (one miR-142-3p binding site and one miR-126-3p binding site), SEQ ID NO: 168 (two miR-142-5p binding sites and one miR-142-3p binding sites) and SEQ ID NO: 171 (two miR-155-5p binding sites and one miR-142-3p binding sites).

In another embodiment, the polynucleotide of the invention comprises at least two miR binding sites for microRNAs expressed in immune cells, wherein one of the miR binding sites is for miR-142-3p. In various embodiments, the polynucleotide of the invention comprises binding sites for miR-142-3p and miR-155 (miR-155-3p or miR-155-5p), miR-142-3p and miR-146 (miR-146-3 or miR-146-5p), or miR-142-3p and miR-126 (miR-126-3p or miR-126-5p).

In another embodiment, the polynucleotide of the invention comprises at least two miR binding sites for microRNAs expressed in immune cells, wherein one of the miR binding sites is for miR-126-3p. In various embodiments, the polynucleotide of the invention comprises binding sites for miR-126-3p and miR-155 (miR-155-3p or miR-155-5p), miR-126-3p and miR-146 (miR-146-3p or miR-146-5p), or miR-126-3p and miR-142 (miR-142-3p or miR-142-5p).

In another embodiment, the polynucleotide of the invention comprises at least two miR binding sites for microRNAs expressed in immune cells, wherein one of the miR binding sites is for miR-142-5p. In various embodiments, the polynucleotide of the invention comprises binding sites for miR-142-5p and miR-155 (miR-155-3p or miR-155-5p), miR-142-5p and miR-146 (miR-146-3 or miR-146-5p), or miR-142-5p and miR-126 (miR-126-3p or miR-126-5p).

In yet another embodiment, the polynucleotide of the invention comprises at least two miR binding sites for microRNAs expressed in immune cells, wherein one of the miR binding sites is for miR-155-5p. In various embodiments, the polynucleotide of the invention comprises binding sites for miR-155-5p and miR-142 (miR-142-3p or miR-142-5p), miR-155-5p and miR-146 (miR-146-3 or miR-146-5p), or miR-155-5p and miR-126 (miR-126-3p or miR-126-5p).

miRNA can also regulate complex biological processes such as angiogenesis (e.g., miR-132) (Anand and Cheresh Curr Opin Hematol 2011 18:171-176). In the polynucleotides of the invention, miRNA binding sites that are involved in such processes can be removed or introduced, in order to tailor the expression of the polynucleotides to biologically relevant cell types or relevant biological processes. In this context, the polynucleotides of the invention are defined as auxotrophic polynucleotides.

In some embodiments, a polynucleotide of the invention comprises a miRNA binding site, wherein the miRNA binding site comprises one or more nucleotide sequences selected from TABLE 3, including one or more copies of any one or more of the miRNA binding site sequences. In some embodiments, a polynucleotide of the invention further comprises at least one, two, three, four, five, six, seven, eight, nine, ten, or more of the same or different miRNA binding sites selected from TABLE 3, including any combination thereof.

In some embodiments, the miRNA binding site binds to miR-142 or is complementary to miR-142. In some embodiments, the miR-142 comprises SEQ ID NO:34. In some embodiments, the miRNA binding site binds to miR-142-3p or miR-142-5p. In some embodiments, the miR-142-3p binding site comprises SEQ ID NO:35. In some embodiments, the miR-142-5p binding site comprises SEQ ID NO:37. In some embodiments, the miRNA binding site comprises a nucleotide sequence at least 80%, at least 85%, at least 90%, at least 95%, or 100% identical to SEQ ID NO:36 or SEQ ID NO:38.

In some embodiments, the miRNA binding site binds to miR-126 or is complementary to miR-126. In some embodiments, the miR-126 comprises SEQ ID NO: 156. In some embodiments, the miRNA binding site binds to miR-126-3p or miR-126-5p. In some embodiments, the miR-126-3p binding site comprises SEQ ID NO: 158. In some embodiments, the miR-126-5p binding site comprises SEQ ID NO: 160. In some embodiments, the miRNA binding site comprises a nucleotide sequence at least 80%, at least 85%, at least 90%, at least 95%, or 100% identical to SEQ ID NO: 158 or SEQ ID NO: 160.

In one embodiment, the 3' UTR comprises two miRNA binding sites, wherein a first miRNA binding site binds to miR-142 and a second miRNA binding site binds to miR-126. In a specific embodiment, the 3' UTR binding to miR-142 and miR-126 comprises, consists, or consists essentially of the sequence of SEQ ID NO: 149 or 150.

TABLE 3 miR-142, miR-126, and miR-142 and miR-126 binding sites

| SEQ ID NO. | Description | Sequence |
| --- | --- | --- |
| 34 | miR-142 | GACAGUGCAGUCACCCAUAAAGU AGAAAGCACUACUAACAGCACUG GAGGGUGUAGUGUUUCCUACUUU AUGGAUGAGUGUACUGUG |
| 35 | miR-142-3p | UGUAGUGUUUCCUACUUUAUGGA |
| 36 | miR-142-3p binding site | UCCAUAAAGUAGGAAACACUACA |
| 37 | miR-142-5p | CAUAAAGUAGAAAGCACUACU |
| 38 | miR-142-5p binding site | AGUAGUGCUUUCUACUUUAUG |
| 156 | miR-126 | CGCUGGCGACGGGACAUUAUUAC UUUUGGUACGCGCUGUGACACUU CAAACUCGUACCGUGAGUAAUAA UGCGCCGUCCACGGCA |
| 157 | miR-126-3p | UCGUACCGUGAGUAAUAAUGCG |
| 158 | miR-126-3p binding site | CGCAUUAUUACUCACGGUACGA |
| 159 | miR-126-5p | CAUUAUUACUUUUGGUACGCG |
| 160 | miR-126-5p binding site | CGCGUACCAAAAGUAAUAAUG |

In some embodiments, a miRNA binding site is inserted in the polynucleotide of the invention in any position of the polynucleotide (e.g., the 5'UTR and/or 3'UTR). In some embodiments, the 5'UTR comprises a miRNA binding site. In some embodiments, the 3'UTR comprises a miRNA binding site. In some embodiments, the 5'UTR and the 3'UTR comprise a miRNA binding site. The insertion site in the polynucleotide can be anywhere in the polynucleotide as long as the insertion of the miRNA binding site in the polynucleotide does not interfere with the translation of a functional polypeptide in the absence of the corresponding miRNA; and in the presence of the miRNA, the insertion of the miRNA binding site in the polynucleotide and the binding of the miRNA binding site to the corresponding miRNA are capable of degrading the polynucleotide or preventing the translation of the polynucleotide.

In some embodiments, a miRNA binding site is inserted in at least about 30 nucleotides downstream from the stop codon of an ORF in a polynucleotide of the invention comprising the ORF. In some embodiments, a miRNA binding site is inserted in at least about 10 nucleotides, at least about 15 nucleotides, at least about 20 nucleotides, at least about 25 nucleotides, at least about 30 nucleotides, at least about 35 nucleotides, at least about 40 nucleotides, at least about 45 nucleotides, at least about 50 nucleotides, at least about 55 nucleotides, at least about 60 nucleotides, at least about 65 nucleotides, at least about 70 nucleotides, at least about 75 nucleotides, at least about 80 nucleotides, at least about 85 nucleotides, at least about 90 nucleotides, at least about 95 nucleotides, or at least about 100 nucleotides downstream from the stop codon of an ORF in a polynucleotide of the invention. In some embodiments, a miRNA binding site is inserted in about 10 nucleotides to about 100 nucleotides, about 20 nucleotides to about 90 nucleotides, about 30 nucleotides to about 80 nucleotides, about 40 nucleotides to about 70 nucleotides, about 50 nucleotides to about 60 nucleotides, about 45 nucleotides to about 65 nucleotides downstream from the stop codon of an ORF in a polynucleotide of the invention.

In some embodiments, a miRNA binding site is inserted within the 3' UTR immediately following the stop codon of the coding region within the polynucleotide of the invention, e.g., mRNA. In some embodiments, if there are multiple copies of a stop codon in the construct, a miRNA binding site is inserted immediately following the final stop codon. in some embodiments, a miRNA binding site is inserted further downstream of the stop codon, in which case there are 3' UTR bases between the stop codon and the miR binding site(s). In some embodiments, three non-limiting examples of possible insertion sites for a miR in a 3' UTR are shown in SEQ ID NOs: 57, 58, and 172, which show a 3' UTR sequence with a miR-142-3p site inserted in one of three different possible insertion sites, respectively, within the 3' UTR.

In some embodiments, one or more miRNA binding sites can be positioned within the 5' UTR at one or more possible insertion sites. For example, three non-limiting examples of possible insertion sites for a miR in a 5' UTR are shown in SEQ ID NOs: 189, 190, and 191, which show a 5' UTR sequence with a miR-142-3p site inserted into one of three different possible insertion sites, respectively, within the 5' UTR.

In one embodiment, a codon optimized open reading frame encoding a polypeptide of interest comprises a stop codon and the at least one microRNA binding site is located within the 3' UTR 1-100 nucleotides after the stop codon. In one embodiment, the codon optimized open reading frame encoding the polypeptide of interest comprises a stop codon and the at least one microRNA binding site for a miR expressed in immune cells is located within the 3' UTR 30-50 nucleotides after the stop codon. In another embodiment, the codon optimized open reading frame encoding the polypeptide of interest comprises a stop codon and the at least one microRNA binding site for a miR expressed in immune cells is located within the 3' UTR at least 50 nucleotides after the stop codon. In other embodiments, the codon optimized open reading frame encoding the polypeptide of interest comprises a stop codon and the at least one microRNA binding site for a miR expressed in immune cells is located within the 3' UTR immediately after the stop codon, or within the 3' UTR 15-20 nucleotides after the stop codon or within the 3' UTR 70-80 nucleotides after the stop codon. In other embodiments, the 3'UTR comprises more than one miRNA bindingsite (e.g., 2-4 miRNA binding sites), wherein there can be a spacer region (e.g., of 10-100, 20-70 or 30-50 nucleotides in length) between each miRNA bindingsite. In another embodiment, the 3' UTR comprises a spacer region between the end of the miRNA bindingsite(s) and the poly A tail nucleotides. For example, a spacer region of 10-100, 20-70 or 30-50 nucleotides in length can be situated between the end of the miRNA bindingsite(s) and the beginning of the poly A tail.

In one embodiment, a codon optimized open reading frame encoding a polypeptide of interest comprises a start codon and the at least one microRNA binding site is located within the 5' UTR 1-100 nucleotides before (upstream of) the start codon. In one embodiment, the codon optimized open reading frame encoding the polypeptide of interest comprises a start codon and the at least one microRNA binding site for a miR expressed in immune cells is located within the 5' UTR 10-50 nucleotides before (upstream of) the start codon. In another embodiment, the codon optimized open reading frame encoding the polypeptide of interest comprises a start codon and the at least one microRNA binding site for a miR expressed in immune cells is located within the 5' UTR at least 25 nucleotides before (upstream of) the start codon. In other embodiments, the codon optimized open reading frame encoding the polypeptide of interest comprises a start codon and the at least one microRNA binding site for a miR expressed in immune cells is located within the 5' UTR immediately before the start codon, or within the 5' UTR 15-20 nucleotides before the start codon or within the 5' UTR 70-80 nucleotides before the start codon. In other embodiments, the 5'UTR comprises more than one miRNA bindingsite (e.g., 2-4 miRNA binding sites), wherein there can be a spacer region (e.g., of 10-100, 20-70 or 30-50 nucleotides in length) between each miRNA bindingsite.

In one embodiment, the 3' UTR comprises more than one stop codon, wherein at least one miRNA bindingsite is positioned downstream of the stop codons. For example, a 3' UTR can comprise 1, 2 or 3 stop codons. Non-limiting examples of triple stop codons that can be used include: UGAUAAUAG, UGAUAGUAA, UAAUGAUAG, UGAUAAUAA, UGAUAGUAG, UAAUGAUGA, UAAUAGUAG, UGAUGAUGA, UAAUAAUAA and UAGUAGUAG. Within a 3' UTR, for example, 1, 2, 3 or 4 miRNA binding sites, e.g., miR-142-3p binding sites, can be positioned immediately adjacent to the stop codon(s) or at any number of nucleotides downstream of the final stop codon. When the 3' UTR comprises multiple miRNA binding sites, these binding sites can be positioned directly next to each other in the construct (i.e., one after the other) or, alternatively, spacer nucleotides can be positioned between each binding site.

In one embodiment, the 3' UTR comprises three stop codons with a single miR-142-3p binding site located downstream of the 3rd stop codon. Non-limiting examples of sequences of 3' UTR having three stop codons and a single miR-142-3p binding site located at different positions downstream of the final stop codon are shown in SEQ ID NOs: 57, 58, 62, and 172.

TABLE 4

3'UTRs, miR sequences, and miR binding sites

| SEQ ID NO: | Sequence |
|---|---|
| 34 | GACAGUGCAGUCACCCAUAAAGUAGAAAGCACUACUAACAGCACUGGAGGGU GUAGUGUUUCCUACUUUAUGGAUGAGUGUACUGUG (miR-142) |
| 35 | UGUAGUGUUUCCUACUUUAUGGA (miR 142-3p sequence) |

TABLE 4-continued

3'UTRs, miR sequences, and miR binding sites

| SEQ ID NO: | Sequence |
|---|---|
| 36 | UCCAUAAAGUAGGAAACACUACA<br>(miR 142-3p binding site) |
| 37 | CAUAAAGUAGAAAGCACUACU<br>(miR 142-5p sequence) |
| 38 | AGUAGUGCUUUCUACUUUAUG<br>(miR-142-5p binding site) |
| 157 | UCGUACCGUGAGUAAUAAUGCG<br>(miR 126-3p sequence) |
| 158 | CGCAUUAUUACUCACGGUACGA<br>(miR 126-3p binding site) |
| 159 | CAUUAUUACUUUUGGUACGCG<br>(miR 126-5p sequence) |
| 173 | CCUCUGAAAUUCAGUUCUUCAG<br>(miR 146-3p sequence) |
| 174 | UGAGAACUGAAUUCCAUGGGUU<br>(miR 146-5p sequence) |
| 175 | CUCCUACAUAUUAGCAUUAACA<br>(miR 155-3p sequence) |
| 176 | UUAAUGCUAAUCGUGAUAGGGGU<br>(miR 155-5p sequence) |
| 177 | CCAGUAUUAACUGUGCUGCUGA<br>(miR 16-3p sequence) |
| 178 | UAGCAGCACGUAAAUAUUGGCG<br>(miR 16-5p sequence) |
| 179 | CAACACCAGUCGAUGGGCUGU<br>(miR 21-3p sequence) |
| 180 | UAGCUUAUCAGACUGAUGUUGA<br>(miR 21-5p sequence) |
| 181 | UGUCAGUUUGUCAAAUACCCCA<br>(miR 223-3p sequence) |
| 182 | CGUGUAUUUGACAAGCUGAGUU<br>(miR 223-5p sequence) |
| 183 | UGGCUCAGUUCAGCAGGAACAG<br>(miR 24-3p sequence) |
| 184 | UGCCUACUGAGCUGAUAUCAGU<br>(miR 24-5p sequence) |
| 185 | UUCACAGUGGCUAAGUUCCGC<br>(miR 27-3p sequence) |
| 186 | AGGGCUUAGCUGCUUGUGAGCA<br>(miR 27-5p sequence) |
| 187 | UUAAUGCUAAUUGUGAUAGGGGU<br>(miR 155-5p sequence) |
| 188 | ACCCCUAUCACAAUUAGCAUUAA<br>(miR 155-5p binding site) |
| 39 | GGGAAAUAAGAGAGAAAAGAAGAGUAAGAAGAAAUAUAAGAGCCACC<br>(5' UTR) |
| 189 | GGGAAAUAAGAGUCCAUAAAGUAGGAAACACUACAAGAAAAGAAGAGUAAGA<br>AGAAAUAUAAGAGCCACC<br>(5' UTR with miR142-3p binding site at position p1) |
| 190 | GGGAAAUAAGAGAGAAAAGAAGAGUAAUCCAUAAAGUAGGAAACACUACAGA<br>AGAAAUAUAAGAGCCACC<br>(5' UTR with miR142-3p binding site at position p2) |

TABLE 4-continued

3'UTRs, miR sequences, and miR binding sites

| SEQ ID NO: | Sequence |
|---|---|
| 191 | GGGAAAUAAGAGAGAAAAGAAGAGUAAGAAGAAAUAUAA<u>UCCAUAAAGUAGG</u><br><u>AAACACUAC</u>AGAGCCACC<br>(5' UTR with miR142-3p binding site at position p3) |
| 57 | UGAUAAUAG<u>UCCAUAAAGUAGGAAACACUAC</u>AGCUGGAGCCUCGGUGGCCAU<br>GCUUCUUGCCCCUUGGGCCUCCCCCAGCCCCUCCUCCCCUUCCUGCACCCG<br>UACCCCCGUGGUCUUUGAAUAAAGUCUGAGUGGGCGGC<br>(3'UTR with miR 142-3p binding site, P1 insertion) |
| 58 | UGAUAAUAGGCUGGAGCCUCGGUGGCU<u>CCAUAAAGUAGGAAACACUAC</u>ACAU<br>GCUUCUUGCCCCUUGGGCCUCCCCCAGCCCCUCCUCCCCUUCCUGCACCCG<br>UACCCCCGUGGUCUUUGAAUAAAGUCUGAGUGGGCGGC<br>(3'UTR with miR 142-3p binding site, P2 insertion) |
| 59 | UGAUAAUAGGCUGGAGCCUCGGUGGCCAUGCUUCUUGCCCC<u>UCCAUAAAGU</u><br><u>AGGAAACACUAC</u>AUGGGCCUCCCCCAGCCCCUCCUCCCCUUCCUGCACCCG<br>UACCCCCGUGGUCUUUGAAUAAAGUCUGAGUGGGCGGC<br>(3'UTR including miR142-3p binding site) |
| 60 | UGAUAAUAGGCUGGAGCCUCGGUGGCCAUGCUUCUUGCCCCUUGGGCCUCCC<br>CCCAGU<u>CCAUAAAGUAGGAAACACUAC</u>ACCCCUCCUCCCCUUCCUGCACCCG<br>UACCCCCGUGGUCUUUGAAUAAAGUCUGAGUGGGCGGC<br>(3'UTR including miR142-3p binding site) |
| 61 | UGAUAAUAGGCUGGAGCCUCGGUGGCCAUGCUUCUUGCCCCUUGGGCCUCCC<br>CCCAGCCCCUCCUCCCCUUC<u>UCCAUAAAGUAGGAAACACUAC</u>ACUGCACCCG<br>UACCCCCGUGGUCUUUGAAUAAAGUCUGAGUGGGCGGC<br>(3'UTR including including miR142-3p binding site) |
| 62 | UGAUAAUAGGCUGGAGCCUCGGUGGCCAUGCUUCUUGCCCCUUGGGCCUCCC<br>CCCAGCCCCUCCUCCCCUUCCUGCACCCGUACCCCC<u>UCCAUAAAGUAGGAAA</u><br><u>CACUAC</u>AGUGGUCUUUGAAUAAAGUCUGAGUGGGCGGC<br>(3'UTR with miR 142-3p binding site) |
| 63 | UGAUAAUAGGCUGGAGCCUCGGUGGCCAUGCUUCUUGCCCCUUGGGCCUCCC<br>CCCAGCCCCUCCUCCCCUUCCUGCACCCGUACCCCCGUGGUCUUUGAAUAAA<br>G<u>UUCCAUAAAGUAGGAAACACUAC</u>ACGAGUGGGCGGC<br>(3'UTR including including miR142-3p binding site) |
| 81 | UGAUAAUAGGCUGGAGCCUCGGUGGCCAUGCUUCUUGCCCCUUGGGCCUCCC<br>CCCAGCCCCUCCUCCCCUUCCUGCACCCGUACCCCCGUGGUCUUUGAAUAAA<br>GUCUGAGUGGGCGGC<br>(3'UTR, no miR binding sites) |
| 149 | UGAUAAUAG<u>UCCAUAAAGUAGGAAACACUAC</u>AGCUGGAGCCUCGGUGGCCAU<br>GCUUCUUGCCCCUUGGGCCUCCCCCAGCCCCUCCUCCCCUUCCUGCACCCG<br>UACCCCC<u>CGCAUUAUUACUCACGGUACGA</u>GUGGUCUUUGAAUAAAGUCUGAG<br>UGGGCGGC<br>(3'UTR with miR 142-3p and miR 126-3p binding<br>sites) |
| 150 | UGAUAAUAG<u>UCCAUAAAGUAGGAAACACUAC</u>AGCUGGAGCCUCGGUGGCCUA<br>GCUUCUUGCCCCUUGGGCCUCCCCCAGCCCCUCCUCCCCUUCCUGCACCCG<br>UACCCCC<u>CGCAUUAUUACUCACGGUACGA</u>GUGGUCUUUGAAUAAAGUCUGAG<br>UGGGCGGC<br>(3'UTR with miR 142-3p and miR 126-3p binding<br>sites variant 2) |
| 151 | UGAUAAUAGGCUGGAGCCUCGGUGGCCUAGCUUCUUGCCCCUUGGGCCUCCC<br>CCCAGCCCCUCCUCCCCUUCCUGCACCCGUACCCCC<u>UCCAUAAAGUAGGAAA</u><br><u>CACUAC</u>AGUGGUCUUUGAAUAAAGUCUGAGUGGGCGGC<br>(3'UTR with miR 142-3p binding site variant 2) |
| 161 | GCUGGAGCCUCGGUGGCCAUGCUUCUUGCCCCUUGGGCCUCCCCCAGCCCC<br>UCCUCCCCUUCCUGCACCCGUACCCCC<u>UCCAUAAAGUAGGAAACACUAC</u>AGU<br>GGUCUUUGAAUAAAGUCUGAGUGGGCGGC<br>(3'UTR with miR 142-3p binding site) |
| 162 | UGAUAAUAGGCUGGAGCCUCGGUGGCCAUGCUUCUUGCCCCUUGGGCCUCCC<br>CCCAGCCCCUCCUCCCCUUCCUGCACCCGUACCCCC<u>CGCAUUAUUACUCACG</u><br><u>GUACGA</u>GUGGUCUUUGAAUAAAGUCUGAGUGGGCGGC<br>(3'UTR with miR 126-3p binding site) |

TABLE 4-continued

3'UTRs, miR sequences, and miR binding sites

| SEQ ID NO: | Sequence |
|---|---|
| 163 | UGAUAAUAGGCUGGAGCCUCGGUGGCCUAGCUUCUUGCCCCUUGGGCCUCCC<br>CCCAGCCCCUCCUCCCCUUCCUGCACCCGUACCCCGUGGUCUUUGAAUAAA<br>GUCUGAGUGGGCGGC<br>(3'UTR, no miR binding sites variant 2) |
| 164 | UGAUAAUAGGCUGGAGCCUCGGUGGCCUAGCUUCUUGCCCCUUGGGCCUCCC<br>CCCAGCCCCUCCUCCCCUUCCUGCACCCGUACCCCC<u>CGCAUUAUUACUCACG</u><br><u>GUACGA</u>GUGGUCUUUGAAUAAAGUCUGAGUGGGCGGC<br>(3'UTR with miR 126-3p binding site variant 3) |
| 165 | UGAUAAUAGUCCAUAAAGUAGGAAACACUACAGCUGGAGCCUCGGUGGCCAU<br>GCUUCUUGCCCCUUGGGCC<u>UCCAUAAAGUAGGAAACACUAC</u>AU<u>CCCCCCAGC<br>CCCUCCUCCCCUUCCUGCACCCGUACCCCCUCCAUAAAGUAGGAAACACUAC</u><br><u>AGUGG</u>UCUUUGAAUAAAGUCUGAGUGGGCGGC<br>(3'UTR with 3 miR 142-3p binding sites) |
| 166 | UGAUAAUAGGCUGGAGCCUCGGUGGCCAUGCUUCUUGCCCCUUGGGCCUCCC<br>CCCAGCCCCUCCUCCCCUUCCUGCACCCGUACCCC*AGUAGUGCUUUCUACU*<br>*UUAUG*GUGGUCUUUGAAUAAAGUCUGAGUGGGCGGC<br>(3'UTR with miR 142-5p binding site) |
| 167 | UGAUAAUAG*AGUAGUGCUUUCUACUUUAUG*GCUGGAGCCUCGGUGGCCAUGC<br>UUCUUGCCCCUUGGGCC*AGUAGUGCUUUCUACUUUAUG*UCCCCCCAGCCCCU<br>CCUCCCCUUCCUGCACCCGUACCCCC*AGUAGUGCUUUCUACUUUAUG*GUGGU<br>CUUUGAAUAAAGUCUGAGUGGGCGGC<br>(3'UTR with 3 miR 142-5p binding sites) |
| 168 | UGAUAAUAG*AGUAGUGCUUUCUACUUUAUG*GCUGGAGCCUCGGUGGCCAUGC<br>UUCUUGCCCCUUGGGCCUCCAUAAAGUAGGAAACACUACAUCCCCCCAGCCC<br>CUCCUCCCCUUCCUGCACCCGUACCCCC*AGUAGUGCUUUCUACUUUAUG*GUG<br>GUCUUUGAAUAAAGUCUGAGUGGGCGGC<br>(3'UTR with 2 miR 142-5p binding sites and<br>1 miR 142-3p binding site) |
| 169 | UGAUAAUAGGCUGGAGCCUCGGUGGCCAUGCUUCUUGCCCCUUGGGCCUCCC<br>CCCAGCCCCUCCUCCCCUUCCUGCACCCGUACCCCC*ACCCCUAUCACAAUUA*<br>*GCAUUAAG*UGGUCUUUGAAUAAAGUCUGAGUGGGCGGC<br>(3'UTR with miR 155-5p binding site) |
| 170 | UGAUAAUAG*ACCCCUAUCACAAUUAGCAUUAAG*CUGGAGCCUCGGUGGCCAU<br>GCUUCUUGCCCCUUGGGCC*ACCCCUAUCACAAUUAGCAUUAA*UCCCCCCAGC<br>CCCUCCUCCCCUUCCUGCACCCGUACCCCC*ACCCCUAUCACAAUUAGCAUUA*<br>*AGUGG*UCUUUGAAUAAAGUCUGAGUGGGCGGC<br>(3'UTR with 3 miR 155-5p binding sites) |
| 171 | UGAUAAUAG*ACCCCUAUCACAAUUAGCAUUAAG*CUGGAGCCUCGGUGGCCAU<br>GCUUCUUGCCCCUUGGGCCUCCAUAAAGUAGGAAACACUACAUCCCCCCAGC<br>CCCUCCUCCCCUUCCUGCACCCGUACCCCC*ACCCCUAUCACAAUUAGCAUUA*<br>*AGUGG*UCUUUGAAUAAAGUCUGAGUGGGCGGC<br>(3'UTR with 2 miR 155-5p binding sites and<br>1 miR 142-3p binding site) |
| 172 | UGAUAAUAGGCUGGAGCCUCGGUGGCCAUGCUUCUUGCCCCUUGGGCC<u>UCCA</u><br><u>UAAAGUAGGAAACACUAC</u>AUCCCCCCAGCCCCUCCUCCCCUUCCUGCA<u>CCCG</u><br>UACCCCGUGGUCUUUGAAUAAAGUCUGAGUGGGCGGC<br>(3'UTR with miR 142-3p binding site, P3 insertion) |
| 192 | UGAUAAUAGU<u>CCAUAAAGUAGGAAACACUAC</u>AGCUGGAGCCUCGGUGGCCUA<br>GCUUCUUGCCCCUUGGGCC<u>UCCAUAAAGUAGGAAACACUAC</u>AUCCCCCCAGC<br>CCCUCCUCCCCUUCCUGC<u>ACCCGUACCCCCUCCAUAAAGUAGGAAACACUAC</u><br><u>AGUGG</u>UCUUUGAAUAAAGUCUGAGUGGGCGGC<br>(3'UTR with 3 miR 142-3p binding sites variant 2) |
| 193 | UGAUAAUAGU<u>CCAUAAAGUAGGAAACACUAC</u>AGCUGGAGCCUCGGUGGCCUA<br>GCUUCUUGCCCCUUGGGCCUCCCCCAGCCCCUCCUCCCCUUCCUGCACCCG<br>UACCCCGUGGUCUUUGAAUAAAGUCUGAGUGGGCGGC<br>(3'UTR with miR 142-3p binding site, P1<br>insertion variant 2) |
| 194 | UGAUAAUAGGCUGGAGCCUCGGUGGC<u>UCCAUAAAGUAGGAAACACUAC</u>UA<br>GCUUCUUGCCCCUUGGGCCUCCCCCAGCCCCUCCUCCCCUUCCUGCACCCG<br>UACCCCGUGGUCUUUGAAUAAAGUCUGAGUGGGCGGC<br>(3'UTR with miR 142-3p binding site, P2<br>insertion variant 2) |

TABLE 4-continued

3'UTRs, miR sequences, and miR binding sites

| SEQ ID NO: | Sequence |
|---|---|
| 195 | UGAUAAUAG<u>*AGUAGUGCUUUCUACUUUAUG*</u>GCUGGAGCCUCGGUGGCCAUGC<br>UUCUUGCCCCUUGGGCC<u>*AGUAGUGCUUUCUACUUUAUG*</u>UCCCCCCAGCCCCU<br>CUCCCCUUCCUGCACCCGUACCCC<u>*AGUAGUGCUUUCUACUUUAUG*</u>GUGGUC<br>UUUGAAUAAAGUCUGAGUGGGCGGC<br>(3'UTR with 3 miR 142-5p binding sites) |
| 196 | UGAUAAUAGGCUGGAGCCUCGGUGGCCUAGCUUCUUGCCCCUUGGGCC<u>UCCA<br>UAAAGUAGGAAACACUACAUCCCCCCAGCCCCUCCUCCCCUUCCUGCACCCG</u><br>UACCCCCGUGGUCUUUGAAUAAAGUCUGAGUGGGCGGC<br>(3'UTR with miR 142-3p binding site, P3<br>insertion variant 2) |
| 197 | UGAUAAUAGGCUGGAGCCUCGGUGGCCUAGCUUCUUGCCCCUUGGGCCUCCC<br>CCCAGCCCCUCCUCCCCUUCCUGCACCCGUACCCCC*ACCCCUAUCACAAUUA<br>GCAUUAAGUGGUCUUUGAAUAAAGUCUGAGUGGGCGGC*<br>(3'UTR with miR 155-5p binding site variant 2) |
| 198 | UGAUAAUAG*ACCCCUAUCACAAUUAGCAUUAAGCUGGAGCCUCGGUGGCCUA<br>GCUUCUUGCCCCUUGGGCCACCCCUAUCACAAUUAGCAUUAAUCCCCCCAGC<br>CCCUCCUCCCCUUCCUGCACCCGUACCCCCACCCCUAUCACAAUUAGCAUUA<br>AGUGGUCUUUGAAUAAAGUCUGAGUGGGCGGC*<br>(3'UTR with 3 miR 155-5p binding sites variant 2) |
| 199 | UGAUAAUAG*ACCCCUAUCACAAUUAGCAUUAAGCUGGAGCCUCGGUGGCCUA<br>GCUUCUUGCCCCUUGGGCC*UCC<u>AUAAAGUAGGAAACACUACAUCCCCCAGC<br>CCCUCCUCCCCUUCCUGC*ACCC*GUACCCCCACCCCUAUCACAAUUAGCAUUA<br>AGUGGUCUUUGAAUAAAGUCUGAGUGGGCGGC*<br>(3'UTR with 2 miR 155-5p binding sites and<br>1 miR 142-3p binding site variant 2) |

Stop codon = bold
miR 142-3p binding site = underline
miR 126-3p binding site = bold underline
miR 155-5p binding site = italicized
miR 142-5p binding site = italicized and bold underline In one embodiment, the polynucleotide of the invention comprises a 5' UTR, a codon optimized open reading frame encoding a polypeptide of interest, a 3' UTR comprising the at least one miRNA binding site for a miR expressed in immune cells, and a 3' tailing region of linked nucleosides. In various embodiments, the 3' UTR comprises 1-4, at least two, one, two, three or four miRNA binding sites for miRs expressed in immune cells, preferably abundantly or preferentially expressed in immune cells.

In one embodiment, the at least one miRNA expressed in immune cells is a miR-142-3p microRNA binding site. In one embodiment, the miR-142-3p microRNA binding site comprises the sequence shown in SEQ ID NO: 36. In one embodiment, the 3' UTR of the mRNA comprising the miR-142-3p microRNA binding site comprises the sequence shown in SEQ ID NO: 161.

In one embodiment, the at least one miRNA expressed in immune cells is a miR-126 microRNA binding site. In one embodiment, the miR-126 binding site is a miR-126-3p binding site. In one embodiment, the miR-126-3p microRNA binding site comprises the sequence shown in SEQ ID NO: 158. In one embodiment, the 3' UTR of the mRNA of the invention comprising the miR-126-3p microRNA binding site comprises the sequence shown in SEQ ID NO: 162.

Non-limiting exemplary sequences for miRs to which a microRNA binding site(s) of the disclosure can bind include the following: miR-142-3p (SEQ ID NO: 35), miR-142-5p (SEQ ID NO: 37), miR-146-3p (SEQ ID NO: 173), miR-146-5p (SEQ ID NO: 174), miR-155-3p (SEQ ID NO: 175), miR-155-5p (SEQ ID NO: 176), miR-126-3p (SEQ ID NO: 157), miR-126-5p (SEQ ID NO: 159), miR-16-3p (SEQ ID NO: 177), miR-16-5p (SEQ ID NO: 178), miR-21-3p (SEQ ID NO: 179), miR-21-5p (SEQ ID NO: 180), miR-223-3p (SEQ ID NO: 181), miR-223-5p (SEQ ID NO: 182), miR-24-3p (SEQ ID NO: 183), miR-24-5p (SEQ ID NO: 184), miR-27-3p (SEQ ID NO: 185) and miR-27-5p (SEQ ID NO: 186). Other suitable miR sequences expressed in immune cells (e.g., abundantly or preferentially expressed in immune cells) are known and available in the art, for example at the University of Manchester's microRNA database, miRBase. Sites that bind any of the aforementioned miRs can be designed based on Watson-Crick complementarity to the miR, typically 100% complementarity to the miR, and inserted into an mRNA construct of the disclosure as described herein.

In another embodiment, a polynucleotide of the present invention (e.g., and mRNA, e.g., the 3' UTR thereof) can comprise at least one miRNA bindingsite to thereby reduce or inhibit accelerated blood clearance, for example by reducing or inhibiting production of IgMs, e.g., against PEG, by B cells and/or reducing or inhibiting proliferation and/or activation of pDCs, and can comprise at least one miRNA bindingsite for modulating tissue expression of an encoded protein of interest.

miRNA gene regulation can be influenced by the sequence surrounding the miRNA such as, but not limited to, the species of the surrounding sequence, the type of sequence (e.g., heterologous, homologous, exogenous, endogenous, or artificial), regulatory elements in the surrounding sequence and/or structural elements in the surrounding sequence. The miRNA can be influenced by the 5'UTR and/or 3'UTR. As a non-limiting example, a non-human 3'UTR can increase the regulatory effect of the miRNA sequence on the expression of a polypeptide of interest compared to a human 3'UTR of the same sequence type.

In one embodiment, other regulatory elements and/or structural elements of the 5'UTR can influence miRNA mediated gene regulation. One example of a regulatory element and/or structural element is a structured IRES (Internal Ribosome Entry Site) in the 5'UTR, which is necessary for the binding of translational elongation factors to initiate protein translation. EIF4A2 binding to this secondarily structured element in the 5'-UTR is necessary for miRNA mediated gene expression (Meijer H A et al., Science, 2013, 340, 82-85, herein incorporated by reference in its entirety). The polynucleotides of the invention can further include this structured 5'UTR in order to enhance microRNA mediated gene regulation.

At least one miRNA binding site can be engineered into the 3'UTR of a polynucleotide of the invention. In this context, at least two, at least three, at least four, at least five, at least six, at least seven, at least eight, at least nine, at least ten, or more miRNA binding sites can be engineered into a 3'UTR of a polynucleotide of the invention. For example, 1 to 10, 1 to 9, 1 to 8, 1 to 7, 1 to 6, 1 to 5, 1 to 4, 1 to 3, 2, or 1 miRNA binding sites can be engineered into the 3'UTR of a polynucleotide of the invention. In one embodiment, miRNA binding sites incorporated into a polynucleotide of the invention can be the same or can be different miRNA sites. A combination of different miRNA binding sites incorporated into a polynucleotide of the invention can include combinations in which more than one copy of any of the different miRNA sites are incorporated. In another embodiment, miRNA binding sites incorporated into a polynucleotide of the invention can target the same or different tissues in the body. As a non-limiting example, through the introduction of tissue-, cell-type-, or disease-specific miRNA binding sites in the 3'-UTR of a polynucleotide of the invention, the degree of expression in specific cell types (e.g., myeloid cells, endothelial cells, etc.) can be reduced.

In one embodiment, a miRNA binding site can be engineered near the 5' terminus of the 3'UTR, about halfway between the 5' terminus and 3' terminus of the 3'UTR and/or near the 3' terminus of the 3'UTR in a polynucleotide of the invention. As a non-limiting example, a miRNA binding site can be engineered near the 5' terminus of the 3'UTR and about halfway between the 5' terminus and 3' terminus of the 3'UTR. As another non-limiting example, a miRNA binding site can be engineered near the 3' terminus of the 3'UTR and about halfway between the 5' terminus and 3' terminus of the 3'UTR. As yet another non-limiting example, a miRNA binding site can be engineered near the 5' terminus of the 3'UTR and near the 3' terminus of the 3'UTR.

In another embodiment, a 3'UTR can comprise 1, 2, 3, 4, 5, 6, 7, 8, 9, or 10 miRNA binding sites. The miRNA binding sites can be complementary to a miRNA, miRNA seed sequence, and/or miRNA sequences flanking the seed sequence.

In some embodiments, the expression of a polynucleotide of the invention can be controlled by incorporating at least one sensor sequence in the polynucleotide and formulating the polynucleotide for administration. As a non-limiting example, a polynucleotide of the invention can be targeted to a tissue or cell by incorporating a miRNA binding site and formulating the polynucleotide in a lipid nanoparticle comprising a ionizable lipid, including any of the lipids described herein.

A polynucleotide of the invention can be engineered for more targeted expression in specific tissues, cell types, or biological conditions based on the expression patterns of miRNAs in the different tissues, cell types, or biological conditions. Through introduction of tissue-specific miRNA binding sites, a polynucleotide of the invention can be designed for optimal protein expression in a tissue or cell, or in the context of a biological condition.

In some embodiments, a polynucleotide of the invention can be designed to incorporate miRNA binding sites that either have 100% identity to known miRNA seed sequences or have less than 100% identity to miRNA seed sequences. In some embodiments, a polynucleotide of the invention can be designed to incorporate miRNA binding sites that have at least: 60%, 65%, 70%, 75%, 80%, 85%, 90%, 95%, 96%, 97%, 98%, or 99% identity to known miRNA seed sequences. The miRNA seed sequence can be partially mutated to decrease miRNA binding affinity and as such result in reduced downmodulation of the polynucleotide. In essence, the degree of match or mis-match between the miRNA binding site and the miRNA seed can act as a rheostat to more finely tune the ability of the miRNA to modulate protein expression. In addition, mutation in the non-seed region of a miRNA binding site can also impact the ability of a miRNA to modulate protein expression.

In one embodiment, a miRNA sequence can be incorporated into the loop of a stem loop.

In another embodiment, a miRNA seed sequence can be incorporated in the loop of a stem loop and a miRNA binding site can be incorporated into the 5' or 3' stem of the stem loop.

In one embodiment, a translation enhancer element (TEE) can be incorporated on the 5'end of the stem of a stem loop and a miRNA seed can be incorporated into the stem of the stem loop. In another embodiment, a TEE can be incorporated on the 5' end of the stem of a stem loop, a miRNA seed can be incorporated into the stem of the stem loop and a miRNA binding site can be incorporated into the 3' end of the stem or the sequence after the stem loop. The miRNA seed and the miRNA binding site can be for the same and/or different miRNA sequences.

In one embodiment, the incorporation of a miRNA sequence and/or a TEE sequence changes the shape of the stem loop region which can increase and/or decrease translation. (see e.g, Kedde et al., "A Pumilio-induced RNA structure switch in p27-3'UTR controls miR-221 and miR-22 accessibility." Nature Cell Biology. 2010, incorporated herein by reference in its entirety).

In one embodiment, the 5'-UTR of a polynucleotide of the invention can comprise at least one miRNA sequence. The miRNA sequence can be, but is not limited to, a 19 or 22 nucleotide sequence and/or a miRNA sequence without the seed.

In one embodiment the miRNA sequence in the 5'UTR can be used to stabilize a polynucleotide of the invention described herein.

In another embodiment, a miRNA sequence in the 5'UTR of a polynucleotide of the invention can be used to decrease the accessibility of the site of translation initiation such as, but not limited to a start codon. See, e.g., Matsuda et al., PLoS One. 2010 11(5):e15057; incorporated herein by reference in its entirety, which used antisense locked nucleic acid (LNA) oligonucleotides and exon junction complexes (EJCs) around a start codon (−4 to +37 where the A of the AUG codons is +1) in order to decrease the accessibility to the first start codon (AUG). Matsuda showed that altering the sequence around the start codon with an LNA or EJC affected the efficiency, length and structural stability of a polynucleotide. A polynucleotide of the invention can comprise a miRNA sequence, instead of the LNA or EJC sequence described by Matsuda et al, near the site of translation initiation in order to decrease the accessibility to the site of translation initiation. The site of translation initiation can be prior to, after or within the miRNA sequence. As a non-limiting example, the site of translation initiation can be located within a miRNA sequence such as a seed sequence or binding site.

In some embodiments, a polynucleotide of the invention can include at least one miRNA in order to dampen the antigen presentation by antigen presenting cells. The miRNA can be the complete miRNA sequence, the miRNA seed sequence, the miRNA sequence without the seed, or a combination thereof. As a non-limiting example, a miRNA incorporated into a polynucleotide of the invention can be specific to the hematopoietic system. As another non-limiting example, a miRNA incorporated into a polynucleotide of the invention to dampen antigen presentation is miR-142-3p.

In some embodiments, a polynucleotide of the invention can include at least one miRNA in order to dampen expression of the encoded polypeptide in a tissue or cell of interest. As a non-limiting example a polynucleotide of the invention can include at least one miR-142-3p binding site, miR-142-3p seed sequence, miR-142-3p binding site without the seed, miR-142-5p binding site, miR-142-5p seed sequence, miR-142-5p binding site without the seed, miR-146 binding site, miR-146 seed sequence and/or miR-146 binding site without the seed sequence.

In some embodiments, a polynucleotide of the invention can comprise at least one miRNA binding site in the 3'UTR in order to selectively degrade mRNA therapeutics in the immune cells to subdue unwanted immunogenic reactions caused by therapeutic delivery. As a non-limiting example, the miRNA binding site can make a polynucleotide of the invention more unstable in antigen presenting cells. Non-limiting examples of these miRNAs include mir-142-5p, mir-142-3p, mir-146a-5p, and mir-146-3p.

In one embodiment, a polynucleotide of the invention comprises at least one miRNA sequence in a region of the polynucleotide that can interact with a RNA binding protein.

In some embodiments, the polynucleotide of the invention (e.g., a RNA, e.g., an mRNA) comprising (i) a sequence-optimized nucleotide sequence (e.g., an ORF) encoding a PBGD polypeptide (e.g., the wild-type sequence, functional fragment, or variant thereof) and (ii) a miRNA binding site (e.g., a miRNA binding site that binds to miR-142).

In some embodiments, the polynucleotide of the invention comprises a uracil-modified sequence encoding a PBGD polypeptide disclosed herein and a miRNA binding site disclosed herein, e.g., a miRNA binding site that binds to miR-142 and/or a miRNA binding site that binds to miR-126. In some embodiments, the polynucleotide of the invention comprises a uracil-modified sequence encoding a polypeptide disclosed herein and a miRNA binding site disclosed herein, e.g., a miRNA binding site that binds to miR-142miR-126, miR-142, miR-144, miR-146, miR-150, miR-155, miR-16, miR-21, miR-223, miR-24, miR-27 or miR-26a. In some embodiments, the miRNA binding site binds to miR126-3p, miR-142-3p, miR-142-5p, or miR-155. In some embodiments, the polynucleotide of the invention comprises a uracil-modified sequence encoding a polypeptide disclosed herein and at least two different microRNA binding sites, wherein the microRNA is expressed in an immune cell of hematopoietic lineage or a cell that expresses TLR7 and/or TLR8 and secretes pro-inflammatory cytokines and/or chemokines, and wherein the polynucleotide comprises one or more modified nucleobases. In some embodiments, the uracil-modified sequence encoding a PBGD polypeptide comprises at least one chemically modified nucleobase, e.g., 5-methoxyuracil. In some embodiments, at least 95% of a type of nucleobase (e.g., uracil) in a uracil-modified sequence encoding a PBGD polypeptide of the invention are modified nucleobases. In some embodiments, at least 95% of uricil in a uracil-modified sequence encoding a PBGD polypeptide is 5-methoxyuridine. In some embodiments, the polynucleotide (e.g., a RNA, e.g., an mRNA) disclosed herein, e.g., comprising an miRNA binding site, is formulated with a delivery agent comprising, e.g., a compound having the Formula (I), e.g., any of Compounds 1-232, e.g., Compound 18; a compound having the Formula (III), (IV), (V), or (VI), e.g., any of Compounds 233-342, e.g., Compound 236; or a compound having the Formula (VIII), e.g., any of Compounds 419-428, e.g., Compound 428, or any combination thereof. In some embodiments, the delivery agent comprises Compound 18, DSPC, Cholesterol, and Compound 428, e.g., with a mole ratio of about 50:10:38.5:1.5.

13. 3' UTRs

In certain embodiments, a polynucleotide of the present invention (e.g., a polynucleotide comprising a nucleotide sequence encoding a PBGD polypeptide of the invention) further comprises a 3' UTR.

3'-UTR is the section of mRNA that immediately follows the translation termination codon and often contains regulatory regions that post-transcriptionally influence gene expression. Regulatory regions within the 3'-UTR can influence polyadenylation, translation efficiency, localization, and stability of the mRNA. In one embodiment, the 3'-UTR useful for the invention comprises a binding site for regulatory proteins or microRNAs.

In certain embodiments, the 3' UTR useful for the polynucleotides of the invention comprises a 3'UTR selected from the group consisting of SEQ ID NO: 57 to 81, 84, 149 to 151, 161 to 172, 192 to 199, or any combination thereof. In some embodiments, the 3' UTR comprises a nucleic acid sequence selected from the group consisting of SEQ ID NOs: 149 to 151, or any combination thereof. In some embodiments, the 3' UTR comprises a nucleic acid sequence of SEQ ID NO: 150. In some embodiments, the 3' UTR comprises a nucleic acid sequence of SEQ ID NO: 151.

In certain embodiments, the 3' UTR sequence useful for the invention comprises a nucleotide sequence at least about 60%, at least about 70%, at least about 80%, at least about 90%, at least about 95%, at least about 96%, at least about 97%, at least about 98%, at least about 99%, or about 100% identical to a sequence selected from the group consisting of SEQ ID NO: 57 to 81, 84, 149 to 151, 161 to 172, 192 to 199, or any combination thereof.

14. REGIONS HAVING A 5' CAP

The invention also includes a polynucleotide that comprises both a 5' Cap and a polynucleotide of the present invention (e.g., a polynucleotide comprising a nucleotide sequence encoding a PBGD polypeptide).

The 5' cap structure of a natural mRNA is involved in nuclear export, increasing mRNA stability and binds the mRNA Cap Binding Protein (CBP), which is responsible for mRNA stability in the cell and translation competency through the association of CBP with poly(A) binding protein to form the mature cyclic mRNA species. The cap further assists the removal of 5' proximal introns during mRNA splicing.

Endogenous mRNA molecules can be 5'-end capped generating a 5'-ppp-5'-triphosphate linkage between a terminal guanosine cap residue and the 5'-terminal transcribed sense nucleotide of the mRNA molecule. This 5'-guanylate cap can then be methylated to generate an N7-methyl-guanylate residue. The ribose sugars of the terminal and/or anteterminal transcribed nucleotides of the 5' end of the mRNA can optionally also be 2'-O-methylated. 5'-decapping through hydrolysis and cleavage of the guanylate cap structure can target a nucleic acid molecule, such as an mRNA molecule, for degradation.

In some embodiments, the polynucleotides of the present invention (e.g., a polynucleotide comprising a nucleotide sequence encoding a PBGD polypeptide) incorporate a cap moiety.

In some embodiments, polynucleotides of the present invention (e.g., a polynucleotide comprising a nucleotide sequence encoding a PBGD polypeptide) comprise a non-hydrolyzable cap structure preventing decapping and thus increasing mRNA half-life. Because cap structure hydrolysis requires cleavage of 5'-ppp-5' phosphorodiester linkages, modified nucleotides can be used during the capping reaction. For example, a Vaccinia Capping Enzyme from New England Biolabs (Ipswich, MA) can be used with α-thio-guanosine nucleotides according to the manufacturer's instructions to create a phosphorothioate linkage in the 5'-ppp-5' cap. Additional modified guanosine nucleotides can be used such as α-methyl-phosphonate and seleno-phosphate nucleotides.

Additional modifications include, but are not limited to, 2'-O-methylation of the ribose sugars of 5'-terminal and/or 5'-anteterminal nucleotides of the polynucleotide (as mentioned above) on the 2'-hydroxyl group of the sugar ring. Multiple distinct 5'-cap structures can be used to generate the 5'-cap of a nucleic acid molecule, such as a polynucleotide that functions as an mRNA molecule. Cap analogs, which herein are also referred to as synthetic cap analogs, chemical caps, chemical cap analogs, or structural or functional cap analogs, differ from natural (i.e., endogenous, wild-type or physiological) 5'-caps in their chemical structure, while retaining cap function. Cap analogs can be chemically (i.e., non-enzymatically) or enzymatically synthesized and/or linked to the polynucleotides of the invention.

For example, the Anti-Reverse Cap Analog (ARCA) cap contains two guanines linked by a 5'-5'-triphosphate group, wherein one guanine contains an N7 methyl group as well as a 3'-O-methyl group (i.e., N7,3'-O-dimethyl-guanosine-5'-triphosphate-5'-guanosine (m$^7$G-3'mppp-G; which can equivalently be designated 3' O-Me-m7G(5')ppp(5')G). The 3'-O atom of the other, unmodified, guanine becomes linked to the 5'-terminal nucleotide of the capped polynucleotide. The N7- and 3'-O-methlyated guanine provides the terminal moiety of the capped polynucleotide.

Another exemplary cap is mCAP, which is similar to ARCA but has a 2'-O-methyl group on guanosine (i.e., N7,2'-O-dimethyl-guanosine-5'-triphosphate-5'-guanosine, m$^7$Gm-ppp-G).

In some embodiments, the cap is a dinucleotide cap analog. As a non-limiting example, the dinucleotide cap analog can be modified at different phosphate positions with a boranophosphate group or a phosphoroselenoate group such as the dinucleotide cap analogs described in U.S. Pat. No. 8,519,110, the contents of which are herein incorporated by reference in its entirety.

In another embodiment, the cap is a cap analog is a N7-(4-chlorophenoxyethyl) substituted dinucleotide form of a cap analog known in the art and/or described herein. Non-limiting examples of a N7-(4-chlorophenoxyethyl) substituted dinucleotide form of a cap analog include a N7-(4-chlorophenoxyethyl)-G(5)ppp(5')G and a N7-(4-chlorophenoxyethyl)-m$^{3'-O}$G(5')ppp(5')G cap analog (See, e.g., the various cap analogs and the methods of synthesizing cap analogs described in Kore et al. Bioorganic & Medicinal Chemistry 2013 21:4570-4574; the contents of which are herein incorporated by reference in its entirety). In another embodiment, a cap analog of the present invention is a 4-chloro/bromophenoxyethyl analog.

While cap analogs allow for the concomitant capping of a polynucleotide or a region thereof, in an in vitro transcription reaction, up to 20% of transcripts can remain uncapped. This, as well as the structural differences of a cap analog from an endogenous 5'-cap structures of nucleic acids produced by the endogenous, cellular transcription machinery, can lead to reduced translational competency and reduced cellular stability.

Polynucleotides of the invention (e.g., a polynucleotide comprising a nucleotide sequence encoding a PBGD polypeptide) can also be capped post-manufacture (whether IVT or chemical synthesis), using enzymes, in order to generate more authentic 5'-cap structures. As used herein, the phrase "more authentic" refers to a feature that closely mirrors or mimics, either structurally or functionally, an endogenous or wild type feature. That is, a "more authentic" feature is better representative of an endogenous, wild-type, natural or physiological cellular function and/or structure as compared to synthetic features or analogs, etc., of the prior art, or which outperforms the corresponding endogenous, wild-type, natural or physiological feature in one or more respects. Non-limiting examples of more authentic 5'cap structures of the present invention are those that, among other things, have enhanced binding of cap binding proteins, increased half-life, reduced susceptibility to 5' endonucleases and/or reduced 5'decapping, as compared to synthetic 5'cap structures known in the art (or to a wild-type, natural or physiological 5'cap structure). For example, recombinant Vaccinia Virus Capping Enzyme and recombinant 2'-O-methyltransferase enzyme can create a canonical 5'-5'-triphosphate linkage between the 5'-terminal nucleotide of a polynucleotide and a guanine cap nucleotide wherein the cap guanine contains an N7 methylation and the 5'-terminal nucleotide of the mRNA contains a 2'-O-methyl. Such a structure is termed the Cap1 structure. This cap results in a higher translational-competency and cellular stability and a reduced activation of cellular pro-inflammatory cytokines, as compared, e.g., to other 5'cap analog structures known in the art. Cap structures include, but are not limited to, 7mG(5')ppp(5')N,pN2p (cap 0), 7mG(5')ppp(5')NlmpNp (cap 1), and 7mG(5')-ppp(5')NlmpN2mp (cap 2).

As a non-limiting example, capping chimeric polynucleotides post-manufacture can be more efficient as nearly 100% of the chimeric polynucleotides can be capped. This is in contrast to ~80% when a cap analog is linked to a chimeric polynucleotide in the course of an in vitro transcription reaction.

According to the present invention, 5' terminal caps can include endogenous caps or cap analogs. According to the present invention, a 5' terminal cap can comprise a guanine analog. Useful guanine analogs include, but are not limited to, inosine, N1-methyl-guanosine, 2'fluoro-guanosine, 7-deaza-guanosine, 8-oxo-guanosine, 2-amino-guanosine, LNA-guanosine, and 2-azido-guanosine.

15. POLY-A TAILS

In some embodiments, the polynucleotides of the present disclosure (e.g., a polynucleotide comprising a nucleotide sequence encoding a PBGD polypeptide) further comprise a poly-A tail. In further embodiments, terminal groups on the poly-A tail can be incorporated for stabilization. In other embodiments, a poly-A tail comprises des-3' hydroxyl tails.

During RNA processing, a long chain of adenine nucleotides (poly-A tail) can be added to a polynucleotide such as an mRNA molecule in order to increase stability. Immediately after transcription, the 3' end of the transcript can be cleaved to free a 3' hydroxyl. Then poly-A polymerase adds a chain of adenine nucleotides to the RNA. The process, called polyadenylation, adds a poly-A tail that can be between, for example, approximately 80 to approximately 250 residues long, including approximately 80, 90, 100, 110, 120, 130, 140, 150, 160, 170, 180, 190, 200, 210, 220, 230, 240 or 250 residues long.

PolyA tails can also be added after the construct is exported from the nucleus.

According to the present invention, terminal groups on the poly A tail can be incorporated for stabilization. Polynucleotides of the present invention can include des-3' hydroxyl tails. They can also include structural moieties or 2'-Omethyl modifications as taught by Junjie Li, et al. (Current Biology, Vol. 15, 1501-1507, Aug. 23, 2005, the contents of which are incorporated herein by reference in its entirety).

The polynucleotides of the present invention can be designed to encode transcripts with alternative polyA tail structures including histone mRNA. According to Norbury, "Terminal uridylation has also been detected on human replication-dependent histone mRNAs. The turnover of these mRNAs is thought to be important for the prevention of potentially toxic histone accumulation following the completion or inhibition of chromosomal DNA replication. These mRNAs are distinguished by their lack of a 3' poly(A) tail, the function of which is instead assumed by a stable stem-loop structure and its cognate stem-loop binding protein (SLBP); the latter carries out the same functions as those of PABP on polyadenylated mRNAs" (Norbury, "Cytoplasmic RNA: a case of the tail wagging the dog," Nature Reviews Molecular Cell Biology; AOP, published online 29 Aug. 2013; doi:10.1038/nrm3645) the contents of which are incorporated herein by reference in its entirety.

Unique poly-A tail lengths provide certain advantages to the polynucleotides of the present invention. Generally, the length of a poly-A tail, when present, is greater than 30 nucleotides in length. In another embodiment, the poly-A tail is greater than 35 nucleotides in length (e.g., at least or greater than about 35, 40, 45, 50, 55, 60, 70, 80, 90, 100, 120, 140, 160, 180, 200, 250, 300, 350, 400, 450, 500, 600, 700, 800, 900, 1,000, 1,100, 1,200, 1,300, 1,400, 1,500, 1,600, 1,700, 1,800, 1,900, 2,000, 2,500, and 3,000 nucleotides).

In some embodiments, the polynucleotide or region thereof includes from about 30 to about 3,000 nucleotides (e.g., from 30 to 50, from 30 to 100, from 30 to 250, from 30 to 500, from 30 to 750, from 30 to 1,000, from 30 to 1,500, from 30 to 2,000, from 30 to 2,500, from 50 to 100, from 50 to 250, from 50 to 500, from 50 to 750, from 50 to 1,000, from 50 to 1,500, from 50 to 2,000, from 50 to 2,500, from 50 to 3,000, from 100 to 500, from 100 to 750, from 100 to 1,000, from 100 to 1,500, from 100 to 2,000, from 100 to 2,500, from 100 to 3,000, from 500 to 750, from 500 to 1,000, from 500 to 1,500, from 500 to 2,000, from 500 to 2,500, from 500 to 3,000, from 1,000 to 1,500, from 1,000 to 2,000, from 1,000 to 2,500, from 1,000 to 3,000, from 1,500 to 2,000, from 1,500 to 2,500, from 1,500 to 3,000, from 2,000 to 3,000, from 2,000 to 2,500, and from 2,500 to 3,000).

In some embodiments, the poly-A tail is designed relative to the length of the overall polynucleotide or the length of a particular region of the polynucleotide. This design can be based on the length of a coding region, the length of a particular feature or region or based on the length of the ultimate product expressed from the polynucleotides.

In this context, the poly-A tail can be 10, 20, 30, 40, 50, 60, 70, 80, 90, or 100% greater in length than the polynucleotide or feature thereof. The poly-A tail can also be designed as a fraction of the polynucleotides to which it belongs. In this context, the poly-A tail can be 10, 20, 30, 40, 50, 60, 70, 80, or 90% or more of the total length of the construct, a construct region or the total length of the construct minus the poly-A tail. Further, engineered binding sites and conjugation of polynucleotides for Poly-A binding protein can enhance expression.

Additionally, multiple distinct polynucleotides can be linked together via the PABP (Poly-A binding protein) through the 3'-end using modified nucleotides at the 3'-terminus of the poly-A tail. Transfection experiments can be conducted in relevant cell lines at and protein production can be assayed by ELISA at 12 hr, 24 hr, 48 hr, 72 hr and day 7 post-transfection.

In some embodiments, the polynucleotides of the present invention are designed to include a polyA-G Quartet region. The G-quartet is a cyclic hydrogen bonded array of four guanine nucleotides that can be formed by G-rich sequences in both DNA and RNA. In this embodiment, the G-quartet is incorporated at the end of the poly-A tail. The resultant polynucleotide is assayed for stability, protein production and other parameters including half-life at various time points. It has been discovered that the polyA-G quartet results in protein production from an mRNA equivalent to at least 75% of that seen using a poly-A tail of 120 nucleotides alone.

16. START CODON REGION

The invention also includes a polynucleotide that comprises both a start codon region and the polynucleotide described herein (e.g., a polynucleotide comprising a nucleotide sequence encoding a PBGD polypeptide). In some embodiments, the polynucleotides of the present invention can have regions that are analogous to or function like a start codon region.

In some embodiments, the translation of a polynucleotide can initiate on a codon that is not the start codon AUG. Translation of the polynucleotide can initiate on an alternative start codon such as, but not limited to, ACG, AGG, AAG, CTG/CUG, GTG/GUG, ATA/AUA, ATT/AUU, TTG/UUG (see Touriol et al. Biology of the Cell 95 (2003) 169-178 and Matsuda and Mauro PLoS ONE, 2010 5:11; the contents of each of which are herein incorporated by reference in its entirety).

As a non-limiting example, the translation of a polynucleotide begins on the alternative start codon ACG. As another non-limiting example, polynucleotide translation begins on the alternative start codon CTG or CUG. As yet another non-limiting example, the translation of a polynucleotide begins on the alternative start codon GTG or GUG.

Nucleotides flanking a codon that initiates translation such as, but not limited to, a start codon or an alternative start codon, are known to affect the translation efficiency, the length and/or the structure of the polynucleotide. (See, e.g., Matsuda and Mauro PLoS ONE, 2010 5:11; the contents of which are herein incorporated by reference in its entirety). Masking any of the nucleotides flanking a codon that initiates translation can be used to alter the position of translation initiation, translation efficiency, length and/or structure of a polynucleotide.

In some embodiments, a masking agent can be used near the start codon or alternative start codon in order to mask or hide the codon to reduce the probability of translation initiation at the masked start codon or alternative start codon. Non-limiting examples of masking agents include antisense locked nucleic acids (LNA) polynucleotides and exon junction complexes (EJCs) (See, e.g., Matsuda and Mauro describing masking agents LNA polynucleotides and EJCs (PLoS ONE, 2010 5:11); the contents of which are herein incorporated by reference in its entirety).

In another embodiment, a masking agent can be used to mask a start codon of a polynucleotide in order to increase the likelihood that translation will initiate on an alternative start codon. In some embodiments, a masking agent can be used to mask a first start codon or alternative start codon in order to increase the chance that translation will initiate on a start codon or alternative start codon downstream to the masked start codon or alternative start codon.

In some embodiments, a start codon or alternative start codon can be located within a perfect complement for a miRNA binding site. The perfect complement of a miRNA binding site can help control the translation, length and/or structure of the polynucleotide similar to a masking agent. As a non-limiting example, the start codon or alternative start codon can be located in the middle of a perfect complement for a miRNA binding site. The start codon or alternative start codon can be located after the first nucleotide, second nucleotide, third nucleotide, fourth nucleotide, fifth nucleotide, sixth nucleotide, seventh nucleotide, eighth nucleotide, ninth nucleotide, tenth nucleotide, eleventh nucleotide, twelfth nucleotide, thirteenth nucleotide, fourteenth nucleotide, fifteenth nucleotide, sixteenth nucleotide, seventeenth nucleotide, eighteenth nucleotide, nineteenth nucleotide, twentieth nucleotide or twenty-first nucleotide.

In another embodiment, the start codon of a polynucleotide can be removed from the polynucleotide sequence in order to have the translation of the polynucleotide begin on a codon that is not the start codon. Translation of the polynucleotide can begin on the codon following the removed start codon or on a downstream start codon or an alternative start codon. In a non-limiting example, the start codon ATG or AUG is removed as the first 3 nucleotides of the polynucleotide sequence in order to have translation initiate on a downstream start codon or alternative start codon. The polynucleotide sequence where the start codon was removed can further comprise at least one masking agent for the downstream start codon and/or alternative start codons in order to control or attempt to control the initiation of translation, the length of the polynucleotide and/or the structure of the polynucleotide.

17. STOP CODON REGION

The invention also includes a polynucleotide that comprises both a stop codon region and the polynucleotide described herein (e.g., a polynucleotide comprising a nucleotide sequence encoding a PBGD polypeptide). In some embodiments, the polynucleotides of the present invention can include at least two stop codons before the 3' untranslated region (UTR). The stop codon can be selected from TGA, TAA and TAG in the case of DNA, or from UGA, UAA and UAG in the case of RNA. In some embodiments, the polynucleotides of the present invention include the stop codon TGA in the case or DNA, or the stop codon UGA in the case of RNA, and one additional stop codon. In a further embodiment the addition stop codon can be TAA or UAA. In another embodiment, the polynucleotides of the present invention include three consecutive stop codons, four stop codons, or more.

18. INSERTIONS AND SUBSTITUTIONS

The invention also includes a polynucleotide of the present disclosure that further comprises insertions and/or substitutions.

In some embodiments, the 5'UTR of the polynucleotide can be replaced by the insertion of at least one region and/or string of nucleosides of the same base. The region and/or string of nucleotides can include, but is not limited to, at least 3, at least 4, at least 5, at least 6, at least 7 or at least 8 nucleotides and the nucleotides can be natural and/or unnatural. As a non-limiting example, the group of nucleotides can include 5-8 adenine, cytosine, thymine, a string of any of the other nucleotides disclosed herein and/or combinations thereof.

In some embodiments, the 5'UTR of the polynucleotide can be replaced by the insertion of at least two regions and/or strings of nucleotides of two different bases such as, but not limited to, adenine, cytosine, thymine, any of the other nucleotides disclosed herein and/or combinations thereof. For example, the 5'UTR can be replaced by inserting 5-8 adenine bases followed by the insertion of 5-8 cytosine bases. In another example, the 5'UTR can be replaced by inserting 5-8 cytosine bases followed by the insertion of 5-8 adenine bases.

In some embodiments, the polynucleotide can include at least one substitution and/or insertion downstream of the transcription start site that can be recognized by an RNA polymerase. As a non-limiting example, at least one substitution and/or insertion can occur downstream of the transcription start site by substituting at least one nucleic acid in the region just downstream of the transcription start site (such as, but not limited to, +1 to +6). Changes to region of nucleotides just downstream of the transcription start site can affect initiation rates, increase apparent nucleotide triphosphate (NTP) reaction constant values, and increase the dissociation of short transcripts from the transcription complex curing initial transcription (Brieba et al, Biochemistry (2002) 41: 5144-5149; herein incorporated by reference in its entirety). The modification, substitution and/or insertion of at least one nucleoside can cause a silent mutation of the sequence or can cause a mutation in the amino acid sequence.

In some embodiments, the polynucleotide can include the substitution of at least 1, at least 2, at least 3, at least 4, at least 5, at least 6, at least 7, at least 8, at least 9, at least 10, at least 11, at least 12 or at least 13 guanine bases downstream of the transcription start site.

In some embodiments, the polynucleotide can include the substitution of at least 1, at least 2, at least 3, at least 4, at least 5 or at least 6 guanine bases in the region just downstream of the transcription start site. As a non-limiting example, if the nucleotides in the region are GGGAGA, the guanine bases can be substituted by at least 1, at least 2, at least 3 or at least 4 adenine nucleotides. In another non-limiting example, if the nucleotides in the region are GGGAGA the guanine bases can be substituted by at least 1, at least 2, at least 3 or at least 4 cytosine bases. In another non-limiting example, if the nucleotides in the region are GGGAGA the guanine bases can be substituted by at least 1, at least 2, at least 3 or at least 4 thymine, and/or any of the nucleotides described herein.

In some embodiments, the polynucleotide can include at least one substitution and/or insertion upstream of the start codon. For the purpose of clarity, one of skill in the art would appreciate that the start codon is the first codon of the protein coding region whereas the transcription start site is the site where transcription begins. The polynucleotide can include, but is not limited to, at least 1, at least 2, at least 3, at least 4, at least 5, at least 6, at least 7 or at least 8 substitutions and/or insertions of nucleotide bases. The nucleotide bases can be inserted or substituted at 1, at least 1, at least 2, at least 3, at least 4 or at least 5 locations upstream of the start codon. The nucleotides inserted and/or substituted can be the same base (e.g., all A or all C or all T or all G), two different bases (e.g., A and C, A and T, or C and T), three different bases (e.g., A, C and T or A, C and T) or at least four different bases.

As a non-limiting example, the guanine base upstream of the coding region in the polynucleotide can be substituted with adenine, cytosine, thymine, or any of the nucleotides described herein. In another non-limiting example the substitution of guanine bases in the polynucleotide can be designed so as to leave one guanine base in the region downstream of the transcription start site and before the start codon (see Esvelt et al. Nature (2011) 472(7344):499-503; the contents of which is herein incorporated by reference in its entirety). As a non-limiting example, at least 5 nucleotides can be inserted at 1 location downstream of the transcription start site but upstream of the start codon and the at least 5 nucleotides can be the same base type.

19. POLYNUCLEOTIDE COMPRISING AN MRNA ENCODING A PBGD POLYPEPTIDE

In certain embodiments, a polynucleotide of the present disclosure, for example a polynucleotide comprising an mRNA nucleotide sequence encoding a PBGD polypeptide, comprises from 5' to 3' end:
(i) a 5' cap provided above;
(ii) a 5' UTR, such as the sequences provided above;
(iii) an open reading frame encoding a PBGD polypeptide, e.g., a sequence optimized nucleic acid sequence encoding PBGD disclosed herein;
(iv) at least one stop codon;
(v) a 3' UTR, such as the sequences provided above; and
(vi) a poly-A tail provided above.

In some embodiments, the polynucleotide further comprises a miRNA binding site, e.g, a miRNA binding site that binds to miRNA-142. In some embodiments, the 5'UTR comprises the miRNA binding site.

In some embodiments, a polynucleotide of the present disclosure comprises a nucleotide sequence encoding a polypeptide sequence at least 70%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to the protein sequence of a wild type PBGD (e.g, isoform 1, 2, 3, or 4).

In some embodiments, a polynucleotide of the present disclosure, for example a polynucleotide comprising an mRNA nucleotide sequence encoding a PBGD polypeptide, comprises (1) a 5' cap provided above, for example, CAP1, (2) a nucleotide sequence selected form the group consisting of SEQ ID NO: 133, 141, 144, and 145, and (3) a poly-A tail provided above, for example, a poly A tail of ~100 residues, wherein SEQ ID NO: 133 comprises from 5' to 3' end: 5' UTR of SEQ ID NO:39, PBGD polypeptide ORF of SEQ ID NO: 104, and 3'UTR of SEQ ID NO: 149; SEQ ID NO: 141 comprises from 5' to 3' end: 5' UTR of SEQ ID NO:39, PBGD polypeptide ORF of SEQ ID NO: 112, and 3'UTR of SEQ ID NO: 149; SEQ ID NO: 144 comprises from 5' to 3' end: 5' UTR of SEQ ID NO:39, PBGD polypeptide ORF of SEQ ID NO: 112, and 3'UTR of SEQ ID NO: 150; and SEQ ID NO: 145 comprises from 5' to 3' end: 5' UTR of SEQ ID NO:39, PBGD polypeptide ORF of SEQ ID NO: 112, and 3'UTR of SEQ ID NO: 151.

In some embodiments, a polynucleotide of the present disclosure, for example a polynucleotide comprising an mRNA nucleotide sequence encoding a PBGD polypeptide, comprises (1) a 5' cap provided above, for example, CAP1, (2) a nucleotide sequence selected form the group consisting of SEQ ID NO: 118-132, 134-140, 142, 143, and 146-148, and (3) a poly-A tail provided above, for example, a poly A tail of ~100 residues, wherein
- SEQ ID NO: 118 comprises from 5' to 3' end: 5' UTR of SEQ ID NO:39, PBGD polypeptide ORF of SEQ ID NO: 89, and 3'UTR of SEQ ID NO: 149;
- SEQ ID NO: 119 comprises from 5' to 3' end: 5' UTR of SEQ ID NO:39, PBGD polypeptide ORF of SEQ ID NO: 90, and 3'UTR of SEQ ID NO: 149;
- SEQ ID NO: 120 comprises from 5' to 3' end: 5' UTR of SEQ ID NO:39, PBGD polypeptide ORF of SEQ ID NO: 91, and 3'UTR of SEQ ID NO: 149;
- SEQ ID NO: 121 comprises from 5' to 3' end: 5' UTR of SEQ ID NO:39, PBGD polypeptide ORF of SEQ ID NO: 92, and 3'UTR of SEQ ID NO: 149;
- SEQ ID NO: 122 comprises from 5' to 3' end: 5' UTR of SEQ ID NO:39, PBGD polypeptide ORF of SEQ ID NO: 93, and 3'UTR of SEQ ID NO: 149;
- SEQ ID NO: 123 comprises from 5' to 3' end: 5' UTR of SEQ ID NO:39, PBGD polypeptide ORF of SEQ ID NO: 94, and 3'UTR of SEQ ID NO: 149;
- SEQ ID NO: 124 comprises from 5' to 3' end: 5' UTR of SEQ ID NO:39, PBGD polypeptide ORF of SEQ ID NO: 95, and 3'UTR of SEQ ID NO: 149;
- SEQ ID NO: 125 comprises from 5' to 3' end: 5' UTR of SEQ ID NO:39, PBGD polypeptide ORF of SEQ ID NO: 96, and 3'UTR of SEQ ID NO: 149;
- SEQ ID NO: 126 comprises from 5' to 3' end: 5' UTR of SEQ ID NO:39, PBGD polypeptide ORF of SEQ ID NO: 97, and 3'UTR of SEQ ID NO: 149;
- SEQ ID NO: 127 comprises from 5' to 3' end: 5' UTR of SEQ ID NO:39, PBGD polypeptide ORF of SEQ ID NO: 98, and 3'UTR of SEQ ID NO: 149;
- SEQ ID NO: 128 comprises from 5' to 3' end: 5' UTR of SEQ ID NO:39, PBGD polypeptide ORF of SEQ ID NO: 99, and 3'UTR of SEQ ID NO: 149;
- SEQ ID NO: 129 comprises from 5' to 3' end: 5' UTR of SEQ ID NO:39, PBGD polypeptide ORF of SEQ ID NO: 100, and 3'UTR of SEQ ID NO: 149;
- SEQ ID NO: 130 comprises from 5' to 3' end: 5' UTR of SEQ ID NO:39, PBGD polypeptide ORF of SEQ ID NO: 101, and 3'UTR of SEQ ID NO: 149;

SEQ ID NO: 131 comprises from 5' to 3' end: 5' UTR of SEQ ID NO:39, PBGD polypeptide ORF of SEQ ID NO: 102, and 3'UTR of SEQ ID NO: 149;

SEQ ID NO: 132 comprises from 5' to 3' end: 5' UTR of SEQ ID NO:39, PBGD polypeptide ORF of SEQ ID NO: 103, and 3'UTR of SEQ ID NO: 149;

SEQ ID NO: 134 comprises from 5' to 3' end: 5' UTR of SEQ ID NO:39, PBGD polypeptide ORF of SEQ ID NO: 105, and 3'UTR of SEQ ID NO: 149;

SEQ ID NO: 135 comprises from 5' to 3' end: 5' UTR of SEQ ID NO:39, PBGD polypeptide ORF of SEQ ID NO: 106, and 3'UTR of SEQ ID NO: 149;

SEQ ID NO: 136 comprises from 5' to 3' end: 5' UTR of SEQ ID NO:39, PBGD polypeptide ORF of SEQ ID NO: 107, and 3'UTR of SEQ ID NO: 149;

SEQ ID NO: 137 comprises from 5' to 3' end: 5' UTR of SEQ ID NO:39, PBGD polypeptide ORF of SEQ ID NO: 108, and 3'UTR of SEQ ID NO: 149;

SEQ ID NO: 138 comprises from 5' to 3' end: 5' UTR of SEQ ID NO:39, PBGD polypeptide ORF of SEQ ID NO: 109, and 3'UTR of SEQ ID NO: 149;

SEQ ID NO: 139 comprises from 5' to 3' end: 5' UTR of SEQ ID NO:39, PBGD polypeptide ORF of SEQ ID NO: 110, and 3'UTR of SEQ ID NO: 149;

SEQ ID NO: 140 comprises from 5' to 3' end: 5' UTR of SEQ ID NO:39, PBGD polypeptide ORF of SEQ ID NO: 111, and 3'UTR of SEQ ID NO: 149;

SEQ ID NO: 142 comprises from 5' to 3' end: 5' UTR of SEQ ID NO:39, PBGD polypeptide ORF of SEQ ID NO: 113, and 3'UTR of SEQ ID NO: 149;

SEQ ID NO: 143 comprises from 5' to 3' end: 5' UTR of SEQ ID NO:39, PBGD polypeptide ORF of SEQ ID NO: 114, and 3'UTR of SEQ ID NO: 149;

SEQ ID NO: 146 comprises from 5' to 3' end: 5' UTR of SEQ ID NO:39, PBGD polypeptide ORF of SEQ ID NO: 115, and 3'UTR of SEQ ID NO: 149;

SEQ ID NO: 147 comprises from 5' to 3' end: 5' UTR of SEQ ID NO:39, PBGD polypeptide ORF of SEQ ID NO: 116, and 3'UTR of SEQ ID NO: 149; and SEQ ID NO: 148 comprises from 5' to 3' end: 5' UTR of SEQ ID NO:39, PBGD polypeptide ORF of SEQ ID NO: 117, and 3'UTR of SEQ ID NO: 149.

TABLE 5 mRNA Constructs

| SEQ ID NO | Con-struct | Sequence (5' UTR = bold underline; 3' UTR comprising a stop codon = bold italics) |
|---|---|---|
| 133 | #16 | <u>GGGAAAUAAGAGAGAAAAGAAGAGUAAGAAGAAAUAUAAGAGCCACC</u>AUGAGCGGCAACGGCAACGCCGCCGCCACCGCCGAGGAGAACAGCCCCAAGAUGCGGGUGAUCCGGGUGGGCACCCGGAAGAGCCAGCUGGCCCGGAUCCAGACCGACAGCGUGGUGGCCACCCUGAAGGCCAGCUACCCCGGCCUGCAGUUCGAGAUCAUCGCCAUGAGCACCACCGGCGACAAGAUCCUGGACACCGCCCUGAGCAAGAUCGGCGAGAAGAGCCUGUUCACCAAGGAGCUGGAGCACGCCCUGGAGAAGAACGAGGUGGACCUGGUGGUGCACAGCCUGAAGGACCUGCCCACCGUGCUGCCCCCCGGCUUCACCAUCGGCGCCAUCUGCAAGCGGGAGAACCCCCACGACGCCGUGGUGUUCCACCCCAAGUUCGUGGGCAAGACCCUGGAGACCCUGCCCGAGAAGAGCGUGGUGGGCACCAGCAGCCUGCGGCGGGCCGCCCAGCUGCAGCGGAAGUUCCCCCACCUGGAGUUCCGGAGCAUCCGGGGCAACCUGAACACCCGGCUGCGGAAGCUGGACGAGCAGCAGGAGUUCAGCGCCAUCAUCCUGGCCACCGCCGGCCUGCAGCGGAUGGGCUGGCACAACCGGGUGGGCCAGAUCCUGCACCCCGAGGAGUGCAUGUACGCCGUGGGCCAGGGCGCCCUGGGCGUGGAGGUGCGGGCCAAGGACCAGGACAUCCUGGACCUGGUGGGCGUGCUGCACGACCCCGAGACCCUGCUGCGGUGCAUCGCCGAGCGGGCCUUCCUGCGGCACCUGGAGGGCGGCUGCAGCGUGCCCGUGGCCGUGCACACCGCCAUGAAGGACGGCCAGCUGUACCUGACCGGCGGCGUGUGGAGCCUGGACGGCAGCGACAGCAUCCAGGAGACCAUGCAGGCCACCAUCCACGUGCCCGCCCAGCACGAGGACGGCCCCGAGGACGACCCCCAGCUGGUGGGCAUCACCGCCCGGAACAUCCCCGGGGCCCCCAGCUGGCCGCCCAGAACCUGGGCAUCAGCCUGGCCAACCUGCUGCUGAGCAAGGGCGCCAAGAACAUCCUGGACGUGGCCCGGCAGCUGAACGACGCCCAC*UGAUAAUAGUCCAUAAAGUAGGAAACACUACAGCUGGAGCCUCGGUGGCCAUGCUUCUUGCCCCUUGGGCUCUCCCCCAGCCCCUCCUCCCCUUCCUGCACCCGUACCCCCCGCAUUAUUACUCACGGUACGAGUGGUCUUUGAAUAAAGUCUGAGUGGGCGGC* |
| 141 | #24 | <u>GGGAAAUAAGAGAGAAAAGAAGAGUAAGAAGAAAUAUAAGAGCCACC</u>AUGAGCGGCAACGGCAACGCCGCCGCCACCGCCGAGGAGAACAGCCCCAAGAUGCGGGUGAUCCGGGUGGGCACCCGGAAGAGCCAGCUGGCCCGGAUCCAGACCGACAGCGUGGUGGCCACCCUGAAGGCCAGCUACCCCGGCCUGCAGUUCGAGAUCAUCGCCAUGAGCACCACCGGCGACAAGAUCCUGGACACCGCCCUGAGCAGAUCGGCGAGAAGAGCCUGUUCACCAAGGAGCUGGAGCACGCCCUGGAGAAGAACGAGGUGGACCUGGUGGUGCACAGCCUGAAGGACCUGCCCACCGUGCUGCCGCCCGGCUUCACCAUCGGCGCCAUCUGCAAGCGGGAGAACCCGCACGACGCCGUGGUGUUCCACCCCAAGUUCGUGGGCAAGACCCUGGAGACCCUGCCCGAGAAGAGCGUGGUGGGCACCAGCAGCCUGCGGCGGGCCGCCCAGCUGCAGCGGAAGUUCCCUCACCUGGAGUUCCGGAGCAUCCGGGGCAACCUGAACACCCGGCUGCGGAAGCUGGACGAGCAGCAGGAGUUCAGCGCCAUCAUCCUGGCCACCGCCGGCCUGCAGCGGAUGGGCUGGCACAACCGGGUGGGCCAGAUCCUGCACCCCGAGGAGUGCAUGUACGCCGUGGGCCAGGGCGCCCUGGGCGUGGAGGUGCGGGCCAAGGACCAGGACAUCCUGGACCUGGUGGGCGUGCUGCACGACCCCGAGACCCUGCUGCGGUGCAUCGCCGAGCGGGCCUUCCUGCGGCACCUGGAGGGCGGCUGCAGCGUGCCCGUGGCCGUGCACACCGCCAUGAAGGACGGCCAGCUGUACCUGACCGGCGGCGUGUGGAGCCUGGACGGCAGCGACAGCAUCCAGGAGACCAUGCAGGCCACCAUCCACGUGCCCGCCCAGCACGAGGACGCCCCGAGGACGACCCUCAGCUGGUGGGCAUCACCGCCCGGAACAUCCCACGGGGCCCUCAGCUGGCCGCCCAGAACCUGGGCAUCAGCCUGGCCAACCUGC |

TABLE 5-continued mRNA Constructs

| SEQ ID NO | Construct | Sequence (5' UTR = bold underline; 3' UTR comprising a stop codon = bold italics) |
|---|---|---|
| | | UGCUGAGCAAGGGCGCCAAGAACAUCCUGGACGUGGCCCGGCAGCUGAACG<br>ACGCCCAC*UGAUAAUAGUCCAUAAAGUAGGAAACACUACAGCUGGAGCCUC<br>GGUGGCCAUGCUUCUUGCCCCUUGGGCCUCCCCCCAGCCCCUCCUCCCCUU<br>CCUGCACCCGUACCCCCGCAUUAUUACUCACGGUACGAGUGGUCUUUGAA<br>UAAAGUCUGAGUGGGCGGC* |
| 144 | #27 | <u>GGGAAAUAAGAGAGAAAAGAAGAGUAAGAAGAAAUAUAAGAGCCACC</u>AUGA<br>GCGGCAACGGCAACGCCGCCGCCACCGCCGAGGAGAACAGCCCCAAGAUGC<br>GGGUGAUCCGGGUGGGCACCCGGAAGAGCCAGCUGGCCCGGAUCCAGACCG<br>ACAGCGUGGUGGCCACCCUGAAGGCCAGCUACCCCGGCCUGCAGUUCGAGA<br>UCAUCGCCAUGAGCACCACCGGCGACAAGAUCCUGGACACCGCCCUGAGCA<br>AGAUCGGCGAGAAGAGCCUGUUCACCAAGGAGCUGGAGCACGCCCUGGAGA<br>AGAACGAGGUGGACCUGGUGGUGCACAGCCUGAAGGACCUGCCCACCGUGC<br>UGCCGCCCGGCUUCACCAUCGGCGCCAUCUGCAAGCGGGAGAACCCGCACG<br>ACGCCGUGGUGUUCCACCCCAAGUUCGUGGGCAAGACCCUGGAGACCCUGC<br>CCGAGAAGAGCGUGGUGGGCACCAGCAGCCUGCGGCGGGCCGCCCAGCUGC<br>AGCGGAAGUUCCCUCACCUGGAGUUCCGGAGCAUCCGGGGCAACCUGAACA<br>CCCGGCUGCGGAAGCUGGACGAGCAGCAGGAGUUCAGCGCCAUCAUCCUGG<br>CCACCGCCGGCCUGCAGCGGAUGGGCUGGCACAACCGGGUGGGCCAGAUCC<br>UGCACCCCGAGGAGUGCAUGUACGCCGUGGGCCAGGGCGCCCUGGGCGUGG<br>AGGUGCGGGCCAAGGACCAGGACAUCCUGGACCUGGUGGGCGUGCUGCACG<br>ACCCCGAGACCCUGCUCGGUGCAUCGCCGAGCGGGCCUUCCUGCGGCACC<br>UGGAGGGCGGCUGCAGCGUGCCCGUGGCCGUGCACACCGCCAUGAAGGACG<br>GCCAGCUGUACCUGACCGGCGGCGUGUGGAGCCUGGACGGCAGCGACAGCA<br>UCCAGGAGACCAUGCAGGCCACCAUCCACGUGCCCGCCCAGCACGAGGACG<br>GCCCCGAGGACGACCCUCAGCUGGUGGGCAUCACCGCCCGGAACAUCCCAC<br>GGGGCCCUCAGCUGGCCGCCCAGAACCUGGGCAUCAGCCUGGCCAACCUGC<br>UGCUGAGCAAGGGCGCCAAGAACAUCCUGGACGUGGCCCGGCAGCUGAACG<br>ACGCCCAC*UGAUAAUAGUCCAUAAAGUAGGAAACACUACAGCUGGAGCCUC<br>GGUGGCCUAGCUUCUUGCCCCUUGGGCCUCCCCCCAGCCCCUCCUCCCCUU<br>CCUGCACCCGUACCCCCGCAUUAUUACUCACGGUACGAGUGGUCUUUGAA<br>UAAAGUCUGAGUGGGCGGC* |
| 145 | #28 | <u>GGGAAAUAAGAGAGAAAAGAAGAGUAAGAAGAAAUAUAAGAGCCACC</u>AUGA<br>GCGGCAACGGCAACGCCGCCGCCACCGCCGAGGAGAACAGCCCCAAGAUGC<br>GGGUGAUCCGGGUGGGCACCCGGAAGAGCCAGCUGGCCCGGAUCCAGACCG<br>ACAGCGUGGUGGCCACCCUGAAGGCCAGCUACCCCGGCCUGCAGUUCGAGA<br>UCAUCGCCAUGAGCACCACCGGCGACAAGAUCCUGGACACCGCCCUGAGCA<br>AGAUCGGCGAGAAGAGCCUGUUCACCAAGGAGCUGGAGCACGCCCUGGAGA<br>AGAACGAGGUGGACCUGGUGGUGCACAGCCUGAAGGACCUGCCCACCGUGC<br>UGCCGCCCGGCUUCACCAUCGGCGCCAUCUGCAAGCGGGAGAACCCGCACG<br>ACGCCGUGGUGUUCCACCCCAAGUUCGUGGGCAAGACCCUGGAGACCCUGC<br>CCGAGAAGAGCGUGGUGGGCACCAGCAGCCUGCGGCGGGCCGCCCAGCUGC<br>AGCGGAAGUUCCCUCACCUGGAGUUCCGGAGCAUCCGGGGCAACCUGAACA<br>CCCGGCUGCGGAAGCUGGACGAGCAGCAGGAGUUCAGCGCCAUCAUCCUGG<br>CCACCGCCGGCCUGCAGCGGAUGGGCUGGCACAACCGGGUGGGCCAGAUCC<br>UGCACCCCGAGGAGUGCAUGUACGCCGUGGGCCAGGGCGCCCUGGGCGUGG<br>AGGUGCGGGCCAAGGACCAGGACAUCCUGGACCUGGUGGGCGUGCUGCACG<br>ACCCCGAGACCCUGCUGCGGUGCAUCGCCGAGCGGGCCUUCCUGCGGCACC<br>UGGAGGGCGGCUGCAGCGUGCCCGUGGCCGUGCACACCGCCAUGAAGGACG<br>GCCAGCUGUACCUGACCGGCGGCGUGUGGAGCCUGGACGGCAGCGACAGCA<br>UCCAGGAGACCAUGCAGGCCACCAUCCACGUGCCCGCCCAGCACGAGGACG<br>GCCCCGAGGACGACCCUCAGCUGGUGGGCAUCACCGCCCGGAACAUCCCAC<br>GGGGCCCUCAGCUGGCCGCCCAGAACCUGGGCAUCAGCCUGGCCAACCUGC<br>UGCUGAGCAAGGGCGCCAAGAACAUCCUGGACGUGGCCCGGCAGCUGAACG<br>ACGCCCAC*UGAUAAUAGGCUGGAGCCUCGGUGGCCUAGCUUCUUGCCCCUU<br>GGGCCUCCCCCCAGCCCCUCCUCCCCUUCCUGCACCCGUACCCCCUCCAUA<br>AAGUAGGAAACACUACAGUGGUCUUUGAAUAAAGUCUGAGUGGGCGGC* |
| 118 | #1 | <u>GGGAAAUAAGAGAGAAAAGAAGAGUAAGAAGAAAUAUAAGAGCCACC</u>AUGA<br>GCGGCAACGGCAACGCCGCAGCCACCGCCGAGGAAAACAGCCCCAAGAUGC<br>GGGUGAUCAGAGUGGGCACCCGGAAGAGCCAGCUGGCCCGGAUCCAGACCG<br>ACAGCGUGGUGGCCACCCUGAAGGCCUCCUACCCCGGCCUGCAGUUCGAGA<br>UCAUUGCCAUGAGCACCACCGGCGACAAGAUCCUGGACACCGCCCUGAGCA<br>AGAUCGGCGAGAAGAGCCUGUUCACAAAAGAGCUGGAACACGCCCUGGAAA<br>AGAACGAGGUGGACCUGGUGGUGCACAGCCUGAAGGACCUGCCCACCGUGC<br>UGCCCCCUGGCUUCACCAUCGGCGCCAUCUGCAAGAGAGAGAACCCCCACG<br>ACGCCGUGGUGUUCCACCCUAAGUUCGUGGGCAAGACACUGGAAACCCUGC<br>CCGAGAAGUCCGUGGUGGGCACCAGCAGCCUGCGGAGAGCCGCCCAGCUGC<br>AGCGGAAGUUCCCCCACCUGGAAUUUCGGAGCAUCCGGGGCAACCUGAACA<br>CCCGGCUGCGGAAGCUGGACGAGCAGCAGGAAUUUCCGCUAUCAUCCUGG<br>CCACAGCCGGACUGCAGCGGAUGGGCUGGCACAACAGAGUGGGCCAGAUCC<br>UGCACCCCGAGGAAUGCAUGUACGCCGUGGGCCAGGGAGCCCUGGGCGUGG<br>AAGUGCGGGCCAAGGACCAGGACAUCCUGGAUCUGGUGGGCGUGCUGCAUG<br>ACCCCGAGACACUGCUCGGUGUAUCGCCGAGCGGGCCUUCCUGCGGCACC |

TABLE 5-continued mRNA Constructs

| SEQ ID NO | Construct | Sequence (5' UTR = bold underline; 3' UTR comprising a stop codon = bold italics) |
|---|---|---|
| | | UGGAAGGCGGCUGCAGCGUGCCCGUGGCCGUGCACACCGCCAUGAAGGACG<br>GACAGCUGUACCUGACAGGCGGCGUGUGGAGCCUGGACGGCAGCGACAGCA<br>UCCAGGAGACCAUGCAGGCCACCAUCCACGUGCCCGCCCAGCACGAGGACG<br>GCCCCGAGGACGACCCUCAGCUGGUCGGCAUCACCGCCGGAACAUCCCCA<br>GAGGCCCCCAGCUGGCCGCCCAGAACCUGGGCAUCAGCCUGGCCAACCUGC<br>UGCUGUCCAAGGGCGCCAAGAACAUCCUGGACGUGGCCCGGCAGCUGAACG<br>ACGCCCAC*UGAUAAUAGUCCAUAAAGUAGGAAACACUACAGCUGGAGCCUC*<br>*GGUGGCCAUGCUUCUUGCCCCUUGGGCCUCCCCCCAGCCCCUCCUCCCCUU*<br>*CCUGCACCCGUACCCCCCGCAUUAUUACUCACGGUACGAGUGGUCUUUGAA*<br>*UAAAGUCUGAGUGGGCGGC* |
| 119 | #2 | <u>GGGAAAUAAGAGAGAAAAGAAGAGUAAGAAGAAAUAUAAGAGCCACC</u>AUGA<br>GCGGCAACGGCAACGCCGCCGCUACCGCCGAAGAGAACAGCCCAAAGAUGC<br>GCGUGAUCAGGGUCGGCACGCGCAAGUCCCAGCUCGCCCGGAUCCAAACCG<br>AUAGCGUGGUGGCCACGCUCAAGGCGAGCUAUCCGGGCUUACAGUUCGAGA<br>UCAUCGCCAUGAGCACCACCGGCGAUAAGAUACUGGACACCGCCCUGUCCA<br>AGAUCGGCGAAAAGAGCCUGUUCACCAAGGAACUGGAGCACGCGCUGGAGA<br>AGAACGAGGUGGACCUGGUGGUGCACAGCCUGAAGGACCUGCCGACCGUGC<br>UGCCGCCGGGAUUCACCAUCGGCGCCAUCUGCAAGAGGGAGAAUCCGCACG<br>AUGCCGUGGUGUUCCACCCAAAGUUCGUGGGCAAGACCUUGGAAACCCUGC<br>CAGAGAAGUCUGUGGUCGGCACCUCCAGCCUGCGGCGAGCCGCCCAGCUGC<br>AGCGAAAGUUCCCGCACCUGGAGUUCAGGUCCAUCCGCGGAAAUCUGAACA<br>CCAGGCUGCGCAAGCUCGACGAGCAGCAGGAGUUCUCCGCCAUCAUCCUGG<br>CCACCGCAGGCCUCCAAAGAAUGGGCUGGCAUAACCGAGUCGGCCAGAUCC<br>UCCACCCGGAGGAGUGCAUGUACGCAGUGGGCCAAGGCGCCCUGGGCGUCG<br>AGGUGCGUGCCAAGGACCAGGACAUCCUGGACCUGGUGGGCGUGCUCCACG<br>AUCCAGAGACACUGCUGAGAUGCAUCGCGGAGCGCGCCUUCCUGCGCCAUC<br>UGGAGGGAGGCUGCUCCGUCCCGGUGGCCGUACAUACCGCCAUGAAGGACG<br>GUCAGCUGUACCUCACCGGCGGCGUAUGGUCCCUCGACGGUAGCGACAGCA<br>UACAGGAGACGAUGCAGGCCACCAUCCACGUGCCGGCGCAGCACGAGGAUG<br>GACCAGAGGACGACCCGCAGCUGGUGGGUAUCACCGCCAGGAAUAUCCCGC<br>GGGGACCUCAGCUGGCCGCCCAGAACCUGGGCAUCUCCCUCGCCAACCUCC<br>UGCUGAGCAAGGGCGCCAAGAACAUCCUGGACGUGGCCAGGCAGCUCAACG<br>AUGCCCAU*UGAUAAUAGUCCAUAAAGUAGGAAACACUACAGCUGGAGCCUC*<br>*GGUGGCCAUGCUUCUUGCCCCUUGGGCCUCCCCCCAGCCCCUCCUCCCCUU*<br>*CCUGCACCCGUACCCCCCGCAUUAUUACUCACGGUACGAGUGGUCUUUGAA*<br>*UAAAGUCUGAGUGGGCGGC* |
| 120 | #3 | <u>GGGAAAUAAGAGAGAAAAGAAGAGUAAGAAGAAAUAUAAGAGCCACC</u>AUGA<br>GCGGCAACGGCAACGCCGCCGCCACCGCCGAGGAAAACAGCCCGAAGAUGC<br>GGGUGAUCAGGGUGGGCACCAGGAAGUCCCAGCUCGCCCGGAUCCAGACCG<br>ACAGCGUGGUCGCCACCUUGAAGGCCUCCUACCCGGGCCUCCAGUUCGAGA<br>UCAUCGCCAUGUCCACAACCGGCGACAAGAUCUGGAUACCGCCCUCAGCA<br>AGAUCGGCGAGAAGUCCCUGUUCACCAAGGAGCUGGAGCACGCCCUGGAGA<br>AGAAUGAGGUGGACCUGGUGGUGCACAGCCUGAAGGACCUGCCCUACCGUGC<br>UGCCACCAGGCUUCACAAUCGGCGCCAUCUGCAAGAGAGAGAACCCGCACG<br>ACGCCGUGGUGUUCCAUCCGAAGUUCGUGGGCAAGACCCUGGAAACCCUGC<br>CGGAGAAGUCCGUAGUGGGAACCUCAAGCCUGAGGCGCCGCCCAGCUCC<br>AGAGGAAGUUCCCUCACCUGGAAUUCCGGUCCAUCAGGGGCAACCUGAACA<br>CGCGCCUGCGGAAGCUCGACGAGCAGCAGGAGUUCUCCGCCAUCAUCCUGG<br>CCACAGCCGGCCUUCAGCGCAUGGGCUGGCACAACAGGGUGGGCCAGAUCC<br>UGCACCCGGAAGAAUGCAUGUACGCCGUGGGCAAGGCGCCCUCGGCGUGG<br>AAGUGCGUGCCAAGGACCAGGACAUCCUGGACCUGGUGGGCGUGCUGCACG<br>ACCCUGAGACGCUGCUCAGGUGCAUCGCCGAACGCGCGUUCCUGCGGCACC<br>UGGAGGGAGGCUGCAGCGUCCCGGUGGCCGUCCACACCGCCAUGAAGGACG<br>GCCAGCUCUACCUGACUGGCGGCGUGUGGAGCCUGGACGGCAGCGACAGCA<br>UUCAGGAAACCAUGCAGGCCACCAUCCACGUGCCUGCCCAGCACGAGGACG<br>GCCCCGAGGACGACCCUCAACUGGUGGGCAUUACUGCGCGAAACAUCCCGC<br>GCGGACCUCAGCUGGCCGCCCAGAACCUGGGCAUCAGCCUGGCCAACCUGC<br>UCCUGUCCAAGGGCGCCAAGAACAUCCUCGACGUGGCCAGGCAGCUGAACG<br>ACGCGCAC*UGAUAAUAGUCCAUAAAGUA*GGAAACAUACAGCUGGAGCCUC<br>*GGUGGCCAUGCUUCUUGCCCCUUGGGCCUCCCCCCAGCCCCUCCUCCCCUU*<br>*CCUGCACCCGUACCCCCCGCAUUAUUACUCACGGUACGAGUGGUCUUUGAA*<br>*UAAAGUCUGAGUGGGCGGC* |
| 121 | #4 | <u>GGGAAAUAAGAGAGAAAAGAAGAGUAAGAAGAAAUAUAAGAGCCACC</u>AUGA<br>GCGGCAACGGAAACGCCGCCGCGACCGCGGAGGAGAACUCGCCUAAGAUGA<br>GAGUGAUAAGGGUAGGCACCCGGAAGUCUCAACUCGCCAGGAUCCAGACCG<br>ACAGCGUGGUGGCCACCCUCAAGGCCAGCUAUCCAGGACUCCAGUUCGAAA<br>UCAUCGCCAUGUCCACCAGGCGAUAAGAUCUGGACACCGCCCUGUCCA<br>AGAUCGGCGAGAAGUCCCUCUUCACCAAGGAACUGGAGCACGCCCUGGAGA<br>AGAACGAGGUCGAUCUGGUCGUGCACAGCCUGAAGGAUCUGCCUACCGUGC<br>UCCCGCCGGGCUUCACCAUCGGCGCCAUCUGCAAGAGGGAGAAUCCUCACG<br>ACGCCGUGGUGUUCCACCCGAAGUUCGUGGGCAAGACCCUGGAGACACUGC<br>CAGAAAAGUCGGUGGUGGGCACCAGCAGCCUGCGGCGGGCGGCCCAGCUGC |

TABLE 5-continued mRNA Constructs

| SEQ ID NO | Construct | Sequence (5' UTR = bold underline; 3' UTR comprising a stop codon = bold italics) |
|---|---|---|
| | | AGCGGAAGUUCCCACACCUGGAGUUCAGGUCCAUCCGUGGCAAUCUGAACA CCCGGCUGCGUAAGCUGGACGAGCAGCAGGAAUUCAGCGCGAUCAUCCUGG CAACCGCCGGUCUGCAAAGGAUGGGCUGGCACAACAGGGUGGGCCAGAUCC UGCACCCUGAGGAGUGCAUGUACGCCGUGGGCCAGGGAGCCCUGGGCGUGG AAGUGCGGGCCAAGGACCAGGACAUCCUGGACCUGGUGGGUGUGCUCCACG ACCCUGAAACCCUGCUGCGGUGCAUCGCCGAAAGGGCCUUCCUGAGGCACC UCGAGGGCGGCUGCAGCGUGCCGGUCGCCGUGCACACCGCCAUGAAGGACG GCCAGCUGUACCUGACCGGAGGAGUGUGGAGCCUGGACGGCUCCGACUCCA UCCAGGAGACUAUGCAGGCCACCAUUCAUGUGCCGGCCCAGCAUGAGGACG GUCCGGAGGACGAUCCACAGCUGGUCGGCAUCACCGCGCGGAACAUCCCAA GAGGCCCGCAACUGGCCGCUCAGAACCUGGGCAUAUCCCUGGCCAACCUGC UCCUGAGCAAGGGCGCCAAGAACAUCCUGGACGUGGCCAGGCAGCUGAAUG ACGCCCAC*UGAUAAUAGUCCAUAAAGUAGGAAACACUACAGCUGGAGCCUC GGUGGCCAUGCUUCUUGCCCCUUGGGCCUCCCCCCAGCCCCUCCUCCCCUU CCUGCACCCGUACCCCCCGCAUUAUUACUCACGGUACGAGUGGUCUUUGAA UAAAGUCUGAGUGGGCGGC* |
| 122 | #5 | <u>GGGAAAUAAGAGAGAAAAGAAGAGUAAGAAGAAAUAUAAGAGCCACC</u>AUGU CCGGCAACGGCAACGCCGCCGCUACCGCCGAGGAGAACUCCCCUAAGAUGC GGGUCAUCAGGGUGGGCACCCGAAAGUCCCAACUUGCCCGGAUCCAGACCG ACUCCGUCGUGGCCACCCUCAAGGCUAGCUAUCCAGGCCUCCAGUUCGAAA UCAUCGCCAUGAGCACCACCGGCGACAAGAUUCUGGACACCGCCCUGUCCA AGAUCGGCGAGAAGAGUCUGUUCACGAAGGAGCUCGAGCACGCCCUGGAAA AGAACGAGGUGGACCUGGUGGUGCAUUCCCUGAAGGACCUGCCAACCUGC UGCCGCCGGGCUUCACUAUAGGAGCCAUCUGCAAGCGGGAGAACCCGCACG ACGCGGUGGUGUUCCAUCCGAAGUUCGUGGGCAAGACUCUGGAAACCCUGC CGGAGAAGUCCGUGGUGGGAACUAGCUCCCUGCGGCGGGCCGCCCAGCUGC AGAGGAAGUUCCGCACCUGGAGUUCAGGAGCAUACGCGGCAACCUGAACA CCCGCCUGCGUAAGCUCGACGAGCAGCAGGAAUUCAGUGCCAUCAUCCUGG CCACGGCGGGCCUGCAGCGGAUGGGCUGGCACAACAGGGUGGGCCAGAUCC UCCACCCGGAGGAAUGUAUGUACGCCGUGGGCCAGGGCGCACUGGGCGUGG AGGUCCGCGCCAAGGACCAAGACAUCCUGGACCUGGUCGGCGUGCUGCACG ACCCUGAAACCCUGCUGAGGUGCAUUGCCGAGAGAGCCUUCCUGAGGCAUC UGGAGGGCGGCUGCAGCGUGCCUGUGGCCGUGCACACAGCCAUGAAGGACG GUCAGCUGUACCUGACCGGCGGCGUGUGGAGCCUGGACGGCAGCGACUCCA UCCAGGAGACAAUGCAGGCCACCAUCCACGUCCCGGCCAACACGAGGACG GACCUGAGGACGAUCCUCAGCUGGUGGGCAUCACCGCCAGGAACAUCCCUC GGGGCCCGCAGCUGGCCGCCCAGAACCUGGGCAUCUCCCUCGCCAACCUGC UGCUGUCCAAGGGCGCCAAGAACAUCCUCGACGUGGCCAGACAGCUGAACG ACGCCCAC*UGAUAAUAGUCCAUAAAGUAGGAAACACUACAGCUGGAGCCUC GGUGGCCAUGCUUCUUGCCCCUUGGGCCUCCCCCCAGCCCCUCCUCCCCUU CCUGCACCCGUACCCCCCGCAUUAUUACUCACGGUACGAGUGGUCUUUGAA UAAAGUCUGAGUGGGCGGC* |
| 123 | #6 | <u>GGGAAAUAAGAGAGAAAAGAAGAGUAAGAAGAAAUAUAAGAGCCACC</u>AUGA GCGGCAACGGCAACGCCGCCGCCACCGCCGAGGAGAACAGCCCGAAGAUGA GGGUGAUAAGGGUGGGCACACGGAAGUCCCAGCUCGCCCGCAUCCAAACCG ACUCCGUGGUGGCCACCCUCAAGGCCAGCUACCCGGGCCUCCAAUUCGAGA UCAUCGCCAUGAGCACCACCGGCGACAAGAUCCUGGACACCGCCCUGUCUA AGAUAGGCGAAAAGAGCCUGUUCACCAAGGAGCUGGAGCAUGCCCUGGAGA AGAACGAGGUGGACCUGGUGGUCCACAGUCUCAAGGACCUGCCAACCGUGC UGCCGCCAGGCUUCACCAUCGGCGCCAUCUGCAAGCGUGAGAACCCGCACG AUGCUGUGGUGUUCCACCCUAAGUUCGUGGGGAAAGACCCUGGAGACGCUGC CGGAAAAGAGCGUGGUCGGCACCUCCAGCCUGCGGAGGGCCGCCCAACUCC AGAGGAAGUUCCGCACCUGGAGUUCAGGAGCAUCCGCGGCAACCUGAACA CCAGGCUGCGAAAGCUGGACGAGCAGCAGGAAUUCUCGGCCAUCAUCCUCG CCACCGCCGGCUUGCAAAGAAUGGGCUGGCAUAAUCGCGUGGGCCAGAUCC UGCACCCUGAGGAGUGCAUGUACGCCGUGGGCCAGGGUGCUCUGGGAGUGG AGGUGCGGGCCAAGGACCAGGAUAUCCUGGACCUGGUCGGCGUGCUUCAUG ACCCGGAGACGCUCCUGAGGUGCAUCGCCGAGCGGGCCUUCCUGAGACACC UGGAGGGCGGCUGCUCCGUGCCAGUGGCCGUGCACACCGCCAUGAAGGACG GACAGCUGUACCUGACCGGCGGCGUGUGGAGCCUGGAAGCGACAGCA UCCAAGAAACCAUGCAGGCGACCAUUCACGUCCCUGCCCAGCACGAGGAUG GACCAGAGGACGACCCGCAGCUGGUGGGCAUCACCGCCCGCAACAUCCCUA GAGGCCCACAGCUGGCCGCCCAGAAUCUGGGCAUCAGCCUGGCCAACCUGC UGCUGUCUAAGGGAGCCAAGAACAUCCUGGACGUGGCCAGGCAGCUGAACG ACGCCCAU*UGAUAAUAGUCCAUAAAGUAGGAAACACUACAGCUGGAGCCUC GGUGGCCAUGCUUCUUGCCCCUUGGGCCUCCCCCCAGCCCCUCCUCCCCUU CCUGCACCCGUACCCCCCGCAUUAUUACUCACGGUACGAGUGGUCUUUGAA UAAAGUCUGAGUGGGCGGC* |
| 124 | #7 | <u>GGGAAAUAAGAGAGAAAAGAAGAGUAAGAAGAAAUAUAAGAGCCACC</u>AUGU CCGGCAACGGCAACGCCGCAGCCACCGCCGAGGAGAAUUCCCCGAAGAUGC GGGUGAUCCGGGUGGGCACCAGAAAGAGCCAGCUCGCCCGCAUCCAAACCG ACUCCGUGGUGGCCACCCUCAAGGCCUCCUACCCAGGCUUGCAGUUCGAAA |

TABLE 5-continued mRNA Constructs

| SEQ ID NO | Con-struct | Sequence (5' UTR = bold underline; 3' UTR comprising a stop codon = bold italics) |
|---|---|---|
| | | UCAUCGCCAUGAGCACCACCGGCGACAAGAUCCUGGACACCGCCCUGAGCA<br>AGAUUGGCGAGAAGUCCCUGUUCACCAAGGAGCUGGAGCAUGCUCUGGAGA<br>GAACGAGGUGGACCUCGUGGUGCACUCCCUGAAGGACCUGCCGACUGUGC<br>UGCCGCCUGGCUUCACGAUCGGCGCCAUAUGCAAGCGGGAAAACCCACACG<br>ACGCCGUGGUCUUCCACCCAAAGUUCGUGGGCAAGACCCUGGAAACCCUGC<br>CGGAAAAGAGCGUGGUCGGCACAAGCUCCCUGAGGAGAGCCGCCCAACUGC<br>AAAGGAAGUUCCCUCACCUCGAGUUCAGGUCCAUCCGGGGCAACCUGAACA<br>CCAGGCUGAGAAAGCUCGACGAACAGCAGGAGUUCAGCGCCAUCAUCCUGG<br>CCACGGCCGGCCUGCAGAGGAUGGGAUGGCAUAACAGGGUGGGCCAGAUCC<br>UGCACCCGGAGGAGUGCAUGUACGCCGUGGGCCAGGGAGCCCUCGGCGUGG<br>AGGUCAGGGCCAAGGAUCAGGAUAUCCUGGACCUGGUGGGGCGUGCUGCACG<br>AUCCUGAGACGCUGCUGAGGUGCAUCGCCGAGCGGGCCUUCCUGCGGCACC<br>UAGAGGGCGGAUGCAGCGUGCCGGUCGCGGUCCACACCGCGAUGAAGGACG<br>GCCAGCUGUACCUGACCGGCGGCGUGUGGUCCCUGGACGGCAGCGAUUCAA<br>UCCAGGAGACGAUGCAGGCCACCAUCCACGUGCCAGCCCAGCACGAGGAUG<br>GCCCGAGGACGACCCGCAGCUGGUGGGCAUUACAGCCAGGAACAUCCCUC<br>GGGGCCCGCAGCUGGCCGCCCAGAAUCUGGGCAUCAGCCUGGCGAACCUGC<br>UGCUCAGCAAGGGAGCGAAGAACAUCCUGGACGUGGCCCGCCAGCUGAACG<br>AUGCCCAC*UGAUAAUAGUCCAUAAAGUAGGAAACACUACAGCUGGAGCCUC<br>GGUGGCCAUGCUUCUUGCCCCUUGGGCCUCCCCCCAGCCCCUCCUCCCCUU<br>CCUGCACCCGUACCCCCCGCAUUAUUACUCACGGUACGAGUGGUCUUUGAA<br>UAAAGUCUGAGUGGGCGGC* |
| 125 | #8 | <u>GGGAAAUAAGAGAGAAAAGAAGAGUAAGAAGAAAUAUAAGAGCCACC</u>AUGA<br>GCGGCAACGGCAACGCCGCCGCCACCGCCGAGGAGAACAGCCCAAAGAUGC<br>GGGUGAUCAGGGUGGGCACCCGCAAGAGCCAACUCGCCAGAAUCCAGACCG<br>ACAGCGUGGUGGCCACCUUGAAGGCCAGCUACCCGGGCCUCCAGUUCGAGA<br>UCAUCGCUAUGUCCACCACCGGCGACAAGAUCCUGGACACCGCGCUGUCCA<br>AGAUCGGCGAAAAGAGCCUGUUCACCAAGGAACUGGAGCACGCCCUCGAGA<br>AGAACGAGGUGGACCUGGUGGUGCACUCCCUGAAGGACCUGCCGACGGUCC<br>UGCCGCCGGGCUUCACCAUCGGCGCCAUCUGCAAGCGGGAAAACCCGCACG<br>ACGCUGUGGUGUUCCACCCAAAGUUCGUGGGCAAGACCCUGGAAACCCUGC<br>CAGAAAAGAGCGUGGUGGGCACCAGCAGCCUCAGGAGAGCCGCCCAGCUGC<br>AGAGGAAGUUCCCGCACCUGGAGUUCAGGAGCAUCAGGGGCAACCUGAACA<br>CCAGGCUGCGUAAGCUGGACGAGCAGCAGGAGUUCUCCGCCAUCAUCCUCG<br>CCACAGCCGGCCUCCAGAGGAUGGGUUGGCACAACAGGGUGGGCCAGAUCC<br>UGCACCCGGAAGAGUGCAUGUACGCCAGUGGGCCAGGGCGCCUUGGCGUGG<br>AAGUGCGAGCCAAGGAUCAGGAUAUCCUGGACCUGGUGGGCGUGCUGCACG<br>ACCCGGAAACUCUGCUGCGGUGCAUCGCCGAAAGGGCCUUCCUGCGCCACC<br>UCGAAGGCGGCUGUAGCGUGCCGGUGGCCGUGCACACCGCCAUGAAGGACG<br>GCCAGCUGUACCUGACCGGCGGCGUGUGGAGCCUCGACGGCAGCGACAGCA<br>UCCAGGAGACAAUGCAGGCCACCAUCCACGUGCCGGCCCAGCAUGAGGAUG<br>GCCCGGAGGACGACCCUCAGCUGGUGGGCAUCACCGCCCGCAACAUCCCAA<br>GAGGACCGCAACUGGCCGCCCAGAACCUGGGCAUCUCCCUGGCCAACCUGC<br>UCCUGAGCAAGGGCGCGAAGAACAUCCUCGACGUCGCACGGCAGCUGAACG<br>ACGCCCAC*UGAUAAUAGUCCAUAAAGUAGGAAACACUACAGCUGGAGCCUC<br>GGUGGCCAUGCUUCUUGCCCCUUGGGCCUCCCCCCAGCCCCUCCUCCCCUU<br>CCUGCACCCGUACCCCCCGCAUUAUUACUCACGGUACGAGUGGUCUUUGAA<br>UAAAGUCUGAGUGGGCGGC* |
| 126 | #9 | <u>GGGAAAUAAGAGAGAAAAGAAGAGUAAGAAGAAAUAUAAGAGCCACC</u>AUGA<br>GCGGCAACGGCAACGCCGCCGCGACGGCCGAGGAAAAUAGCCCGAAGAUGC<br>GGGUGAUCAGGGUGGGCACCAGGAAGUCCCAGCUCGCCAGGAUCCAGACCG<br>ACAGCGUGGUGGCCACCCUCAAGGCCUCCUACCCGGGCCUCCAAUUCGAGA<br>UCAUCGCCAUGUCCACCACCGGCGACAAGAUCCUCGACACCGCCCUGAGCA<br>AGAUCGGCGAAAAGUCGCUGUUCACCAAGGAGCUGGAGCACGCCCUCGAGA<br>AGAACGAGGUGGACCUGGUAGUGCACUCCCUAAAGGACCUGCCGACCGUGC<br>UGCCGCCGGGCUUCACGAUCGGCGCCAUCUGCAAGCGCGAGAACCCGCAUG<br>AUGCCGUCGUUUCCACCCUAAGUUCGUGGGCAAGACCCUGGAGACGCUGC<br>CGGAGAAGUCGGUGGUGGGAACCAGCAGCCUGAGGAGGGCCGCACAACUGC<br>AGAGGAAGUUCCCGCAUCUGGAGUUCCGCAGCAUUCGAGGCAACCUGAACA<br>CGCGCCUGAGAAAGCUCGAUGAACAGCAGGAGUUCAGCGCCAUCAUUCUGG<br>CCACUGCCGGACUGCAGCGGAUGGGCUGGCACAACAGAGUGGGCCAGAUCC<br>UGCAUCCGGAAGAGUGUAUGUACGCCGUGGGCCAGGGUGCCCUGGGCGUGG<br>AGGUGCGGGCCAAGGACCAGGAUAUACUGGAUCUGGUCGGCGUGCUCCACG<br>ACCCAGAAACACUCCUGAGGUGCAUCGCUGAGAGAGCCUUCCUCCGGCACC<br>UCGAGGGCGGCUGUUCCGUGCCGGUGGCCGUCCAUACCGCCAUGAAGGACG<br>GUCAGCUGUACCUGACCGGAGGCGUUUGGUCCCUGGACGGCAGCGACAGCA<br>UCCAGGAAACCAUGCAGGCCACCAUCCACGUGCCGGCGCAGCACGAGGACG |

TABLE 5-continued mRNA Constructs

| SEQ ID NO | Construct | Sequence (5' UTR = bold underline; 3' UTR comprising a stop codon = bold italics) |
|---|---|---|

|  |  | GCCCGGAAGACGACCCGCAGCUGGUCGGCAUCACGGCCAGAAACAUCCCGC<br>GGGGCCCGCAGCUGGCGGCCCAGAACCUGGGAAUCUCCCUGGCCAACCUGC<br>UGCUGAGCAAGGGCGCGAAGAACAUCCUGGACGUGGCCAGGCAGCUGAACG<br>AUGCCCAC*UGAUAAUAGUCCAUAAAGUAGGAAACACUACAGCUGGAGCCUC<br>GGUGGCCAUGCUUCUUGCCCCUUGGGCCUCCCCCCAGCCCCUCCUCCCCUU<br>CCUGCACCCGUACCCCCCGCAUUAUUACUCACGGUACGAGUGGUCUUUGAA<br>CCUGCACCCGUACCCCCCGCAUUAUUACUAAAGUCUGAGUGGGCGGC* |
| 127 | #10 | <u>GGGAAAUAAGAGAGAAAAGAAGAGUAAGAAGAAAUAUAAGAGCCACC</u>AUGA<br>GCGGUAACGGCAACGCCGCCGCCACCGCCGAGGAGAACUCCCCGAAGAUGC<br>GCGUGAUUCGGGUCGGCACAAGAAAGUCUCAACUCGCCCGAAUCCAAACGG<br>ACAGCGUGGUGGCCACCCUCAAGGCGAGCUACCCGGGCCUCCAGUUCGAAA<br>UCAUCGCCAUGAGCACCACCGGCGACAAGAUCCUGGACACCGCCCUGUCGA<br>AGAUUGGCGAAAAGUCCCUGUUCACCAAGGAGCUGGAGCACGCCCUGGAGA<br>AGAACGAAGUCGACCUGGUCGUGCACAGCCUGAAGGACCUGCCGACCGUUC<br>UGCCGCCGGGCUUCACCAUCGGAGCCAUCUGCAAGCGGGAGAAUCCGCACG<br>ACGCCGUGGUCUUCCACCCAAAGUUCGUGGGAAAGACCCUCGAGACACUGC<br>CGGAGAAGUCCGUGGUGGGAACCUCCUCCCUGCGGAGGGCCGCCCAACUGC<br>AGCGGAAGUUCCCACACCUGGAAUUCCGGUCCAUCAGAGGCAACCUCAACA<br>CCCAGGCUGAGGAAGCUCGAUGAGCAGCAGGAGUUCAGCGCCAUCAUCCUGG<br>CCACAGCCGGACUGCAGCGCAUGGGCUGGCAUAACAGAGUGGGCCAGAUCC<br>UCCACCCGGAGGAGUGCAUGUACGCCGUGGGACAAGGCGCGCUGGGCGUGG<br>AAGUUCGGGCCAAGGACCAGGAUAUCCUGGACCUGGUGGGCGUGCUCCACG<br>ACCCAGAGACGCUGCUGCGGUGCAUCGCCGAGCGCGCCUUCCUGCGGCACC<br>UCGAGGGCGGCUGCAGCGUGCCGGUCGCUGUGCACACAGCCAUGAAGGACG<br>GCCAGCUGUACCUGACCGGCGGCGUGUGGAGUCUGGACGGCAGCGACUCCA<br>UCCAGGAGACUAUGCAAGCCACCAUCCAUGUGCCGGCCCAACAUGAGGACG<br>GCCCGGAGGACGACCCGCAACUGGUGGGCAUCACCGCCCGGAACAUCCCGA<br>GGGGCCCGCAGCUGGCCGCCCAGAACCUGGGCAUUAGCCUGGCCAACCUGC<br>UCCUGAGCAAGGGCGCUAAGAACAUCCUGGACGUCGCCAGACAGCUGAACG<br>ACGCCCAC*UGAUAAUAGUCCAUAAAGUAGGAAACACUACAGCUGGAGCCUC<br>GGUGGCCAUGCUUCUUGCCCCUUGGGCCUCCCCCCAGCCCCUCCUCCCCUU<br>CCUGCACCCGUACCCCCCGCAUUAUUACUCACGGUACGAGUGGUCUUUGAA<br>UAAAGUCUGAGUGGGCGGC* |
| 128 | #11 | <u>GGGAAAUAAGAGAGAAAAGAAGAGUAAGAAGAAAUAUAAGAGCCACC</u>AUGA<br>GCGGCAACGGCAACGCCGCCGCCACCGCCGAGGAGAACAGCCCCAAGAUGC<br>GGGUGAUCCGGGUGGGCACCCGUAAGAGCCAGCUGGCCCGGAUCCAGACCG<br>ACAGCGUGGUGGCCACCCUGAAGGCCAGCUACCCCGGCCUGCAGUUCGAGA<br>UCAUCGCCAUGAGCACCACCGGCGACAAGAUCCUGGACACCGCCCUGAGCA<br>AGAUCGGCGAGAAGUCCCUGUUCACCAAGGAGCUGGAGCACGCCCUGGAGA<br>AGAACGAGGUGGACCUGGUGGUGCACAGCCUGAAGGACCUGCCCACCGUGC<br>UGCCUCCAGGCUUCACCAUCGGCGCCAUCUGCAAGCGGGAGAACCCCCACG<br>ACGCCGUGGUGUUCCACCCCAAGUUCGUGGGCAAGACCCUGGAAACCCUGC<br>CUGAGAAGUCCGUCGUAGGAACCAGCAGCCUGCGGCGGGCCGCCCAGCUGC<br>AGCGGAAGUUCCCCCACCUGGAGUUCCGGAGCAUCCGGGGCAACCUGAACA<br>CCCGGCUGCGGAAGCUGGACGAGCAGCAGGAGUUCAGCGCCAUCAUCCUGG<br>CUACCGCCGGUCUGCAACGAAUGGGCUGGCACAAUAGGGUGGGCCAGAUCC<br>UGCACCCCGAGGAGUGCAUGUACGCGGUGGGACAGGGCGCCUGGGCGUGG<br>AGGUGCGGGCCAAGGACCAGGACAUCCUUGAUCUGGUGGGCGUGCUGCACG<br>ACCCCGAGACGCUGCUGCGGUGCAUCGCCGAGCGGGCCUUCCUGCGGCAUU<br>UGGAGGGCGGAUGCAGCGUGCCCGUGGCCGUGCACACCGCCAUGAAGGACG<br>GCCAGCUGUACCUGACCGGCGGCGUGUGGAGCCUGGACGGCAGCGACAGCA<br>UCCAGGAAACCAUGCAGGCCACCAUCCACGUGCCUGCUCAGCACGAAGACG<br>GCCCAGAGGACGACCCCAGCUGGUAGGCAUCACCGCCCGGAACAUCCCCC<br>GGGGCCCUCAGCUCGCCGCACAGAACCUUGGAAUCAGCCUGGCCAACCUGC<br>UGUUGUCAAAGGGCGCCAAGAAUAUCCUCGACGUGGCCCGGCAGCUGAACG<br>ACGCCCAC*UGAUAAUAGUCCAUAAAGUAGGAAACACUACAGCUGGAGCCUC<br>GGUGGCCAUGCUUCUUGCCCCUUGGGCCUCCCCCCAGCCCCUCCUCCCCUU<br>CCUGCACCCGUACCCCCCGCAUUAUUACUCACGGUACGAGUGGUCUUUGAA<br>UAAAGUCUGAGUGGGCGGC* |
| 129 | #12 | <u>GGGAAAUAAGAGAGAAAAGAAGAGUAAGAAGAAAUAUAAGAGCCACC</u>AUGA<br>GCGGCAACGGCAACGCCGCCGCCACCGCCGAGGAGAACAGCCCCAAGAUGC<br>GGGUGAUCCGGGUGGGCACCAGAAAGAGCCAGCUGGCCCGGAUCCAGACCG<br>ACAGCGUGGUGGCCACCCUGAAGGCCAGCUACCCCGGCCUGCAGUUCGAGA<br>UCAUCGCCAUGAGCACCACCGGCGACAAGAUCCUGGACACCGCCCUGAGCA<br>AGAUCGGCGAGAAGAGUCUGUUCACCAAGGAGCUGGAGCACGCCCUGGAGA<br>AGAACGAGGUGGACCUGGUGGUGCACAGCCUGAAGGACCUGCCCACCGUGC<br>UGCCGCCUGGCUUCACCAUCGGCGCCAUCUGCAAGCGGGAGAACCCCCACG<br>ACGCCGUGGUGUUCCACCCCAAGUUCGUGGGCAAGACUCUGGAAACCCUGC<br>CUGAGAAGUCCGUGGUCGGAACAAGCAGCCUGCGGCGGGCCGCCCAGCUGC<br>AGCGGAAGUUCCCCCACCUGGAGUUCCGGAGCAUCCGGGGCAACCUGAACA<br>CCCGGCUGCGGAAGCUGGACGAGCAGCAGGAGUUCAGCGCCAUCAUCCUGG<br>CCACAGCCGGCCUUCAGAGGAUGGGCUGGCACAAUCGGGUAGGCCAGAUCC |

TABLE 5-continued mRNA Constructs

| SEQ ID NO | Construct | Sequence (5' UTR = bold underline; 3' UTR comprising a stop codon = bold italics) |
|---|---|---|
|  |  | UGCACCCCGAGGAGUGCAUGUACGCGGUAGGUCAGGGCGCCCUGGGCGUGG<br>AGGUGCGGGCCAAGGACCAGGACAUCUUAGAUCUGGUUGGCGUGCUGCACG<br>ACCCCGAAACACUGCUGCGGUGCAUCGCCGAGCGGGCCUUCCUGCGGCACC<br>UCGAGGGCGGCUGCAGUGUGCCCGUGGCCGUGCACACCGCCAUGAAGGACG<br>GCCAGCUGUACCUGACCGGCGGCGUGUGGAGCCUGGACGGCAGCGACAGCA<br>UCCAGGAGACAAUGCAGGCCACCAUCCACGUGCCAGCUCAGCACGAAGACG<br>GACCAGAGGACGACCCCCAGUUAGUGGGAAUCACCGCCCGGAACAUCCCCC<br>GGGGCCCUCAGCUCGCGGCCCAGAACCUGGGCAUCAGCCUGGCCAACCUGC<br>UGCUGUCUAAGGGCGCCAAGAACAUCCUAGACGUGGCCCGGCAGCUGAACG<br>ACGCCCAC*UGAUAAUAGUCCAUAAAGUAGGAAACACUACAGCUGGAGCCUC**GGUGGCCAUGCUUCUUGCCCCUUGGGCCUCCCCCCAGCCCCUCCUCCCCUU**CCUGCACCCGUACCCCCCGCAUUAUUACUCACGGUACGAGUGGUCUUUGAA**UAAAGUCUGAGUGGGCGGC* |
| 130 | #13 | <u>GGGAAAUAAGAGAGAAAAGAAGAGUAAGAAGAAAUAUAAGAGCCACC</u>AUGA<br>GCGGCAACGGCAACGCCGCCGCCACCGCCGAGGAGAACAGCCCCAAGAUGC<br>GGGUGAUCCGGGUGGGCACCAGGAAGUCACAGCUGGCCCGGAUCCAGACCG<br>ACAGCGUGGUGGCCACCCUGAAGGCCAGCUACCCCGGCCUGCAGUUCGAGA<br>UCAUCGCCAUGAGCACCACCGGCGACAAGAUCCUGGACACCGCCCUGAGCA<br>AGAUCGGCGAGAAGUCCCUGUUCACCAAGGAGCUGGAGCACGCCCUGGAGA<br>AGAACGAGGUGGACCUGGUGGUGCACAGCCUGAAGGACCUGCCCACCGUGC<br>UGCCGCCAGGCUUCACCAUCGGCGCCAUCUGCAAGCGGGAGAACCCCCACG<br>ACGCCGUGGUGUUCCACCCCAAGUUCGUGGGCAAGACCCUUGAAACCCUGC<br>CAGAGAAGUCUGUGGUCGGCACCAGCAGCCUGCGGCGGGCCGCCCAGCUGC<br>AGCGGAAGUUCCCCCACCUGGAGUUCCGGAGCAUCCGGGGCAACCUGAACA<br>CCCGGCUGCGGAAGCUGGACGAGCAGCAGGAGUUCAGCGCCAUCAUCCUGG<br>CCACCGCUGGCCUACAGCGGAUGGGCUGGCACAAUAGAGUUGGUCAGAUCC<br>UGCACCCCGAGGAGUGCAUGUACGCCGUCGGCCAGGGCGCCUGGGCGUGG<br>AGGUGCGGGCCAAGGACCAGGACAUACUAGACCUCGUGGGCGUGCUGCACG<br>ACCCCGAAACCUUGCUGCGGUGCAUCGCCGAGCGGGCCUUCCUGCGGCACC<br>UGGAAGGCGGUUGCAGCGUGCCCGUGGCCGUGCACACCGCCAUGAAGGACG<br>GCCAGCUGUACCUGACCGGCGGCGUGUGGAGCCUGGACGGCAGCGACAGCA<br>UCCAGGAGACAAUGCAGGCCACCAUCCACGUGCCGCCCAACACGAGGACG<br>GACCUGAGGACGACCCCCAGCUUGUGGGAAUCACCGCCCGGAACAUCCCCC<br>GGGGCCCUCAACUGGCAGCCCAGAACUUAGGCAUAAGCCUGGCCAACCUGC<br>UGCUGUCCAAGGGCGCCAAGAACAUCCUCGAUGUGGCCCGGCAGCUGAACG<br>ACGCCCAC*UGAUAAUAGUCCAUAAAGUAGGAAACACUACAGCUGGAGCCUC**GGUGGCCAUGCUUCUUGCCCCUUGGGCCUCCCCCCAGCCCCUCCUCCCCUU**CCUGCACCCGUACCCCCCGCAUUAUUACUCACGGUACGAGUGGUCUUUGAA**UAAAGUCUGAGUGGGCGGC* |
| 131 | #14 | <u>GGGAAAUAAGAGAGAAAAGAAGAGUAAGAAGAAAUAUAAGAGCCACC</u>AUGA<br>GCGGCAACGGCAACGCCGCCGCCACCGCCGAGGAGAACAGCCCCAAGAUGC<br>GGGUGAUCCGGGUGGGCACCCGCAAGAGUCAGCUGGCCCGGAUCCAGACCG<br>ACAGCGUGGUGGCCACCCUGAAGGCCAGCUACCCCGGCCUGCAGUUCGAGA<br>UCAUCGCCAUGAGCACCACCGGCGACAAGAUCCUGGACACCGCCCUGAGCA<br>AGAUCGGCGAGAAGAGUCUGUUCACCAAGGAGCUGGAGCACGCCCUGGAGA<br>AGAACGAGGUGGACCUGGUGGUGCACAGCCUGAAGGACCUGCCCACCGUGC<br>UGCCACCUGGCUUCACCAUCGGCGCCAUCUGCAAGCGGGAGAACCCCCACG<br>ACGCCGUGGUGUUCCACCCCAAGUUCGUGGGCAAGACACUGGAAACCCUGC<br>CGGAGAAGUCCGUGGUAGGCACCAGCAGCCUGCGGCGGGCCGCCCAGCUGC<br>AGCGGAAGUUCCCCCACCUGGAGUUCCGGAGCAUCCGGGGCAACCUGAACA<br>CCCGGCUGCGGAAGCUGGACGAGCAGCAGGAGUUCAGCGCCAUCAUCCUGG<br>CAACAGCCGGCUUACAGCGUAUGGGCUGGCACAACAGGGUGGGACAGAUCC<br>UGCACCCCGAGGAGUGCAUGUACGCUGUGGGCAGGGCGCCCUGGGCGUGG<br>AGGUGCGGGCCAAGGACCAGGACAUCUUAGAUCUCGUCGGCGUGCUGCACG<br>ACCCCGAAACCUUGCUGCGGUGCAUCGCCGAGCGGGCCUUCCUGCGGCAUC<br>UUGAGGGCGGAUGCUCCGUGCCCGUGGCCGUGCACACCGCCAUGAAGGACG<br>GCCAGCUGUACCUGACCGGCGGCGUGUGGAGCCUGGACGGCAGCGACAGCA<br>UCCAGGAGACUAUGCAGGCCACCAUCCACGUGCCAGCCCAGCACGAAGACG<br>GCCCAGAGGACGACCCCCAGCUGGUGGGAAUCACCGCCCGGAACAUCCCCC<br>GGGGCCCUCAACUGGCCGCACAGAACCUAGGCAUCAGCCUGGCCAACCUGC<br>UGCUCAGCAAGGGCGCCAAGAAUAUCUUGGACGUGGCCCGGCAGCUGAACG<br>ACGCCCAC*UGAUAAUAGUCCAUAAAGUAGGAAACACUACAGCUGGAGCCUC**GGUGGCCAUGCUUCUUGCCCCUUGGGCCUCCCCCCAGCCCCUCCUCCCCUU**CCUGCACCCGUACCCCCCGCAUUAUUACUCACGGUACGAGUGGUCUUUGAA**UAAAGUCUGAGUGGGCGGC* |
| 132 | #15 | <u>GGGAAAUAAGAGAGAAAAGAAGAGUAAGAAGAAAUAUAAGAGCCACC</u>AUGA<br>GCGGCAACGGCAACGCCGCCGCCACCGCCGAGGAGAACAGCCCCAAGAUGC<br>GGGUGAUCCGGGUGGGCACCAGAAAGAGCCAGCUGGCCCGGAUCCAGACCG<br>ACAGCGUGGUGGCCACCCUGAAGGCCAGCUACCCCGGCCUGCAGUUCGAGA<br>UCAUCGCCAUGAGCACCACCGGCGACAAGAUCCUGGACACCGCCCUGAGCA<br>AGAUCGGCGAGAAGUCUCUGUUCACCAAGGAGCUGGAGCACGCCCUGGAGA<br>AGAACGAGGUGGACCUGGUGGUGCACAGCCUGAAGGACCUGCCCACCGUGC |

TABLE 5-continued mRNA Constructs

| SEQ ID NO | Construct | Sequence (5' UTR = bold underline; 3' UTR comprising a stop codon = bold italics) |
|---|---|---|
| | | UGCCUCCUGGCUUCACCAUCGGCGCCAUCUGCAAGCGGGAGAACCCCCACG<br>ACGCCGUGGUGUUCCACCCCAAGUUCGUGGGCAAGACCCUUGAGACUCUGC<br>CAGAGAAGUCUGUAGUGGGAACCAGCAGCCUGCGGCGGGCCGCCCAGCUGC<br>AGCGGAAGUUCCCCCACCUGGAGUUCCGGAGCAUCGGGGCAACCUGAACA<br>CCCGGCUGCGGAAGCUGGACGAGCAGCAGGAGUUCAGCGCCAUCAUCCUGG<br>CCACGGCCGGAUUACAGAGAAUGGGCUGGCACAACCGAGUGGGACAGAUCC<br>UGCACCCCGAGGAGUGCAUGUAUGCCGUUGGCCAAGGCGCCCUGGGCGUGG<br>AGGUGCGGGCCAAGGACCAGGACAUCCUCGAUCUCGUGGGCGUGCUGCACG<br>ACCCCGAGACUUUGCUGCGGUGCAUCGCCGAGCGGGCCUUCCUGCGGCACC<br>UAGAGGGCGGCUGCUCGUGCCCGUGGCCGUGCACACCGCCAUGAAGGACG<br>GCCAGCUGUACCUGACCGGCGGCGUGUGGAGCCUGGACGGCAGCGACAGCA<br>UCCAGGAGACAAUGCAGGCCACCAUCCACGUGCCAGCCCAGCACGAGGAUG<br>GCCCUGAAGACGACCCCAGCUGGUGGGCAUCACCGCCCGGAACAUCCCCC<br>GGGGCCCACAAUUGGCCGCUCAGAACUUAGGCAUUAGCCUGGCCAACCUGC<br>UGCUGUCUAAGGGCGCCAAGAACAUACUGGACGUGGCCCGGCAGCUGAACG<br>ACGCCCAC*UGAUAAUAGUCCAUAAAGUAGGAAACACUACAGCUGGAGCCUC*<br>*GGUGGCCAUGCUUCUUGCCCCUUGGGCCUCCCCCCAGCCCCUCCUCCCCUU*<br>*CCUGCACCCGUACCCCCCGCAUUAUUACUCACGGUACGAGUGGUCUUUGAA*<br>*UAAAGUCUGAGUGGGCGGC* |
| 134 | #17 | <u>GGGAAAUAAGAGAGAAAAGAAGAGUAAGAAGAAAUAUAAGAGCCACC</u>AUGA<br>GCGGCAACGGCAACGCCGCCGCCACCGCCGAGGAGAACAGCCCCAAGAUGC<br>GGGUGAUCCGGGUGGGCACCCGGAAGAGCCAGCUGGCGAGGAUCCAGACGG<br>ACAGCGUGGUGGCGACGCUGAAGGCGAGCUACCCGGGGCUGCAGUUCGAGA<br>UCAUCGCGAUGAGCACGACGGGGGACAAGAUCCUGGACACGGCGCUGAGCA<br>AGAUCGGGGAGAAGAGCCUGUUCACGAAGGAGCUGGAGCACGCGCUGGAGA<br>AGAACGAGGUGGACCUGGUGGUGCACAGCCUGAAGGACCUGCCGACGGUGC<br>UGCCGCCGGGGUUCACGAUCGGGGCGAUCUGCAAGAGGGAGAACCCGCACG<br>ACGCGGUGGUGUUCCACCCGAAGUUCGUGGGGAAGACGCUGGAGACGCUGC<br>GGAGAAGAGCGUGGUGGGACGAGCAGCCUGAGGAGGCGGCGCAGCUGC<br>AGAGGAAGUUCCCGCACCUGGAGUUCAGGAGCAUCAGGGGGAACCUGAACA<br>CGAGGCUGAGGAAGCUGGACGAGCAGCAGGAGUUCAGCGCGAUCAUCCUGG<br>CGACGGCGGGGCUGCAGAGGAUGGGUGGCACAACAGGGUGGGGCAGAUCC<br>UGCACCCGGAGGAGUGCAUGUACGCGGUGGGGCAGGGGGCGCUGGGGGUGG<br>AGGUGAGGGCGAAGGACCAGGACAUCCUGGACCUGGUGGGGGUGCUGCACG<br>ACCCGGAGACGCUGCUGAGGUGCAUCGCGGAGAGGGCGUUCCUGAGGCACC<br>UGGAGGGGGGUGCAGCGUGCCGGUGGCGGUGCACACGGCGAUGAAGGACG<br>GCCAGCUGUACCUGACGGGGGGGUGUGGAGCCUGGACGGAGCGACAGCA<br>UCCAGGAGACGAUGCAGGCGACGAUCCACGUGCCGGCGCAGCACGAGGACG<br>GCCGGAGGACGACCCGCAGCUGGUGGGAUCACGGCGAGGAACAUCCCGA<br>GGGGGCCGCAGCUGGCGGCGCAGAACCUGGGGAUCAGCCUGGCGAACCUGC<br>UGCUGAGCAAGGGGGCGAAGAACAUCCUGGACGUGGCGAGGCAGCUGAACG<br>ACGCGCAC*UGAUAAUAGUCCAUAAAGUAGGAAACACUACAGCUGGAGCCUC*<br>*GGUGGCCAUGCUUCUUGCCCCUUGGGCCUCCCCCCAGCCCCUCCUCCCCUU*<br>*CCUGCACCCGUACCCCCCGCAUUAUUACUCACGGUACGAGUGGUCUUUGAA*<br>*UAAAGUCUGAGUGGGCGGC* |
| 135 | #18 | <u>GGGAAAUAAGAGAGAAAAGAAGAGUAAGAAGAAAUAUAAGAGCCACC</u>AUGA<br>GCGGCAACGGCAACGCCGCCGCCACCGCCGAGGAGAACAGCCCCAAGAUGC<br>GGGUGAUCCGGGUGGGCACCCGGAAGAGCCAGCUGGCCCGCAUCCAGACCG<br>ACUCCGUCGUCGCCACCCUCAAGGCCUCCUACCCCGGCCUCCAGUUCGAGA<br>UCAUCGCCAUGUCCACCACCGGCGACAAGAUCCUCGACACCGCCCUCUCCA<br>AGAUCGGCGAGAAGUCCCUCUUCACCAAGGAGCUCGAGCACGCCCUCGAGA<br>AGAACGAGGUCGACCUCGUCGUCCACUCCCUCAAGGACCUCCCCACCGUCC<br>UCCCCCCCGGCUUCACCAUCGGCGCCAUCUGCAAGCGCGAGAACCCCCACG<br>ACGCCGUCGUCUUCCACCCCAAGUUCGUCGGCAAGACCCUCGAGACCCUCC<br>GCGAGAAGUCCGUCGUCGGCACCUCCUCCCCCGCCGCCCGCCCAGCUCC<br>AGCGCAAGUUCCCCCACCUCGAGUUCCGCUCCAUCCGCGGCAACCUCAACA<br>CCCGCCUCCGCAAGCUCGACGAGCAGCAGGAGUUCUCCGCCAUCAUCCUCG<br>CCACCGCCGGCCUCCAGCGCAUGGGCUGGCACAACCGCGUCGGCCAGAUCC<br>UCCACCCCGAGGAGUGCAUGUACGCCGUCGGCAGGGCGCCCUCGGCGUCG<br>AGGUCCGCGCCAAGGACCAGGACAUCCUCGACCUCGUCGGCGUCCUCCACG<br>ACCCCGAGACCCUCCUCGCUGCAUCGCCGAGCGCGCCUUCCUCCGCCACC<br>UCGAGGGCGGCUGCUCCGUCCCGUCGCCGUCCACACCGCCAUGAAGGACG<br>GCCAGCUCUACCUCACCGGCGGCGUCUGGUCCCUCGACGGCUCCGACUCCA<br>UCCAGGAGACCAUGCAGGCCACCAUCCACGUCCCCGCCCAGCACGAGGACG<br>GCCCCGAGGACGACCCCAGCUCGUCGGCAUCACCGCCCGCAACAUCCCCC<br>GCGGCCCCCAGCUCGCCGCCCAGAACCUCGGCAUCUCCCUCGCCAACCUCC<br>UCCUCUCCAAGGGCGCCAAGAACAUCCUCGACGUCGCCCGCCAGCUCAACG<br>ACGCCCAC*UGAUAAUAGUCCAUAAAGUAGGAAACACUACAGCUGGAGCCUC*<br>*GGUGGCCAUGCUUCUUGCCCCUUGGGCCUCCCCCCAGCCCCUCCUCCCCUU*<br>*CCUGCACCCGUACCCCCCGCAUUAUUACUCACGGUACGAGUGGUCUUUGAA*<br>*UAAAGUCUGAGUGGGCGGC* |

TABLE 5-continued mRNA Constructs

| SEQ ID NO | Construct | Sequence (5' UTR = bold underline; 3' UTR comprising a stop codon = bold italics) |
|---|---|---|
| 136 | #19 | <u>GGGAAAUAAGAGAGAAAAGAAGAGUAAGAAGAAAUAUAAGAGCCACC</u>AUGA<br>GCGGCAACGGCAACGCCGCCGCCACCGCCGAGGAGAACAGCCCCAAGAUGC<br>GGGUGAUCCGGGUGGGCACCCGUAAGAGCCAGCUGGCCCGGAUCCAGACCG<br>ACAGCGUGGUGGCCACCCUGAAGGCCAGCUACCCCGGCCUGCAGUUCGAGA<br>UCAUCGCCAUGAGCACCACCGGCGACAAGAUCCUGGACACCGCCCUGAGCA<br>AGAUCGGCGAGAAGUCCCUGUUCACCAAGGAGCUGGAGCACGCCCUGGAGA<br>AGAACGAGGUGGACCUGGUGGUGCACAGCCUGAAGGACCUGCCCACCGUGC<br>UGCCUCCAGGCUUCACCAUCGGCGCCAUCUGCAAGCGGGAGAACCCUCACG<br>ACGCCGUGGUGUUCCACCCCAAGUUCGUGGGCAAGACCCUGGAAACCCUGC<br>CUGAGAAGUCCGUCGUAGGAACCAGCAGCCUGCGGCGGGCCGCCCAGCUGC<br>AGCGGAAGUUCCCACACCUGGAGUUCCGGAGCAUCCGGGGCAACCUGAACA<br>CCCCGGCUGCGGAAGCUGGACGAGCAGCAGGAGUUCAGCGCCAUCAUCCUGG<br>CUACCGCCGGUCUGCAACGAAUGGGCUGGCACAAUAGGGUGGGCCAGAUCC<br>UGCACCCCGAGGAGUGCAUGUACGCGGUGGACAGGGCGCCCUGGGCGUGG<br>AGGUGCGGGCCAAGGACCAGGACAUCCUUGAUCUGGUGGGCGUGCUGCACG<br>ACCCCGAGACGCUGCUGCGGUGCAUCGCCGAGCGGGCCUUCCUGCGGCAUU<br>UGGAGGGCGGAUGCAGCGUGCCCGUGGCCGUGCACACCGCCAUGAAGGACG<br>GCCAGCUGUACCUGACCGGCGGCGUGUGGAGCCUGGACGGCAGCGACAGCA<br>UCCAGGAAACCAUGCAGGCCACCAUCCACGUGCCUGCUCAGCACGAAGACG<br>GCCCAGAGGACGACCCUCAGCUGGUAGGCAUCACCGCCCGGAACAUCCCUC<br>GGGGCCCUCAGCUCGCCGCACAGAACCUUGGAAUCAGCCUGGCCAACCUGC<br>UGUUGUCAAAGGGCGCCAAGAAUAUCCUCGACGUGGCCCGGCAGCUGAACG<br>ACGCCCAC*UGAUAAUAGUCCAUAAAGUAGGAAACACUACAGCUGGAGCCUC<br>GGUGGCCAUGCUUCUUGCCCCUUGGGCCUCCCCCCAGCCCCUCCUCCCCUU<br>CCUGCACCCGUACCCCCCGCAUUAUUACUCACGGUACGAGUGGUCUUUGAA<br>UAAAGUCUGAGUGGGCGGC* |
| 137 | #20 | <u>GGGAAAUAAGAGAGAAAAGAAGAGUAAGAAGAAAUAUAAGAGCCACC</u>AUGA<br>GCGGCAACGGCAACGCCGCCGCCACCGCCGAGGAGAACAGCCCCAAGAUGC<br>GGGUGAUCCGGGUGGGCACCAGAAAGAGCCAGCUGGCCCGGAUCCAGACCG<br>ACAGCGUGGUGGCCACCCUGAAGGCCAGCUACCCCGGCCUGCAGUUCGAGA<br>UCAUCGCCAUGAGCACCACCGGCGACAAGAUCCUGGACACCGCCCUGAGCA<br>AGAUCGGCGAGAAGAGUCUGUUCACCAAGGAGCUGGAGCACGCCCUGGAGA<br>AGAACGAGGUGGACCUGGUGGUGCACAGCCUGAAGGACCUGCCCACCGUGC<br>UGCCGCCUGGCUUCACCAUCGGCGCCAUCUGCAAGCGGGAGAACCCGCACG<br>ACGCCGUGGUGUUCCACCCCAAGUUCGUGGGCAAGACUCUGGAAACCCUGC<br>CUGAGAAGUCCGUGGUCGGAACAAGCAGCCUGCGGCGGGCCGCCCAGCUGC<br>AGCGGAAGUUCCCACACCUGGAGUUCCGGAGCAUCCGGGGCAACCUGAACA<br>CCCCGGCUGCGGAAGCUGGACGAGCAGCAGGAGUUCAGCGCCAUCAUCCUGG<br>CCACAGCCGGCCUUCAGAGGAUGGGCUGGCACAAUCGGGUAGGCCAGAUCC<br>UGCACCCCGAGGAGUGCAUGUACGCGGUUGGACAGGGCGCCCUGGGCGUGG<br>AGGUGCGGGCCAAGGACCAGGACAUCUUAGAUCUGGUUGGCGUGCUGCACG<br>ACCCCGAAACACUGCUGCGGUGCAUCGCCGAGCGGGCCUUCCUGCGGCACC<br>UCGAGGGCGGCUGCAGUGUGCCCGUGGCCGUGCACACCGCCAUGAAGGACG<br>GCCAGCUGUACCUGACCGGCGGCGUGUGGAGCCUGGACGGCAGCGACAGCA<br>UCCAGGAGACAAUGCAGGCCACCAUCCACGUGCCAGCUCAGCACGAAGACG<br>GACCAGAGGACGACCCACAGUUAGUGGGAAUCACCGCCCGGAACAUCCCGC<br>GGGGCCCUCAGCUCGCGCCCAGAACCUGGGCAUCAGCCUGGCCAACCUGC<br>UGCUGUCUAAGGGCGCCAAGAACAUCCUAGACGUGGCCCGGCAGCUGAACG<br>ACGCCCAC*UGAUAAUAGUCCAUAAAGUAGGAAACACUACAGCUGGAGCCUC<br>GGUGGCCAUGCUUCUUGCCCCUUGGGCCUCCCCCCAGCCCCUCCUCCCCUU<br>CCUGCACCCGUACCCCCCGCAUUAUUACUCACGGUACGAGUGGUCUUUGAA<br>UAAAGUCUGAGUGGGCGGC* |
| 138 | #21 | <u>GGGAAAUAAGAGAGAAAAGAAGAGUAAGAAGAAAUAUAAGAGCCACC</u>AUGA<br>GCGGCAACGGCAACGCCGCCGCCACCGCCGAGGAGAACAGCCCCAAGAUGC<br>GGGUGAUCCGGGUGGGCACCAGGAAGUCACAGCUGGCCCGGAUCCAGACCG<br>ACAGCGUGGUGGCCACCCUGAAGGCCAGCUACCCCGGCCUGCAGUUCGAGA<br>UCAUCGCCAUGAGCACCACCGGCGACAAGAUCCUGGACACCGCCCUGAGCA<br>AGAUCGGCGAGAAGUCCCUGUUCACCAAGGAGCUGGAGCACGCCCUGGAGA<br>AGAACGAGGUGGACCUGGUGGUGCACAGCCUGAAGGACCUGCCCACCGUGC<br>UGCCGCCAGGCUUCACCAUCGGCGCCAUCUGCAAGCGGGAGAACCCGCACG<br>ACGCCGUGGUGUUCCACCCCAAGUUCGUGGGCAAGACCCUUGAAACCCUGC<br>CAGAGAAGUCUGUGGUCGGCACCAGCAGCCUGCGGCGGGCCGCCCAGCUGC<br>AGCGGAAGUUCCCGCACCUGGAGUUCCGGAGCAUCCGGGGCAACCUGAACA<br>CCCCGGCUGCGGAAGCUGGACGAGCAGCAGGAGUUCAGCGCCAUCAUCCUGG<br>CCACCGCUGGCCUACAGCGGAUGGGCUGGCACAAUAGAGUUGGUCAGAUCC<br>UGCACCCCGAGGAGUGCAUGUACGCCGUCGGCCAGGGCGCCCUGGGCGUGG<br>AGGUGCGGGCCAAGGACCAGGACAUACUAGACCUCGUGGGCGUGCUGCACG<br>ACCCCGAAACCUUGCUGCGGUGCAUCGCCGAGCGGGCCUUCCUGCGGCACC<br>UGGAAGGCGGUUGCAGCGUGCCCGUGGCCGUGCACACCGCCAUGAAGGACG<br>GCCAGCUGUACCUGACCGGCGGCGUGUGGAGCCUGGACGGCAGCGACAGCA<br>UCCAGGAGACAAUGCAGGCCACCAUCCACGUGCCGGCCAACACGAGGACG<br>GACCUGAGGACGACCCACAGCUUGUGGGAAUCACCGCCCGGAACAUCCCAC<br>GGGGCCCUCAACUGGCAGCCCAGAACUUAGGCAUAAGCCUGGCCAACCUGC |

TABLE 5-continued mRNA Constructs

| SEQ ID NO | Construct | Sequence (5' UTR = bold underline; 3' UTR comprising a stop codon = bold italics) |
|---|---|---|
| | | UGCUGUCCAAGGGCGCCAAGAACAUCCUCGAUGUGGCCCGGCAGCUGAACG ACGCCCAC*UGAUAAUAGUCCAUAAAGUAGGAAACACUACAGCUGGAGCCUC GGUGGCCAUGCUUCUUGCCCCUUGGGCCUCCCCCCAGCCCCUCCUCCCCUU CCUGCACCCGUACCCCCGCAUUAUUACUCACGGUACGAGUGGUCUUUGAA UAAAGUCUGAGUGGGCGGC* |
| 139 | #22 | <u>GGGAAAUAAGAGAGAAAAGAAGAGUAAGAAGAAAUAUAAGAGCCACC</u>AUGA GCGGCAACGGCAACGCCGCCGCCACCGCCGAGGAGAACAGCCCCAAGAUGC GGGUGAUCCGGGUGGGCACCCGCAAGAGUCAGCUGGCCCGGAUCCAGACCG ACAGCGUGGUGGCCACCCUGAAGGCCAGCUACCCCGGCCUGCAGUUCGAGA UCAUCGCCAUGAGCACCACCGGCGACAAGAUCCUGGACACCGCCCUGAGCA AGAUCGGCGAGAAGAGUCUGUUCACCAAGGAGCUGGAGCACGCCCUGGAGA AGAACGAGGUGGACCUGGUGGUGCACAGCCUGAAGGACCUGCCCACCGUGC UGCCACCUGGCUUCACCAUCGGCGCCAUCUGCAAGCGGGAGAACCCACACG ACGCCGUGGUGUUCCACCCCAAGUUCGUGGGCAAGACACUGGAAACCCUGC GGAGAAGUCCGUGGUAGGCACCAGCAGCCUGCGGCGGGCCGCCCAGCUGC AGCGGAAGUUCCCGCACCUGGAGUUCCGGAGCAUCCGGGGCAACCUGAACA CCCGGCUGCGGAAGCUGGACGAGCAGCAGGAGUUCAGCGCCAUCAUCCUGG CAACAGCCGGCUUACAGCGUAUGGGCUGGCACAACAGGGUGGGACAGAUCC UGCACCCCGAGGAGUGCAUGUACGCUGUGGGCCAGGGCGCCCUGGGCGUGG AGGUGCGGGCCAAGGACCAGGACAUCUUAGAUCUCGUCGGCGUGCUGCACG ACCCCGAAACCUUGCUGCGGUGCAUCGCCGAGCGGGCCUUCCUGCGGCAUC UUGAGGGCGGAUGCUCCGUGCCCGUGGCCGUGCACACCGCCAUGAAGGACG GCCAGCUGUACCUGACCGGCGGCGUGUGGAGCCUGGACGGCAGCGACAGCA UCCAGGAGACUAUGCAGGCCACCAUCCACGUGCCAGCCCAGCACGAAGACG GCCCAGAGGACGACCCACAGCUGGUGGGAAUCACCGCCCGGAACAUCCCGC GGGGCCCUCAACUGGCCGCACAGAACCUAGGCAUCAGCCUGGCCAACCUGC UGCUCAGCAAGGGCGCCAAGAAUAUCUUGGACGUGGCCCGGCAGCUGAACG ACGCCCAC*UGAUAAUAGUCCAUAAAGUAGGAAACACUACAGCUGGAGCCUC GGUGGCCAUGCUUCUUGCCCCUUGGGCCUCCCCCCAGCCCCUCCUCCCCUU CCUGCACCCGUACCCCCGCAUUAUUACUCACGGUACGAGUGGUCUUUGAA UAAAGUCUGAGUGGGCGGC* |
| 140 | #23 | <u>GGGAAAUAAGAGAGAAAAGAAGAGUAAGAAGAAAUAUAAGAGCCACC</u>AUGA GCGGCAACGGCAACGCCGCCGCCACCGCCGAGGAGAACAGCCCCAAGAUGC GGGUGAUCCGGGUGGGCACCAGAAAGAGCCAGCUGGCCCGGAUCCAGACCG ACAGCGUGGUGGCCACCCUGAAGGCCAGCUACCCCGGCCUGCAGUUCGAGA UCAUCGCCAUGAGCACCACCGGCGACAAGAUCCUGGACACCGCCCUGAGCA AGAUCGGCGAGAAGUCUCUGUUCACCAAGGAGCUGGAGCACGCCCUGGAGA AGAACGAGGUGGACCUGGUGGUGCACAGCCUGAAGGACCUGCCCACCGUGC UGCCUCCUGGCUUCACCAUCGGCGCCAUCUGCAAGCGGGAGAACCCACACG ACGCCGUGGUGUUCCACCCCAAGUUCGUGGGCAAGACCCUUGAGACUCUGC CAGAGAAGUCUGUAGUGGGAACCAGCAGCCUGCGGCGGGCCGCCCAGCUGC AGCGGAAGUUCCCUCACCUGGAGUUCCGGAGCAUCCGGGGCAACCUGAACA CCCGGCUGCGGAAGCUGGACGAGCAGCAGGAGUUCAGCGCCAUCAUCCUGG CCACGGCCGGAUUACAGAGAAUGGGCUGGCACAACCGAGUGGGACAGAUCC UGCACCCCGAGGAGUGCAUGUAUGCCGUUGGCCAAGGCGCCCUGGGCGUGG AGGUGCGGGCCAAGGACCAGGACAUCCUCGAUCUCGUGGGCGUGCUGCACG ACCCCGAGACUUUGCUGCGGUGCAUCGCCGAGCGGGCCUUCCUGCGGCACC UAGAGGGCGGCUGCUCGGUGCCCGUGGCCGUGCACACCGCCAUGAAGGACG GCCAGCUGUACCUGACCGGCGGCGUGUGGAGCCUGGACGGCAGCGACAGCA UCCAGGAGACAAUGCAGGCCACCAUCCACGUGCCAGCCCAGCACGAGGAUG GCCCUGAAGACGACCCACAGCUGGUGGGCAUCACCGCCCGGAACAUCCCGC GGGGCCCACAAUUGGCCGCUCAGAACUUAGGCAUUAGCCUGGCCAACCUGC UGCUGUCUAAGGGCGCCAAGAACAUACUGGACGUGGCCCGGCAGCUGAACG ACGCCCAC*UGAUAAUAGUCCAUAAAGUAGGAAACACUACAGCUGGAGCCUC GGUGGCCAUGCUUCUUGCCCCUUGGGCCUCCCCCCAGCCCCUCCUCCCCUU CCUGCACCCGUACCCCCGCAUUAUUACUCACGGUACGAGUGGUCUUUGAA UAAAGUCUGAGUGGGCGGC* |
| 142 | #25 | <u>GGGAAAUAAGAGAGAAAAGAAGAGUAAGAAGAAAUAUAAGAGCCACC</u>AUGA GCGGCAACGGCAACGCCGCCGCCACCGCCGAGGAGAACAGCCCCAAGAUGC GGGUGAUCCGGGUGGGCACCCGCAAGAGCCAGCUGGCGAGGAUCCAGACGG ACAGCGUGGUGGCGACGCUGAAGGCGAGCUACCCCGGGCUGCAGUUCGAGA UCAUCGCGAUGAGCACGACCGGCGACAAGAUCCUGGACACGGCGCUGAGCA AGAUCGGGGAGAAGAGCCUGUUCACGAAGGAGCUGGAGCACGCGCUGGAGA AGAACGAGGUGGACCUGGUGGUGCACAGCCUGAAGGACCUGCCGACGGUGC UGCCGCCGGGGUUCACGAUCGGGGCGAUCUGCAAGAGGGAGAACCCGCACG ACGCGGUGGUGUUCCACCCCAAGUUCGUGGGGAAGACGCUGGAGACGCUGC GGGAGAAGAGCGUGGUGGGGACGAGCAGCCUGAGGAGGGCCGCCCAGCUGC AGAGGAAGUUCCCGCACCUGGAGUUCAGGAGCAUCAGGGGUAACCUGAACA CGAGGCUGAGGAAGCUGGACGAGCAGCAGGAGUUCAGCGCGAUCAUCCUGG CGACGGCGGGCUGCAGAGGAUGGGGUGGCACAACAGGGUGGGGCAGAUCC UGCACCCCGAGGAGUGCAUGUACGCGGUGGGGCAGGGCGCGCUGGGCGUGG AGGUGAGGGCGAAGGACCAGGACAUCCUGGACCUGGUGGGCGUGCUGCACG TABLE 5-continued mRNA Constructs

| SEQ ID NO | Construct | Sequence (5' UTR = bold underline; 3' UTR comprising a stop codon = bold italics) |
|---|---|---|
| | | ACCCGGAGACGCUGCUGAGGUGCAUCGCGGAGAGGGCGUUCCUGAGGCACC<br>UGGAGGGCGGGUGCAGCGUGCCGGUGGCGGUGCACACGGCGAUGAAGGACG<br>GGCAGCUGUACCUGACGGGAGGGGUGUGGAGCCUGGACGGGAGCGACAGCA<br>UCCAGGAGACGAUGCAGGCGACGAUCCACGUGCCGGCGCAGCACGAGGACG<br>GGCCGGAGGACGACCCGCAGCUGGUGGGGAUCACGGCGAGGAACAUCCCGA<br>GGGGUCCGCAGCUGGCGGCGCAGAACCUGGGGAUCAGCCUGGCGAACCUGC<br>UGCUGAGCAAGGGGAGCGAAGAACAUCCUGGACGUGGCGAGGCAGCUGAACG<br>ACGCCAC*UGAUAAUAGUCCAUAAAGUAGGAAACACUACAGCUGGAGCCUC*<br>*GGUGGCCAUGCUUCUUGCCCCUUGGGCCUCCCCCCAGCCCCUCCUCCCCUU*<br>*CCUGCACCCGUACCCCCCGCAUUAUUACUCACGGUACGAGUGGUCUUUGAA*<br>*UAAAGUCUGAGUGGGCGGC* |
| 143 | #26 | <u>GGGAAAUAAGAGAGAAAAGAAGAGUAAGAAGAAAUAUAAGAGCCACC</u>AUGA<br>GCGGCAACGGCAACGCCGCCGCCACCGCCGAGGAGAACAGCCCCAAGAUGC<br>GGGUGAUCCGGGUGGGCACCCGGAAGAGCCAGCUGGCCCGCAUCCAGACCG<br>ACUCCGUCGUCGCCACCCUCAAGGCCUCCUACCCCGGCCUCCAGUUCGAGA<br>UCAUCGCCAUGUCCACCACCGGCGACAAGAUCCUCGACACCGCCCUCUCCA<br>AGAUCGGCGAGAAGUCCCUCUUCACCAAGGAGCUCGAGCACGCCCUCGAGA<br>AGAACGAGGUCGACCUCGUCGUCCACUCCCUCAAGGACCUCCCCACCGUCC<br>UCCCACCCGGCUUCACCAUCGGCGCCAUCUGCAAGCGCGAGAACCCUCACG<br>ACGCCGUCGUCUUCCACCCCAAGUUCGUCGGCAAGACCCUCGAGACCCUCC<br>CCGAGAAGUCCGUCGUCGGCACCUCCUCCCUCCGCCGCCGCCCAGCUCC<br>AGCGCAAGUUCCCACACCUCGAGUUCCGCUCCAUCCGCGGCAACCUCAACA<br>CCCGCCUCCGCAAGCUCGACGAGCAGCAGGAGUUCUCCGCCAUCAUCCUCG<br>CCACCGCCGGCCUCCAGCGCAUGGGCUGGCACAACCGCGUCGGCCAGAUCC<br>UCCACCCCGAGGAGUGCAUGUACGCCGUCGGCCAGGGCGCCCUCGGCGUCG<br>AGGUCCGCGCCAAGGACCAGGACAUCCUCGACCUCGUCGGCGUCCUCCACG<br>ACCCCGAGACCCUCCUCCGCUGCAUCGCCGAGCGCGCCUUCCUCCGCCACC<br>UCGAGGGCGGCUGCUCCGUCCCCGUCGCCGUCCACACCGCCAUGAAGGACG<br>GCCAGCUCUACCUCACCGGCGGCGUCUGGUCCCUCGACGGCUCCGACUCCA<br>UCCAGGAGACCAUGCAGGCCACCAUCCACGUCCCCGCCCAGCACGAGGACG<br>GCCCCGAGGACGACCCGCUCAGCUGCGUCGGCAUCACCGCCCGCAACAUCCCGC<br>GCGGCCCUCAGCUCGCCGCCCAGAACCUCGGCAUCUCCCUCGCCAACCUCC<br>UCCUCUCCAAGGGCGCCAAGAACAUCCUCGACGUCGCCCGCCAGCUCAACG<br>ACGCCCAC*UGAUAAUAGUCCAUAAAGUAGGAAACACUACAGCUGGAGCCUC*<br>*GGUGGCCAUGCUUCUUGCCCCUUGGGCCUCCCCCCAGCCCCUCCUCCCCUU*<br>*CCUGCACCCGUACCCCCCGCAUUAUUACUCACGGUACGAGUGGUCUUUGAA*<br>*UAAAGUCUGAGUGGGCGGC* |
| 146 | #29 | <u>GGGAAAUAAGAGAGAAAAGAAGAGUAAGAAGAAAUAUAAGAGCCACC</u>AUGU<br>CCGGAAACGGAAACGCCGCCGCUACCGCCGAGGAAAAUAGCCCGAAGAUGA<br>GAGUGAUCCGGGUGGGUACCAGGAAGUCCCAGCUCGCCAGGAUCCAAACGG<br>ACUCGGUGGUGGCCACCCUCAAGGCUAGCUACCCGGGCCUGCAAUUCGAGA<br>UCAUUGCUAUGUCCACCACCGGCGACAAGAUCCUGGAUACGGCCCUGUCCA<br>AGAUCGGCGAAAAGAGCCUCUUCACCAAGGAGCUGGAACACGCGCUCGAGA<br>AGAACGAGGUGGACCUGGUCGUCCACAGCCUCAAGGACCUGCCUACGGUGC<br>UGCCGCCGGGAUUCACCAUCGGCGCCAUCUGUAAGCGGGAGAAUCCGCACG<br>ACGCCGUGGUGUUCCACCCUAAGUUCGUGGGCAAGACCCUCGAGACACUGC<br>CGGAAAAGUCCGUCGUGGGCACCUCCUCCCUGAGAAGGGCCGCUCAGCUCC<br>AGAGAAAGUUCCCGCACCUGGAAUUCAGGAGCAUCCGGGGCAACCUGAAUA<br>CCCGGCUUCGCAAGCUGGACGAGCAGCAGGAGUUCAGCGCCAUCAUCCUGG<br>CCACCGCCGGCCUGCAGCGGAUGGGCUGGCACAACCGGGUGGGCCAGAUCC<br>UGCACCCGGAGGAGUGCAUGUAUGCCGUGGGUCAGGGAGCCCUGGGCGUGG<br>AGGUCCGGGCCAAGGACCAGGACAUCCUGGACCUCGUGGGCGUGCUCCACG<br>ACCCUGAAACCCUCCUGAGGUGCAUCGCCGAGAGGGCCUUCCUCCGGCACC<br>UGGAGGGCGGCUGUUCCGUCCCUGUGGCCGUGCAUACCGCCAUGAAGGACG<br>GACAGCUGUACCUGACCGGCGGCGUGUGGUCCCUGGACGGCUCCGACAGCA<br>UCCAGGAGACCAUGCAGGCCACUAUCCACGUGCCGCCCAGCACGAAGACG<br>GCCCAGAGGAUGACCCGCAACUGGUCGGCAUUACCGCCAGGAACAUACCAA<br>GGGGCCCGCAGCUGGCCGCCCAGAACCUGGGCAUCUCCCUGGCCAACCUGC<br>UGCUGUCCAAGGGAGCCAAGAACAUUCUGGACGUGGCCAGGCAGCUCAAUG<br>AUGCCCAC*UGAUAAUAGUCCAUAAAGUAGGAAACACUACAGCUGGAGCCUC*<br>*GGUGGCCAUGCUUCUUGCCCCUUGGGCCUCCCCCCAGCCCCUCCUCCCCUU*<br>*CCUGCACCCGUACCCCCCGCAUUAUUACUCACGGUACGAGUGGUCUUUGAA*<br>*UAAAGUCUGAGUGGGCGGC* |
| 147 | #30 | <u>GGGAAAUAAGAGAGAAAAGAAGAGUAAGAAGAAAUAUAAGAGCCACC</u>AUGA<br>GCGGCAACGGCAACGCCGCCGCCACCGCAGAGGAGAAUAGCCCGAAGAUGA<br>GGGUGAUCCGAGUGGGCACCAGGAAGUCCCAGCUUGCGCGAAUUCAGACCG<br>ACAGCGUGGUGGCCACCCUCAAGGCCUCCUACCCGGGACUCCAGUUCGAGA<br>UCAUCGCCAUGAGCACCACGGGAGACAAGAUCCUGGACACCGCCCUGUCCA<br>AGAUCGGCGAAAAGAGCCUCUUCACCAAGGAGCUGGAGCACGCCCUGGAGA<br>AGAACGAGGUCGAUCUGGUGGUGCACAGCCUGAAGGACCUGCCGACCGUCC<br>UGCCGCCGGGAUUCACCAUCGGUGCCAUCUGUAAGCGGGAGAACCCGCACG<br>ACGCCGUGGUGUUCCACCCGAAGUUCGUCGGCAAGACCCUGGAAACCCUGC |

TABLE 5-continued mRNA Constructs

| SEQ ID NO | Construct | Sequence (5' UTR = bold underline; 3' UTR comprising a stop codon = bold italics) |
|---|---|---|
| | | CGGAGAAGUCCGUGGUGGGCACCAGCAGCCUGAGGCGGGCCGCCCAGCUGC<br>AGCGGAAGUUCCCGCACCUGGAAUUCAGGAGCAUCCGGGGCAACCUGAACA<br>CCCGGCUGCGGAAGCUGGACGAGCAGCAGGAGUUCAGCGCCAUCAUCCUGG<br>CCACCGCAGGCCUCCAGCGCAUGGGAUGGCACAACAGGGUAGGCCAAAUCC<br>UGCACCCGGAGGAGUGUAUGUACGCCGUGGGCCAGGGAGCCCUGGGCGUGG<br>AGGUGAGAGCCAAGGACCAGGACAUCCUAGACCUGGUCGGCGUGCUGCACG<br>ACCCGGAGACACUGCUGAGAUGCAUCGCGGAGAGAGCCUUCCUGCGACACC<br>UGGAGGGCGGCUGCUCCGUGCCGGUGGCCGUGCACACCGCCAUGAAGGACG<br>GCCAGCUGUAUCUGACCGGCGGCGUGUGGAGCCUGGACGGCAGCGACUCCA<br>UCCAAGAAACCAUGCAGGCUACCAUCCACGUGCCGGCCCAGCACGAGGAUG<br>GACCAGAGGACGAUCCUCAACUGGUGGGCAUCACUGCCAGGAACAUCCCAA<br>GAGGCCCGCAGCUGGCCGCCCAGAACCUGGGCAUCAGCCUGGCCAACCUGC<br>UGCUGUCCAAGGGCGCCAAGAACAUUCUCGAUGUGGCCAGGCAGCUGAACG<br>AUGCCCAC*UGAUAAUAGUCCAUAAAGUAGGAAACACUACAGCUGGAGCCUC*<br>*GGUGGCCAUGCUUCUUGCCCCUUGGGCCUCCCCCCAGCCCCUCCUCCCCUU*<br>*CCUGCACCCGUACCCCCCGCAUUAUUACUCACGGUACGAGUGGUCUUUGAA*<br>*UAAAGUCUGAGUGGGCGGC* |
| 148 | #31 | <u>GGGAAAUAAGAGAGAAAAGAAGAGUAAGAAGAAAUAUAAGAGCCACC</u>AUGU<br>CGGGAAACGGCAACGCCGCCGCCACGGCCGAGGAGAACAGCCCGAAGAUGA<br>GAGUGAUUAGGGUGGGCACCCGGAAGUCCCAACUCGCGCGGAUCCAGACCG<br>ACUCCGUGGUGGCCACCCUCAAGGCCAGCUACCCGGGCCUCCAGUUCGAGA<br>UUAUCGCCAUGUCCACCACAGGCGACAAGAUCCUCGACACCGCACUCUCGA<br>AGAUCGGCGAGAAGUCCCUGUUCACCAAGGAACUGGAGCACGCCCUGGAGA<br>AGAACGAGGUGGACCUGGUGGUGCACUCCCUGAAGGACCUGCCGACCGUGC<br>UCCCACCAGGCUUCACCAUCGGCGCAAUCUGUAAGCGCGAGAAUCCGCACG<br>ACGCCGUGGUGUUCCACCCAAAGUUCGUGGGCAAGACCCUCGAAACCCUCC<br>CGGAAAAGAGCGUGGUGGGUACCAGCUCCCUGCGGAGAGCUGCCCAGCUGC<br>AGAGAAAGUUCCCGCAUCUGGAAUUCAGGAGCAUCAGGGGAAAUCUGAAUA<br>CCAGACUGCGCAAGCUGGACGAGCAGCAGGAGUUCAGCGCCAUCAUCCUGG<br>CCACCGCCGGCCUGCAGCGGAUGGGCUGGCACAACAGGGUGGGCCAGAUAC<br>UGCAUCCGGAGGAGUGUAUGUACGCCGUGGGCCAGGGCGCCCUCGGCGUGG<br>AGGUGAGAGCCAAGGACCAAGACAUCCUGGACCUAGUGGGCGUGCUGCAUG<br>ACCCUGAAACCCUGCUCAGGUGCAUCGCCGAGAGGGCCUUCCUGCGGCACC<br>UGGAGGGCGGCUGCAGCGUGCCGGUGGCCGUCCACACCGCCAUGAAGGACG<br>GCCAGCUGUACCUGACCGGCGGCGUCUGGAGCCUGGACGGAUCCGACAGCA<br>UCCAGGAAACCAUGCAGGCCACCAUCCACGUGCCGGCCCAGCACGAGGACG<br>GCCCUGAGGACGACCCUCAGCUGGUGGGCAUCACCGCUAGGAACAUCCCAA<br>GGGGCCCGCAGCUGGCCGCCCAGAACCUCGGCAUCAGCCUGGCCAACCUGC<br>UGCUGUCCAAGGGCGCCAAGAAUAUCCUGGACGUGGCCAGGCAGCUGAACG<br>ACGCCCAC*UGAUAAUAGUCCAUAAAGUAGGAAACACUACAGCUGGAGCCUC*<br>*GGUGGCCAUGCUUCUUGCCCCUUGGGCCUCCCCCCAGCCCCUCCUCCCCUU*<br>*CCUGCACCCGUACCCCCCGCAUUAUUACUCACGGUACGAGUGGUCUUUGAA*<br>*UAAAGUCUGAGUGGGCGGC* |

20. METHODS OF MAKING POLYNUCLEOTIDES

The present disclosure also provides methods for making a polynucleotide of the invention (e.g., a polynucleotide comprising a nucleotide sequence encoding a PBGD polypeptide) or a complement thereof.

In some aspects, a polynucleotide (e.g., a RNA, e.g., an mRNA) disclosed herein, and encoding a PBGD polypeptide, can be constructed using in vitro transcription. In other aspects, a polynucleotide (e.g., a RNA, e.g., an mRNA) disclosed herein, and encoding a PBGD polypeptide, can be constructed by chemical synthesis using an oligonucleotide synthesizer.

In other aspects, a polynucleotide (e.g., a RNA, e.g., an mRNA) disclosed herein, and encoding a PBGD polypeptide is made by using a host cell. In certain aspects, a polynucleotide (e.g., a RNA, e.g., an mRNA) disclosed herein, and encoding a PBGD polypeptide is made by one or more combination of the IVT, chemical synthesis, host cell expression, or any other methods known in the art.

Naturally occurring nucleosides, non-naturally occurring nucleosides, or combinations thereof, can totally or partially naturally replace occurring nucleosides present in the candidate nucleotide sequence and can be incorporated into a sequence-optimized nucleotide sequence (e.g., a RNA, e.g., an mRNA) encoding a PBGD polypeptide. The resultant polynucleotides, e.g., mRNAs, can then be examined for their ability to produce protein and/or produce a therapeutic outcome.

a. In Vitro Transcription/Enzymatic Synthesis

The polynucleotides of the present invention disclosed herein (e.g., a polynucleotide comprising a nucleotide sequence encoding a PBGD polypeptide) can be transcribed using an in vitro transcription (IVT) system. The system typically comprises a transcription buffer, nucleotide triphosphates (NTPs), an RNase inhibitor and a polymerase. The NTPs can be selected from, but are not limited to, those described herein including natural and unnatural (modified) NTPs. The polymerase can be selected from, but is not limited to, T7 RNA polymerase, T3 RNA polymerase and mutant polymerases such as, but not limited to, polymerases able to incorporate polynucleotides disclosed herein. See U.S. Publ. No. US20130259923, which is herein incorporated by reference in its entirety.

Any number of RNA polymerases or variants can be used in the synthesis of the polynucleotides of the present invention. RNA polymerases can be modified by inserting or deleting amino acids of the RNA polymerase sequence. As a non-limiting example, the RNA polymerase can be modified to exhibit an increased ability to incorporate a 2'-modified nucleotide triphosphate compared to an unmodified RNA polymerase (see International Publication WO2008078180 and U.S. Pat. No. 8,101,385; herein incorporated by reference in their entireties).

Variants can be obtained by evolving an RNA polymerase, optimizing the RNA polymerase amino acid and/or nucleic acid sequence and/or by using other methods known in the art. As a non-limiting example, T7 RNA polymerase variants can be evolved using the continuous directed evolution system set out by Esvelt et al. (Nature 472:499-503 (2011); herein incorporated by reference in its entirety) where clones of T7 RNA polymerase can encode at least one mutation such as, but not limited to, lysine at position 93 substituted for threonine (K93T), I4M, A7T, E63V, V64D, A65E, D66Y, T76N, C125R, S128R, A136T, N165S, G175R, H176L, Y178H, F182L, L196F, G198V, D208Y, E222K, S228A, Q239R, T243N, G259D, M267I, G280C, H300R, D351A, A354S, E356D, L360P, A383V, Y385C, D388Y, S397R, M401T, N410S, K450R, P451T, G452V, E484A, H523L, H524N, G542V, E565K, K577E, K577M, N601S, S684Y, L699I, K713E, N748D, Q754R, E775K, A827V, D851N or L864F. As another non-limiting example, T7 RNA polymerase variants can encode at least mutation as described in U.S. Pub. Nos. 20100120024 and 20070117112; herein incorporated by reference in their entireties. Variants of RNA polymerase can also include, but are not limited to, substitutional variants, conservative amino acid substitution, insertional variants, and/or deletional variants.

In one aspect, the polynucleotide can be designed to be recognized by the wild type or variant RNA polymerases. In doing so, the polynucleotide can be modified to contain sites or regions of sequence changes from the wild type or parent chimeric polynucleotide.

Polynucleotide or nucleic acid synthesis reactions can be carried out by enzymatic methods utilizing polymerases. Polymerases catalyze the creation of phosphodiester bonds between nucleotides in a polynucleotide or nucleic acid chain. Currently known DNA polymerases can be divided into different families based on amino acid sequence comparison and crystal structure analysis. DNA polymerase I (pol I) or A polymerase family, including the Klenow fragments of *E. coli, Bacillus* DNA polymerase I, *Thermus aquaticus* (Taq) DNA polymerases, and the T7 RNA and DNA polymerases, is among the best studied of these families. Another large family is DNA polymerase a (pol a) or B polymerase family, including all eukaryotic replicating DNA polymerases and polymerases from phages T4 and RB69. Although they employ similar catalytic mechanism, these families of polymerases differ in substrate specificity, substrate analog-incorporating efficiency, degree and rate for primer extension, mode of DNA synthesis, exonuclease activity, and sensitivity against inhibitors.

DNA polymerases are also selected based on the optimum reaction conditions they require, such as reaction temperature, pH, and template and primer concentrations. Sometimes a combination of more than one DNA polymerases is employed to achieve the desired DNA fragment size and synthesis efficiency. For example, Cheng et al. increase pH, add glycerol and dimethyl sulfoxide, decrease denaturation times, increase extension times, and utilize a secondary thermostable DNA polymerase that possesses a 3' to 5' exonuclease activity to effectively amplify long targets from cloned inserts and human genomic DNA. (Cheng et al., PNAS 91:5695-5699 (1994), the contents of which are incorporated herein by reference in their entirety). RNA polymerases from bacteriophage T3, T7, and SP6 have been widely used to prepare RNAs for biochemical and biophysical studies. RNA polymerases, capping enzymes, and poly-A polymerases are disclosed in the co-pending International Publication No. WO2014028429, the contents of which are incorporated herein by reference in their entirety.

In one aspect, the RNA polymerase which can be used in the synthesis of the polynucleotides of the present invention is a Syn5 RNA polymerase (see Zhu et al. Nucleic Acids Research 2013, doi:10.1093/nar/gkt1193, which is herein incorporated by reference in its entirety). The Syn5 RNA polymerase was recently characterized from marine cyanophage Syn5 by Zhu et al. where they also identified the promoter sequence (see Zhu et al. Nucleic Acids Research 2013, the contents of which is herein incorporated by reference in its entirety). Zhu et al. found that Syn5 RNA polymerase catalyzed RNA synthesis over a wider range of temperatures and salinity as compared to T7 RNA polymerase. Additionally, the requirement for the initiating nucleotide at the promoter was found to be less stringent for Syn5 RNA polymerase as compared to the T7 RNA polymerase making Syn5 RNA polymerase promising for RNA synthesis.

In one aspect, a Syn5 RNA polymerase can be used in the synthesis of the polynucleotides described herein. As a non-limiting example, a Syn5 RNA polymerase can be used in the synthesis of the polynucleotide requiring a precise 3'-terminus.

In one aspect, a Syn5 promoter can be used in the synthesis of the polynucleotides. As a non-limiting example, the Syn5 promoter can be 5'-ATTGGGCACCCGTAAGGG-3' (SEQ ID NO: 82 as described by Zhu et al. (Nucleic Acids Research 2013).

In one aspect, a Syn5 RNA polymerase can be used in the synthesis of polynucleotides comprising at least one chemical modification described herein and/or known in the art (see e.g., the incorporation of pseudo-UTP and 5Me-CTP described in Zhu et al. Nucleic Acids Research 2013).

In one aspect, the polynucleotides described herein can be synthesized using a Syn5 RNA polymerase which has been purified using modified and improved purification procedure described by Zhu et al. (Nucleic Acids Research 2013).

Various tools in genetic engineering are based on the enzymatic amplification of a target gene which acts as a template. For the study of sequences of individual genes or specific regions of interest and other research needs, it is necessary to generate multiple copies of a target gene from a small sample of polynucleotides or nucleic acids. Such methods can be applied in the manufacture of the polynucleotides of the invention.

For example, polymerase chain reaction (PCR), strand displacement amplification (SDA),nucleic acid sequence-based amplification (NASBA), also called transcription mediated amplification (TMA), and/or rolling-circle amplification (RCA) can be utilized in the manufacture of one or more regions of the polynucleotides of the present invention. Assembling polynucleotides or nucleic acids by a ligase is also widely used.

b. Chemical Synthesis

Standard methods can be applied to synthesize an isolated polynucleotide sequence encoding an isolated polypeptide of interest, such as a polynucleotide of the invention (e.g., a polynucleotide comprising a nucleotide sequence encoding a PBGD polypeptide). For example, a single DNA or RNA oligomer containing a codon-optimized nucleotide sequence coding for the particular isolated polypeptide can be synthesized. In other aspects, several small oligonucleotides coding for portions of the desired polypeptide can be synthesized and then ligated. In some aspects, the individual oligonucleotides typically contain 5' or 3' overhangs for complementary assembly.

A polynucleotide disclosed herein (e.g., a RNA, e.g., an mRNA) can be chemically synthesized using chemical synthesis methods and potential nucleobase substitutions known in the art. See, for example, International Publication Nos. WO2014093924, WO2013052523; WO2013039857, WO2012135805, WO2013151671; U.S. Publ. No. US20130115272; or U.S. Pat. No. 8,999,380 or 8,710,200, all of which are herein incorporated by reference in their entireties.

c. Purification of Polynucleotides Encoding PBGD

Purification of the polynucleotides described herein (e.g., a polynucleotide comprising a nucleotide sequence encoding a PBGD polypeptide) can include, but is not limited to, polynucleotide clean-up, quality assurance and quality control. Clean-up can be performed by methods known in the arts such as, but not limited to, AGENCOURT® beads (Beckman Coulter Genomics, Danvers, MA), poly-T beads, LNA™ oligo-T capture probes (EXIQON® Inc., Vedbaek, Denmark) or HPLC based purification methods such as, but not limited to, strong anion exchange HPLC, weak anion exchange HPLC, reverse phase HPLC (RP-HPLC), and hydrophobic interaction HPLC (HIC-HPLC).

The term "purified" when used in relation to a polynucleotide such as a "purified polynucleotide" refers to one that is separated from at least one contaminant. As used herein, a "contaminant" is any substance that makes another unfit, impure or inferior. Thus, a purified polynucleotide (e.g., DNA and RNA) is present in a form or setting different from that in which it is found in nature, or a form or setting different from that which existed prior to subjecting it to a treatment or purification method.

In some embodiments, purification of a polynucleotide of the invention (e.g., a polynucleotide comprising a nucleotide sequence encoding a PBGD polypeptide) removes impurities that can reduce or remove an unwanted immune response, e.g., reducing cytokine activity.

In some embodiments, the polynucleotide of the invention (e.g., a polynucleotide comprising a nucleotide sequence encoding a PBGD polypeptide) is purified prior to administration using column chromatography (e.g., strong anion exchange HPLC, weak anion exchange HPLC, reverse phase HPLC (RP-HPLC), and hydrophobic interaction HPLC (HIC-HPLC), or (LCMS)).

In some embodiments, the polynucleotide of the invention (e.g., a polynucleotide comprising a nucleotide sequence a PBGD polypeptide) purified using column chromatography (e.g., strong anion exchange HPLC, weak anion exchange HPLC, reverse phase HPLC (RP-HPLC, hydrophobic interaction HPLC (HIC-HPLC), or (LCMS)) presents increased expression of the encoded PBGD protein compared to the expression level obtained with the same polynucleotide of the present disclosure purified by a different purification method.

In some embodiments, a column chromatography (e.g., strong anion exchange HPLC, weak anion exchange HPLC, reverse phase HPLC (RP-HPLC), hydrophobic interaction HPLC (HIC-HPLC), or (LCMS)) purified polynucleotide comprises a nucleotide sequence encoding a PBGD polypeptide comprising one or more of the point mutations known in the art.

In some embodiments, the use of RP-HPLC purified polynucleotide increases PBGD protein expression levels in cells when introduced into those cells, e.g., by 10-100%, i.e., at least about 10%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 90%, at least about 95%, or at least about 100% with respect to the expression levels of PBGD protein in the cells before the RP-HPLC purified polynucleotide was introduced in the cells, or after a non-RP-HPLC purified polynucleotide was introduced in the cells.

In some embodiments, the use of RP-HPLC purified polynucleotide increases functional PBGD protein expression levels in cells when introduced into those cells, e.g., by 10-100%, i.e., at least about 10%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 90%, at least about 95%, or at least about 100% with respect to the functional expression levels of PBGD protein in the cells before the RP-HPLC purified polynucleotide was introduced in the cells, or after a non-RP-HPLC purified polynucleotide was introduced in the cells.

In some embodiments, the use of RP-HPLC purified polynucleotide increases detectable PBGD activity in cells when introduced into those cells, e.g., by 10-100%, i.e., at least about 10%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 90%, at least about 95%, or at least about 100% with respect to the activity levels of functional PBGD in the cells before the RP-HPLC purified polynucleotide was introduced in the cells, or after a non-RP-HPLC purified polynucleotide was introduced in the cells.

In some embodiments, the purified polynucleotide is at least about 80% pure, at least about 85% pure, at least about 90% pure, at least about 95% pure, at least about 96% pure, at least about 97% pure, at least about 98% pure, at least about 99% pure, or about 100% pure.

A quality assurance and/or quality control check can be conducted using methods such as, but not limited to, gel electrophoresis, UV absorbance, or analytical HPLC. In another embodiment, the polynucleotide can be sequenced by methods including, but not limited to reverse-transcriptase-PCR.

d. Quantification of Expressed Polynucleotides Encoding PBGD

In some embodiments, the polynucleotides of the present invention (e.g., a polynucleotide comprising a nucleotide sequence encoding a PBGD polypeptide), their expression products, as well as degradation products and metabolites can be quantified according to methods known in the art.

In some embodiments, the polynucleotides of the present invention can be quantified in exosomes or when derived from one or more bodily fluid. As used herein "bodily fluids" include peripheral blood, serum, plasma, ascites, urine, cerebrospinal fluid (CSF), sputum, saliva, bone marrow, synovial fluid, aqueous humor, amniotic fluid, cerumen, breast milk, broncheoalveolar lavage fluid, semen, prostatic fluid, cowper's fluid or pre-ejaculatory fluid, sweat, fecal matter, hair, tears, cyst fluid, pleural and peritoneal fluid, pericardial fluid, lymph, chyme, chyle, bile, interstitial fluid, menses, pus, sebum, vomit, vaginal secretions, mucosal secretion, stool water, pancreatic juice, lavage fluids from sinus cavities, bronchopulmonary aspirates, blastocyl cavity fluid, and umbilical cord blood. Alternatively, exosomes can be retrieved from an organ selected from the group consisting of lung, heart, pancreas, stomach, intestine, bladder, kidney, ovary, testis, skin, colon, breast, prostate, brain, esophagus, liver, and placenta.

In the exosome quantification method, a sample of not more than 2 mL is obtained from the subject and the exosomes isolated by size exclusion chromatography, density gradient centrifugation, differential centrifugation, nanomembrane ultrafiltration, immunoabsorbent capture, affinity purification, microfluidic separation, or combinations thereof. In the analysis, the level or concentration of a polynucleotide can be an expression level, presence, absence, truncation or alteration of the administered construct. It is advantageous to correlate the level with one or more clinical phenotypes or with an assay for a human disease biomarker.

The assay can be performed using construct specific probes, cytometry, qRT-PCR, real-time PCR, PCR, flow cytometry, electrophoresis, mass spectrometry, or combinations thereof while the exosomes can be isolated using immunohistochemical methods such as enzyme linked immunosorbent assay (ELISA) methods. Exosomes can also be isolated by size exclusion chromatography, density gradient centrifugation, differential centrifugation, nanomembrane ultrafiltration, immunoabsorbent capture, affinity purification, microfluidic separation, or combinations thereof.

These methods afford the investigator the ability to monitor, in real time, the level of polynucleotides remaining or delivered. This is possible because the polynucleotides of the present invention differ from the endogenous forms due to the structural or chemical modifications.

In some embodiments, the polynucleotide can be quantified using methods such as, but not limited to, ultraviolet visible spectroscopy (UV/Vis). A non-limiting example of a UV/Vis spectrometer is a NANODROP® spectrometer (ThermoFisher, Waltham, MA). The quantified polynucleotide can be analyzed in order to determine if the polynucleotide can be of proper size, check that no degradation of the polynucleotide has occurred. Degradation of the polynucleotide can be checked by methods such as, but not limited to, agarose gel electrophoresis, HPLC based purification methods such as, but not limited to, strong anion exchange HPLC, weak anion exchange HPLC, reverse phase HPLC (RP-HPLC), and hydrophobic interaction HPLC (HIC-HPLC), liquid chromatography-mass spectrometry (LCMS), capillary electrophoresis (CE) and capillary gel electrophoresis (CGE).

21. PHARMACEUTICAL COMPOSITIONS AND FORMULATIONS

The present invention provides pharmaceutical compositions and formulations that comprise any of the polynucleotides described above. In some embodiments, the composition or formulation further comprises a delivery agent.

In some embodiments, the composition or formulation can contain a polynucleotide comprising a sequence optimized nucleic acid sequence disclosed herein which encodes a PBGD polypeptide. In some embodiments, the composition or formulation can contain a polynucleotide (e.g., a RNA, e.g., an mRNA) comprising a polynucleotide (e.g., an ORF) having significant sequence identity to a sequence optimized nucleic acid sequence disclosed herein which encodes a PBGD polypeptide. In some embodiments, the polynucleotide further comprises a miRNA binding site, e.g., a miRNA binding site that binds miR-126, miR-142, miR-144, miR-146, miR-150, miR-155, miR-16, miR-21, miR-223, miR-24, miR-27 and miR-26a.

Pharmaceutical compositions or formulation can optionally comprise one or more additional active substances, e.g., therapeutically and/or prophylactically active substances. Pharmaceutical compositions or formulation of the present invention can be sterile and/or pyrogen-free. General considerations in the formulation and/or manufacture of pharmaceutical agents can be found, for example, in *Remington: The Science and Practice of Pharmacy* 21$^{st}$ ed., Lippincott Williams & Wilkins, 2005 (incorporated herein by reference in its entirety). In some embodiments, compositions are administered to humans, human patients or subjects. For the purposes of the present disclosure, the phrase "active ingredient" generally refers to polynucleotides to be delivered as described herein.

Formulations and pharmaceutical compositions described herein can be prepared by any method known or hereafter developed in the art of pharmacology. In general, such preparatory methods include the step of associating the active ingredient with an excipient and/or one or more other accessory ingredients, and then, if necessary and/or desirable, dividing, shaping and/or packaging the product into a desired single- or multi-dose unit.

A pharmaceutical composition or formulation in accordance with the present disclosure can be prepared, packaged, and/or sold in bulk, as a single unit dose, and/or as a plurality of single unit doses. As used herein, a "unit dose" refers to a discrete amount of the pharmaceutical composition comprising a predetermined amount of the active ingredient. The amount of the active ingredient is generally equal to the dosage of the active ingredient that would be administered to a subject and/or a convenient fraction of such a dosage such as, for example, one-half or one-third of such a dosage.

Relative amounts of the active ingredient, the pharmaceutically acceptable excipient, and/or any additional ingredients in a pharmaceutical composition in accordance with the present disclosure can vary, depending upon the identity, size, and/or condition of the subject being treated and further depending upon the route by which the composition is to be administered.

In some embodiments, the compositions and formulations described herein can contain at least one polynucleotide of the invention. As a non-limiting example, the composition or formulation can contain 1, 2, 3, 4 or 5 polynucleotides of the invention. In some embodiments, the compositions or formulations described herein can comprise more than one type of polynucleotide. In some embodiments, the composition or formulation can comprise a polynucleotide in linear and circular form. In another embodiment, the composition or formulation can comprise a circular polynucleotide and an in vitro transcribed (IVT) polynucleotide. In yet another embodiment, the composition or formulation can comprise an IVT polynucleotide, a chimeric polynucleotide and a circular polynucleotide.

Although the descriptions of pharmaceutical compositions and formulations provided herein are principally directed to pharmaceutical compositions and formulations that are suitable for administration to humans, it will be understood by the skilled artisan that such compositions are generally suitable for administration to any other animal, e.g., to non-human animals, e.g. non-human mammals.

The present invention provides pharmaceutical formulations that comprise a polynucleotide described herein (e.g., a polynucleotide comprising a nucleotide sequence encoding a PBGD polypeptide). The polynucleotides described herein can be formulated using one or more excipients to: (1) increase stability; (2) increase cell transfection; (3) permit the sustained or delayed release (e.g., from a depot formulation of the polynucleotide); (4) alter the biodistribution (e.g., target the polynucleotide to specific tissues or cell types); (5) increase the translation of encoded protein in vivo; and/or (6) alter the release profile of encoded protein in vivo. In some embodiments, the pharmaceutical formulation disclosed herein further comprises a delivery agent comprising, e.g., a compound having the Formula (I), e.g., any of Compounds 1-232, e.g., Compound 18; a compound having the Formula (III), (IV), (V), or (VI), e.g., any of Compounds 233-342, e.g., Compound 236; or a compound having the Formula (VIII), e.g., any of Compounds 419-428, e.g., Compound 428, or any combination thereof. In some embodiments, the delivery agent comprises Compound 18, DSPC, Cholesterol, and Compound 428, e.g., with a mole ratio of about 50:10:38.5:1.5.

A pharmaceutically acceptable excipient, as used herein, includes, but are not limited to, any and all solvents, dispersion media, or other liquid vehicles, dispersion or suspension aids, diluents, granulating and/or dispersing agents, surface active agents, isotonic agents, thickening or emulsifying agents, preservatives, binders, lubricants or oil, coloring, sweetening or flavoring agents, stabilizers, antioxidants, antimicrobial or antifungal agents, osmolality adjusting agents, pH adjusting agents, buffers, chelants, cyoprotectants, and/or bulking agents, as suited to the particular dosage form desired. Various excipients for formulating pharmaceutical compositions and techniques for preparing the composition are known in the art (see Remington: The Science and Practice of Pharmacy, 21st Edition, A. R. Gennaro (Lippincott, Williams & Wilkins, Baltimore, MD, 2006; incorporated herein by reference in its entirety).

Exemplary diluents include, but are not limited to, calcium or sodium carbonate, calcium phosphate, calcium hydrogen phosphate, sodium phosphate, lactose, sucrose, cellulose, microcrystalline cellulose, kaolin, mannitol, sorbitol, etc., and/or combinations thereof.

Exemplary granulating and/or dispersing agents include, but are not limited to, starches, pregelatinized starches, or microcrystalline starch, alginic acid, guar gum, agar, poly(vinyl-pyrrolidone), providone, cross-linked poly(vinyl-pyrrolidone) (crospovidone), cellulose, methylcellulose, carboxymethyl cellulose, cross-linked sodium carboxymethyl cellulose (croscarmellose), magnesium aluminum silicate (VEEGUM®), sodium lauryl sulfate, etc., and/or combinations thereof.

Exemplary surface active agents and/or emulsifiers include, but are not limited to, natural emulsifiers (e.g., acacia, agar, alginic acid, sodium alginate, tragacanth, chondrux, cholesterol, xanthan, pectin, gelatin, egg yolk, casein, wool fat, cholesterol, wax, and lecithin), sorbitan fatty acid esters (e.g., polyoxyethylene sorbitan monooleate [TWEEN®80], sorbitan monopalmitate [SPAN®40], glyceryl monooleate, polyoxyethylene esters, polyethylene glycol fatty acid esters (e.g., CREMOPHOR®), polyoxyethylene ethers (e.g., polyoxyethylene lauryl ether [BRIJ®30]), PLUORINC®F 68, POLOXAMER®188, etc. and/or combinations thereof.

Exemplary binding agents include, but are not limited to, starch, gelatin, sugars (e.g., sucrose, glucose, dextrose, dextrin, molasses, lactose, lactitol, mannitol), amino acids (e.g., glycine), natural and synthetic gums (e.g., acacia, sodium alginate), ethylcellulose, hydroxyethylcellulose, hydroxypropyl methylcellulose, etc., and combinations thereof.

Oxidation is a potential degradation pathway for mRNA, especially for liquid mRNA formulations. In order to prevent oxidation, antioxidants can be added to the formulations. Exemplary antioxidants include, but are not limited to, alpha tocopherol, ascorbic acid, ascorbyl palmitate, benzyl alcohol, butylated hydroxyanisole, m-cresol, methionine, butylated hydroxytoluene, monothioglycerol, sodium or potassium metabisulfite, propionic acid, propyl gallate, sodium ascorbate, etc., and combinations thereof.

Exemplary chelating agents include, but are not limited to, ethylenediaminetetraacetic acid (EDTA), citric acid monohydrate, disodium edetate, fumaric acid, malic acid, phosphoric acid, sodium edetate, tartaric acid, trisodium edetate, etc., and combinations thereof.

Exemplary antimicrobial or antifungal agents include, but are not limited to, benzalkonium chloride, benzethonium chloride, methyl paraben, ethyl paraben, propyl paraben, butyl paraben, benzoic acid, hydroxybenzoic acid, potassium or sodium benzoate, potassium or sodium sorbate, sodium propionate, sorbic acid, etc., and combinations thereof.

Exemplary preservatives include, but are not limited to, vitamin A, vitamin C, vitamin E, beta-carotene, citric acid, ascorbic acid, butylated hydroxyanisol, ethylenediamine, sodium lauryl sulfate (SLS), sodium lauryl ether sulfate (SLES), etc., and combinations thereof.

In some embodiments, the pH of polynucleotide solutions are maintained between pH 5 and pH 8 to improve stability. Exemplary buffers to control pH can include, but are not limited to sodium phosphate, sodium citrate, sodium succinate, histidine (or histidine-HCl), sodium malate, sodium carbonate, etc., and/or combinations thereof.

Exemplary lubricating agents include, but are not limited to, magnesium stearate, calcium stearate, stearic acid, silica, talc, malt, hydrogenated vegetable oils, polyethylene glycol, sodium benzoate, sodium or magnesium lauryl sulfate, etc., and combinations thereof.

The pharmaceutical composition or formulation described here can contain a cryoprotectant to stabilize a polynucleotide described herein during freezing. Exemplary cryoprotectants include, but are not limited to mannitol, sucrose, trehalose, lactose, glycerol, dextrose, etc., and combinations thereof.

The pharmaceutical composition or formulation described here can contain a bulking agent in lyophilized polynucleotide formulations to yield a "pharmaceutically elegant" cake, stabilize the lyophilized polynucleotides during long term (e.g., 36 month) storage. Exemplary bulking agents of the present invention can include, but are not limited to sucrose, trehalose, mannitol, glycine, lactose, raffinose, and combinations thereof.

In some embodiments, the pharmaceutical composition or formulation further comprises a delivery agent. The delivery agent of the present disclosure can include, without limitation, liposomes, lipid nanoparticles, lipidoids, polymers, lipoplexes, microvesicles, exosomes, peptides, proteins, cells transfected with polynucleotides, hyaluronidase, nanoparticle mimics, nanotubes, conjugates, and combinations thereof.

22. DELIVERY AGENTS a. Lipid Compound

The present disclosure provides pharmaceutical compositions with advantageous properties. The lipid compositions described herein may be advantageously used in lipid nanoparticle compositions for the delivery of therapeutic and/or prophylactic agents, e.g., mRNAs, to mammalian cells or organs. For example, the lipids described herein have little or no immunogenicity. For example, the lipid compounds disclosed herein have a lower immunogenicity as compared to a reference lipid (e.g., MC3, KC2, or DLinDMA). For example, a formulation comprising a lipid disclosed herein and a therapeutic or prophylactic agent, e.g., mRNA, has an increased therapeutic index as compared to a corresponding formulation which comprises a reference lipid (e.g., MC3, KC2, or DLinDMA) and the same therapeutic or prophylactic agent.

In certain embodiments, the present application provides pharmaceutical compositions comprising:
(a) a polynucleotide comprising a nucleotide sequence encoding a PBGD polypeptide; and
(b) a delivery agent.

In some embodiments, the delivery agent comprises a lipid compound having the Formula (I)

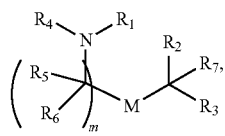

(I)

wherein
$R_1$ is selected from the group consisting of $C_{5-30}$ alkyl, $C_{5-20}$ alkenyl, —R*YR", —YR", and —R"M'R';
$R_2$ and $R_3$ are independently selected from the group consisting of H, $C_{1-14}$ alkyl, $C_{2-14}$ alkenyl, —R*YR", —YR", and —R*OR", or $R_2$ and $R_3$, together with the atom to which they are attached, form a heterocycle or carbocycle;
$R_4$ is selected from the group consisting of a $C_{3-6}$ carbocycle, —$(CH_2)_nQ$, —$(CH_2)_n$CHQR, —CHQR, —$CQ(R)_2$, and unsubstituted $C_{1-6}$ alkyl, where Q is selected from a carbocycle, heterocycle, —OR, —$O(CH_2)_nN(R)_2$, —C(O)OR, —OC(O)R, —$CX_3$, —$CX_2H$, —$CXH_2$, —CN, —$N(R)_2$, —$C(O)N(R)_2$, —N(R)C(O)R, —N(R)S(O)$_2$R, —N(R)C(O)N(R)$_2$, —N(R)C(S)N(R)$_2$, —N(R)R$_8$, —$O(CH_2)_n$OR, —N(R)C(=NR$_9$)N(R)$_2$, —N(R)C(=CHR$_9$)N(R)$_2$, —OC(O)N(R)$_2$, —N(R)C(O)OR, —N(OR)C(O)R, —N(OR)S(O)$_2$R, —N(OR)C(O)OR, —N(OR)C(O)N(R)$_2$, —N(OR)C(S)N(R)$_2$, —N(OR)C(=NR$_9$)N(R)$_2$, —N(OR)C(=CHR$_9$)N(R)$_2$, —C(=NR$_9$)N(R)$_2$, —C(=NR$_9$)R, —C(O)N(R)OR, and —C(R)N(R)$_2$C(O)OR, and each n is independently selected from 1, 2, 3, 4, and 5;
each $R_5$ is independently selected from the group consisting of $C_{1-3}$ alkyl, $C_{2-3}$ alkenyl, and H;
each $R_6$ is independently selected from the group consisting of $C_{1-3}$ alkyl, $C_{2-3}$ alkenyl, and H;
M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —S(O)$_2$—, —S—S—, an aryl group, and a heteroaryl group;
$R_7$ is selected from the group consisting of $C_{1-3}$ alkyl, $C_{2-3}$ alkenyl, and H;
$R_8$ is selected from the group consisting of $C_{3-6}$ carbocycle and heterocycle;
$R_9$ is selected from the group consisting of H, CN, NO$_2$, $C_{1-6}$ alkyl, —OR, —S(O)$_2$R, —S(O)$_2$N(R)$_2$, $C_{2-6}$ alkenyl, $C_{3-6}$ carbocycle and heterocycle;
each R is independently selected from the group consisting of $C_{1-3}$ alkyl, $C_{2-3}$ alkenyl, and H;
each R' is independently selected from the group consisting of $C_{1-18}$ alkyl, $C_{2-18}$ alkenyl, —R*YR", —YR", and H;
each R" is independently selected from the group consisting of $C_{3-14}$ alkyl and $C_{3-14}$ alkenyl;
each R* is independently selected from the group consisting of $C_{1-12}$ alkyl and $C_{2-12}$ alkenyl;
each Y is independently a $C_{3-6}$ carbocycle;
each X is independently selected from the group consisting of F, Cl, Br, and I; and
m is selected from 5, 6, 7, 8, 9, 10, 11, 12, and 13,
or salts or stereoisomers thereof.

In some embodiments, a subset of compounds of Formula (I) includes those in which
$R_1$ is selected from the group consisting of $C_{5-20}$ alkyl, $C_{5-20}$ alkenyl, —R*YR", —YR", and —R"M'R';
$R_2$ and $R_3$ are independently selected from the group consisting of H, $C_{1-14}$ alkyl, $C_{2-14}$ alkenyl, —R*YR", —YR", and —R*OR", or $R_2$ and $R_3$, together with the atom to which they are attached, form a heterocycle or carbocycle;
$R_4$ is selected from the group consisting of a $C_{3-6}$ carbocycle, —$(CH_2)_nQ$, —$(CH_2)_n$CHQR, —CHQR, —$CQ(R)_2$, and unsubstituted $C_{1-6}$ alkyl, where Q is selected from a carbocycle, heterocycle, —OR, —$O(CH_2)_nN(R)_2$, —C(O)OR, —OC(O)R, —$CX_3$, —$CX_2H$, —$CXH_2$, —CN, —$N(R)_2$, —$C(O)N(R)_2$, —N(R)C(O)R, —N(R)S(O)$_2$R, —N(R)C(O)N(R)$_2$, —N(R)C(S)N(R)$_2$, and —C(R)N(R)$_2$C(O)OR, and each n is independently selected from 1, 2, 3, 4, and 5;
each $R_5$ is independently selected from the group consisting of $C_{1-3}$ alkyl, $C_{2-3}$ alkenyl, and H;
each $R_6$ is independently selected from the group consisting of $C_{1-3}$ alkyl, $C_{2-3}$ alkenyl, and H;
M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —S(O)$_2$—, an aryl group, and a heteroaryl group;
$R_7$ is selected from the group consisting of $C_{1-3}$ alkyl, $C_{2-3}$ alkenyl, and H; each R is independently selected from the group consisting of $C_{1-3}$ alkyl, $C_{2-3}$ alkenyl, and H;
each R' is independently selected from the group consisting of $C_{1-18}$ alkyl, $C_{2-18}$ alkenyl, —R*YR", —YR", and H;
each R" is independently selected from the group consisting of $C_{3-14}$ alkyl and $C_{3-14}$ alkenyl;
each R* is independently selected from the group consisting of $C_{1-12}$ alkyl and $C_{2-12}$ alkenyl;
each Y is independently a $C_{3-6}$ carbocycle;
each X is independently selected from the group consisting of F, Cl, Br, and I; and
m is selected from 5, 6, 7, 8, 9, 10, 11, 12, and 13,
or salts or stereoisomers thereof, wherein alkyl and alkenyl groups may be linear or branched.

In some embodiments, a subset of compounds of Formula (I) includes those in which when $R_4$ is —$(CH_2)_nQ$, —$(CH_2)_n$CHQR, —CHQR, or —$CQ(R)_2$, then (i) Q is not —$N(R)_2$ when n is 1, 2, 3, 4 or 5, or (ii) Q is not 5, 6, or 7-membered heterocycloalkyl when n is 1 or 2.

In another embodiments, another subset of compounds of Formula (I) includes those in which $R_1$ is selected from the group consisting of $C_{5-30}$ alkyl, $C_{5-20}$ alkenyl, —R*YR", —YR", and —R"M'R';

$R_2$ and $R_3$ are independently selected from the group consisting of H, $C_{1-14}$ alkyl, $C_{2-14}$ alkenyl, —R*YR", —YR", and —R*OR", or $R_2$ and $R_3$, together with the atom to which they are attached, form a heterocycle or carbocycle;

$R_4$ is selected from the group consisting of a $C_{3-6}$ carbocycle, —$(CH_2)_nQ$, —$(CH_2)_n$CHQR, —CHQR, —CQ$(R)_2$, and unsubstituted $C_{1-6}$ alkyl, where Q is selected from a $C_{3-6}$ carbocycle, a 5- to 14-membered heteroaryl having one or more heteroatoms selected from N, O, and S, —OR, —O$(CH_2)_nN(R)_2$, —C(O)OR, —OC(O)R, —$CX_3$, —$CX_2H$, —$CXH_2$, —CN, —C(O)N$(R)_2$, —N(R)C(O)R, —N(R)S(O)$_2$R, —N(R)C(O)N$(R)_2$, —N(R)C(S)N$(R)_2$, —CRN$(R)_2$C(O)OR, —N(R)$R_8$, —O$(CH_2)_n$OR, —N(R)C(=$NR_9$)N$(R)_2$, —N(R)C(=$CHR_9$)N$(R)_2$, —OC(O)N$(R)_2$, —N(R)C(O)OR, —N(OR)C(O)R, —N(OR)S(O)$_2$R, —N(OR)C(O)OR, —N(OR)C(O)N$(R)_2$, —N(OR)C(S)N$(R)_2$, —N(OR)C(=$NR_9$)N$(R)_2$, —N(OR)C(=$CHR_9$)N$(R)_2$, —C(=$NR_9$)N$(R)_2$, —C(=$NR_9$)R, —C(O)N(R)OR, and a 5- to 14-membered heterocycloalkyl having one or more heteroatoms selected from N, O, and S which is substituted with one or more substituents selected from oxo (=O), OH, amino, and $C_{1-3}$ alkyl, and each n is independently selected from 1, 2, 3, 4, and 5;

each $R_5$ is independently selected from the group consisting of $C_{1-3}$ alkyl, $C_{2-3}$ alkenyl, and H;

each $R_6$ is independently selected from the group consisting of $C_{1-3}$ alkyl, $C_{2-3}$ alkenyl, and H;

M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —S(O)$_2$—, —S—S—, an aryl group, and a heteroaryl group;

$R_7$ is selected from the group consisting of $C_{1-3}$ alkyl, $C_{2-3}$ alkenyl, and H;

$R_8$ is selected from the group consisting of $C_{3-6}$ carbocycle and heterocycle;

$R_9$ is selected from the group consisting of H, CN, $NO_2$, $C_{1-6}$ alkyl, —OR, —S(O)$_2$R, —S(O)$_2$N$(R)_2$, $C_{2-6}$ alkenyl, $C_{3-6}$ carbocycle and heterocycle;

each R is independently selected from the group consisting of $C_{1-3}$ alkyl, $C_{2-3}$ alkenyl, and H;

each R' is independently selected from the group consisting of $C_{1-18}$ alkyl, $C_{2-18}$ alkenyl, —R*YR", —YR", and H;

each R" is independently selected from the group consisting of $C_{3-14}$ alkyl and $C_{3-14}$ alkenyl;

each R* is independently selected from the group consisting of $C_{1-12}$ alkyl and $C_{2-12}$ alkenyl;

each Y is independently a $C_{3-6}$ carbocycle;

each X is independently selected from the group consisting of F, Cl, Br, and I; and m is selected from 5, 6, 7, 8, 9, 10, 11, 12, and 13, or salts or stereoisomers thereof.

In another embodiments, another subset of compounds of Formula (I) includes those in which $R_1$ is selected from the group consisting of $C_{5-20}$ alkyl, $C_{5-20}$ alkenyl, —R*YR", —YR", and —R"M'R';

$R_2$ and $R_3$ are independently selected from the group consisting of H, $C_{1-14}$ alkyl, $C_{2-14}$ alkenyl, —R*YR", —YR", and —R*OR", or $R_2$ and $R_3$, together with the atom to which they are attached, form a heterocycle or carbocycle;

$R_4$ is selected from the group consisting of a $C_{3-6}$ carbocycle, —$(CH_2)_nQ$, —$(CH_2)_n$CHQR, —CHQR, —CQ$(R)_2$, and unsubstituted $C_{1-6}$ alkyl, where Q is selected from a $C_{3-6}$ carbocycle, a 5- to 14-membered heteroaryl having one or more heteroatoms selected from N, O, and S, —OR, —O$(CH_2)_nN(R)_2$, —C(O)OR, —OC(O)R, —$CX_3$, —$CX_2H$, —$CXH_2$, —CN, —C(O)N$(R)_2$, —N(R)C(O)R, —N(R)S(O)$_2$R, —N(R)C(O)N$(R)_2$, —N(R)C(S)N$(R)_2$, —CRN$(R)_2$C(O)OR, and a 5- to 14-membered heterocycloalkyl having one or more heteroatoms selected from N, O, and S which is substituted with one or more substituents selected from oxo (=O), OH, amino, and $C_{1-3}$ alkyl, and each n is independently selected from 1, 2, 3, 4, and 5;

each $R_5$ is independently selected from the group consisting of $C_{1-3}$ alkyl, $C_{2-3}$ alkenyl, and H;

each $R_6$ is independently selected from the group consisting of $C_{1-3}$ alkyl, $C_{2-3}$ alkenyl, and H;

M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —S(O)$_2$—, an aryl group, and a heteroaryl group;

$R_7$ is selected from the group consisting of $C_{1-3}$ alkyl, $C_{2-3}$ alkenyl, and H;

each R is independently selected from the group consisting of $C_{1-3}$ alkyl, $C_{2-3}$ alkenyl, and H;

each R' is independently selected from the group consisting of $C_{1-18}$ alkyl, $C_{2-18}$ alkenyl, —R*YR", —YR", and H;

each R" is independently selected from the group consisting of $C_{3-14}$ alkyl and $C_{3-14}$ alkenyl;

each R* is independently selected from the group consisting of $C_{1-12}$ alkyl and $C_{2-12}$ alkenyl;

each Y is independently a $C_{3-6}$ carbocycle;

each X is independently selected from the group consisting of F, Cl, Br, and I; and m is selected from 5, 6, 7, 8, 9, 10, 11, 12, and 13, or salts or stereoisomers thereof.

In yet another embodiments, another subset of compounds of Formula (I) includes those in which $R_1$ is selected from the group consisting of $C_{5-30}$ alkyl, $C_{5-20}$ alkenyl, —R*YR", —YR", and —R"M'R';

$R_2$ and $R_3$ are independently selected from the group consisting of H, $C_{1-14}$ alkyl, $C_{2-14}$ alkenyl, —R*YR", —YR", and —R*OR", or $R_2$ and $R_3$, together with the atom to which they are attached, form a heterocycle or carbocycle;

$R_4$ is selected from the group consisting of a $C_{3-6}$ carbocycle, —$(CH_2)_nQ$, —$(CH_2)_n$CHQR, —CHQR, —CQ$(R)_2$, and unsubstituted $C_{1-6}$ alkyl, where Q is selected from a $C_{3-6}$ carbocycle, a 5- to 14-membered heterocycle having one or more heteroatoms selected from N, O, and S, —OR, —O$(CH_2)_nN(R)_2$, —C(O)OR, —OC(O)R, —$CX_3$, —$CX_2H$, —$CXH_2$, —CN, —C(O)N$(R)_2$, —N(R)C(O)R, —N(R)S(O)$_2$R, —N(R)C(O)N$(R)_2$, —N(R)C(S)N$(R)_2$, —CRN$(R)_2$C(O)OR, —N(R)$R_8$, —O$(CH_2)_n$OR, —N(R)C(=$NR_9$)N$(R)_2$, —N(R)C(=$CHR_9$)N$(R)_2$, —OC(O)N$(R)_2$, —N(R)C(O)OR, —N(OR)C(O)R, —N(OR)S(O)$_2$R, —N(OR)C(O)OR, —N(OR)C(O)N$(R)_2$, —N(OR)C(S)N$(R)_2$, —N(OR)C(=$NR_9$)N$(R)_2$, —N(OR)C(=$CHR_9$)N$(R)_2$, —C(=$NR_9$)R, —C(O)N(R)OR, and —C(=$NR_9$)N$(R)_2$, and each n is independently selected from 1, 2, 3, 4, and 5; and when Q is a 5- to 14-membered heterocycle and (i) $R_4$ is —$(CH_2)_nQ$ in which n is 1 or 2, or (ii) $R_4$ is —$(CH_2)_n$CHQR in which n is 1, or (iii) $R_4$ is —CHQR, and —CQ(R)$_2$, then Q is either a 5- to 14-membered heteroaryl or 8- to 14-membered heterocycloalkyl;

each $R_5$ is independently selected from the group consisting of $C_{1-3}$ alkyl, $C_{2-3}$ alkenyl, and H;

each $R_6$ is independently selected from the group consisting of $C_{1-3}$ alkyl, $C_{2-3}$ alkenyl, and H;

M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —S(O)$_2$—, —S—S—, an aryl group, and a heteroaryl group;

$R_7$ is selected from the group consisting of $C_{1-3}$ alkyl, $C_{2-3}$ alkenyl, and H;

$R_8$ is selected from the group consisting of $C_{3-6}$ carbocycle and heterocycle;

$R_9$ is selected from the group consisting of H, CN, NO$_2$, $C_{1-6}$ alkyl, —OR, —S(O)$_2$R, —S(O)$_2$N(R)$_2$, $C_{2-6}$ alkenyl, $C_{3-6}$ carbocycle and heterocycle;

each R is independently selected from the group consisting of $C_{1-3}$ alkyl, $C_{2-3}$ alkenyl, and H;

each R' is independently selected from the group consisting of $C_{1-18}$ alkyl, $C_{2-18}$ alkenyl, —R*YR", —YR", and H;

each R" is independently selected from the group consisting of $C_{3-14}$ alkyl and $C_{3-14}$ alkenyl;

each R* is independently selected from the group consisting of $C_{1-12}$ alkyl and $C_{2-12}$ alkenyl;

each Y is independently a $C_{3-6}$ carbocycle;

each X is independently selected from the group consisting of F, Cl, Br, and I; and m is selected from 5, 6, 7, 8, 9, 10, 11, 12, and 13, or salts or stereoisomers thereof.

In yet another embodiments, another subset of compounds of Formula (I) includes those in which $R_1$ is selected from the group consisting of $C_{5-20}$ alkyl, $C_{5-20}$ alkenyl, —R*YR", —YR", and —R"M'R';

$R_2$ and $R_3$ are independently selected from the group consisting of H, $C_{1-14}$ alkyl, $C_{2-14}$ alkenyl, —R*YR", —YR", and —R*OR", or $R_2$ and $R_3$, together with the atom to which they are attached, form a heterocycle or carbocycle;

$R_4$ is selected from the group consisting of a $C_{3-6}$ carbocycle, —(CH$_2$)$_n$Q, —(CH$_2$)$_n$CHQR, —CHQR, —CQ(R)$_2$, and unsubstituted $C_{1-6}$ alkyl, where Q is selected from a $C_{3-6}$ carbocycle, a 5- to 14-membered heterocycle having one or more heteroatoms selected from N, O, and S, —OR, —O(CH$_2$)$_n$N(R)$_2$, —C(O)OR, —OC(O)R, —CX$_3$, —CX$_2$H, —CXH$_2$, —CN, —C(O)N(R)$_2$, —N(R)C(O)R, —N(R)S(O)$_2$R, —N(R)C(O)N(R)$_2$, —N(R)C(S)N(R)$_2$, —CRN(R)$_2$C(O)OR, and each n is independently selected from 1, 2, 3, 4, and 5; and when Q is a 5- to 14-membered heterocycle and (i) $R_4$ is —(CH$_2$)$_n$Q in which n is 1 or 2, or (ii) $R_4$ is —(CH$_2$)$_n$CHQR in which n is 1, or (iii) $R_4$ is —CHQR, and —CQ(R)$_2$, then Q is either a 5- to 14-membered heteroaryl or 8- to 14-membered heterocycloalkyl;

each $R_5$ is independently selected from the group consisting of $C_{1-3}$ alkyl, $C_{2-3}$ alkenyl, and H;

each $R_6$ is independently selected from the group consisting of $C_{1-3}$ alkyl, $C_{2-3}$ alkenyl, and H;

M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —S(O)$_2$—, an aryl group, and a heteroaryl group;

$R_7$ is selected from the group consisting of $C_{1-3}$ alkyl, $C_{2-3}$ alkenyl, and H;

each R is independently selected from the group consisting of $C_{1-3}$ alkyl, $C_{2-3}$ alkenyl, and H;

each R' is independently selected from the group consisting of $C_{1-18}$ alkyl, $C_{2-18}$ alkenyl, —R*YR", —YR", and H;

each R" is independently selected from the group consisting of $C_{3-14}$ alkyl and $C_{3-14}$ alkenyl;

each R* is independently selected from the group consisting of $C_{1-12}$ alkyl and $C_{2-12}$ alkenyl;

each Y is independently a $C_{3-6}$ carbocycle;

each X is independently selected from the group consisting of F, Cl, Br, and I; and m is selected from 5, 6, 7, 8, 9, 10, 11, 12, and 13, or salts or stereoisomers thereof.

In still another embodiments, another subset of compounds of Formula (I) includes those in which $R_1$ is selected from the group consisting of $C_{5-30}$ alkyl, $C_{5-20}$ alkenyl, —R*YR", —YR", and —R"M'R';

$R_2$ and $R_3$ are independently selected from the group consisting of H, $C_{1-14}$ alkyl, $C_{2-14}$ alkenyl, —R*YR", —YR", and —R*OR", or $R_2$ and $R_3$, together with the atom to which they are attached, form a heterocycle or carbocycle;

$R_4$ is selected from the group consisting of a $C_{3-6}$ carbocycle, —(CH$_2$)$_n$Q, —(CH$_2$)$_n$CHQR, —CHQR, —CQ(R)$_2$, and unsubstituted $C_{1-6}$ alkyl, where Q is selected from a $C_{3-6}$ carbocycle, a 5- to 14-membered heteroaryl having one or more heteroatoms selected from N, O, and S, —OR, —O(CH$_2$)$_n$N(R)$_2$, —C(O)OR, —OC(O)R, —CX$_3$, —CX$_2$H, —CXH$_2$, —CN, —C(O)N(R)$_2$, —N(R)C(O)R, —N(R)S(O)$_2$R, —N(R)C(O)N(R)$_2$, —N(R)C(S)N(R)$_2$, —CRN(R)$_2$C(O)OR, —N(R)R$_8$, —O(CH$_2$)$_n$OR, —N(R)C(=NR$_9$)N(R)$_2$, —N(R)C(=CHR$_9$)N(R)$_2$, —OC(O)N(R)$_2$, —N(R)C(O)OR, —N(OR)C(O)R, —N(OR)S(O)$_2$R, —N(OR)C(O)OR, —N(OR)C(O)N(R)$_2$, —N(OR)C(S)N(R)$_2$, —N(OR)C(=NR$_9$)N(R)$_2$, —N(OR)C(=CHR$_9$)N(R)$_2$, —C(=NR$_9$)R, —C(O)N(R)OR, and —C(=NR$_9$)N(R)$_2$, and each n is independently selected from 1, 2, 3, 4, and 5;

each $R_5$ is independently selected from the group consisting of $C_{1-3}$ alkyl, $C_{2-3}$ alkenyl, and H;

each $R_6$ is independently selected from the group consisting of $C_{1-3}$ alkyl, $C_{2-3}$ alkenyl, and H;

M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —S(O)$_2$—, —S—S—, an aryl group, and a heteroaryl group;

$R_7$ is selected from the group consisting of $C_{1-3}$ alkyl, $C_{2-3}$ alkenyl, and H;

$R_8$ is selected from the group consisting of $C_{3-6}$ carbocycle and heterocycle;

$R_9$ is selected from the group consisting of H, CN, NO$_2$, $C_{1-6}$ alkyl, —OR, —S(O)$_2$R, —S(O)$_2$N(R)$_2$, $C_{2-6}$ alkenyl, $C_{3-6}$ carbocycle and heterocycle;

each R is independently selected from the group consisting of $C_{1-3}$ alkyl, $C_{2-3}$ alkenyl, and H;

each R' is independently selected from the group consisting of $C_{1-18}$ alkyl, $C_{2-18}$ alkenyl, —R*YR", —YR", and H;

each R" is independently selected from the group consisting of $C_{3-14}$ alkyl and $C_{3-14}$ alkenyl;

each R* is independently selected from the group consisting of $C_{1-12}$ alkyl and $C_{2-12}$ alkenyl;

each Y is independently a $C_{3-6}$ carbocycle;
each X is independently selected from the group consisting of F, Cl, Br, and I; and
m is selected from 5, 6, 7, 8, 9, 10, 11, 12, and 13, or salts or stereoisomers thereof.

In still another embodiments, another subset of compounds of Formula (I) includes those in which
$R_1$ is selected from the group consisting of $C_{5-20}$ alkyl, $C_{5-20}$ alkenyl, —R*YR", —YR", and —R"M'R';
$R_2$ and $R_3$ are independently selected from the group consisting of H, $C_{1-14}$ alkyl, $C_{2-14}$ alkenyl, —R*YR", —YR", and —R*OR", or $R_2$ and $R_3$, together with the atom to which they are attached, form a heterocycle or carbocycle;
$R_4$ is selected from the group consisting of a $C_{3-6}$ carbocycle, —(CH$_2$)$_n$Q, —(CH$_2$)$_n$CHQR, —CHQR, —CQ(R)$_2$, and unsubstituted $C_{1-6}$ alkyl, where Q is selected from a $C_{3-6}$ carbocycle, a 5- to 14-membered heteroaryl having one or more heteroatoms selected from N, O, and S, —OR, —O(CH$_2$)$_n$N(R)$_2$, —C(O)OR, —OC(O)R, —CX$_3$, —CX$_2$H, —CXH$_2$, —CN, —C(O)N(R)$_2$, —N(R)C(O)R, —N(R)S(O)$_2$R, —N(R)C(O)N(R)$_2$, —N(R)C(S)N(R)$_2$, —CRN(R)$_2$C(O)OR, and each n is independently selected from 1, 2, 3, 4, and 5;
each $R_5$ is independently selected from the group consisting of $C_{1-3}$ alkyl, $C_{2-3}$ alkenyl, and H;
each $R_6$ is independently selected from the group consisting of $C_{1-3}$ alkyl, $C_{2-3}$ alkenyl, and H;
M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —S(O)$_2$—, an aryl group, and a heteroaryl group;
$R_7$ is selected from the group consisting of $C_{1-3}$ alkyl, $C_{2-3}$ alkenyl, and H;
each R is independently selected from the group consisting of $C_{1-3}$ alkyl, $C_{2-3}$ alkenyl, and H;
each R' is independently selected from the group consisting of $C_{1-18}$ alkyl, $C_{2-18}$ alkenyl, —R*YR", —YR", and H;
each R" is independently selected from the group consisting of $C_{3-14}$ alkyl and $C_{3-14}$ alkenyl;
each R* is independently selected from the group consisting of $C_{1-12}$ alkyl and $C_{2-12}$ alkenyl;
each Y is independently a $C_{3-6}$ carbocycle;
each X is independently selected from the group consisting of F, Cl, Br, and I; and
m is selected from 5, 6, 7, 8, 9, 10, 11, 12, and 13, or salts or stereoisomers thereof.

In yet another embodiments, another subset of compounds of Formula (I) includes those in which
$R_1$ is selected from the group consisting of $C_{5-30}$ alkyl, $C_{5-20}$ alkenyl, —R*YR", —YR", and —R"M'R';
$R_2$ and $R_3$ are independently selected from the group consisting of H, $C_{2-14}$ alkyl, $C_{2-14}$ alkenyl, —R*YR", —YR", and —R*OR", or $R_2$ and $R_3$, together with the atom to which they are attached, form a heterocycle or carbocycle;
$R_4$ is —(CH$_2$)$_n$Q or —(CH$_2$)$_n$CHQR, where Q is —N(R)$_2$, and n is selected from 3, 4, and 5;
each $R_5$ is independently selected from the group consisting of $C_{1-3}$ alkyl, $C_{2-3}$ alkenyl, and H;
each $R_6$ is independently selected from the group consisting of $C_{1-3}$ alkyl, $C_{2-3}$ alkenyl, and H;
M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —S(O)$_2$—, —S—S—, an aryl group, and a heteroaryl group;
$R_7$ is selected from the group consisting of $C_{1-3}$ alkyl, $C_{2-3}$ alkenyl, and H; each R is independently selected from the group consisting of $C_{1-3}$ alkyl, $C_{2-3}$ alkenyl, and H;
each R' is independently selected from the group consisting of $C_{1-18}$ alkyl, $C_{2-18}$ alkenyl, —R*YR", —YR", and H;
each R" is independently selected from the group consisting of $C_{3-14}$ alkyl and $C_{3-14}$ alkenyl;
each R* is independently selected from the group consisting of $C_{1-12}$ alkyl and $C_{1-12}$ alkenyl;
each Y is independently a $C_{3-6}$ carbocycle;
each X is independently selected from the group consisting of F, Cl, Br, and I; and
m is selected from 5, 6, 7, 8, 9, 10, 11, 12, and 13, or salts or stereoisomers thereof.

In yet another embodiments, another subset of compounds of Formula (I) includes those in which
$R_1$ is selected from the group consisting of $C_{5-20}$ alkyl, $C_{5-20}$ alkenyl, —R*YR", —YR", and —R"M'R';
$R_2$ and $R_3$ are independently selected from the group consisting of H, $C_{2-14}$ alkyl, $C_{2-14}$ alkenyl, —R*YR", —YR", and —R*OR", or $R_2$ and $R_3$, together with the atom to which they are attached, form a heterocycle or carbocycle;
$R_4$ is —(CH$_2$)$_n$Q or —(CH$_2$)$_n$CHQR, where Q is —N(R)$_2$, and n is selected from 3, 4, and 5;
each $R_5$ is independently selected from the group consisting of $C_{1-3}$ alkyl, $C_{2-3}$ alkenyl, and H;
each $R_6$ is independently selected from the group consisting of $C_{1-3}$ alkyl, $C_{2-3}$ alkenyl, and H;
M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —S(O)$_2$—, an aryl group, and a heteroaryl group;
$R_7$ is selected from the group consisting of $C_{1-3}$ alkyl, $C_{2-3}$ alkenyl, and H;
each R is independently selected from the group consisting of $C_{1-3}$ alkyl, $C_{2-3}$ alkenyl, and H;
each R' is independently selected from the group consisting of $C_{1-18}$ alkyl, $C_{2-18}$ alkenyl, —R*YR", —YR", and H;
each R" is independently selected from the group consisting of $C_{3-14}$ alkyl and $C_{3-14}$ alkenyl;
each R* is independently selected from the group consisting of $C_{1-12}$ alkyl and $C_{1-12}$ alkenyl;
each Y is independently a $C_{3-6}$ carbocycle;
each X is independently selected from the group consisting of F, Cl, Br, and I; and
m is selected from 5, 6, 7, 8, 9, 10, 11, 12, and 13, or salts or stereoisomers thereof.

In still other embodiments, another subset of compounds of Formula (I) includes those in which
$R_1$ is selected from the group consisting of $C_{5-30}$ alkyl, $C_{5-20}$ alkenyl, —R*YR", —YR", and —R"M'R';
$R_2$ and $R_3$ are independently selected from the group consisting of $C_{1-14}$ alkyl, $C_{2-14}$ alkenyl, —R*YR", —YR", and —R*OR", or $R_2$ and $R_3$, together with the atom to which they are attached, form a heterocycle or carbocycle;
$R_4$ is selected from the group consisting of —(CH$_2$)$_n$Q, —(CH$_2$)$_n$CHQR, —CHQR, and —CQ(R)$_2$, where Q is —N(R)$_2$, and n is selected from 1, 2, 3, 4, and 5;
each $R_5$ is independently selected from the group consisting of $C_{1-3}$ alkyl, $C_{2-3}$ alkenyl, and H;

each $R_6$ is independently selected from the group consisting of $C_{1-3}$ alkyl, $C_{2-3}$ alkenyl, and H;

M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —S(O)$_2$—, —S—S—, an aryl group, and a heteroaryl group;

$R_7$ is selected from the group consisting of $C_{1-3}$ alkyl, $C_{2-3}$ alkenyl, and H;

each R is independently selected from the group consisting of $C_{1-3}$ alkyl, $C_{2-3}$ alkenyl, and H;

each R' is independently selected from the group consisting of $C_{1-18}$ alkyl, $C_{2-18}$ alkenyl, —R*YR", —YR", and H;

each R" is independently selected from the group consisting of $C_{3-14}$ alkyl and $C_{3-14}$ alkenyl;

each R* is independently selected from the group consisting of $C_{1-12}$ alkyl and $C_{1-12}$ alkenyl;

each Y is independently a $C_{3-6}$ carbocycle;

each X is independently selected from the group consisting of F, Cl, Br, and I; and m is selected from 5, 6, 7, 8, 9, 10, 11, 12, and 13, or salts or stereoisomers thereof.

In still other embodiments, another subset of compounds of Formula (I) includes those in which $R_1$ is selected from the group consisting of $C_{5-20}$ alkyl, $C_{5-20}$ alkenyl, —R*YR", —YR", and —R"M'R';

$R_2$ and $R_3$ are independently selected from the group consisting of $C_{1-14}$ alkyl, $C_{2-14}$ alkenyl, —R*YR", —YR", and —R*OR", or $R_2$ and $R_3$, together with the atom to which they are attached, form a heterocycle or carbocycle;

$R_4$ is selected from the group consisting of —(CH$_2$)$_n$Q, —(CH$_2$)$_n$CHQR, —CHQR, and —CQ(R)$_2$, where Q is —N(R)$_2$, and n is selected from 1, 2, 3, 4, and 5;

each $R_5$ is independently selected from the group consisting of $C_{1-3}$ alkyl, $C_{2-3}$ alkenyl, and H;

each $R_6$ is independently selected from the group consisting of $C_{1-3}$ alkyl, $C_{2-3}$ alkenyl, and H;

M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —S(O)$_2$—, an aryl group, and a heteroaryl group;

$R_7$ is selected from the group consisting of $C_{1-3}$ alkyl, $C_{2-3}$ alkenyl, and H;

each R is independently selected from the group consisting of $C_{1-3}$ alkyl, $C_{2-3}$ alkenyl, and H;

each R' is independently selected from the group consisting of $C_{1-18}$ alkyl, $C_{2-18}$ alkenyl, —R*YR", —YR", and H;

each R" is independently selected from the group consisting of $C_{3-14}$ alkyl and $C_{3-14}$ alkenyl;

each R* is independently selected from the group consisting of $C_{1-12}$ alkyl and $C_{1-12}$ alkenyl;

each Y is independently a $C_{3-6}$ carbocycle;

each X is independently selected from the group consisting of F, Cl, Br, and I; and m is selected from 5, 6, 7, 8, 9, 10, 11, 12, and 13, or salts or stereoisomers thereof.

In certain embodiments, a subset of compounds of Formula (I) includes those of Formula (IA):

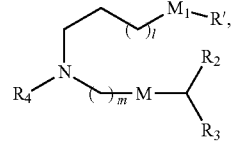

(IA)

or a salt or stereoisomer thereof, wherein l is selected from 1, 2, 3, 4, and 5; m is selected from 5, 6, 7, 8, and 9; $M_1$ is a bond or M'; $R_4$ is unsubstituted $C_{1-3}$ alkyl, or —(CH$_2$)$_n$Q, in which Q is OH, —NHC(S)N(R)$_2$, —NHC(O)N(R)$_2$, —N(R)C(O)R, —N(R)S(O)$_2$R, —N(R)R$_8$, —NHC(=NR$_9$)N(R)$_2$, —NHC(=CHR$_9$)N(R)$_2$, —OC(O)N(R)$_2$, —N(R)C(O)OR, heteroaryl, or heterocycloalkyl; M and M' are independently selected from —C(O)O—, —OC(O)—, —C(O)N(R')—, —P(O)(OR')O—, —S—S—, an aryl group, and a heteroaryl group; and $R_2$ and $R_3$ are independently selected from the group consisting of H, $C_{1-14}$ alkyl, and $C_{2-14}$ alkenyl.

In some embodiments, a subset of compounds of Formula (I) includes those of Formula (IA), or a salt or stereoisomer thereof, wherein l is selected from 1, 2, 3, 4, and 5; m is selected from 5, 6, 7, 8, and 9; $M_1$ is a bond or M';

$R_4$ is unsubstituted $C_{1-3}$ alkyl, or —(CH$_2$)$_n$Q, in which Q is OH, —NHC(S)N(R)$_2$, or —NHC(O)N(R)$_2$;

M and M' are independently selected from —C(O)O—, —OC(O)—, —C(O)N(R')—, —P(O)(OR')O—, an aryl group, and a heteroaryl group; and $R_2$ and $R_3$ are independently selected from the group consisting of H, $C_{1-14}$ alkyl, and $C_{2-14}$ alkenyl.

In certain embodiments, a subset of compounds of Formula (I) includes those of Formula (II):

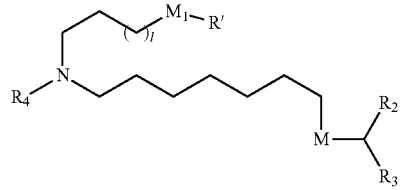

(II)

or a salt or stereoisomer thereof, wherein l is selected from 1, 2, 3, 4, and 5; $M_1$ is a bond or M'; $R_4$ is unsubstituted $C_{1-3}$ alkyl, or —(CH$_2$)$_n$Q, in which n is 2, 3, or 4, and Q is OH, —NHC(S)N(R)$_2$, —NHC(O)N(R)$_2$, —N(R)C(O)R, —N(R)S(O)$_2$R, —N(R)R$_8$, —NHC(=NR$_9$)N(R)$_2$, —NHC(=CHR$_9$)N(R)$_2$, —OC(O)N(R)$_2$, —N(R)C(O)OR, heteroaryl, or heterocycloalkyl; M and M' are independently selected from —C(O)O—, —OC(O)—, —C(O)N(R')—, —P(O)(OR')O—, —S—S—, an aryl group, and a heteroaryl group; and $R_2$ and $R_3$ are independently selected from the group consisting of H, $C_{1-14}$ alkyl, and $C_{2-14}$ alkenyl.

In some embodiments, a subset of compounds of Formula (I) includes those of Formula (II), or a salt or stereoisomer thereof, wherein l is selected from 1, 2, 3, 4, and 5;

$M_1$ is a bond or M';

$R_4$ is unsubstituted $C_{1-3}$ alkyl, or —(CH$_2$)$_n$Q, in which n is 2, 3, or 4, and Q is OH, —NHC(S)N(R)$_2$, or —NHC(O)N(R)$_2$;

M and M' are independently selected from —C(O)O—, —OC(O)—, —C(O)N(R')—, —P(O)(OR')O—, an aryl group, and a heteroaryl group; and R$_2$ and R$_3$ are independently selected from the group consisting of H, C$_{1-14}$ alkyl, and C$_{2-14}$ alkenyl.

In some embodiments, the compound of Formula (I) is of the Formula (IIa),

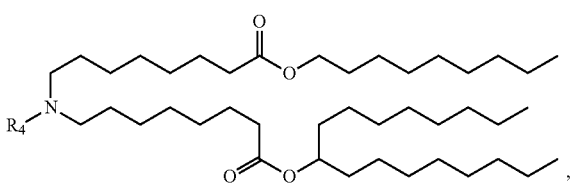

(IIa)

or a salt thereof, wherein R$_4$ is as described above.

In some embodiments, the compound of Formula (I) is of the Formula (IIb),

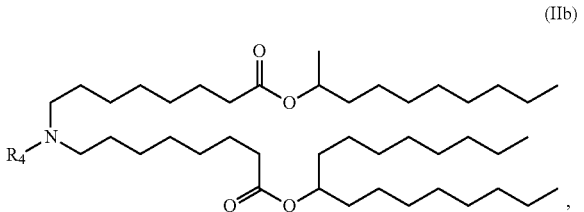

(IIb)

or a salt thereof, wherein R$_4$ is as described above.

In some embodiments, the compound of Formula (I) is of the Formula (IIc),

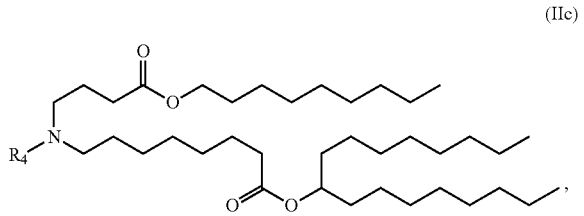

(IIc)

or a salt thereof, wherein R$_4$ is as described above.

In some embodiments, the compound of Formula (I) is of the Formula (IIe):

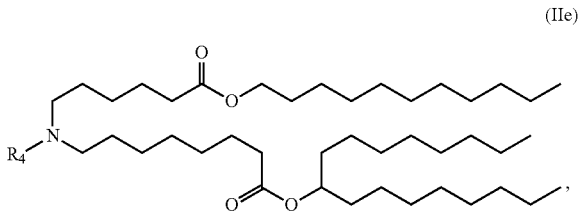

(IIe)

or a salt thereof, wherein R$_4$ is as described above.

In some embodiments, the compound of Formula (IIa), (IIb), (IIc), or (IIe) comprises an R$_4$ which is selected from —(CH$_2$)$_n$Q and —(CH$_2$)$_n$CHQR, wherein Q, R and n are as defined above.

In some embodiments, Q is selected from the group consisting of —OR, —OH, —O(CH$_2$)$_n$N(R)$_2$, —OC(O)R, —CX$_3$, —CN, —N(R)C(O)R, —N(H)C(O)R, —N(R)S(O)$_2$R, —N(H)S(O)$_2$R, —N(R)C(O)N(R)$_2$, —N(H)C(O)N(R)$_2$, —N(H)C(O)N(H)(R), —N(R)C(S)N(R)$_2$, —N(H)C(S)N(R)$_2$, —N(H)C(S)N(H)(R), and a heterocycle, wherein R is as defined above. In some aspects, n is 1 or 2. In some embodiments, Q is OH, —NHC(S)N(R)$_2$, or —NHC(O)N(R)$_2$.

In some embodiments, the compound of Formula (I) is of the Formula (IId),

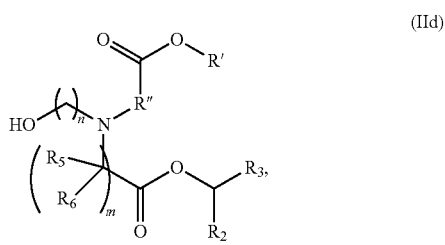

(IId)

or a salt thereof, wherein R$_2$ and R$_3$ are independently selected from the group consisting of C$_{5-14}$ alkyl and C$_{5-14}$ alkenyl, n is selected from 2, 3, and 4, and R', R'', R$_5$, R$_6$ and m are as defined above.

In some aspects of the compound of Formula (IId), R$_2$ is C$_8$ alkyl. In some aspects of the compound of Formula (IId), R$_3$ is C$_5$-C$_9$ alkyl. In some aspects of the compound of Formula (IId), m is 5, 7, or 9. In some aspects of the compound of Formula (IId), each R$_5$ is H. In some aspects of the compound of Formula (IId), each R$_6$ is H.

In another aspect, the present application provides a lipid composition (e.g., a lipid nanoparticle (LNP)) comprising: (1) a compound having the Formula (I); (2) optionally a helper lipid (e.g. a phospholipid); (3) optionally a structural lipid (e.g. a sterol); and (4) optionally a lipid conjugate (e.g. a PEG-lipid). In exemplary embodiments, the lipid composition (e.g., LNP) further comprises a polynucleotide encoding a PBGD polypeptide, e.g., a polynucleotide encapsulated therein.

As used herein, the term "alkyl" or "alkyl group" means a linear or branched, saturated hydrocarbon including one or more carbon atoms (e.g., one, two, three, four, five, six, seven, eight, nine, ten, eleven, twelve, thirteen, fourteen, fifteen, sixteen, seventeen, eighteen, nineteen, twenty, or more carbon atoms).

The notation "C$_{1-14}$ alkyl" means a linear or branched, saturated hydrocarbon including 1-14 carbon atoms. An alkyl group can be optionally substituted.

As used herein, the term "alkenyl" or "alkenyl group" means a linear or branched hydrocarbon including two or more carbon atoms (e.g., two, three, four, five, six, seven, eight, nine, ten, eleven, twelve, thirteen, fourteen, fifteen, sixteen, seventeen, eighteen, nineteen, twenty, or more carbon atoms) and at least one double bond.

The notation "C$_{2-14}$ alkenyl" means a linear or branched hydrocarbon including 2-14 carbon atoms and at least one double bond. An alkenyl group can include one, two, three, four, or more double bonds. For example, C$_{18}$ alkenyl can include one or more double bonds. A C$_{18}$ alkenyl group including two double bonds can be a linoleyl group. An alkenyl group can be optionally substituted.

As used herein, the term "carbocycle" or "carbocyclic group" means a mono- or multi-cyclic system including one or more rings of carbon atoms. Rings can be three, four, five, six, seven, eight, nine, ten, eleven, twelve, thirteen, fourteen, or fifteen membered rings.

The notation "$C_{3-6}$ carbocycle" means a carbocycle including a single ring having 3-6 carbon atoms. Carbocycles can include one or more double bonds and can be aromatic (e.g., aryl groups). Examples of carbocycles include cyclopropyl, cyclopentyl, cyclohexyl, phenyl, naphthyl, and 1,2-dihydronaphthyl groups. Carbocycles can be optionally substituted.

As used herein, the term "heterocycle" or "heterocyclic group" means a mono- or multi-cyclic system including one or more rings, where at least one ring includes at least one heteroatom. Heteroatoms can be, for example, nitrogen, oxygen, or sulfur atoms. Rings can be three, four, five, six, seven, eight, nine, ten, eleven, or twelve membered rings. Heterocycles can include one or more double bonds and can be aromatic (e.g., heteroaryl groups). Examples of heterocycles include imidazolyl, imidazolidinyl, oxazolyl, oxazolidinyl, thiazolyl, thiazolidinyl, pyrazolidinyl, pyrazolyl, isoxazolidinyl, isoxazolyl, isothiazolidinyl, isothiazolyl, morpholinyl, pyrrolyl, pyrrolidinyl, furyl, tetrahydrofuryl, thiophenyl, pyridinyl, piperidinyl, quinolyl, and isoquinolyl groups. Heterocycles can be optionally substituted.

As used herein, a "biodegradable group" is a group that can facilitate faster metabolism of a lipid in a subject. A biodegradable group can be, but is not limited to, —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —S(O)$_2$—, an aryl group, and a heteroaryl group.

As used herein, an "aryl group" is a carbocyclic group including one or more aromatic rings. Examples of aryl groups include phenyl and naphthyl groups.

As used herein, a "heteroaryl group" is a heterocyclic group including one or more aromatic rings. Examples of heteroaryl groups include pyrrolyl, furyl, thiophenyl, imidazolyl, oxazolyl, and thiazolyl. Both aryl and heteroaryl groups can be optionally substituted. For example, M and M' can be selected from the non-limiting group consisting of optionally substituted phenyl, oxazole, and thiazole. In the formulas herein, M and M' can be independently selected from the list of biodegradable groups above.

Alkyl, alkenyl, and cyclyl (e.g., carbocyclyl and heterocyclyl) groups can be optionally substituted unless otherwise specified. Optional substituents can be selected from the group consisting of, but are not limited to, a halogen atom (e.g., a chloride, bromide, fluoride, or iodide group), a carboxylic acid (e.g., —C(O)OH), an alcohol (e.g., a hydroxyl, —OH), an ester (e.g., —C(O)OR or —OC(O)R), an aldehyde (e.g., —C(O)H), a carbonyl (e.g., —C(O)R, alternatively represented by C=O), an acyl halide (e.g., —C(O)X, in which X is a halide selected from bromide, fluoride, chloride, and iodide), a carbonate (e.g., —OC(O)OR), an alkoxy (e.g., —OR), an acetal (e.g., —C(OR)$_2$R"", in which each OR are alkoxy groups that can be the same or different and R"" is an alkyl or alkenyl group), a phosphate (e.g., P(O)$_4^{3-}$), a thiol (e.g., —SH), a sulfoxide (e.g., —S(O)R), a sulfinic acid (e.g., —S(O)OH), a sulfonic acid (e.g., —S(O)$_2$OH), a thial (e.g., —C(S)H), a sulfate (e.g., S(O)$_4^{2-}$), a sulfonyl (e.g., —S(O)$_2$—), an amide (e.g., —C(O)NR$_2$, or —N(R)C(O)R), an azido (e.g., —N$_3$), a nitro (e.g., —NO$_2$), a cyano (e.g., —CN), an isocyano (e.g., —NC), an acyloxy (e.g., —OC(O)R), an amino (e.g., —NR$_2$, —NRH, or —NH$_2$), a carbamoyl (e.g., —OC(O)NR$_2$, —OC(O)NRH, or —OC(O)NH$_2$), a sulfonamide (e.g., —S(O)$_2$NR$_2$, —S(O)$_2$NRH, —S(O)$_2$NH$_2$, —N(R)S(O)$_2$R, —N(H)S(O)$_2$R, —N(R)S(O)$_2$H, or —N(H)S(O)$_2$H), an alkyl group, an alkenyl group, and a cyclyl (e.g., carbocyclyl or heterocyclyl) group.

In any of the preceding, R is an alkyl or alkenyl group, as defined herein. In some embodiments, the substituent groups themselves can be further substituted with, for example, one, two, three, four, five, or six substituents as defined herein. For example, a $C_{1-6}$ alkyl group can be further substituted with one, two, three, four, five, or six substituents as described herein.

The compounds of any one of Formulae (I), (IA), (II), (IIa), (IIb), (IIc), (IId), and (IIe) include one or more of the following features when applicable.

In some embodiments, $R_4$ is selected from the group consisting of a $C_{3-6}$ carbocycle, —(CH$_2$)$_n$Q, —(CH$_2$)$_n$CHQR, —CHQR, and —CQ(R)$_2$, where Q is selected from a $C_{3-6}$ carbocycle, 5- to 14-membered aromatic or non-aromatic heterocycle having one or more heteroatoms selected from N, O, S, and P, —OR, —O(CH$_2$)$_n$N(R)$_2$, —C(O)OR, —OC(O)R, —CX$_3$, —CX$_2$H, —CXH$_2$, —CN, —N(R)$_2$, —C(O)N(R)$_2$, —N(R)C(O)R, —N(R)S(O)$_2$R, —N(R)C(O)N(R)$_2$, —N(R)C(S)N(R)$_2$, and —C(R)N(R)$_2$C(O)OR, and each n is independently selected from 1, 2, 3, 4, and 5.

In another embodiment, $R_4$ is selected from the group consisting of a $C_{3-6}$ carbocycle, —(CH$_2$)$_n$Q, —(CH$_2$)$_n$CHQR, —CHQR, and —CQ(R)$_2$, where Q is selected from a $C_{3-6}$ carbocycle, a 5- to 14-membered heteroaryl having one or more heteroatoms selected from N, O, and S, —OR, —O(CH$_2$)$_n$N(R)$_2$, —C(O)OR, —OC(O)R, —CX$_3$, —CX$_2$H, —CXH$_2$, —CN, —C(O)N(R)$_2$, —N(R)C(O)R, —N(R)S(O)$_2$R, —N(R)C(O)N(R)$_2$, —N(R)C(S)N(R)$_2$, —C(R)N(R)$_2$C(O)OR, and a 5- to 14-membered heterocycloalkyl having one or more heteroatoms selected from N, O, and S which is substituted with one or more substituents selected from oxo (=O), OH, amino, and $C_{1-3}$ alkyl, and each n is independently selected from 1, 2, 3, 4, and 5.

In another embodiment, $R_4$ is selected from the group consisting of a $C_{3-6}$ carbocycle, —(CH$_2$)$_n$Q, —(CH$_2$)$_n$CHQR, —CHQR, and —CQ(R)$_2$, where Q is selected from a $C_{3-6}$ carbocycle, a 5- to 14-membered heterocycle having one or more heteroatoms selected from N, O, and S, —OR, —O(CH$_2$)$_n$N(R)$_2$, —C(O)OR, —OC(O)R, —CX$_3$, —CX$_2$H, —CXH$_2$, —CN, —C(O)N(R)$_2$, —N(R)C(O)R, —N(R)S(O)$_2$R, —N(R)C(O)N(R)$_2$, —N(R)C(S)N(R)$_2$, —C(R)N(R)$_2$C(O)OR, and each n is independently selected from 1, 2, 3, 4, and 5; and when Q is a 5- to 14-membered heterocycle and (i) $R_4$ is —(CH$_2$)$_n$Q in which n is 1 or 2, or (ii) $R_4$ is —(CH$_2$)$_n$CHQR in which n is 1, or (iii) $R_4$ is —CHQR, and —CQ(R)$_2$, then Q is either a 5- to 14-membered heteroaryl or 8- to 14-membered heterocycloalkyl.

In another embodiment, $R_4$ is selected from the group consisting of a $C_{3-6}$ carbocycle, —(CH$_2$)$_n$Q, —(CH$_2$)$_n$CHQR, —CHQR, and —CQ(R)$_2$, where Q is selected from a $C_{3-6}$ carbocycle, a 5- to 14-membered heteroaryl having one or more heteroatoms selected from N, O, and S, —OR, —O(CH$_2$)$_n$N(R)$_2$, —C(O)OR, —OC(O)R, —CX$_3$, —CX$_2$H, —CXH$_2$, —CN, —C(O)N(R)$_2$, —N(R)C(O)R, —N(R)S(O)$_2$R, —N(R)C(O)N(R)$_2$, —N(R)C(S)N(R)$_2$, —C(R)N(R)$_2$C(O)OR, and each n is independently selected from 1, 2, 3, 4, and 5.

In another embodiment, $R_4$ is unsubstituted $C_{1-4}$ alkyl, e.g., unsubstituted methyl.

In certain embodiments, the disclosure provides a compound having the Formula (I), wherein $R_4$ is —(CH$_2$)$_n$Q or —(CH$_2$)$_n$CHQR, where Q is —N(R)$_2$, and n is selected from 3, 4, and 5.

In certain embodiments, the disclosure provides a compound having the Formula (I), wherein $R_4$ is selected from the group consisting of —$(CH_2)_nQ$, —$(CH_2)_nCHQR$, —CHQR, and —$CQ(R)_2$, where Q is —$N(R)_2$, and n is selected from 1, 2, 3, 4, and 5.

In certain embodiments, the disclosure provides a compound having the Formula (I), wherein $R_2$ and $R_3$ are independently selected from the group consisting of $C_{2-14}$ alkyl, $C_{2-14}$ alkenyl, —R*YR", —YR", and —R*OR", or $R_2$ and $R_3$, together with the atom to which they are attached, form a heterocycle or carbocycle, and $R_4$ is —$(CH_2)_nQ$ or —$(CH_2)_nCHQR$, where Q is —$N(R)_2$, and n is selected from 3, 4, and 5.

In certain embodiments, $R_2$ and $R_3$ are independently selected from the group consisting of $C_{2-14}$ alkyl, $C_{2-14}$ alkenyl, —R*YR", —YR", and —R*OR", or $R_2$ and $R_3$, together with the atom to which they are attached, form a heterocycle or carbocycle.

In some embodiments, $R_1$ is selected from the group consisting of $C_{5-20}$ alkyl and $C_{5-20}$ alkenyl.

In other embodiments, $R_1$ is selected from the group consisting of —R*YR", —YR", and —R"M'R'.

In certain embodiments, $R_1$ is selected from —R*YR" and —YR". In some embodiments, Y is a cyclopropyl group. In some embodiments, R* is $C_8$ alkyl or $C_8$ alkenyl. In certain embodiments, R" is $C_{3-12}$ alkyl. For example, R" can be $C_3$ alkyl. For example, R" can be $C_{4-8}$ alkyl (e.g., $C_4$, $C_5$, $C_6$, $C_7$, or $C_8$ alkyl).

In some embodiments, $R_1$ is $C_{5-20}$ alkyl. In some embodiments, $R_1$ is $C_6$ alkyl. In some embodiments, $R_1$ is $C_8$ alkyl. In other embodiments, $R_1$ is $C_9$ alkyl. In certain embodiments, $R_1$ is $C_{14}$ alkyl. In other embodiments, $R_1$ is $C_{18}$ alkyl.

In some embodiments, $R_1$ is $C_{5-20}$ alkenyl. In certain embodiments, $R_1$ is Cis alkenyl. In some embodiments, $R_1$ is linoleyl.

In certain embodiments, $R_1$ is branched (e.g., decan-2-yl, undecan-3-yl, dodecan-4-yl, tridecan-5-yl, tetradecan-6-yl, 2-methylundecan-3-yl, 2-methyldecan-2-yl, 3-methylundecan-3-yl, 4-methyldodecan-4-yl, or heptadeca-9-yl). In certain embodiments, $R_1$ is

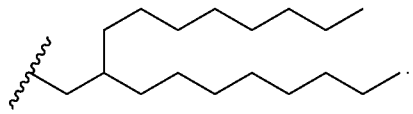 [SMILES: *CC(CCCCCCCC)CCCCCCCC]

In certain embodiments, $R_1$ is unsubstituted $C_{5-20}$ alkyl or $C_{5-20}$ alkenyl. In certain embodiments, R' is substituted $C_{5-20}$ alkyl or $C_{5-20}$ alkenyl (e.g., substituted with a $C_{3-6}$ carbocycle such as 1-cyclopropylnonyl).

In other embodiments, $R_1$ is —R"M'R'.

In some embodiments, R' is selected from —R*YR" and —YR". In some embodiments, Y is $C_{3-8}$ cycloalkyl. In some embodiments, Y is $C_{6-10}$ aryl. In some embodiments, Y is a cyclopropyl group. In some embodiments, Y is a cyclohexyl group. In certain embodiments, R* is $C_1$ alkyl.

In some embodiments, R" is selected from the group consisting of $C_{3-12}$ alkyl and $C_{3-12}$ alkenyl. In some embodiments, R" adjacent to Y is $C_1$ alkyl. In some embodiments, R" adjacent to Y is $C_{4-9}$ alkyl (e.g., $C_4$, $C_5$, $C_6$, $C_7$ or $C_8$ or $C_9$ alkyl).

In some embodiments, R' is selected from $C_4$ alkyl and $C_4$ alkenyl. In certain embodiments, R' is selected from $C_5$ alkyl and $C_5$ alkenyl. In some embodiments, R' is selected from $C_6$ alkyl and $C_6$ alkenyl. In some embodiments, R' is selected from $C_7$ alkyl and $C_7$ alkenyl. In some embodiments, R' is selected from $C_9$ alkyl and $C_9$ alkenyl.

In other embodiments, R' is selected from $C_{11}$ alkyl and $C_{11}$ alkenyl. In other embodiments, R' is selected from $C_{12}$ alkyl, $C_{12}$ alkenyl, $C_{13}$ alkyl, $C_{13}$ alkenyl, $C_{14}$ alkyl, $C_{14}$ alkenyl, $C_{15}$ alkyl, $C_{15}$ alkenyl, $C_{16}$ alkyl, $C_{16}$ alkenyl, $C_{17}$ alkyl, $C_{17}$ alkenyl, $C_{18}$ alkyl, and $C_{18}$ alkenyl. In certain embodiments, R' is branched (e.g., decan-2-yl, undecan-3-yl, dodecan-4-yl, tridecan-5-yl, tetradecan-6-yl, 2-methylundecan-3-yl, 2-methyldecan-2-yl, 3-methylundecan-3-yl, 4-methyldodecan-4-yl or heptadeca-9-yl). In certain embodiments, R' is

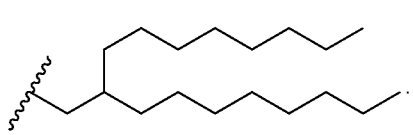 [SMILES: *CC(CCCCCCCC)CCCCCCCC]

In certain embodiments, R' is unsubstituted $C_{1-18}$ alkyl. In certain embodiments, R' is substituted $C_{1-18}$ alkyl (e.g., $C_{1-15}$ alkyl substituted with a $C_{3-6}$ carbocycle such as 1-cyclopropylnonyl).

In some embodiments, R" is selected from the group consisting of $C_{3-14}$ alkyl and $C_{3-14}$ alkenyl. In some embodiments, R" is $C_3$ alkyl, $C_4$ alkyl, $C_5$ alkyl, $C_6$ alkyl, $C_7$ alkyl, or $C_8$ alkyl. In some embodiments, R" is $C_9$ alkyl, $C_{10}$ alkyl, $C_{11}$ alkyl, $C_{12}$ alkyl, $C_{13}$ alkyl, or $C_{14}$ alkyl.

In some embodiments, M' is —C(O)O—. In some embodiments, M' is —OC(O)—.

In other embodiments, M' is an aryl group or heteroaryl group. For example, M' can be selected from the group consisting of phenyl, oxazole, and thiazole.

In some embodiments, M is —C(O)O— In some embodiments, M is —OC(O)—. In some embodiments, M is —C(O)N(R')—. In some embodiments, M is —P(O)(OR')O—.

In other embodiments, M is an aryl group or heteroaryl group. For example, M can be selected from the group consisting of phenyl, oxazole, and thiazole.

In some embodiments, M is the same as M'. In other embodiments, M is different from M'.

In some embodiments, each $R_5$ is H. In certain such embodiments, each $R_6$ is also H.

In some embodiments, $R_7$ is H. In other embodiments, $R_7$ is $C_{1-3}$ alkyl (e.g., methyl, ethyl, propyl, or i-propyl).

In some embodiments, $R_2$ and $R_3$ are independently $C_{5-14}$ alkyl or $C_{5-14}$ alkenyl.

In some embodiments, $R_2$ and $R_3$ are the same. In some embodiments, $R_2$ and $R_3$ are $C_8$ alkyl. In certain embodiments, $R_2$ and $R_3$ are $C_2$ alkyl. In other embodiments, $R_2$ and $R_3$ are $C_3$ alkyl. In some embodiments, $R_2$ and $R_3$ are $C_4$ alkyl. In certain embodiments, $R_2$ and $R_3$ are $C_5$ alkyl. In other embodiments, $R_2$ and $R_3$ are $C_6$ alkyl. In some embodiments, $R_2$ and $R_3$ are $C_7$ alkyl.

In other embodiments, $R_2$ and $R_3$ are different. In certain embodiments, $R_2$ is $C_8$ alkyl. In some embodiments, $R_3$ is $C_{1-7}$ (e.g., $C_1$, $C_2$, $C_3$, $C_4$, $C_5$, $C_6$, or $C_7$ alkyl) or $C_9$ alkyl.

In some embodiments, $R_7$ and $R_3$ are H.

In certain embodiments, $R_2$ is H.

In some embodiments, m is 5, 7, or 9.

In some embodiments, $R_4$ is selected from —$(CH_2)_nQ$ and —$(CH_2)_nCHQR$.

In some embodiments, Q is selected from the group consisting of —OR, —OH, —$O(CH_2)_nN(R)_2$, —OC(O)R, —CX₃, —CN, —N(R)C(O)R, —N(H)C(O)R, —N(R)S(O)₂R, —N(H)S(O)₂R, —N(R)C(O)N(R)₂, —N(H)C(O)N(R)₂, —N(H)C(O)N(H)(R), —N(R)C(S)N(R)₂, —N(H)C(S)N(R)₂, —N(H)C(S)N(H)(R), —C(R)N(R)₂C(O)OR, a carbocycle, and a heterocycle.

In certain embodiments, Q is —OH.

In certain embodiments, Q is a substituted or unsubstituted 5- to 10-membered heteroaryl, e.g., Q is an imidazole, a pyrimidine, a purine, 2-amino-1,9-dihydro-6H-purin-6-one-9-yl (or guanin-9-yl), adenin-9-yl, cytosin-1-yl, or uracil-1-yl. In certain embodiments, Q is a substituted 5- to 14-membered heterocycloalkyl, e.g., substituted with one or more substituents selected from oxo (=O), OH, amino, and $C_{1-3}$ alkyl. For example, Q is 4-methylpiperazinyl, 4-(4-methoxybenzyl)piperazinyl, or isoindolin-2-yl-1,3-dione.

In certain embodiments, Q is an unsubstituted or substituted $C_{6-10}$ aryl (such as phenyl) or $C_{3-6}$ cycloalkyl.

In some embodiments, n is 1. In other embodiments, n is 2. In further embodiments, n is 3. In certain other embodiments, n is 4. For example, $R_4$ can be —(CH₂)₂OH. For example, $R_4$ can be —(CH₂)₃OH. For example, $R_4$ can be —(CH₂)₄OH. For example, $R_4$ can be benzyl. For example, $R_4$ can be 4-methoxybenzyl.

In some embodiments, $R_4$ is a $C_{3-6}$ carbocycle. In some embodiments, $R_4$ is a $C_{3-6}$ cycloalkyl. For example, $R_4$ can be cyclohexyl optionally substituted with e.g., OH, halo, $C_{1-6}$ alkyl, etc. For example, $R_4$ can be 2-hydroxycyclohexyl.

In some embodiments, R is H.

In some embodiments, R is unsubstituted $C_{1-3}$ alkyl or unsubstituted $C_{2-3}$ alkenyl. For example, $R_4$ can be —CH₂CH(OH)CH₃ or —CH₂CH(OH)CH₂CH₃.

In some embodiments, R is substituted $C_{1-3}$ alkyl, e.g., CH₂OH. For example, $R_4$ can be —CH₂CH(OH)CH₂OH.

In some embodiments, $R_2$ and $R_3$, together with the atom to which they are attached, form a heterocycle or carbocycle. In some embodiments, $R_2$ and $R_3$, together with the atom to which they are attached, form a 5- to 14-membered aromatic or non-aromatic heterocycle having one or more heteroatoms selected from N, O, S, and P. In some embodiments, $R_2$ and $R_3$, together with the atom to which they are attached, form an optionally substituted $C_{3-20}$ carbocycle (e.g., $C_{3-18}$ carbocycle, $C_{3-15}$ carbocycle, $C_{3-12}$ carbocycle, or $C_{3-10}$ carbocycle), either aromatic or non-aromatic. In some embodiments, $R_2$ and $R_3$, together with the atom to which they are attached, form a $C_{3-6}$ carbocycle. In other embodiments, $R_2$ and $R_3$, together with the atom to which they are attached, form a $C_6$ carbocycle, such as a cyclohexyl or phenyl group. In certain embodiments, the heterocycle or $C_{3-6}$ carbocycle is substituted with one or more alkyl groups (e.g., at the same ring atom or at adjacent or non-adjacent ring atoms). For example, $R_2$ and $R_3$, together with the atom to which they are attached, can form a cyclohexyl or phenyl group bearing one or more $C_5$ alkyl substitutions. In certain embodiments, the heterocycle or $C_{3-6}$ carbocycle formed by $R_2$ and $R_3$, is substituted with a carbocycle groups. For example, $R_2$ and $R_3$, together with the atom to which they are attached, can form a cyclohexyl or phenyl group that is substituted with cyclohexyl. In some embodiments, $R_2$ and $R_3$, together with the atom to which they are attached, form a $C_{7-15}$ carbocycle, such as a cycloheptyl, cyclopentadecanyl, or naphthyl group.

In some embodiments, $R_4$ is selected from —(CH₂)$_n$Q and —(CH₂)$_n$CHQR. In some embodiments, Q is selected from the group consisting of —OR, —OH, —O(CH₂)$_n$N(R)₂, —OC(O)R, —CX₃, —CN, —N(R)C(O)R, —N(H)C(O)R, —N(R)S(O)₂R, —N(H)S(O)₂R, —N(R)C(O)N(R)₂, —N(H)C(O)N(R)₂, —N(H)C(O)N(H)(R), —N(R)C(S)N(R)₂, —N(H)C(S)N(R)₂, —N(H)C(S)N(H)(R), and a heterocycle. In other embodiments, Q is selected from the group consisting of an imidazole, a pyrimidine, and a purine.

In some embodiments, $R_2$ and $R_3$, together with the atom to which they are attached, form a heterocycle or carbocycle. In some embodiments, $R_2$ and $R_3$, together with the atom to which they are attached, form a $C_{3-6}$ carbocycle, such as a phenyl group. In certain embodiments, the heterocycle or $C_{3-6}$ carbocycle is substituted with one or more alkyl groups (e.g., at the same ring atom or at adjacent or non-adjacent ring atoms). For example, $R_2$ and $R_3$, together with the atom to which they are attached, can form a phenyl group bearing one or more $C_5$ alkyl substitutions.

In some embodiments, the pharmaceutical compositions of the present disclosure, the compound of Formula (I) is selected from the group consisting of:

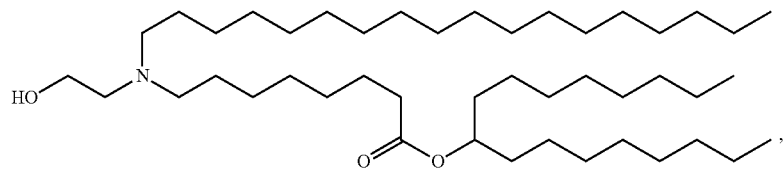

(Compound 1)

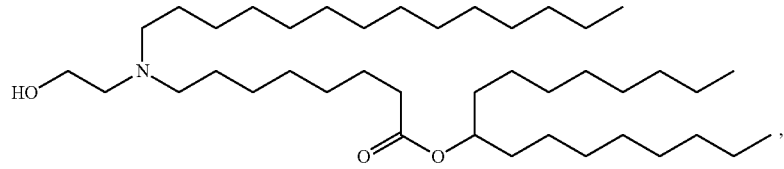

(Compound 2)

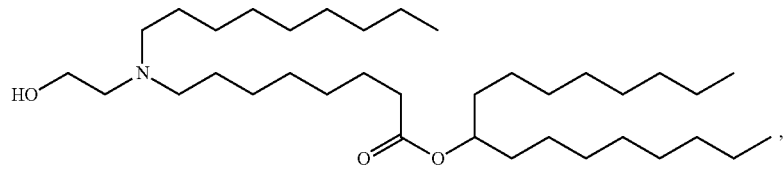

(Compound 3)

(Compound 4)
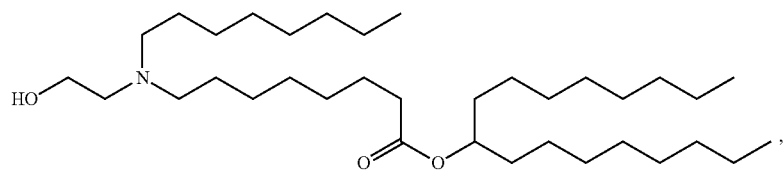
(Compound 5)
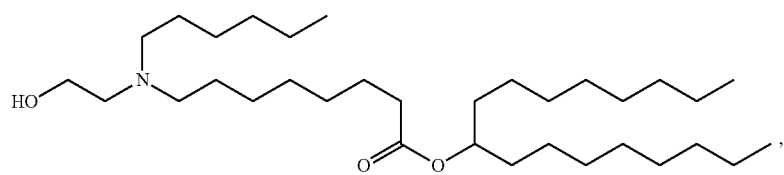
(Compound 6)
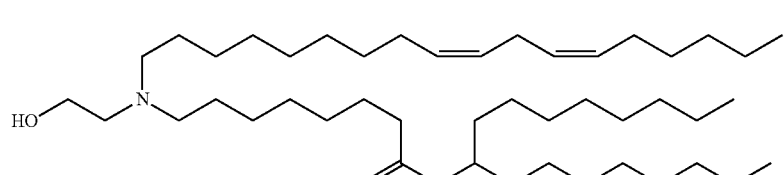
(Compound 7)
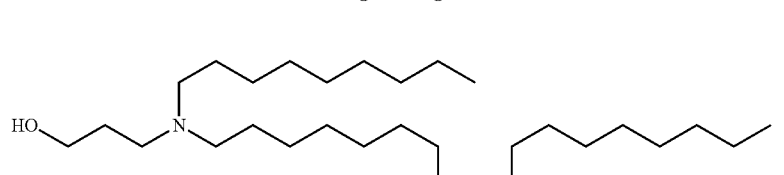
(Compound 8)
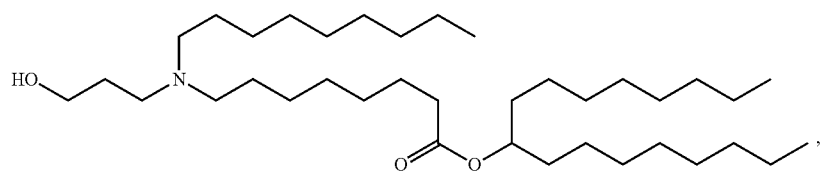
(Compound 9)
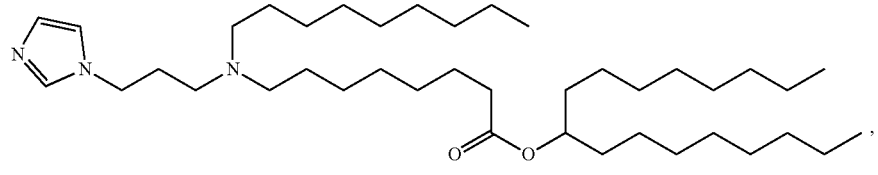
(Compound 10)
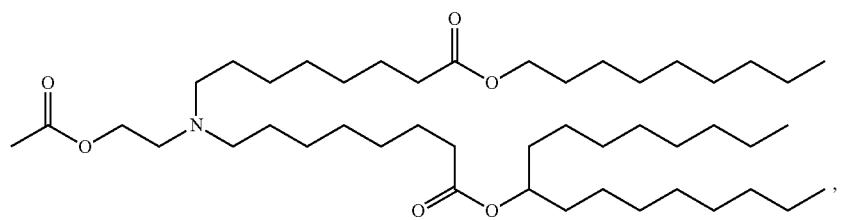
(Compound 11)
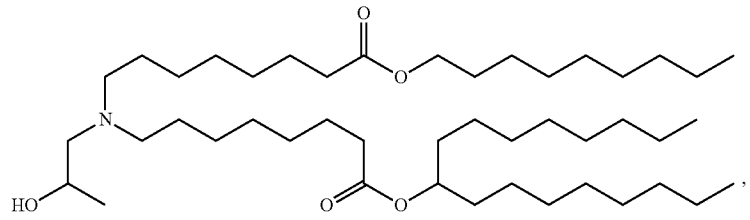
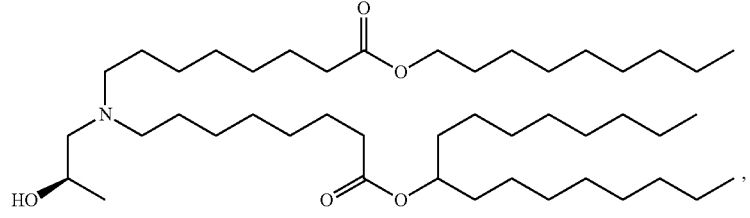

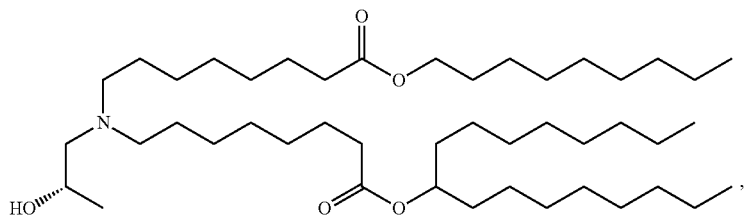
(Compound 12)
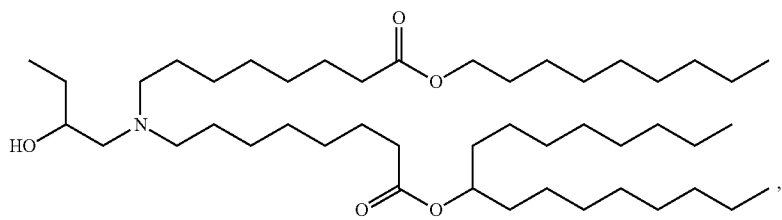
(Compound 13)
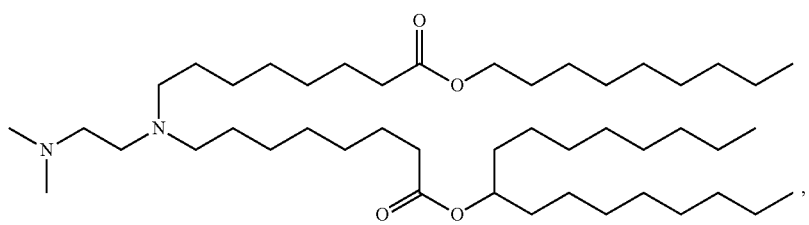
(Compound 14)
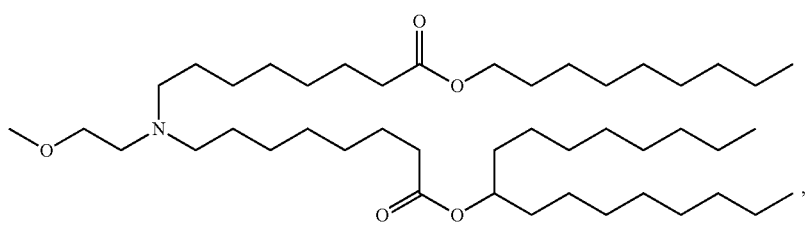
(Compound 15)
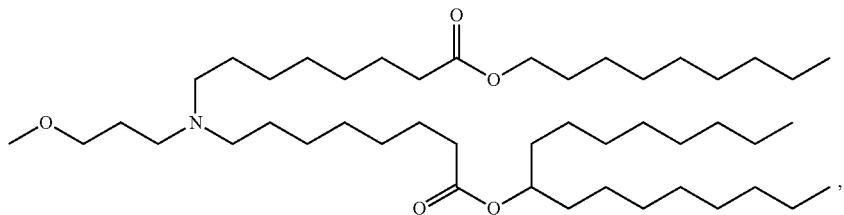
(Compound 16)
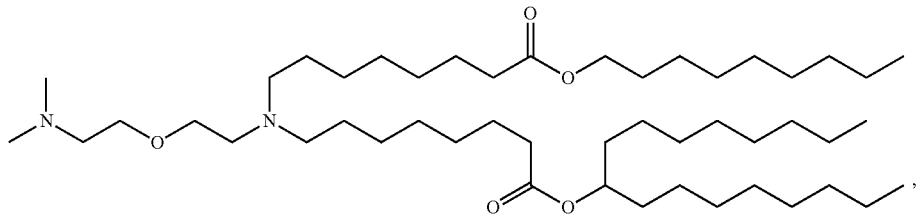
(Compound 17)
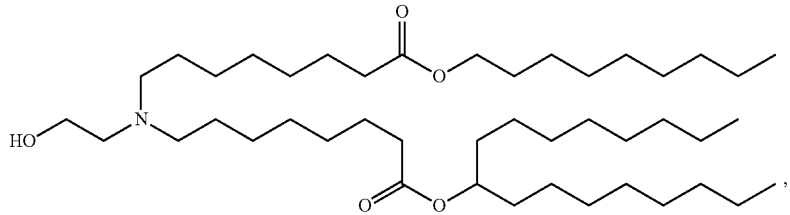
(Compound 18)

(Compound 19)
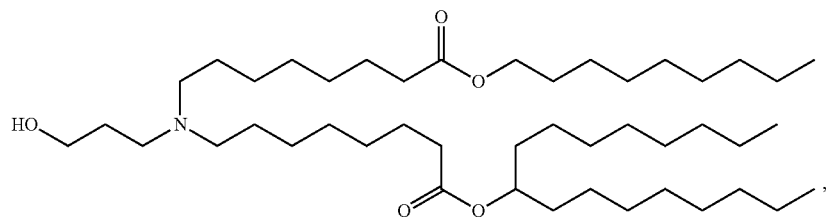
(Compound 20)
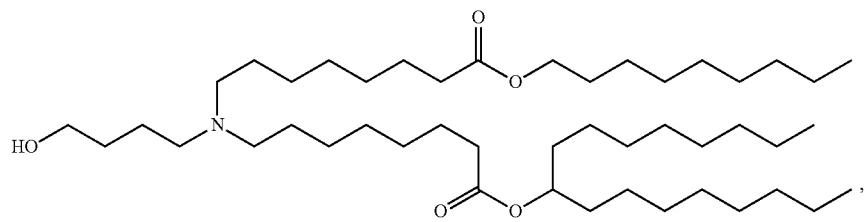
(Compound 21)
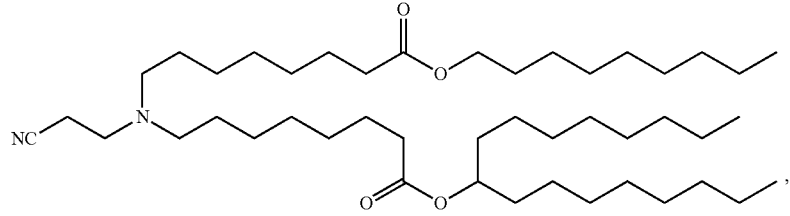
(Compound 22)
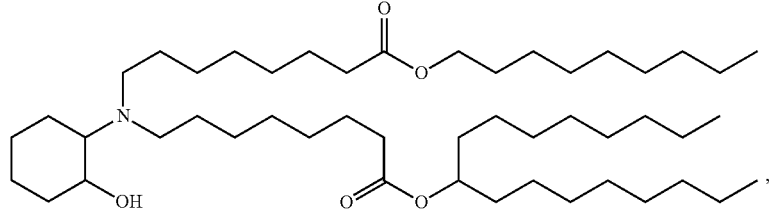
(Compound 23)
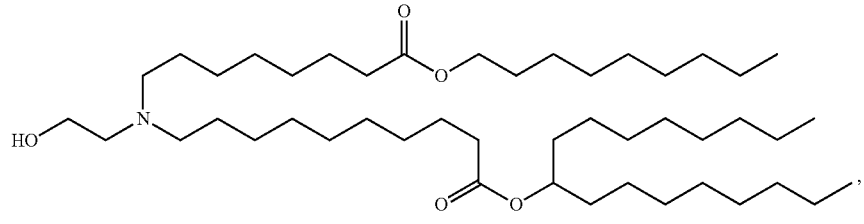
(Compound 24)
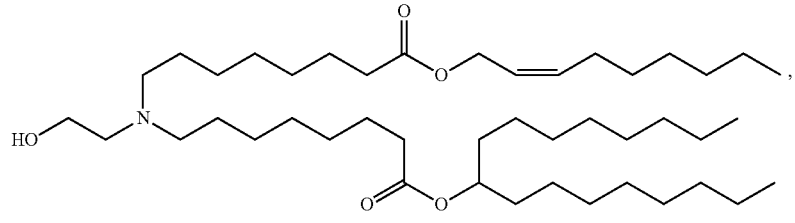
(Compound 25)
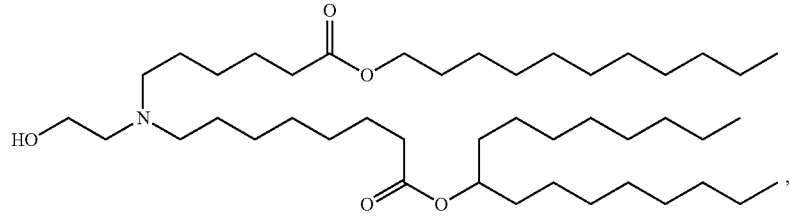

(Compound 26)
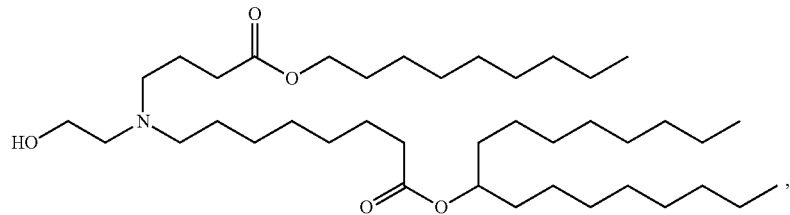
(Compound 27)
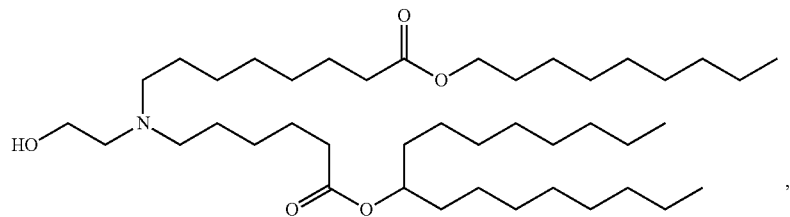
(Compound 28)
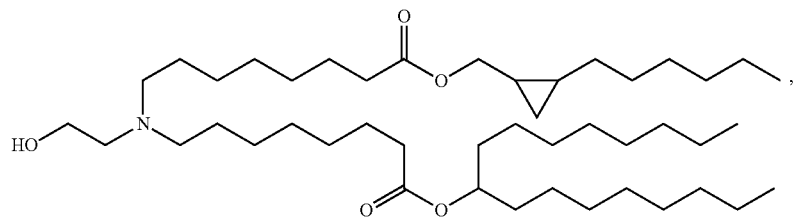
(Compound 29)
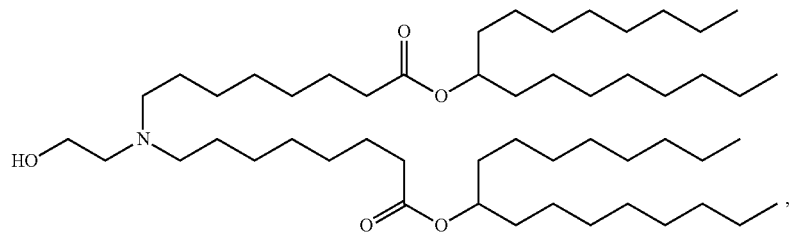
(Compound 30)
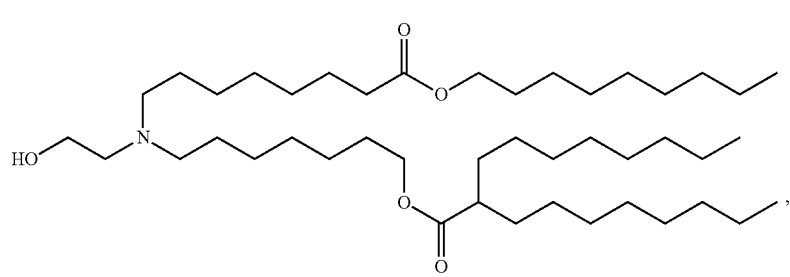
(Compound 31)
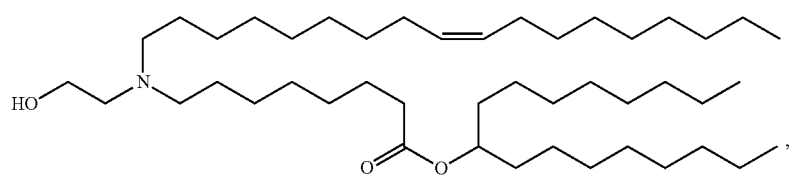
(Compound 32)
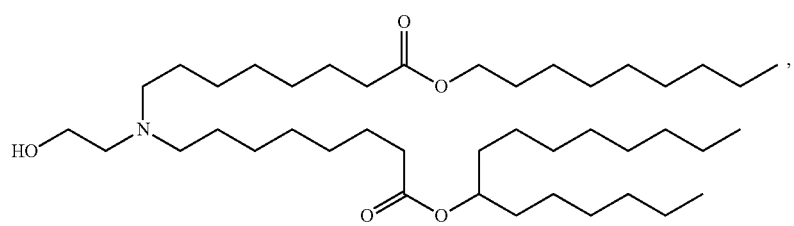

-continued
(Compound 33)
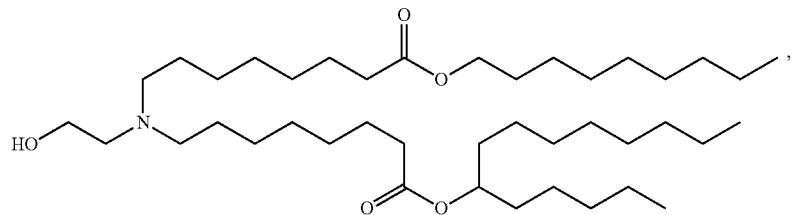
(Compound 34)
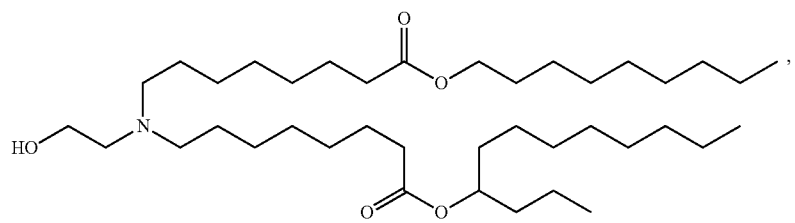
(Compound 35)
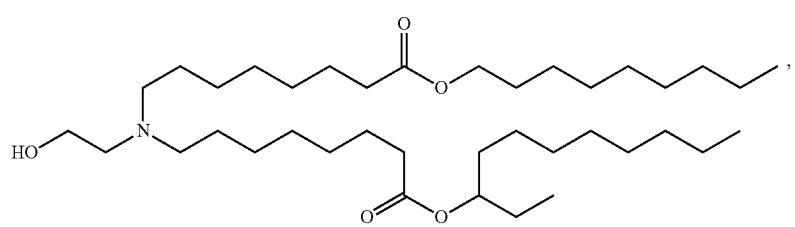
(Compound 36)
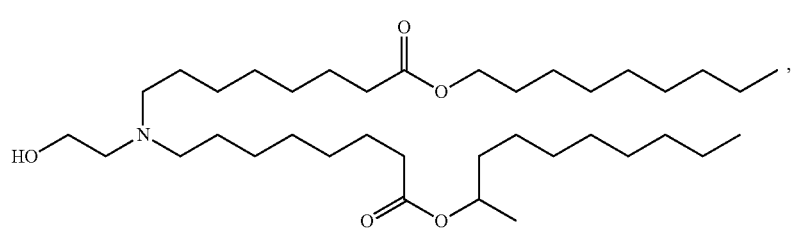
(Compound 37)
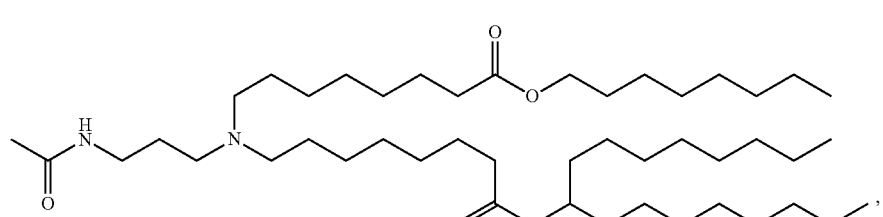
(Compound 38)
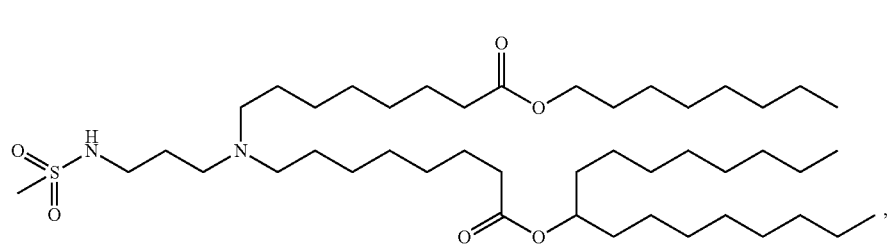
(Compound 39)
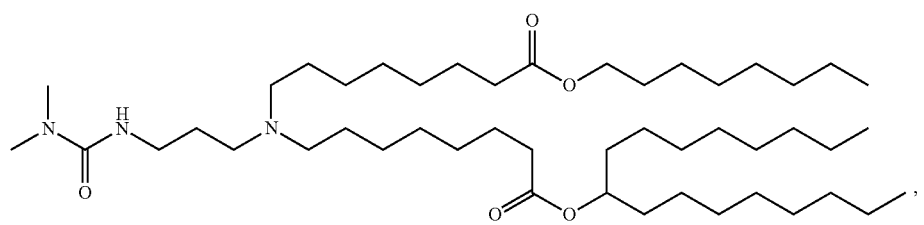

(Compound 40)
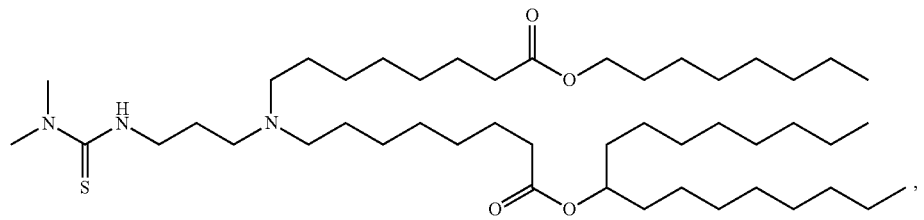
(Compound 41)
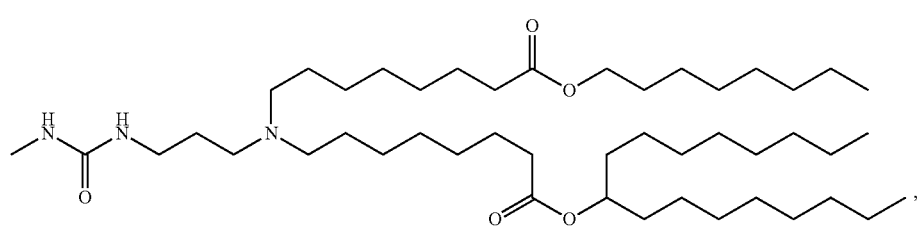
(Compound 42)
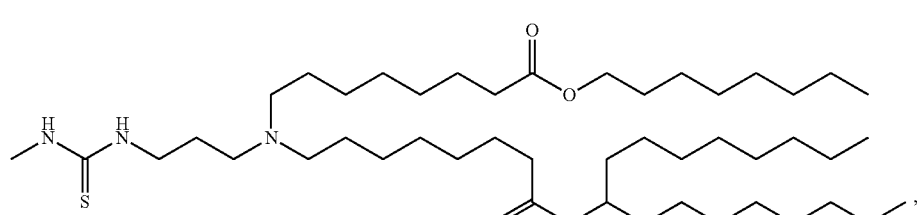
(Compound 43)
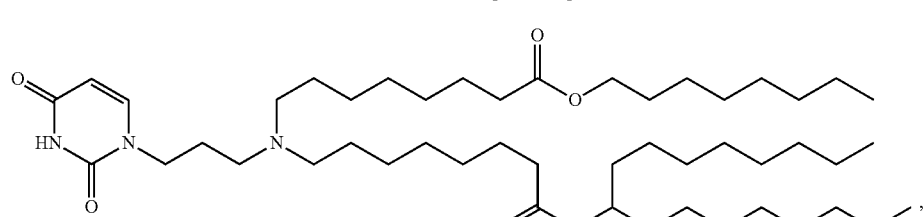
(Compound 44)
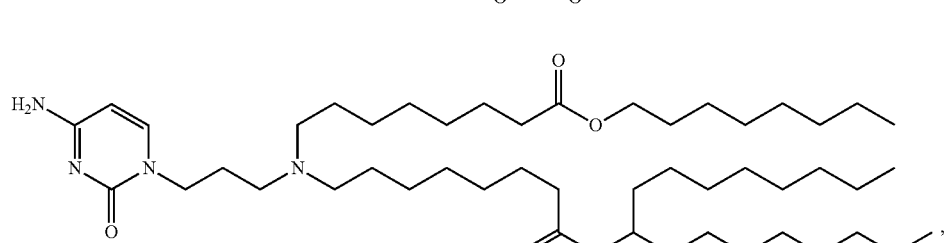
(Compound 45)
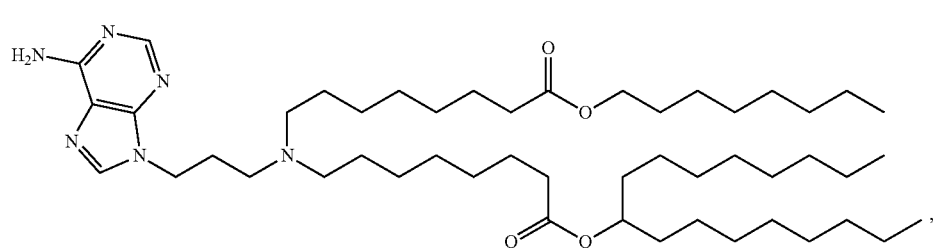
(Compound 46)
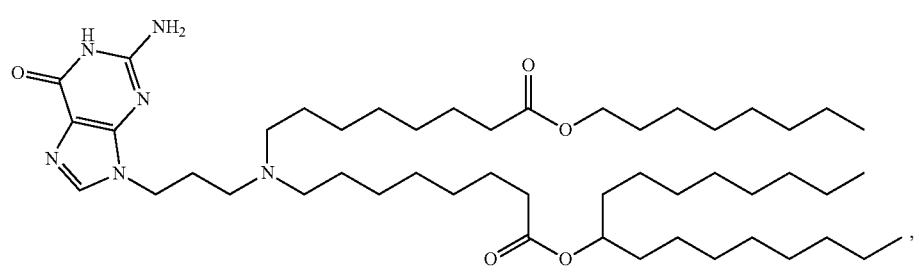

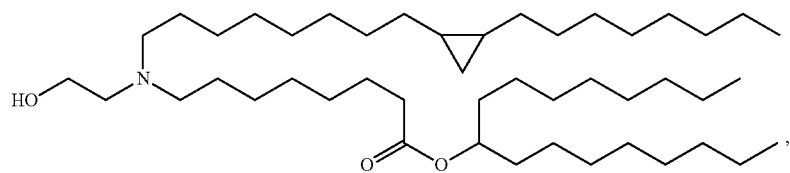
(Compound 47)
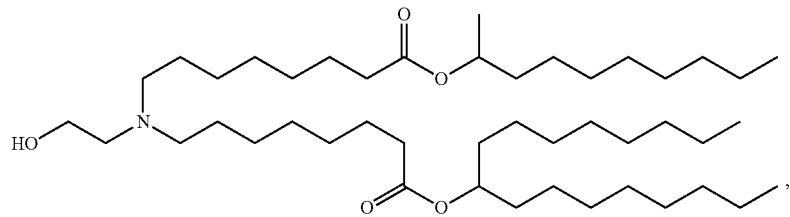
(Compound 48)
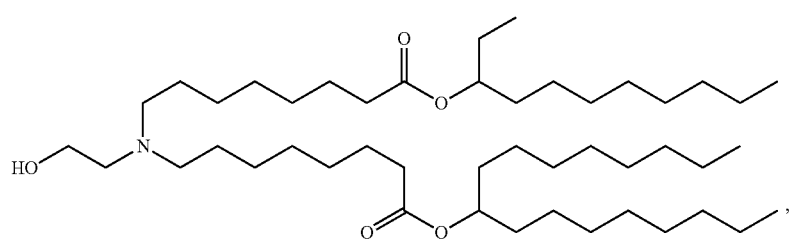
(Compound 49)
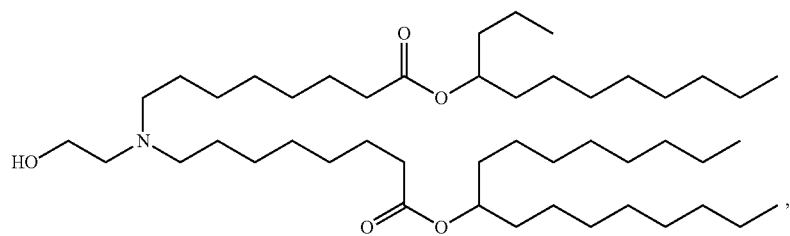
(Compound 50)
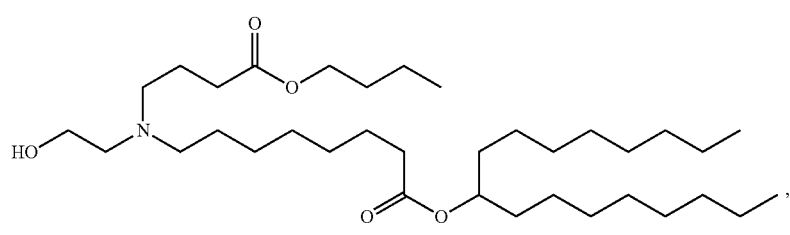
(Compound 51)
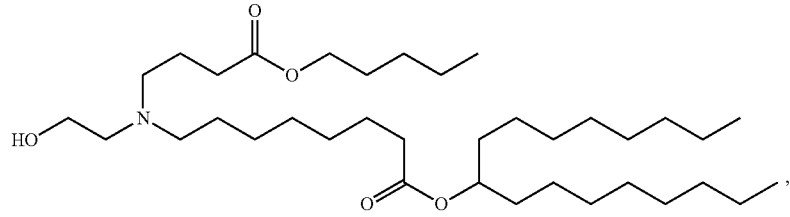
(Compound 52)
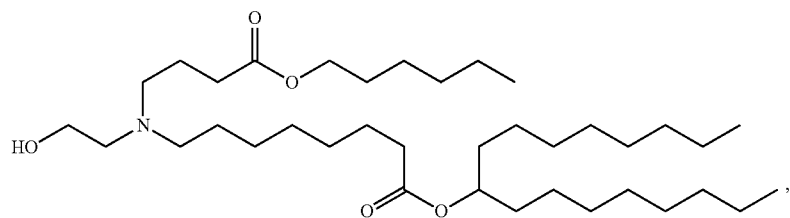
(Compound 53)

-continued
(Compound 54)
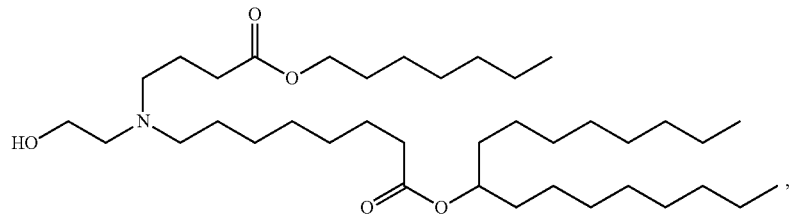
(Compound 55)
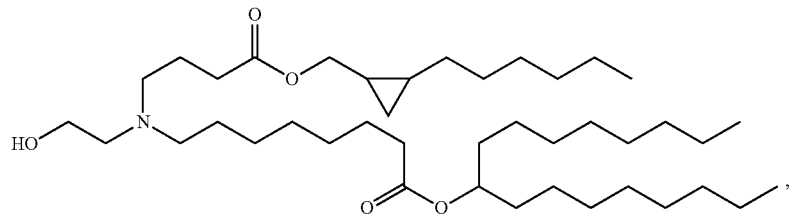
(Compound 56)
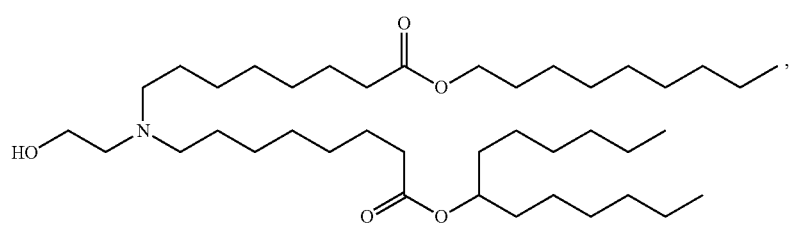
(Compound 57)
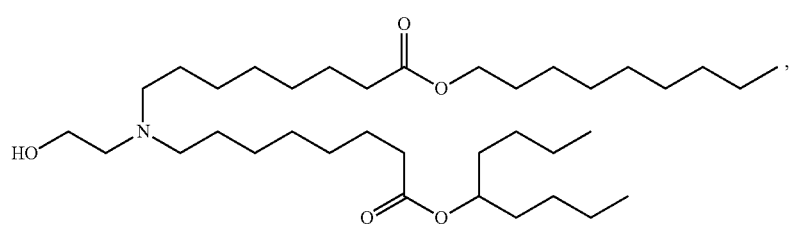
(Compound 58)
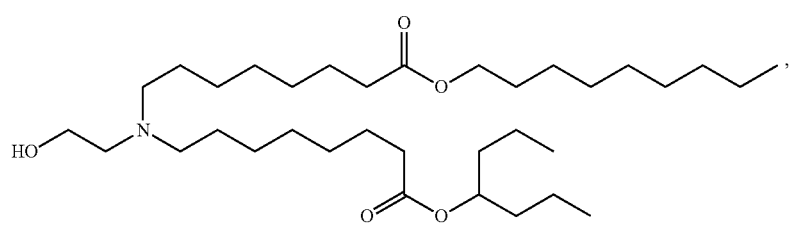
(Compound 59)
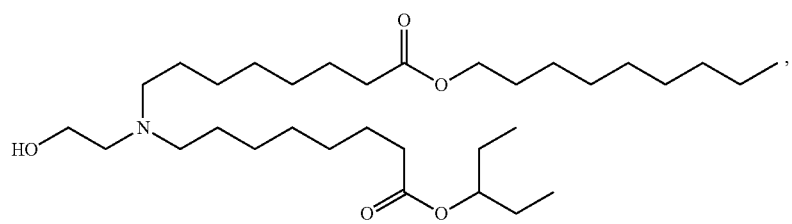
(Compound 60)
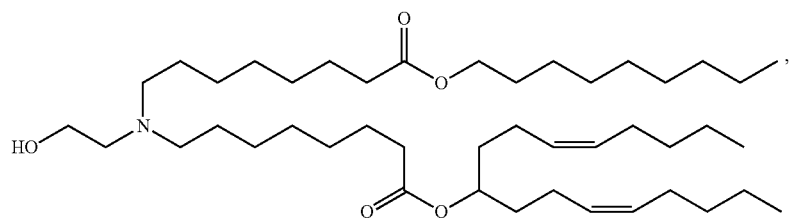

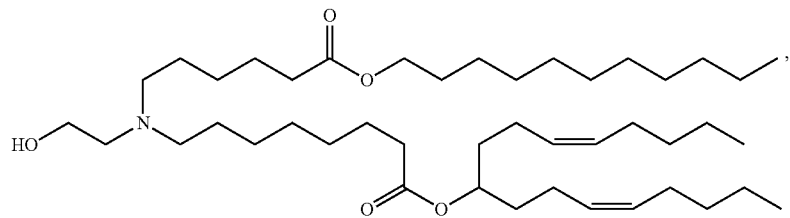
(Compound 61)
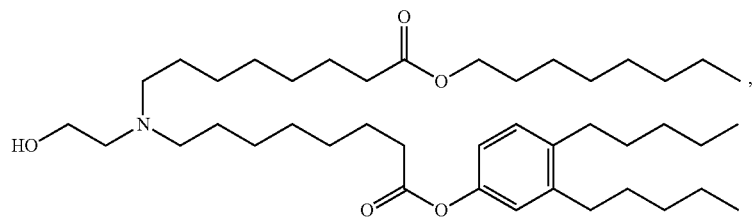
(Compound 62)
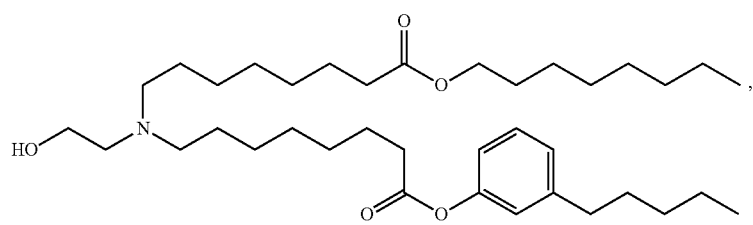
(Compound 63)
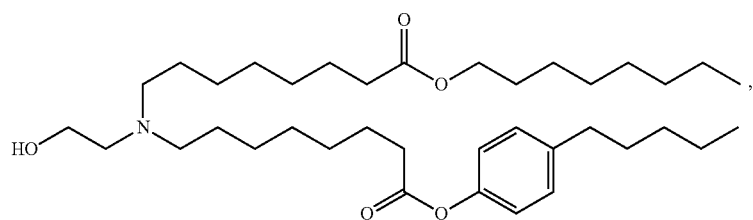
(Compound 64)
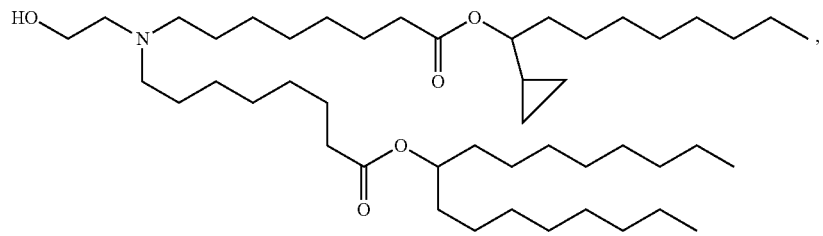
(Compound 65)
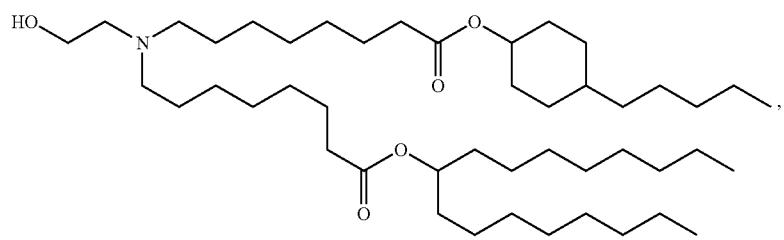
(Compound 66)

(Compound 67)
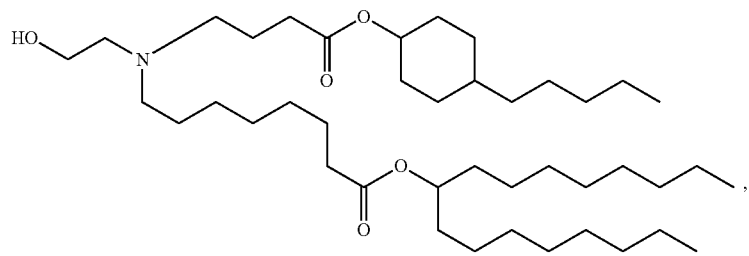
(Compound 68)
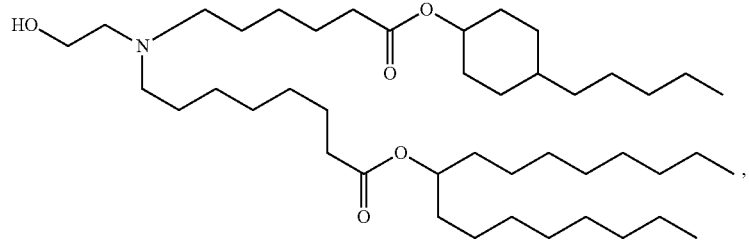
(Compound 69)
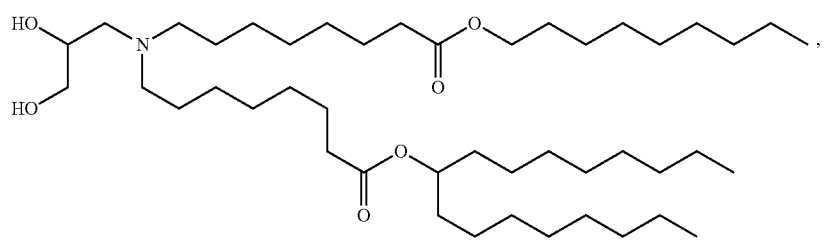
(Compound 70)
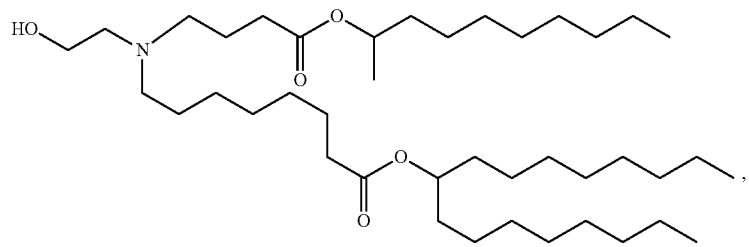
(Compound 71)
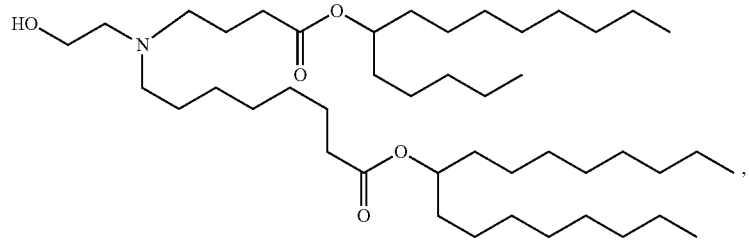
(Compound 72)
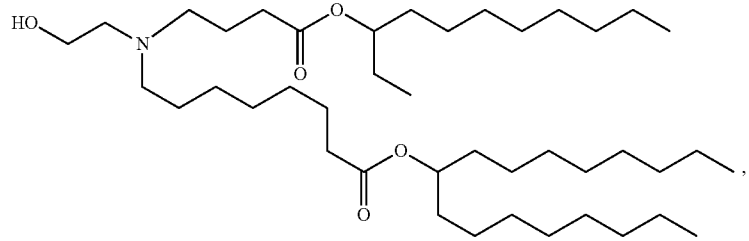

-continued
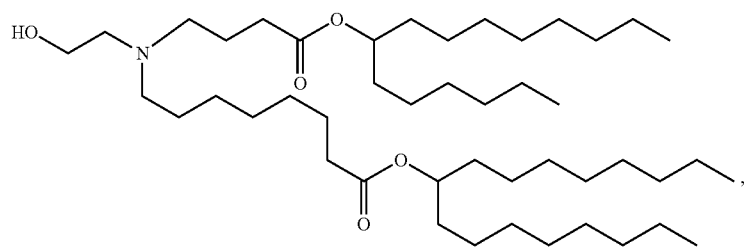
(Compound 73)
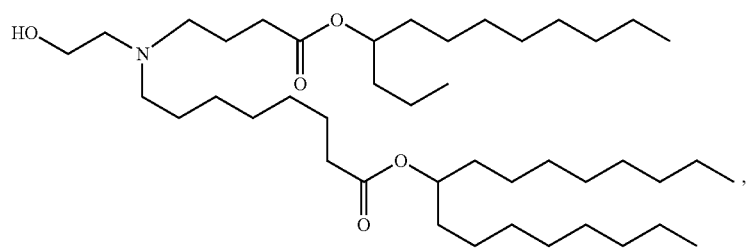
(Compound 74)
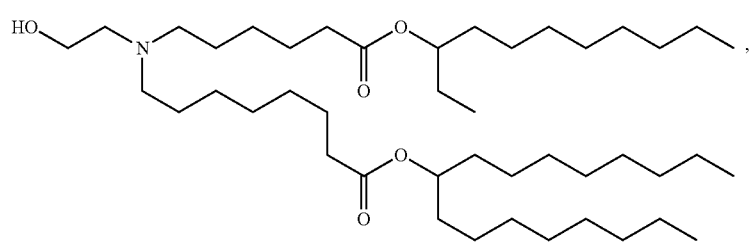
(Compound 75)
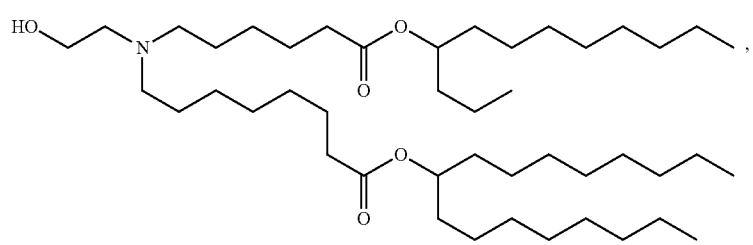
(Compound 76)
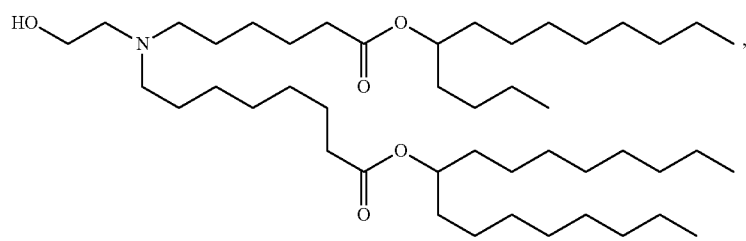
(Compound 77)
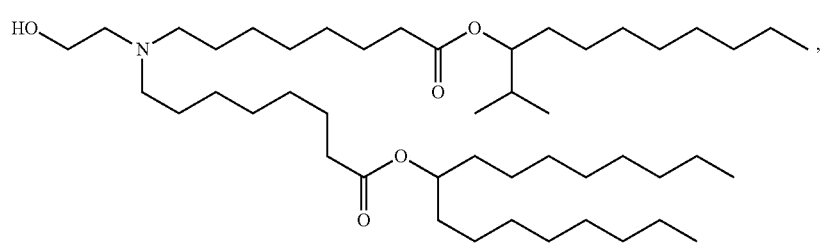
(Compound 78)

-continued
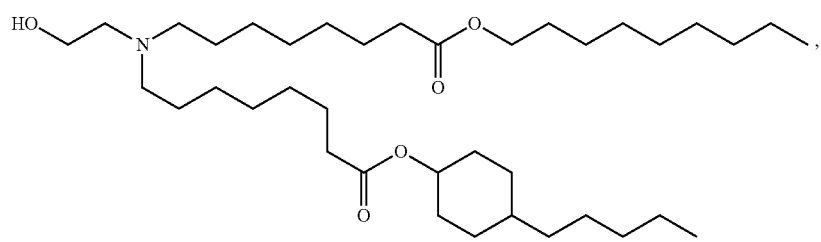
(Compound 79)
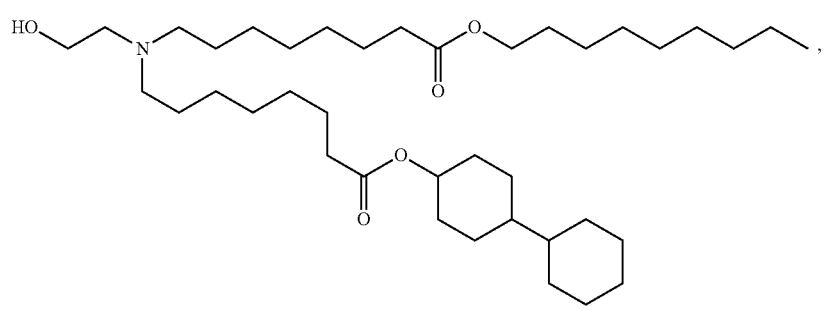
(Compound 80)
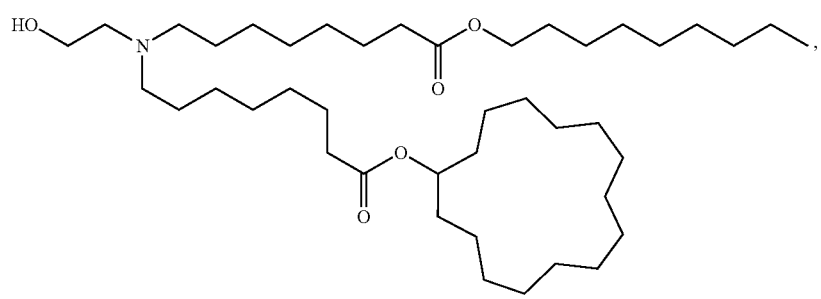
(Compound 81)
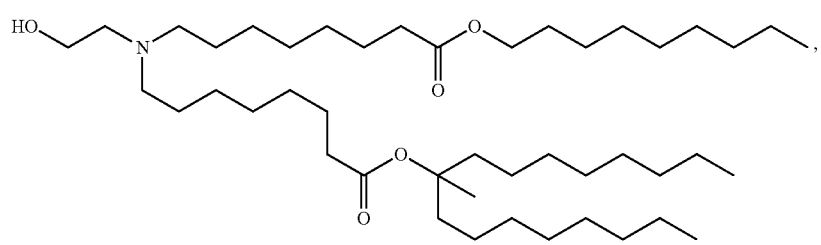
(Compound 82)
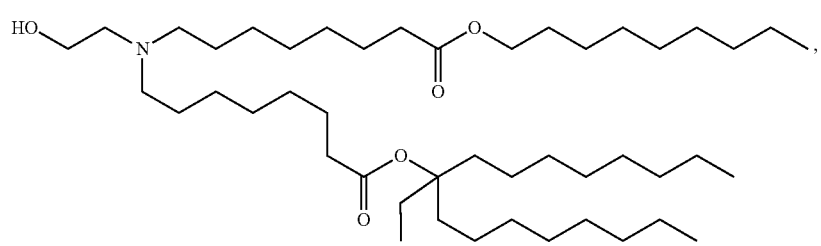
(Compound 83)
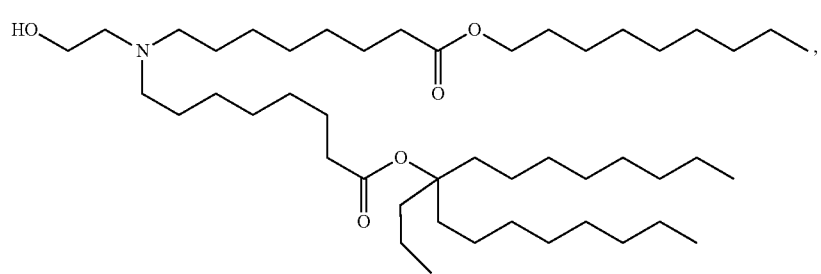
(Compound 84)

-continued
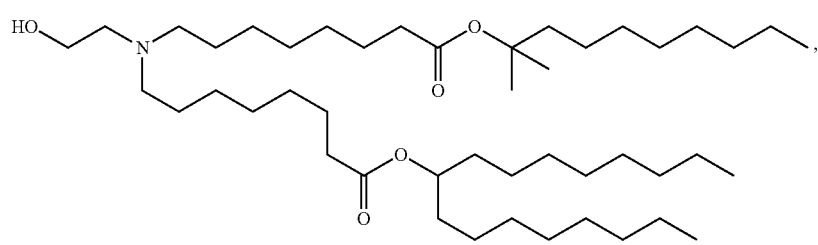
(Compound 85)
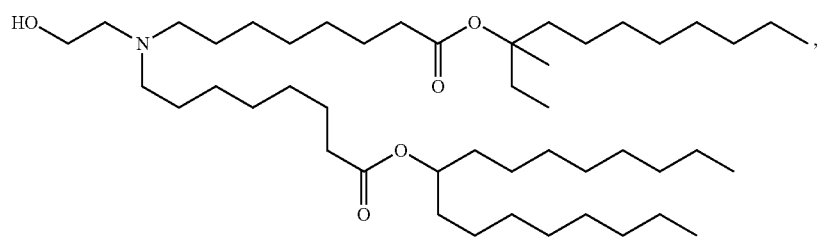
(Compound 86)
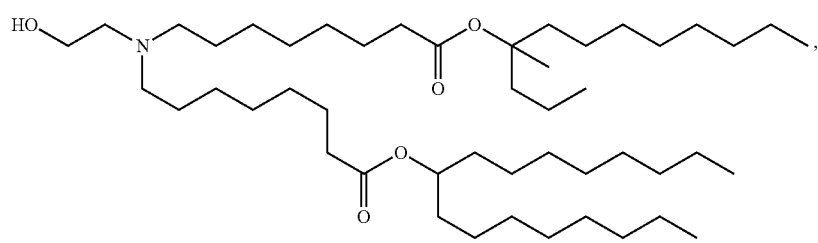
(Compound 87)
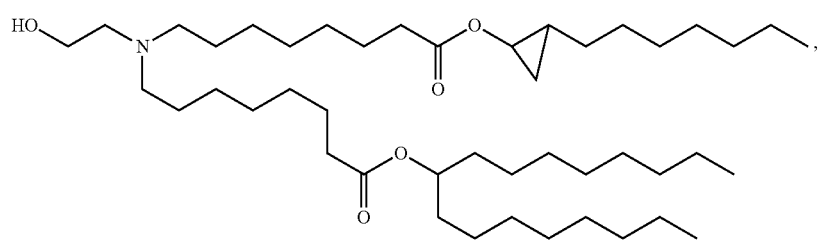
(Compound 88)
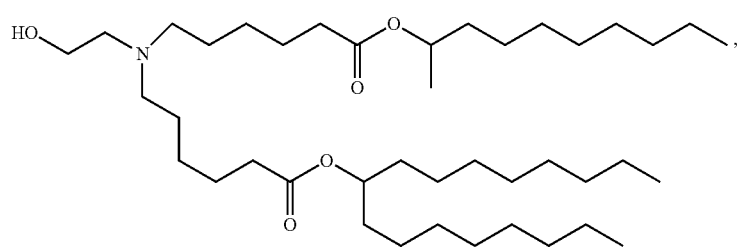
(Compound 89)
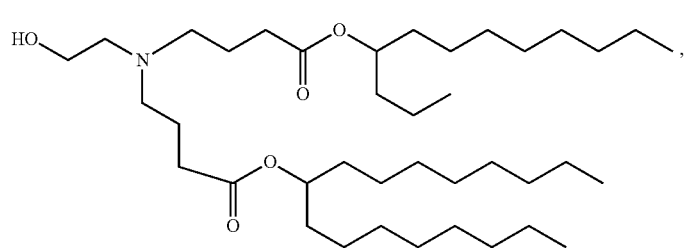
(Compound 90)

-continued
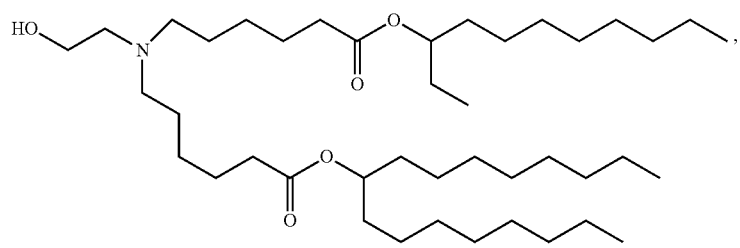
(Compound 91)
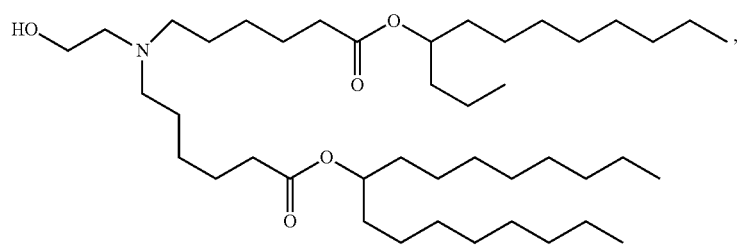
(Compound 92)
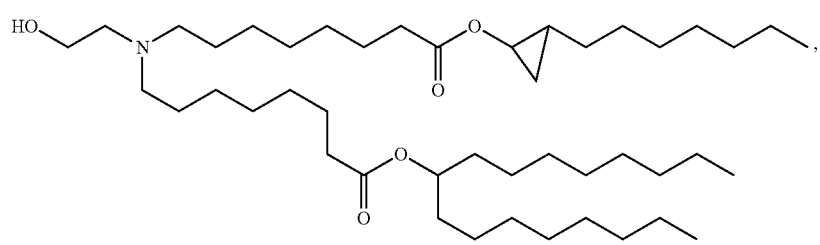
(Compound 93)
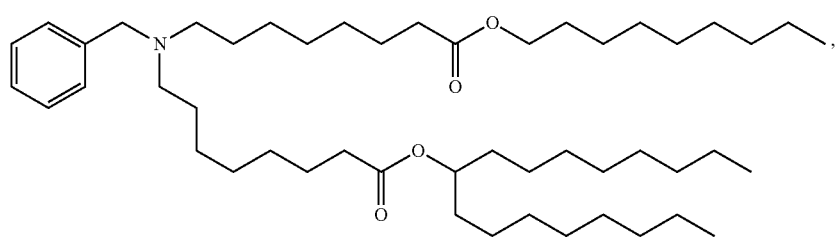
(Compound 94)
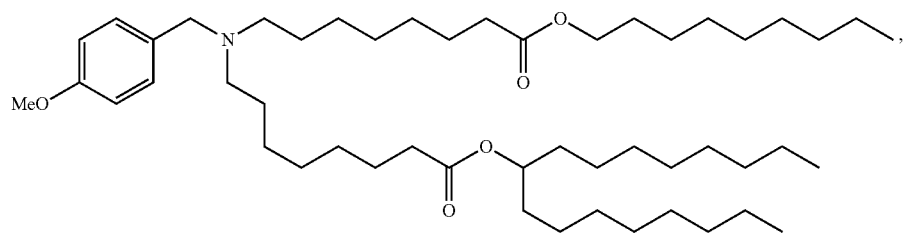
(Compound 95)
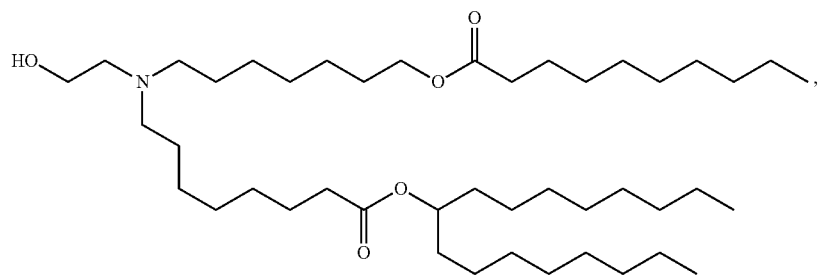
(Compound 96)

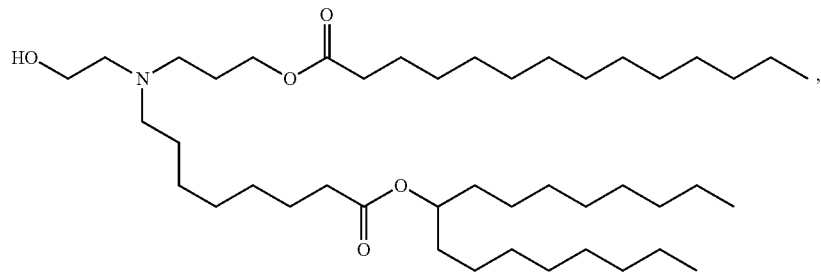
(Compound 97)
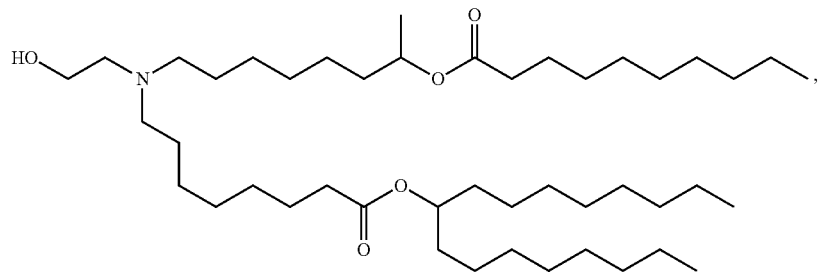
(Compound 98)
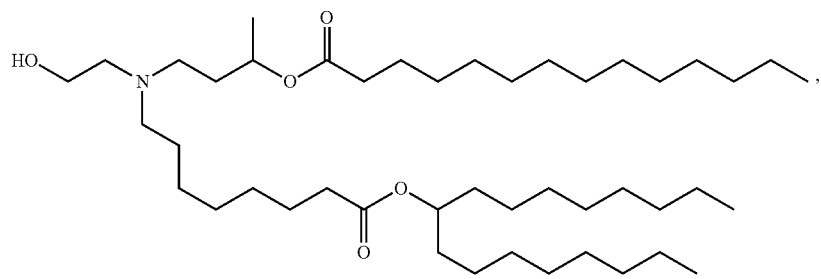
(Compound 99)
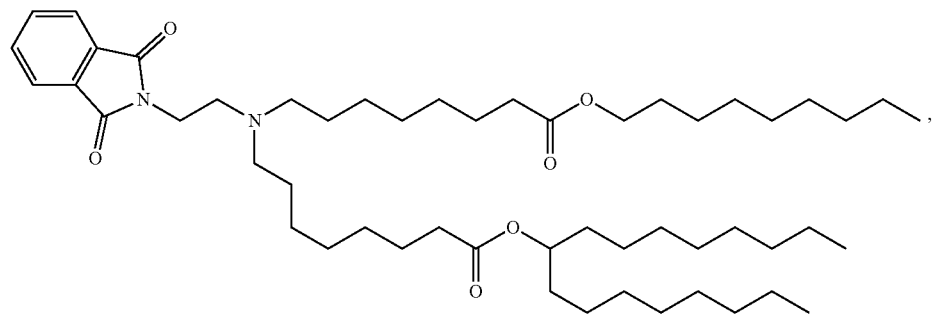
(Compound 100)
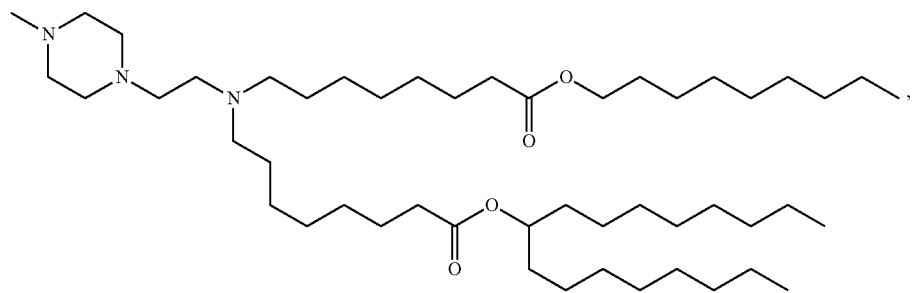
(Compound 101)

(Compound 102)
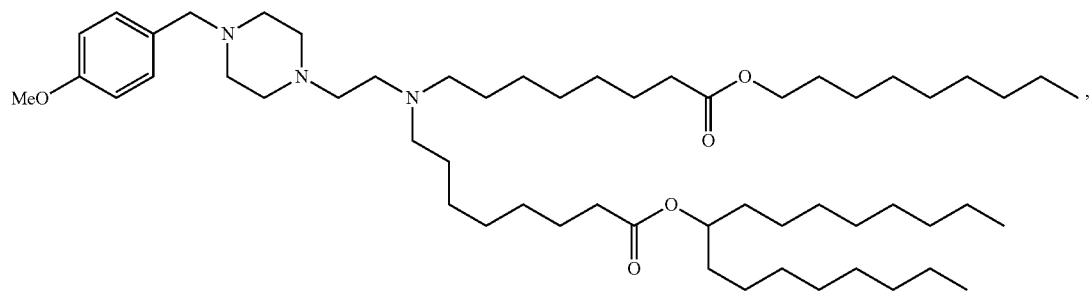
(Compound 103)
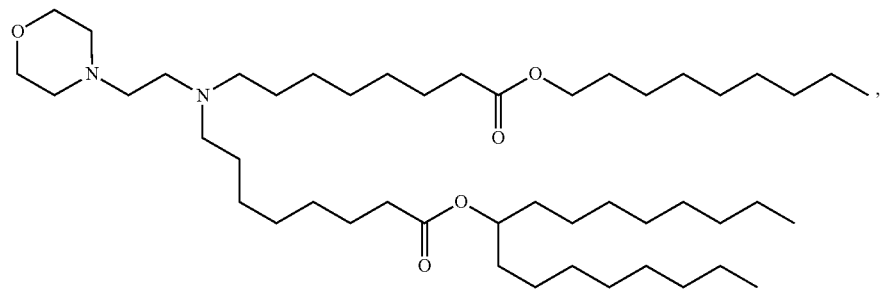
(Compound 104)
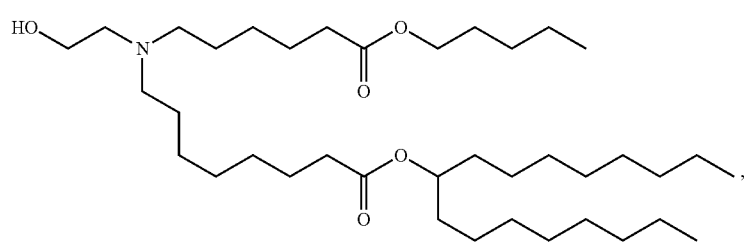
(Compound 105)
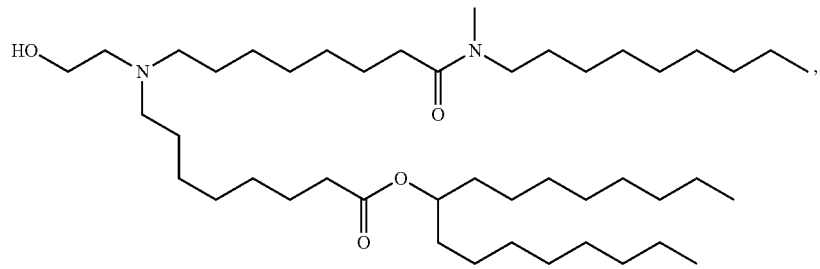
(Compound 106)
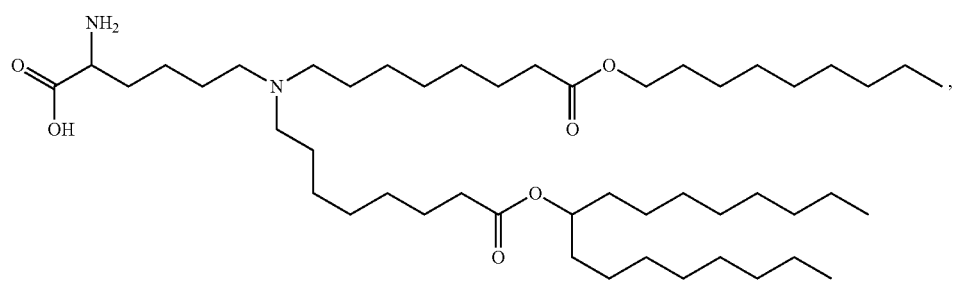

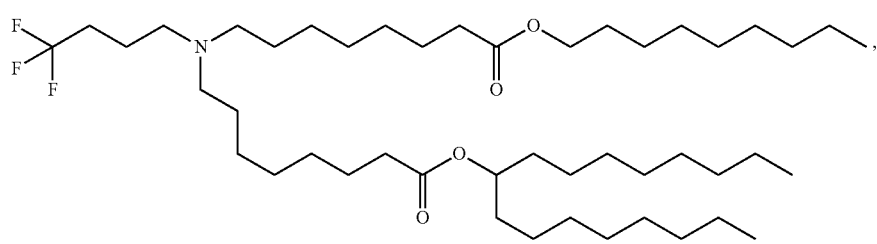
(Compound 107)
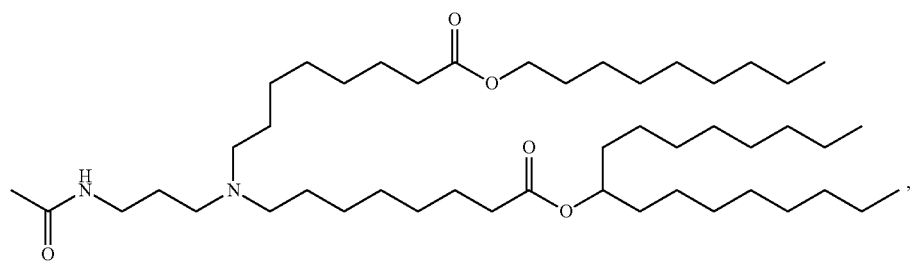
(Compound 108)
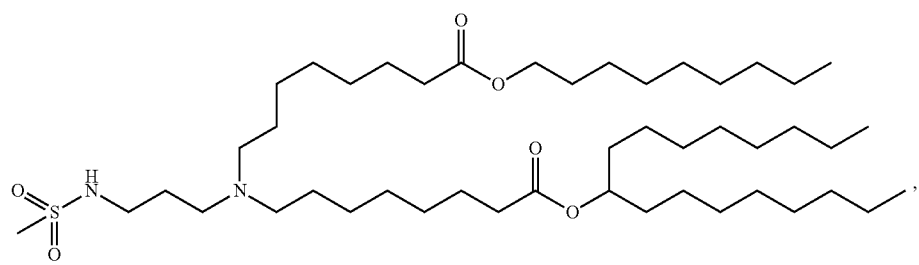
(Compound 109)
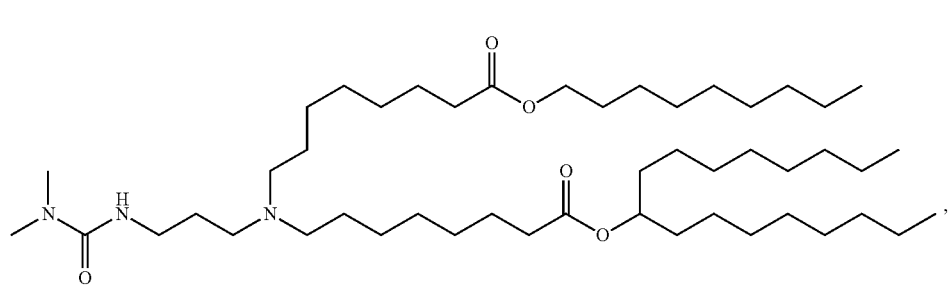
(Compound 110)
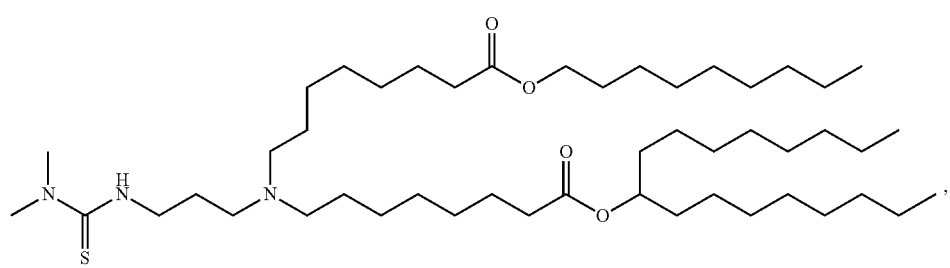
(Compound 111)
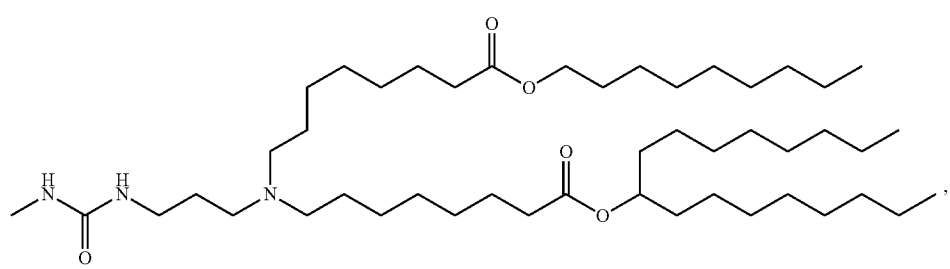
(Compound 112)

(Compound 113)
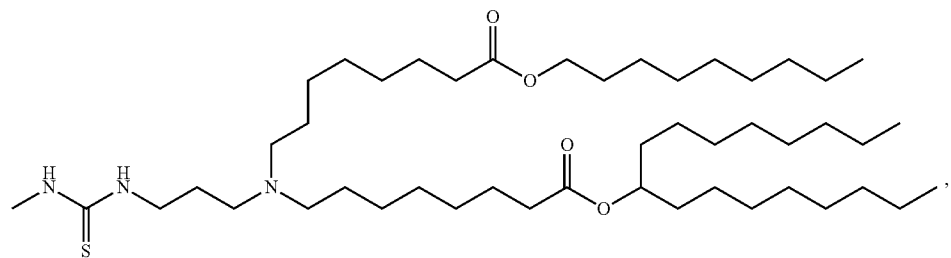
(Compound 114)
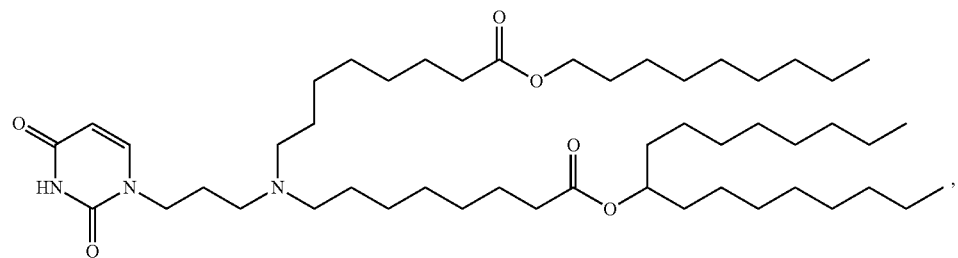
(Compound 115)
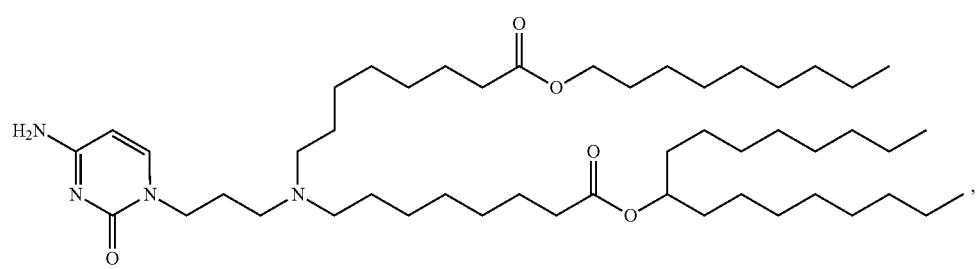
(Compound 116)
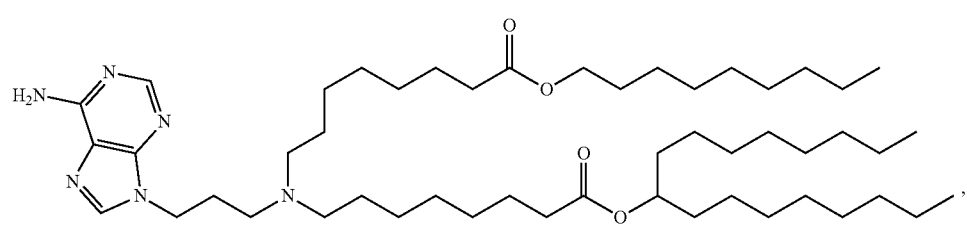
(Compound 117)
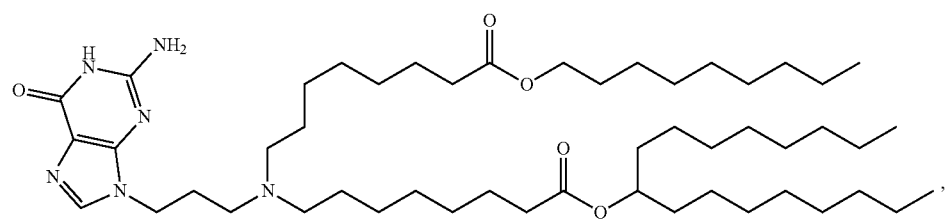
(Compound 118)
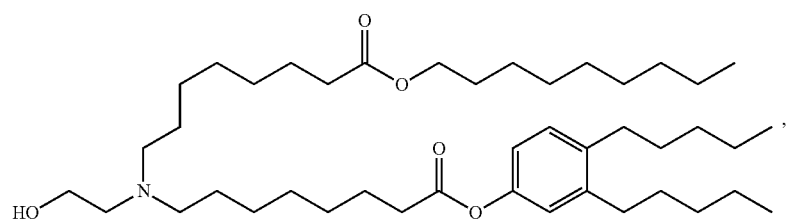

-continued
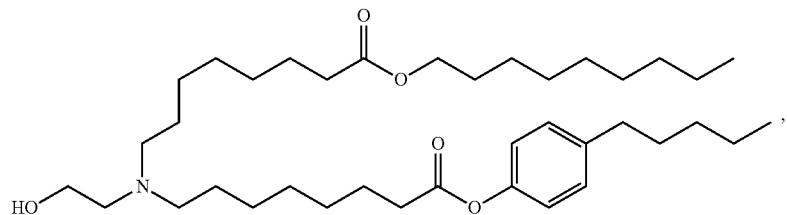
(Compound 119)
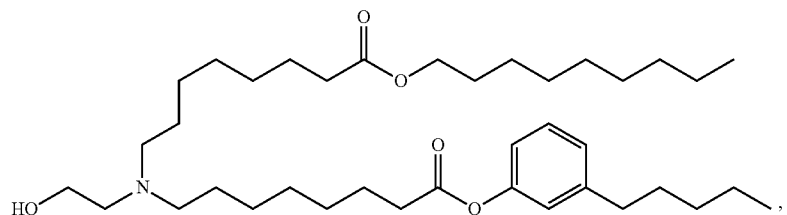
(Compound 120)
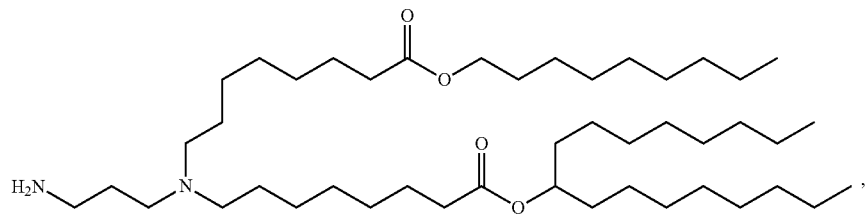
(Compound 121)
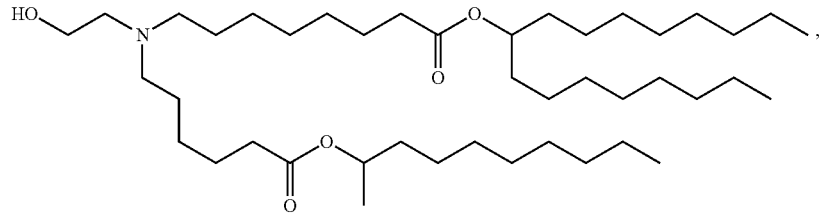
(Compound 122)
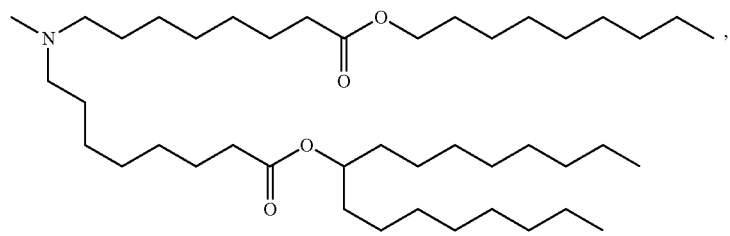
(Compound 123)
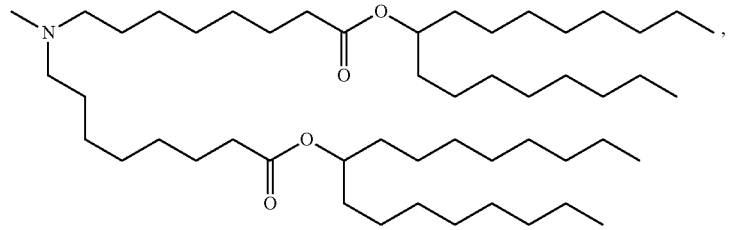
(Compound 124)

(Compound 125)
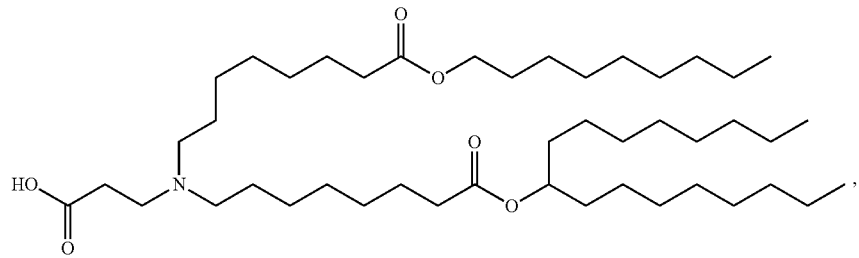
(Compound 126)
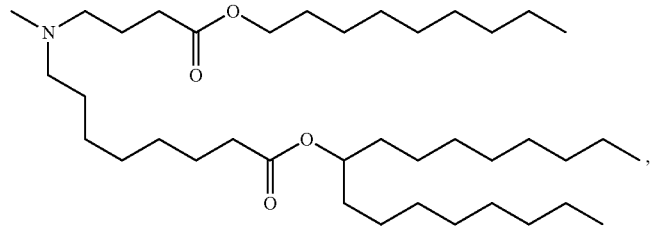
(Compound 127)
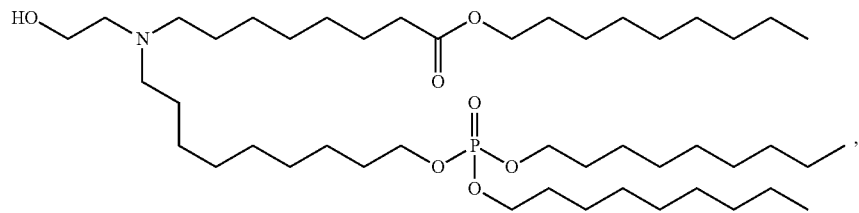
(Compound 128)
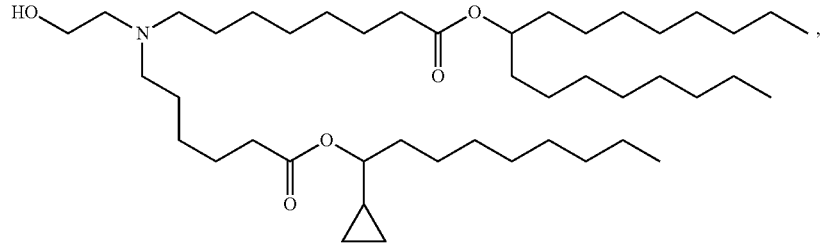
(Compound 129)
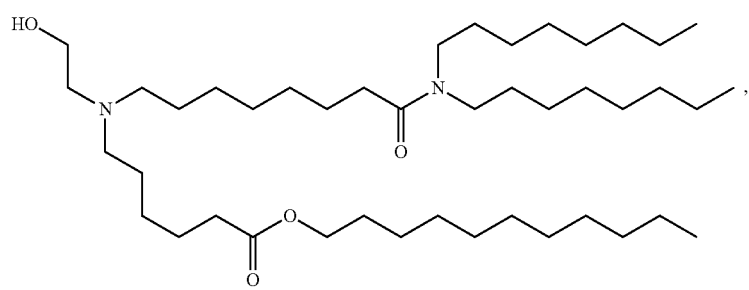
(Compound 130)
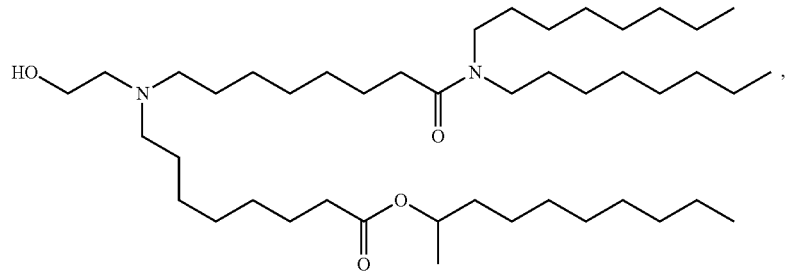

-continued
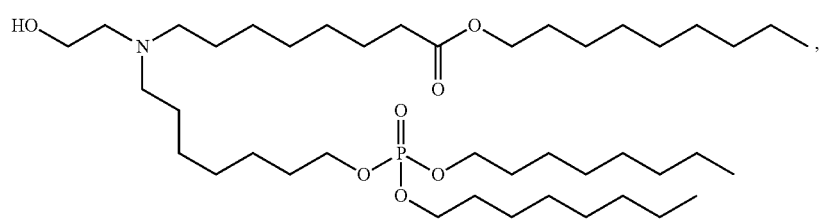
(Compound 131)
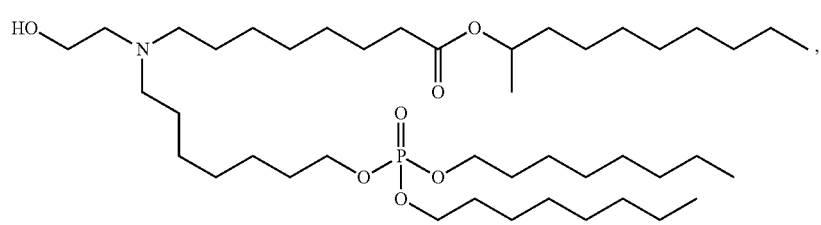
(Compound 132)
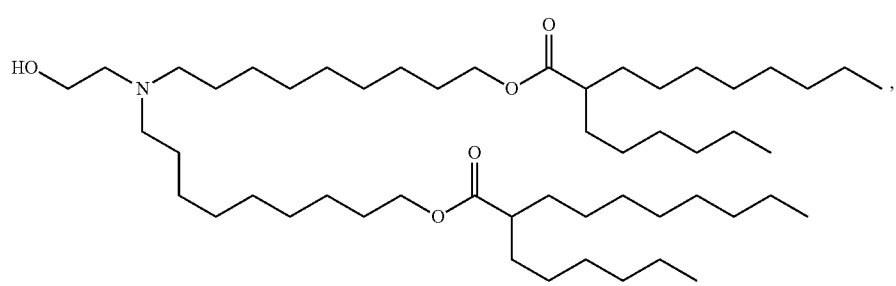
(Compound 133)
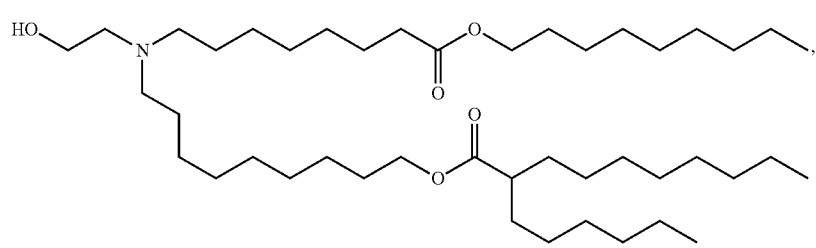
(Compound 134)
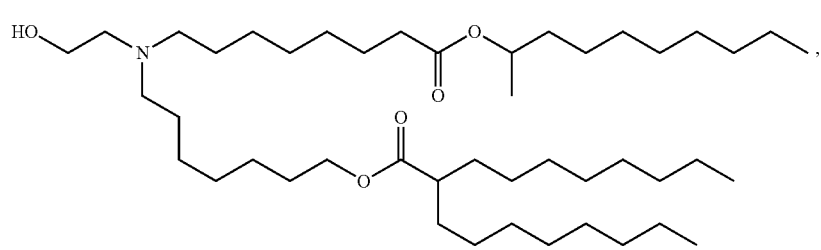
(Compound 135)
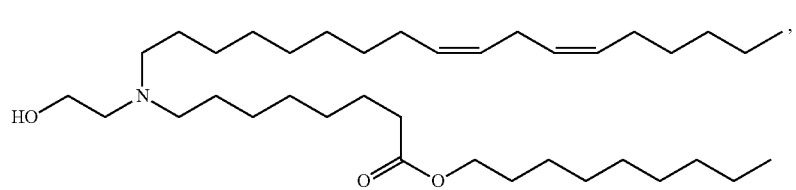
(Compound 136)
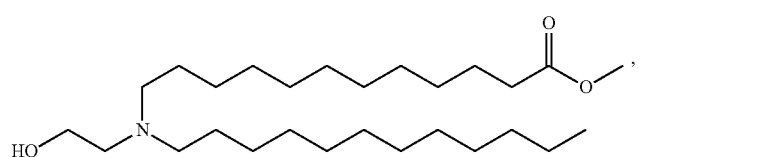
(Compound 137)

-continued
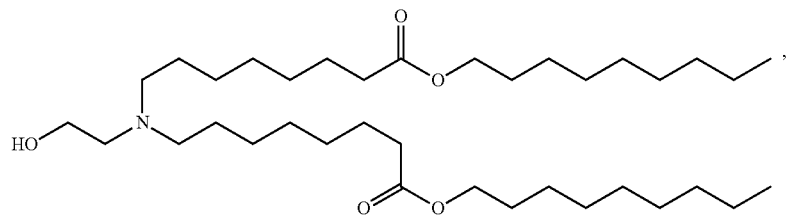
(Compound 138)
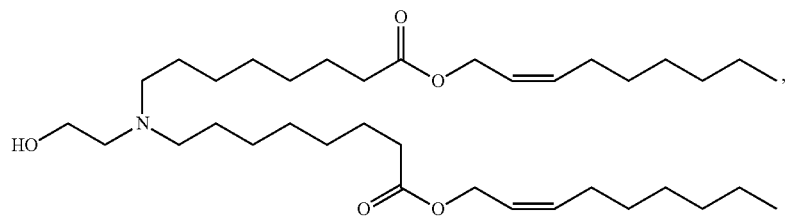
(Compound 139)
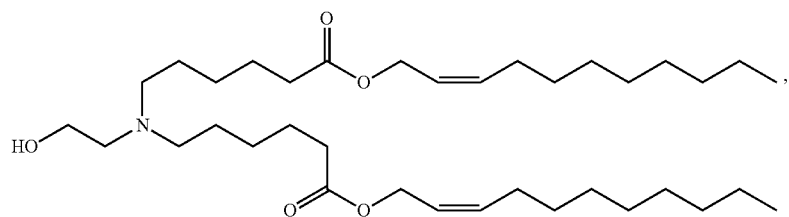
(Compound 140)
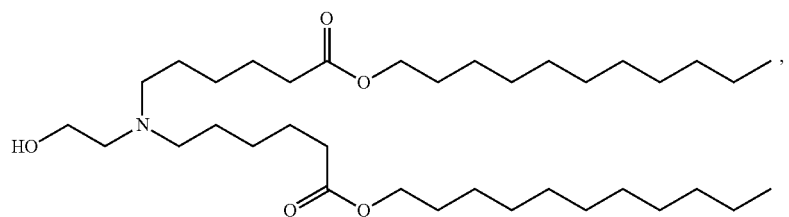
(Compound 141)
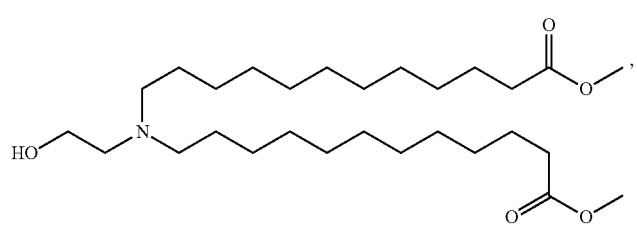
(Compound 142)
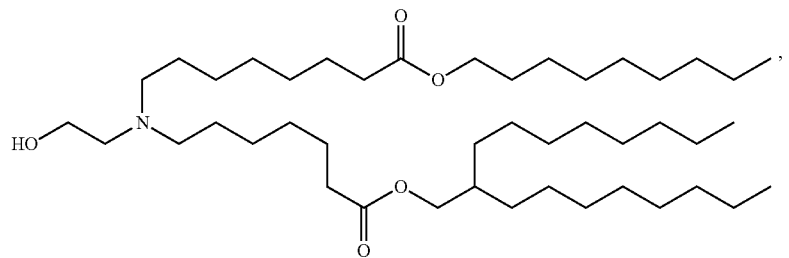
(Compound 143)

-continued
(Compound 144)
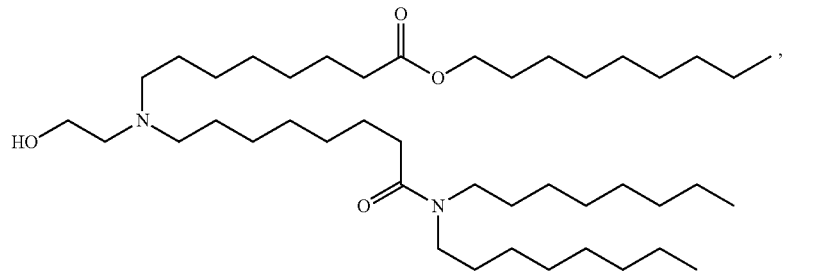
(Compound 145)
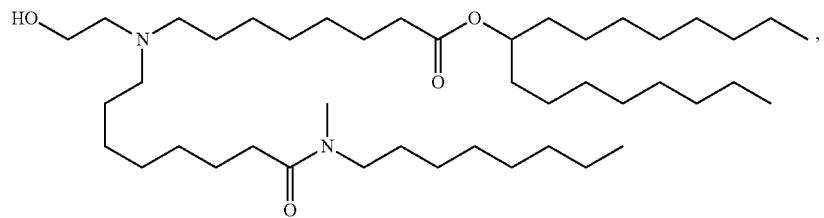
(Compound 146)
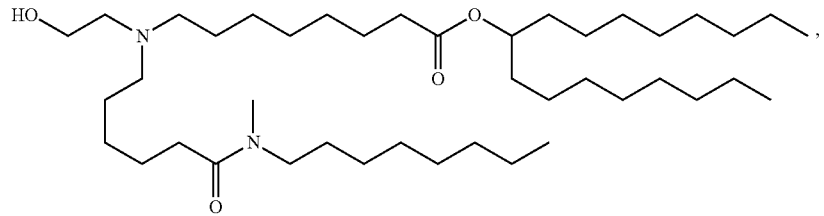
(Compound 147)
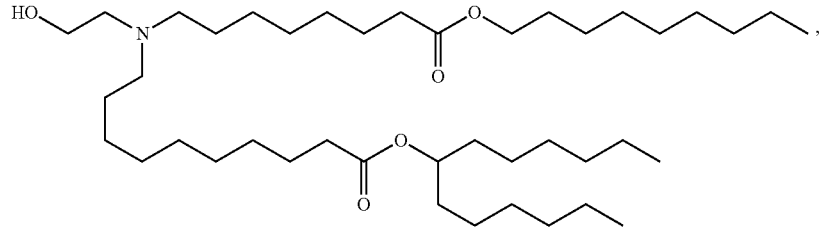
(Compound 148)
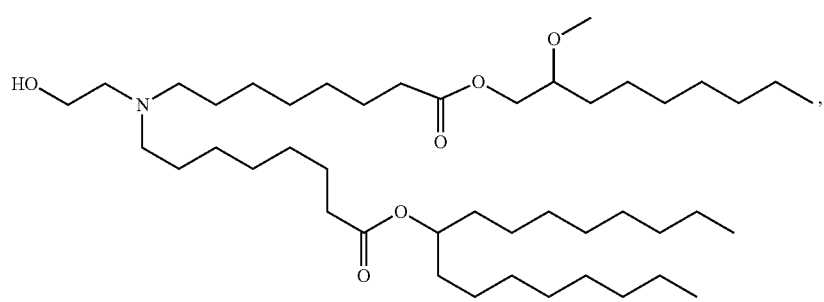
(Compound 149)
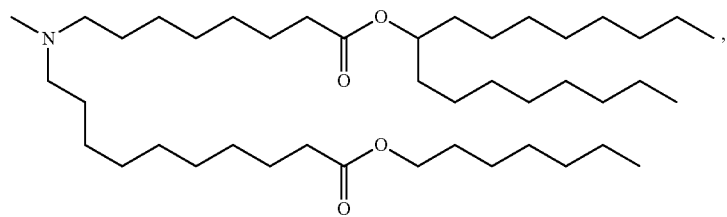

-continued
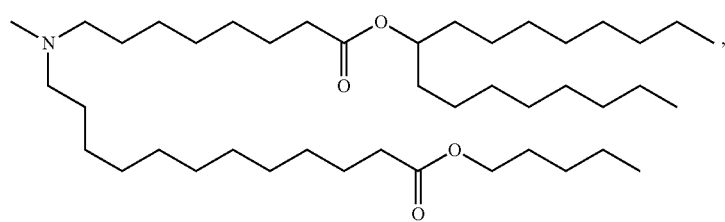
(Compound 150)
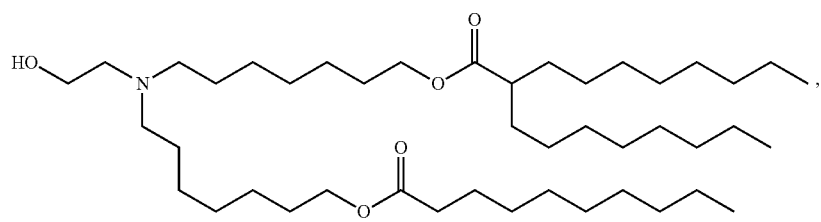
(Compound 151)
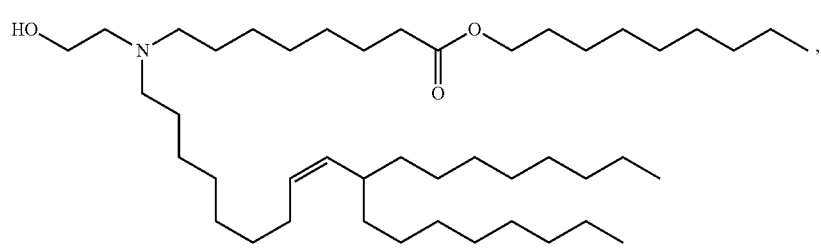
(Compound 152)
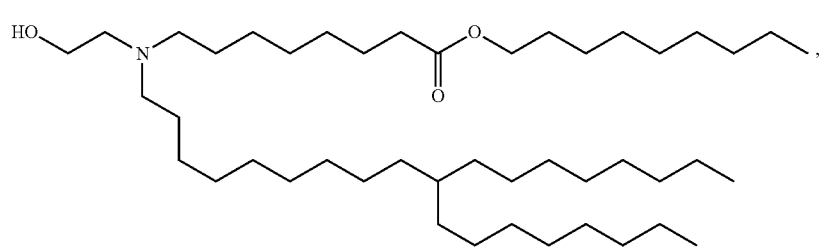
(Compound 153)
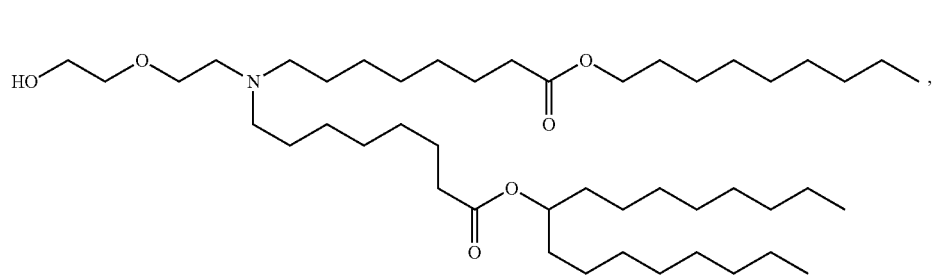
(Compound 154)
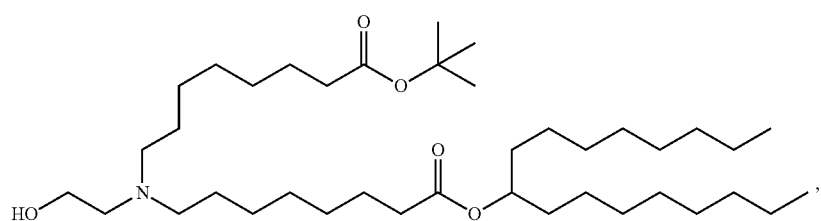
(Compound 155)

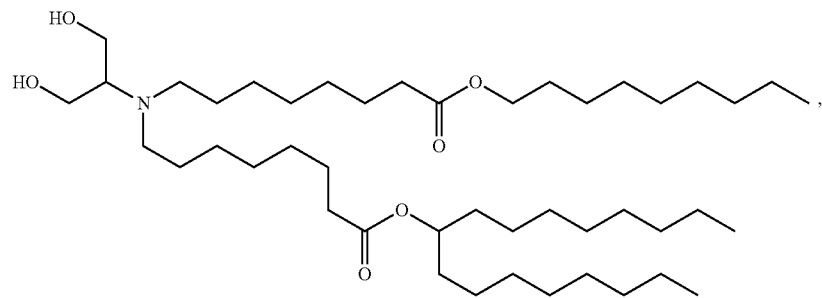
(Compound 156)
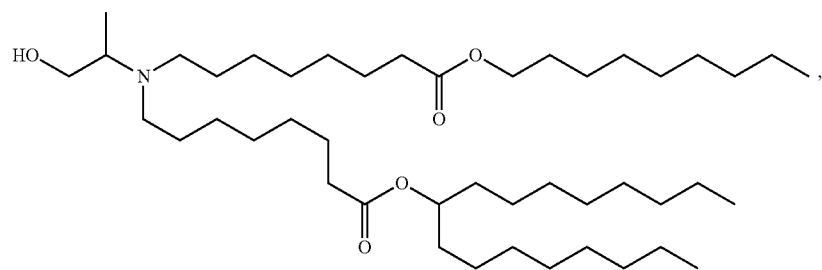
(Compound 157)
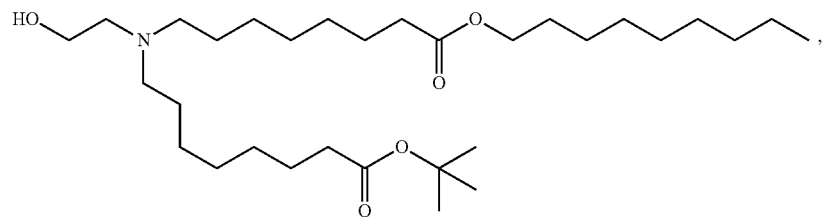
(Compound 158)
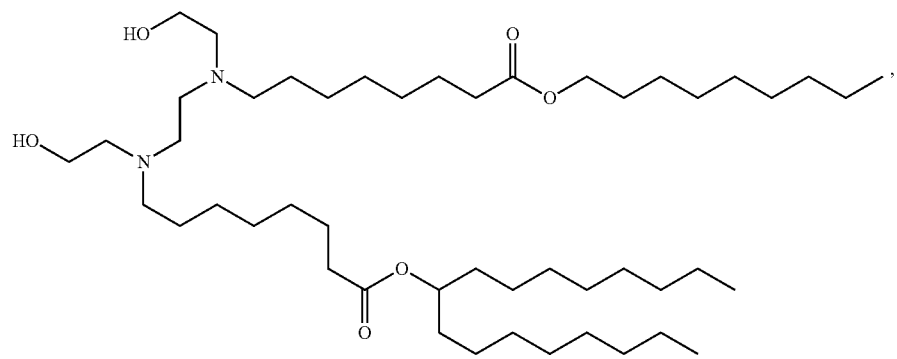
(Compound 159)

-continued
(Compound 160)
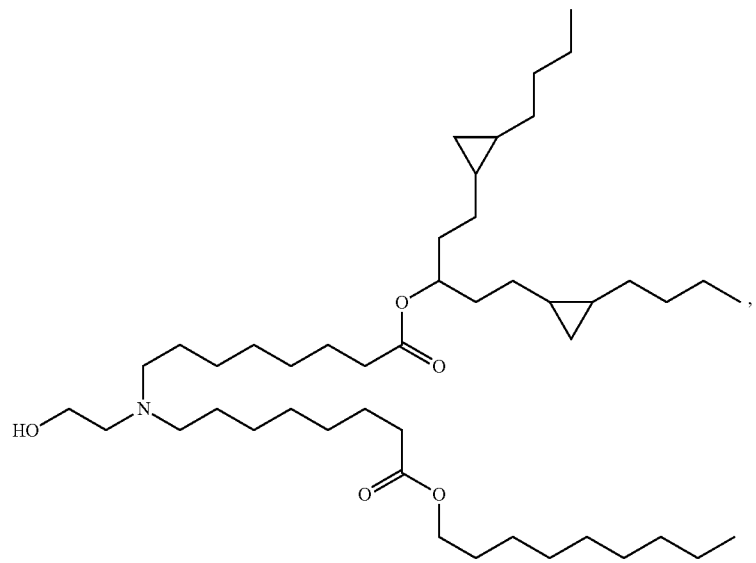
(Compound 161)
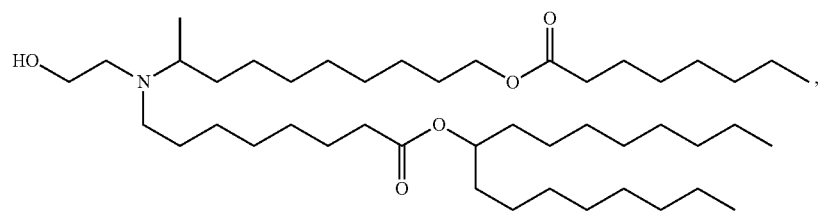
(Compound 162)
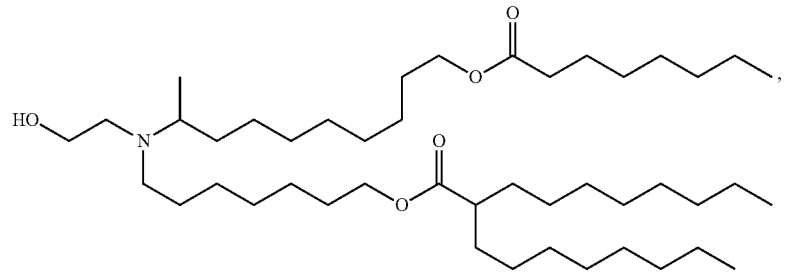
(Compound 163)
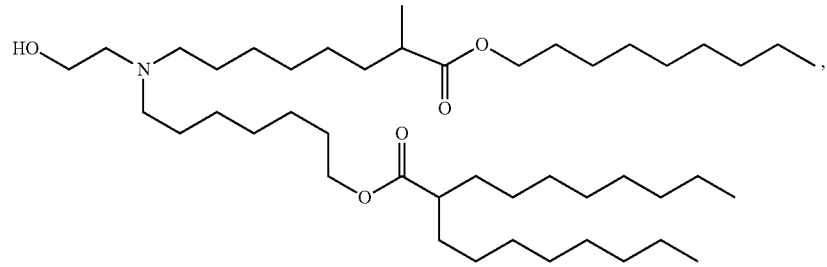
(Compound 164)
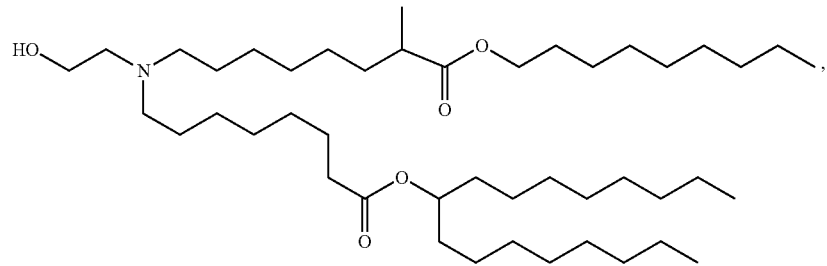

-continued
(Compound 165)
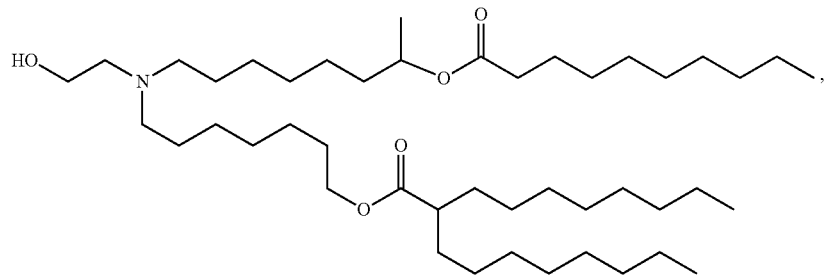
(Compound 166)
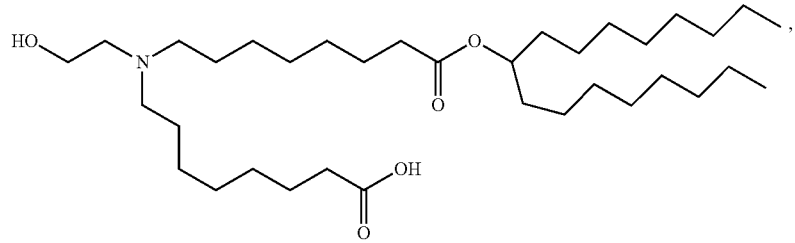
(Compound 167)
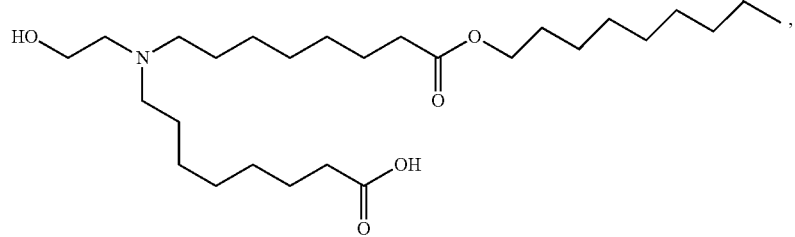
(Compound 168)
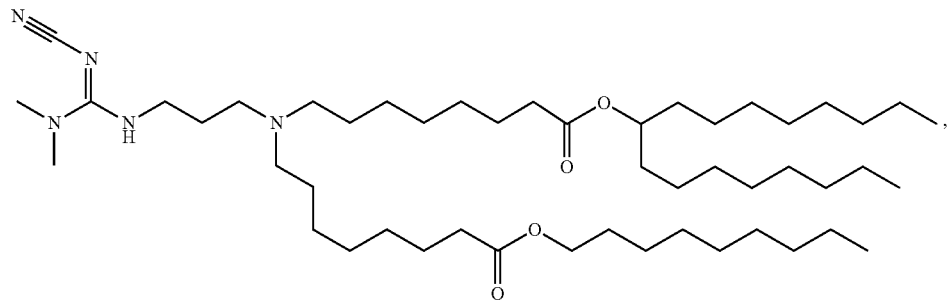
(Compound 169)
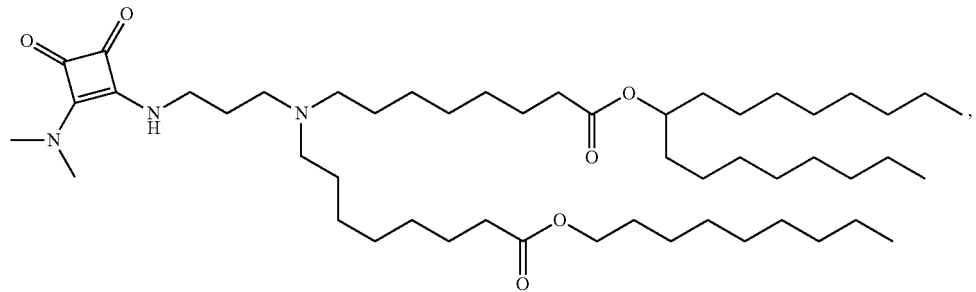

-continued
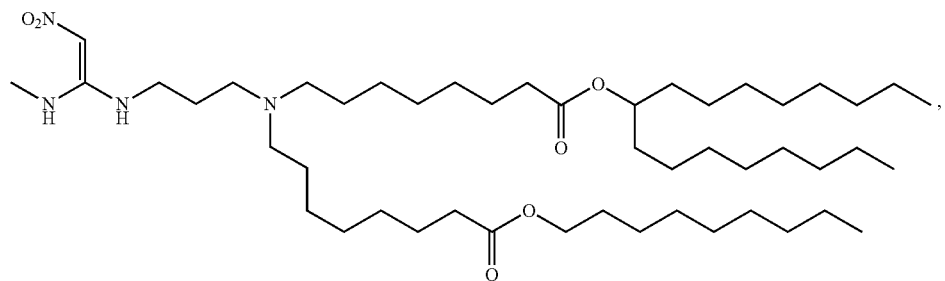
(Compound 170)
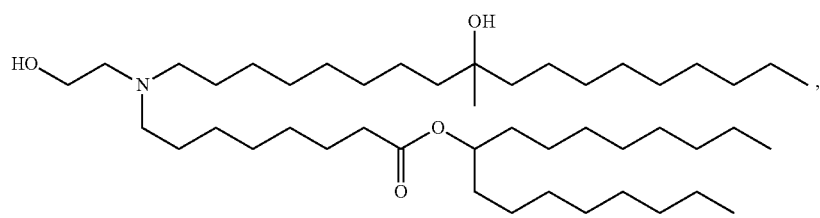
(Compound 171)
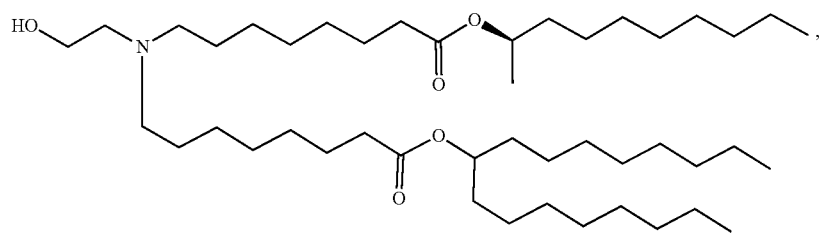
(Compound 172)
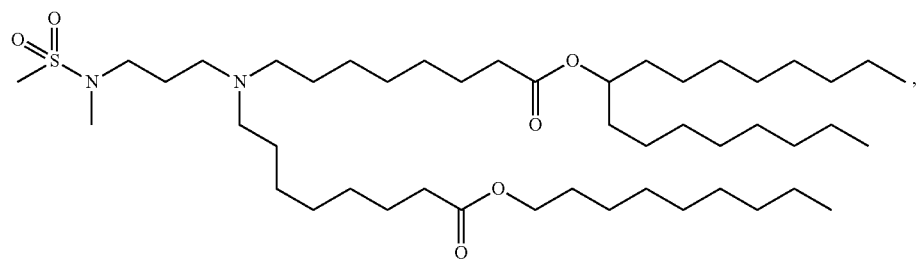
(Compound 173)
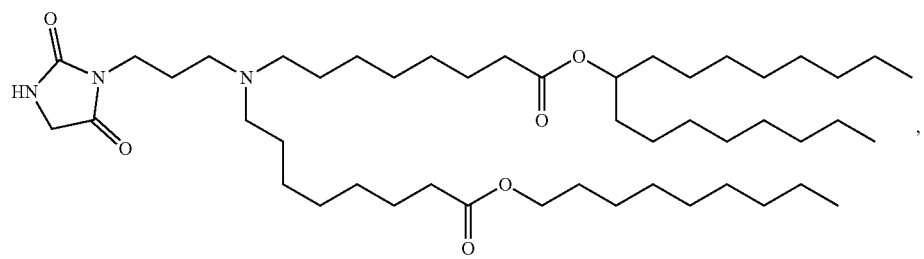
(Compound 174)
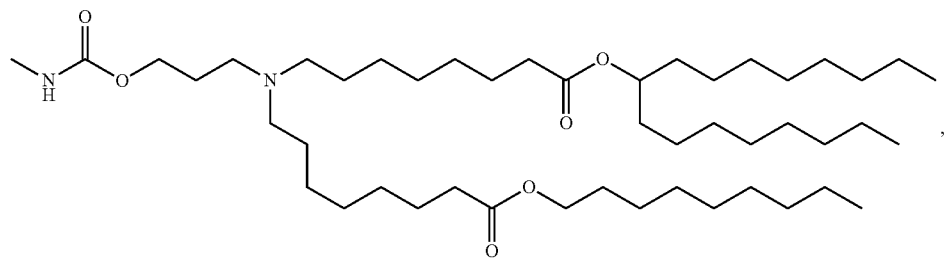
(Compound 175)

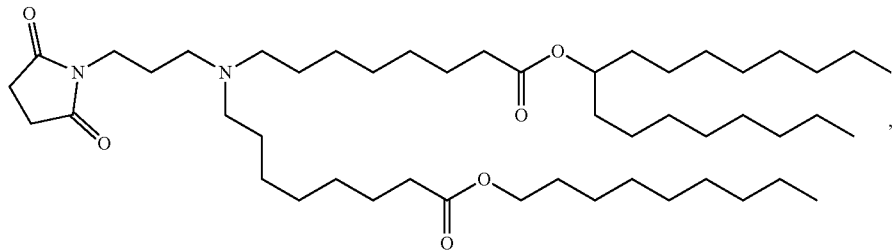
(Compound 176)
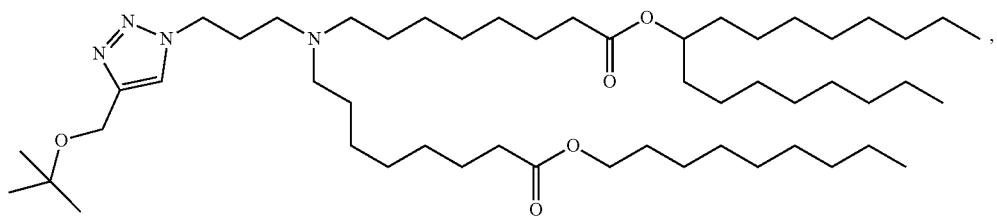
(Compound 177)
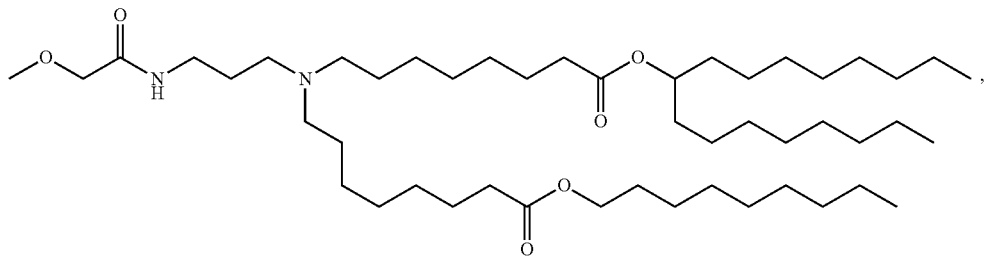
(Compound 178)
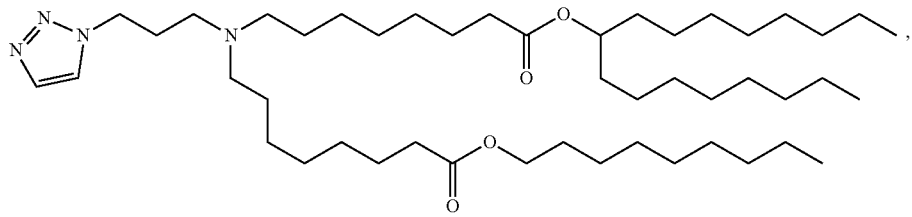
(Compound 179)
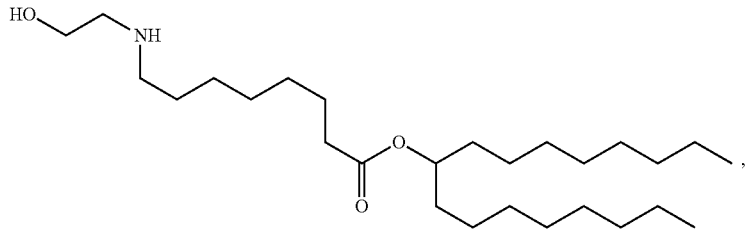
(Compound 180)
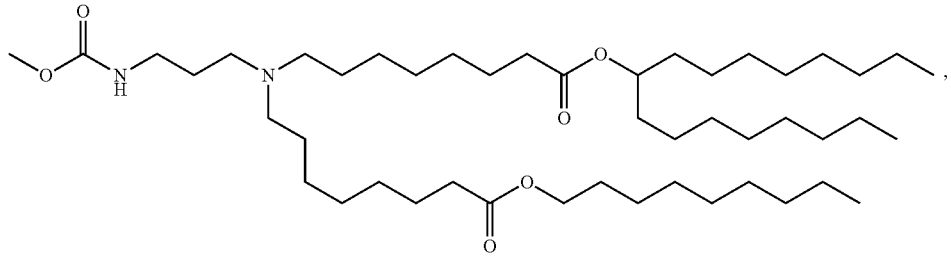
(Compound 181)

(Compound 182)
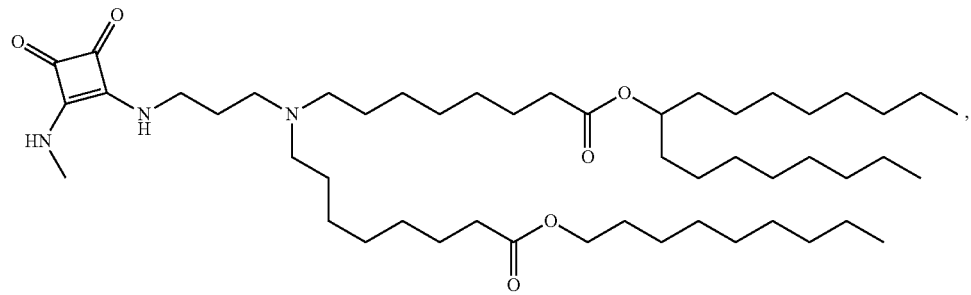
(Compound 183)
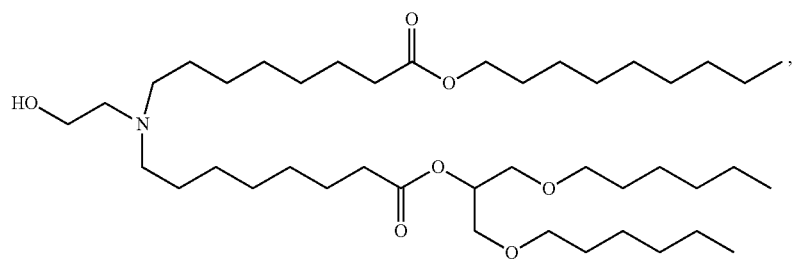
(Compound 184)
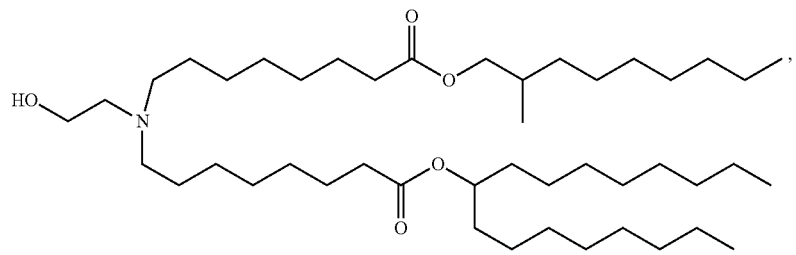
(Compound 185)
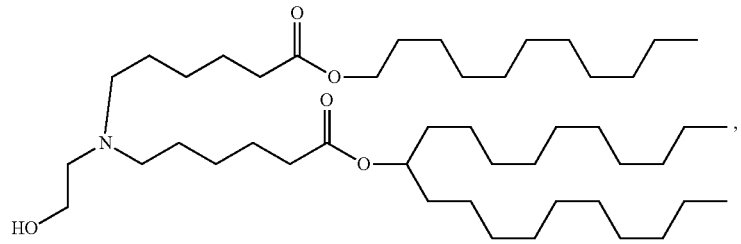
(Compound 186)
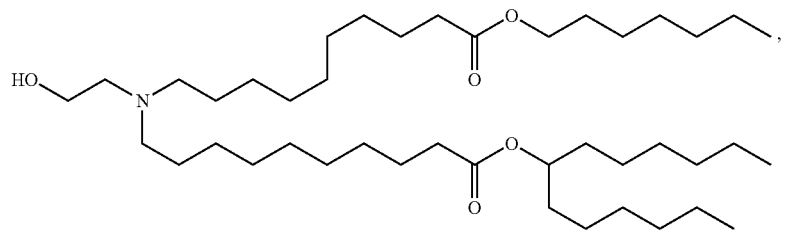
(Compound 187)
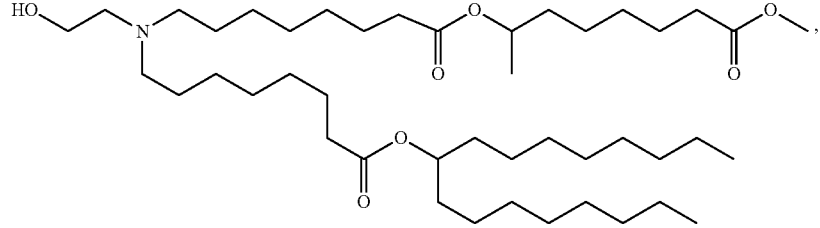

-continued
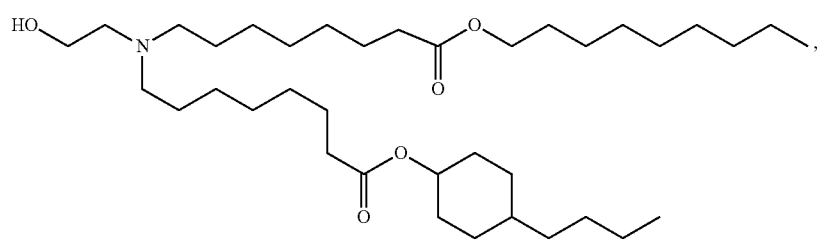
(Compound 188)
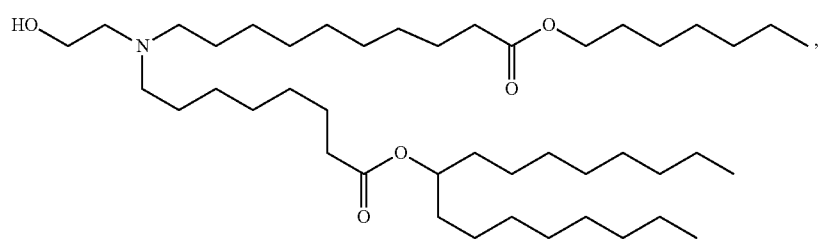
(Compound 189)
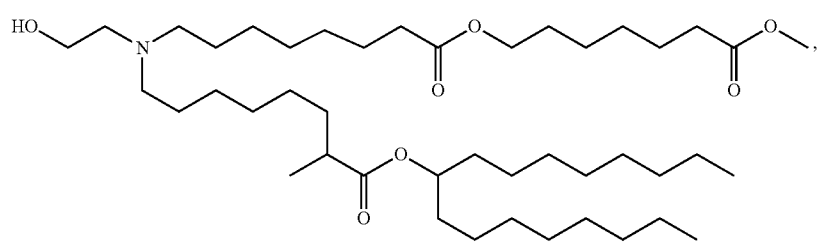
(Compound 190)
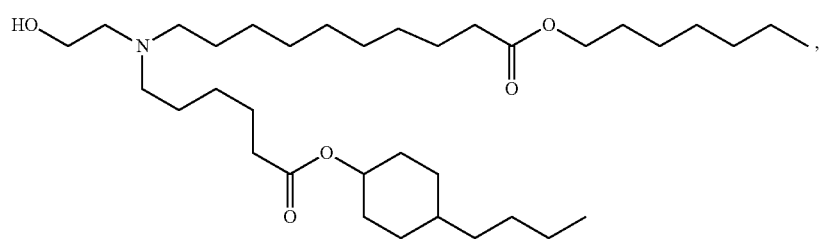
(Compound 191)
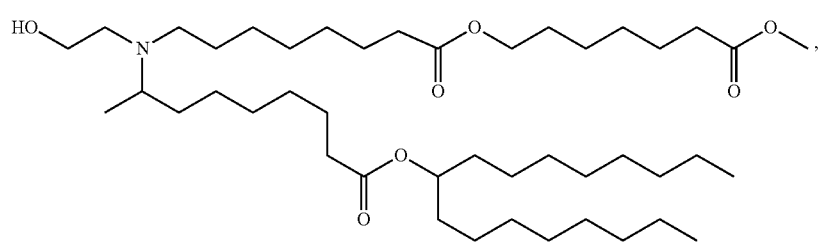
(Compound 192)
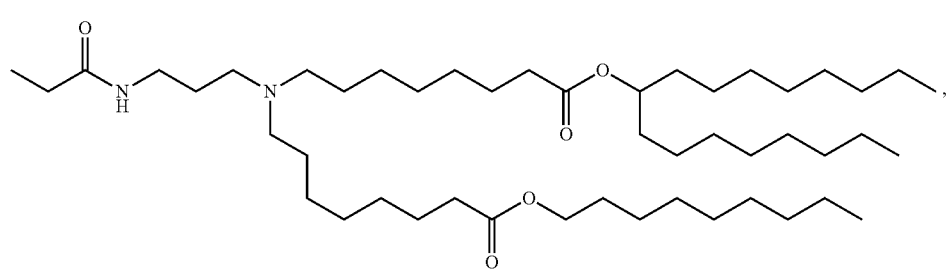
(Compound 193)

-continued
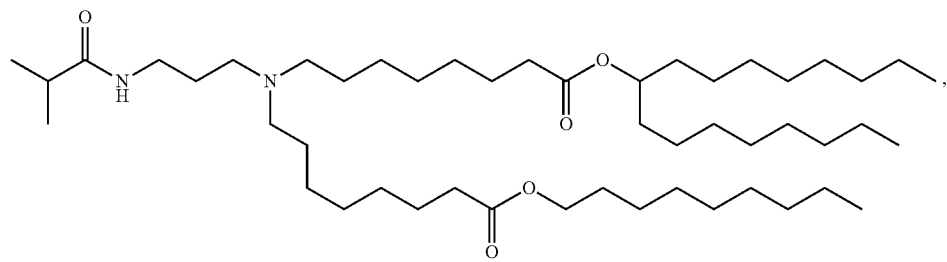
(Compound 194)
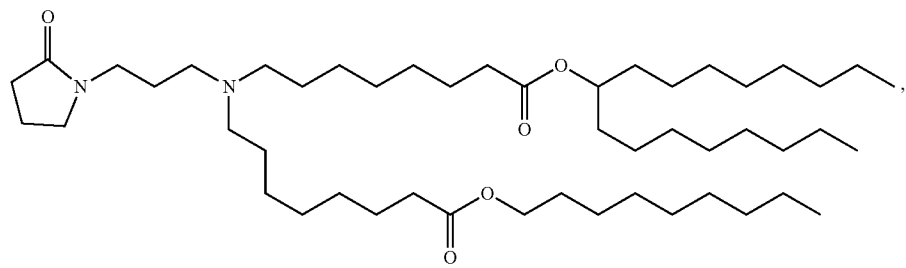
(Compound 195)
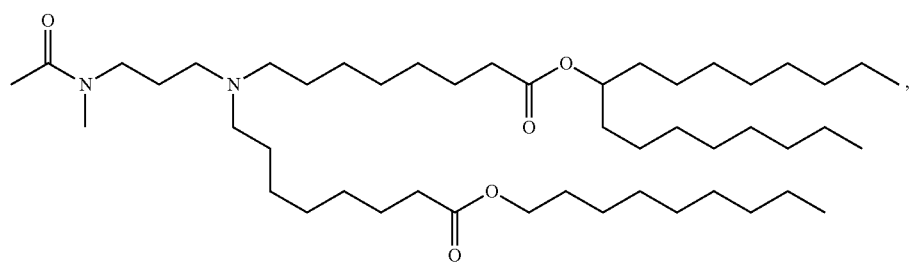
(Compouond 196)
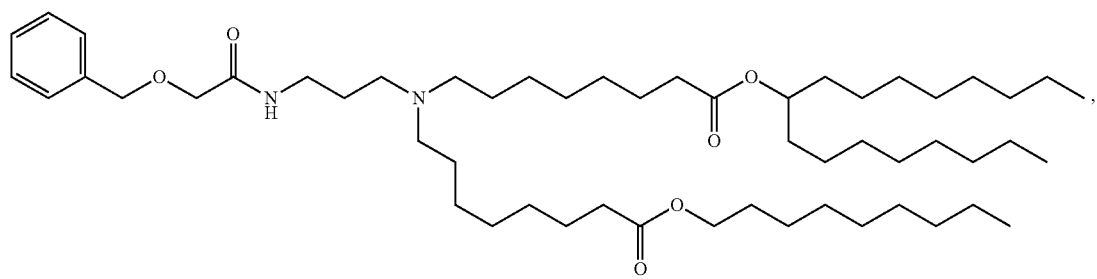
(Compound 197)
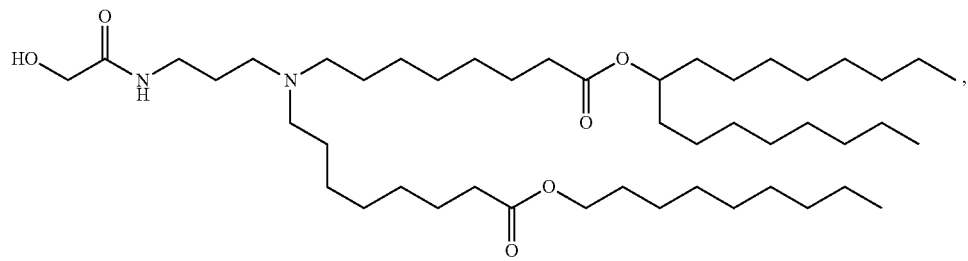
(Compound 198)
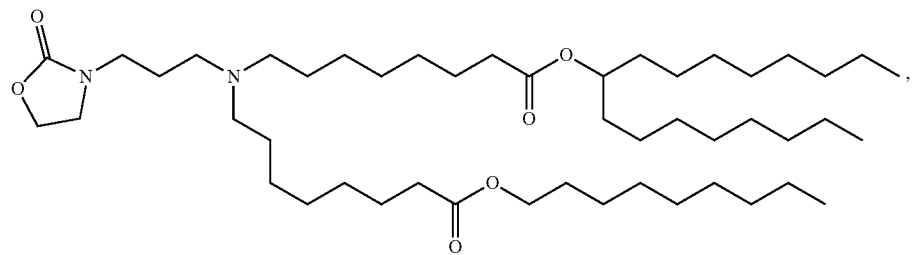
(Compound 199)

-continued
(Compound 200)
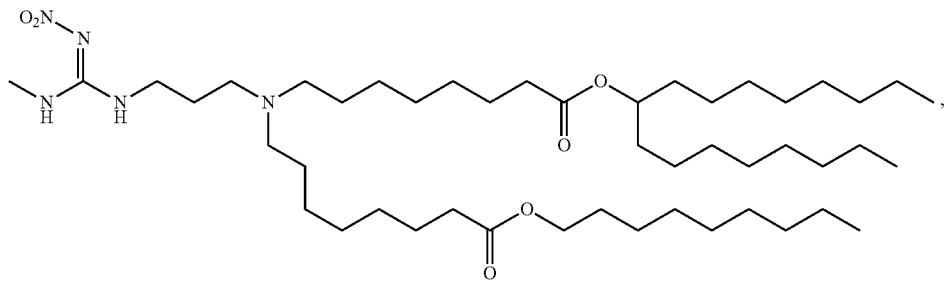
(Compound 201)
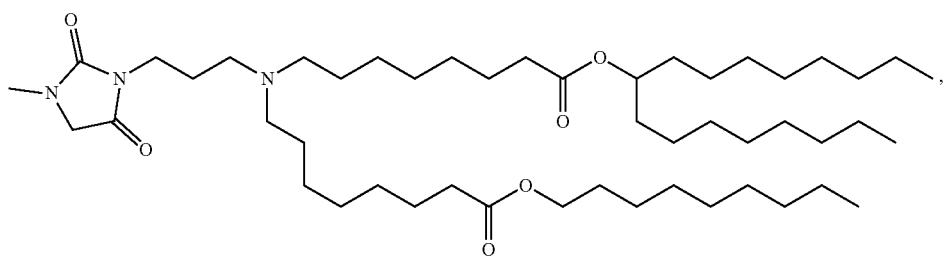
(Compound 202)
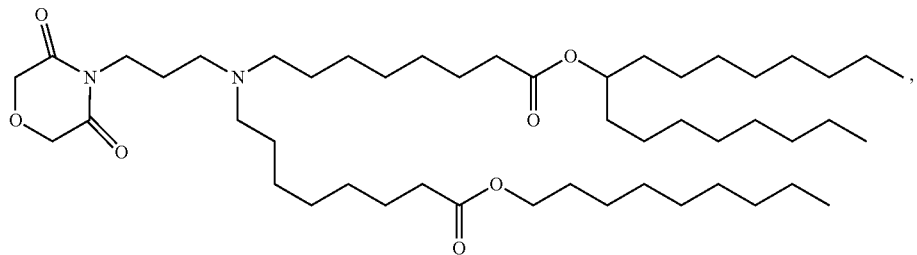
(Compound 203)
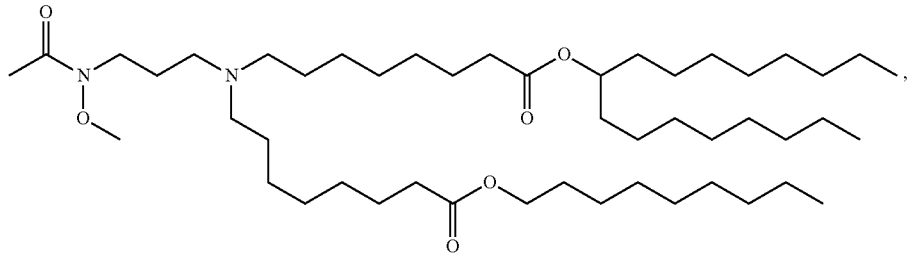
(Compound 204)
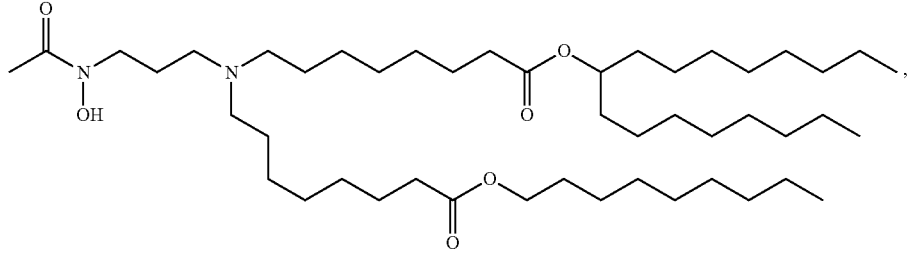
(Compound 205)
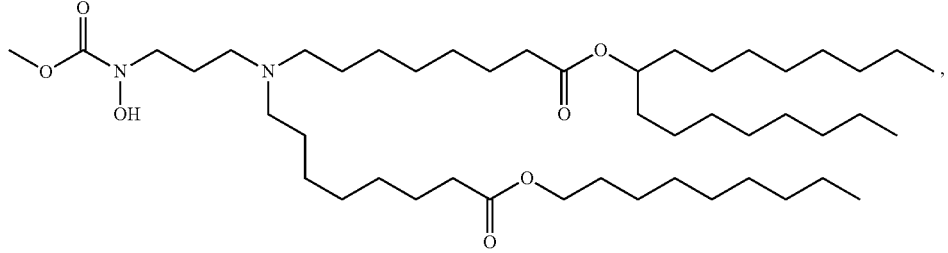

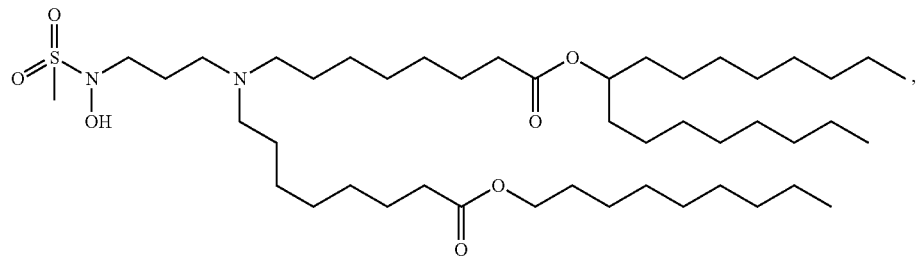
(Compound 206)
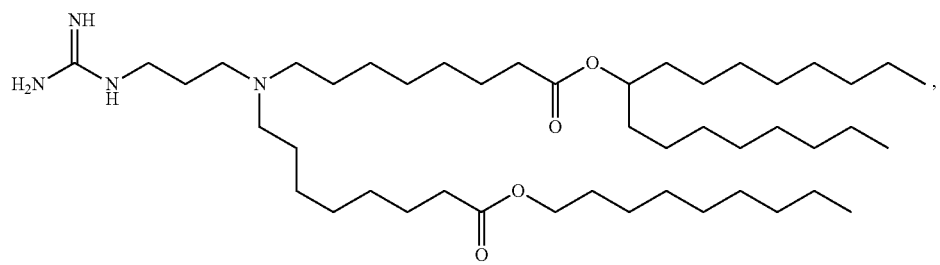
(Compound 207)
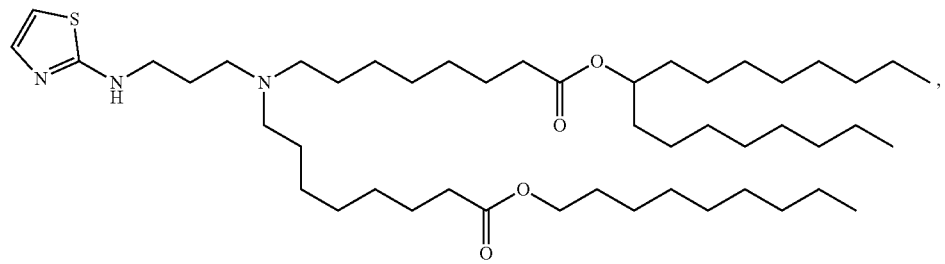
(Compound 208)
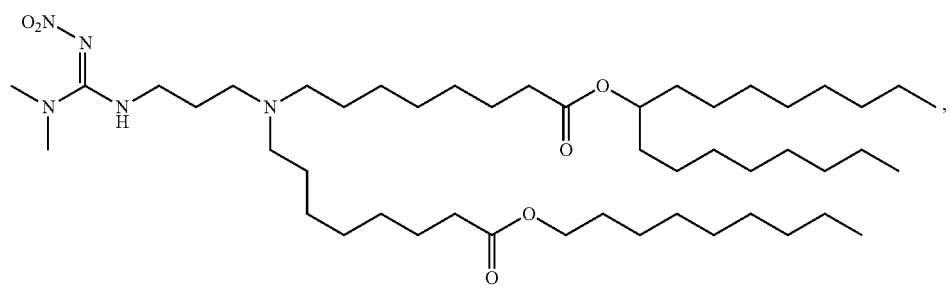
(Compound 209)
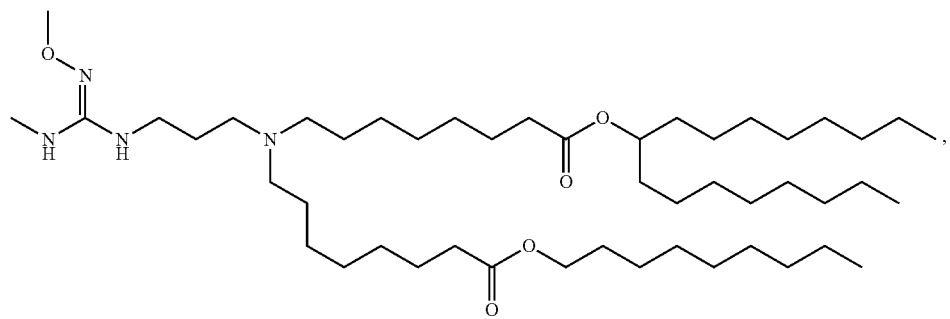
(Compound 210)

(Compound 211)
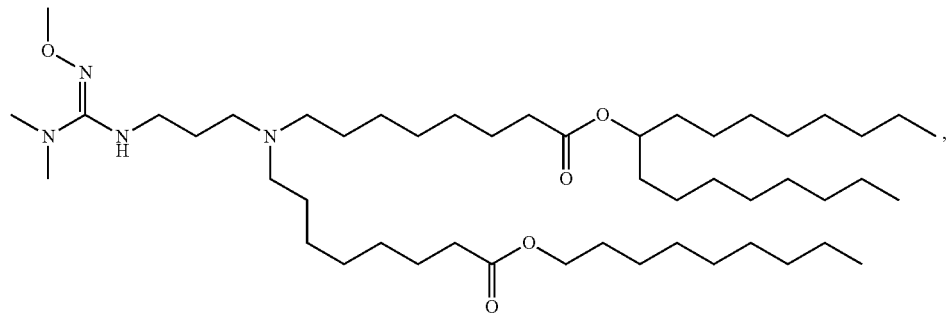
(Compound 212)
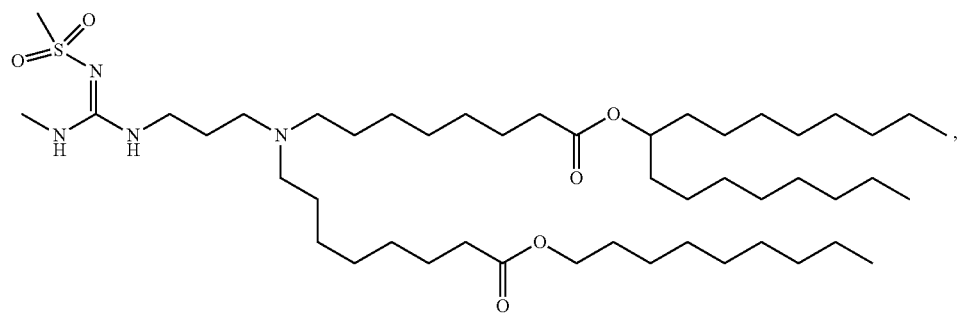
(Compound 213)
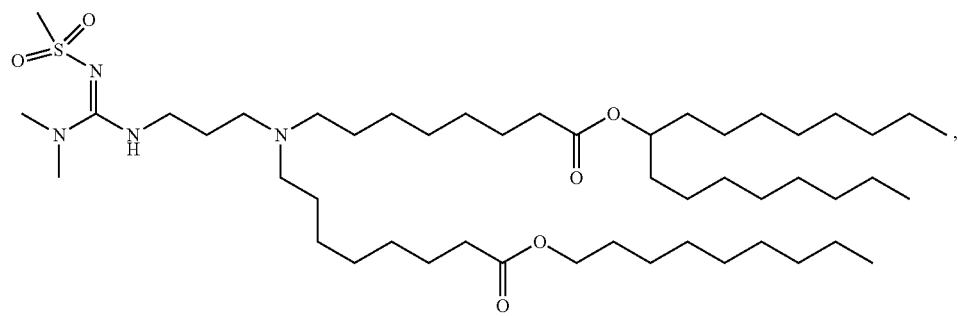
(Compound 214)
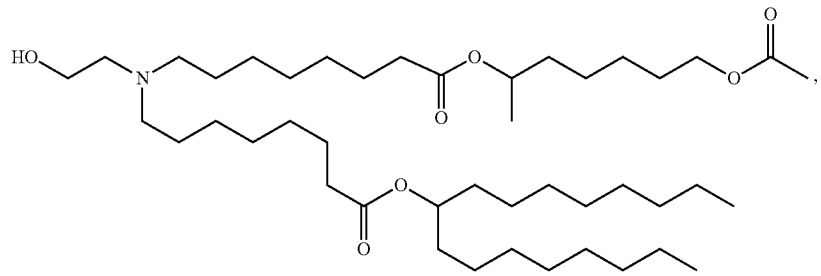
(Compound 215)
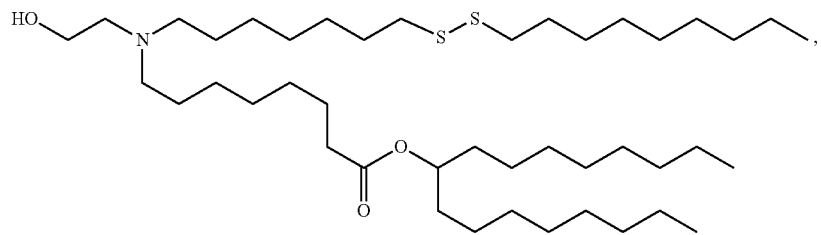

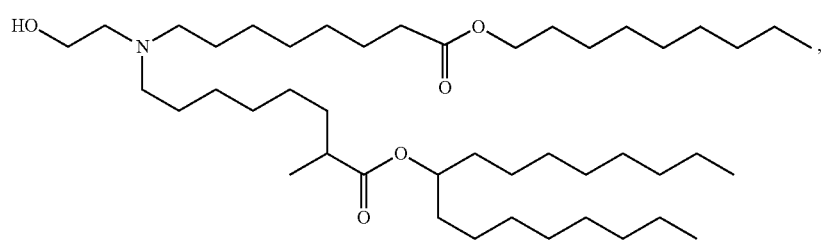
(Compound 216)
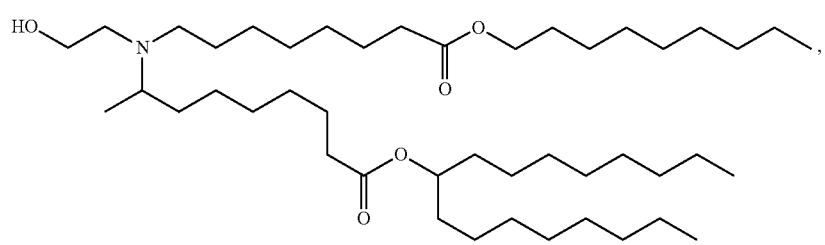
(Compound 217)
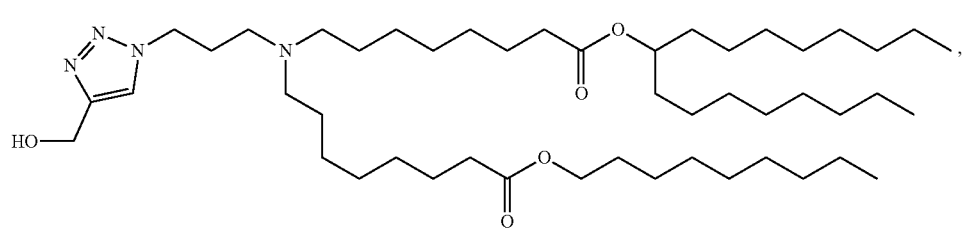
(Compound 218)
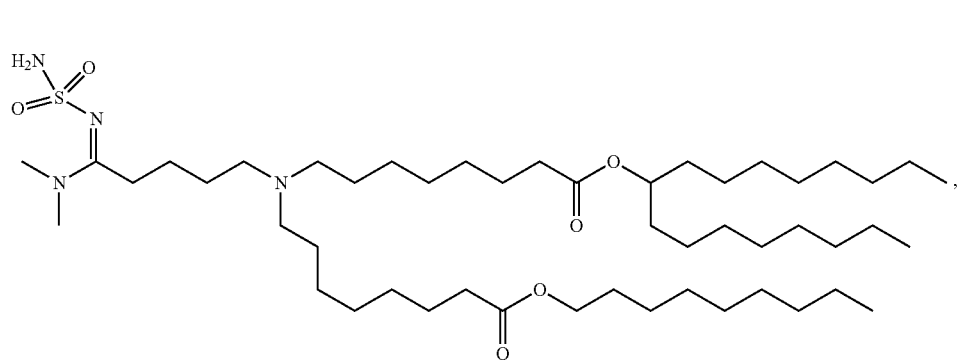
(Compound 219)
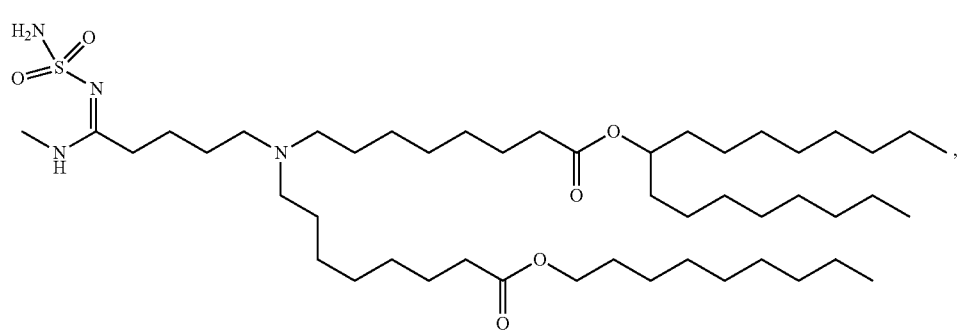
(Compound 220)

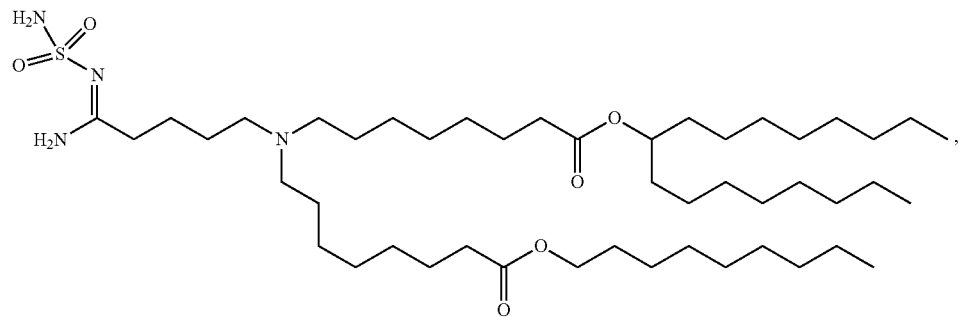
(Compound 221)
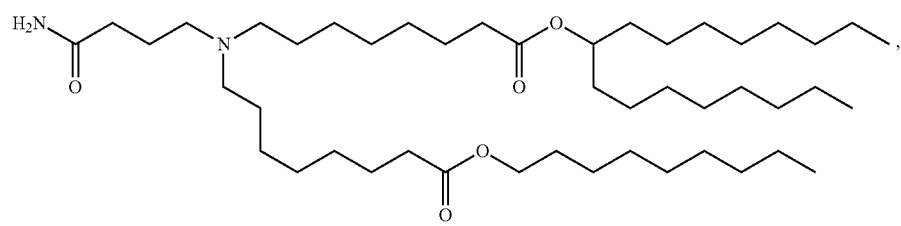
(Compound 222)
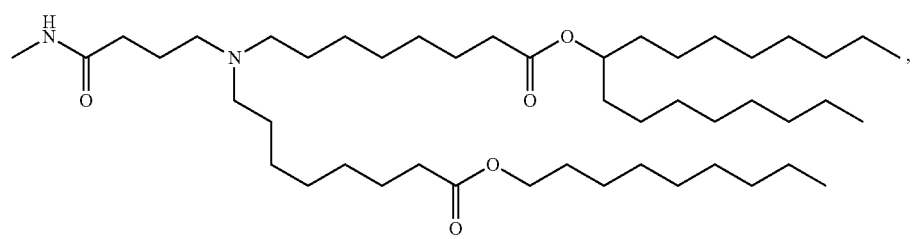
(Compound 223)
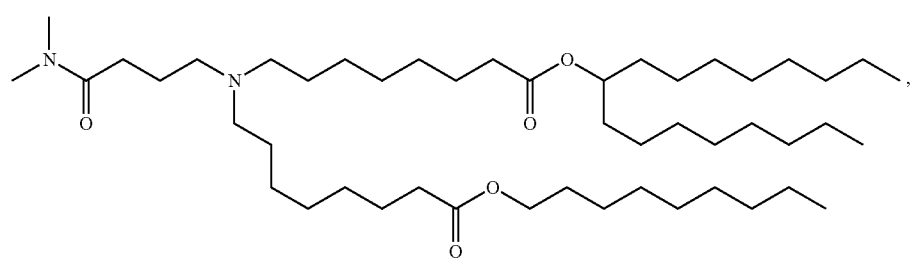
(Compound 224)
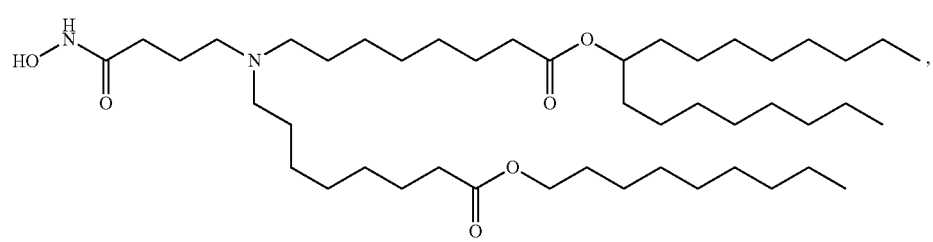
(Compound 225)
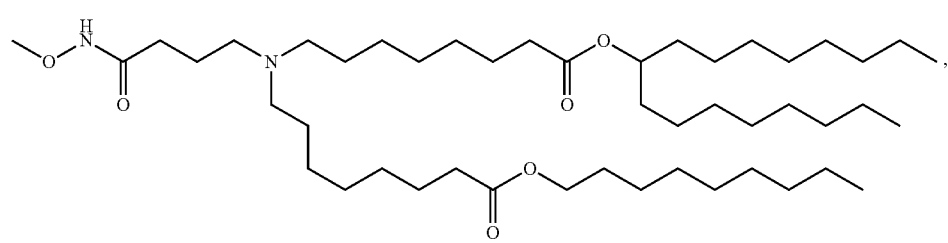
(Compound 226)

-continued
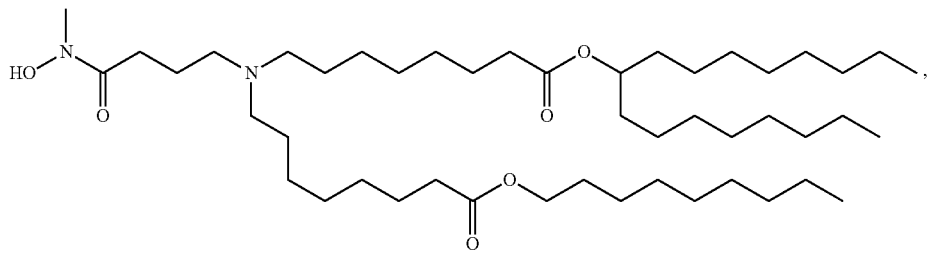
(Compound 227)
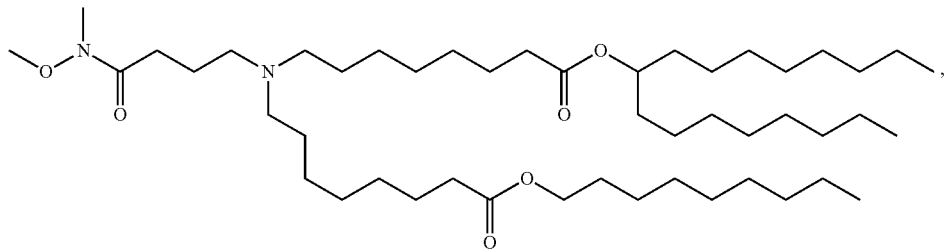
(Compound 228)
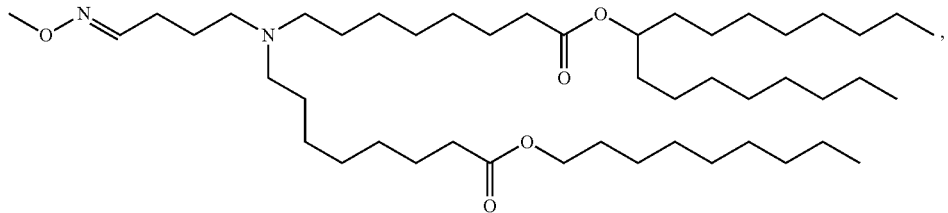
(Compound 229)
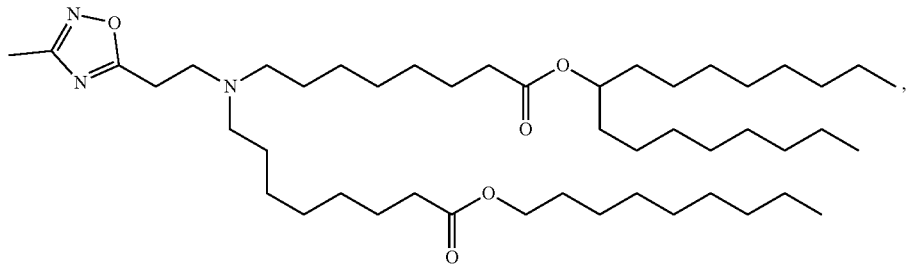
(Compound 230)
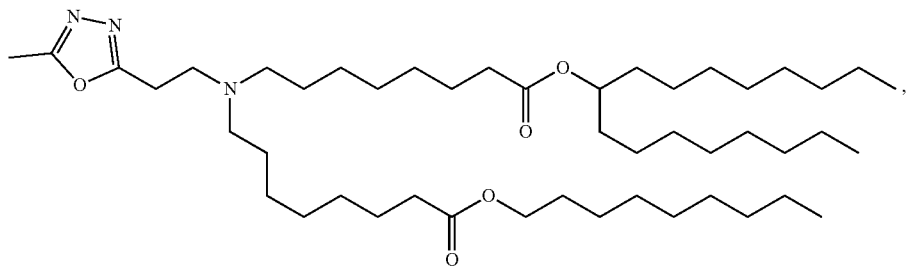
(Compound 231)
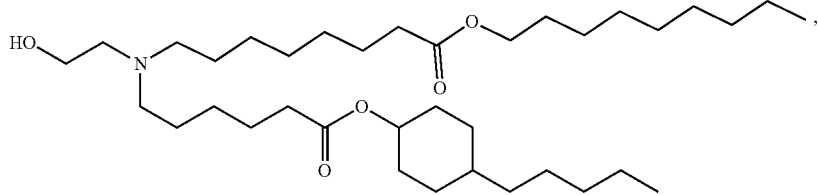
(Compound 232)
and salts or stereoisomers thereof.

In other embodiments, the compound of Formula (I) is selected from the group consisting of Compound 1-Compound 147, or salt or stereoisomers thereof.

In some embodiments ionizable lipids including a central piperazine moiety are provided.

In some embodiments, the delivery agent comprises a lipid compound having the Formula (III)

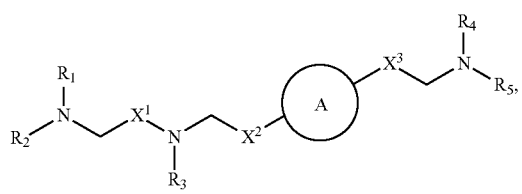

(III)

or salts or stereoisomers thereof, wherein
ring A is

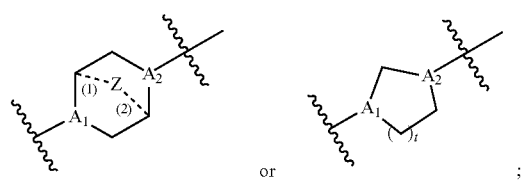

t is 1 or 2;

$A_1$ and $A_2$ are each independently selected from CH or N;

Z is $CH_2$ or absent wherein when Z is $CH_2$, the dashed lines (1) and (2) each represent a single bond; and when Z is absent, the dashed lines (1) and (2) are both absent;

$R_1$, $R_2$, $R_3$, $R_4$, and $R_5$ are independently selected from the group consisting of $C_{5-20}$ alkyl, $C_{5-20}$ alkenyl, —R"MR', —R*YR", —YR", and —R*OR";

each M is independently selected from the group consisting of —C(O)O—, —OC(O)—, —OC(O)O—, —C(O)N(R')—, —N(R')C(O)—, —C(O)—, —C(S)—, —C(S)S—, —SC(S)—, —CH(OH)—, —P(O)(OR')O—, —S(O)$_2$—, an aryl group, and a heteroaryl group;

$X^1$, $X^2$, and $X^3$ are independently selected from the group consisting of a bond, —CH$_2$—, —(CH$_2$)$_2$—, —CHR—, —CHY—, —C(O)—, —C(O)O—, —OC(O)—, —C(O)—CH$_2$—, —CH$_2$—C(O)—, —C(O)O—CH$_2$—, —OC(O)—CH$_2$—, —CH$_2$—C(O)O—, —CH$_2$—OC(O)—, —CH(OH)—, —C(S)—, and —CH(SH)—;

each Y is independently a $C_{3-6}$ carbocycle;

each R* is independently selected from the group consisting of $C_{1-12}$ alkyl and $C_{2-12}$ alkenyl;

each R is independently selected from the group consisting of $C_{1-3}$ alkyl and a $C_{3-6}$ carbocycle;

each R' is independently selected from the group consisting of $C_{1-12}$ alkyl, $C_{2-12}$ alkenyl, and H; and each R" is independently selected from the group consisting of $C_{3-12}$ alkyl and $C_{3-12}$ alkenyl, wherein when ring A is

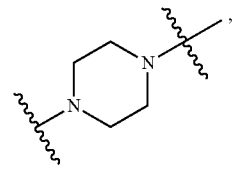 [SMILES: *N1CCN(*)CC1]

then
i) at least one of $X^1$, $X^2$, and $X^3$ is not —CH$_2$—; and/or
ii) at least one of $R_1$, $R_2$, $R_3$, $R_4$, and $R_5$ is —R"MR'.

In some embodiments, the compound is of any of Formulae (IIIa1)-(IIIa6):

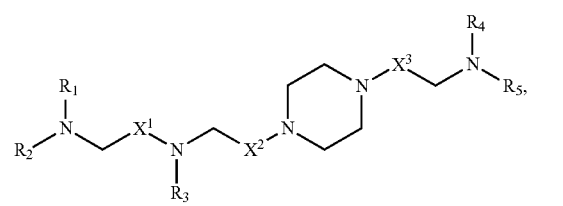

(IIIa1)

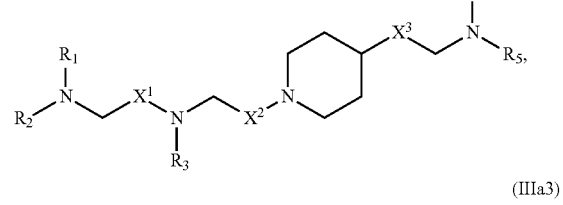

(IIIa2)

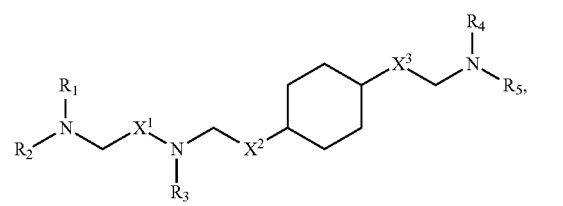

(IIIa3)

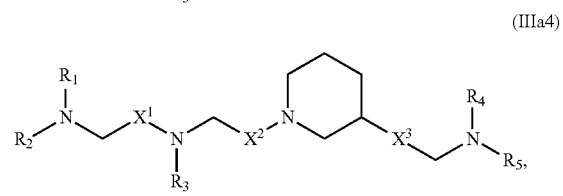

(IIIa4)

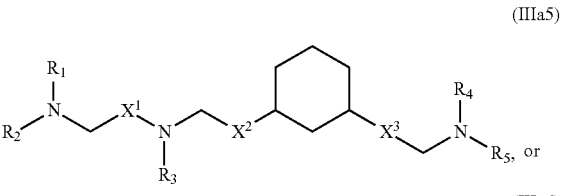

(IIIa5)

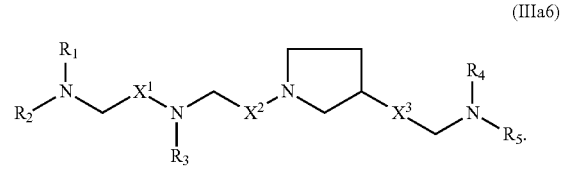

(IIIa6)

The compounds of Formula (III) or any of (IIIa1)-(IIIa6) include one or more of the following features when applicable.

In some embodiments, ring A is

In some embodiments, ring A is or

In some embodiments, ring A is

In some embodiments, ring A is

In some embodiments, ring A is

, or

In some embodiments, ring A is or wherein ring, in which the N atom is connected with $X^2$.

In some embodiments, Z is $CH_2$

In some embodiments, Z is absent.

In some embodiments, at least one of $A_1$ and $A_2$ is N.

In some embodiments, each of $A_1$ and $A_2$ is N.

In some embodiments, each of $A_1$ and $A_2$ is CH.

In some embodiments, $A_1$ is N and $A_2$ is CH.

In some embodiments, $A_1$ is CH and $A_2$ is N.

In some embodiments, at least one of $X^1$, $X^2$, and $X^3$ is not —$CH_2$—. For example, in certain embodiments, $X^1$ is not —$CH_2$—. In some embodiments, at least one of $X^1$, $X^2$, and $X^3$ is —C(O)—.

In some embodiments, $X^2$ is —C(O)—, —C(O)O—, —OC(O)—, —C(O)—$CH_2$—, —$CH_2$—C(O)—, —C(O)O—$CH_2$—, —OC(O)—$CH_2$—, —$CH_2$—C(O)O—, or —$CH_2$—OC(O)—.

In some embodiments, $X^3$ is —C(O)—, —C(O)O—, —OC(O)—, —C(O)—$CH_2$—, —$CH_2$—C(O)—, —C(O)O—$CH_2$—, —OC(O)—$CH_2$—, —$CH_2$—C(O)O—, or —$CH_2$—OC(O)—. In other embodiments, $X^3$ is —$CH_2$—.

In some embodiments, $X^3$ is a bond or —$(CH_2)_2$—.

In some embodiments, $R_1$ and $R_2$ are the same. In certain embodiments, $R_1$, $R_2$, and $R_3$ are the same. In some embodiments, $R_4$ and $R_5$ are the same. In certain embodiments, $R_1$, $R_2$, $R_3$, $R_4$, and $R_5$ are the same.

In some embodiments, at least one of $R_1$, $R_2$, $R_3$, $R_4$, and $R_5$ is —R"MR'. In some embodiments, at most one of $R_1$, $R_2$, $R_3$, $R_4$, and $R_5$ is —R"MR'. For example, at least one of $R_1$, $R_2$, and $R_3$ may be —R"MR', and/or at least one of $R_4$ and $R_5$ is —R"MR'. In certain embodiments, at least one M is —C(O)O—. In some embodiments, each M is —C(O)O—. In some embodiments, at least one M is —OC(O)—. In some embodiments, each M is —OC(O)—. In some embodiments, at least one M is —OC(O)O—. In some embodiments, each M is —OC(O)O—. In some embodiments, at least one R" is $C_3$ alkyl. In certain embodiments, each R" is $C_3$ alkyl. In some embodiments, at least one R" is $C_5$ alkyl. In certain embodiments, each R" is $C_5$ alkyl. In some embodiments, at least one R" is $C_6$ alkyl. In certain embodiments, each R" is $C_6$ alkyl. In some embodiments, at least one R" is $C_7$ alkyl. In certain embodiments, each R" is $C_7$ alkyl. In some embodiments, at least one R' is $C_5$ alkyl. In certain embodiments, each R' is $C_5$ alkyl. In other embodiments, at least one R' is $C_1$ alkyl. In certain embodiments, each R' is $C_1$ alkyl. In some embodiments, at least one R' is $C_2$ alkyl. In certain embodiments, each R' is $C_2$ alkyl.

In some embodiments, at least one of $R_1$, $R_2$, $R_3$, $R_4$, and $R_5$ is $C_{12}$ alkyl. In certain embodiments, each of $R_1$, $R_2$, $R_3$, $R_4$, and $R_5$ are $C_{12}$ alkyl.

In certain embodiments, the compound is selected from the group consisting of:

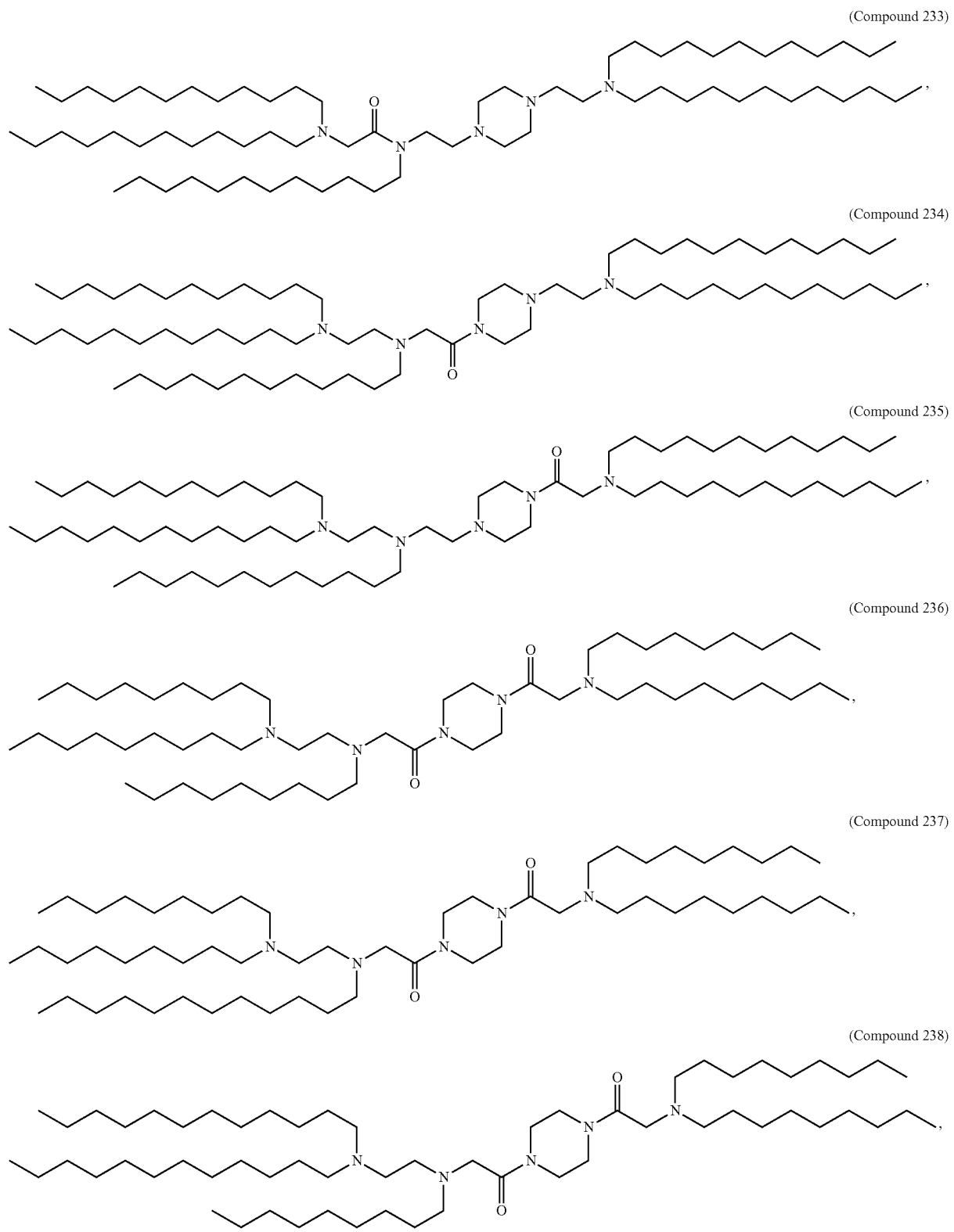

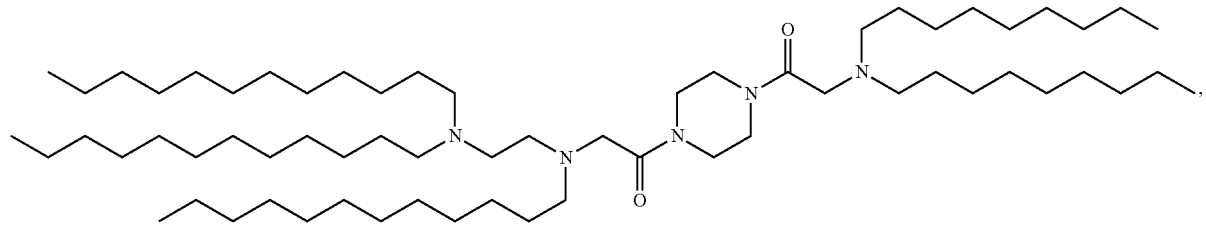
(Compound 239)
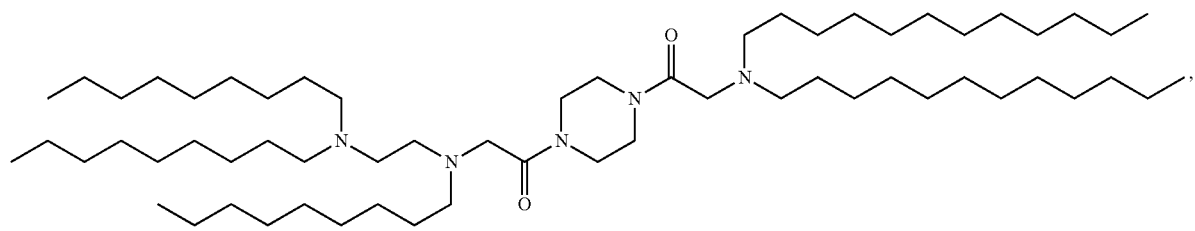
(Compound 240)
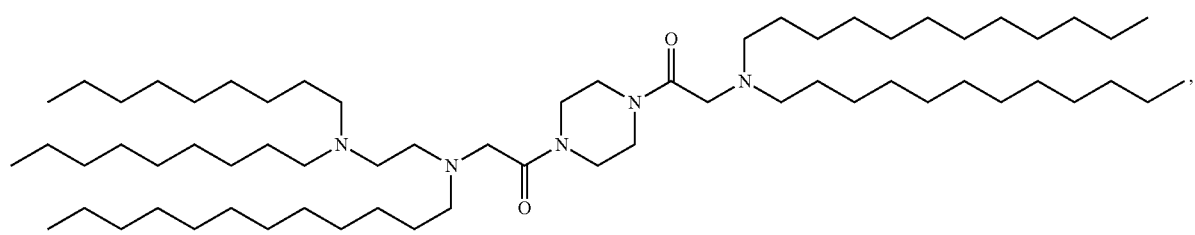
(Compound 241)
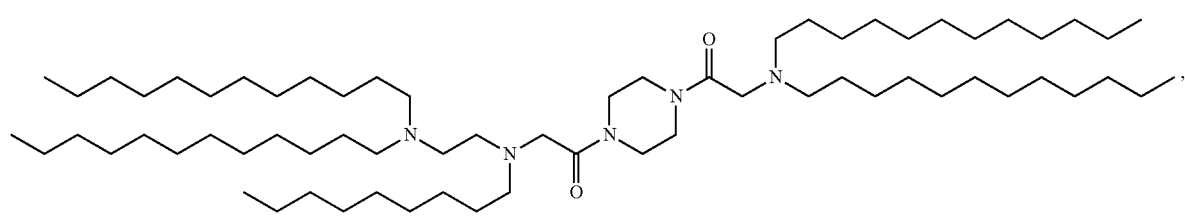
(Compound 242)
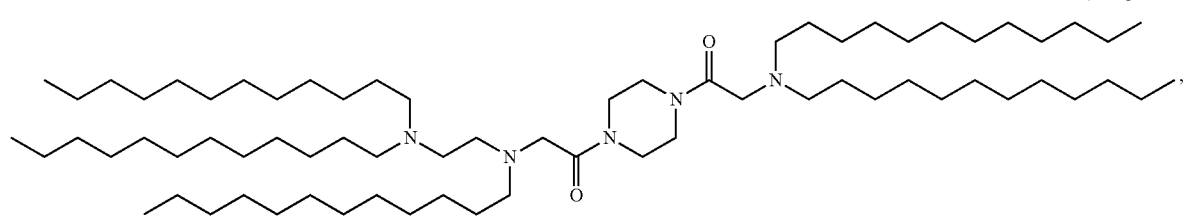
(Compound 243)
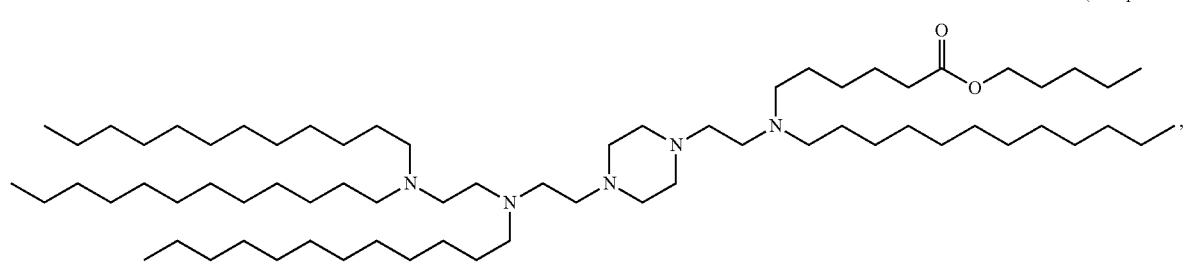
(Compound 244)

-continued
(Compound 245)
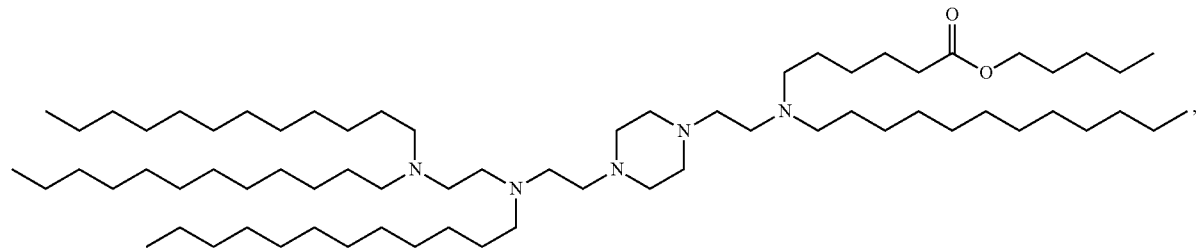
(Compound 246)
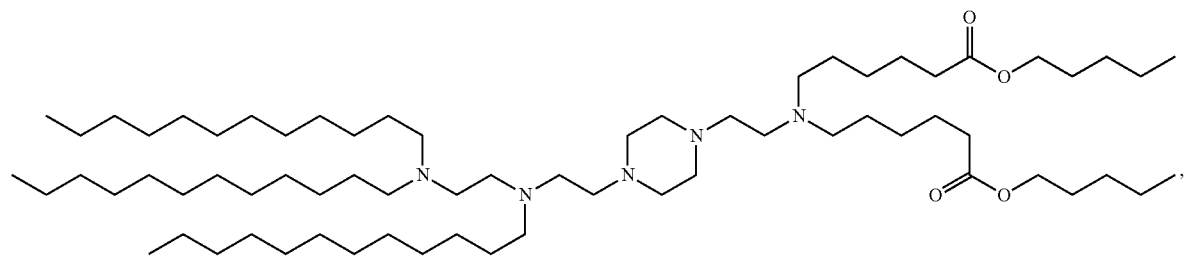
(Compound 247)
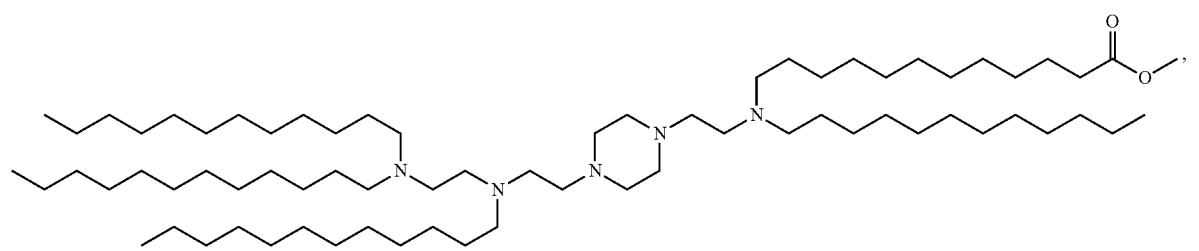
(Compound 248)
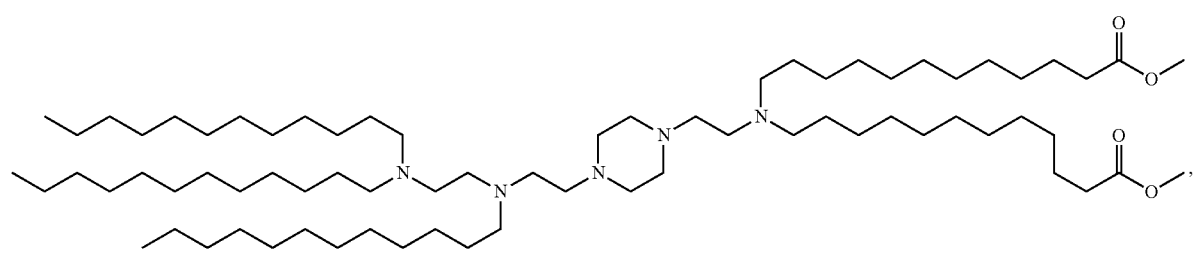
(Compound 274)
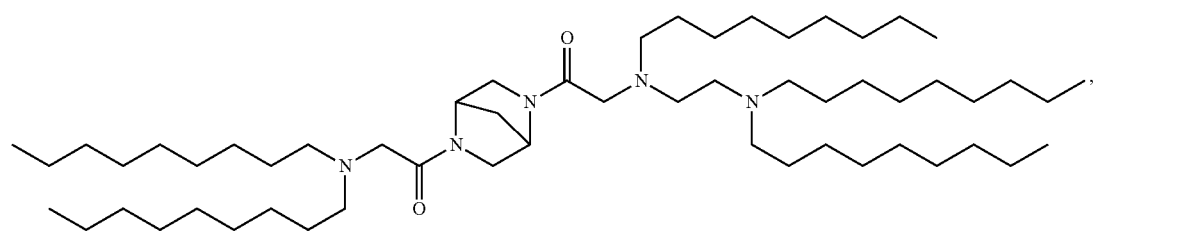
(Compound 275)
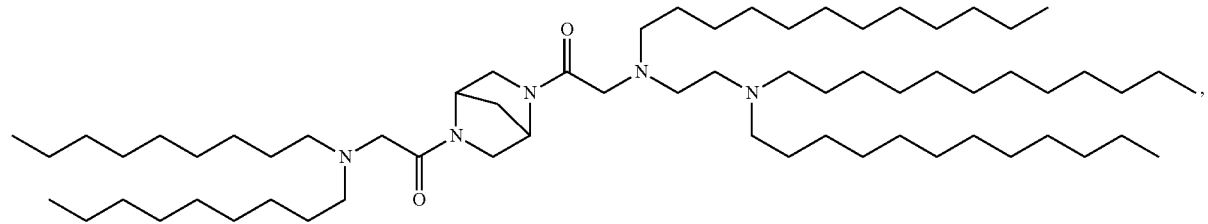

-continued
(Compound 276)
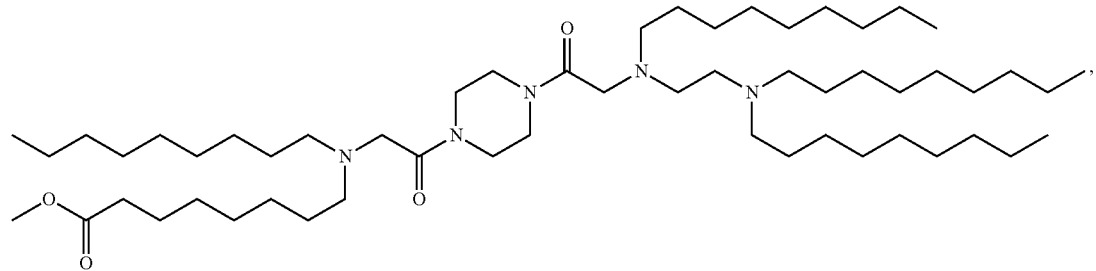
(Compound 277)
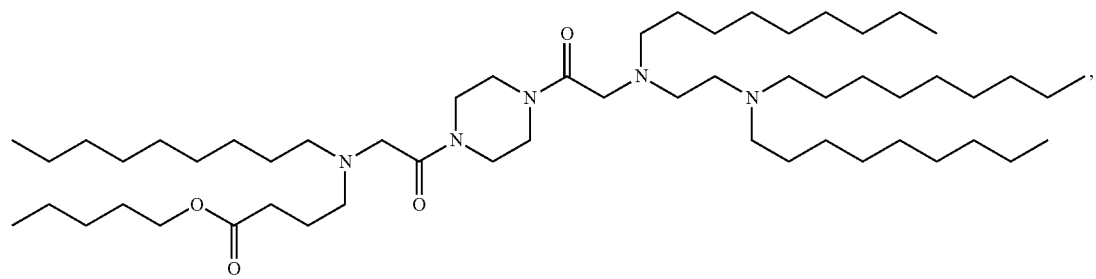
(Compound 278)
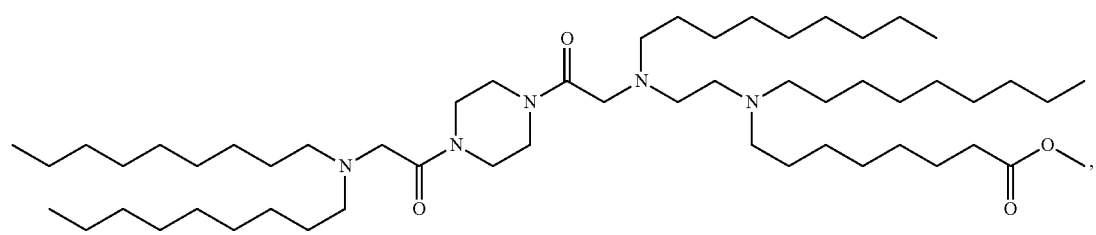
(Compound 279)
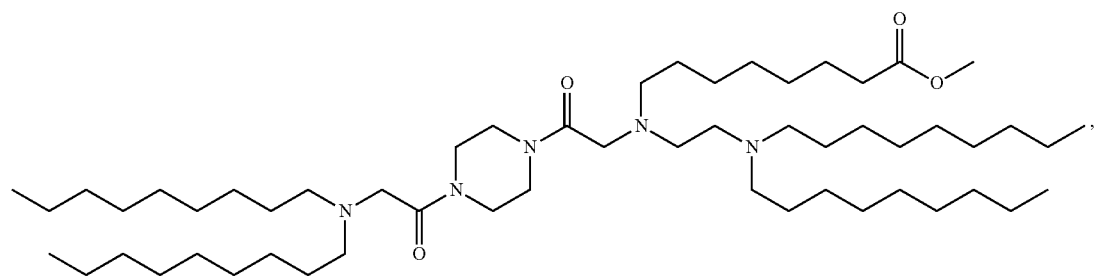
(Compound 280)
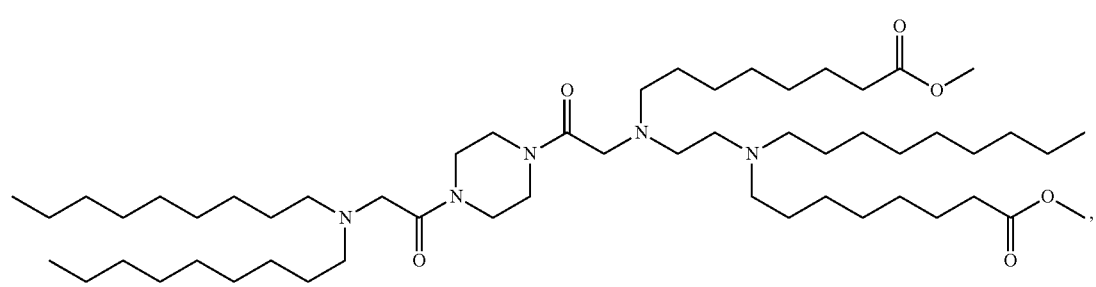

-continued
(Compound 281)
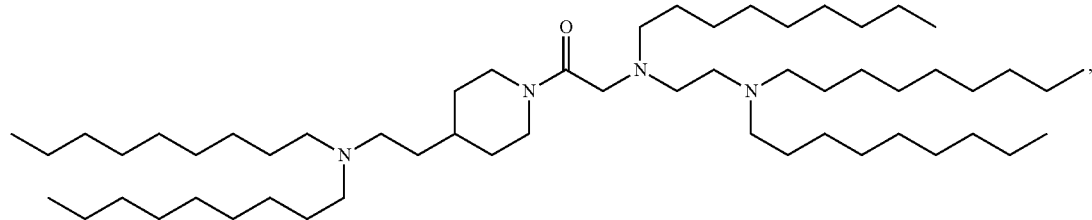
(Compound 282)
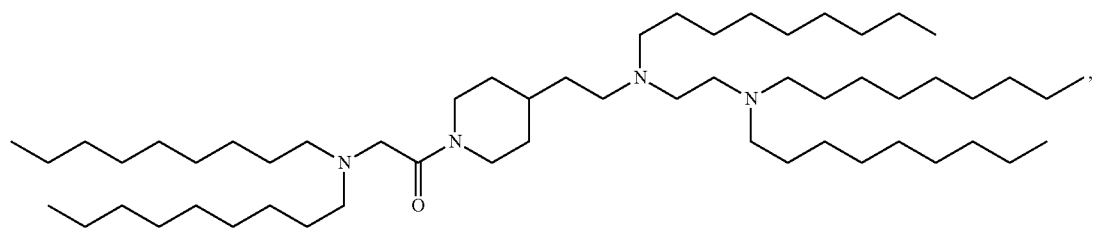
(Compound 283)
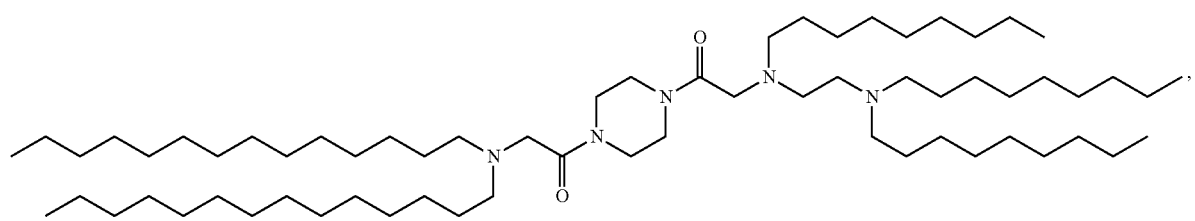
(Compound 284)
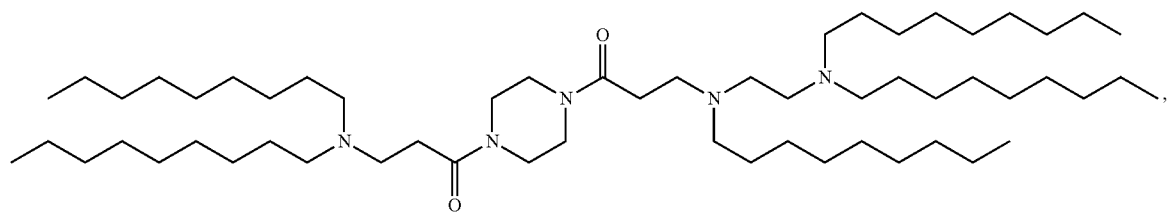
(Compound 285)
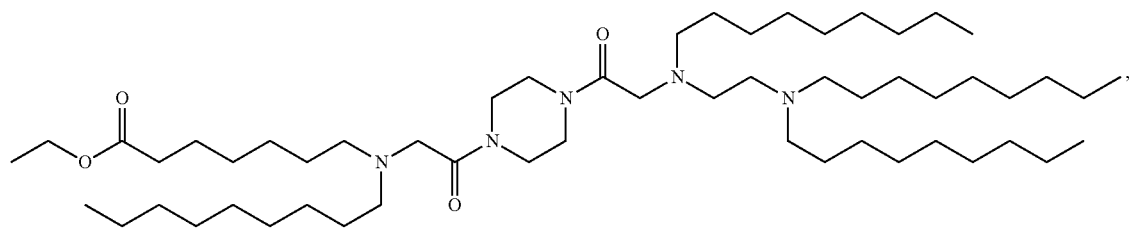
(Compound 286)
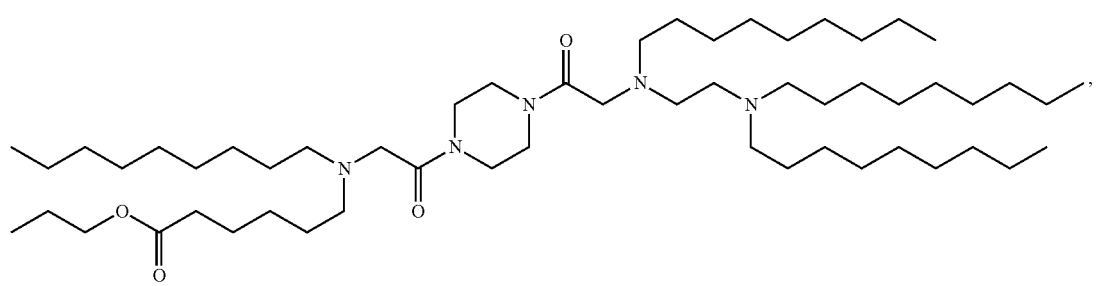

-continued
(Compound 287)
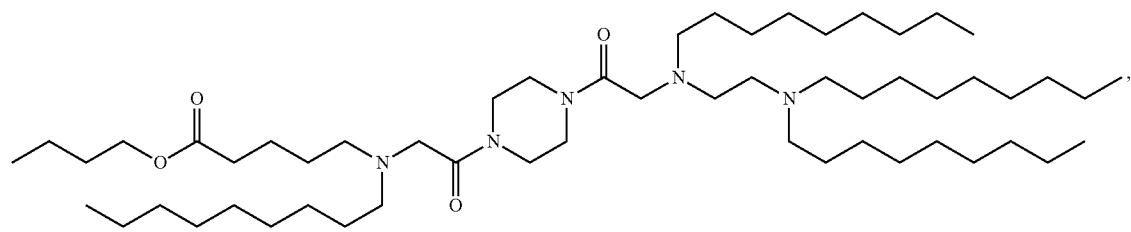
(Compound 288)
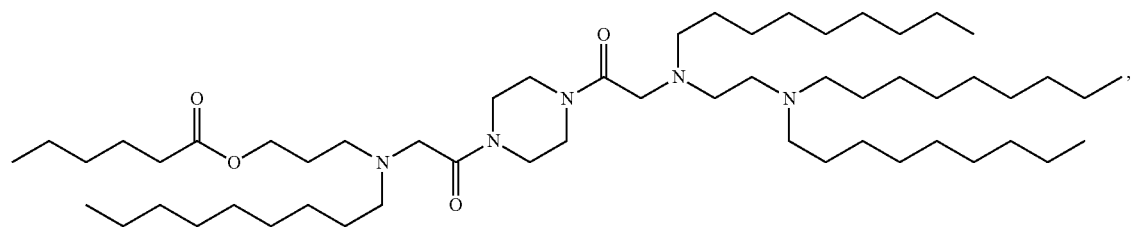
(Compound 289)
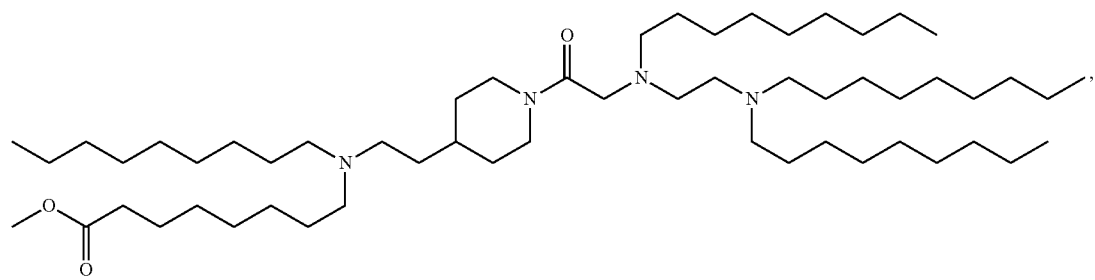
(Compound 290)
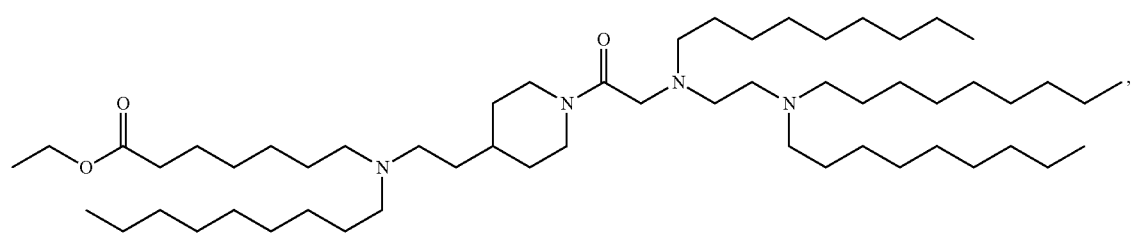
(Compound 291)
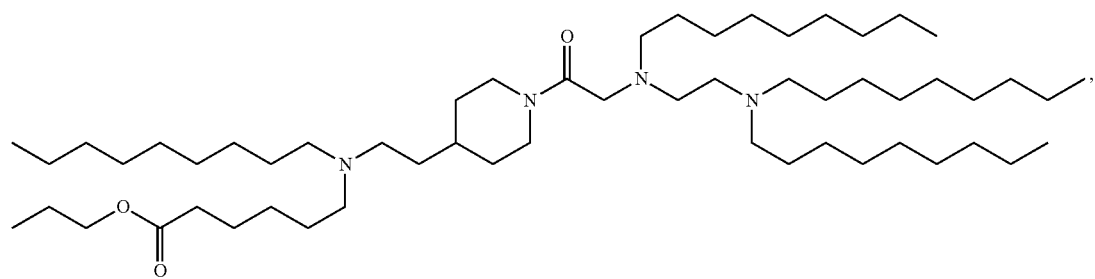
(Compound 292)
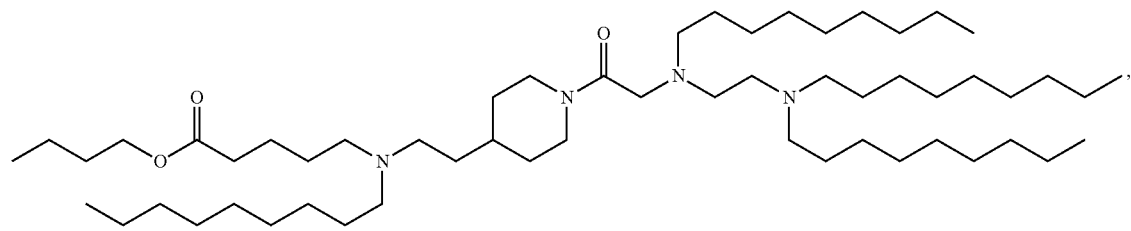

-continued
(Compound 293)
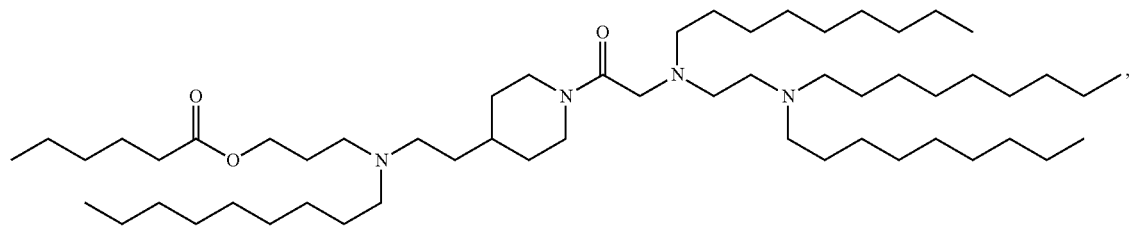
(Compound 294)
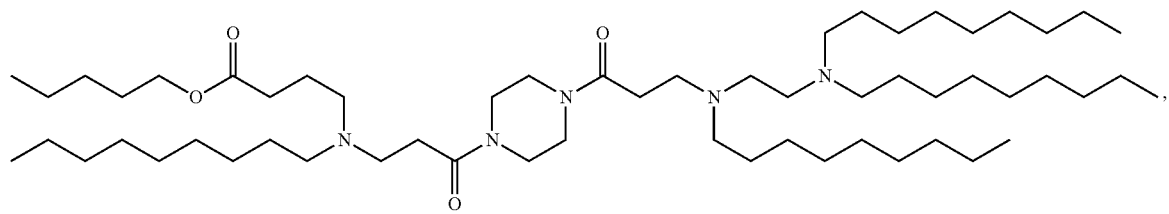
(Compound 295)
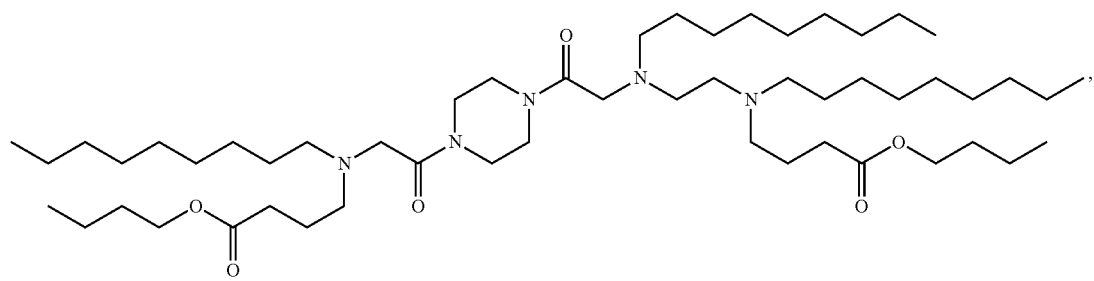
(Compound 296)
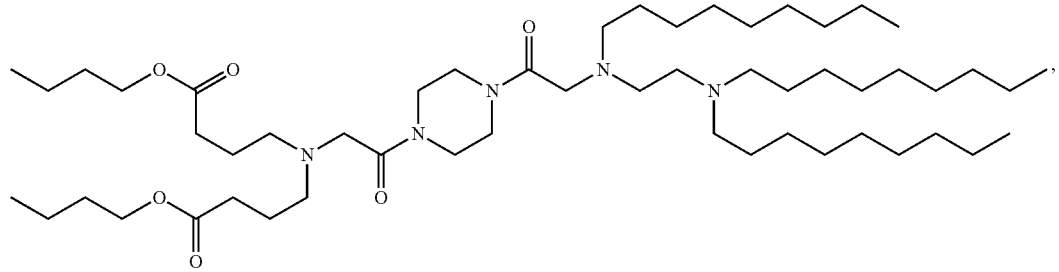
(Compound 297)
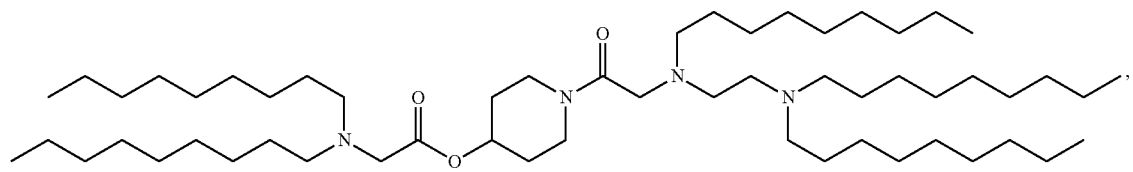
(Compound 298)
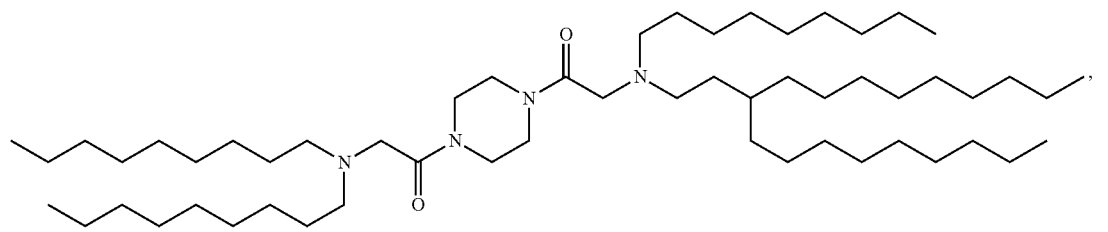

-continued
(Compound 300)
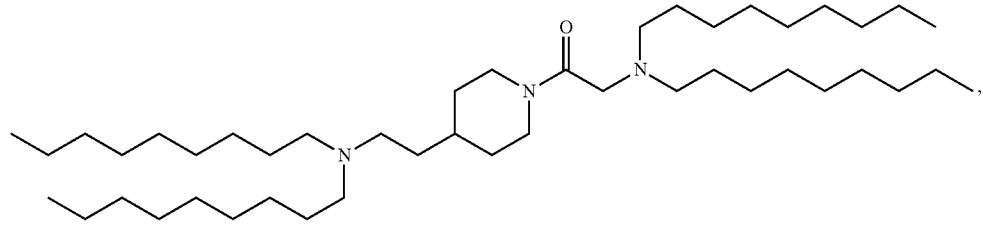
(Compound 301)
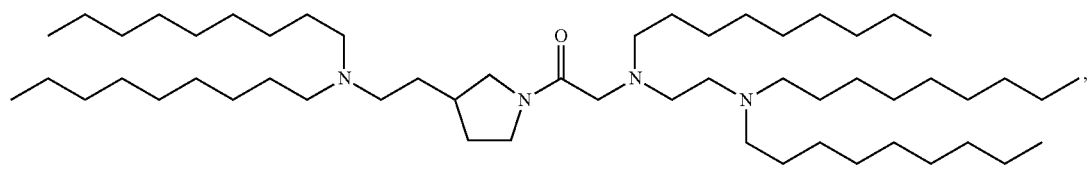
(Compound 302)
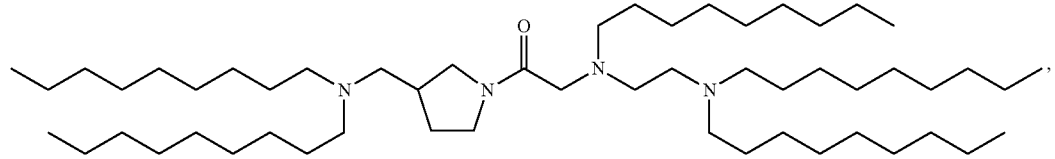
(Compound 303)
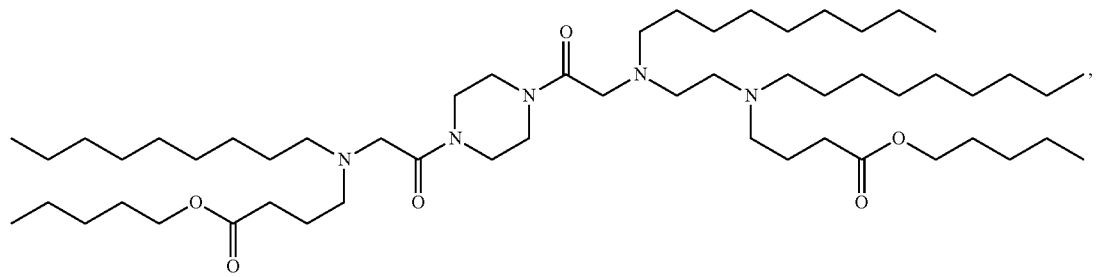
(Compound 304)
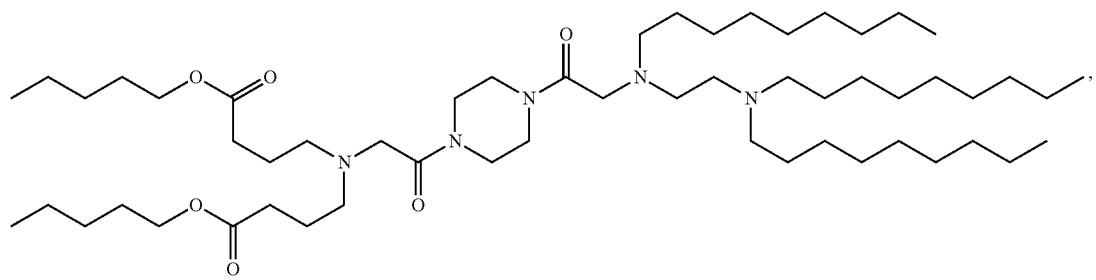
(Compound 305)
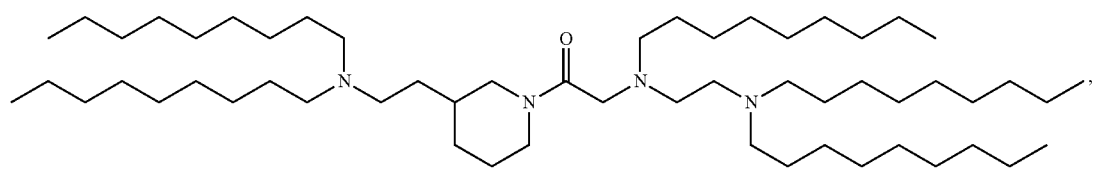
(Compound 306)
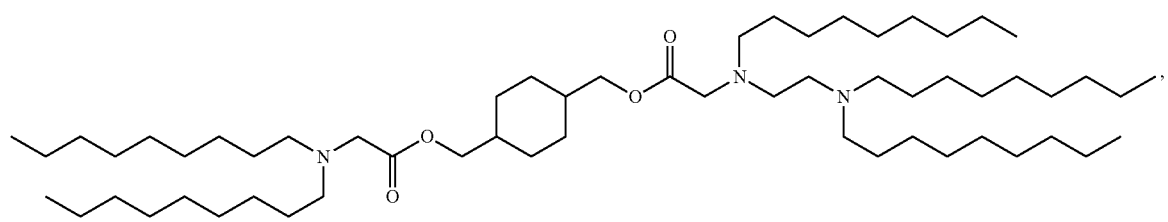

-continued
(Compound 307)
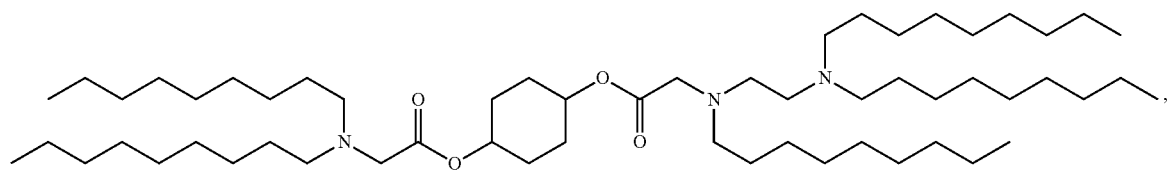
(Compound 308)
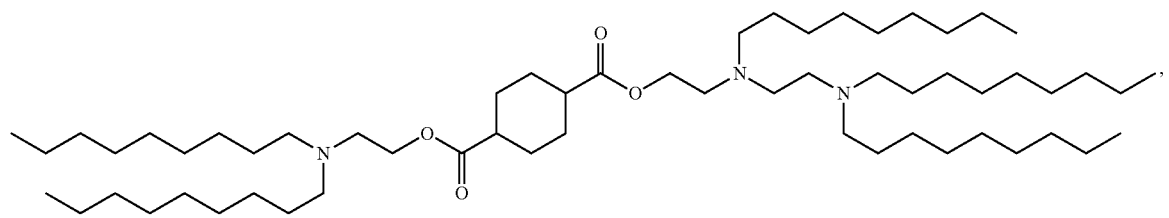
(Compound 310)
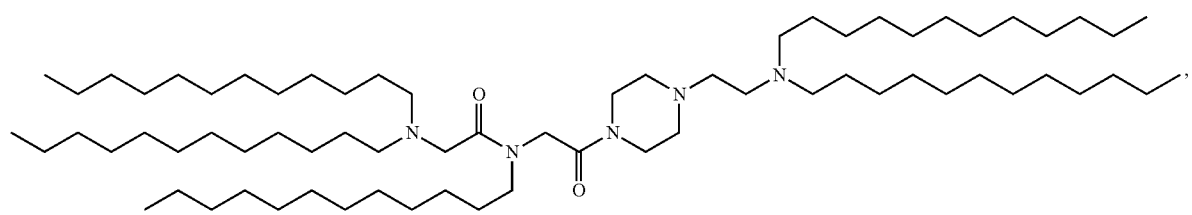
(Compound 311)
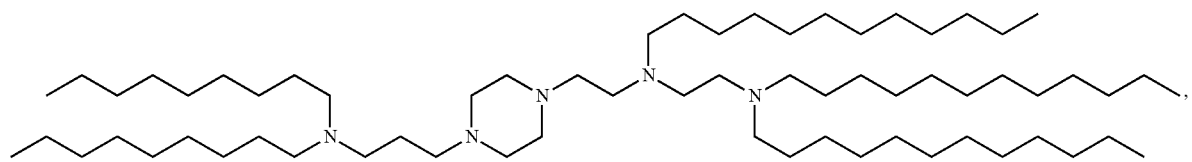
(Compound 312)
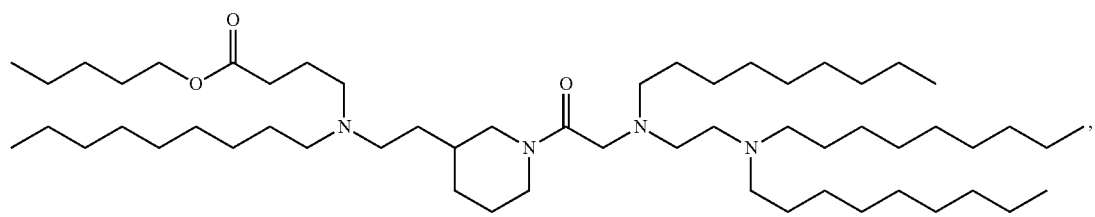
(Compound 313)
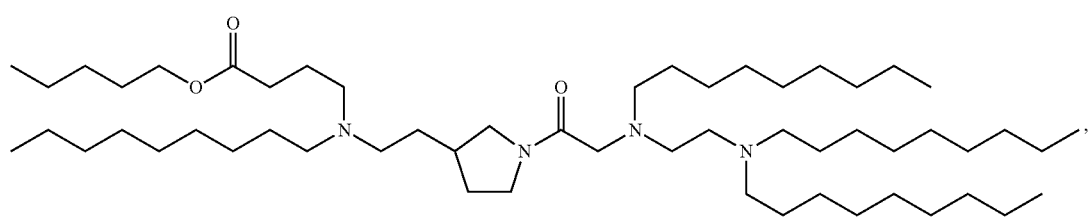
(Compound 314)
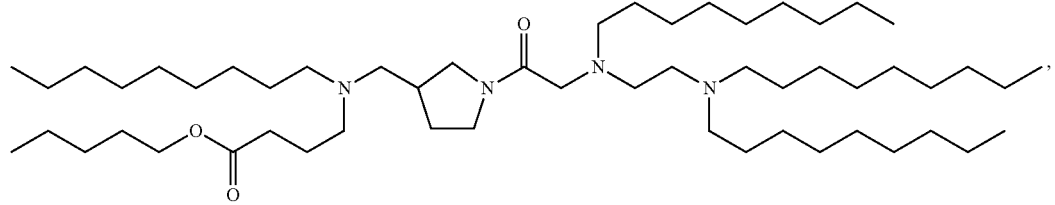

(Compound 315)
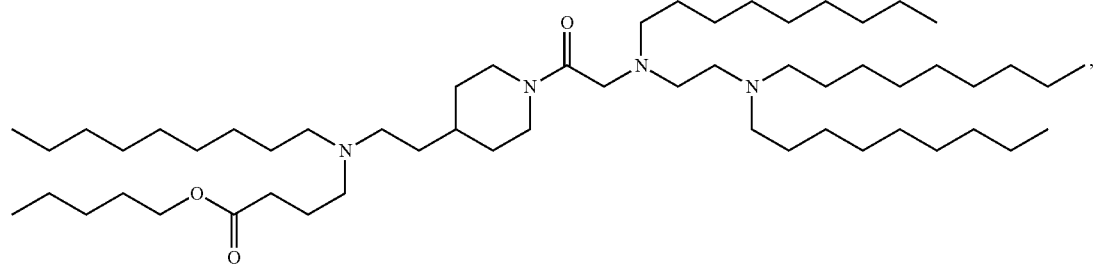
(Compound 316)
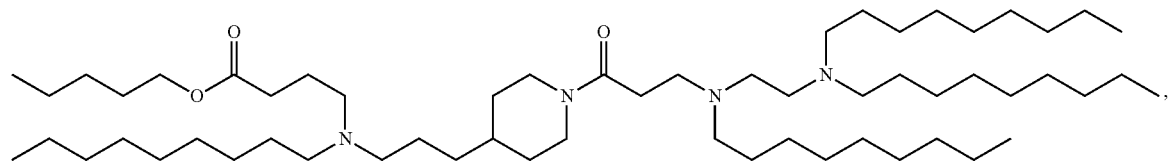
(Compound 317)
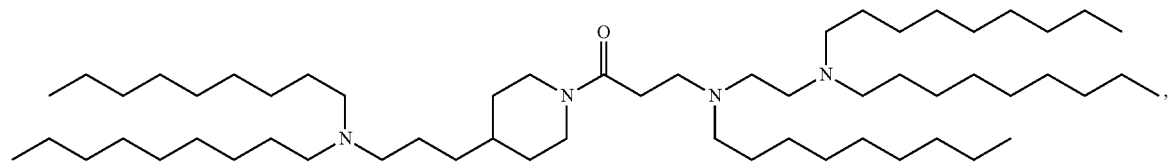
(Compound 318)
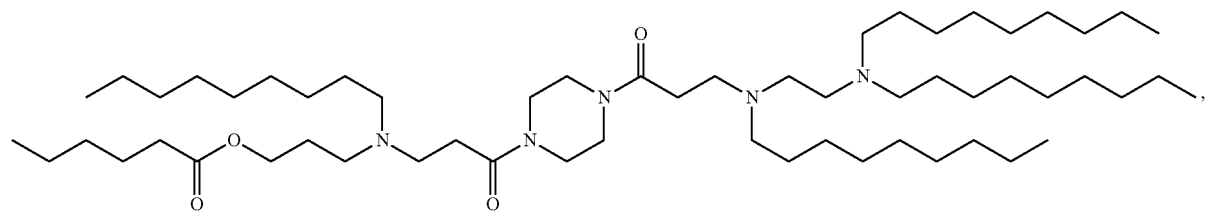
(Compound 319)
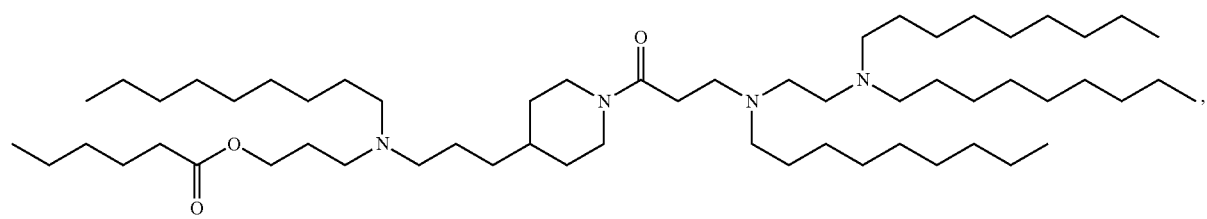
(Compound 320)
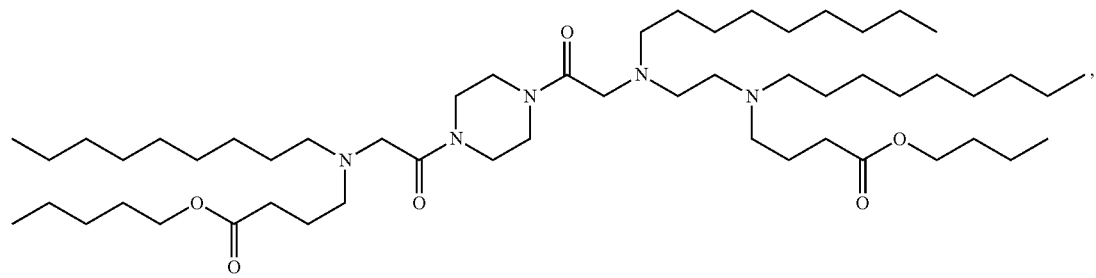

(Compound 321)
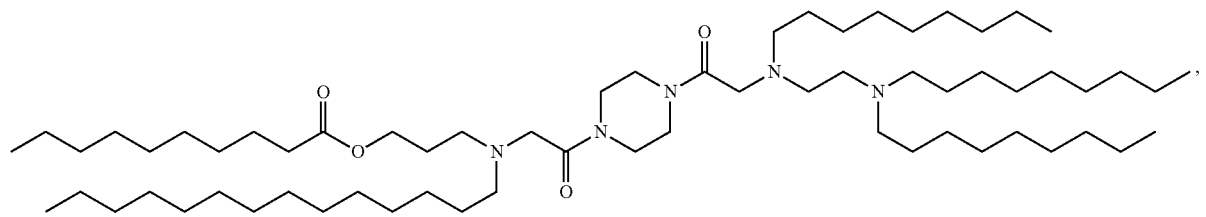
(Compound 322)
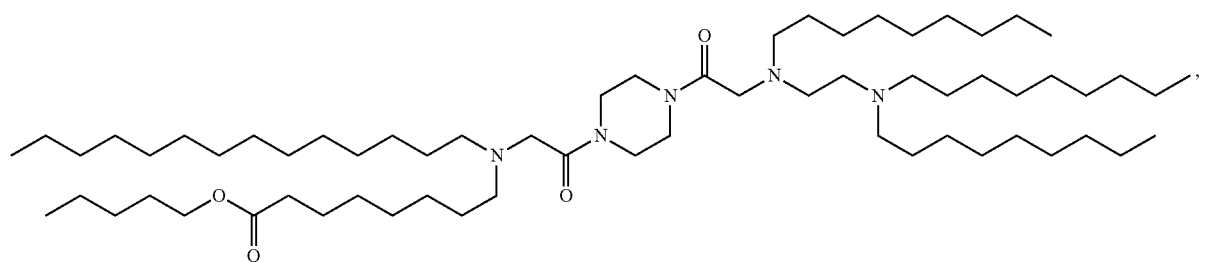
(Compound 323)
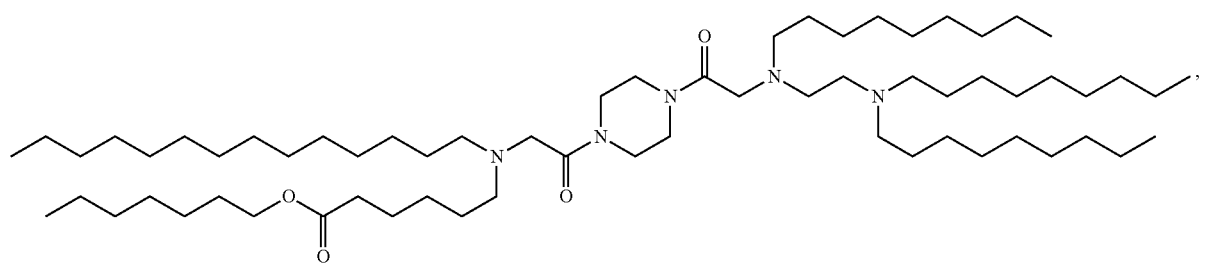
(Compound 324)
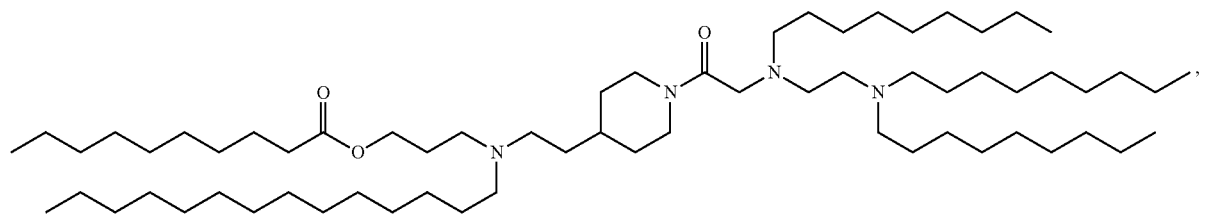
(Compound 325)
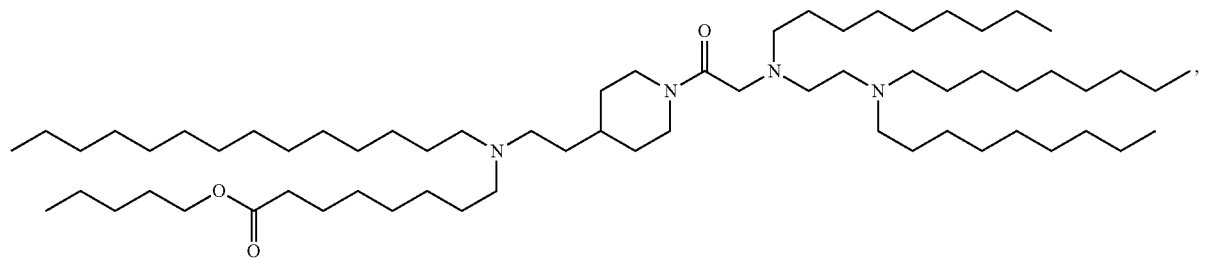
(Compound 326)
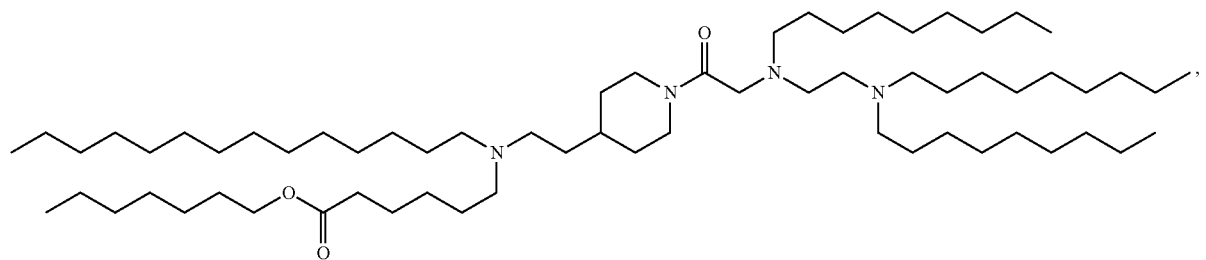

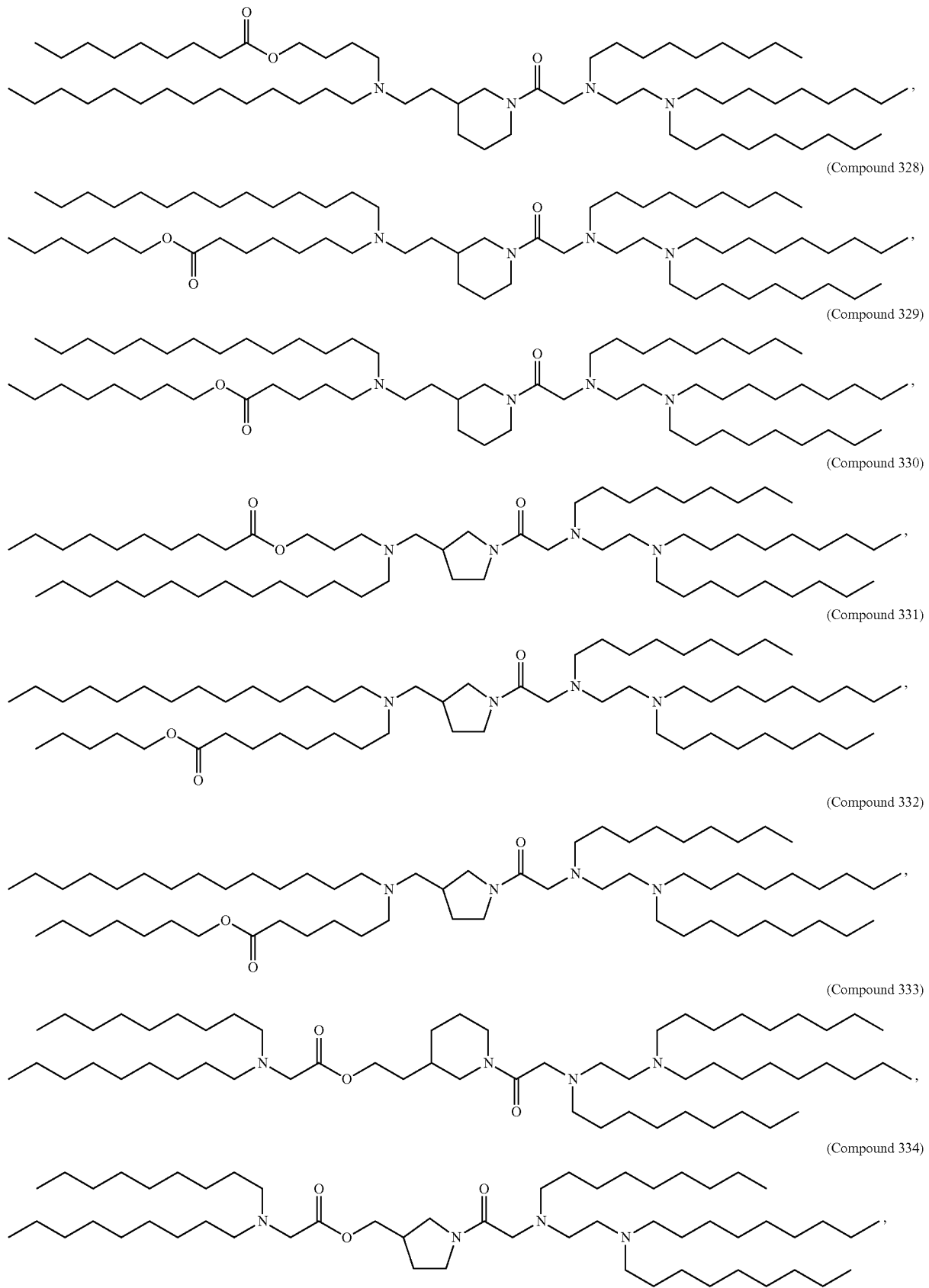

-continued
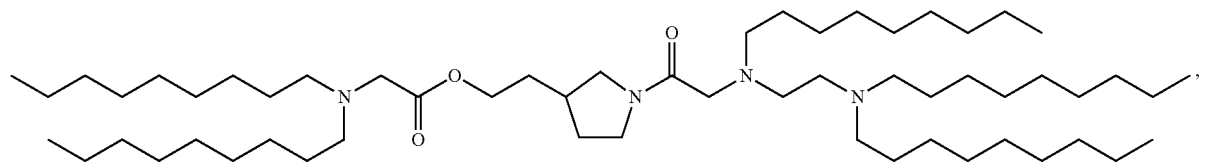
(Compound 335)
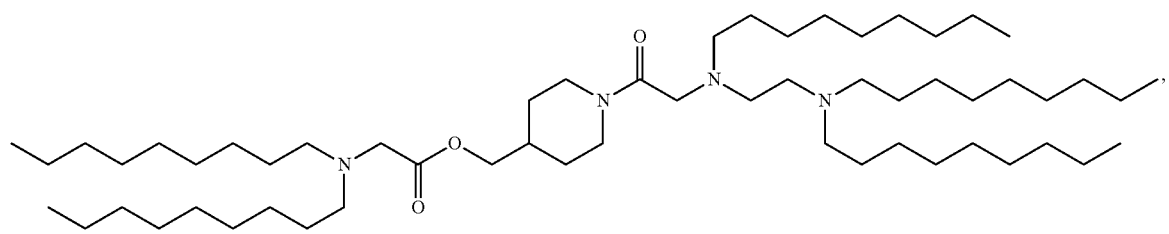
(Compound 336)
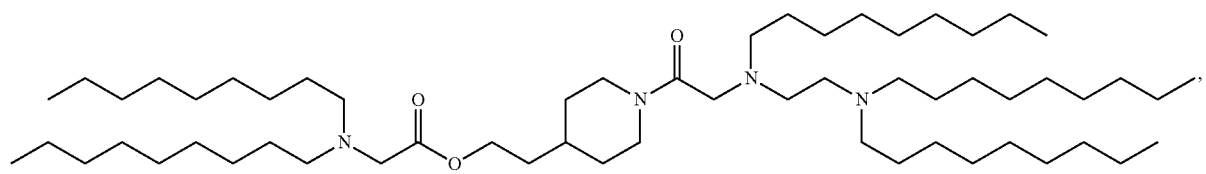
(Compound 337)
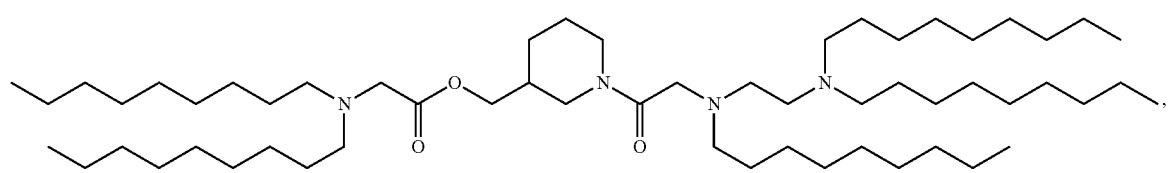
(Compound 338)
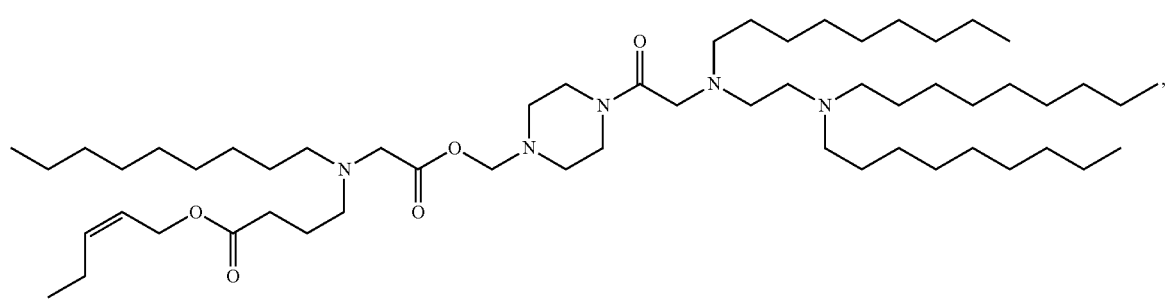
(Compound 339)
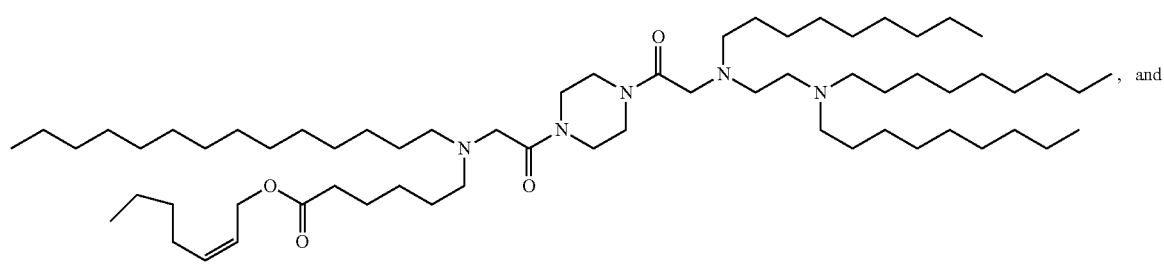
(Compound 340) , and (Compound 341)

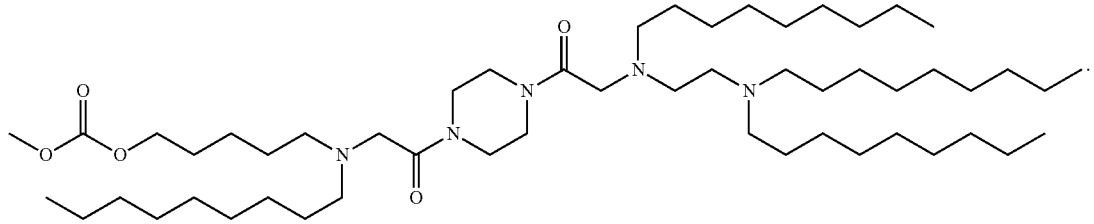

In some embodiments, the delivery agent comprises Compound 236.

In some embodiments, the delivery agent comprises a compound having the Formula (IV)

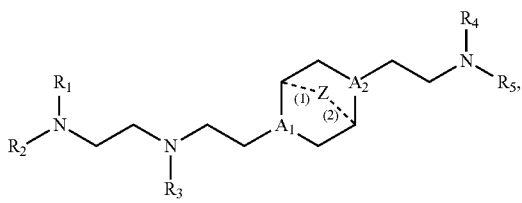

(IV)

or salts or stereoisomer thereof, wherein $A_1$ and $A_2$ are each independently selected from CH or N and at least one of $A_1$ and $A_2$ is N;

Z is $CH_2$ or absent wherein when Z is $CH_2$, the dashed lines (1) and (2) each represent a single bond; and when Z is absent, the dashed lines (1) and (2) are both absent;

$R_1$, $R_2$, $R_3$, $R_4$, and $R_5$ are independently selected from the group consisting of $C_{6-20}$ alkyl and $C_{6-20}$ alkenyl;

wherein when ring A is

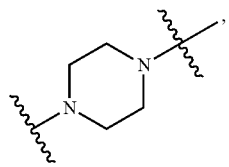 [SMILES: *N1CCN(*)CC1]

then i) $R_1$, $R_2$, $R_3$, $R_4$, and $R_5$ are the same, wherein $R_1$ is not $C_{12}$ alkyl, $C_{18}$ alkyl, or $C_{18}$ alkenyl;

ii) only one of $R_1$, $R_2$, $R_3$, $R_4$, and $R_5$ is selected from $C_{6-20}$ alkenyl;

iii) at least one of $R_1$, $R_2$, $R_3$, $R_4$, and $R_5$ have a different number of carbon atoms than at least one other of $R_1$, $R_2$, $R_3$, $R_4$, and $R_5$;

iv) $R_1$, $R_2$, and $R_3$ are selected from $C_{6-20}$ alkenyl, and $R_4$ and $R_5$ are selected from $C_{6-20}$ alkyl; or v) $R_1$, $R_2$, and $R_3$ are selected from $C_{6-20}$ alkyl, and $R_4$ and $R_5$ are selected from $C_{6-20}$ alkenyl.

In some embodiments, the compound is of Formula (IVa):

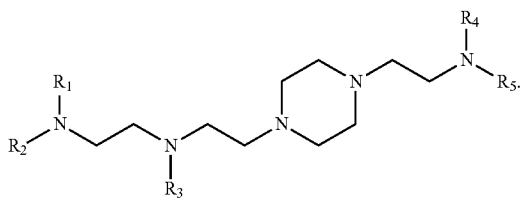

(IVa)

The compounds of Formula (IV) or (IVa) include one or more of the following features when applicable.

In some embodiments, Z is $CH_2$.
In some embodiments, Z is absent.
In some embodiments, at least one of $A_1$ and $A_2$ is N.
In some embodiments, each of $A_1$ and $A_2$ is N.
In some embodiments, each of $A_1$ and $A_2$ is CH.
In some embodiments, $A_1$ is N and $A_2$ is CH.
In some embodiments, $A_1$ is CH and $A_2$ is N.
In some embodiments, $R_1$, $R_2$, $R_3$, $R_4$, and $R_5$ are the same, and are not $C_{12}$ alkyl, $C_{18}$ alkyl, or $C_{18}$ alkenyl. In some embodiments, $R_1$, $R_2$, $R_3$, $R_4$, and $R_5$ are the same and are $C_9$ alkyl or $C_{14}$ alkyl.

In some embodiments, only one of $R_1$, $R_2$, $R_3$, $R_4$, and $R_5$ is selected from $C_{6-20}$ alkenyl. In certain such embodiments, $R_1$, $R_2$, $R_3$, $R_4$, and $R_5$ have the same number of carbon atoms. In some embodiments, $R_4$ is selected from $C_{5-20}$ alkenyl. For example, $R_4$ may be $C_{12}$ alkenyl or $C_{18}$ alkenyl.

In some embodiments, at least one of $R_1$, $R_2$, $R_3$, $R_4$, and $R_5$ have a different number of carbon atoms than at least one other of $R_1$, $R_2$, $R_3$, $R_4$, and $R_5$.

In certain embodiments, $R_1$, $R_2$, and $R_3$ are selected from $C_{6-20}$ alkenyl, and $R_4$ and $R_5$ are selected from $C_{6-20}$ alkyl. In other embodiments, $R_1$, $R_2$, and $R_3$ are selected from $C_{6-20}$ alkyl, and $R_4$ and $R_5$ are selected from $C_{6-20}$ alkenyl. In some embodiments, $R_1$, $R_2$, and $R_3$ have the same number of carbon atoms, and/or $R_4$ and $R_5$ have the same number of carbon atoms. For example, $R_1$, $R_2$, and $R_3$, or $R_4$ and $R_5$, may have 6, 8, 9, 12, 14, or 18 carbon atoms. In some embodiments, $R_1$, $R_2$, and $R_3$, or $R_4$ and $R_5$, are Cis alkenyl (e.g., linoleyl). In some embodiments, $R_1$, $R_2$, and $R_3$, or $R_4$ and $R_5$, are alkyl groups including 6, 8, 9, 12, or 14 carbon atoms.

In some embodiments, $R_1$ has a different number of carbon atoms than $R_2$, $R_3$, $R_4$, and $R_5$. In other embodiments, $R_3$ has a different number of carbon atoms than $R_1$, $R_2$, $R_4$, and $R_5$. In further embodiments, $R_4$ has a different number of carbon atoms than $R_1$, $R_2$, $R_3$, and $R_5$.

In some embodiments, the compound is selected from the group consisting of:

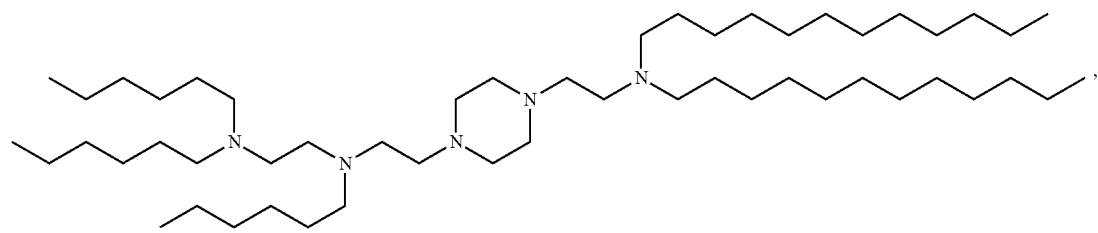
(Compound 249)
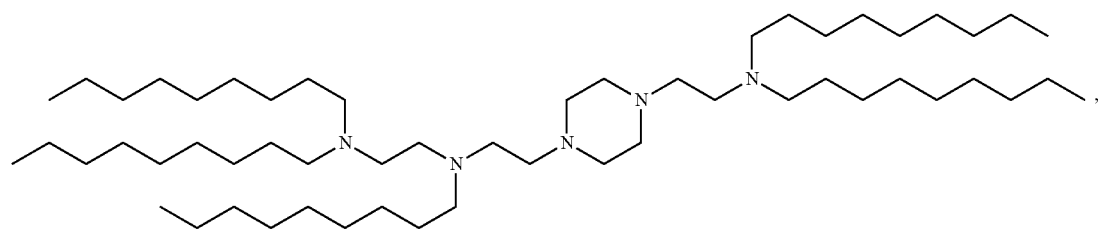
(Compound 250)
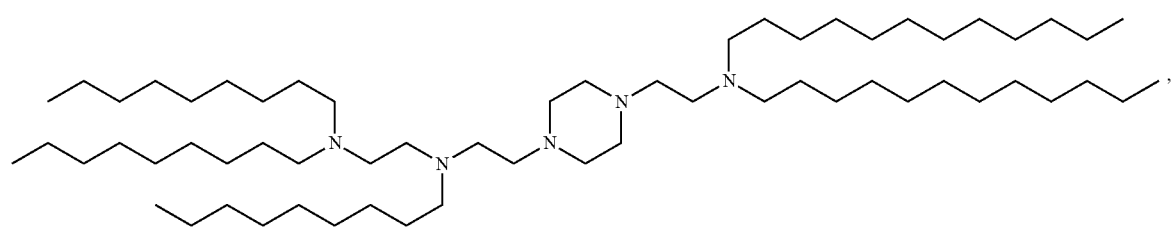
(Compound 251)
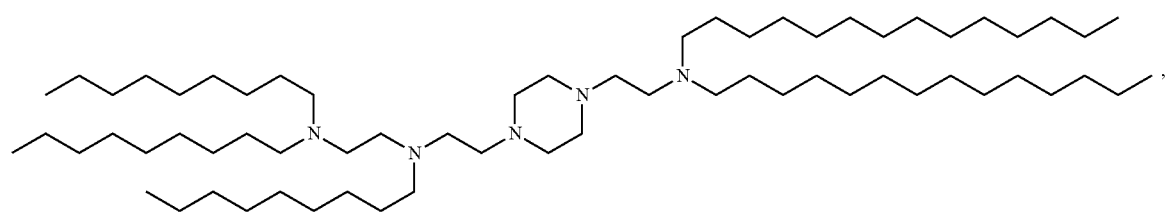
(Compound 252)
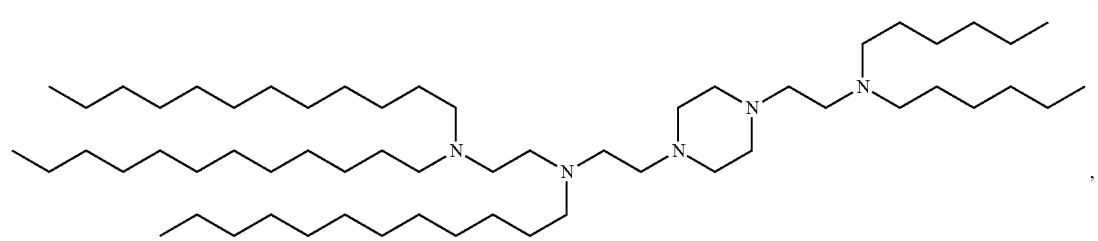
(Compound 253)
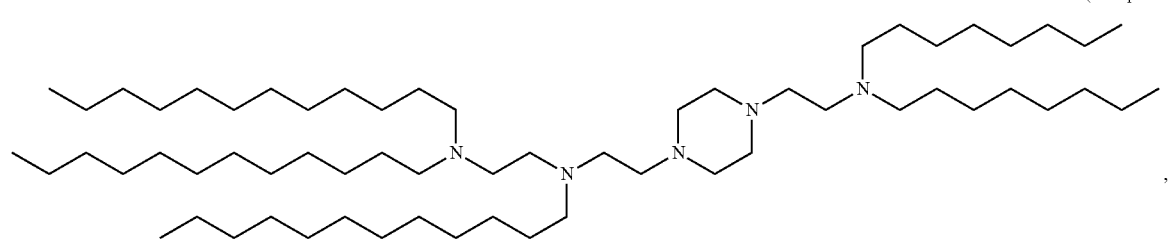
(Compound 254)

(Compound 255)
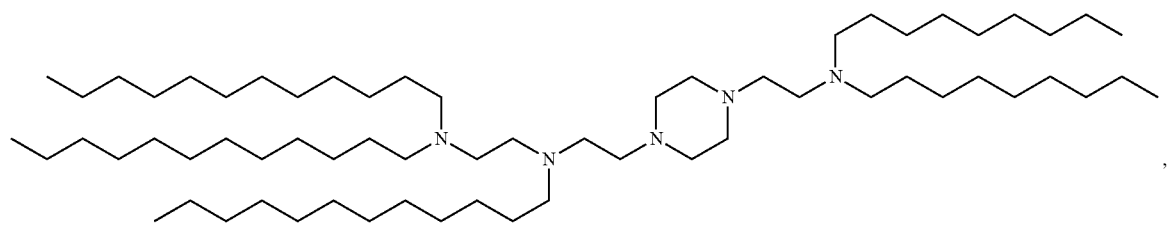
,
(Compound 256)
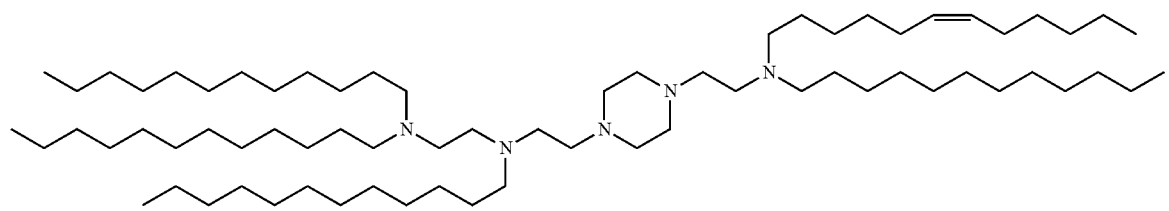
,
(Compound 257)
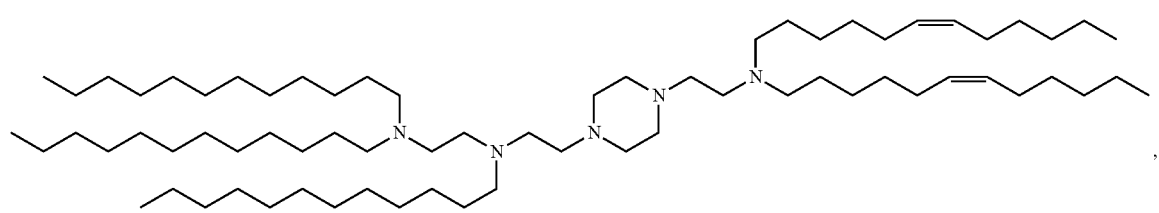
,
(Compound 258)
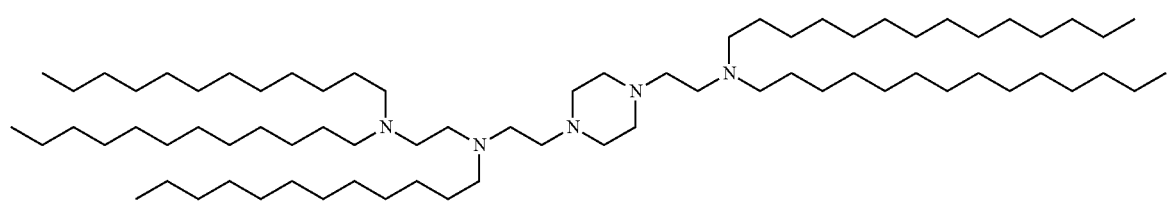
,
(Compound 259)
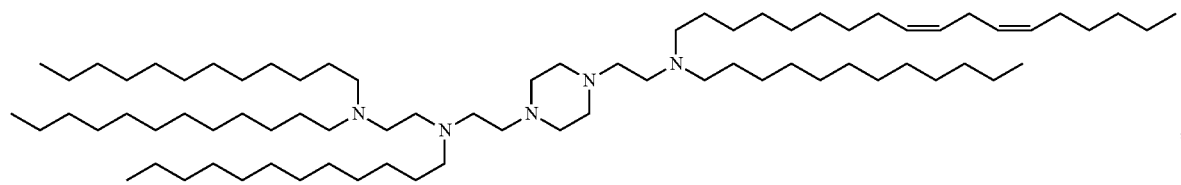
,
(Compound 260)
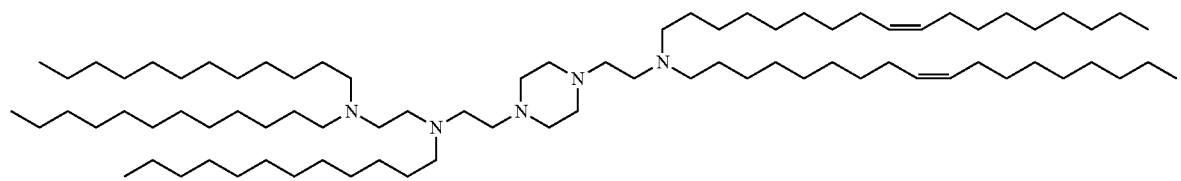
,
(Compound 261)
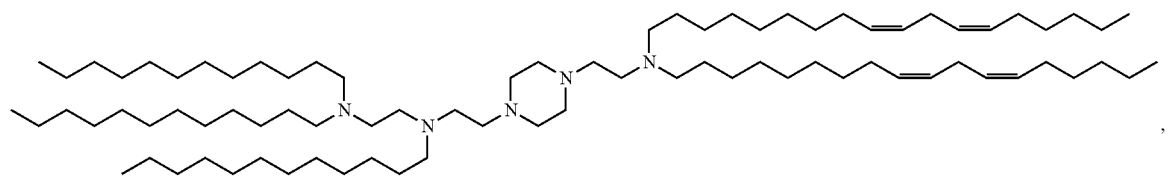
,

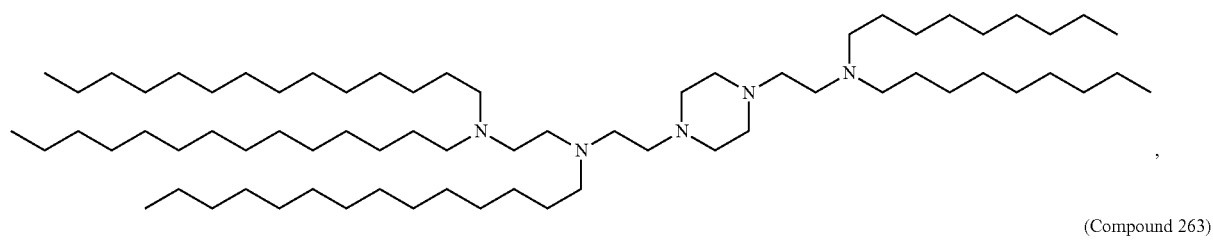
(Compound 262)

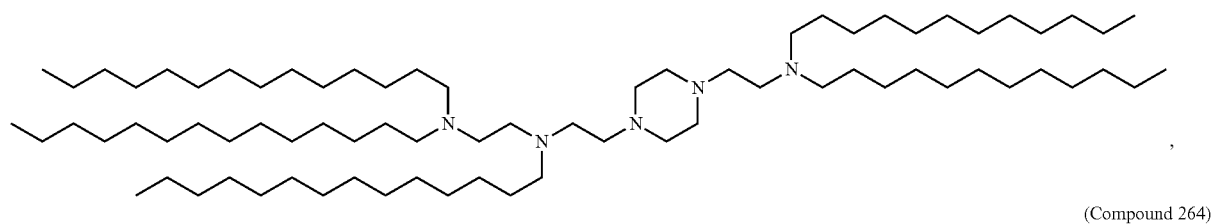
(Compound 263)

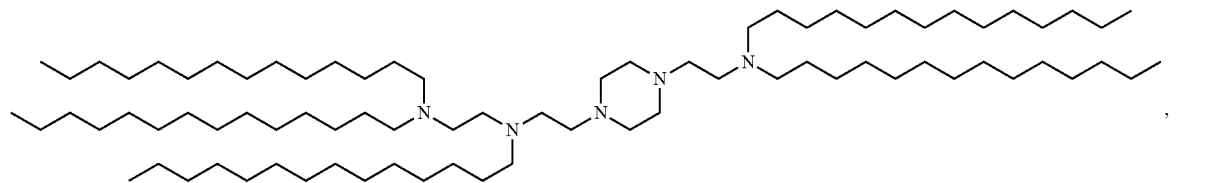
(Compound 264)

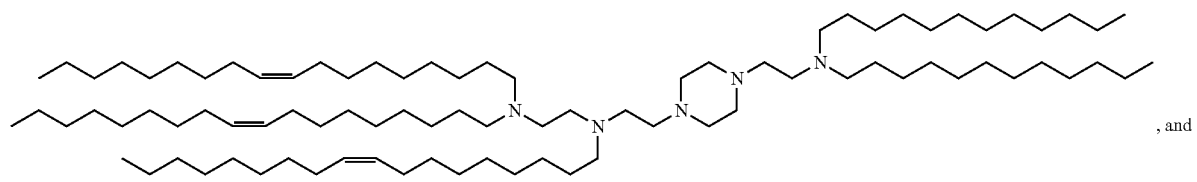
(Compound 265), and

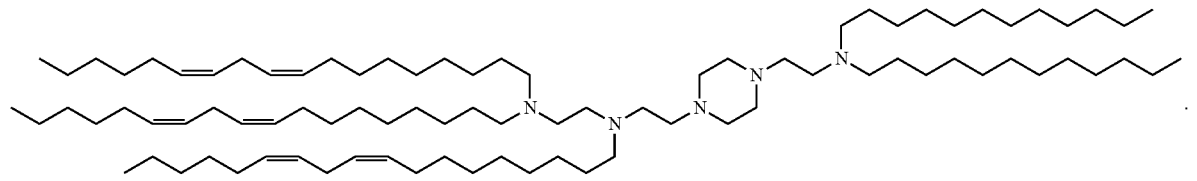
(Compound 266)

In other embodiments, the delivery agent comprises a compound having the Formula (V)

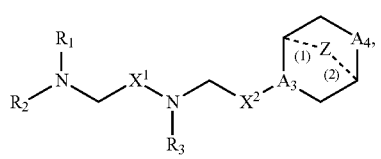
(V)

or salts or stereoisomers thereof, in which
- $A_3$ is CH or N;
- $A_4$ is $CH_2$ or NH; and at least one of $A_3$ and $A_4$ is N or NH;
- Z is $CH_2$ or absent wherein when Z is $CH_2$, the dashed lines (1) and (2) each represent a single bond; and when Z is absent, the dashed lines (1) and (2) are both absent;
- $R_1$, $R_2$, and $R_3$ are independently selected from the group consisting of $C_{5-20}$ alkyl, $C_{5-20}$ alkenyl, —R"MR', —R*YR", —YR", and —R*OR";
- each M is independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —S(O)$_2$—, an aryl group, and a heteroaryl group;
- $X^1$ and $X^2$ are independently selected from the group consisting of —CH$_2$—, —(CH$_2$)$_2$—, —CHR—, —CHY—, —C(O)—, —C(O)O—, —OC(O)—, —C(O)—CH$_2$—, —CH$_2$—C(O)—, —C(O)O—CH$_2$—, —OC(O)—CH$_2$—, —CH$_2$—C(O)O—, —CH$_2$—OC(O)—, —CH(OH)—, —C(S)—, and —CH(SH)—;
- each Y is independently a $C_{3-6}$ carbocycle;
- each R* is independently selected from the group consisting of $C_{1-12}$ alkyl and $C_{2-12}$ alkenyl;
- each R is independently selected from the group consisting of $C_{1-3}$ alkyl and a $C_{3-6}$ carbocycle;
- each R' is independently selected from the group consisting of $C_{1-12}$ alkyl, $C_{2-12}$ alkenyl, and H; and
- each R" is independently selected from the group consisting of $C_{3-12}$ alkyl and $C_{3-12}$ alkenyl.

In some embodiments, the compound is of Formula (Va):

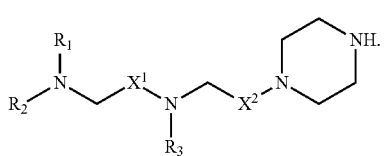
(Va)

The compounds of Formula (V) or (Va) include one or more of the following features when applicable.

In some embodiments, Z is CH$_2$.
In some embodiments, Z is absent.
In some embodiments, at least one of A$_3$ and A$_4$ is N or NH.
In some embodiments, A$_3$ is N and A$_4$ is NH.
In some embodiments, A$_3$ is N and A$_4$ is CH$_2$.
In some embodiments, A$_3$ is CH and A$_4$ is NH.
In some embodiments, at least one of X$^1$ and X$^2$ is not —CH$_2$—. For example, in certain embodiments, X$^1$ is not —CH$_2$—. In some embodiments, at least one of X$^1$ and X$^2$ is —C(O)—.

In some embodiments, X$^2$ is —C(O)—, —C(O)O—, —OC(O)—, —C(O)—CH$_2$—, —CH$_2$—C(O)—, —C(O)O—CH$_2$—, —OC(O)—CH$_2$—, —CH$_2$—C(O)O—, or —CH$_2$—OC(O)—.

In some embodiments, R$_1$, R$_2$, and R$_3$ are independently selected from the group consisting of C$_{5-20}$ alkyl and C$_{5-20}$ alkenyl. In some embodiments, R$_1$, R$_2$, and R$_3$ are the same. In certain embodiments, R$_1$, R$_2$, and R$_3$ are C$_6$, C$_9$, C$_{12}$, or C$_{14}$ alkyl. In other embodiments, R$_1$, R$_2$, and R$_3$ are Cis alkenyl. For example, R$_1$, R$_2$, and R$_3$ may be linoleyl.

In some embodiments, the compound is selected from the group consisting of:

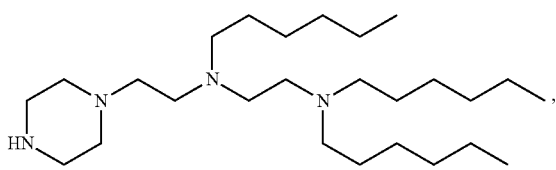
(Compound 267)

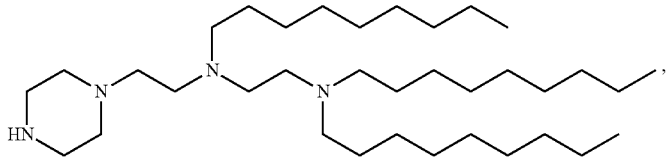
(Compound 268)

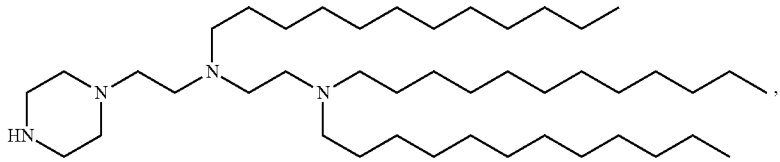
(Compound 269)

(Compound 270)

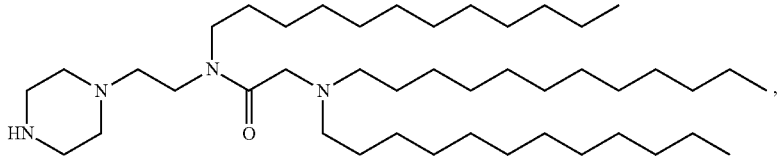
(Compound 271)

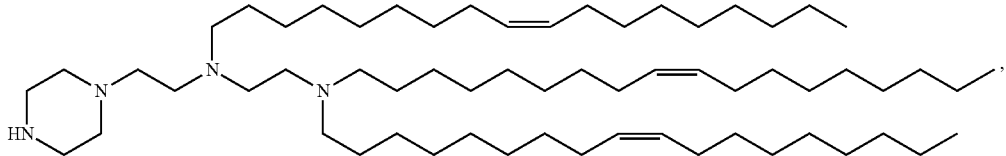
(Compound 272)

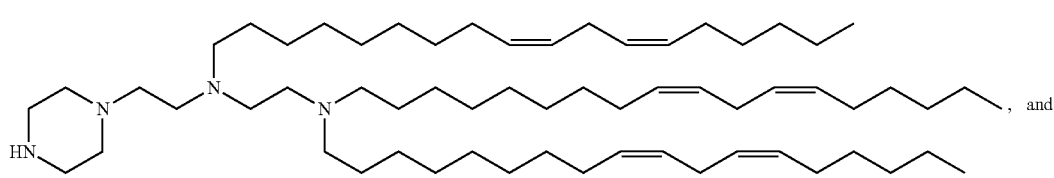

(Compound 273)

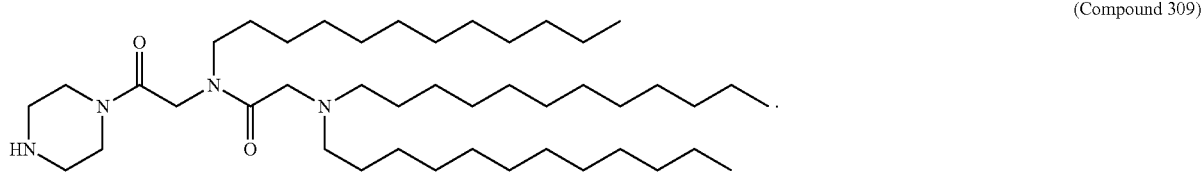

, and (Compound 309)

In other embodiments, the delivery agent comprises a compound having the Formula (VI):

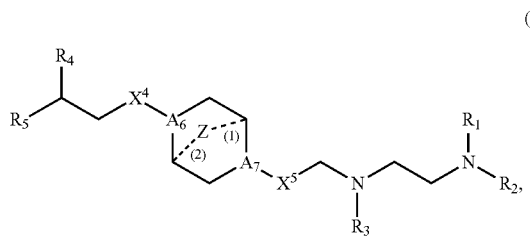

(VI)

or salts or stereoisomers thereof, in which

A$_6$ and A$_7$ are each independently selected from CH or N, wherein at least one of A$_6$ and A$_7$ is N;

Z is CH$_2$ or absent wherein when Z is CH$_2$, the dashed lines (1) and (2) each represent a single bond; and when Z is absent, the dashed lines (1) and (2) are both absent;

X$^4$ and X$^5$ are independently selected from the group consisting of —CH$_2$—, —CH$_2$)$_2$—, —CHR—, —CHY—, —C(O)—, —C(O)O—, —OC(O)—, —C(O)—CH$_2$—, —CH$_2$—C(O)—, —C(O)O—CH$_2$—, —OC(O)—CH$_2$—, —CH$_2$—C(O)O—, —CH$_2$—OC(O)—, —CH(OH)—, —C(S)—, and —CH(SH)—;

R$_1$, R$_2$, R$_3$, R$_4$, and R$_5$ each are independently selected from the group consisting of C$_{5-20}$ alkyl, C$_{5-20}$ alkenyl, —R"MR', —R*YR", —YR", and —R*OR";

each M is independently selected from the group consisting of —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —S(O)$_2$— an aryl group, and a heteroaryl group;

each Y is independently a C$_{3-6}$ carbocycle;

each R* is independently selected from the group consisting of C$_{1-12}$ alkyl and C$_{2-12}$ alkenyl;

each R is independently selected from the group consisting of C$_{1-3}$ alkyl and a C$_{3-6}$ carbocycle;

each R' is independently selected from the group consisting of C$_{1-12}$ alkyl, C$_{2-12}$ alkenyl, and H; and each R" is independently selected from the group consisting of C$_{3-12}$ alkyl and C$_{3-12}$ alkenyl.

In some embodiments, R$_1$, R$_2$, R$_3$, R$_4$, and R$_5$ each are independently selected from the group consisting of C$_{6-20}$ alkyl and C$_{6-20}$ alkenyl.

In some embodiments, R$_1$ and R$_2$ are the same. In certain embodiments, R$_1$, R$_2$, and R$_3$ are the same. In some embodiments, R$_4$ and R$_5$ are the same. In certain embodiments, R$_1$, R$_2$, R$_3$, R$_4$, and R$_5$ are the same.

In some embodiments, at least one of R$_1$, R$_2$, R$_3$, R$_4$, and R$_5$ is C$_{9-12}$ alkyl. In certain embodiments, each of R$_1$, R$_2$, R$_3$, R$_4$, and R$_5$ independently is C$_9$, C$_{12}$ or C$_{14}$ alkyl. In certain embodiments, each of R$_1$, R$_2$, R$_3$, R$_4$, and R$_5$ is C$_9$ alkyl.

In some embodiments, A$_6$ is N and A$_7$ is N. In some embodiments, A$_6$ is CH and A$_7$ is N.

In some embodiments, X$^4$ is —CH$_2$— and X$^5$ is —C(O)—. In some embodiments, X$^4$ and X$^5$ are —C(O)—.

In some embodiments, when A$_6$ is N and A$_7$ is N, at least one of X$^4$ and X$^5$ is not —CH$_2$—, e.g., at least one of X$^4$ and X$^5$ is —C(O)—. In some embodiments, when A$_6$ is N and A$_7$ is N, at least one of R$_1$, R$_2$, R$_3$, R$_4$, and R$_5$ is —R"MR'.

In some embodiments, at least one of R$_1$, R$_2$, R$_3$, R$_4$, and R$_5$ is not —R"MR'. In some embodiments, the compound is (Compound 299)

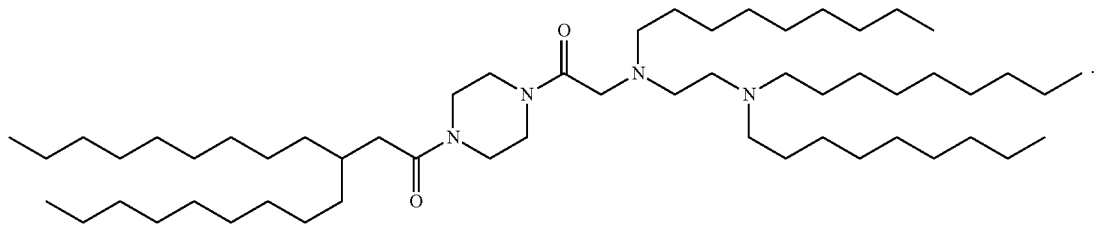

In other embodiments, the delivery agent comprises a compound having the formula:

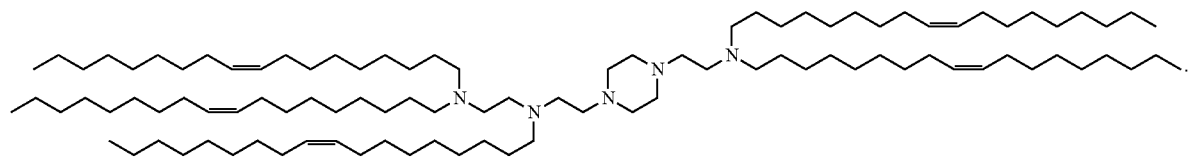

(Compound 342)

Amine moieties of the lipid compounds disclosed herein can be protonated under certain conditions. For example, the central amine moiety of a lipid according to Formula (I) is typically protonated (i.e., positively charged) at a pH below the pKa of the amino moiety and is substantially not charged at a pH above the pKa. Such lipids can be referred to ionizable amino lipids.

In one specific embodiment, the ionizable amino lipid is Compound 18. In another embodiment, the ionizable amino lipid is Compound 236.

In some embodiments, the amount the ionizable amino lipid, e.g., compound of Formula (I) ranges from about 1 mol % to 99 mol % in the lipid composition.

In one embodiment, the amount of the ionizable amino lipid, e.g., compound of Formula (I) is at least about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99 mol % in the lipid composition.

In one embodiment, the amount of the ionizable amino lipid, e.g., the compound of Formula (I) ranges from about 30 mol % to about 70 mol %, from about 35 mol % to about 65 mol %, from about 40 mol % to about 60 mol %, and from about 45 mol % to about 55 mol % in the lipid composition.

In one specific embodiment, the amount of the ionizable amino lipid, e.g., compound of Formula (I) is about 50 mol % in the lipid composition.

In addition to the ionizable amino lipid disclosed herein, e.g., compound of Formula (I), the lipid composition of the pharmaceutical compositions disclosed herein can comprise additional components such as phospholipids, structural lipids, PEG-lipids, and any combination thereof.

b. Additional Components in the Lipid Composition
(i) Phospholipids

The lipid composition of the pharmaceutical composition disclosed herein can comprise one or more phospholipids, for example, one or more saturated or (poly)unsaturated phospholipids or a combination thereof. In general, phospholipids comprise a phospholipid moiety and one or more fatty acid moieties.

A phospholipid moiety can be selected, for example, from the non-limiting group consisting of phosphatidyl choline, phosphatidyl ethanolamine, phosphatidyl glycerol, phosphatidyl serine, phosphatidic acid, 2-lysophosphatidyl choline, and a sphingomyelin.

A fatty acid moiety can be selected, for example, from the non-limiting group consisting of lauric acid, myristic acid, myristoleic acid, palmitic acid, palmitoleic acid, stearic acid, oleic acid, linoleic acid, alpha-linolenic acid, erucic acid, phytanoic acid, arachidic acid, arachidonic acid, eicosapentaenoic acid, behenic acid, docosapentaenoic acid, and docosahexaenoic acid.

Particular phospholipids can facilitate fusion to a membrane. For example, a cationic phospholipid can interact with one or more negatively charged phospholipids of a membrane (e.g., a cellular or intracellular membrane). Fusion of a phospholipid to a membrane can allow one or more elements (e.g., a therapeutic agent) of a lipid-containing composition (e.g., LNPs) to pass through the membrane permitting, e.g., delivery of the one or more elements to a target tissue.

Non-natural phospholipid species including natural species with modifications and substitutions including branching, oxidation, cyclization, and alkynes are also contemplated. For example, a phospholipid can be functionalized with or cross-linked to one or more alkynes (e.g., an alkenyl group in which one or more double bonds is replaced with a triple bond). Under appropriate reaction conditions, an alkyne group can undergo a copper-catalyzed cycloaddition upon exposure to an azide. Such reactions can be useful in functionalizing a lipid bilayer of a nanoparticle composition to facilitate membrane permeation or cellular recognition or in conjugating a nanoparticle composition to a useful component such as a targeting or imaging moiety (e.g., a dye).

Phospholipids include, but are not limited to, glycerophospholipids such as phosphatidylcholines, phosphatidylethanolamines, phosphatidylserines, phosphatidylinositols, phosphatidy glycerols, and phosphatidic acids. Phospholipids also include phosphosphingolipid, such as sphingomyelin.

Examples of phospholipids include, but are not limited to, the following:

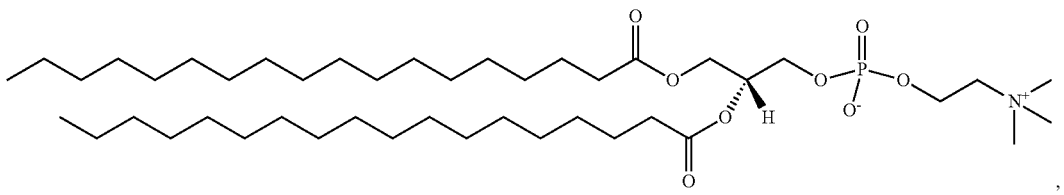

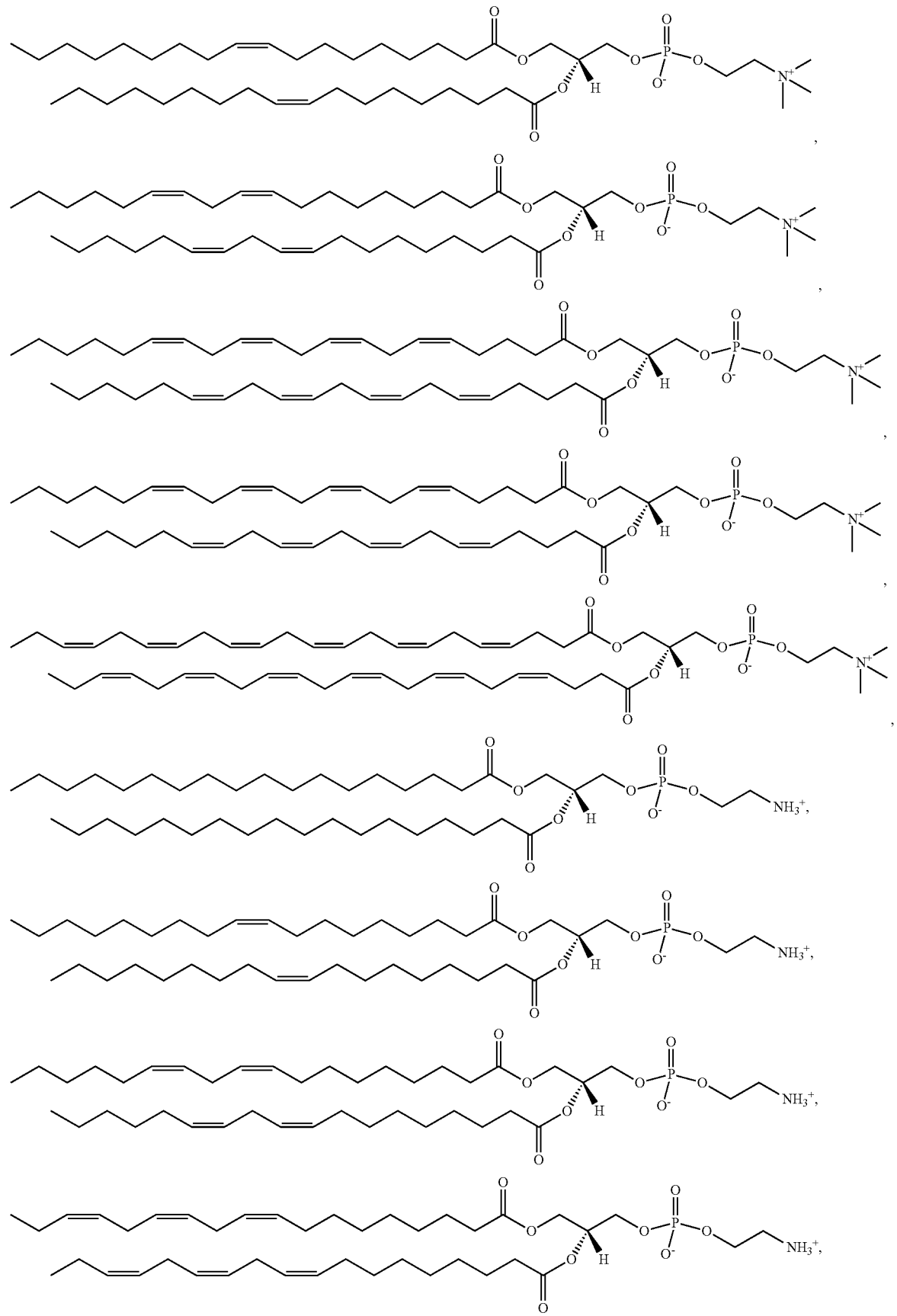

-continued

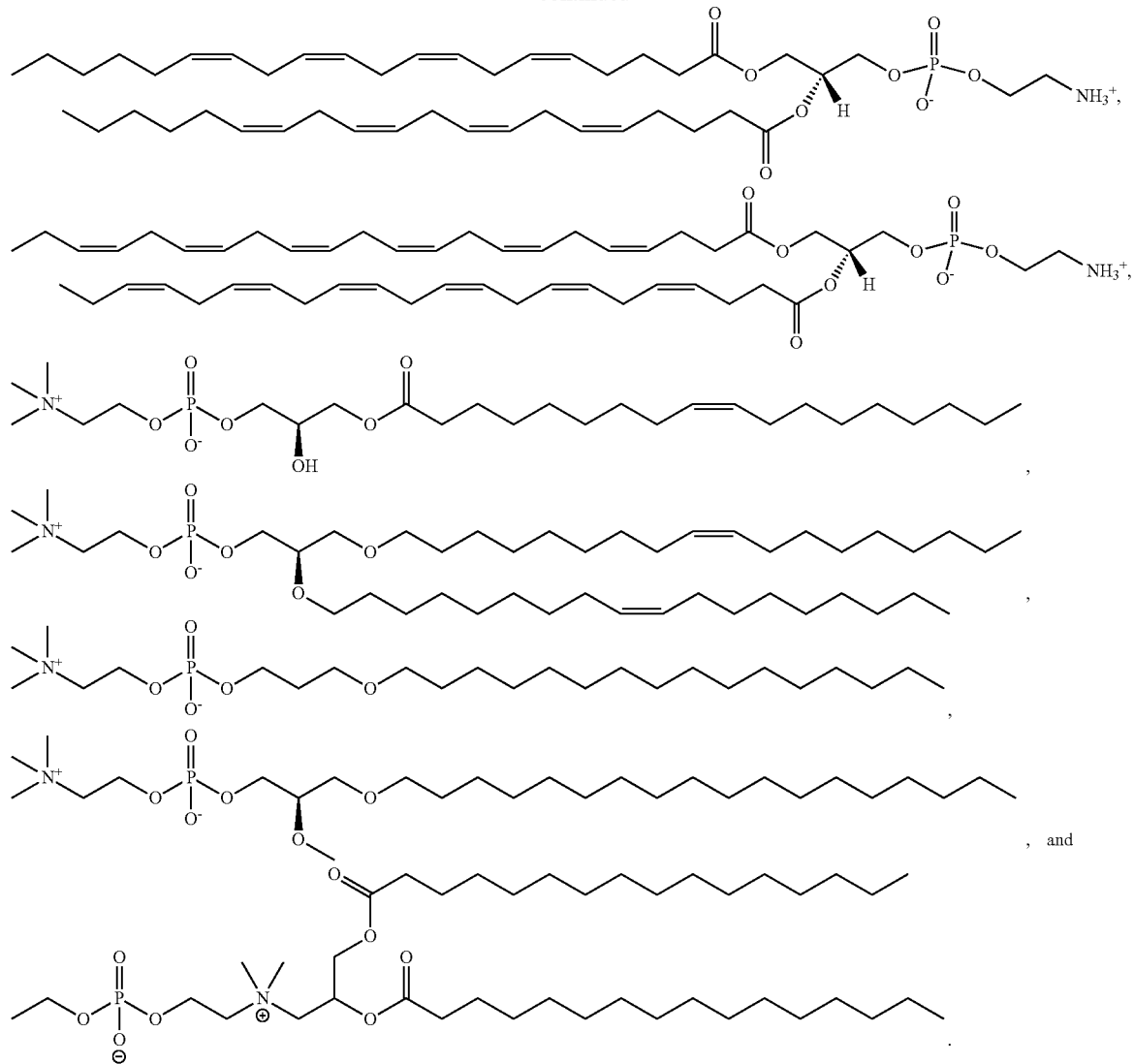

, and

.

In certain embodiments, a phospholipid useful or potentially useful in the present invention is an analog or variant of DSPC. In certain embodiments, a phospholipid useful or potentially useful in the present invention is a compound of Formula (IX):

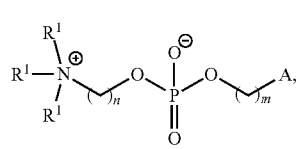

or a salt thereof, wherein:
each $R^1$ is independently optionally substituted alkyl; or optionally two $R^1$ are joined together with the intervening atoms to form optionally substituted monocyclic carbocyclyl or optionally substituted monocyclic heterocyclyl; or optionally three $R^1$ are joined together with the intervening atoms to form optionally substituted bicyclic carbocyclyl or optionally substitute bicyclic heterocyclyl;
n is 1, 2, 3, 4, 5, 6, 7, 8, 9, or 10;
m is 0, 1, 2, 3, 4, 5, 6, 7, 8, 9, or 10;
A is of the formula:

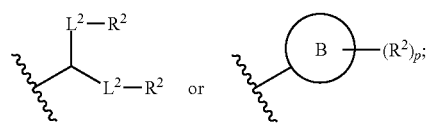

each instance of $L^2$ is independently a bond or optionally substituted $C_{1-6}$ alkylene, wherein one methylene unit of the optionally substituted $C_{1-6}$ alkylene is optionally replaced with —O—, —N($R^N$)—, —S—, —C(O)—, —C(O)N($R^N$)—, —$NR^N$C(O)—, —C(O)O—, —OC(O)—, —OC(O)O—, —OC(O)N($R^N$)—, —$NR^N$C(O)O—, or —$NR^N$C(O)N($R^N$)—;
each instance of $R^2$ is independently optionally substituted $C_{1-30}$ alkyl, optionally substituted $C_{1-30}$ alkenyl, or optionally substituted $C_{1-30}$ alkynyl; optionally wherein one or more methylene units of $R^2$ are independently replaced with optionally substituted carbocyclylene, optionally substituted heterocyclylene, optionally substituted arylene, optionally substituted heteroarylene, —N($R^N$)—, —O—, —S—, —C(O)—, —C(O)N($R^N$)—, —$NR^N$C(O)—, —$NR^N$C(O)N($R^N$)—, —C(O)O—, —OC(O)—, —OC(O)O—, —OC(O)N($R^N$)—, —$NR^N$C(O)O—, —C(O)S—, —SC(O)—, —C(=$NR^N$)—, —C(=$NR^N$)N($R^N$)—, —$NR^N$C(=$NR^N$)—, —$NR^N$C(=$NR^N$)N($R^N$)—, —C(S)—, —C(S)N($R^N$)—, —$NR^N$C(S)—, —$NR^N$C(S)N($R^N$)—, —S(O)—, —OS(O)—, —S(O)O—, —OS(O)O—, —OS(O)$_2$—, —S(O)$_2$O—, —OS(O)$_2$O—, —N($R^N$)S(O)—, —S(O)N($R^N$)—, —N($R^N$)S(O)N($R^N$)—, —OS(O)N($R^N$)—, —N($R^N$)S(O)O—, —S(O)$_2$—, —N($R^N$)S(O)$_2$—, —S(O)$_2$N($R^N$)—, —N($R^N$)S(O)$_2$N($R^N$)—, —OS(O)$_2$N($R^N$)—, or —N($R^N$)S(O)$_2$O—;

each instance of $R^N$ is independently hydrogen, optionally substituted alkyl, or a nitrogen protecting group;

Ring B is optionally substituted carbocyclyl, optionally substituted heterocyclyl, optionally substituted aryl, or optionally substituted heteroaryl; and p is 1 or 2;

provided that the compound is not of the formula:

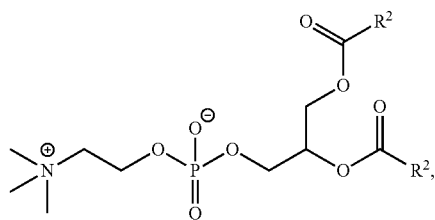

wherein each instance of $R^2$ is independently unsubstituted alkyl, unsubstituted alkenyl, or unsubstituted alkynyl.

Phospholipid Head Modifications

In certain embodiments, a phospholipid useful or potentially useful in the present invention comprises a modified phospholipid head (e.g., a modified choline group). In certain embodiments, a phospholipid with a modified head is DSPC, or analog thereof, with a modified quaternary amine. For example, in embodiments of Formula (IX), at least one of $R^1$ is not methyl. In certain embodiments, at least one of $R^1$ is not hydrogen or methyl. In certain embodiments, the compound of Formula (IX) is of one of the following formulae:

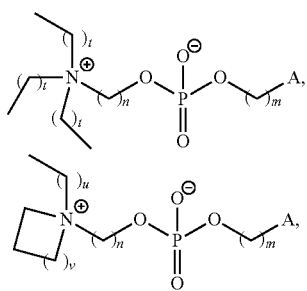

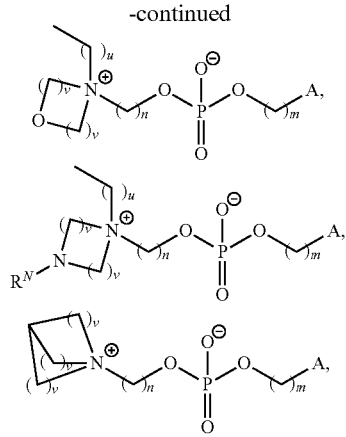

or a salt thereof, wherein:

each t is independently 1, 2, 3, 4, 5, 6, 7, 8, 9, or 10;

each u is independently 0, 1, 2, 3, 4, 5, 6, 7, 8, 9, or 10; and each v is independently 1, 2, or 3.

In certain embodiments, the compound of Formula (IX) is of one of the following formulae:

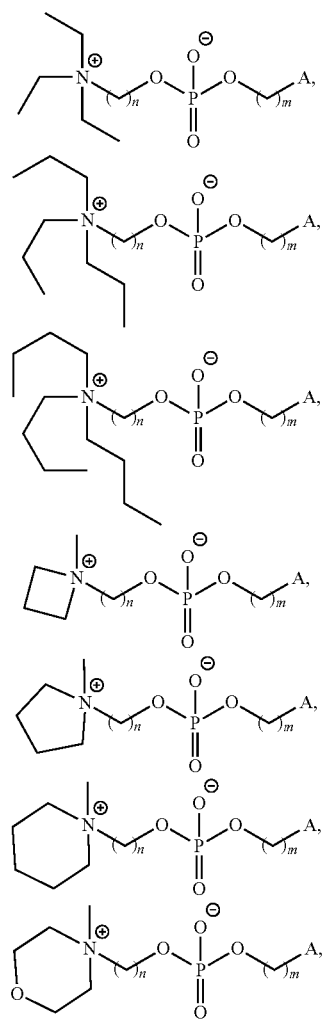

321
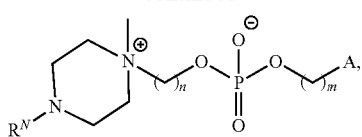
322
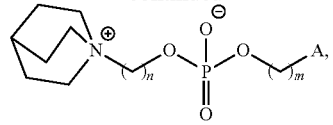
or a salt thereof.
In certain embodiments, a compound of Formula (IX) is one of the following:
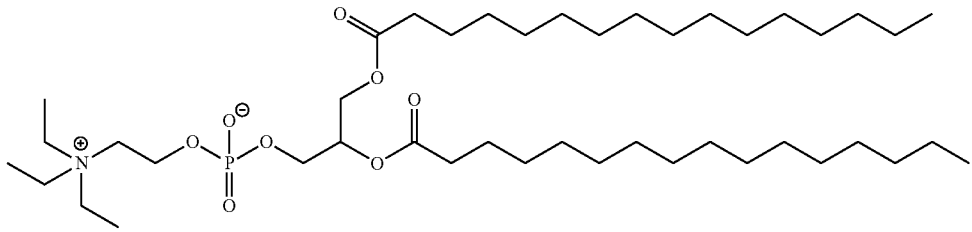
(Compound 400)
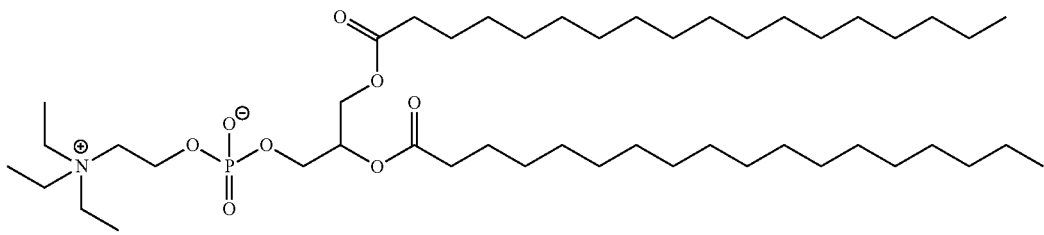
(Compound 401)
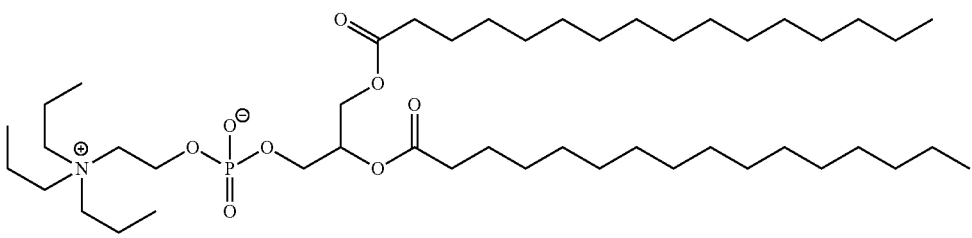
(Compound 402)
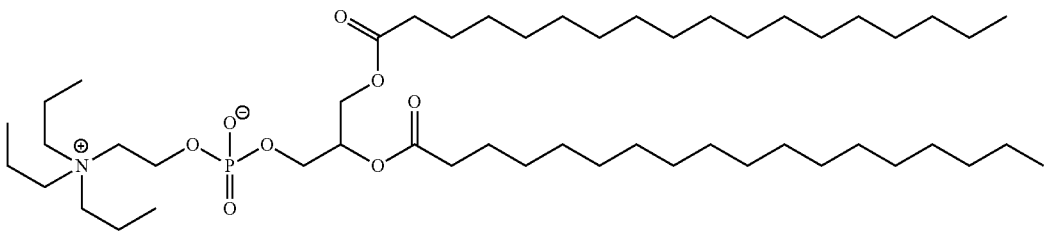
(Compound 403)
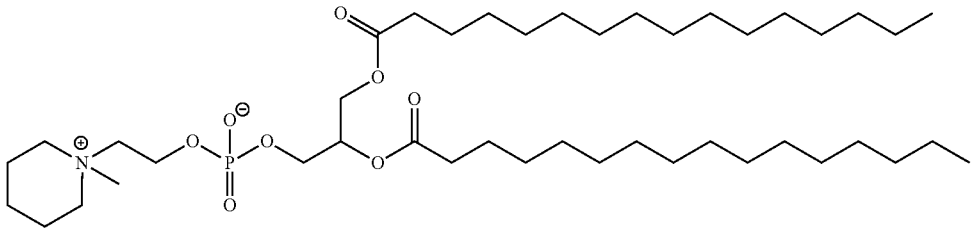
(Compound 404)

-continued

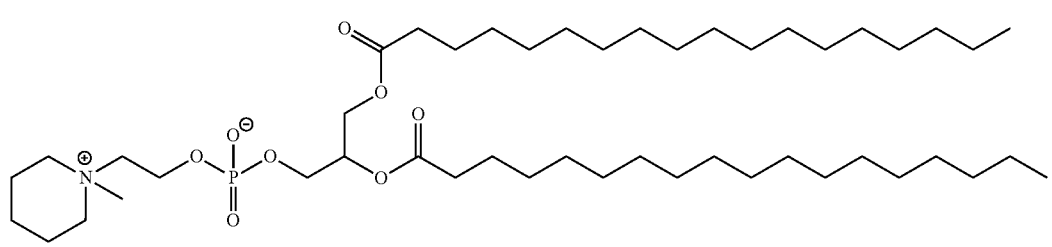
(Compound 405)

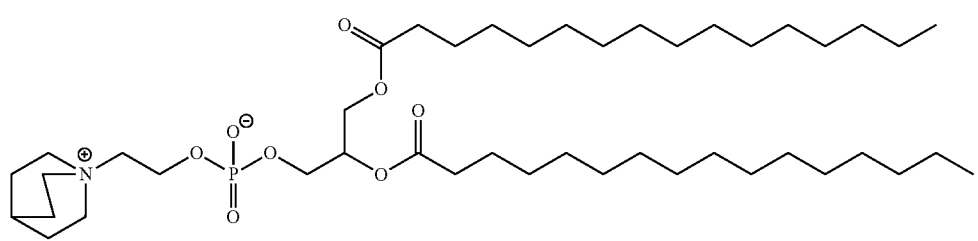
(Compound 406)

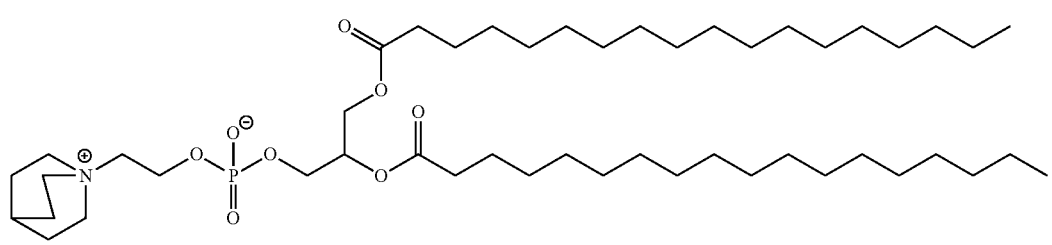
(Compound 407)

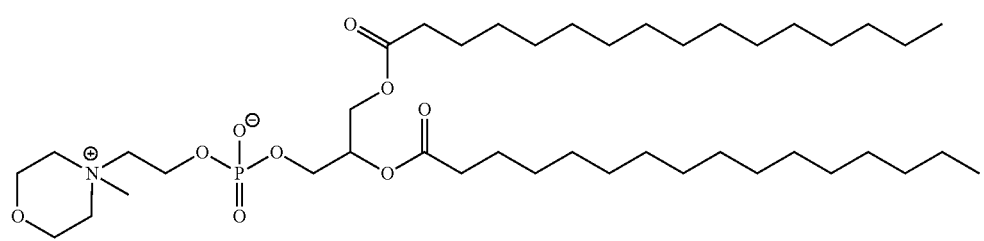
(Compound 408)

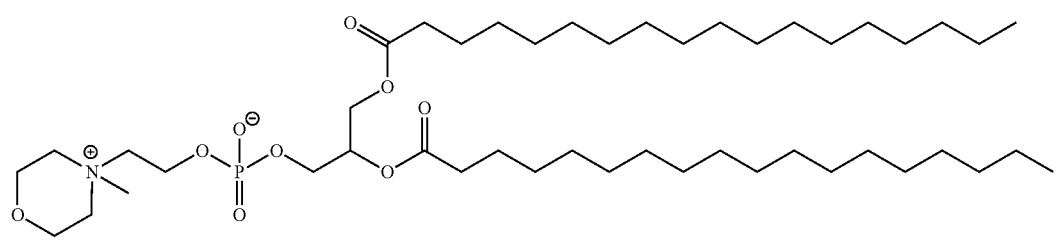
(Compound 409)

, or a salt thereof.

In certain embodiments, a compound of Formula (IX) is of Formula (IX-a):

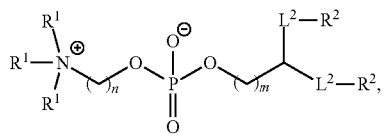
(IX-a)

or a salt thereof.

In certain embodiments, phospholipids useful or potentially useful in the present invention comprise a modified core. In certain embodiments, a phospholipid with a modified core described herein is DSPC, or analog thereof, with a modified core structure. For example, in certain embodiments of Formula (IX-a), group A is not of the following formula:

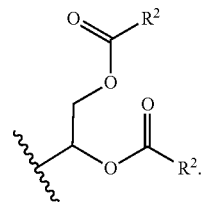

In certain embodiments, the compound of Formula (IX-a) is of one of the following formulae:
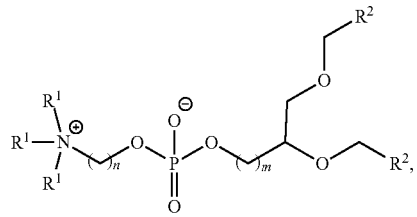
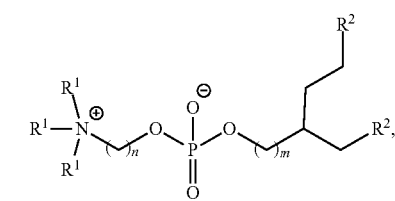
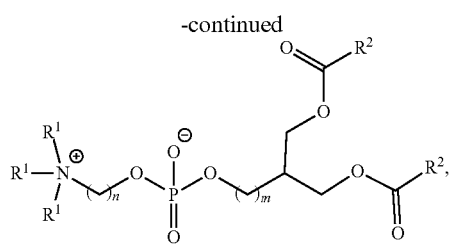
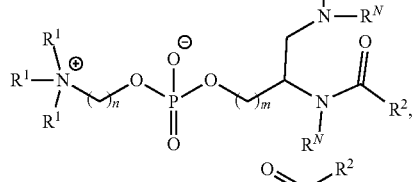
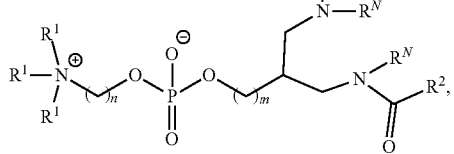
or a salt thereof.
In certain embodiments, a compound of Formula (IX) is one of the following:
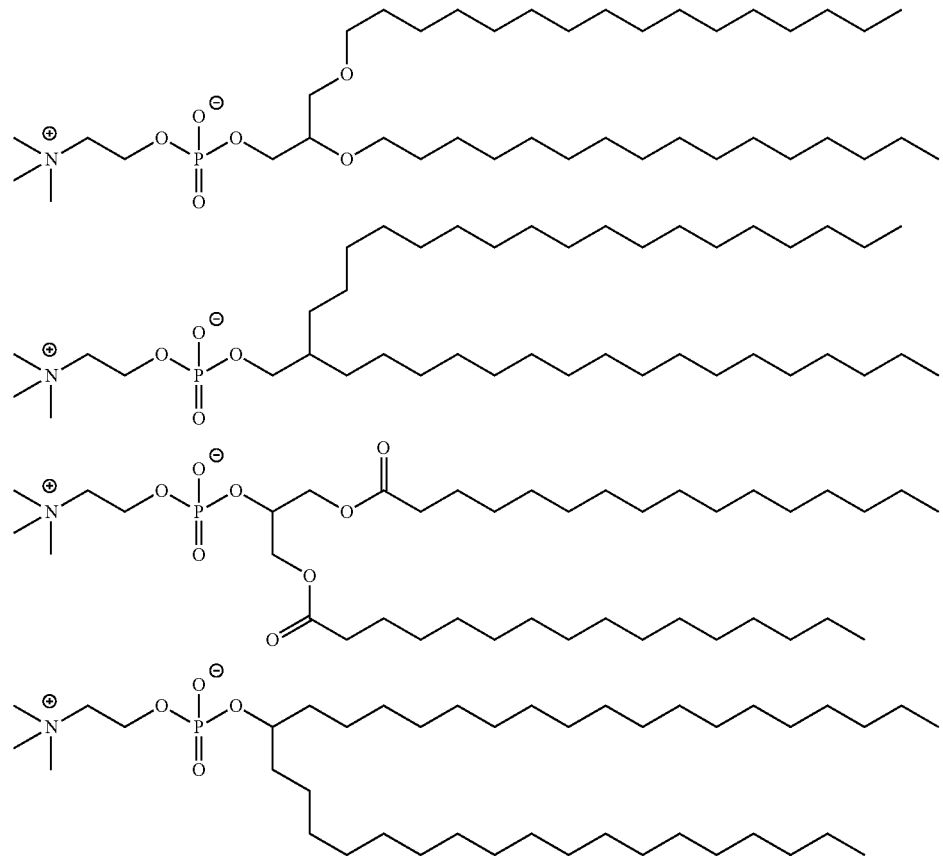

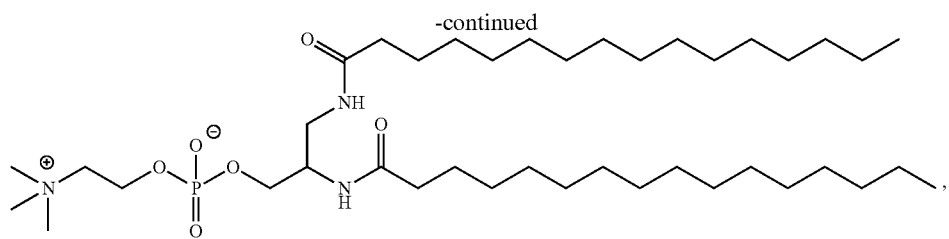

or salts thereof.

In certain embodiments, a phospholipid useful or potentially useful in the present invention comprises a cyclic moiety in place of the glyceride moiety. In certain embodiments, a phospholipid useful in the present invention is DSPC, or analog thereof, with a cyclic moiety in place of the glyceride moiety. In certain embodiments, the compound of Formula (IX) is of Formula (IX-b):

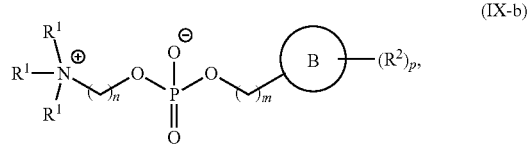

(IX-b)

or a salt thereof.

In certain embodiments, the compound of Formula (IX-b) is of Formula (IX-b-1):

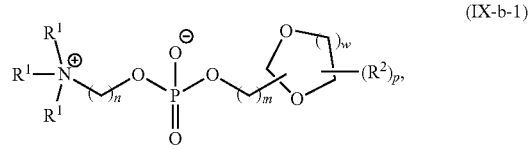

(IX-b-1)

or a salt thereof, wherein:

w is 0, 1, 2, or 3.

In certain embodiments, the compound of Formula (IX-b) is of Formula (IX-b-2):

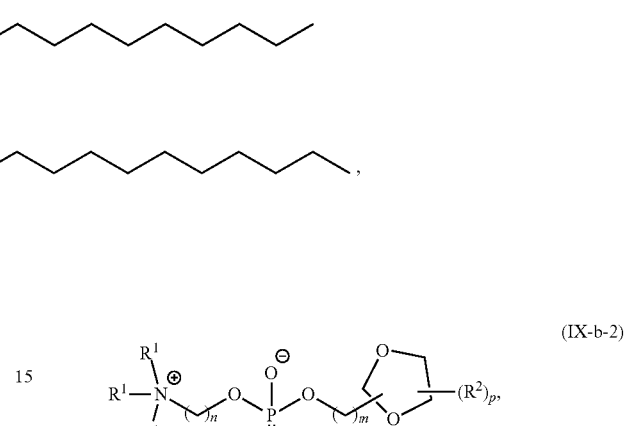

(IX-b-2)

or a salt thereof.

In certain embodiments, the compound of Formula (IX-b) is of Formula (IX-b-3):

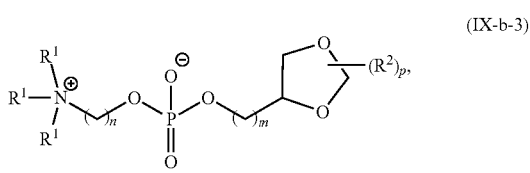

(IX-b-3)

or a salt thereof.

In certain embodiments, the compound of Formula (IX-b) is of Formula (IX-b-4):

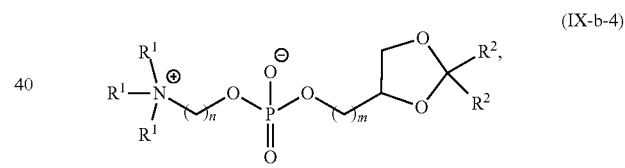

(IX-b-4)

or a salt thereof.

In certain embodiments, the compound of Formula (IX-b) is one of the following:

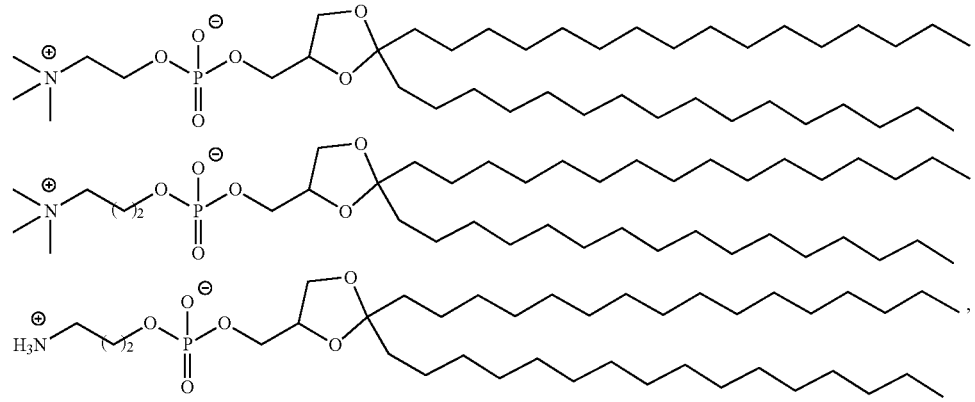

or salts thereof.

Phospholipid Tail Modifications

In certain embodiments, a phospholipid useful or potentially useful in the present invention comprises a modified tail. In certain embodiments, a phospholipid useful or potentially useful in the present invention is DSPC, or analog thereof, with a modified tail. As described herein, a "modified tail" may be a tail with shorter or longer aliphatic chains, aliphatic chains with branching introduced, aliphatic chains with substituents introduced, aliphatic chains wherein one or more methylenes are replaced by cyclic or heteroatom groups, or any combination thereof. For example, in certain embodiments, the compound of (IX) is of Formula (IX-a), or a salt thereof, wherein at least one instance of $R^2$ is each instance of $R^2$ is optionally substituted $C_{1-30}$ alkyl, wherein one or more methylene units of $R^2$ are independently replaced with optionally substituted carbocyclylene, optionally substituted heterocyclylene, optionally substituted arylene, optionally substituted heteroarylene, —N($R^N$)—, —O—, —S—, —C(O)—, —C(O)N($R^N$)—, —N$R^N$C(O)—, —N$R^N$C(O)N($R^N$)—, —C(O)O—, —OC(O)—, —OC(O)O—, —OC(O)N($R^N$)—, —N$R^N$C(O)O—, —C(O)S—, —SC(O)—, —C(=N$R^N$)—, —C(=N$R^N$)N($R^N$)—, —N$R^N$C(=N$R^N$)—, —N$R^N$C(=N$R^N$)N($R^N$)—, —C(S)—, —C(S)N($R^N$)—, —N$R^N$C(S)—, —N$R^N$C(S)N($R^N$)—, —S(O)—, —OS(O)—, —S(O)O—, —OS(O)O—, —OS(O)$_2$—, —S(O)$_2$O—, —OS(O)$_2$O—, —N($R^N$)S(O)—, —S(O)N($R^N$)—, —N($R^N$)S(O)N($R^N$)—, —OS(O)N($R^N$)—, —N($R^N$)S(O)O—, —S(O)$_2$—, —N($R^N$)S(O)$_2$—, —S(O)$_2$N($R^N$)—, —N($R^N$)S(O)$_2$N($R^N$)—, —OS(O)$_2$N($R^N$)—, or —N($R^N$)S(O)$_2$O—.

In certain embodiments, the compound of Formula (IX) is of Formula (IX-c):

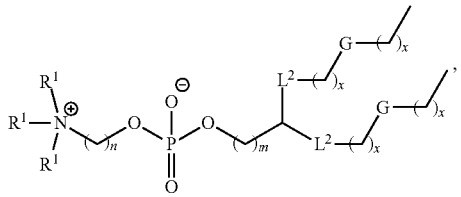

(IX-c)

or a salt thereof, wherein:
each x is independently an integer between 0-30, inclusive; and
each instance is G is independently selected from the group consisting of optionally substituted carbocyclylene, optionally substituted heterocyclylene, optionally substituted arylene, optionally substituted heteroarylene, —N($R^N$)—, —O—, —S—, —C(O)—, —C(O)N($R^N$)—, —N$R^N$C(O)—, —N$R^N$C(O)N($R^N$)—, —C(O)O—, —OC(O)—, —OC(O)O—, —OC(O)N($R^N$)—, —N$R^N$C(O)O—, —C(O)S—, —SC(O)—, —C(=N$R^N$)—, —C(=N$R^N$)N($R^N$)—, —N$R^N$C(=N$R^N$)—, —N$R^N$C(=N$R^N$)N($R^N$)—, —C(S)—, —C(S)N($R^N$)—, —N$R^N$C(S)—, —N$R^N$C(S)N($R^N$)—, —S(O)—, —OS(O)—, —S(O)O—, —OS(O)O—, —OS(O)$_2$—, —S(O)$_2$O—, —OS(O)$_2$O—, —N($R^N$)S(O)—, —S(O)N($R^N$)—, —N($R^N$)S(O)N($R^N$)—, —OS(O)N($R^N$)—, —N($R^N$)S(O)O—, —S(O)$_2$—, —N($R^N$)S(O)$_2$—, —S(O)$_2$N($R^N$)—, —N($R^N$)S(O)$_2$N($R^N$)—, —OS(O)$_2$N($R^N$)—, or —N($R^N$)S(O)$_2$O—. Each possibility represents a separate embodiment of the present invention.

In certain embodiments, the compound of Formula (IX-c) is of Formula (IX-c-1):

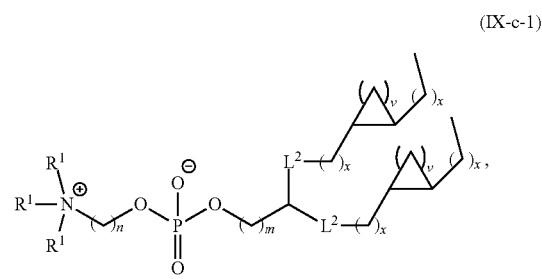

(IX-c-1)

or salt thereof, wherein:
each instance of v is independently 1, 2, or 3.

In certain embodiments, the compound of Formula (IX-c) is of Formula (IX-c-2):

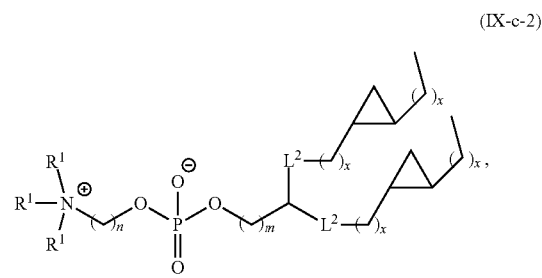

(IX-c-2)

or a salt thereof.

In certain embodiments, the compound of Formula (IX-c) is of the following formula:

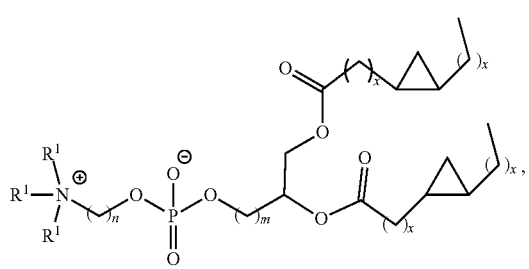

or a salt thereof.

In certain embodiments, the compound of Formula (IX-c) is the following:

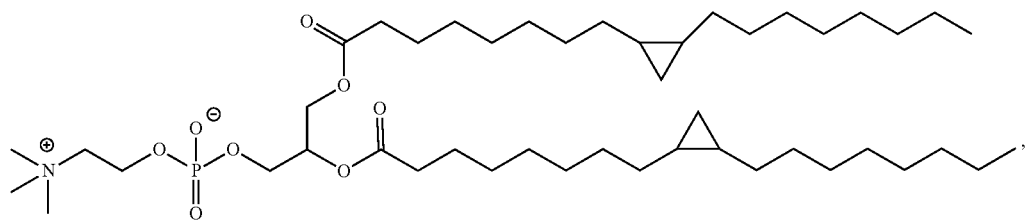 [SMILES: CCCCCCCCC1CC1CCCCCCCC(=O)OCC(COP(=O)([O-])OCC[N+](C)(C)C)OC(=O)CCCCCCCC1CC1CCCCCCCC]

or a salt thereof.

In certain embodiments, the compound of Formula (IX-c) is of Formula (IX-c-3):

(IX-c-3)

or a salt thereof.

In certain embodiments, the compound of Formula (IX-c) is of the following formulae:

or a salt thereof.

In certain embodiments, the compound of Formula (IX-c) is the following:

In certain embodiments, a phospholipid useful or potentially useful in the present invention comprises a modified phosphocholine moiety, wherein the alkyl chain linking the quaternary amine to the phosphoryl group is not ethylene (e.g., n is not 2). Therefore, in certain embodiments, a phospholipid useful or potentially useful in the present invention is a compound of Formula (IX), wherein n is 1, 3, 4, 5, 6, 7, 8, 9, or 10. For example, in certain embodiments, a compound of Formula (IX) is of one of the following formulae:

or a salt thereof.

In certain embodiments, a compound of Formula (IX) is one of the following:

or a salt thereof.

333 334
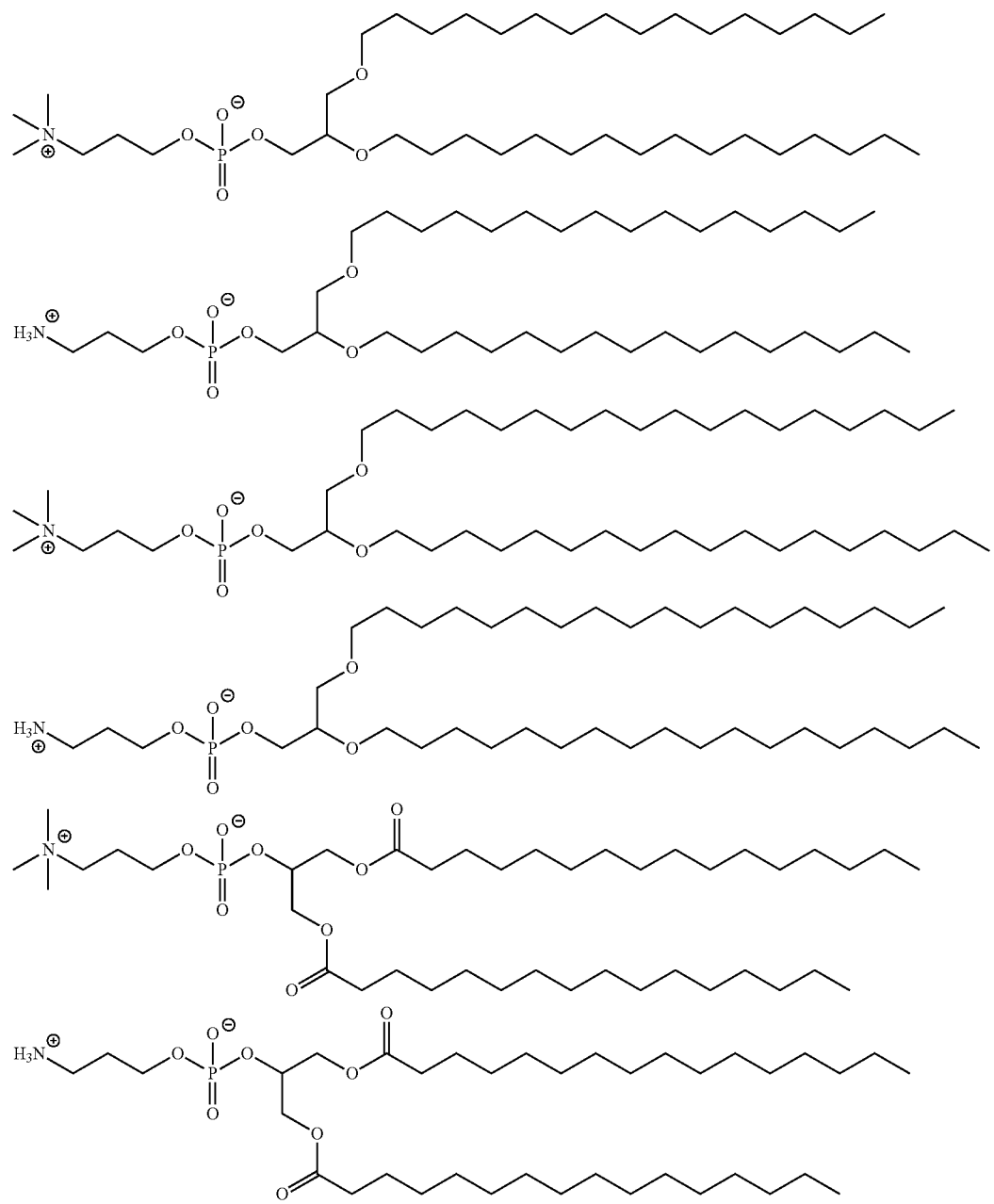
(Compound 411)
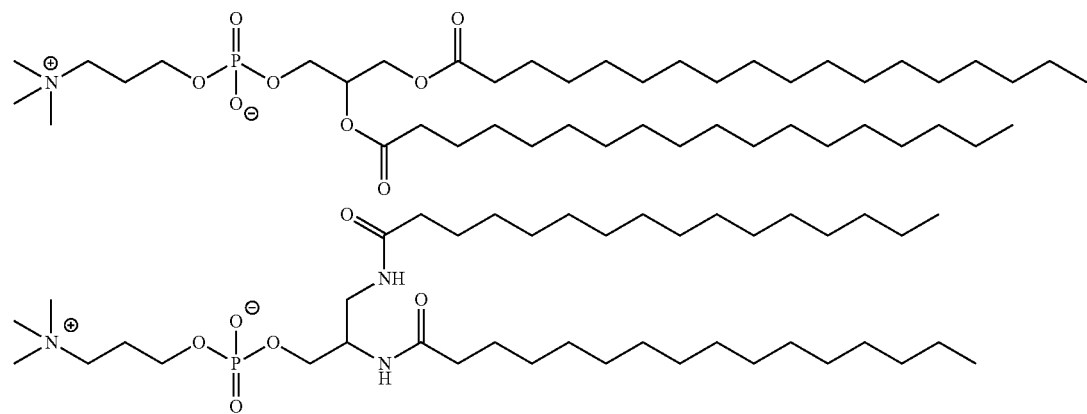

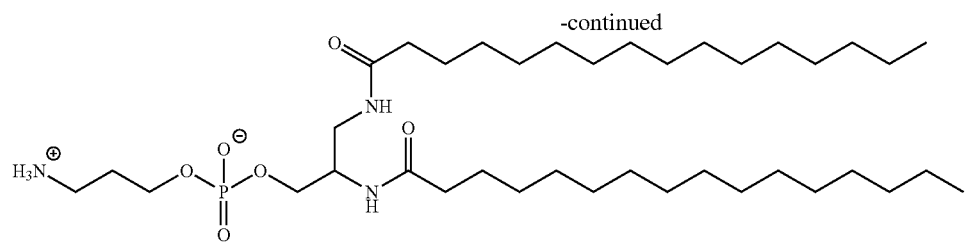
(Compound 412)
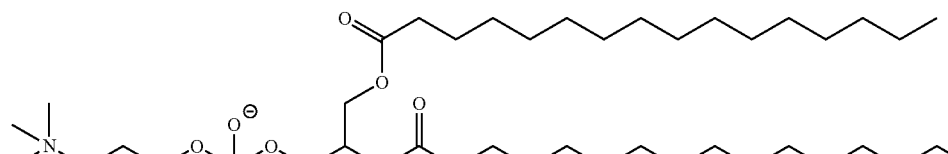
(Compound 413)
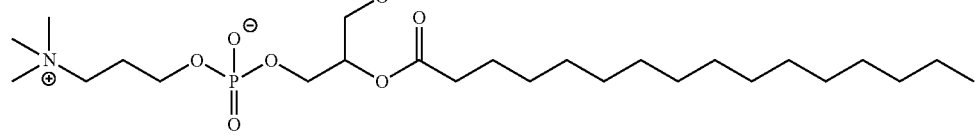
(Compound 414)
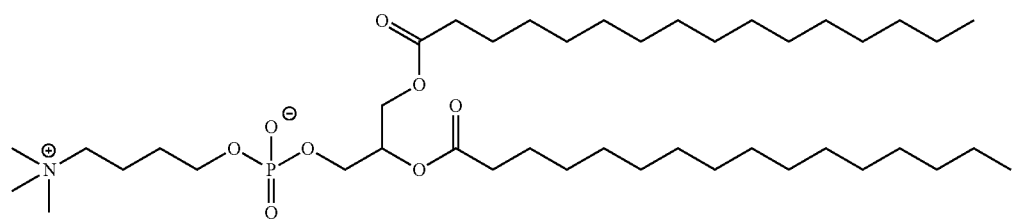
,
or salts thereof.
(ii) Alternative Lipids
In certain embodiments, an alternative lipid is used in place of a phospholipid of the invention. Non-limiting examples of such alternative lipids include the following:
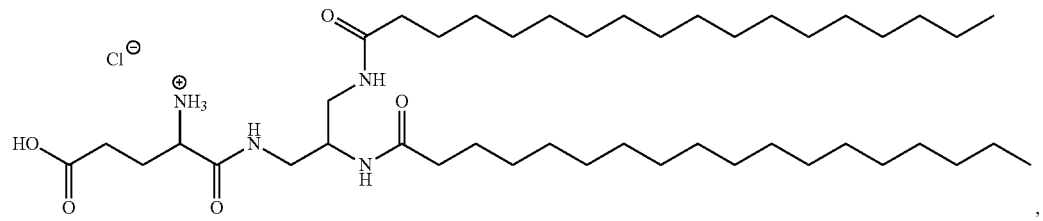
,
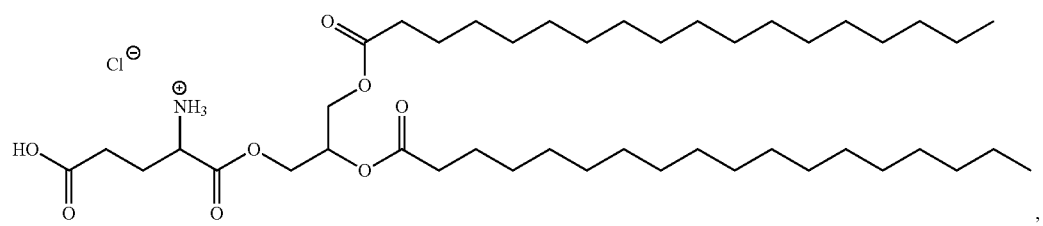
,

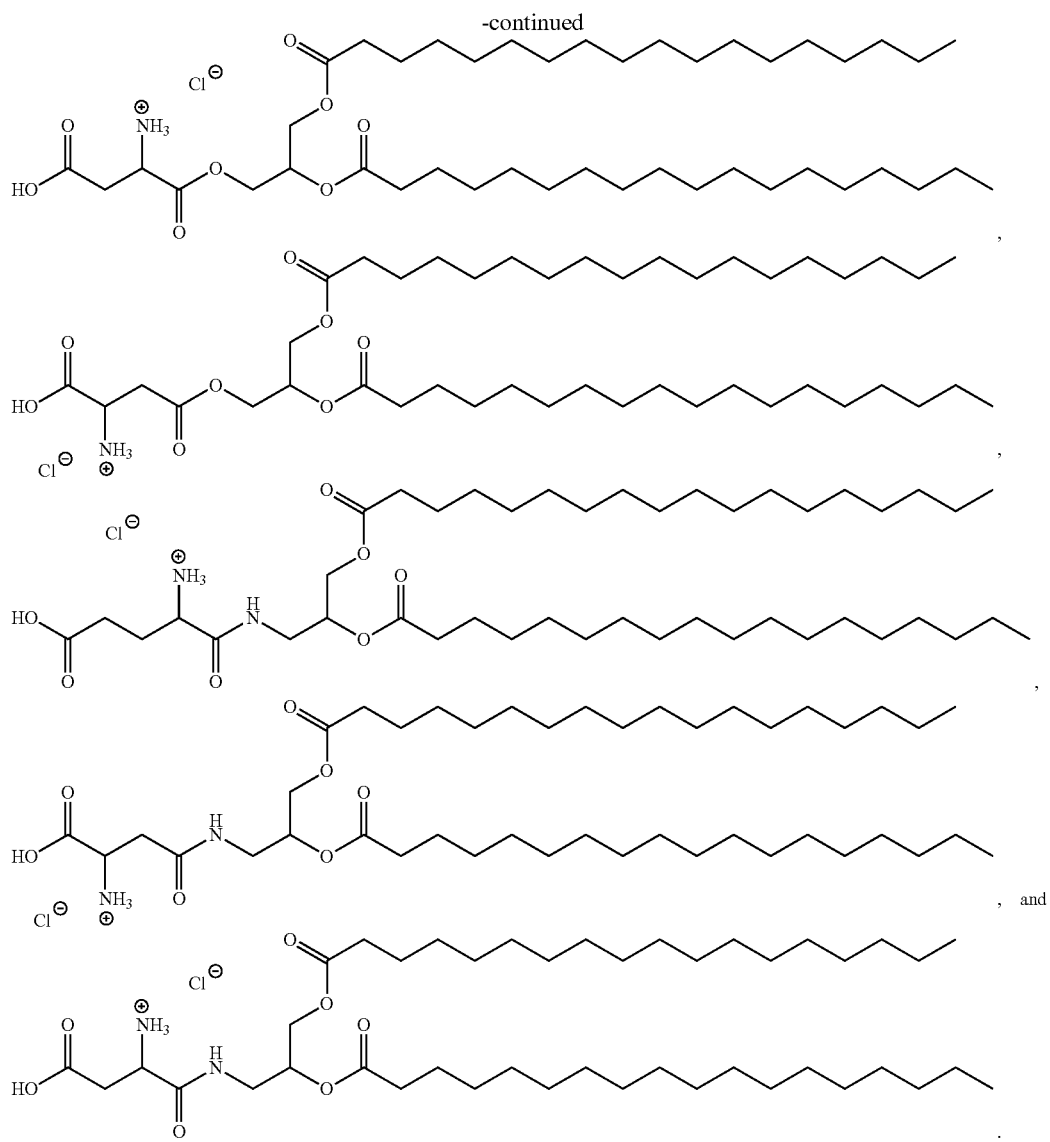

(iii) Structural Lipids

The lipid composition of a pharmaceutical composition disclosed herein can comprise one or more structural lipids. As used herein, the term "structural lipid" refers to sterols and also to lipids containing sterol moieties.

Incorporation of structural lipids in the lipid nanoparticle may help mitigate aggregation of other lipids in the particle. Structural lipids can be selected from the group including but not limited to, cholesterol, fecosterol, sitosterol, ergosterol, campesterol, stigmasterol, brassicasterol, tomatidine, tomatine, ursolic acid, alpha-tocopherol, hopanoids, phytosterols, steroids, and mixtures thereof. In some embodiments, the structural lipid is a sterol. As defined herein, "sterols" are a subgroup of steroids consisting of steroid alcohols. In certain embodiments, the structural lipid is a steroid. In certain embodiments, the structural lipid is cholesterol. In certain embodiments, the structural lipid is an analog of cholesterol. In certain embodiments, the structural lipid is alpha-tocopherol. Examples of structural lipids include, but are not limited to, the following:

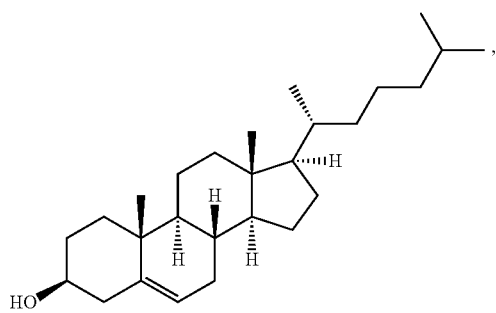

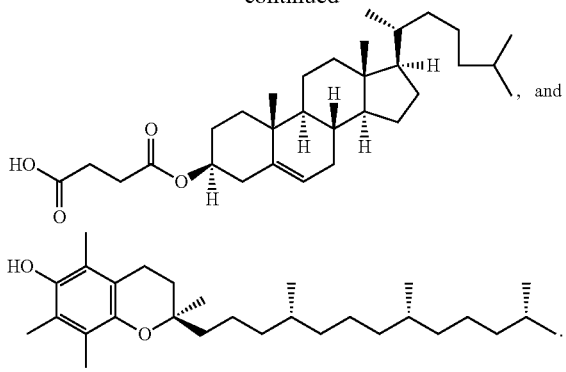

In one embodiment, the amount of the structural lipid (e.g., an sterol such as cholesterol) in the lipid composition of a pharmaceutical composition disclosed herein ranges from about 20 mol % to about 60 mol %, from about 25 mol % to about 55 mol %, from about 30 mol % to about 50 mol %, or from about 35 mol % to about 45 mol %.

In one embodiment, the amount of the structural lipid (e.g., an sterol such as cholesterol) in the lipid composition disclosed herein ranges from about 25 mol % to about 30 mol %, from about 30 mol % to about 35 mol %, or from about 35 mol % to about 40 mol %.

In one embodiment, the amount of the structural lipid (e.g., a sterol such as cholesterol) in the lipid composition disclosed herein is about 24 mol %, about 29 mol %, about 34 mol %, or about 39 mol %.

In some embodiments, the amount of the structural lipid (e.g., an sterol such as cholesterol) in the lipid composition disclosed herein is at least about 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, or 60 mol %.

(iv) Polyethylene Glycol (PEG)-Lipids

The lipid composition of a pharmaceutical composition disclosed herein can comprise one or more a polyethylene glycol (PEG) lipid.

As used herein, the term "PEG-lipid" refers to polyethylene glycol (PEG)-modified lipids. Non-limiting examples of PEG-lipids include PEG-modified phosphatidylethanolamine and phosphatidic acid, PEG-ceramide conjugates (e.g., PEG-CerC14 or PEG-CerC20), PEG-modified dialkylamines and PEG-modified 1,2-diacyloxypropan-3-amines. Such lipids are also referred to as PEGylated lipids. For example, a PEG lipid can be PEG-c-DOMG, PEG-DMG, PEG-DLPE, PEG-DMPE, PEG-DPPC, or a PEG-DSPE lipid.

In some embodiments, the PEG-lipid includes, but not limited to 1,2-dimyristoyl-sn-glycerol methoxypolyethylene glycol (PEG-DMG), 1,2-distearoyl-sn-glycero-3-phosphoethanolamine-N-[amino(polyethylene glycol)] (PEG-DSPE), PEG-disteryl glycerol (PEG-DSG), PEG-dipalmetoleyl, PEG-dioleyl, PEG-distearyl, PEG-diacylglycamide (PEG-DAG), PEG-dipalmitoyl phosphatidylethanolamine (PEG-DPPE), or PEG-1,2-dimyristyloxlpropyl-3-amine (PEG-c-DMA).

In one embodiment, the PEG-lipid is selected from the group consisting of a PEG-modified phosphatidylethanolamine, a PEG-modified phosphatidic acid, a PEG-modified ceramide, a PEG-modified dialkylamine, a PEG-modified diacylglycerol, a PEG-modified dialkylglycerol, and mixtures thereof.

In some embodiments, the lipid moiety of the PEG-lipids includes those having lengths of from about $C_{14}$ to about $C_{22}$, preferably from about $C_{14}$ to about $C_{16}$. In some embodiments, a PEG moiety, for example an mPEG-NH$_2$, has a size of about 1000, 2000, 5000, 10,000, 15,000 or 20,000 daltons. In one embodiment, the PEG-lipid is PEG2k-DMG.

In one embodiment, the lipid nanoparticles described herein can comprise a PEG lipid which is a non-diffusible PEG. Non-limiting examples of non-diffusible PEGs include PEG-DSG and PEG-DSPE.

PEG-lipids are known in the art, such as those described in U.S. Pat. No. 8,158,601 and International Publ. No. WO 2015/130584 A2, which are incorporated herein by reference in their entirety.

In general, some of the other lipid components (e.g., PEG lipids) of various formulae, described herein may be synthesized as described International Patent Application No. PCT/US2016/000129, filed Dec. 10, 2016, entitled "Compositions and Methods for Delivery of Therapeutic Agents," which is incorporated by reference in its entirety.

The lipid component of a lipid nanoparticle composition may include one or more molecules comprising polyethylene glycol, such as PEG or PEG-modified lipids. Such species may be alternately referred to as PEGylated lipids. A PEG lipid is a lipid modified with polyethylene glycol. A PEG lipid may be selected from the non-limiting group including PEG-modified phosphatidylethanolamines, PEG-modified phosphatidic acids, PEG-modified ceramides, PEG-modified dialkylamines, PEG-modified diacylglycerols, PEG-modified dialkylglycerols, and mixtures thereof. For example, a PEG lipid may be PEG-c-DOMG, PEG-DMG, PEG-DLPE, PEG-DMPE, PEG-DPPC, or a PEG-DSPE lipid.

In some embodiments the PEG-modified lipids are a modified form of PEG DMG. PEG-DMG has the following structure:

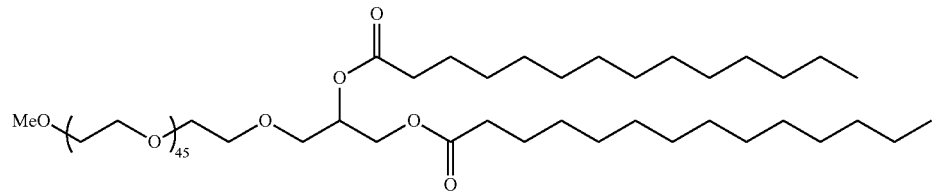

In one embodiment, PEG lipids useful in the present invention can be PEGylated lipids described in International Publication No. WO2012099755, the contents of which is herein incorporated by reference in its entirety. Any of these exemplary PEG lipids described herein may be modified to comprise a hydroxyl group on the PEG chain. In certain embodiments, the PEG lipid is a PEG-OH lipid. As generally defined herein, a "PEG-OH lipid" (also referred to herein as "hydroxy-PEGylated lipid") is a PEGylated lipid having one or more hydroxyl (—OH) groups on the lipid. In certain embodiments, the PEG-OH lipid includes one or more hydroxyl groups on the PEG chain. In certain embodiments, a PEG-OH or hydroxy-PEGylated lipid comprises an —OH group at the terminus of the PEG chain. Each possibility represents a separate embodiment of the present invention.

In certain embodiments, a PEG lipid useful in the present invention is a compound of Formula (VII). Provided herein are compounds of Formula (VII):

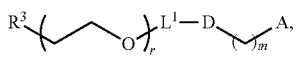
(VII)

or salts thereof, wherein:
  $R^3$ is —$OR^O$;
  $R^O$ is hydrogen, optionally substituted alkyl, or an oxygen protecting group;
  r is an integer between 1 and 100, inclusive;
  $L^1$ is optionally substituted $C_{1-10}$ alkylene, wherein at least one methylene of the optionally substituted $C_{1-10}$ alkylene is independently replaced with optionally substituted carbocyclylene, optionally substituted heterocyclylene, optionally substituted arylene, optionally substituted heteroarylene, —O—, —N($R^N$)—, —S—, —C(O)—, —C(O)N($R^N$)—, —$NR^N$C(O)—, —C(O)O—, —OC(O)—, —OC(O)O—, —OC(O)N($R^N$)—, —$NR^N$C(O)O—, or —$NR^N$C(O)N($R^N$)—;
  D is a moiety obtained by click chemistry or a moiety cleavable under physiological conditions;
  m is 0, 1, 2, 3, 4, 5, 6, 7, 8, 9, or 10;
  A is of the formula:

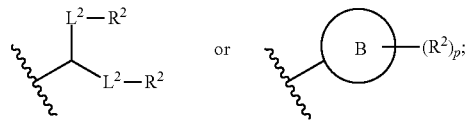

each instance of $L^2$ is independently a bond or optionally substituted $C_{1-6}$ alkylene, wherein one methylene unit of the optionally substituted $C_{1-6}$ alkylene is optionally replaced with —O—, —N($R^N$)—, —S—, —C(O)—, —C(O)N($R^N$)—, —$NR^N$C(O)—, —C(O)O—, —OC(O)—, —OC(O)O—, —OC(O)N($R^N$)—, —$NR^N$C(O)O—, or —$NR^N$C(O)N($R^N$)—;
  each instance of $R^2$ is independently optionally substituted $C_{1-30}$ alkyl, optionally substituted $C_{1-30}$ alkenyl, or optionally substituted $C_{1-30}$ alkynyl; optionally wherein one or more methylene units of $R^2$ are independently replaced with optionally substituted carbocyclylene, optionally substituted heterocyclylene, optionally substituted arylene, optionally substituted heteroarylene, —N($R^N$)—, —O—, —S—, —C(O)—, —C(O)N($R^N$)—, —$NR^N$C(O)—, —$NR^N$C(O)N($R^N$)—, —C(O)O—, —OC(O)—, —OC(O)O—, —OC(O)N($R^N$)—, —$NR^N$C(O)O—, —C(O)S—, —SC(O)—, —C(=$NR^N$)—, —C(=$NR^N$)N($R^N$)—, —$NR^N$C(=$NR^N$)—, —$NR^N$C(=$NR^N$)N($R^N$)—, —C(S)—, —C(S)N($R^N$)—, —$NR^N$C(S)—, —$NR^N$C(S)N($R^N$)—, —S(O)—, —OS(O)—, —S(O)O—, —OS(O)O—, —OS(O)$_2$—, —S(O)$_2$O—, —OS(O)$_2$O—, —N($R^N$)S(O)—, —S(O)N($R^N$)—, —N($R^N$)S(O)N($R^N$)—, —OS(O)N($R^N$)—, —N($R^N$)S(O)O—, —S(O)$_2$—, —N($R^N$)S(O)$_2$—, —S(O)$_2$N($R^N$)—, —N($R^N$)S(O)$_2$N($R^N$)—, —OS(O)$_2$N($R^N$)—, or —N($R^N$)S(O)$_2$O—;
  each instance of $R^N$ is independently hydrogen, optionally substituted alkyl, or a nitrogen protecting group;
  Ring B is optionally substituted carbocyclyl, optionally substituted heterocyclyl, optionally substituted aryl, or optionally substituted heteroaryl; and
  p is 1 or 2.

In certain embodiments, the compound of Formula (VII) is a PEG-OH lipid (i.e.,
  $R^3$ is —$OR^O$, and $R^O$ is hydrogen). In certain embodiments, the compound of Formula (VII) is of Formula (VII-OH):

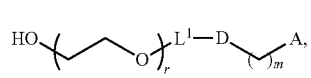
(VII-OH)

or a salt thereof.

In certain embodiments, D is a moiety obtained by click chemistry (e.g., triazole). In certain embodiments, the compound of Formula (VII) is of Formula (VII-a-1) or (VII-a-2):

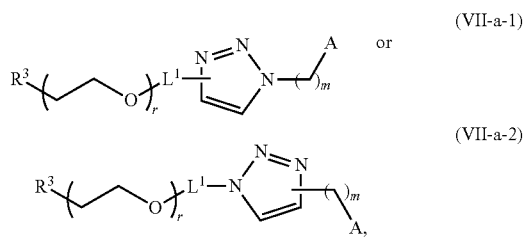

or a salt thereof.

In certain embodiments, the compound of Formula (VII) is of one of the following formulae:

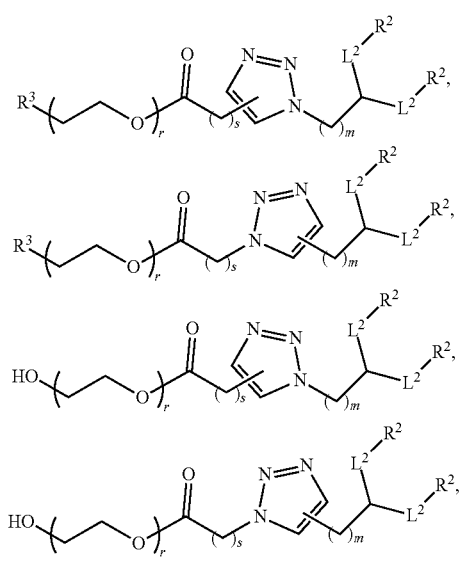

or a salt thereof, wherein
s is 0, 1, 2, 3, 4, 5, 6, 7, 8, 9, or 10.
In certain embodiments, the compound of Formula (VII) is of one of the following formulae:
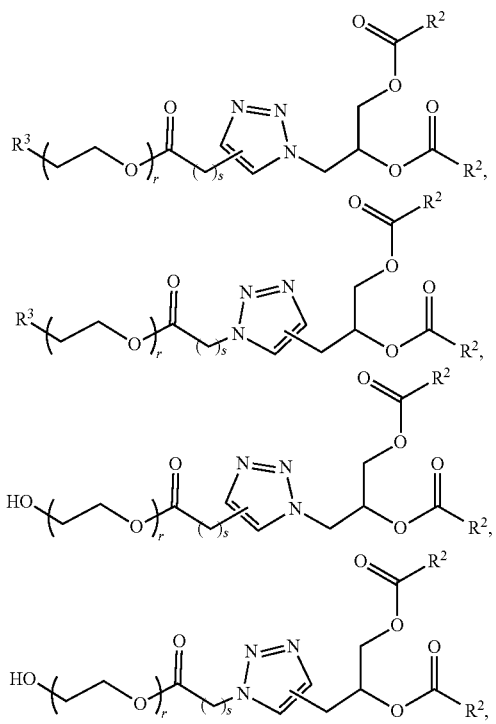
or a salt thereof.
In certain embodiments, a compound of Formula (VII) is of one of the following formulae:
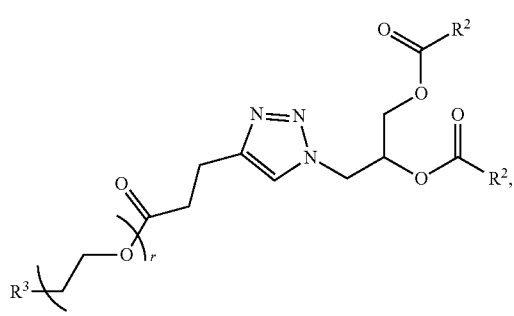
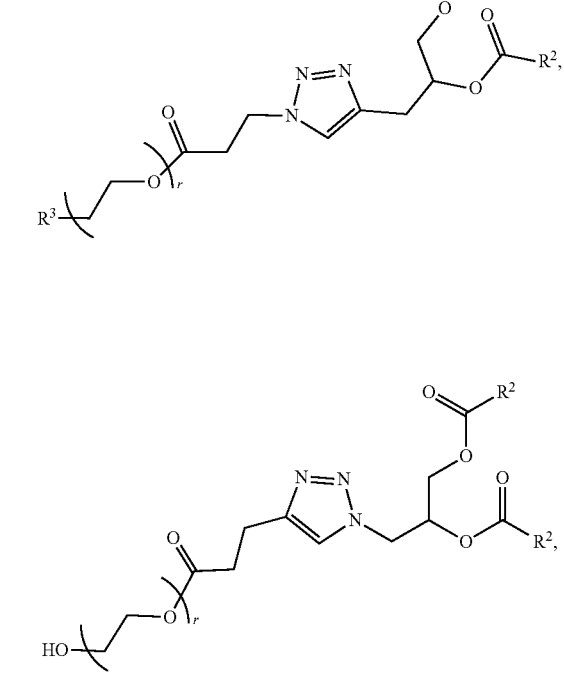
or a salt thereof.
In certain embodiments, a compound of Formula (VII) is of one of the following formulae:
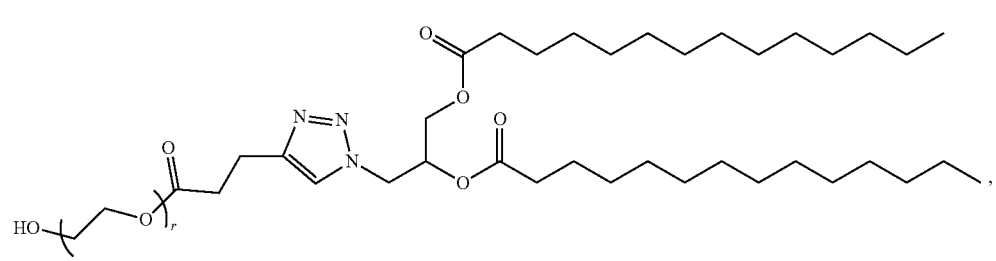
(Compound 415)

-continued

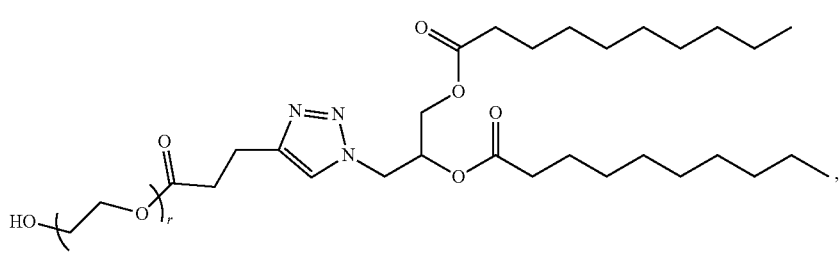
(Compound 416)

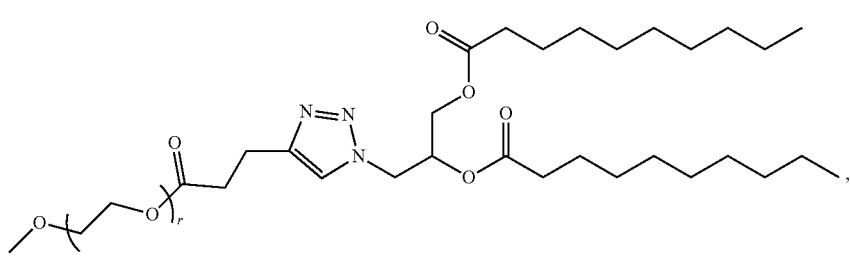
(Compound 417)

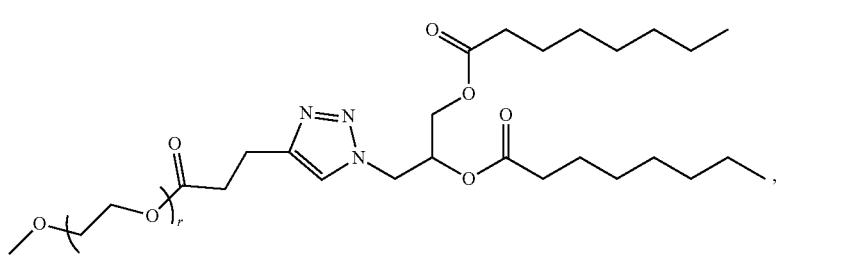
(Compound 418)

or a salt thereof.

In certain embodiments, D is a moiety cleavable under physiological conditions (e.g., ester, amide, carbonate, carbamate, urea). In certain embodiments, a compound of Formula (VII) is of Formula (VII-b-1) or (VII-b-2):

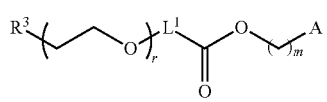
(VII-b-1)

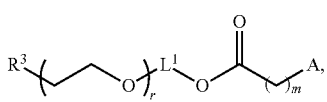
(VII-b-2)

or a salt thereof.

In certain embodiments, a compound of Formula (VII) is of Formula (VII-b-1-OH) or (VII-b-2-OH):

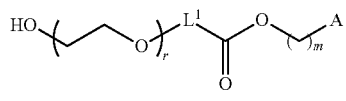
(VII-b-1-OH)

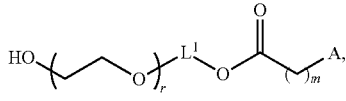
(VII-b-2-OH)

or a salt thereof.

In certain embodiments, the compound of Formula (VII) is of one of the following formulae:

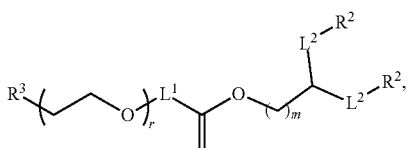

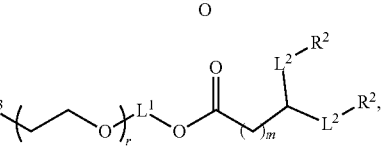

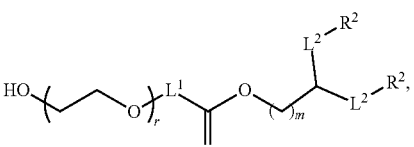

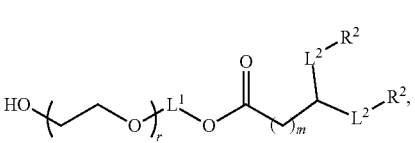

or a salt thereof.

In certain embodiments, a compound of Formula (VII) is of one of the following formulae:

347

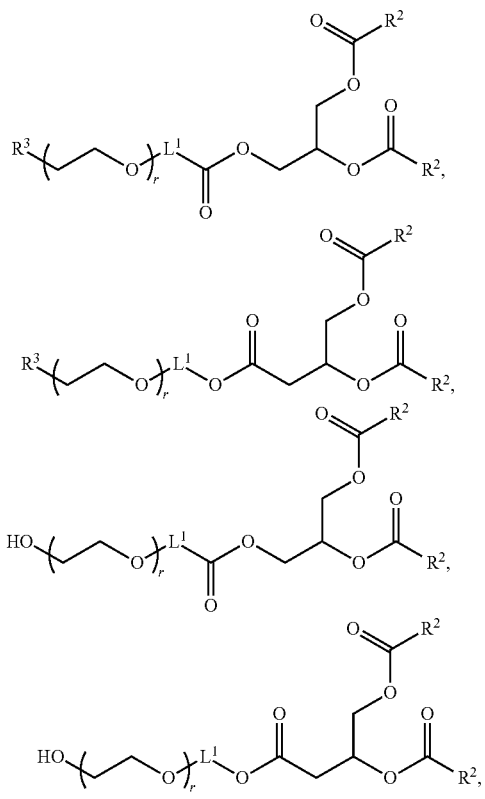

or a salt thereof.

In certain embodiments, a compound of Formula (VII) is of one of the following formulae:

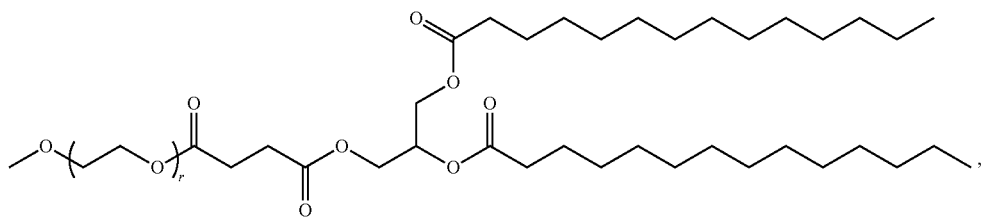

or salts thereof.

348

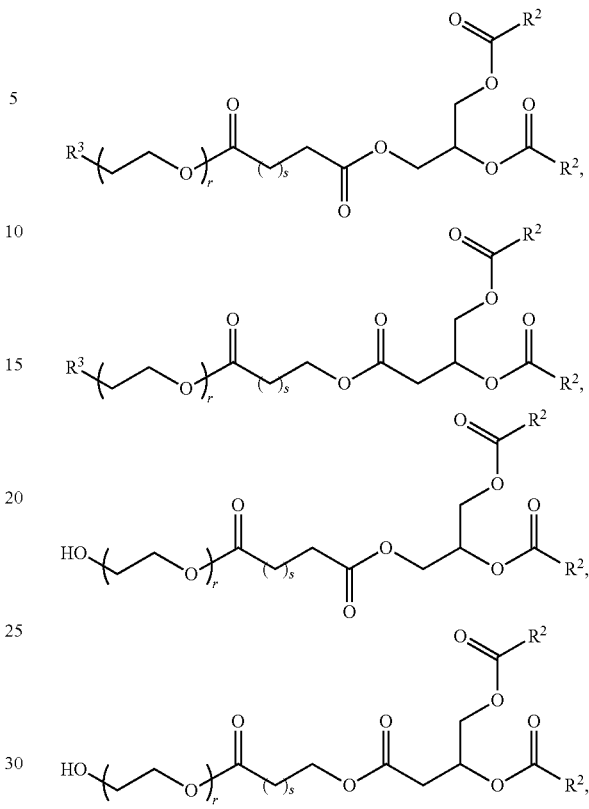

or a salt thereof.

In certain embodiments, a compound of Formula (VII) is of one of the following formulae:

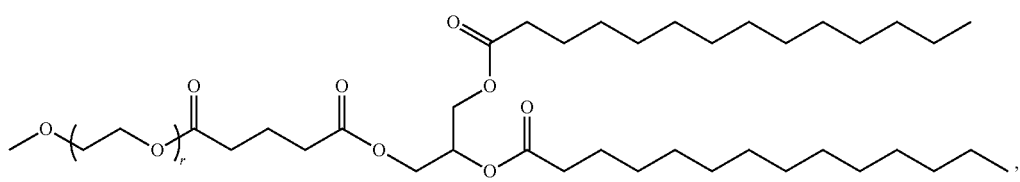

In certain embodiments, a PEG lipid useful in the present invention is a PEGylated fatty acid. In certain embodiments, a PEG lipid useful in the present invention is a compound of Formula (VIII). Provided herein are compounds of Formula (VIII):

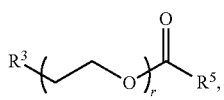

(VIII)

or a salts thereof, wherein:

$R^3$ is $—OR^O$;

$R^O$ is hydrogen, optionally substituted alkyl or an oxygen protecting group;

r is an integer between 1 and 100, inclusive;

$R^5$ is optionally substituted $C_{10\text{-}40}$ alkyl, optionally substituted $C_{10\text{-}40}$ alkenyl, or optionally substituted $C_{10\text{-}40}$ alkynyl; and optionally one or more methylene groups of $R^5$ are replaced with optionally substituted carbocyclylene, optionally substituted heterocyclylene, optionally substituted arylene, optionally substituted heteroarylene, $—N(R^N)—$, $—O—$, $—S—$, $—C(O)—$, $—C(O)N(R^N)—$, $—NR^NC(O)—$, $—NR^NC(O)N(R^N)—$, $—C(O)O—$, $—OC(O)—$, $—OC(O)O—$, $—OC(O)N(R^N)—$, $—NR^NC(O)O—$, $—C(O)S—$, $—SC(O)—$, $—C(=NR^N)—$, $—C(=NR^N)N(R^N)—$, $—NR^NC(=NR^N)—$, $—NR^NC(=NR^N)N(R^N)—$, $—C(S)—$, $—C(S)N(R^N)—$, $—NR^NC(S)—$, $—NR^NC(S)N(R^N)—$, $—S(O)—$, $—OS(O)—$, $—S(O)O—$, $—OS(O)O—$, $—OS(O)_2—$, $—S(O)_2O—$, $—OS(O)_2O—$, $—N(R^N)S(O)—$, $—S(O)N(R^N)—$, $—N(R^N)S(O)N(R^N)—$, $—OS(O)N(R^N)—$, $—N(R^N)S(O)O—$, $—S(O)_2—$, $—N(R^N)S(O)_2—$, $—S(O)_2N(R^N)—$, $—N(R^N)S(O)_2N(R^N)—$, $—OS(O)_2N(R^N)—$, or $—N(R^N)S(O)_2O—$; and each instance of $R^N$ is independently hydrogen, optionally substituted alkyl, or a nitrogen protecting group.

In certain embodiments, the compound of Formula (VIII) is of Formula (VIII-OH):

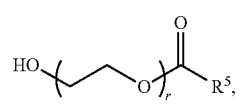

(VIII-OH)

or a salt thereof. In some embodiments, r is 45.

In certain embodiments, a compound of Formula (VIII) is of one of the following formulae:

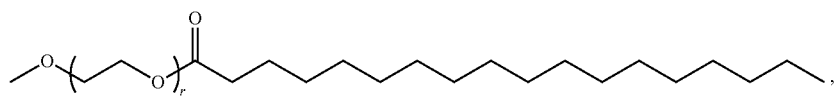

(Compound 419)

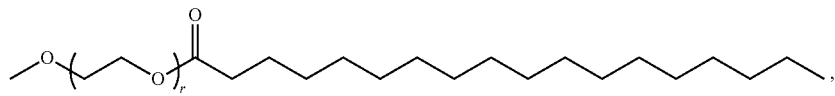

(Compound 420)

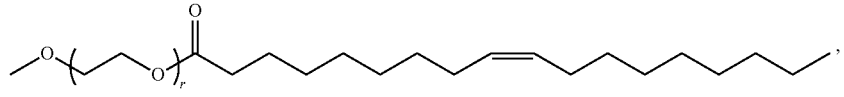

(Compound 421)

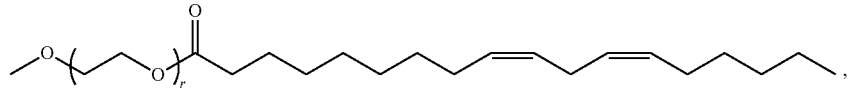

(Compound 422)

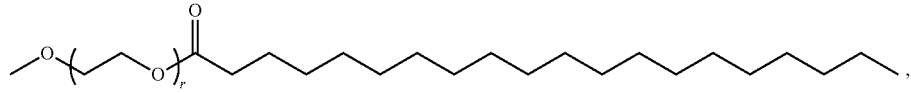

(Compound 423)

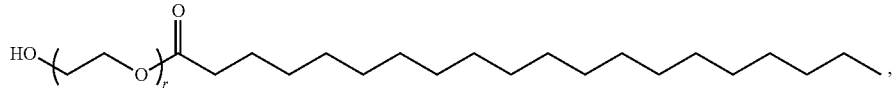

(Compound 424)

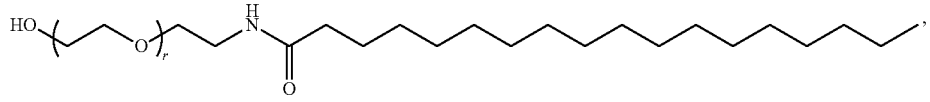

(Compound 425)

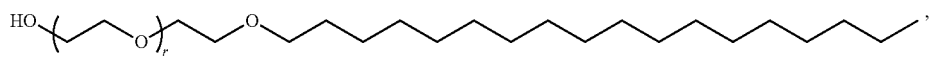

(Compound 426)

or a salt thereof. In some embodiments, r is 45.

In yet other embodiments the compound of Formula (VIII) is:

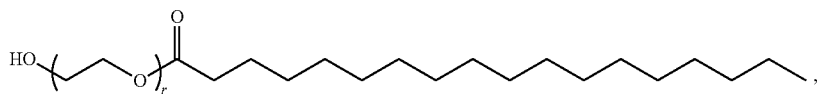

(Compound 427)

or a salt thereof.

In one embodiment, the compound of Formula (VIII) is

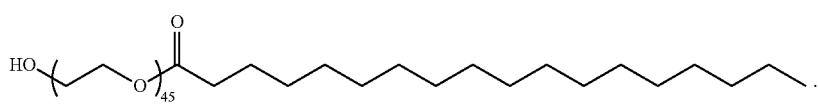

(Compound 428)

In one embodiment, the amount of PEG-lipid in the lipid composition of a pharmaceutical composition disclosed herein ranges from about 0.1 mol % to about 5 mol %, from about 0.5 mol % to about 5 mol %, from about 1 mol % to about 5 mol %, from about 1.5 mol % to about 5 mol %, from about 2 mol % to about 5 mol % mol %, from about 0.1 mol % to about 4 mol %, from about 0.5 mol % to about 4 mol %, from about 1 mol % to about 4 mol %, from about 1.5 mol % to about 4 mol %, from about 2 mol % to about 4 mol %, from about 0.1 mol % to about 3 mol %, from about 0.5 mol % to about 3 mol %, from about 1 mol % to about 3 mol %, from about 1.5 mol % to about 3 mol %, from about 2 mol % to about 3 mol %, from about 0.1 mol % to about 2 mol %, from about 0.5 mol % to about 2 mol %, from about 1 mol % to about 2 mol %, from about 1.5 mol % to about 2 mol %, from about 0.1 mol % to about 1.5 mol %, from about 0.5 mol % to about 1.5 mol %, or from about 1 mol % to about 1.5 mol %.

In one embodiment, the amount of PEG-lipid in the lipid composition disclosed herein is about 2 mol %. In one embodiment, the amount of PEG-lipid in the lipid composition disclosed herein is about 1.5 mol %.

In one embodiment, the amount of PEG-lipid in the lipid composition disclosed herein is at least about 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, or 5 mol %.

In some aspects, the lipid composition of the pharmaceutical compositions disclosed herein does not comprise a PEG-lipid.

(v) Other Ionizable Amino Lipids

The lipid composition of the pharmaceutical composition disclosed herein can comprise one or more ionizable amino lipids in addition to a lipid according to Formula (I), (III), (IV), (V), or (VI).

Ionizable lipids can be selected from the non-limiting group consisting of 3-(didodecylamino)-N1,N1,4-tridodecyl-1-piperazineethanamine (KL10), N1-[2-(didodecylamino)ethyl]-N1,N4,N4-tridodecyl-1,4-piperazinediethanamine (KL22), 14,25-ditridecyl-15,18,21,24-tetraaza-octatriacontane (KL25), 1,2-dilinoleyloxy-N,N-dimethylaminopropane (DLin-DMA), 2,2-dilinoleyl-4-dimethylaminomethyl-[1,3]-dioxolane (DLin-K-DMA), heptatriaconta-6,9,28,31-tetraen-19-yl 4-(dimethylamino)butanoate (DLin-MC3-DMA), 2,2-dilinoleyl-4-(2-dimethylaminoethyl)[1,3]-dioxolane (DLin-KC2-DMA), 1,2-dioleyloxy-N,N-dimethylaminopropane (DODMA), (13Z,16SZ)—N,N-dimethyl-3-nonydocosa-13-16-dien-1-amine (L608), 2-({8-[(3β)-cholest-5-en-3-yloxy]octyl}oxy)-N,N-dimethyl-3-[(9Z,12Z)-octadeca-9,12-di en-1-yloxy]propan-1-amine (Octyl-CLinDMA), (2R)-2-({8-[(3β)-cholest-5-en-3-yloxy]octyl}oxy)-N,N-dimethyl-3-[(9Z,12Z)-octadeca-9, 12-dien-1-yloxy]propan-1-amine (Octyl-CLinDMA (2R)), and (2S)-2-({8-[(3β)-cholest-5-en-3-yloxy]octyl}oxy)-N,N-dimethyl-3-[(9Z,12Z)-octadeca-9, 12-dien-1-yloxy]propan-1-amine (Octyl-CLinDMA (2S)). In addition to these, an ionizable amino lipid can also be a lipid including a cyclic amine group.

Ionizable lipids can also be the compounds disclosed in International Publication No. WO 2017/075531 A1, hereby incorporated by reference in its entirety. For example, the ionizable amino lipids include, but not limited to:

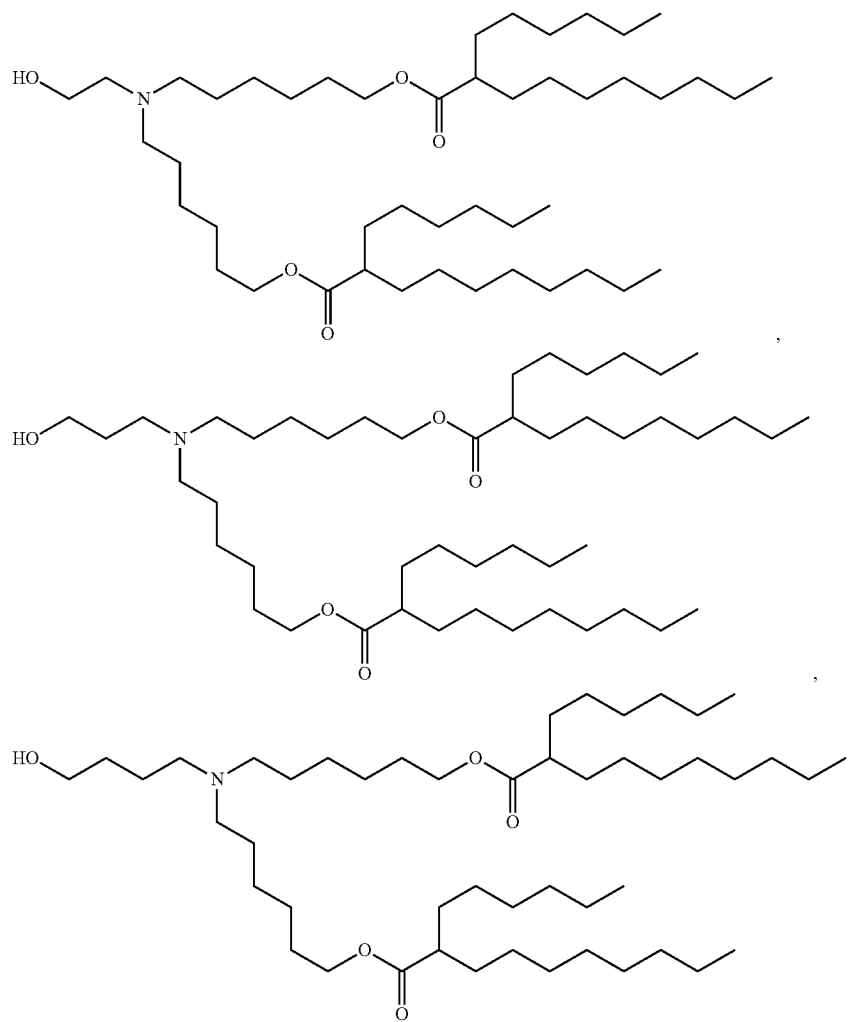
and any combination thereof.
Ionizable lipids can also be the compounds disclosed in International Publication No. WO 2015/199952 A1, hereby incorporated by reference in its entirety. For example, the ionizable amino lipids include, but not limited to:
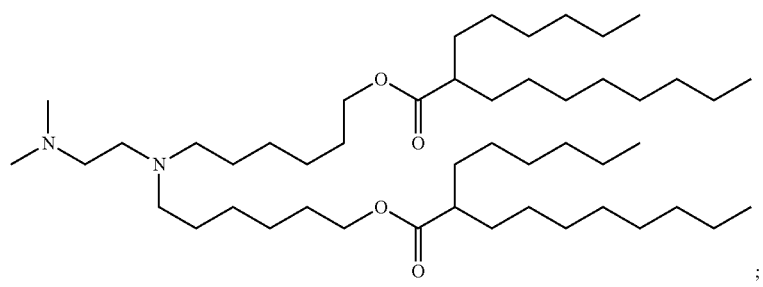

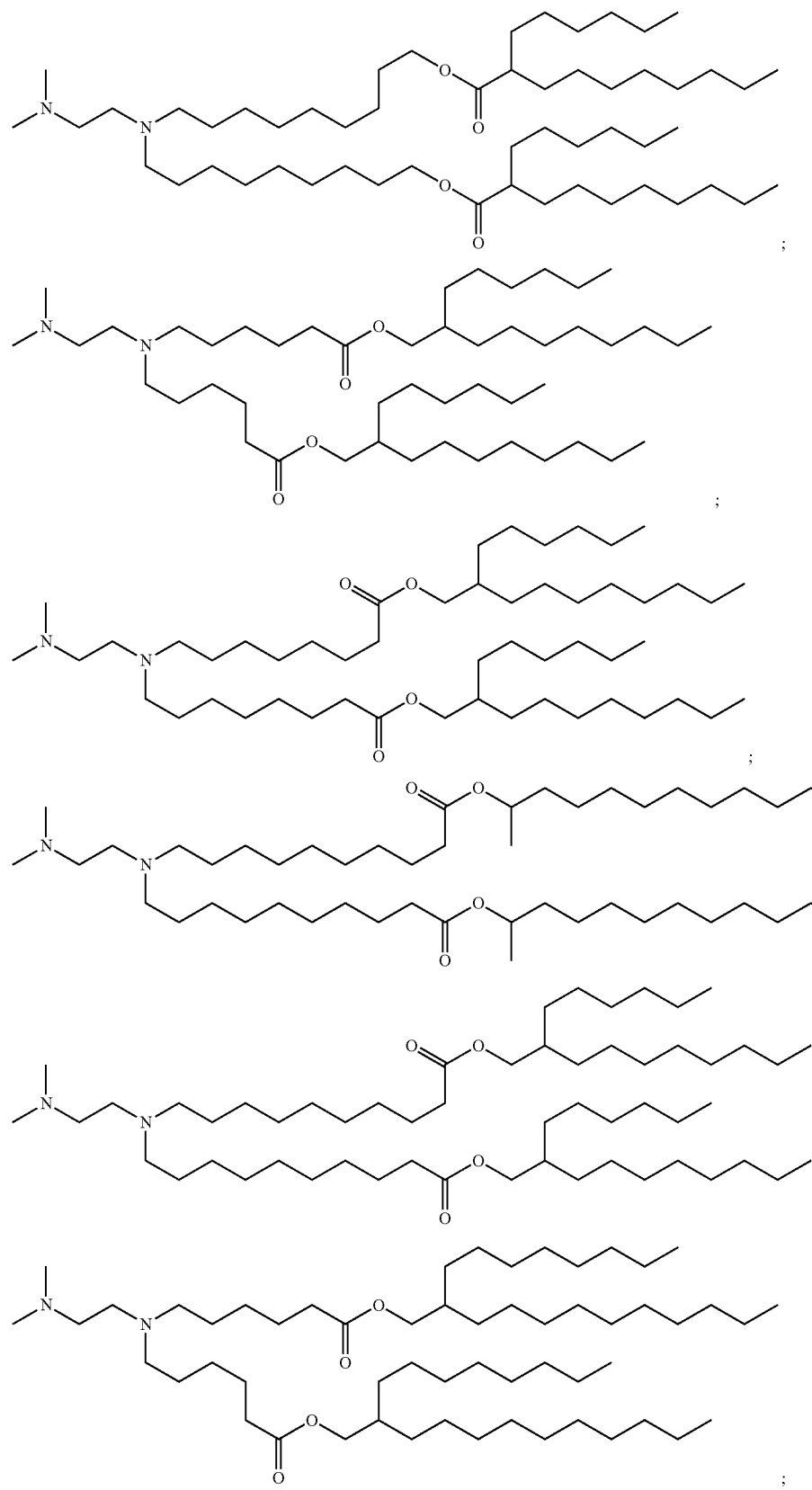

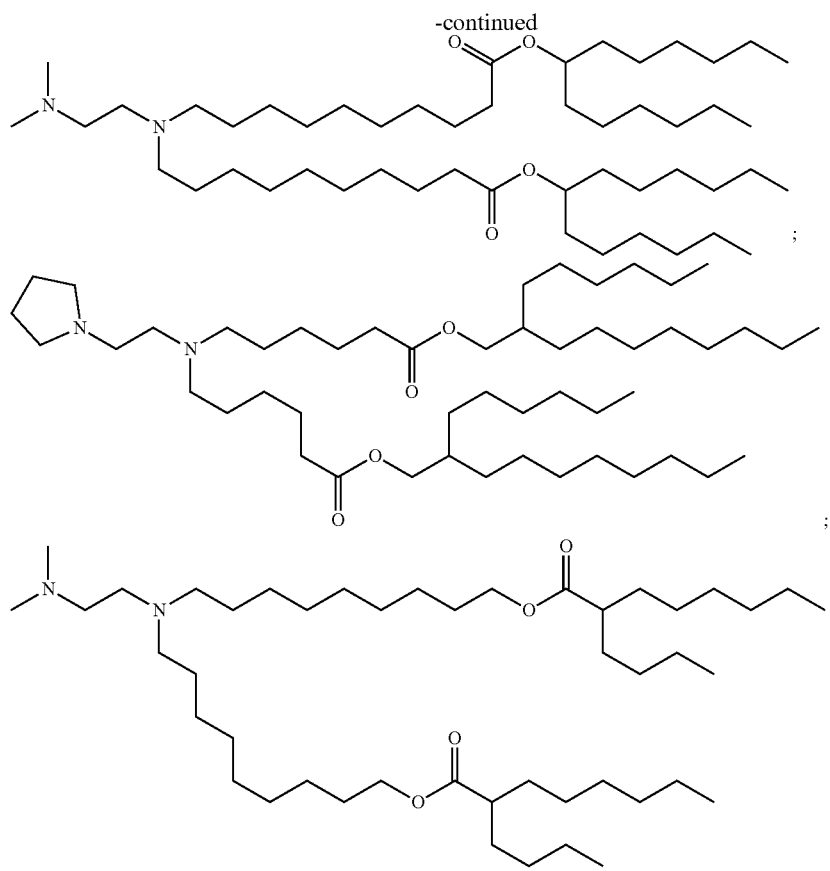
and any combination thereof.
Ionizable lipids can further include, but are not limited to:
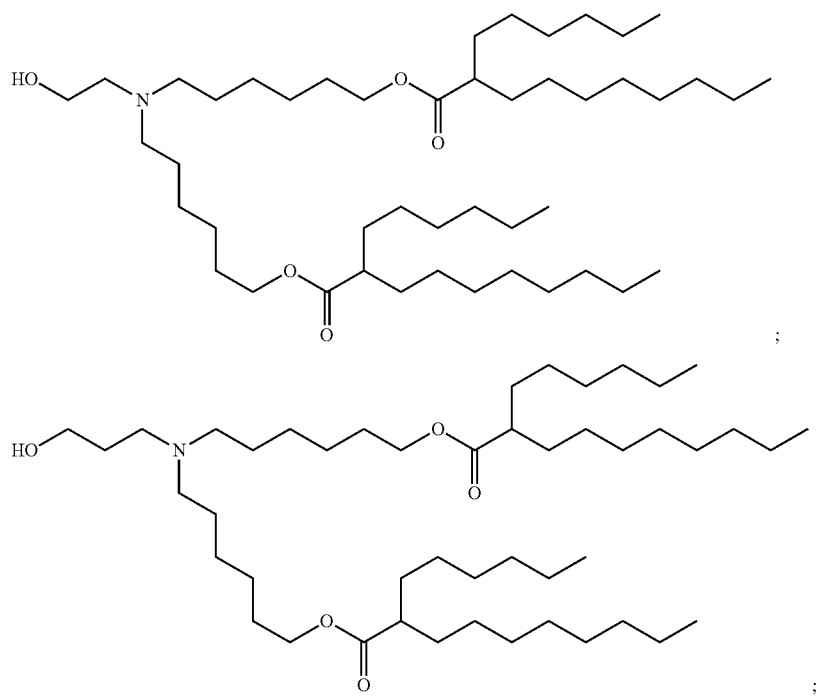

-continued

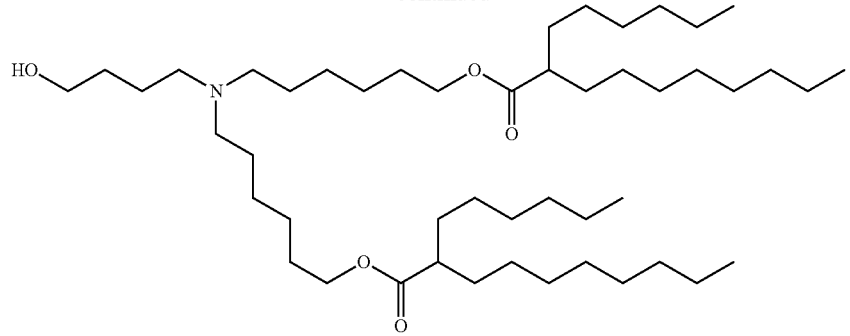

and any combination thereof.

(vi) Other Lipid Composition Components

The lipid composition of a pharmaceutical composition disclosed herein can include one or more components in addition to those described above. For example, the lipid composition can include one or more permeability enhancer molecules, carbohydrates, polymers, surface altering agents (e.g., surfactants), or other components. For example, a permeability enhancer molecule can be a molecule described by U.S. Patent Application Publication No. 2005/0222064. Carbohydrates can include simple sugars (e.g., glucose) and polysaccharides (e.g., glycogen and derivatives and analogs thereof).

A polymer can be included in and/or used to encapsulate or partially encapsulate a pharmaceutical composition disclosed herein (e.g., a pharmaceutical composition in lipid nanoparticle form). A polymer can be biodegradable and/or biocompatible. A polymer can be selected from, but is not limited to, polyamines, polyethers, polyamides, polyesters, polycarbamates, polyureas, polycarbonates, polystyrenes, polyimides, polysulfones, polyurethanes, polyacetylenes, polyethylenes, polyethyleneimines, polyisocyanates, polyacrylates, polymethacrylates, polyacrylonitriles, and polyarylates.

The ratio between the lipid composition and the polynucleotide range can be from about 10:1 to about 60:1 (wt/wt).

In some embodiments, the ratio between the lipid composition and the polynucleotide can be about 10:1, 11:1, 12:1, 13:1, 14:1, 15:1, 16:1, 17:1, 18:1, 19:1, 20:1, 21:1, 22:1, 23:1, 24:1, 25:1, 26:1, 27:1, 28:1, 29:1, 30:1, 31:1, 32:1, 33:1, 34:1, 35:1, 36:1, 37:1, 38:1, 39:1, 40:1, 41:1, 42:1, 43:1, 44:1, 45:1, 46:1, 47:1, 48:1, 49:1, 50:1, 51:1, 52:1, 53:1, 54:1, 55:1, 56:1, 57:1, 58:1, 59:1 or 60:1 (wt/wt). In some embodiments, the wt/wt ratio of the lipid composition to the polynucleotide encoding a therapeutic agent is about 20:1 or about 15:1.

In some embodiments, the pharmaceutical composition disclosed herein can contain more than one polypeptides. For example, a pharmaceutical composition disclosed herein can contain two or more polynucleotides (e.g., RNA, e.g., mRNA).

In one embodiment, the lipid nanoparticles described herein can comprise polynucleotides (e.g., mRNA) in a lipid:polynucleotide weight ratio of 5:1, 10:1, 15:1, 20:1, 25:1, 30:1, 35:1, 40:1, 45:1, 50:1, 55:1, 60:1 or 70:1, or a range or any of these ratios such as, but not limited to, 5:1 to about 10:1, from about 5:1 to about 15:1, from about 5:1 to about 20:1, from about 5:1 to about 25:1, from about 5:1 to about 30:1, from about 5:1 to about 35:1, from about 5:1 to about 40:1, from about 5:1 to about 45:1, from about 5:1 to about 50:1, from about 5:1 to about 55:1, from about 5:1 to about 60:1, from about 5:1 to about 70:1, from about 10:1 to about 15:1, from about 10:1 to about 20:1, from about 10:1 to about 25:1, from about 10:1 to about 30:1, from about 10:1 to about 35:1, from about 10:1 to about 40:1, from about 10:1 to about 45:1, from about 10:1 to about 50:1, from about 10:1 to about 55:1, from about 10:1 to about 60:1, from about 10:1 to about 70:1, from about 15:1 to about 20:1, from about 15:1 to about 25:1, from about 15:1 to about 30:1, from about 15:1 to about 35:1, from about 15:1 to about 40:1, from about 15:1 to about 45:1, from about 15:1 to about 50:1, from about 15:1 to about 55:1, from about 15:1 to about 60:1 or from about 15:1 to about 70:1.

In one embodiment, the lipid nanoparticles described herein can comprise the polynucleotide in a concentration from approximately 0.1 mg/ml to 2 mg/ml such as, but not limited to, 0.1 mg/ml, 0.2 mg/ml, 0.3 mg/ml, 0.4 mg/ml, 0.5 mg/ml, 0.6 mg/ml, 0.7 mg/ml, 0.8 mg/ml, 0.9 mg/ml, 1.0 mg/ml, 1.1 mg/ml, 1.2 mg/ml, 1.3 mg/ml, 1.4 mg/ml, 1.5 mg/ml, 1.6 mg/ml, 1.7 mg/ml, 1.8 mg/ml, 1.9 mg/ml, 2.0 mg/ml or greater than 2.0 mg/ml.

(vii) Nanoparticle Compositions

In some embodiments, the pharmaceutical compositions disclosed herein are formulated as lipid nanoparticles (LNP). Accordingly, the present disclosure also provides nanoparticle compositions comprising (i) a lipid composition comprising a delivery agent such as a compound of Formula (I) or (III) as described herein, and (ii) a polynucleotide encoding a PBGD polypeptide. In such nanoparticle composition, the lipid composition disclosed herein can encapsulate the polynucleotide encoding a PBGD polypeptide.

Nanoparticle compositions are typically sized on the order of micrometers or smaller and can include a lipid bilayer. Nanoparticle compositions encompass lipid nanoparticles (LNPs), liposomes (e.g., lipid vesicles), and lipoplexes. For example, a nanoparticle composition can be a liposome having a lipid bilayer with a diameter of 500 nm or less.

Nanoparticle compositions include, for example, lipid nanoparticles (LNPs), liposomes, and lipoplexes. In some embodiments, nanoparticle compositions are vesicles including one or more lipid bilayers. In certain embodiments, a nanoparticle composition includes two or more concentric bilayers separated by aqueous compartments. Lipid bilayers can be functionalized and/or crosslinked to one another. Lipid bilayers can include one or more ligands, proteins, or channels.

In some embodiments, the nanoparticle compositions of the present disclosure comprise at least one compound according to Formula (I), (III), (IV), (V), or (VI). For example, the nanoparticle composition can include one or more of Compounds 1-147, or one or more of Compounds 1-342. Nanoparticle compositions can also include a variety of other components. For example, the nanoparticle composition may include one or more other lipids in addition to a lipid according to Formula (I), (III), (IV), (V), or (VI), such as (i) at least one phospholipid, (ii) at least one structural lipid, (iii) at least one PEG-lipid, or (iv) any combination thereof. Inclusion of structural lipid can be optional, for example when lipids according to Formula III are used in the lipid nanoparticle compositions of the invention.

In some embodiments, the nanoparticle composition comprises a compound of Formula (I), (e.g., Compounds 18, 25, 26 or 48). In some embodiments, the nanoparticle composition comprises a compound of Formula (I) (e.g., Compounds 18, 25, 26 or 48) and a phospholipid (e.g., DSPC).

In some embodiments, the nanoparticle composition comprises a compound of Formula (III) (e.g., Compound 236). In some embodiments, the nanoparticle composition comprises a compound of Formula (III) (e.g., Compound 236) and a phospholipid (e.g., DOPE or DSPC).

In some embodiments, the nanoparticle composition comprises a lipid composition consisting or consisting essentially of compound of Formula (I) (e.g., Compounds 18, 25, 26 or 48). In some embodiments, the nanoparticle composition comprises a lipid composition consisting or consisting essentially of a compound of Formula (I) (e.g., Compounds 18, 25, 26 or 48) and a phospholipid (e.g., DSPC).

In some embodiments, the nanoparticle composition comprises a lipid composition consisting or consisting essentially of compound of Formula (III) (e.g., Compound 236). In some embodiments, the nanoparticle composition comprises a lipid composition consisting or consisting essentially of a compound of Formula (III) (e.g., Compound 236) and a phospholipid (e.g., DOPE or DSPC).

In one embodiment, a lipid nanoparticle comprises an ionizable lipid, a structural lipid, a phospholipid, and mRNA. In some embodiments, the LNP comprises an ionizable lipid, a PEG-modified lipid, a sterol and a structural lipid. In some embodiments, the LNP has a molar ratio of about 20-60% ionizable lipid:about 5-25% structural lipid: about 25-55% sterol; and about 0.5-15% PEG-modified lipid. In some embodiments, the LNP comprises a molar ratio of about 50% ionizable lipid, about 1.5% PEG-modified lipid, about 38.5% cholesterol and about 10% structural lipid. In some embodiments, the LNP comprises a molar ratio of about 55% ionizable lipid, about 2.5% PEG lipid, about 32.5% cholesterol and about 10% structural lipid. In some embodiments, the ionizable lipid is an ionizable amino lipid and the structural lipid is a neutral lipid, and the sterol is a cholesterol. In some embodiments, the LNP has a molar ratio of 50:38.5:10:1.5 of ionizable lipid: cholesterol: DSPC: PEG lipid. In some embodiments, the ionizable lipid is Compound 18 or Compound 236, and the PEG lipid is Compound 428.

In some embodiments, the LNP has a molar ratio of 50:38.5:10:1.5 of Compound 18:Cholesterol:Phospholipid:Compound 428. In some embodiments, the LNP has a molar ratio of 50:38.5:10:1.5 of Compound 18:Cholesterol:DSPC:Compound 428.

In some embodiments, the LNP has a molar ratio of 50:38.5:10:1.5 of Compound 236:Cholesterol:Phospholipid:Compound 428. In some embodiments, the LNP has a molar ratio of 50:38.5:10:1.5 of Compound 236:Cholesterol:DSPC:Compound 428.

In some embodiments, the LNP has a polydispersity value of less than 0.4. In some embodiments, the LNP has a net neutral charge at a neutral pH. In some embodiments, the LNP has a mean diameter of 50-150 nm. In some embodiments, the LNP has a mean diameter of 80-100 nm.

As generally defined herein, the term "lipid" refers to a small molecule that has hydrophobic or amphiphilic properties. Lipids may be naturally occurring or synthetic. Examples of classes of lipids include, but are not limited to, fats, waxes, sterol-containing metabolites, vitamins, fatty acids, glycerolipids, glycerophospholipids, sphingolipids, saccharolipids, and polyketides, and prenol lipids. In some instances, the amphiphilic properties of some lipids leads them to form liposomes, vesicles, or membranes in aqueous media.

In some embodiments, a lipid nanoparticle (LNP) may comprise an ionizable lipid. As used herein, the term "ionizable lipid" has its ordinary meaning in the art and may refer to a lipid comprising one or more charged moieties. In some embodiments, an ionizable lipid may be positively charged or negatively charged. An ionizable lipid may be positively charged, in which case it can be referred to as "cationic lipid." In certain embodiments, an ionizable lipid molecule may comprise an amine group, and can be referred to as an ionizable amino lipid. As used herein, a "charged moiety" is a chemical moiety that carries a formal electronic charge, e.g., monovalent (+1, or −1), divalent (+2, or −2), trivalent (+3, or −3), etc. The charged moiety may be anionic (i.e., negatively charged) or cationic (i.e., positively charged). Examples of positively-charged moieties include amine groups (e.g., primary, secondary, and/or tertiary amines), ammonium groups, pyridinium group, guanidine groups, and imidizolium groups. In a particular embodiment, the charged moieties comprise amine groups. Examples of negatively-charged groups or precursors thereof, include carboxylate groups, sulfonate groups, sulfate groups, phosphonate groups, phosphate groups, hydroxyl groups, and the like. The charge of the charged moiety may vary, in some cases, with the environmental conditions, for example, changes in pH may alter the charge of the moiety, and/or cause the moiety to become charged or uncharged. In general, the charge density of the molecule may be selected as desired.

It should be understood that the terms "charged" or "charged moiety" does not refer to a "partial negative charge" or "partial positive charge" on a molecule. The terms "partial negative charge" and "partial positive charge" are given its ordinary meaning in the art. A "partial negative charge" may result when a functional group comprises a bond that becomes polarized such that electron density is pulled toward one atom of the bond, creating a partial negative charge on the atom. Those of ordinary skill in the art will, in general, recognize bonds that can become polarized in this way.

In some embodiments, the ionizable lipid is an ionizable amino lipid, sometimes referred to in the art as an "ionizable cationic lipid". In one embodiment, the ionizable amino lipid may have a positively charged hydrophilic head and a hydrophobic tail that are connected via a linker structure.

In addition to these, an ionizable lipid may also be a lipid including a cyclic amine group.

In one embodiment, the ionizable lipid may be selected from, but not limited to, a ionizable lipid described in International Publication Nos. WO2013086354 and WO2013116126; the contents of each of which are herein incorporated by reference in their entirety.

In yet another embodiment, the ionizable lipid may be selected from, but not limited to, formula CLI-CLXXXXII of U.S. Pat. No. 7,404,969; each of which is herein incorporated by reference in their entirety.

In one embodiment, the lipid may be a cleavable lipid such as those described in International Publication No. WO2012170889, herein incorporated by reference in its entirety. In one embodiment, the lipid may be synthesized by methods known in the art and/or as described in International Publication Nos. WO2013086354; the contents of each of which are herein incorporated by reference in their entirety.

Nanoparticle compositions can be characterized by a variety of methods. For example, microscopy (e.g., transmission electron microscopy or scanning electron microscopy) can be used to examine the morphology and size distribution of a nanoparticle composition. Dynamic light scattering or potentiometry (e.g., potentiometric titrations) can be used to measure zeta potentials. Dynamic light scattering can also be utilized to determine particle sizes. Instruments such as the Zetasizer Nano ZS (Malvern Instruments Ltd, Malvern, Worcestershire, UK) can also be used to measure multiple characteristics of a nanoparticle composition, such as particle size, polydispersity index, and zeta potential.

The size of the nanoparticles can help counter biological reactions such as, but not limited to, inflammation, or can increase the biological effect of the polynucleotide.

As used herein, "size" or "mean size" in the context of nanoparticle compositions refers to the mean diameter of a nanoparticle composition.

In one embodiment, the polynucleotide encoding a PBGD polypeptide are formulated in lipid nanoparticles having a diameter from about 10 to about 100 nm such as, but not limited to, about 10 to about 20 nm, about 10 to about 30 nm, about 10 to about 40 nm, about 10 to about 50 nm, about 10 to about 60 nm, about 10 to about 70 nm, about 10 to about 80 nm, about 10 to about 90 nm, about 20 to about 30 nm, about 20 to about 40 nm, about 20 to about 50 nm, about 20 to about 60 nm, about 20 to about 70 nm, about 20 to about 80 nm, about 20 to about 90 nm, about 20 to about 100 nm, about 30 to about 40 nm, about 30 to about 50 nm, about 30 to about 60 nm, about 30 to about 70 nm, about 30 to about 80 nm, about 30 to about 90 nm, about 30 to about 100 nm, about 40 to about 50 nm, about 40 to about 60 nm, about 40 to about 70 nm, about 40 to about 80 nm, about 40 to about 90 nm, about 40 to about 100 nm, about 50 to about 60 nm, about 50 to about 70 nm, about 50 to about 80 nm, about 50 to about 90 nm, about 50 to about 100 nm, about 60 to about 70 nm, about 60 to about 80 nm, about 60 to about 90 nm, about 60 to about 100 nm, about 70 to about 80 nm, about 70 to about 90 nm, about 70 to about 100 nm, about 80 to about 90 nm, about 80 to about 100 nm and/or about 90 to about 100 nm.

In one embodiment, the nanoparticles have a diameter from about 10 to 500 nm. In one embodiment, the nanoparticle has a diameter greater than 100 nm, greater than 150 nm, greater than 200 nm, greater than 250 nm, greater than 300 nm, greater than 350 nm, greater than 400 nm, greater than 450 nm, greater than 500 nm, greater than 550 nm, greater than 600 nm, greater than 650 nm, greater than 700 nm, greater than 750 nm, greater than 800 nm, greater than 850 nm, greater than 900 nm, greater than 950 nm or greater than 1000 nm.

In some embodiments, the largest dimension of a nanoparticle composition is 1 μm or shorter (e.g., 1 μm, 900 nm, 800 nm, 700 nm, 600 nm, 500 nm, 400 nm, 300 nm, 200 nm, 175 nm, 150 nm, 125 nm, 100 nm, 75 nm, 50 nm, or shorter).

A nanoparticle composition can be relatively homogenous. A polydispersity index can be used to indicate the homogeneity of a nanoparticle composition, e.g., the particle size distribution of the nanoparticle composition. A small (e.g., less than 0.3) polydispersity index generally indicates a narrow particle size distribution. A nanoparticle composition can have a polydispersity index from about 0 to about 0.25, such as 0.01, 0.02, 0.03, 0.04, 0.05, 0.06, 0.07, 0.08, 0.09, 0.10, 0.11, 0.12, 0.13, 0.14, 0.15, 0.16, 0.17, 0.18, 0.19, 0.20, 0.21, 0.22, 0.23, 0.24, or 0.25. In some embodiments, the polydispersity index of a nanoparticle composition disclosed herein can be from about 0.10 to about 0.20.

The zeta potential of a nanoparticle composition can be used to indicate the electrokinetic potential of the composition. For example, the zeta potential can describe the surface charge of a nanoparticle composition. Nanoparticle compositions with relatively low charges, positive or negative, are generally desirable, as more highly charged species can interact undesirably with cells, tissues, and other elements in the body. In some embodiments, the zeta potential of a nanoparticle composition disclosed herein can be from about −10 mV to about +20 mV, from about −10 mV to about +15 mV, from about 10 mV to about +10 mV, from about −10 mV to about +5 mV, from about −10 mV to about 0 mV, from about −10 mV to about −5 mV, from about −5 mV to about +20 mV, from about −5 mV to about +15 mV, from about −5 mV to about +10 mV, from about −5 mV to about +5 mV, from about −5 mV to about 0 mV, from about 0 mV to about +20 mV, from about 0 mV to about +15 mV, from about 0 mV to about +10 mV, from about 0 mV to about +5 mV, from about +5 mV to about +20 mV, from about +5 mV to about +15 mV, or from about +5 mV to about +10 mV.

In some embodiments, the zeta potential of the lipid nanoparticles can be from about 0 mV to about 100 mV, from about 0 mV to about 90 mV, from about 0 mV to about 80 mV, from about 0 mV to about 70 mV, from about 0 mV to about 60 mV, from about 0 mV to about 50 mV, from about 0 mV to about 40 mV, from about 0 mV to about 30 mV, from about 0 mV to about 20 mV, from about 0 mV to about 10 mV, from about 10 mV to about 100 mV, from about 10 mV to about 90 mV, from about 10 mV to about 80 mV, from about 10 mV to about 70 mV, from about 10 mV to about 60 mV, from about 10 mV to about 50 mV, from about 10 mV to about 40 mV, from about 10 mV to about 30 mV, from about 10 mV to about 20 mV, from about 20 mV to about 100 mV, from about 20 mV to about 90 mV, from about 20 mV to about 80 mV, from about 20 mV to about 70 mV, from about 20 mV to about 60 mV, from about 20 mV to about 50 mV, from about 20 mV to about 40 mV, from about 20 mV to about 30 mV, from about 30 mV to about 100 mV, from about 30 mV to about 90 mV, from about 30 mV to about 80 mV, from about 30 mV to about 70 mV, from about 30 mV to about 60 mV, from about 30 mV to about 50 mV, from about 30 mV to about 40 mV, from about 40 mV to about 100 mV, from about 40 mV to about 90 mV, from about 40 mV to about 80 mV, from about 40 mV to about 70 mV, from about 40 mV to about 60 mV, and from about 40 mV to about 50 mV. In some embodiments, the zeta potential of the lipid nanoparticles can be from about 10 mV to about 50 mV, from about 15 mV to about 45 mV, from about 20 mV to about 40 mV, and from about 25 mV to about 35 mV. In some embodiments, the zeta potential of the lipid nanoparticles can be about 10 mV, about 20 mV, about 30 mV, about 40 mV, about 50 mV, about 60 mV, about 70 mV, about 80 mV, about 90 mV, and about 100 mV.

The term "encapsulation efficiency" of a polynucleotide describes the amount of the polynucleotide that is encapsulated by or otherwise associated with a nanoparticle composition after preparation, relative to the initial amount provided. As used herein, "encapsulation" can refer to complete, substantial, or partial enclosure, confinement, surrounding, or encasement.

Encapsulation efficiency is desirably high (e.g., close to 100%). The encapsulation efficiency can be measured, for example, by comparing the amount of the polynucleotide in a solution containing the nanoparticle composition before and after breaking up the nanoparticle composition with one or more organic solvents or detergents.

Fluorescence can be used to measure the amount of free polynucleotide in a solution. For the nanoparticle compositions described herein, the encapsulation efficiency of a polynucleotide can be at least 50%, for example 50%, 55%, 60%, 65%, 70%, 75%, 80%, 85%, 90%, 91%, 92%, 93%, 94%, 95%, 96%, 97%, 98%, 99%, or 100%. In some embodiments, the encapsulation efficiency can be at least 80%. In certain embodiments, the encapsulation efficiency can be at least 90%.

The amount of a polynucleotide present in a pharmaceutical composition disclosed herein can depend on multiple factors such as the size of the polynucleotide, desired target and/or application, or other properties of the nanoparticle composition as well as on the properties of the polynucleotide.

For example, the amount of an mRNA useful in a nanoparticle composition can depend on the size (expressed as length, or molecular mass), sequence, and other characteristics of the mRNA. The relative amounts of a polynucleotide in a nanoparticle composition can also vary.

The relative amounts of the lipid composition and the polynucleotide present in a lipid nanoparticle composition of the present disclosure can be optimized according to considerations of efficacy and tolerability. For compositions including an mRNA as a polynucleotide, the N:P ratio can serve as a useful metric.

As the N:P ratio of a nanoparticle composition controls both expression and tolerability, nanoparticle compositions with low N:P ratios and strong expression are desirable. N:P ratios vary according to the ratio of lipids to RNA in a nanoparticle composition.

In general, a lower N:P ratio is preferred. The one or more RNA, lipids, and amounts thereof can be selected to provide an N:P ratio from about 2:1 to about 30:1, such as 2:1, 3:1, 4:1, 5:1, 6:1, 7:1, 8:1, 9:1, 10:1, 12:1, 14:1, 16:1, 18:1, 20:1, 22:1, 24:1, 26:1, 28:1, or 30:1. In certain embodiments, the N:P ratio can be from about 2:1 to about 8:1. In other embodiments, the N:P ratio is from about 5:1 to about 8:1. In certain embodiments, the N:P ratio is between 5:1 and 6:1. In one specific aspect, the N:P ratio is about is about 5.67:1.

In addition to providing nanoparticle compositions, the present disclosure also provides methods of producing lipid nanoparticles comprising encapsulating a polynucleotide. Such method comprises using any of the pharmaceutical compositions disclosed herein and producing lipid nanoparticles in accordance with methods of production of lipid nanoparticles known in the art. See, e.g., Wang et al. (2015) "Delivery of oligonucleotides with lipid nanoparticles" Adv. Drug Deliv. Rev. 87:68-80; Silva et al. (2015) "Delivery Systems for Biopharmaceuticals. Part I: Nanoparticles and Microparticles" Curr. Pharm. Technol. 16: 940-954; Naseri et al. (2015) "Solid Lipid Nanoparticles and Nanostructured Lipid Carriers: Structure, Preparation and Application" Adv. Pharm. Bull. 5:305-13; Silva et al. (2015) "Lipid nanoparticles for the delivery of biopharmaceuticals" Curr. Pharm. Biotechnol. 16:291-302, and references cited therein.

23. OTHER DELIVERY AGENTS a. Liposomes, Lipoplexes, and Lipid Nanoparticles

In some embodiments, the compositions or formulations of the present disclosure comprise a delivery agent, e.g., a liposome, a lioplexes, a lipid nanoparticle, or any combination thereof. The polynucleotides described herein (e.g., a polynucleotide comprising a nucleotide sequence encoding a PBGD polypeptide) can be formulated using one or more liposomes, lipoplexes, or lipid nanoparticles. Liposomes, lipoplexes, or lipid nanoparticles can be used to improve the efficacy of the polynucleotides directed protein production as these formulations can increase cell transfection by the polynucleotide; and/or increase the translation of encoded protein. The liposomes, lipoplexes, or lipid nanoparticles can also be used to increase the stability of the polynucleotides.

Liposomes are artificially-prepared vesicles that can primarily be composed of a lipid bilayer and can be used as a delivery vehicle for the administration of pharmaceutical formulations. Liposomes can be of different sizes. A multilamellar vesicle (MLV) can be hundreds of nanometers in diameter, and can contain a series of concentric bilayers separated by narrow aqueous compartments. A small unicellular vesicle (SUV) can be smaller than 50 nm in diameter, and a large unilamellar vesicle (LUV) can be between 50 and 500 nm in diameter. Liposome design can include, but is not limited to, opsonins or ligands to improve the attachment of liposomes to unhealthy tissue or to activate events such as, but not limited to, endocytosis. Liposomes can contain a low or a high pH value in order to improve the delivery of the pharmaceutical formulations.

The formation of liposomes can depend on the pharmaceutical formulation entrapped and the liposomal ingredients, the nature of the medium in which the lipid vesicles are dispersed, the effective concentration of the entrapped substance and its potential toxicity, any additional processes involved during the application and/or delivery of the vesicles, the optimal size, polydispersity and the shelf-life of the vesicles for the intended application, and the batch-to-batch reproducibility and scale up production of safe and efficient liposomal products, etc.

As a non-limiting example, liposomes such as synthetic membrane vesicles can be prepared by the methods, apparatus and devices described in U.S. Pub. Nos. US20130177638, US20130177637, US20130177636, US20130177635, US20130177634, US20130177633, US20130183375, US20130183373, and US20130183372. In some embodiments, the polynucleotides described herein can be encapsulated by the liposome and/or it can be contained in an aqueous core that can then be encapsulated by the liposome as described in, e.g., Intl. Pub. Nos. WO2012031046, WO2012031043, WO2012030901, WO2012006378, and WO2013086526; and U.S. Pub. Nos. US20130189351, US20130195969 and US20130202684. Each of the references in herein incorporated by reference in its entirety.

In some embodiments, the polynucleotides described herein can be formulated in a cationic oil-in-water emulsion where the emulsion particle comprises an oil core and a cationic lipid that can interact with the polynucleotide anchoring the molecule to the emulsion particle. In some embodiments, the polynucleotides described herein can be formulated in a water-in-oil emulsion comprising a continuous hydrophobic phase in which the hydrophilic phase is dispersed. Exemplary emulsions can be made by the methods described in Intl. Pub. Nos. WO2012006380 and WO201087791, each of which is herein incorporated by reference in its entirety.

In some embodiments, the polynucleotides described herein can be formulated in a lipid-polycation complex. The formation of the lipid-polycation complex can be accomplished by methods as described in, e.g., U.S. Pub. No. US20120178702. As a non-limiting example, the polycation can include a cationic peptide or a polypeptide such as, but not limited to, polylysine, polyornithine and/or polyarginine and the cationic peptides described in Intl. Pub. No. WO2012013326 or U.S. Pub. No. US20130142818. Each of the references is herein incorporated by reference in its entirety.

In some embodiments, the polynucleotides described herein can be formulated in a lipid nanoparticle (LNP) such as those described in Intl. Pub. Nos. WO2013123523, WO2012170930, WO2011127255 and WO2008103276; and U.S. Pub. No. US20130171646, each of which is herein incorporated by reference in its entirety.

Lipid nanoparticle formulations typically comprise one or more lipids. In some embodiments, the lipid is an ionizable lipid (e.g., an ionizable amino lipid), sometimes referred to in the art as an "ionizable cationic lipid". In some embodiments, lipid nanoparticle formulations further comprise other components, including a phospholipid, a structural lipid, and a molecule capable of reducing particle aggregation, for example a PEG or PEG-modified lipid.

Exemplary ionizable lipids include, but are not limited to, any one of Compounds 1-342 disclosed herein, DLin-MC3-DMA (MC3), DLin-DMA, DLenDMA, DLin-D-DMA, DLin-K-DMA, DLin-M-C2-DMA, DLin-K-DMA, DLin-KC2-DMA, DLin-KC3-DMA, DLin-KC4-DMA, DLin-C2K-DMA, DLin-MP-DMA, DODMA, 98N12-5, C12-200, DLin-C-DAP, DLin-DAC, DLinDAP, DLinAP, DLin-EG-DMA, DLin-2-DMAP, KL10, KL22, KL25, Octyl-CLinDMA, Octyl-CLinDMA (2R), Octyl-CLinDMA (2S), and any combination thereof. Other exemplary ionizable lipids include, (13Z,16Z)—N,N-dimethyl-3-nonyldocosa-13,16-dien-1-amine (L608), (20Z,23Z)—N,N-dimethyl-nonacosa-20,23-dien-10-amine, (17Z,20Z)—N,N-dimemyl-hexacosa-17,20-dien-9-amine, (16Z,19Z)—N5N-dimethylpentacosa-16,19-dien-8-amine, (13Z,16Z)—N,N-dimethyldocosa-13,16-dien-5-amine, (12Z,15Z)—N,N-dimethylhenicosa-12,15-dien-4-amine, (14Z,17Z)—N,N-dimethyltricosa-14,17-dien-6-amine, (15Z,18Z)—N,N-dimethyltetracosa-15,18-dien-7-amine, (18Z,21Z)—N,N-dimethylheptacosa-18,21-dien-10-amine, (15Z,18Z)—N,N-dimethyltetracosa-15,18-dien-5-amine, (14Z,17Z)—N,N-dimethyltricosa-14,17-dien-4-amine, (19Z,22Z)—N,N-dimethyloctacosa-19,22-dien-9-amine, (18Z,21Z)—N,N-dimethylheptacosa-18,21-dien-8-amine, (17Z,20Z)—N,N-dimethylhexacosa-17,20-dien-7-amine, (16Z,19Z)—N,N-dimethylpentacosa-16,19-dien-6-amine, (22Z,25Z)—N,N-dimethylhentriaconta-22,25-dien-10-amine, (21Z,24Z)—N,N-dimethyltriaconta-21,24-dien-9-amine, (18Z)—N,N-dimetylheptacos-18-en-10-amine, (17Z)—N,N-dimethylhexacos-17-en-9-amine, (19Z,22Z)—N,N-dimethyloctacosa-19,22-dien-7-amine, N,N-dimethylheptacosan-10-amine, (20Z,23Z)—N-ethyl-N-methylnonacosa-20,23-dien-10-amine, 1-[(11Z,14Z)-1-nonylicosa-11,14-dien-1-yl]pyrrolidine, (20Z)—N,N-dimethylheptacos-20-en-10-amine, (15Z)—N,N-dimethyl eptacos-15-en-10-amine, (14Z)—N,N-dimethylnonacos-14-en-10-amine, (17Z)—N,N-dimethylnonacos-17-en-10-amine, (24Z)—N,N-dimethyltritriacont-24-en-10-amine, (20Z)—N,N-dimethylnonacos-20-en-10-amine, (22Z)—N,N-dimethylhentriacont-22-en-10-amine, (16Z)—N,N-dimethylpentacos-16-en-8-amine, (12Z,15Z)—N,N-dimethyl-2-nonylhenicosa-12,15-dien-1-amine, N,N-dimethyl-1-[(1S,2R)-2-octylcyclopropyl] eptadecan-8-amine, 1-[(1S,2R)-2-hexylcyclopropyl]-N,N-dimethylnonadecan-10-amine, N,N-dimethyl-1-[(1S,2R)-2-octylcyclopropyl] nonadecan-10-amine, N,N-dimethyl-21-[(1S,2R)-2-octylcyclopropyl]henicosan-10-amine, N,N-dimethyl-1-[(1S,2S)-2-{[(1R,2R)-2-pentylcyclopropyl]methyl}cyclopropyl]nonadecan-10-amine, N,N-dimethyl-1-[(1S,2R)-2-octylcyclopropyl]hexadecan-8-amine, N,N-dimethyl-[(1R,2S)-2-undecylcyclopropyl]tetradecan-5-amine, N,N-dimethyl-3-{7-[(1S,2R)-2-octylcyclopropyl]heptyl}dodecan-1-amine, 1-[(1R,2S)-2-heptylcyclopropyl]-N,N-dimethyloctadecan-9-amine, 1-[(1S,2R)-2-decylcyclopropyl]-N,N-dimethylpentadecan-6-amine, N,N-dimethyl-1-[(1S,2R)-2-octylcyclopropyl]pentadecan-8-amine, R—N,N-dimethyl-1-[(9Z,12Z)-octadeca-9,12-dien-1-yloxy]-3-(octyloxy)propan-2-amine, S—N,N-dimethyl-1-[(9Z,12Z)-octadeca-9,12-dien-1-yloxy]-3-(octyloxy) propan-2-amine, 1-{2-[(9Z,12Z)-octadeca-9,12-dien-1-yloxy]-1-[(octyloxy)methyl]ethyl}pyrrolidine, (2S)—N,N-dimethyl-1-[(9Z,12Z)-octadeca-9,12-dien-1-yloxy]-3-[(5Z)-oct-5-en-1-yloxy]propan-2-amine, 1-{2-[(9Z,12Z)-octadeca-9,12-dien-1-yloxy]-1-[(octyloxy)methyl]ethyl}azetidine, (2S)-1-(hexyloxy)-N,N-dimethyl-3-[(9Z,12Z)-octadeca-9,12-dien-1-yloxy]propan-2-amine, (2S)-1-(heptyloxy)-N,N-dimethyl-3-[(9Z,12Z)-octadeca-9,12-dien-1-yloxy]propan-2-amine, N,N-dimethyl-1-(nonyloxy)-3-[(9Z,12Z)-octadeca-9,12-dien-1-yloxy]propan-2-amine, N,N-dimethyl-1-[(9Z)-octadec-9-en-1-yloxy]-3-(octyloxy)propan-2-amine; (2S)—N,N-dimethyl-1-[(6Z,9Z,12Z)-octadeca-6,9,12-trien-1-yloxy]-3-(octyloxy)propan-2-amine, (2S)-1-[(11Z,14Z)-icosa-11,14-dien-1-yloxy]-N,N-dimethyl-3-(pentyloxy)propan-2-amine, (2S)-1-(hexyloxy)-3-[(11Z,14Z)-icosa-11,14-dien-1-yloxy]-N,N-dimethylpropan-2-amine, 1-[(11Z,14Z)-icosa-11,14-dien-1-yloxy]-N,N-dimethyl-3-(octyloxy)propan-2-amine, 1-[(13Z,16Z)-docosa-13,16-dien-1-yloxy]-N,N-dimethyl-3-(octyloxy) propan-2-amine, (2S)-1-[(13Z, 16Z)-docosa-13,16-dien-1-yloxy]-3-(hexyloxy)-N,N-dimethylpropan-2-amine, (2S)-1-[(13Z)-docos-13-en-1-yloxy]-3-(hexyloxy)-N,N-dimethylpropan-2-amine, 1-[(13Z)-docos-13-en-1-yloxy]-N,N-dimethyl-3-(octyloxy)propan-2-amine, 1-[(9Z)-hexadec-9-en-1-yloxy]-N,N-dimethyl-3-(octyloxy)propan-2-amine, (2R)—N,N-dimethyl-H(1-metoyloctyl)oxy]-3-[(9Z,12Z)-octadeca-9,12-dien-1-yloxy]propan-2-amine, (2R)-1-[(3,7-dimethyloctyl)oxy]-N,N-dimethyl-3-[(9Z, 12Z)-octadeca-9,12-dien-1-yloxy]propan-2-amine, N,N-dimethyl-1-(octyloxy)-3-({8-[(1S,2S)-2-{[(1R,2R)-2-pentyl-cyclopropyl]methyl}cyclopropyl]octyl}oxy)propan-2-amine, N,N-dimethyl-1-{[8-(2-octlylcyclopropyl)octyl]oxy}-3-(octyloxy)propan-2-amine, and (11E,20Z,23Z)—N,N-dimethylnonacosa-11,20,2-trien-10-amine, and any combination thereof.

Phospholipids include, but are not limited to, glycerophospholipids such as phosphatidylcholines, phosphatidylethanolamines, phosphatidylserines, phosphatidylinositols, phosphatidy glycerols, and phosphatidic acids. Phospholipids also include phosphosphingolipid, such as sphingomyelin. In some embodiments, the phospholipids are DLPC, DMPC, DOPC, DPPC, DSPC, DUPC, 18:0 Diether PC, DLnPC, DAPC, DHAPC, DOPE, 4ME 16:0 PE, DSPE, DLPE, DLnPE, DAPE, DHAPE, DOPG, and any combination thereof. In some embodiments, the phospholipids are MPPC, MSPC, PMPC, PSPC, SMPC, SPPC, DHAPE, DOPG, and any combination thereof. In some embodiments, the amount of phospholipids (e.g., DSPC) in the lipid composition ranges from about 1 mol % to about 20 mol %.

The structural lipids include sterols and lipids containing sterol moieties. In some embodiments, the structural lipids include cholesterol, fecosterol, sitosterol, ergosterol, campesterol, stigmasterol, brassicasterol, tomatidine, tomatine, ursolic acid, alpha-tocopherol, and mixtures thereof. In some embodiments, the structural lipid is cholesterol. In some embodiments, the amount of the structural lipids (e.g., cholesterol) in the lipid composition ranges from about 20 mol % to about 60 mol %.

The PEG-modified lipids include PEG-modified phosphatidylethanolamine and phosphatidic acid, PEG-ceramide conjugates (e.g., PEG-CerC14 or PEG-CerC20), PEG-modified dialkylamines and PEG-modified 1,2-diacyloxypropan-3-amines. Such lipids are also referred to as PEGylated lipids. For example, a PEG lipid can be PEG-c-DOMG, PEG-DMG, PEG-DLPE, PEG DMPE, PEG-DPPC, or a PEG-DSPE lipid. In some embodiments, the PEG-lipid are 1,2-dimyristoyl-sn-glycerol methoxypolyethylene glycol (PEG-DMG), 1,2-distearoyl-sn-glycero-3-phosphoethanolamine-N-[amino(polyethylene glycol)] (PEG-DSPE), PEG-disteryl glycerol (PEG-DSG), PEG-dipalmetoleyl, PEG-dioleyl, PEG-distearyl, PEG-diacylglycamide (PEG-DAG), PEG-dipalmitoyl phosphatidylethanolamine (PEG-DPPE), or PEG-1,2-dimyristyloxlpropyl-3-amine (PEG-c-DMA). In some embodiments, the PEG moiety has a size of about 1000, 2000, 5000, 10,000, 15,000 or 20,000 daltons. In some embodiments, the amount of PEG-lipid in the lipid composition ranges from about 0.1 mol % to about 5 mol %.

In some embodiments, the LNP formulations described herein can additionally comprise a permeability enhancer molecule. Non-limiting permeability enhancer molecules are described in U.S. Pub. No. US20050222064, herein incorporated by reference in its entirety.

The LNP formulations can further contain a phosphate conjugate. The phosphate conjugate can increase in vivo circulation times and/or increase the targeted delivery of the nanoparticle. Phosphate conjugates can be made by the methods described in, e.g., Intl. Pub. No. WO2013033438 or U.S. Pub. No. US20130196948. The LNP formulation can also contain a polymer conjugate (e.g., a water soluble conjugate) as described in, e.g., U.S. Pub. Nos. US20130059360, US20130196948, and US20130072709. Each of the references is herein incorporated by reference in its entirety.

The LNP formulations can comprise a conjugate to enhance the delivery of nanoparticles of the present invention in a subject. Further, the conjugate can inhibit phagocytic clearance of the nanoparticles in a subject. In some embodiments, the conjugate can be a "self" peptide designed from the human membrane protein CD47 (e.g., the "self" particles described by Rodriguez et al, Science 2013 339, 971-975, herein incorporated by reference in its entirety). As shown by Rodriguez et al. the self peptides delayed macrophage-mediated clearance of nanoparticles which enhanced delivery of the nanoparticles.

The LNP formulations can comprise a carbohydrate carrier. As a non-limiting example, the carbohydrate carrier can include, but is not limited to, an anhydride-modified phytoglycogen or glycogen-type material, phytoglycogen octenyl succinate, phytoglycogen beta-dextrin, anhydride-modified phytoglycogen beta-dextrin (e.g., Intl. Pub. No. WO2012109121, herein incorporated by reference in its entirety).

The LNP formulations can be coated with a surfactant or polymer to improve the delivery of the particle. In some embodiments, the LNP can be coated with a hydrophilic coating such as, but not limited to, PEG coatings and/or coatings that have a neutral surface charge as described in U.S. Pub. No. US20130183244, herein incorporated by reference in its entirety.

The LNP formulations can be engineered to alter the surface properties of particles so that the lipid nanoparticles can penetrate the mucosal barrier as described in U.S. Pat. No. 8,241,670 or Intl. Pub. No. WO2013110028, each of which is herein incorporated by reference in its entirety.

The LNP engineered to penetrate mucus can comprise a polymeric material (i.e., a polymeric core) and/or a polymer-vitamin conjugate and/or a tri-block co-polymer. The polymeric material can include, but is not limited to, polyamines, polyethers, polyamides, polyesters, polycarbamates, polyureas, polycarbonates, poly(styrenes), polyimides, polysulfones, polyurethanes, polyacetylenes, polyethylenes, polyethyeneimines, polyisocyanates, polyacrylates, polymethacrylates, polyacrylonitriles, and polyarylates.

LNP engineered to penetrate mucus can also include surface altering agents such as, but not limited to, polynucleotides, anionic proteins (e.g., bovine serum albumin), surfactants (e.g., cationic surfactants such as for example dimethyldioctadecyl-ammonium bromide), sugars or sugar derivatives (e.g., cyclodextrin), nucleic acids, polymers (e.g., heparin, polyethylene glycol and poloxamer), mucolytic agents (e.g., N-acetylcysteine, mugwort, bromelain, papain, clerodendrum, acetylcysteine, bromhexine, carbocisteine, eprazinone, mesna, ambroxol, sobrerol, domiodol, letosteine, stepronin, tiopronin, gelsolin, thymosin dornase alfa, neltenexine, erdosteine) and various DNases including rhDNase.

In some embodiments, the mucus penetrating LNP can be a hypotonic formulation comprising a mucosal penetration enhancing coating. The formulation can be hypotonic for the epithelium to which it is being delivered. Non-limiting examples of hypotonic formulations can be found in, e.g., Intl. Pub. No. WO2013110028, herein incorporated by reference in its entirety.

In some embodiments, the polynucleotide described herein is formulated as a lipoplex, such as, without limitation, the ATUPLEX™ system, the DACC system, the DBTC system and other siRNA-lipoplex technology from Silence Therapeutics (London, United Kingdom), STEMFECT™ from STEMGENT® (Cambridge, MA), and polyethylenimine (PEI) or protamine-based targeted and non-targeted delivery of nucleic acids (Aleku et al. Cancer Res. 2008 68:9788-9798; Strumberg et al. Int J Clin Pharmacol Ther 2012 50:76-78; Santel et al., Gene Ther 2006 13:1222-1234; Santel et al., Gene Ther 2006 13:1360-1370; Gutbier et al., Pulm Pharmacol. Ther. 2010 23:334-344; Kaufmann et al. Microvasc Res 2010 80:286-293 Weide et al. J Immunother. 2009 32:498-507; Weide et al. J Immunother. 2008 31:180-188; Pascolo Expert Opin. Biol. Ther. 4:1285-1294; Fotin-Mleczek et al., 2011 J. Immunother. 34:1-15; Song et al., Nature Biotechnol. 2005, 23:709-717; Peer et al., Proc Natl Acad Sci USA. 2007 6; 104:4095-4100; deFougerolles Hum Gene Ther. 2008 19:125-132; all of which are incorporated herein by reference in its entirety).

In some embodiments, the polynucleotides described herein are formulated as a solid lipid nanoparticle (SLN), which can be spherical with an average diameter between 10 to 1000 nm. SLN possess a solid lipid core matrix that can solubilize lipophilic molecules and can be stabilized with surfactants and/or emulsifiers. Exemplary SLN can be those as described in Intl. Pub. No. WO2013105101, herein incorporated by reference in its entirety.

In some embodiments, the polynucleotides described herein can be formulated for controlled release and/or targeted delivery. As used herein, "controlled release" refers to a pharmaceutical composition or compound release profile that conforms to a particular pattern of release to effect a therapeutic outcome. In one embodiment, the polynucleotides can be encapsulated into a delivery agent described herein and/or known in the art for controlled release and/or targeted delivery. As used herein, the term "encapsulate" means to enclose, surround or encase. As it relates to the formulation of the compounds of the invention, encapsulation can be substantial, complete or partial. The term "substantially encapsulated" means that at least greater than 50, 60, 70, 80, 85, 90, 95, 96, 97, 98, 99, 99.9, 99.9 or greater than 99.999% of the pharmaceutical composition or compound of the invention can be enclosed, surrounded or encased within the delivery agent. "Partially encapsulation" means that less than 10, 10, 20, 30, 40 50 or less of the pharmaceutical composition or compound of the invention can be enclosed, surrounded or encased within the delivery agent.

Advantageously, encapsulation can be determined by measuring the escape or the activity of the pharmaceutical composition or compound of the invention using fluorescence and/or electron micrograph. For example, at least 1, 5, 10, 20, 30, 40, 50, 60, 70, 80, 85, 90, 95, 96, 97, 98, 99, 99.9, 99.99 or greater than 99.99% of the pharmaceutical composition or compound of the invention are encapsulated in the delivery agent.

In some embodiments, the polynucleotide controlled release formulation can include at least one controlled release coating (e.g., OPADRY®, EUDRAGIT RL®, EUDRAGIT RS® and cellulose derivatives such as ethylcellulose aqueous dispersions (AQUACOAT® and SURELEASE®)). In some embodiments, the polynucleotide controlled release formulation can comprise a polymer system as described in U.S. Pub. No. US20130130348, or a PEG and/or PEG related polymer derivative as described in U.S. Pat. No. 8,404,222, each of which is incorporated by reference in its entirety.

In some embodiments, the polynucleotides described herein can be encapsulated in a therapeutic nanoparticle, referred to herein as "therapeutic nanoparticle polynucleotides." Therapeutic nanoparticles can be formulated by methods described in, e.g., Intl. Pub. Nos. WO2010005740, WO2010030763, WO2010005721, WO2010005723, and WO2012054923; and U.S. Pub. Nos. US20110262491, US20100104645, US20100087337, US20100068285, US20110274759, US20100068286, US20120288541, US20120140790, US20130123351 and US20130230567; and U.S. Pat. Nos. 8,206,747, 8,293,276, 8,318,208 and 8,318,211, each of which is herein incorporated by reference in its entirety.

In some embodiments, the therapeutic nanoparticle polynucleotide can be formulated for sustained release. As used herein, "sustained release" refers to a pharmaceutical composition or compound that conforms to a release rate over a specific period of time. The period of time can include, but is not limited to, hours, days, weeks, months and years. As a non-limiting example, the sustained release nanoparticle of the polynucleotides described herein can be formulated as disclosed in Intl. Pub. No. WO2010075072 and U.S. Pub. Nos. US20100216804, US20110217377, US20120201859 and US20130150295, each of which is herein incorporated by reference in their entirety.

In some embodiments, the therapeutic nanoparticle polynucleotide can be formulated to be target specific, such as those described in Intl. Pub. Nos. WO2008121949, WO2010005726, WO2010005725, WO2011084521 and WO2011084518; and U.S. Pub. Nos. US20100069426, US20120004293 and US20100104655, each of which is herein incorporated by reference in its entirety.

The LNPs can be prepared using microfluidic mixers or micromixers. Exemplary microfluidic mixers can include, but are not limited to, a slit interdigital micromixer including, but not limited to those manufactured by Microinnova (Allerheiligen bei Wildon, Austria) and/or a staggered herringbone micromixer (SHM) (see Zhigaltsev et al., "Bottom-up design and synthesis of limit size lipid nanoparticle systems with aqueous and triglyceride cores using millisecond microfluidic mixing," Langmuir 28:3633-40 (2012); Belliveau et al., "Microfluidic synthesis of highly potent limit-size lipid nanoparticles for in vivo delivery of siRNA," Molecular Therapy-Nucleic Acids. 1:e37 (2012); Chen et al., "Rapid discovery of potent siRNA-containing lipid nanoparticles enabled by controlled microfluidic formulation," J. Am. Chem. Soc. 134(16):6948-51 (2012); each of which is herein incorporated by reference in its entirety). Exemplary micromixers include Slit Interdigital Microstructured Mixer (SIMM-V2) or a Standard Slit Interdigital Micro Mixer (SSIMM) or Caterpillar (CPMM) or Impinging-jet (IJMM,) from the Institut für Mikrotechnik Mainz GmbH, Mainz Germany. In some embodiments, methods of making LNP using SHM further comprise mixing at least two input streams wherein mixing occurs by microstructure-induced chaotic advection (MICA). According to this method, fluid streams flow through channels present in a herringbone pattern causing rotational flow and folding the fluids around each other. This method can also comprise a surface for fluid mixing wherein the surface changes orientations during fluid cycling. Methods of generating LNPs using SHM include those disclosed in U.S. Pub. Nos. US20040262223 and US20120276209, each of which is incorporated herein by reference in their entirety.

In some embodiments, the polynucleotides described herein can be formulated in lipid nanoparticles using microfluidic technology (see Whitesides, George M., "The Origins and the Future of Microfluidics," Nature 442: 368-373 (2006); and Abraham et al., "Chaotic Mixer for Microchannels," Science 295: 647-651 (2002); each of which is herein incorporated by reference in its entirety). In some embodiments, the polynucleotides can be formulated in lipid nanoparticles using a micromixer chip such as, but not limited to, those from Harvard Apparatus (Holliston, MA) or Dolomite Microfluidics (Royston, UK). A micromixer chip can be used for rapid mixing of two or more fluid streams with a split and recombine mechanism.

In some embodiments, the polynucleotides described herein can be formulated in lipid nanoparticles having a diameter from about 1 nm to about 100 nm such as, but not limited to, about 1 nm to about 20 nm, from about 1 nm to about 30 nm, from about 1 nm to about 40 nm, from about 1 nm to about 50 nm, from about 1 nm to about 60 nm, from about 1 nm to about 70 nm, from about 1 nm to about 80 nm, from about 1 nm to about 90 nm, from about 5 nm to about from 100 nm, from about 5 nm to about 10 nm, about 5 nm to about 20 nm, from about 5 nm to about 30 nm, from about 5 nm to about 40 nm, from about 5 nm to about 50 nm, from about 5 nm to about 60 nm, from about 5 nm to about 70 nm, from about 5 nm to about 80 nm, from about 5 nm to about 90 nm, about 10 to about 20 nm, about 10 to about 30 nm, about 10 to about 40 nm, about 10 to about 50 nm, about 10 to about 60 nm, about 10 to about 70 nm, about 10 to about 80 nm, about 10 to about 90 nm, about 20 to about 30 nm, about 20 to about 40 nm, about 20 to about 50 nm, about 20 to about 60 nm, about 20 to about 70 nm, about 20 to about 80 nm, about 20 to about 90 nm, about 20 to about 100 nm, about 30 to about 40 nm, about 30 to about 50 nm, about 30 to about 60 nm, about 30 to about 70 nm, about 30 to about 80 nm, about 30 to about 90 nm, about 30 to about 100 nm, about 40 to about 50 nm, about 40 to about 60 nm, about 40 to about 70 nm, about 40 to about 80 nm, about 40 to about 90 nm, about 40 to about 100 nm, about 50 to about 60 nm, about 50 to about 70 nm about 50 to about 80 nm, about 50 to about 90 nm, about 50 to about 100 nm, about 60 to about 70 nm, about 60 to about 80 nm, about 60 to about 90 nm, about 60 to about 100 nm, about 70 to about 80 nm, about 70 to about 90 nm, about 70 to about 100 nm, about 80 to about 90 nm, about 80 to about 100 nm and/or about 90 to about 100 nm.

In some embodiments, the lipid nanoparticles can have a diameter from about 10 to 500 nm. In one embodiment, the lipid nanoparticle can have a diameter greater than 100 nm, greater than 150 nm, greater than 200 nm, greater than 250 nm, greater than 300 nm, greater than 350 nm, greater than 400 nm, greater than 450 nm, greater than 500 nm, greater than 550 nm, greater than 600 nm, greater than 650 nm, greater than 700 nm, greater than 750 nm, greater than 800 nm, greater than 850 nm, greater than 900 nm, greater than 950 nm or greater than 1000 nm.

In some embodiments, the polynucleotides can be delivered using smaller LNPs. Such particles can comprise a diameter from below 0.1 µm up to 100 nm such as, but not limited to, less than 0.1 µm, less than 1.0 µm, less than 5 µm, less than 10 µm, less than 15 um, less than 20 um, less than 25 um, less than 30 um, less than 35 um, less than 40 um, less than 50 um, less than 55 um, less than 60 um, less than 65 um, less than 70 um, less than 75 um, less than 80 um, less than 85 um, less than 90 um, less than 95 um, less than 100 um, less than 125 um, less than 150 um, less than 175 um, less than 200 um, less than 225 um, less than 250 um, less than 275 um, less than 300 um, less than 325 um, less than 350 um, less than 375 um, less than 400 um, less than 425 um, less than 450 um, less than 475 um, less than 500 um, less than 525 um, less than 550 um, less than 575 um, less than 600 um, less than 625 um, less than 650 um, less than 675 um, less than 700 um, less than 725 um, less than 750 um, less than 775 um, less than 800 um, less than 825 um, less than 850 um, less than 875 um, less than 900 um, less than 925 um, less than 950 um, or less than 975 um.

The nanoparticles and microparticles described herein can be geometrically engineered to modulate macrophage and/or the immune response. The geometrically engineered particles can have varied shapes, sizes and/or surface charges to incorporate the polynucleotides described herein for targeted delivery such as, but not limited to, pulmonary delivery (see, e.g., Intl. Pub. No. WO2013082111, herein incorporated by reference in its entirety). Other physical features the geometrically engineering particles can include, but are not limited to, fenestrations, angled arms, asymmetry and surface roughness, charge that can alter the interactions with cells and tissues.

In some embodiment, the nanoparticles described herein are stealth nanoparticles or target-specific stealth nanoparticles such as, but not limited to, those described in U.S. Pub. No. US20130172406, herein incorporated by reference in its entirety. The stealth or target-specific stealth nanoparticles can comprise a polymeric matrix, which can comprise two or more polymers such as, but not limited to, polyethylenes, polycarbonates, polyanhydrides, polyhydroxyacids, polypropylfumerates, polycaprolactones, polyamides, polyacetals, polyethers, polyesters, poly(orthoesters), polycyanoacrylates, polyvinyl alcohols, polyurethanes, polyphosphazenes, polyacrylates, polymethacrylates, polycyanoacrylates, polyureas, polystyrenes, polyamines, polyesters, polyanhydrides, polyethers, polyurethanes, polymethacrylates, polyacrylates, polycyanoacrylates, or combinations thereof.

b. Lipidoids

In some embodiments, the compositions or formulations of the present disclosure comprise a delivery agent, e.g., a lipidoid. The polynucleotides described herein (e.g., a polynucleotide comprising a nucleotide sequence encoding a PBGD polypeptide) can be formulated with lipidoids. Complexes, micelles, liposomes or particles can be prepared containing these lipidoids and therefore to achieve an effective delivery of the polynucleotide, as judged by the production of an encoded protein, following the injection of a lipidoid formulation via localized and/or systemic routes of administration. Lipidoid complexes of polynucleotides can be administered by various means including, but not limited to, intravenous, intramuscular, or subcutaneous routes.

The synthesis of lipidoids is described in literature (see Mahon et al., Bioconjug. Chem. 2010 21:1448-1454; Schroeder et al., J Intern Med. 2010 267:9-21; Akinc et al., Nat Biotechnol. 2008 26:561-569; Love et al., Proc Natl Acad Sci USA. 2010 107:1864-1869; Siegwart et al., Proc Natl Acad Sci USA. 2011 108:12996-3001; all of which are incorporated herein in their entireties).

Formulations with the different lipidoids, including, but not limited to penta[3-(1-laurylaminopropionyl)]-triethylenetetramine hydrochloride (TETA-SLAP; also known as 98N12-5, see Murugaiah et al., Analytical Biochemistry, 401:61 (2010)), C12-200 (including derivatives and variants), and MD1, can be tested for in vivo activity. The lipidoid "98N12-5" is disclosed by Akinc et al., Mol Ther. 2009 17:872-879. The lipidoid "C12-200" is disclosed by Love et al., Proc Natl Acad Sci USA. 2010 107:1864-1869 and Liu and Huang, Molecular Therapy. 2010 669-670. Each of the references is herein incorporated by reference in its entirety.

In one embodiment, the polynucleotides described herein can be formulated in an aminoalcohol lipidoid. Aminoalcohol lipidoids can be prepared by the methods described in U.S. Pat. No. 8,450,298 (herein incorporated by reference in its entirety).

The lipidoid formulations can include particles comprising either 3 or 4 or more components in addition to polynucleotides. Lipidoids and polynucleotide formulations comprising lipidoids are described in Intl. Pub. No. WO 2015051214 (herein incorporated by reference in its entirety.

c. Hyaluronidase

In some embodiments, the polynucleotides described herein (e.g., a polynucleotide comprising a nucleotide sequence encoding a PBGD polypeptide) and hyaluronidase for injection (e.g., intramuscular or subcutaneous injection). Hyaluronidase catalyzes the hydrolysis of hyaluronan, which is a constituent of the interstitial barrier. Hyaluronidase lowers the viscosity of hyaluronan, thereby increases tissue permeability (Frost, Expert Opin. Drug Deliv. (2007) 4:427-440). Alternatively, the hyaluronidase can be used to increase the number of cells exposed to the polynucleotides administered intramuscularly or subcutaneously.

d. Nanoparticle Mimics

In some embodiments, the polynucleotides described herein (e.g., a polynucleotide comprising a nucleotide sequence encoding a PBGD polypeptide) is encapsulated within and/or absorbed to a nanoparticle mimic. A nanoparticle mimic can mimic the delivery function organisms or particles such as, but not limited to, pathogens, viruses, bacteria, fungus, parasites, prions and cells. As a non-limiting example, the polynucleotides described herein can be encapsulated in a non-viron particle that can mimic the delivery function of a virus (see e.g., Intl. Pub. No. WO2012006376 and U.S. Pub. Nos. US20130171241 and US20130195968, each of which is herein incorporated by reference in its entirety).

e. Nanotubes

In some embodiments, the compositions or formulations of the present disclosure comprise the polynucleotides described herein (e.g., a polynucleotide comprising a nucleotide sequence encoding a PBGD polypeptide) attached or otherwise bound to (e.g., through steric, ionic, covalent and/or other forces) at least one nanotube, such as, but not limited to, rosette nanotubes, rosette nanotubes having twin bases with a linker, carbon nanotubes and/or single-walled carbon nanotubes. Nanotubes and nanotube formulations comprising a polynucleotide are described in, e.g., Intl. Pub. No. WO2014152211, herein incorporated by reference in its entirety.

f. Self-Assembled Nanoparticles, or Self-Assembled Macromolecules

In some embodiments, the compositions or formulations of the present disclosure comprise the polynucleotides described herein (e.g., a polynucleotide comprising a nucleotide sequence encoding a PBGD polypeptide) in self-assembled nanoparticles, or amphiphilic macromolecules (AMs) for delivery. AMs comprise biocompatible amphiphilic polymers that have an alkylated sugar backbone covalently linked to poly(ethylene glycol). In aqueous solution, the AMs self-assemble to form micelles. Nucleic acid self-assembled nanoparticles are described in Intl. Appl. No. PCT/US2014/027077, and AMs and methods of forming AMs are described in U.S. Pub. No. US20130217753, each of which is herein incorporated by reference in its entirety.

g. Inorganic Nanoparticles, Semi-Conductive and Metallic Nanoparticles

In some embodiments, the compositions or formulations of the present disclosure comprise the polynucleotides described herein (e.g., a polynucleotide comprising a nucleotide sequence encoding a PBGD polypeptide) in inorganic nanoparticles, or water-dispersible nanoparticles comprising a semiconductive or metallic material. The inorganic nanoparticles can include, but are not limited to, clay substances that are water swellable. The water-dispersible nanoparticles can be hydrophobic or hydrophilic nanoparticles. As a non-limiting example, the inorganic, semi-conductive and metallic nanoparticles are described in, e.g., U.S. Pat. Nos. 5,585,108 and 8,257,745; and U.S. Pub. Nos. US20120228565, US 20120265001 and US 20120283503, each of which is herein incorporated by reference in their entirety.

h. Surgical Sealants: Gels and Hydrogels

In some embodiments, the compositions or formulations of the present disclosure comprise the polynucleotides described herein (e.g., a polynucleotide comprising a nucleotide sequence encoding a PBGD polypeptide) in a surgical sealant. Surgical sealants such as gels and hydrogels are described in Intl. Appl. No. PCT/US2014/027077, herein incorporated by reference in its entirety.

i. Suspension formulations

In some embodiments, the compositions or formulations of the present disclosure comprise the polynucleotides described herein (e.g., a polynucleotide comprising a nucleotide sequence encoding a PBGD polypeptide) in suspensions. In some embodiments, suspensions comprise a polynucleotide, water immiscible oil depots, surfactants and/or co-surfactants and/or co-solvents. Suspensions can be formed by first preparing an aqueous solution of a polynucleotide and an oil-based phase comprising one or more surfactants, and then mixing the two phases (aqueous and oil-based).

Exemplary oils for suspension formulations can include, but are not limited to, sesame oil and Miglyol (comprising esters of saturated coconut and palmkernel oil-derived caprylic and capric fatty acids and glycerin or propylene glycol), corn oil, soybean oil, peanut oil, beeswax and/or palm seed oil. Exemplary surfactants can include, but are not limited to Cremophor, polysorbate 20, polysorbate 80, polyethylene glycol, transcutol, Capmul®, labrasol, isopropyl myristate, and/or Span 80. In some embodiments, suspensions can comprise co-solvents including, but not limited to ethanol, glycerol and/or propylene glycol.

In some embodiments, suspensions can provide modulation of the release of the polynucleotides into the surrounding environment by diffusion from a water immiscible depot followed by resolubilization into a surrounding environment (e.g., an aqueous environment).

In some embodiments, the polynucleotides can be formulated such that upon injection, an emulsion forms spontaneously (e.g., when delivered to an aqueous phase), which can provide a high surface area to volume ratio for release of polynucleotides from an oil phase to an aqueous phase. In some embodiments, the polynucleotide is formulated in a nanoemulsion, which can comprise a liquid hydrophobic core surrounded by or coated with a lipid or surfactant layer. Exemplary nanoemulsions and their preparations are described in, e.g., U.S. Pat. No. 8,496,945, herein incorporated by reference in its entirety.

j. Cations and Anions

In some embodiments, the compositions or formulations of the present disclosure comprise the polynucleotides described herein (e.g., a polynucleotide comprising a nucleotide sequence encoding a PBGD polypeptide) and a cation or anion, such as $Zn^{2+}$, $Ca^{2+}$, $Cu^{2+}$, $Mg^{2+}$ and combinations thereof. Exemplary formulations can include polymers and a polynucleotide complexed with a metal cation as described in, e.g., U.S. Pat. Nos. 6,265,389 and 6,555,525, each of which is herein incorporated by reference in its entirety. In some embodiments, cationic nanoparticles can contain a combination of divalent and monovalent cations. The delivery of polynucleotides in cationic nanoparticles or in one or more depot comprising cationic nanoparticles can improve polynucleotide bioavailability by acting as a long-acting depot and/or reducing the rate of degradation by nucleases.

k. Molded Nanoparticles and Microparticles

In some embodiments, the compositions or formulations of the present disclosure comprise the polynucleotides described herein (e.g., a polynucleotide comprising a nucleotide sequence encoding a PBGD polypeptide) in molded nanoparticles in various sizes, shapes and chemistry. For example, the nanoparticles and/or microparticles can be made using the PRINT® technology by LIQUIDA TECH- NOLOGIES® (Morrisville, NC) (e.g., International Pub. No. WO2007024323, herein incorporated by reference in its entirety).

In some embodiments, the polynucleotides described herein (e.g., a polynucleotide comprising a nucleotide sequence encoding a PBGD polypeptide) is formulated in microparticles. The microparticles can contain a core of the polynucleotide and a cortex of a biocompatible and/or biodegradable polymer, including but not limited to, poly (α-hydroxy acid), a polyhydroxy butyric acid, a polycaprolactone, a polyorthoester and a polyanhydride. The microparticle can have adsorbent surfaces to adsorb polynucleotides. The microparticles can have a diameter of from at least 1 micron to at least 100 microns (e.g., at least 1 micron, at least 10 micron, at least 20 micron, at least 30 micron, at least 50 micron, at least 75 micron, at least 95 micron, and at least 100 micron). In some embodiment, the compositions or formulations of the present disclosure are microemulsions comprising microparticles and polynucleotides. Exemplary microparticles, microemulsions and their preparations are described in, e.g., U.S. Pat. Nos. 8,460,709, 8,309,139 and 8,206,749; U.S. Pub. Nos. US20130129830, US2013195923 and US20130195898; and Intl. Pub. No. WO2013075068, each of which is herein incorporated by reference in its entirety.

l. NanoJackets and NanoLiposomes

In some embodiments, the compositions or formulations of the present disclosure comprise the polynucleotides described herein (e.g., a polynucleotide comprising a nucleotide sequence encoding a PBGD polypeptide) in NanoJackets and NanoLiposomes by Keystone Nano (State College, PA). NanoJackets are made of materials that are naturally found in the body including calcium, phosphate and can also include a small amount of silicates. Nanojackets can have a size ranging from 5 to 50 nm.

NanoLiposomes are made of lipids such as, but not limited to, lipids that naturally occur in the body. NanoLiposomes can have a size ranging from 60-80 nm. In some embodiments, the polynucleotides disclosed herein are formulated in a NanoLiposome such as, but not limited to, Ceramide NanoLiposomes.

m. Cells or Minicells

In some embodiments, the compositions or formulations of the present disclosure comprise the polynucleotides described herein (e.g., a polynucleotide comprising a nucleotide sequence encoding a PBGD polypeptide) that is transfected ex vivo into cells, which are subsequently transplanted into a subject. Cell-based formulations of the polynucleotide disclosed herein can be used to ensure cell transfection (e.g., in the cellular carrier), alter the biodistribution of the polynucleotide (e.g., by targeting the cell carrier to specific tissues or cell types), and/or increase the translation of encoded protein.

Exemplary cells include, but are not limited to, red blood cells, virosomes, and electroporated cells (see e.g., Godfrin et al., Expert Opin Biol Ther. 2012 12:127-133; Fang et al., Expert Opin Biol Ther. 2012 12:385-389; Hu et al., Proc Natl Acad Sci USA. 2011 108:10980-10985; Lund et al., Pharm Res. 2010 27:400-420; Huckriede et al., J Liposome Res. 2007; 17:39-47; Cusi, Hum Vaccin. 2006 2:1-7; de Jonge et al., Gene Ther. 2006 13:400-411; all of which are herein incorporated by reference in its entirety).

A variety of methods are known in the art and are suitable for introduction of nucleic acid into a cell, including viral and non-viral mediated techniques. Examples of typical non-viral mediated techniques include, but are not limited to, electroporation, calcium phosphate mediated transfer, nucleofection, sonoporation, heat shock, magnetofection, liposome mediated transfer, microinjection, microprojectile mediated transfer (nanoparticles), cationic polymer mediated transfer (DEAE-dextran, polyethylenimine, polyethylene glycol (PEG) and the like) or cell fusion.

In some embodiments, the polynucleotides described herein can be delivered in synthetic virus-like particles (VLPs) synthesized by the methods as described in Intl. Pub Nos. WO2011085231 and WO2013116656; and U.S. Pub. No. 20110171248, each of which is herein incorporated by reference in its entirety.

The technique of sonoporation, or cellular sonication, is the use of sound (e.g., ultrasonic frequencies) for modifying the permeability of the cell plasma membrane. Sonoporation methods are known to deliver nucleic acids in vivo (Yoon and Park, Expert Opin Drug Deliv. 2010 7:321-330; Postema and Gilja, Curr Pharm Biotechnol. 2007 8:355-361; Newman and Bettinger, Gene Ther. 2007 14:465-475; U.S. Pub. Nos. US20100196983 and US20100009424; all herein incorporated by reference in their entirety).

In some embodiments, the polynucleotides described herein can be delivered by electroporation. Electroporation techniques are known to deliver nucleic acids in vivo and clinically (Andre et al., Curr Gene Ther. 2010 10:267-280; Chiarella et al., Curr Gene Ther. 2010 10:281-286; Hojman, Curr Gene Ther. 2010 10:128-138; all herein incorporated by reference in their entirety). Electroporation devices are sold by many companies worldwide including, but not limited to BTX® Instruments (Holliston, MA) (e.g., the AgilePulse In Vivo System) and Inovio (Blue Bell, PA) (e.g., Inovio SP-5P intramuscular delivery device or the CEL-LECTRA® 3000 intradermal delivery device).

In some embodiments, the cells are selected from the group consisting of mammalian cells, bacterial cells, plant, microbial, algal and fungal cells. In some embodiments, the cells are mammalian cells, such as, but not limited to, human, mouse, rat, goat, horse, rabbit, hamster or cow cells. In a further embodiment, the cells can be from an established cell line, including, but not limited to, HeLa, NSO, SP2/0, KEK 293T, Vero, Caco, Caco-2, MDCK, COS-1, COS-7, K562, Jurkat, CHO-K1, DG44, CHOK1SV, CHO-S, Huvec, CV-1, Huh-7, NIH3T3, HEK293, 293, A549, HepG2, IMR-90, MCF-7, U-20S, Per.C6, SF9, SF21 or Chinese Hamster Ovary (CHO) cells.

In certain embodiments, the cells are fungal cells, such as, but not limited to, *Chrysosporium* cells, *Aspergillus* cells, *Trichoderma* cells, Dictyostelium cells, *Candida* cells, *Saccharomyces* cells, *Schizosaccharomyces* cells, and *Penicillium* cells.

In certain embodiments, the cells are bacterial cells such as, but not limited to, *E. coli, B. subtilis*, or BL21 cells. Primary and secondary cells to be transfected by the methods of the invention can be obtained from a variety of tissues and include, but are not limited to, all cell types that can be maintained in culture. The primary and secondary cells include, but are not limited to, fibroblasts, keratinocytes, epithelial cells (e.g., mammary epithelial cells, intestinal epithelial cells), endothelial cells, glial cells, neural cells, formed elements of the blood (e.g., lymphocytes, bone marrow cells), muscle cells and precursors of these somatic cell types. Primary cells can also be obtained from a donor of the same species or from another species (e.g., mouse, rat, rabbit, cat, dog, pig, cow, bird, sheep, goat, horse).

In some embodiments, the compositions or formulations of the present disclosure comprise the polynucleotides described herein in bacterial minicells. As a non-limiting example, bacterial minicells can be those described in Intl.

Pub. No. WO2013088250 or U.S. Pub. No. US20130177499, each of which is herein incorporated by reference in its entirety.

n. Semi-Solid Compositions

In some embodiments, the compositions or formulations of the present disclosure comprise the polynucleotides described herein (e.g., a polynucleotide comprising a nucleotide sequence encoding a PBGD polypeptide) in a hydrophobic matrix to form a semi-solid or paste-like composition. As a non-limiting example, the semi-solid or paste-like composition can be made by the methods described in Intl. Pub. No. WO201307604, herein incorporated by reference in its entirety.

o. Exosomes

In some embodiments, the compositions or formulations of the present disclosure comprise the polynucleotides described herein (e.g., a polynucleotide comprising a nucleotide sequence encoding a PBGD polypeptide) in exosomes, which can be loaded with at least one polynucleotide and delivered to cells, tissues and/or organisms. As a non-limiting example, the polynucleotides can be loaded in the exosomes as described in Intl. Pub. No. WO2013084000, herein incorporated by reference in its entirety.

p. Silk-Based Delivery

In some embodiments, the compositions or formulations of the present disclosure comprise the polynucleotides described herein (e.g., a polynucleotide comprising a nucleotide sequence encoding a PBGD polypeptide) that is formulated for silk-based delivery. The silk-based delivery system can be formed by contacting a silk fibroin solution with a polynucleotide described herein. As a non-limiting example, a sustained release silk-based delivery system and methods of making such system are described in U.S. Pub. No. US20130177611, herein incorporated by reference in its entirety.

q. Amino Acid Lipids

In some embodiments, the compositions or formulations of the present disclosure comprise the polynucleotides described herein (e.g., a polynucleotide comprising a nucleotide sequence encoding a PBGD polypeptide) that is formulation with an amino acid lipid. Amino acid lipids are lipophilic compounds comprising an amino acid residue and one or more lipophilic tails. Non-limiting examples of amino acid lipids and methods of making amino acid lipids are described in U.S. Pat. No. 8,501,824. The amino acid lipid formulations can deliver a polynucleotide in releasable form that comprises an amino acid lipid that binds and releases the polynucleotides. As a non-limiting example, the release of the polynucleotides described herein can be provided by an acid-labile linker as described in, e.g., U.S. Pat. Nos. 7,098,032, 6,897,196, 6,426,086, 7,138,382, 5,563,250, and 5,505,931, each of which is herein incorporated by reference in its entirety.

r. Microvesicles

In some embodiments, the compositions or formulations of the present disclosure comprise the polynucleotides described herein (e.g., a polynucleotide comprising a nucleotide sequence encoding a PBGD polypeptide) in a microvesicle formulation. Exemplary microvesicles include those described in U.S. Pub. No. US20130209544 (herein incorporated by reference in its entirety). In some embodiments, the microvesicle is an ARRDC1-mediated microvesicles (ARMMs) as described in Intl. Pub. No. WO2013119602 (herein incorporated by reference in its entirety).

s. Interpolyelectrolyte Complexes

In some embodiments, the compositions or formulations of the present disclosure comprise the polynucleotides described herein (e.g., a polynucleotide comprising a nucleotide sequence encoding a PBGD polypeptide) in an interpolyelectrolyte complex. Interpolyelectrolyte complexes are formed when charge-dynamic polymers are complexed with one or more anionic molecules. Non-limiting examples of charge-dynamic polymers and interpolyelectrolyte complexes and methods of making interpolyelectrolyte complexes are described in U.S. Pat. No. 8,524,368, herein incorporated by reference in its entirety.

t. Crystalline Polymeric Systems

In some embodiments, the compositions or formulations of the present disclosure comprise the polynucleotides described herein (e.g., a polynucleotide comprising a nucleotide sequence encoding a PBGD polypeptide) in crystalline polymeric systems. Crystalline polymeric systems are polymers with crystalline moieties and/or terminal units comprising crystalline moieties. Exemplary polymers are described in U.S. Pat. No. 8,524,259 (herein incorporated by reference in its entirety).

u. Polymers, Biodegradable Nanoparticles, and Core-Shell Nanoparticles

In some embodiments, the compositions or formulations of the present disclosure comprise the polynucleotides described herein (e.g., a polynucleotide comprising a nucleotide sequence encoding a PBGD polypeptide) and a natural and/or synthetic polymer. The polymers include, but not limited to, polyethenes, polyethylene glycol (PEG), poly(l-lysine)(PLL), PEG grafted to PLL, cationic lipopolymer, biodegradable cationic lipopolymer, polyethyleneimine (PEI), cross-linked branched poly(alkylene imines), a polyamine derivative, a modified poloxamer, elastic biodegradable polymer, biodegradable copolymer, biodegradable polyester copolymer, biodegradable polyester copolymer, multiblock copolymers, poly[$\alpha$-(4-aminobutyl)-L-glycolic acid] (PAGA), biodegradable cross-linked cationic multiblock copolymers, polycarbonates, polyanhydrides, polyhydroxyacids, polypropylfumerates, polycaprolactones, polyamides, polyacetals, polyethers, polyesters, poly(orthoesters), polycyanoacrylates, polyvinyl alcohols, polyurethanes, polyphosphazenes, polyureas, polystyrenes, polyamines, polylysine, poly(ethylene imine), poly(serine ester), poly(L-lactide-co-L-lysine), poly(4-hydroxy-L-proline ester), amine-containing polymers, dextran polymers, dextran polymer derivatives or combinations thereof.

Exemplary polymers include, DYNAMIC POLYCONJUGATE® (Arrowhead Research Corp., Pasadena, CA) formulations from MIRUS® Bio (Madison, WI) and Roche Madison (Madison, WI), PHASERX™ polymer formulations such as, without limitation, SMARTT POLYMER TECHNOLOGY™ (PHASERX®, Seattle, WA), DMRI/DOPE, poloxamer, VAXFECTIN® adjuvant from Vical (San Diego, CA), chitosan, cyclodextrin from Calando Pharmaceuticals (Pasadena, CA), dendrimers and poly(lactic-co-glycolic acid) (PLGA) polymers. RONDEL™ (RNAi/Oligonucleotide Nanoparticle Delivery) polymers (Arrowhead Research Corporation, Pasadena, CA) and pH responsive co-block polymers such as PHASERX® (Seattle, WA).

The polymer formulations allow a sustained or delayed release of the polynucleotide (e.g., following intramuscular or subcutaneous injection). The altered release profile for the polynucleotide can result in, for example, translation of an encoded protein over an extended period of time. The polymer formulation can also be used to increase the stability of the polynucleotide. Sustained release formulations can include, but are not limited to, PLGA microspheres, ethylene vinyl acetate (EVAc), poloxamer, GELSITE® (Nanotherapeutics, Inc. Alachua, FL), HYLENEX® (Halozyme Therapeutics, San Diego CA), surgical sealants such as fibrinogen polymers (Ethicon Inc. Cornelia, GA), TISSELL® (Baxter International, Inc. Deerfield, IL), PEG-based sealants, and COSEAL® (Baxter International, Inc. Deerfield, IL).

As a non-limiting example modified mRNA can be formulated in PLGA microspheres by preparing the PLGA microspheres with tunable release rates (e.g., days and weeks) and encapsulating the modified mRNA in the PLGA microspheres while maintaining the integrity of the modified mRNA during the encapsulation process. EVAc are non-biodegradable, biocompatible polymers that are used extensively in pre-clinical sustained release implant applications (e.g., extended release products Ocusert a pilocarpine ophthalmic insert for glaucoma or progestasert a sustained release progesterone intrauterine device; transdermal delivery systems Testoderm, Duragesic and Selegiline; catheters). Poloxamer F-407 NF is a hydrophilic, non-ionic surfactant triblock copolymer of polyoxyethylene-polyoxypropylene-polyoxyethylene having a low viscosity at temperatures less than 5° C. and forms a solid gel at temperatures greater than 15° C.

As a non-limiting example, the polynucleotides described herein can be formulated with the polymeric compound of PEG grafted with PLL as described in U.S. Pat. No. 6,177,274. As another non-limiting example, the polynucleotides described herein can be formulated with a block copolymer such as a PLGA-PEG block copolymer (see e.g., U.S. Pub. No. US20120004293 and U.S. Pat. Nos. 8,236,330 and 8,246,968), or a PLGA-PEG-PLGA block copolymer (see e.g., U.S. Pat. No. 6,004,573). Each of the references is herein incorporated by reference in its entirety.

In some embodiments, the polynucleotides described herein can be formulated with at least one amine-containing polymer such as, but not limited to polylysine, polyethylene imine, poly(amidoamine) dendrimers, poly(amine-co-esters) or combinations thereof. Exemplary polyamine polymers and their use as delivery agents are described in, e.g., U.S. Pat. Nos. 8,460,696, 8,236,280, each of which is herein incorporated by reference in its entirety.

In some embodiments, the polynucleotides described herein can be formulated in a biodegradable cationic lipopolymer, a biodegradable polymer, or a biodegradable copolymer, a biodegradable polyester copolymer, a biodegradable polyester polymer, a linear biodegradable copolymer, PAGA, a biodegradable cross-linked cationic multi-block copolymer or combinations thereof as described in, e.g., U.S. Pat. Nos. 6,696,038, 6,517,869, 6,267,987, 6,217,912, 6,652,886, 8,057,821, and 8,444,992; U.S. Pub. Nos. US20030073619, US20040142474, US20100004315, US2012009145 and US20130195920; and Intl Pub. Nos. WO2006063249 and WO2013086322, each of which is herein incorporated by reference in its entirety.

In some embodiments, the polynucleotides described herein can be formulated in or with at least one cyclodextrin polymer as described in U.S. Pub. No. US20130184453. In some embodiments, the polynucleotides described herein can be formulated in or with at least one crosslinked cation-binding polymers as described in Intl. Pub. Nos. WO2013106072, WO2013106073 and WO2013106086. In some embodiments, the polynucleotides described herein can be formulated in or with at least PEGylated albumin polymer as described in U.S. Pub. No. US20130231287. Each of the references is herein incorporated by reference in its entirety.

In some embodiments, the polynucleotides disclosed herein can be formulated as a nanoparticle using a combination of polymers, lipids, and/or other biodegradable agents, such as, but not limited to, calcium phosphate. Components can be combined in a core-shell, hybrid, and/or layer-by-layer architecture, to allow for fine-tuning of the nanoparticle for delivery (Wang et al., Nat Mater. 2006 5:791-796; Fuller et al., Biomaterials. 2008 29:1526-1532; DeKoker et al., Adv Drug Deliv Rev. 2011 63:748-761; Endres et al., Biomaterials. 2011 32:7721-7731; Su et al., Mol Pharm. 2011 Jun. 6; 8(3):774-87; herein incorporated by reference in their entireties). As a non-limiting example, the nanoparticle can comprise a plurality of polymers such as, but not limited to hydrophilic-hydrophobic polymers (e.g., PEG-PLGA), hydrophobic polymers (e.g., PEG) and/or hydrophilic polymers (Intl. Pub. No. WO20120225129, herein incorporated by reference in its entirety).

The use of core-shell nanoparticles has additionally focused on a high-throughput approach to synthesize cationic cross-linked nanogel cores and various shells (Siegwart et al., Proc Natl Acad Sci USA. 2011 108:12996-13001; herein incorporated by reference in its entirety). The complexation, delivery, and internalization of the polymeric nanoparticles can be precisely controlled by altering the chemical composition in both the core and shell components of the nanoparticle. For example, the core-shell nanoparticles can efficiently deliver siRNA to mouse hepatocytes after they covalently attach cholesterol to the nanoparticle.

In some embodiments, a hollow lipid core comprising a middle PLGA layer and an outer neutral lipid layer containing PEG can be used to delivery of the polynucleotides as described herein. In some embodiments, the lipid nanoparticles can comprise a core of the polynucleotides disclosed herein and a polymer shell, which is used to protect the polynucleotides in the core. The polymer shell can be any of the polymers described herein and are known in the art. The polymer shell can be used to protect the polynucleotides in the core.

Core-shell nanoparticles for use with the polynucleotides described herein are described in U.S. Pat. No. 8,313,777 or Intl. Pub. No. WO2013124867, each of which is herein incorporated by reference in their entirety.

v. Peptides and Proteins

In some embodiments, the compositions or formulations of the present disclosure comprise the polynucleotides described herein (e.g., a polynucleotide comprising a nucleotide sequence encoding a PBGD polypeptide) that is formulated with peptides and/or proteins to increase transfection of cells by the polynucleotide, and/or to alter the biodistribution of the polynucleotide (e.g., by targeting specific tissues or cell types), and/or increase the translation of encoded protein (e.g., Intl. Pub. Nos. WO2012110636 and WO2013123298. In some embodiments, the peptides can be those described in U.S. Pub. Nos. US20130129726, US20130137644 and US20130164219. Each of the references is herein incorporated by reference in its entirety.

w. Conjugates

In some embodiments, the compositions or formulations of the present disclosure comprise the polynucleotides described herein (e.g., a polynucleotide comprising a nucleotide sequence encoding a PBGD polypeptide) that is covalently linked to a carrier or targeting group, or including two encoding regions that together produce a fusion protein (e.g., bearing a targeting group and therapeutic protein or peptide) as a conjugate. The conjugate can be a peptide that selectively directs the nanoparticle to neurons in a tissue or organism, or assists in crossing the blood-brain barrier.

The conjugates include a naturally occurring substance, such as a protein (e.g., human serum albumin (HSA), low-density lipoprotein (LDL), high-density lipoprotein (HDL), or globulin); an carbohydrate (e.g., a dextran, pullulan, chitin, chitosan, inulin, cyclodextrin or hyaluronic acid); or a lipid. The ligand can also be a recombinant or synthetic molecule, such as a synthetic polymer, e.g., a synthetic polyamino acid, an oligonucleotide (e.g., an aptamer). Examples of polyamino acids include polyamino acid is a polylysine (PLL), poly L-aspartic acid, poly L-glutamic acid, styrene-maleic acid anhydride copolymer, poly (L-lactide-co-glycolied) copolymer, divinyl ether-maleic anhydride copolymer, N-(2-hydroxypropyl)methacrylamide copolymer (HMPA), polyethylene glycol (PEG), polyvinyl alcohol (PVA), polyurethane, poly(2-ethylacryllic acid), N-isopropylacrylamide polymers, or polyphosphazine. Example of polyamines include: polyethylenimine, polylysine (PLL), spermine, spermidine, polyamine, pseudopeptide-polyamine, peptidomimetic polyamine, dendrimer polyamine, arginine, amidine, protamine, cationic lipid, cationic porphyrin, quaternary salt of a polyamine, or an alpha helical peptide.

In some embodiments, the conjugate can function as a carrier for the polynucleotide disclosed herein. The conjugate can comprise a cationic polymer such as, but not limited to, polyamine, polylysine, polyalkylenimine, and polyethylenimine that can be grafted to with poly(ethylene glycol). Exemplary conjugates and their preparations are described in U.S. Pat. No. 6,586,524 and U.S. Pub. No. US20130211249, each of which herein is incorporated by reference in its entirety.

The conjugates can also include targeting groups, e.g., a cell or tissue targeting agent, e.g., a lectin, glycoprotein, lipid or protein, e.g., an antibody, that binds to a specified cell type such as a kidney cell. A targeting group can be a thyrotropin, melanotropin, lectin, glycoprotein, surfactant protein A, Mucin carbohydrate, multivalent lactose, multivalent galactose, N-acetyl-galactosamine, N-acetyl-glucosamine multivalent mannose, multivalent fucose, glycosylated polyaminoacids, multivalent galactose, transferrin, bisphosphonate, polyglutamate, polyaspartate, a lipid, cholesterol, a steroid, bile acid, folate, vitamin B12, biotin, an RGD peptide, an RGD peptide mimetic or an aptamer.

Targeting groups can be proteins, e.g., glycoproteins, or peptides, e.g., molecules having a specific affinity for a co-ligand, or antibodies e.g., an antibody, that binds to a specified cell type such as a cancer cell, endothelial cell, or bone cell. Targeting groups can also include hormones and hormone receptors. They can also include non-peptidic species, such as lipids, lectins, carbohydrates, vitamins, cofactors, multivalent lactose, multivalent galactose, N-acetyl-galactosamine, N-acetyl-glucosamine multivalent mannose, multivalent frucose, or aptamers. The ligand can be, for example, a lipopolysaccharide, or an activator of p38 MAP kinase.

The targeting group can be any ligand that is capable of targeting a specific receptor. Examples include, without limitation, folate, GalNAc, galactose, mannose, mannose-6P, apatamers, integrin receptor ligands, chemokine receptor ligands, transferrin, biotin, serotonin receptor ligands, PSMA, endothelin, GCPII, somatostatin, LDL, and HDL ligands. In particular embodiments, the targeting group is an aptamer. The aptamer can be unmodified or have any combination of modifications disclosed herein. As a non-limiting example, the targeting group can be a glutathione receptor (GR)-binding conjugate for targeted delivery across the blood-central nervous system barrier as described in, e.g., U.S. Pub. No. US2013021661012 (herein incorporated by reference in its entirety).

In some embodiments, the conjugate can be a synergistic biomolecule-polymer conjugate, which comprises a long-acting continuous-release system to provide a greater therapeutic efficacy. The synergistic biomolecule-polymer conjugate can be those described in U.S. Pub. No. US20130195799. In some embodiments, the conjugate can be an aptamer conjugate as described in Intl. Pat. Pub. No. WO2012040524. In some embodiments, the conjugate can be an amine containing polymer conjugate as described in U.S. Pat. No. 8,507,653. Each of the references is herein incorporated by reference in its entirety. In some embodiments, the polynucleotides can be conjugated to SMARTT POLYMER TECHNOLOGY® (PHASERX®, Inc. Seattle, WA).

In some embodiments, the polynucleotides described herein are covalently conjugated to a cell penetrating polypeptide, which can also include a signal sequence or a targeting sequence. The conjugates can be designed to have increased stability, and/or increased cell transfection; and/or altered the biodistribution (e.g., targeted to specific tissues or cell types).

In some embodiments, the polynucleotides described herein can be conjugated to an agent to enhance delivery. In some embodiments, the agent can be a monomer or polymer such as a targeting monomer or a polymer having targeting blocks as described in Intl. Pub. No. WO2011062965. In some embodiments, the agent can be a transport agent covalently coupled to a polynucleotide as described in, e.g., U.S. Pat. Nos. 6,835,393 and 7,374,778. In some embodiments, the agent can be a membrane barrier transport enhancing agent such as those described in U.S. Pat. Nos. 7,737,108 and 8,003,129. Each of the references is herein incorporated by reference in its entirety.

x. Micro-Organs

In some embodiments, the compositions or formulations of the present disclosure comprise the polynucleotides described herein (e.g., a polynucleotide comprising a nucleotide sequence encoding a PBGD polypeptide) in a micro-organ that can then express an encoded polypeptide of interest in a long-lasting therapeutic formulation. Exemplary micro-organs and formulations are described in Intl. Pub. No. WO2014152211 (herein incorporated by reference in its entirety).

y. Pseudovirions

In some embodiments, the compositions or formulations of the present disclosure comprise the polynucleotides described herein (e.g., a polynucleotide comprising a nucleotide sequence encoding a PBGD polypeptide) in pseudovirions (e.g., pseudovirions developed by Aura Biosciences, Cambridge, MA).

In some embodiments, the pseudovirion used for delivering the polynucleotides can be derived from viruses such as, but not limited to, herpes and papillomaviruses as described in, e.g., U.S. Pub. Nos. US20130012450, US20130012566, US21030012426 and US20120207840; and Intl. Pub. No. WO2013009717, each of which is herein incorporated by reference in its entirety.

The pseudovirion can be a virus-like particle (VLP) prepared by the methods described in U.S. Pub. Nos. US20120015899 and US20130177587, and Intl. Pub. Nos. WO2010047839, WO2013116656, WO2013106525 and WO2013122262. In one aspect, the VLP can be bacteriophages MS, Qβ, R17, fr, GA, Sp, MI, I, MXI, NL95, AP205, f2, PP7, and the plant viruses Turnip crinkle virus (TCV), Tomato bushy stunt virus (TBSV), Southern bean mosaic virus (SBMV) and members of the genus *Bromovirus* including Broad bean mottle virus, Brome mosaic virus, Cassia yellow blotch virus, Cowpea chlorotic mottle virus (CCMV), Melandrium yellow fleck virus, and Spring beauty latent virus. In another aspect, the VLP can be derived from the influenza virus as described in U.S. Pub. No. US20130177587 and U.S. Pat. No. 8,506,967. In one aspect, the VLP can comprise a B7-1 and/or B7-2 molecule anchored to a lipid membrane or the exterior of the particle such as described in Intl. Pub. No. WO2013116656. In one aspect, the VLP can be derived from norovirus, rotavirus recombinant VP6 protein or double layered VP2/VP6 such as the VLP as described in Intl. Pub. No. WO2012049366. Each of the references is herein incorporated by reference in its entirety.

In some embodiments, the pseudovirion can be a human papilloma virus-like particle as described in Intl. Pub. No. WO2010120266 and U.S. Pub. No. US20120171290. In some embodiments, the virus-like particle (VLP) can be a self-assembled particle. In one aspect, the pseudovirions can be virion derived nanoparticles as described in U.S. Pub. Nos. US20130116408 and US20130115247; and Intl. Pub. No. WO2013119877. Each of the references is herein incorporated by reference in their entirety.

Non-limiting examples of formulations and methods for formulating the polynucleotides described herein are also provided in Intl. Pub. No WO2013090648 (incorporated herein by reference in their entirety).

24. ACCELERATED BLOOD CLEARANCE

The invention provides compounds, compositions and methods of use thereof for reducing the effect of ABC on a repeatedly administered active agent such as a biologically active agent. As will be readily apparent, reducing or eliminating altogether the effect of ABC on an administered active agent effectively increases its half-life and thus its efficacy.

In some embodiments the term reducing ABC refers to any reduction in ABC in comparison to a positive reference control ABC inducing LNP such as an MC3 LNP. ABC inducing LNPs cause a reduction in circulating levels of an active agent upon a second or subsequent administration within a given time frame. Thus a reduction in ABC refers to less clearance of circulating agent upon a second or subsequent dose of agent, relative to a standard LNP. The reduction may be, for instance, at least 10%, 15%, 20%, 25%, 30%, 35%, 40%, 45%, 50%, 55%, 60%, 65%, 70%, 75%, 80%, 85%, 90%, 95%, 98%, or 100%. In some embodiments the reduction is 10-100%, 10-50%, 20-100%, 20-50%, 30-100%, 30-50%, 40%-100%, 40-80%, 50-90%, or 50-100%. Alternatively the reduction in ABC may be characterized as at least a detectable level of circulating agent following a second or subsequent administration or at least a 2 fold, 3 fold, 4 fold, 5 fold increase in circulating agent relative to circulating agent following administration of a standard LNP. In some embodiments the reduction is a 2-100 fold, 2-50 fold, 3-100 fold, 3-50 fold, 3-20 fold, 4-100 fold, 4-50 fold, 4-40 fold, 4-30 fold, 4-25 fold, 4-20 fold, 4-15 fold, 4-10 fold, 4-5 fold, 5-100 fold, 5-50 fold, 5-40 fold, 5-30 fold, 5-25 fold, 5-20 fold, 5-15 fold, 5-10 fold, 6-100 fold, 6-50 fold, 6-40 fold, 6-30 fold, 6-25 fold, 6-20 fold, 6-15 fold, 6-10 fold, 8-100 fold, 8-50 fold, 8-40 fold, 8-30 fold, 8-25 fold, 8-20 fold, 8-15 fold, 8-10 fold, 10-100 fold, 10-50 fold, 10-40 fold, 10-30 fold, 10-25 fold, 10-20 fold, 10-15 fold, 20-100 fold, 20-50 fold, 20-40 fold, 20-30 fold, or 20-25 fold.

The disclosure provides lipid-comprising compounds and compositions that are less susceptible to clearance and thus have a longer half-life in vivo. This is particularly the case where the compositions are intended for repeated including chronic administration, and even more particularly where such repeated administration occurs within days or weeks.

Significantly, these compositions are less susceptible or altogether circumvent the observed phenomenon of accelerated blood clearance (ABC). ABC is a phenomenon in which certain exogenously administered agents are rapidly cleared from the blood upon second and subsequent administrations. This phenomenon has been observed, in part, for a variety of lipid-containing compositions including but not limited to lipidated agents, liposomes or other lipid-based delivery vehicles, and lipid-encapsulated agents. Heretofore, the basis of ABC has been poorly understood and in some cases attributed to a humoral immune response and accordingly strategies for limiting its impact in vivo particularly in a clinical setting have remained elusive.

This disclosure provides compounds and compositions that are less susceptible, if at all susceptible, to ABC. In some important aspects, such compounds and compositions are lipid-comprising compounds or compositions. The lipid-containing compounds or compositions of this disclosure, surprisingly, do not experience ABC upon second and subsequent administration in vivo. This resistance to ABC renders these compounds and compositions particularly suitable for repeated use in vivo, including for repeated use within short periods of time, including days or 1-2 weeks. This enhanced stability and/or half-life is due, in part, to the inability of these compositions to activate B1a and/or B1b cells and/or conventional B cells, pDCs and/or platelets.

This disclosure therefore provides an elucidation of the mechanism underlying accelerated blood clearance (ABC). It has been found, in accordance with this disclosure and the inventions provided herein, that the ABC phenomenon at least as it relates to lipids and lipid nanoparticles is mediated, at least in part an innate immune response involving B1a and/or B1b cells, pDC and/or platelets. B1a cells are normally responsible for secreting natural antibody, in the form of circulating IgM. This IgM is poly-reactive, meaning that it is able to bind to a variety of antigens, albeit with a relatively low affinity for each.

It has been found in accordance with the invention that some lipidated agents or lipid-comprising formulations such as lipid nanoparticles administered in vivo trigger and are subject to ABC. It has now been found in accordance with the invention that upon administration of a first dose of the LNP, one or more cells involved in generating an innate immune response (referred to herein as sensors) bind such agent, are activated, and then initiate a cascade of immune factors (referred to herein as effectors) that promote ABC and toxicity. For instance, B1a and B1b cells may bind to LNP, become activated (alone or in the presence of other sensors such as pDC and/or effectors such as IL6) and secrete natural IgM that binds to the LNP. Pre-existing natural IgM in the subject may also recognize and bind to the LNP, thereby triggering complement fixation. After administration of the first dose, the production of natural IgM begins within 1-2 hours of administration of the LNP. Typically by about 2-3 weeks the natural IgM is cleared from the system due to the natural half-life of IgM. Natural IgG is produced beginning around 96 hours after administration of the LNP. The agent, when administered in a naïve setting, can exert its biological effects relatively unencumbered by the natural IgM produced post-activation of the B1a cells or B1b cells or natural IgG. The natural IgM and natural IgG are non-specific and thus are distinct from anti-PEG IgM and anti-PEG IgG.

Although Applicant is not bound by mechanism, it is proposed that LNPs trigger ABC and/or toxicity through the following mechanisms. It is believed that when an LNP is administered to a subject the LNP is rapidly transported through the blood to the spleen. The LNPs may encounter immune cells in the blood and/or the spleen. A rapid innate immune response is triggered in response to the presence of the LNP within the blood and/or spleen. Applicant has shown herein that within hours of administration of an LNP several immune sensors have reacted to the presence of the LNP. These sensors include but are not limited to immune cells involved in generating an immune response, such as B cells, pDC, and platelets. The sensors may be present in the spleen, such as in the marginal zone of the spleen and/or in the blood. The LNP may physically interact with one or more sensors, which may interact with other sensors. In such a case the LNP is directly or indirectly interacting with the sensors. The sensors may interact directly with one another in response to recognition of the LNP. For instance many sensors are located in the spleen and can easily interact with one another. Alternatively one or more of the sensors may interact with LNP in the blood and become activated. The activated sensor may then interact directly with other sensors or indirectly (e.g., through the stimulation or production of a messenger such as a cytokine e.g., IL6).

In some embodiments the LNP may interact directly with and activate each of the following sensors: pDC, B1a cells, B1b cells, and platelets. These cells may then interact directly or indirectly with one another to initiate the production of effectors which ultimately lead to the ABC and/or toxicity associated with repeated doses of LNP. For instance, Applicant has shown that LNP administration leads to pDC activation, platelet aggregation and activation and B cell activation. In response to LNP platelets also aggregate and are activated and aggregate with B cells. pDC cells are activated. LNP has been found to interact with the surface of platelets and B cells relatively quickly. Blocking the activation of any one or combination of these sensors in response to LNP is useful for dampening the immune response that would ordinarily occur. This dampening of the immune response results in the avoidance of ABC and/or toxicity.

The sensors once activated produce effectors. An effector, as used herein, is an immune molecule produced by an immune cell, such as a B cell. Effectors include but are not limited to immunoglobulin such as natural IgM and natural IgG and cytokines such as IL6. B1a and B1b cells stimulate the production of natural IgMs within 2-6 hours following administration of an LNP. Natural IgG can be detected within 96 hours. IL6 levels are increased within several hours. The natural IgM and IgG circulate in the body for several days to several weeks. During this time the circulating effectors can interact with newly administered LNPs, triggering those LNPs for clearance by the body. For instance, an effector may recognize and bind to an LNP. The Fc region of the effector may be recognized by and trigger uptake of the decorated LNP by macrophage. The macrophage are then transported to the spleen. The production of effectors by immune sensors is a transient response that correlates with the timing observed for ABC.

If the administered dose is the second or subsequent administered dose, and if such second or subsequent dose is administered before the previously induced natural IgM and/or IgG is cleared from the system (e.g., before the 2-3 window time period), then such second or subsequent dose is targeted by the circulating natural IgM and/or natural IgG or Fc which trigger alternative complement pathway activation and is itself rapidly cleared. When LNP are administered after the effectors have cleared from the body or are reduced in number, ABC is not observed.

Thus, it is useful according to aspects of the invention to inhibit the interaction between LNP and one or more sensors, to inhibit the activation of one or more sensors by LNP (direct or indirect), to inhibit the production of one or more effectors, and/or to inhibit the activity of one or more effectors. In some embodiments the LNP is designed to limit or block interaction of the LNP with a sensor. For instance the LNP may have an altered PC and/or PEG to prevent interactions with sensors. Alternatively or additionally an agent that inhibits immune responses induced by LNPs may be used to achieve any one or more of these effects.

It has also been determined that conventional B cells are also implicated in ABC. Specifically, upon first administration of an agent, conventional B cells, referred to herein as CD19(+), bind to and react against the agent. Unlike B1a and B1b cells though, conventional B cells are able to mount first an IgM response (beginning around 96 hours after administration of the LNPs) followed by an IgG response (beginning around 14 days after administration of the LNPs) concomitant with a memory response. Thus conventional B cells react against the administered agent and contribute to IgM (and eventually IgG) that mediates ABC. The IgM and IgG are typically anti-PEG IgM and anti-PEG IgG.

It is contemplated that in some instances, the majority of the ABC response is mediated through B1a cells and B1a-mediated immune responses. It is further contemplated that in some instances, the ABC response is mediated by both IgM and IgG, with both conventional B cells and B1a cells mediating such effects. In yet still other instances, the ABC response is mediated by natural IgM molecules, some of which are capable of binding to natural IgM, which may be produced by activated B1a cells. The natural IgMs may bind to one or more components of the LNPs, e.g., binding to a phospholipid component of the LNPs (such as binding to the PC moiety of the phospholipid) and/or binding to a PEG-lipid component of the LNPs (such as binding to PEG-DMG, in particular, binding to the PEG moiety of PEG-DMG). Since B1a expresses CD36, to which phosphatidylcholine is a ligand, it is contemplated that the CD36 receptor may mediate the activation of B1a cells and thus production of natural IgM. In yet still other instances, the ABC response is mediated primarily by conventional B cells.

It has been found in accordance with the invention that the ABC phenomenon can be reduced or abrogated, at least in part, through the use of compounds and compositions (such as agents, delivery vehicles, and formulations) that do not activate B1a cells. Compounds and compositions that do not activate B1a cells may be referred to herein as B1a inert compounds and compositions. It has been further found in accordance with the invention that the ABC phenomenon can be reduced or abrogated, at least in part, through the use of compounds and compositions that do not activate conventional B cells. Compounds and compositions that do not activate conventional B cells may in some embodiments be referred to herein as CD19-inert compounds and compositions. Thus, in some embodiments provided herein, the compounds and compositions do not activate B1a cells and they do not activate conventional B cells. Compounds and compositions that do not activate B1a cells and conventional B cells may in some embodiments be referred to herein as B1a/CD19-inert compounds and compositions.

These underlying mechanisms were not heretofore understood, and the role of B1a and B1b cells and their interplay with conventional B cells in this phenomenon was also not appreciated.

Accordingly, this disclosure provides compounds and compositions that do not promote ABC. These may be further characterized as not capable of activating B1a and/or B1b cells, platelets and/or pDC, and optionally conventional B cells also. These compounds (e.g., agents, including biologically active agents such as prophylactic agents, therapeutic agents and diagnostic agents, delivery vehicles, including liposomes, lipid nanoparticles, and other lipid-based encapsulating structures, etc.) and compositions (e.g., formulations, etc.) are particularly desirable for applications requiring repeated administration, and in particular repeated administrations that occur within with short periods of time (e.g., within 1-2 weeks). This is the case, for example, if the agent is a nucleic acid based therapeutic that is provided to a subject at regular, closely-spaced intervals. The findings provided herein may be applied to these and other agents that are similarly administered and/or that are subject to ABC.

Of particular interest are lipid-comprising compounds, lipid-comprising particles, and lipid-comprising compositions as these are known to be susceptible to ABC. Such lipid-comprising compounds particles, and compositions have been used extensively as biologically active agents or as delivery vehicles for such agents. Thus, the ability to improve their efficacy of such agents, whether by reducing the effect of ABC on the agent itself or on its delivery vehicle, is beneficial for a wide variety of active agents.

Also provided herein are compositions that do not stimulate or boost an acute phase response (ARP) associated with repeat dose administration of one or more biologically active agents.

The composition, in some instances, may not bind to IgM, including but not limited to natural IgM.

The composition, in some instances, may not bind to an acute phase protein such as but not limited to C-reactive protein.

The composition, in some instances, may not trigger a CD5(+) mediated immune response. As used herein, a CD5(+) mediated immune response is an immune response that is mediated by B1a and/or B1b cells. Such a response may include an ABC response, an acute phase response, induction of natural IgM and/or IgG, and the like.

The composition, in some instances, may not trigger a CD19(+) mediated immune response. As used herein, a CD19(+) mediated immune response is an immune response that is mediated by conventional CD19(+), CD5(−) B cells. Such a response may include induction of IgM, induction of IgG, induction of memory B cells, an ABC response, an anti-drug antibody (ADA) response including an anti-protein response where the protein may be encapsulated within an LNP, and the like.

B1a cells are a subset of B cells involved in innate immunity. These cells are the source of circulating IgM, referred to as natural antibody or natural serum antibody. Natural IgM antibodies are characterized as having weak affinity for a number of antigens, and therefore they are referred to as "poly-specific" or "poly-reactive", indicating their ability to bind to more than one antigen. B1a cells are not able to produce IgG. Additionally, they do not develop into memory cells and thus do not contribute to an adaptive immune response. However, they are able to secrete IgM upon activation. The secreted IgM is typically cleared within about 2-3 weeks, at which point the immune system is rendered relatively naïve to the previously administered antigen. If the same antigen is presented after this time period (e.g., at about 3 weeks after the initial exposure), the antigen is not rapidly cleared. However, significantly, if the antigen is presented within that time period (e.g., within 2 weeks, including within 1 week, or within days), then the antigen is rapidly cleared. This delay between consecutive doses has rendered certain lipid-containing therapeutic or diagnostic agents unsuitable for use.

In humans, B1a cells are CD19(+), CD20(+), CD27(+), CD43(+), CD70(−) and CD5(+). In mice, B1a cells are CD19(+), CD5(+), and CD45 B cell isoform B220(+). It is the expression of CD5 which typically distinguishes B1a cells from other convention B cells. B1a cells may express high levels of CD5, and on this basis may be distinguished from other B-1 cells such as B-1b cells which express low or undetectable levels of CD5. CD5 is a pan-T cell surface glycoprotein. B1a cells also express CD36, also known as fatty acid translocase. CD36 is a member of the class B scavenger receptor family. CD36 can bind many ligands, including oxidized low density lipoproteins, native lipoproteins, oxidized phospholipids, and long-chain fatty acids.

B1b cells are another subset of B cells involved in innate immunity. These cells are another source of circulating natural IgM. Several antigens, including PS, are capable of inducing T cell independent immunity through B1b activation. CD27 is typically upregulated on B1b cells in response to antigen activation. Similar to B1a cells, the B1b cells are typically located in specific body locations such as the spleen and peritoneal cavity and are in very low abundance in the blood. The B1b secreted natural IgM is typically cleared within about 2-3 weeks, at which point the immune system is rendered relatively naïve to the previously administered antigen. If the same antigen is presented after this time period (e.g., at about 3 weeks after the initial exposure), the antigen is not rapidly cleared. However, significantly, if the antigen is presented within that time period (e.g., within 2 weeks, including within 1 week, or within days), then the antigen is rapidly cleared. This delay between consecutive doses has rendered certain lipid-containing therapeutic or diagnostic agents unsuitable for use.

In some embodiments it is desirable to block B1a and/or B1b cell activation. One strategy for blocking B1a and/or B1b cell activation involves determining which components of a lipid nanoparticle promote B cell activation and neutralizing those components. It has been discovered herein that at least PEG and phosphatidylcholine (PC) contribute to B1a and B1b cell interaction with other cells and/or activation. PEG may play a role in promoting aggregation between B1 cells and platelets, which may lead to activation. PC (a helper lipid in LNPs) is also involved in activating the B1 cells, likely through interaction with the CD36 receptor on the B cell surface. Numerous particles have PEG-lipid alternatives, PEG-less, and/or PC replacement lipids (e.g. oleic acid or analogs thereof) have been designed and tested. Applicant has established that replacement of one or more of these components within an LNP that otherwise would promote ABC upon repeat administration, is useful in preventing ABC by reducing the production of natural IgM and/or B cell activation. Thus, the invention encompasses LNPs that have reduced ABC as a result of a design which eliminates the inclusion of B cell triggers.

Another strategy for blocking B1a and/or B1b cell activation involves using an agent that inhibits immune responses induced by LNPs. These types of agents are discussed in more detail below. In some embodiments these agents block the interaction between B1a/B1b cells and the LNP or platelets or pDC. For instance the agent may be an antibody or other binding agent that physically blocks the interaction. An example of this is an antibody that binds to CD36 or CD6. The agent may also be a compound that prevents or disables the B1a/B1b cell from signaling once activated or prior to activation. For instance, it is possible to block one or more components in the B1a/B1b signaling cascade the results from B cell interaction with LNP or other immune cells. In other embodiments the agent may act one or more effectors produced by the B1a/B1b cells following activation. These effectors include for instance, natural IgM and cytokines.

It has been demonstrated according to aspects of the invention that when activation of pDC cells is blocked, B cell activation in response to LNP is decreased. Thus, in order to avoid ABC and/or toxicity, it may be desirable to prevent pDC activation. Similar to the strategies discussed above, pDC cell activation may be blocked by agents that interfere with the interaction between pDC and LNP and/or B cells/platelets. Alternatively agents that act on the pDC to block its ability to get activated or on its effectors can be used together with the LNP to avoid ABC.

Platelets may also play an important role in ABC and toxicity. Very quickly after a first dose of LNP is administered to a subject platelets associate with the LNP, aggregate and are activated. In some embodiments it is desirable to block platelet aggregation and/or activation. One strategy for blocking platelet aggregation and/or activation involves determining which components of a lipid nanoparticle promote platelet aggregation and/or activation and neutralizing those components. It has been discovered herein that at least PEG contribute to platelet aggregation, activation and/or interaction with other cells. Numerous particles have PEG-lipid alternatives and PEG-less have been designed and tested. Applicant has established that replacement of one or more of these components within an LNP that otherwise would promote ABC upon repeat administration, is useful in preventing ABC by reducing the production of natural IgM and/or platelet aggregation. Thus, the invention encompasses LNPs that have reduced ABC as a result of a design which eliminates the inclusion of platelet triggers. Alternatively agents that act on the platelets to block its activity once it is activated or on its effectors can be used together with the LNP to avoid ABC.

(i) Measuring ABC Activity and Related Activities

Various compounds and compositions provided herein, including LNPs, do not promote ABC activity upon administration in vivo. These LNPs may be characterized and/or identified through any of a number of assays, such as but not limited to those described below, as well as any of the assays disclosed in the Examples section, include the methods subsection of the Examples.

In some embodiments the methods involve administering an LNP without producing an immune response that promotes ABC. An immune response that promotes ABC involves activation of one or more sensors, such as B1 cells, pDC, or platelets, and one or more effectors, such as natural IgM, natural IgG or cytokines such as IL6. Thus administration of an LNP without producing an immune response that promotes ABC, at a minimum involves administration of an LNP without significant activation of one or more sensors and significant production of one or more effectors. Significant used in this context refers to an amount that would lead to the physiological consequence of accelerated blood clearance of all or part of a second dose with respect to the level of blood clearance expected for a second dose of an ABC triggering LNP. For instance, the immune response should be dampened such that the ABC observed after the second dose is lower than would have been expected for an ABC triggering LNP.

(ii) B1a or B1b Activation Assay

Certain compositions provided in this disclosure do not activate B cells, such as B1a or B1b cells (CD19+CD5+) and/or conventional B cells (CD19+CD5−). Activation of B1a cells, B1b cells, or conventional B cells may be determined in a number of ways, some of which are provided below. B cell population may be provided as fractionated B cell populations or unfractionated populations of splenocytes or peripheral blood mononuclear cells (PBMC). If the latter, the cell population may be incubated with the LNP of choice for a period of time, and then harvested for further analysis. Alternatively, the supernatant may be harvested and analyzed.

(iii) Upregulation of Activation Marker Cell Surface Expression

Activation of B1a cells, B1b cells, or conventional B cells may be demonstrated as increased expression of B cell activation markers including late activation markers such as CD86. In an exemplary non-limiting assay, unfractionated B cells are provided as a splenocyte population or as a PBMC population, incubated with an LNP of choice for a particular period of time, and then stained for a standard B cell marker such as CD19 and for an activation marker such as CD86, and analyzed using for example flow cytometry. A suitable negative control involves incubating the same population with medium, and then performing the same staining and visualization steps. An increase in CD86 expression in the test population compared to the negative control indicates B cell activation.

(iv) Pro-Inflammatory Cytokine Release

B cell activation may also be assessed by cytokine release assay. For example, activation may be assessed through the production and/or secretion of cytokines such as IL-6 and/or TNF-alpha upon exposure with LNPs of interest.

Such assays may be performed using routine cytokine secretion assays well known in the art. An increase in cytokine secretion is indicative of B cell activation.

(v) LNP Binding/Association to and/or Uptake by B Cells

LNP association or binding to B cells may also be used to assess an LNP of interest and to further characterize such LNP. Association/binding and/or uptake/internalization may be assessed using a detectably labeled, such as fluorescently labeled, LNP and tracking the location of such LNP in or on B cells following various periods of incubation.

The invention further contemplates that the compositions provided herein may be capable of evading recognition or detection and optionally binding by downstream mediators of ABC such as circulating IgM and/or acute phase response mediators such as acute phase proteins (e.g., C-reactive protein (CRP).

(vi) Methods of Use for Reducing ABC

Also provided herein are methods for delivering LNPs, which may encapsulate an agent such as a therapeutic agent, to a subject without promoting ABC.

In some embodiments, the method comprises administering any of the LNPs described herein, which do not promote ABC, for example, do not induce production of natural IgM binding to the LNPs, do not activate B1a and/or B1b cells. As used herein, an LNP that "does not promote ABC" refers to an LNP that induces no immune responses that would lead to substantial ABC or a substantially low level of immune responses that is not sufficient to lead to substantial ABC. An LNP that does not induce the production of natural IgMs binding to the LNP refers to LNPs that induce either no natural IgM binding to the LNPs or a substantially low level of the natural IgM molecules, which is insufficient to lead to substantial ABC. An LNP that does not activate B1a and/or B1b cells refer to LNPs that induce no response of B1a and/or B1b cells to produce natural IgM binding to the LNPs or a substantially low level of B1a and/or B1b responses, which is insufficient to lead to substantial ABC.

In some embodiments the terms do not activate and do not induce production are a relative reduction to a reference value or condition. In some embodiments the reference value or condition is the amount of activation or induction of production of a molecule such as IgM by a standard LNP such as an MC3 LNP. In some embodiments the relative reduction is a reduction of at least 30%, for example at least 30%, 35%, 40%, 45%, 50%, 55%, 60%, 65%, 70%, 75%, 80%, 85%, 90%, 91%, 92%, 93%, 94%, 95%, 96%, 97%, 98%, 99%, or 100%. In other embodiments the terms do not activate cells such as B cells and do not induce production of a protein such as IgM may refer to an undetectable amount of the active cells or the specific protein.

(vii) Platelet Effects and Toxicity

The invention is further premised in part on the elucidation of the mechanism underlying dose-limiting toxicity associated with LNP administration. Such toxicity may involve coagulopathy, disseminated intravascular coagulation (DIC, also referred to as consumptive coagulopathy), whether acute or chronic, and/or vascular thrombosis. In some instances, the dose-limiting toxicity associated with LNPs is acute phase response (APR) or complement activation-related psudoallergy (CARPA).

As used herein, coagulopathy refers to increased coagulation (blood clotting) in vivo. The findings reported in this disclosure are consistent with such increased coagulation and significantly provide insight on the underlying mechanism. Coagulation is a process that involves a number of different factors and cell types, and heretofore the relationship between and interaction of LNPs and platelets has not been understood in this regard. This disclosure provides evidence of such interaction and also provides compounds and compositions that are modified to have reduced platelet effect, including reduced platelet association, reduced platelet aggregation, and/or reduced platelet aggregation. The ability to modulate, including preferably down-modulate, such platelet effects can reduce the incidence and/or severity of coagulopathy post-LNP administration. This in turn will reduce toxicity relating to such LNP, thereby allowing higher doses of LNPs and importantly their cargo to be administered to patients in need thereof.

CARPA is a class of acute immune toxicity manifested in hypersensitivity reactions (HSRs), which may be triggered by nanomedicines and biologicals. Unlike allergic reactions, CARPA typically does not involve IgE but arises as a consequence of activation of the complement system, which is part of the innate immune system that enhances the body's abilities to clear pathogens. One or more of the following pathways, the classical complement pathway (CP), the alternative pathway (AP), and the lectin pathway (LP), may be involved in CARPA. Szebeni, Molecular Immunology, 61:163-173 (2014).

The classical pathway is triggered by activation of the C1-complex, which contains. C1q, C1r, C1s, or C1qr2s2. Activation of the C1-complex occurs when C1q binds to IgM or IgG complexed with antigens, or when C1q binds directly to the surface of the pathogen. Such binding leads to conformational changes in the C1q molecule, which leads to the activation of C1r, which in turn, cleave C1s. The C1r2s2 component now splits C4 and then C2, producing C4a, C4b, C2a, and C2b. C4b and C2b bind to form the classical pathway C3-convertase (C4b2b complex), which promotes cleavage of C3 into C3a and C3b. C3b then binds the C3 convertase to from the C5 convertase (C4b2b3b complex). The alternative pathway is continuously activated as a result of spontaneous C3 hydrolysis. Factor P (properdin) is a positive regulator of the alternative pathway. Oligomerization of properdin stabilizes the C3 convertase, which can then cleave much more C3. The C3 molecules can bind to surfaces and recruit more B, D, and P activity, leading to amplification of the complement activation.

Acute phase response (APR) is a complex systemic innate immune responses for preventing infection and clearing potential pathogens. Numerous proteins are involved in APR and C-reactive protein is a well-characterized one.

It has been found, in accordance with the invention, that certain LNP are able to associate physically with platelets almost immediately after administration in vivo, while other LNP do not associate with platelets at all or only at background levels. Significantly, those LNPs that associate with platelets also apparently stabilize the platelet aggregates that are formed thereafter. Physical contact of the platelets with certain LNPs correlates with the ability of such platelets to remain aggregated or to form aggregates continuously for an extended period of time after administration. Such aggregates comprise activated platelets and also innate immune cells such as macrophages and B cells.

25. METHODS OF USE

The polynucleotides, pharmaceutical compositions and formulations described herein are used in the preparation, manufacture and therapeutic use to treat and/or prevent PBGD-related diseases, disorders or conditions. In some embodiments, the polynucleotides, compositions and formulations of the invention are used to treat AIP. AIP patients can suffer from acute attacks and can be treated during or after an acute attack (e.g., severe pain). Patients having reoccurring attacks, e.g., several attacks per year, can be treated "prophylactically", i.e., to reduce the risk of and/or prevent recurring attacks.

In some embodiments, the polynucleotides, pharmaceutical compositions and formulations of the invention are used in methods for reducing the levels of porphobilinogen in a subject in need thereof. For instance, one aspect of the invention provides a method of alleviating the signs or symptoms of AIP in a subject comprising the administration of a composition or formulation comprising a polynucleotide encoding PBGD to that subject (e.g, an mRNA encoding a PBGD polypeptide).

In some embodiments, the polynucleotides, pharmaceutical compositions and formulations of the invention are used to reduce the level of a metabolite associated with AIP (e.g., the substrate or product, i.e., hydroxymethylbilane or porphobilinogen), the method comprising administering to the subject an effective amount of a polynucleotide encoding a PBGD polypeptide.

In some embodiments, the administration of an effective amount of a polynucleotide, pharmaceutical composition or formulation of the invention reduces the levels of a biomarker of AIP, e.g., porphobilinogen (PBG), aminolevulinate acid (ALA), porphyrin, alanine transaminase (ALT), aspartate transaminase (AST), bilirubin, or any combination thereof. In some embodiments, the administration of the polynucleotide, pharmaceutical composition or formulation of the invention results in reduction in the level of one or more biomarkers of AIP, e.g., porphobilinogen, within a short period of time (e.g., within about 6 hours, within about 8 hours, within about 12 hours, within about 16 hours, within about 20 hours, or within about 24 hours) after administration of the polynucleotide, pharmaceutical composition or formulation of the invention.

Replacement therapy is a potential treatment for AIP. Thus, in certain aspects of the invention, the polynucleotides, e.g., mRNA, disclosed herein comprise one or more sequences encoding a PBGD polypeptide that is suitable for use in gene replacement therapy for AIP. In some embodiments, the present disclosure treats a lack of PBGD or PBGD activity, or decreased or abnormal PBGD activity in a subject by providing a polynucleotide, e.g., mRNA, that encodes a PBGD polypeptide to the subject. In some embodiments, the polynucleotide is sequence-optimized. In some embodiments, the polynucleotide (e.g., an mRNA) comprises a nucleic acid sequence (e.g., an ORF) encoding a PBGD polypeptide, wherein the nucleic acid is sequence-optimized, e.g., by modifying its G/C, uridine, or thymidine content, and/or the polynucleotide comprises at least one chemically modified nucleoside. In some embodiments, the polynucleotide comprises a miRNA binding site, e.g., a miRNA binding site that binds miRNA-142 and/or a miRNA binding site that binds miRNA-126.

In some embodiments, the administration of a composition or formulation comprising polynucleotide, pharmaceutical composition or formulation of the invention to a subject results in a decrease in porphobilinogen in cells to a level at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or to 100% lower than the level observed prior to the administration of the composition or formulation.

In some embodiments, the administration of the polynucleotide, pharmaceutical composition or formulation of the invention results in expression of PBGD protein in cells of the subject. In some embodiments, administering the polynucleotide, pharmaceutical composition or formulation of the invention results in an increase of PBGD expression and/or enzymatic activity in the subject. For example, in some embodiments, the polynucleotides of the present invention are used in methods of administering a composition or formulation comprising an mRNA encoding a PBGD polypeptide to a subject, wherein the method results in an increase of PBGD expression and/or enzymatic activity in at least some cells of a subject.

In some embodiments, the administration of a composition or formulation comprising an mRNA encoding a PBGD polypeptide to a subject results in an increase of PBGD expression and/or enzymatic activity in cells subject to a level at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or to 100% or more of the expression and/or activity level expected in a normal subject, e.g., a human not suffering from AIP.

In some embodiments, the administration of the polynucleotide, pharmaceutical composition or formulation of the invention results in expression of PBGD protein in at least some of the cells of a subject that persists for a period of time sufficient to allow significant porphobilinogen metabolism to occur.

In some embodiments, the expression and/or enzymatic activity of the encoded polypeptide is increased. In some embodiments, the polynucleotide increases PBGD expression and/or enzymatic activity levels in cells when introduced into those cells, e.g., by at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or to 100% with respect to the PBGD expression and/or enzymatic activity level in the cells before the polypeptide is introduced in the cells.

In some embodiments, the method or use comprises administering a polynucleotide, e.g., mRNA, comprising a nucleotide sequence having sequence similarity to a polynucleotide selected from the group of SEQ ID NOs: 9 to 33 and 89 to 117 (See TABLE 2) or a polynucleotide selected from the group of SEQ ID NOs: 118-148, e.g., 133, 141, 144, or 145 (See TABLE 5), wherein the polynucleotide encodes an PBGD polypeptide.

Other aspects of the present disclosure relate to transplantation of cells containing polynucleotides to a mammalian subject. Administration of cells to mammalian subjects is known to those of ordinary skill in the art, and includes, but is not limited to, local implantation (e.g., topical or subcutaneous administration), organ delivery or systemic injection (e.g., intravenous injection or inhalation), and the formulation of cells in pharmaceutically acceptable carriers.

The present disclosure also provides methods to increase hepatic PBGD activity (for example, expressed as pmol uroporphyrinogen/mg protein/hour) in a subject in need thereof, e.g., a subject with AIP, comprising administering to the subject a therapeutically effective amount of a composition or formulation comprising mRNA encoding a PBGD polypeptide disclosed herein, e.g., a human PBGD isoform, a mutant thereof (such as gain of function SM double mutant), or a fusion protein comprising a human PBGD isoform or a mutant thereof (for example a fusion protein comprising a PBGD moiety and a human apoliprotein A1 moeity).

In some aspects, the hepatic PBGD activity measured after administration to a subject in need thereof, e.g., a subject with AIP, is at least the normal PBGD activity level observed in healthy human subjects. In some aspects, such normal PBGD activity level observed in healthy human subjects is 5±0.2 units (pmol uroporphyrinogen/mg protein/hour units). In some aspects, the hepatic PBGD activity measured after administration is at higher than the PBGD activity level observed in AIP patients, e.g., untreated AIP patients. In some aspects, the hepatic PBGD activity level observed in AIP patients is 2±0.2 units (pmol uroporphyrinogen/mg protein/hour units). In some aspects, the increase in hepatic PBGD activity (for example, expressed as pmol uroporphyrinogen/mg protein/hour) in a subject in need thereof, e.g., a subject with AIP, after administering to the subject a therapeutically effective amount of a composition or formulation comprising mRNA encoding a PBGD polypeptide disclosed herein is at least about 0.1, 0.2, 0.3, 0.4, 0.5, 0.6, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, or 10 pmol uroporphyrinogen/mg protein/hour units (i) above the normal PBGD activity level observed in healthy human subjects or (ii) above the PBGD activity level observed in AIP patients, e.g., untreated AIP patients. In some aspects, the increase in hepatic PBGD activity above the PBGD activity level observed in AIP patients (e.g., about 2 pmol uroporphyrinogen/mg protein/hour units) after administering to the subject a composition or formulation comprising an mRNA encoding a PBGD polypeptide disclosed herein (e.g., after a single dose administration) is maintained for at least 1 day, 2 days, 3 days, 4 days, 5 days, 6 days, 7 days, 8 days, 9 days, or 10 days.

When an AIP attack occurs there is an accumulation of the porphyrin precursors ALA (aminolevulinate) and PBG (Porphobilinogen). ALA and PBG can be measured in urine using methods known in the art. The present disclosure also provides a method to decrease ALA levels in a subject in need thereof, e.g., untreated AIP patients, comprising administering to the subject a therapeutically effective amount of a composition or formulation comprising mRNA encoding a PBGD polypeptide disclosed herein. In some aspects, the ALA levels are urinary ALA excretion levels. Also provided is a method to decrease PBG levels in a subject in need thereof, e.g., untreated AIP patients, comprising administering to the subject a therapeutically effection amount of a composition or formulation comprising mRNA encoding a PBGD polypeptide disclosed herein. In some aspects, the PBG levels are urinary PBG excretion levels.

In some aspects, the present disclosure provides a method to protect a subject suffering from AIP against an increase in heme precursors (e.g., ALA and/or PBG) in an AIP attack comprising administering to the subject a therapeutically effective amount of a composition or formulation comprising mRNA encoding a PBGD polypeptide disclosed herein. Also provided is a method to reduce the accumulation of heme precursors (e.g., ALA and/or PBG) in a subject suffering from AIP comprising administering to the subject a therapeutically effective amount of a composition or formulation comprising mRNA encoding a PBGD polypeptide disclosed herein.

The present disclosure also provides a method to treat, prevent, or ameliorate pain in an AIP patient comprising administering to the subject a therapeutically effective amount of a composition or formulation comprising mRNA encoding a PBGD polypeptide disclosed herein. In some aspects, the administration of a therapeutically effective amount of a composition or formulation comprising mRNA encoding a PBGD polypeptide disclosed herein to subject suffering from AIP results in a reduction in pain. In some aspects, the reduction in pain is complete (pain annulment). In some aspects, the pain is severe pain.

Also provided is a method to treat, prevent, or ameliorate neuropathy in an AIP patient comprising administering to the subject a therapeutically effective amount of a composition or formulation comprising mRNA encoding a PBGD polypeptide disclosed herein. In some aspects, the administration of a therapeutically effective amount of a composition or formulation comprising mRNA encoding a PBGD polypeptide disclosed herein to subject suffering from AIP results in a reduction in neuropathy. In some aspects, the reduction in neuropathy is complete (neuropathy annulment). In some aspects the neuropathy is peripheral neuropathy.

Also provided is a method to increase survival an AIP patient comprising administering to the subject a therapeutically effective amount of a composition or formulation comprising mRNA encoding a PBGD polypeptide disclosed herein.

In some aspects, the dose of mRNA encoding a PBGD polypeptide disclosed herein is at least about 0.1 nmol/kg, at least about 0.2 nmol/kg, at least about 0.3 nmol/kg, at least about 0.4 nmol/kg, at least about 0.5 nmol/kg, at least about 0.6 nmol/kg, at least about 0.7 nmol/kg, at least about 0.8 nmol/kg, at least about 0.9 nmol/kg, at least about 1 nmol/kg, at least about 1.1 nmol/kg, at least about 1.2 nmol/kg, at least about 1.3 nmol/kg, at least about 1.4 nmol/kg, at least about 1.5 nmol/kg, at least about 1.6 nmol/kg, at least about 1.7 nmol/kg, at least about 1.8 nmol/kg, at least about 1.9 nmol/kg, at least about 2 nmol/kg, at least about 2.5 nmol/kg, at least about 3 nmol/kg, at least about 3.5 nmol/kg, at least about 4 nmol/kg, at least about 4.5 nmol/kg, or at least about 5 nmol/kg. In some aspects, the dose of mRNA encoding a PBGD polypeptide disclosed herein is at least about 0.05 mg/kg, at least about 0.1 mg/kg, at least about 0.15 mg/kg, at least about 0.2 mg/kg, at least about 0.25 mg/kg, at least about 0.3 mg/kg, at least about 0.35 mg/kg, at least about 0.4 mg/kg, at least about 0.45 mg/kg, at least about 0.5 mg/kg, at least about 0.55 mg/kg, at least about 0.6 mg/kg, at least about 0.7 mg/kg, at least about 0.75 mg/kg, at least about 0.8 mg/kg, at least about 0.85 mg/kg, at least about 0.9 mg/kg, at least about 0.95 mg/kg, or at least about 1 mg/kg.

In some aspects of the method disclosed herein, the AIP patient is an ayrnptomatic patient.

In some embodiments, the polynucleotides (e.g., mRNA), pharmaceutical compositions and formulations used in the methods of the invention comprise a uracil-modified sequence encoding a PBGD polypeptide disclosed herein and a miRNA binding site disclosed herein, e.g., a miRNA binding site that binds to miR-142 and/or a miRNA binding site that binds to miR-126. In some embodiments, the uracil-modified sequence encoding a PBGD polypeptide comprises at least one chemically modified nucleobase, e.g., 5-methoxyuracil. In some embodiments, at least 95% of a type of nucleobase (e.g., uracil) in a uracil-modified sequence encoding a PBGD polypeptide of the invention are modified nucleobases. In some embodiments, at least 95% of uricil in a uracil-modified sequence encoding a PBGD polypeptide is 5-methoxyuridine. In some embodiments, the polynucleotide (e.g., a RNA, e.g., an mRNA) disclosed herein is formulated with a delivery agent comprising, e.g., a compound having the Formula (I), e.g., any of Compounds 1-232, e.g., Compound 18; a compound having the Formula (III), (IV), (V), or (VI), e.g., any of Compounds 233-342, e.g., Compound 236; or a compound having the Formula (VIII), e.g., any of Compounds 419-428, e.g., Compound 428, or any combination thereof. In some embodiments, the delivery agent comprises Compound 18, DSPC, Cholesterol, and Compound 428, e.g., with a mole ratio of about 50:10:38.5:1.5.

The skilled artisan will appreciate that the therapeutic effectiveness of a drug or a treatment of the instant invention can be characterized or determined by measuring the level of expression of an encoded protein (e.g., enzyme) in a sample or in samples taken from a subject (e.g., from a preclinical test subject (rodent, primate, etc.) or from a clinical subject (human). Likewise, the therapeutic effectiveness of a drug or a treatment of the instant invention can be characterized or determined by measuring the level of activity of an encoded protein (e.g., enzyme) in a sample or in samples taken from a subject (e.g., from a preclinical test subject (rodent, primate, etc.) or from a clinical subject (human). Furthermore, the therapeutic effectiveness of a drug or a treatment of the instant invention can be characterized or determined by measuring the level of an appropriate biomarker in sample(s) taken from a subject. Levels of protein and/or biomarkers can be determined post-administration with a single dose of an mRNA therapeutic of the invention or can be determined and/or monitored at several time points following administration with a single dose or can be determined and/or monitored throughout a course of treatment, e.g., a multi-dose treatment.

AIP is characterized by acute episodes and asymptomatic periods. Accordingly, AIP patients can be asymptomatic carriers or suffer from recurrent acute attack. AIP patients commonly show high aminolevulinic acid (ALA) and porphobilinogen (PBG) blood and urinary levels and their concentrations further increase during acute attacks. Unless otherwise specified, the methods of treating AIP patients or human subjects disclosed herein include treatment of both asymptomatic "high excreter" (ASHE) patients, who carry a genetic mutation of acute intermittent porphyria (AIP) and have elevated levels of biomarkers, e.g., ALA and PBG, and recurrent acute attack patients.

PBGD Protein Expression Levels

Certain aspects of the invention feature measurement, determination and/or monitoring of the expression level or levels of porphobilinogen deaminase (PBGD) protein in a subject, for example, in an animal (e.g., rodents, primates, and the like) or in a human subject. Animals include normal, healthy or wildtype animals, as well as animal models for use in understanding acute intermittent porphyria (AIP) and treatments thereof. Exemplary animal models include rodent models, for example, PBGD deficient mice also referred to as AIP mice. AIP mice are compound heterozygotes of two different disruptions of the PBGD gene: T1 strain [C57BL/6-pbgdtm1(neo)Uam and T2 strain (C57BL/6-pbgdtm2(neo)Uam] (Lindberg R L, et al. "Porphobilinogen deaminase deficiency in mice causes a neuropathy resembling that of human hepatic porphyria." Nat Genet. 1996; 12:195-199). Acute porphyria attacks are triggered by phenobarbital challenges in AIP mice. AIP mice subjected to phenobarbital challenge biochemically mimic AIP, e.g., induction of the porphyrin precursors, and develop physical signs and symptoms that mimic those in human subjects with AIP.

PBGD protein expression levels can be measured or determined by any art-recognized method for determining protein levels in biological samples, e.g., needle liver biopsy. The term "level" or "level of a protein" as used herein, preferably means the weight, mass or concentration of the protein within a sample or a subject. It will be understood by the skilled artisan that in certain embodiments the sample may be subjected, e.g., to any of the following: purification, precipitation, separation, e.g. centrifugation and/or HPLC, and subsequently subjected to determining the level of the protein, e.g., using mass and/or spectrometric analysis. In exemplary embodiments, enzyme-linked immunosorbent assay (ELISA) can be used to determine protein expression levels. In other exemplary embodiments, protein purification, separation and LC-MS can be used as a means for determining the level of a protein according to the invention. In some embodiments, an mRNA therapy of the invention (e.g., a single intravenous dose) results in increased PBGD protein expression levels in the liver tissue of the subject (e.g., 2-fold, 3-fold, 4-fold, 5-fold, 6-fold, 7-fold, 8-fold, 9-fold, 10-fold, 20-fold, 30-fold, 40-fold, 50-fold increase and/or increased to at least 50%, at least 60%, at least 70%, at least 75%, 80%, at least 85%, at least 90%, at least 95%, or at least 100% of normal levels) for at least 6 hours, at least 12 hours, at least 24 hours, at least 36 hours, at least 48 hours, at least 60 hours, at least 72 hours, at least 84 hours, at least 96 hours, at least 108 hours, at least 122 hours after administration of a single dose of the mRNA therapy.

PBGD Protein Activity

In AIP patients, PBGD enzymatic activity is reduced, e.g., to about 50% of normal. Further aspects of the invention feature measurement, determination and/or monitoring of the activity level(s) (i.e., enzymatic activity level(s)) of PBGD protein in a subject, for example, in an animal (e.g., rodent, primate, and the like) or in a human subject. Activity levels can be measured or determined by any art-recognized method for determining enzymatic activity levels in biological samples. The term "activity level" or "enzymatic activity level" as used herein, preferably means the activity of the enzyme per volume, mass or weight of sample or total protein within a sample. In exemplary embodiments, the "activity level" or "enzymatic activity level" is described in terms of units per milliliter of fluid (e.g., bodily fluid, e.g., serum, plasma, urine and the like) or is described in terms of units per weight of tissue or per weight of protein (e.g., total protein) within a sample. Units ("U") of enzyme activity can be described in terms of weight or mass of substrate hydrolyzed per unit time. Exemplary embodiments of the invention feature PBGD activity described in terms of U/ml plasma or U/mg protein (tissue), where units ("U") are described in terms of nmol substrate hydrolyzed per hour (or nmol/hr). An exemplary enzymatic assay features uroporphyrin production (URO). PBGD activity in tissue (e.g., liver) can be quantitated, e.g., as pmol of uroporphyrin produced per mg of protein per hour.

In exemplary embodiments, an mRNA therapy of the invention features a pharmaceutical composition comprising a dose of mRNA effective to result in at least 5 U/mg, at least 10 U/mg, at least 20 U/mg, at least 30 U/mg, at least 40 U/mg, at least 50 U/mg, at least 60 U/mg, at least 70 U/mg, at least 80 U/mg, at least 90 U/mg, at least 100 U/mg, or at least 150 U/mg of PBGD activity in tissue (e.g., liver) between 6 and 12 hours, or between 12 and 24, between 24 and 48, or between 48 and 72 hours post administration (e.g., at 48 or at 72 hours post administration).

In exemplary embodiments, an mRNA therapy of the invention features a pharmaceutical composition comprising a single intravenous dose of mRNA that results in the above-described levels of activity. In another embodiment, an mRNA therapy of the invention features a pharmaceutical composition which can be administered in multiple single unit intravenous doses of mRNA that maintain the above-described levels of activity.

PBGD Biomarkers

Further aspects of the invention feature determining the level (or levels) of a biomarker, e.g., urinary aminolevulinate acid (ALA) excretion, urinary porphobilinogen (PBG) excretion, urinary porphyrin excretion, serum transaminases (e.g., alanine transaminase (ALT) or aspartate transaminase (AST)) and/or serum bilirubin, determined in a sample as compared to a level (e.g., a reference level) of the same or another biomarker in another sample, e.g., from the same patient, from another patient, from a control and/or from the same or different time points, and/or a physiologic level, and/or an elevated level, and/or a supraphysiologic level, and/or a level of a control. The skilled artisan will be familiar with physiologic levels of biomarkers, for example, levels in normal or wildtype animals, normal or healthy subjects, and the like, in particular, the level or levels characteristic of subjects who are healthy and/or normal functioning. As used herein, the phrase "elevated level" means amounts greater than normally found in a normal or wildtype preclinical animal or in a normal or healthy subject, e.g. a human subject. As used herein, the term "supraphysiologic" means amounts greater than normally found in a normal or wildtype preclinical animal or in a normal or healthy subject, e.g. a human subject, optionally producing a significantly enhanced physiologic response. As used herein, the term "comparing" or "compared to" preferably means the mathematical comparison of the two or more values, e.g., of the levels of the biomarker(s). It will thus be readily apparent to the skilled artisan whether one of the values is higher, lower or identical to another value or group of values if at least two of such values are compared with each other. Comparing or comparison to can be in the context, for example, of comparing to a control value, e.g., as compared to a reference serum ALT level, a reference serum AST level and/or a reference serum bilirubin level in said subject prior to administration (e.g., in a person suffering from AIP) or in a normal or healthy subject. Comparing or comparison to can also be in the context, for example, of comparing to a control value, e.g., as compared to a reference urinary ALA, PBG, and/or porphyrin excretion level in said subject prior to administration (e.g., in a person suffering from AIP) or in a normal or healthy subject.

As used herein, a "control" is preferably a sample from a subject wherein the AIP status of said subject is known. In one embodiment, a control is a sample of a healthy patient. In another embodiment, the control is a sample from at least one subject having a known AIP status, for example, a severe, mild, or healthy AIP status, e.g. a control patient. In another embodiment, the control is a sample from a subject not being treated for AIP. In a still further embodiment, the control is a sample from a single subject or a pool of samples from different subjects and/or samples taken from the subject(s) at different time points.

The term "level" or "level of a biomarker" as used herein, preferably means the mass, weight or concentration of a biomarker of the invention within a sample or a subject. Biomarkers of the invention include, for example, aminolevulinate acid (ALA) (e.g., normal urinary excretion levels <about 3.9 mmol ALA/mol creatinine), porphobilinogen (PBG) (e.g., normal urinary excretion levels <about 1.6 or 1.5 mmol PBG/mol creatinine or 0-4 mg/L), porphyrin (e.g., normal urinary excretion levels <145 transaminases (e.g., alanine transaminase (ALT) (e.g., normal serum levels <about 10-35 U/L) or aspartate transaminase (AST) (e.g., normal serum levels <about 15-41 U/L)) and/or bilirubin (e.g., normal serum levels <about 1.2 mg/dl). It will be understood by the skilled artisan that in certain embodiments the sample may be subjected to, e.g., one or more of the following: substance purification, precipitation, separation, e.g. centrifugation and/or HPLC and subsequently subjected to determining the level of the biomarker, e.g. using mass spectrometric analysis. In exemplary embodiments, LC-MS can be used as a means for determining the level of a biomarker according to the invention.

Certain embodiments an mRNA of the invention can be used express a PBGD polypeptide at a level sufficient to reduce urinary excretion of: (i) aminolevulinate acid (ALA) to less than about 20, 19, 18, 17, 16, 15, 14, 13, 12, 11, 10, 9, 8, 7, 6, 5, 4, 3, 2, or 1 mmol ALA/mol creatinine for at least 24 hours, at least 48 hours, at least 72 hours, at least 96 hours, or at least 120 hours post-administration, and/or (ii) porphobilinogen (PBG) to less than about 15, 14, 13, 12, 11, 10, 9, 8, 7, 6, 5, 4, 3, 2, or 1 mmol PBG/mol creatinine for at least 24 hours, at least 48 hours, at least 72 hours, at least 96 hours, or at least 120 hours post-administration.

The term "determining the level" of a biomarker as used herein can mean methods which include quantifying an amount of at least one substance in a sample from a subject, for example, in a bodily fluid from the subject (e.g., serum, plasma, urine, blood, lymph, fecal, etc.) or in a tissue of the subject (e.g., liver, heart, spleen kidney, etc.).

The term "reference level" as used herein can refer to levels (e.g., of a biomarker) in a subject prior to administration of an mRNA therapy of the invention (e.g., in a person suffering from AIP) or in a normal or healthy subject.

As used herein, the term "normal subject" or "healthy subject" refers to a subject not suffering from symptoms associated with AIP. Moreover, a subject will be considered to be normal (or healthy) if it has no mutation of the functional portions or domains of the porphobilinogen deaminase (PBGD) gene (also referred to as hydroxymethylbilane synthase (HMBS) and uroporphyrinogen I synthase) and/or no mutation of the PBGD gene resulting in a reduction of or deficiency of the enzyme PBGD (also known as uroporphyrinogen I synthase or hydroxymethylbilane synthase) or the activity thereof, resulting in symptoms associated with AIP. Said mutations will be detected if a sample from the subject is subjected to a genetic testing for such PBGD mutations. In exemplary embodiments of the present invention, a sample from a healthy subject is used as a control sample, or the known or standardized value for the level of biomarker from samples of healthy or normal subjects is used as a control.

In some embodiments, comparing the level of the biomarker in a sample from a subject in need of treatment for AIP and/or prevention of an acute porphyria attack, or in a subject being treated for AIP to a control level of the biomarker comprises comparing the level of the biomarker in the sample from the subject (in need of treatment or being treated for AIP) to a baseline or reference level, wherein if a level of the biomarker in the sample from the subject (in need of treatment or being treated for AIP) is elevated, increased or higher compared to the baseline or reference level, this is indicative that the subject is suffering from AIP and/or is in need of treatment; and/or wherein if a level of the biomarker in the sample from the subject (in need of treatment or being treated for AIP) is decreased or lower compared to the baseline level this is indicative that the subject is not suffering from, is successfully being treated for AIP, or is not in need of treatment for AIP. The stronger the reduction (e.g., at least 2-fold, at least 3-fold, at least 4-fold, at least 5-fold, at least 6-fold, at least 7-fold, at least 8-fold, at least 10-fold, at least 20-fold, at least-30 fold, at least 40-fold, at least 50-fold reduction and/or at least 10%, at least 20%, at least 30% at least 40%, at least 50%, at least 60%, at least 70%, at least 80%, at least 90%, at least 95%, at least 98%, at least 99%, or at least 100% reduction) of the level of a biomarker, e.g., aminolevulinate acid (ALA), porphobilinogen (PBG), porphyrin, transaminases (e.g., alanine transaminase (ALT) or aspartate transaminase (AST)) and/or bilirubin, within a certain time period, e.g., within 6 hours, within 12 hours, 24 hours, 36 hours, 48 hours, 60 hours, or 72 hours, and/or for a certain duration of time, e.g., 48 hours, 72 hours, 96 hours, 120 hours, 144 hours, 1 week, 2 weeks, 3 weeks, 4 weeks, 1 month, 2 months, 3 months, 4 months, 5 months, 6 months, 7 months, 8 months, 9 months, 10 months, 11 months, 12 months, 18 months, 24 months, etc. the more successful is a therapy, such as for example an mRNA therapy of the invention (e.g., a single dose or a multiple regimen).

A reduction of at least about 20%, at least about 30%, at least about 40%, at least about 50%, at least about 60%, at least about 70%, at least about 80%, at least about 90%, at least 95%, at least 98%, at least 99%, at least 100% or more of the level of biomarker, in particular, in bodily fluid (e.g., plasma, serum, urine, e.g., urinary sediment) or in tissue(s)

in a subject (e.g., liver, heart, spleen, kidney, brain or lung), for example a ALA, PBG, porphyrin, a transaminases (e.g., ALT or AST), and/or serum bilirubin, within 1, 2, 3, 4, 5, 6 or more days following administration is indicative of a dose suitable for successful treatment AIP, wherein reduction as used herein, preferably means that the level of biomarker determined at the end of a specified time period (e.g., post-administration, for example, of a single intravenous dose) is compared to the level of the same biomarker determined at the beginning of said time period (e.g., pre-administration of said dose). Exemplary time periods include 12, 24, 48, 72, 96, 120 or 144 hours post administration, in particular 24, 48, 72 or 96 hours post administration.

A sustained reduction in substrate levels (e.g., biomarkers such as ALA, PBG, porphyrin, a transaminases (e.g., ALT or AST), and/or serum bilirubin) is particularly indicative of mRNA therapeutic dosing and/or administration regimens successful for treatment of AIP. Such sustained reduction can be referred to herein as "duration" of effect. In exemplary embodiments, a reduction of at least about 40%, at least about 50%, at least about 60%, at least about 65%, at least about 70%, at least about 75%, at least about 80%, at least about 85%, at least about 90%, or at least about 95% at least about 96%, at least about 97%, at least about 98%, at least about 99%, at least about 100% or more of the level of biomarker, in particular, in a bodily fluid (e.g., plasma, serum, urine, e.g., urinary sediment) or in tissue(s) in a subject (e.g., liver, heart, spleen, kidney, brain or lung), for example ALA, PBG, porphyrin, a transaminases (e.g., ALT or AST), and/or serum bilirubin, within 1, 2, 3, 4, 5, 6, 7, 8 or more days following administration is indicative of a successful therapeutic approach. In exemplary embodiments, sustained reduction in substrate (e.g., biomarker) levels in one or more samples (e.g., fluids and/or tissues) is preferred. For example, mRNA therapies resulting in sustained reduction in ALA, PBG, porphyrin, a transaminases (e.g., ALT or AST), and/or serum bilirubin (as defined herein), optionally in combination with sustained reduction of said biomarker in at least one tissue, preferably two, three, four, five or more tissues, is indicative of successful treatment.

In some embodiments, a single dose of an mRNA therapy of the invention is about 0.2 to about 0.8 mpk. about 0.3 to about 0.7 mpk, about 0.4 to about 0.8 mpk, or about 0.5 mpk. In another embodiment, a single dose of an mRNA therapy of the invention is less than 1.5 mpk, less than 1.25 mpk, less than 1 mpk, or less than 0.75 mpk.

26. COMPOSITIONS AND FORMULATIONS FOR USE

Certain aspects of the invention are directed to compositions or formulations comprising any of the polynucleotides disclosed above.

In some embodiments, the composition or formulation comprises:

(i) a polynucleotide (e.g., a RNA, e.g., an mRNA) comprising a sequence-optimized nucleotide sequence (e.g., an ORF) encoding a PBGD polypeptide (e.g., the wild-type sequence, functional fragment, or variant thereof), wherein the polynucleotide comprises at least one chemically modified nucleobase, e.g., 5-methoxyuracil (e.g., wherein at least about 25%, at least about 30%, at least about 40%, at least about 50%, at least about 60%, at least about 70%, at least about 80%, at least about 90%, at least about 95%, at least about 99%, or 100% of the uracils are 5-methoxyuracils), and wherein the polynucleotide further comprises a miRNA binding site, e.g., a miRNA binding site that binds to miR-142 (e.g., a miR-142-3p or miR-142-5p binding site) and/or a miRNA binding site that binds to miR-126 (e.g., a miR-126-3p or miR-126-5p binding site); and (ii) a delivery agent comprising, e.g., a compound having the Formula (I), e.g., any of Compounds 1-232, e.g., Compound 18; a compound having the Formula (III), (IV), (V), or (VI), e.g., any of Compounds 233-342, e.g., Compound 236; or a compound having the Formula (VIII), e.g., any of Compounds 419-428, e.g., Compound 428, or any combination thereof.

In some embodiments, the uracil or thymine content of the ORF relative to the theoretical minimum uracil or thymine content of a nucleotide sequence encoding the PBGD polypeptide (% $U_{TM}$ or % $T_{TM}$), is between about 100% and about 150%.

In some embodiments, the polynucleotides, compositions or formulations above are used to treat and/or prevent a PBGD-related diseases, disorders or conditions, e.g., AIP.

27. FORMS OF ADMINISTRATION

The polynucleotides, pharmaceutical compositions and formulations of the invention described above can be administered by any route that results in a therapeutically effective outcome. These include, but are not limited to enteral (into the intestine), gastroenteral, epidural (into the dura matter), oral (by way of the mouth), transdermal, peridural, intracerebral (into the cerebrum), intracerebroventricular (into the cerebral ventricles), epicutaneous (application onto the skin), intradermal, (into the skin itself), subcutaneous (under the skin), nasal administration (through the nose), intravenous (into a vein), intravenous bolus, intravenous drip, intraarterial (into an artery), intramuscular (into a muscle), intracardiac (into the heart), intraosseous infusion (into the bone marrow), intrathecal (into the spinal canal), intraperitoneal, (infusion or injection into the peritoneum), intravesical infusion, intravitreal, (through the eye), intracavernous injection (into a pathologic cavity) intracavitary (into the base of the penis), intravaginal administration, intrauterine, extra-amniotic administration, transdermal (diffusion through the intact skin for systemic distribution), transmucosal (diffusion through a mucous membrane), transvaginal, insufflation (snorting), sublingual, sublabial, enema, eye drops (onto the conjunctiva), in ear drops, auricular (in or by way of the ear), buccal (directed toward the cheek), conjunctival, cutaneous, dental (to a tooth or teeth), electroosmosis, endocervical, endosinusial, endotracheal, extracorporeal, hemodialysis, infiltration, interstitial, intraabdominal, intra-amniotic, intra-articular, intrabiliary, intrabronchial, intrabursal, intracartilaginous (within a cartilage), intracaudal (within the cauda equine), intracisternal (within the cisterna magna cerebellomedularis), intracorneal (within the cornea), dental intracornal, intracoronary (within the coronary arteries), intracorporus cavernosum (within the dilatable spaces of the corporus cavernosa of the penis), intradiscal (within a disc), intraductal (within a duct of a gland), intraduodenal (within the duodenum), intradural (within or beneath the dura), intraepidermal (to the epidermis), intraesophageal (to the esophagus), intragastric (within the stomach), intragingival (within the gingivae), intraileal (within the distal portion of the small intestine), intralesional (within or introduced directly to a localized lesion), intraluminal (within a lumen of a tube), intralymphatic (within the lymph), intramedullary (within the marrow cavity of a bone), intrameningeal (within the meninges), intraocular (within the eye), intraovarian (within the ovary), intrapericardial (within the pericardium), intrapleural (within the pleura), intraprostatic (within the prostate gland), intrapulmonary (within the lungs or its bronchi), intrasinal (within the nasal or periorbital sinuses), intraspinal (within the vertebral column), intrasynovial (within the synovial cavity of a joint), intratendinous (within a tendon), intratesticular (within the testicle), intrathecal (within the cerebrospinal fluid at any level of the cerebrospinal axis), intrathoracic (within the thorax), intratubular (within the tubules of an organ), intratympanic (within the aurus media), intravascular (within a vessel or vessels), intraventricular (within a ventricle), iontophoresis (by means of electric current where ions of soluble salts migrate into the tissues of the body), irrigation (to bathe or flush open wounds or body cavities), laryngeal (directly upon the larynx), nasogastric (through the nose and into the stomach), occlusive dressing technique (topical route administration that is then covered by a dressing that occludes the area), ophthalmic (to the external eye), oropharyngeal (directly to the mouth and pharynx), parenteral, percutaneous, periarticular, peridural, perineural, periodontal, rectal, respiratory (within the respiratory tract by inhaling orally or nasally for local or systemic effect), retrobulbar (behind the pons or behind the eyeball), intramyocardial (entering the myocardium), soft tissue, subarachnoid, subconjunctival, submucosal, topical, transplacental (through or across the placenta), transtracheal (through the wall of the trachea), transtympanic (across or through the tympanic cavity), ureteral (to the ureter), urethral (to the urethra), vaginal, caudal block, diagnostic, nerve block, biliary perfusion, cardiac perfusion, photopheresis or spinal. In specific embodiments, compositions can be administered in a way that allows them cross the blood-brain barrier, vascular barrier, or other epithelial barrier. In some embodiments, a formulation for a route of administration can include at least one inactive ingredient.

The polynucleotides of the present invention (e.g., a polynucleotide comprising a nucleotide sequence encoding a PBGD polypeptide or a functional fragment or variant thereof) can be delivered to a cell naked. As used herein in, "naked" refers to delivering polynucleotides free from agents that promote transfection. The naked polynucleotides can be delivered to the cell using routes of administration known in the art and described herein.

The polynucleotides of the present invention (e.g., a polynucleotide comprising a nucleotide sequence encoding a PBGD polypeptide or a functional fragment or variant thereof) can be formulated, using the methods described herein. The formulations can contain polynucleotides that can be modified and/or unmodified. The formulations can further include, but are not limited to, cell penetration agents, a pharmaceutically acceptable carrier, a delivery agent, a bioerodible or biocompatible polymer, a solvent, and a sustained-release delivery depot. The formulated polynucleotides can be delivered to the cell using routes of administration known in the art and described herein.

A pharmaceutical composition for parenteral administration can comprise at least one inactive ingredient. Any or none of the inactive ingredients used can have been approved by the US Food and Drug Administration (FDA). A non-exhaustive list of inactive ingredients for use in pharmaceutical compositions for parenteral administration includes hydrochloric acid, mannitol, nitrogen, sodium acetate, sodium chloride and sodium hydroxide.

Injectable preparations, for example, sterile injectable aqueous or oleaginous suspensions can be formulated according to the known art using suitable dispersing agents, wetting agents, and/or suspending agents. Sterile injectable preparations can be sterile injectable solutions, suspensions, and/or emulsions in nontoxic parenterally acceptable diluents and/or solvents, for example, as a solution in 1,3-butanediol. Among the acceptable vehicles and solvents that can be employed are water, Ringer's solution, U.S.P., and isotonic sodium chloride solution. Sterile, fixed oils are conventionally employed as a solvent or suspending medium. For this purpose any bland fixed oil can be employed including synthetic mono- or diglycerides. Fatty acids such as oleic acid can be used in the preparation of injectables. The sterile formulation can also comprise adjuvants such as local anesthetics, preservatives and buffering agents.

Injectable formulations can be sterilized, for example, by filtration through a bacterial-retaining filter, and/or by incorporating sterilizing agents in the form of sterile solid compositions that can be dissolved or dispersed in sterile water or other sterile injectable medium prior to use.

Injectable formulations can be for direct injection into a region of a tissue, organ and/or subject. As a non-limiting example, a tissue, organ and/or subject can be directly injected a formulation by intramyocardial injection into the ischemic region. (See, e.g., Zangi et al. Nature Biotechnology 2013; the contents of which are herein incorporated by reference in its entirety).

In order to prolong the effect of an active ingredient, it is often desirable to slow the absorption of the active ingredient from subcutaneous or intramuscular injection. This can be accomplished by the use of a liquid suspension of crystalline or amorphous material with poor water solubility. The rate of absorption of the drug then depends upon its rate of dissolution which, in turn, can depend upon crystal size and crystalline form. Alternatively, delayed absorption of a parenterally administered drug form is accomplished by dissolving or suspending the drug in an oil vehicle. Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides). Depot injectable formulations are prepared by entrapping the drug in liposomes or microemulsions that are compatible with body tissues.

28. KITS AND DEVICES a. Kits

The invention provides a variety of kits for conveniently and/or effectively using the claimed nucleotides of the present invention. Typically kits will comprise sufficient amounts and/or numbers of components to allow a user to perform multiple treatments of a subject(s) and/or to perform multiple experiments.

In one aspect, the present invention provides kits comprising the molecules (polynucleotides) of the invention.

Said kits can be for protein production, comprising a first polynucleotide comprising a translatable region. The kit can further comprise packaging and instructions and/or a delivery agent to form a formulation composition. The delivery agent can comprise a saline, a buffered solution, a lipidoid or any delivery agent disclosed herein.

In some embodiments, the buffer solution can include sodium chloride, calcium chloride, phosphate and/or EDTA. In another embodiment, the buffer solution can include, but is not limited to, saline, saline with 2 mM calcium, 5% sucrose, 5% sucrose with 2 mM calcium, 5% Mannitol, 5% Mannitol with 2 mM calcium, Ringer's lactate, sodium chloride, sodium chloride with 2 mM calcium and mannose (See, e.g., U.S. Pub. No. 20120258046; herein incorporated by reference in its entirety). In a further embodiment, the buffer solutions can be precipitated or it can be lyophilized. The amount of each component can be varied to enable consistent, reproducible higher concentration saline or simple buffer formulations. The components can also be varied in order to increase the stability of modified RNA in the buffer solution over a period of time and/or under a variety of conditions. In one aspect, the present invention provides kits for protein production, comprising: a polynucleotide comprising a translatable region, provided in an amount effective to produce a desired amount of a protein encoded by the translatable region when introduced into a target cell; a second polynucleotide comprising an inhibitory nucleic acid, provided in an amount effective to substantially inhibit the innate immune response of the cell; and packaging and instructions.

In one aspect, the present invention provides kits for protein production, comprising a polynucleotide comprising a translatable region, wherein the polynucleotide exhibits reduced degradation by a cellular nuclease, and packaging and instructions.

In one aspect, the present invention provides kits for protein production, comprising a polynucleotide comprising a translatable region, wherein the polynucleotide exhibits reduced degradation by a cellular nuclease, and a mammalian cell suitable for translation of the translatable region of the first nucleic acid.

b. Devices

The present invention provides for devices that can incorporate polynucleotides that encode polypeptides of interest. These devices contain in a stable formulation the reagents to synthesize a polynucleotide in a formulation available to be immediately delivered to a subject in need thereof, such as a human patient Devices for administration can be employed to deliver the polynucleotides of the present invention according to single, multi- or split-dosing regimens taught herein. Such devices are taught in, for example, International Application Publ. No. WO2013151666, the contents of which are incorporated herein by reference in their entirety.

Method and devices known in the art for multi-administration to cells, organs and tissues are contemplated for use in conjunction with the methods and compositions disclosed herein as embodiments of the present invention. These include, for example, those methods and devices having multiple needles, hybrid devices employing for example lumens or catheters as well as devices utilizing heat, electric current or radiation driven mechanisms.

According to the present invention, these multi-administration devices can be utilized to deliver the single, multi- or split doses contemplated herein. Such devices are taught for example in, International Application Publ. No. WO2013151666, the contents of which are incorporated herein by reference in their entirety.

In some embodiments, the polynucleotide is administered subcutaneously or intramuscularly via at least 3 needles to three different, optionally adjacent, sites simultaneously, or within a 60 minutes period (e.g., administration to 4, 5, 6, 7, 8, 9, or 10 sites simultaneously or within a 60 minute period).

c. Methods and Devices Utilizing Catheters and/or Lumens

Methods and devices using catheters and lumens can be employed to administer the polynucleotides of the present invention on a single, multi- or split dosing schedule. Such methods and devices are described in International Application Publication No. WO2013151666, the contents of which are incorporated herein by reference in their entirety.

d. Methods and Devices Utilizing Electrical Current

Methods and devices utilizing electric current can be employed to deliver the polynucleotides of the present invention according to the single, multi- or split dosing regimens taught herein. Such methods and devices are described in International Application Publication No. WO2013151666, the contents of which are incorporated herein by reference in their entirety.

29. DEFINITIONS

In order that the present disclosure can be more readily understood, certain terms are first defined. As used in this application, except as otherwise expressly provided herein, each of the following terms shall have the meaning set forth below. Additional definitions are set forth throughout the application.

The invention includes embodiments in which exactly one member of the group is present in, employed in, or otherwise relevant to a given product or process. The invention includes embodiments in which more than one, or all of the group members are present in, employed in, or otherwise relevant to a given product or process.

In this specification and the appended claims, the singular forms "a", "an" and "the" include plural referents unless the context clearly dictates otherwise. The terms "a" (or "an"), as well as the terms "one or more," and "at least one" can be used interchangeably herein. In certain aspects, the term "a" or "an" means "single." In other aspects, the term "a" or "an" includes "two or more" or "multiple."

Furthermore, "and/or" where used herein is to be taken as specific disclosure of each of the two specified features or components with or without the other. Thus, the term "and/or" as used in a phrase such as "A and/or B" herein is intended to include "A and B," "A or B," "A" (alone), and "B" (alone). Likewise, the term "and/or" as used in a phrase such as "A, B, and/or C" is intended to encompass each of the following aspects: A, B, and C; A, B, or C; A or C; A or B; B or C; A and C; A and B; B and C; A (alone); B (alone); and C (alone).

Unless defined otherwise, all technical and scientific terms used herein have the same meaning as commonly understood by one of ordinary skill in the art to which this disclosure is related. For example, the Concise Dictionary of Biomedicine and Molecular Biology, Juo, Pei-Show, 2nd ed., 2002, CRC Press; The Dictionary of Cell and Molecular Biology, 3rd ed., 1999, Academic Press; and the Oxford Dictionary Of Biochemistry And Molecular Biology, Revised, 2000, Oxford University Press, provide one of skill with a general dictionary of many of the terms used in this disclosure.

Wherever aspects are described herein with the language "comprising," otherwise analogous aspects described in terms of "consisting of" and/or "consisting essentially of" are also provided.

Units, prefixes, and symbols are denoted in their Système International de Unites (SI) accepted form. Numeric ranges are inclusive of the numbers defining the range. Where a range of values is recited, it is to be understood that each intervening integer value, and each fraction thereof, between the recited upper and lower limits of that range is also specifically disclosed, along with each subrange between such values. The upper and lower limits of any range can independently be included in or excluded from the range, and each range where either, neither or both limits are included is also encompassed within the invention. Where a value is explicitly recited, it is to be understood that values which are about the same quantity or amount as the recited value are also within the scope of the invention. Where a combination is disclosed, each subcombination of the elements of that combination is also specifically disclosed and is within the scope of the invention. Conversely, where different elements or groups of elements are individually disclosed, combinations thereof are also disclosed. Where any element of an invention is disclosed as having a plurality of alternatives, examples of that invention in which each alternative is excluded singly or in any combination with the other alternatives are also hereby disclosed; more than one element of an invention can have such exclusions, and all combinations of elements having such exclusions are hereby disclosed.

Nucleotides are referred to by their commonly accepted single-letter codes. Unless otherwise indicated, nucleic acids are written left to right in 5' to 3' orientation. Nucleobases are referred to herein by their commonly known one-letter symbols recommended by the IUPAC-IUB Biochemical Nomenclature Commission. Accordingly, A represents adenine, C represents cytosine, G represents guanine, T represents thymine, U represents uracil.

Amino acids are referred to herein by either their commonly known three letter symbols or by the one-letter symbols recommended by the IUPAC-IUB Biochemical Nomenclature Commission. Unless otherwise indicated, amino acid sequences are written left to right in amino to carboxy orientation.

About: The term "about" as used in connection with a numerical value throughout the specification and the claims denotes an interval of accuracy, familiar and acceptable to a person skilled in the art. Such interval of accuracy is ±10%.

Where ranges are given, endpoints are included. Furthermore, unless otherwise indicated or otherwise evident from the context and understanding of one of ordinary skill in the art, values that are expressed as ranges can assume any specific value or subrange within the stated ranges in different embodiments of the invention, to the tenth of the unit of the lower limit of the range, unless the context clearly dictates otherwise.

Administered in combination: As used herein, the term "administered in combination" or "combined administration" means that two or more agents are administered to a subject at the same time or within an interval such that there can be an overlap of an effect of each agent on the patient. In some embodiments, they are administered within about 60, 30, 15, 10, 5, or 1 minute of one another. In some embodiments, the administrations of the agents are spaced sufficiently closely together such that a combinatorial (e.g., a synergistic) effect is achieved.

Amino acid substitution: The term "amino acid substitution" refers to replacing an amino acid residue present in a parent or reference sequence (e.g., a wild type PBGD sequence) with another amino acid residue. An amino acid can be substituted in a parent or reference sequence (e.g., a wild type PBGD polypeptide sequence), for example, via chemical peptide synthesis or through recombinant methods known in the art. Accordingly, a reference to a "substitution at position X" refers to the substitution of an amino acid present at position X with an alternative amino acid residue. In some aspects, substitution patterns can be described according to the schema AnY, wherein A is the single letter code corresponding to the amino acid naturally or originally present at position n, and Y is the substituting amino acid residue. In other aspects, substitution patterns can be described according to the schema An(YZ), wherein A is the single letter code corresponding to the amino acid residue substituting the amino acid naturally or originally present at position X, and Y and Z are alternative substituting amino acid residue, i.e., and Y and Z are alternative substituting amino acid residues.

In the context of the present disclosure, substitutions (even when they referred to as amino acid substitution) are conducted at the nucleic acid level, i.e., substituting an amino acid residue with an alternative amino acid residue is conducted by substituting the codon encoding the first amino acid with a codon encoding the second amino acid.

Animal: As used herein, the term "animal" refers to any member of the animal kingdom. In some embodiments, "animal" refers to humans at any stage of development. In some embodiments, "animal" refers to non-human animals at any stage of development. In certain embodiments, the non-human animal is a mammal (e.g., a rodent, a mouse, a rat, a rabbit, a monkey, a dog, a cat, a sheep, cattle, a primate, or a pig). In some embodiments, animals include, but are not limited to, mammals, birds, reptiles, amphibians, fish, and worms. In some embodiments, the animal is a transgenic animal, genetically-engineered animal, or a clone.

Approximately: As used herein, the term "approximately," as applied to one or more values of interest, refers to a value that is similar to a stated reference value. In certain embodiments, the term "approximately" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

Associated with: As used herein with respect to a disease, the term "associated with" means that the symptom, measurement, characteristic, or status in question is linked to the diagnosis, development, presence, or progression of that disease. As association can, but need not be causatively linked to the disease. For example, signs, symptoms, sequelae, or any effects causing a decrease in the quality of life of a patient of AIP are considered associated with AIP and in some embodiments of the present invention can be treated, ameliorated, or prevented by administering the polynucleotides of the present invention to a subject in need thereof.

When used with respect to two or more moieties, the terms "associated with," "conjugated," "linked," "attached," and "tethered," when used with respect to two or more moieties, means that the moieties are physically associated or connected with one another, either directly or via one or more additional moieties that serves as a linking agent, to form a structure that is sufficiently stable so that the moieties remain physically associated under the conditions in which the structure is used, e.g., physiological conditions. An "association" need not be strictly through direct covalent chemical bonding. It can also suggest ionic or hydrogen bonding or a hybridization based connectivity sufficiently stable such that the "associated" entities remain physically associated.

Bifunctional: As used herein, the term "bifunctional" refers to any substance, molecule or moiety that is capable of or maintains at least two functions. The functions can affect the same outcome or a different outcome. The structure that produces the function can be the same or different. For example, bifunctional modified RNAs of the present invention can encode a PBGD peptide (a first function) while those nucleosides that comprise the encoding RNA are, in and of themselves, capable of extending the half-life of the RNA (second function). In this example, delivery of the bifunctional modified RNA to a subject suffering from a protein deficiency would produce not only a peptide or protein molecule that can ameliorate or treat a disease or conditions, but would also maintain a population modified RNA present in the subject for a prolonged period of time. In other aspects, a bifunction modified mRNA can be a chimeric or quimeric molecule comprising, for example, an RNA encoding a PBGD peptide (a first function) and a second protein either fused to first protein or co-expressed with the first protein, for example, and ApoA1 protein.

Biocompatible: As used herein, the term "biocompatible" means compatible with living cells, tissues, organs or systems posing little to no risk of injury, toxicity or rejection by the immune system.

Biodegradable: As used herein, the term "biodegradable" means capable of being broken down into innocuous products by the action of living things.

Biologically active: As used herein, the phrase "biologically active" refers to a characteristic of any substance that has activity in a biological system and/or organism. For instance, a substance that, when administered to an organism, has a biological effect on that organism, is considered to be biologically active. In particular embodiments, a polynucleotide of the present invention can be considered biologically active if even a portion of the polynucleotide is biologically active or mimics an activity considered biologically relevant.

Chimera: As used herein, "chimera" is an entity having two or more incongruous or heterogeneous parts or regions. For example, a chimeric molecule can comprise a first part comprising a PBGD polypeptide, and a second part (e.g., genetically fused to the first part) comprising a second therapeutic protein (e.g., a protein with a distinct enzymatic activity, an antigen binding moiety, or a moiety capable of extending the plasma half life of PBGD, for example, an Fc region of an antibody).

Sequence Optimization: The term "sequence optimization" refers to a process or series of processes by which nucleobases in a reference nucleic acid sequence are replaced with alternative nucleobases, resulting in a nucleic acid sequence with improved properties, e.g., improved protein expression or decreased immunogenicity.

In general, the goal in sequence optimization is to produce a synonymous nucleotide sequence than encodes the same polypeptide sequence encoded by the reference nucleotide sequence. Thus, there are no amino acid substitutions (as a result of codon optimization) in the polypeptide encoded by the codon optimized nucleotide sequence with respect to the polypeptide encoded by the reference nucleotide sequence.

Codon substitution: The terms "codon substitution" or "codon replacement" in the context of sequence optimization refer to replacing a codon present in a reference nucleic acid sequence with another codon. A codon can be substituted in a reference nucleic acid sequence, for example, via chemical peptide synthesis or through recombinant methods known in the art. Accordingly, references to a "substitution" or "replacement" at a certain location in a nucleic acid sequence (e.g., an mRNA) or within a certain region or subsequence of a nucleic acid sequence (e.g., an mRNA) refer to the substitution of a codon at such location or region with an alternative codon.

As used herein, the terms "coding region" and "region encoding" and grammatical variants thereof, refer to an Open Reading Frame (ORF) in a polynucleotide that upon expression yields a polypeptide or protein.

Compound: As used herein, the term "compound," is meant to include all stereoisomers and isotopes of the structure depicted. As used herein, the term "stereoisomer" means any geometric isomer (e.g., cis- and trans-isomer), enantiomer, or diastereomer of a compound. The present disclosure encompasses any and all stereoisomers of the compounds described herein, including stereomerically pure forms (e.g., geometrically pure, enantiomerically pure, or diastereomerically pure) and enantiomeric and stereoisomeric mixtures, e.g., racemates. Enantiomeric and stereomeric mixtures of compounds and means of resolving them into their component enantiomers or stereoisomers are well-known. "Isotopes" refers to atoms having the same atomic number but different mass numbers resulting from a different number of neutrons in the nuclei. For example, isotopes of hydrogen include tritium and deuterium. Further, a compound, salt, or complex of the present disclosure can be prepared in combination with solvent or water molecules to form solvates and hydrates by routine methods.

Contacting: As used herein, the term "contacting" means establishing a physical connection between two or more entities. For example, contacting a mammalian cell with a nanoparticle composition means that the mammalian cell and a nanoparticle are made to share a physical connection. Methods of contacting cells with external entities both in vivo and ex vivo are well known in the biological arts. For example, contacting a nanoparticle composition and a mammalian cell disposed within a mammal can be performed by varied routes of administration (e.g., intravenous, intramuscular, intradermal, and subcutaneous) and can involve varied amounts of nanoparticle compositions. Moreover, more than one mammalian cell can be contacted by a nanoparticle composition.

Conservative amino acid substitution: A "conservative amino acid substitution" is one in which the amino acid residue in a protein sequence is replaced with an amino acid residue having a similar side chain. Families of amino acid residues having similar side chains have been defined in the art, including basic side chains (e.g., lysine, arginine, or histidine), acidic side chains (e.g., aspartic acid or glutamic acid), uncharged polar side chains (e.g., glycine, asparagine, glutamine, serine, threonine, tyrosine, or cysteine), nonpolar side chains (e.g., alanine, valine, leucine, isoleucine, proline, phenylalanine, methionine, or tryptophan), beta-branched side chains (e.g., threonine, valine, isoleucine) and aromatic side chains (e.g., tyrosine, phenylalanine, tryptophan, or histidine). Thus, if an amino acid in a polypeptide is replaced with another amino acid from the same side chain family, the amino acid substitution is considered to be conservative. In another aspect, a string of amino acids can be conservatively replaced with a structurally similar string that differs in order and/or composition of side chain family members.

Non-conservative amino acid substitution: Non-conservative amino acid substitutions include those in which (i) a residue having an electropositive side chain (e.g., Arg, His or Lys) is substituted for, or by, an electronegative residue (e.g., Glu or Asp), (ii) a hydrophilic residue (e.g., Ser or Thr) is substituted for, or by, a hydrophobic residue (e.g., Ala, Leu, Ile, Phe or Val), (iii) a cysteine or proline is substituted for, or by, any other residue, or (iv) a residue having a bulky hydrophobic or aromatic side chain (e.g., Val, His, Ile or Trp) is substituted for, or by, one having a smaller side chain (e.g., Ala or Ser) or no side chain (e.g., Gly).

Other amino acid substitutions can be readily identified by workers of ordinary skill. For example, for the amino acid alanine, a substitution can be taken from any one of D-alanine, glycine, beta-alanine, L-cysteine and D-cysteine. For lysine, a replacement can be any one of D-lysine, arginine, D-arginine, homo-arginine, methionine, D-methionine, ornithine, or D-ornithine. Generally, substitutions in functionally important regions that can be expected to induce changes in the properties of isolated polypeptides are those in which (i) a polar residue, e.g., serine or threonine, is substituted for (or by) a hydrophobic residue, e.g., leucine, isoleucine, phenylalanine, or alanine; (ii) a cysteine residue is substituted for (or by) any other residue; (iii) a residue having an electropositive side chain, e.g., lysine, arginine or histidine, is substituted for (or by) a residue having an electronegative side chain, e.g., glutamic acid or aspartic acid; or (iv) a residue having a bulky side chain, e.g., phenylalanine, is substituted for (or by) one not having such a side chain, e.g., glycine. The likelihood that one of the foregoing non-conservative substitutions can alter functional properties of the protein is also correlated to the position of the substitution with respect to functionally important regions of the protein: some non-conservative substitutions can accordingly have little or no effect on biological properties.

Conserved: As used herein, the term "conserved" refers to nucleotides or amino acid residues of a polynucleotide sequence or polypeptide sequence, respectively, that are those that occur unaltered in the same position of two or more sequences being compared. Nucleotides or amino acids that are relatively conserved are those that are conserved amongst more related sequences than nucleotides or amino acids appearing elsewhere in the sequences.

In some embodiments, two or more sequences are said to be "completely conserved" if they are 100% identical to one another. In some embodiments, two or more sequences are said to be "highly conserved" if they are at least 70% identical, at least 80% identical, at least 90% identical, or at least 95% identical to one another. In some embodiments, two or more sequences are said to be "highly conserved" if they are about 70% identical, about 80% identical, about 90% identical, about 95%, about 98%, or about 99% identical to one another. In some embodiments, two or more sequences are said to be "conserved" if they are at least 30% identical, at least 40% identical, at least 50% identical, at least 60% identical, at least 70% identical, at least 80% identical, at least 90% identical, or at least 95% identical to one another. In some embodiments, two or more sequences are said to be "conserved" if they are about 30% identical, about 40% identical, about 50% identical, about 60% identical, about 70% identical, about 80% identical, about 90% identical, about 95% identical, about 98% identical, or about 99% identical to one another. Conservation of sequence can apply to the entire length of an polynucleotide or polypeptide or can apply to a portion, region or feature thereof.

Controlled Release: As used herein, the term "controlled release" refers to a pharmaceutical composition or compound release profile that conforms to a particular pattern of release to effect a therapeutic outcome.

Cyclic or Cyclized: As used herein, the term "cyclic" refers to the presence of a continuous loop. Cyclic molecules need not be circular, only joined to form an unbroken chain of subunits. Cyclic molecules such as the engineered RNA or mRNA of the present invention can be single units or multimers or comprise one or more components of a complex or higher order structure.

Cytotoxic: As used herein, "cytotoxic" refers to killing or causing injurious, toxic, or deadly effect on a cell (e.g., a mammalian cell (e.g., a human cell)), bacterium, virus, fungus, protozoan, parasite, prion, or a combination thereof.

Delivering: As used herein, the term "delivering" means providing an entity to a destination. For example, delivering a polynucleotide to a subject can involve administering a nanoparticle composition including the polynucleotide to the subject (e.g., by an intravenous, intramuscular, intradermal, or subcutaneous route). Administration of a nanoparticle composition to a mammal or mammalian cell can involve contacting one or more cells with the nanoparticle composition.

Delivery Agent: As used herein, "delivery agent" refers to any substance that facilitates, at least in part, the in vivo, in vitro, or ex vivo delivery of a polynucleotide to targeted cells.

Destabilized: As used herein, the term "destable," "destabilize," or "destabilizing region" means a region or molecule that is less stable than a starting, wild-type or native form of the same region or molecule.

Diastereomer: As used herein, the term "diastereomer," means stereoisomers that are not mirror images of one another and are non-superimposable on one another.

Digest: As used herein, the term "digest" means to break apart into smaller pieces or components. When referring to polypeptides or proteins, digestion results in the production of peptides.

Distal: As used herein, the term "distal" means situated away from the center or away from a point or region of interest.

Domain: As used herein, when referring to polypeptides, the term "domain" refers to a motif of a polypeptide having one or more identifiable structural or functional characteristics or properties (e.g., binding capacity, serving as a site for protein-protein interactions).

Dosing regimen: As used herein, a "dosing regimen" or a "dosing regimen" is a schedule of administration or physician determined regimen of treatment, prophylaxis, or palliative care.

Effective Amount: As used herein, the term "effective amount" of an agent is that amount sufficient to effect beneficial or desired results, for example, clinical results, and, as such, an "effective amount" depends upon the context in which it is being applied. For example, in the context of administering an agent that treats a protein deficiency (e.g., a PBGD deficiency), an effective amount of an agent is, for example, an amount of mRNA expressing sufficient PBGD to ameliorate, reduce, eliminate, or prevent the signs and symptoms associated with the PBGD deficiency, as compared to the severity of the symptom observed without administration of the agent. The term "effective amount" can be used interchangeably with "effective dose," "therapeutically effective amount," or "therapeutically effective dose."

Enantiomer: As used herein, the term "enantiomer" means each individual optically active form of a compound of the invention, having an optical purity or enantiomeric excess (as determined by methods standard in the art) of at least 80% (i.e., at least 90% of one enantiomer and at most 10% of the other enantiomer), at least 90%, or at least 98%.

Encapsulate: As used herein, the term "encapsulate" means to enclose, surround or encase.

Encapsulation Efficiency: As used herein, "encapsulation efficiency" refers to the amount of a polynucleotide that becomes part of a nanoparticle composition, relative to the initial total amount of polynucleotide used in the preparation of a nanoparticle composition. For example, if 97 mg of polynucleotide are encapsulated in a nanoparticle composition out of a total 100 mg of polynucleotide initially provided to the composition, the encapsulation efficiency can be given as 97%. As used herein, "encapsulation" can refer to complete, substantial, or partial enclosure, confinement, surrounding, or encasement.

Encoded protein cleavage signal: As used herein, "encoded protein cleavage signal" refers to the nucleotide sequence that encodes a protein cleavage signal.

Engineered: As used herein, embodiments of the invention are "engineered" when they are designed to have a feature or property, whether structural or chemical, that varies from a starting point, wild type or native molecule.

Enhanced Delivery: As used herein, the term "enhanced delivery" means delivery of more (e.g., at least 1.5 fold more, at least 2-fold more, at least 3-fold more, at least 4-fold more, at least 5-fold more, at least 6-fold more, at least 7-fold more, at least 8-fold more, at least 9-fold more, at least 10-fold more) of a polynucleotide by a nanoparticle to a target tissue of interest (e.g., mammalian liver) compared to the level of delivery of a polynucleotide by a control nanoparticle to a target tissue of interest (e.g., MC3, KC2, or DLinDMA). The level of delivery of a nanoparticle to a particular tissue can be measured by comparing the amount of protein produced in a tissue to the weight of said tissue, comparing the amount of polynucleotide in a tissue to the weight of said tissue, comparing the amount of protein produced in a tissue to the amount of total protein in said tissue, or comparing the amount of polynucleotide in a tissue to the amount of total polynucleotide in said tissue. It will be understood that the enhanced delivery of a nanoparticle to a target tissue need not be determined in a subject being treated, it can be determined in a surrogate such as an animal model (e.g., a rat model).

Exosome: As used herein, "exosome" is a vesicle secreted by mammalian cells or a complex involved in RNA degradation.

Expression: As used herein, "expression" of a nucleic acid sequence refers to one or more of the following events: (1) production of an mRNA template from a DNA sequence (e.g., by transcription); (2) processing of an mRNA transcript (e.g., by splicing, editing, 5' cap formation, and/or 3' end processing); (3) translation of an mRNA into a polypeptide or protein; and (4) post-translational modification of a polypeptide or protein.

Ex Vivo: As used herein, the term "ex vivo" refers to events that occur outside of an organism (e.g., animal, plant, or microbe or cell or tissue thereof). Ex vivo events can take place in an environment minimally altered from a natural (e.g., in vivo) environment.

Feature: As used herein, a "feature" refers to a characteristic, a property, or a distinctive element. When referring to polypeptides, "features" are defined as distinct amino acid sequence-based components of a molecule. Features of the polypeptides encoded by the polynucleotides of the present invention include surface manifestations, local conformational shape, folds, loops, half-loops, domains, half-domains, sites, termini or any combination thereof.

Formulation: As used herein, a "formulation" includes at least a polynucleotide and one or more of a carrier, an excipient, and a delivery agent.

Fragment: A "fragment," as used herein, refers to a portion. For example, fragments of proteins can comprise polypeptides obtained by digesting full-length protein isolated from cultured cells. In some embodiments, a fragment is a subsequences of a full length protein (e.g., PBGD) wherein N-terminal, and/or C-terminal, and/or internal subsequences have been deleted. In some preferred aspects of the present invention, the fragments of a protein of the present invention are functional fragments.

Functional: As used herein, a "functional" biological molecule is a biological molecule in a form in which it exhibits a property and/or activity by which it is characterized. Thus, a functional fragment of a polynucleotide of the present invention is a polynucleotide capable of expressing a functional PBGD fragment. As used herein, a functional fragment of PBGD refers to a fragment of wild type PBGD (i.e., a fragment of any of its naturally occurring isoforms), or a mutant or variant thereof, wherein the fragment retains a least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, or at least about 95% of the biological activity of the corresponding full length protein.

Helper Lipid: As used herein, the term "helper lipid" refers to a compound or molecule that includes a lipidic moiety (for insertion into a lipid layer, e.g., lipid bilayer) and a polar moiety (for interaction with physiologic solution at the surface of the lipid layer). Typically the helper lipid is a phospholipid. A function of the helper lipid is to "complement" the amino lipid and increase the fusogenicity of the bilayer and/or to help facilitate endosomal escape, e.g., of nucleic acid delivered to cells. Helper lipids are also believed to be a key structural component to the surface of the LNP.

Homology: As used herein, the term "homology" refers to the overall relatedness between polymeric molecules, e.g. between nucleic acid molecules (e.g. DNA molecules and/or RNA molecules) and/or between polypeptide molecules. Generally, the term "homology" implies an evolutionary relationship between two molecules. Thus, two molecules that are homologous will have a common evolutionary ancestor. In the context of the present invention, the term homology encompasses both to identity and similarity.

In some embodiments, polymeric molecules are considered to be "homologous" to one another if at least 25%, 30%, 35%, 40%, 45%, 50%, 55%, 60%, 65%, 70%, 75%, 80%, 85%, 90%, 95%, or 99% of the monomers in the molecule are identical (exactly the same monomer) or are similar (conservative substitutions). The term "homologous" necessarily refers to a comparison between at least two sequences (polynucleotide or polypeptide sequences).

Identity: As used herein, the term "identity" refers to the overall monomer conservation between polymeric molecules, e.g., between polynucleotide molecules (e.g. DNA molecules and/or RNA molecules) and/or between polypeptide molecules. Calculation of the percent identity of two polynucleotide sequences, for example, can be performed by aligning the two sequences for optimal comparison purposes (e.g., gaps can be introduced in one or both of a first and a second nucleic acid sequences for optimal alignment and non-identical sequences can be disregarded for comparison purposes). In certain embodiments, the length of a sequence aligned for comparison purposes is at least 30%, at least 40%, at least 50%, at least 60%, at least 70%, at least 80%, at least 90%, at least 95%, or 100% of the length of the reference sequence. The nucleotides at corresponding nucleotide positions are then compared. When a position in the first sequence is occupied by the same nucleotide as the corresponding position in the second sequence, then the molecules are identical at that position. The percent identity between the two sequences is a function of the number of identical positions shared by the sequences, taking into account the number of gaps, and the length of each gap, which needs to be introduced for optimal alignment of the two sequences. The comparison of sequences and determination of percent identity between two sequences can be accomplished using a mathematical algorithm. When comparing DNA and RNA, thymine (T) and uracil (U) can be considered equivalent.

Suitable software programs are available from various sources, and for alignment of both protein and nucleotide sequences. One suitable program to determine percent sequence identity is bl2seq, part of the BLAST suite of program available from the U.S. government's National Center for Biotechnology Information BLAST web site (blast.ncbi.nlm.nih.gov). Bl2seq performs a comparison between two sequences using either the BLASTN or BLASTP algorithm. BLASTN is used to compare nucleic acid sequences, while BLASTP is used to compare amino acid sequences. Other suitable programs are, e.g., Needle, Stretcher, Water, or Matcher, part of the EMBOSS suite of bioinformatics programs and also available from the European Bioinformatics Institute (EBI) at www.ebi.ac.uk/Tools/psa.

Sequence alignments can be conducted using methods known in the art such as MAFFT, Clustal (ClustalW, Clustal X or Clustal Omega), MUSCLE, etc.

Different regions within a single polynucleotide or polypeptide target sequence that aligns with a polynucleotide or polypeptide reference sequence can each have their own percent sequence identity. It is noted that the percent sequence identity value is rounded to the nearest tenth. For example, 80.11, 80.12, 80.13, and 80.14 are rounded down to 80.1, while 80.15, 80.16, 80.17, 80.18, and 80.19 are rounded up to 80.2. It also is noted that the length value will always be an integer.

In certain aspects, the percentage identity "% ID" of a first amino acid sequence (or nucleic acid sequence) to a second amino acid sequence (or nucleic acid sequence) is calculated as % ID=100×(Y/Z), where Y is the number of amino acid residues (or nucleobases) scored as identical matches in the alignment of the first and second sequences (as aligned by visual inspection or a particular sequence alignment program) and Z is the total number of residues in the second sequence. If the length of a first sequence is longer than the second sequence, the percent identity of the first sequence to the second sequence will be higher than the percent identity of the second sequence to the first sequence.

One skilled in the art will appreciate that the generation of a sequence alignment for the calculation of a percent sequence identity is not limited to binary sequence-sequence comparisons exclusively driven by primary sequence data. It will also be appreciated that sequence alignments can be generated by integrating sequence data with data from heterogeneous sources such as structural data (e.g., crystallographic protein structures), functional data (e.g., location of mutations), or phylogenetic data. A suitable program that integrates heterogeneous data to generate a multiple sequence alignment is T-Coffee, available at www.tcoffee.org, and alternatively available, e.g., from the EBI. It will also be appreciated that the final alignment used to calculate percent sequence identity can be curated either automatically or manually.

Immune response: The term "immune response" refers to the action of, for example, lymphocytes, antigen presenting cells, phagocytic cells, granulocytes, and soluble macromolecules produced by the above cells or the liver (including antibodies, cytokines, and complement) that results in selective damage to, destruction of, or elimination from the human body of invading pathogens, cells or tissues infected with pathogens, cancerous cells, or, in cases of autoimmunity or pathological inflammation, normal human cells or tissues. In some cases, the administration of a nanoparticle comprising a lipid component and an encapsulated therapeutic agent can trigger an immune response, which can be caused by (i) the encapsulated therapeutic agent (e.g., an mRNA), (ii) the expression product of such encapsulated therapeutic agent (e.g., a polypeptide encoded by the mRNA), (iii) the lipid component of the nanoparticle, or (iv) a combination thereof.

Inflammatory response: "Inflammatory response" refers to immune responses involving specific and non-specific defense systems. A specific defense system reaction is a specific immune system reaction to an antigen. Examples of specific defense system reactions include antibody responses. A non-specific defense system reaction is an inflammatory response mediated by leukocytes generally incapable of immunological memory, e.g., macrophages, eosinophils and neutrophils. In some aspects, an immune response includes the secretion of inflammatory cytokines, resulting in elevated inflammatory cytokine levels.

Inflammatory cytokines: The term "inflammatory cytokine" refers to cytokines that are elevated in an inflammatory response. Examples of inflammatory cytokines include interleukin-6 (IL-6), CXCL1 (chemokine (C—X—C motif) ligand 1; also known as GROα, interferon-γ (IFNγ), tumor necrosis factor α (TNFα), interferon γ-induced protein 10 (IP-10), or granulocyte-colony stimulating factor (G-CSF). The term inflammatory cytokines includes also other cytokines associated with inflammatory responses known in the art, e.g., interleukin-1 (IL-1), interleukin-8 (IL-8), interleukin-12 (IL-12), interleukin-13 (Il-13), interferon α (IFN-α), etc.

In Vitro: As used herein, the term "in vitro" refers to events that occur in an artificial environment, e.g., in a test tube or reaction vessel, in cell culture, in a Petri dish, etc., rather than within an organism (e.g., animal, plant, or microbe).

In Vivo: As used herein, the term "in vivo" refers to events that occur within an organism (e.g., animal, plant, or microbe or cell or tissue thereof).

Insertional and deletional variants: "Insertional variants" when referring to polypeptides are those with one or more amino acids inserted immediately adjacent to an amino acid at a particular position in a native or starting sequence. "Immediately adjacent" to an amino acid means connected to either the alpha-carboxy or alpha-amino functional group of the amino acid. "Deletional variants" when referring to polypeptides are those with one or more amino acids in the native or starting amino acid sequence removed. Ordinarily, deletional variants will have one or more amino acids deleted in a particular region of the molecule.

Intact: As used herein, in the context of a polypeptide, the term "intact" means retaining an amino acid corresponding to the wild type protein, e.g., not mutating or substituting the wild type amino acid. Conversely, in the context of a nucleic acid, the term "intact" means retaining a nucleobase corresponding to the wild type nucleic acid, e.g., not mutating or substituting the wild type nucleobase.

Ionizable amino lipid: The term "ionizable amino lipid" includes those lipids having one, two, three, or more fatty acid or fatty alkyl chains and a pH-titratable amino head group (e.g., an alkylamino or dialkylamino head group). An ionizable amino lipid is typically protonated (i.e., positively charged) at a pH below the pKa of the amino head group and is substantially not charged at a pH above the pKa. Such ionizable amino lipids include, but are not limited to DLin-MC3-DMA (MC3) and (13Z,16Z)—N,N-dimethyl-3-nonydocosa-13-16-dien-1-amine (L608).

Isolated: As used herein, the term "isolated" refers to a substance or entity that has been separated from at least some of the components with which it was associated (whether in nature or in an experimental setting). Isolated substances (e.g., polynucleotides or polypeptides) can have varying levels of purity in reference to the substances from which they have been isolated. Isolated substances and/or entities can be separated from at least about 10%, about 20%, about 30%, about 40%, about 50%, about 60%, about 70%, about 80%, about 90%, or more of the other components with which they were initially associated. In some embodiments, isolated substances are more than about 80%, about 85%, about 90%, about 91%, about 92%, about 93%, about 94%, about 95%, about 96%, about 97%, about 98%, about 99%, or more than about 99% pure. As used herein, a substance is "pure" if it is substantially free of other components.

Substantially isolated: By "substantially isolated" is meant that the compound is substantially separated from the environment in which it was formed or detected. Partial separation can include, for example, a composition enriched in the compound of the present disclosure. Substantial separation can include compositions containing at least about 50%, at least about 60%, at least about 70%, at least about 80%, at least about 90%, at least about 95%, at least about 97%, or at least about 99% by weight of the compound of the present disclosure, or salt thereof.

A polynucleotide, vector, polypeptide, cell, or any composition disclosed herein which is "isolated" is a polynucleotide, vector, polypeptide, cell, or composition which is in a form not found in nature. Isolated polynucleotides, vectors, polypeptides, or compositions include those which have been purified to a degree that they are no longer in a form in which they are found in nature. In some aspects, a polynucleotide, vector, polypeptide, or composition which is isolated is substantially pure.

Isomer: As used herein, the term "isomer" means any tautomer, stereoisomer, enantiomer, or diastereomer of any compound of the invention. It is recognized that the compounds of the invention can have one or more chiral centers and/or double bonds and, therefore, exist as stereoisomers, such as double-bond isomers (i.e., geometric E/Z isomers) or diastereomers (e.g., enantiomers (i.e., (+) or (−)) or cis/trans isomers). According to the invention, the chemical structures depicted herein, and therefore the compounds of the invention, encompass all of the corresponding stereoisomers, that is, both the stereomerically pure form (e.g., geometrically pure, enantiomerically pure, or diastereomerically pure) and enantiomeric and stereoisomeric mixtures, e.g., racemates. Enantiomeric and stereoisomeric mixtures of compounds of the invention can typically be resolved into their component enantiomers or stereoisomers by well-known methods, such as chiral-phase gas chromatography, chiral-phase high performance liquid chromatography, crystallizing the compound as a chiral salt complex, or crystallizing the compound in a chiral solvent. Enantiomers and stereoisomers can also be obtained from stereomerically or enantiomerically pure intermediates, reagents, and catalysts by well-known asymmetric synthetic methods.

Linker: As used herein, a "linker" refers to a group of atoms, e.g., 10-1,000 atoms, and can be comprised of the atoms or groups such as, but not limited to, carbon, amino, alkylamino, oxygen, sulfur, sulfoxide, sulfonyl, carbonyl, and imine. The linker can be attached to a modified nucleoside or nucleotide on the nucleobase or sugar moiety at a first end, and to a payload, e.g., a detectable or therapeutic agent, at a second end. The linker can be of sufficient length as to not interfere with incorporation into a nucleic acid sequence. The linker can be used for any useful purpose, such as to form polynucleotide multimers (e.g., through linkage of two or more chimeric polynucleotides molecules or IVT polynucleotides) or polynucleotides conjugates, as well as to administer a payload, as described herein. Examples of chemical groups that can be incorporated into the linker include, but are not limited to, alkyl, alkenyl, alkynyl, amido, amino, ether, thioether, ester, alkylene, heteroalkylene, aryl, or heterocyclyl, each of which can be optionally substituted, as described herein. Examples of linkers include, but are not limited to, unsaturated alkanes, polyethylene glycols (e.g., ethylene or propylene glycol monomeric units, e.g., diethylene glycol, dipropylene glycol, triethylene glycol, tripropylene glycol, tetraethylene glycol, or tetraethylene glycol), and dextran polymers and derivatives thereof, Other examples include, but are not limited to, cleavable moieties within the linker, such as, for example, a disulfide bond (—S—S—) or an azo bond (—N=N—), which can be cleaved using a reducing agent or photolysis. Non-limiting examples of a selectively cleavable bond include an amido bond can be cleaved for example by the use of tris(2-carboxyethyl)phosphine (TCEP), or other reducing agents, and/or photolysis, as well as an ester bond can be cleaved for example by acidic or basic hydrolysis.

Methods of Administration: As used herein, "methods of administration" can include intravenous, intramuscular, intradermal, subcutaneous, or other methods of delivering a composition to a subject. A method of administration can be selected to target delivery (e.g., to specifically deliver) to a specific region or system of a body.

Modified: As used herein "modified" refers to a changed state or structure of a molecule of the invention. Molecules can be modified in many ways including chemically, structurally, and functionally. In some embodiments, the mRNA molecules of the present invention are modified by the introduction of non-natural nucleosides and/or nucleotides, e.g., as it relates to the natural ribonucleotides A, U, G, and C. Noncanonical nucleotides such as the cap structures are not considered "modified" although they differ from the chemical structure of the A, C, G, U ribonucleotides.

Mucus: As used herein, "mucus" refers to the natural substance that is viscous and comprises mucin glycoproteins.

Nanoparticle Composition: As used herein, a "nanoparticle composition" is a composition comprising one or more lipids. Nanoparticle compositions are typically sized on the order of micrometers or smaller and can include a lipid bilayer. Nanoparticle compositions encompass lipid nanoparticles (LNPs), liposomes (e.g., lipid vesicles), and lipoplexes. For example, a nanoparticle composition can be a liposome having a lipid bilayer with a diameter of 500 nm or less.

Naturally occurring: As used herein, "naturally occurring" means existing in nature without artificial aid.

Non-human vertebrate: As used herein, a "non-human vertebrate" includes all vertebrates except *Homo sapiens*, including wild and domesticated species. Examples of non-human vertebrates include, but are not limited to, mammals, such as alpaca, banteng, bison, camel, cat, cattle, deer, dog, donkey, gayal, goat, guinea pig, horse, llama, mule, pig, rabbit, reindeer, sheep water buffalo, and yak.

Nucleic acid sequence: The terms "nucleic acid sequence," "nucleotide sequence," or "polynucleotide sequence" are used interchangeably and refer to a contiguous nucleic acid sequence. The sequence can be either single stranded or double stranded DNA or RNA, e.g., an mRNA.

The term "nucleic acid," in its broadest sense, includes any compound and/or substance that comprises a polymer of nucleotides. These polymers are often referred to as polynucleotides. Exemplary nucleic acids or polynucleotides of the invention include, but are not limited to, ribonucleic acids (RNAs), deoxyribonucleic acids (DNAs), threose nucleic acids (TNAs), glycol nucleic acids (GNAs), peptide nucleic acids (PNAs), locked nucleic acids (LNAs, including LNA having a β-D-ribo configuration, α-LNA having an α-L-ribo configuration (a diastereomer of LNA), 2'-amino-LNA having a 2'-amino functionalization, and 2'-amino-α-LNA having a 2'-amino functionalization), ethylene nucleic acids (ENA), cyclohexenyl nucleic acids (CeNA) or hybrids or combinations thereof.

The phrase "nucleotide sequence encoding" refers to the nucleic acid (e.g., an mRNA or DNA molecule) coding sequence which encodes a polypeptide. The coding sequence can further include initiation and termination signals operably linked to regulatory elements including a promoter and polyadenylation signal capable of directing expression in the cells of an individual or mammal to which the nucleic acid is administered. The coding sequence can further include sequences that encode signal peptides.

Off-target: As used herein, "off target" refers to any unintended effect on any one or more target, gene, or cellular transcript.

Open reading frame: As used herein, "open reading frame" or "ORF" refers to a sequence which does not contain a stop codon in a given reading frame.

Operably linked: As used herein, the phrase "operably linked" refers to a functional connection between two or more molecules, constructs, transcripts, entities, moieties or the like.

Optionally substituted: Herein a phrase of the form "optionally substituted X" (e.g., optionally substituted alkyl) is intended to be equivalent to "X, wherein X is optionally substituted" (e.g., "alkyl, wherein said alkyl is optionally substituted"). It is not intended to mean that the feature "X" (e.g., alkyl) per se is optional.

Part: As used herein, a "part" or "region" of a polynucleotide is defined as any portion of the polynucleotide that is less than the entire length of the polynucleotide.

Patient: As used herein, "patient" refers to a subject who can seek or be in need of treatment, requires treatment, is receiving treatment, will receive treatment, or a subject who is under care by a trained professional for a particular disease or condition. For example, AIP patients can suffer from acute attacks and can be treated during or after an acute attack (e.g., severe pain). Patients having reoccurring attacks can be treated "prophylactically", i.e., to reduce the risk of or prevent recurring attacks.

PBGD Associated Disease: As use herein the terms "PBGD-associated disease" or "PBGD-associated disorder" refer to diseases or disorders, respectively, which result from aberrant PBGD activity (e.g., decreased activity or increased activity). As a non-limiting example, acute intermittent porphyria is a PBGD associated disease. Numerous clinical variants of acute intermittent porphyria are know in the art. See, e.g., www.omim.org/entry/609806.

The terms "PBGD enzymatic activity," "PBGD activity," and "porphobilinogen deaminase activity" are used interchangeably in the present disclosure and refer to PBGD's ability to catalyze the stepwise enzymatic condensation of 4 porphobilinogen units into hydroxymethylbilane. Accordingly, a fragment or variant retaining or having PBGD enzymatic activity or PBGD activity refers to a fragment or variant that has measurable enzymatic catalyzing the enzymatic condensation of porphobilinogen units into hydroxymethylbilane.

Pharmaceutically acceptable: The phrase "pharmaceutically acceptable" is employed herein to refer to those compounds, materials, compositions, and/or dosage forms that are, within the scope of sound medical judgment, suitable for use in contact with the tissues of human beings and animals without excessive toxicity, irritation, allergic response, or other problem or complication, commensurate with a reasonable benefit/risk ratio.

Pharmaceutically acceptable excipients: The phrase "pharmaceutically acceptable excipient," as used herein, refers any ingredient other than the compounds described herein (for example, a vehicle capable of suspending or dissolving the active compound) and having the properties of being substantially nontoxic and non-inflammatory in a patient. Excipients can include, for example: antiadherents, antioxidants, binders, coatings, compression aids, disintegrants, dyes (colors), emollients, emulsifiers, fillers (diluents), film formers or coatings, flavors, fragrances, glidants (flow enhancers), lubricants, preservatives, printing inks, sorbents, suspending or dispersing agents, sweeteners, and waters of hydration. Exemplary excipients include, but are not limited to: butylated hydroxytoluene (BHT), calcium carbonate, calcium phosphate (dibasic), calcium stearate, croscarmellose, crosslinked polyvinyl pyrrolidone, citric acid, crospovidone, cysteine, ethylcellulose, gelatin, hydroxypropyl cellulose, hydroxypropyl methylcellulose, lactose, magnesium stearate, maltitol, mannitol, methionine, methylcellulose, methyl paraben, microcrystalline cellulose, polyethylene glycol, polyvinyl pyrrolidone, povidone, pregelatinized starch, propyl paraben, retinyl palmitate, shellac, silicon dioxide, sodium carboxymethyl cellulose, sodium citrate, sodium starch glycolate, sorbitol, starch (corn), stearic acid, sucrose, talc, titanium dioxide, vitamin A, vitamin E, vitamin C, and xylitol.

Pharmaceutically acceptable salts: The present disclosure also includes pharmaceutically acceptable salts of the compounds described herein. As used herein, "pharmaceutically acceptable salts" refers to derivatives of the disclosed compounds wherein the parent compound is modified by converting an existing acid or base moiety to its salt form (e.g., by reacting the free base group with a suitable organic acid). Examples of pharmaceutically acceptable salts include, but are not limited to, mineral or organic acid salts of basic residues such as amines; alkali or organic salts of acidic residues such as carboxylic acids; and the like. Representative acid addition salts include acetate, acetic acid, adipate, alginate, ascorbate, aspartate, benzenesulfonate, benzene sulfonic acid, benzoate, bisulfate, borate, butyrate, camphorate, camphorsulfonate, citrate, cyclopentanepropionate, digluconate, dodecylsulfate, ethanesulfonate, fumarate, glucoheptonate, glycerophosphate, hemisulfate, heptonate, hexanoate, hydrobromide, hydrochloride, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, toluenesulfonate, undecanoate, valerate salts, and the like. Representative alkali or alkaline earth metal salts include sodium, lithium, potassium, calcium, magnesium, and the like, as well as nontoxic ammonium, quaternary ammonium, and amine cations, including, but not limited to ammonium, tetramethylammonium, tetraethylammonium, methylamine, dimethylamine, trimethylamine, triethylamine, ethylamine, and the like. The pharmaceutically acceptable salts of the present disclosure include the conventional non-toxic salts of the parent compound formed, for example, from non-toxic inorganic or organic acids. The pharmaceutically acceptable salts of the present disclosure can be synthesized from the parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are used. Lists of suitable salts are found in *Remington's Pharmaceutical Sciences*, 17$^{th}$ ed., Mack Publishing Company, Easton, Pa., 1985, p. 1418, *Pharmaceutical Salts: Properties, Selection, and Use*, P. H. Stahl and C. G. Wermuth (eds.), Wiley-VCH, 2008, and Berge et al., *Journal of Pharmaceutical Science*, 66, 1-19 (1977), each of which is incorporated herein by reference in its entirety.

Pharmaceutically acceptable solvate: The term "pharmaceutically acceptable solvate," as used herein, means a compound of the invention wherein molecules of a suitable solvent are incorporated in the crystal lattice. A suitable solvent is physiologically tolerable at the dosage administered. For example, solvates can be prepared by crystallization, recrystallization, or precipitation from a solution that includes organic solvents, water, or a mixture thereof. Examples of suitable solvents are ethanol, water (for example, mono-, di-, and tri-hydrates), N-methylpyrrolidinone (NMP), dimethyl sulfoxide (DMSO), N,N'-dimethylformamide (DMF), N,N'-dimethylacetamide (DMAC), 1,3-dimethyl-2-imidazolidinone (DMEU), 1,3-dimethyl-3,4,5,6-tetrahydro-2-(1H)-pyrimidinone (DMPU), acetonitrile (ACN), propylene glycol, ethyl acetate, benzyl alcohol, 2-pyrrolidone, benzyl benzoate, and the like. When water is the solvent, the solvate is referred to as a "hydrate."

Pharmacokinetic: As used herein, "pharmacokinetic" refers to any one or more properties of a molecule or compound as it relates to the determination of the fate of substances administered to a living organism. Pharmacokinetics is divided into several areas including the extent and rate of absorption, distribution, metabolism and excretion. This is commonly referred to as ADME where: (A) Absorption is the process of a substance entering the blood circulation; (D) Distribution is the dispersion or dissemination of substances throughout the fluids and tissues of the body; (M) Metabolism (or Biotransformation) is the irreversible transformation of parent compounds into daughter metabolites; and (E) Excretion (or Elimination) refers to the elimination of the substances from the body. In rare cases, some drugs irreversibly accumulate in body tissue.

Physicochemical: As used herein, "physicochemical" means of or relating to a physical and/or chemical property.

Polynucleotide: The term "polynucleotide" as used herein refers to polymers of nucleotides of any length, including ribonucleotides, deoxyribonucleotides, analogs thereof, or mixtures thereof. This term refers to the primary structure of the molecule. Thus, the term includes triple-, double- and single-stranded deoxyribonucleic acid ("DNA"), as well as triple-, double- and single-stranded ribonucleic acid ("RNA"). It also includes modified, for example by alkylation, and/or by capping, and unmodified forms of the polynucleotide. More particularly, the term "polynucleotide" includes polydeoxyribonucleotides (containing 2-deoxy-D-ribose), polyribonucleotides (containing D-ribose), including tRNA, rRNA, hRNA, siRNA and mRNA, whether spliced or unspliced, any other type of polynucleotide which is an N- or C-glycoside of a purine or pyrimidine base, and other polymers containing normucleotidic backbones, for example, polyamide (e.g., peptide nucleic acids "PNAs") and polymorpholino polymers, and other synthetic sequence-specific nucleic acid polymers providing that the polymers contain nucleobases in a configuration which allows for base pairing and base stacking, such as is found in DNA and RNA. In particular aspects, the polynucleotide comprises an mRNA. In other aspect, the mRNA is a synthetic mRNA. In some aspects, the synthetic mRNA comprises at least one unnatural nucleobase. In some aspects, all nucleobases of a certain class have been replaced with unnatural nucleobases (e.g., all uridines in a polynucleotide disclosed herein can be replaced with an unnatural nucleobase, e.g., 5-methoxyuridine). In some aspects, the polynucleotide (e.g., a synthetic RNA or a synthetic DNA) comprises only natural nucleobases, i.e., A (adenosine), G (guanosine), C (cytidine), and T (thymidine) in the case of a synthetic DNA, or A, C, G, and U (uridine) in the case of a synthetic RNA.

The skilled artisan will appreciate that the T bases in the codon maps disclosed herein are present in DNA, whereas the T bases would be replaced by U bases in corresponding RNAs. For example, a codon-nucleotide sequence disclosed herein in DNA form, e.g., a vector or an in-vitro translation (IVT) template, would have its T bases transcribed as U based in its corresponding transcribed mRNA. In this respect, both codon-optimized DNA sequences (comprising T) and their corresponding mRNA sequences (comprising U) are considered codon-optimized nucleotide sequence of the present invention. A skilled artisan would also understand that equivalent codon-maps can be generated by replaced one or more bases with non-natural bases. Thus, e.g., a TTC codon (DNA map) would correspond to a UUC codon (RNA map), which in turn would correspond to a ΨΨC codon (RNA map in which U has been replaced with pseudouridine).

Standard A-T and G-C base pairs form under conditions which allow the formation of hydrogen bonds between the N3-H and C4-oxy of thymidine and the N1 and C6-NH2, respectively, of adenosine and between the C2-oxy, N3 and C4-NH2, of cytidine and the C2-NH2, N'—H and C6-oxy, respectively, of guanosine. Thus, for example, guanosine (2-amino-6-oxy-9-β-D-ribofuranosyl-purine) can be modified to form isoguanosine (2-oxy-6-amino-9-β-D-ribofuranosyl-purine). Such modification results in a nucleoside base which will no longer effectively form a standard base pair with cytosine. However, modification of cytosine (1β-D-ribofuranosyl-2-oxy-4-amino-pyrimidine) to form isocytosine (1β-D-ribofuranosyl-2-amino-4-oxy-pyrimidine-) results in a modified nucleotide which will not effectively base pair with guanosine but will form a base pair with isoguanosine (U.S. Pat. No. 5,681,702 to Collins et al.). Isocytosine is available from Sigma Chemical Co. (St. Louis, Mo.); isocytidine can be prepared by the method described by Switzer et al. (1993) Biochemistry 32:10489-10496 and references cited therein; 2'-deoxy-5-methyl-isocytidine can be prepared by the method of Tor et al., 1993, J. Am. Chem. Soc. 115:4461-4467 and references cited therein; and isoguanine nucleotides can be prepared using the method described by Switzer et al., 1993, supra, and Mantsch et al., 1993, Biochem. 14:5593-5601, or by the method described in U.S. Pat. No. 5,780,610 to Collins et al. Other nonnatural base pairs can be synthesized by the method described in Piccirilli et al., 1990, Nature 343:33-37, for the synthesis of 2,6-diaminopyrimidine and its complement (1-methylpyrazolo-[4,3]pyrimidine-5,7-(4H,6H)-dione. Other such modified nucleotide units which form unique base pairs are known, such as those described in Leach et al. (1992) J. Am. Chem. Soc. 114:3675-3683 and Switzer et al., supra.

Polypeptide: The terms "polypeptide," "peptide," and "protein" are used interchangeably herein to refer to polymers of amino acids of any length. The polymer can comprise modified amino acids. The terms also encompass an amino acid polymer that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids such as homocysteine, ornithine, p-acetylphenylalanine, D-amino acids, and creatine), as well as other modifications known in the art.

The term, as used herein, refers to proteins, polypeptides, and peptides of any size, structure, or function. Polypeptides include encoded polynucleotide products, naturally occurring polypeptides, synthetic polypeptides, homologs, orthologs, paralogs, fragments and other equivalents, variants, and analogs of the foregoing. A polypeptide can be a monomer or can be a multi-molecular complex such as a dimer, trimer or tetramer. They can also comprise single chain or multichain polypeptides. Most commonly disulfide linkages are found in multichain polypeptides. The term polypeptide can also apply to amino acid polymers in which one or more amino acid residues are an artificial chemical analogue of a corresponding naturally occurring amino acid. In some embodiments, a "peptide" can be less than or equal to 50 amino acids long, e.g., about 5, 10, 15, 20, 25, 30, 35, 40, 45, or 50 amino acids long.

Polypeptide variant: As used herein, the term "polypeptide variant" refers to molecules that differ in their amino acid sequence from a native or reference sequence. The amino acid sequence variants can possess substitutions, deletions, and/or insertions at certain positions within the amino acid sequence, as compared to a native or reference sequence. Ordinarily, variants will possess at least about 50% identity, at least about 60% identity, at least about 70% identity, at least about 80% identity, at least about 90% identity, at least about 95% identity, at least about 99% identity to a native or reference sequence. In some embodiments, they will be at least about 80%, or at least about 90% identical to a native or reference sequence.

Polypeptide per unit drug (PUD): As used herein, a PUD or product per unit drug, is defined as a subdivided portion of total daily dose, usually 1 mg, pg, kg, etc., of a product (such as a polypeptide) as measured in body fluid or tissue, usually defined in concentration such as pmol/mL, mmol/mL, etc. divided by the measure in the body fluid.

Preventing: As used herein, the term "preventing" refers to partially or completely delaying onset of an infection, disease, disorder and/or condition; partially or completely delaying onset of one or more signs, symptoms, features, or clinical manifestations of a particular infection, disease, disorder, and/or condition; partially or completely delaying onset of one or more signs, symptoms, features, or manifestations of a particular infection, disease, disorder, and/or condition; partially or completely delaying progression from an infection, a particular disease, disorder and/or condition; and/or decreasing the risk of developing pathology associated with the infection, the disease, disorder, and/or condition.

Proliferate: As used herein, the term "proliferate" means to grow, expand or increase or cause to grow, expand or increase rapidly. "Proliferative" means having the ability to proliferate. "Anti-proliferative" means having properties counter to or inapposite to proliferative properties.

Prophylactic: As used herein, "prophylactic" refers to a therapeutic or course of action used to prevent the spread of disease.

Prophylaxis: As used herein, a "prophylaxis" refers to a measure taken to maintain health and prevent the spread of disease. An "immune prophylaxis" refers to a measure to produce active or passive immunity to prevent the spread of disease.

Protein cleavage site: As used herein, "protein cleavage site" refers to a site where controlled cleavage of the amino acid chain can be accomplished by chemical, enzymatic or photochemical means.

Protein cleavage signal: As used herein "protein cleavage signal" refers to at least one amino acid that flags or marks a polypeptide for cleavage.

Protein of interest: As used herein, the terms "proteins of interest" or "desired proteins" include those provided herein and fragments, mutants, variants, and alterations thereof.

Proximal: As used herein, the term "proximal" means situated nearer to the center or to a point or region of interest.

Pseudouridine: As used herein, pseudouridine ($\psi$) refers to the C-glycoside isomer of the nucleoside uridine. A "pseudouridine analog" is any modification, variant, isoform or derivative of pseudouridine. For example, pseudouridine analogs include but are not limited to 1-carboxymethyl-pseudouridine, 1-propynyl-pseudouridine, 1-taurinomethyl-pseudouridine, 1-taurinomethyl-4-thio-pseudouridine, 1-methylpseudouridine ($m^1\psi$), 1-methyl-4-thio-pseudouridine ($m^1s^4\psi$), 4-thio-1-methyl-pseudouridine, 3-methyl-pseudouridine ($m^3\psi$), 2-thio-1-methyl-pseudouridine, 1-methyl-1-deaza-pseudouridine, 2-thio-1-methyl-1-deaza-pseudouridine, dihydropseudouridine, 2-thio-dihydropseudouridine, 2-methoxyuridine, 2-methoxy-4-thio-uridine, 4-methoxy-pseudouridine, 4-methoxy-2-thio-pseudouridine, N1-methyl-pseudouridine, 1-methyl-3-(3-amino-3-carboxypropyl)pseudouridine ($acp^3\psi$), and 2'-O-methyl-pseudouridine ($\psi m$).

Purified: As used herein, "purify," "purified," "purification" means to make substantially pure or clear from unwanted components, material defilement, admixture or imperfection.

Reference Nucleic Acid Sequence: The term "reference nucleic acid sequence" or "reference nucleic acid" or "reference nucleotide sequence" or "reference sequence" refers to a starting nucleic acid sequence (e.g., a RNA, e.g., an mRNA sequence) that can be sequence optimized. In some embodiments, the reference nucleic acid sequence is a wild type nucleic acid sequence, a fragment or a variant thereof. In some embodiments, the reference nucleic acid sequence is a previously sequence optimized nucleic acid sequence.

Salts: In some aspects, the pharmaceutical composition for delivery disclosed herein and comprises salts of some of their lipid constituents. The term "salt" includes any anionic and cationic complex. Non-limiting examples of anions include inorganic and organic anions, e.g., fluoride, chloride, bromide, iodide, oxalate (e.g., hemioxalate), phosphate, phosphonate, hydrogen phosphate, dihydrogen phosphate, oxide, carbonate, bicarbonate, nitrate, nitrite, nitride, bisulfate, sulfide, sulfite, bisulfate, sulfate, thiosulfate, hydrogen sulfate, borate, formate, acetate, benzoate, citrate, tartrate, lactate, acrylate, polyacrylate, fumarate, maleate, itaconate, glycolate, gluconate, malate, mandelate, tiglate, ascorbate, salicylate, polymethacrylate, perchlorate, chlorate, chlorite, hypochlorite, bromate, hypobromite, iodate, an alkylsulfonate, an arylsulfonate, arsenate, arsenite, chromate, dichromate, cyanide, cyanate, thiocyanate, hydroxide, peroxide, permanganate, and mixtures thereof.

Sample: As used herein, the term "sample" or "biological sample" refers to a subset of its tissues, cells or component parts (e.g., body fluids, including but not limited to blood, mucus, lymphatic fluid, synovial fluid, cerebrospinal fluid, saliva, amniotic fluid, amniotic cord blood, urine, vaginal fluid and semen). A sample further can include a homogenate, lysate or extract prepared from a whole organism or a subset of its tissues, cells or component parts, or a fraction or portion thereof, including but not limited to, for example, plasma, serum, spinal fluid, lymph fluid, the external sections of the skin, respiratory, intestinal, and genitourinary tracts, tears, saliva, milk, blood cells, tumors, or organs. A sample further refers to a medium, such as a nutrient broth or gel, which can contain cellular components, such as proteins or nucleic acid molecule.

Signal Sequence: As used herein, the phrases "signal sequence," "signal peptide," and "transit peptide" are used interchangeably and refer to a sequence that can direct the transport or localization of a protein to a certain organelle, cell compartment, or extracellular export. The term encompasses both the signal sequence polypeptide and the nucleic acid sequence encoding the signal sequence. Thus, references to a signal sequence in the context of a nucleic acid refer in fact to the nucleic acid sequence encoding the signal sequence polypeptide.

Signal transduction pathway: A "signal transduction pathway" refers to the biochemical relationship between a variety of signal transduction molecules that play a role in the transmission of a signal from one portion of a cell to another portion of a cell. As used herein, the phrase "cell surface receptor" includes, for example, molecules and complexes of molecules capable of receiving a signal and the transmission of such a signal across the plasma membrane of a cell.

Similarity: As used herein, the term "similarity" refers to the overall relatedness between polymeric molecules, e.g. between polynucleotide molecules (e.g. DNA molecules and/or RNA molecules) and/or between polypeptide molecules. Calculation of percent similarity of polymeric molecules to one another can be performed in the same manner as a calculation of percent identity, except that calculation of percent similarity takes into account conservative substitutions as is understood in the art.

Single unit dose: As used herein, a "single unit dose" is a dose of any therapeutic administered in one dose/at one time/single route/single point of contact, i.e., single administration event.

Split dose: As used herein, a "split dose" is the division of single unit dose or total daily dose into two or more doses.

Specific delivery: As used herein, the term "specific delivery," "specifically deliver," or "specifically delivering" means delivery of more (e.g., at least 1.5 fold more, at least 2-fold more, at least 3-fold more, at least 4-fold more, at least 5-fold more, at least 6-fold more, at least 7-fold more, at least 8-fold more, at least 9-fold more, at least 10-fold more) of a polynucleotide by a nanoparticle to a target tissue of interest (e.g., mammalian liver) compared to an off-target tissue (e.g., mammalian spleen). The level of delivery of a nanoparticle to a particular tissue can be measured by comparing the amount of protein produced in a tissue to the weight of said tissue, comparing the amount of polynucleotide in a tissue to the weight of said tissue, comparing the amount of protein produced in a tissue to the amount of total protein in said tissue, or comparing the amount of polynucleotide in a tissue to the amount of total polynucleotide in said tissue. For example, for renovascular targeting, a polynucleotide is specifically provided to a mammalian kidney as compared to the liver and spleen if 1.5, 2-fold, 3-fold, 5-fold, 10-fold, 15 fold, or 20 fold more polynucleotide per 1 g of tissue is delivered to a kidney compared to that delivered to the liver or spleen following systemic administration of the polynucleotide. It will be understood that the ability of a nanoparticle to specifically deliver to a target tissue need not be determined in a subject being treated, it can be determined in a surrogate such as an animal model (e.g., a rat model).

Stable: As used herein "stable" refers to a compound that is sufficiently robust to survive isolation to a useful degree of purity from a reaction mixture, and in some cases capable of formulation into an efficacious therapeutic agent.

Stabilized: As used herein, the term "stabilize," "stabilized," "stabilized region" means to make or become stable.

Stereoisomer: As used herein, the term "stereoisomer" refers to all possible different isomeric as well as conformational forms that a compound can possess (e.g., a compound of any formula described herein), in particular all possible stereochemically and conformationally isomeric forms, all diastereomers, enantiomers and/or conformers of the basic molecular structure. Some compounds of the present invention can exist in different tautomeric forms, all of the latter being included within the scope of the present invention.

Subject: By "subject" or "individual" or "animal" or "patient" or "mammal," is meant any subject, particularly a mammalian subject, for whom diagnosis, prognosis, or therapy is desired. Mammalian subjects include, but are not limited to, humans, domestic animals, farm animals, zoo animals, sport animals, pet animals such as dogs, cats, guinea pigs, rabbits, rats, mice, horses, cattle, cows; primates such as apes, monkeys, orangutans, and chimpanzees; canids such as dogs and wolves; felids such as cats, lions, and tigers; equids such as horses, donkeys, and zebras; bears, food animals such as cows, pigs, and sheep; ungulates such as deer and giraffes; rodents such as mice, rats, hamsters and guinea pigs; and so on. In certain embodiments, the mammal is a human subject. In other embodiments, a subject is a human patient. In a particular embodiment, a subject is a human patient in need of treatment.

Substantially: As used herein, the term "substantially" refers to the qualitative condition of exhibiting total or near-total extent or degree of a characteristic or property of interest. One of ordinary skill in the biological arts will understand that biological and chemical characteristics rarely, if ever, go to completion and/or proceed to completeness or achieve or avoid an absolute result. The term "substantially" is therefore used herein to capture the potential lack of completeness inherent in many biological and chemical characteristics.

Substantially equal: As used herein as it relates to time differences between doses, the term means plus/minus 2%.

Substantially simultaneous: As used herein and as it relates to plurality of doses, the term means within 2 seconds.

Suffering from: An individual who is "suffering from" a disease, disorder, and/or condition has been diagnosed with or displays one or more signs or symptoms of the disease, disorder, and/or condition.

Susceptible to: An individual who is "susceptible to" a disease, disorder, and/or condition has not been diagnosed with and/or cannot exhibit signs or symptoms of the disease, disorder, and/or condition but harbors a propensity to develop a disease or its signs or symptoms. In some embodiments, an individual who is susceptible to a disease, disorder, and/or condition (for example, AIP) can be characterized by one or more of the following: (1) a genetic mutation associated with development of the disease, disorder, and/or condition; (2) a genetic polymorphism associated with development of the disease, disorder, and/or condition; (3) increased and/or decreased expression and/or activity of a protein and/or nucleic acid associated with the disease, disorder, and/or condition; (4) habits and/or lifestyles associated with development of the disease, disorder, and/or condition; (5) a family history of the disease, disorder, and/or condition; and (6) exposure to and/or infection with a microbe associated with development of the disease, disorder, and/or condition. In some embodiments, an individual who is susceptible to a disease, disorder, and/or condition will develop the disease, disorder, and/or condition. In some embodiments, an individual who is susceptible to a disease, disorder, and/or condition will not develop the disease, disorder, and/or condition.

Sustained release: As used herein, the term "sustained release" refers to a pharmaceutical composition or compound release profile that conforms to a release rate over a specific period of time.

Synthetic: The term "synthetic" means produced, prepared, and/or manufactured by the hand of man. Synthesis of polynucleotides or other molecules of the present invention can be chemical or enzymatic.

Targeted Cells: As used herein, "targeted cells" refers to any one or more cells of interest. The cells can be found in vitro, in vivo, in situ or in the tissue or organ of an organism. The organism can be an animal, for example a mammal, a human, a subject or a patient.

Target tissue: As used herein "target tissue" refers to any one or more tissue types of interest in which the delivery of a polynucleotide would result in a desired biological and/or pharmacological effect. Examples of target tissues of interest include specific tissues, organs, and systems or groups thereof. In particular applications, a target tissue can be a liver, a kidney, a lung, a spleen, or vascular endothelium in vessels (e.g., intra-coronary or intra-femoral). An "off-target tissue" refers to any one or more tissue types in which the expression of the encoded protein does not result in a desired biological and/or pharmacological effect.

The presence of a therapeutic agent in an off-target issue can be the result of: (i) leakage of a polynucleotide from the administration site to peripheral tissue or distant off-target tissue via diffusion or through the bloodstream (e.g., a polynucleotide intended to express a polypeptide in a certain tissue would reach the off-target tissue and the polypeptide would be expressed in the off-target tissue); or (ii) leakage of an polypeptide after administration of a polynucleotide encoding such polypeptide to peripheral tissue or distant off-target tissue via diffusion or through the bloodstream (e.g., a polynucleotide would expressed a polypeptide in the target tissue, and the polypeptide would diffuse to peripheral tissue).

Targeting sequence: As used herein, the phrase "targeting sequence" refers to a sequence that can direct the transport or localization of a protein or polypeptide.

Terminus: As used herein the terms "termini" or "terminus," when referring to polypeptides, refers to an extremity of a peptide or polypeptide. Such extremity is not limited only to the first or final site of the peptide or polypeptide but can include additional amino acids in the terminal regions. The polypeptide based molecules of the invention can be characterized as having both an N-terminus (terminated by an amino acid with a free amino group ($NH_2$)) and a C-terminus (terminated by an amino acid with a free carboxyl group (COOH)). Proteins of the invention are in some cases made up of multiple polypeptide chains brought together by disulfide bonds or by non-covalent forces (multimers, oligomers). These sorts of proteins will have multiple N- and C-termini. Alternatively, the termini of the polypeptides can be modified such that they begin or end, as the case can be, with a non-polypeptide based moiety such as an organic conjugate.

Therapeutic Agent: The term "therapeutic agent" refers to an agent that, when administered to a subject, has a therapeutic, diagnostic, and/or prophylactic effect and/or elicits a desired biological and/or pharmacological effect. For example, in some embodiments, an mRNA encoding a PBGD polypeptide can be a therapeutic agent.

Therapeutically effective amount: As used herein, the term "therapeutically effective amount" means an amount of an agent to be delivered (e.g., nucleic acid, drug, therapeutic agent, diagnostic agent, prophylactic agent, etc.) that is sufficient, when administered to a subject suffering from or susceptible to an infection, disease, disorder, and/or condition, to treat, improve signs or symptoms of, diagnose, prevent, and/or delay the onset of the infection, disease, disorder, and/or condition.

Therapeutically effective outcome: As used herein, the term "therapeutically effective outcome" means an outcome that is sufficient in a subject suffering from or susceptible to an infection, disease, disorder, and/or condition, to treat, improve signs or symptoms of, diagnose, prevent, and/or delay the onset of the infection, disease, disorder, and/or condition.

Total daily dose: As used herein, a "total daily dose" is an amount given or prescribed in 24 hr. period. The total daily dose can be administered as a single unit dose or a split dose.

Transcription factor: As used herein, the term "transcription factor" refers to a DNA-binding protein that regulates transcription of DNA into RNA, for example, by activation or repression of transcription. Some transcription factors effect regulation of transcription alone, while others act in concert with other proteins. Some transcription factor can both activate and repress transcription under certain conditions. In general, transcription factors bind a specific target sequence or sequences highly similar to a specific consensus sequence in a regulatory region of a target gene. Transcription factors can regulate transcription of a target gene alone or in a complex with other molecules.

Transcription: As used herein, the term "transcription" refers to methods to produce mRNA (e.g., an mRNA sequence or template) from DNA (e.g., a DNA template or sequence).

Transfection: As used herein, "transfection" refers to the introduction of a polynucleotide (e.g., exogenous nucleic acids) into a cell wherein a polypeptide encoded by the polynucleotide is expressed (e.g., mRNA) or the polypeptide modulates a cellular function (e.g., siRNA, miRNA). As used herein, "expression" of a nucleic acid sequence refers to translation of a polynucleotide (e.g., an mRNA) into a polypeptide or protein and/or post-translational modification of a polypeptide or protein. Methods of transfection include, but are not limited to, chemical methods, physical treatments and cationic lipids or mixtures.

Treating, treatment, therapy: As used herein, the term "treating" or "treatment" or "therapy" refers to partially or completely alleviating, ameliorating, improving, relieving, delaying onset of, inhibiting progression of, reducing severity of, and/or reducing incidence of one or more signs, symptoms or features of a disease, e.g., acute intermittent porphyria. For example, "treating" acute intermittent porphyria can refer to diminishing signs or symptoms associate with the disease, prolong the lifespan (increase the survival rate) of patients, reducing the severity of the disease, preventing or delaying the onset of the disease, etc. Treatment can be administered to a subject who does not exhibit signs of a disease, disorder, and/or condition and/or to a subject who exhibits only early signs of a disease, disorder, and/or condition for the purpose of decreasing the risk of developing pathology associated with the disease, disorder, and/or condition.

Unmodified: As used herein, "unmodified" refers to any substance, compound or molecule prior to being changed in some way. Unmodified can, but does not always, refer to the wild type or native form of a biomolecule. Molecules can undergo a series of modifications whereby each modified molecule can serve as the "unmodified" starting molecule for a subsequent modification.

Uracil: Uracil is one of the four nucleobases in the nucleic acid of RNA, and it is represented by the letter U. Uracil can be attached to a ribose ring, or more specifically, a ribofuranose via a $\beta$-$N_1$-glycosidic bond to yield the nucleoside uridine. The nucleoside uridine is also commonly abbreviated according to the one letter code of its nucleobase, i.e., U. Thus, in the context of the present disclosure, when a monomer in a polynucleotide sequence is U, such U is designated interchangeably as a "uracil" or a "uridine."

Uridine Content: The terms "uridine content" or "uracil content" are interchangeable and refer to the amount of uracil or uridine present in a certain nucleic acid sequence. Uridine content or uracil content can be expressed as an absolute value (total number of uridine or uracil in the sequence) or relative (uridine or uracil percentage respect to the total number of nucleobases in the nucleic acid sequence).

Uridine-Modified Sequence: The terms "uridine-modified sequence" refers to a sequence optimized nucleic acid (e.g., a synthetic mRNA sequence) with a different overall or local uridine content (higher or lower uridine content) or with different uridine patterns (e.g., gradient distribution or clustering) with respect to the uridine content and/or uridine patterns of a candidate nucleic acid sequence. In the content of the present disclosure, the terms "uridine-modified sequence" and "uracil-modified sequence" are considered equivalent and interchangeable.

A "high uridine codon" is defined as a codon comprising two or three uridines, a "low uridine codon" is defined as a codon comprising one uridine, and a "no uridine codon" is a codon without any uridines. In some embodiments, a uridine-modified sequence comprises substitutions of high uridine codons with low uridine codons, substitutions of high uridine codons with no uridine codons, substitutions of low uridine codons with high uridine codons, substitutions of low uridine codons with no uridine codons, substitution of no uridine codons with low uridine codons, substitutions of no uridine codons with high uridine codons, and combinations thereof. In some embodiments, a high uridine codon can be replaced with another high uridine codon. In some embodiments, a low uridine codon can be replaced with another low uridine codon. In some embodiments, a no uridine codon can be replaced with another no uridine codon. A uridine-modified sequence can be uridine enriched or uridine rarefied.

Uridine Enriched: As used herein, the terms "uridine enriched" and grammatical variants refer to the increase in uridine content (expressed in absolute value or as a percentage value) in an sequence optimized nucleic acid (e.g., a synthetic mRNA sequence) with respect to the uridine content of the corresponding candidate nucleic acid sequence. Uridine enrichment can be implemented by substituting codons in the candidate nucleic acid sequence with synonymous codons containing less uridine nucleobases. Uridine enrichment can be global (i.e., relative to the entire length of a candidate nucleic acid sequence) or local (i.e., relative to a subsequence or region of a candidate nucleic acid sequence).

Uridine Rarefied: As used herein, the terms "uridine rarefied" and grammatical variants refer to a decrease in uridine content (expressed in absolute value or as a percentage value) in an sequence optimized nucleic acid (e.g., a synthetic mRNA sequence) with respect to the uridine content of the corresponding candidate nucleic acid sequence. Uridine rarefication can be implemented by substituting codons in the candidate nucleic acid sequence with synonymous codons containing less uridine nucleobases. Uridine rarefication can be global (i.e., relative to the entire length of a candidate nucleic acid sequence) or local (i.e., relative to a subsequence or region of a candidate nucleic acid sequence).

Variant: The term variant as used in present disclosure refers to both natural variants (e.g, polymorphisms, isoforms, etc) and artificial variants in which at least one amino acid residue in a native or starting sequence (e.g., a wild type sequence) has been removed and a different amino acid inserted in its place at the same position. These variants can de described as "substitutional variants." The substitutions can be single, where only one amino acid in the molecule has been substituted, or they can be multiple, where two or more amino acids have been substituted in the same molecule. If amino acids are inserted or deleted, the resulting variant would be an "insertional variant" or a "deletional variant" respectively.

30. EMBODIMENTS

Throughout this section, the term embodiment is abbreviated as 'E' followed by an ordinal. For example, E1 is equivalent to Embodiment 1.

E1. A polynucleotide comprising an open reading frame (ORF) encoding a porphobilinogen deaminase (PBGD) polypeptide, wherein the uracil or thymine content of the ORF relative to the theoretical minimum uracil or thymine content of a nucleotide sequence encoding the PBGD polypeptide (% $U_{TM}$ or % $T_{TM}$), is between about 100% and about 150%.

E2. The polynucleotide of E1, wherein the % $U_{TM}$ or % $T_{TM}$ is between about 105% and about 145%, between about 105% and about 140%, between about 110% and about 140%, between about 110% and about 145%, between about 115% and about 135%, between about 105% and about 135%, between about 110% and about 135%, between about 115% and about 145%, or between about 115% and about 140%.

E3. The polynucleotide of E2, wherein the % $U_{TM}$ or % $T_{TM}$ is between (i) 110%, 111%, 112%, 113%, 114%, 115%, 116%, 117%, or 118% and (ii) 132%, 133%, 134%, 135%, 136%, 137%, 138%, 139%, or 140%.

E4. The polynucleotide of any one of E1 to E3, wherein the uracil or thymine content of the ORF relative to the uracil or thymine content of the corresponding wild-type ORF (% $U_{WT}$ or % $T_{WT}$) is less than 100%.

E5. The polynucleotide of E4, wherein the % $U_{WT}$ or % $T_{WT}$ is less than about 95%, less than about 90%, less than about 85%, less than 80%, less than 79%, less than 78%, less than 77%, less than 76%, less than 75%, less than 74%, or less than 73%.

E6. The polynucleotide of E4, wherein the % $U_{WT}$ or % $T_{WT}$ is between 65% and 73%.

E7. The polynucleotide of any one of E1 to E6, wherein the uracil or thymine content in the ORF relative to the total nucleotide content in the ORF (% $U_{TL}$ or % $T_{TL}$) is less than about 50%, less than about 40%, less than about 30%, or less than about 19%.

E8. The polynucleotide of E7, wherein the % $U_{TL}$ or % $T_{TL}$ is less than about 19%.

E9. The polynucleotide of any one of E1 to E8, wherein the % $U_{TL}$ or % $T_{TL}$ is between about 13% and about 15%.

E10. The polynucleotide of any one of E1 to E9, wherein the guanine content of the ORF with respect to the theoretical maximum guanine content of a nucleotide sequence encoding the PBGD polypeptide (% $G_{TMX}$) is at least 69%, at least 70%, at least 75%, at least about 80%, at least about 85%, at least about 90%, at least about 95%, or about 100%.

E11. The polynucleotide of E10, wherein the % $G_{TMX}$ is between about 70% and about 80%, between about 71% and about 79%, between about 71% and about 78%, or between about 71% and about 77%.

E12. The polynucleotide of any one of E1 to E11, wherein the cytosine content of the ORF relative to the theoretical maximum cytosine content of a nucleotide sequence encoding the PBGD polypeptide (% $C_{TMX}$) is at least 59%, at least 60%, at least about 65%, at least about 70%, at least about 75%, at least about 80%, at least about 85%, at least about 90%, at least about 95%, or about 100%.

E13. The polynucleotide of E12, wherein the % $C_{TMX}$ is between about 60% and about 80%, between about 62% and about 80%, between about 63% and about 79%, or between about 68% and about 76%.

E14. The polynucleotide of any one of E1 to E13, wherein the guanine and cytosine content (G/C) of the ORF relative to the theoretical maximum G/C content in a nucleotide sequence encoding the PBGD polypeptide (% $G/C_{TMX}$) is at least about 81%, at least about 85%, at least about 90%, at least about 95%, or about 100%.

E15. The polynucleotide of any one of E1 to E13, wherein the % $G/C_{TMX}$ is between about 80% and about 100%, between about 85% and about 99%, between about 90% and about 97%, or between about 91% and about 96%.

E16. The polynucleotide of any one of E1 to E15, wherein the G/C content in the ORF relative to the G/C content in the corresponding wild-type ORF (% $G/C_{WT}$) is at least 102%, at least 103%, at least 104%, at least 105%, at least 106%, at least 107%, at least 110%, at least 115%, or at least 120%.

E17. The polynucleotide of any one of E1 to E15, wherein the average G/C content in the $3^{rd}$ codon position in the ORF is at least 20%, at least 21%, at least 22%, at least 23%, at least 24%, at least 25%, at least 26%, at least 27%, at least 28%, at least 29%, or at least 30% higher than the average G/C content in the $3^{rd}$ codon position in the corresponding wild-type ORF.

E18. The polynucleotide of any one of E1 to E17, wherein the ORF further comprises at least one low-frequency codon.

E19. The polynucleotide of any one of E1 to E18,
(i) wherein the ORF is at least 87%, at least 88%, at least 89%, at least 90%, at least 91%, at least 92%, at least 93%, at least 94%, at least 95%, at least 96%, at least 97%, at least 98%, at least 99%, or 100% identical to PBGD-CO3 or PBGD-CO25,
(ii) wherein the ORF is at least 88%, at least 89%, at least 90%, at least 91%, at least 92%, at least 93%, at least 94%, at least 95%, at least 96%, at least 97%, at least 98%, at least 99%, or 100% identical to PBGD-CO1, PBGD-CO2, PBGD-CO7, PBGD-CO11, PBGD-CO13, PBGD-CO14, PBGD-CO16, or PBGD-CO24,
(iii) wherein the ORF is at least 89%, at least 90%, at least 91%, at least 92%, at least 93%, at least 94%, at least 95%, at least 96%, at least 97%, at least 98%, at least 99%, or 100% identical to PBGD-COS, PBGD-CO9, PBGD-CO10, PBGD-CO12, PBGD-CO15, PBGD-CO17, PBGD-CO18, PBGD-CO19, PBGD-CO20, PBGD-CO21, or PBGD-CO22,
(iv) wherein the ORF is at least 90%, at least 91%, at least 92%, at least 93%, at least 94%, at least 95%, at least 96%, at least 97%, at least 98%, at least 99%, or 100% identical to PBGD-CO6, PBGD-CO8, PBGD-CO23, or
(v) wherein the ORF is at least 91%, at least 91%, at least 92%, at least 93%, at least 94%, at least 95%, at least 96%, at least 97%, at least 98%, at least 99%, or 100% identical to PBGD-CO4.

E20. A polynucleotide comprising an ORF,
(i) wherein the ORF is at least 87%, at least 88%, at least 89%, at least 90%, at least 91%, at least 92%, at least 93%, at least 94%, at least 95%, at least 96%, at least 97%, at least 98%, at least 99%, or 100% identical to PBGD-CO3 or PBGD-CO25,
(ii) wherein the ORF is at least 88%, at least 89%, at least 90%, at least 91%, at least 92%, at least 93%, at least 94%, at least 95%, at least 96%, at least 97%, at least 98%, at least 99%, or 100% identical to PBGD-CO1, PBGD-CO2, PBGD-CO7, PBGD-CO11, PBGD-CO13, PBGD-CO14, PBGD-CO16, or PBGD-CO24,
(iii) wherein the ORF is at least 89%, at least 90%, at least 91%, at least 92%, at least 93%, at least 94%, at least 95%, at least 96%, at least 97%, at least 98%, at least 99%, or 100% identical to PBGD-COS, PBGD-CO9, PBGD-CO10, PBGD-CO12, PBGD-CO15, PBGD-CO17, PBGD-CO18, PBGD-CO19, PBGD-CO20, PBGD-CO21, or PBGD-CO22,
(iv) wherein the ORF is at least 90%, at least 91%, at least 92%, at least 93%, at least 94%, at least 95%, at least 96%, at least 97%, at least 98%, at least 99%, or 100% identical to PBGD-CO6, PBGD-CO8, PBGD-CO23, or
(v) wherein the ORF is at least 91%, at least 91%, at least 92%, at least 93%, at least 94%, at least 95%, at least 96%, at least 97%, at least 98%, at least 99%, or 100% identical to PBGD-CO4.

E21. The polynucleotide of any one of E1 to E20, wherein the ORF has at least 87%, at least 88%, at least 89%, at least 90%, at least 91%, at least 92%, at least 93%, at least 94%, at least 95%, at least 96%, at least 97%, at least 98%, at least 99%, or 100% sequence identity to a sequence selected from the group consisting of SEQ ID NOs: 9 to 33.

E22. The polynucleotide of any one of E1 to E21, wherein the PBGD polypeptide comprises an amino acid sequence at least about 95%, at least about 96%, at least about 97%, at least about 98%, at least about 99%, or about 100% identical to (i) the polypeptide sequence of wild type PBGD, isoform 1 (SEQ ID NO: 1), (ii) the polypeptide sequence of wild type PBGD, isoform 2 (SEQ ID NO: 3), the polypeptide sequence of wild type PBGD, isoform 3 (SEQ ID NO: 5), or the polypeptide sequence of wild type PBGD, isoform 4 (SEQ ID NO: 7), and wherein the PBGD polypeptide has porphobilinogen deaminase activity.

E23. The polynucleotide of E22, wherein the PBGD polypeptide is a variant, derivative, or mutant having a porphobilinogen deaminase activity.

E24. The polynucleotide of any one of E1 to E23, wherein the polynucleotide sequence further comprises a nucleotide sequence encoding a transit peptide.

E25. The polynucleotide of any one of E1 to E24, wherein the polynucleotide is single stranded.

E26. The polynucleotide of any one of E1 to E24, wherein the polynucleotide is double stranded.

E27. The polynucleotide of any one of E1 to E26, wherein the polynucleotide is DNA.

E28. The polynucleotide of any one of E1 to E26, wherein the polynucleotide is RNA.

E29. The polynucleotide of E28, wherein the polynucleotide is mRNA.

E30. The polynucleotide of any one of E1 to E29, wherein the polynucleotide comprises at least one chemically modified nucleobase, sugar, backbone, or any combination thereof.

E31. The polynucleotide of E30, wherein the at least one chemically modified nucleobase is selected from the group consisting of pseudouracil (ψ), N1-methylpseudouracil (m1ψ), 2-thiouracil (s2U), 4'-thiouracil, 5-methylcytosine, 5-methyluracil, and any combination thereof.

E32. The polynucleotide of E30, wherein the at least one chemically modified nucleobase is 5-methoxyuracil.

E33. The polynucleotide of E32, wherein at least about 25%, at least about 30%, at least about 40%, at least about 50%, at least about 60%, at least about 70%, at least about 80%, at least about 90%, at least about 95%, at least about 99%, or 100% of the uracils are 5-methoxyuracils.

E34. The polynucleotide of any one of E1 to E33, wherein the polynucleotide further comprises a miRNA binding site.

E35. The polynucleotide of E34, wherein the miRNA binding site comprises one or more nucleotide sequences selected from SEQ ID NO:36 and SEQ ID NO:38

E36. The polynucleotide of E34, wherein the miRNA binding site binds to miR-142.

E37. The polynucleotide of E35 or E36, wherein the miRNA binding site binds to miR-142-3p or miR-142-5p.

E38. The polynucleotide of E36 or E37, wherein the miR142 comprises SEQ ID NO: 34.

E39. The polynucleotide of any one of E1 to E38, wherein the polynucleotide further comprises a 5' UTR.

E40. The polynucleotide of E39, wherein the 5' UTR comprises a nucleic acid sequence at least 90%, at least about 95%, at least about 96%, at least about 97%, at least about 98%, at least about 99%, or about 100% identical to a 5'UTR sequence selected from the group consisting of SEQ ID NO: 39-56, or any combination thereof.

E41. The polynucleotide of any one of E1 to E40, wherein the polynucleotide further comprises a 3' UTR.

E42. The polynucleotide of E41, wherein the 3' UTR comprises a nucleic acid sequence at least about 90%, at least about 95%, at least about 96%, at least about 97%, at least about 98%, at least about 99%, or about 100% identical to a 3'UTR sequence selected from the group consisting of SEQ ID NO: 57-81, or any combination thereof.

E43. The polynucleotide of E41 or E42, wherein the miRNA binding site is located within the 3' UTR.

E44. The polynucleotide of any one of E1 to E43, wherein the polynucleotide further comprises a 5' terminal cap.

E45. The polynucleotide of E44, wherein the 5' terminal cap comprises a Cap0, Cap1, ARCA, inosine, N1-methylguanosine, 2'-fluoro-guanosine, 7-deaza-guanosine, 8-oxoguanosine, 2-amino-guanosine, LNA-guanosine, 2-azidoguanosine, Cap2, Cap4, 5' methylG cap, or an analog thereof.

E46. The polynucleotide of any one of E1 to E45, wherein the polynucleotide further comprises a poly-A region.

E47. The polynucleotide of E46, wherein the poly-A region is at least about 10, at least about 20, at least about 30, at least about 40, at least about 50, at least about 60, at least about 70, at least about 80, or at least about 90 nucleotides in length.

E48. The polynucleotide of E47, wherein the poly-A region has about 10 to about 200, about 20 to about 180, about 50 to about 160, about 70 to about 140, about 80 to about 120 nucleotides in length.

E49. The polynucleotide of any one of E1 to E48, wherein the polynucleotide encodes a PBGD polypeptide that is fused to one or more heterologous polypeptides.

E50. The polynucleotide of E49, wherein the one or more heterologous polypeptides increase a pharmacokinetic property of the PBGD polypeptide.

E51. The polynucleotide of any one of E1 to E50, wherein upon administration to a subject, the polynucleotide has:
  (i) a longer plasma half-life;
  (ii) increased expression of a PBGD polypeptide encoded by the ORF;
  (iii) a lower frequency of arrested translation resulting in an expression fragment;
  (iv) greater structural stability; or
  (v) any combination thereof, relative to a corresponding polynucleotide comprising SEQ ID NO: 2, 4, 6, or 8.

E52. The polynucleotide of any one of E1 to E51, wherein the polynucleotide comprises:
  (i) a 5'-terminal cap;
  (ii) a 5'-UTR;
  (iii) an ORF encoding a PBGD polypeptide;
  (iv) a 3'-UTR; and
  (v) a poly-A region.

E53. The polynucleotide of E52, wherein the 3'-UTR comprises a miRNA binding site.

E54. A method of producing the polynucleotide of any one of E1 to E53, the method comprising modifying an ORF encoding a PBGD polypeptide by substituting at least one uracil nucleobase with an adenine, guanine, or cytosine nucleobase, or by substituting at least one adenine, guanine, or cytosine nucleobase with a uracil nucleobase, wherein all the substitutions are synonymous substitutions.

E55. The method of E54, wherein the method further comprises replacing at least about 90%, at least about 95%, at least about 99%, or about 100% of uracils with 5-methoxyuracils.

E56. A composition comprising
  (a) the polynucleotide of any one of E1 to E53; and
  (b) a delivery agent.

E57. The composition of E56, wherein the delivery agent comprises a lipidoid, a liposome, a lipoplex, a lipid nanoparticle, a polymeric compound, a peptide, a protein, a cell, a nanoparticle mimic, a nanotube, or a conjugate.

E58. The composition of E56, wherein the delivery agent comprises a lipid nanoparticle.

E59. The composition of E58, wherein the lipid nanoparticle comprises a lipid selected from the group consisting of 3-(didodecylamino)-N1,N1,4-tridodecyl-1-piperazineethanamine (KL10),
N1-[2-(didodecylamino)ethyl]-N1,N4,N4-tridodecyl-1,4-piperazinediethanamine (KL22),
14,25-ditridecyl-15,18,21,24-tetraaza-octatriacontane (KL25),
1,2-dilinoleyloxy-N,N-dimethylaminopropane (DLin-DMA),
2,2-dilinoleyl-4-dimethylaminomethyl-[1,3]-dioxolane (DLin-K-DMA),
heptatriaconta-6,9,28,31-tetraen-19-yl 4-(dimethylamino)butanoate (DLin-MC3-DMA),
2,2-dilinoleyl-4-(2-dimethylaminoethyl)[1,3]-dioxolane (DLin-KC2-DMA),
1,2-dioleyloxy-N,N-dimethylaminopropane (DODMA),
(13Z,16SZ)—N,N-dimethyl-3-nonydocosa-13-16-dien-1-amine (L608),
2-({8-[(3β)-cholest-5-en-3-yloxy]octyl}oxy)-N,N-dimethyl-3-[(9Z,12Z)-octadeca-9,12-dien-1-yloxy]propan-1-amine (Octyl-CLinDMA),
(2R)-2-({8-[(3β)-cholest-5-en-3-yloxy]octyl}oxy)-N,N-dimethyl-3-[(9Z,12Z)-octadeca-9, 12-dien-1-yloxy]propan-1-amine (Octyl-CLinDMA (2R)),
(2S)-2-({8-[(3β)-cholest-5-en-3-yloxy]octyl}oxy)-N,N-dimethyl-3-[(9Z,12Z)-octadeca-9, 12-dien-1-yloxy]propan-1-amine (Octyl-CLinDMA (2S)), and any combinations thereof.

E60. The composition of any one of E56 to E59, wherein the delivery agent comprises a compound having the Formula (I)

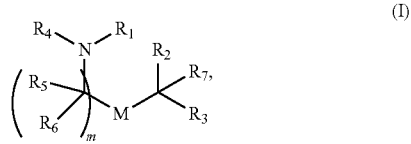

(I)

or a salt or stereoisomer thereof, wherein $R_1$ is selected from the group consisting of $C_{5-20}$ alkyl, $C_{5-20}$ alkenyl, —R*YR", —YR", and —R"M'R';

$R_2$ and $R_3$ are independently selected from the group consisting of H, $C_{1-14}$ alkyl, $C_{2-14}$ alkenyl, —R*YR", —YR", and —R*OR", or $R_2$ and $R_3$, together with the atom to which they are attached, form a heterocycle or carbocycle;

$R_4$ is selected from the group consisting of a $C_{3-6}$ carbocycle, —(CH$_2$)$_n$Q, —(CH$_2$)$_n$CHQR, —CHQR, —CQ(R)$_2$, and unsubstituted $C_{1-6}$ alkyl, where Q is selected from a carbocycle, heterocycle, —OR, —O(CH$_2$)$_n$N(R)$_2$, —C(O)OR, —OC(O)R, —CX$_3$, —CX$_2$H, —CXH$_2$, —CN, —N(R)$_2$, —C(O)N(R)$_2$, —N(R)C(O)R, —N(R)S(O)$_2$R, —N(R)C(O)N(R)$_2$, —N(R)C(S)N(R)$_2$, and —C(R)N(R)$_2$C(O)OR, and each n is independently selected from 1, 2, 3, 4, and 5;

each $R_5$ is independently selected from the group consisting of $C_{1-3}$ alkyl, $C_{2-3}$ alkenyl, and H;

each $R_6$ is independently selected from the group consisting of $C_{1-3}$ alkyl, $C_{2-3}$ alkenyl, and H;

M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —S(O)$_2$—, an aryl group, and a heteroaryl group;

$R_7$ is selected from the group consisting of $C_{1-3}$ alkyl, $C_{2-3}$ alkenyl, and H; each R is independently selected from the group consisting of $C_{1-3}$ alkyl, $C_{2-3}$ alkenyl, and H;

each R' is independently selected from the group consisting of $C_{1-18}$ alkyl, $C_{2-18}$ alkenyl, —R*YR", —YR", and H;

each R" is independently selected from the group consisting of $C_{3-14}$ alkyl and $C_{3-14}$ alkenyl;

each R* is independently selected from the group consisting of $C_{1-12}$ alkyl and $C_{2-12}$ alkenyl;

each Y is independently a $C_{3-6}$ carbocycle;

each X is independently selected from the group consisting of F, Cl, Br, and I; and m is selected from 5, 6, 7, 8, 9, 10, 11, 12, and 13; and provided when $R_4$ is —(CH$_2$)$_n$Q, —(CH$_2$)$_n$CHQR, —CHQR, or —CQ(R)$_2$, then (i) Q is not —N(R)$_2$ when n is 1, 2, 3, 4 or 5, or (ii) Q is not 5, 6, or 7-membered heterocycloalkyl when n is 1 or 2.

E61. A composition comprising a nucleotide sequence encoding a PBGD polypeptide and a delivery agent, wherein the delivery agent comprises a compound having the Formula (I)

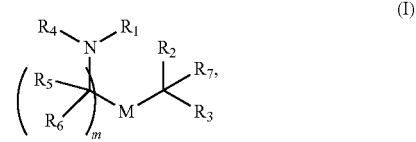

(I)

or a salt or stereoisomer thereof, wherein $R_1$ is selected from the group consisting of $C_{5-20}$ alkyl, $C_{5-20}$ alkenyl, —R*YR", —YR", and —R"M'R';

$R_2$ and $R_3$ are independently selected from the group consisting of H, $C_{1-14}$ alkyl, $C_{2-14}$ alkenyl, —R*YR", —YR", and —R*OR", or $R_2$ and $R_3$, together with the atom to which they are attached, form a heterocycle or carbocycle;

$R_4$ is selected from the group consisting of a $C_{3-6}$ carbocycle, —CH$_2$)$_n$Q, —(CH$_2$)$_n$CHQR, —CHQR, —CQ(R)$_2$, and unsubstituted $C_{1-6}$ alkyl, where Q is selected from a carbocycle, heterocycle, —OR, —O(CH$_2$)$_n$N(R)$_2$, —C(O)OR, —OC(O)R, —CX$_3$, —CX$_2$H, —CXH$_2$, —CN, —N(R)$_2$, —C(O)N(R)$_2$, —N(R)C(O)R, —N(R)S(O)$_2$R, —N(R)C(O)N(R)$_2$, —N(R)C(S)N(R)$_2$, and —C(R)N(R)$_2$C(O)OR, and each n is independently selected from 1, 2, 3, 4, and 5;

each $R_5$ is independently selected from the group consisting of $C_{1-3}$ alkyl, $C_{2-3}$ alkenyl, and H;

each $R_6$ is independently selected from the group consisting of $C_{1-3}$ alkyl, $C_{2-3}$ alkenyl, and H;

M and M' are independently selected from —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —S(O)$_2$—, an aryl group, and a heteroaryl group;

$R_7$ is selected from the group consisting of $C_{1-3}$ alkyl, $C_{2-3}$ alkenyl, and H; each R is independently selected from the group consisting of $C_{1-3}$ alkyl, $C_{2-3}$ alkenyl, and H;

each R' is independently selected from the group consisting of $C_{1-18}$ alkyl, $C_{2-18}$ alkenyl, —R*YR", —YR", and H;

each R" is independently selected from the group consisting of $C_{3-14}$ alkyl and $C_{3-14}$ alkenyl;

each R* is independently selected from the group consisting of $C_{1-12}$ alkyl and $C_{2-12}$ alkenyl;

each Y is independently a $C_{3-6}$ carbocycle;

each X is independently selected from the group consisting of F, Cl, Br, and I; and m is selected from 5, 6, 7, 8, 9, 10, 11, 12, and 13; and provided when $R_4$ is —$(CH_2)_nQ$, —$(CH_2)_n$CHQR, —CHQR, or —$CQ(R)_2$, then (i) Q is not —$N(R)_2$ when n is 1, 2, 3, 4 or 5, or (ii) Q is not 5, 6, or 7-membered heterocycloalkyl when n is 1 or 2.

E62. The composition of E60 or E61, wherein the compound is of Formula (IA):

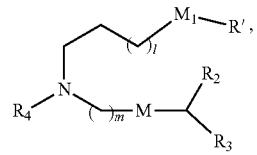

or a salt or stereoisomer thereof, wherein
l is selected from 1, 2, 3, 4, and 5;
m is selected from 5, 6, 7, 8, and 9;
$M_1$ is a bond or M';
$R_4$ is unsubstituted $C_{1-3}$ alkyl, or —$(CH_2)_nQ$, in which n is 1, 2, 3, 4, or 5 and Q is OH, —$NHC(S)N(R)_2$, or —$NHC(O)N(R)_2$;
M and M' are independently selected from —C(O)O—, —OC(O)—, —C(O)N(R')—, —P(O)(OR')O—, an aryl group, and a heteroaryl group; and
$R_2$ and $R_3$ are independently selected from the group consisting of H, $C_{1-14}$ alkyl, and $C_{2-14}$ alkenyl.

E63. The composition of any one of E60 to E62, wherein m is 5, 7, or 9.

E64. The composition of any one of E60 to E63, wherein the compound is of Formula (II):

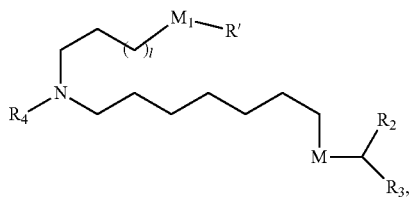

or a salt or stereoisomer thereof, wherein
l is selected from 1, 2, 3, 4, and 5;
$M_1$ is a bond or M';
$R_4$ is unsubstituted $C_{1-3}$ alkyl, or —$(CH_2)_nQ$, in which n is 2, 3, or 4 and Q is OH, —$NHC(S)N(R)_2$, or —$NHC(O)N(R)_2$;
M and M' are independently selected from —C(O)O—, —OC(O)—, —C(O)N(R')—, —P(O)(OR')O—, an aryl group, and a heteroaryl group; and
$R_2$ and $R_3$ are independently selected from the group consisting of H, $C_{1-14}$ alkyl, and $C_{2-14}$ alkenyl.

E65. The composition of any one of E62 to E64, wherein $M_1$ is M'.

E66. The composition of E65, wherein M and M' are independently —C(O)O— or —OC(O)—.

E67. The composition of any one of E62 to E66, wherein l is 1, 3, or 5.

E68. The composition of E60 or E61, wherein the compound is selected from the group consisting of Compound 1 to Compound 147, salts and stereoisomers thereof, and any combination thereof.

E69. The composition of E60 or E61, wherein the compound is of the Formula (IIa),

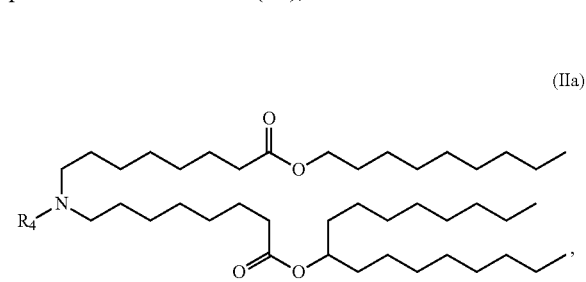

or a salt or stereoisomer thereof.

E70. The composition of E60 or E61, wherein the compound is of the Formula (IIb),

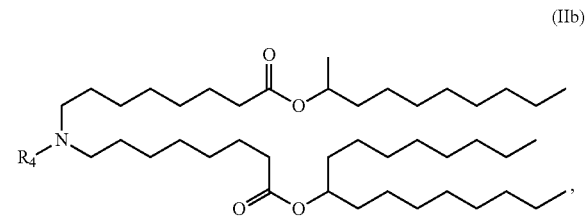

or a salt or stereoisomer thereof.

E71. The composition of E60 or E61, wherein the compound is of the Formula (IIc) or (IIe),

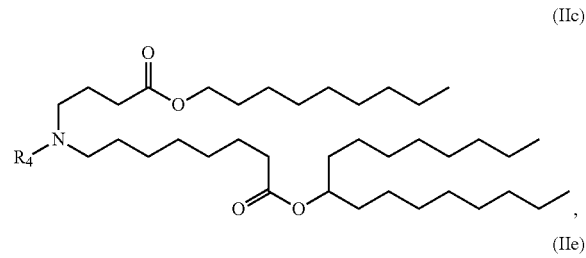

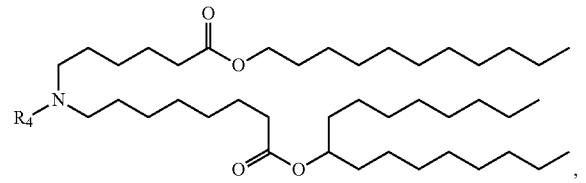

or a salt or stereoisomer thereof.

E72. The composition of any one of E69 to E71, wherein $R_4$ is selected from —$(CH_2)_nQ$ and —$(CH_2)_n$CHQR.

E73. The composition of E60 or E61, wherein the compound is of the Formula (IId),

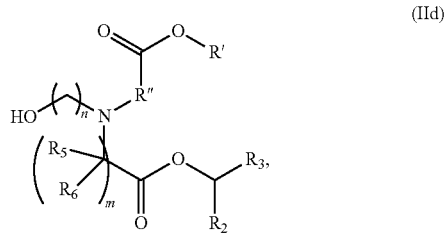

(IId)

or a salt or stereoisomer thereof, wherein $R_2$ and $R_3$ are independently selected from the group consisting of $C_{5-14}$ alkyl and $C_{5-14}$ alkenyl, n is selected from 2, 3, and 4, and R', R", $R_5$, $R_6$ and m are as defined in claim 60 or 61.

E74. The composition of E73, wherein $R_2$ is $C_8$ alkyl.

E75. The composition of E74, wherein $R_3$ is $C_5$ alkyl, $C_6$ alkyl, $C_7$ alkyl, $C_8$ alkyl, or $C_9$ alkyl.

E76. The composition of any one of E73 to E75, wherein m is 5, 7, or 9.

E77. The composition of any one of E73 to E76, wherein each $R_5$ is H.

E78. The composition of E77, wherein each $R_6$ is H.

E79. The composition of any one of E60 to E78, which is a nanoparticle composition.

E80. The composition of E79, wherein the delivery agent further comprises a phospholipid.

E81. The composition of E80, wherein the phospholipid is selected from the group consisting of 1,2-dilinoleoyl-sn-glycero-3-phosphocholine (DLPC),
1,2-dimyristoyl-sn-glycero-phosphocholine (DMPC),
1,2-dioleoyl-sn-glycero-3-phosphocholine (DOPC),
1,2-dipalmitoyl-sn-glycero-3-phosphocholine (DPPC),
1,2-distearoyl-sn-glycero-3-phosphocholine (DSPC),
1,2-diundecanoyl-sn-glycero-phosphocholine (DUPC),
1-palmitoyl-2-oleoyl-sn-glycero-3-phosphocholine (POPC),
1,2-di-O-octadecenyl-sn-glycero-3-phosphocholine (18:0 Diether PC),
1-oleoyl-2-cholesterylhemisuccinoyl-sn-glycero-3-phosphocholine (OChemsPC),
1-hexadecyl-sn-glycero-3-phosphocholine (C16 Lyso PC),
1,2-dilinolenoyl-sn-glycero-3-phosphocholine,
1,2-diarachidonoyl-sn-glycero-3-phosphocholine,
1,2-didocosahexaenoyl-sn-glycero-3-phosphocholine,
1,2-dioleoyl-sn-glycero-3-phosphoethanolamine (DOPE),
1,2-diphytanoyl-sn-glycero-3-phosphoethanolamine (ME 16:0 PE),
1,2-distearoyl-sn-glycero-3-phosphoethanolamine,
1,2-dilinoleoyl-sn-glycero-3-phosphoethanolamine,
1,2-dilinolenoyl-sn-glycero-3-phosphoethanolamine,
1,2-diarachidonoyl-sn-glycero-3-phosphoethanolamine,
1,2-didocosahexaenoyl-sn-glycero-3-phosphoethanolamine,
1,2-dioleoyl-sn-glycero-3-phospho-rac-(1-glycerol) sodium salt (DOPG), sphingomyelin, and any mixtures thereof.

E82. The composition of any one of E60 to E81, wherein the delivery agent further comprises a structural lipid.

E83. The composition of E82, wherein the structural lipid is selected from the group consisting of cholesterol, fecosterol, sitosterol, ergosterol, campesterol, stigmasterol, brassicasterol, tomatidine, ursolic acid, alpha-tocopherol, and any mixtures thereof.

E84. The composition of any one of E60 to E83, wherein the delivery agent further comprises a PEG lipid.

E85. The composition of E84, wherein the PEG lipid is selected from the group consisting of a PEG-modified phosphatidylethanolamine, a PEG-modified phosphatidic acid, a PEG-modified ceramide, a PEG-modified dialkylamine, a PEG-modified diacylglycerol, a PEG-modified dialkylglycerol, and any mixtures thereof.

E86. The composition of any one of E60 to E85, wherein the delivery agent further comprises an ionizable lipid selected from the group consisting of
3-(didodecylamino)-N1,N1,4-tridodecyl-1-piperazineethanamine (KL10),
N1-[2-(didodecylamino)ethyl]-N1,N4,N4-tridodecyl-1,4-piperazinediethanamine (KL22),
14,25-ditridecyl-15,18,21,24-tetraaza-octatriacontane (KL25),
1,2-dilinoleyloxy-N,N-dimethylaminopropane (DLin-DMA),
2,2-dilinoleyl-4-dimethylaminomethyl-[1,3]-dioxolane (DLin-K-DMA),
heptatriaconta-6,9,28,31-tetraen-19-yl 4-(dimethylamino)butanoate (DLin-MC3-DMA),
2,2-dilinoleyl-4-(2-dimethylaminoethyl)-[1,3]-dioxolane (DLin-KC2-DMA),
1,2-dioleyloxy-N,N-dimethylaminopropane (DODMA),
2-({8-[(3β)-cholest-5-en-3-yloxy]octyl}oxy)-N,N-dimethyl-3-[(9Z,12Z)-octadeca-9,12-dien-1-yloxy]propan-1-amine (Octyl-CLinDMA),
(2R)-2-({8-[(3β)-cholest-5-en-3-yloxy]octyl}oxy)-N,N-dimethyl-3-[(9Z,12Z)-octadeca-9, 12-dien-1-yloxy]propan-1-amine (Octyl-CLinDMA (2R)), and
(2S)-2-({8-[(3β)-cholest-5-en-3-yloxy]octyl}oxy)-N,N-dimethyl-3-[(9Z,12Z)-octadeca-9, 12-dien-1-yloxy]propan-1-amine (Octyl-CLinDMA (2S)).

E87. The composition of any one of E60 to E86, wherein the delivery agent further comprises a phospholipid, a structural lipid, a PEG lipid, or any combination thereof.

E88. The composition of any one of E60 to E87, wherein the composition is formulated for in vivo delivery.

E89. The composition according any one of E60 to E88, which is formulated for intramuscular, subcutaneous, or intradermal delivery.

E90. A host cell comprising the polynucleotide of any one of E1 to E53.

E91. The host cell of E90, wherein the host cell is a eukaryotic cell.

E92. A vector comprising the polynucleotide of any one of E1 to E53.

E93. A method of making a polynucleotide comprising enzymatically or chemically synthesizing the polynucleotide of any one of E1 to E53.

E94. A polypeptide encoded by the polynucleotide of any one of E1 to E53, the composition of any one of E56 to E89, the host cell of E90 or E91, or the vector of E92 or produced by the method of E93.

E95. A method of expressing in vivo an active PBGD polypeptide in a subject in need thereof comprising administering to the subject an effective amount of the polynucleotide of any one of E1 to E53, the composition of any one of E56 to E89, the host cell of E90 or E91, or the vector of E92.

E96. A method of treating acute intermittent porphyria (AIP) in a subject in need thereof comprising administering to the subject a therapeutically effective amount of the polynucleotide of any one of E1 to E53, the composition of any one of E56 to E89, the host cell of E90 or E91, or the vector of E92, wherein the administration alleviates the signs or symptoms of AIP in the subject.

E97. A method to prevent or delay the onset of AIP signs or symptoms in a subject in need thereof comprising administering to the subject a prophylactically effective amount of the polynucleotide of any one of E1 to E53, the composition of any one of E56 to E89, the host cell of E90 or E91, or the vector of E92 before AIP signs or symptoms manifest, wherein the administration prevents or delays the onset of AIP signs or symptoms in the subject.

E98. A method to ameliorate the signs or symptoms of AIP in a subject in need thereof comprising administering to the subject a therapeutically effective amount of the polynucleotide of any one of E1 to E53, the composition of any one of E56 to E89, the host cell of E90 or E91, or the vector of E92 before AIP signs or symptoms manifest, wherein the administration ameliorates AIP signs or symptoms in the subject.

E99. A method to increase hepatic PBGD activity in a subject in need thereof comprising administering to the subject an effective amount of the polynucleotide of any one of E1 to E53, the composition of any one of E56 to E89, the host cell of E90 or E91, or the vector of E92.

E100. A method to decrease ALA (aminolevulinate) and/or PBG (porphobilinogen) in a subject in need thereof comprising administering to the subject an effective amount of the polynucleotide of any one of E1 to E53, the composition of any one of E56 to E89, the host cell of E90 or E91, or the vector of E92.

E101. The method according to E100, wherein the ALA and/or PBG levels are urinary excretion levels.

E102, A method to protect a subject in need thereof against the increase in heme precursors in an AIP attack comprising administering to the subject an effective amount of the polynucleotide of any one of E1 to E53, the composition of any one of E56 to E89, the host cell of E90 or E91, or the vector of E92.

E103. A method to reduce the accumulation of heme precursors in a subject in need thereof comprising administering to the subject an effective amount of the polynucleotide of any one of E1 to E53, the composition of any one of E56 to E89, the host cell of E90 or E91, or the vector of E92.

E104. The method according to E102 or E103, wherein the heme precursors are
ALA and/or PBG.

E105. A method to treat, prevent, or ameliorate pain in a subject in need thereof comprising administering to the subject an effective amount of the polynucleotide of any one of E1 to E53, the composition of any one of E56 to E89, the host cell of E90 or E91, or the vector of E92.

E106. The method according to E105, wherein the pain is severe pain.

E107. The method according to E105, wherein the treatment, prevention or amelioration in pain results in pain annulment.

E108. A method to treat, prevent, or ameliorate neuropathy in a subject in need thereof comprising administering to the subject an effective amount of the polynucleotide of any one of E1 to E53, the composition of any one of E56 to E89, the host cell of E90 or E91, or the vector of E92.

E109. The method according to E108, wherein the treatment, prevention or amelioration in neuropathy results in neuropathy annulment.

E110. The method according to E108 or E109, wherein the neuropathy is peripheral neuropathy.

E111. A method to increase survival in a subject in need thereof comprising administering to the subject an effective amount of the polynucleotide of any one of E1 to E53, the composition of any one of E56 to E89, the host cell of E90 or E91, or the vector of E92.

E112. The method according to any one of E95 to E111, wherein the subject is an AIP patient.

E113. The method according to E112, wherein the AIP patient is an asymptomatic patient.

E114. The method according to any one of E95 to E114, wherein the polynucleotide comprises PBGD-CO3 (SEQ ID NO:11).

31. EQUIVALENTS AND SCOPE

Those skilled in the art will recognize, or be able to ascertain using no more than routine experimentation, many equivalents to the specific embodiments in accordance with the invention described herein. The scope of the present invention is not intended to be limited to the above Description, but rather is as set forth in the appended claims.

In the claims, articles such as "a," "an," and "the" can mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

It is also noted that the term "comprising" is intended to be open and permits but does not require the inclusion of additional elements or steps. When the term "comprising" is used herein, the term "consisting of" is thus also encompassed and disclosed.

Where ranges are given, endpoints are included. Furthermore, it is to be understood that unless otherwise indicated or otherwise evident from the context and understanding of one of ordinary skill in the art, values that are expressed as ranges can assume any specific value or subrange within the stated ranges in different embodiments of the invention, to the tenth of the unit of the lower limit of the range, unless the context clearly dictates otherwise.

In addition, it is to be understood that any particular embodiment of the present invention that falls within the prior art can be explicitly excluded from any one or more of the claims. Since such embodiments are deemed to be known to one of ordinary skill in the art, they can be excluded even if the exclusion is not set forth explicitly herein. Any particular embodiment of the compositions of the invention (e.g., any nucleic acid or protein encoded thereby; any method of production; any method of use; etc.) can be excluded from any one or more claims, for any reason, whether or not related to the existence of prior art.

All cited sources, for example, references, publications, databases, database entries, and art cited herein, are incorporated into this application by reference, even if not expressly stated in the citation. In case of conflicting statements of a cited source and the instant application, the statement in the instant application shall control.

Section and table headings are not intended to be limiting.

EXAMPLES

Example 1

Chimeric Polynucleotide Synthesis
A. Triphosphate Route

Two regions or parts of a chimeric polynucleotide can be joined or ligated using triphosphate chemistry. According to this method, a first region or part of 100 nucleotides or less can be chemically synthesized with a 5' monophosphate and terminal 3'desOH or blocked OH. If the region is longer than 80 nucleotides, it can be synthesized as two strands for ligation.

If the first region or part is synthesized as a non-positionally modified region or part using in vitro transcription (IVT), conversion the 5'monophosphate with subsequent capping of the 3' terminus can follow. Monophosphate protecting groups can be selected from any of those known in the art.

The second region or part of the chimeric polynucleotide can be synthesized using either chemical synthesis or IVT methods. IVT methods can include an RNA polymerase that can utilize a primer with a modified cap. Alternatively, a cap of up to 80 nucleotides can be chemically synthesized and coupled to the IVT region or part.

It is noted that for ligation methods, ligation with DNA T4 ligase, followed by treatment with DNase should readily avoid concatenation.

The entire chimeric polynucleotide need not be manufactured with a phosphate-sugar backbone. If one of the regions or parts encodes a polypeptide, then such region or part can comprise a phosphate-sugar backbone.

Ligation can then be performed using any known click chemistry, orthoclick chemistry, solulink, or other bioconjugate chemistries known to those in the art.

B. Synthetic Route

The chimeric polynucleotide can be made using a series of starting segments. Such segments include:
(a) Capped and protected 5' segment comprising a normal 3'OH (SEG. 1)
(b) 5' triphosphate segment which can include the coding region of a polypeptide and comprising a normal 3'OH (SEG. 2)
(c) 5' monophosphate segment for the 3' end of the chimeric polynucleotide (e.g., the tail) comprising cordycepin or no 3'OH (SEG. 3)

After synthesis (chemical or IVT), segment 3 (SEG. 3) can be treated with cordycepin and then with pyrophosphatase to create the 5'monophosphate.

Segment 2 (SEG. 2) can then be ligated to SEG. 3 using RNA ligase. The ligated polynucleotide can then be purified and treated with pyrophosphatase to cleave the diphosphate. The treated SEG. 2-SEG. 3 construct is then purified and SEG. 1 is ligated to the 5' terminus. A further purification step of the chimeric polynucleotide can be performed.

Where the chimeric polynucleotide encodes a polypeptide, the ligated or joined segments can be represented as: 5'UTR (SEG. 1), open reading frame or ORF (SEG. 2) and 3'UTR+PolyA (SEG. 3).

The yields of each step can be as much as 90-95%.

Example 2

PCR for cDNA Production

PCR procedures for the preparation of cDNA can be performed using 2×KAPA HIFI™ HotStart ReadyMix by Kapa Biosystems (Woburn, MA). This system includes 2× KAPA ReadyMix 12.5 µl; Forward Primer (10 µM) 0.75 µl; Reverse Primer (10 µM) 0.75 µl; Template cDNA ~100 ng; and dH$_2$0 diluted to 25.0 µl. The PCR reaction conditions can be: at 95° C. for 5 min. and 25 cycles of 98° C. for 20 sec, then 58° C. for 15 sec, then 72° C. for 45 sec, then 72° C. for 5 min. then 4° C. to termination.

The reverse primer of the instant invention can incorporate a poly-Tim for a poly-Atm in the mRNA. Other reverse primers with longer or shorter poly(T) tracts can be used to adjust the length of the poly(A) tail in the polynucleotide mRNA.

The reaction can be cleaned up using Invitrogen's PURELINK™ PCR Micro Kit (Carlsbad, CA) per manufacturer's instructions (up to 5 µg). Larger reactions will require a cleanup using a product with a larger capacity. Following the cleanup, the cDNA can be quantified using the NANODROP™ and analyzed by agarose gel electrophoresis to confirm the cDNA is the expected size. The cDNA can then be submitted for sequencing analysis before proceeding to the in vitro transcription reaction.

Example 3

In Vitro Transcription (IVT)

The in vitro transcription reactions can generate polynucleotides containing uniformly modified polynucleotides. Such uniformly modified polynucleotides can comprise a region or part of the polynucleotides of the invention. The input nucleotide triphosphate (NTP) mix can be made using natural and un-natural NTPs.

A typical in vitro transcription reaction can include the following:
1 Template cDNA—1.0 µg
2 10× transcription buffer (400 mM Tris-HCl pH 8.0, 190 mM MgCl$_2$, 50 mM DTT, 10 mM Spermidine)—2.0
3 Custom NTPs (25 mM each)—7.2 µl
4 RNase Inhibitor—20 U
5 T7 RNA polymerase—3000 U
6 dH$_2$0—Up to 20.0 µl and
7 Incubation at 37° C. for 3 hr-5 hrs.

The crude IVT mix can be stored at 4° C. overnight for cleanup the next day. 1 U of RNase-free DNase can then be used to digest the original template. After 15 minutes of incubation at 37° C., the mRNA can be purified using Ambion's MEGACLEAR™ Kit (Austin, TX) following the manufacturer's instructions. This kit can purify up to 500 µg of RNA. Following the cleanup, the RNA can be quantified using the NanoDrop and analyzed by agarose gel electrophoresis to confirm the RNA is the proper size and that no degradation of the RNA has occurred.

Example 4

Enzymatic Capping

Capping of a polynucleotide can be performed with a mixture includes: IVT RNA 60 µg-180 µg and dH$_2$0 up to 72 µl. The mixture can be incubated at 65° C. for 5 minutes to denature RNA, and then can be transferred immediately to ice.

The protocol can then involve the mixing of 10× Capping Buffer (0.5 M Tris-HCl (pH 8.0), 60 mM KCl, 12.5 mM MgCl$_2$) (10.0 µl); 20 mM GTP (5.0 µl); 20 mM S-Adenosyl Methionine (2.5 µl); RNase Inhibitor (100 U); 2'-O-Methyltransferase (400U); Vaccinia capping enzyme (Guanylyl transferase) (40 U); dH$_2$0 (Up to 28 µl); and incubation at 37° C. for 30 minutes for 60 µg RNA or up to 2 hours for 180 µg of RNA.

The polynucleotide can then be purified using Ambion's MEGACLEAR™ Kit (Austin, TX) following the manufacturer's instructions. Following the cleanup, the RNA can be quantified using the NANODROP™ (ThermoFisher, Waltham, MA) and analyzed by agarose gel electrophoresis to confirm the RNA is the proper size and that no degradation of the RNA has occurred. The RNA product can also be sequenced by running a reverse-transcription-PCR to generate the cDNA for sequencing.

Example 5

PolyA Tailing Reaction

Without a poly-T in the cDNA, a poly-A tailing reaction must be performed before cleaning the final product. This can be done by mixing Capped IVT RNA (100 µl); RNase Inhibitor (20 U); 10× Tailing Buffer (0.5 M Tris-HCl (pH 8.0), 2.5 M NaCl, 100 mM $MgCl_2$)(12.0 µl); 20 mM ATP (6.0 µl); Poly-A Polymerase (20 U); $dH_2O$ up to 123.5 IA and incubating at 37° C. for 30 min. If the poly-A tail is already in the transcript, then the tailing reaction can be skipped and proceed directly to cleanup with Ambion's MEGA-CLEAR™ kit (Austin, TX) (up to 500 µg). Poly-A Polymerase is, in some cases, a recombinant enzyme expressed in yeast.

It should be understood that the processivity or integrity of the polyA tailing reaction does not always result in an exact size polyA tail. Hence polyA tails of approximately between 40-200 nucleotides, e.g., about 40, 50, 60, 70, 80, 90, 91, 92, 93, 94, 95, 96, 97, 98, 99, 100, 101, 102, 103, 104, 105, 106, 107, 108, 109, 110, 150-165, 155, 156, 157, 158, 159, 160, 161, 162, 163, 164 or 165 are within the scope of the invention.

Example 6

Natural 5' Caps and 5' Cap Analogues

5'-capping of polynucleotides can be completed concomitantly during the in vitro-transcription reaction using the following chemical RNA cap analogs to generate the 5'-guanosine cap structure according to manufacturer protocols: 3'-O-Me-m7G(5')ppp(5') G [the ARCA cap]; G(5)ppp(5')A; G(5')ppp(5')G; m7G(5')ppp(5')A; m7G(5')ppp(5')G (New England BioLabs, Ipswich, MA). 5'-capping of modified RNA can be completed post-transcriptionally using a Vaccinia Virus Capping Enzyme to generate the "Cap 0" structure: m7G(5')ppp(5')G (New England BioLabs, Ipswich, MA). Cap 1 structure can be generated using both Vaccinia Virus Capping Enzyme and a 2'-O methyl-transferase to generate: m7G(5')ppp(5')G-2'-O-methyl. Cap 2 structure can be generated from the Cap 1 structure followed by the 2'-O-methylation of the 5'-antepenultimate nucleotide using a 2'-O methyl-transferase. Cap 3 structure can be generated from the Cap 2 structure followed by the 2'-O-methylation of the 5'-preantepenultimate nucleotide using a 2'-O methyl-transferase. Enzymes can be derived from a recombinant source.

When transfected into mammalian cells, the modified mRNAs can have a stability of between 12-18 hours or more than 18 hours, e.g., 24, 36, 48, 60, 72 or greater than 72 hours.

Example 7

Capping Assays
A. Protein Expression Assay

Polynucleotides encoding a polypeptide, containing any of the caps taught herein, can be transfected into cells at equal concentrations. After 6, 12, 24 and 36 hours post-transfection, the amount of protein secreted into the culture medium can be assayed by ELISA. Synthetic polynucleotides that secrete higher levels of protein into the medium would correspond to a synthetic polynucleotide with a higher translationally-competent Cap structure.
B. Purity Analysis Synthesis Polynucleotides encoding a polypeptide, containing any of the caps taught herein, can be compared for purity using denaturing Agarose-Urea gel electrophoresis or HPLC analysis. Polynucleotides with a single, consolidated band by electrophoresis correspond to the higher purity product compared to polynucleotides with multiple bands or streaking bands. Synthetic polynucleotides with a single HPLC peak would also correspond to a higher purity product. The capping reaction with a higher efficiency would provide a more pure polynucleotide population.
C. Cytokine Analysis Polynucleotides encoding a polypeptide, containing any of the caps taught herein, can be transfected into cells at multiple concentrations. After 6, 12, 24 and 36 hours post-transfection the amount of pro-inflammatory cytokines such as TNF-alpha and IFN-beta secreted into the culture medium can be assayed by ELISA. Polynucleotides resulting in the secretion of higher levels of pro-inflammatory cytokines into the medium would correspond to polynucleotides containing an immune-activating cap structure.
D. Capping Reaction Efficiency Polynucleotides encoding a polypeptide, containing any of the caps taught herein, can be analyzed for capping reaction efficiency by LC-MS after nuclease treatment. Nuclease treatment of capped polynucleotides would yield a mixture of free nucleotides and the capped 5'-5-triphosphate cap structure detectable by LC-MS. The amount of capped product on the LC-MS spectra can be expressed as a percent of total polynucleotide from the reaction and would correspond to capping reaction efficiency. The cap structure with higher capping reaction efficiency would have a higher amount of capped product by LC-MS.

Example 8

Agarose Gel Electrophoresis of Modified RNA or RT PCR Products

Individual polynucleotides (200-400 ng in a 20 µl volume) or reverse transcribed PCR products (200-400 ng) can be loaded into a well on a non-denaturing 1.2% Agarose E-Gel (Invitrogen, Carlsbad, CA) and run for 12-15 minutes according to the manufacturer protocol.

Example 9

Nanodrop Modified RNA Quantification and UV Spectral Data

Modified polynucleotides in TE buffer (1 µl) can be used for Nanodrop UV absorbance readings to quantitate the yield of each polynucleotide from an chemical synthesis or in vitro transcription reaction.

Example 10

Formulation of Modified mRNA Using Lipidoids

Polynucleotides can be formulated for in vitro experiments by mixing the polynucleotides with the lipidoid at a set ratio prior to addition to cells. In vivo formulation can require the addition of extra ingredients to facilitate circulation throughout the body. To test the ability of these lipidoids to form particles suitable for in vivo work, a standard formulation process used for siRNA-lipidoid formulations can be used as a starting point. After formation of the particle, polynucleotide can be added and allowed to integrate with the complex. The encapsulation efficiency can be determined using a standard dye exclusion assays.

Example 11

Method of Screening for Protein Expression
A. Electrospray Ionization
A biological sample that can contain proteins encoded by a polynucleotide administered to the subject can be prepared and analyzed according to the manufacturer protocol for electrospray ionization (ESI) using 1, 2, 3 or 4 mass analyzers. A biologic sample can also be analyzed using a tandem ESI mass spectrometry system.
Patterns of protein fragments, or whole proteins, can be compared to known controls for a given protein and identity can be determined by comparison.
B. Matrix-Assisted Laser Desorption/Ionization
A biological sample that can contain proteins encoded by one or more polynucleotides administered to the subject can be prepared and analyzed according to the manufacturer protocol for matrix-assisted laser desorption/ionization (MALDI).
Patterns of protein fragments, or whole proteins, can be compared to known controls for a given protein and identity can be determined by comparison.
C. Liquid Chromatography-Mass Spectrometry-Mass Spectrometry
A biological sample, which can contain proteins encoded by one or more polynucleotides, can be treated with a trypsin enzyme to digest the proteins contained within. The resulting peptides can be analyzed by liquid chromatography-mass spectrometry-mass spectrometry (LC/MS/MS). The peptides can be fragmented in the mass spectrometer to yield diagnostic patterns that can be matched to protein sequence databases via computer algorithms. The digested sample can be diluted to achieve 1 ng or less starting material for a given protein. Biological samples containing a simple buffer background (e.g., water or volatile salts) are amenable to direct in-solution digest; more complex backgrounds (e.g., detergent, non-volatile salts, glycerol) require an additional clean-up step to facilitate the sample analysis.
Patterns of protein fragments, or whole proteins, can be compared to known controls for a given protein and identity can be determined by comparison.

Example 12

Synthesis of mRNA Encoding PBGD
Sequence optimized polynucleotides encoding PBGD polypeptides, i.e., SEQ ID NOs: 1, 3, 5, or 7, were synthesized and characterized as described in Examples 1 to 11. mRNAs encoding both human PBGD isoforms were prepared for the Examples described below, and were synthesized and characterized as described in Examples 1 to 11.
An mRNA encoding human PBGD can be constructed, e.g., by using the ORF sequence provided in SEQ ID NO: 2, 4, 6, or 8. The mRNA sequence includes both 5' and 3' UTR regions (see, e.g., SEQ ID NOs: 83 and 84, respectively). In a construct, the 5'UTR and 3'UTR sequences are:

```
5'UTR
                                   (SEQ ID NO: 83)
TCAAGCTTTTGGACCCTCGTACAGAAGCTAATACGACTCACTATAGG

GAAATAAGAGAGAAAAGAAGAGTAAGAAGAAATATAAGAGCCACC

3'UTR
                                   (SEQ ID NO: 84)
TGATAATAGGCTGGAGCCTCGGTGGCCATGCTTCTTGCCCCTTGGGC

CTCCCCCCAGCCCCTCCTCCCCTTCCTGCACCCGTACCCCCGTGGTC

TTTGAATAAAGTCTGAGTGGGCGGC
or

3'UTR
                                   (SEQ ID NO: 149)
TGATAATAGTCCATAAAGTAGGAAACACTACAGCTGGAGCCTCGGTG

GCCATGCTTCTTGCCCCTTGGGCCTCCCCCCAGCCCCTCCTCCCCTT

CCTGCACCCGTACCCCCGCATTATTACTCACGGTACGAGTGGTCTT

TGAATAAAGTCTGAGTGGGCGGC
[[miR142 + miR126 3'UTR]]
```

The PBGD mRNA sequence was prepared as modified mRNA. Specifically, during in vitro translation, modified mRNA can be generated using 5-methoxy-UTP to ensure that the mRNAs contain 100% 5-methoxy-uridine instead of uridine. Further, PBGD-mRNA can be synthesized with a primer that introduces a polyA-tail, and a Cap 1 structure is generated on both mRNAs using Vaccinia Virus Capping Enzyme and a 2'-O methyl-transferase to generate: m7G(5') ppp(5')G-2'-O-methyl.

Example 13

Detecting Endogenous PBGD Expression In Vitro
PBGD expression is characterized in a variety of cell lines derived from both mice and human sources. Cells are cultured in standard conditions and cell extracts are obtained by placing the cells in lysis buffer. For comparison purposes, appropriate controls are also prepared. To analyze PBGD expression, lysate samples are prepared from the tested cells and mixed with lithium dodecyl sulfate sample loading buffer and subjected to standard Western blot analysis. For detection of PBGD, the antibody used is a commercial anti-PBGD antibody. For detection of a load control, the antibody used is anti-β-Actin (mouse monoclonal; A2228; Sigma). To examine the localization of endogenous PBGD, immunofluorescence analysis is performed on cells. PBGD expression is detected using a commercial anti-PBGD. The location of specific organelles can be detected with existing commercial products. For example, mitochondria can be detected using Mitotracker, and the nucleus can be stained with DAPI. Image analysis is performed on a Zeiss ELYRA imaging system.
Endogenous PBGD expression can be used as a base line to determine changes in PBGD expression resulting from transfection with mRNAs comprising nucleic acids encoding PBGD.

Example 14

In Vitro Expression of PBGD in HeLa Cells
To measure in vitro expression of human PBGD in HeLa cells, those cells are seeded on 12-well plates (BD Biosciences, San Jose, USA) one day prior to transfection. mRNA formulations comprising human PBGD or a GFP control are transfected using 800 ng mRNA and 2 μL Lipofectamin 2000 in 60 μL OPTI-MEM per well and incubated.

After 24 hours, the cells in each well are lysed using a consistent amount of lysis buffer. Appropriate controls are used. Protein concentrations of each are determined using a BCA assay according to manufacturer's instructions. To analyze PBGD expression, equal loads of each lysate (50 μg) are prepared in a loading buffer and subjected to standard Western blot analysis. For detection of PBGD, a commercial anti-PBGD antibody is used according to the manufacturer's instructions.

Example 15

In Vitro PBGD Activity in HeLa Cells

An in vitro PBGD activity assay is performed to determine whether PBGD exogenously-expressed after introduction of mRNA comprising a PBGD sequence is active.
A. Expression Assay HeLa cells are transfected with mRNA formulations comprising human PBGD or a GFP control. Cells are transfected with Lipofectamin 2000 and lysed as described in Example 14 above. Appropriate controls are also prepared.
B. Activity Assay To assess whether exogenous PBGD can function, an in vitro activity assay is performed using transfected HeLa cell lysates as the source of enzymatic activity. To begin, lysate is mixed PBGD substrate. The reaction is stopped by 5% TCA and vortexing. The reaction tubes are then centrifuged at 2,000 g for 10 min, and the supernatant is exposed to light for 20 min and analyzed for the presence of oxidized enzymatic products resulting from the activity of PBGD using fluorometric quantification.

Example 16

Measuring In Vitro Expression of PBGD in Cells

Cells from normal subjects and acute intermittent porphyria patients are examined for their capacity to express exogenous PBGD. Cells are transfected with mRNA formulations comprising human PBGD, mouse PBGD, or a GFP control via electroporation using a standard protocol. Each construct is tested separately. After incubation, cells are lysed and protein concentration in each lysate is measured using a suitable assay, e.g., by BCA assay. To analyze PBGD expression, equal loads of each lysate are prepared in a loading buffer and subjected to standard Western blot analysis. For detection of PBGD, an anti-PBGD is used. For detection of a load control, the antibody used is anti-β-Actin (mouse monoclonal; A2228; Sigma).

Example 17

Measuring In Vitro PBGD Activity in Lysates
A. Expression

Cells from normal human subjects and acute intermittent porphyria patients are cultured. Cells are transfected with mRNA formulations comprising human PBGD, mouse PBGD, or a GFP control via electroporation using a standard protocol.
B. Activity Assay To assess whether exogenous PBGD function, an in vitro activity assay is performed using transfected cell lysates as the source of enzymatic activity. Lysate containing expressed PBGD protein is incubated with PBGD substrate, and the activity of PBGD is quantified by measuring the levels of oxidized products resulting from the enzymatic activity of PBGD.

Example 18

In Vivo PBGD Expression in Animal Models

To assess the ability of PBGD-containing mRNA's to facilitate PBGD expression in vivo, mRNA encoding human PBGD is introduced into CD1 mice. CD1 mice are injected intravenously with either control mRNA (Luciferase) or human PBGD mRNA. The mRNA is formulated in lipid nanoparticles for delivery into the mice. Mice are sacrificed after 24 or 48 hrs. and PBGD protein levels in liver lysates are determined by capillary electrophoresis (CE). β-Actin expression is examined for use as a load control. For control Luciferase injections, 4 mice are tested for each time point. For human PBGD mRNA injections, 4 mice are tested for each time point.

Example 19

Human PBGD Mutant and Chimeric Constructs

A polynucleotide of the present invention can comprise at least a first region of linked nucleosides encoding human PBGD, which can be constructed, expressed, and characterized according to the examples above. Similarly, the polynucleotide sequence can contain one or more mutations that results in the expression of a PBGD with increased or decreased activity. Furthermore, the polynucleotide sequence encoding PBGD can be part of a construct encoding a chimeric fusion protein.

Example 20

Production of Nanoparticle Compositions
A. Production of Nanoparticle Compositions Nanoparticles can be made with mixing processes such as microfluidics and T-junction mixing of two fluid streams, one of which contains the polynucleotide and the other has the lipid components.

Lipid compositions can be prepared by combining an ionizable amino lipid disclosed herein, e.g., a lipid according to Formula (I) such as Compound 18 or a lipid according to Formula (III) such as Compound 236, a phospholipid (such as DOPE or DSPC, obtainable from Avanti Polar Lipids, Alabaster, AL), a PEG lipid (such as 1,2-dimyristoyl-sn-glycerol methoxypolyethylene glycol, also known as PEG-DMG, obtainable from Avanti Polar Lipids, Alabaster, AL or Compound 428), and a structural lipid (such as cholesterol, obtainable from Sigma-Aldrich, Taufkirchen, Germany, or a corticosteroid (such as prednisolone, dexamethasone, prednisone, and hydrocortisone), or a combination thereof) at concentrations of about 50 mM in ethanol. Solutions should be refrigerated for storage at, for example, −20° C. Lipids are combined to yield desired molar ratios and diluted with water and ethanol to a final lipid concentration of between about 5.5 mM and about 25 mM.

Nanoparticle compositions including a polynucleotide and a lipid composition can be prepared by combining the lipid solution with a solution including the a polynucleotide at lipid composition to polynucleotide wt:wt ratios between about 5:1 and about 50:1. The lipid solution is rapidly injected using a NanoAssemblr microfluidic based system at flow rates between about 10 ml/min and about 18 ml/min into the polynucleotide solution to produce a suspension with a water to ethanol ratio between about 1:1 and about 4:1.

For nanoparticle compositions including an RNA, solutions of the RNA at concentrations of 0.1 mg/ml in deionized water are diluted in 50 mM sodium citrate buffer at a pH between 3 and 4 to form a stock solution.

Nanoparticle compositions can be processed by dialysis to remove ethanol and achieve buffer exchange. Formulations are dialyzed twice against phosphate buffered saline (PBS), pH 7.4, at volumes 200 times that of the primary product using Slide-A-Lyzer cassettes (Thermo Fisher Scientific Inc., Rockford, IL) with a molecular weight cutoff of 10 kD. The first dialysis is carried out at room temperature for 3 hours. The formulations are then dialyzed overnight at 4° C. The resulting nanoparticle suspension is filtered through 0.2 μm sterile filters (Sarstedt, Nümbrecht, Germany) into glass vials and sealed with crimp closures. Nanoparticle composition solutions of 0.01 mg/ml to 0.10 mg/ml are generally obtained.

The method described above induces nano-precipitation and particle formation. Alternative processes including, but not limited to, T-junction and direct injection, can be used to achieve the same nano-precipitation.

B. Characterization of Nanoparticle Compositions

A Zetasizer Nano ZS (Malvern Instruments Ltd, Malvern, Worcestershire, UK) can be used to determine the particle size, the polydispersity index (PDI) and the zeta potential of the nanoparticle compositions in 1×PBS in determining particle size and 15 mM PBS in determining zeta potential.

Ultraviolet-visible spectroscopy can be used to determine the concentration of a polynucleotide (e.g., RNA) in nanoparticle compositions. 100 μL of the diluted formulation in 1×PBS is added to 900 μL of a 4:1 (v/v) mixture of methanol and chloroform. After mixing, the absorbance spectrum of the solution is recorded, for example, between 230 nm and 330 nm on a DU 800 spectrophotometer (Beckman Coulter, Beckman Coulter, Inc., Brea, CA). The concentration of polynucleotide in the nanoparticle composition can be calculated based on the extinction coefficient of the polynucleotide used in the composition and on the difference between the absorbance at a wavelength of, for example, 260 nm and the baseline value at a wavelength of, for example, 330 nm.

For nanoparticle compositions including an RNA, a QUANT-IT™ RIBOGREEN® RNA assay (Invitrogen Corporation Carlsbad, CA) can be used to evaluate the encapsulation of an RNA by the nanoparticle composition. The samples are diluted to a concentration of approximately 5 μg/mL in a TE buffer solution (10 mM Tris-HCl, 1 mM EDTA, pH 7.5). 50 μL of the diluted samples are transferred to a polystyrene 96 well plate and either 50 μL of TE buffer or 50 μL of a 2% Triton X-100 solution is added to the wells. The plate is incubated at a temperature of 37° C. for 15 minutes. The RIBOGREEN® reagent is diluted 1:100 in TE buffer, and 100 μL of this solution is added to each well. The fluorescence intensity can be measured using a fluorescence plate reader (Wallac Victor 1420 Multilablel Counter; Perkin Elmer, Waltham, MA) at an excitation wavelength of, for example, about 480 nm and an emission wavelength of, for example, about 520 nm. The fluorescence values of the reagent blank are subtracted from that of each of the samples and the percentage of free RNA is determined by dividing the fluorescence intensity of the intact sample (without addition of Triton X-100) by the fluorescence value of the disrupted sample (caused by the addition of Triton X-100).

Exemplary formulations of the nanoparticle compositions are presented in the TABLE 6 below. The term "Compound" refers to an ionizable lipid such as MC3, Compound 18, or Compound 236. "Phospholipid" can be DSPC or DOPE. "PEG-lipid" can be PEG-DMG or Compound 428.

TABLE 6

Exemplary Formulations of Nanoparticles

| Composition (mol %) | Components |
| --- | --- |
| 40:20:38.5:1.5 | Compound:Phospholipid:Chol:PEG-lipid |
| 45:15:38.5:1.5 | Compound:Phospholipid:Chol:PEG-lipid |
| 50:10:38.5:1.5 | Compound:Phospholipid:Chol:PEG-lipid |
| 55:5:38.5:1.5 | Compound:Phospholipid:Chol:PEG-Lipid |
| 60:5:33.5:1.5 | Compound:Phospholipid:Chol:PEG-lipid |
| 45:20:33.5:1.5 | Compound:Phospholipid:Chol:PEG-lipid |
| 50:20:28.5:1.5 | Compound:Phospholipid:Chol:PEG-lipid |
| 55:20:23.5:1.5 | Compound:Phospholipid:Chol:PEG-lipid |
| 60:20:18.5:1.5 | Compound:Phospholipid:Chol:PEG-lipid |
| 40:15:43.5:1.5 | Compound:Phospholipid:Chol:PEG-lipid |
| 50:15:33.5:1.5 | Compound:Phospholipid:Chol:PEG-lipid |
| 55:15:28.5:1.5 | Compound:Phospholipid:Chol:PEG-lipid |
| 60:15:23.5:1.5 | Compound:Phospholipid:Chol:PEG-lipid |
| 40:10:48.5:1.5 | Compound:Phospholipid:Chol:PEG-lipid |
| 45:10:43.5:1.5 | Compound:Phospholipid:Chol:PEG-lipid |
| 55:10:33.5:1.5 | Compound:Phospholipid:Chol:PEG-lipid |
| 60:10:28.5:1.5 | Compound:Phospholipid:Chol:PEG-lipid |
| 40:5:53.5:1.5 | Compound:Phospholipid:Chol:PEG-lipid |
| 45:5:48.5:1.5 | Compound:Phospholipid:Chol:PEG-lipid |
| 50:5:43.5:1.5 | Compound:Phospholipid:Chol:PEG-lipid |
| 40:20:40:0 | Compound:Phospholipid:Chol:PEG-lipid |
| 45:20:35:0 | Compound:Phospholipid:Chol:PEG-lipid |
| 50:20:30:0 | Compound:Phospholipid:Chol:PEG-lipid |
| 55:20:25:0 | Compound:Phospholipid:Chol:PEG-lipid |
| 60:20:20:0 | Compound:Phospholipid:Chol:PEG-lipid |
| 40:15:45:0 | Compound:Phospholipid:Chol:PEG-lipid |
| 45:15:40:0 | Compound:Phospholipid:Chol:PEG-lipid |
| 50:15:35:0 | Compound:Phospholipid:Chol:PEG-lipid |
| 55:15:30:0 | Compound:Phospholipid:Chol:PEG-lipid |
| 60:15:25:0 | Compound:Phospholipid:Chol:PEG-lipid |
| 40:10:50:0 | Compound:Phospholipid:Chol:PEG-lipid |
| 45:10:45:0 | Compound:Phospholipid:Chol:PEG-lipid |
| 50:10:40:0 | Compound:Phospholipid:Chol:PEG-lipid |
| 55:10:35:0 | Compound:Phospholipid:Chol:PEG-lipid |
| 60:10:30:0 | Compound:Phospholipid:Chol:PEG-lipid |

Example 21

Hepatic PBGD Activity in AIP Mice after Administration of Modified mRNA Encoding PBGD Hepatic PBGD activity was determined in AIP mice administered mRNA encoding PBGD. AIP mice are compound heterozygotes of two different disruptions of the PBGD gene: T1 strain [C57BL/6-pbgd$^{tm1(neo)Uam}$ and T2 strain (C57BL/6-pbgd$^{tm2(neo)Uam}$] (Lindberg R L, et al. "Porphobilinogen deaminase deficiency in mice causes a neuropathy resembling that of human hepatic porphyria." Nat Genet. 1996; 12:195-199). These AIP mice develop symptoms that mimic those in humans with AIP. For example, the AIP mouse phenotype includes, e.g., overproduction of aminolevulinic acid in response to phenobarbital treatment, increased urinary excretion of aminolevulinic acid and porphobilinogen in response to phenobarbital treatment, slightly increased excretion of uroporphyrins, pain, ataxia, slower movements, shorter stride length, skeletal muscle degeneration, and erythruria.

Sequence modified (1-methyl-pseudouridine) mRNAs comprising an ORF encoding wild-type PBGD (PBGD COV1 or PBGD COV2), PBGD-SM (gain of function PBGD mutant with SM mutation), and ApoA1-PBGD-SM (gain of function PBGD mutant with SM mutation fused to apolipoprotein A1) at 1 nmol/kg were intravenously administered to AIP mice (n=4), and hepatic PBGD activity was measured by a fluorimetric assay (pmol uroporphyrin I/mg protein/hour). The modified mRNA encoding PBGD-SM included a miR-142 binding site. The modified mRNAs encoding wild type PBGD, PBGD COV1 (codon optimized variant 1) and PBGD COV2 (codon optimized variant 2), did not include a miR-142 binding site. mRNAs were formulated in MC3 lipid nanoparticles.

PBGD activity in tissue homogenates was determined by measuring the conversion of PBG to uroporphyrin. Briefly, 1 g of tissue was homogenized at 4° C. in 4 vol of KCl solution 1.15%. The homogenate was centrifuged at 12.000 rpm at 4° C. for 20 minutes and the clear supernatant without any cellular debris was used the same day for protein determination (Bradford assay using albumin standard) and PBGD activity. The supernatant samples were diluted 1:3 with phosphate buffer (pH 7.6), DTT, $Cl_2Mg$ and Triton X-100; and 100 µl of this mixture were pre-incubated with 1.8 ml of Tris-HCl 0.1M (pH 8.1) for 3 min at 37° C. Next the mixture was incubated in the dark with 0.5 ml PBG substrate 1 mM 60 min at 37° C. The reaction was stopped with 350 µl cold TCA 40% and the uroporphyrinogen formed was oxidised to uroporphyrin after light exposure. Uroporphyrins were measured quantitatively in a spectrofluorometer with an excitation peak at 405 nm and window emission peak values between 550-660 nm. PBGD activity was expressed in terms of pmol uroporphyrin/mg protein/h using appropriate standards.

Figure 13:
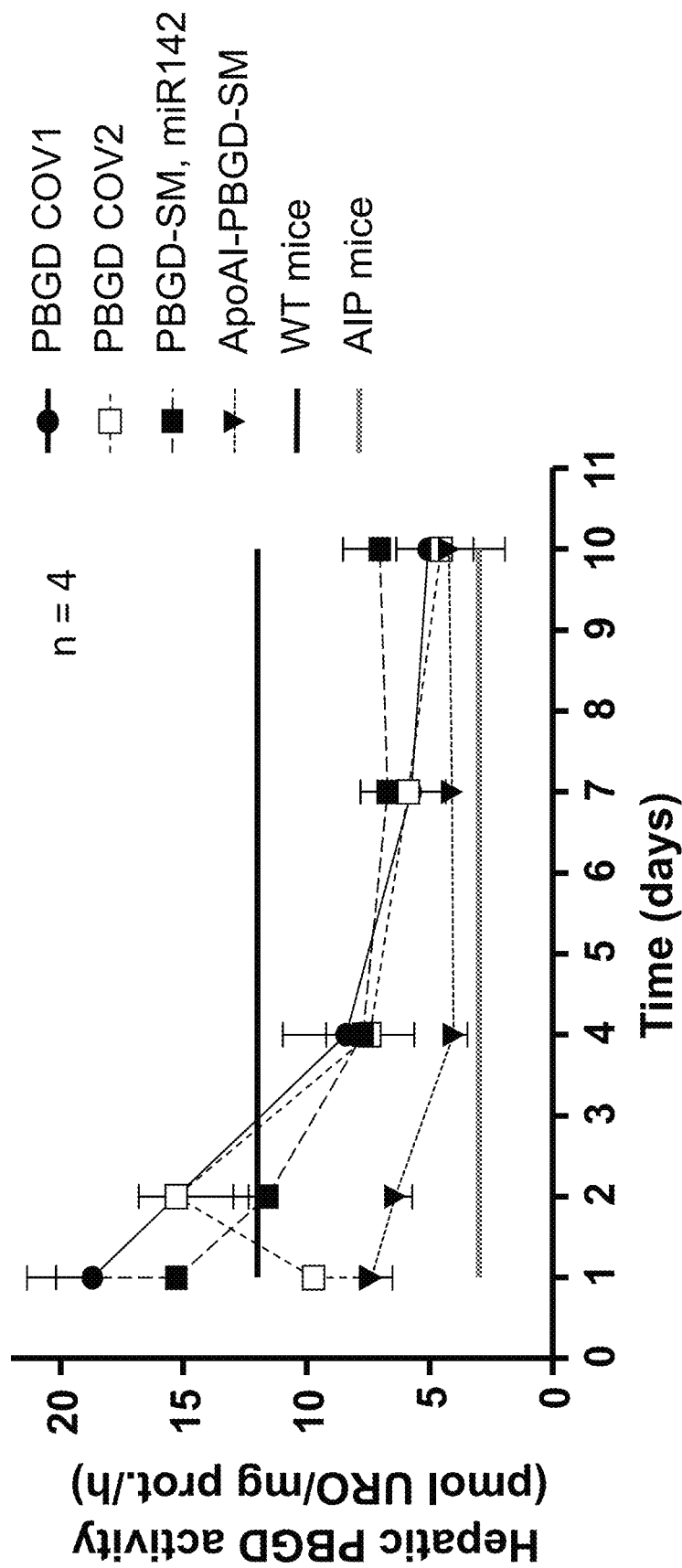

The hepatic PBGD activity in AIP mice following administration of PBGD mRNA is shown in FIG. 13. For comparison, the 12 units threshold line in FIG. 13 is the level of PBGD observed in livers of wild-type mice (C57BL/6), and the 3 units threshold line is the level of PBGD in livers of AIP mice without treatment.

The results show that after 24 hours, hepatic PBGD activity was within the therapeutic window for up to 7 days after administration. An acute porphyria attack in a human lasts between 5 and 7 days. In humans, the increase from 2 units to 5 units completely restores the PBGD activity in the liver. Accordingly, these results suggest that a single administration of mRNA encoding wild-type PBGD could protect against an acute porphyria attack.

Example 22

Single Dose IV Administration of mRNA Encoding PBGD to AIP Mice

Figure 14:
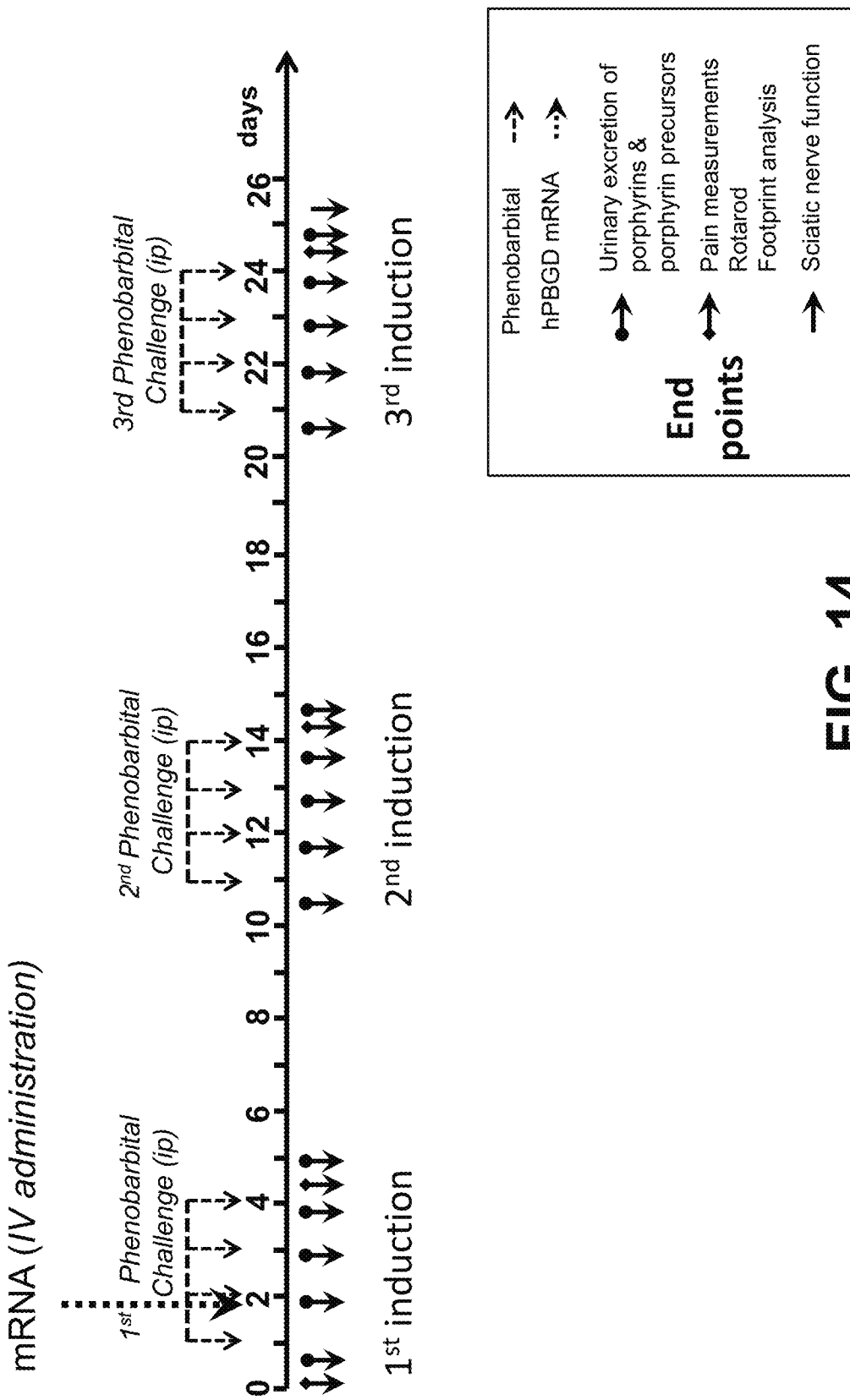

The ability of PBGD mRNA to reduce symptoms in AIP mice after multiple phenobarbital induced attacks was tested. 0.5 mg/kg doses of 1-methyl-pseudouridine modified mRNAs comprising an ORF encoding wild-type or SM variant of human PBGD or 0.5 mg/kg doses of control luciferase mRNA were formulated in lipid nanoparticles (MC3) and administered to AIP mice (n=4) according to the dosing schedule presented in FIG. 14. The mRNAs were administered as a single intravenous dose on day 2 of the study. Mice were subjected to 3 phenobarbital challenges, each of which consisted of 4 separate intraperitoneal injections of phenobarbital. The end points of the study included (A) urinary excretion of porphyrins and porphyrin precursors, (B) pain measurements, (C) peripheral neuropathy using rotarod and footprint analysis, and (D) sciatic nerve function.

A. Reduction of urinary ALA and PBG excretion: Urinary aminolevulinic acid (ALA) excretion and urinary porphobilinogen (PBG) excretion were measured in the AIP mice administered PBGD mRNA or luciferase control.

Urinary excretion of aminolevulinate acid (ALA) and porphobilinogen (PBG) were quantified using a quantitative ion exchange column method (BioSystems SA, Barcelona) and measured at 555 nm in an Ultrospc 3000 spectrophotometer (Pharmacia Biotech, Buckinghamshire, UK). Unzu et al., Mol Ther. 19(2):243-50 (2011).

Figure 15:
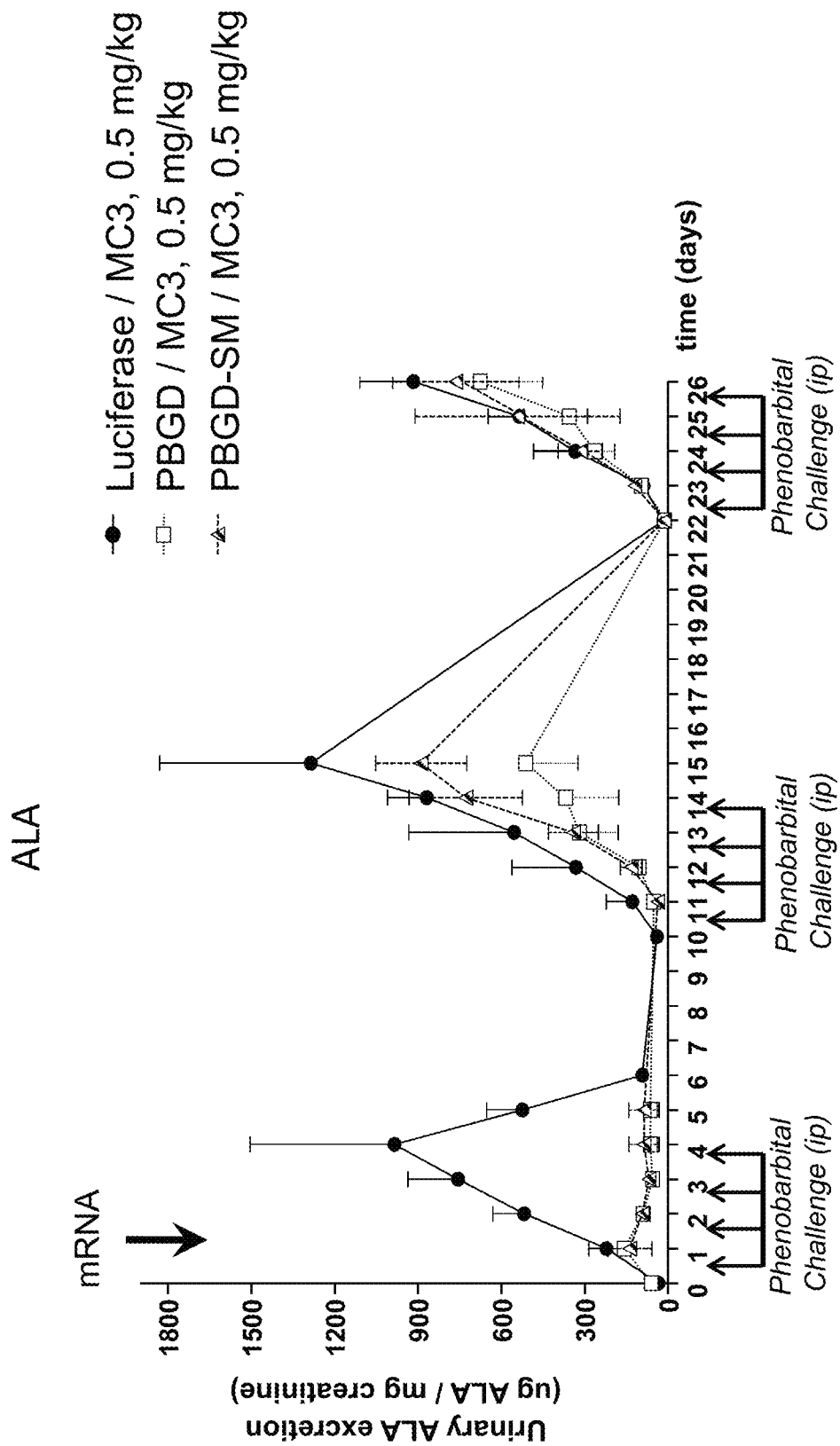
Figure 16:
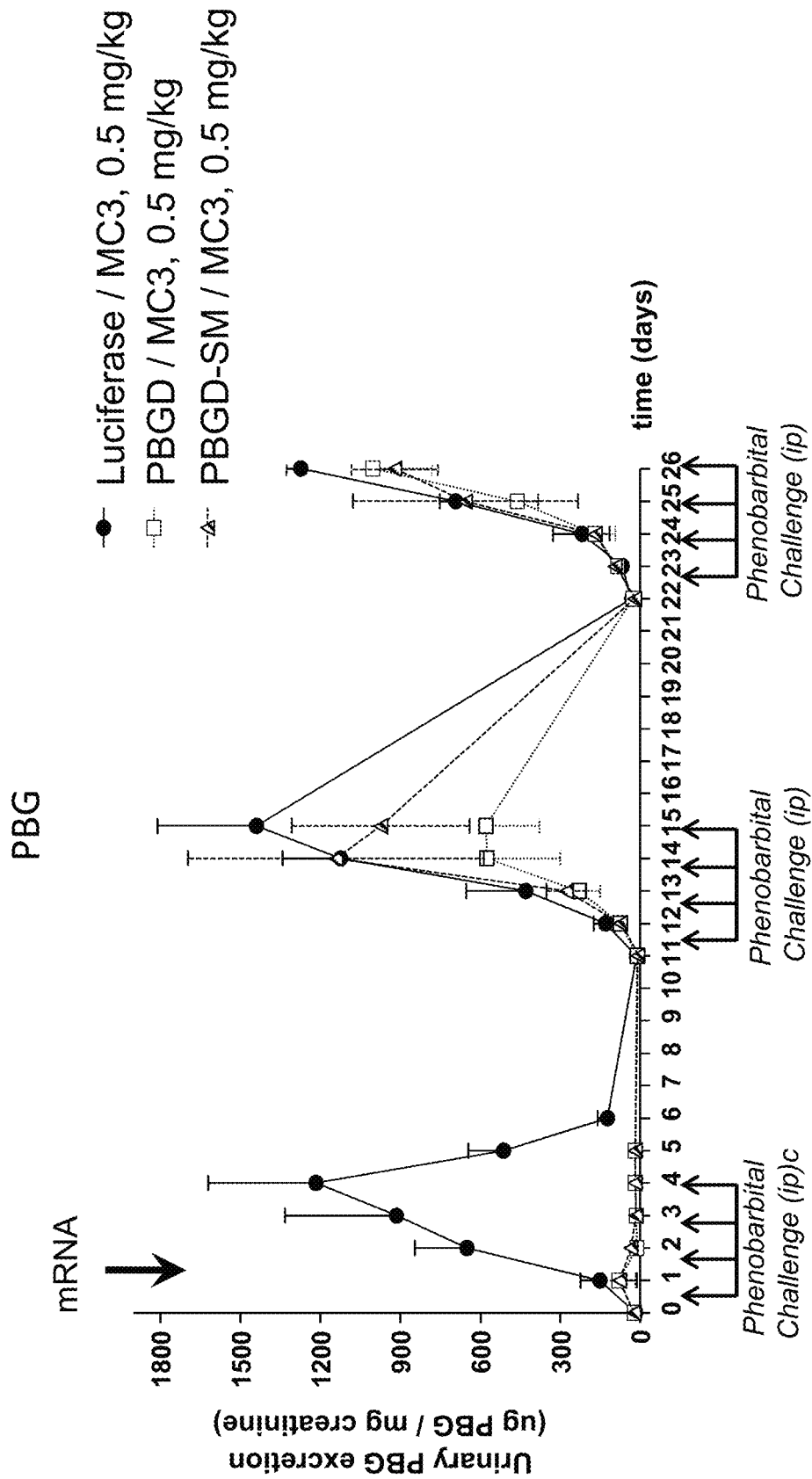

Urinary ALA excretion (µg ALA/mg creatinine) and urinary PBG excretion (µg PBG/mg creatinine) levels over time are shown in FIG. 15 and FIG. 16, respectively. Both urinary ALA and PBG increased markedly in AIP mice treated with control luciferase mRNA, reaching levels of twenty-fold and sixty-fold greater, respectively, compared to mean baseline values. In contrast, after the first phenobarbital challenge, full protection against the ALA and PBG over-excretion was obtained in mice administered PBGD mRNA. After the administration of PBGD mRNA, ALA and PBG levels were maintained close to baseline levels. A protective effect was observed in PBGD mRNA treated mice after the second phenobarbital challenge, which took place about 2 weeks after mRNA administration. After three weeks, the protective effect was no longer observed.

These results indicate that (i) there was a very fast onset of the protective effect (within one day) by PBGD mRNA administration, (ii) the observed effect on ALA and PBG urinary excretion was very potent (close to baseline levels), and (iii) the observed protective effect was long lasting, indicating that the half-life of the modified PBGD mRNA is very long (at least two weeks).

Figure 17:
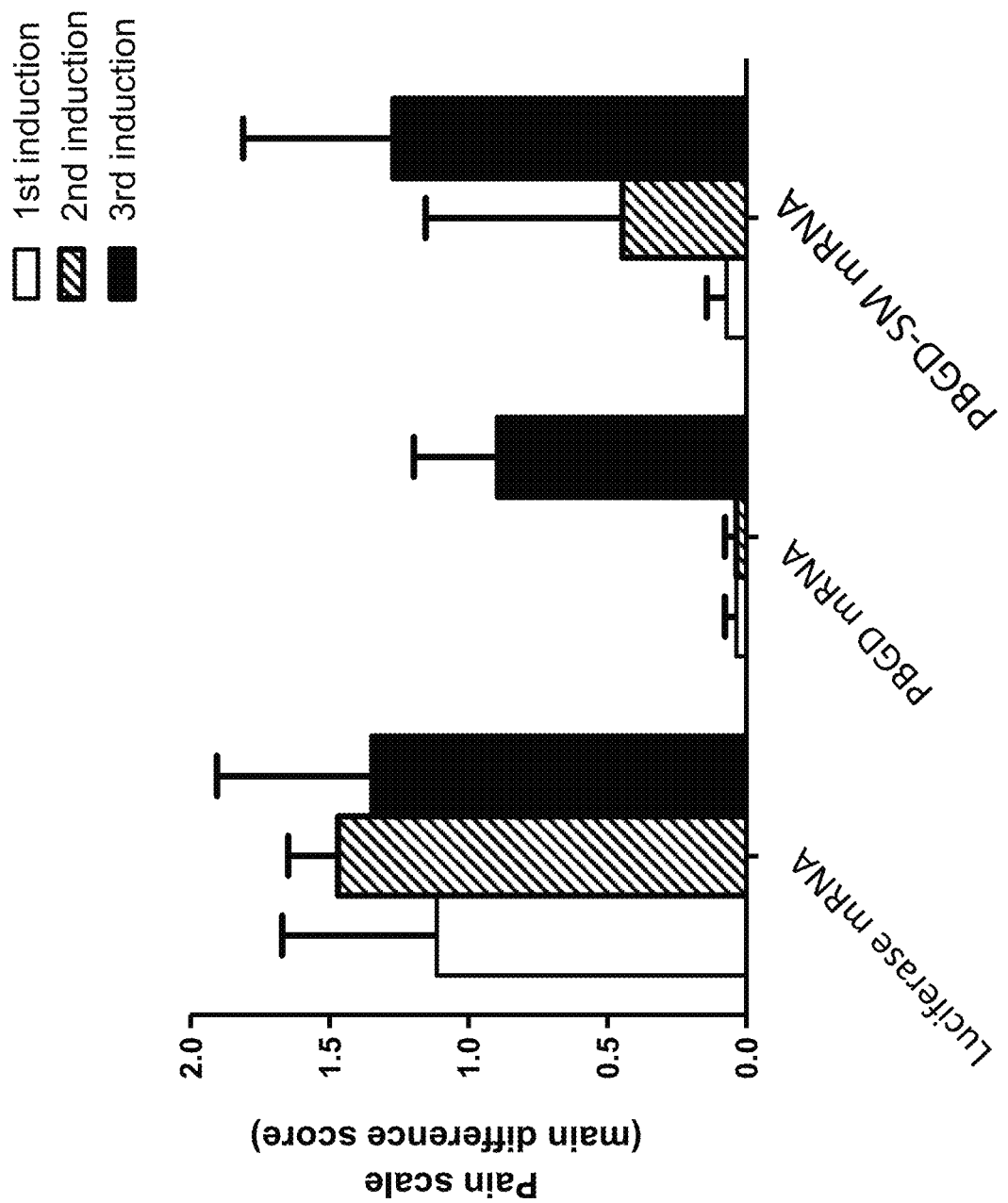

B. Protection against pain: 95% of human patients suffering from AIP experience severe pain. The effect of mRNA encoding wild-type or SM variant of PBGD on pain in AIP mice was tested. Pain was measured based on observations of orbital tightening, nose bulge, cheek bulge, ear position, whisker change, abdominal grooming, and respiratory distress (Langford et al. Nat Methods. 7(6):447-9 (2010)). The data presented in FIG. 17 shows that a single administration of mRNA encoding wild-type or SM variant of human PBGD protected against pain induced after the first phenobarbital challenge, and extended protection against recurrent phenobarbital-induced pain was observed in the AIP mice after the second phenobarbital challenge. Control luciferase mRNA provided no pain protection in AIP mice following phenobarbital challenge.

C. Protection against peripheral neuropathy: Peripheral neuropathy was assessed by evaluating rotarod performance (movement and balance) and gait patterns (stride length and base of support) after phenobarbital challenge. Motor coordination was evaluated by the rotarod test, which measures the time (in seconds) that a mouse can stay on a rotating dowel turning at increasing speed (Unzu et al., Mol Ther. 19(2):243-50 (2011)). To assess gait pattern, the stride length and base of support (i.e., distance between the central pads of the hind feet) was determined substantially as described in Lindberg R L et al., Nat Genet, 12: 195-99 (1996). The time spent on the rotarod (seconds) for each group is shown in FIG. 18A, and stride length (cm) for each group is shown in FIG. 18B.

Figure 18A:
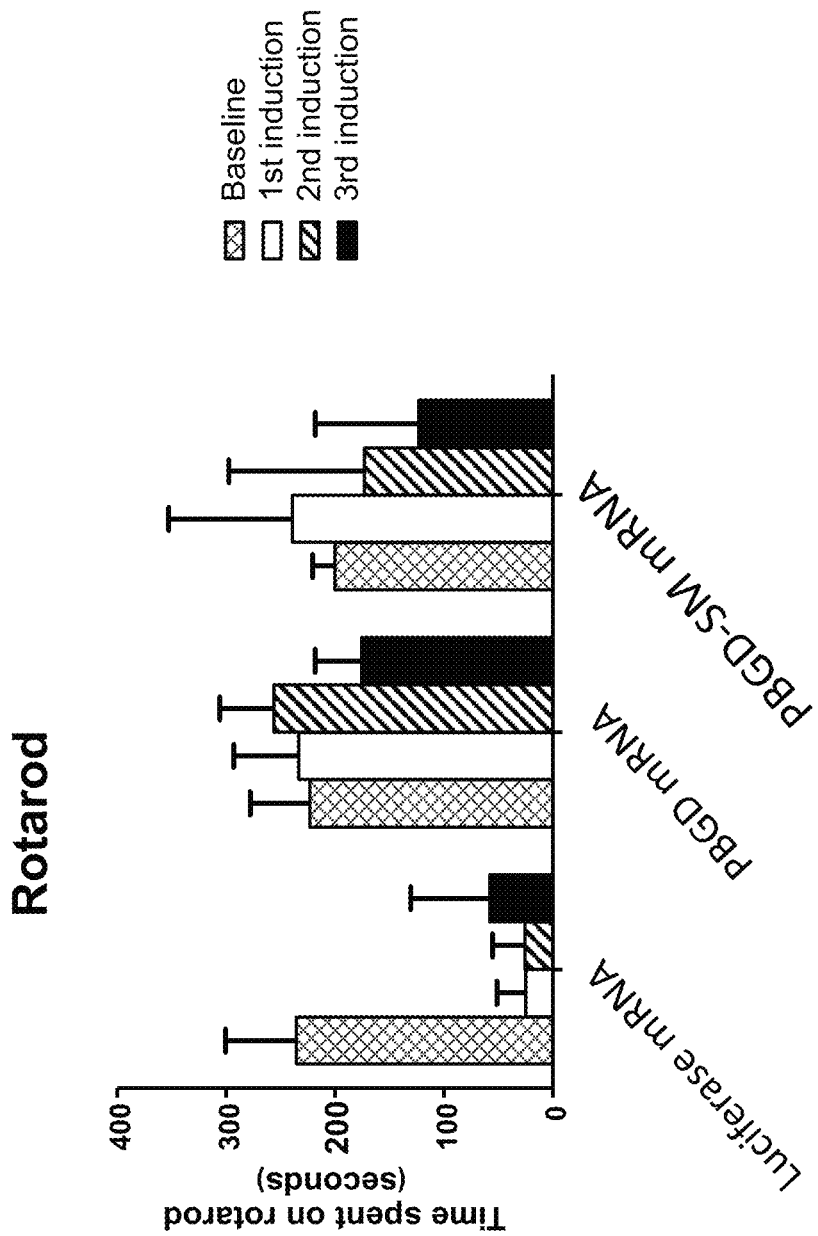

As shown in FIG. 18A, after the each phenobarbital challenge, the time that AIP mice administered control luciferase mRNA were able to stay on the rotarod significantly decreased. On the other hand, after the each phenobarbital challenge, the time that AIP mice administered PBGD mRNA were able to stay on the rotarod was comparable to the time observed under baseline conditions (no phenobarbital challenge).

Figure 18B:
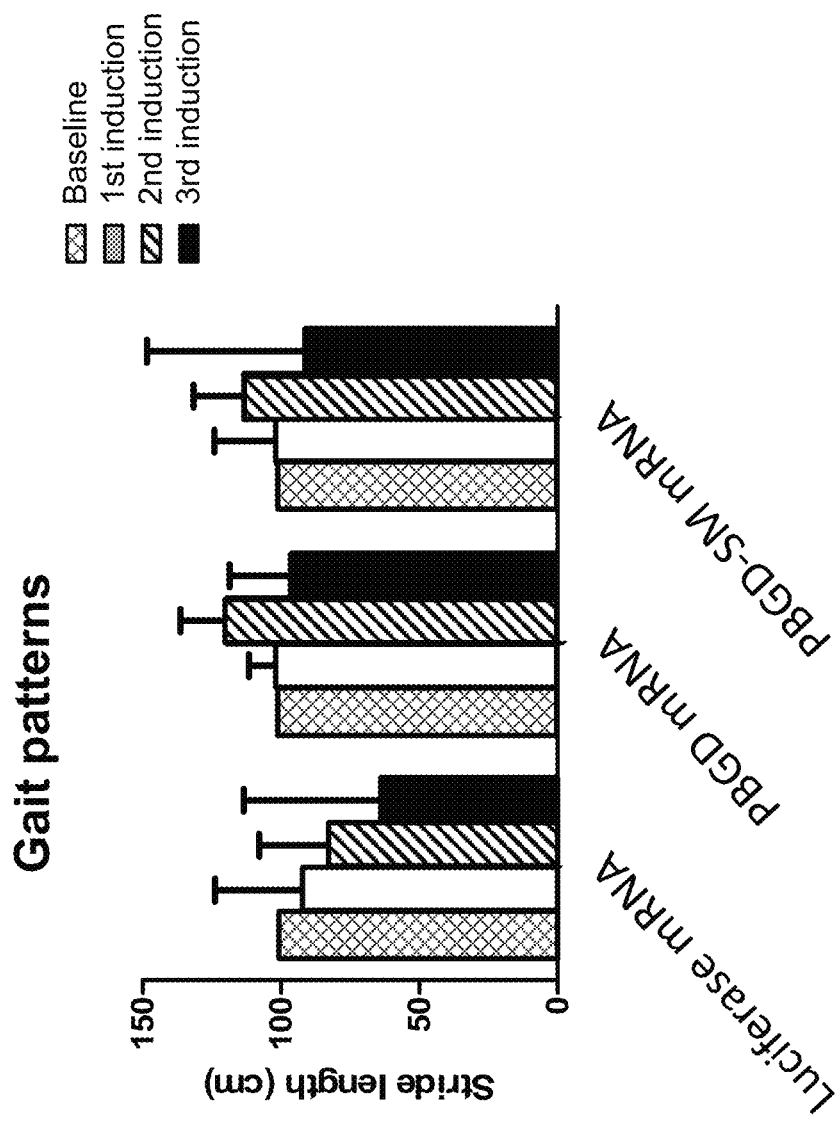

As shown in FIG. 18B, AIP mice administered control luciferase mRNA had decreased stride length compared to animals administered PBGD mRNA. The gait of AIP mice treated with control luciferase mRNA deteriorated with each phenobarbital challenge. On the other hand, the gait maintained in AIP mice treated with PBGD mRNA. Thus, these results show that the administration of modified mRNA encoding wild-type or SM variant of human PBGD protected AIP against peripheral motor disturbance induced by phenobarbital.

D. Improvement in sciatic nerve dysfunction caused by recurrent acute attacks: Sciatic nerve function was assessed in AIP mice administered control luciferase mRNA or PBGD mRNA using substantially the methods disclosed in Unzu et al., Mol Ther. 19(2):243-50, 2011.

Axon measurement. Sciatic nerves were fixed overnight at 4° C. in 4% glutaraldehyde in 0.1 M sodium cacodylate buffer, pH 7.2, and post-fixed for 2.5 h at 4° C. in 1% phosphate-buffered osmium tetroxide. Samples were dehydrated with ethanol, washed with propylene oxide and embedded in Epon 812. Semithin (1 mm thick) sections were cut and stained with 1% toluidine blue for examination by light microscopy. Axon sections were acquired in a M1 Zeiss microscope and an INSIGHT AxioCamm ICc3 camera using AxioVision Zeiss Imaging software. The image analysis software has been developed using MATLAB v.7.1.0 and DIPlib v1.6 C libraries under OS Red Hat Linux AS 2.6.18-53.e15. Caliber and density of axons were quantified by computer-assisted image analysis.

Neurophysiological studies. Electrophysiological studies included measurements of nerve conduction velocity and action potential amplitude of the sciatic nerve. The electrical stimuli were delivered by means of pairs of needles placed subcutaneously near the exit point of the sciatic nerve at the hip, with a separation of 0.5 mm and the cathode located distally. Stimuli were delivered by a Grass S180 stimulator with a Grass constant current unit (Grass-AstroMed, W. Worwick, USA), synchronized with the recording equipment. Stimulus intensity was progressively increased to ensure the maximal response amplitude. The motor potential was recorded by means of steel needle electrodes (Viasys Heathcare, UK) located at the center of the soleus muscle (active) (midpoint between the ankle and the knee) and near the insertion of the Achilles tendon. The responses were amplified by a Grass P511 amplifier (Grass Astromed, USA), digitized by means of a CED power 1401 A/D converter (Cambridge Electronic Design, Cambridge, UK), and stored in a PC using Signal 3 software (Cambridge Electronic Design, Cambridge, UK). Stimulation intensity was increased gradually until the amplitude of the response did not increase any further. The intensity used for the measured potentials was at least 20% higher than the minimal value associated with a maximal response. The best response out of 10 adequate potentials was selected for the analysis. The response analyzed consisted of a biphasic potential negative/positive in all cases. Amplitude, latency and duration of the compound muscle action potential were measured and double-checked by a different person.

Increased latency and loss of amplitude correlate with motor dysfunction and axonal loss developed in AIP mice after repeated phenobarbital induction of acute attacks (Unzu et al. Mol Ther. 2011). In AIP mice, abnormalities in the nerve conduction velocities occur with aging and after recurrent acute attacks induced by increasing doses of phenobarbital. In the human porphyria, peripheral neuropathy is observed in patients after maintained high levels of porphyrin precursors over-time. Peripheral neuropathy can be asymmetric in acute porphyrias.

Figure 19B:
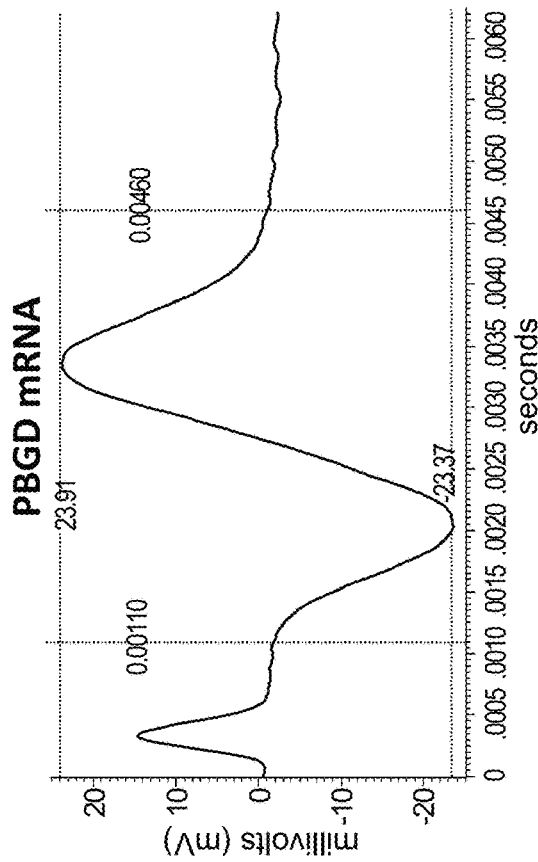
Figure 19A:
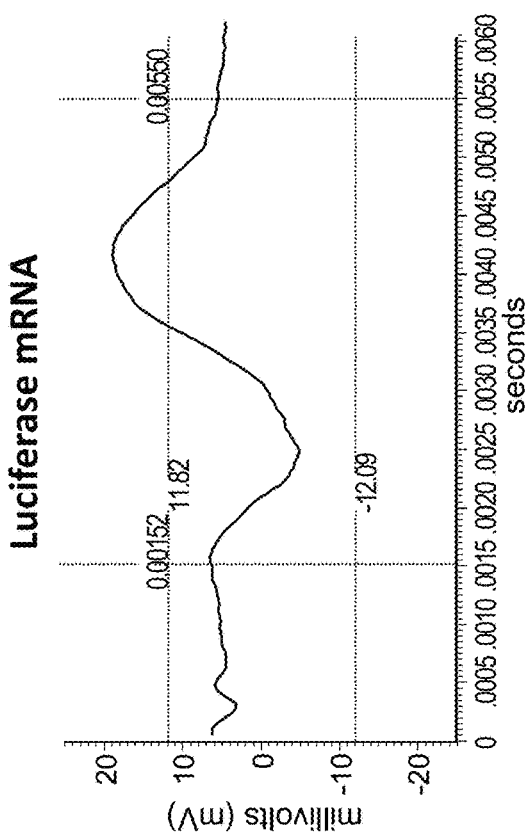
Figure 19C:
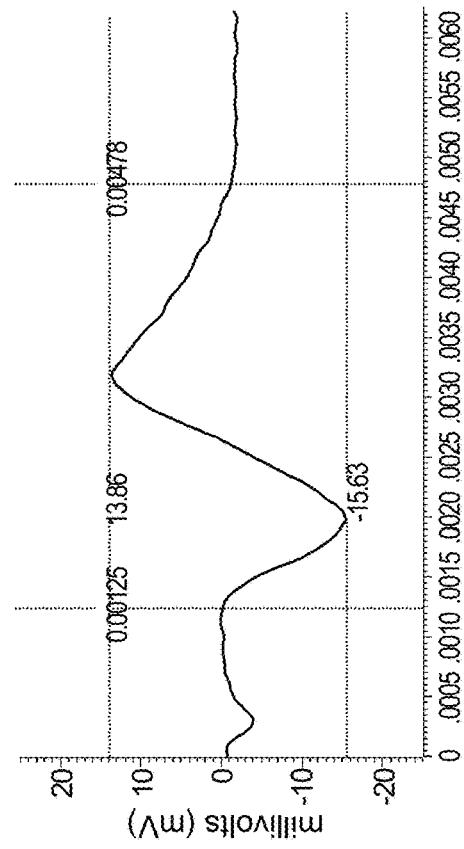
Figure 19E:
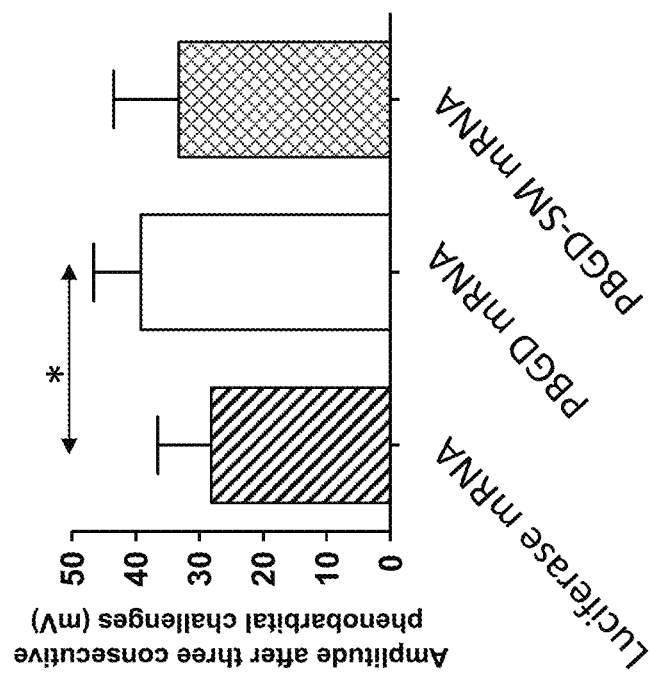
Figure 19D:
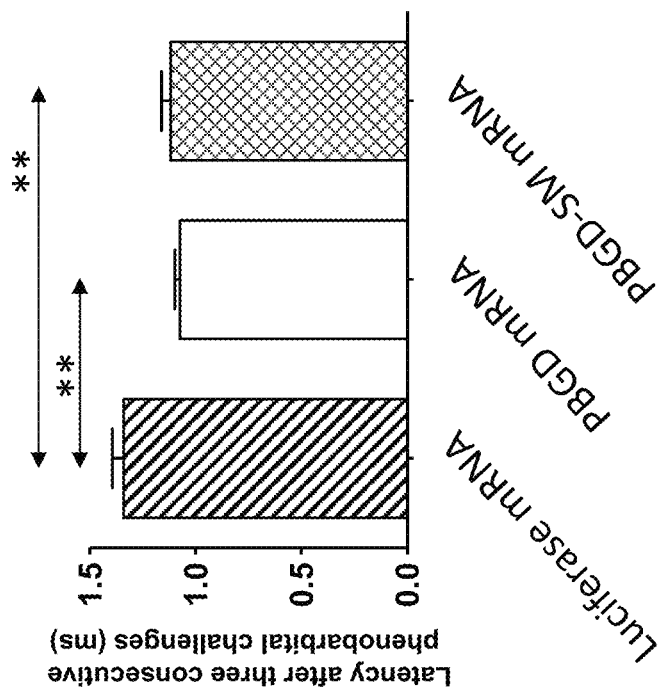

The compound-muscle action potentials evoked by proximal stimulation of the sciatic nerve were measured at day 27 post-injection), 8 hour last phenobarbital challenge in the two hind legs of AIP mice administered mRNA encoding luciferase or mRNA encoding wild type PBGD or mRNA encoding PBGD-SM protein variant. FIG. 19A, FIG. 19B and FIG. 19C show examples of the amplitude over time (right leg) for control, PBGD mRNA and PGBD-SM mRNA treated mice, respectively. The control luciferase mRNA group had short amplitude and long latency measurements and the PBGD mRNA group had longer amplitude and shorter latency measurements. The latency after three consecutive phenobarbital challenges (ms) for each group is shown in FIG. 19D. The amplitude after three consecutive phenobarbital challenges (mV) for each group is shown in FIG. 19E. Thus, the administration of a single dose of modified mRNA encoding wild-type human PBGD protected against increased latency and loss of amplitude in AIP mice following recurrent acute attacks. The administration of a single dose of modified mRNA encoding human PBGD-SM protected against increased latency in AIP mice following recurrent acute attacks.

These results show significant therapeutic efficacy of mRNA encoding PBGD for treatment of AIP signs and symptoms in vivo. The PBGD mRNA treated AIP mouse, although challenged with phenobarbital, showed no signs of pain and was able to move around as actively as a wild type mouse. On the contrary, the luciferase mRNA treated AIP mouse during phenobarbital induced attack appeared to be in great pain and could not move freely and showed balancing problems in the movement.

Example 23

Hepatic Expression of PBGD Protein after Administration of AAV-PBGD DNA and PBGD mRNA Liver tissue from AIP mice injected with an AAV-PBGD vector or with mRNA comprising an ORF encoding PBGD were analyzed by immunohistochemistry (IHC) using a rabbit polyclonal anti-PBGD antibody (Santa cruz #sc-67037) and compared to liver from untreated AIP mice.

Histology and PBGD Immunohistochemical staining. Formalin-fixed/paraffin embedded sections (5 μm) of right and left liver lobes were stained with hematoxylin eosin. Immunohistochemistry was used to determine the proportion of cells highly stained with the polyclonal anti-PBGD antibody produced in rabbit (dilution 1:800). The secondary antibody used was goat anti-rabbit coupled to a peroxidase-labelled dextran polymer (Dako, K4003). Peroxidase was visualized using DAB+ (Dako, K3468). After counterstaining with hematoxylin to give a blue background contrast to brown colour of the positive cells, the percentage of PBGD-positive cells was calculated in at least 1000 cells from 4-6 fields of vision for each sample under microscope with 40× magnifications. Hepatocytes and non-parenchymal cells were readily differentiated based upon morphological criteria: hepatocytes have a polyhedral shape, round nucleus and are larger than the non-parenchymal cells, which have an irregular shape.

As shown in FIG. 20A, administration of gene therapy vector AAV-PBGD in AIP mice induced aggregate staining in the liver suggesting high PBGD protein levels (>60 U) in some hepatocytes. A representative liver tissue sample from an untreated AIP mouse is shown in FIG. 20B, which confirmed essentially very low PBGD protein level (about 3 U) was detected in the liver of AIP mice. In the liver of PBGD mRNA treated AIP mice, PBGD protein expression was homogeneous throughout all hepatocytes and decreased over time. Increased protein expression was observed at day 1 (about 19U), day 2 (about 14 U), and day 4 (about 4.7 U) after injection of the PBGD mRNA, as shown in FIG. 20C, FIG. 20D, and FIG. 20E, respectively. The expression of PBGD protein observed by IHC was consistent with the PBGD hepatic activity shown in Example 21.

Example 24

Lipid Nanoparticle Delivery Systems for Administering mRNAs Encoding Wild-Type Human PBGD Different formulations of lipid nanoparticles encapsulating PBGD mRNA were tested for the ability to reduce symptoms in AIP mice after multiple phenobarbital induced attacks. 0.5 or 0.1 mg/kg doses of 1-methyl-pseudouridine modified mRNAs comprising an ORF encoding wild-type human PBGD or 0.5 mg/kg does of control mRNA comprising an ORF encoding luciferase were formulated in lipid nanoparticles (either MC3 or Compound 18) and administered to AIP mice. The mRNAs were administered as a single intravenous dose on day 2 of the study. Mice were subjected to 3 phenobarbital challenges, each of which consisted of 4 separate intraperitoneal injections of phenobarbital. The end points of the study included (A) urinary excretion of porphyrins and porphyrin precursors, (B) pain measurements, (C) peripheral neuropathy using rotarod, which were tested according to the same methods described in Example 22 above. A mouse from the luciferase mRNA-MC3 (control) group, a mouse from the luciferase mRNA-Compound 18 (control) group, and a mouse from the PBGD mRNA-MC3 group died after the administration of the third dose during the second phenobarbital challenge. All three showed symptoms of an acute porphyria attack before their deaths.

Figure 21A:
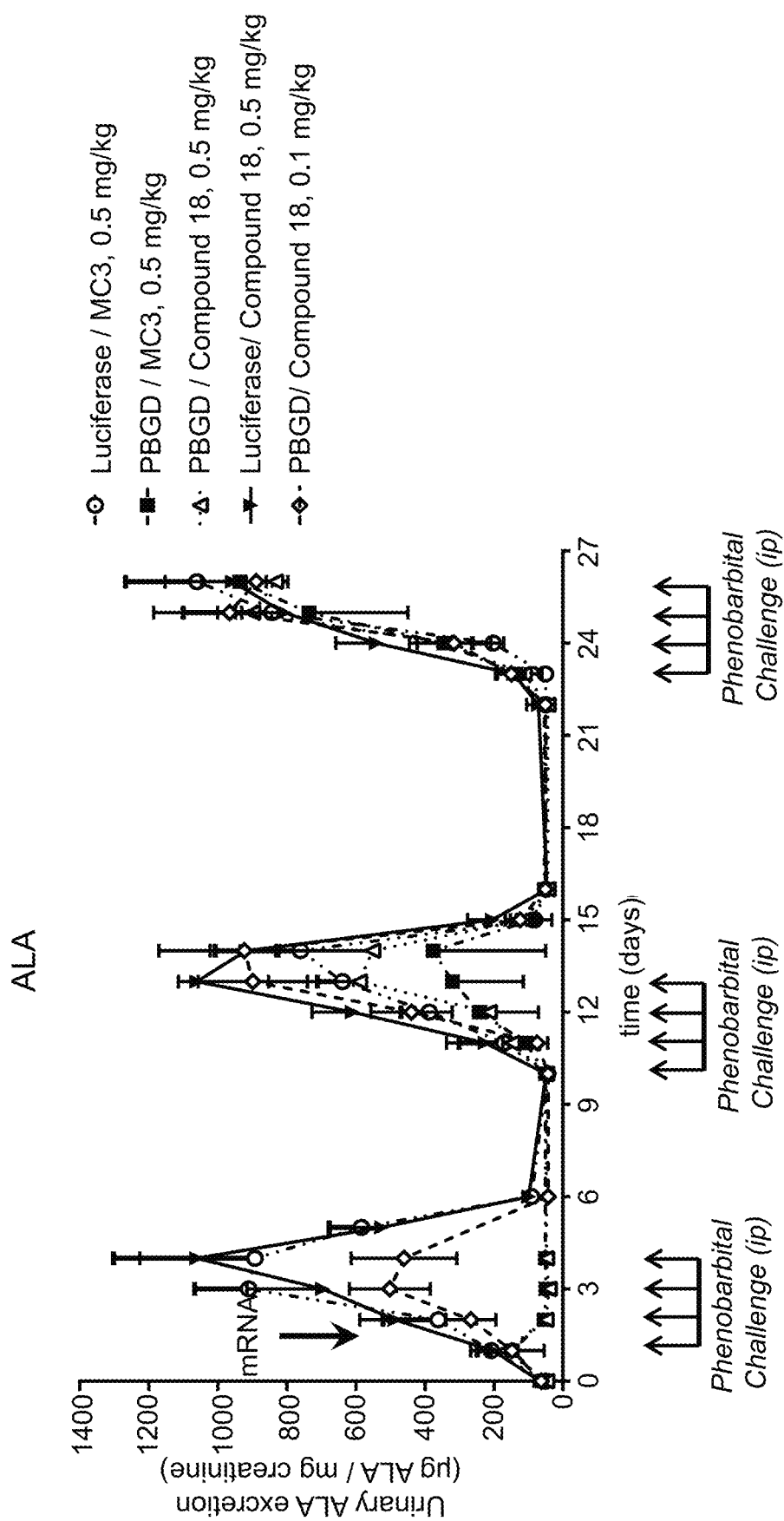
Figure 21B:
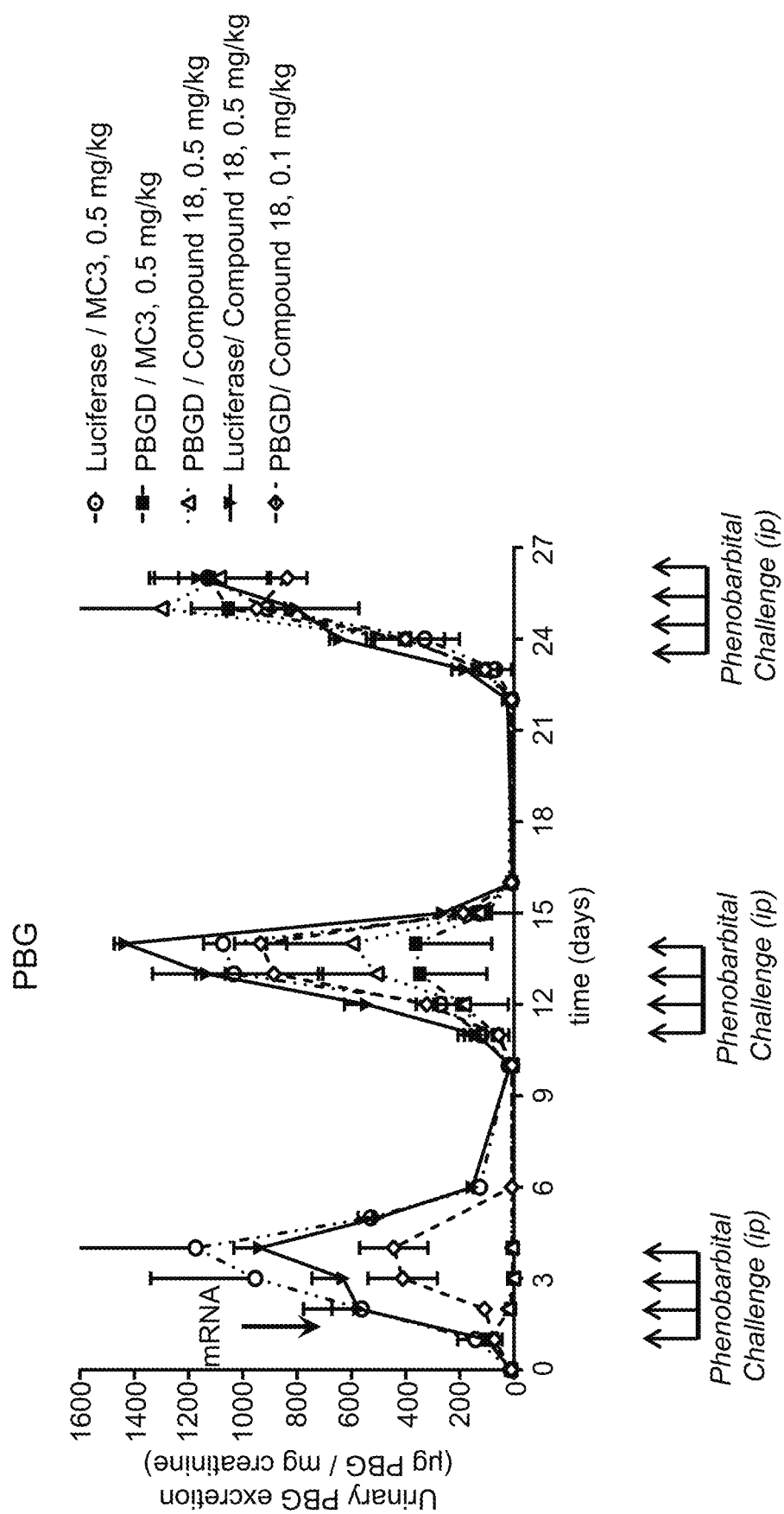

A. Reduction of urinary ALA and PBG excretion: mRNAs encoding wild-type PBGD formulated in either MC3 or Compound 18 fully protected against the increase of porphyrin precursors ALA and PBG induced after a first phenobarbital challenge, and significantly reduced their accumulation in the second phenobarbital challenge as shown in FIG. 21A and FIG. 21B, respectively. The administration of the lower 0.1 mg/kg dose of PBGD mRNA formulated with Compound 18 showed a partial reduction of porphyrin excretion after the first induction. Control luciferase mRNA provided no reduction in ALA or PBG increase following phenobarbital challenge when formulated with either lipid nanoparticle.

Figure 22A:
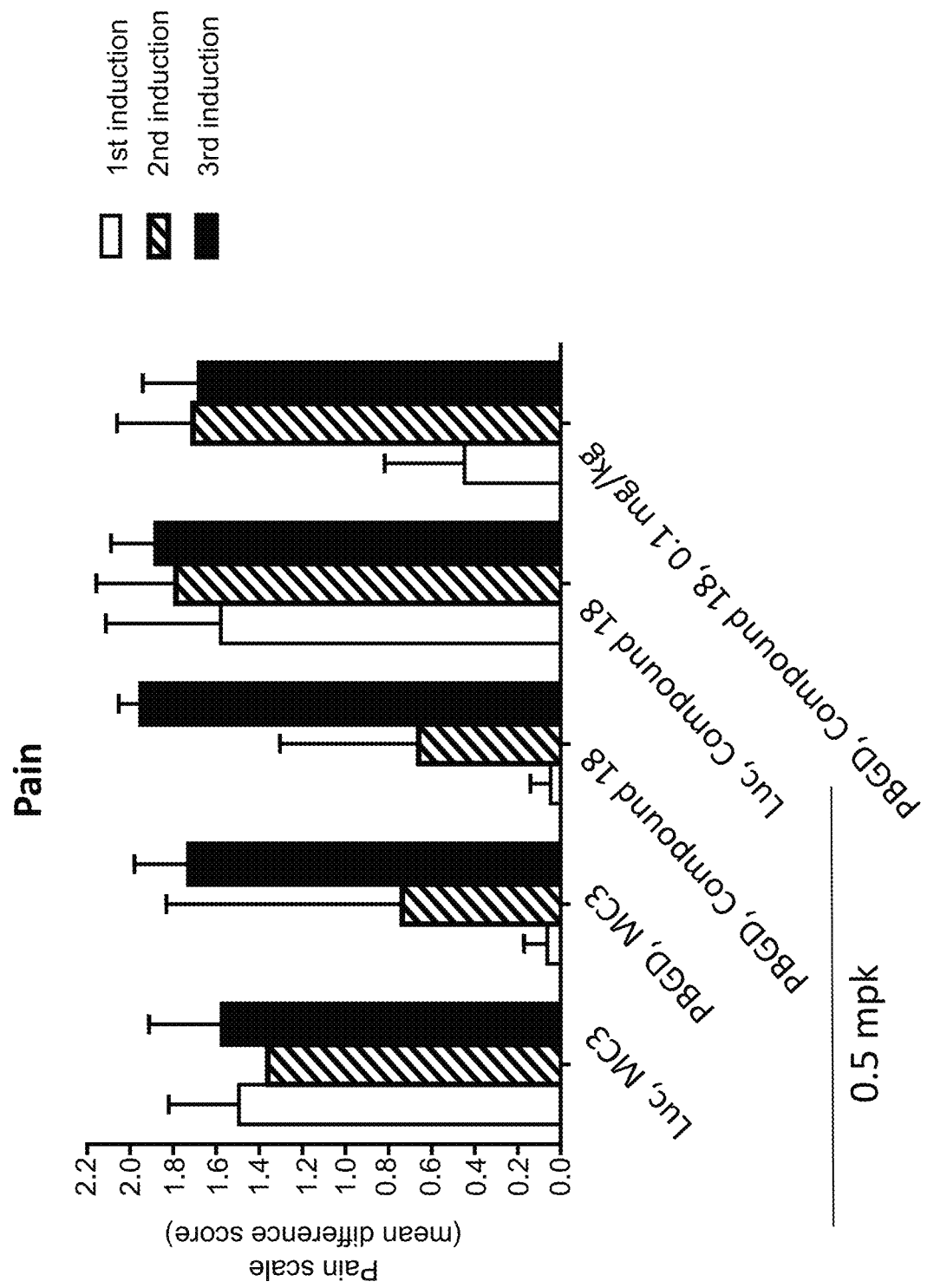

B. Protection against pain: The effect of the administration of mRNAs encoding wild-type PBGD formulated with either MC3 or Compound 18 on pain in AIP mice was evaluated. mRNA encoding luciferase formulated in MC3 or Compound 18 was used as a control. As shown in FIG. 22A, mRNA encoding wild-type PBGD formulated with MC3 at 0.5 mg/kg and formulated with Compound 18 at 0.5 mg/kg or 0.1 mg/k doses, all showed a reduction in pain. Administration of 0.1 mg/mg PBGD mRNA formulated with Compound 18 showed a significant reduction in pain when the first phenobarbital challenge was applied, but there was no significant difference with respect to the controls when the second or third phenobarbital challenge was applied. The pain reduction with 0.5 mg/kg PBGD mRNA formulated in either MC3 or Compound 18 was similar after the first and second phenobarbital inductions. No pain reduction with either formulation was observed after the third phenobarbital induction. Control luciferase mRNA provided no protection against pain.

Figure 22B:
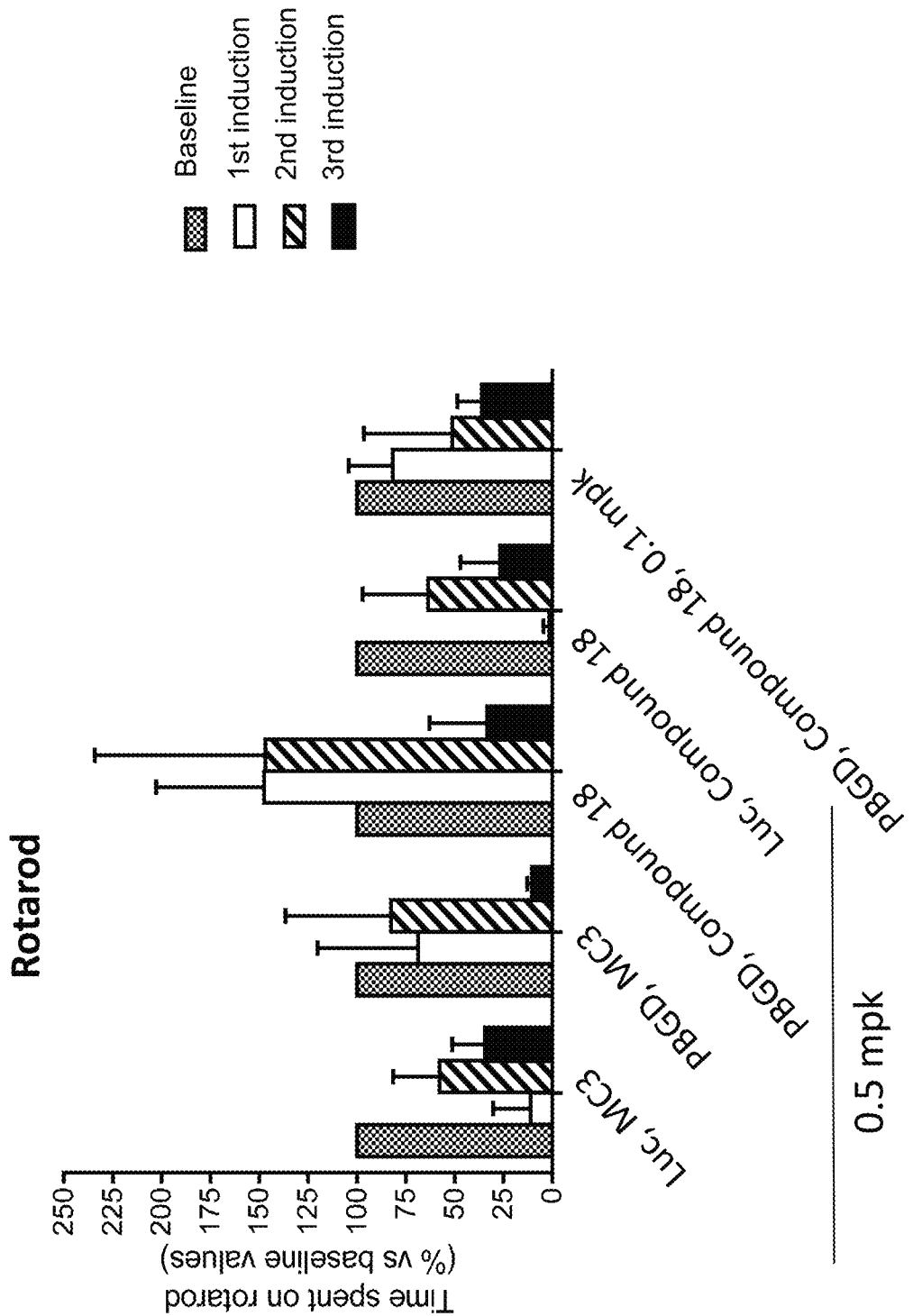

C. Protection against peripheral neuropathy: The time spent on the rotarod (% vs baseline values) for each group is shown in FIG. 22B. The rotarod results after the first and second inductions indicated that the 0.5 mg/kg PBGD mRNA formulation in Compound 18 resulted in longest time spent on the rotarod. The 0.5 mg/kg PBGD mRNA formulation in MC3 also resulted in a time spent on the rotarod close to baseline. Control luciferase treated mice had significantly reduced times on the rotarod compared to baseline.

Example 25

PBGD Activity in Wild-Type Mice Administered Modified PBGD mRNA Constructs

The ability of sequence optimized, chemically modified PBGD-encoding mRNAs to facilitate PBGD activity in vivo was tested. Wild-type CD1 mice were injected intravenously with (i) control 1-methyl-pseudouridine modified luciferase mRNA (ORF SEQ ID NO: 86) (N=3), (ii) 1-methyl-pseudouridine modified mRNA comprising an ORF without sequence engineering (wt PBGD (ORF SEQ ID NO: 87) in Table 8) encoding human PBGD (N=3); (iii) 1-methyl-pseudouridine modified mRNA comprising a sequence optimized ORF encoding human PBGD (constructs PBGD COV2 and PBGD COV1, ORF SEQ ID NO: 88 and 89, respectively) (N=3); or (iv) 5-methoxyuridine modified mRNA comprising a sequence optimized ORF encoding human PBGD (constructs #1 to #26 and #29 to #31 in Table 7) (N=4). The 5-methoxyuridine modified PBGD mRNA included mir-142 and mir-126 binding sites in the 3' untranslated region for Constructs #1 to #27 and #29 to #31, whereas Construct #28 included mir-142 binding site in the 3' untranslated region (Table 7). The mRNAs were formulated in lipid nanoparticles (Compound 18) for delivery into each mouse.

TABLE 7

Modified mRNA constructs including optimized ORFs encoding human PBGD. Each of constructs #1-#28 comprises a Cap1 5' terminal cap and a 3' terminal polyA region.

| PBGD mRNA construct | 5'UTR SEQ ID NO | PBGD ORF Name | SEQ ID NO | 3'UTR SEQ ID NO |
|---|---|---|---|---|
| #1 | 39 | PBGD-CO30 | 89 | 149 |
| #2 | 39 | PBGD-CO31 | 90 | 149 |
| #3 | 39 | PBGD-CO32 | 91 | 149 |
| #4 | 39 | PBGD-CO33 | 92 | 149 |
| #5 | 39 | PBGD-CO34 | 93 | 149 |
| #6 | 39 | PBGD-CO35 | 94 | 149 |
| #7 | 39 | PBGD-CO36 | 95 | 149 |
| #8 | 39 | PBGD-CO37 | 96 | 149 |
| #9 | 39 | PBGD-CO38 | 97 | 149 |
| #10 | 39 | PBGD-CO39 | 98 | 149 |
| #11 | 39 | PBGD-CO40A | 99 | 149 |
| #12 | 39 | PBGD-CO41A | 100 | 149 |
| #13 | 39 | PBGD-CO42A | 101 | 149 |
| #14 | 39 | PBGD-CO43A | 102 | 149 |
| #15 | 39 | PBGD-CO44A | 103 | 149 |
| #16 | 39 | PBGD-CO45A | 104 | 149 |
| #17 | 39 | PBGD-CO46A | 105 | 149 |
| #18 | 39 | PBGD-CO47A | 106 | 149 |
| #19 | 39 | PBGD-CO40B | 107 | 149 |
| #20 | 39 | PBGD-CO41B | 108 | 149 |
| #21 | 39 | PBGD-CO42B | 109 | 149 |
| #22 | 39 | PBGD-CO43B | 110 | 149 |
| #23 | 39 | PBGD-CO44B | 111 | 149 |

TABLE 7-continued

Modified mRNA constructs including optimized ORFs encoding human PBGD. Each of constructs #1-#28 comprises a Cap1 5' terminal cap and a 3' terminal polyA region.

| PBGD mRNA construct | 5'UTR SEQ ID NO | PBGD ORF Name | SEQ ID NO | 3'UTR SEQ ID NO |
|---|---|---|---|---|
| #24 | 39 | PBGD-CO45B | 112 | 149 |
| #25 | 39 | PBGD-CO46B | 113 | 149 |
| #26 | 39 | PBGD-CO47B | 114 | 149 |
| #27 | 39 | PBGD-CO45B | 112 | 150 |
| #28 | 39 | PBGD-CO45B | 112 | 151 |
| wt | 39 | wt ORF | 87 | 81 |
| PBGD COV2 | 39 | PBGD COV2 | 88 | 81 |
| PBGD COV1 | 39 | PBGD COV1 | 89 | 81 |
| #29 | 39 | PBGD-CO48 | 115 | 149 |
| #30 | 39 | PBGD-CO49 | 116 | 149 |
| #31 | 39 | PBGD-CO50 | 117 | 149 |

The hepatic PBGD activity in the wild-type mice at 24 hours post-injection for sequence optimized, chemically modified PBGD mRNA Constructs #1-18 formulated in Compound 18 compared to controls is shown in Table 8.

TABLE 8

PBGD activity in PBGD mRNA constructs

| Construct | Average PBGD activity (uroporphyrin I (nM)) | StdDev |
|---|---|---|
| #1 | 358.4 | 23.5 |
| #2 | 242.7 | 17.9 |
| #3 | 375.0 | 76.8 |
| #4 | 244.0 | 87.4 |
| #5 | 266.7 | 66.9 |
| #6 | 181.0 | 24.7 |
| #7 | 383.9 | 260.3 |
| #8 | 265.7 | 39.9 |
| #9 | 296.9 | 96.0 |
| #10 | 323.9 | 113.9 |
| #11 | 401.1 | 33.8 |
| #12 | 289.9 | 39.2 |
| #13 | 348.0 | 73.5 |
| #14 | 501.8 | 40.6 |
| #15 | 216.4 | 52.8 |
| #16 | 631.7 | 141.9 |
| #17 | 400.9 | 146.8 |
| #18 | 375.1 | 67.9 |
| wt PBGD | 272.6 | 10.4 |
| PBGD COV2 | 493.6 | 67.7 |
| PBGD COV1 | 297.3 | 110.6 |
| luciferase | 103.4 | 11.6 |

The sequence optimized, chemically modified PBGD mRNAs facilitated increased PBGD activity compared to controls. Notably, sequence optimized, 5-methoxyuridine modified PBGD mRNA Constructs #14 and #16 formulated in Compound 18 resulted in PBGD activity significantly higher than the other 5-methoxyuridine modified constructs. Sequence optimized, 5-methoxyuridine modified PBGD mRNA (construct #14) formulated in Compound 18 was used in the further studies described in Examples 26-27 below. Sequence optimized, 5-methoxyuridine modified PBGD mRNA (construct #16) formulated in Compound 18 was used in the further studies described in Examples 28-31 below.

Figure 23A:
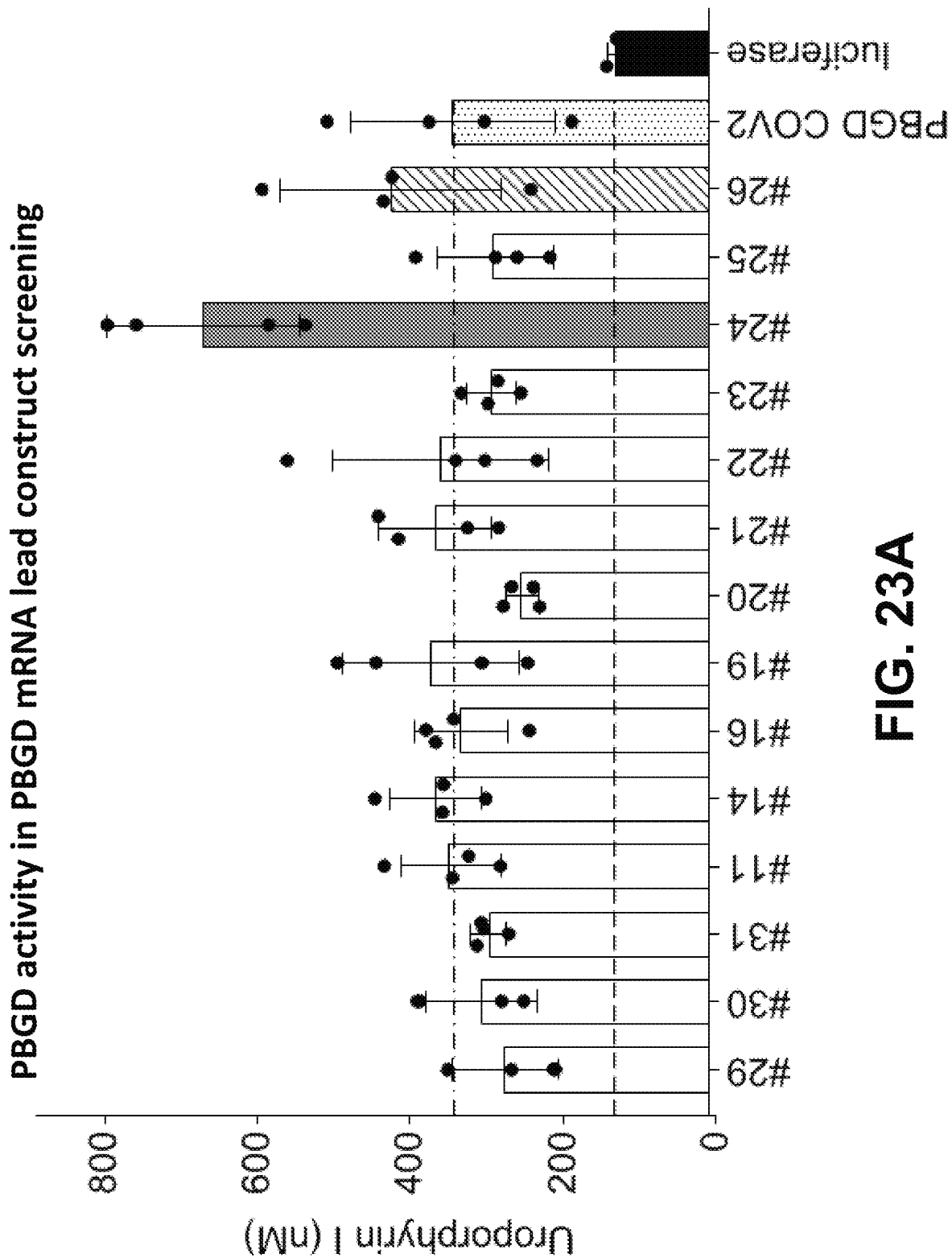
Figure 23B:
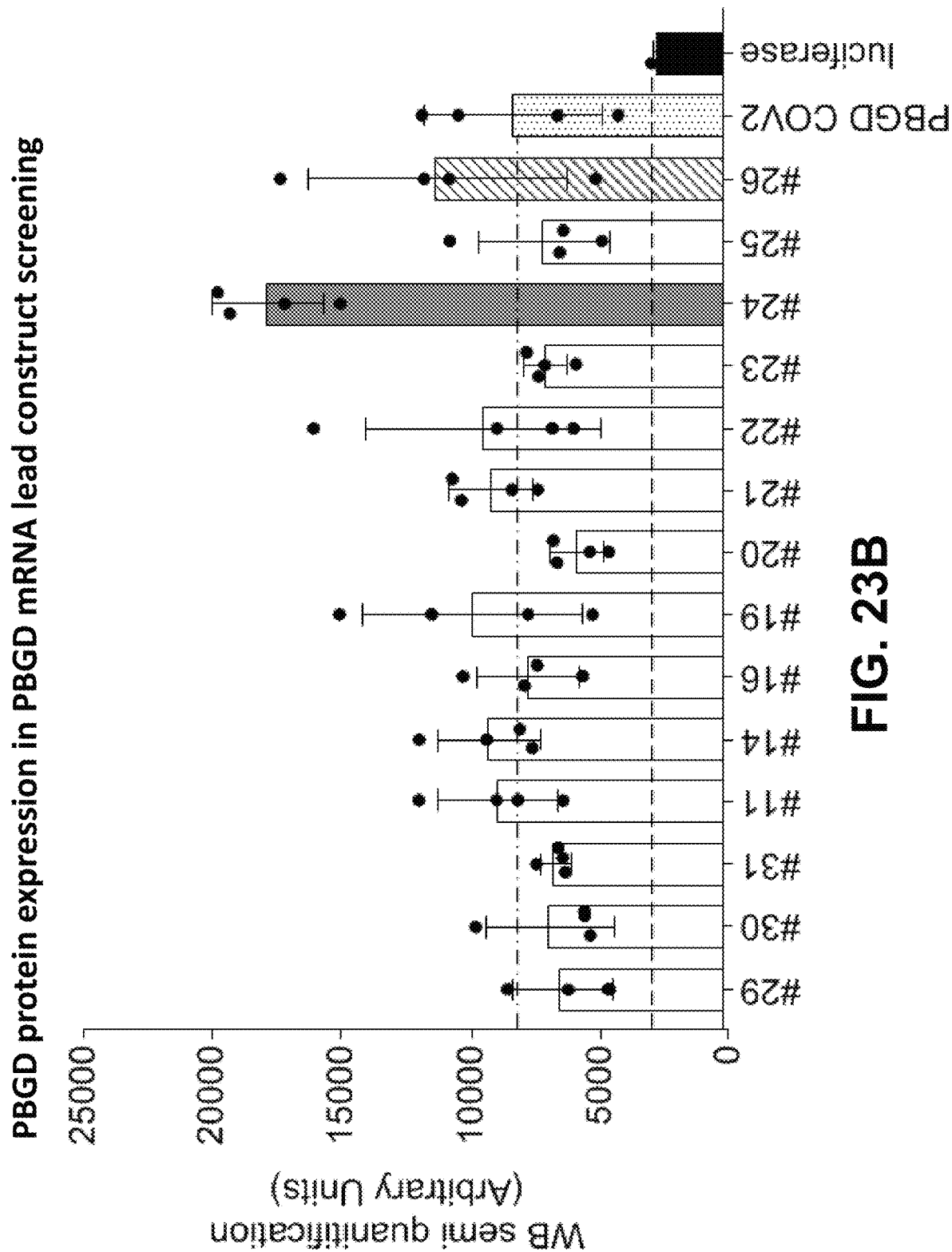

FIGS. 23A and 23B, respectively, show hepatic PBGD activity and PBGD protein expression in the wild-type mice at 24 hours post-injection with sequence optimized, chemically modified PBGD mRNA Constructs #11, #14, #16, #19 to #26, and #29 to #31 formulated in Compound 18. All constructs tested resulted in PBGD activity and protein expression well above the control luciferase construct. Notably, sequence optimized, 5-methoxyuridine modified PBGD mRNAs Constructs #24 and #26 formulated in Compound 18 resulted in PBGD activity and protein expression significantly higher than the other 5-methoxyuridine modified constructs tested.

Example 26

Multi-Dose Study in AIP Mice Administered Modified PBGD mRNA

The ability of multi-dose administration of mRNA encoding human PBGD formulated in lipid nanoparticle to reduce disease-associated biomarkers, pain and peripheral neuropathy in AIP mice after multiple phenobarbital induced attacks was tested. Three doses (0.5 mg/kg, 0.2 mg/kg, or 0.05 mg/kg) of sequence optimized, 5-methoxyuridine modified (miR-142 and miR-126) mRNA encoding PBGD (construct #14 in Table 7) formulated in Compound 18-containing lipid nanoparticles (Compound 18:Cholesterol:DSPC:DMG:PEG) (N=5, each dose) or a 0.5 mg/kg dose of control 1-methyl-pseudouridine modified (no miR) mRNA encoding luciferase formulated in Compound 18 (N=5) were administered intravenously to AIP mice according to the dosing schedule presented in FIG. 24. The mRNAs were administered as an IV bolus once every two weeks (i.e., on days 2, 15, and 29) of the study. AIP mice administered PBS control were included for comparision (N=4). Mice were subjected to 3 phenobarbital challenges, each of which consisted of 4 separate intraperitoneal injections of phenobarbital. The end points of the study included (A) urinary excretion of porphyrins and porphyrin precursors, (B) pain measurements, (C) peripheral neuropathy using rotarod and footprint analysis, (D) sciatic nerve function, (E) liver function test, and (F) anti-PBGD antibody levels.

Figure 25:
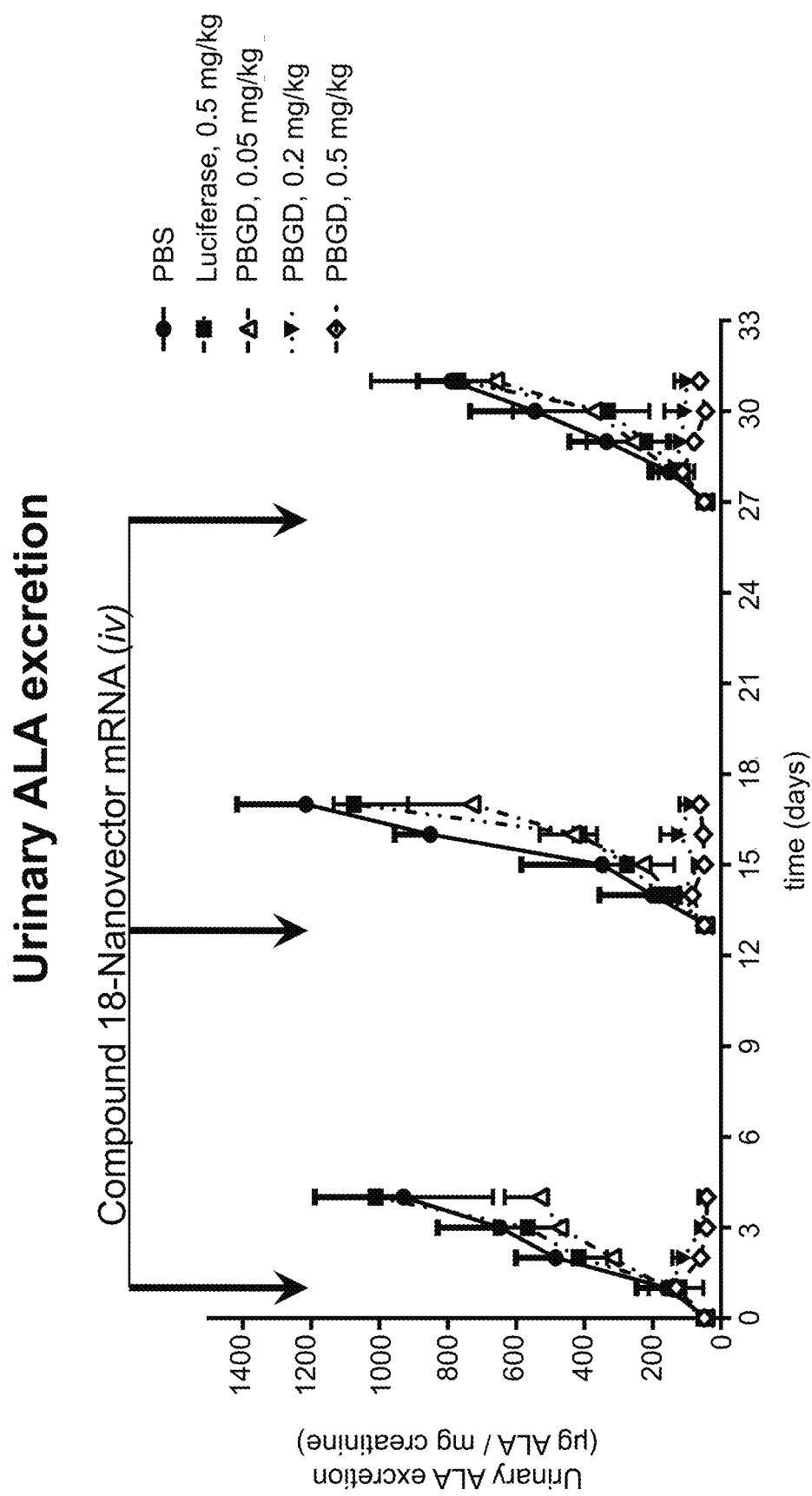
FIG. 25 shows urinary ALA excretion levels (micrograms of ALA per mg of creatinine) in AIP mice subjected to multiple porphyria attacks induced by intraperitoneal phenobarbital challenges according to the study design shown in FIG. 24. Data are expressed as mean±SD.
Figure 26:
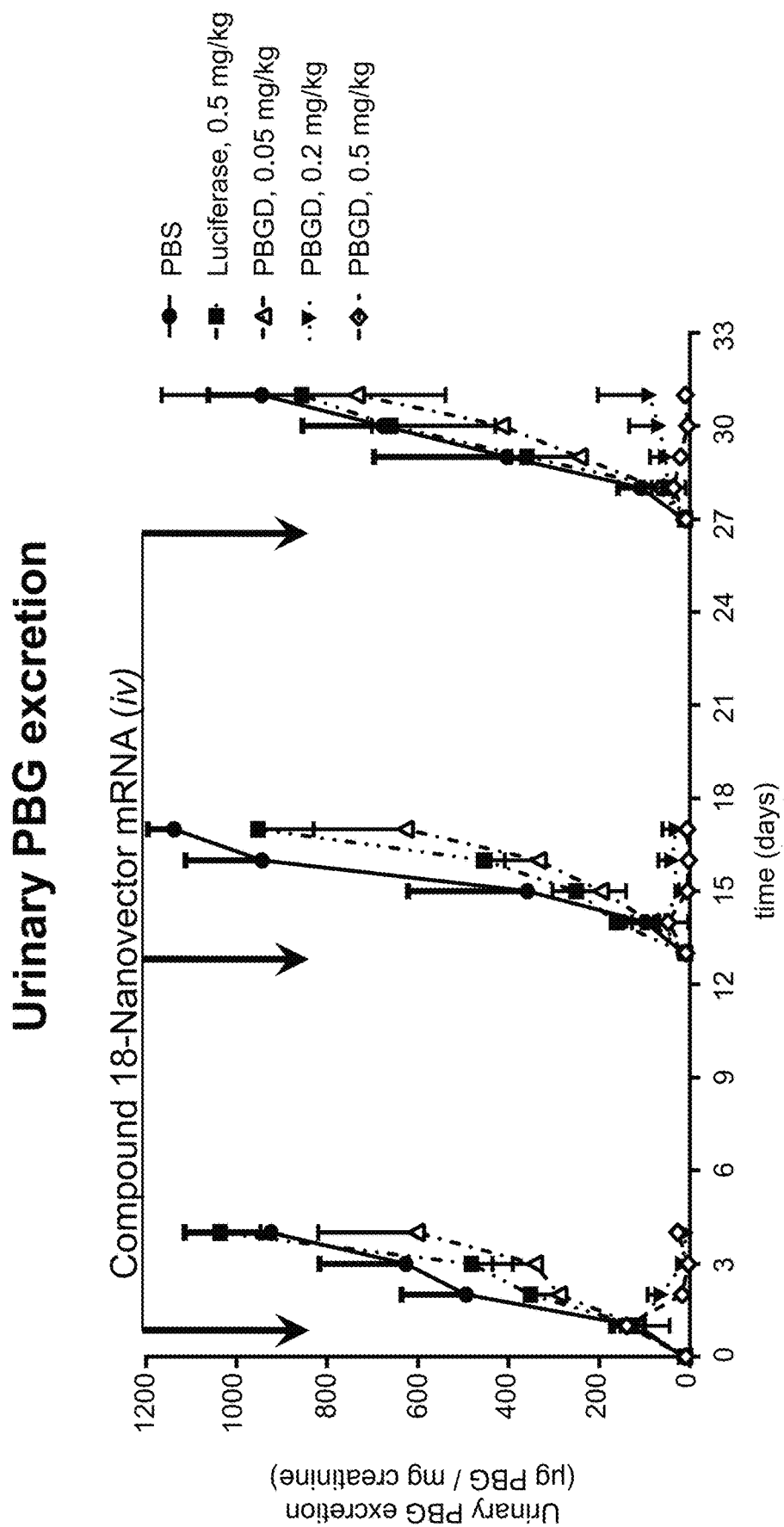
FIG. 26 shows urinary PBG excretion levels (micrograms of PBG per mg of creatinine) in AIP mice subjected to multiple porphyria attacks induced by intraperitoneal phenobarbital challenges according to the study design shown in FIG. 24. Data are expressed as mean±SD.
Figure 27:
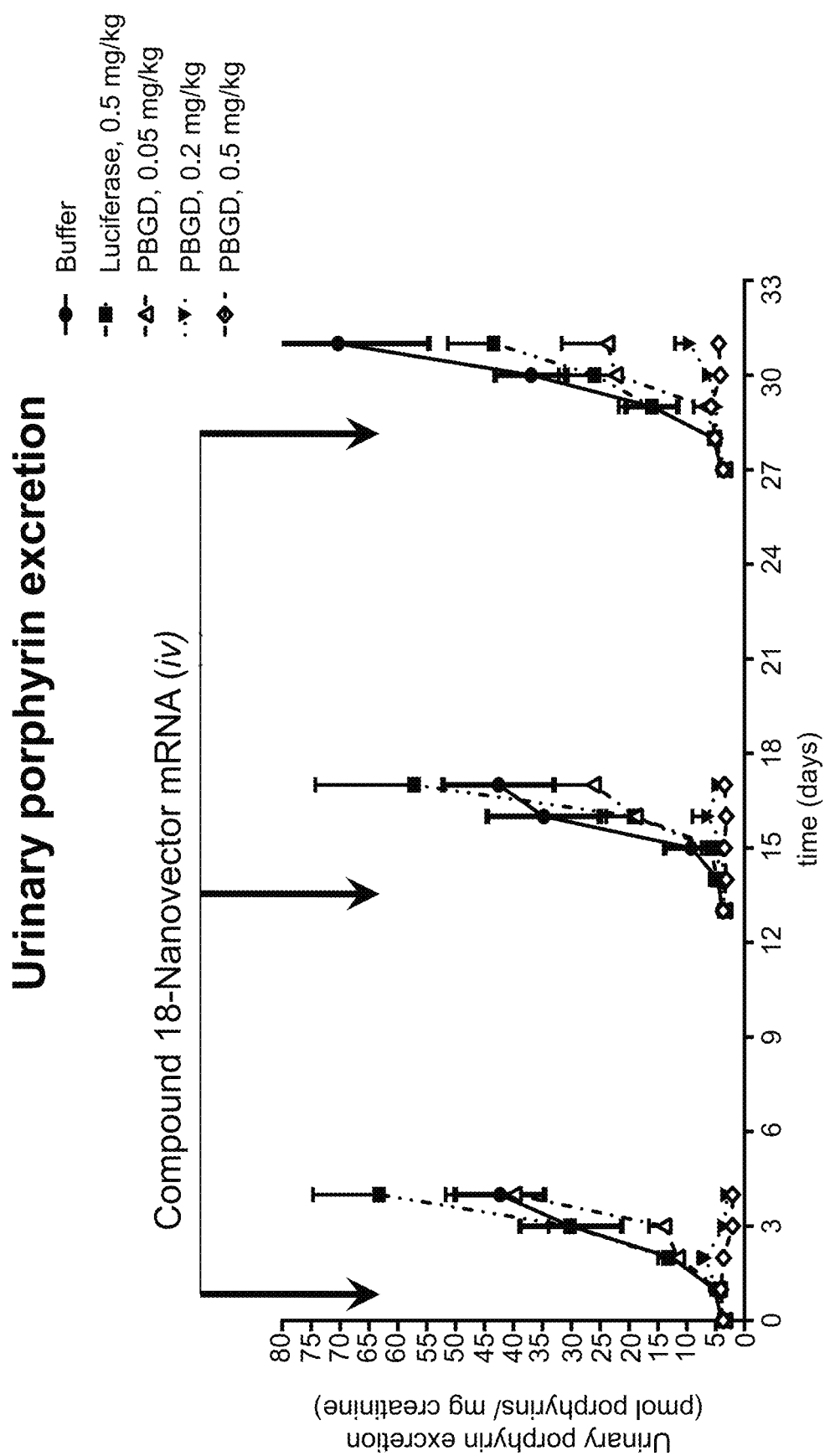
FIG. 27 shows urinary porphyrin excretion levels (micrograms of porphyrin per mg of creatinine) in AIP mice subjected to multiple porphyria attacks induced by intraperitoneal phenobarbital challenges according to the study design shown in FIG. 24. Data are expressed as mean±SD.

A. Reduction of urinary ALA, PBG, and porphyrin excretion: Urinary excretion levels of ALA, PBG, and porphyrin in AIP mice following phenobarbital challenge were measured as described in Example 22 above. The results for urinary excretion of ALA are shown in FIG. 25, PBG excretion is shown in FIG. 26, and porphyrin excretion is shown in FIG. 27. Urinary ALA, PBG, and porphyrin increased in AIP control mice administered control luciferase mRNA or PBS after phenobarbital challenge. There was a dose-response effect for AIP mice administered PBGD mRNA. The 0.05 mg/kg doses of PBGD had no significant effect. Both the 0.2 mg/kg and 0.5 mg/kg doses of PBGD mRNA reduced biomarker excretion after each phenobarbital challenge, but the 0.5 mg/kg dose consistently achieved the greatest reduction throughout all three challenges. After the administration of the PBGD mRNA at 0.2 mg/kg and 0.5 mg/kg doses, ALA, PBG and prophyrin levels were close to baseline levels. These results show that (i) there was a very fast onset of the protective effect of the PBGD mRNA after administration, (ii) the observed effect on ALA, PBG, and porphyrin urinary excretion levels was very potent, and (iii) the observed protective effect was achieved during each attack after multiple dosing.

B. Protection against pain: The effect administering multiple 0.5 mg/kg, 0.2 mg/kg, and 0.05 mg/kg doses of PBGD mRNAs on pain in AIP mice after phenobarbital induction was evaluated. Pain was assessed by measuring orbital tightening, nose bulge, cheek bulge, ear position, whisker change, abdominal grooming, and respiratory distress. Pain measurement results (mean difference score) are presented in FIG. 28. Data were log transformed prior to a repeated measures ANOVA analysis to equalize variances and pairwise comparisons were made using Bonferroni's multiple comparisons.

The results show that administration of PBGD mRNA at 0.2 mg/kg and 0.5 mg/kg doses protected against the pain induced after all three phenobarbital challenges.

C. Protection against peripheral neuropathy: Improvement in peripheral neuropathy was assessed by rotarod and footprint measurements (gait patterns). The rotarod (time spent in seconds) and gait patterns (stride length in cm) are shown in FIG. 29 and FIG. 30, respectively. Data are expressed as mean with SD. In case of the statistical analysis, data were log transformed prior to repeated measures ANOVA analysis to equalize variances and comparisons between baseline and marks obtained after each induction were made using Bonferroni's multiple comparisons. Some animals increase their mark on the third induction due to training. These results show that when administered a dose of 0.05 mg/kg the PBGD mRNA had a weak effect. However, administration of PBGD mRNA at doses of 0.2 mg/kg and 0.5 mg/kg protected against peripheral motor disturbance induced after all three phenobarbital challenges.

D. Improvement in sciatic nerve dysfunction caused by recurrent acute attacks: Sciatic nerve function was assessed in AIP mice as described in Example 22 above. The compound action potentials were measured in the two hind legs of each animal. The amplitude parameter shown in FIG. 31 gives an estimation of the total volume of fibers. AIP mice administered PBS or control luciferase mRNA showed a reduction in amplitude after three consecutive phenobarbital challenges. The administration of 0.5 mg/kg of PBGD mRNA showed the most protection against this loss of amplitude AIP challenged mice.

E. Evaluation of serum transaminases and bilirubin: Levels of serum transaminases (FIG. 32A and FIG. 32B) and serum bilirubin (FIG. 32C) were assessed in AIP mice at the end of the study.

Serum levels of the ALT (alanine transaminase) and AST (aspartate transaminase) transaminases at sacrifice (six days after the third administration of modified mRNA encoding wild type PBGD, and three days after the last phenobarbital dose) showed no significant variations among the groups and were similar to WT mouse levels. There was no dose dependent effect.

Serum bilirubin levels were similar between groups as well.

F. Anti-Drug Antibody (ADA) Assay: The presence of anti-PBGD antibodies in the serum of the AIP mice injected with doses of PBGD mRNA used in the experiments described in this Example was determined using the following protocol:

1. Coat with antigen (0.1 µg in 50 µl per well) in carbonate buffer 0.1 M at 4° C. overnight.
2. Wash three times with PBS-Tween 0.05% (200 µl per well).
3. Block with blocking solution PBS-Tween 0.05% with 5% milk (200 µl per well), 1 hour at room temperature.
4. Make 12 dilutions for each serum sample, starting with a 1:20 dilution, in blocking solution and incubate for 1 hour 30 minutes at 37° C. (Vf=50 µl). The serum was diluted 1:2, 50 µl serum were combined with 50 µl assay diluent, and 50 µL were used.
5. Wash five times with PBS-Tween 0.05% (200 µl per well).
6. Add protein A HPRO in blocking solution with a dilution 1:5,000, and incubate for 1 hour 30 minutes at 37° C.
7. Wash five times with PBS-Tween 0.05% (200 µl per well).
8. Add TMB (50 µl per well) and incubate 3 min.
9. Stop the reaction with sulfuric acid 2 M (30 µl per well).
10. Read the absorbance at 450 nm.

The ADA assay did not detect the presence of anti-PBGD antibodies in the serum of the AIP mice (data not shown).

Example 27

Acute Treatment Study in AIP Mice Administered Modified PBGD mRNA

In the treatment of acute AIP attacks, it is important to reduce the very high levels of porphyrin precursors (ALA and PBG) and porphyrin as fast as possible. Accordingly, a study was designed to assess the speed of onset to drop urinary levels of ALA, PBG and prophyrin after the administration of mRNA encoding human PBGD.

AIP mice were subjected to a single phenobarbital challenge to induce an acute AIP episode. After three intraperitoneal injections of phenobarbital (at days 1, 2 and 3), but 2 hours prior to the fourth phenobarbital injection in the challenge (at day 4), sequence optimized, 5-methoxyuridine modified (miR-142/126) mRNA encoding PBGD (construct #14 in Table 7) formulated in Compound 18-containing lipid nanoparticles (Compound 18:Cholesterol:DSPC:DMG:PEG) was administered intravenously as a single-dose (0.5 mg/kg) intravenous bolus (N=5). Luciferase mRNA also formulated in Compound 18-containing lipid nanoparticles (Compound 18:Cholesterol:DSPC:DMG:PEG) administered with phenobarbital challenge (N=4) and PBS administered without phenobarbital challenge (N=3) were included as controls. An additional fifth phenobarbital injection was given (at day 5) to sustain the high levels of urinary biomarkers in luciferase controls at days 4 and 5. The design of the study dosing is summarized in FIGS. 33A-33C. After each phenobarbital injection, mice were installed in a metabolic cage to obtain whole urine during the next 24 hours for measurement of ALA, PBG and porphyrin levels.

The results show a rapid lowering of urinary porphyrin precursors ALA (FIG. 33A) and PBG (FIG. 33B) as well as the levels of porphyrin (FIG. 33C) against an established acute attack with administration of 0.5 mg/kg PBGD mRNA. ALA and PBG excretion levels rapidly returned to basal values within 2 hours at day 4 between PBGD mRNA and fourth phenobarbital injections, and porphyrin levels returned to basal level 1 day after administration of PBGD mRNA (at day 5). In contrast, ALA and PBG levels continued to rise and porphyrin levels remained elevated at day 5 in mice administered control luciferase mRNA.

In this study the modified mRNA was administered late during the acute AIP episode when the biomarkers had reached peak levels (as indicated by the values corresponding to the luciferase control). Under these acute AIP attack conditions, PBGD mRNA rapidly lowered all the biomarker levels to baseline.

Example 28

Pharmacokinetics Study of Modified mRNA Encoding Wild Type PBGD in Wild Type CD-1 Mice A study was conducted to evaluate the duration and pharmacokinetics of PBGD mRNA administration in vivo. Sequence optimized, 5-methoxyuridine modified (miR-142/

126) mRNA encoding PBGD (construct #16 in Table 7) formulated in lipid nanoparticles (Compound 18) was administered to wild-type mice (CD-1, 9 weeks old) as a single 0.5 mg/kg intravenous bolus. The time points of the study were 2 hours, 6 hours, 10 hours, 16 hours, 24 hours, 2 days, 4 days, 7 days, 10 days, and 14 days. Upon sacrifice, livers and spleens of the animals were perfused. mRNA levels were determined using bDNA testing. Two samples were collected for bDNA testing from the left and right medial lobes of the liver of each animal for each time point (up to 4 days). PBGD activity and protein levels were measured in liver (1 gram of liver tissue in 3.5 ml KCl solution in 15 ml tubes) and spleen (half spleen, i.e., approximately 50-100 mg, in 200 µl KCl solution in 1.5 ml Eppendorf tubes). Pieces of liver and spleen tissue were fixed in 10% formalin for histology analysis (both RNAscope and IHC). Liver samples were taken from the left and right medial lobes and immediately fixed in 10% formalin. Spleen samples were first cut cross-sectionally and then fixed in 10% formalin. Small pieces of liver tissue samples were snap frozen for absolute quantification by LC/MSMS (n=2, left and right medial lobe sample samples for each time point).

The hepatic PBGD activity over time in mice administered PBGD mRNA compared to mice administered control luciferase mRNA is shown in FIG. 34. As shown in FIG. 35A, the terminal $t_{1/2}$ (by noncompartmental analysis) of mRNA-encoded PBGD activity was 8 days. PBGD activity peaked between 6 and 10 hours, and then decayed until it reached baseline levels at approximately 7 days post injection. The half-life of mRNA-encoded PBGD activity was consistent with the half-life of the protein encoded by the PBGD construct used in Example 21 (see FIG. 13 and FIG. 35B). A single dose of the modified mRNA encoding wild type PBGD appears to have sufficient half-life to treat a full AIP acute attack. PBGD protein levels in liver (FIG. 36) was consistent with the activity data. The hepatic levels of human PBGD mRNA also correlated well with the PBGD activity levels in liver (FIG. 37).

The PK data of splenic PBGD activity in mice showed no increase in splenic PBGD (data not shown) indicating that the increase in PBGD activity was specific to liver tissue. PBGD protein levels in spleen were consistent with the activity data (data not shown).

In the livers of PBGD mRNA treated WT CD1 mice, the PBGD protein expression observed by IHC was consistent with the PBGD activity shown in FIG. 34, and was also consistent with the human PBGD protein levels detected by LC/MSMS shown in FIG. 36. The expression of exogenous PBGD was homogeneous throughout all hepatocytes and decreased after 16 hours post-injection. Increased expression of PBGD protein above the basal level was observed at 2 hours, 6 hours, 10 hours, 16 hours, and 24 hours after injection of the PBGD mRNA, as shown in FIGS. 38A, 38B, 38C, 38D, and 38E, respectively. A representative liver tissue sample from a luciferase mRNA treated WT CD1 mouse is shown in FIG. 38F to assess the PBGD basal level. No PBGD protein expression was detected in the luciferase control, which indicated no cross-reaction of the Novus anti-PBGD antibody used for IHC analysis with mouse species.

Example 29

Pharmacokinetics Study of Modified mRNA Encoding Wild Type PBGD in AIP Mice

A study was conducted to evaluate the duration and pharmacokinetics of PBGD mRNA administration in vivo. Wild-type PBGD-encoding 1-methyl-pseudouridine modified mRNA comprising a codon optimized ORF (PBGD COV1; ORF SEQ ID NO: 89) formulated in MC3 was administered at 0.5 mg/kg, and sequence optimized, 5-methoxyuridine modified (miR-142 and miR-126) mRNA encoding PBGD (construct #16 in Table 7) formulated in lipid nanoparticles (Compound 18) was administered at 0.5 mg/kg and 0.2 mg/kg doses to AIP mice as a single intravenous bolus. The time points of the study were 10 hours, 1 day, 2 days, 4 days, 7 days, and 10 days. The hepatic PBGD activity in AIP mice following administration of PBGD mRNA is shown in FIG. 39. For comparison, the 12 units threshold line in FIG. 39 is the level of PBGD observed in livers of wild-type mice (C57BL/6), and the 3 units threshold line is the level of PBGD in livers of AIP mice without treatment.

The results show that hepatic PBGD activity was within the therapeutic window for up to 7 days after administration. An acute porphyria attack in a human lasts between 5 and 7 days. In humans, the increase from 2 units to 5 units completely restores the PBGD activity in the liver. Accordingly, these results suggests that a single administration of mRNA encoding wild-type PBGD could protect against an acute porphyria attack.

Example 30

Blood Pressure in AIP Mice Administered Modified PBGD mRNA

The ability of administration of PBGD mRNA formulated in lipid nanoparticle to reduce blood pressure in AIP mice during the phenobarbital induced attack was tested (FIG. 40A and FIG. 40B). AIP mice were subjected to 4 intraperitoneal injections of phenobarbital to induce the acute attack. Wild-type PBGD-encoding 1-methyl-pseudouridine modified mRNA comprising a codon optimized ORF (PBGD COV1) formulated in MC3 (N=5) and wild-type PBGD-encoding 1-methyl-pseudouridine modified mRNA comprising a codon optimized ORF (PBGD COV1; ORF SEQ ID NO: 89) formulated in MC3 (N=5) and wild-type PBGD-encoding 1-methyl-pseudouridine modified mRNA comprising a codon optimized ORF (PBGD COV2; ORF SEQ ID NO: 88) formulated in Compound 18-containing lipid nanoparticles (Compound 18:Cholesterol:DSPC:DMG:PEG) (N=6) were administered intravenously to AIP mice at a dose of 0.5 mg/kg and 1 mg/kg, respectively, before the first phenobarbital injection. AIP mice subjected to phenobarbital challenge but with no administration of PBGD mRNA were included for comparison (N=9). AIP mice (N=11) and wild type C57BL/6 mice (N=9) without any treatment were included as control.

AIP mice have blood pressure readings in the range of wild type mice. Four phenobarbital injections in AIP mice significantly increased both systolic and diastolic blood pressure values. Full protection against hypertension and porphyrin precursors accumulation induced by phenobarbital challenge was achieved in AIP mice injected with a therapeutic dose of PBGD mRNA in both MC3 and compound 18 formulations. These data show for the first time that porphyrin precursors generated in the liver correlated with blood hypertension.

Example 31

Pharmacokinetics Study of Modified mRNA Encoding Wild Type PBGD in Wild-Type Sprague Dawley Rats Hepatic PBGD activity was determined in WT Sprague Dayley rats administered sequence optimized, 5-methoxyuridine modified PBGD mRNA (construct #16 in Table 7) formulated in lipid nanoparticles (Compound 18) at a dose of 0.5 mg/kg as a single intravenous bolus. The hepatic PBGD activity at 24 hours and 48 hours following administration of PBGD mRNA is shown in FIG. 41. The increase of PBGD activity in rats as a result of PBGD mRNA injection, compared to the basal PBGD activity level in rats administered control luciferase mRNA, was to similar extent of that in WT CD1 mice at 24 hours and 48 hours post administration as shown in FIG. 34.

In the livers of PBGD mRNA treated WT Sprague Dawley rats, the expression level of PBGD protein was assessed by IHC as shown in FIGS. 42A and 42B. The expression of exogenous PBGD was homogeneous throughout all hepatocytes. Increased expression of PBGD protein above the basal level was observed at 24 hours after injection of the PBGD mRNA formulated in compound 18 at 1 mg/kg as shown in FIG. 42A. A representative liver tissue sample from a control PBS injected WT Sprague Dawley rat is shown in FIG. 42B. Minimal PBGD protein expression (about U) was detected in the PBS control, which indicated very low level of cross-reaction of the Novus anti-PBGD antibody used for IHC analysis with rat species.

Example 32

PBGD Activity in a Non-human Primate After Administration of a Modified PBGD mRNA Construct Hepatic PBGD activity was determined in Cynomolgus macaque 24 hours after IV-administration of 5-methoxyuridine modified PBGD mRNA comprising miR142 and miR126 binding sites. The mRNAs were formulated in lipid nanoparticles comprising Compound 18 or Compound 236. Animals were administered a single intravenous bolus of (i) 0.5 mg/kg mRNA formulated with Compound 236 or (ii) 1 mg/kg mRNA formulated with Compound 18. Control animals were administered PBS. Hepatic PBGD activity and expression at 24 hours following administration of PBGD mRNA is shown in FIGS. 43A and 43B, respectively. Animals administered 0.5 mg/kg mRNA formulated in lipid nanoparticles comprising Compound 236 showed about 40% increase in PBGD activity and about 90% increase in PBGD expression compared to the level seen in control animals administered PBS.

It is to be appreciated that the Detailed Description section, and not the Summary and Abstract sections, is intended to be used to interpret the claims. The Summary and Abstract sections can set forth one or more but not all exemplary embodiments of the present invention as contemplated by the inventor(s), and thus, are not intended to limit the present invention and the appended claims in any way.

The present invention has been described above with the aid of functional building blocks illustrating the implementation of specified functions and relationships thereof. The boundaries of these functional building blocks have been arbitrarily defined herein for the convenience of the description. Alternate boundaries can be defined so long as the specified functions and relationships thereof are appropriately performed.

The foregoing description of the specific embodiments will so fully reveal the general nature of the invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present invention should not be limited by any of the above-described exemplary embodiments, but should be defined only in accordance with the following claims and their equivalents.

All publications, patent applications, patents, and other references mentioned herein are incorporated by reference in their entirety. In case of conflict, the present specification, including definitions, will control.

What is claimed is:

1. A method of treating an acute *Porphyria* attack in a human subject in need thereof, the method comprising administering to the human subject a lipid nanoparticle comprising a therapeutically effective amount of a messenger RNA (mRNA) encoding a porphobilinogen deaminase (PBGD) polypeptide, wherein the mRNA comprises an open reading frame comprising the nucleotide sequence set forth in SEQ ID NO: 102 or SEQ ID NO: 104, and wherein the human subject has acute intermittent *Porphyria*.

2. The method of claim 1, wherein the mRNA comprises at least one chemically modified nucleobase.

3. The method of claim 2, wherein the at least one chemically modified nucleobase is selected from the group consisting of pseudouracil, N1-methylpseudouracil, 1-ethylpseudouracil, 2-thiouracil, 4'-thiouracil, 5-methylcytosine, 5-methyluracil, 5-methoxyuracil, and any combination thereof.

4. The method of claim 3, wherein the at least one chemically modified nucleobase is 5-methoxyuracil.

5. The method of claim 4, wherein at least 95% of uracil in the mRNA is 5-methoxyuracil.

6. The method of claim 4, wherein 100% of uracil in the mRNA is 5-methoxyuracil.

7. The method of claim 3, wherein the at least one chemically modified nucleobase is N1-methylpseudouracil.

8. The method of claim 1, wherein the lipid nanoparticle is administered intravenously.

9. The method of claim 1, wherein the lipid nanoparticle is administered to the human subject about once every two weeks.

10. The method of claim 1, wherein the open reading frame comprises the nucleotide sequence set forth in SEQ ID NO: 102.

11. The method of claim 1, wherein the open reading frame comprises the nucleotide sequence set forth in SEQ ID NO: 104.

* * * * *

UNITED STATES PATENT AND TRADEMARK OFFICE
CERTIFICATE OF CORRECTION

PATENT NO. : 12,377,136 B2
APPLICATION NO. : 17/813984
DATED : August 5, 2025
INVENTOR(S) : Paolo Martini et al.

Page 1 of 1

It is certified that error appears in the above-identified patent and that said Letters Patent is hereby corrected as shown below:

On the Title Page

Column 1, (Related U.S. Application Data), Line 4, below "abandoned." insert -- (60) Provisional application No. 62/338,161, filed on May 18, 2016. --, as a new field entry.

In the Claims

Column 573, Line 14, Claim 1, delete "Porphyria" and insert -- porphyria --.

Column 573, Line 22, Claim 1, delete "Porphyria." and insert -- porphyria. --.

Signed and Sealed this
Twenty-eighth Day of October, 2025

John A. Squires
*Director of the United States Patent and Trademark Office*